(12) United States Patent
Komori et al.

(10) Patent No.: US 10,759,781 B2
(45) Date of Patent: Sep. 1, 2020

(54) SUBSTITUTED GUANIDINE DERIVATIVES

(71) Applicant: UBE INDUSTRIES, LTD., Ube-shi, Yamaguchi (JP)

(72) Inventors: Ken-ichi Komori, Ube (JP); Akishi Ninomiya, Ube (JP); Shigeru Ushiyama, Ube (JP); Masaru Shinohara, Ube (JP); Koji Ito, Ube (JP); Tetsuo Kawaguchi, Ube (JP); Yasunori Tokunaga, Ube (JP); Hiroyoshi Kawada, Ube (JP); Haruka Yamada, Ube (JP); Yusuke Shiraishi, Ube (JP); Masahiro Kojima, Ube (JP); Masaaki Ito, Ube (JP); Tomio Kimura, Tokyo (JP)

(73) Assignee: UBE INDUSTRIES, LTD., Ube-Shi, Yamaguchi (JP)

( * ) Notice: Subject to any disclaimer, the term of this patent is extended or adjusted under 35 U.S.C. 154(b) by 0 days.

(21) Appl. No.: 15/750,583

(22) PCT Filed: Aug. 5, 2016

(86) PCT No.: PCT/JP2016/073184
§ 371 (c)(1),
(2) Date: Feb. 6, 2018

(87) PCT Pub. No.: WO2017/022861
PCT Pub. Date: Feb. 9, 2017

(65) Prior Publication Data
US 2019/0152953 A1 May 23, 2019

(30) Foreign Application Priority Data

Aug. 6, 2015 (JP) .................................. 2015-156120
Oct. 27, 2015 (JP) .................................. 2015-210695

(51) Int. Cl.
| | | |
|---|---|---|
| *C07D 403/04* | (2006.01) | |
| *C07D 401/04* | (2006.01) | |
| *A61K 31/4427* | (2006.01) | |
| *A61K 31/506* | (2006.01) | |
| *C07D 401/14* | (2006.01) | |
| *C07D 405/14* | (2006.01) | |
| *C07D 413/14* | (2006.01) | |
| *C07F 7/18* | (2006.01) | |
| *A61K 31/695* | (2006.01) | |
| *A61K 31/4433* | (2006.01) | |
| *A61K 31/5377* | (2006.01) | |
| *A61K 31/443* | (2006.01) | |
| *C07C 55/10* | (2006.01) | |
| *C07C 57/145* | (2006.01) | |
| *C07C 59/255* | (2006.01) | |
| *C07D 403/14* | (2006.01) | |
| *C07F 7/08* | (2006.01) | |

(52) U.S. Cl.
CPC .......... *C07D 403/04* (2013.01); *A61K 31/443* (2013.01); *A61K 31/4427* (2013.01); *A61K 31/4433* (2013.01); *A61K 31/506* (2013.01); *A61K 31/5377* (2013.01); *A61K 31/695* (2013.01); *C07C 55/10* (2013.01); *C07C 57/145* (2013.01); *C07C 59/255* (2013.01); *C07D 401/04* (2013.01); *C07D 401/14* (2013.01); *C07D 403/14* (2013.01); *C07D 405/14* (2013.01); *C07D 413/14* (2013.01); *C07F 7/0892* (2013.01); *C07F 7/18* (2013.01); *Y02P 20/55* (2015.11)

(58) Field of Classification Search
CPC ........................... C07D 403/04; C07D 401/04
See application file for complete search history.

(56) References Cited

U.S. PATENT DOCUMENTS

| | | |
|---|---|---|
| 6,482,920 B1 | 11/2002 | Cozzi et al. |
| 6,974,813 B2 | 12/2005 | Hamanaka et al. |
| 2007/0254931 A1 | 11/2007 | Inoue et al. |
| 2008/0312208 A1 | 12/2008 | Andersen et al. |
| 2011/0166116 A1 | 7/2011 | Dyck et al. |
| 2011/0263567 A1 | 10/2011 | Mátyus et al. |
| 2012/0184520 A1 | 7/2012 | Yoshihara et al. |
| 2013/0143860 A1 | 6/2013 | Yoshihara et al. |
| 2014/0100210 A1 | 4/2014 | Yoshihara et al. |
| 2015/0203480 A1 | 7/2015 | Yoshihara et al. |

FOREIGN PATENT DOCUMENTS

| | | |
|---|---|---|
| CN | 1109468 A | 10/1995 |
| CN | 1226232 A | 8/1999 |
| CN | 1289326 A | 3/2001 |
| CN | 101031555 A | 9/2007 |
| RU | 2008101924 A | 8/2009 |
| WO | WO 2010/029379 A1 | 3/2010 |
| WO | WO 2010/149684 A1 | 12/2010 |

(Continued)

OTHER PUBLICATIONS

Smith, David. Ann. N.Y. Acad. Sci. 1110: 382-388 (2007) 382-388.*
WebMD. Inherited Metabolic Disorders.: Types, Causes, Symptoms and Treatments. (2014). Web: <http://www.webmd.com/a-to-z-guides/inherited-metabolic-disorder-types-and-treatments?page=2>.*
International Search Report (PCT/ISA/210) issued in PCT/JP2016/073184, dated Sep. 20, 2016.
Weston et al., "Vascular adhesion protein-1 promotes liver inflammation and drives hepatic fibrosis", The Journal of Clinical Investigation, vol. 125, No. 2, Feb. 2015. pp. 501-520.
Yu et al., "Aminoguanidine inhibits semicarbazide-sensitive amine oxidase activity: implications for advanced glycation and diabetic complications", Diabetologia, vol. 40, 1997, pp. 1243-1250.

(Continued)

*Primary Examiner* — Emily A Bernhardt
*Assistant Examiner* — Laura M Daniel
(74) *Attorney, Agent, or Firm* — Jianjie Hu

(57) ABSTRACT

The present invention provides a compound of general formula (I) (wherein, $R^1$, X, p and q are as described in the present description and claims), or a pharmacologically acceptable salt thereof, and a pharmaceutical composition containing that compound.

30 Claims, No Drawings

(56) References Cited

FOREIGN PATENT DOCUMENTS

WO    WO 2011/034078 A1    3/2011
WO    WO 2012/124696 A1    9/2012

OTHER PUBLICATIONS

Yu et al., "Involvement of semicarbazide-sensitive amine oxidase-mediated deamination in atherogenesis in KKAy diabetic mice fed with high cholesterol diet", Diabetologia, vol. 45, 2002, pp. 1255-1262.

* cited by examiner

SUBSTITUTED GUANIDINE DERIVATIVES

TECHNICAL FIELD

The present invention relates to substituted guanidine derivatives, a pharmaceutical composition containing the same, and particularly substituted guanidine derivatives and a pharmaceutical composition containing the same for treating diseases prevented, alleviated and/or treated by inhibiting VAP-1.

BACKGROUND ART

Type 2 diabetes is a type of lifestyle disease for which the number of patients with this disease has continued to increase in recent years. A prolonged hyperglycemic state gradually destroys microvessels throughout the body, resulting in the risk of causing serious damage to various organs including the oculus and kidney. These types of serious damage are referred to as diabetic complications, and among these, preventing the onset and inhibiting the progression of the three major diabetic complications consisting of diabetic neuropathy, diabetic retinopathy and diabetic nephropathy are becoming important issues.

Although the prevention of onset and inhibition of progression of diabetic complications are foremost based on the control of blood glucose level, increases in the activity of VAP-1 (vascular adhesion protein-1, also referred to as semicarbazide-sensitive amine oxidase (SSAO)) in blood and the correlation thereof with plasma glycosylated hemoglobin levels has been observed in diabetes patients in recent years. This enzyme, which is selectively located in vascular tissue, catalyzes deamination of methylamine and aminoacetone, respectively producing formaldehyde and methylglyoxal in addition to $H_2O_2$ and ammonia. Since each of these substances has cytotoxicity, increases in VAP-1 in blood are attracting attention as one of the causes of the onset of inflammatory diseases or diabetic complications (see, for example, Non-Patent Documents 1 and 2).

Various VAP-1 enzyme inhibitors have been reported thus far. A compound of the following formula:

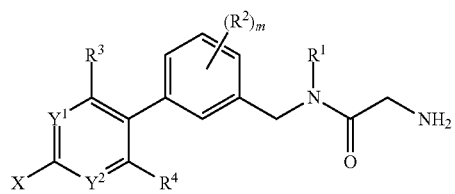

is described to have VAP-1 inhibitory activity and being useful for the prevention and/or treatment of VAP-1-associated diseases including various types of inflammatory diseases and diabetic complications, and particularly diabetic nephropathy or diabetic macular edema (see, for example, Patent Document 1).

Moreover, a compound of the following formula:

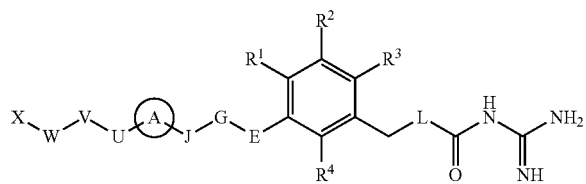

is described to have VAP-1 inhibitory activity and being useful for the prevention and/or treatment of VAP-1-associated diseases including various types of inflammatory diseases and diabetic complications, and particularly diabetic nephropathy or diabetic macular edema (see, for example, Patent Document 2).

On the other hand, it has also been reported that expression of VAP-1 increases in the liver of patients with chronic liver disease, that soluble VAP-1 concentration in serum and expression of VAP-1 in the liver of patients with non-alcoholic fatty liver disease increase in comparison with that of patients not having non-alcoholic fatty liver disease, and that there is a correlation between soluble VAP-1 concentration in serum and the severity of fibrosis based on liver biopsies performed on patients with non-alcoholic fatty liver disease (see, for example, Non-Patent Document 3). On the basis thereof, in addition to the aforementioned diabetic complications, non-alcoholic fatty liver disease, and particularly non-alcoholic steatohepatitis, is expected to be prevented, alleviated and/or treated by inhibiting VAP-1.

PRIOR ART DOCUMENTS

Patent Documents

Patent Document 1: International Publication No. WO 2011/034078

Patent Document 2: International Publication No. WO 2012/124696

Non-Patent Documents

Non-Patent Document 1: Diabetologia (1997), 40: 1243-1250

Non-Patent Document 2: Diabetologia (2002), 45: 1255-1262

Non-Patent Document 3: The Journal of Clinical Investigation (2015), 2: 501-520

SUMMARY OF INVENTION

Problems to be Solved by the Invention

The present invention provides a useful novel compound for treating diseases prevented, alleviated and/or treated by inhibiting VAP-1, and a pharmaceutical composition containing the same.

Means for Solving the Problems

As a result of conducting extensive research on compounds having VAP-1 inhibitory activity, the present inventors found that a series of substituted guanidine derivatives, or salts thereof, having an oxime structure (=N—O—) in a molecule thereof has superior VAP-1 inhibitory activity and is useful for the treatment of diseases prevented, alleviated and/or treated by inhibiting VAP-1, and particularly diabetic nephropathy and non-alcoholic steatohepatitis, thereby leading to completion of the present invention.

The present invention provides the following inventions of [1] to [34].

[1] A compound of general formula (I):

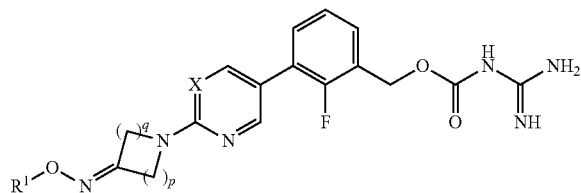

(I)

wherein, $R^1$ represents a hydrogen atom, protecting group, optionally substituted $C_1$-$C_6$ alkyl group, optionally substituted $C_2$-$C_6$ alkenyl group, optionally substituted $C_3$-$C_8$ cycloalkyl group, optionally substituted $C_1$-$C_6$ alkoxy-$C_1$-$C_6$ alkyl group, —$CONR^{11}R^{12}$, optionally substituted heterocyclyl group, optionally substituted heterocyclyl-$C_1$-$C_6$ alkyl group, optionally substituted aryl group or optionally substituted $C_7$-$C_{16}$ aralkyl group, and X represents N or C—$R^2$ wherein, $R^2$ represents a hydrogen atom, halogen atom, optionally substituted $C_1$-$C_6$ alkyl group, optionally substituted $C_3$-$C_8$ cycloalkyl group, optically substituted $C_1$-$C_6$ alkoxy group or cyano group, and p and q, independently of each other, represent a natural number of 1 to 3, provided that the sum of p and q is a natural number of 2 to 4, wherein, the term "substituted" refers to being substituted with at least one substituent selected from the group consisting of a deuterium atom, halogen atom, $C_1$-$C_6$ alkyl group, $C_1$-$C_6$ alkoxy group, $C_1$-$C_6$ alkoxy-$C_1$-$C_6$ alkyl group, $R^{13}O$—$C_1$-$C_6$ alkyl group, halo-$C_1$-$C_6$ alkyl group, $C_7$-$C_{16}$ aralkyl group, $C_1$-$C_7$ acyl group, cyano group, oxo group, —$CONR^{11}R^{12}$, —$OR^{13}$, —$COOR^{14}$, —$NR^{15}R^{16}$ and —$S(O)_nR^{17}$, $R^{11}$ and $R^{12}$ independently represent a hydrogen atom or $C_1$-$C_6$ alkyl group, $R^{13}$ represents a hydrogen atom, $C_1$-$C_7$ acyl group or protecting group, $R^{14}$ represents a hydrogen atom or $C_1$-$C_6$ alkyl group, $R^{15}$ and $R^{16}$ independently represent a hydrogen atom, $C_1$-$C_6$ alkyl group, $C_7$-$C_{16}$ aralkyl group, $C_1$-$C_7$ acyl group, —$COOR^{14}$ or —$S(O)_nR^{17}$, $R^{17}$ represents a $C_1$-$C_6$ alkyl group, and n represents 0, 1 or 2;

or a pharmacologically acceptable salt thereof.

[2] The compound described in [1], of general formula (II):

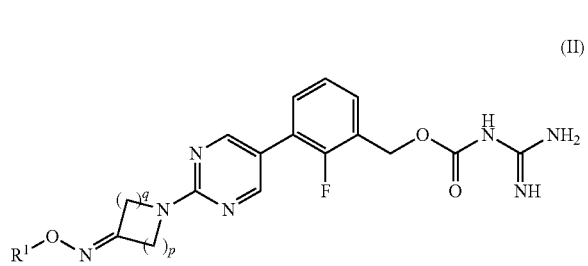

(II)

wherein, $R^1$ represents a hydrogen atom, protecting group, optionally substituted $C_1$-$C_6$ alkyl group, optionally substituted $C_2$-$C_6$ alkenyl group, optionally substituted $C_3$-$C_8$ cycloalkyl group, optionally substituted $C_1$-$C_6$ alkoxy-$C_1$-$C_6$ alkyl group, —$CONR^{11}R^{12}$, optionally substituted heterocyclyl group, optionally substituted heterocyclyl-$C_1$-$C_6$ alkyl group, optionally substituted aryl group or optionally substituted $C_7$-$C_{16}$ aralkyl group, and p and q, independently of each other, represent a natural number of 1 to 3, provided that the sum of p and q is a natural number of 2 to 4, wherein, the term "substituted" refers to being substituted with at least one substituent selected from the group consisting of a deuterium atom, halogen atom, $C_1$-$C_6$ alkyl group, $C_1$-$C_6$ alkoxy group, $C_1$-$C_6$ alkoxy-$C_1$-$C_6$ alkyl group, $R^{13}O$—$C_1$-$C_6$ alkyl group, halo-$C_1$-$C_6$ alkyl group, $C_7$-$C_{16}$ aralkyl group, $C_1$-$C_7$ acyl group, cyano group, oxo group, —$CONR^{11}R^{12}$, —$OR^{13}$, —$COOR^{14}$, —$NR^{15}R^{16}$ and —$S(O)_nR^{17}$, $R^{11}$ and $R^{12}$ independently represent a hydrogen atom or $C_1$-$C_6$ alkyl group, $R^{13}$ represents a hydrogen atom, $C_1$-$C_7$ acyl group or protecting group, $R^{14}$ represents a hydrogen atom or $C_1$-$C_6$ alkyl group, $R^{15}$ and $R^{16}$ independently represent a hydrogen atom, $C_1$-$C_6$ alkyl group, $C_7$-$C_{16}$ aralkyl group, $C_1$-$C_7$ acyl group, —$COOR^{14}$ or —$S(O)_nR^{17}$, $R^{17}$ represents a $C_1$-$C_6$ alkyl group, and n represents 0, 1 or 2;

or a pharmacologically acceptable salt thereof.

[3] The compound described in [2], or a pharmacologically acceptable salt thereof, wherein $R^1$ represents a hydrogen atom, optionally substituted $C_1$-$C_6$ alkyl group, $C_2$-$C_6$ alkenyl group, optionally substituted $C_3$-$C_8$ cycloalkyl group, optionally substituted $C_1$-$C_6$ alkoxy-$C_1$-$C_6$ alkyl group or optionally substituted heterocyclyl group, wherein, the term "substituted" refers to being substituted with at least one substituent selected from the group consisting of a deuterium atom, halogen atom, —$OR^{13}$ and —$S(O)_nR^{17}$, and $R^{13}$ represents a hydrogen atom, $C_1$-$C_7$ acyl group or protecting group, $R^{17}$ represents a $C_1$-$C_6$ alkyl group, and n represents 0, 1 or 2.

[4] The compound described in [3], or a pharmacologically acceptable salt thereof, wherein p and q represent 1.

[5] The compound described in [4], or a pharmacologically acceptable salt thereof, wherein $R^1$ represents a $C_1$-$C_4$ alkyl group, or a $C_1$-$C_4$ alkyl group substituted with at least one substituent selected from the group consisting of a deuterium atom, fluorine atom and hydroxyl group.

[6] The compound described in [1], of general formula (III):

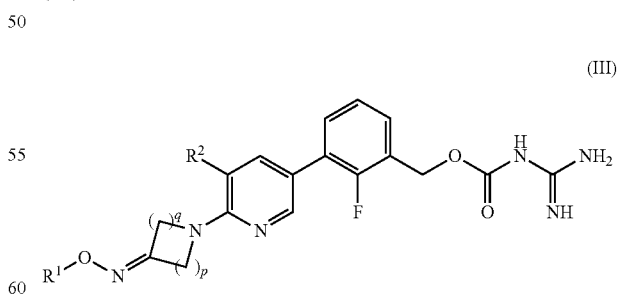

(III)

wherein, $R^1$ represents a hydrogen atom, protecting group, optionally substituted $C_1$-$C_6$ alkyl group, optionally substituted $C_2$-$C_6$ alkenyl group, optionally substituted $C_3$-$C_8$ cycloalkyl group, optionally substituted $C_1$-$C_6$ alkoxy-$C_1$-$C_6$ alkyl group, —$CONR^{11}R^{12}$, optionally substituted heterocyclyl group, optionally substituted heterocyclyl-$C_1$-$C_6$ alkyl group, optionally substituted aryl group or optionally substituted $C_7$-$C_{16}$ aralkyl group, and $R^2$ represents a hydrogen atom, halogen atom, optionally substituted $C_1$-$C_6$ alkyl group, optionally substituted $C_3$-$C_8$ cycloalkyl group, optionally substituted $C_1$-$C_6$ alkoxy group or cyano group, and p and q, independently of each other, represent a natural number of 1 to 3, provided that the sum of p and q is a natural number of 2 to 4, wherein, the term "substituted" refers to being substituted with at least one substituent selected from the group consisting of a deuterium atom, halogen atom, $C_1$-$C_6$ alkyl group, $C_1$-$C_6$ alkoxy group, $C_1$-$C_6$ alkoxy-$C_1$-$C_6$ alkyl group, $R^{13}O$—$C_1$-$C_6$ alkyl group, halo-$C_1$-$C_6$ alkyl group, $C_7$-$C_{16}$ aralkyl group, $C_1$-$C_7$ acyl group, cyano group, oxo group, —$CONR^{11}R^{12}$, —$OR^{13}$, —$COOR^{14}$, —$NR^{15}R^{16}$ and —$S(O)_nR^{17}$, $R^{11}$ and $R^{12}$ independently represent a hydrogen atom or $C_1$-$C_6$ alkyl group, $R^{13}$ represents a hydrogen atom, $C_1$-$C_7$ acyl group or protecting group, $R^{14}$ represents a hydrogen atom or $C_1$-$C_6$ alkyl group, $R^{15}$ and $R^{16}$ independently represent a hydrogen atom, $C_1$-$C_6$ alkyl group, $C_7$-$C_{16}$ aralkyl group, $C_1$-$C_7$ acyl group, —$COOR^{14}$ or —$S(O)_nR^{17}$, $R^{17}$ represents a $C_1$-$C_6$ alkyl group, and n represents 0, 1 or 2;

or a pharmacologically acceptable salt thereof.

[7] The compound described in [6], or a pharmacologically acceptable salt thereof, wherein $R^1$ represents a hydrogen atom, optionally substituted $C_1$-$C_6$ alkyl group, $C_2$-$C_6$ alkenyl group, optionally substituted $C_3$-$C_8$ cycloalkyl group, optionally substituted $C_1$-$C_6$ alkoxy-$C_1$-$C_6$ alkyl group or optionally substituted heterocyclyl group, wherein, the term "substituted" refers to being substituted with at least one substituent selected from the group consisting of a deuterium atom, halogen atom, —$OR^{13}$ and —$S(O)R^{17}$, $R^{13}$ represents a hydrogen atom, $C_1$-$C_7$ acyl group or protecting group, $R^{17}$ represents a $C_1$-$C_6$ alkyl group, and n represents 0, 1 or 2.

[8] The compound described in [7], or a pharmacologically acceptable salt thereof, wherein $R^2$ represents a halogen atom.

[9] The compound described in [8], or a pharmacologically acceptable salt thereof, wherein $R^2$ represents a fluorine atom.

[10] The compound described in [9], or a pharmacologically acceptable salt thereof, wherein p and q represent 1.

[11] The compound described in [10], or a pharmacologically acceptable salt thereof, wherein $R^1$ represents a $C_1$-$C_4$ alkyl group, or a $C_1$-$C_4$ alkyl group substituted with at least one substituent selected from the group consisting of a deuterium atom, fluorine atom and hydroxyl group.

[12] The compound described in [1], or a pharmacologically acceptable salt thereof, wherein the compound is:

2-fluoro-3-{2-[3-(methoxyimino)azetidin-1-yl]pyrimidin-5-yl}benzyl carbamimidoylcarbamate, 3-{2-[3-(ethoxyimino)azetidin-1-yl]pyrimidin-5-yl}-2-fluorobenzyl carbamimidoylcarbamate, 2-fluoro-3-(2-{3-[(methoxy-$d_3$)imino]azetidin-1-yl}pyrimidin-5-yl)benzyl carbamimidoylcarbamate, 2-fluoro-3-(2-{3-[(2-fluoroethoxy)imino]azetidin-1-yl}pyrimidin-5-yl)benzyl carbamimidoylcarbamate, 3-{2-[3-[(2,2-difluoroethoxy)imino]azetidin-1-yl}pyrimidin-5-yl}-2-fluorobenzyl carbamimidoylcarbamate, 2-fluoro-3-(2-{3-[(2,2,2-trifluoroethoxy)imino]azetidin-1-yl}pyrimidin-5-yl)benzyl carbamimidoylcarbamate, 2-fluoro-3-(2-{3-[(3-fluoropropoxy)imino]azetidin-1-yl}pyrimidin-5-yl)benzyl carbamimidoylcarbamate, 2-fluoro-3-{2-[3-({4-[(tetrahydropyran-2-yl)oxy]butoxy}imino)azetidin-1-yl]pyrimidin-5-yl}benzyl carbamimidoylcarbamate, 2-fluoro-3-(2-{3-[(2-methoxyethoxy)imino]azetidin-1-yl}pyrimidin-5-yl)benzyl carbamimidoylcarbamate,

[({1-[5-(3-{[(carbamimidoylcarbamoyl)oxy]methyl}-2-fluorophenyl)pyrimidin-2-yl]azetidin-3-ylidene}amino)oxy]methyl pivalate, 1-[({1-[5-(3-{[(carbamimidoylcarbamoyl)oxy]methyl}-2-fluorophenyl)pyrimidin-2-yl]azetidin-3-ylidene}amino)oxy]-3-methoxypropan-2-yl acetate, 4-[({1-[5-(3-{[(carbamimidoylcarbamoyl)oxy]methyl}-2-fluorophenyl)pyrimidin-2-yl]azetidin-3-ylidene}amino)oxy]butan-1,2-diyl diacetate, 2-[({1-[5-(3-{[(carbamimidoylcarbamoyl)oxy]methyl}-2-fluorophenyl)pyrimidin-2-yl]azetidin-3-ylidene}amino)oxy]ethyl acetate, 2-[({1-[5-(3-{[(carbamimidoylcarbamoyl)oxy]methyl}-2-fluorophenyl)pyrimidin-2-yl]azetidin-3-ylidene}amino)oxy]ethyl propionate, 2-[({1-[5-(3-{[(carbamimidoylcarbamoyl)oxy]methyl}-2-fluorophenyl)pyrimidin-2-yl]azetidin-3-ylidene}amino)oxy]ethyl butyrate, 2-[({1-[5-(3-{[(carbamimidoylcarbamoyl)oxy]methyl}-2-fluorophenyl)pyrimidin-2-yl]azetidin-3-ylidene}amino)oxy]ethyl benzoate, 2-fluoro-3-{5-fluoro-6-[3-(methoxyimino)azetidin-1-yl]pyridin-3-yl}benzyl carbamimidoylcarbamate, 2-fluoro-3-{5-fluoro-6-{3-[(methoxy-$d_3$)imino]azetidin-1-yl}pyridine-3-yl}benzyl carbamimidoylcarbamate, 2-fluoro-3-{6-[3-(methoxyimino)azetidin-1-yl]pyridin-3-yl}benzyl carbamimidoylcarbamate, 2-fluoro-3-{6-[3-(methoxyimino)azetidin-1-yl]-5-methyl-pyridin-3-yl}benzyl carbamimidoylcarbamate, 3-{5-cyano-6-[3-(methoxyimino)azetidin-1-yl]pyridin-3-yl}-2-fluorobenzyl carbamimidoylcarbamate, 3-{5-chloro-6-[3-(methoxyimino)azetidin-1-yl]pyridin-3-yl}-2-fluorobenzyl carbamimidoylcarbamate, 3-{5-(difluoromethyl)-6-[3-(methoxyimino)azetidin-1-yl]pyridin-3-yl}-2-fluorobenzyl carbamimidoylcarbamate, 3-{5-(cyclopropyl)-6-[3-(methoxyimino)azetidin-1-yl]pyridin-3-yl}-2-fluorobenzyl carbamimidoylcarbamate, 3-{5-ethyl-6-[3-(methoxyimino)azetidin-1-yl]pyridin-3-yl}-2-fluorobenzyl carbamimidoylcarbamate, 2-fluoro-3-{6-[3-(methoxymino)azetidin-1-yl]-5-(methoxymethyl)pyridin-3-yl}benzyl carbamimidoylcarbamate, 2-fluoro-3-{5-methoxy-6-[3-(methoxyimino)azetidin-1-yl]pyridin-3-yl}benzyl carbamimidoylcarbamate, 2-fluoro-3-{2-[4-(methoxymino)piperidin-1-yl]pyrimidin-5-yl}benzyl carbamimidoylcarbamate, 3-{2-[4-(ethoxyimino)piperidin-1-yl]pyridimin-5-yl}-2-fluorobenzyl carbamimidoylcarbamate, 2-fluoro-3-{2-[4-(isopropoxyimino)piperidin-1-yl]pyrimidin-5-yl}benzyl carbamimidoylcarbamate, 2-fluoro-3-{2-[4-(propoxyimino)piperidin-1-yl]pyrimidin-5-yl}benzyl carbamimidoylcarbamate, 3-(2-{4-[(allyloxy)imino]piperidin-1-yl}pyridimin-5-yl)-2-fluorobenzyl carbamimidoylcarbamate, 2-fluoro-3-{2-[4-({2-[(tetrahydropyran-2-yl)oxy]ethoxy}imino)piperidin-1-yl]pyrimidin-5-yl}benzyl carbamimidoylcarbamate, 2-fluoro-3-(2-{4-[(2-methoxyethoxy)imino]piperidin-1-yl}pyridimin-5-yl)benzyl carbamimidoylcarbamate,
2-[({1-[5-(3-{[(carbamimidoylcarbamoyl)oxy]methyl}-2-fluorophenyl)pyrimidin-2-yl]piperidin-4-ylidene}amino)oxy]ethyl acetate,
(E/Z)-2-fluoro-3-{2-[3-(methoxyimino)pyrrolidin-1-yl]pyrimidin-5-yl}benzyl carbamimidoylcarbamate,
2-fluoro-3-{2-[3-(hydroxymino)azetidin-1-yl]pyrimidin-5-yl}benzyl carbamimidoylcarbamate,
2-fluoro-3-(2-{3-[(2-hydroxyethoxy)imino]azetidin-1-yl}pyrimidin-5-yl)benzyl carbamimidoylcarbamate,
2-fluoro-3-(2-{3-[(3-hydroxypropoxy)imino]azetidin-1-yl}pyrimidin-5-yl)benzyl carbamimidoylcarbamate,
2-fluoro-3-(2-{3-[(4-hydroxybutoxy)imino]azetidin-1-yl}pyrimidin-5-yl)benzyl carbamimidoylcarbamate,
2-fluoro-3-[2-(3-{[2-(2-hydroxyethoxy)ethoxy]imino}azetidin-1-yl)pyrimidin-5-yl]benzyl carbamimidoylcarbamate,
2-fluoro-3-[2-(3-{[3-fluoro-2-(hydroxymethyl)propoxy]imino}azetidin-1-yl)pyrimidin-5-yl]benzyl carbamimidoylcarbamate,
2-fluoro-3-(2-{3-[(4-hydroxy-3-methoxybutoxy)imino]azetidin-1-yl}pyrimidin-5-yl)benzyl carbamimidoylcarbamate,
3-[({1-[5-(3-{[(carbamimidoylcarbamoyl)oxy]methyl}-2-fluorophenyl)pyrimidin-2-yl]azetidin-3-ylidene}amino)oxy]-2-(hydroxymethyl)propyl acetate,
3-[({1-[5-(3-{[(carbamimidoylcarbamoyl)oxy]methyl}-2-fluorophenyl)pyrimidin-2-yl]azetidin-3-ylidene}amino)oxy]-2-(hydroxymethyl)propyl propionate,
3-[({1-[5-(3-{[(carbamimidoylcarbamoyl)oxy]methyl}-2-fluorophenyl)pyrimidin-2-yl]azetidin-3-ylidene}amino)oxy]-2-(hydroxymethyl)propyl butyrate,
3-[({1-[5-(3-{[(carbamimidoylcarbamoyl)oxy]methyl}-2-fluorophenyl)pyrimidin-2-yl]azetidin-3-ylidene}amino)oxy]-2-(hydroxymethyl)propyl isobutyrate,
3-[({1-[5-(3-{[(carbamimidoylcarbamoyl)oxy]methyl}-2-fluorophenyl)pyrimidin-2-yl]azetidin-3-ylidene}amino)oxy]-2-(hydroxymethyl)propyl pivalate,
3-[({1-[5-(3-{[(carbamimidoylcarbamoyl)oxy]methyl}-2-fluorophenyl)pyrimidin-2-yl]azetidin-3-ylidene}amino)oxy]-2-(hydroxymethyl)propyl hexanoate,
3-[({1-[5-(3-{[(carbamimidoylcarbamoyl)oxy]methyl}-2-fluorophenyl)pyrimidin-2-yl]azetidin-3-ylidene}amino)oxy]-2-(hydroxymethyl)propyl benzoate,
2-fluoro-3-{5-(2-hydroxypropan-2-yl)-6-[3-(methoxyimino)azetidin-1-yl]pyrid in-3-yl}benzyl carbamimidoylcarbamate,
2-fluoro-3-(2-{4-[(2-hydroxyethoxy)imino]piperidin-1-yl}pyrimidin-5-yl)benzyl carbamimidoylcarbamate,
2-fluoro-3-(2-{4-[(3-hydroxypropoxy)imino]piperidin-1-yl}pyrimidin-5-yl)benzyl carbamimidoylcarbamate,
2-fluoro-3-(2-{4-[(4-hydroxybutoxy)imino]piperidin-1-yl}pyrimidin-5-yl)benzyl carbamimidoylcarbamate,
2-fluoro-3-(2-{4-[(3-hydroxy-2,2-dimethylpropoxy)imino]piperidin-1-yl}pyrimidin-5-yl)benzyl carbamimidoylcarbamate,
2-fluoro-3-(2-{4-[(3-hydroxy-3-methylbutoxy)imino]piperidin-1-yl}pyrimidin-5-yl)benzyl carbamimidoylcarbamate,
2-fluoro-3-(2-{4-[(2-hydroxypropoxy)imino]piperidin-1-yl}pyrimidin-5-yl)benzyl carbamimidoylcarbamate,
2-fluoro-3-(2-{4-[(3-hydroxy-2-methylpropoxy)imino]piperidin-1-yl}pyrimidin-5-yl)benzyl carbamimidoylcarbamate,
2-fluoro-3-[2-(3-{[3-hydroxy-2-(hydroxymethyl)propoxy]imino}azetidin-1-yl)pyrimidin-5-yl]benzyl carbamimidoylcarbamate,
3-(2-{3-[(2,3-dihydroxypropoxy)imino]azetidin-1-yl}pyrimidin-5-yl)-2-fluorobenzyl carbamimidoylcarbamate,
3-(2-{3-[(3,4-dihydroxybutoxy)imino]azetidin-1-yl}pyrimidin-5-yl)-2-fluorobenzyl carbamimidoylcarbamate,
3-(6-{3-[(3,4-dihydroxybutoxy)imino]azetidin-1-yl}-5-fluoropyridin-3-yl)-2-fluorobenzyl carbamimidoylcarbamate,
2-fluoro-3-{5-fluoro-6-[3-{[3-hydroxy-2-(hydroxymethyl)propoxy]imino}azetidin-1-yl]pyridin-3-yl}benzyl carbamimidoylcarbamate,
2-fluoro-3-[2-(4-{[3-hydroxy-2-(hydroxymethyl)propoxy]imino}piperidin-1-yl)pyrimidin-5-yl]benzyl carbamimidoylcarbamate,
2-fluoro-3-[2-(4-{[3-hydroxy-2-(hydroxymethyl)-2-methylpropoxy]imino}piperidin-1-yl)pyrimidin-5-yl]benzyl carbamimidoylcarbamate,
3-(2-{4-[(2,3-dihydroxypropoxy)imino]piperidin-1-yl}pyrimidin-5-yl)-2-fluorobenzyl carbamimidoylcarbamate,
2-fluoro-3-[2-(3-{[3-hydroxy-2-(methoxymethyl)propoxy]imino}azetidin-1-yl)pyrimidin-5-yl]benzyl carbamimidoylcarbamate,
2-fluoro-3-(2-{3-[(3-hydroxy-2-methoxypropoxy)imino]azetidin-1-yl}pyrimidin-5-yl)benzyl carbamimidoylcarbamate,
2-fluoro-3-(2-{3-[(2-fluoro-3-hydroxypropoxy)imino]azetidin-1-yl}pyrimidin-5-yl)benzyl carbamimidoylcarbamate,
2-fluoro-3-(5-fluoro-6-{3-[(2-fluoro-3-hydroxypropoxy)imino]azetidin-1-yl}pyridin-3-yl)benzyl carbamimidoylcarbamate,
2-fluoro-3-(2-{3-[(2-hydroxy-3-methoxypropoxy)imino]azetidin-1-yl}pyrimidin-5-yl)benzyl carbamimidoylcarbamate,
2-fluoro-3-{2-[4-(hydroxyimino)piperidin-1-yl]pyrimidin-5-yl}benzyl carbamimidoylcarbamate,
2-fluoro-3-{5-fluoro-6-[3-(hydroxyimino)azetidin-1-yl]pyridin-3-yl}benzyl carbamimidoylcarbamate,
tert-butyl 2-[({1-[5-(3-{[(carbamimidoylcarbamoyl)oxy]methyl}-2-fluorophenyl)pyrimidin-2-yl]azetidin-3-ylidene}amino)oxy]acetate,
2-[({1-[5-(3-{[(carbamimidoylcarbamoyl)oxy]methyl}-2-fluorophenyl)pyrimidin-2-yl]azetidin-3-ylidene}amino)oxy]acetic acid,
3-[2-(3-{[(dimethylcarbamoyl)oxy]imino}azetidin-1-yl)pyrimidin-5-yl]-2-fluorobenzyl carbamimidoylcarbamate,
2-fluoro-3-[2-(3-{[2-(methylamino)-2-oxoethoxy]imino}azetidin-1-yl)pyrimidin-5-yl]benzyl carbamimidoylcarbamate,
3-(2-{3-[(3-amino-3-oxopropoxy)imino]azetidin-1-yl}pyrimidin-5-yl)-2-fluorobenzyl carbamimidoylcarbamate,
2-fluoro-3-[2-(3-{[3-(methylamino)-3-oxopropoxy]imino}azetidin-1-yl)pyrimidin-5-yl]benzyl carbamimidoylcarbamate,
ethyl 4-[({1-[5-(3-{[(carbamimidoylcarbamoyl)oxy]methyl}-2-fluorophenyl)pyrimidin-2-yl]azetidin-3-ylidene}amino)oxy]butanoate,
4-[({1-[5-(3-{[(carbamimidoylcarbamoyl)oxy]methyl}-2-fluorophenyl)pyrimidin-2-yl]azetidin-3-ylidene}amino)oxy]butanoic acid, 2-fluoro-3-[2-(3-{[4-(methylamino)-4-oxobutoxy]imino}azetidin-1-yl)pyrimidin-5-yl]benzyl carbamimidoylcarbamate, 3-[2-(3-{[2-(dimethylamino)ethoxy]imino}azetidin-1-yl)pyrimidin-5-yl]-2-fluorobenzyl carbamimidoylcarbamate, 3-{2-[3-{{2-[benzyl(methyl)amino]ethoxy}imino}azetidin-1-yl]pyrimidin-5-yl}-2-fluorobenzyl carbamimidoylcarbamate, 3-[2-(3-{[3-(acetamido-2-(hydroxymethyl)propoxy]imino}azetidin-1-yl)pyrimidin-5-yl]-2-fluorobenzyl carbamimidoylcarbamate, 3-[2-(3-{[3-(dimethylamino)-2-(hydroxymethyl)propoxy]imino}azetidin-1-yl)pyrimidin-5-yl]-2-fluorobenzyl carbamimidoylcarbamate, 3-(2-{3-[(3-acetamido-2-methoxypropoxy)imino]azetidin-1-yl}pyrimidin-5-yl)-2-fluorobenzyl carbamimidoylcarbamate, 2-fluoro-3-[2-(3-{[2-(piperidin-1-yl)ethoxy]imino}azetidin-1-yl)pyrimidin-5-yl]benzyl carbamimidoylcarbamate, 2-fluoro-3-(2-{3-[(morpholinoethoxy)imino]azetidin-1-yl}pyrimidin-5-yl)benzyl carbamimidoylcarbamate, 3-[2-(3-{[2-(azetidin-1-yl)ethoxy]imino}azetidin-1-yl)pyrimidin-5-yl]-2-fluorobenzyl carbamimidoylcarbamate, 3-[2-(3-{[2-(3,3-difluoroazetidin-1-yl)ethoxy]imino}azetidin-1-yl)pyrimidin-5-yl]-2-fluorobenzyl carbamimidoylcarbamate, 2-fluoro-3-[2-(3-{[2-(3-fluoroazetidin-1-yl)ethoxy]imino}azetidin-1-yl)pyrimidin-5-yl]benzyl carbamimidoylcarbamate, 2-fluoro-3-[2-(3-{[2-(3-methoxyazetidin-1-yl)ethoxy]imino}azetidin-1-yl)pyrimidin-5-yl]benzyl carbamimidoylcarbamate, 2-fluoro-3-[2-(3-{[(4-methylmorpholin-2-yl)methoxy]imino}azetidin-1-yl)pyrimidin-5-yl]benzyl carbamimidoylcarbamate, 3-[2-(3-{[(4-acetylmorpholin-2-yl)methoxy]imino}azetidin-1-yl)pyrimidin-5-yl]-2-fluorobenzyl carbamimidoylcarbamate, 2-fluoro-3-[2-(3-{[(5-oxotetrahydrofuran-2-yl)methoxy]imino}azetidin-1-yl)pyrimidin-5-yl]benzyl carbamimidoylcarbamate, 3-[({1-[5-(3-{[(carbamimidoylcarbamoyl)oxy]methyl}-2-fluorophenyl)pyrimidin-2-yl]azetidin-3-ylidene}amino)oxy]cyclobutyl acetate, 2-fluoro-3-(2-{3-[(3-hydroxycyclobutoxy)imino]azetidin-1-yl}pyrimidin-5-yl)benzyl carbamimidoylcarbamate, 3-(2-{3-[(benzyloxy)imino]azetidin-1-yl}pyrimidin-5-yl)-2-fluorobenzyl carbamimidoylcarbamate, 2-fluoro-3-[2-(3-{[(4-methoxybenzyl)oxy]imino}azetidin-1-yl)pyrimidin-5-yl]benzyl carbamimidoylcarbamate, 2-fluoro-3-[2-(3-{[(1-methylazetidin-3-yl)oxy]imino}azetidin-1-yl)pyrimidin-5-yl]benzyl carbamimidoylcarbamate, 3-[2-(3-{[(1-acetylazetidin-3-yl)oxy]imino}azetidin-1-yl)pyrimidin-5-yl]-2-fluorobenzyl carbamimidoylcarbamate, 3-[2-(3-{[(1-benzylazetidin-3-yl)oxy]imino}azetidin-1-yl)pyrimidin-5-yl]-2-fluorobenzyl carbamimidoylcarbamate, 2-fluoro-3-{2-{3-({[1-(2,2,2-trifluoroethyl)azetidin-3-yl]oxy}imino)azetidin-1-yl]pyrimidin-5-yl}benzyl carbamimidoylcarbamate, 2-fluoro-3-{2-[3-({[1-(methylsulfonyl)azetidin-3-yl]oxy}imino)azetidin-1-yl]pyrimidin-5-yl}benzyl carbamimidoylcarbamate, 3-[2-(3-{[(1-ethylazetidin-3-yl)oxy]imino}azetidin-1-yl)pyrimidin-5-yl]-2-fluorobenzyl carbamimidoylcarbamate, methyl 3-[({1-[5-(3-{[(carbamimidoylcarbamoyl)oxy]methyl}-2-fluorophenyl)pyrimidin-2-yl]azetidin-3-ylidene}amino)oxy]azetidin-1-carboxylate, 2-fluoro-3-(2-{3-[(oxetan-3-yloxy)imino]azetidin-1-yl}pyrimidin-5-yl)benzyl carbamimidoylcarbamate, 2-{3-[({1-[5-(3-{[(carbamimidoylcarbamoyl)oxy]methyl}-2-fluorophenyl)pyrimidin-2-yl]azetidin-3-ylidene}amino)oxy]azetidin-1-yl}ethyl acetate, 2-fluoro-3-{2-[3-({[1-(2-hydroxyethyl)azetidin-3-yl]oxy}imino)azetidin-1-yl]pyrimidin-5-yl}benzyl carbamimidoylcarbamate, 2-fluoro-3-{2-[3-({[1-(2-methoxyethyl)azetidin-3-yl]oxy}imino)azetidin-1-yl]pyrimidin-5-yl}benzyl carbamimidoylcarbamate, 2-fluoro-3-{2-[3-({[1-(2-fluoroethyl)azetidin-3-yl]oxy}imino)azetidin-1-yl]pyrimidin-5-yl}benzyl carbamimidoylcarbamate, ethyl 3-[({1-[5-(3-{[(carbamimidoylcarbamoyl)oxy]methyl}-2-fluorophenyl)pyrimidin-2-yl]piperidin-4-ylidene}amino)oxy]propanoate, 3-(2-{4-[(3-amino-3-oxopropoxy)imino]piperidin-1-yl}pyrimidin-5-yl)-2-fluorobenzyl carbamimidoylcarbamate, 2-fluoro-3-[2-(4-{[3-(methylamino)-3-oxopropoxy]imino}piperidin-1-yl)pyrimidin-5-yl]benzyl carbamimidoylcarbamate, ethyl 4-[({1-[5-(3-{[(carbamimidoylcarbamoyl)oxy]methyl}-2-fluorophenyl)pyrimidin-2-yl]piperidin-4-ylidene}amino)oxy]butanoate, 4-[({1-[5-(3-{[(carbamimidoylcarbamoyl)oxy]methyl}-2-fluorophenyl)pyrimidin-2-yl]piperidin-4-ylidene}amino)oxy]butanoic acid, 3-[2-(4-{[3-(dimethylamino)-3-oxopropoxy]imino}piperidin-1-yl)pyrimidin-5-yl]-2-fluorobenzyl carbamimidoylcarbamate, 3-(2-{4-[(2-acetamidoethoxy)imino]piperidin-1-yl}pyrimidin-5-yl)-2-fluorobenzyl carbamimidoylcarbamate, 2-fluoro-3-[2-(4-{[2-(N-methylacetamido)ethoxy]imino}piperidin-1-yl)pyrimidin-5-yl]benzyl carbamimidoylcarbamate, 2-fluoro-3-[2-(4-{[2-(N-methylmethylsulfonamido)ethoxy]imino}piperidin-1-yl)pyrimidin-5-yl]benzyl carbamimidoylcarbamate, 2-fluoro-3-[2-(4-{[2-(methylsulfonamido)ethoxy]imino}piperidin-1-yl)pyrimidin-5-yl]benzyl carbamimidoylcarbamate, 3-[2-(4-{[2-(dimethylamino)ethoxy]imino}piperidin-1-yl)pyrimidin-5-yl]-2-fluorobenzyl carbamimidoylcarbamate, 2-fluoro-3-[2-(4-{[2-(methylamino)ethoxy]imino}piperidin-1-yl)pyrimidin-5-yl]benzyl carbamimidoylcarbamate, 3-(2-{4-[(2-aminoethoxy)imino]piperidin-1-yl}pyrimidin-5-yl)-2-fluorobenzyl carbamimidoylcarbamate, 3-(2-{4-[(2-cyanoethoxy)imino]piperidin-1-yl}pyrimidin-5-yl)-2-fluorobenzyl carbamimidoylcarbamate, 3-(2-{4-[(3-cyanopropoxy)imino]piperidin-1-yl}pyrimidin-5-yl)-2-fluorobenzyl carbamimidoylcarbamate, 2-fluoro-3-[2-(4-{[2-(methylsulfonyl)ethoxy]imino}piperidin-1-yl)pyrimidin-5-yl]benzyl carbamimidoylcarbamate, 2-fluoro-3-[2-(4-{[3-(methylsulfonyl)propoxy]
imino}piperidin-1-yl)pyrimidin-5-yl]benzyl carbamimidoylcarbamate,
2-fluoro-3-[2-(4-{[1-(methyl-1H-pyrazol-3-yl)methoxy]
imino}piperidin-1-yl)pyrimidin-5-yl]benzyl carbamimidoylcarbamate,
3-[2-(4-{[(1H-pyrazol-3-yl)methoxy]imino}piperidin-1-yl)
pyrimidin-5-yl]-2-fluorobenzyl carbamimidoylcarbamate,
2-fluoro-3-{2-[4-({[1-(tetrahydropyran-2-yl)-1H-pyrazol-4-yl]methoxy}imino) piperidin-1-yl]pyrimidin-5-yl}benzyl carbamimidoylcarbamate,
3-[2-(4-{[(1H-pyrazol-4-yl)methoxy]imino}piperidin-1-yl)
pyrimidin-5-yl]-2-fluorobenzyl carbamimidoylcarbamate,
2-fluoro-3-[2-(4-{[1-(methyl-1H-pyrazol-4-yl)methoxy]
imino}piperidin-1-yl)pyrimidin-5-yl]benzyl carbamimidoylcarbamate,
3-[2-(4-{[2-(1H-pyrazol-1-yl)ethoxy]imino}piperidin-1-yl)
pyrimidin-5-yl]-2-fluorobenzyl carbamimidoylcarbamate,
2-fluoro-3-(2-{4-[(pyridin-4-ylmethoxy)imino}piperidin-1-yl)pyrimidin-5-yl]benzyl carbamimidoylcarbamate,
3-[2-(4-{[2-(2,5-dioxopyrrolidin-1-yl)ethoxy]
imino}piperidin-1-yl)pyrimidin-5-yl]-2-fluorobenzyl carbamimidoylcarbamate,
2-fluoro-3-[2-(4-{[2-(2-oxopyrrolidin-1-yl)ethoxy]
imino}piperidin-1-yl)pyrimidin-5-yl]benzyl carbamimidoylcarbamate,
2-fluoro-3-[2-(4-{[2-(2-oxooxazolidin-3-yl)ethoxy]
imino}piperidin-1-yl)pyrimidin-5-yl]benzyl carbamimidoylcarbamate,
2-fluoro-3-[2-(4-{[2-(3-oxomorpholino)ethoxy]
imino}piperidin-1-yl)pyrimidin-5-yl]benzyl carbamimidoylcarbamate,
2-fluoro-3-{2-[4-(phenoxyimino)piperidin-1-yl]pyrimidin-5-yl}benzyl carbamimidoylcarbamate,
2-fluoro-3-(2-{4-[(pyrimidin-5-yloxy)imino]piperidin-1-yl}pyrimidin-5-yl)benzyl carbamimidoylcarbamate, or
2-fluoro-3-(2-{4-[(pyrimidin-2-yloxy)imino]piperidin-1-yl}pyrimidin-5-yl)benzyl carbamimidoylcarbamate.

[13] 2-fluoro-3-{2-[3-(methoxyimino)azetidin-1-yl]pyrimidin-5-yl}benzyl carbamimidoylcarbamate, or a pharmacologically acceptable salt thereof.

[14] 3-{2-[3-(ethoxyimino)azetidin-1-yl]pyrimidin-5-yl}-2-fluorobenzyl carbamimidoylcarbamate or a pharmacologically acceptable salt thereof.

[15] 2-fluoro-3-(2-{3-[(methoxy-$d_3$)imino]azetidin-1-yl}pyrimidin-5-yl)benzyl carbamimidoylcarbamate or a pharmacologically acceptable salt thereof.

[16] 2-fluoro-3-(2-{3-[(2-fluoroethoxy)imino]azetidin-1-yl}pyrimidin-5-yl)benzyl carbamimidoylcarbamate or a pharmacologically acceptable salt thereof.

[17] 2-fluoro-3-{5-fluoro-6-[3-(methoxyimino)azetidin-1-yl]pyridin-3-yl}benzyl carbamimidoylcarbamate or a pharmacologically acceptable salt thereof.

[18] 2-fluoro-3-{5-fluoro-6-{3-[(methoxy-$d_3$)imino]azetidin-1-yl}pyridine-3-yl}benzyl carbamimidoylcarbamate or a pharmacologically acceptable salt thereof.

[19] 3-(6-{3-[(3,4-dihydroxybutoxy)imino]azetidin-1-yl}-5-fluoropyridin-3-yl)-2-fluorobenzyl carbamimidoylcarbamate or a pharmacologically acceptable salt thereof.

[20] 2-fluoro-3-{5-fluoro-6-[3-{[hydroxy-2-(hydroxymethyl)propoxy]imino}azetidin-1-yl]pyridin-3-yl}benzyl carbamimidoylcarbamate or a pharmacologically acceptable salt thereof.

[21] 2-fluoro-3-(2-{3-[(2-fluoro-3-hydroxypropoxy)imino]azetidin-1-yl}pyrimidin-5-yl)benzyl carbamimidoylcarbamate or a pharmacologically acceptable salt thereof.

[22] 3-[({1-[5-(3-{[(carbamimidoylcarbamoyl)oxy]
methyl}-2-fluorophenyl)pyrimidin-2-yl]azetidin-3-ylidene}amino)oxy]cyclobutyl acetate or a pharmacologically acceptable salt thereof.

[23] 2-fluoro-3-(2-{3-[(3-hydroxycyclobutoxy)imino]
azetidin-1-yl}pyrimidin-5-yl)benzyl carbamimidoylcarbamate or a pharmacologically acceptable salt thereof.

[24] 2-fluoro-3-{2-[3-({[1-(methylsulfonyl)azetidin-3-yl]
oxy}imino)azetidin-1-yl]pyrimidin-5-yl}benzyl carbamimidoylcarbamate or a pharmacologically acceptable salt thereof.

[25] 2-fluoro-3-(2-{3-[(oxetan-3-yloxy)imino]azetidin-1-yl}pyrimidin-5-yl)benzyl carbamimidoylcarbamate or a pharmacologically acceptable salt thereof.

[26] The compound described in any of [1] to [25], or a pharmacologically acceptable salt thereof, wherein the pharmacologically acceptable salt is a salt of an organic acid.

[27] The compound described in any of [1] to [25], or a pharmacologically acceptable salt thereof, wherein the pharmacologically acceptable salt is a salt of a dicarboxylic acid.

[28] A pharmaceutical composition containing the compound described in any of [1] to [27], or a pharmacologically acceptable salt thereof, and at least one type of pharmacologically acceptable additive.

[29] The pharmaceutical composition described in [28] for treating a disease prevented, alleviated and/or treated by inhibiting VAP-1.

[30] The pharmaceutical composition described in [29], wherein the disease is diabetic nephropathy.

[31] The pharmaceutical composition described in [29], wherein the disease is non-alcoholic steatohepatitis.

[32] The compound described in any of [1] to [27], or a pharmacologically acceptable salt thereof, for use in treating a disease prevented, alleviated and/or treated by inhibiting VAP-1.

[33] The compound described in any of [1] to [27], or a pharmacologically acceptable salt thereof, for producing a medicament for treating a disease prevented, alleviated and/or treated by inhibiting VAP-1.

[34] A method for treating a disease prevented, alleviated and/or treated by inhibiting VAP-1, which includes administering a therapeutically effective amount of the compound described in any of [1] to [27], or a pharmacologically acceptable salt thereof, to a patient in need thereof.

Effects of the Invention

Since the compound of general formula (I) of the present invention, or a pharmacologically acceptable salt thereof, has high VAP-1 inhibitory activity and superior pharmacokinetic properties, it is useful in treating a disease prevented, alleviated and/or treated by inhibiting VAP-1, and typically non-alcoholic fatty liver diseases such as non-alcoholic steatohepatitis, inflammatory diseases such as atopic dermatitis or psoriasis, diabetic complications such as diabetic neuropathy, diabetic retinopathy (and particularly, diabetic macular edema) or diabetic nephropathy, vascular diseases such as atherosclerosis, heart diseases such as myocardial infarction, and metabolic diseases such as obesity.

DESCRIPTION OF EMBODIMENTS

The meanings of terms used in the present description and claims are as explained below. Terms used in the present description and claims have the meanings indicated below unless specifically indicated otherwise.

In the present description, numerical ranges indicated using the symbol "-" indicate a range that includes values indicated before and after the "-" symbol as the minimum and maximum values, respectively, of that range.

In the present invention, the compound of general formula (I) includes isotopic isomers thereof. Namely, all or a portion of the atoms of the compound of general formula (I) may be substituted with isotopic atoms corresponding respectively thereto. An isotopic atom refers to an atom having a different mass number from the mass number found in nature. Examples of such isotopic atoms include hydrogen atoms ($^2$H, $^3$H), carbon atoms ($^{13}$C, $^{14}$C), nitrogen atoms ($^{15}$N), and oxygen atoms ($^{17}$O, $^{18}$O). Deuterium atoms ($^2$H) in particular may be represented with a "D". In such cases, in the compound of general formula (I), all of the hydrogen atoms at specific locations indicated by D are substituted by deuterium atoms, and indicate a molecular weight that differs from the molecular weight calculated from the mass number found in nature.

"Halogen atom" or "halo" refers to a fluorine atom, chlorine atom, bromine atom or iodine atom either alone or in combination with other groups.

A "$C_1$-$C_6$ alkyl group" refers to a monovalent group of linear or branched, saturated aliphatic hydrocarbon having 1 to 6 carbon atoms either alone or in combination with other groups. Examples of $C_1$-$C_6$ alkyl groups include a methyl group, ethyl group, propyl group, butyl group, pentyl group and hexyl group (including various isomers thereof). A preferable aspect of a $C_1$-$C_6$ alkyl group is a $C_1$-$C_4$ alkyl group, and examples thereof include a methyl group, ethyl group, propyl group, isopropyl group, butyl group, isobutyl group, sec-butyl group and tert-butyl group.

A "$C_1$-$C_6$ alkoxy group" refers to a group of —O—$R^4$ (wherein, $R^4$ represents the aforementioned $C_1$-$C_6$ alkyl group) either alone or in combination with other groups. Examples of $C_1$-$C_6$ alkoxy groups include a methoxy group, ethoxy group, propoxy group, butyloxy group, pentyloxy group and hexyloxy group (including various isomers thereof). A preferable aspect of a $C_1$-$C_6$ alkoxy group is a $C_1$-$C_4$ alkoxy group, and examples thereof include a methoxy group, ethoxy group, propoxy group, isopropoxy group, butyloxy group, isobutyloxy group, sec-butyloxy group and tert-butyloxy group.

A "$C_1$-$C_6$ alkoxy-$C_1$-$C_6$ alkyl group" refers to the aforementioned $C_1$-$C_6$ alkyl group substituted with the aforementioned $C_1$-$C_6$ alkoxy group. Examples of $C_1$-$C_6$ alkoxy-$C_1$-$C_6$ alkyl groups include a methoxymethyl group, ethoxymethyl group, propoxymethyl group, butyloxymethyl group, pentyloxymethyl group, hexyloxymethyl group, methoxyethyl group, ethoxyethyl group, propoxyethyl group, butyloxyethyl group, pentyloxyethyl group, hexyloxyethyl group, methoxypropyl group, ethoxypropyl group, propoxypropyl group and butoxybutyl group (including various isomers thereof). A preferable aspect of a $C_1$-$C_6$ alkoxy-$C_1$-$C_6$ alkyl group is a $C_1$-$C_4$ alkoxy-$C_1$-$C_4$ alkyl group, and examples thereof include a methoxymethyl group, ethoxymethyl group, 2-methoxyethyl group, 2-ethoxyethyl group, 3-methoxypropyl group, 2-methosypropyl group and 3-methoxybutyl group.

A "halo-$C_1$-$C_6$ alkyl group" refers to the aforementioned $C_1$-$C_6$ alkyl group substituted with at least one of the above-mentioned same or different halogen atoms. Examples of halo-$C_1$-$C_6$ alkyl groups include linear or branched halo-$C_1$-$C_6$ alkyl groups such as a fluoromethyl group, chloromethyl group, bromomethyl group, difluoromethyl group, dichloromethyl group, dibromomethyl group, trifluoromethyl group, trichloromethyl group, tribromomethyl group, 2-fluoroethyl group, 2-chloroethyl group, 2-bromoethyl group, 2,2-difluoroethyl group, 2,2-dichloroethyl group, 2,2-dibromoethyl group, 2,2,2-trifluoroethyl group, 2,2,2-trichloroethyl group, 2,2,2-tribromoethyl group, pentafluoroethyl group, pentachloroethyl group, pentabromoethyl group, 3-fluoropropyl group, 3-chloropropyl group, 3-bromopropyl group or 2,3-difluoropropyl group.

A "$C_3$-$C_8$ cycloalkyl group" refers to a monovalent group of cyclic, saturated aliphatic hydrocarbon having 3 to 8 carbon atoms. Examples of $C_3$-$C_8$ cycloalkyl groups include a cyclopropyl group, cyclobutyl group, cyclopentyl group, cyclohexyl group, cycloheptyl group and cyclooctyl group. A preferable aspect of a $C_3$-$C_8$ cycloalkyl group is a $C_3$-$C_6$ cycloalkyl group, and examples thereof include a cyclopropyl group, cyclobutyl group, cyclopentyl group and cyclohexyl group.

A "$C_2$-$C_6$ alkenyl group" refers to a monovalent group of linear or branched, unsaturated aliphatic hydrocarbon having 2 to 6 carbon atoms and containing at least one double bond. Examples of $C_2$-$C_6$ alkenyl groups include a vinyl group, allyl group, isopropenyl group, 1-butenyl group, 2-butenyl group, 1,3-butadienyl group and 2-pentenyl group. A preferable aspect of a $C_2$-$C_6$ alkenyl group is a $C_2$-$C_4$ alkenyl group, and examples thereof include a vinyl group, allyl group, isopropenyl group, 1-butenyl group, 2-butenyl group and 1,3-butadienyl group.

An "aryl group" refers to a monovalent group of aromatic hydrocarbon having 6 to 10 carbon atoms. Examples of aryl groups include a phenyl group, 1-naphthyl group and 2-naphthyl group.

A "$C_7$-$C_{16}$ aralkyl group" refers to the aforementioned $C_1$-$C_6$ alkyl group substituted with an aforementioned aryl group. Examples of $C_7$-$C_{16}$ aralkyl groups include a benzyl group, 1-phenylethyl group, 2-phenylethyl group, 1-naphthylmethyl group and 2-naphthylmethyl group.

A "heterocyclyl group" refers to a monovalent group of 4-member to 7-member, saturated, partially unsaturated or unsaturated monocyclic heterocycle containing one to four heteroatoms independently selected from the group consisting of a nitrogen atom, oxygen atom and sulfur atom, or a monovalent group of bicyclic heterocycle obtained by condensing the aforementioned monocyclic heterocycle with benzene or cyclohexane. Examples of such heterocyclyl groups include a group of monocyclic heterocycle such as an azetidinyl group, pyrrolidinyl group, pyrrolinyl group, pyrrolyl group, piperidyl group, pyridyl group, azepanyl group, azepinyl group, imidazolidinyl group, imidazolinyl group, imidazolyl group, pyrazolidinyl group, pyrazolinyl group, pyrazolyl group, piperazinyl group, pyrazinyl group, pyrimidinyl group, pyridazinyl group, triazolyl group, tetrazolyl group, oxetanyl group, tetrahydrofuryl group, furyl group, pyranyl group, tetrahydropyranyl group, thienyl group, thiazolyl group, isothiazolyl group, oxazolidinyl group, oxazolinyl group, oxazolyl group, isoxazolidinyl group, isoxazolinyl group, isoxazolyl group or morpholinyl group, and a group of bicyclic heterocycle such as indolyl, benzofuran, benzothiophene, quinoline, isoquinoline, tetrahydroquinoline or tetrahydroisoquinoline.

A "heterocyclyl-$C_1$-$C_6$ alkyl group" refers to the aforementioned $C_1$-$C_6$ alkyl group substituted with an aforementioned heterocyclyl group. Examples of heterocyclyl-$C_1$-$C_6$ alkyl groups include a 2-(piperidin-1-yl)ethyl group, 2-morpholinoethyl group, 2-(azetidin-1-yl)ethyl group, morpholin-2-yl methyl group, (tetrahydrofuran-2-yl)methyl group, 1H-pyrazol-3-yl methyl group, 1H-pyrazol-4-yl methyl group, 2-(1H-pyrazol-1-yl)ethyl group, pyridin-4-yl methyl group, pyridin-3-yl methyl group, pyridin-2-yl methyl group, 2-(pyrrolidin-1-yl)ethyl group, 2-(oxazolidin-3-yl) ethyl group, 2-(3-oxomorpholino)ethyl group and 2-(1H-tetrazol-5-yl)ethyl group.

A "$C_1$-$C_7$ acyl group" refers to a group of —CO—$R^5$ (wherein, $R^5$ represents a hydrogen atom, the aforementioned $C_1$-$C_6$ alkyl group or a phenyl group). Examples of a $C_1$-$C_7$ acyl group include a formyl group, acetyl group, propionyl group, butyryl group, isobutyryl group, valeryl group, isovaleryl group, pivaloyl group, hexanoyl group and benzoyl group.

A "protecting group" refers to a protecting group of a hydroxyl group and can be arbitrarily selected by a person with ordinary skill in the art from among hydroxyl group protecting groups described in the known art such as Protective Groups in Organic Synthesis, 4th Edition, T. W. Greene and P. G. M. Wuts, ed., John Wiley & Sons Inc. (2006). Examples of protecting groups of a hydroxyl group include acyl-based protecting groups such as $C_1$-$C_7$ acyl groups (such as a formyl group, acetyl group, propionyl group, butyryl group, isobutyryl group, valeryl group, isovaleryl group, pivaloyl group, hexanoyl group or benzoyl group), acetal-based protecting groups such as a methoxymethyl group, 1-ethoxyethyl group, methylthiomethyl group, benzyloxymethyl group, tetrahydropyranyl group, silyl-based protecting groups such as a tri($C_1$-$C_4$ alkyl)silyl group (such as a trimethylsilyl group, triethylsilyl group, triisopropylsilyl group, dimethylisopropylsilyl group or tert-butyldimethylsilyl group), a ($C_1$-$C_4$ alkyl)diarylsilyl group (such as a tert-butyldiphenylsilyl group or diphenylmethylsilyl group), a triarylsilyl group (such as a triphenylsilyl group), or a tribenzylsilyl group, and benzyl-based protecting groups such as a benzyl group, p-methoxybenzyl group or triphenylmethyl group. Examples of preferable aspects of protecting groups include a $C_1$-$C_7$ acyl group, tetrahydropyranyl group, tri($C_1$-$C_4$ alkyl)silyl group, benzyl group, p-methoxybenzyl group and triphenylmethyl group.

In addition, in the case the compound of general formula (I) contains a 1,2- or 1,3-diol structure, the protecting group may be a cyclic acetal that protects the two hydroxyl groups in the form of a 5-member or 6-member cyclic compound. Examples of cyclic acetals include methylene acetal, ethylidene acetal, acetonide, benzylidene acetal and p-methoxybenzylidene acetal. In the case $R^1$ is substituted with two —$OR^{13}$ groups and a 1,2- or 1,3-diol structure is contained, a preferable aspect of the protecting group is an acetonide.

In the present invention, the phase "optionally substituted" refers to a certain group not being substituted or being substituted with at least one substituent selected from a group of given substituents such as the group consisting of a deuterium atom, halogen atom, $C_1$-$C_6$ alkyl group, $C_1$-$C_6$ alkoxy group, $C_1$-$C_6$ alkoxy-$C_1$-$C_6$ alkyl group, $R^{13}$O—$C_1$-$C_6$ alkyl group, halo-$C_1$-$C_6$ alkyl group, $C_7$-$C_{16}$ aralkyl group, $C_1$-$C_7$ acyl group, cyano group, oxo group, —$CONR^{11}R^{12}$, —$OR^{13}$, —$COOR^{14}$, —$NR^{15}R^{16}$ and —$S(O)_nR^{17}$ (wherein, $R^{11}$ and $R^{12}$ independently represent a hydrogen atom or $C_1$-$C_6$ alkyl group, $R^{13}$ represents a hydrogen atom, $C_1$-$C_7$ acyl group or protecting group, $R^{14}$ represents a hydrogen atom or $C_1$-$C_6$ alkyl group, $R^{15}$ and $R^{16}$ independently represent a hydrogen atom, $C_1$-$C_6$ alkyl group, $C_7$-$C_{16}$ aralkyl group, $C_1$-$C_7$ acyl group, —$COOR^{14}$ or —$S(O)_nR^{17}$, $R^{17}$ represents a $C_1$-$C_6$ alkyl group, and n represents 0, 1 or 2).

In the present invention, a preferable aspect of an "optionally substituted $C_1$-$C_6$ alkyl group" is an (unsubstituted) $C_1$-$C_6$ alkyl group or $C_1$-$C_6$ alkyl group substituted with at least one substituent selected from the group consisting of a deuterium atom, halogen atom, $C_1$-$C_7$ acyl group, cyano group, oxo group, —$CONR^{11}R^{12}$, —$OR^{13}$, —$COOR^{14}$, —$NR^{15}R^{16}$ and —$S(O)_nR^{17}$ (wherein, $R^{11}$ and $R^{12}$ independently represent a hydrogen atom or $C_1$-$C_6$ alkyl group, $R^{13}$ represents a hydrogen atom, $C_1$-$C_7$ acyl group or protecting group, $R^{14}$ represents a hydrogen atom or $C_1$-$C_6$ alkyl group, $R^{15}$ and $R^{16}$ independently represent a hydrogen atom, $C_1$-$C_6$ alkyl group, $C_7$-$C_{16}$ aralkyl group, $C_1$-$C_7$ acyl group, —$COOR^{14}$ or —$S(O)_nR^{17}$, $R^{17}$ represents a $C_1$-$C_6$ alkyl group, and n represents 0, 1 or 2). A more preferable aspect of an "optionally substituted $C_1$-$C_6$ alkyl group" is an (unsubstituted) $C_1$-$C_6$ alkyl group or $C_1$-$C_6$ alkyl group substituted with at least one substituent selected from the group consisting of a deuterium atom, halogen atom, cyano group, —$CONR^{11}R^{12}$, —$OR^{13}$, —$COOR^{14}$, —$NR^{15}R^{16}$ and —$S(O)_nR^{17}$. An even more preferable aspect of an "optionally substituted $C_1$-$C_6$ alkyl group" is an (unsubstituted) $C_1$-$C_6$ alkyl group or $C_1$-$C_6$ alkyl group substituted with at least one substituent selected from the group consisting of a deuterium atom, halogen atom, —$OR^{13}$ and —$S(O)_nR^{17}$. A particularly preferable aspect of an "optionally substituted $C_1$-$C_6$ alkyl group" is an (unsubstituted) $C_1$-$C_6$ alkyl group or $C_1$-$C_6$ alkyl group substituted with at least one substituent selected from the group consisting of a deuterium atom, fluorine atom and hydroxyl group.

In the present invention, a preferable aspect of an "optionally substituted $C_2$-$C_6$ alkenyl group" is an (unsubstituted) $C_2$-$C_6$ alkenyl group or $C_2$-$C_6$ alkenyl group substituted with at least one substituent selected from the group consisting of a deuterium atom, halogen atom, —$OR^{13}$ and —$S(O)_nR^{17}$ (wherein, $R^{13}$ represents a hydrogen atom, $C_1$-$C_7$ acyl group or protecting group, $R^{17}$ represents a $C_1$-$C_6$ alkyl group, and n represents 0, 1 or 2). A more preferable aspect of an "optionally substituted $C_2$-$C_6$ alkenyl group" is an (unsubstituted) $C_2$-$C_6$ alkenyl group.

In the present invention, a preferable aspect of an "optionally substituted $C_3$-$C_8$ cycloalkyl group" is an (unsubstituted) $C_3$-$C_8$ cycloalkyl group or $C_3$-$C_8$ cycloalkyl group substituted with at least one substituent selected from the group consisting of a deuterium atom, halogen atom, —$OR^{13}$ and —$S(O)_nR^{17}$ (wherein, $R^{13}$ represents a hydrogen atom, $C_1$-$C_7$ acyl group or protecting group, $R^{17}$ represents a $C_1$-$C_6$ alkyl group, and n represents 0, 1 or 2). A more preferable aspect of an "optionally substituted $C_3$-$C_8$ cycloalkyl group" is an (unsubstituted) $C_3$-$C_8$ cycloalkyl group or a $C_3$-$C_8$ cycloalkyl group substituted with at least one —$OR^{13}$ group.

In the present invention, a preferable aspect of an "optionally substituted $C_1$-$C_6$ alkoxy-$C_1$-$C_6$ alkyl group" is an (unsubstituted) $C_1$-$C_6$ alkoxy-$C_1$-$C_6$ alkyl group or $C_1$-$C_6$ alkoxy-$C_1$-$C_6$ alkyl group substituted with at least one substituent selected from the group consisting of a deuterium atom, halogen atom, —$OR^{13}$, —$NR^{15}R^{16}$ and —$S(O)_nR^{17}$ (wherein, $R^{13}$ represents a hydrogen atom, $C_1$-$C_7$ acyl group or protecting group, $R^{15}$ and $R^{16}$ independently represent a hydrogen atom, $C_1$-$C_6$ alkyl group, $C_7$-$C_{16}$ aralkyl group, $C_1$-$C_7$ acyl group, —$COOR^{14}$ or —$S(O)_nR^{17}$, $R^{17}$ represents a $C_1$-$C_6$ alkyl group, and n represents 0, 1 or 2). A more preferable aspect of an "optionally substituted $C_1$-$C_6$ alkoxy-$C_1$-$C_6$ alkyl group" is an (unsubstituted) $C_1$-$C_6$ alkoxy-$C_1$-$C_6$ alkyl group or $C_1$-$C_6$ alkoxy-$C_1$-$C_6$ alkyl group substituted with at least one substituent selected from the group consisting of —$OR^{13}$ and —$NR^{15}R^{16}$ In the present invention, preferable aspects of an "optionally substituted heterocyclyl group" and "optionally substituted heterocyclyl-$C_1$-$C_6$ alkyl group" consist of an (unsubstituted) heterocyclyl group and (unsubstituted) heterocyclyl-$C_1$-$C_6$ alkyl group or a heterocyclyl group and heterocyclyl-$C_1$-$C_6$ alkyl group in which the heterocyclyl moiety is substituted with at least one substituent selected from the group consisting of a deuterium atom, halogen atom, $C_1$-$C_6$ alkyl group, $C_1$-$C_6$ alkoxy group, $C_1$-$C_6$ alkoxy-$C_1$-$C_6$ alkyl group, $R^{13}O$—$C_1$-$C_6$ alkyl group, halo-$C_1$-$C_6$ alkyl group, $C_7$-$C_{16}$ aralkyl group, $C_1$-$C_7$ acyl group, oxo group, —$COOR^{14}$, and —$S(O)_nR^{17}$ (wherein, $R^{13}$ represents a hydrogen atom, $C_1$-$C_7$ acyl group or protecting group, $R^{14}$ represents a hydrogen atom or $C_1$-$C_6$ alkyl group, $R^{17}$ represents a $C_1$-$C_6$ alkyl group, and n represents 0, 1 or 2). More preferable aspects of an "optionally substituted heterocyclyl group" and "optionally substituted heterocyclyl-$C_1$-$C_6$ alkyl group" consist of an (unsubstituted) heterocyclyl group and (unsubstituted) heterocyclyl-$C_1$-$C_6$ alkyl group or a heterocyclyl group and heterocyclyl-$C_1$-$C_6$ alkyl group in which the heterocyclyl moiety is substituted with at least one substituent selected from the group consisting of a halogen atom and —$S(O)_nR^{17}$.

In the present invention, a preferable aspect of an "optionally substituted aryl group" is an (unsubstituted) aryl group or an aryl group substituted with at least one substituent selected from the group consisting of a deuterium atom, halogen atom, —$OR^{13}$ and —$S(O)_nR^{17}$ (wherein, $R^{13}$ represents a hydrogen atom, $C_1$-$C_7$ acyl group or protecting group, $R^{17}$ represents a $C_1$-$C_6$ alkyl group, and n represents 0, 1 or 2). A more preferable aspect of an "optionally substituted aryl group" is an (unsubstituted) aryl group.

The compound of general formula (I) of the present invention includes stereoisomers thereof (if such stereoisomers exist). Stereoisomers refer to isomers having different spatial configurations of atoms, and examples thereof include optical isomers such as diastereomers and enantiomers, and geometric isomers. For example, in the case the compound of general formula (I) of the present invention has one or more chiral centers, the compound of general formula (I) of the present invention can be present in the form of optically pure enantiomers, a mixture of enantiomers such as racemates, optically pure diastereomers, a mixture of diastereomers, racemates of diastereomers or a mixture of racemates of diastereomers. In addition, in the case a geometric isomer based on a double bond such as a C=C or C=N double bond is present in the compound of general formula (I) of the present invention, the compound of general formula (I) of the present invention can be present in the form of a geometric isomer of pure E forms and Z forms or a mixture of geometric isomers of E forms and Z forms.

Examples of pharmacologically acceptable salts of the compound of general formula (I) of the present invention include inorganic acid salts such as hydrochlorides, hydrobromides, hydroiodides, nitrates, sulfates or phosphates, and organic acid salts such as acetates, trifluoroacetates, benzoates, oxalates, malonates, succinates, maleates, fumarates, tartrates, citrates, methanesulfonates, ethanesulfonates, trifluoromethanesulfonates, benzenesulfonates, p-toluenesulfonates, glutamates or aspartates. Preferable aspects of organic acid salts consist of salts of dicarboxylic acids such as oxalates, malonates, succinates, maleates, fumarates and tartrates.

Other examples of pharmacologically acceptable salts of the compound of general formula (I) of the present invention include metal salts such as sodium salts, potassium salts, calcium salts or magnesium salts, inorganic salts such as ammonium salts, and organic amine salts such as triethylamine salts or guanidine salts.

The compound of general formula (I) of the present invention, or a pharmacologically acceptable salt thereof, includes pharmacologically acceptable solvates. A preferable aspect of a solvate is a hydrate. Furthermore, a hydrate may be that the compound of general formula (I) of the present invention or a pharmacologically acceptable salt thereof adsorbs moisture to result in.

The compound of general formula (I) of the present invention or a pharmacologically acceptable salt thereof may exhibit crystal polymorphism in the case of being a crystal. Crystal polymorphism refers to the same substance having different crystal structures. Each crystal or a mixture thereof at any arbitrary ratio is included in the present invention.

The following provides a detailed explanation of embodiments of the present invention.

The present invention relates to a compound of general formula (I):

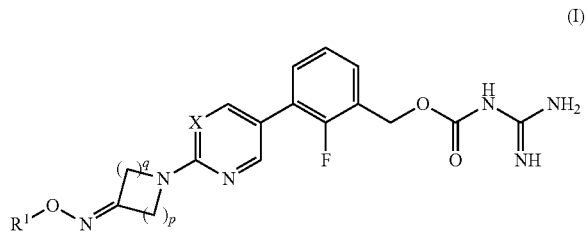

(I)

wherein,
$R^1$ represents a hydrogen atom, protecting group, optionally substituted $C_1$-$C_6$ alkyl group, optionally substituted $C_2$-$C_6$ alkenyl group, optionally substituted $C_3$-$C_8$ cycloalkyl group, optionally substituted $C_1$-$C_6$ alkoxy-$C_1$-$C_6$ alkyl group, —$CONR^{11}R^{12}$, optionally substituted heterocyclyl group, optionally substituted heterocyclyl-$C_1$-$C_6$ alkyl group, optionally substituted aryl group or optionally substituted $C_7$-$C_{16}$ aralkyl group, and X represents N or C—$R^2$, wherein, $R^2$ represents a hydrogen atom, halogen atom, optionally substituted $C_1$-$C_6$ alkyl group, optionally substituted $C_3$-$C_8$ cycloalkyl group, optionally substituted $C_1$-$C_6$ alkoxy group or cyano group, and p and q, independently of each other, represent a natural number of 1 to 3, provided that the sum of p and q is a natural number of 2 to 4, wherein, the term "substituted" refers to being substituted with at least one substituent selected from the group consisting of a deuterium atom, halogen atom, $C_1$-$C_6$ alkyl group, $C_1$-$C_6$ alkoxy group, $C_1$-$C_6$ alkoxy-$C_1$-$C_6$ alkyl group, $R^{13}O$—$C_1$-$C_6$ alkyl group, halo-$C_1$-$C_6$ alkyl group, $C_7$-$C_{16}$ aralkyl group, $C_1$-$C_7$ acyl group, cyano group, oxo group, —$CONR^{11}R^{12}$, —$OR^{13}$, —$COOR^{14}$, —$NR^{15}R^{16}$ and —$S(O)_nR^{17}$, $R^{11}$ and $R^{12}$ independently represent a hydrogen atom or $C_1$-$C_6$ alkyl group, $R^{13}$ represents a hydrogen atom, $C_1$-$C_7$ acyl group or protecting group, $R^{14}$ represents a hydrogen atom or $C_1$-$C_6$ alkyl group, $R^{15}$ and $R^{16}$ independently represent a hydrogen atom, $C_1$-$C_6$ alkyl group, $C_7$-$C_{16}$ aralkyl group, $C_1$-$C_7$ acyl group, —$COOR^{14}$ or —$S(O)_nR^{17}$, $R^{17}$ represents a $C_1$-$C_6$ alkyl group, and n represents 0, 1 or 2;

or a pharmacologically acceptable salt thereof.

In a specific embodiment, the present invention relates to the compound of general formula (I), or a pharmacologically acceptable salt thereof, wherein p and q represent 1.

In a specific embodiment, the present invention relates to the compound of general formula (I), or a pharmacologically acceptable salt thereof, wherein p represents 1 and q represents 2 (or p represents 2 and q represents 1).

In a specific embodiment, the present invention relates to the compound of general formula (I), or a pharmacologically acceptable salt thereof, wherein p and q represent 2.

In a specific embodiment, the present invention relates to the compound of general formula (I), or a pharmacologically acceptable salt thereof, wherein p represents 1 and q represents 3 (or p represents 3 and q represents 1).

In a specific embodiment, the present invention relates to the compound of general formula (I), or a pharmacologically acceptable salt thereof, wherein $R^1$ represents a hydrogen atom, protecting group, $C_1$-$C_6$ alkyl group (which may be substituted with at least one substituent selected from the group consisting of a deuterium atom, halogen atom, cyano group, —$CONR^{11}R^{12}$, —$OR^{13}$, —$COOR^{14}$, —$NR^{15}R^{16}$ and —$S(O)_nR^{17}$), $C_2$-$C_6$ alkenyl group, $C_3$-$C_8$ cycloalkyl group (which may be substituted with at least one —$OR^{13}$ group), $C_1$-$C_6$ alkoxy-$C_1$-$C_6$ alkyl group (which may be substituted with at least one substituent selected from the group consisting of —$OR^{13}$ and —$NR^{15}R^{16}$), —$CONR^{11}R^{12}$, heterocyclyl group or heterocyclyl-$C_1$-$C_6$ alkyl group (in which the heterocyclyl moiety may be substituted with at least one substituent selected from the group consisting of a halogen atom, $C_1$-$C_6$ alkyl group, $C_1$-$C_6$ alkoxy group, $C_1$-$C_6$ alkoxy-$C_1$-$C_6$ alkyl group, $R^{13}$O—$C_1$-$C_6$ alkyl group, halo-$C_1$-$C_6$ alkyl group, $C_7$-$C_{16}$ aralkyl group, $C_1$-$C_7$ acyl group, oxo group, —$COOR^{14}$ and —$S(O)_nR^{17}$), or aryl group; wherein, $R^{11}$ and $R^{12}$ independently represent a hydrogen atom or $C_1$-$C_6$ alkyl group, $R^{13}$ represents a hydrogen atom, $C_1$-$C_7$ acyl group or protecting group, $R^{14}$ represents a hydrogen atom or $C_1$-$C_6$ alkyl group, $R^{15}$ and $R^{16}$ independently represent a hydrogen atom, $C_1$-$C_6$ alkyl group, $C_7$-$C_{16}$ aralkyl group, $C_1$-$C_7$ acyl group, —$COOR^{14}$ or —$S(O)_nR^{17}$, $R^{17}$ represents a $C_1$-$C_6$ alkyl group, and n represents 0, 1 or 2.

In a specific embodiment, the present invention relates to the compound of general formula (I), or a pharmacologically acceptable salt thereof, wherein $R^1$ represents a hydrogen atom, optionally substituted $C_1$-$C_6$ alkyl group, $C_2$-$C_6$ alkenyl group, optionally substituted $C_3$-$C_8$ cycloalkyl group, optionally substituted $C_1$-$C_6$ alkoxy-$C_1$-$C_6$ alkyl group or optionally substituted heterocyclyl group, wherein the aforementioned term "substituted" refers to being substituted with at least one substituent selected from the group consisting of a deuterium atom, halogen atom, —$OR^{13}$ and —$S(O)_nR^{17}$, $R^{13}$ represents a hydrogen atom, $C_1$-$C_7$ acyl group or protecting group, and $R^{17}$ represents a $C_1$-$C_6$ alkyl group.

In a specific embodiment, the present invention relates to the compound of general formula (I) of the present invention, or a pharmacologically acceptable salt thereof, wherein $R^1$ represents a hydrogen atom, $C_1$-$C_6$ alkyl group (which may be substituted with at least one substituent selected from the group consisting of a deuterium atom, halogen atom, —$OR^{13}$ and —$S(O)_nR^{17}$), $C_2$-$C_6$ alkenyl group, $C_3$-$C_8$ cycloalkyl group (which may be substituted with at least one —$OR^{13}$ group), $C_1$-$C_6$ alkoxy-$C_1$-$C_6$ alkyl group (which may be substituted with at least one —$OR^{13}$ group), or heterocyclyl group (in which the heterocyclyl moiety may be substituted with at least one substituent selected from the group consisting of a halogen atom and —$S(O)_nR^{17}$);

wherein, $R^{13}$ represents a hydrogen atom, $C_1$-$C_7$ acyl group or protecting group, $R^{17}$ represents a $C_1$-$C_6$ alkyl group, and n represents 0, 1 or 2.

In a specific embodiment, the present invention relates to the compound of general formula (I) of the present invention, or a pharmacologically acceptable salt thereof, wherein $R^1$ represents a $C_1$-$C_4$ alkyl group or a $C_1$-$C_4$ alkyl group substituted with at least one substituent selected from the group consisting of a deuterium atom, fluorine atom and hydroxyl group.

In a specific embodiment, the present invention relates to the compound of general formula (II), or a pharmacologically acceptable salt thereof.

General Formula (II):

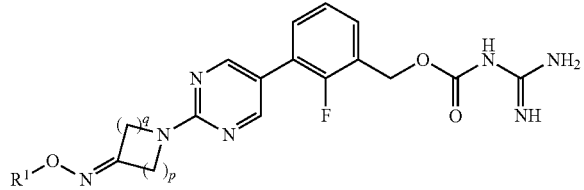

(II)

In general formula (II), $R^1$, p and q are the same as previously defined in general formula (I).

In a specific embodiment, the present invention relates to the compound of general formula (II), or a pharmacologically acceptable salt thereof, wherein p and q represent 1.

In a specific embodiment, the present invention relates to the compound of general formula (II), or a pharmacologically acceptable salt thereof, wherein p represents 1 and q represents 2 (or p represents 2 and q represents 1).

In a specific embodiment, the present invention relates to the compound of general formula (II), or a pharmacologically acceptable salt thereof, wherein p and q represent 2.

In a specific embodiment, the present invention relates to the compound of general formula (II), or a pharmacologically acceptable salt thereof, wherein p represents 1 and q represents 3 (or p represents 3 and q represents 1).

In a specific embodiment, the present invention relates to the compound of general formula (II), or a pharmacologically acceptable salt thereof, wherein $R^1$ represents a hydrogen atom, protecting group, $C_1$-$C_6$ alkyl group (which may be substituted with at least one substituent selected from the group consisting of a deuterium atom, halogen atom, cyano group, —$CONR^{11}R^{12}$, —$OR^{13}$, —$COOR^{14}$, —$NR^{15}R^{16}$ and —$S(O)_nR^{17}$), $C_2$-$C_6$ alkenyl group, $C_3$-$C_8$ cycloalkyl group (which may be substituted with at least one —$OR^{13}$ group), $C_1$-$C_6$ alkoxy-$C_1$-$C_6$ alkyl group (which may be substituted with at least one substituent selected from the group consisting of —$OR^{13}$ and —$NR^{15}R^{16}$), —$CONR^{11}R^{12}$, heterocyclyl group or heterocyclyl-$C_1$-$C_6$ alkyl group (in which the heterocyclyl moiety may be substituted with at least one substituent selected from the group consisting of a halogen atom, $C_1$-$C_6$ alkyl group, $C_1$-$C_6$ alkoxy group, $C_1$-$C_6$ alkoxy-$C_1$-$C_6$ alkyl group, $R^{13}$O—$C_1$-$C_6$ alkyl group, halo-$C_1$-$C_6$ alkyl group, $C_7$-$C_{16}$ aralkyl group, $C_1$-$C_7$ acyl group, oxo group, —$COOR^{14}$ and —$S(O)_nR^7$), or aryl group; wherein, $R^{11}$ and $R^{12}$ independently represent a hydrogen atom or $C_1$-$C_6$ alkyl group, $R^{13}$ represents a hydrogen atom, $C_1$-$C_7$ acyl group or protecting group, $R^{14}$ represents a hydrogen atom or $C_1$-$C_6$ alkyl group, $R^{15}$ and $R^{16}$ independently represent a hydrogen atom, $C_1$-$C_6$ alkyl group, $C_7$-$C_{16}$ aralkyl group, $C_1$-$C_7$ acyl group, —COOR$^{14}$ or —S(O)$_n$R$^7$, R$^{17}$ represents a $C_1$-$C_6$ alkyl group, and n represents 0, 1 or 2.

In a specific embodiment, the present invention relates to the compound of general formula (II), or a pharmacologically acceptable salt thereof, wherein R$^1$ represents a hydrogen atom, optionally substituted $C_1$-$C_6$ alkyl group, $C_2$-$C_6$ alkenyl group, optionally substituted $C_3$-$C_8$ cycloalkyl group, optionally substituted $C_1$-$C_6$ alkoxy-$C_1$-$C_6$ alkyl group or optionally substituted heterocyclyl group, wherein the aforementioned term "substituted" refers to being substituted with at least one substituent selected from the group consisting of a deuterium atom, halogen atom, —OR$^{13}$ and —S(O)$_n$R$^{17}$, R$^{13}$ represents a hydrogen atom, $C_1$-$C_7$ acyl group or protecting group, and R$^{17}$ represents a $C_1$-$C_6$ alkyl group.

In a specific embodiment, the present invention relates to the compound of general formula (II) of the present invention, or a pharmacologically acceptable salt thereof, wherein R$^1$ represents a hydrogen atom, $C_1$-$C_6$ alkyl group (which may be substituted with at least one substituent selected from the group consisting of a deuterium atom, halogen atom, —OR$^{13}$ and —S(O)$_n$R$^{17}$), $C_2$-$C_6$ alkenyl group, $C_3$-$C_8$ cycloalkyl group (which may be substituted with at least one —OR$^{13}$ group), $C_1$-$C_6$ alkoxy-$C_1$-$C_6$ alkyl group (which may be substituted with at least one —OR$^{13}$ group), or heterocyclyl group (in which the heterocyclyl moiety may be substituted with at least one substituent selected from the group consisting of a halogen atom and —S(O)$_n$R$^{17}$); wherein, R$^{13}$ represents a hydrogen atom, $C_1$-$C_7$ acyl group or protecting group, R$^{17}$ represents a $C_1$-$C_6$ alkyl group, and n represents 0, 1 or 2.

In a specific embodiment, the present invention relates to the compound of general formula (II) of the present invention, or a pharmacologically acceptable salt thereof, wherein R$^1$ represents a $C_1$-$C_4$ alkyl group or a $C_1$-$C_4$ alkyl group substituted with at least one substituent selected from the group consisting of a deuterium atom, fluorine atom and hydroxyl group.

In a specific embodiment, the present invention relates to the compound of general formula (III), or a pharmacologically acceptable salt thereof.

General Formula (III):

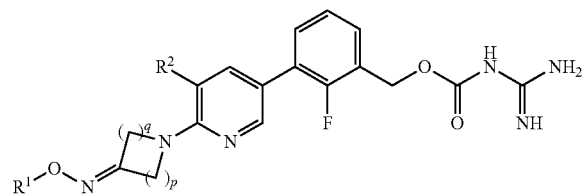

(III)

In general formula (III), R$^1$, R$^2$, p and q are the same as previously defined in general formula (I).

In a specific embodiment, the present invention relates to the compound of general formula (III), or a pharmacologically acceptable salt thereof, wherein p and q represent 1.

In a specific embodiment, the present invention relates to the compound of general formula (III), or a pharmacologically acceptable salt thereof, wherein p represents 1 and q represents 2 (or p represents 2 and q represents 1).

In a specific embodiment, the present invention relates to the compound of general formula (III); or a pharmacologically acceptable salt thereof, wherein p and q represent 2.

In a specific embodiment, the present invention relates to the compound of general formula (III), or a pharmacologically acceptable salt thereof, wherein p represents 1 and q represents 3 (or p represents 3 and q represents 1).

In a specific embodiment, the present invention relates to the compound of general formula (III) of the present invention, or a pharmacologically acceptable salt thereof, wherein R$^2$ represents a hydrogen atom, halogen atom, $C_1$-$C_6$ alkyl group (which may be substituted with at least one substituent selected from the group consisting of a halogen atom, —OR$^{13}$ and $C_1$-$C_6$ alkoxy group), $C_3$-$C_8$ cycloalkyl group, $C_1$-$C_6$ alkoxy group or cyano group, wherein R$^{13}$ represents a hydrogen atom, $C_1$-$C_7$ acyl group or protecting group.

In a specific embodiment, the present invention relates to the compound of general formula (III) of the present invention, or a pharmacologically acceptable salt thereof, wherein R$^2$ represents a hydrogen atom, fluorine atom, chlorine atom, $C_1$-$C_4$ alkyl group, $C_1$-$C_4$ alkyl group substituted with at least one fluorine atom, $C_1$-$C_4$ alkyl group substituted with at least one hydroxyl group, $C_1$-$C_4$ alkyl group substituted with at least one protected hydroxyl group, $C_1$-$C_4$ alkyl group substituted with at least one $C_1$-$C_4$ alkoxy group, $C_3$-$C_6$ cycloalkyl group, $C_1$-$C_4$ alkoxy group or cyano group.

In a specific embodiment, the present invention relates to the compound of general formula (III) of the present invention, or a pharmacologically acceptable salt thereof, wherein R$^2$ represents a hydrogen atom, fluorine atom, chlorine atom, methyl group, ethyl group, difluoromethyl group, 2-[(tetrafluoropyran-2-yl)oxy]propan-2-yl group, 2-hydroxypropan-2-yl group, methoxymethyl group, cyclopropyl group, methoxy group or cyano group.

In a specific embodiment, the present invention relates to the compound of general formula (III) of the present invention, or a pharmacologically acceptable salt thereof, wherein R$^2$ represents a fluorine atom.

In a specific embodiment, the present invention relates to the compound of general formula (III) of the present invention, or a pharmacologically acceptable salt thereof, wherein R$^1$ represents a hydrogen atom, protecting group, $C_1$-$C_6$ alkyl group (which may be substituted with at least one substituent selected from the group consisting of a deuterium atom, halogen atom, cyano group, —CONR$^{11}$R$^{12}$, —OR$^{13}$, —COOR$^{14}$, —NR$^{15}$R$^{16}$ and —S(O)$_n$R$^{17}$), $C_2$-$C_6$ alkenyl group, $C_3$-$C_8$ cycloalkyl group (which may be substituted with at least one —OR$^{13}$ group), $C_1$-$C_6$ alkoxy-$C_1$-$C_6$ alkyl group (which may be substituted with at least one substituent selected from the group consisting of —OR$^{13}$ and —NR$^{15}$R$^{16}$), —CONR$^{11}$R$^{12}$, heterocyclyl group or heterocyclyl-$C_1$-$C_6$ alkyl group (in which the heterocyclyl moiety may be substituted with at least one substituent selected from the group consisting of a halogen atom, $C_1$-$C_6$ alkyl group, $C_1$-$C_6$ alkoxy group, $C_1$-$C_6$ alkoxy-$C_1$-$C_6$ alkyl group, R$^{13}$O—$C_1$-$C_6$ alkyl group, halo-$C_1$-$C_6$ alkyl group, $C_7$-$C_{16}$ aralkyl group, $C_1$-$C_7$ acyl group, oxo group, —COOR$^{14}$ and —S(O)$_n$R$^{17}$), or aryl group; wherein, R$^{11}$ and R$^{12}$ independently represent a hydrogen atom or $C_1$-$C_6$ alkyl group, R$^{13}$ represents a hydrogen atom, $C_1$-$C_7$ acyl group or protecting group, R$^{14}$ represents a hydrogen atom or $C_1$-$C_6$ alkyl group, R$^{15}$ and R$^{16}$ independently represent a hydrogen atom, $C_1$-$C_6$ alkyl group, $C_7$-$C_{16}$ aralkyl group, $C_1$-$C_7$ acyl group, —COOR$^{14}$ or —S(O)$_n$R$^{17}$, R$^{17}$ represents a $C_1$-$C_6$ alkyl group, and n represents 0, 1 or 2.

In a specific embodiment, the present invention relates to the compound of general formula (III), or a pharmacologically acceptable salt thereof, wherein $R^1$ represents a hydrogen atom, optionally substituted $C_1$-$C_6$ alkyl group, $C_2$-$C_6$ alkenyl group, optionally substituted $C_3$-$C_8$ cycloalkyl group, optionally substituted $C_1$-$C_6$ alkoxy-$C_1$-$C_6$ alkyl group or optionally substituted heterocyclyl group, wherein the aforementioned term "substituted" refers to being substituted with at least one substituent selected from the group consisting of a deuterium atom, halogen atom, —$OR^{13}$ and —$S(O)_nR^{17}$, $R^{13}$ represents a hydrogen atom, $C_1$-$C_7$ acyl group or protecting group, and $R^{17}$ represents a $C_1$-$C_6$ alkyl group.

In a specific embodiment, the present invention relates to the compound of general formula (III) of the present invention, or a pharmacologically acceptable salt thereof, wherein $R^1$ represents a hydrogen atom, $C_1$-$C_6$ alkyl group (which may be substituted with at least one substituent selected from the group consisting of a deuterium atom, halogen atom, —$OR^{13}$ and —$S(O)_nR^{17}$), $C_2$-$C_6$ alkenyl group, $C_3$-$C_8$ cycloalkyl group (which may be substituted with at least one —$OR^{13}$ group), $C_1$-$C_6$ alkoxy-$C_1$-$C_6$ alkyl group (which may be substituted with at least one —$OR^{13}$ group), or heterocyclyl group (in which the heterocyclyl moiety may be substituted with at least one substituent selected from the group consisting of a halogen atom and —$S(O)_nR^{17}$); wherein, $R^{13}$ represents a hydrogen atom, $C_1$-$C_7$ acyl group or protecting group, $R^{17}$ represents a $C_1$-$C_6$ alkyl group, and n represents 0, 1 or 2.

In a specific embodiment, the present invention relates to the compound of general formula (III) of the present invention, or a pharmacologically acceptable salt thereof, wherein $R^1$ represents a $C_1$-$C_4$ alkyl group or a $C_1$-$C_4$ alkyl group substituted with at least one substituent selected from the group consisting of a deuterium atom, fluorine atom and hydroxyl group.

In a specific embodiment, the present invention relates to the compound of general formula (III) of the present invention, or a pharmacologically acceptable salt thereof, wherein $R^1$ represents a $C_1$-$C_4$ alkyl group or a $C_1$-$C_4$ alkyl group substituted with at least one substituent selected from the group consisting of a deuterium atom, fluorine atom and hydroxyl group, and $R^2$ represents a fluorine atom.

In a specific embodiment, the present invention relates to the compound of general formula (I), (II) or (III) of the present invention, or a pharmacologically acceptable salt thereof, wherein $R^1$ represents a hydrogen atom, tetrahydropyran-2-yl group, tert-butyldimethylsilyl group, methyl group, ethyl group, isopropyl group, propyl group, allyl group, 2-methoxyethyl group, deuterated methyl group, 2-fluoroethyl group, 2,2-difluoroethyl group, 2,2,2-trifluoroethyl group, 3-fluoropropyl group, 2-hydroxyethyl group, 2-hydroxypropyl group, 3-hydroxypropyl group, 3-hydroxy-2-methylpropyl group, 4-hydroxybutyl group, 3-hydroxy-3-methylbutyl group, 3-hydroxy-2,2-dimethylpropyl group, 2,3-dihydroxypropyl group, 3-hydroxy-2-(hydroxymethyl)-propyl group, 3-hydroxy-2-(hydroxymethyl)-2-methylpropyl group, 3,4-dihydroxybutyl group, 3-fluoro-2-(hydroxymethyl)propyl group, 2-fluoro-3-hydroxypropyl group, 3-acetyloxy-2-(hydroxymethyl)propyl group, 2-(hydroxymethyl)-3-propanoyloxypropyl group, 3-butanoyloxy-2-(hydroxymethyl)propyl group, 2-(hydroxymethyl)-3-isobutyryloxypropyl group, 2-(hydroxymethyl)-3-pivaloyloxypropyl group, 3-hexanoyloxy-2-(hydroxymethyl)propyl group, 3-benzoyloxy-2-(hydroxymethyl)propyl group, 3-fluoro-2-{[(tetrahydropyran-2-yl)oxy]methyl}propyl group, 2-fluoro-3-(trityloxy)propyl group, 2-[(tetrahydropyran-2-yl)oxy]ethyl group, 2-[(tetrahydropyran-2-yl)oxy]propyl group, 3-[(tetrahydropyran-2-yl)oxy]propyl group, 2-methyl-3-[(tetrahydropyran-2-yl)oxy]propyl group, 4-[(tetrahydropyran-2-yl)oxy]butyl group, 2,2-dimethyl-3-[(tetrahydropyran-2-yl)oxy]propyl group, 3-methyl-3-[(tetrahydropyran-2-yl)oxy]butyl group, pivaloyloxymethyl group, 2-(acetyloxy)ethyl group, 2-(propanoyloxy)ethyl group, 2-(butanoyloxy)ethyl group, 2-(benzoyloxy)ethyl group, 3,4-di(acetyloxy)butyl group, 2,2-dimethyl-1,3-dioxan-5-ylmethyl group, 2,2-dimethyl-1,3-dioxolan-4-ylmethyl group, 2-(2,2-dimethyl-1,3-dioxolan-4-yl)ethyl group, 2,2,5-trimethyl-1,3-dioxan-5-ylmethyl group, 3-acetyloxy-2-{[(tetrahydropyran-2-yl)oxy]methyl}propyl group, 3-propanoyloxy-2-{[(tetrahydropyran-2-yl)oxy]methyl}propyl group, 3-butanoyloxy-2-{[(tetrahydropyran-2-yl)oxy]methyl}propyl group, 3-isobutyryloxy-2-{[(tetrahydropyran-2-yl)oxy]methyl}propyl group, 3-pivaloyloxy-2-{[(tetrahydropyran-2-yl)oxy]methyl}propyl group, 3-hexanoyloxy-2-{[(tetrahydropyran-2-yl)oxy]methyl}propyl group, 3-benzoyloxy-2-{[(tetrahydropyran-2-yl)oxy]methyl}propyl group, 2-(2-hydroxyethoxy)ethyl group, 2-hydroxy-3-methoxypropyl group, 3-hydroxy-2-methoxypropyl group, 3-hydroxy-2-(methoxymethyl)propyl group, 4-hydroxy-3-methoxybutyl group, 2-methoxy-3-(trityloxy)propyl group, 2-acetyloxy-3-methoxypropyl group, 2-{2-[(tetrahydropyran-2-yl)oxy]ethoxy}ethyl group, 3-methoxy-2-{[(tetrahydropyran-2-yl)oxy]methyl}propyl group, or 3-methoxy-4-[(tetrahydropyran-2-yl)oxy]butyl group.

Moreover, in a specific embodiment, the present invention relates to the compound of general formula (I), (II) or (III) of the present invention, or a pharmacologically acceptable salt thereof, wherein $R^1$ represents a 2-tert-butoxy-2-oxoethyl group, carboxymethyl group, dimethylcarbamoyl group, 2-(methylamino)-2-oxoethyl group, 3-amino-3-oxopropyl group, 3-(methylamino-3-oxopropyl group, 4-ethoxy-4-oxobutyl group, 3-carboxypropyl group, 4-(methylamino)-4-oxobutyl group, 2-(dimethylamino)ethyl group, 2-[benzyl(methyl)amino]ethyl group, 3-acetamido-2-{[(tetrahydropyran-2-yl)oxy]methyl}propyl group, 3-acetamido-2-(hydroxymethyl)propyl group, 3-(dimethylamino)-2-{[(tetrahydropyran-2-yl)oxy]methyl}propyl group, 3-(dimethylamino)-2-(hydroxymethyl)propyl group, 3-acetamido-2-methoxypropyl group, 2-(piperidin-1-yl)ethyl group, 2-morpholinoethyl group, 2-(azetidin-1-yl)ethyl group, 2-(3,3-difluoroazetidin-1-yl)ethyl group, 2-(3-fluoroazetidin-1-yl)ethyl group, 2-(3-methoxyazetidin-1-yl)ethyl group, (4-methylmorpholin-2-yl)methyl group, (4-acetylmorpholin-2-yl)methyl group, (5-oxotetrahydrofuran-2-yl)methyl group, 3-acetyloxycyclobutan-1-yl group, 3-hydroxycyclobutan-1-yl group, benzyl group, 4-methoxybenzyl group, 1-methylazetidin-3-yl group, 1-acetylazetidin-3-yl group, 1-benzylazetidin-3-yl group, 1-(2,2,2-trifluoroethyl)azetidin-3-yl group, 1-(methylsulfonyl)azetidin-3-yl group, 1-ethylazetidin-3-yl group, 1-(methoxycarbonyl)azetidin-3-yl group, oxetan-3-yl group, 1-[2-(acetyloxy)ethyl]azetidin-3-yl group, 1-(2-hydroxyethyl)azetidin-3-yl group, 1-(2-methoxyethyl)azetidin-3-yl group, 1-(2-fluoroethyl)azetidin-3-yl group, 3-ethoxy-3-oxopropyl group, 3-amino-3-oxopropyl group, 3-(methylamino)-3-oxopropyl group, 3-(dimethylamino)-3-oxopropyl group, 2-acetamidoethyl group, 2-(N-methylacetamido)ethyl group, 2-(N-methylmethylsulfonamido)ethyl group, 2-[N-(tert-butoxycarbonyl)methylsulfonamido]ethyl group, 2-(methylsulfonamido)ethyl group, 2-[N-(tert-butoxycarbonyl)(methyl)amino]ethyl group, 2-(methylamino)ethyl group, 2-[N-di(tert-butoxycarbonyl)amino]ethyl group, 2-aminoethyl group, 2-cyanoethyl group, 3-cyanopropyl group, 2-(methylsulfonyl)ethyl group, 3-(methylsulfonyl)propyl group, (1-methyl-1H-pyrazol-3-yl)methyl group, [1-(tetrahydropyran-2-yl)-1H-pyrazol-3-yl]methyl group, (1H-pyrazol-3-yl)methyl group, [1-(tetrahydropyran-2-yl)-1H-pyrazol-4-yl]methyl group, (1H-pyrazol-4-yl)methyl group, (1-methyl-1H-pyrazol-4-yl)methyl group, 2-(1H-pyrazol-1-yl)ethyl group, pyridin-4-ylmethyl group, 2-(2,5-dioxopyrrolidin-1-yl)ethyl group, 2-(2-oxopyrrolidin-1-yl)ethyl group, 2-(2-oxooxazolidin-3-yl)ethyl group, 2-(3-oxomorpholino)ethyl group, phenyl group, pyrimidin-5-yl group or pyrimidin-2-yl group.

In a specific embodiment, the present invention relates to the compound of general formula (I), or a pharmacologically acceptable salt thereof, which is 2-fluoro-3-{2-[3-(methoxyimino)azetidin-1-yl]pyrimidin-5-yl}benzyl carbamimidoylcarbamate, 3-{2-[3-(ethoxyimino)azetidin-1-yl]pyrimidin-5-yl}-2-fluorobenzyl carbamimidoylcarbamate, 2-fluoro-3-(2-{3-[(methoxy-$d_3$)imino]azetidin-1-yl}pyrimidin-5-yl)benzyl carbamimidoylcarbamate, 2-fluoro-3-(2-{3-[(2-fluoroethoxy)imino]azetidin-1-yl}pyrimidin-5-yl)benzyl carbamimidoylcarbamate, 3-{2-{3-[(2,2-difluoroethoxy)imino]azetidin-1-yl}pyrimidin-5-yl}-2-fluorobenzyl carbamimidoylcarbamate, 2-fluoro-3-(2-{3-[(2,2,2-trifluoroethoxy)imino]azetidin-1-yl}pyrimidin-5-yl)benzyl carbamimidoylcarbamate, 2-fluoro-3-(2-{3-[(3-fluoropropoxy)imino]azetidin-1-yl}pyrimidin-5-yl)benzyl carbamimidoylcarbamate, 2-fluoro-3-{2-[3-({4-[(tetrahydropyran-2-yl)oxy]butoxy}imino)azetidin-1-yl]pyrimidin-5-yl}benzyl carbamimidoylcarbamate, 2-fluoro-3-(2-{3-[(2-methoxyethoxy)imino]azetidin-1-yl}pyrimidin-5-yl)benzyl carbamimidoylcarbamate,

[({1-[5-(3-{[(carbamimidoylcarbamoyl)oxy]methyl}-2-fluorophenyl)pyrimidin-2-yl]azetidin-3-ylidene}amino)oxy]methyl pivalate, 1-[({1-[5-(3-{[(carbamimidoylcarbamoyl)oxy]methyl}-2-fluorophenyl)pyrimidin-2-yl]azetidin-3-ylidene}amino)oxy]-3-methoxypropan-2-yl acetate, 4-[({1-[5-(3-{[(carbamimidoylcarbamoyl)oxy]methyl}-2-fluorophenyl)pyrimidin-2-yl]azetidin-3-ylidene}amino)oxy]butan-1,2-diyl diacetate, 2-[({1-[5-(3-{[(carbamimidoylcarbamoyl)oxy]methyl}-2-fluorophenyl)pyrimidin-2-yl]azetidin-3-ylidene}amino)oxy]ethyl acetate, 2-[({1-[5-(3-{[(carbamimidoylcarbamoyl)oxy]methyl}-2-fluorophenyl)pyrimidin-2-yl]azetidin-3-ylidene}amino)oxy]ethyl propionate, 2-[({1-[5-(3-{[(carbamimidoylcarbamoyl)oxy]methyl}-2-fluorophenyl)pyrimidin-2-yl]azetidin-3-ylidene}amino)oxy]ethyl butyrate, 2-[({1-[5-(3-{[(carbamimidoylcarbamoyl)oxy]methyl}-2-fluorophenyl)pyrimidin-2-yl]azetidin-3-ylidene}amino)oxy]ethyl benzoate, 2-fluoro-3-{5-fluoro-6-[3-(methoxyimino)azetidin-1-yl]pyridin-3-yl}benzyl carbamimidoylcarbamate, 2-fluoro-3-{5-fluoro-6-{3-[(methoxy-$d_3$)imino]azetidin-1-yl}pyridine-3-yl}benzyl carbamimidoylcarbamate, 2-fluoro-3-{6-[3-(methoxyimino)azetidin-1-yl]pyridin-3-yl}benzyl carbamimidoylcarbamate, 2-fluoro-3-{6-[3-(methoxyimino)azetidin-1-yl]-5-methyl-pyridin-3-yl}benzyl carbamimidoylcarbamate, 3-{5-cyano-6-[3-(methoxyimino)azetidin-1-yl]pyridin-3-yl}-2-fluorobenzyl carbamimidoylcarbamate, 3-{5-chloro-6-[3-(methoxyimino)azetidin-1-yl]pyridin-3-yl}-2-fluorobenzyl carbamimidoylcarbamate, 3-{5-(difluoromethyl)-6-[3-(methoxyimino)azetidin-1-yl]pyridin-3-yl}-2-fluorobenzyl carbamimidoylcarbamate, 3-{5-(cyclopropyl)-6-[3-(methoxyimino)azetidin-1-yl]pyridin-3-yl}-2-fluorobenzyl carbamimidoylcarbamate, 3-{5-ethyl-6-[3-(methoxyimino)azetidin-1-yl]pyridin-3-yl}-2-fluorobenzyl carbamimidoylcarbamate, 2-fluoro-3-{6-[3-(methoxyimino)azetidin-1-yl]-5-(methoxymethyl)pyridin-3-yl}benzyl carbamimidoylcarbamate, 2-fluoro-3-{5-methoxy-6-[3-(methoxyimino)azetidin-1-yl]pyridin-3-yl}benzyl carbamimidoylcarbamate, 2-fluoro-3-{2-[4-(methoxyimino)piperidin-1-yl]pyrimidin-5-yl}benzyl carbamimidoylcarbamate, 3-{2-[4-(ethoxyimino)piperidin-1-yl]pyridimin-5-yl}-2-fluoro benzyl carbamimidoylcarbamate, 2-fluoro-3-{2-[4-(isopropoxyimino)piperidin-1-yl]pyrimidin-5-yl}benzyl carbamimidoylcarbamate, 2-fluoro-3-{2-[4-(propoxyimino)piperidin-1-yl]pyrimidin-5-yl}benzyl carbamimidoylcarbamate, 3-(2-{4-[(allyloxy)imino]piperidin-1-yl}pyridimin-5-yl)-2-fluorobenzyl carbamimidoylcarbamate, 2-fluoro-3-{2-[4-({2-[(tetrahydropyran-2-yl)oxy]ethoxy}imino)piperidin-1-yl]pyrimidin-5-yl}benzyl carbamimidoylcarbamate, 2-fluoro-3-(2-{4-[(2-methoxyethoxy)imino]piperidin-1-yl}pyridimin-5-yl)benzyl carbamimidoylcarbamate, 2-[({1-[5-(3-{[(carbamimidoylcarbamoyl)oxy]methyl}-2-fluorophenyl)pyrimidin-2-yl]piperidin-4-ylidene}amino)oxy]ethyl acetate, (E/Z)-2-fluoro-3-{2-[3-(methoxyimino)pyrrolidin-1-yl]pyrimidin-5-yl}benzyl carbamimidoylcarbamate, 2-fluoro-3-{2-[3-(hydroxymino)azetidin-1-yl]pyrimidin-5-yl}benzyl carbamimidoylcarbamate, 2-fluoro-3-(2-{3-[(2-hydroxyethoxy)imino]azetidin-1-yl}pyrimidin-5-yl)benzyl carbamimidoylcarbamate, 2-fluoro-3-(2-{3-[(3-hydroxypropoxy)imino]azetidin-1-yl}pyrimidin-5-yl)benzyl carbamimidoylcarbamate, 2-fluoro-3-(2-{3-[(4-hydroxybutoxy)imino]azetidin-1-yl}pyrimidin-5-yl)benzyl carbamimidoylcarbamate, 2-fluoro-3-[2-(3-{[2-(2-hydroxyethoxy)ethoxy]imino}azetidin-1-yl)pyrimidin-5-yl]benzyl carbamimidoylcarbamate, 2-fluoro-3-[2-(3-{[3-fluoro-2-(hydroxymethyl)propoxy]imino}azetidin-1-yl)pyrimidin-5-yl]benzyl carbamimidoylcarbamate, 2-fluoro-3-(2-{3-[(4-hydroxy-3-methoxybutoxy)imino]azetidin-1-yl}pyrimidin-5-yl)benzyl carbamimidoylcarbamate, 3-[({1-[5-(3-{[(carbamimidoylcarbamoyl)oxy]methyl}-2-fluorophenyl)pyrimidin-2-yl]azetidin-3-ylidene}amino)oxy]-2-(hydroxymethyl)propyl acetate, 3-[({1-[5-(3-{[(carbamimidoylcarbamoyl)oxy]methyl}-2-fluorophenyl)pyrimidin-2-yl]azetidin-3-ylidene}amino)oxy]-2-(hydroxymethyl)propyl propionate, 3-[({1-[5-(3-{[(carbamimidoylcarbamoyl)oxy]methyl}-2-fluorophenyl)pyrimidin-2-yl]azetidin-3-ylidene}amino)oxy]-2-(hydroxymethyl)propyl butyrate, 3-[({1-[5-(3-{[(carbamimidoylcarbamoyl)oxy]methyl}-2-fluorophenyl)pyrimidin-2-yl]azetidin-3-ylidene}amino)oxy]-2-(hydroxymethyl)propyl isobutyrate, 3-[({1-[5-(3-{[(carbamimidoylcarbamoyl)oxy]methyl}-2-fluorophenyl)pyrimidin-2-yl]azetidin-3-ylidene}amino)oxy]-2-(hydroxymethyl)propyl pivalate, 3-[({1-[5-(3-{[(carbamimidoylcarbamoyl)oxy]methyl}-2-fluorophenyl)pyrimidin-2-yl]azetidin-3-ylidene}amino)oxy]-2-(hydroxymethyl)propyl hexanoate, 3-[({1-[5-(3-{[(carbamimidoylcarbamoyl)oxy]methyl}-2-fluorophenyl)pyrimidin-2-yl]azetidin-3-ylidene}amino)oxy]-2-(hydroxymethyl)propyl benzoate, 2-fluoro-3-{5-(2-hydroxypropan-2-yl)-6-[3-(methoxyimino)azetidin-1-yl]pyrid in-3-yl}benzyl carbamimidoylcarbamate, 2-fluoro-3-(2-{4-[(2-hydroxyethoxy)imino]piperidin-1-yl}pyrimidin-5-yl)benzyl carbamimidoylcarbamate, 2-fluoro-3-(2-{4-[(3-hydroxypropoxy)imino]piperidin-1-yl}pyrimidin-5-yl)benzyl carbamimidoylcarbamate, 2-fluoro-3-(2-{4-[(4-hydroxybutoxy)imino]piperidin-1-yl}pyrimidin-5-yl)benzyl carbamimidoylcarbamate, 2-fluoro-3-(2-{4-[(3-hydroxy-2,2-dimethylpropoxy)imino]piperidin-1-yl}pyrimidin-5-yl)benzyl carbamimidoylcarbamate, 2-fluoro-3-(2-{4-[(3-hydroxy-3-methylbutoxy)imino]piperidin-1-yl}pyrimidin-5-yl)benzyl carbamimidoylcarbamate, 2-fluoro-3-(2-{4-[(2-hydroxypropoxy)imino]piperidin-1-yl}pyrimidin-5-yl)benzyl carbamimidoylcarbamate, 2-fluoro-3-(2-{4-[(3-hydroxy-2-methylpropoxy)imino]piperidin-1-yl}pyrimidin-5-yl)benzyl carbamimidoylcarbamate, 2-fluoro-3-[2-(3-{[3-hydroxy-2-(hydroxymethyl)propoxy]imino}azetidin-1-yl)pyrimidin-5-yl]benzyl carbamimidoylcarbamate, 3-(2-{3-[(2,3-dihydroxypropoxy)imino]azetidin-1-yl}pyrimidin-5-yl)-2-fluorobenzyl carbamimidoylcarbamate, 3-(2-{3-[(3,4-dihydroxybutoxy)imino]azetidin-1-yl}pyrimidin-5-yl)-2-fluorobenzyl carbamimidoylcarbamate, 3-(6-{3-[(3,4-dihydroxybutoxy)imino]azetidin-1-yl}-5-fluoropyridin-3-yl)-2-fluorobenzyl carbamimidoylcarbamate, 2-fluoro-3-{5-fluoro-6-[3-{[hydroxy-2-(hydroxymethyl)propoxy]imino}azetidin-1-yl]pyridin-3-yl}benzyl carbamimidoylcarbamate, 2-fluoro-3-[2-(4-{[3-hydroxy-2-(hydroxymethyl)propoxy]imino}piperidin-1-yl)pyrimidin-5-yl]benzyl carbamimidoylcarbamate, 2-fluoro-3-[2-(4-{[3-hydroxy-2-(hydroxymethyl)-2-methylpropoxy]imino}piperidin-1-yl)pyrimidin-5-yl]benzyl carbamimidoylcarbamate, 3-(2-{4-[(2,3-dihydroxypropoxy)imino]piperidin-1-yl}pyrimidin-5-yl)-2-fluorobenzyl carbamimidoylcarbamate, 2-fluoro-3-[2-(3-{[3-hydroxy-2-(methoxymethyl)propoxy]imino}azetidin-1-yl)pyrimidin-5-yl]benzyl carbamimidoylcarbamate, 2-fluoro-3-(2-{3-[(3-hydroxy-2-methoxypropoxy)imino]azetidin-1-yl}pyrimidin-5-yl)benzyl carbamimidoylcarbamate, 2-fluoro-3-(2-{3-[(2-fluoro-3-hydroxypropoxy)imino]azetidin-1-yl}pyrimidin-5-yl)benzyl carbamimidoylcarbamate, 2-fluoro-3-(5-fluoro-6-{3-[(2-fluoro-3-hydroxypropoxy)imino]azetidin-1-yl}pyridin-3-yl)benzyl carbamimidoylcarbamate, 2-fluoro-3-(2-{3-[(2-hydroxy-3-methoxypropoxy)imino]azetidin-1-yl}pyrimidin-5-yl)benzyl carbamimidoylcarbamate, 2-fluoro-3-{2-[4-(hydroxyimino)piperidin-1-yl]pyrimidin-5-yl}benzyl carbamimidoylcarbamate, 2-fluoro-3-{5-fluoro-6-[3-(hydroxyimino)azetidin-1-yl]pyridin-3-yl}benzyl carbamimidoylcarbamate, tert-butyl 2-[({1-[5-(3-{[(carbamimidoylcarbamoyl)oxy]methyl}-2-fluorophenyl)pyrimidin-2-yl]azetidin-3-ylidene}amino)oxy]acetate, 2-[({1-[5-(3-{[(carbamimidoylcarbamoyl)oxy]methyl}-2-fluorophenyl)pyrimidin-2-yl]azetidin-3-ylidene}amino)oxy]acetic acid, 3-[2-(3-{[(dimethylcarbamoyl)oxy]imino}azetidin-1-yl)pyrimidin-5-yl]-2-fluorobenzyl carbamimidoylcarbamate, 2-fluoro-3-[2-(3-{[2-(methylamino)-2-oxoethoxy]imino}azetidin-1-yl)pyrimidin-5-yl]benzyl carbamimidoylcarbamate, 3-(2-{3-[(3-amino-3-oxopropoxy)imino]azetidin-1-yl}pyrimidin-5-yl)-2-fluorobenzyl carbamimidoylcarbamate, 2-fluoro-3-[2-(3-{[3-(methylamino)-3-oxopropoxy]imino}azetidin-1-yl)pyrimidin-5-yl]benzyl carbamimidoylcarbamate, ethyl 4-[({1-[5-(3-{[(carbamimidoylcarbamoyl)oxy]methyl}-2-fluorophenyl)pyrimidin-2-yl]azetidin-3-ylidene}amino)oxy]butanoate, 4-[({1-[5-(3-{[(carbamimidoylcarbamoyl)oxy]methyl}-2-fluorophenyl)pyrimidin-2-yl]azetidin-3-ylidene}amino)oxy]butanoic acid, 2-fluoro-3-[2-(3-{[4-(methylamino)-4-oxobutoxy]imino}azetidin-1-yl)pyrimidin-5-yl]benzyl carbamimidoylcarbamate, 3-[2-(3-{[2-(dimethylamino)ethoxy]imino}azetidin-1-yl)pyrimidin-5-yl]-2-fluorobenzyl carbamimidoylcarbamate, 3-{2-[3-{{2-[benzyl(methyl)amino]ethoxy}imino}azetidin-1-yl]pyrimidin-5-yl}-2-fluorobenzyl carbamimidoylcarbamate, 3-[2-(3-{[3-(acetamido-2-(hydroxymethyl)propoxy]imino}azetidin-1-yl)pyrimidin-5-yl]-2-fluorobenzyl carbamimidoylcarbamate, 3-[2-(3-{[3-(dimethylamino)-2-(hydroxymethyl)propoxy]imino}azetidin-1-yl)pyrimidin-5-yl]-2-fluorobenzyl carbamimidoylcarbamate, 3-(2-{3-[(3-acetamido-2-methoxypropoxy)imino]azetidin-1-yl}pyrimidin-5-yl)-2-fluorobenzyl carbamimidoylcarbamate, 2-fluoro-3-[2-(3-{[2-(piperidin-1-yl)ethoxy]imino}azetidin-1-yl)pyrimidin-5-yl]benzyl carbamimidoylcarbamate, 2-fluoro-3-(2-{3-[(morpholinoethoxy)imino]azetidin-1-yl}pyrimidin-5-yl)benzyl carbamimidoylcarbamate, 3-[2-(3-{[2-(azetidin-1-yl)ethoxy]imino}azetidin-1-yl)pyrimidin-5-yl]-2-fluorobenzyl carbamimidoylcarbamate, 3-[2-(3-{[2-(3,3-difluoroazetidin-1-yl)ethoxy]imino}azetidin-1-yl)pyrimidin-5-yl]-2-fluorobenzyl carbamimidoylcarbamate, 2-fluoro-3-[2-(3-{[2-(3-fluoroazetidin-1-yl)ethoxy]imino}azetidin-1-yl)pyrimidin-5-yl]benzyl carbamimidoylcarbamate, 2-fluoro-3-[2-(3-{[2-(3-methoxyazetidin-1-yl)ethoxy]imino}azetidin-1-yl)pyrimidin-5-yl]benzyl carbamimidoylcarbamate, 2-fluoro-3-[2-(3-{[(4-methylmorpholin-2-yl)methoxy]imino}azetidin-1-yl)pyrimidin-5-yl]benzyl carbamimidoylcarbamate, 3-[2-(3-{[(4-acetylmorpholin-2-yl)methoxy]imino}azetidin-1-yl)pyrimidin-5-yl]-2-fluorobenzyl carbamimidoylcarbamate, 2-fluoro-3-[2-(3-{[(5-oxotetrahydrofuran-2-yl)methoxy] imino}azetidin-1-yl)pyrimidin-5-yl]benzyl carbamimidoylcarbamate,
3-[({1-[5-(3-{[(carbamimidoylcarbamoyl)oxy]methyl}-2-fluorophenyl)pyrimidin-2-yl]azetidin-3-ylidene}amino) oxy]cyclobutyl acetate,
2-fluoro-3-(2-{3-[(3-hydroxycyclobutoxy)imino]azetidin-1-yl}pyrimidin-5-yl)benzyl carbamimidoylcarbamate,
3-(2-{3-[(benzyloxy)imino]azetidin-1-yl}pyrimidin-5-yl)-2-fluorobenzyl carbamimidoylcarbamate,
2-fluoro-3-[2-(3-{[(4-methoxybenzyl)oxy]imino}azetidin-1-yl)pyrimidin-5-yl]benzyl carbamimidoylcarbamate,
2-fluoro-3-[2-(3-{[(1-methylazetidin-3-yl)oxy] imino}azetidin-1-yl)pyrimidin-5-yl]benzyl carbamimidoylcarbamate,
3-[2-(3-{[(1-acetylazetidin-3-yl)oxy]imino}azetidin-1-yl) pyrimidin-5-yl]-2-fluorobenzyl carbamimidoylcarbamate,
3-[2-(3-{[(1-benzylazetidin-3-yl)oxy]imino}azetidin-1-yl) pyrimidin-5-yl]-2-fluorobenzyl carbamimidoylcarbamate,
2-fluoro-3-{2-{3-({[1-(2,2,2-trifluoroethyl)azetidin-3-yl] oxy}imino)azetidin-1-yl]pyrimidin-5-yl}benzyl carbamimidoylcarbamate,
2-fluoro-3-{2-[3-({[1-(methylsulfonyl)azetidin-3-yl] oxy}imino)azetidin-1-yl]pyrimidin-5-yl}benzyl carbamimidoylcarbamate,
3-[2-(3-{[(1-ethylazetidin-3-yl)oxy]imino}azetidin-1-yl) pyrimidin-5-yl]-2-fluorobenzyl carbamimidoylcarbamate,
methyl 3-[({1-[5-(3-{[(carbamimidoylcarbamoyl)oxy] methyl}-2-fluorophenyl)pyrimidin-2-yl]azetidin-3-ylidene}amino)oxy]azetidin-1-carboxylate,
2-fluoro-3-(2-{3-[(oxetan-3-yloxy)imino]azetidin-1-yl}pyrimidin-5-yl)benzyl carbamimidoylcarbamate,
2-{3-[({1-[5-(3-{[(carbamimidoylcarbamoyl)oxy]methyl}-2-fluorophenyl)pyrimidin-2-yl]azetidin-3-ylidene}amino)oxy]azetidin-1-yl}ethyl acetate,
2-fluoro-3-{2-[3-({[1-(2-hydroxyethyl)azetidin-3-yl] oxy}imino)azetidin-1-yl]pyrimidin-5-yl}benzyl carbamimidoylcarbamate,
2-fluoro-3-{2-[3-({[1-(2-methoxyethyl)azetidin-3-yl] oxy}imino)azetidin-1-yl]pyrimidin-5-yl}benzyl carbamimidoylcarbamate,
2-fluoro-3-{2-[3-({[1-(2-fluoroethyl)azetidin-3-yl] oxy}imino)azetidin-1-yl]pyrimidin-5-yl}benzyl carbamimidoylcarbamate,
ethyl 3-[({1-[5-(3-{[(carbamimidoylcarbamoyl)oxy] methyl}-2-fluorophenyl)pyrimidin-2-yl]piperidin-4-ylidene}amino)oxy]propanoate,
3-(2-{4-[(3-amino-3-oxopropoxy)imino]piperidin-1-yl}pyrimidin-5-yl)-2-fluorobenzyl carbamimidoylcarbamate,
2-fluoro-3-[2-(4-{[3-(methylamino)-3-oxopropoxy] imino}piperidin-1-yl)pyrimidin-5-yl]benzyl carbamimidoylcarbamate,
ethyl 4-[({1-[5-(3-{[(carbamimidoylcarbamoyl)oxy]methyl}-2-fluorophenyl)pyrimidin-2-yl]piperidin-4-ylidene}amino) oxy]butanoate,
4-[({1-[5-(3-{[(carbamimidoylcarbamoyl)oxy]methyl}-2-fluorophenyl)pyrimidin-2-yl]piperidin-4-ylidene}amino) oxy]butanoic acid,
3-[2-(4-{[3-(dimethylamino)-3-oxopropoxy] imino}piperidin-1-yl)pyrimidin-5-yl]-2-fluorobenzyl carbamimidoylcarbamate,
3-(2-{4-[(2-acetamidoethoxy)imino]piperidin-1-yl}pyrimidin-5-yl)-2-fluorobenzyl carbamimidoylcarbamate,
2-fluoro-3-[2-(4-{[2-(N-methylacetamido)ethoxy] imino}piperidin-1-yl)pyrimidin-5-yl]benzyl carbamimidoylcarbamate,
2-fluoro-3-[2-(4-{[2-(N-methylmethylsulfonamido)ethoxy] imino}piperidin-1-yl)pyrimidin-5-yl]benzyl carbamimidoylcarbamate,
2-fluoro-3-[2-(4-{[2-(methylsulfonamido)ethoxy] imino}piperidin-1-yl)pyrimidin-5-yl]benzyl carbamimidoylcarbamate,
3-[2-(4-{[2-(dimethylamino)ethoxy]imino}piperidin-1-yl) pyrimidin-5-yl]-2-fluorobenzyl carbamimidoylcarbamate,
2-fluoro-3-[2-(4-{[2-(methylamino)ethoxy] imino}piperidin-1-yl)pyrimidin-5-yl]benzyl carbamimidoylcarbamate,
3-(2-{4-[(2-aminoethoxy)imino]piperidin-1-yl}pyrimidin-5-yl)-2-fluorobenzyl carbamimidoylcarbamate,
3-(2-{4-[(2-cyanoethoxy)imino]piperidin-1-yl}pyrimidin-5-yl)-2-fluorobenzyl carbamimidoylcarbamate,
3-(2-{4-[(3-cyanopropoxy)imino]piperidin-1-yl}pyrimidin-5-yl)-2-fluorobenzyl carbamimidoylcarbamate,
2-fluoro-3-[2-(4-{[2-(methylsulfonyl)ethoxy] imino}piperidin-1-yl)pyrimidin-5-yl]benzyl carbamimidoylcarbamate,
2-fluoro-3-[2-(4-{[3-(methylsulfonyl)propoxy] imino}piperidin-1-yl)pyrimidin-5-yl]benzyl carbamimidoylcarbamate,
2-fluoro-3-[2-(4-{[(1-methyl-1H-pyrazol-3-yl)methoxy] imino}piperidin-1-yl)pyrimidin-5-yl]benzyl carbamimidoylcarbamate,
3-[2-(4-{[(1H-pyrazol-3-yl)methoxy]imino}piperidin-1-yl) pyrimidin-5-yl]-2-fluorobenzyl carbamimidoylcarbamate,
2-fluoro-3-{2-[4-({[1-(tetrahydropyran-2-yl)-1H-pyrazol-4-yl]methoxy}imino) piperidin-1-yl]pyrimidin-5-yl}benzyl carbamimidoylcarbamate,
3-[2-(4-{[(1H-pyrazol-4-yl)methoxy]imino}piperidin-1-yl) pyrimidin-5-yl]-2-fluorobenzyl carbamimidoylcarbamate,
2-fluoro-3-[2-(4-{[(1-methyl-1H-pyrazol-4-yl)methoxy] imino}piperidin-1-yl)pyrimidin-5-yl]benzyl carbamimidoylcarbamate,
3-[2-(4-{[2-(1H-pyrazol-1-yl)ethoxy]imino}piperidin-1-yl) pyrimidin-5-yl]-2-fluorobenzyl carbamimidoylcarbamate,
2-fluoro-3-(2-{4-[(pyridin-4-ylmethoxy)imino]piperidin-1-yl}pyrimidin-5-yl)benzyl carbamimidoylcarbamate,
3-[2-(4-{[2-(2,5-dioxopyrrolidin-1-yl)ethoxy] imino}piperidin-1-yl)pyrimidin-5-yl]-2-fluorobenzyl carbamimidoylcarbamate,
2-fluoro-3-[2-(4-{[2-(2-oxopyrrolidin-1-yl)ethoxy] imino}piperidin-1-yl)pyrimidin-5-yl]benzyl carbamimidoylcarbamate,
2-fluoro-3-[2-(4-{[2-(2-oxooxazolidin-3-yl)ethoxy] imino}piperidin-1-yl)pyrimidin-5-yl]benzyl carbamimidoylcarbamate,
2-fluoro-3-[2-(4-{[2-(3-oxomorpholino)ethoxy] imino}piperidin-1-yl)pyrimidin-5-yl]benzyl carbamimidoylcarbamate,
2-fluoro-3-{2-[4-(phenoxyimino)piperidin-1-yl]pyrimidin-5-yl}benzyl carbamimidoylcarbamate,
2-fluoro-3-(2-{4-[(pyrimidin-5-yloxy)imino]piperidin-1-yl}pyrimidin-5-yl)benzyl carbamimidoylcarbamate, or 2-fluoro-3-(2-{4-[(pyrimidin-2-yloxy)imino]piperidin-1-yl}pyrimidin-5-yl)benzyl carbamimidoylcarbamate.

In a specific embodiment, the present invention relates to 2-fluoro-3-{2-[3-(methoxyimino)azetidin-1-yl]pyrimidin-5-yl}benzyl carbamimidoylcarbamate, or a pharmacologically acceptable salt thereof.

In a specific embodiment, the present invention relates to 3-{2-[3-(ethoxyimino)azetidin-1-yl]pyrimidin-5-yl}-2-fluorobenzyl carbamimidoylcarbamate, or a pharmacologically acceptable salt thereof.

In a specific embodiment, the present invention relates to 2-fluoro-3-(2-{3-[(methoxy-$d_3$)imino]azetidin-1-yl}pyrimidin-5-yl)benzyl carbamimidoylcarbamate, or a pharmacologically acceptable salt thereof.

In a specific embodiment, the present invention relates to 2-fluoro-3-(2-{3-[(2-fluoroethoxy)imino]azetidin-1-yl}pyrimidin-5-yl)benzyl carbamimidoylcarbamate, or a pharmacologically acceptable salt thereof.

In a specific embodiment, the present invention relates to 2-fluoro-3-{5-fluoro-6-[3-(methoxyimino)azetidin-1-yl]pyridin-3-yl}benzyl carbamimidoylcarbamate, or a pharmacologically acceptable salt thereof.

In a specific embodiment, the present invention relates to 2-fluoro-3-{5-fluoro-6-{3-[(methoxy-$d_3$)imino]azetidin-1-yl}pyridine-3-yl}benzyl carbamimidoylcarbamate, or a pharmacologically acceptable salt thereof.

In a specific embodiment, the present invention relates to 3-(6-{3-[(3,4-dihydroxybutoxy)imino]azetidin-1-yl}-5-fluoropyridin-3-yl)-2-fluorobenzyl carbamimidoylcarbamate, or a pharmacologically acceptable salt thereof.

In a specific embodiment, the present invention relates to 2-fluoro-3-{5-fluoro-6-[3-{[3-hydroxy-2-(hydroxymethyl)propoxy]imino}azetidin-1-yl]pyridin-3-yl}benzyl carbamimidoylcarbamate, or a pharmacologically acceptable salt thereof.

In a specific embodiment, the present invention relates to 2-fluoro-3-(2-{3-[(2-fluoro-3-hydroxypropoxy)imino]azetidin-1-yl}pyrimidin-5-yl)benzyl carbamimidoylcarbamate, or a pharmacologically acceptable salt thereof.

In a specific embodiment, the present invention relates to 3-[({1-[5-(3-{[(carbamimidoylcarbamoyl)oxy]methyl}-2-fluorophenyl)pyrimidin-2-yl]azetidin-3-ylidene}amino)oxy]cyclobutyl acetate, or a pharmacologically acceptable salt thereof.

In a specific embodiment, the present invention relates to 2-fluoro-3-(2-{3-[(3-hydroxycyclobutoxy)imino]azetidin-1-yl}pyrimidin-5-yl)benzyl carbamimidoylcarbamate, or a pharmacologically acceptable salt thereof.

In a specific embodiment, the present invention relates to 2-fluoro-3-{2-[3-({[1-(methylsulfonyl)azetidin-3-yl]oxy}imino)azetidin-1-yl]pyrimidin-5-yl}benzyl carbamimidoylcarbamate, or a pharmacologically acceptable salt thereof.

In a specific embodiment, the present invention relates to 2-fluoro-3-(2-{3-[(oxetan-3-yloxy)imino]azetidin-1-yl}pyrimidin-5-yl)benzyl carbamimidoylcarbamate, or a pharmacologically acceptable salt thereof.

Specific examples of the compound of general formula (I) of the present invention further include the compounds listed in Table 1 and Table 2. Further, in the following Tables 1 and 2, $R^1$ group represents a group of the following formulas A1 to A90 or formulas B1 to B95. Furthermore, D represents a deuterium atom and Ph represents a phenyl group in the following formulas A1 to A90. Moreover, in the following Table 2, F represents a fluorine atom, Cl represents a chlorine atom, Br represents a bromine atom, I represents an iodine atom, Me represents a methyl group, Et represents an ethyl group, nPr represents an n-propyl group, iPr represents an isopropyl group, $CH_2F$ represents a fluoromethyl group, $CHF_2$ represents a difluoromethyl group, $CF_3$ represents a trifluoromethyl group, $HOCH_2$ represents a hydroxymethyl group, HOCHMe represents a 1-hydroxyethyl group, $HOC(Me)_2$ represents a 2-hydroxypropan-2-yl group, $THPOC(Me)_2$ represents a 2-[(tetrahydropyran-2-yl)oxy]propan-2-yl group, $MeOCH_2$ represents a methoxymethyl group, $EtOCH_2$ represents an ethoxymethyl group, cPr represents a cyclopropyl group, cBu represents a cyclobutyl group, MeO represents a methoxy group, EtO represents an ethoxy group and NC represents a cyano group.

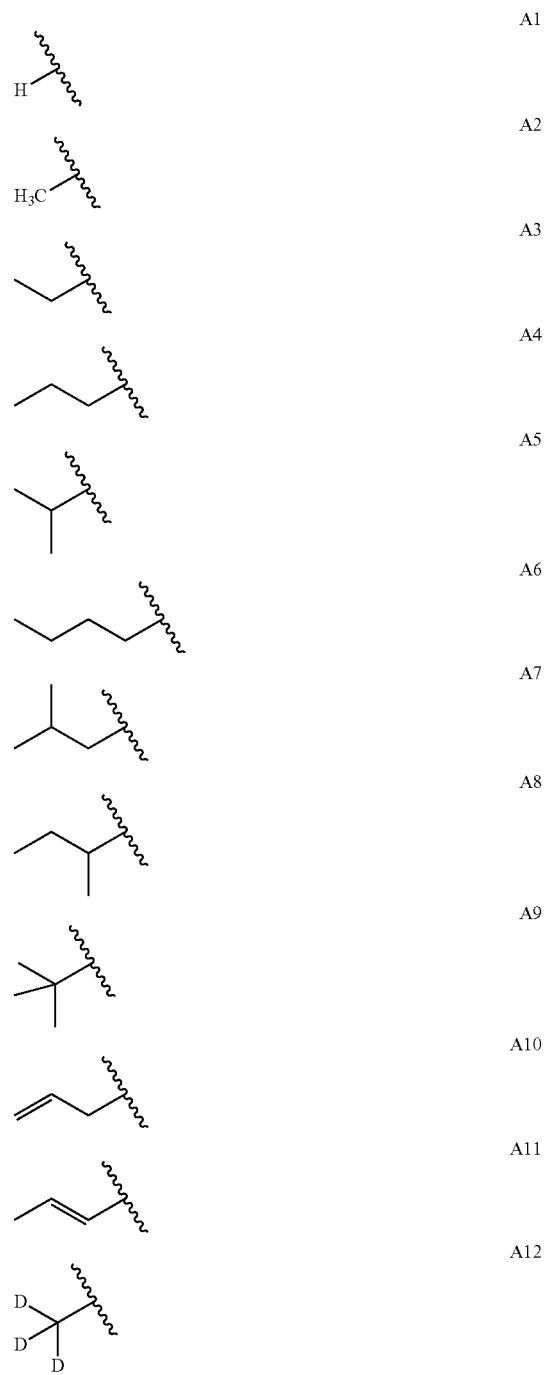

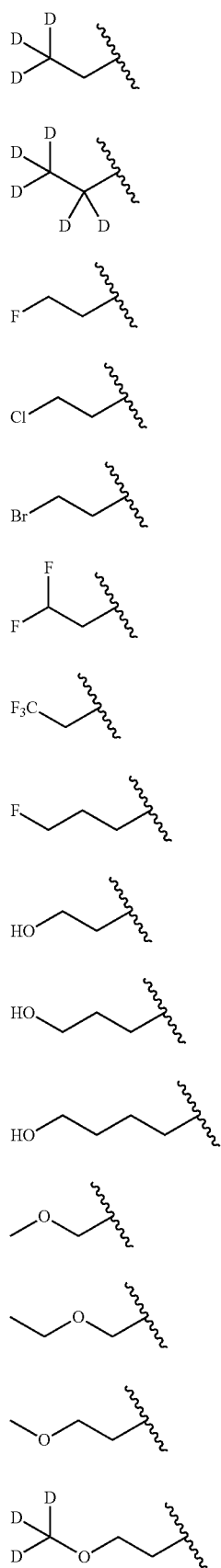
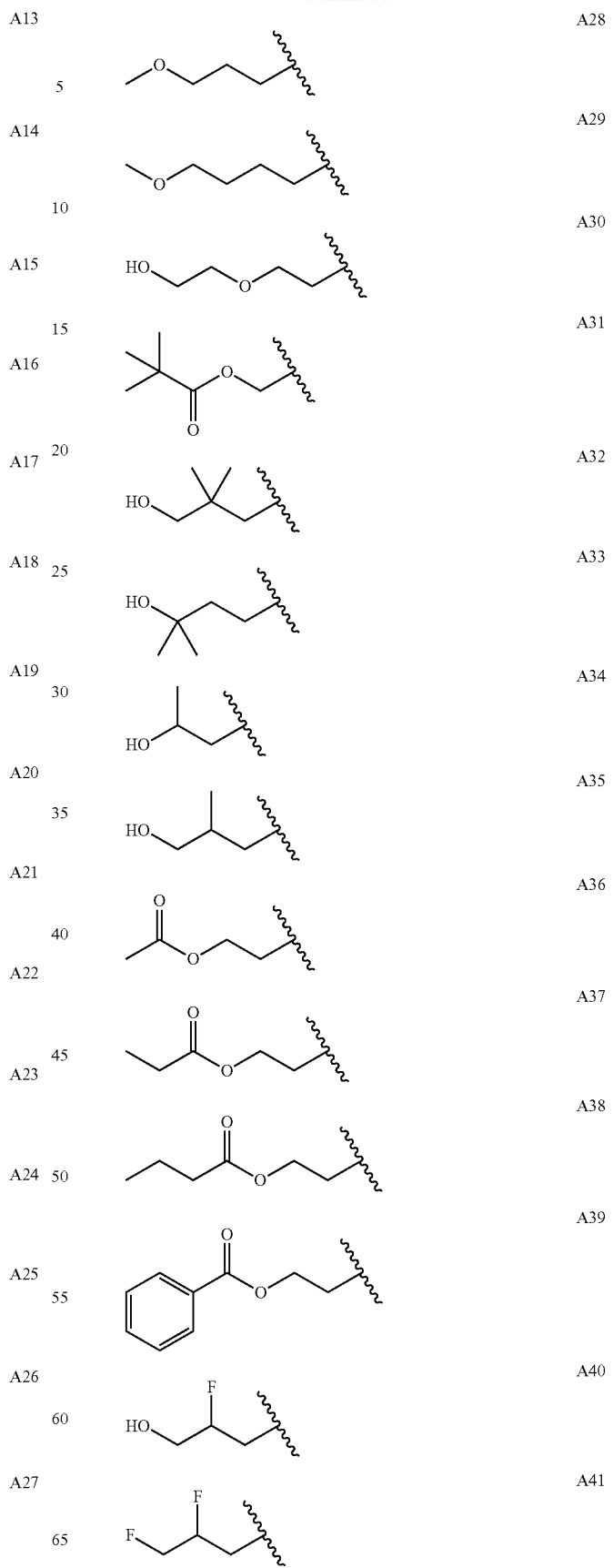

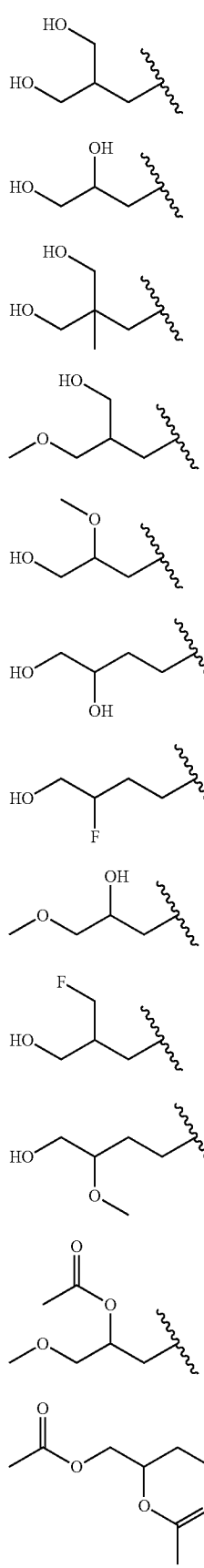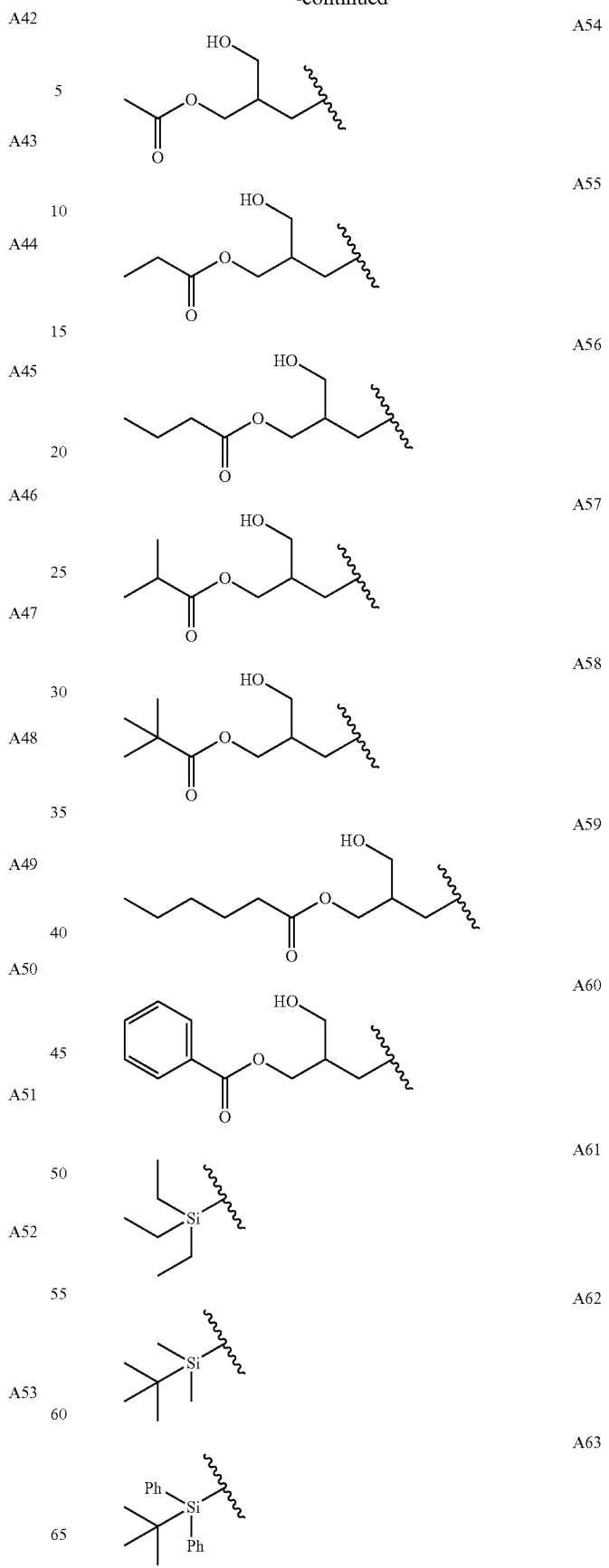

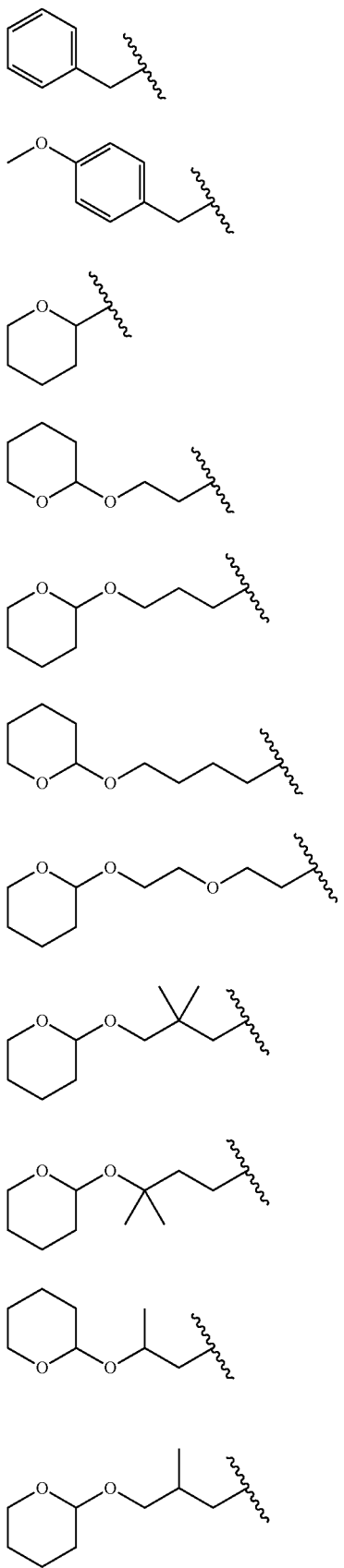
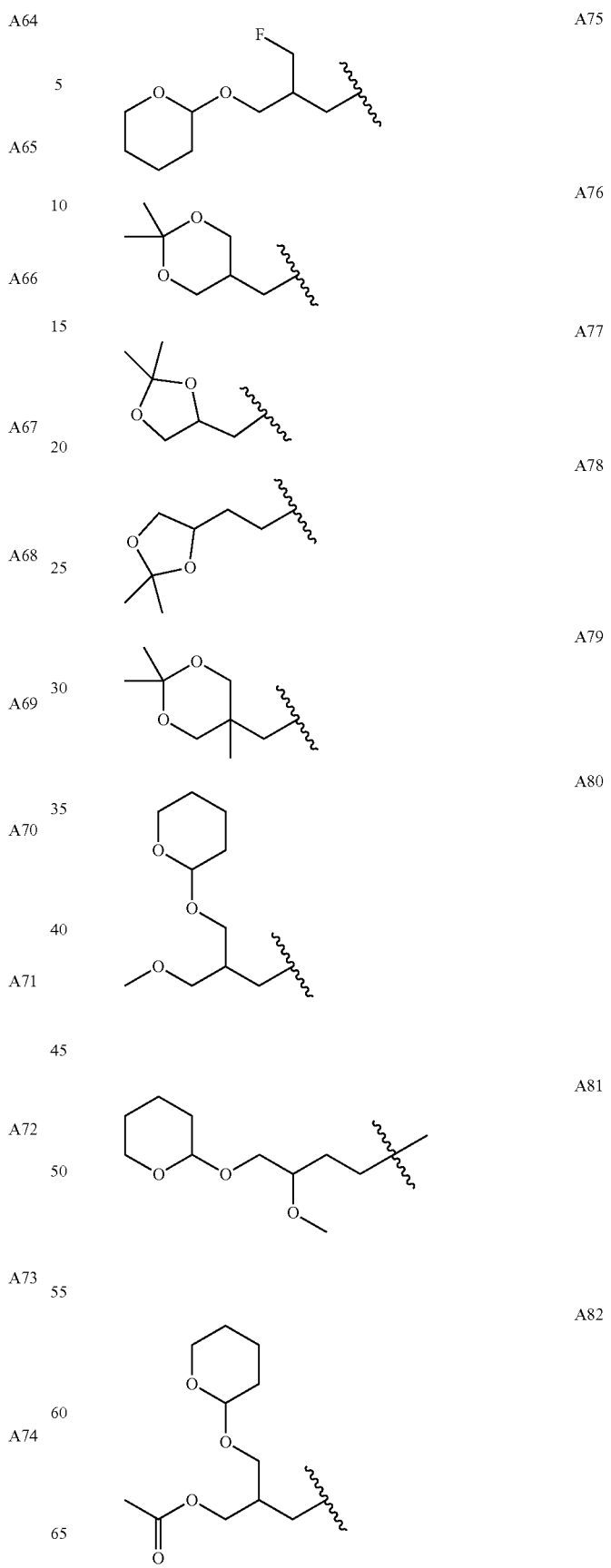

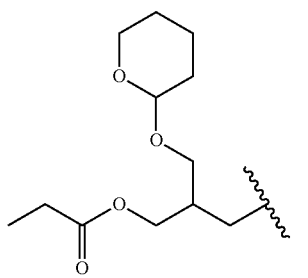
A83
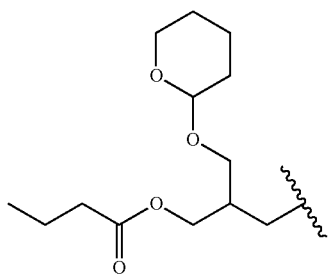
A84
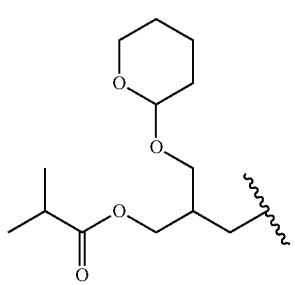
A85
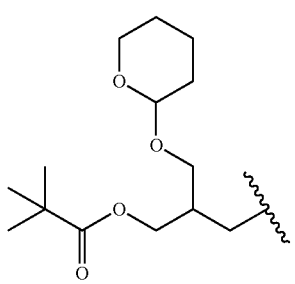
A86
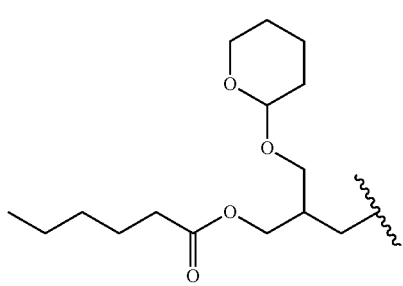
A87
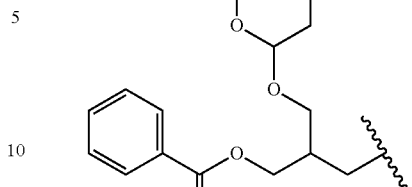
A88

A89
A90
B1
B2
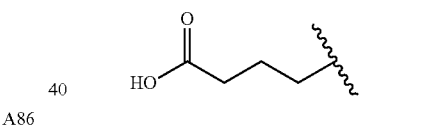
B3
B4
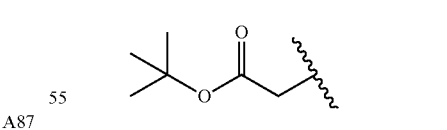
B5
B6
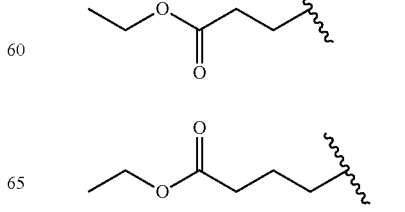
B7
B8

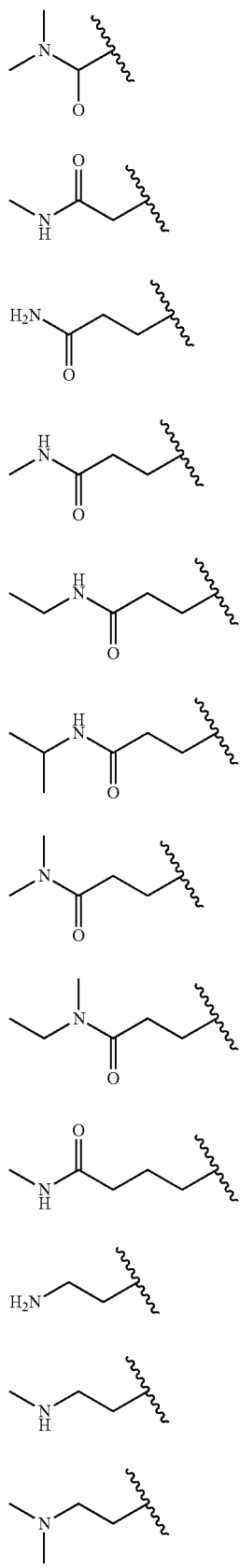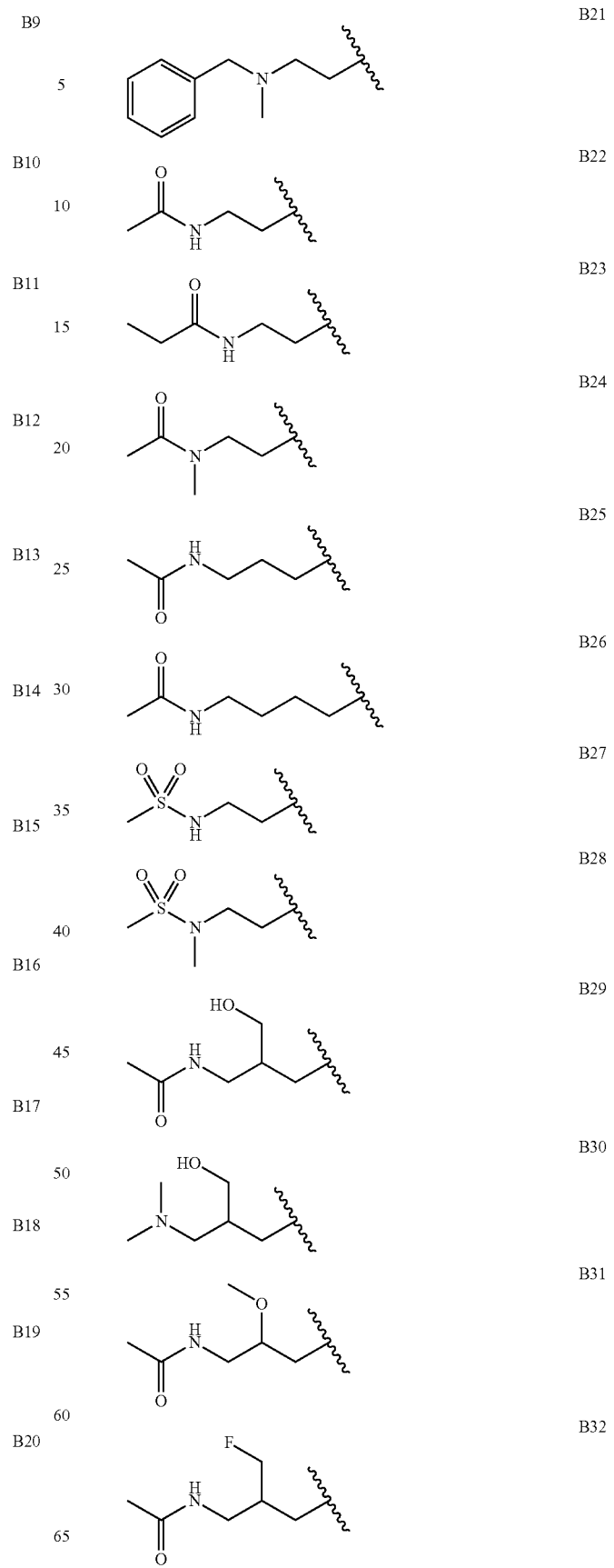

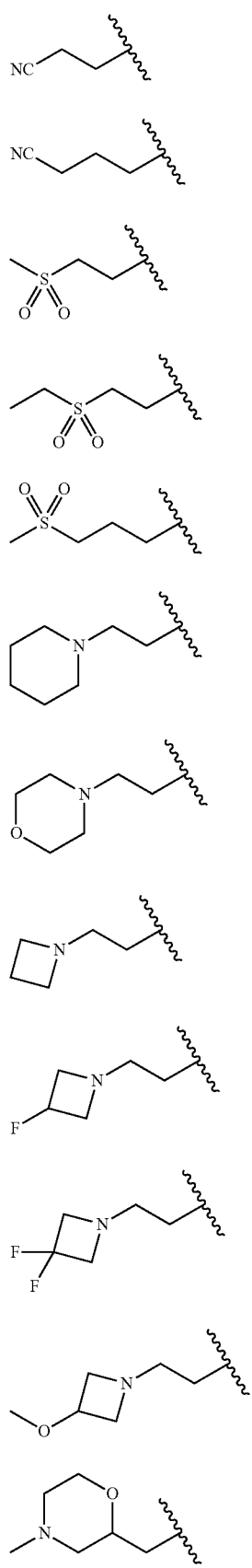
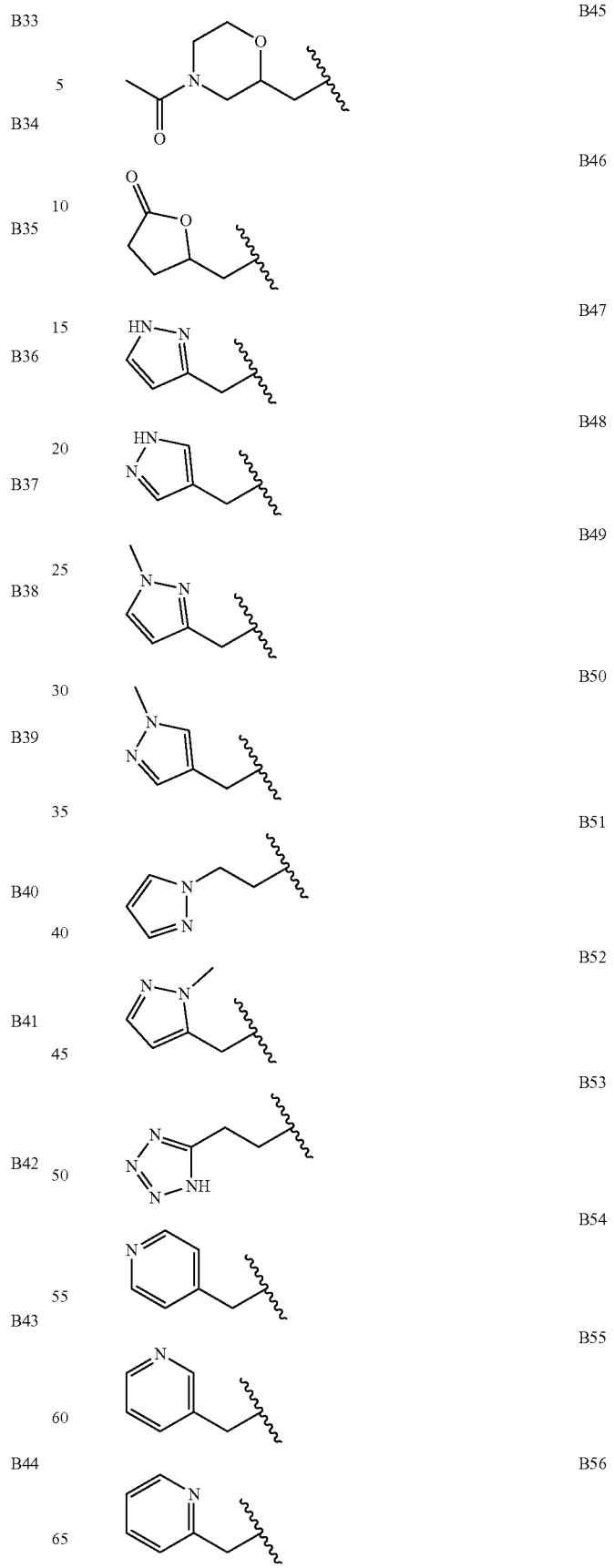

B57 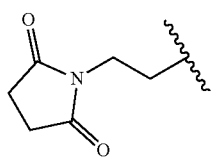
B58 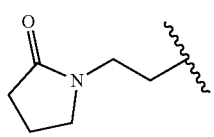
B59 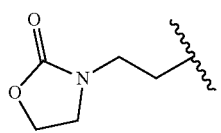
B60 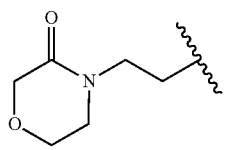
B61 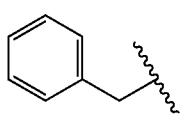
B62 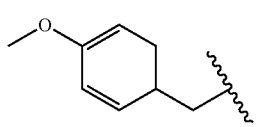
B63 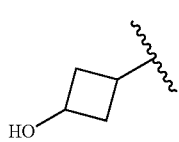
B64 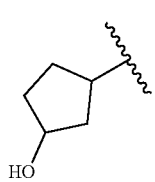
B65 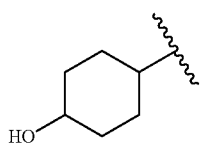
B66 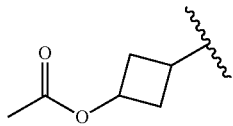
B67 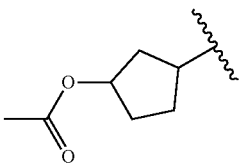
B68 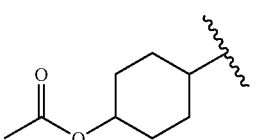
B69 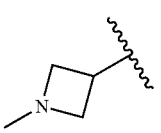
B70 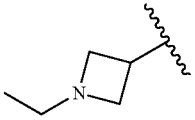
B71 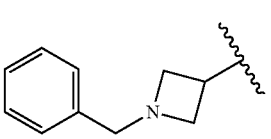
B72 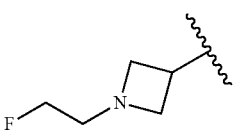
B73 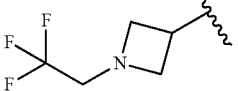
B74 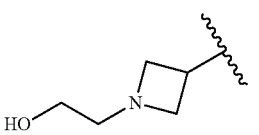
B75 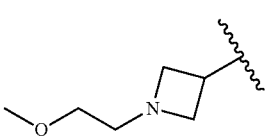
B76 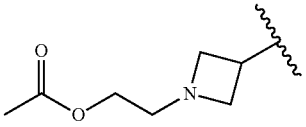
B77

B78 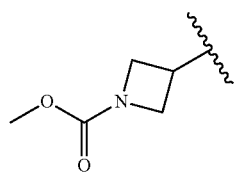
B79 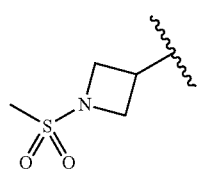
B80 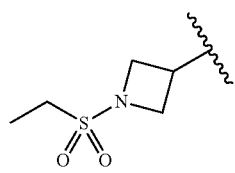
B81 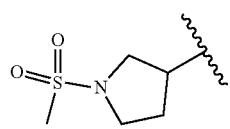
B82 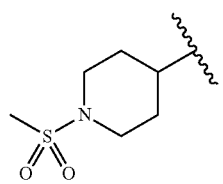
B83 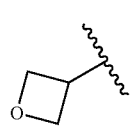
B84 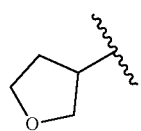
B85 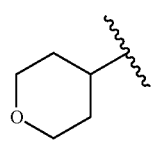
B86 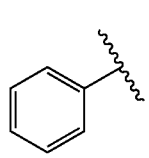
B87 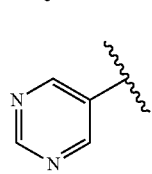
B88 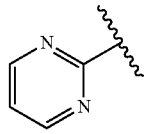
B89 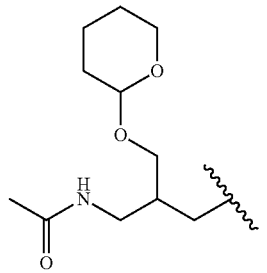
B90 
B91 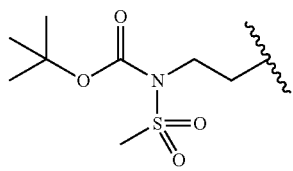
B92 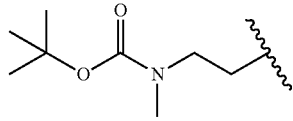
B93 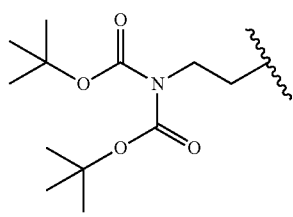
B94 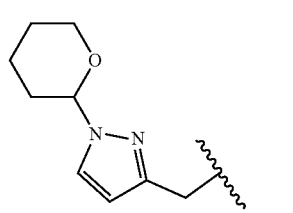
B95 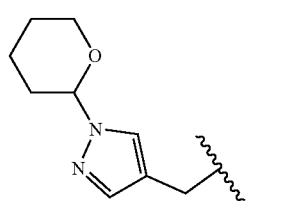

TABLE 1

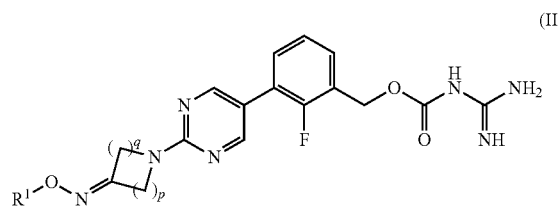

(II)

| Compound No. | R¹ | p | q |
|---|---|---|---|
| II-1 | A1 | 1 | 1 |
| II-2 | A2 | 1 | 1 |
| II-3 | A3 | 1 | 1 |
| II-4 | A4 | 1 | 1 |
| II-5 | A5 | 1 | 1 |
| II-6 | A6 | 1 | 1 |
| II-7 | A7 | 1 | 1 |
| II-8 | A8 | 1 | 1 |
| II-9 | A9 | 1 | 1 |
| II-10 | A10 | 1 | 1 |
| II-11 | A11 | 1 | 1 |
| II-12 | A12 | 1 | 1 |
| II-13 | A13 | 1 | 1 |
| II-14 | A14 | 1 | 1 |
| II-15 | A15 | 1 | 1 |
| II-16 | A16 | 1 | 1 |
| II-17 | A17 | 1 | 1 |
| II-18 | A18 | 1 | 1 |
| II-19 | A19 | 1 | 1 |
| II-20 | A20 | 1 | 1 |
| II-21 | A21 | 1 | 1 |
| II-22 | A22 | 1 | 1 |
| II-23 | A23 | 1 | 1 |
| II-24 | A24 | 1 | 1 |
| II-25 | A25 | 1 | 1 |
| II-26 | A26 | 1 | 1 |
| II-27 | A27 | 1 | 1 |
| II-28 | A28 | 1 | 1 |
| II-29 | A29 | 1 | 1 |
| II-30 | A30 | 1 | 1 |
| II-31 | A31 | 1 | 1 |
| II-32 | A32 | 1 | 1 |
| II-33 | A33 | 1 | 1 |
| II-34 | A34 | 1 | 1 |
| II-35 | A35 | 1 | 1 |
| II-36 | A36 | 1 | 1 |
| II-37 | A37 | 1 | 1 |
| II-38 | A38 | 1 | 1 |
| II-39 | A39 | 1 | 1 |
| II-40 | A40 | 1 | 1 |
| II-41 | A41 | 1 | 1 |
| II-42 | A42 | 1 | 1 |
| II-43 | A43 | 1 | 1 |
| II-44 | A44 | 1 | 1 |
| II-45 | A45 | 1 | 1 |
| II-46 | A46 | 1 | 1 |
| II-47 | A47 | 1 | 1 |
| II-48 | A48 | 1 | 1 |
| II-49 | A49 | 1 | 1 |
| II-50 | A50 | 1 | 1 |
| II-51 | A51 | 1 | 1 |
| II-52 | A52 | 1 | 1 |
| II-53 | A53 | 1 | 1 |
| II-54 | A54 | 1 | 1 |
| II-55 | A55 | 1 | 1 |

TABLE 2

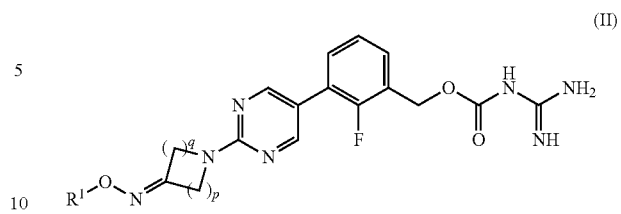

(II)

| Compound No. | R¹ | p | q |
|---|---|---|---|
| II-56 | A56 | 1 | 1 |
| II-57 | A57 | 1 | 1 |
| II-58 | A58 | 1 | 1 |
| II-59 | A59 | 1 | 1 |
| II-60 | A60 | 1 | 1 |
| II-61 | A61 | 1 | 1 |
| II-62 | A62 | 1 | 1 |
| II-63 | A63 | 1 | 1 |
| II-64 | A64 | 1 | 1 |
| II-65 | A65 | 1 | 1 |
| II-66 | A66 | 1 | 1 |
| II-67 | A67 | 1 | 1 |
| II-68 | A68 | 1 | 1 |
| II-69 | A69 | 1 | 1 |
| II-70 | A70 | 1 | 1 |
| II-71 | A71 | 1 | 1 |
| II-72 | A72 | 1 | 1 |
| II-73 | A73 | 1 | 1 |
| II-74 | A74 | 1 | 1 |
| II-75 | A75 | 1 | 1 |
| II-76 | A76 | 1 | 1 |
| II-77 | A77 | 1 | 1 |
| II-78 | A78 | 1 | 1 |
| II-79 | A79 | 1 | 1 |
| II-80 | A80 | 1 | 1 |
| II-81 | A81 | 1 | 1 |
| II-82 | A82 | 1 | 1 |
| II-83 | A83 | 1 | 1 |
| II-84 | A84 | 1 | 1 |
| II-85 | A85 | 1 | 1 |
| II-86 | A86 | 1 | 1 |
| II-87 | A87 | 1 | 1 |
| II-88 | A88 | 1 | 1 |
| II-89 | A89 | 1 | 1 |
| II-90 | A90 | 1 | 1 |
| II-91 | A1 | 2 | 1 |
| II-92 | A2 | 2 | 1 |
| II-93 | A3 | 2 | 1 |
| II-94 | A4 | 2 | 1 |
| II-95 | A5 | 2 | 1 |
| II-96 | A10 | 2 | 1 |
| II-97 | A12 | 2 | 1 |
| II-98 | A15 | 2 | 1 |
| II-99 | A18 | 2 | 1 |
| II-100 | A19 | 2 | 1 |
| II-101 | A20 | 2 | 1 |
| II-102 | A21 | 2 | 1 |
| II-103 | A22 | 2 | 1 |
| II-104 | A23 | 2 | 1 |
| II-105 | A26 | 2 | 1 |
| II-106 | A30 | 2 | 1 |
| II-107 | A31 | 2 | 1 |
| II-108 | A32 | 2 | 1 |
| II-109 | A33 | 2 | 1 |
| II-110 | A34 | 2 | 1 |

TABLE 3

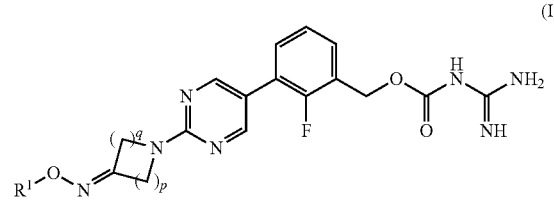
(II)

| Compound No. | R¹ | p | q |
|---|---|---|---|
| II-111 | A35 | 2 | 1 |
| II-112 | A36 | 2 | 1 |
| II-113 | A37 | 2 | 1 |
| II-114 | A38 | 2 | 1 |
| II-115 | A39 | 2 | 1 |
| II-116 | A40 | 2 | 1 |
| II-117 | A42 | 2 | 1 |
| II-118 | A43 | 2 | 1 |
| II-119 | A44 | 2 | 1 |
| II-120 | A45 | 2 | 1 |
| II-121 | A46 | 2 | 1 |
| II-122 | A47 | 2 | 1 |
| II-123 | A49 | 2 | 1 |
| II-124 | A50 | 2 | 1 |
| II-125 | A51 | 2 | 1 |
| II-126 | A52 | 2 | 1 |
| II-127 | A53 | 2 | 1 |
| II-128 | A54 | 2 | 1 |
| II-129 | A55 | 2 | 1 |
| II-130 | A56 | 2 | 1 |
| II-131 | A57 | 2 | 1 |
| II-132 | A58 | 2 | 1 |
| II-133 | A59 | 2 | 1 |
| II-134 | A60 | 2 | 1 |
| II-135 | A62 | 2 | 1 |
| II-136 | A66 | 2 | 1 |
| II-137 | A67 | 2 | 1 |
| II-138 | A68 | 2 | 1 |
| II-139 | A69 | 2 | 1 |
| II-140 | A70 | 2 | 1 |
| II-141 | A71 | 2 | 1 |
| II-142 | A72 | 2 | 1 |
| II-143 | A73 | 2 | 1 |
| II-144 | A74 | 2 | 1 |
| II-145 | A75 | 2 | 1 |
| II-146 | A76 | 2 | 1 |
| II-147 | A77 | 2 | 1 |
| II-148 | A78 | 2 | 1 |
| II-149 | A79 | 2 | 1 |
| II-150 | A80 | 2 | 1 |
| II-151 | A81 | 2 | 1 |
| II-152 | A82 | 2 | 1 |
| II-153 | A83 | 2 | 1 |
| II-154 | A84 | 2 | 1 |
| II-155 | A85 | 2 | 1 |
| II-156 | A86 | 2 | 1 |
| II-157 | A87 | 2 | 1 |
| II-158 | A88 | 2 | 1 |
| II-159 | A89 | 2 | 1 |
| II-160 | A90 | 2 | 1 |
| II-161 | A1 | 3 | 1 |
| II-162 | A2 | 3 | 1 |
| II-163 | A3 | 3 | 1 |
| II-164 | A4 | 3 | 1 |
| II-165 | A5 | 3 | 1 |

TABLE 4

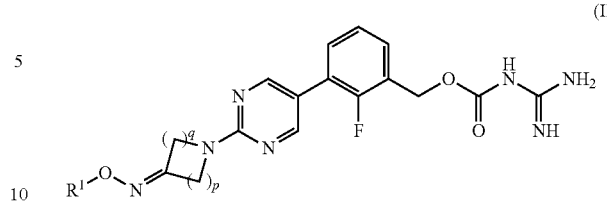
(II)

| Compound No. | R¹ | p | q |
|---|---|---|---|
| II-166 | A10 | 3 | 1 |
| II-167 | A12 | 3 | 1 |
| II-168 | A15 | 3 | 1 |
| II-169 | A18 | 3 | 1 |
| II-170 | A19 | 3 | 1 |
| II-171 | A20 | 3 | 1 |
| II-172 | A21 | 3 | 1 |
| II-173 | A22 | 3 | 1 |
| II-174 | A23 | 3 | 1 |
| II-175 | A26 | 3 | 1 |
| II-176 | A30 | 3 | 1 |
| II-177 | A31 | 3 | 1 |
| II-178 | A32 | 3 | 1 |
| II-179 | A33 | 3 | 1 |
| II-180 | A34 | 3 | 1 |
| II-181 | A35 | 3 | 1 |
| II-182 | A36 | 3 | 1 |
| II-183 | A37 | 3 | 1 |
| II-184 | A38 | 3 | 1 |
| II-185 | A39 | 3 | 1 |
| II-186 | A40 | 3 | 1 |
| II-187 | A42 | 3 | 1 |
| II-188 | A43 | 3 | 1 |
| II-189 | A44 | 3 | 1 |
| II-190 | A45 | 3 | 1 |
| II-191 | A46 | 3 | 1 |
| II-192 | A47 | 3 | 1 |
| II-193 | A49 | 3 | 1 |
| II-194 | A50 | 3 | 1 |
| II-195 | A51 | 3 | 1 |
| II-196 | A52 | 3 | 1 |
| II-197 | A53 | 3 | 1 |
| II-198 | A54 | 3 | 1 |
| II-199 | A55 | 3 | 1 |
| II-200 | A76 | 3 | 1 |
| II-201 | A77 | 3 | 1 |
| II-202 | A78 | 3 | 1 |
| II-203 | A79 | 3 | 1 |
| II-204 | A1 | 2 | 2 |
| II-205 | A2 | 2 | 2 |
| II-206 | A3 | 2 | 2 |
| II-207 | A4 | 2 | 2 |
| II-208 | A5 | 2 | 2 |
| II-209 | A10 | 2 | 2 |
| II-210 | A12 | 2 | 2 |
| II-211 | A15 | 2 | 2 |
| II-212 | A18 | 2 | 2 |
| II-213 | A19 | 2 | 2 |
| II-214 | A20 | 2 | 2 |
| II-215 | A21 | 2 | 2 |
| II-216 | A22 | 2 | 2 |
| II-217 | A23 | 2 | 2 |
| II-218 | A26 | 2 | 2 |
| II-219 | A30 | 2 | 2 |
| II-220 | A31 | 2 | 2 |

TABLE 5

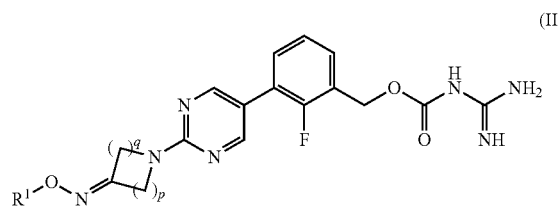
(II)

| Compound No. | R¹ | p | q |
|---|---|---|---|
| II-221 | A32 | 2 | 2 |
| II-222 | A33 | 2 | 2 |
| II-223 | A34 | 2 | 2 |
| II-224 | A35 | 2 | 2 |
| II-225 | A36 | 2 | 2 |
| II-226 | A37 | 2 | 2 |
| II-227 | A38 | 2 | 2 |
| II-228 | A39 | 2 | 2 |
| II-229 | A40 | 2 | 2 |
| II-230 | A42 | 2 | 2 |
| II-231 | A43 | 2 | 2 |
| II-232 | A44 | 2 | 2 |
| II-233 | A45 | 2 | 2 |
| II-234 | A46 | 2 | 2 |
| II-235 | A47 | 2 | 2 |
| II-236 | A49 | 2 | 2 |
| II-237 | A50 | 2 | 2 |
| II-238 | A51 | 2 | 2 |
| II-239 | A52 | 2 | 2 |
| II-240 | A53 | 2 | 2 |
| II-241 | A54 | 2 | 2 |
| II-242 | A55 | 2 | 2 |
| II-243 | A56 | 2 | 2 |
| II-244 | A57 | 2 | 2 |
| II-245 | A58 | 2 | 2 |
| II-246 | A59 | 2 | 2 |
| II-247 | A60 | 2 | 2 |
| II-248 | A62 | 2 | 2 |
| II-249 | A66 | 2 | 2 |
| II-250 | A67 | 2 | 2 |
| II-251 | A68 | 2 | 2 |
| II-252 | A69 | 2 | 2 |
| II-253 | A70 | 2 | 2 |
| II-254 | A71 | 2 | 2 |
| II-255 | A72 | 2 | 2 |
| II-256 | A73 | 2 | 2 |
| II-257 | A74 | 2 | 2 |
| II-258 | A75 | 2 | 2 |
| II-259 | A76 | 2 | 2 |
| II-260 | A77 | 2 | 2 |
| II-261 | A78 | 2 | 2 |
| II-262 | A79 | 2 | 2 |
| II-263 | A80 | 2 | 2 |
| II-264 | A81 | 2 | 2 |
| II-265 | A82 | 2 | 2 |
| II-266 | A83 | 2 | 2 |
| II-267 | A84 | 2 | 2 |
| II-268 | A85 | 2 | 2 |
| II-269 | A86 | 2 | 2 |
| II-270 | A87 | 2 | 2 |
| II-271 | A88 | 2 | 2 |
| II-272 | A89 | 2 | 2 |
| II-273 | A90 | 2 | 2 |

TABLE 6

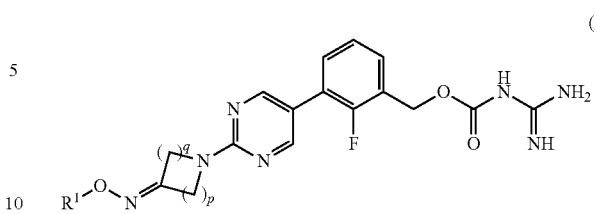
(II)

| Compound No. | R¹ | p | q |
|---|---|---|---|
| II-274 | B1 | 1 | 1 |
| II-275 | B2 | 1 | 1 |
| II-276 | B3 | 1 | 1 |
| II-277 | B4 | 1 | 1 |
| II-278 | B5 | 1 | 1 |
| II-279 | B6 | 1 | 1 |
| II-280 | B7 | 1 | 1 |
| II-281 | B8 | 1 | 1 |
| II-282 | B9 | 1 | 1 |
| II-283 | B10 | 1 | 1 |
| II-284 | B11 | 1 | 1 |
| II-285 | B12 | 1 | 1 |
| II-286 | B13 | 1 | 1 |
| II-287 | B14 | 1 | 1 |
| II-288 | B15 | 1 | 1 |
| II-289 | B16 | 1 | 1 |
| II-290 | B17 | 1 | 1 |
| II-291 | B18 | 1 | 1 |
| II-292 | B19 | 1 | 1 |
| II-293 | B20 | 1 | 1 |
| II-294 | B21 | 1 | 1 |
| II-295 | B22 | 1 | 1 |
| II-296 | B23 | 1 | 1 |
| II-297 | B24 | 1 | 1 |
| II-298 | B25 | 1 | 1 |
| II-299 | B26 | 1 | 1 |
| II-300 | B27 | 1 | 1 |
| II-301 | B28 | 1 | 1 |
| II-302 | B29 | 1 | 1 |
| II-303 | B30 | 1 | 1 |
| II-304 | B31 | 1 | 1 |
| II-305 | B32 | 1 | 1 |
| II-306 | B33 | 1 | 1 |
| II-307 | B34 | 1 | 1 |
| II-308 | B35 | 1 | 1 |
| II-309 | B36 | 1 | 1 |
| II-310 | B37 | 1 | 1 |
| II-311 | B38 | 1 | 1 |
| II-312 | B39 | 1 | 1 |
| II-313 | B40 | 1 | 1 |
| II-314 | B41 | 1 | 1 |
| II-315 | B42 | 1 | 1 |
| II-316 | B43 | 1 | 1 |
| II-317 | B44 | 1 | 1 |
| II-318 | B45 | 1 | 1 |
| II-319 | B46 | 1 | 1 |
| II-320 | B47 | 1 | 1 |
| II-321 | B48 | 1 | 1 |
| II-322 | B49 | 1 | 1 |
| II-323 | B50 | 1 | 1 |
| II-324 | B51 | 1 | 1 |
| II-325 | B52 | 1 | 1 |

TABLE 7

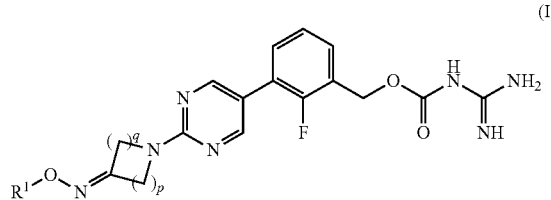

(II)

| Compound No. | R¹ | p | q |
|---|---|---|---|
| II-326 | B53 | 1 | 1 |
| II-327 | B54 | 1 | 1 |
| II-328 | B55 | 1 | 1 |
| II-329 | B56 | 1 | 1 |
| II-330 | B57 | 1 | 1 |
| II-331 | B58 | 1 | 1 |
| II-332 | B59 | 1 | 1 |
| II-333 | B60 | 1 | 1 |
| II-334 | B61 | 1 | 1 |
| II-335 | B62 | 1 | 1 |
| II-336 | B63 | 1 | 1 |
| II-337 | B64 | 1 | 1 |
| II-338 | B65 | 1 | 1 |
| II-339 | B66 | 1 | 1 |
| II-340 | B67 | 1 | 1 |
| II-341 | B68 | 1 | 1 |
| II-342 | B69 | 1 | 1 |
| II-343 | B70 | 1 | 1 |
| II-344 | B71 | 1 | 1 |
| II-345 | B72 | 1 | 1 |
| II-346 | B73 | 1 | 1 |
| II-347 | B74 | 1 | 1 |
| II-348 | B75 | 1 | 1 |
| II-349 | B76 | 1 | 1 |
| II-350 | B77 | 1 | 1 |
| II-351 | B78 | 1 | 1 |
| II-352 | B79 | 1 | 1 |
| II-353 | B80 | 1 | 1 |
| II-354 | B81 | 1 | 1 |
| II-355 | B82 | 1 | 1 |
| II-356 | B83 | 1 | 1 |
| II-357 | B84 | 1 | 1 |
| II-358 | B85 | 1 | 1 |
| II-359 | B86 | 1 | 1 |
| II-360 | B87 | 1 | 1 |
| II-361 | B88 | 1 | 1 |
| II-362 | B89 | 1 | 1 |
| II-363 | B90 | 1 | 1 |
| II-364 | B91 | 1 | 1 |
| II-365 | B92 | 1 | 1 |
| II-366 | B93 | 1 | 1 |
| II-367 | B94 | 1 | 1 |
| II-368 | B95 | 1 | 1 |
| II-369 | B1 | 2 | 1 |
| II-370 | B3 | 2 | 1 |
| II-371 | B6 | 2 | 1 |
| II-372 | B7 | 2 | 1 |
| II-373 | B8 | 2 | 1 |
| II-374 | B9 | 2 | 1 |
| II-375 | B10 | 2 | 1 |

TABLE 8

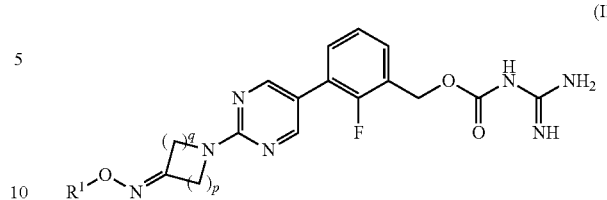

(II)

| Compound No. | R¹ | p | q |
|---|---|---|---|
| II-376 | B11 | 2 | 1 |
| II-377 | B12 | 2 | 1 |
| II-378 | B15 | 2 | 1 |
| II-379 | B17 | 2 | 1 |
| II-380 | B18 | 2 | 1 |
| II-381 | B19 | 2 | 1 |
| II-382 | B20 | 2 | 1 |
| II-383 | B21 | 2 | 1 |
| II-384 | B22 | 2 | 1 |
| II-385 | B24 | 2 | 1 |
| II-386 | B27 | 2 | 1 |
| II-387 | B28 | 2 | 1 |
| II-388 | B29 | 2 | 1 |
| II-389 | B30 | 2 | 1 |
| II-390 | B31 | 2 | 1 |
| II-391 | B33 | 2 | 1 |
| II-392 | B34 | 2 | 1 |
| II-393 | B35 | 2 | 1 |
| II-394 | B37 | 2 | 1 |
| II-395 | B38 | 2 | 1 |
| II-396 | B39 | 2 | 1 |
| II-397 | B40 | 2 | 1 |
| II-398 | B41 | 2 | 1 |
| II-399 | B42 | 2 | 1 |
| II-400 | B43 | 2 | 1 |
| II-401 | B44 | 2 | 1 |
| II-402 | B45 | 2 | 1 |
| II-403 | B46 | 2 | 1 |
| II-404 | B47 | 2 | 1 |
| II-405 | B48 | 2 | 1 |
| II-406 | B49 | 2 | 1 |
| II-407 | B50 | 2 | 1 |
| II-408 | B51 | 2 | 1 |
| II-409 | B54 | 2 | 1 |
| II-410 | B57 | 2 | 1 |
| II-411 | B58 | 2 | 1 |
| II-412 | B59 | 2 | 1 |
| II-413 | B60 | 2 | 1 |
| II-414 | B61 | 2 | 1 |
| II-415 | B62 | 2 | 1 |
| II-416 | B63 | 2 | 1 |
| II-417 | B66 | 2 | 1 |
| II-418 | B69 | 2 | 1 |
| II-419 | B70 | 2 | 1 |
| II-420 | B71 | 2 | 1 |
| II-421 | B72 | 2 | 1 |
| II-422 | B73 | 2 | 1 |
| II-423 | B74 | 2 | 1 |
| II-424 | B75 | 2 | 1 |
| II-425 | B76 | 2 | 1 |

TABLE 9

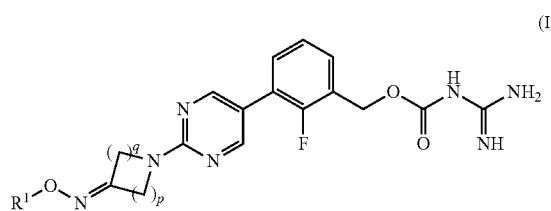

(II)

| Compound No. | R¹ | p | q |
|---|---|---|---|
| II-426 | B77 | 2 | 1 |
| II-427 | B78 | 2 | 1 |
| II-428 | B79 | 2 | 1 |
| II-429 | B83 | 2 | 1 |
| II-430 | B86 | 2 | 1 |
| II-431 | B87 | 2 | 1 |
| II-432 | B88 | 2 | 1 |
| II-433 | B89 | 2 | 1 |
| II-434 | B90 | 2 | 1 |
| II-435 | B91 | 2 | 1 |
| II-436 | B92 | 2 | 1 |
| II-437 | B93 | 2 | 1 |
| II-438 | B94 | 2 | 1 |
| II-439 | B95 | 2 | 1 |
| II-440 | B1 | 3 | 1 |
| II-441 | B3 | 3 | 1 |
| II-442 | B6 | 3 | 1 |
| II-443 | B7 | 3 | 1 |
| II-444 | B8 | 3 | 1 |
| II-445 | B9 | 3 | 1 |
| II-446 | B10 | 3 | 1 |
| II-447 | B11 | 3 | 1 |
| II-448 | B12 | 3 | 1 |
| II-449 | B15 | 3 | 1 |
| II-450 | B17 | 3 | 1 |
| II-451 | B18 | 3 | 1 |
| II-452 | B19 | 3 | 1 |
| II-453 | B20 | 3 | 1 |
| II-454 | B21 | 3 | 1 |
| II-455 | B22 | 3 | 1 |
| II-456 | B24 | 3 | 1 |
| II-457 | B27 | 3 | 1 |
| II-458 | B28 | 3 | 1 |
| II-459 | B29 | 3 | 1 |
| II-460 | B30 | 3 | 1 |
| II-461 | B31 | 3 | 1 |
| II-462 | B33 | 3 | 1 |
| II-463 | B34 | 3 | 1 |
| II-464 | B35 | 3 | 1 |
| II-465 | B37 | 3 | 1 |
| II-466 | B38 | 3 | 1 |
| II-467 | B39 | 3 | 1 |
| II-468 | B40 | 3 | 1 |
| II-469 | B41 | 3 | 1 |
| II-470 | B42 | 3 | 1 |
| II-471 | B43 | 3 | 1 |
| II-472 | B44 | 3 | 1 |
| II-473 | B45 | 3 | 1 |
| II-474 | B46 | 3 | 1 |
| II-475 | B47 | 3 | 1 |

TABLE 10

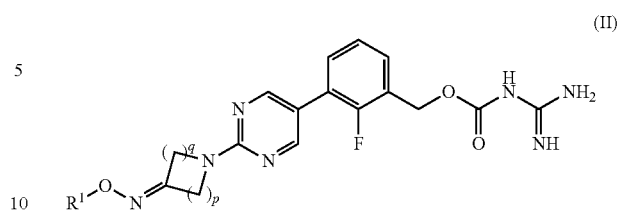

(II)

| Compound No. | R¹ | p | q |
|---|---|---|---|
| II-476 | B48 | 3 | 1 |
| II-477 | B49 | 3 | 1 |
| II-478 | B50 | 3 | 1 |
| II-479 | B51 | 3 | 1 |
| II-480 | B54 | 3 | 1 |
| II-481 | B57 | 3 | 1 |
| II-482 | B58 | 3 | 1 |
| II-483 | B59 | 3 | 1 |
| II-484 | B60 | 3 | 1 |
| II-485 | B61 | 3 | 1 |
| II-486 | B62 | 3 | 1 |
| II-487 | B63 | 3 | 1 |
| II-488 | B66 | 3 | 1 |
| II-489 | B69 | 3 | 1 |
| II-490 | B70 | 3 | 1 |
| II-491 | B71 | 3 | 1 |
| II-492 | B72 | 3 | 1 |
| II-493 | B73 | 3 | 1 |
| II-494 | B74 | 3 | 1 |
| II-495 | B75 | 3 | 1 |
| II-496 | B76 | 3 | 1 |
| II-497 | B77 | 3 | 1 |
| II-498 | B78 | 3 | 1 |
| II-499 | B79 | 3 | 1 |
| II-500 | B83 | 3 | 1 |
| II-501 | B86 | 3 | 1 |
| II-502 | B87 | 3 | 1 |
| II-503 | B88 | 3 | 1 |
| II-504 | B1 | 2 | 2 |
| II-505 | B3 | 2 | 2 |
| II-506 | B6 | 2 | 2 |
| II-507 | B7 | 2 | 2 |
| II-508 | B8 | 2 | 2 |
| II-509 | B9 | 2 | 2 |
| II-510 | B10 | 2 | 2 |
| II-511 | B11 | 2 | 2 |
| II-512 | B12 | 2 | 2 |
| II-513 | B15 | 2 | 2 |
| II-514 | B17 | 2 | 2 |
| II-515 | B18 | 2 | 2 |
| II-516 | B19 | 2 | 2 |
| II-517 | B20 | 2 | 2 |
| II-518 | B21 | 2 | 2 |
| II-519 | B22 | 2 | 2 |
| II-520 | B24 | 2 | 2 |
| II-521 | B27 | 2 | 2 |
| II-522 | B28 | 2 | 2 |
| II-523 | B29 | 2 | 2 |
| II-524 | B30 | 2 | 2 |
| II-525 | B31 | 2 | 2 |

TABLE 11

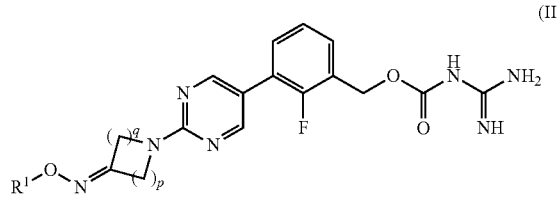
(II)

| Compound No. | R¹ | p | q |
|---|---|---|---|
| II-526 | B33 | 2 | 2 |
| II-527 | B34 | 2 | 2 |
| II-528 | B35 | 2 | 2 |
| II-529 | B37 | 2 | 2 |
| II-530 | B38 | 2 | 2 |
| II-531 | B39 | 2 | 2 |
| II-532 | B40 | 2 | 2 |
| II-533 | B41 | 2 | 2 |
| II-534 | B42 | 2 | 2 |
| II-535 | B43 | 2 | 2 |
| II-536 | B44 | 2 | 2 |
| II-537 | B45 | 2 | 2 |
| II-538 | B46 | 2 | 2 |
| II-539 | B47 | 2 | 2 |
| II-540 | B48 | 2 | 2 |
| II-541 | B49 | 2 | 2 |
| II-542 | B50 | 2 | 2 |
| II-543 | B51 | 2 | 2 |
| II-544 | B54 | 2 | 2 |
| II-545 | B57 | 2 | 2 |
| II-546 | B58 | 2 | 2 |
| II-547 | B59 | 2 | 2 |
| II-548 | B60 | 2 | 2 |
| II-549 | B61 | 2 | 2 |
| II-550 | B62 | 2 | 2 |
| II-551 | B63 | 2 | 2 |
| II-552 | B66 | 2 | 2 |
| II-553 | B69 | 2 | 2 |
| II-554 | B70 | 2 | 2 |
| II-555 | B71 | 2 | 2 |
| II-556 | B72 | 2 | 2 |
| II-557 | B73 | 2 | 2 |
| II-558 | B74 | 2 | 2 |
| II-559 | B75 | 2 | 2 |
| II-560 | B76 | 2 | 2 |
| II-561 | B77 | 2 | 2 |
| II-562 | B78 | 2 | 2 |
| II-563 | B79 | 2 | 2 |
| II-564 | B83 | 2 | 2 |
| II-565 | B86 | 2 | 2 |
| II-566 | B87 | 2 | 2 |
| II-567 | B88 | 2 | 2 |
| II-568 | B89 | 2 | 2 |
| II-569 | B90 | 2 | 2 |
| II-570 | B91 | 2 | 2 |
| II-571 | B92 | 2 | 2 |
| II-572 | B93 | 2 | 2 |
| II-573 | B94 | 2 | 2 |
| II-574 | B95 | 2 | 2 |

TABLE 12

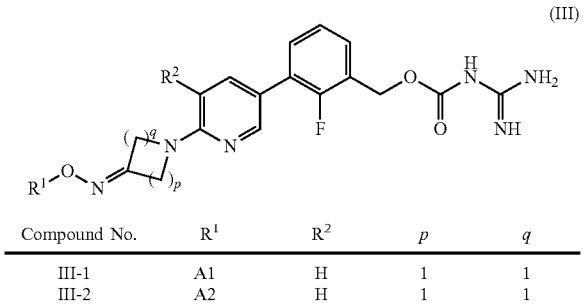
(III)

| Compound No. | R¹ | R² | p | q |
|---|---|---|---|---|
| III-1 | A1 | H | 1 | 1 |
| III-2 | A2 | H | 1 | 1 |
| III-3 | A3 | H | 1 | 1 |
| III-4 | A4 | H | 1 | 1 |
| III-5 | A5 | H | 1 | 1 |
| III-6 | A10 | H | 1 | 1 |
| III-7 | A12 | H | 1 | 1 |
| III-8 | A15 | H | 1 | 1 |
| III-9 | A18 | H | 1 | 1 |
| III-10 | A19 | H | 1 | 1 |
| III-11 | A20 | H | 1 | 1 |
| III-12 | A21 | H | 1 | 1 |
| III-13 | A22 | H | 1 | 1 |
| III-14 | A23 | H | 1 | 1 |
| III-15 | A26 | H | 1 | 1 |
| III-16 | A30 | H | 1 | 1 |
| III-17 | A31 | H | 1 | 1 |
| III-18 | A32 | H | 1 | 1 |
| III-19 | A33 | H | 1 | 1 |
| III-20 | A34 | H | 1 | 1 |
| III-21 | A35 | H | 1 | 1 |
| III-22 | A36 | H | 1 | 1 |
| III-23 | A37 | H | 1 | 1 |
| III-24 | A38 | H | 1 | 1 |
| III-25 | A39 | H | 1 | 1 |
| III-26 | A40 | H | 1 | 1 |
| III-27 | A42 | H | 1 | 1 |
| III-28 | A43 | H | 1 | 1 |
| III-29 | A44 | H | 1 | 1 |
| III-30 | A45 | H | 1 | 1 |
| III-31 | A46 | H | 1 | 1 |
| III-32 | A47 | H | 1 | 1 |
| III-33 | A49 | H | 1 | 1 |
| III-34 | A50 | H | 1 | 1 |
| III-35 | A51 | H | 1 | 1 |
| III-36 | A52 | H | 1 | 1 |
| III-37 | A53 | H | 1 | 1 |
| III-38 | A54 | H | 1 | 1 |
| III-39 | A55 | H | 1 | 1 |
| III-40 | A76 | H | 1 | 1 |
| III-41 | A77 | H | 1 | 1 |
| III-42 | A78 | H | 1 | 1 |
| III-43 | A79 | H | 1 | 1 |
| III-44 | A1 | H | 2 | 1 |
| III-45 | A2 | H | 2 | 1 |
| III-46 | A3 | H | 2 | 1 |
| III-47 | A4 | H | 2 | 1 |
| III-48 | A12 | H | 2 | 1 |
| III-49 | A15 | H | 2 | 1 |
| III-50 | A26 | H | 2 | 1 |
| III-51 | A40 | H | 2 | 1 |
| III-52 | A42 | H | 2 | 1 |
| III-53 | A43 | H | 2 | 1 |
| III-54 | A47 | H | 2 | 1 |

TABLE 13

(III)

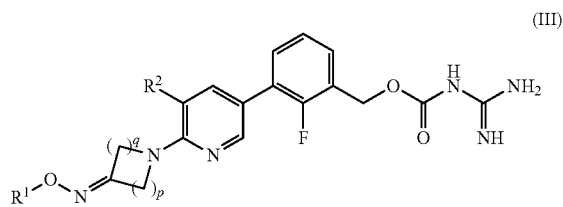

| Compound No. | R¹ | R² | p | q |
|---|---|---|---|---|
| III-55 | A1 | H | 3 | 1 |
| III-56 | A2 | H | 3 | 1 |
| III-57 | A3 | H | 3 | 1 |
| III-58 | A4 | H | 3 | 1 |
| III-59 | A12 | H | 3 | 1 |
| III-60 | A15 | H | 3 | 1 |
| III-61 | A26 | H | 3 | 1 |
| III-62 | A40 | H | 3 | 1 |
| III-63 | A42 | H | 3 | 1 |
| III-64 | A43 | H | 3 | 1 |
| III-65 | A47 | H | 3 | 1 |
| III-66 | A1 | H | 2 | 2 |
| III-67 | A2 | H | 2 | 2 |
| III-68 | A3 | H | 2 | 2 |
| III-69 | A4 | H | 2 | 2 |
| III-70 | A12 | H | 2 | 2 |
| III-71 | A15 | H | 2 | 2 |
| III-72 | A26 | H | 2 | 2 |
| III-73 | A40 | H | 2 | 2 |
| III-74 | A42 | H | 2 | 2 |
| III-75 | A43 | H | 2 | 2 |
| III-76 | A47 | H | 2 | 2 |
| III-77 | A1 | F | 1 | 1 |
| III-78 | A2 | F | 1 | 1 |
| III-79 | A3 | F | 1 | 1 |
| III-80 | A4 | F | 1 | 1 |
| III-81 | A5 | F | 1 | 1 |
| III-82 | A6 | F | 1 | 1 |
| III-83 | A7 | F | 1 | 1 |
| III-84 | A8 | F | 1 | 1 |
| III-85 | A9 | F | 1 | 1 |
| III-86 | A10 | F | 1 | 1 |
| III-87 | A11 | F | 1 | 1 |
| III-88 | A12 | F | 1 | 1 |
| III-89 | A13 | F | 1 | 1 |
| III-90 | A14 | F | 1 | 1 |
| III-91 | A15 | F | 1 | 1 |
| III-92 | A16 | F | 1 | 1 |
| III-93 | A17 | F | 1 | 1 |
| III-94 | A18 | F | 1 | 1 |
| III-95 | A19 | F | 1 | 1 |
| III-96 | A20 | F | 1 | 1 |
| III-97 | A21 | F | 1 | 1 |
| III-98 | A22 | F | 1 | 1 |
| III-99 | A23 | F | 1 | 1 |
| III-100 | A24 | F | 1 | 1 |
| III-101 | A25 | F | 1 | 1 |
| III-102 | A26 | F | 1 | 1 |
| III-103 | A27 | F | 1 | 1 |
| III-104 | A28 | F | 1 | 1 |
| III-105 | A29 | F | 1 | 1 |
| III-106 | A30 | F | 1 | 1 |
| III-107 | A31 | F | 1 | 1 |
| III-108 | A32 | F | 1 | 1 |
| III-109 | A33 | F | 1 | 1 |
| III-110 | A34 | F | 1 | 1 |

TABLE 14

(III)

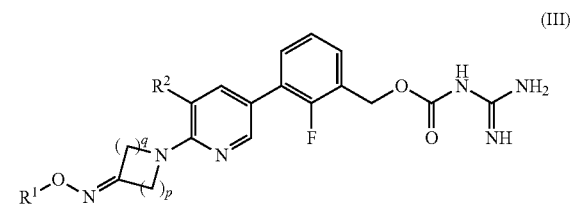

| Compound No. | R¹ | R² | p | q |
|---|---|---|---|---|
| III-111 | A35 | F | 1 | 1 |
| III-112 | A36 | F | 1 | 1 |
| III-113 | A37 | F | 1 | 1 |
| III-114 | A38 | F | 1 | 1 |
| III-115 | A39 | F | 1 | 1 |
| III-116 | A40 | F | 1 | 1 |
| III-117 | A41 | F | 1 | 1 |
| III-118 | A42 | F | 1 | 1 |
| III-119 | A43 | F | 1 | 1 |
| III-120 | A44 | F | 1 | 1 |
| III-121 | A45 | F | 1 | 1 |
| III-122 | A46 | F | 1 | 1 |
| III-123 | A47 | F | 1 | 1 |
| III-124 | A48 | F | 1 | 1 |
| III-125 | A49 | F | 1 | 1 |
| III-126 | A50 | F | 1 | 1 |
| III-127 | A51 | F | 1 | 1 |
| III-128 | A52 | F | 1 | 1 |
| III-129 | A53 | F | 1 | 1 |
| III-130 | A54 | F | 1 | 1 |
| III-131 | A55 | F | 1 | 1 |
| III-132 | A56 | F | 1 | 1 |
| III-133 | A57 | F | 1 | 1 |
| III-134 | A58 | F | 1 | 1 |
| III-135 | A59 | F | 1 | 1 |
| III-136 | A60 | F | 1 | 1 |
| III-137 | A61 | F | 1 | 1 |
| III-138 | A62 | F | 1 | 1 |
| III-139 | A63 | F | 1 | 1 |
| III-140 | A64 | F | 1 | 1 |
| III-141 | A65 | F | 1 | 1 |
| III-142 | A66 | F | 1 | 1 |
| III-143 | A67 | F | 1 | 1 |
| III-144 | A68 | F | 1 | 1 |
| III-145 | A69 | F | 1 | 1 |
| III-146 | A70 | F | 1 | 1 |
| III-147 | A71 | F | 1 | 1 |
| III-148 | A72 | F | 1 | 1 |
| III-149 | A73 | F | 1 | 1 |
| III-150 | A74 | F | 1 | 1 |
| III-151 | A75 | F | 1 | 1 |
| III-152 | A76 | F | 1 | 1 |
| III-153 | A77 | F | 1 | 1 |
| III-154 | A78 | F | 1 | 1 |
| III-155 | A79 | F | 1 | 1 |
| III-156 | A80 | F | 1 | 1 |
| III-157 | A81 | F | 1 | 1 |
| III-158 | A82 | F | 1 | 1 |
| III-159 | A83 | F | 1 | 1 |
| III-160 | A84 | F | 1 | 1 |
| III-161 | A85 | F | 1 | 1 |
| III-162 | A86 | F | 1 | 1 |
| III-163 | A87 | F | 1 | 1 |
| III-164 | A88 | F | 1 | 1 |
| III-165 | A89 | F | 1 | 1 |
| III-166 | A90 | F | 1 | 1 |

TABLE 15

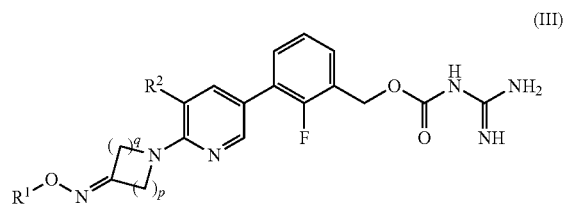
(III)

| Compound No. | R¹ | R² | p | q |
|---|---|---|---|---|
| III-167 | A1 | F | 2 | 1 |
| III-168 | A2 | F | 2 | 1 |
| III-169 | A3 | F | 2 | 1 |
| III-170 | A4 | F | 2 | 1 |
| III-171 | A5 | F | 2 | 1 |
| III-172 | A10 | F | 2 | 1 |
| III-173 | A12 | F | 2 | 1 |
| III-174 | A15 | F | 2 | 1 |
| III-175 | A18 | F | 2 | 1 |
| III-176 | A19 | F | 2 | 1 |
| III-177 | A20 | F | 2 | 1 |
| III-178 | A21 | F | 2 | 1 |
| III-179 | A22 | F | 2 | 1 |
| III-180 | A23 | F | 2 | 1 |
| III-181 | A26 | F | 2 | 1 |
| III-182 | A30 | F | 2 | 1 |
| III-183 | A31 | F | 2 | 1 |
| III-184 | A32 | F | 2 | 1 |
| III-185 | A33 | F | 2 | 1 |
| III-186 | A34 | F | 2 | 1 |
| III-187 | A35 | F | 2 | 1 |
| III-188 | A36 | F | 2 | 1 |
| III-189 | A37 | F | 2 | 1 |
| III-190 | A38 | F | 2 | 1 |
| III-191 | A39 | F | 2 | 1 |
| III-192 | A40 | F | 2 | 1 |
| III-193 | A42 | F | 2 | 1 |
| III-194 | A43 | F | 2 | 1 |
| III-195 | A44 | F | 2 | 1 |
| III-196 | A45 | F | 2 | 1 |
| III-197 | A46 | F | 2 | 1 |
| III-198 | A47 | F | 2 | 1 |
| III-199 | A49 | F | 2 | 1 |
| III-200 | A50 | F | 2 | 1 |
| III-201 | A51 | F | 2 | 1 |
| III-202 | A52 | F | 2 | 1 |
| III-203 | A53 | F | 2 | 1 |
| III-204 | A54 | F | 2 | 1 |
| III-205 | A55 | F | 2 | 1 |
| III-206 | A56 | F | 2 | 1 |
| III-207 | A57 | F | 2 | 1 |
| III-208 | A58 | F | 2 | 1 |
| III-209 | A59 | F | 2 | 1 |
| III-210 | A60 | F | 2 | 1 |
| III-211 | A62 | F | 2 | 1 |
| III-212 | A66 | F | 2 | 1 |
| III-213 | A67 | F | 2 | 1 |
| III-214 | A68 | F | 2 | 1 |
| III-215 | A69 | F | 2 | 1 |
| III-216 | A70 | F | 2 | 1 |
| III-217 | A71 | F | 2 | 1 |
| III-218 | A72 | F | 2 | 1 |
| III-219 | A73 | F | 2 | 1 |
| III-220 | A74 | F | 2 | 1 |
| III-221 | A75 | F | 2 | 1 |
| III-222 | A76 | F | 2 | 1 |

TABLE 16

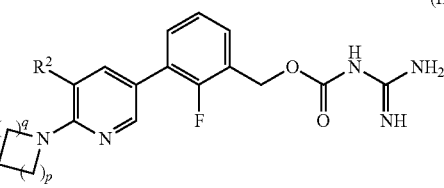
(III)

| Compound No. | R¹ | R² | p | q |
|---|---|---|---|---|
| III-223 | A77 | F | 2 | 1 |
| III-224 | A78 | F | 2 | 1 |
| III-225 | A79 | F | 2 | 1 |
| III-226 | A80 | F | 2 | 1 |
| III-227 | A81 | F | 2 | 1 |
| III-228 | A82 | F | 2 | 1 |
| III-229 | A83 | F | 2 | 1 |
| III-230 | A84 | F | 2 | 1 |
| III-231 | A85 | F | 2 | 1 |
| III-232 | A86 | F | 2 | 1 |
| III-233 | A87 | F | 2 | 1 |
| III-234 | A88 | F | 2 | 1 |
| III-235 | A89 | F | 2 | 1 |
| III-236 | A90 | F | 2 | 1 |
| III-237 | A1 | F | 3 | 1 |
| III-238 | A2 | F | 3 | 1 |
| III-239 | A3 | F | 3 | 1 |
| III-240 | A4 | F | 3 | 1 |
| III-241 | A5 | F | 3 | 1 |
| III-242 | A10 | F | 3 | 1 |
| III-243 | A12 | F | 3 | 1 |
| III-244 | A15 | F | 3 | 1 |
| III-245 | A18 | F | 3 | 1 |
| III-246 | A19 | F | 3 | 1 |
| III-247 | A20 | F | 3 | 1 |
| III-248 | A21 | F | 3 | 1 |
| III-249 | A22 | F | 3 | 1 |
| III-250 | A23 | F | 3 | 1 |
| III-251 | A26 | F | 3 | 1 |
| III-252 | A30 | F | 3 | 1 |
| III-253 | A31 | F | 3 | 1 |
| III-254 | A32 | F | 3 | 1 |
| III-255 | A33 | F | 3 | 1 |
| III-256 | A34 | F | 3 | 1 |
| III-257 | A35 | F | 3 | 1 |
| III-258 | A36 | F | 3 | 1 |
| III-259 | A37 | F | 3 | 1 |
| III-260 | A38 | F | 3 | 1 |
| III-261 | A39 | F | 3 | 1 |
| III-262 | A40 | F | 3 | 1 |
| III-263 | A42 | F | 3 | 1 |
| III-264 | A43 | F | 3 | 1 |
| III-265 | A44 | F | 3 | 1 |
| III-266 | A45 | F | 3 | 1 |
| III-267 | A46 | F | 3 | 1 |
| III-268 | A47 | F | 3 | 1 |
| III-269 | A49 | F | 3 | 1 |
| III-270 | A50 | F | 3 | 1 |
| III-271 | A51 | F | 3 | 1 |
| III-272 | A52 | F | 3 | 1 |
| III-273 | A53 | F | 3 | 1 |
| III-274 | A54 | F | 3 | 1 |
| III-275 | A55 | F | 3 | 1 |
| III-276 | A76 | F | 3 | 1 |
| III-277 | A77 | F | 3 | 1 |
| III-278 | A78 | F | 3 | 1 |
| III-279 | A79 | F | 3 | 1 |

TABLE 17

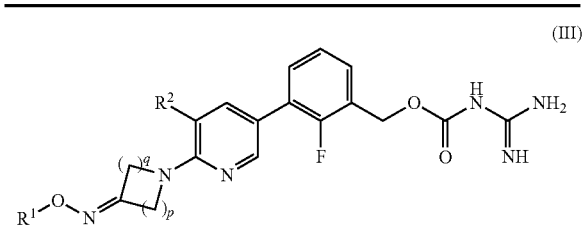
(III)

| Compound No. | R¹ | R² | p | q |
|---|---|---|---|---|
| III-280 | A1 | F | 2 | 2 |
| III-281 | A2 | F | 2 | 2 |
| III-282 | A3 | F | 2 | 2 |
| III-283 | A4 | F | 2 | 2 |
| III-284 | A5 | F | 2 | 2 |
| III-285 | A10 | F | 2 | 2 |
| III-286 | A12 | F | 2 | 2 |
| III-287 | A15 | F | 2 | 2 |
| III-288 | A18 | F | 2 | 2 |
| III-289 | A19 | F | 2 | 2 |
| III-290 | A20 | F | 2 | 2 |
| III-291 | A21 | F | 2 | 2 |
| III-292 | A22 | F | 2 | 2 |
| III-293 | A23 | F | 2 | 2 |
| III-294 | A26 | F | 2 | 2 |
| III-295 | A30 | F | 2 | 2 |
| III-296 | A31 | F | 2 | 2 |
| III-297 | A32 | F | 2 | 2 |
| III-298 | A33 | F | 2 | 2 |
| III-299 | A34 | F | 2 | 2 |
| III-300 | A35 | F | 2 | 2 |
| III-301 | A36 | F | 2 | 2 |
| III-302 | A37 | F | 2 | 2 |
| III-303 | A38 | F | 2 | 2 |
| III-304 | A39 | F | 2 | 2 |
| III-305 | A40 | F | 2 | 2 |
| III-306 | A42 | F | 2 | 2 |
| III-307 | A43 | F | 2 | 2 |
| III-308 | A44 | F | 2 | 2 |
| III-309 | A45 | F | 2 | 2 |
| III-310 | A46 | F | 2 | 2 |
| III-311 | A47 | F | 2 | 2 |
| III-312 | A49 | F | 2 | 2 |
| III-313 | A50 | F | 2 | 2 |
| III-314 | A51 | F | 2 | 2 |
| III-315 | A52 | F | 2 | 2 |
| III-316 | A53 | F | 2 | 2 |
| III-317 | A54 | F | 2 | 2 |
| III-318 | A55 | F | 2 | 2 |
| III-319 | A76 | F | 2 | 2 |
| III-320 | A77 | F | 2 | 2 |
| III-321 | A78 | F | 2 | 2 |
| III-322 | A79 | F | 2 | 2 |
| III-323 | A1 | Cl | 1 | 1 |
| III-324 | A2 | Cl | 1 | 1 |
| III-325 | A3 | Cl | 1 | 1 |
| III-326 | A4 | Cl | 1 | 1 |
| III-327 | A5 | Cl | 1 | 1 |
| III-328 | A6 | Cl | 1 | 1 |
| III-329 | A7 | Cl | 1 | 1 |
| III-330 | A8 | Cl | 1 | 1 |
| III-331 | A9 | Cl | 1 | 1 |
| III-332 | A10 | Cl | 1 | 1 |

TABLE 18

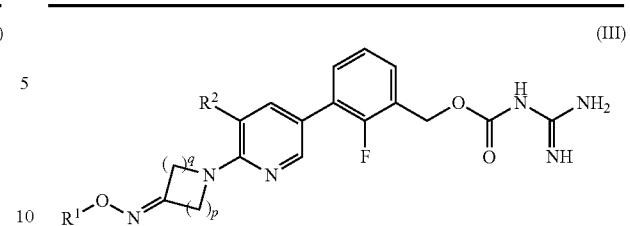
(III)

| Compound No. | R¹ | R² | p | q |
|---|---|---|---|---|
| III-333 | A11 | Cl | 1 | 1 |
| III-334 | A12 | Cl | 1 | 1 |
| III-335 | A13 | Cl | 1 | 1 |
| III-336 | A14 | Cl | 1 | 1 |
| III-337 | A15 | Cl | 1 | 1 |
| III-338 | A16 | Cl | 1 | 1 |
| III-339 | A17 | Cl | 1 | 1 |
| III-340 | A18 | Cl | 1 | 1 |
| III-341 | A19 | Cl | 1 | 1 |
| III-342 | A20 | Cl | 1 | 1 |
| III-343 | A21 | Cl | 1 | 1 |
| III-344 | A22 | Cl | 1 | 1 |
| III-345 | A23 | Cl | 1 | 1 |
| III-346 | A24 | Cl | 1 | 1 |
| III-347 | A25 | Cl | 1 | 1 |
| III-348 | A26 | Cl | 1 | 1 |
| III-349 | A27 | Cl | 1 | 1 |
| III-350 | A28 | Cl | 1 | 1 |
| III-351 | A29 | Cl | 1 | 1 |
| III-352 | A30 | Cl | 1 | 1 |
| III-353 | A31 | Cl | 1 | 1 |
| III-354 | A32 | Cl | 1 | 1 |
| III-355 | A33 | Cl | 1 | 1 |
| III-356 | A34 | Cl | 1 | 1 |
| III-357 | A35 | Cl | 1 | 1 |
| III-358 | A36 | Cl | 1 | 1 |
| III-359 | A37 | Cl | 1 | 1 |
| III-360 | A38 | Cl | 1 | 1 |
| III-361 | A39 | Cl | 1 | 1 |
| III-362 | A40 | Cl | 1 | 1 |
| III-363 | A41 | Cl | 1 | 1 |
| III-364 | A42 | Cl | 1 | 1 |
| III-365 | A43 | Cl | 1 | 1 |
| III-366 | A44 | Cl | 1 | 1 |
| III-367 | A45 | Cl | 1 | 1 |
| III-368 | A46 | Cl | 1 | 1 |
| III-369 | A47 | Cl | 1 | 1 |
| III-370 | A48 | Cl | 1 | 1 |
| III-371 | A49 | Cl | 1 | 1 |
| III-372 | A50 | Cl | 1 | 1 |
| III-373 | A51 | Cl | 1 | 1 |
| III-374 | A52 | Cl | 1 | 1 |
| III-375 | A53 | Cl | 1 | 1 |
| III-376 | A54 | Cl | 1 | 1 |
| III-377 | A55 | Cl | 1 | 1 |
| III-378 | A56 | Cl | 1 | 1 |
| III-379 | A57 | Cl | 1 | 1 |
| III-380 | A58 | Cl | 1 | 1 |
| III-381 | A59 | Cl | 1 | 1 |
| III-382 | A60 | Cl | 1 | 1 |
| III-383 | A61 | Cl | 1 | 1 |
| III-384 | A62 | Cl | 1 | 1 |
| III-385 | A63 | Cl | 1 | 1 |

TABLE 19

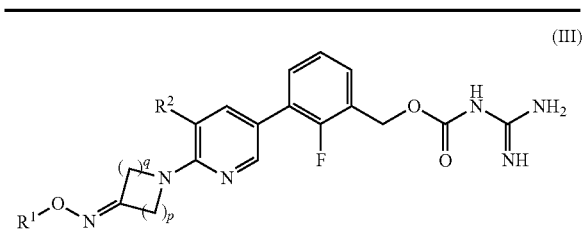

(III)

| Compound No. | R¹ | R² | p | q |
|---|---|---|---|---|
| III-386 | A64 | Cl | 1 | 1 |
| III-387 | A65 | Cl | 1 | 1 |
| III-388 | A66 | Cl | 1 | 1 |
| III-389 | A67 | Cl | 1 | 1 |
| III-390 | A68 | Cl | 1 | 1 |
| III-391 | A69 | Cl | 1 | 1 |
| III-392 | A70 | Cl | 1 | 1 |
| III-393 | A71 | Cl | 1 | 1 |
| III-394 | A72 | Cl | 1 | 1 |
| III-395 | A73 | Cl | 1 | 1 |
| III-396 | A74 | Cl | 1 | 1 |
| III-397 | A75 | Cl | 1 | 1 |
| III-398 | A76 | Cl | 1 | 1 |
| III-399 | A77 | Cl | 1 | 1 |
| III-400 | A78 | Cl | 1 | 1 |
| III-401 | A79 | Cl | 1 | 1 |
| III-402 | A80 | Cl | 1 | 1 |
| III-403 | A81 | Cl | 1 | 1 |
| III-404 | A82 | Cl | 1 | 1 |
| III-405 | A83 | Cl | 1 | 1 |
| III-406 | A84 | Cl | 1 | 1 |
| III-407 | A85 | Cl | 1 | 1 |
| III-408 | A86 | Cl | 1 | 1 |
| III-409 | A87 | Cl | 1 | 1 |
| III-410 | A88 | Cl | 1 | 1 |
| III-411 | A89 | Cl | 1 | 1 |
| III-412 | A90 | Cl | 1 | 1 |
| III-413 | A1 | Cl | 2 | 1 |
| III-414 | A2 | Cl | 2 | 1 |
| III-415 | A3 | Cl | 2 | 1 |
| III-416 | A4 | Cl | 2 | 1 |
| III-417 | A5 | Cl | 2 | 1 |
| III-418 | A10 | Cl | 2 | 1 |
| III-419 | A12 | Cl | 2 | 1 |
| III-420 | A15 | Cl | 2 | 1 |
| III-421 | A18 | Cl | 2 | 1 |
| III-422 | A19 | Cl | 2 | 1 |
| III-423 | A20 | Cl | 2 | 1 |
| III-424 | A21 | Cl | 2 | 1 |
| III-425 | A22 | Cl | 2 | 1 |
| III-426 | A23 | Cl | 2 | 1 |
| III-427 | A26 | Cl | 2 | 1 |
| III-428 | A30 | Cl | 2 | 1 |
| III-429 | A31 | Cl | 2 | 1 |
| III-430 | A32 | Cl | 2 | 1 |
| III-431 | A33 | Cl | 2 | 1 |
| III-432 | A34 | Cl | 2 | 1 |
| III-433 | A35 | Cl | 2 | 1 |
| III-434 | A36 | Cl | 2 | 1 |
| III-435 | A37 | Cl | 2 | 1 |
| III-436 | A38 | Cl | 2 | 1 |
| III-437 | A39 | Cl | 2 | 1 |
| III-438 | A40 | Cl | 2 | 1 |
| III-439 | A42 | Cl | 2 | 1 |
| III-440 | A43 | Cl | 2 | 1 |

TABLE 20

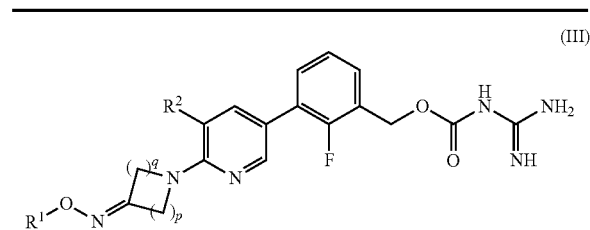

(III)

| Compound No. | R¹ | R² | p | q |
|---|---|---|---|---|
| III-441 | A44 | Cl | 2 | 1 |
| III-442 | A45 | Cl | 2 | 1 |
| III-443 | A46 | Cl | 2 | 1 |
| III-444 | A47 | Cl | 2 | 1 |
| III-445 | A49 | Cl | 2 | 1 |
| III-446 | A50 | Cl | 2 | 1 |
| III-447 | A51 | Cl | 2 | 1 |
| III-448 | A52 | Cl | 2 | 1 |
| III-449 | A53 | Cl | 2 | 1 |
| III-450 | A54 | Cl | 2 | 1 |
| III-451 | A55 | Cl | 2 | 1 |
| III-452 | A56 | Cl | 2 | 1 |
| III-453 | A57 | Cl | 2 | 1 |
| III-454 | A58 | Cl | 2 | 1 |
| III-455 | A59 | Cl | 2 | 1 |
| III-456 | A60 | Cl | 2 | 1 |
| III-457 | A62 | Cl | 2 | 1 |
| III-458 | A66 | Cl | 2 | 1 |
| III-459 | A67 | Cl | 2 | 1 |
| III-460 | A68 | Cl | 2 | 1 |
| III-461 | A69 | Cl | 2 | 1 |
| III-462 | A70 | Cl | 2 | 1 |
| III-463 | A71 | Cl | 2 | 1 |
| III-464 | A72 | Cl | 2 | 1 |
| III-465 | A73 | Cl | 2 | 1 |
| III-466 | A74 | Cl | 2 | 1 |
| III-467 | A75 | Cl | 2 | 1 |
| III-468 | A76 | Cl | 2 | 1 |
| III-469 | A77 | Cl | 2 | 1 |
| III-470 | A78 | Cl | 2 | 1 |
| III-471 | A79 | Cl | 2 | 1 |
| III-472 | A80 | Cl | 2 | 1 |
| III-473 | A81 | Cl | 2 | 1 |
| III-474 | A82 | Cl | 2 | 1 |
| III-475 | A83 | Cl | 2 | 1 |
| III-476 | A84 | Cl | 2 | 1 |
| III-477 | A85 | Cl | 2 | 1 |
| III-478 | A86 | Cl | 2 | 1 |
| III-479 | A87 | Cl | 2 | 1 |
| III-480 | A88 | Cl | 2 | 1 |
| III-481 | A89 | Cl | 2 | 1 |
| III-482 | A90 | Cl | 2 | 1 |
| III-483 | A1 | Cl | 3 | 1 |
| III-484 | A2 | Cl | 3 | 1 |
| III-485 | A3 | Cl | 3 | 1 |
| III-486 | A4 | Cl | 3 | 1 |
| III-487 | A5 | Cl | 3 | 1 |
| III-488 | A10 | Cl | 3 | 1 |
| III-489 | A12 | Cl | 3 | 1 |
| III-490 | A15 | Cl | 3 | 1 |
| III-491 | A18 | Cl | 3 | 1 |
| III-492 | A19 | Cl | 3 | 1 |
| III-493 | A20 | Cl | 3 | 1 |
| III-494 | A21 | Cl | 3 | 1 |
| III-495 | A22 | Cl | 3 | 1 |

TABLE 21

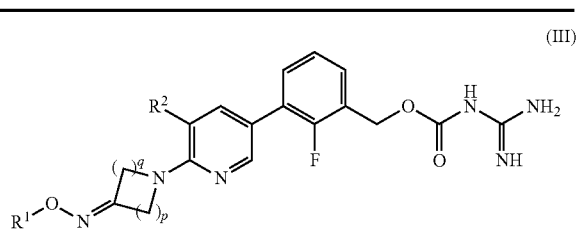

(III)

| Compound No. | R¹ | R² | p | q |
|---|---|---|---|---|
| III-496 | A23 | Cl | 3 | 1 |
| III-497 | A26 | Cl | 3 | 1 |
| III-498 | A30 | Cl | 3 | 1 |
| III-499 | A31 | Cl | 3 | 1 |
| III-500 | A32 | Cl | 3 | 1 |
| III-501 | A33 | Cl | 3 | 1 |
| III-502 | A34 | Cl | 3 | 1 |
| III-503 | A35 | Cl | 3 | 1 |
| III-504 | A36 | Cl | 3 | 1 |
| III-505 | A37 | Cl | 3 | 1 |
| III-506 | A38 | Cl | 3 | 1 |
| III-507 | A39 | Cl | 3 | 1 |
| III-508 | A40 | Cl | 3 | 1 |
| III-509 | A42 | Cl | 3 | 1 |
| III-510 | A43 | Cl | 3 | 1 |
| III-511 | A44 | Cl | 3 | 1 |
| III-512 | A45 | Cl | 3 | 1 |
| III-513 | A46 | Cl | 3 | 1 |
| III-514 | A47 | Cl | 3 | 1 |
| III-515 | A49 | Cl | 3 | 1 |
| III-516 | A50 | Cl | 3 | 1 |
| III-517 | A51 | Cl | 3 | 1 |
| III-518 | A52 | Cl | 3 | 1 |
| III-519 | A53 | Cl | 3 | 1 |
| III-520 | A54 | Cl | 3 | 1 |
| III-521 | A55 | Cl | 3 | 1 |
| III-522 | A76 | Cl | 3 | 1 |
| III-523 | A77 | Cl | 3 | 1 |
| III-524 | A78 | Cl | 3 | 1 |
| III-525 | A79 | Cl | 3 | 1 |
| III-526 | A1 | Cl | 2 | 2 |
| III-527 | A2 | Cl | 2 | 2 |
| III-528 | A3 | Cl | 2 | 2 |
| III-529 | A4 | Cl | 2 | 2 |
| III-530 | A5 | Cl | 2 | 2 |
| III-531 | A10 | Cl | 2 | 2 |
| III-532 | A12 | Cl | 2 | 2 |
| III-533 | A15 | Cl | 2 | 2 |
| III-534 | A18 | Cl | 2 | 2 |
| III-535 | A19 | Cl | 2 | 2 |
| III-536 | A20 | Cl | 2 | 2 |
| III-537 | A21 | Cl | 2 | 2 |
| III-538 | A22 | Cl | 2 | 2 |
| III-539 | A23 | Cl | 2 | 2 |
| III-540 | A26 | Cl | 2 | 2 |
| III-541 | A30 | Cl | 2 | 2 |
| III-542 | A31 | Cl | 2 | 2 |
| III-543 | A32 | Cl | 2 | 2 |
| III-544 | A33 | Cl | 2 | 2 |
| III-545 | A34 | Cl | 2 | 2 |
| III-546 | A35 | Cl | 2 | 2 |
| III-547 | A36 | Cl | 2 | 2 |
| III-548 | A37 | Cl | 2 | 2 |
| III-549 | A38 | Cl | 2 | 2 |
| III-550 | A39 | Cl | 2 | 2 |

TABLE 22

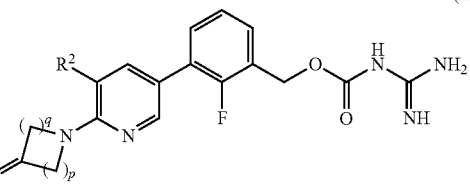

(III)

| Compound No. | R¹ | R² | p | q |
|---|---|---|---|---|
| III-551 | A40 | Cl | 2 | 2 |
| III-552 | A42 | Cl | 2 | 2 |
| III-553 | A43 | Cl | 2 | 2 |
| III-554 | A44 | Cl | 2 | 2 |
| III-555 | A45 | Cl | 2 | 2 |
| III-556 | A46 | Cl | 2 | 2 |
| III-557 | A47 | Cl | 2 | 2 |
| III-558 | A49 | Cl | 2 | 2 |
| III-559 | A50 | Cl | 2 | 2 |
| III-560 | A51 | Cl | 2 | 2 |
| III-561 | A52 | Cl | 2 | 2 |
| III-562 | A53 | Cl | 2 | 2 |
| III-563 | A54 | Cl | 2 | 2 |
| III-564 | A55 | Cl | 2 | 2 |
| III-565 | A76 | Cl | 2 | 2 |
| III-566 | A77 | Cl | 2 | 2 |
| III-567 | A78 | Cl | 2 | 2 |
| III-568 | A79 | Cl | 2 | 2 |
| III-569 | A1 | Br | 1 | 1 |
| III-570 | A2 | Br | 1 | 1 |
| III-571 | A3 | Br | 1 | 1 |
| III-572 | A4 | Br | 1 | 1 |
| III-573 | A5 | Br | 1 | 1 |
| III-574 | A10 | Br | 1 | 1 |
| III-575 | A12 | Br | 1 | 1 |
| III-576 | A15 | Br | 1 | 1 |
| III-577 | A18 | Br | 1 | 1 |
| III-578 | A19 | Br | 1 | 1 |
| III-579 | A20 | Br | 1 | 1 |
| III-580 | A21 | Br | 1 | 1 |
| III-581 | A22 | Br | 1 | 1 |
| III-582 | A23 | Br | 1 | 1 |
| III-583 | A26 | Br | 1 | 1 |
| III-584 | A30 | Br | 1 | 1 |
| III-585 | A31 | Br | 1 | 1 |
| III-586 | A32 | Br | 1 | 1 |
| III-587 | A33 | Br | 1 | 1 |
| III-588 | A34 | Br | 1 | 1 |
| III-589 | A35 | Br | 1 | 1 |
| III-590 | A36 | Br | 1 | 1 |
| III-591 | A37 | Br | 1 | 1 |
| III-592 | A38 | Br | 1 | 1 |
| III-593 | A39 | Br | 1 | 1 |
| III-594 | A40 | Br | 1 | 1 |
| III-595 | A42 | Br | 1 | 1 |
| III-596 | A43 | Br | 1 | 1 |
| III-597 | A44 | Br | 1 | 1 |
| III-598 | A45 | Br | 1 | 1 |
| III-599 | A46 | Br | 1 | 1 |
| III-600 | A47 | Br | 1 | 1 |
| III-601 | A49 | Br | 1 | 1 |
| III-602 | A50 | Br | 1 | 1 |
| III-603 | A51 | Br | 1 | 1 |
| III-604 | A52 | Br | 1 | 1 |
| III-605 | A53 | Br | 1 | 1 |

TABLE 23

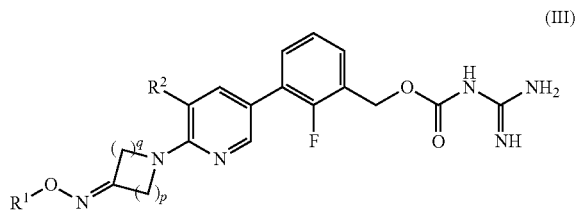

(III)

| Compound No. | R¹ | R² | p | q |
|---|---|---|---|---|
| III-606 | A54 | Br | 1 | 1 |
| III-607 | A55 | Br | 1 | 1 |
| III-608 | A56 | Br | 1 | 1 |
| III-609 | A57 | Br | 1 | 1 |
| III-610 | A58 | Br | 1 | 1 |
| III-611 | A59 | Br | 1 | 1 |
| III-612 | A60 | Br | 1 | 1 |
| III-613 | A62 | Br | 1 | 1 |
| III-614 | A66 | Br | 1 | 1 |
| III-615 | A67 | Br | 1 | 1 |
| III-616 | A68 | Br | 1 | 1 |
| III-617 | A69 | Br | 1 | 1 |
| III-618 | A70 | Br | 1 | 1 |
| III-619 | A71 | Br | 1 | 1 |
| III-620 | A72 | Br | 1 | 1 |
| III-621 | A73 | Br | 1 | 1 |
| III-622 | A74 | Br | 1 | 1 |
| III-623 | A75 | Br | 1 | 1 |
| III-624 | A76 | Br | 1 | 1 |
| III-625 | A77 | Br | 1 | 1 |
| III-626 | A78 | Br | 1 | 1 |
| III-627 | A79 | Br | 1 | 1 |
| III-628 | A80 | Br | 1 | 1 |
| III-629 | A81 | Br | 1 | 1 |
| III-630 | A82 | Br | 1 | 1 |
| III-631 | A83 | Br | 1 | 1 |
| III-632 | A84 | Br | 1 | 1 |
| III-633 | A85 | Br | 1 | 1 |
| III-634 | A86 | Br | 1 | 1 |
| III-635 | A87 | Br | 1 | 1 |
| III-636 | A88 | Br | 1 | 1 |
| III-637 | A89 | Br | 1 | 1 |
| III-638 | A90 | Br | 1 | 1 |
| III-639 | A1 | Br | 2 | 1 |
| III-640 | A2 | Br | 2 | 1 |
| III-641 | A3 | Br | 2 | 1 |
| III-642 | A4 | Br | 2 | 1 |
| III-643 | A5 | Br | 2 | 1 |
| III-644 | A10 | Br | 2 | 1 |
| III-645 | A12 | Br | 2 | 1 |
| III-646 | A15 | Br | 2 | 1 |
| III-647 | A18 | Br | 2 | 1 |
| III-648 | A19 | Br | 2 | 1 |
| III-649 | A20 | Br | 2 | 1 |
| III-650 | A21 | Br | 2 | 1 |
| III-651 | A22 | Br | 2 | 1 |
| III-652 | A23 | Br | 2 | 1 |
| III-653 | A26 | Br | 2 | 1 |
| III-654 | A30 | Br | 2 | 1 |
| III-655 | A31 | Br | 2 | 1 |
| III-656 | A32 | Br | 2 | 1 |
| III-657 | A33 | Br | 2 | 1 |
| III-658 | A34 | Br | 2 | 1 |
| III-659 | A35 | Br | 2 | 1 |
| III-660 | A36 | Br | 2 | 1 |

TABLE 24

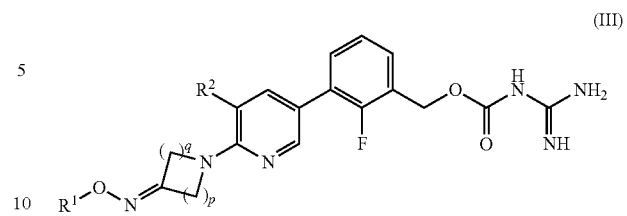

(III)

| Compound No. | R¹ | R² | p | q |
|---|---|---|---|---|
| III-661 | A37 | Br | 2 | 1 |
| III-662 | A38 | Br | 2 | 1 |
| III-663 | A39 | Br | 2 | 1 |
| III-664 | A40 | Br | 2 | 1 |
| III-665 | A42 | Br | 2 | 1 |
| III-666 | A43 | Br | 2 | 1 |
| III-667 | A44 | Br | 2 | 1 |
| III-668 | A45 | Br | 2 | 1 |
| III-669 | A46 | Br | 2 | 1 |
| III-670 | A47 | Br | 2 | 1 |
| III-671 | A49 | Br | 2 | 1 |
| III-672 | A50 | Br | 2 | 1 |
| III-673 | A51 | Br | 2 | 1 |
| III-674 | A52 | Br | 2 | 1 |
| III-675 | A53 | Br | 2 | 1 |
| III-676 | A54 | Br | 2 | 1 |
| III-677 | A55 | Br | 2 | 1 |
| III-678 | A76 | Br | 2 | 1 |
| III-679 | A77 | Br | 2 | 1 |
| III-680 | A78 | Br | 2 | 1 |
| III-681 | A79 | Br | 2 | 1 |
| III-682 | A1 | Br | 3 | 1 |
| III-683 | A2 | Br | 3 | 1 |
| III-684 | A3 | Br | 3 | 1 |
| III-685 | A4 | Br | 3 | 1 |
| III-686 | A12 | Br | 3 | 1 |
| III-687 | A15 | Br | 3 | 1 |
| III-688 | A26 | Br | 3 | 1 |
| III-689 | A40 | Br | 3 | 1 |
| III-690 | A42 | Br | 3 | 1 |
| III-691 | A43 | Br | 3 | 1 |
| III-692 | A47 | Br | 3 | 1 |
| III-693 | A1 | Br | 2 | 2 |
| III-694 | A2 | Br | 2 | 2 |
| III-695 | A3 | Br | 2 | 2 |
| III-696 | A4 | Br | 2 | 2 |
| III-697 | A12 | Br | 2 | 2 |
| III-698 | A15 | Br | 2 | 2 |
| III-699 | A26 | Br | 2 | 2 |
| III-700 | A40 | Br | 2 | 2 |
| III-701 | A42 | Br | 2 | 2 |
| III-702 | A43 | Br | 2 | 2 |
| III-703 | A47 | Br | 2 | 2 |
| III-704 | A1 | I | 1 | 1 |
| III-705 | A2 | I | 1 | 1 |
| III-706 | A3 | I | 1 | 1 |
| III-707 | A4 | I | 1 | 1 |
| III-708 | A12 | I | 1 | 1 |
| III-709 | A15 | I | 1 | 1 |
| III-710 | A26 | I | 1 | 1 |
| III-711 | A40 | I | 1 | 1 |
| III-712 | A42 | I | 1 | 1 |
| III-713 | A43 | I | 1 | 1 |
| III-714 | A47 | I | 1 | 1 |

TABLE 25

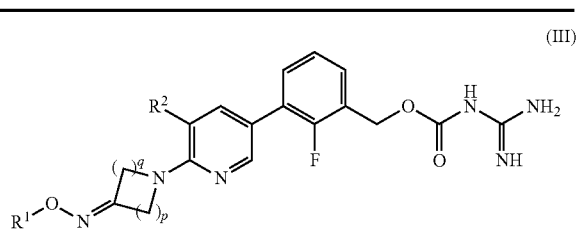
(III)

| Compound No. | R¹ | R² | p | q |
|---|---|---|---|---|
| III-715 | A1 | Me | 1 | 1 |
| III-716 | A2 | Me | 1 | 1 |
| III-717 | A3 | Me | 1 | 1 |
| III-718 | A4 | Me | 1 | 1 |
| III-719 | A5 | Me | 1 | 1 |
| III-720 | A10 | Me | 1 | 1 |
| III-721 | A12 | Me | 1 | 1 |
| III-722 | A15 | Me | 1 | 1 |
| III-723 | A18 | Me | 1 | 1 |
| III-724 | A19 | Me | 1 | 1 |
| III-725 | A20 | Me | 1 | 1 |
| III-726 | A21 | Me | 1 | 1 |
| III-727 | A22 | Me | 1 | 1 |
| III-728 | A23 | Me | 1 | 1 |
| III-729 | A26 | Me | 1 | 1 |
| III-730 | A30 | Me | 1 | 1 |
| III-731 | A31 | Me | 1 | 1 |
| III-732 | A32 | Me | 1 | 1 |
| III-733 | A33 | Me | 1 | 1 |
| III-734 | A34 | Me | 1 | 1 |
| III-735 | A35 | Me | 1 | 1 |
| III-736 | A36 | Me | 1 | 1 |
| III-737 | A37 | Me | 1 | 1 |
| III-738 | A38 | Me | 1 | 1 |
| III-739 | A39 | Me | 1 | 1 |
| III-740 | A40 | Me | 1 | 1 |
| III-741 | A42 | Me | 1 | 1 |
| III-742 | A43 | Me | 1 | 1 |
| III-743 | A44 | Me | 1 | 1 |
| III-744 | A45 | Me | 1 | 1 |
| III-745 | A46 | Me | 1 | 1 |
| III-746 | A47 | Me | 1 | 1 |
| III-747 | A49 | Me | 1 | 1 |
| III-748 | A50 | Me | 1 | 1 |
| III-749 | A51 | Me | 1 | 1 |
| III-750 | A52 | Me | 1 | 1 |
| III-751 | A53 | Me | 1 | 1 |
| III-752 | A54 | Me | 1 | 1 |
| III-753 | A55 | Me | 1 | 1 |
| III-754 | A56 | Me | 1 | 1 |
| III-755 | A57 | Me | 1 | 1 |
| III-756 | A58 | Me | 1 | 1 |
| III-757 | A59 | Me | 1 | 1 |
| III-758 | A60 | Me | 1 | 1 |
| III-759 | A62 | Me | 1 | 1 |
| III-760 | A66 | Me | 1 | 1 |
| III-761 | A67 | Me | 1 | 1 |
| III-762 | A68 | Me | 1 | 1 |
| III-763 | A69 | Me | 1 | 1 |
| III-764 | A70 | Me | 1 | 1 |
| III-765 | A71 | Me | 1 | 1 |
| III-766 | A72 | Me | 1 | 1 |
| III-767 | A73 | Me | 1 | 1 |
| III-768 | A74 | Me | 1 | 1 |
| III-769 | A75 | Me | 1 | 1 |

TABLE 26

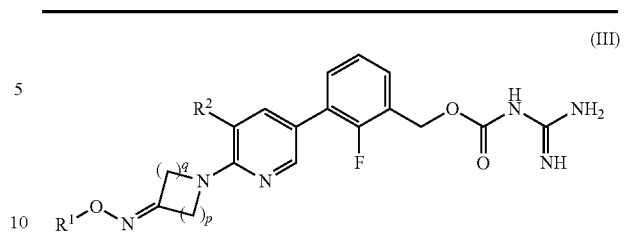
(III)

| Compound No. | R¹ | R² | p | q |
|---|---|---|---|---|
| III-770 | A76 | Me | 1 | 1 |
| III-771 | A77 | Me | 1 | 1 |
| III-772 | A78 | Me | 1 | 1 |
| III-773 | A79 | Me | 1 | 1 |
| III-774 | A80 | Me | 1 | 1 |
| III-775 | A81 | Me | 1 | 1 |
| III-776 | A82 | Me | 1 | 1 |
| III-777 | A83 | Me | 1 | 1 |
| III-778 | A84 | Me | 1 | 1 |
| III-779 | A85 | Me | 1 | 1 |
| III-780 | A86 | Me | 1 | 1 |
| III-781 | A87 | Me | 1 | 1 |
| III-782 | A88 | Me | 1 | 1 |
| III-783 | A89 | Me | 1 | 1 |
| III-784 | A90 | Me | 1 | 1 |
| III-785 | A1 | Me | 2 | 1 |
| III-786 | A2 | Me | 2 | 1 |
| III-787 | A3 | Me | 2 | 1 |
| III-788 | A4 | Me | 2 | 1 |
| III-789 | A5 | Me | 2 | 1 |
| III-790 | A10 | Me | 2 | 1 |
| III-791 | A12 | Me | 2 | 1 |
| III-792 | A15 | Me | 2 | 1 |
| III-793 | A18 | Me | 2 | 1 |
| III-794 | A19 | Me | 2 | 1 |
| III-795 | A20 | Me | 2 | 1 |
| III-796 | A21 | Me | 2 | 1 |
| III-797 | A22 | Me | 2 | 1 |
| III-798 | A23 | Me | 2 | 1 |
| III-799 | A26 | Me | 2 | 1 |
| III-800 | A30 | Me | 2 | 1 |
| III-801 | A31 | Me | 2 | 1 |
| III-802 | A32 | Me | 2 | 1 |
| III-803 | A33 | Me | 2 | 1 |
| III-804 | A34 | Me | 2 | 1 |
| III-805 | A35 | Me | 2 | 1 |
| III-806 | A36 | Me | 2 | 1 |
| III-807 | A37 | Me | 2 | 1 |
| III-808 | A38 | Me | 2 | 1 |
| III-809 | A39 | Me | 2 | 1 |
| III-810 | A40 | Me | 2 | 1 |
| III-811 | A42 | Me | 2 | 1 |
| III-812 | A43 | Me | 2 | 1 |
| III-813 | A44 | Me | 2 | 1 |
| III-814 | A45 | Me | 2 | 1 |
| III-815 | A46 | Me | 2 | 1 |
| III-816 | A47 | Me | 2 | 1 |
| III-817 | A49 | Me | 2 | 1 |
| III-818 | A50 | Me | 2 | 1 |
| III-819 | A51 | Me | 2 | 1 |
| III-820 | A52 | Me | 2 | 1 |
| III-821 | A53 | Me | 2 | 1 |
| III-822 | A54 | Me | 2 | 1 |
| III-823 | A55 | Me | 2 | 1 |

TABLE 27

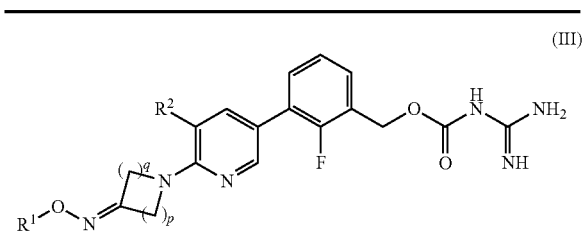

(III)

| Compound No. | R¹ | R² | p | q |
|---|---|---|---|---|
| III-824 | A76 | Me | 2 | 1 |
| III-825 | A77 | Me | 2 | 1 |
| III-826 | A78 | Me | 2 | 1 |
| III-827 | A79 | Me | 2 | 1 |
| III-828 | A1 | Me | 3 | 1 |
| III-829 | A2 | Me | 3 | 1 |
| III-830 | A3 | Me | 3 | 1 |
| III-831 | A4 | Me | 3 | 1 |
| III-832 | A12 | Me | 3 | 1 |
| III-833 | A15 | Me | 3 | 1 |
| III-834 | A26 | Me | 3 | 1 |
| III-835 | A40 | Me | 3 | 1 |
| III-836 | A42 | Me | 3 | 1 |
| III-837 | A43 | Me | 3 | 1 |
| III-838 | A47 | Me | 3 | 1 |
| III-839 | A1 | Me | 2 | 2 |
| III-840 | A2 | Me | 2 | 2 |
| III-841 | A3 | Me | 2 | 2 |
| III-842 | A4 | Me | 2 | 2 |
| III-843 | A12 | Me | 2 | 2 |
| III-844 | A15 | Me | 2 | 2 |
| III-845 | A26 | Me | 2 | 2 |
| III-846 | A40 | Me | 2 | 2 |
| III-847 | A42 | Me | 2 | 2 |
| III-848 | A43 | Me | 2 | 2 |
| III-849 | A47 | Me | 2 | 2 |
| III-850 | A1 | Et | 1 | 1 |
| III-851 | A2 | Et | 1 | 1 |
| III-852 | A3 | Et | 1 | 1 |
| III-853 | A4 | Et | 1 | 1 |
| III-854 | A5 | Et | 1 | 1 |
| III-855 | A10 | Et | 1 | 1 |
| III-856 | A12 | Et | 1 | 1 |
| III-857 | A15 | Et | 1 | 1 |
| III-858 | A18 | Et | 1 | 1 |
| III-859 | A19 | Et | 1 | 1 |
| III-860 | A20 | Et | 1 | 1 |
| III-861 | A21 | Et | 1 | 1 |
| III-862 | A22 | Et | 1 | 1 |
| III-863 | A23 | Et | 1 | 1 |
| III-864 | A26 | Et | 1 | 1 |
| III-865 | A30 | Et | 1 | 1 |
| III-866 | A31 | Et | 1 | 1 |
| III-867 | A32 | Et | 1 | 1 |
| III-868 | A33 | Et | 1 | 1 |
| III-869 | A34 | Et | 1 | 1 |
| III-870 | A35 | Et | 1 | 1 |
| III-871 | A36 | Et | 1 | 1 |
| III-872 | A37 | Et | 1 | 1 |
| III-873 | A38 | Et | 1 | 1 |
| III-874 | A39 | Et | 1 | 1 |
| III-875 | A40 | Et | 1 | 1 |

TABLE 28

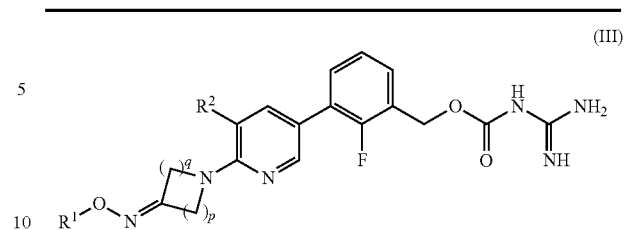

(III)

| Compound No. | R¹ | R² | p | q |
|---|---|---|---|---|
| III-876 | A42 | Et | 1 | 1 |
| III-877 | A43 | Et | 1 | 1 |
| III-878 | A44 | Et | 1 | 1 |
| III-879 | A45 | Et | 1 | 1 |
| III-880 | A46 | Et | 1 | 1 |
| III-881 | A47 | Et | 1 | 1 |
| III-882 | A49 | Et | 1 | 1 |
| III-883 | A50 | Et | 1 | 1 |
| III-884 | A51 | Et | 1 | 1 |
| III-885 | A52 | Et | 1 | 1 |
| III-886 | A53 | Et | 1 | 1 |
| III-887 | A54 | Et | 1 | 1 |
| III-888 | A55 | Et | 1 | 1 |
| III-889 | A76 | Et | 1 | 1 |
| III-890 | A77 | Et | 1 | 1 |
| III-891 | A78 | Et | 1 | 1 |
| III-892 | A79 | Et | 1 | 1 |
| III-893 | A1 | Et | 2 | 1 |
| III-894 | A2 | Et | 2 | 1 |
| III-895 | A3 | Et | 2 | 1 |
| III-896 | A4 | Et | 2 | 1 |
| III-897 | A12 | Et | 2 | 1 |
| III-898 | A15 | Et | 2 | 1 |
| III-899 | A26 | Et | 2 | 1 |
| III-900 | A40 | Et | 2 | 1 |
| III-901 | A42 | Et | 2 | 1 |
| III-902 | A43 | Et | 2 | 1 |
| III-903 | A47 | Et | 2 | 1 |
| III-904 | A1 | Et | 3 | 1 |
| III-905 | A2 | Et | 3 | 1 |
| III-906 | A3 | Et | 3 | 1 |
| III-907 | A4 | Et | 3 | 1 |
| III-908 | A12 | Et | 3 | 1 |
| III-909 | A15 | Et | 3 | 1 |
| III-910 | A26 | Et | 3 | 1 |
| III-911 | A40 | Et | 3 | 1 |
| III-912 | A42 | Et | 3 | 1 |
| III-913 | A43 | Et | 3 | 1 |
| III-914 | A47 | Et | 3 | 1 |
| III-915 | A1 | Et | 2 | 2 |
| III-916 | A2 | Et | 2 | 2 |
| III-917 | A3 | Et | 2 | 2 |
| III-918 | A4 | Et | 2 | 2 |
| III-919 | A12 | Et | 2 | 2 |
| III-920 | A15 | Et | 2 | 2 |
| III-921 | A26 | Et | 2 | 2 |
| III-922 | A40 | Et | 2 | 2 |
| III-923 | A42 | Et | 2 | 2 |
| III-924 | A43 | Et | 2 | 2 |
| III-925 | A47 | Et | 2 | 2 |
| III-926 | A1 | nPr | 1 | 1 |
| III-927 | A2 | nPr | 1 | 1 |
| III-928 | A3 | nPr | 1 | 1 |
| III-929 | A4 | nPr | 1 | 1 |
| III-930 | A12 | nPr | 1 | 1 |

TABLE 29

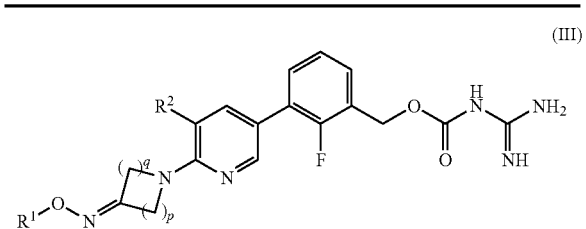

(III)

| Compound No. | R¹ | R² | p | q |
|---|---|---|---|---|
| III-931 | A15 | nPr | 1 | 1 |
| III-932 | A26 | nPr | 1 | 1 |
| III-933 | A40 | nPr | 1 | 1 |
| III-934 | A42 | nPr | 1 | 1 |
| III-935 | A43 | nPr | 1 | 1 |
| III-936 | A47 | nPr | 1 | 1 |
| III-937 | A1 | Pr | 1 | 1 |
| III-938 | A2 | Pr | 1 | 1 |
| III-939 | A3 | Pr | 1 | 1 |
| III-940 | A4 | Pr | 1 | 1 |
| III-941 | A12 | Pr | 1 | 1 |
| III-942 | A15 | Pr | 1 | 1 |
| III-943 | A26 | Pr | 1 | 1 |
| III-944 | A40 | Pr | 1 | 1 |
| III-945 | A42 | Pr | 1 | 1 |
| III-946 | A43 | Pr | 1 | 1 |
| III-947 | A47 | Pr | 1 | 1 |
| III-948 | A1 | $CH_2F$ | 1 | 1 |
| III-949 | A2 | $CH_2F$ | 1 | 1 |
| III-950 | A3 | $CH_2F$ | 1 | 1 |
| III-951 | A4 | $CH_2F$ | 1 | 1 |
| III-952 | A12 | $CH_2F$ | 1 | 1 |
| III-953 | A15 | $CH_2F$ | 1 | 1 |
| III-954 | A26 | $CH_2F$ | 1 | 1 |
| III-955 | A40 | $CH_2F$ | 1 | 1 |
| III-956 | A42 | $CH_2F$ | 1 | 1 |
| III-957 | A43 | $CH_2F$ | 1 | 1 |
| III-958 | A47 | $CH_2F$ | 1 | 1 |
| III-959 | A1 | $CH_2F$ | 1 | 1 |
| III-960 | A2 | $CH_2F$ | 1 | 1 |
| III-961 | A3 | $CH_2F$ | 1 | 1 |
| III-962 | A4 | $CH_2F$ | 1 | 1 |
| III-963 | A5 | $CH_2F$ | 1 | 1 |
| III-964 | A10 | $CH_2F$ | 1 | 1 |
| III-965 | A12 | $CH_2F$ | 1 | 1 |
| III-966 | A15 | $CH_2F$ | 1 | 1 |
| III-967 | A18 | $CH_2F$ | 1 | 1 |
| III-968 | A19 | $CH_2F$ | 1 | 1 |
| III-969 | A20 | $CH_2F$ | 1 | 1 |
| III-970 | A21 | $CH_2F$ | 1 | 1 |
| III-971 | A22 | $CH_2F$ | 1 | 1 |
| III-972 | A23 | $CH_2F$ | 1 | 1 |
| III-973 | A26 | $CH_2F$ | 1 | 1 |
| III-974 | A30 | $CH_2F$ | 1 | 1 |
| III-975 | A31 | $CH_2F$ | 1 | 1 |
| III-976 | A32 | $CH_2F$ | 1 | 1 |
| III-977 | A33 | $CH_2F$ | 1 | 1 |
| III-978 | A34 | $CH_2F$ | 1 | 1 |
| III-979 | A35 | $CH_2F$ | 1 | 1 |
| III-980 | A36 | $CH_2F$ | 1 | 1 |

TABLE 30

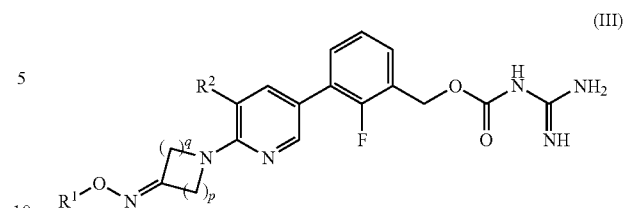

(III)

| Compound No. | R¹ | R² | p | q |
|---|---|---|---|---|
| III-981 | A37 | $CHF_2$ | 1 | 1 |
| III-982 | A38 | $CHF_2$ | 1 | 1 |
| III-983 | A39 | $CHF_2$ | 1 | 1 |
| III-984 | A40 | $CHF_2$ | 1 | 1 |
| III-985 | A42 | $CHF_2$ | 1 | 1 |
| III-986 | A43 | $CHF_2$ | 1 | 1 |
| III-987 | A44 | $CHF_2$ | 1 | 1 |
| III-988 | A45 | $CHF_2$ | 1 | 1 |
| III-989 | A46 | $CHF_2$ | 1 | 1 |
| III-990 | A47 | $CHF_2$ | 1 | 1 |
| III-991 | A49 | $CHF_2$ | 1 | 1 |
| III-992 | A50 | $CHF_2$ | 1 | 1 |
| III-993 | A51 | $CHF_2$ | 1 | 1 |
| III-994 | A52 | $CHF_2$ | 1 | 1 |
| III-995 | A53 | $CHF_2$ | 1 | 1 |
| III-996 | A54 | $CHF_2$ | 1 | 1 |
| III-997 | A55 | $CHF_2$ | 1 | 1 |
| III-998 | A76 | $CHF_2$ | 1 | 1 |
| III-999 | A77 | $CHF_2$ | 1 | 1 |
| III-1000 | A78 | $CHF_2$ | 1 | 1 |
| III-1001 | A79 | $CHF_2$ | 1 | 1 |
| III-1002 | A1 | $CHF_2$ | 2 | 1 |
| III-1003 | A2 | $CHF_2$ | 2 | 1 |
| III-1004 | A3 | $CHF_2$ | 2 | 1 |
| III-1005 | A4 | $CHF_2$ | 2 | 1 |
| III-1006 | A12 | $CHF_2$ | 2 | 1 |
| III-1007 | A15 | $CHF_2$ | 2 | 1 |
| III-1008 | A26 | $CHF_2$ | 2 | 1 |
| III-1009 | A40 | $CHF_2$ | 2 | 1 |
| III-1010 | A42 | $CHF_2$ | 2 | 1 |
| III-1011 | A43 | $CHF_2$ | 2 | 1 |
| III-1012 | A47 | $CHF_2$ | 2 | 1 |
| III-1013 | A1 | $CHF_2$ | 3 | 1 |
| III-1014 | A2 | $CHF_2$ | 3 | 1 |
| III-1015 | A3 | $CHF_2$ | 3 | 1 |
| III-1016 | A4 | $CHF_2$ | 3 | 1 |
| III-1017 | A12 | $CHF_2$ | 3 | 1 |
| III-1018 | A15 | $CHF_2$ | 3 | 1 |
| III-1019 | A26 | $CHF_2$ | 3 | 1 |
| III-1020 | A40 | $CHF_2$ | 3 | 1 |
| III-1021 | A42 | $CHF_2$ | 3 | 1 |
| III-1022 | A43 | $CHF_2$ | 3 | 1 |
| III-1023 | A47 | $CHF_2$ | 3 | 1 |

TABLE 31

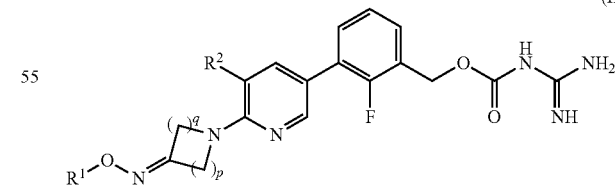

(III)

| Compound No. | R¹ | R² | p | q |
|---|---|---|---|---|
| III-1024 | A1 | $CHF_2$ | 2 | 2 |
| III-1025 | A2 | $CHF_2$ | 2 | 2 |
| III-1026 | A3 | $CHF_2$ | 2 | 2 |
| III-1027 | A4 | $CHF_2$ | 2 | 2 |
| III-1028 | A12 | $CHF_2$ | 2 | 2 |
| III-1029 | A15 | $CHF_2$ | 2 | 2 |

TABLE 31-continued (III)

| Compound No. | R¹ | R² | p | q |
|---|---|---|---|---|
| III-1030 | A26 | CHF$_2$ | 2 | 2 |
| III-1031 | A40 | CHF$_2$ | 2 | 2 |
| III-1032 | A42 | CHF$_2$ | 2 | 2 |
| III-1033 | A43 | CHF$_2$ | 2 | 2 |
| III-1034 | A47 | CHF$_2$ | 2 | 2 |
| III-1035 | A1 | CF$_3$ | 1 | 1 |
| III-1036 | A2 | CF$_3$ | 1 | 1 |
| III-1037 | A3 | CF$_3$ | 1 | 1 |
| III-1038 | A4 | CF$_3$ | 1 | 1 |
| III-1039 | A12 | CF$_3$ | 1 | 1 |
| III-1040 | A15 | CF$_3$ | 1 | 1 |
| III-1041 | A26 | CF$_3$ | 1 | 1 |
| III-1042 | A40 | CF$_3$ | 1 | 1 |
| III-1043 | A42 | CF$_3$ | 1 | 1 |
| III-1044 | A43 | CF$_3$ | 1 | 1 |
| III-1045 | A47 | CF$_3$ | 1 | 1 |
| III-1046 | A1 | HOCH$_2$ | 1 | 1 |
| III-1047 | A2 | HOCH$_2$ | 1 | 1 |
| III-1048 | A3 | HOCH$_2$ | 1 | 1 |
| III-1049 | A4 | HOCH$_2$ | 1 | 1 |
| III-1050 | A12 | HOCH$_2$ | 1 | 1 |
| III-1051 | A15 | HOCH$_2$ | 1 | 1 |
| III-1052 | A26 | HOCH$_2$ | 1 | 1 |
| III-1053 | A40 | HOCH$_2$ | 1 | 1 |
| III-1054 | A42 | HOCH$_2$ | 1 | 1 |
| III-1055 | A43 | HOCH$_2$ | 1 | 1 |
| III-1056 | A47 | HOCH$_2$ | 1 | 1 |
| III-1057 | A1 | HOCHMe | 1 | 1 |
| III-1058 | A2 | HOCHMe | 1 | 1 |
| III-1059 | A3 | HOCHMe | 1 | 1 |
| III-1060 | A4 | HOCHMe | 1 | 1 |
| III-1061 | A5 | HOCHMe | 1 | 1 |
| III-1062 | A10 | HOCHMe | 1 | 1 |
| III-1063 | A12 | HOCHMe | 1 | 1 |
| III-1064 | A15 | HOCHMe | 1 | 1 |
| III-1065 | A18 | HOCHMe | 1 | 1 |
| III-1066 | A19 | HOCHMe | 1 | 1 |
| III-1067 | A20 | HOCHMe | 1 | 1 |
| III-1068 | A21 | HOCHMe | 1 | 1 |
| III-1069 | A22 | HOCHMe | 1 | 1 |
| III-1070 | A23 | HOCHMe | 1 | 1 |

TABLE 32

(III)

| Compound No. | R¹ | R² | p | q |
|---|---|---|---|---|
| III-1071 | A26 | HOCHMe | 1 | 1 |
| III-1072 | A30 | HOCHMe | 1 | 1 |
| III-1073 | A31 | HOCHMe | 1 | 1 |
| III-1074 | A32 | HOCHMe | 1 | 1 |
| III-1075 | A33 | HOCHMe | 1 | 1 |
| III-1076 | A34 | HOCHMe | 1 | 1 |
| III-1077 | A35 | HOCHMe | 1 | 1 |
| III-1078 | A36 | HOCHMe | 1 | 1 |

TABLE 32-continued (III)

| Compound No. | R¹ | R² | p | q |
|---|---|---|---|---|
| III-1079 | A37 | HOCHMe | 1 | 1 |
| III-1080 | A38 | HOCHMe | 1 | 1 |
| III-1081 | A39 | HOCHMe | 1 | 1 |
| III-1082 | A40 | HOCHMe | 1 | 1 |
| III-1083 | A42 | HOCHMe | 1 | 1 |
| III-1084 | A43 | HOCHMe | 1 | 1 |
| III-1085 | A44 | HOCHMe | 1 | 1 |
| III-1086 | A45 | HOCHMe | 1 | 1 |
| III-1087 | A46 | HOCHMe | 1 | 1 |
| III-1088 | A47 | HOCHMe | 1 | 1 |
| III-1089 | A49 | HOCHMe | 1 | 1 |
| III-1090 | A50 | HOCHMe | 1 | 1 |
| III-1091 | A51 | HOCHMe | 1 | 1 |
| III-1092 | A52 | HOCHMe | 1 | 1 |
| III-1093 | A53 | HOCHMe | 1 | 1 |
| III-1094 | A54 | HOCHMe | 1 | 1 |
| III-1095 | A55 | HOCHMe | 1 | 1 |
| III-1096 | A76 | HOCHMe | 1 | 1 |
| III-1097 | A77 | HOCHMe | 1 | 1 |
| III-1098 | A78 | HOCHMe | 1 | 1 |
| III-1099 | A79 | HOCHMe | 1 | 1 |
| III-1100 | A1 | HOCHMe | 2 | 1 |
| III-1101 | A2 | HOCHMe | 2 | 1 |
| III-1102 | A3 | HOCHMe | 2 | 1 |
| III-1103 | A4 | HOCHMe | 2 | 1 |
| III-1104 | A12 | HOCHMe | 2 | 1 |
| III-1105 | A15 | HOCHMe | 2 | 1 |
| III-1106 | A26 | HOCHMe | 2 | 1 |
| III-1107 | A40 | HOCHMe | 2 | 1 |
| III-1108 | A42 | HOCHMe | 2 | 1 |
| III-1109 | A43 | HOCHMe | 2 | 1 |
| III-1110 | A47 | HOCHMe | 2 | 1 |
| III-1111 | A1 | HOCHMe | 3 | 1 |
| III-1112 | A2 | HOCHMe | 3 | 1 |
| III-1113 | A3 | HOCHMe | 3 | 1 |
| III-1114 | A4 | HOCHMe | 3 | 1 |
| III-1115 | A12 | HOCHMe | 3 | 1 |
| III-1116 | A15 | HOCHMe | 3 | 1 |
| III-1117 | A26 | HOCHMe | 3 | 1 |
| III-1118 | A40 | HOCHMe | 3 | 1 |
| III-1119 | A42 | HOCHMe | 3 | 1 |
| III-1120 | A43 | HOCHMe | 3 | 1 |
| III-1121 | A47 | HOCHMe | 3 | 1 |

TABLE 33

(III)

| Compound No. | R¹ | R² | p | q |
|---|---|---|---|---|
| III-1122 | A1 | HOCHMe | 2 | 2 |
| III-1123 | A2 | HOCHMe | 2 | 2 |
| III-1124 | A3 | HOCHMe | 2 | 2 |
| III-1125 | A4 | HOCHMe | 2 | 2 |
| III-1126 | A12 | HOCHMe | 2 | 2 |
| III-1127 | A15 | HOCHMe | 2 | 2 |

TABLE 33-continued (III)

| Compound No. | R¹ | R² | p | q |
|---|---|---|---|---|
| III-1128 | A26 | HOCHMe | 2 | 2 |
| III-1129 | A40 | HOCHMe | 2 | 2 |
| III-1130 | A42 | HOCHMe | 2 | 2 |
| III-1131 | A43 | HOCHMe | 2 | 2 |
| III-1132 | A47 | HOCHMe | 2 | 2 |
| III-1133 | A1 | HOC(Me)$_2$ | 1 | 1 |
| III-1134 | A2 | HOC(Me)$_2$ | 1 | 1 |
| III-1135 | A3 | HOC(Me)$_2$ | 1 | 1 |
| III-1136 | A4 | HOC(Me)$_2$ | 1 | 1 |
| III-1137 | A5 | HOC(Me)$_2$ | 1 | 1 |
| III-1138 | A10 | HOC(Me)$_2$ | 1 | 1 |
| III-1139 | A12 | HOC(Me)$_2$ | 1 | 1 |
| III-1140 | A15 | HOC(Me)$_2$ | 1 | 1 |
| III-1141 | A18 | HOC(Me)$_2$ | 1 | 1 |
| III-1142 | A19 | HOC(Me)$_2$ | 1 | 1 |
| III-1143 | A20 | HOC(Me)$_2$ | 1 | 1 |
| III-1144 | A21 | HOC(Me)$_2$ | 1 | 1 |
| III-1145 | A22 | HOC(Me)$_2$ | 1 | 1 |
| III-1146 | A23 | HOC(Me)$_2$ | 1 | 1 |
| III-1147 | A26 | HOC(Me)$_2$ | 1 | 1 |
| III-1148 | A30 | HOC(Me)$_2$ | 1 | 1 |
| III-1149 | A31 | HOC(Me)$_2$ | 1 | 1 |
| III-1150 | A32 | HOC(Me)$_2$ | 1 | 1 |
| III-1151 | A33 | HOC(Me)$_2$ | 1 | 1 |
| III-1152 | A34 | HOC(Me)$_2$ | 1 | 1 |
| III-1153 | A35 | HOC(Me)$_2$ | 1 | 1 |
| III-1154 | A36 | HOC(Me)$_2$ | 1 | 1 |
| III-1155 | A37 | HOC(Me)$_2$ | 1 | 1 |
| III-1156 | A38 | HOC(Me)$_2$ | 1 | 1 |
| III-1157 | A39 | HOC(Me)$_2$ | 1 | 1 |
| III-1158 | A40 | HOC(Me)$_2$ | 1 | 1 |
| III-1159 | A42 | HOC(Me)$_2$ | 1 | 1 |
| III-1160 | A43 | HOC(Me)$_2$ | 1 | 1 |
| III-1161 | A44 | HOC(Me)$_2$ | 1 | 1 |
| III-1162 | A45 | HOC(Me)$_2$ | 1 | 1 |
| III-1163 | A46 | HOC(Me)$_2$ | 1 | 1 |
| III-1164 | A47 | HOC(Me)$_2$ | 1 | 1 |
| III-1165 | A49 | HOC(Me)$_2$ | 1 | 1 |
| III-1166 | A50 | HOC(Me)$_2$ | 1 | 1 |

TABLE 34

(III)

| Compound No. | R¹ | R² | p | q |
|---|---|---|---|---|
| III-1167 | A51 | HOC(Me)$_2$ | 1 | 1 |
| III-1168 | A52 | HOC(Me)$_2$ | 1 | 1 |
| III-1169 | A53 | HOC(Me)$_2$ | 1 | 1 |
| III-1170 | A54 | HOC(Me)$_2$ | 1 | 1 |
| III-1171 | A55 | HOC(Me)$_2$ | 1 | 1 |
| III-1172 | A76 | HOC(Me)$_2$ | 1 | 1 |
| III-1173 | A77 | HOC(Me)$_2$ | 1 | 1 |
| III-1174 | A78 | HOC(Me)$_2$ | 1 | 1 |
| III-1175 | A79 | HOC(Me)$_2$ | 1 | 1 |
| III-1176 | A1 | HOC(Me)$_2$ | 2 | 1 |

TABLE 34-continued (III)

| Compound No. | R¹ | R² | p | q |
|---|---|---|---|---|
| III-1177 | A2 | HOC(Me)$_2$ | 2 | 1 |
| III-1178 | A3 | HOC(Me)$_2$ | 2 | 1 |
| III-1179 | A4 | HOC(Me)$_2$ | 2 | 1 |
| III-1180 | A12 | HOC(Me)$_2$ | 2 | 1 |
| III-1181 | A15 | HOC(Me)$_2$ | 2 | 1 |
| III-1182 | A26 | HOC(Me)$_2$ | 2 | 1 |
| III-1183 | A40 | HOC(Me)$_2$ | 2 | 1 |
| III-1184 | A42 | HOC(Me)$_2$ | 2 | 1 |
| III-1185 | A43 | HOC(Me)$_2$ | 2 | 1 |
| III-1186 | A47 | HOC(Me)$_2$ | 2 | 1 |
| III-1187 | A1 | HOC(Me)$_2$ | 3 | 1 |
| III-1188 | A2 | HOC(Me)$_2$ | 3 | 1 |
| III-1189 | A3 | HOC(Me)$_2$ | 3 | 1 |
| III-1190 | A4 | HOC(Me)$_2$ | 3 | 1 |
| III-1191 | A12 | HOC(Me)$_2$ | 3 | 1 |
| III-1192 | A15 | HOC(Me)$_2$ | 3 | 1 |
| III-1193 | A26 | HOC(Me)$_2$ | 3 | 1 |
| III-1194 | A40 | HOC(Me)$_2$ | 3 | 1 |
| III-1195 | A42 | HOC(Me)$_2$ | 3 | 1 |
| III-1196 | A43 | HOC(Me)$_2$ | 3 | 1 |
| III-1197 | A47 | HOC(Me)$_2$ | 3 | 1 |
| III-1198 | A1 | HOC(Me)$_2$ | 2 | 2 |
| III-1199 | A2 | HOC(Me)$_2$ | 2 | 2 |
| III-1200 | A3 | HOC(Me)$_2$ | 2 | 2 |
| III-1201 | A4 | HOC(Me)$_2$ | 2 | 2 |
| III-1202 | A12 | HOC(Me)$_2$ | 2 | 2 |
| III-1203 | A15 | HOC(Me)$_2$ | 2 | 2 |
| III-1204 | A26 | HOC(Me)$_2$ | 2 | 2 |
| III-1205 | A40 | HOC(Me)$_2$ | 2 | 2 |
| III-1206 | A42 | HOC(Me)$_2$ | 2 | 2 |
| III-1207 | A43 | HOC(Me)$_2$ | 2 | 2 |
| III-1208 | A47 | HOC(Me)$_2$ | 2 | 2 |

TABLE 35

(III)

| Compound No. | R¹ | R² | p | q |
|---|---|---|---|---|
| III-1209 | A1 | THPOC(Me)$_2$ | 1 | 1 |
| III-1210 | A2 | THPOC(Me)$_2$ | 1 | 1 |
| III-1211 | A3 | THPOC(Me)$_2$ | 1 | 1 |
| III-1212 | A4 | THPOC(Me)$_2$ | 1 | 1 |
| III-1213 | A12 | THPOC(Me)$_2$ | 1 | 1 |
| III-1214 | A15 | THPOC(Me)$_2$ | 1 | 1 |
| III-1215 | A26 | THPOC(Me)$_2$ | 1 | 1 |
| III-1216 | A40 | THPOC(Me)$_2$ | 1 | 1 |
| III-1217 | A42 | THPOC(Me)$_2$ | 1 | 1 |
| III-1218 | A43 | THPOC(Me)$_2$ | 1 | 1 |
| III-1219 | A47 | THPOC(Me)$_2$ | 1 | 1 |
| III-1220 | A1 | MeOCH$_2$ | 1 | 1 |
| III-1221 | A2 | MeOCH$_2$ | 1 | 1 |
| III-1222 | A3 | MeOCH$_2$ | 1 | 1 |
| III-1223 | A4 | MeOCH$_2$ | 1 | 1 |
| III-1224 | A5 | MeOCH$_2$ | 1 | 1 |
| III-1225 | A10 | MeOCH$_2$ | 1 | 1 |

TABLE 35-continued (III)

| Compound No. | R¹ | R² | p | q |
|---|---|---|---|---|
| III-1226 | A12 | MeOCH$_2$ | 1 | 1 |
| III-1227 | A15 | MeOCH$_2$ | 1 | 1 |
| III-1228 | A18 | MeOCH$_2$ | 1 | 1 |
| III-1229 | A19 | MeOCH$_2$ | 1 | 1 |
| III-1230 | A20 | MeOCH$_2$ | 1 | 1 |
| III-1231 | A21 | MeOCH$_2$ | 1 | 1 |
| III-1232 | A22 | MeOCH$_2$ | 1 | 1 |
| III-1233 | A23 | MeOCH$_2$ | 1 | 1 |
| III-1234 | A26 | MeOCH$_2$ | 1 | 1 |
| III-1235 | A30 | MeOCH$_2$ | 1 | 1 |
| III-1236 | A31 | MeOCH$_2$ | 1 | 1 |
| III-1237 | A32 | MeOCH$_2$ | 1 | 1 |
| III-1238 | A33 | MeOCH$_2$ | 1 | 1 |
| III-1239 | A34 | MeOCH$_2$ | 1 | 1 |
| III-1240 | A35 | MeOCH$_2$ | 1 | 1 |
| III-1241 | A36 | MeOCH$_2$ | 1 | 1 |
| III-1242 | A37 | MeOCH$_2$ | 1 | 1 |
| III-1243 | A38 | MeOCH$_2$ | 1 | 1 |
| III-1244 | A39 | MeOCH$_2$ | 1 | 1 |
| III-1245 | A40 | MeOCH$_2$ | 1 | 1 |
| III-1246 | A42 | MeOCH$_2$ | 1 | 1 |
| III-1247 | A43 | MeOCH$_2$ | 1 | 1 |
| III-1248 | A44 | MeOCH$_2$ | 1 | 1 |
| III-1249 | A45 | MeOCH$_2$ | 1 | 1 |
| III-1250 | A46 | MeOCH$_2$ | 1 | 1 |
| III-1251 | A47 | MeOCH$_2$ | 1 | 1 |
| III-1252 | A49 | MeOCH$_2$ | 1 | 1 |
| III-1253 | A50 | MeOCH$_2$ | 1 | 1 |

TABLE 36

(III)

| Compound No. | R¹ | R² | p | q |
|---|---|---|---|---|
| III-1254 | A51 | MeOCH$_2$ | 1 | 1 |
| III-1255 | A52 | MeOCH$_2$ | 1 | 1 |
| III-1256 | A53 | MeOCH$_2$ | 1 | 1 |
| III-1257 | A54 | MeOCH$_2$ | 1 | 1 |
| III-1258 | A55 | MeOCH$_2$ | 1 | 1 |
| III-1259 | A76 | MeOCH$_2$ | 1 | 1 |
| III-1260 | A77 | MeOCH$_2$ | 1 | 1 |
| III-1261 | A78 | MeOCH$_2$ | 1 | 1 |
| III-1262 | A79 | MeOCH$_2$ | 1 | 1 |
| III-1263 | A1 | MeOCH$_2$ | 2 | 1 |
| III-1264 | A2 | MeOCH$_2$ | 2 | 1 |
| III-1265 | A3 | MeOCH$_2$ | 2 | 1 |
| III-1266 | A4 | MeOCH$_2$ | 2 | 1 |
| III-1267 | A12 | MeOCH$_2$ | 2 | 1 |
| III-1268 | A15 | MeOCH$_2$ | 2 | 1 |
| III-1269 | A26 | MeOCH$_2$ | 2 | 1 |
| III-1270 | A40 | MeOCH$_2$ | 2 | 1 |
| III-1271 | A42 | MeOCH$_2$ | 2 | 1 |
| III-1272 | A43 | MeOCH$_2$ | 2 | 1 |
| III-1273 | A47 | MeOCH$_2$ | 2 | 1 |
| III-1274 | A1 | MeOCH$_2$ | 3 | 1 |

TABLE 36-continued (III)

| Compound No. | R¹ | R² | p | q |
|---|---|---|---|---|
| III-1275 | A2 | MeOCH$_2$ | 3 | 1 |
| III-1276 | A3 | MeOCH$_2$ | 3 | 1 |
| III-1277 | A4 | MeOCH$_2$ | 3 | 1 |
| III-1278 | A12 | MeOCH$_2$ | 3 | 1 |
| III-1279 | A15 | MeOCH$_2$ | 3 | 1 |
| III-1280 | A26 | MeOCH$_2$ | 3 | 1 |
| III-1281 | A40 | MeOCH$_2$ | 3 | 1 |
| III-1282 | A42 | MeOCH$_2$ | 3 | 1 |
| III-1283 | A43 | MeOCH$_2$ | 3 | 1 |
| III-1284 | A47 | MeOCH$_2$ | 3 | 1 |
| III-1285 | A1 | MeOCH$_2$ | 2 | 2 |
| III-1286 | A2 | MeOCH$_2$ | 2 | 2 |
| III-1287 | A3 | MeOCH$_2$ | 2 | 2 |
| III-1288 | A4 | MeOCH$_2$ | 2 | 2 |
| III-1289 | A12 | MeOCH$_2$ | 2 | 2 |
| III-1290 | A15 | MeOCH$_2$ | 2 | 2 |
| III-1291 | A26 | MeOCH$_2$ | 2 | 2 |
| III-1292 | A40 | MeOCH$_2$ | 2 | 2 |
| III-1293 | A42 | MeOCH$_2$ | 2 | 2 |
| III-1294 | A43 | MeOCH$_2$ | 2 | 2 |
| III-1295 | A47 | MeOCH$_2$ | 2 | 2 |

TABLE 37

(III)

| Compound No. | R¹ | R² | p | q |
|---|---|---|---|---|
| III-1296 | A1 | EtOCH$_2$ | 1 | 1 |
| III-1297 | A2 | EtOCH$_2$ | 1 | 1 |
| III-1298 | A3 | EtOCH$_2$ | 1 | 1 |
| III-1299 | A4 | EtOCH$_2$ | 1 | 1 |
| III-1300 | A12 | EtOCH$_2$ | 1 | 1 |
| III-1301 | A15 | EtOCH$_2$ | 1 | 1 |
| III-1302 | A26 | EtOCH$_2$ | 1 | 1 |
| III-1303 | A40 | EtOCH$_2$ | 1 | 1 |
| III-1304 | A42 | EtOCH$_2$ | 1 | 1 |
| III-1305 | A43 | EtOCH$_2$ | 1 | 1 |
| III-1306 | A47 | EtOCH$_2$ | 1 | 1 |
| III-1307 | A1 | cPr | 1 | 1 |
| III-1308 | A2 | cPr | 1 | 1 |
| III-1309 | A3 | cPr | 1 | 1 |
| III-1310 | A4 | cPr | 1 | 1 |
| III-1311 | A5 | cPr | 1 | 1 |
| III-1312 | A10 | cPr | 1 | 1 |
| III-1313 | A12 | cPr | 1 | 1 |
| III-1314 | A15 | cPr | 1 | 1 |
| III-1315 | A18 | cPr | 1 | 1 |
| III-1316 | A19 | cPr | 1 | 1 |
| III-1317 | A20 | cPr | 1 | 1 |
| III-1318 | A21 | cPr | 1 | 1 |
| III-1319 | A22 | cPr | 1 | 1 |
| III-1320 | A23 | cPr | 1 | 1 |
| III-1321 | A26 | cPr | 1 | 1 |
| III-1322 | A30 | cPr | 1 | 1 |
| III-1323 | A31 | cPr | 1 | 1 |

TABLE 37-continued (III)

| Compound No. | R¹ | R² | p | q |
|---|---|---|---|---|
| III-1324 | A32 | cPr | 1 | 1 |
| III-1325 | A33 | cPr | 1 | 1 |
| III-1326 | A34 | cPr | 1 | 1 |
| III-1327 | A35 | cPr | 1 | 1 |
| III-1328 | A36 | cPr | 1 | 1 |
| III-1329 | A37 | cPr | 1 | 1 |
| III-1330 | A38 | cPr | 1 | 1 |
| III-1331 | A39 | cPr | 1 | 1 |
| III-1332 | A40 | cPr | 1 | 1 |
| III-1333 | A42 | cPr | 1 | 1 |
| III-1334 | A43 | cPr | 1 | 1 |
| III-1335 | A44 | cPr | 1 | 1 |
| III-1336 | A45 | cPr | 1 | 1 |
| III-1337 | A46 | cPr | 1 | 1 |
| III-1338 | A47 | cPr | 1 | 1 |
| III-1339 | A49 | cPr | 1 | 1 |
| III-1340 | A50 | cPr | 1 | 1 |
| III-1341 | A51 | cPr | 1 | 1 |
| III-1342 | A52 | cPr | 1 | 1 |
| III-1343 | A53 | cPr | 1 | 1 |
| III-1344 | A54 | cPr | 1 | 1 |
| III-1345 | A55 | cPr | 1 | 1 |
| III-1346 | A76 | cPr | 1 | 1 |
| III-1347 | A77 | cPr | 1 | 1 |
| III-1348 | A78 | cPr | 1 | 1 |
| III-1349 | A79 | cPr | 1 | 1 |

TABLE 38

(III)

| Compound No. | R1 | R2 | p | q |
|---|---|---|---|---|
| III-1350 | A1 | cPr | 2 | 1 |
| III-1351 | A2 | cPr | 2 | 1 |
| III-1352 | A3 | cPr | 2 | 1 |
| III-1353 | A4 | cPr | 2 | 1 |
| III-1354 | A12 | cPr | 2 | 1 |
| III-1355 | A15 | cPr | 2 | 1 |
| III-1356 | A26 | cPr | 2 | 1 |
| III-1357 | A40 | cPr | 2 | 1 |
| III-1358 | A42 | cPr | 2 | 1 |
| III-1359 | A43 | cPr | 2 | 1 |
| III-1360 | A47 | cPr | 2 | 1 |
| III-1361 | A1 | cPr | 3 | 1 |
| III-1362 | A2 | cPr | 3 | 1 |
| III-1363 | A3 | cPr | 3 | 1 |
| III-1364 | A4 | cPr | 3 | 1 |
| III-1365 | A12 | cPr | 3 | 1 |
| III-1366 | A15 | cPr | 3 | 1 |
| III-1367 | A26 | cPr | 3 | 1 |
| III-1368 | A40 | cPr | 3 | 1 |
| III-1369 | A42 | cPr | 3 | 1 |
| III-1370 | A43 | cPr | 3 | 1 |
| III-1371 | A47 | cPr | 3 | 1 |
| III-1372 | A1 | cPr | 2 | 2 |

TABLE 38-continued (III)

| Compound No. | R1 | R2 | p | q |
|---|---|---|---|---|
| III-1373 | A2 | cPr | 2 | 2 |
| III-1374 | A3 | cPr | 2 | 2 |
| III-1375 | A4 | cPr | 2 | 2 |
| III-1376 | A12 | cPr | 2 | 2 |
| III-1377 | A15 | cPr | 2 | 2 |
| III-1378 | A26 | cPr | 2 | 2 |
| III-1379 | A40 | cPr | 2 | 2 |
| III-1380 | A42 | cPr | 2 | 2 |
| III-1381 | A43 | cPr | 2 | 2 |
| III-1382 | A47 | cPr | 2 | 2 |
| III-1383 | A1 | cBu | 1 | 1 |
| III-1384 | A2 | cBu | 1 | 1 |
| III-1385 | A3 | cBu | 1 | 1 |
| III-1386 | A4 | cBu | 1 | 1 |
| III-1387 | A12 | cBu | 1 | 1 |
| III-1388 | A15 | cBu | 1 | 1 |
| III-1389 | A26 | cBu | 1 | 1 |
| III-1390 | A40 | cBu | 1 | 1 |
| III-1391 | A42 | cBu | 1 | 1 |
| III-1392 | A43 | cBu | 1 | 1 |
| III-1393 | A47 | cBu | 1 | 1 |

TABLE 39

(III)

| Compound No. | R¹ | R² | p | q |
|---|---|---|---|---|
| III-1394 | A1 | MeO | 1 | 1 |
| III-1395 | A2 | MeO | 1 | 1 |
| III-1396 | A3 | MeO | 1 | 1 |
| III-1397 | A4 | MeO | 1 | 1 |
| III-1398 | A5 | MeO | 1 | 1 |
| III-1399 | A10 | MeO | 1 | 1 |
| III-1400 | A12 | MeO | 1 | 1 |
| III-1401 | A15 | MeO | 1 | 1 |
| III-1402 | A18 | MeO | 1 | 1 |
| III-1403 | A19 | MeO | 1 | 1 |
| III-1404 | A20 | MeO | 1 | 1 |
| III-1405 | A21 | MeO | 1 | 1 |
| III-1406 | A22 | MeO | 1 | 1 |
| III-1407 | A23 | MeO | 1 | 1 |
| III-1408 | A26 | MeO | 1 | 1 |
| III-1409 | A30 | MeO | 1 | 1 |
| III-1410 | A31 | MeO | 1 | 1 |
| III-1411 | A32 | MeO | 1 | 1 |
| III-1412 | A33 | MeO | 1 | 1 |
| III-1413 | A34 | MeO | 1 | 1 |
| III-1414 | A35 | MeO | 1 | 1 |
| III-1415 | A36 | MeO | 1 | 1 |
| III-1416 | A37 | MeO | 1 | 1 |
| III-1417 | A38 | MeO | 1 | 1 |
| III-1418 | A39 | MeO | 1 | 1 |
| III-1419 | A40 | MeO | 1 | 1 |
| III-1420 | A42 | MeO | 1 | 1 |
| III-1421 | A43 | MeO | 1 | 1 |

TABLE 39-continued (III) [structure: R² and pyridine linked to fluorophenyl-CH₂-O-C(=O)-NH-C(=NH)-NH₂; azetidine with R¹-O-N= substituent, (p) and (q) subscripts]

| Compound No. | R¹ | R² | p | q |
|---|---|---|---|---|
| III-1422 | A44 | MeO | 1 | 1 |
| III-1423 | A45 | MeO | 1 | 1 |
| III-1424 | A46 | MeO | 1 | 1 |
| III-1425 | A47 | MeO | 1 | 1 |
| III-1426 | A49 | MeO | 1 | 1 |
| III-1427 | A50 | MeO | 1 | 1 |
| III-1428 | A51 | MeO | 1 | 1 |
| III-1429 | A52 | MeO | 1 | 1 |
| III-1430 | A53 | MeO | 1 | 1 |
| III-1431 | A54 | MeO | 1 | 1 |
| III-1432 | A55 | MeO | 1 | 1 |
| III-1433 | A76 | MeO | 1 | 1 |
| III-1434 | A77 | MeO | 1 | 1 |
| III-1435 | A78 | MeO | 1 | 1 |
| III-1436 | A79 | MeO | 1 | 1 |
| III-1437 | A1 | MeO | 2 | 1 |
| III-1438 | A2 | MeO | 2 | 1 |
| III-1439 | A3 | MeO | 2 | 1 |
| III-1440 | A4 | MeO | 2 | 1 |
| III-1441 | A12 | MeO | 2 | 1 |
| III-1442 | A15 | MeO | 2 | 1 |
| III-1443 | A26 | MeO | 2 | 1 |
| III-1444 | A40 | MeO | 2 | 1 |
| III-1445 | A42 | MeO | 2 | 1 |
| III-1446 | A43 | MeO | 2 | 1 |
| III-1447 | A47 | MeO | 2 | 1 |

TABLE 40

(III)

| Compound No. | R¹ | R² | p | q |
|---|---|---|---|---|
| III-1448 | A1 | MeO | 3 | 1 |
| III-1449 | A2 | MeO | 3 | 1 |
| III-1450 | A3 | MeO | 3 | 1 |
| III-1451 | A4 | MeO | 3 | 1 |
| III-1452 | A12 | MeO | 3 | 1 |
| III-1453 | A15 | MeO | 3 | 1 |
| III-1454 | A26 | MeO | 3 | 1 |
| III-1455 | A40 | MeO | 3 | 1 |
| III-1456 | A42 | Me0 | 3 | 1 |
| III-1457 | A43 | MeO | 3 | 1 |
| III-1458 | A47 | MeO | 3 | 1 |
| III-1459 | A1 | MeO | 2 | 2 |
| III-1460 | A2 | MeO | 2 | 2 |
| III-1461 | A3 | MeO | 2 | 2 |
| III-1462 | A4 | MeO | 2 | 2 |
| III-1463 | A12 | MeO | 2 | 2 |
| III-1464 | A15 | MeO | 2 | 2 |
| III-1465 | A26 | MeO | 2 | 2 |
| III-1466 | A40 | MeO | 2 | 2 |
| III-1467 | A42 | MeO | 2 | 2 |
| III-1468 | A43 | MeO | 2 | 2 |
| III-1469 | A47 | MeO | 2 | 2 |
| III-1470 | A1 | EtO | 1 | 1 |

TABLE 40-continued (III)

| Compound No. | R¹ | R² | p | q |
|---|---|---|---|---|
| III-1471 | A2 | EtO | 1 | 1 |
| III-1472 | A3 | EtO | 1 | 1 |
| III-1473 | A4 | EtO | 1 | 1 |
| III-1474 | A12 | EtO | 1 | 1 |
| III-1475 | A15 | EtO | 1 | 1 |
| III-1476 | A26 | EtO | 1 | 1 |
| III-1477 | A40 | EtO | 1 | 1 |
| III-1478 | A42 | EtO | 1 | 1 |
| III-1479 | A43 | EtO | 1 | 1 |
| III-1480 | A47 | EtO | 1 | 1 |
| III-1481 | A1 | NC | 1 | 1 |
| III-1482 | A2 | NC | 1 | 1 |
| III-1483 | A3 | NC | 1 | 1 |
| III-1484 | A4 | NC | 1 | 1 |
| III-1485 | A5 | NC | 1 | 1 |
| III-1486 | A10 | NC | 1 | 1 |
| III-1487 | A12 | NC | 1 | 1 |
| III-1488 | A15 | NC | 1 | 1 |
| III-1489 | A18 | NC | 1 | 1 |
| III-1490 | A19 | NC | 1 | 1 |
| III-1491 | A20 | NC | 1 | 1 |
| III-1492 | A21 | NC | 1 | 1 |
| III-1493 | A22 | NC | 1 | 1 |
| III-1494 | A23 | NC | 1 | 1 |
| III-1495 | A26 | NC | 1 | 1 |
| III-1496 | A30 | NC | 1 | 1 |
| III-1497 | A31 | NC | 1 | 1 |
| III-1498 | A32 | NO | 1 | 1 |
| III-1499 | A33 | NC | 1 | 1 |
| III-1500 | A34 | NO | 1 | 1 |
| III-1501 | A35 | NC | 1 | 1 |
| III-1502 | A36 | NC | 1 | 1 |
| III-1503 | A37 | NC | 1 | 1 |

TABLE 41

(III)

| Compound No. | R¹ | R² | p | q |
|---|---|---|---|---|
| III-1504 | A38 | NC | 1 | 1 |
| III-1505 | A39 | NC | 1 | 1 |
| III-1506 | A40 | NC | 1 | 1 |
| III-1507 | A42 | NC | 1 | 1 |
| III-1508 | A43 | NC | 1 | 1 |
| III-1509 | A44 | NC | 1 | 1 |
| III-1510 | A45 | NC | 1 | 1 |
| III-1511 | A46 | NC | 1 | 1 |
| III-1512 | A47 | NC | 1 | 1 |
| III-1513 | A49 | NC | 1 | 1 |
| III-1514 | A50 | NC | 1 | 1 |
| III-1515 | A51 | NC | 1 | 1 |
| III-1516 | A52 | NC | 1 | 1 |
| III-1517 | A53 | NC | 1 | 1 |
| III-1518 | A54 | NC | 1 | 1 |
| III-1519 | A55 | NC | 1 | 1 |

TABLE 41-continued (III)

| Compound No. | R¹ | R² | p | q |
|---|---|---|---|---|
| III-1520 | A76 | NC | 1 | 1 |
| III-1521 | A77 | NC | 1 | 1 |
| III-1522 | A78 | NC | 1 | 1 |
| III-1523 | A79 | NC | 1 | 1 |
| III-1524 | A1 | NC | 2 | 1 |
| III-1525 | A2 | NC | 2 | 1 |
| III-1526 | A3 | NC | 2 | 1 |
| III-1527 | A4 | NC | 2 | 1 |
| III-1528 | A12 | NC | 2 | 1 |
| III-1529 | A15 | NC | 2 | 1 |
| III-1530 | A26 | NC | 2 | 1 |
| III-1531 | A40 | NC | 2 | 1 |
| III-1532 | A42 | NC | 2 | 1 |
| III-1533 | A43 | NC | 2 | 1 |
| III-1534 | A47 | NC | 2 | 1 |
| III-1535 | A1 | NC | 3 | 1 |
| III-1536 | A2 | NC | 3 | 1 |
| III-1537 | A3 | NC | 3 | 1 |
| III-1538 | A4 | NC | 3 | 1 |
| III-1539 | A12 | NC | 3 | 1 |
| III-1540 | A15 | NC | 3 | 1 |
| III-1541 | A26 | NC | 3 | 1 |
| III-1542 | A40 | NC | 3 | 1 |
| III-1543 | A42 | NC | 3 | 1 |
| III-1544 | A43 | NC | 3 | 1 |
| III-1545 | A47 | NC | 3 | 1 |
| III-1546 | A1 | NC | 2 | 2 |
| III-1547 | A2 | NC | 2 | 2 |
| III-1548 | A3 | NC | 2 | 2 |
| III-1549 | A4 | NC | 2 | 2 |
| III-1550 | A12 | NC | 2 | 2 |
| III-1551 | A15 | NC | 2 | 2 |
| III-1552 | A26 | NC | 2 | 2 |
| III-1553 | A40 | NC | 2 | 2 |
| III-1554 | A42 | NC | 2 | 2 |
| III-1555 | A43 | NC | 2 | 2 |
| III-1556 | A47 | NC | 2 | 2 |

TABLE 42

(III)

| Compound No. | R¹ | R² | p | q |
|---|---|---|---|---|
| III-1557 | B1 | H | 1 | 1 |
| III-1558 | B3 | H | 1 | 1 |
| III-1559 | B6 | H | 1 | 1 |
| III-1560 | B7 | H | 1 | 1 |
| III-1561 | B8 | H | 1 | 1 |
| III-1562 | B9 | H | 1 | 1 |
| III-1563 | B10 | H | 1 | 1 |
| III-1564 | B11 | H | 1 | 1 |
| III-1565 | B12 | H | 1 | 1 |
| III-1566 | B15 | H | 1 | 1 |
| III-1567 | B17 | H | 1 | 1 |
| III-1568 | B18 | H | 1 | 1 |
| III-1569 | B19 | H | 1 | 1 |
| III-1570 | B20 | H | 1 | 1 |
| III-1571 | B21 | H | 1 | 1 |
| III-1572 | B22 | H | 1 | 1 |
| III-1573 | B24 | H | 1 | 1 |
| III-1574 | B27 | H | 1 | 1 |
| III-1575 | B28 | H | 1 | 1 |
| III-1576 | B29 | H | 1 | 1 |
| III-1577 | B30 | H | 1 | 1 |
| III-1578 | B31 | H | 1 | 1 |
| III-1579 | B33 | H | 1 | 1 |
| III-1580 | B34 | H | 1 | 1 |
| III-1581 | B35 | H | 1 | 1 |
| III-1582 | B37 | H | 1 | 1 |
| III-1583 | B38 | H | 1 | 1 |
| III-1584 | B39 | H | 1 | 1 |
| III-1585 | B40 | H | 1 | 1 |
| III-1586 | B41 | H | 1 | 1 |
| III-1587 | B42 | H | 1 | 1 |
| III-1588 | B43 | H | 1 | 1 |
| III-1589 | B44 | H | 1 | 1 |
| III-1590 | B45 | H | 1 | 1 |
| III-1591 | B46 | H | 1 | 1 |
| III-1592 | B47 | H | 1 | 1 |
| III-1593 | B48 | H | 1 | 1 |
| III-1594 | B49 | H | 1 | 1 |
| III-1595 | B50 | H | 1 | 1 |
| III-1596 | B51 | H | 1 | 1 |
| III-1597 | B54 | H | 1 | 1 |
| III-1598 | B57 | H | 1 | 1 |
| III-1599 | B58 | H | 1 | 1 |
| III-1600 | B59 | H | 1 | 1 |
| III-1601 | B60 | H | 1 | 1 |
| III-1602 | B61 | H | 1 | 1 |
| III-1603 | B62 | H | 1 | 1 |
| III-1604 | B63 | H | 1 | 1 |
| III-1605 | B66 | H | 1 | 1 |
| III-1606 | B69 | H | 1 | 1 |
| III-1607 | B70 | H | 1 | 1 |
| III-1608 | B71 | H | 1 | 1 |
| III-1609 | B72 | H | 1 | 1 |
| III-1610 | B73 | H | 1 | 1 |

TABLE 43

(III)

| Compound No. | R¹ | R² | p | q |
|---|---|---|---|---|
| III-1611 | B74 | H | 1 | 1 |
| III-1612 | B75 | H | 1 | 1 |
| III-1613 | B76 | H | 1 | 1 |
| III-1614 | B77 | H | 1 | 1 |
| III-1615 | B78 | H | 1 | 1 |
| III-1616 | B79 | H | 1 | 1 |
| III-1617 | B83 | H | 1 | 1 |

TABLE 43-continued (III)

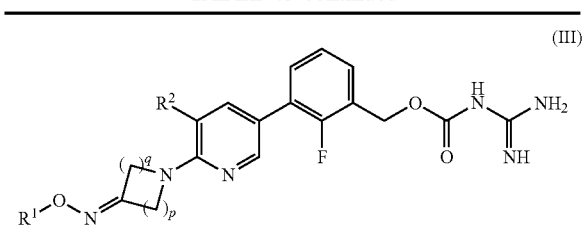

| Compound No. | R¹ | R² | p | q |
|---|---|---|---|---|
| III-1618 | B86 | H | 1 | 1 |
| III-1619 | B87 | H | 1 | 1 |
| III-1620 | B88 | H | 1 | 1 |
| III-1621 | B63 | H | 2 | 1 |
| III-1622 | B66 | H | 2 | 1 |
| III-1623 | B69 | H | 2 | 1 |
| III-1624 | B77 | H | 2 | 1 |
| III-1625 | B79 | H | 2 | 1 |
| III-1626 | B83 | H | 2 | 1 |
| III-1627 | B87 | H | 2 | 1 |
| III-1628 | B88 | H | 2 | 1 |
| III-1629 | B63 | H | 3 | 1 |
| III-1630 | B66 | H | 3 | 1 |
| III-1631 | B69 | H | 3 | 1 |
| III-1632 | B77 | H | 3 | 1 |
| III-1633 | B79 | H | 3 | 1 |
| III-1634 | B83 | H | 3 | 1 |
| III-1635 | B87 | H | 3 | 1 |
| III-1636 | B88 | H | 3 | 1 |
| III-1637 | B63 | H | 2 | 2 |
| III-1638 | B66 | H | 2 | 2 |
| III-1639 | B69 | H | 2 | 2 |
| III-1640 | B77 | H | 2 | 2 |
| III-1641 | B79 | H | 2 | 2 |
| III-1642 | B83 | H | 2 | 2 |
| III-1643 | B87 | H | 2 | 2 |
| III-1644 | B88 | H | 2 | 2 |
| III-1645 | B1 | F | 1 | 1 |
| III-1646 | B2 | F | 1 | 1 |
| III-1647 | B3 | F | 1 | 1 |
| III-1648 | B4 | F | 1 | 1 |
| III-1649 | B5 | F | 1 | 1 |
| III-1650 | B6 | F | 1 | 1 |
| III-1651 | B7 | F | 1 | 1 |
| III-1652 | B8 | F | 1 | 1 |
| III-1653 | B9 | F | 1 | 1 |
| III-1654 | B10 | F | 1 | 1 |
| III-1655 | B11 | F | 1 | 1 |
| III-1656 | B12 | F | 1 | 1 |
| III-1657 | B13 | F | 1 | 1 |
| III-1658 | B14 | F | 1 | 1 |
| III-1659 | B15 | F | 1 | 1 |
| III-1660 | B16 | F | 1 | 1 |
| III-1661 | B17 | F | 1 | 1 |
| III-1662 | B18 | F | 1 | 1 |
| III-1663 | B19 | F | 1 | 1 |
| III-1664 | B20 | F | 1 | 1 |
| III-1665 | B21 | F | 1 | 1 |

TABLE 44

(III)

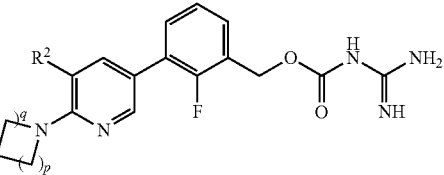

| Compound No. | R¹ | R² | p | q |
|---|---|---|---|---|
| III-1666 | B22 | F | 1 | 1 |
| III-1667 | B23 | F | 1 | 1 |
| III-1668 | B24 | F | 1 | 1 |
| III-1669 | B25 | F | 1 | 1 |
| III-1670 | B26 | F | 1 | 1 |
| III-1671 | B27 | F | 1 | 1 |
| III-1672 | B28 | F | 1 | 1 |
| III-1673 | B29 | F | 1 | 1 |
| III-1674 | B30 | F | 1 | 1 |
| III-1675 | B31 | F | 1 | 1 |
| III-1676 | B32 | F | 1 | 1 |
| III-1677 | B33 | F | 1 | 1 |
| III-1678 | B34 | F | 1 | 1 |
| III-1679 | B35 | F | 1 | 1 |
| III-1680 | B36 | F | 1 | 1 |
| III-1681 | B37 | F | 1 | 1 |
| III-1682 | B38 | F | 1 | 1 |
| III-1683 | B39 | F | 1 | 1 |
| III-1684 | B40 | F | 1 | 1 |
| III-1685 | B41 | F | 1 | 1 |
| III-1686 | B42 | F | 1 | 1 |
| III-1687 | B43 | F | 1 | 1 |
| III-1688 | B44 | F | 1 | 1 |
| III-1689 | B45 | F | 1 | 1 |
| III-1690 | B46 | F | 1 | 1 |
| III-1691 | B47 | F | 1 | 1 |
| III-1692 | B48 | F | 1 | 1 |
| III-1693 | B49 | F | 1 | 1 |
| III-1694 | B50 | F | 1 | 1 |
| III-1695 | B51 | F | 1 | 1 |
| III-1696 | B52 | F | 1 | 1 |
| III-1697 | B53 | F | 1 | 1 |
| III-1698 | B54 | F | 1 | 1 |
| III-1699 | B55 | F | 1 | 1 |
| III-1700 | B56 | F | 1 | 1 |
| III-1701 | B57 | F | 1 | 1 |
| III-1702 | B58 | F | 1 | 1 |
| III-1703 | B59 | F | 1 | 1 |
| III-1704 | B60 | F | 1 | 1 |
| III-1705 | B61 | F | 1 | 1 |
| III-1706 | B62 | F | 1 | 1 |
| III-1707 | B63 | F | 1 | 1 |
| III-1708 | B64 | F | 1 | 1 |
| III-1709 | B65 | F | 1 | 1 |
| III-1710 | B66 | F | 1 | 1 |
| III-1711 | B67 | F | 1 | 1 |
| III-1712 | B68 | F | 1 | 1 |
| III-1713 | B69 | F | 1 | 1 |
| III-1714 | B70 | F | 1 | 1 |
| III-1715 | B71 | F | 1 | 1 |
| III-1716 | B72 | F | 1 | 1 |
| III-1717 | B73 | F | 1 | 1 |
| III-1718 | B74 | F | 1 | 1 |
| III-1719 | B75 | F | 1 | 1 |
| III-1720 | B76 | F | 1 | 1 |

TABLE 45

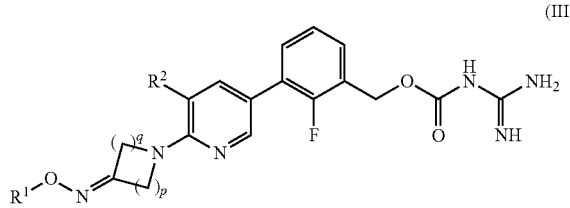

(III)

| Compound No. | R¹ | R² | p | q |
|---|---|---|---|---|
| III-1721 | B77 | F | 1 | 1 |
| III-1722 | B78 | F | 1 | 1 |
| III-1723 | B79 | F | 1 | 1 |
| III-1724 | B80 | F | 1 | 1 |
| III-1725 | B81 | F | 1 | 1 |
| III-1726 | B82 | F | 1 | 1 |
| III-1727 | B83 | F | 1 | 1 |
| III-1728 | B84 | F | 1 | 1 |
| III-1729 | B85 | F | 1 | 1 |
| III-1730 | B86 | F | 1 | 1 |
| III-1731 | B87 | F | 1 | 1 |
| III-1732 | B88 | F | 1 | 1 |
| III-1733 | B89 | F | 1 | 1 |
| III-1734 | B90 | F | 1 | 1 |
| III-1735 | B91 | F | 1 | 1 |
| III-1736 | B92 | F | 1 | 1 |
| III-1737 | B93 | F | 1 | 1 |
| III-1738 | B94 | F | 1 | 1 |
| III-1739 | B95 | F | 1 | 1 |
| III-1740 | B1 | F | 2 | 1 |
| III-1741 | B3 | F | 2 | 1 |
| III-1742 | B6 | F | 2 | 1 |
| III-1743 | B7 | F | 2 | 1 |
| III-1744 | B8 | F | 2 | 1 |
| III-1745 | B9 | F | 2 | 1 |
| III-1746 | B10 | F | 2 | 1 |
| III-1747 | B11 | F | 2 | 1 |
| III-1748 | B12 | F | 2 | 1 |
| III-1749 | B15 | F | 2 | 1 |
| III-1750 | B17 | F | 2 | 1 |
| III-1751 | B18 | F | 2 | 1 |
| III-1752 | B19 | F | 2 | 1 |
| III-1753 | B20 | F | 2 | 1 |
| III-1754 | B21 | F | 2 | 1 |
| III-1755 | B22 | F | 2 | 1 |
| III-1756 | B24 | F | 2 | 1 |
| III-1757 | B27 | F | 2 | 1 |
| III-1758 | B28 | F | 2 | 1 |
| III-1759 | B29 | F | 2 | 1 |
| III-1760 | B30 | F | 2 | 1 |
| III-1761 | B31 | F | 2 | 1 |
| III-1762 | B33 | F | 2 | 1 |
| III-1763 | B34 | F | 2 | 1 |
| III-1764 | B35 | F | 2 | 1 |
| III-1765 | B37 | F | 2 | 1 |
| III-1766 | B38 | F | 2 | 1 |
| III-1767 | B39 | F | 2 | 1 |
| III-1768 | B40 | F | 2 | 1 |
| III-1769 | B41 | F | 2 | 1 |
| III-1770 | B42 | F | 2 | 1 |
| III-1771 | B43 | F | 2 | 1 |
| III-1772 | B44 | F | 2 | 1 |
| III-1773 | B45 | F | 2 | 1 |
| III-1774 | B46 | F | 2 | 1 |
| III-1775 | B47 | F | 2 | 1 |

TABLE 46

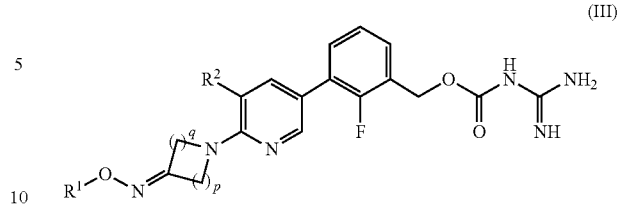

(III)

| Compound No. | R¹ | R² | p | q |
|---|---|---|---|---|
| III-1776 | B48 | F | 2 | 1 |
| III-1777 | B49 | F | 2 | 1 |
| III-1778 | B50 | F | 2 | 1 |
| III-1779 | B51 | F | 2 | 1 |
| III-1780 | B54 | F | 2 | 1 |
| III-1781 | B57 | F | 2 | 1 |
| III-1782 | B58 | F | 2 | 1 |
| III-1783 | B59 | F | 2 | 1 |
| III-1784 | B60 | F | 2 | 1 |
| III-1785 | B61 | F | 2 | 1 |
| III-1786 | B62 | F | 2 | 1 |
| III-1787 | B63 | F | 2 | 1 |
| III-1788 | B66 | F | 2 | 1 |
| III-1789 | B69 | F | 2 | 1 |
| III-1790 | B70 | F | 2 | 1 |
| III-1791 | B71 | F | 2 | 1 |
| III-1792 | B72 | F | 2 | 1 |
| III-1793 | B73 | F | 2 | 1 |
| III-1794 | B74 | F | 2 | 1 |
| III-1795 | B75 | F | 2 | 1 |
| III-1796 | B76 | F | 2 | 1 |
| III-1797 | B77 | F | 2 | 1 |
| III-1798 | B78 | F | 2 | 1 |
| III-1799 | B79 | F | 2 | 1 |
| III-1800 | B83 | F | 2 | 1 |
| III-1801 | B86 | F | 2 | 1 |
| III-1802 | B87 | F | 2 | 1 |
| III-1803 | B88 | F | 2 | 1 |
| III-1804 | B89 | F | 2 | 1 |
| III-1805 | B90 | F | 2 | 1 |
| III-1806 | B91 | F | 2 | 1 |
| III-1807 | B92 | F | 2 | 1 |
| III-1808 | B93 | F | 2 | 1 |
| III-1809 | B94 | F | 2 | 1 |
| III-1810 | B95 | F | 2 | 1 |
| III-1811 | B1 | F | 3 | 1 |
| III-1812 | B3 | F | 3 | 1 |
| III-1813 | B6 | F | 3 | 1 |
| III-1814 | B7 | F | 3 | 1 |
| III-1815 | B8 | F | 3 | 1 |
| III-1816 | B9 | F | 3 | 1 |
| III-1817 | B10 | F | 3 | 1 |
| III-1818 | B11 | F | 3 | 1 |
| III-1819 | B12 | F | 3 | 1 |
| III-1820 | B15 | F | 3 | 1 |
| III-1821 | B17 | F | 3 | 1 |
| III-1822 | B18 | F | 3 | 1 |
| III-1823 | B19 | F | 3 | 1 |
| III-1824 | B20 | F | 3 | 1 |
| III-1825 | B21 | F | 3 | 1 |
| III-1826 | B22 | F | 3 | 1 |
| III-1827 | B24 | F | 3 | 1 |
| III-1828 | B27 | F | 3 | 1 |
| III-1829 | B28 | F | 3 | 1 |
| III-1830 | B29 | F | 3 | 1 |

TABLE 47

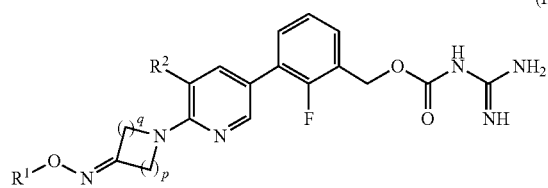
(III)

| Compound No. | R¹ | R² | p | q |
|---|---|---|---|---|
| III-1831 | B30 | F | 3 | 1 |
| III-1832 | B31 | F | 3 | 1 |
| III-1833 | B33 | F | 3 | 1 |
| III-1834 | B34 | F | 3 | 1 |
| III-1835 | B35 | F | 3 | 1 |
| III-1836 | B37 | F | 3 | 1 |
| III-1837 | B38 | F | 3 | 1 |
| III-1838 | B39 | F | 3 | 1 |
| III-1839 | B40 | F | 3 | 1 |
| III-1840 | B41 | F | 3 | 1 |
| III-1841 | B42 | F | 3 | 1 |
| III-1842 | B43 | F | 3 | 1 |
| III-1843 | B44 | F | 3 | 1 |
| III-1844 | B45 | F | 3 | 1 |
| III-1845 | B46 | F | 3 | 1 |
| III-1846 | B47 | F | 3 | 1 |
| III-1847 | B48 | F | 3 | 1 |
| III-1848 | B49 | F | 3 | 1 |
| III-1849 | B50 | F | 3 | 1 |
| III-1850 | B51 | F | 3 | 1 |
| III-1851 | B54 | F | 3 | 1 |
| III-1852 | B57 | F | 3 | 1 |
| III-1853 | B58 | F | 3 | 1 |
| III-1854 | B59 | F | 3 | 1 |
| III-1855 | B60 | F | 3 | 1 |
| III-1856 | B61 | F | 3 | 1 |
| III-1857 | B62 | F | 3 | 1 |
| III-1858 | B63 | F | 3 | 1 |
| III-1859 | B66 | F | 3 | 1 |
| III-1860 | B69 | F | 3 | 1 |
| III-1861 | B70 | F | 3 | 1 |
| III-1862 | B71 | F | 3 | 1 |
| III-1863 | B72 | F | 3 | 1 |
| III-1864 | B73 | F | 3 | 1 |
| III-1865 | B74 | F | 3 | 1 |
| III-1866 | B75 | F | 3 | 1 |
| III-1867 | B76 | F | 3 | 1 |
| III-1868 | B77 | F | 3 | 1 |
| III-1869 | B78 | F | 3 | 1 |
| III-1870 | B79 | F | 3 | 1 |
| III-1871 | B83 | F | 3 | 1 |
| III-1872 | B86 | F | 3 | 1 |
| III-1873 | B87 | F | 3 | 1 |
| III-1874 | B88 | F | 3 | 1 |
| III-1875 | B1 | F | 2 | 2 |
| III-1876 | B3 | F | 2 | 2 |
| III-1877 | B6 | F | 2 | 2 |
| III-1878 | B7 | F | 2 | 2 |
| III-1879 | B8 | F | 2 | 2 |
| III-1880 | B9 | F | 2 | 2 |
| III-1881 | B10 | F | 2 | 2 |
| III-1882 | B11 | F | 2 | 2 |
| III-1883 | B12 | F | 2 | 2 |
| III-1884 | B15 | F | 2 | 2 |
| III-1885 | B17 | F | 2 | 2 |

TABLE 48

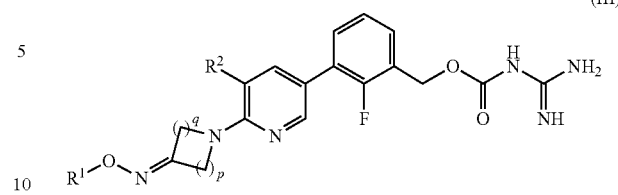
(III)

| Compound No. | R¹ | R² | p | q |
|---|---|---|---|---|
| III-1886 | B18 | F | 2 | 2 |
| III-1887 | B19 | F | 2 | 2 |
| III-1888 | B20 | F | 2 | 2 |
| III-1889 | B21 | F | 2 | 2 |
| III-1890 | B22 | F | 2 | 2 |
| III-1891 | B24 | F | 2 | 2 |
| III-1892 | B27 | F | 2 | 2 |
| III-1893 | B28 | F | 2 | 2 |
| III-1894 | B29 | F | 2 | 2 |
| III-1895 | B30 | F | 2 | 2 |
| III-1896 | B31 | F | 2 | 2 |
| III-1897 | B33 | F | 2 | 2 |
| III-1898 | B34 | F | 2 | 2 |
| III-1899 | B35 | F | 2 | 2 |
| III-1900 | B37 | F | 2 | 2 |
| III-1901 | B38 | F | 2 | 2 |
| III-1902 | B39 | F | 2 | 2 |
| III-1903 | B40 | F | 2 | 2 |
| III-1904 | B41 | F | 2 | 2 |
| III-1905 | B42 | F | 2 | 2 |
| III-1906 | B43 | F | 2 | 2 |
| III-1907 | B44 | F | 2 | 2 |
| III-1908 | B45 | F | 2 | 2 |
| III-1909 | B46 | F | 2 | 2 |
| III-1910 | B47 | F | 2 | 2 |
| III-1911 | B48 | F | 2 | 2 |
| III-1912 | B49 | F | 2 | 2 |
| III-1913 | B50 | F | 2 | 2 |
| III-1914 | B51 | F | 2 | 2 |
| III-1915 | B54 | F | 2 | 2 |
| III-1916 | B57 | F | 2 | 2 |
| III-1917 | B58 | F | 2 | 2 |
| III-1918 | B59 | F | 2 | 2 |
| III-1919 | B60 | F | 2 | 2 |
| III-1920 | B61 | F | 2 | 2 |
| III-1921 | B62 | F | 2 | 2 |
| III-1922 | B63 | F | 2 | 2 |
| III-1923 | B66 | F | 2 | 2 |
| III-1924 | B69 | F | 2 | 2 |
| III-1925 | B70 | F | 2 | 2 |
| III-1926 | B71 | F | 2 | 2 |
| III-1927 | B72 | F | 2 | 2 |
| III-1928 | B73 | F | 2 | 2 |
| III-1929 | B74 | F | 2 | 2 |
| III-1930 | B75 | F | 2 | 2 |
| III-1931 | B76 | F | 2 | 2 |
| III-1932 | B77 | F | 2 | 2 |
| III-1933 | B78 | F | 2 | 2 |
| III-1934 | B79 | F | 2 | 2 |
| III-1935 | B83 | F | 2 | 2 |
| III-1936 | B86 | F | 2 | 2 |
| III-1937 | B87 | F | 2 | 2 |
| III-1938 | B88 | F | 2 | 2 |
| III-1939 | B89 | F | 2 | 2 |
| III-1940 | B90 | F | 2 | 2 |

TABLE 49

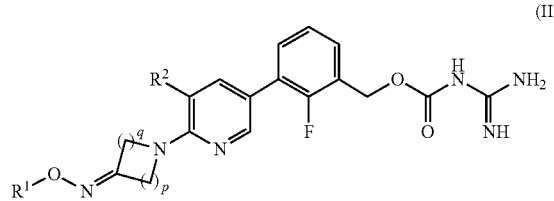
(III)

| Compound No. | R¹ | R² | p | q |
|---|---|---|---|---|
| III-1941 | B91 | F | 2 | 2 |
| III-1942 | B92 | F | 2 | 2 |
| III-1943 | B93 | F | 2 | 2 |
| III-1944 | B94 | F | 2 | 2 |
| III-1945 | B95 | F | 2 | 2 |
| III-1946 | B1 | Cl | 1 | 1 |
| III-1947 | B2 | Cl | 1 | 1 |
| III-1948 | B3 | Cl | 1 | 1 |
| III-1949 | B4 | Cl | 1 | 1 |
| III-1950 | B5 | Cl | 1 | 1 |
| III-1951 | B6 | Cl | 1 | 1 |
| III-1952 | B7 | Cl | 1 | 1 |
| III-1953 | B8 | Cl | 1 | 1 |
| III-1954 | B9 | Cl | 1 | 1 |
| III-1955 | B10 | Cl | 1 | 1 |
| III-1956 | B11 | Cl | 1 | 1 |
| III-1957 | B12 | Cl | 1 | 1 |
| III-1958 | B13 | Cl | 1 | 1 |
| III-1959 | B14 | Cl | 1 | 1 |
| III-1960 | B15 | Cl | 1 | 1 |
| III-1961 | B16 | Cl | 1 | 1 |
| III-1962 | B17 | Cl | 1 | 1 |
| III-1963 | B18 | Cl | 1 | 1 |
| III-1964 | B19 | Cl | 1 | 1 |
| III-1965 | B20 | Cl | 1 | 1 |
| III-1966 | B21 | Cl | 1 | 1 |
| III-1967 | B22 | Cl | 1 | 1 |
| III-1968 | B23 | Cl | 1 | 1 |
| III-1969 | B24 | Cl | 1 | 1 |
| III-1970 | B25 | Cl | 1 | 1 |
| III-1971 | B26 | Cl | 1 | 1 |
| III-1972 | B27 | Cl | 1 | 1 |
| III-1973 | B28 | Cl | 1 | 1 |
| III-1974 | B29 | Cl | 1 | 1 |
| III-1975 | B30 | Cl | 1 | 1 |
| III-1976 | B31 | Cl | 1 | 1 |
| III-1977 | B32 | Cl | 1 | 1 |
| III-1978 | B33 | Cl | 1 | 1 |
| III-1979 | B34 | Cl | 1 | 1 |
| III-1980 | B35 | Cl | 1 | 1 |
| III-1981 | B36 | Cl | 1 | 1 |
| III-1982 | B37 | Cl | 1 | 1 |
| III-1983 | B38 | Cl | 1 | 1 |
| III-1984 | B39 | Cl | 1 | 1 |
| III-1985 | B40 | Cl | 1 | 1 |
| III-1986 | B41 | Cl | 1 | 1 |
| III-1987 | B42 | Cl | 1 | 1 |
| III-1988 | B43 | Cl | 1 | 1 |
| III-1989 | B44 | Cl | 1 | 1 |
| III-1990 | B45 | Cl | 1 | 1 |
| III-1991 | B46 | Cl | 1 | 1 |
| III-1992 | B47 | Cl | 1 | 1 |
| III-1993 | B48 | Cl | 1 | 1 |
| III-1994 | B49 | Cl | 1 | 1 |
| III-1995 | B50 | Cl | 1 | 1 |

TABLE 50

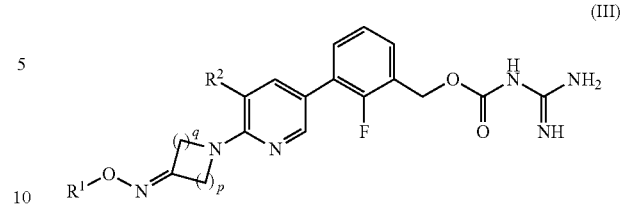
(III)

| Compound No. | R¹ | R² | p | q |
|---|---|---|---|---|
| III-1996 | B51 | Cl | 1 | 1 |
| III-1997 | B52 | Cl | 1 | 1 |
| III-1998 | B53 | Cl | 1 | 1 |
| III-1999 | B54 | Cl | 1 | 1 |
| III-2000 | B55 | Cl | 1 | 1 |
| III-2001 | B56 | Cl | 1 | 1 |
| III-2002 | B57 | Cl | 1 | 1 |
| III-2003 | B58 | Cl | 1 | 1 |
| III-2004 | B59 | Cl | 1 | 1 |
| III-2005 | B60 | Cl | 1 | 1 |
| III-2006 | B61 | Cl | 1 | 1 |
| III-2007 | B62 | Cl | 1 | 1 |
| III-2008 | B63 | Cl | 1 | 1 |
| III-2009 | B64 | Cl | 1 | 1 |
| III-2010 | B65 | Cl | 1 | 1 |
| III-2011 | B66 | Cl | 1 | 1 |
| III-2012 | B67 | Cl | 1 | 1 |
| III-2013 | B68 | Cl | 1 | 1 |
| III-2014 | B69 | Cl | 1 | 1 |
| III-2015 | B70 | Cl | 1 | 1 |
| III-2016 | B71 | Cl | 1 | 1 |
| III-2017 | B72 | Cl | 1 | 1 |
| III-2018 | B73 | Cl | 1 | 1 |
| III-2019 | B74 | Cl | 1 | 1 |
| III-2020 | B75 | Cl | 1 | 1 |
| III-2021 | B76 | Cl | 1 | 1 |
| III-2022 | B77 | Cl | 1 | 1 |
| III-2023 | B78 | Cl | 1 | 1 |
| III-2024 | B79 | Cl | 1 | 1 |
| III-2025 | B80 | Cl | 1 | 1 |
| III-2026 | B81 | Cl | 1 | 1 |
| III-2027 | B82 | Cl | 1 | 1 |
| III-2028 | B83 | Cl | 1 | 1 |
| III-2029 | B84 | Cl | 1 | 1 |
| III-2030 | B85 | Cl | 1 | 1 |
| III-2031 | B86 | Cl | 1 | 1 |
| III-2032 | B87 | Cl | 1 | 1 |
| III-2033 | B88 | Cl | 1 | 1 |
| III-2034 | B89 | Cl | 1 | 1 |
| III-2035 | B90 | Cl | 1 | 1 |
| III-2036 | B91 | Cl | 1 | 1 |
| III-2037 | B92 | Cl | 1 | 1 |
| III-2038 | B93 | Cl | 1 | 1 |
| III-2039 | B94 | Cl | 1 | 1 |
| III-2040 | B95 | Cl | 1 | 1 |
| III-2041 | B1 | Cl | 2 | 1 |
| III-2042 | B3 | Cl | 2 | 1 |
| III-2043 | B6 | Cl | 2 | 1 |
| III-2044 | B7 | Cl | 2 | 1 |
| III-2045 | B8 | Cl | 2 | 1 |
| III-2046 | B9 | Cl | 2 | 1 |
| III-2047 | B10 | Cl | 2 | 1 |
| III-2048 | B11 | Cl | 2 | 1 |
| III-2049 | B12 | Cl | 2 | 1 |
| III-2050 | B15 | Cl | 2 | 1 |

TABLE 51

(III)

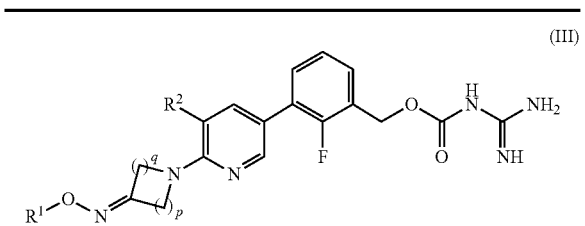

| Compound No. | R¹ | R² | p | q |
|---|---|---|---|---|
| III-2051 | B17 | Cl | 2 | 1 |
| III-2052 | B18 | Cl | 2 | 1 |
| III-2053 | B19 | Cl | 2 | 1 |
| III-2054 | B20 | Cl | 2 | 1 |
| III-2055 | B21 | Cl | 2 | 1 |
| III-2056 | B22 | Cl | 2 | 1 |
| III-2057 | B24 | Cl | 2 | 1 |
| III-2058 | B27 | Cl | 2 | 1 |
| III-2059 | B28 | Cl | 2 | 1 |
| III-2060 | B29 | Cl | 2 | 1 |
| III-2061 | B30 | Cl | 2 | 1 |
| III-2062 | B31 | Cl | 2 | 1 |
| III-2063 | B33 | Cl | 2 | 1 |
| III-2064 | B34 | Cl | 2 | 1 |
| III-2065 | B35 | Cl | 2 | 1 |
| III-2066 | B37 | Cl | 2 | 1 |
| III-2067 | B38 | Cl | 2 | 1 |
| III-2068 | B39 | Cl | 2 | 1 |
| III-2069 | B40 | Cl | 2 | 1 |
| III-2070 | B41 | Cl | 2 | 1 |
| III-2071 | B42 | Cl | 2 | 1 |
| III-2072 | B43 | Cl | 2 | 1 |
| III-2073 | B44 | Cl | 2 | 1 |
| III-2074 | B45 | Cl | 2 | 1 |
| III-2075 | B46 | Cl | 2 | 1 |
| III-2076 | B47 | Cl | 2 | 1 |
| III-2077 | B48 | Cl | 2 | 1 |
| III-2078 | B49 | Cl | 2 | 1 |
| III-2079 | B50 | Cl | 2 | 1 |
| III-2080 | B51 | Cl | 2 | 1 |
| III-2081 | B54 | Cl | 2 | 1 |
| III-2082 | B57 | Cl | 2 | 1 |
| III-2083 | B58 | Cl | 2 | 1 |
| III-2084 | B59 | Cl | 2 | 1 |
| III-2085 | B60 | Cl | 2 | 1 |
| III-2086 | B61 | Cl | 2 | 1 |
| III-2087 | B62 | Cl | 2 | 1 |
| III-2088 | B63 | Cl | 2 | 1 |
| III-2089 | B66 | Cl | 2 | 1 |
| III-2090 | B69 | Cl | 2 | 1 |
| III-2091 | B70 | Cl | 2 | 1 |
| III-2092 | B71 | Cl | 2 | 1 |
| III-2093 | B72 | Cl | 2 | 1 |
| III-2094 | B73 | Cl | 2 | 1 |
| III-2095 | B74 | Cl | 2 | 1 |
| III-2096 | B75 | Cl | 2 | 1 |
| III-2097 | B76 | Cl | 2 | 1 |
| III-2098 | B77 | Cl | 2 | 1 |
| III-2099 | B78 | Cl | 2 | 1 |
| III-2100 | B79 | Cl | 2 | 1 |
| III-2101 | B83 | Cl | 2 | 1 |
| III-2102 | B86 | Cl | 2 | 1 |
| III-2103 | B87 | Cl | 2 | 1 |
| III-2104 | B88 | Cl | 2 | 1 |
| III-2105 | B89 | Cl | 2 | 1 |

TABLE 52

(III)

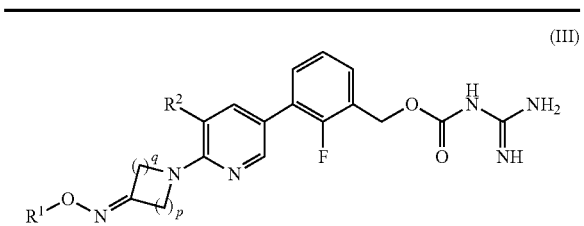

| Compound No. | R¹ | R² | p | q |
|---|---|---|---|---|
| III-2106 | B90 | Cl | 2 | 1 |
| III-2107 | B91 | Cl | 2 | 1 |
| III-2108 | B92 | Cl | 2 | 1 |
| III-2109 | B93 | Cl | 2 | 1 |
| III-2110 | B94 | Cl | 2 | 1 |
| III-2111 | B95 | Cl | 2 | 1 |
| III-2112 | B1 | Cl | 3 | 1 |
| III-2113 | B3 | Cl | 3 | 1 |
| III-2114 | B6 | Cl | 3 | 1 |
| III-2115 | B7 | Cl | 3 | 1 |
| III-2116 | B8 | Cl | 3 | 1 |
| III-2117 | B9 | Cl | 3 | 1 |
| III-2118 | B10 | Cl | 3 | 1 |
| III-2119 | B11 | Cl | 3 | 1 |
| III-2120 | B12 | Cl | 3 | 1 |
| III-2121 | B15 | Cl | 3 | 1 |
| III-2122 | B17 | Cl | 3 | 1 |
| III-2123 | B18 | Cl | 3 | 1 |
| III-2124 | B19 | Cl | 3 | 1 |
| III-2125 | B20 | Cl | 3 | 1 |
| III-2126 | B21 | Cl | 3 | 1 |
| III-2127 | B22 | Cl | 3 | 1 |
| III-2128 | B24 | Cl | 3 | 1 |
| III-2129 | B27 | Cl | 3 | 1 |
| III-2130 | B28 | Cl | 3 | 1 |
| III-2131 | B29 | Cl | 3 | 1 |
| III-2132 | B30 | Cl | 3 | 1 |
| III-2133 | B31 | Cl | 3 | 1 |
| III-2134 | B33 | Cl | 3 | 1 |
| III-2135 | B34 | Cl | 3 | 1 |
| III-2136 | B35 | Cl | 3 | 1 |
| III-2137 | B37 | Cl | 3 | 1 |
| III-2138 | B38 | Cl | 3 | 1 |
| III-2139 | B39 | Cl | 3 | 1 |
| III-2140 | B40 | Cl | 3 | 1 |
| III-2141 | B41 | Cl | 3 | 1 |
| III-2142 | B42 | Cl | 3 | 1 |
| III-2143 | B43 | Cl | 3 | 1 |
| III-2144 | B44 | Cl | 3 | 1 |
| III-2145 | B45 | Cl | 3 | 1 |
| III-2146 | B46 | Cl | 3 | 1 |
| III-2147 | B47 | Cl | 3 | 1 |
| III-2148 | B48 | Cl | 3 | 1 |
| III-2149 | B49 | Cl | 3 | 1 |
| III-2150 | B50 | Cl | 3 | 1 |
| III-2151 | B51 | Cl | 3 | 1 |
| III-2152 | B54 | Cl | 3 | 1 |
| III-2153 | B57 | Cl | 3 | 1 |
| III-2154 | B58 | Cl | 3 | 1 |
| III-2155 | B59 | Cl | 3 | 1 |
| III-2156 | B60 | Cl | 3 | 1 |
| III-2157 | B61 | Cl | 3 | 1 |
| III-2158 | B62 | Cl | 3 | 1 |
| III-2159 | B63 | Cl | 3 | 1 |
| III-2160 | B66 | Cl | 3 | 1 |

TABLE 53

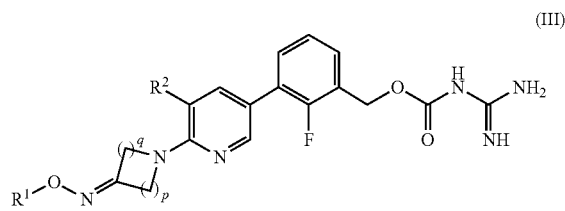

(III)

| Compound No. | R¹ | R² | p | q |
|---|---|---|---|---|
| III-2161 | B69 | Cl | 3 | 1 |
| III-2162 | B70 | Cl | 3 | 1 |
| III-2163 | B71 | Cl | 3 | 1 |
| III-2164 | B72 | Cl | 3 | 1 |
| III-2165 | B73 | Cl | 3 | 1 |
| III-2166 | B74 | Cl | 3 | 1 |
| III-2167 | B75 | Cl | 3 | 1 |
| III-2168 | B76 | Cl | 3 | 1 |
| III-2169 | B77 | Cl | 3 | 1 |
| III-2170 | B78 | Cl | 3 | 1 |
| III-2171 | B79 | Cl | 3 | 1 |
| III-2172 | B83 | Cl | 3 | 1 |
| III-2173 | B86 | Cl | 3 | 1 |
| III-2174 | B87 | Cl | 3 | 1 |
| III-2175 | B88 | Cl | 3 | 1 |
| III-2176 | B1 | Cl | 2 | 2 |
| III-2177 | B3 | Cl | 2 | 2 |
| III-2178 | B6 | Cl | 2 | 2 |
| III-2179 | B7 | Cl | 2 | 2 |
| III-2180 | B8 | Cl | 2 | 2 |
| III-2181 | B9 | Cl | 2 | 2 |
| III-2182 | B10 | Cl | 2 | 2 |
| III-2183 | B11 | Cl | 2 | 2 |
| III-2184 | B12 | Cl | 2 | 2 |
| III-2185 | B15 | Cl | 2 | 2 |
| III-2186 | B17 | Cl | 2 | 2 |
| III-2187 | B18 | Cl | 2 | 2 |
| III-2188 | B19 | Cl | 2 | 2 |
| III-2189 | B20 | Cl | 2 | 2 |
| III-2190 | B21 | Cl | 2 | 2 |
| III-2191 | B22 | Cl | 2 | 2 |
| III-2192 | B24 | Cl | 2 | 2 |
| III-2193 | B27 | Cl | 2 | 2 |
| III-2194 | B28 | Cl | 2 | 2 |
| III-2195 | B29 | Cl | 2 | 2 |
| III-2196 | B30 | Cl | 2 | 2 |
| III-2197 | B31 | Cl | 2 | 2 |
| III-2198 | B33 | Cl | 2 | 2 |
| III-2199 | B34 | Cl | 2 | 2 |
| III-2200 | B35 | Cl | 2 | 2 |
| III-2201 | B37 | Cl | 2 | 2 |
| III-2202 | B38 | Cl | 2 | 2 |
| III-2203 | B39 | Cl | 2 | 2 |
| III-2204 | B40 | Cl | 2 | 2 |
| III-2205 | B41 | Cl | 2 | 2 |
| III-2206 | B42 | Cl | 2 | 2 |
| III-2207 | B43 | Cl | 2 | 2 |
| III-2208 | B44 | Cl | 2 | 2 |
| III-2209 | B45 | Cl | 2 | 2 |
| III-2210 | B46 | Cl | 2 | 2 |
| III-2211 | B47 | Cl | 2 | 2 |
| III-2212 | B48 | Cl | 2 | 2 |
| III-2213 | B49 | Cl | 2 | 2 |
| III-2214 | B50 | Cl | 2 | 2 |
| III-2215 | B51 | Cl | 2 | 2 |

TABLE 54

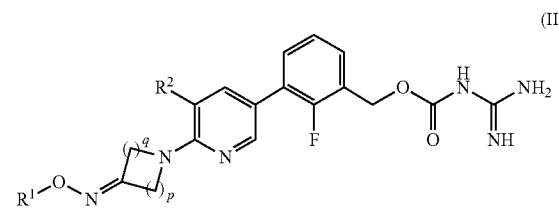

(III)

| Compound No. | R¹ | R² | p | q |
|---|---|---|---|---|
| III-2216 | B54 | Cl | 2 | 2 |
| III-2217 | B57 | Cl | 2 | 2 |
| III-2218 | B58 | Cl | 2 | 2 |
| III-2219 | B59 | Cl | 2 | 2 |
| III-2220 | B60 | Cl | 2 | 2 |
| III-2221 | B61 | Cl | 2 | 2 |
| III-2222 | B62 | Cl | 2 | 2 |
| III-2223 | B63 | Cl | 2 | 2 |
| III-2224 | B66 | Cl | 2 | 2 |
| III-2225 | B69 | Cl | 2 | 2 |
| III-2226 | B70 | Cl | 2 | 2 |
| III-2227 | B71 | Cl | 2 | 2 |
| III-2228 | B72 | Cl | 2 | 2 |
| III-2229 | B73 | Cl | 2 | 2 |
| III-2230 | B74 | Cl | 2 | 2 |
| III-2231 | B75 | Cl | 2 | 2 |
| III-2232 | B76 | Cl | 2 | 2 |
| III-2233 | B77 | Cl | 2 | 2 |
| III-2234 | B78 | Cl | 2 | 2 |
| III-2235 | B79 | Cl | 2 | 2 |
| III-2236 | B83 | Cl | 2 | 2 |
| III-2237 | B86 | Cl | 2 | 2 |
| III-2238 | B87 | Cl | 2 | 2 |
| III-2239 | B88 | Cl | 2 | 2 |
| III-2240 | B1 | Br | 1 | 1 |
| III-2241 | B3 | Br | 1 | 1 |
| III-2242 | B6 | Br | 1 | 1 |
| III-2243 | B7 | Br | 1 | 1 |
| III-2244 | B8 | Br | 1 | 1 |
| III-2245 | B39 | Br | 1 | 1 |
| III-2246 | B10 | Br | 1 | 1 |
| III-2247 | B11 | Br | 1 | 1 |
| III-2248 | B12 | Br | 1 | 1 |
| III-2249 | B15 | Br | 1 | 1 |
| III-2250 | B17 | Br | 1 | 1 |
| III-2251 | B18 | Br | 1 | 1 |
| III-2252 | B19 | Br | 1 | 1 |
| III-2253 | B20 | Br | 1 | 1 |
| III-2254 | B21 | Br | 1 | 1 |
| III-2255 | B22 | Br | 1 | 1 |
| III-2256 | B24 | Br | 1 | 1 |
| III-2257 | B27 | Br | 1 | 1 |
| III-2258 | B28 | Br | 1 | 1 |
| III-2259 | B29 | Br | 1 | 1 |
| III-2260 | B30 | Br | 1 | 1 |
| III-2261 | B31 | Br | 1 | 1 |
| III-2262 | B33 | Br | 1 | 1 |
| III-2263 | B34 | Br | 1 | 1 |
| III-2264 | B35 | Br | 1 | 1 |
| III-2265 | B37 | Br | 1 | 1 |
| III-2266 | B38 | Br | 1 | 1 |
| III-2267 | B39 | Br | 1 | 1 |
| III-2268 | B40 | Br | 1 | 1 |
| III-2269 | B41 | Br | 1 | 1 |
| III-2270 | B42 | Br | 1 | 1 |

TABLE 55

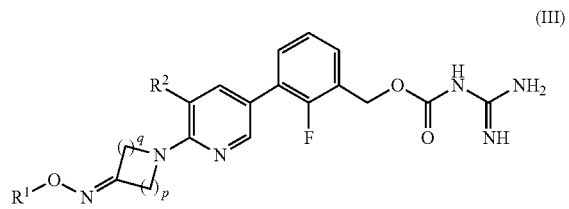
(III)

| Compound No. | R¹ | R² | p | q |
|---|---|---|---|---|
| III-2271 | B43 | Br | 1 | 1 |
| III-2272 | B44 | Br | 1 | 1 |
| III-2273 | B45 | Br | 1 | 1 |
| III-2274 | B46 | Br | 1 | 1 |
| III-2275 | B47 | Br | 1 | 1 |
| III-2276 | B48 | Br | 1 | 1 |
| III-2277 | B49 | Br | 1 | 1 |
| III-2278 | B50 | Br | 1 | 1 |
| III-2279 | B51 | Br | 1 | 1 |
| III-2280 | B54 | Br | 1 | 1 |
| III-2281 | B57 | Br | 1 | 1 |
| III-2282 | B58 | Br | 1 | 1 |
| III-2283 | B59 | Br | 1 | 1 |
| III-2284 | B60 | Br | 1 | 1 |
| III-2285 | B61 | Br | 1 | 1 |
| III-2286 | B62 | Br | 1 | 1 |
| III-2287 | B63 | Br | 1 | 1 |
| III-2288 | B66 | Br | 1 | 1 |
| III-2289 | B69 | Br | 1 | 1 |
| III-2290 | B70 | Br | 1 | 1 |
| III-2291 | B71 | Br | 1 | 1 |
| III-2292 | B72 | Br | 1 | 1 |
| III-2293 | B73 | Br | 1 | 1 |
| III-2294 | B74 | Br | 1 | 1 |
| III-2295 | B75 | Br | 1 | 1 |
| III-2296 | B76 | Br | 1 | 1 |
| III-2297 | B77 | Br | 1 | 1 |
| III-2298 | B78 | Br | 1 | 1 |
| III-2299 | B79 | Br | 1 | 1 |
| III-2300 | B83 | Br | 1 | 1 |
| III-2301 | B86 | Br | 1 | 1 |
| III-2302 | B87 | Br | 1 | 1 |
| III-2303 | B88 | Br | 1 | 1 |
| III-2304 | B89 | Br | 1 | 1 |
| III-2305 | B90 | Br | 1 | 1 |
| III-2306 | B91 | Br | 1 | 1 |
| III-2307 | B92 | Br | 1 | 1 |
| III-2308 | B93 | Br | 1 | 1 |
| III-2309 | B94 | Br | 1 | 1 |
| III-2310 | B95 | Br | 1 | 1 |
| III-2311 | B1 | Br | 2 | 1 |
| III-2312 | B3 | Br | 2 | 1 |
| III-2313 | B6 | Br | 2 | 1 |
| III-2314 | B7 | Br | 2 | 1 |
| III-2315 | B8 | Br | 2 | 1 |
| III-2316 | B9 | Br | 2 | 1 |
| III-2317 | B10 | Br | 2 | 1 |
| III-2318 | B11 | Br | 2 | 1 |
| III-2319 | B12 | Br | 2 | 1 |
| III-2320 | B15 | Br | 2 | 1 |
| III-2321 | B17 | Br | 2 | 1 |
| III-2322 | B18 | Br | 2 | 1 |
| III-2323 | B19 | Br | 2 | 1 |
| III-2324 | B20 | Br | 2 | 1 |
| III-2325 | B21 | Br | 2 | 1 |
| III-2326 | B22 | Br | 2 | 1 |

TABLE 56

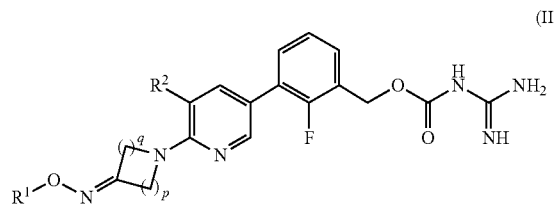
(III)

| Compound No. | R¹ | R² | p | q |
|---|---|---|---|---|
| III-2327 | B24 | Br | 2 | 1 |
| III-2328 | B27 | Br | 2 | 1 |
| III-2329 | B28 | Br | 2 | 1 |
| III-2330 | B29 | Br | 2 | 1 |
| III-2331 | B30 | Br | 2 | 1 |
| III-2332 | B31 | Br | 2 | 1 |
| III-2333 | B33 | Br | 2 | 1 |
| III-2334 | B34 | Br | 2 | 1 |
| III-2335 | B35 | Br | 2 | 1 |
| III-2336 | B37 | Br | 2 | 1 |
| III-2337 | B38 | Br | 2 | 1 |
| III-2338 | B39 | Br | 2 | 1 |
| III-2339 | B40 | Br | 2 | 1 |
| III-2340 | B41 | Br | 2 | 1 |
| III-2341 | B42 | Br | 2 | 1 |
| III-2342 | B43 | Br | 2 | 1 |
| III-2343 | B44 | Br | 2 | 1 |
| III-2344 | B45 | Br | 2 | 1 |
| III-2345 | B46 | Br | 2 | 1 |
| III-2346 | B47 | Br | 2 | 1 |
| III-2347 | B48 | Br | 2 | 1 |
| III-2348 | B49 | Br | 2 | 1 |
| III-2349 | B50 | Br | 2 | 1 |
| III-2350 | B51 | Br | 2 | 1 |
| III-2351 | B54 | Br | 2 | 1 |
| III-2352 | B57 | Br | 2 | 1 |
| III-2353 | B58 | Br | 2 | 1 |
| III-2354 | B59 | Br | 2 | 1 |
| III-2355 | B60 | Br | 2 | 1 |
| III-2356 | B61 | Br | 2 | 1 |
| III-2357 | B62 | Br | 2 | 1 |
| III-2358 | B63 | Br | 2 | 1 |
| III-2359 | B66 | Br | 2 | 1 |
| III-2360 | B69 | Br | 2 | 1 |
| III-2361 | B70 | Br | 2 | 1 |
| III-2362 | B71 | Br | 2 | 1 |
| III-2363 | B72 | Br | 2 | 1 |
| III-2364 | B73 | Br | 2 | 1 |
| III-2365 | B74 | Br | 2 | 1 |
| III-2366 | B75 | Br | 2 | 1 |
| III-2367 | B76 | Br | 2 | 1 |
| III-2368 | B77 | Br | 2 | 1 |
| III-2369 | B78 | Br | 2 | 1 |
| III-2370 | B79 | Br | 2 | 1 |
| III-2371 | B83 | Br | 2 | 1 |
| III-2372 | B86 | Br | 2 | 1 |
| III-2373 | B87 | Br | 2 | 1 |
| III-2374 | B88 | Br | 2 | 1 |
| III-2375 | B63 | Br | 3 | 1 |
| III-2376 | B66 | Br | 3 | 1 |
| III-2377 | B69 | Br | 3 | 1 |
| III-2378 | B77 | Br | 3 | 1 |
| III-2379 | B79 | Br | 3 | 1 |
| III-2380 | B83 | Br | 3 | 1 |
| III-2381 | B87 | Br | 3 | 1 |
| III-2382 | B88 | Br | 3 | 1 |

TABLE 57

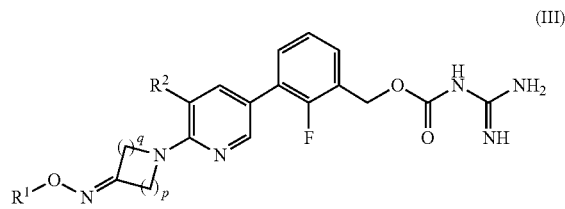
(III)

| Compound No. | R¹ | R² | p | q |
|---|---|---|---|---|
| III-2383 | B63 | Br | 2 | 2 |
| III-2384 | B66 | Br | 2 | 2 |
| III-2385 | B69 | Br | 2 | 2 |
| III-2386 | B77 | Br | 2 | 2 |
| III-2387 | B79 | Br | 2 | 2 |
| III-2388 | B83 | Br | 2 | 2 |
| III-2389 | B87 | Br | 2 | 2 |
| III-2390 | B88 | Br | 2 | 2 |
| III-2391 | B63 | I | 1 | 1 |
| III-2392 | B66 | I | 1 | 1 |
| III-2393 | B69 | I | 1 | 1 |
| III-2394 | B77 | I | 1 | 1 |
| III-2395 | B79 | I | 1 | 1 |
| III-2396 | B83 | I | 1 | 1 |
| III-2397 | B87 | I | 1 | 1 |
| III-2398 | B88 | I | 1 | 1 |
| III-2399 | B1 | Me | 1 | 1 |
| III-2400 | B3 | Me | 1 | 1 |
| III-2401 | B6 | Me | 1 | 1 |
| III-2402 | B7 | Me | 1 | 1 |
| III-2403 | B8 | Me | 1 | 1 |
| III-2404 | B9 | Me | 1 | 1 |
| III-2405 | B10 | Me | 1 | 1 |
| III-2406 | B11 | Me | 1 | 1 |
| III-2407 | B12 | Me | 1 | 1 |
| III-2408 | B15 | Me | 1 | 1 |
| III-2409 | B17 | Me | 1 | 1 |
| III-2410 | B18 | Me | 1 | 1 |
| III-2411 | B19 | Me | 1 | 1 |
| III-2412 | B20 | Me | 1 | 1 |
| III-2413 | B21 | Me | 1 | 1 |
| III-2414 | B22 | Me | 1 | 1 |
| III-2415 | B24 | Me | 1 | 1 |
| III-2416 | B27 | Me | 1 | 1 |
| III-2417 | B28 | Me | 1 | 1 |
| III-2418 | B29 | Me | 1 | 1 |
| III-2419 | B30 | Me | 1 | 1 |
| III-2420 | B31 | Me | 1 | 1 |
| III-2421 | B33 | Me | 1 | 1 |
| III-2422 | B34 | Me | 1 | 1 |
| III-2423 | B35 | Me | 1 | 1 |
| III-2424 | B37 | Me | 1 | 1 |
| III-2425 | B38 | Me | 1 | 1 |
| III-2426 | B39 | Me | 1 | 1 |
| III-2427 | B40 | Me | 1 | 1 |
| III-2428 | B41 | Me | 1 | 1 |
| III-2429 | B42 | Me | 1 | 1 |
| III-2430 | B43 | Me | 1 | 1 |
| III-2431 | B44 | Me | 1 | 1 |
| III-2432 | B45 | Me | 1 | 1 |
| III-2433 | B46 | Me | 1 | 1 |
| III-2434 | B47 | Me | 1 | 1 |
| III-2435 | B48 | Me | 1 | 1 |
| III-2436 | B49 | Me | 1 | 1 |
| III-2437 | B50 | Me | 1 | 1 |

TABLE 581

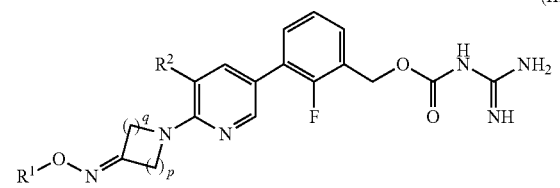
(III)

| Compound No. | R¹ | R² | p | q |
|---|---|---|---|---|
| III-2438 | B51 | Me | 1 | 1 |
| III-2439 | B54 | Me | 1 | 1 |
| III-2440 | B57 | Me | 1 | 1 |
| III-2441 | B58 | Me | 1 | 1 |
| III-2442 | B59 | Me | 1 | 1 |
| III-2443 | B60 | Me | 1 | 1 |
| III-2444 | B61 | Me | 1 | 1 |
| III-2445 | B62 | Me | 1 | 1 |
| III-2446 | B63 | Me | 1 | 1 |
| III-2447 | B66 | Me | 1 | 1 |
| III-2448 | B69 | Me | 1 | 1 |
| III-2449 | B70 | Me | 1 | 1 |
| III-2450 | B71 | Me | 1 | 1 |
| III-2451 | B72 | Me | 1 | 1 |
| III-2452 | B73 | Me | 1 | 1 |
| III-2453 | B74 | Me | 1 | 1 |
| III-2454 | B75 | Me | 1 | 1 |
| III-2455 | B76 | Me | 1 | 1 |
| III-2456 | B77 | Me | 1 | 1 |
| III-2457 | B78 | Me | 1 | 1 |
| III-2458 | B79 | Me | 1 | 1 |
| III-2459 | B83 | Me | 1 | 1 |
| III-2460 | B86 | Me | 1 | 1 |
| III-2461 | B87 | Me | 1 | 1 |
| III-2462 | B88 | Me | 1 | 1 |
| III-2463 | B89 | Me | 1 | 1 |
| III-2464 | B90 | Me | 1 | 1 |
| III-2465 | B91 | Me | 1 | 1 |
| III-2466 | B92 | Me | 1 | 1 |
| III-2467 | B93 | Me | 1 | 1 |
| III-2468 | B94 | Me | 1 | 1 |
| III-2469 | B95 | Me | 1 | 1 |
| III-2470 | B1 | Me | 2 | 1 |
| III-2471 | B3 | Me | 2 | 1 |
| III-2472 | B6 | Me | 2 | 1 |
| III-2473 | B7 | Me | 2 | 1 |
| III-2474 | B8 | Me | 2 | 1 |
| III-2475 | B9 | Me | 2 | 1 |
| III-2476 | B10 | Me | 2 | 1 |
| III-2477 | B11 | Me | 2 | 1 |
| III-2478 | B12 | Me | 2 | 1 |
| III-2479 | B15 | Me | 2 | 1 |
| III-2480 | B17 | Me | 2 | 1 |
| III-2481 | B18 | Me | 2 | 1 |
| III-2482 | B19 | Me | 2 | 1 |
| III-2483 | B20 | Me | 2 | 1 |
| III-2484 | B21 | Me | 2 | 1 |
| III-2485 | B22 | Me | 2 | 1 |
| III-2486 | B24 | Me | 2 | 1 |
| III-2487 | B27 | Me | 2 | 1 |
| III-2488 | B28 | Me | 2 | 1 |
| III-2489 | B29 | Me | 2 | 1 |
| III-2490 | B30 | Me | 2 | 1 |
| III-2491 | B31 | Me | 2 | 1 |
| III-2492 | B33 | Me | 2 | 1 |
| III-2493 | B34 | Me | 2 | 1 |

TABLE 59

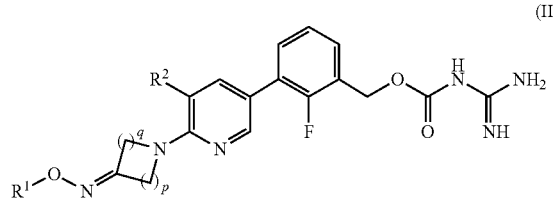
(III)

| Compound No. | R¹ | R² | p | q |
|---|---|---|---|---|
| III-2494 | B35 | Me | 2 | 1 |
| III-2495 | B37 | Me | 2 | 1 |
| III-2496 | B38 | Me | 2 | 1 |
| III-2497 | B39 | Me | 2 | 1 |
| III-2498 | B40 | Me | 2 | 1 |
| III-2499 | B41 | Me | 2 | 1 |
| III-2500 | B42 | Me | 2 | 1 |
| III-2501 | B43 | Me | 2 | 1 |
| III-2502 | B44 | Me | 2 | 1 |
| III-2503 | B45 | Me | 2 | 1 |
| III-2504 | B46 | Me | 2 | 1 |
| III-2505 | B47 | Me | 2 | 1 |
| III-2506 | B48 | Me | 2 | 1 |
| III-2507 | B49 | Me | 2 | 1 |
| III-2508 | B50 | Me | 2 | 1 |
| III-2509 | B51 | Me | 2 | 1 |
| III-2510 | B54 | Me | 2 | 1 |
| III-2511 | B57 | Me | 2 | 1 |
| III-2512 | B58 | Me | 2 | 1 |
| III-2513 | B59 | Me | 2 | 1 |
| III-2514 | B60 | Me | 2 | 1 |
| III-2515 | B61 | Me | 2 | 1 |
| III-2516 | B62 | Me | 2 | 1 |
| III-2517 | B63 | Me | 2 | 1 |
| III-2518 | B66 | Me | 2 | 1 |
| III-2519 | B69 | Me | 2 | 1 |
| III-2520 | B70 | Me | 2 | 1 |
| III-2521 | B71 | Me | 2 | 1 |
| III-2522 | B72 | Me | 2 | 1 |
| III-2523 | B73 | Me | 2 | 1 |
| III-2524 | B74 | Me | 2 | 1 |
| III-2525 | B75 | Me | 2 | 1 |
| III-2526 | B76 | Me | 2 | 1 |
| III-2527 | B77 | Me | 2 | 1 |
| III-2528 | B78 | Me | 2 | 1 |
| III-2529 | B79 | Me | 2 | 1 |
| III-2530 | B83 | Me | 2 | 1 |
| III-2531 | B86 | Me | 2 | 1 |
| III-2532 | B87 | Me | 2 | 1 |
| III-2533 | B88 | Me | 2 | 1 |
| III-2534 | B63 | Me | 3 | 1 |
| III-2535 | B66 | Me | 3 | 1 |
| III-2536 | B69 | Me | 3 | 1 |
| III-2537 | B77 | Me | 3 | 1 |
| III-2538 | B79 | Me | 3 | 1 |
| III-2539 | B83 | Me | 3 | 1 |
| III-2540 | B87 | Me | 3 | 1 |
| III-2541 | B88 | Me | 3 | 1 |
| III-2542 | B63 | Me | 2 | 2 |
| III-2543 | B66 | Me | 2 | 2 |
| III-2544 | B69 | Me | 2 | 2 |
| III-2545 | B77 | Me | 2 | 2 |
| III-2546 | B79 | Me | 2 | 2 |
| III-2547 | B83 | Me | 2 | 2 |
| III-2548 | B87 | Me | 2 | 2 |
| III-2549 | B88 | Me | 2 | 2 |

TABLE 60

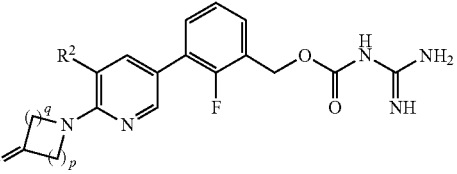
(III)

| Compound No. | R¹ | R² | p | q |
|---|---|---|---|---|
| III-2550 | B1 | Et | 1 | 1 |
| III-2551 | B3 | Et | 1 | 1 |
| III-2552 | B6 | Et | 1 | 1 |
| III-2553 | B7 | Et | 1 | 1 |
| III-2554 | B8 | Et | 1 | 1 |
| III-2555 | B9 | Et | 1 | 1 |
| III-2556 | B10 | Et | 1 | 1 |
| III-2557 | B11 | Et | 1 | 1 |
| III-2558 | B12 | Et | 1 | 1 |
| III-2559 | B15 | Et | 1 | 1 |
| III-2560 | B17 | Et | 1 | 1 |
| III-2561 | B18 | Et | 1 | 1 |
| III-2562 | B19 | Et | 1 | 1 |
| III-2563 | B20 | Et | 1 | 1 |
| III-2564 | B21 | Et | 1 | 1 |
| III-2565 | B22 | Et | 1 | 1 |
| III-2566 | B24 | Et | 1 | 1 |
| III-2567 | B27 | Et | 1 | 1 |
| III-2568 | B28 | Et | 1 | 1 |
| III-2569 | B29 | Et | 1 | 1 |
| III-2570 | B30 | Et | 1 | 1 |
| III-2571 | B31 | Et | 1 | 1 |
| III-2572 | B33 | Et | 1 | 1 |
| III-2573 | B34 | Et | 1 | 1 |
| III-2574 | B35 | Et | 1 | 1 |
| III-2575 | B37 | Et | 1 | 1 |
| III-2576 | B38 | Et | 1 | 1 |
| III-2577 | B39 | Et | 1 | 1 |
| III-2578 | B40 | Et | 1 | 1 |
| III-2579 | B41 | Et | 1 | 1 |
| III-2580 | B42 | Et | 1 | 1 |
| III-2581 | B43 | Et | 1 | 1 |
| III-2582 | B44 | Et | 1 | 1 |
| III-2583 | B45 | Et | 1 | 1 |
| III-2584 | B46 | Et | 1 | 1 |
| III-2585 | B47 | Et | 1 | 1 |
| III-2586 | B48 | Et | 1 | 1 |
| III-2587 | B49 | Et | 1 | 1 |
| III-2588 | B50 | Et | 1 | 1 |
| III-2589 | B51 | Et | 1 | 1 |
| III-2590 | B54 | Et | 1 | 1 |
| III-2591 | B57 | Et | 1 | 1 |
| III-2592 | B58 | Et | 1 | 1 |
| III-2593 | B59 | Et | 1 | 1 |
| III-2594 | B60 | Et | 1 | 1 |
| III-2595 | B61 | Et | 1 | 1 |
| III-2596 | B62 | Et | 1 | 1 |
| III-2597 | B63 | Et | 1 | 1 |
| III-2598 | B66 | Et | 1 | 1 |
| III-2599 | B69 | Et | 1 | 1 |
| III-2600 | B70 | Et | 1 | 1 |

TABLE 61

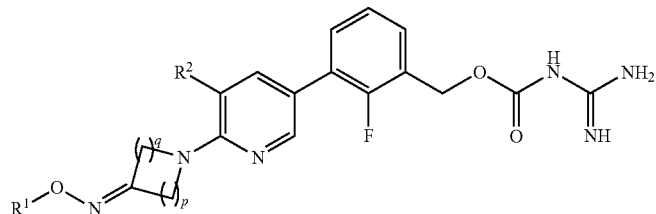

(III)

| Compound No. | R¹ | R² | p | q |
|---|---|---|---|---|
| III-2601 | B71 | Et | 1 | 1 |
| III-2602 | B72 | Et | 1 | 1 |
| III-2603 | B73 | Et | 1 | 1 |
| III-2604 | B74 | Et | 1 | 1 |
| III-2605 | B75 | Et | 1 | 1 |
| III-2606 | B76 | Et | 1 | 1 |
| III-2607 | B77 | Et | 1 | 1 |
| III-2608 | B78 | Et | 1 | 1 |
| III-2609 | B79 | Et | 1 | 1 |
| III-2610 | B83 | Et | 1 | 1 |
| III-2611 | B86 | Et | 1 | 1 |
| III-2612 | B87 | Et | 1 | 1 |
| III-2613 | B88 | Et | 1 | 1 |
| III-2614 | B63 | Et | 2 | 1 |
| III-2615 | B66 | Et | 2 | 1 |
| III-2616 | B69 | Et | 2 | 1 |
| III-2617 | B77 | Et | 2 | 1 |
| III-2618 | B79 | Et | 2 | 1 |
| III-2619 | B83 | Et | 2 | 1 |
| III-2620 | B87 | Et | 2 | 1 |
| III-2621 | B88 | Et | 2 | 1 |
| III-2622 | B63 | Et | 3 | 1 |
| III-2623 | B66 | Et | 3 | 1 |
| III-2624 | B69 | Et | 3 | 1 |
| III-2625 | B77 | Et | 3 | 1 |
| III-2626 | B79 | Et | 3 | 1 |
| III-2627 | B83 | Et | 3 | 1 |
| III-2628 | B87 | Et | 3 | 1 |
| III-2629 | B88 | Et | 3 | 1 |
| III-2630 | B63 | Et | 2 | 2 |
| III-2631 | B66 | Et | 2 | 2 |
| III-2632 | B69 | Et | 2 | 2 |
| III-2633 | B77 | Et | 2 | 2 |
| III-2634 | B79 | Et | 2 | 2 |
| III-2635 | B83 | Et | 2 | 2 |
| III-2636 | B87 | Et | 2 | 2 |
| III-2637 | B88 | Et | 2 | 2 |
| III-2638 | B63 | nPr | 1 | 1 |
| III-2639 | B66 | nPr | 1 | 1 |
| III-2640 | B69 | nPr | 1 | 1 |
| III-2641 | B77 | nPr | 1 | 1 |
| III-2642 | B79 | nPr | 1 | 1 |
| III-2643 | B83 | nPr | 1 | 1 |
| III-2644 | B87 | nPr | 1 | 1 |
| III-2645 | B88 | nPr | 1 | 1 |
| III-2646 | B63 | iPr | 1 | 1 |
| III-2647 | B66 | Pr | 1 | 1 |
| III-2648 | B69 | Pr | 1 | 1 |
| III-2649 | B77 | Pr | 1 | 1 |
| III-2650 | B79 | Pr | 1 | 1 |
| III-2651 | B83 | iPr | 1 | 1 |
| III-2652 | B87 | Pr | 1 | 1 |
| III-2653 | B88 | Pr | 1 | 1 |

TABLE 62

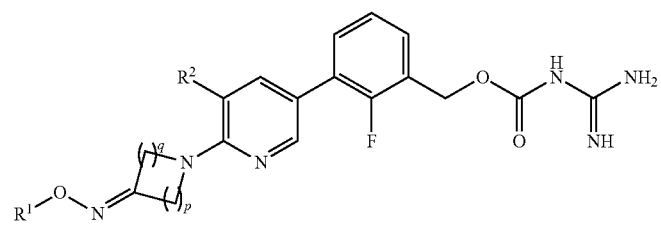

(III)

| Compound No. | R¹ | R² | p | q |
|---|---|---|---|---|
| III-2654 | B63 | $CH_2F$ | 1 | 1 |
| III-2655 | B66 | $CH_2F$ | 1 | 1 |
| III-2656 | B69 | $CH_2F$ | 1 | 1 |
| III-2657 | B77 | $CH_2F$ | 1 | 1 |
| III-2658 | B79 | $CH_2F$ | 1 | 1 |
| III-2659 | B83 | $CH_2F$ | 1 | 1 |
| III-2660 | B87 | $CH_2F$ | 1 | 1 |
| III-2661 | B88 | $CH_2F$ | 1 | 1 |
| III-2662 | B1 | $CHF_2$ | 1 | 1 |
| III-2663 | B3 | $CHF_2$ | 1 | 1 |
| III-2664 | B6 | $CHF_2$ | 1 | 1 |
| III-2665 | B7 | $CHF_2$ | 1 | 1 |
| III-2666 | B8 | $CHF_2$ | 1 | 1 |
| III-2667 | B9 | $CHF_2$ | 1 | 1 |
| III-2668 | B10 | $CHF_2$ | 1 | 1 |
| III-2669 | B11 | $CHF_2$ | 1 | 1 |
| III-2670 | B12 | $CHF_2$ | 1 | 1 |
| III-2671 | B15 | $CHF_2$ | 1 | 1 |
| III-2672 | B17 | $CHF_2$ | 1 | 1 |
| III-2673 | B18 | $CHF_2$ | 1 | 1 |
| III-2674 | B19 | $CHF_2$ | 1 | 1 |
| III-2675 | B20 | $CHF_2$ | 1 | 1 |
| III-2676 | B21 | $CHF_2$ | 1 | 1 |
| III-2677 | B22 | $CHF_2$ | 1 | 1 |
| III-2678 | B24 | $CHF_2$ | 1 | 1 |
| III-2679 | B27 | $CHF_2$ | 1 | 1 |
| III-2680 | B28 | $CHF_2$ | 1 | 1 |
| III-2681 | B29 | $CHF_2$ | 1 | 1 |
| III-2682 | B30 | $CHF_2$ | 1 | 1 |
| III-2683 | B31 | $CHF_2$ | 1 | 1 |
| III-2684 | B33 | $CHF_2$ | 1 | 1 |
| III-2685 | B34 | $CHF_2$ | 1 | 1 |
| III-2686 | B35 | $CHF_2$ | 1 | 1 |
| III-2687 | B37 | $CHF_2$ | 1 | 1 |
| III-2688 | B38 | $CHF_2$ | 1 | 1 |
| III-2689 | B39 | $CHF_2$ | 1 | 1 |
| III-2690 | B40 | $CHF_2$ | 1 | 1 |
| III-2691 | B41 | $CHF_2$ | 1 | 1 |
| III-2692 | B42 | $CHF_2$ | 1 | 1 |
| III-2693 | B43 | $CHF_2$ | 1 | 1 |
| III-2694 | B44 | $CHF_2$ | 1 | 1 |

TABLE 63

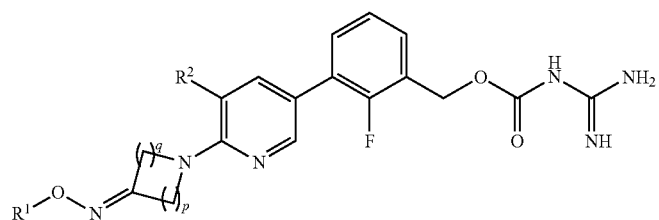

(III)

| Compound No. | R¹ | R² | p | q |
| --- | --- | --- | --- | --- |
| III-2695 | B45 | $CHF_2$ | 1 | 1 |
| III-2696 | B46 | $CHF_2$ | 1 | 1 |
| III-2697 | B47 | $CHF_2$ | 1 | 1 |
| III-2698 | B48 | $CHF_2$ | 1 | 1 |
| III-2699 | B49 | $CHF_2$ | 1 | 1 |
| III-2700 | B50 | $CHF_2$ | 1 | 1 |
| III-2701 | B51 | $CHF_2$ | 1 | 1 |
| III-2702 | B54 | $CHF_2$ | 1 | 1 |
| III-2703 | B57 | $CHF_2$ | 1 | 1 |
| III-2704 | B58 | $CHF_2$ | 1 | 1 |
| III-2705 | B59 | $CHF_2$ | 1 | 1 |
| III-2706 | B60 | $CHF_2$ | 1 | 1 |
| III-2707 | B61 | $CHF_2$ | 1 | 1 |
| III-2708 | B62 | $CHF_2$ | 1 | 1 |
| III-2709 | B63 | $CHF_2$ | 1 | 1 |
| III-2710 | B66 | $CHF_2$ | 1 | 1 |
| III-2711 | B69 | $CHF_2$ | 1 | 1 |
| III-2712 | B70 | $CHF_2$ | 1 | 1 |
| III-2713 | B71 | $CHF_2$ | 1 | 1 |
| III-2714 | B72 | $CHF_2$ | 1 | 1 |
| III-2715 | B73 | $CHF_2$ | 1 | 1 |
| III-2716 | B74 | $CHF_2$ | 1 | 1 |
| III-2717 | B75 | $CHF_2$ | 1 | 1 |
| III-2718 | B76 | $CHF_2$ | 1 | 1 |
| III-2719 | B77 | $CHF_2$ | 1 | 1 |
| III-2720 | B78 | $CHF_2$ | 1 | 1 |
| III-2721 | B79 | $CHF_2$ | 1 | 1 |
| III-2722 | B83 | $CHF_2$ | 1 | 1 |
| III-2723 | B86 | $CHF_2$ | 1 | 1 |
| III-2724 | B87 | $CHF_2$ | 1 | 1 |
| III-2725 | B88 | $CHF_2$ | 1 | 1 |
| III-2726 | B63 | $CHF_2$ | 2 | 1 |
| III-2727 | B66 | $CHF_2$ | 2 | 1 |
| III-2728 | B69 | $CHF_2$ | 2 | 1 |
| III-2729 | B77 | $CHF_2$ | 2 | 1 |
| III-2730 | B79 | $CHF_2$ | 2 | 1 |
| III-2731 | B83 | $CHF_2$ | 2 | 1 |
| III-2732 | B87 | $CHF_2$ | 2 | 1 |
| III-2733 | B88 | $CHF_2$ | 2 | 1 |

TABLE 64

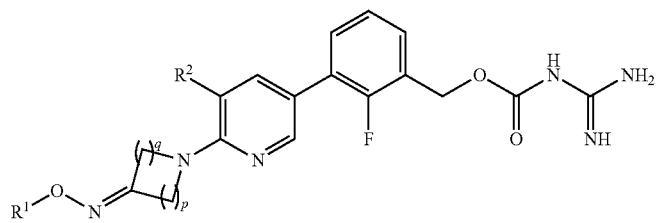

(III)

| Compound No. | R¹ | R² | p | q |
| --- | --- | --- | --- | --- |
| III-2734 | B63 | CHF$_2$ | 3 | 1 |
| III-2735 | B66 | CHF$_2$ | 3 | 1 |
| III-2736 | B69 | CHF$_2$ | 3 | 1 |
| III-2737 | B77 | CHF$_2$ | 3 | 1 |
| III-2738 | B79 | CHF$_2$ | 3 | 1 |
| III-2739 | B83 | CHF$_2$ | 3 | 1 |
| III-2740 | B87 | CHF$_2$ | 3 | 1 |
| III-2741 | B88 | CHF$_2$ | 3 | 1 |
| III-2742 | B63 | CHF$_2$ | 2 | 2 |
| III-2743 | B66 | CHF$_2$ | 2 | 2 |
| III-2744 | B69 | CHF$_2$ | 2 | 2 |
| III-2745 | B77 | CHF$_2$ | 2 | 2 |
| III-2746 | B79 | CHF$_2$ | 2 | 2 |
| III-2747 | B83 | CHF$_2$ | 2 | 2 |
| III-2748 | B87 | CHF$_2$ | 2 | 2 |
| III-2749 | B88 | CHF$_2$ | 2 | 2 |
| III-2750 | B63 | CF$_3$ | 1 | 1 |
| III-2751 | B66 | CF$_3$ | 1 | 1 |
| III-2752 | B69 | CF$_3$ | 1 | 1 |
| III-2753 | B77 | CF$_3$ | 1 | 1 |
| III-2754 | B79 | CF$_3$ | 1 | 1 |
| III-2755 | B83 | CF$_3$ | 1 | 1 |
| III-2756 | B87 | CF$_3$ | 1 | 1 |
| III-2757 | B88 | CF$_3$ | 1 | 1 |
| III-2758 | B63 | HOCH$_2$ | 1 | 1 |
| III-2759 | B66 | HOCH$_2$ | 1 | 1 |
| III-2760 | B69 | HOCH$_2$ | 1 | 1 |
| III-2761 | B77 | HOCH$_2$ | 1 | 1 |
| III-2762 | B79 | HOCH$_2$ | 1 | 1 |
| III-2763 | B83 | HOCH$_2$ | 1 | 1 |
| III-2764 | B87 | HOCH$_2$ | 1 | 1 |
| III-2765 | B88 | HOCH$_2$ | 1 | 1 |
| III-2766 | B1 | HOCHMe | 1 | 1 |
| III-2767 | B3 | HOCHMe | 1 | 1 |
| III-2768 | B6 | HOCHMe | 1 | 1 |
| III-2769 | B7 | HOCHMe | 1 | 1 |
| III-2770 | B8 | HOCHMe | 1 | 1 |
| III-2771 | B9 | HOCHMe | 1 | 1 |
| III-2772 | B10 | HOCHMe | 1 | 1 |
| III-2773 | B11 | HOCHMe | 1 | 1 |
| III-2774 | B12 | HOCHMe | 1 | 1 |
| III-2775 | B15 | HOCHMe | 1 | 1 |
| III-2776 | B17 | HOCHMe | 1 | 1 |
| III-2777 | B18 | HOCHMe | 1 | 1 |
| III-2778 | B19 | HOCHMe | 1 | 1 |
| III-2779 | B20 | HOCHMe | 1 | 1 |
| III-2780 | B21 | HOCHMe | 1 | 1 |

TABLE 65

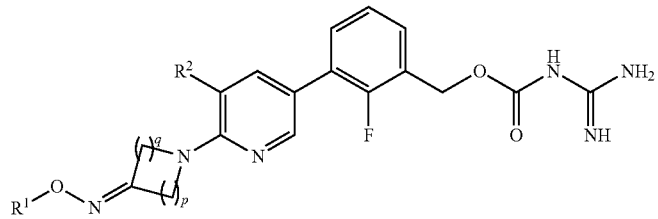

(III)

| Compound No. | R¹ | R² | p | q |
|---|---|---|---|---|
| III-2781 | B22 | HOCHMe | 1 | 1 |
| III-2782 | B24 | HOCHMe | 1 | 1 |
| III-2783 | B27 | HOCHMe | 1 | 1 |
| III-2784 | B28 | HOCHMe | 1 | 1 |
| III-2785 | B29 | HOCHMe | 1 | 1 |
| III-2786 | B30 | HOCHMe | 1 | 1 |
| III-2787 | B31 | HOCHMe | 1 | 1 |
| III-2788 | B33 | HOCHMe | 1 | 1 |
| III-2789 | B34 | HOCHMe | 1 | 1 |
| III-2790 | B35 | HOCHMe | 1 | 1 |
| III-2791 | B37 | HOCHMe | 1 | 1 |
| III-2792 | B38 | HOCHMe | 1 | 1 |
| III-2793 | B39 | HOCHMe | 1 | 1 |
| III-2794 | B40 | HOCHMe | 1 | 1 |
| III-2795 | B41 | HOCHMe | 1 | 1 |
| III-2796 | B42 | HOCHMe | 1 | 1 |
| III-2797 | B43 | HOCHMe | 1 | 1 |
| III-2798 | B44 | HOCHMe | 1 | 1 |
| III-2799 | B45 | HOCHMe | 1 | 1 |
| III-2800 | B46 | HOCHMe | 1 | 1 |
| III-2801 | B47 | HOCHMe | 1 | 1 |
| III-2802 | B48 | HOCHMe | 1 | 1 |
| III-2803 | B49 | HOCHMe | 1 | 1 |
| III-2804 | B50 | HOCHMe | 1 | 1 |
| III-2805 | B51 | HOCHMe | 1 | 1 |
| III-2806 | B54 | HOCHMe | 1 | 1 |
| III-2807 | B57 | HOCHMe | 1 | 1 |
| III-2808 | B58 | HOCHMe | 1 | 1 |
| III-2809 | B59 | HOCHMe | 1 | 1 |
| III-2810 | B60 | HOCHMe | 1 | 1 |
| III-2811 | B61 | HOCHMe | 1 | 1 |
| III-2812 | B62 | HOCHMe | 1 | 1 |
| III-2813 | B63 | HOCHMe | 1 | 1 |
| III-2814 | B66 | HOCHMe | 1 | 1 |
| III-2815 | B69 | HOCHMe | 1 | 1 |
| III-2816 | B70 | HOCHMe | 1 | 1 |
| III-2817 | B71 | HOCHMe | 1 | 1 |
| III-2818 | B72 | HOCHMe | 1 | 1 |
| III-2819 | B73 | HOCHMe | 1 | 1 |
| III-2820 | B74 | HOCHMe | 1 | 1 |
| III-2821 | B75 | HOCHMe | 1 | 1 |
| III-2822 | B76 | HOCHMe | 1 | 1 |
| III-2823 | B77 | HOCHMe | 1 | 1 |
| III-2824 | B78 | HOCHMe | 1 | 1 |
| III-2825 | B79 | HOCHMe | 1 | 1 |
| III-2826 | B83 | HOCHMe | 1 | 1 |
| III-2827 | B86 | HOCHMe | 1 | 1 |
| III-2828 | B87 | HOCHMe | 1 | 1 |
| III-2829 | B88 | HOCHMe | 1 | 1 |

TABLE 66

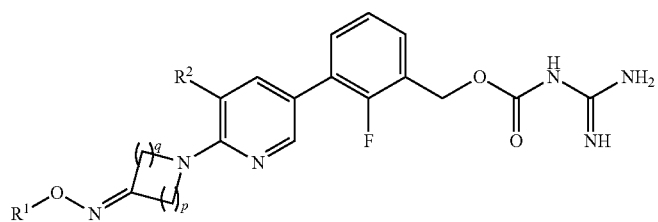

(III)

| Compound No. | R¹ | R² | p | q |
|---|---|---|---|---|
| III-2830 | B63 | HOCHMe | 2 | 1 |
| III-2831 | B66 | HOCHMe | 2 | 1 |
| III-2832 | B69 | HOCHMe | 2 | 1 |
| III-2833 | B77 | HOCHMe | 2 | 1 |
| III-2834 | B79 | HOCHMe | 2 | 1 |
| III-2835 | B83 | HOCHMe | 2 | 1 |
| III-2836 | B87 | HOCHMe | 2 | 1 |
| III-2837 | B88 | HOCHMe | 2 | 1 |
| III-2838 | B63 | HOCHMe | 3 | 1 |
| III-2839 | B66 | HOCHMe | 3 | 1 |
| III-2840 | B69 | HOCHMe | 3 | 1 |
| III-2841 | B77 | HOCHMe | 3 | 1 |
| III-2842 | B79 | HOCHMe | 3 | 1 |
| III-2843 | B83 | HOCHMe | 3 | 1 |
| III-2844 | B87 | HOCHMe | 3 | 1 |
| III-2845 | B88 | HOCHMe | 3 | 1 |
| III-2846 | B63 | HOCHMe | 2 | 2 |
| III-2847 | B66 | HOCHMe | 2 | 2 |
| III-2848 | B69 | HOCHMe | 2 | 2 |
| III-2849 | B77 | HOCHMe | 2 | 2 |
| III-2850 | B79 | HOCHMe | 2 | 2 |
| III-2851 | B83 | HOCHMe | 2 | 2 |
| III-2852 | B87 | HOCHMe | 2 | 2 |
| III-2853 | B88 | HOCHMe | 2 | 2 |
| III-2854 | B1 | HOC(Me)$_2$ | 1 | 1 |
| III-2855 | B3 | HOC(Me)$_2$ | 1 | 1 |
| III-2856 | B6 | HOC(Me)$_2$ | 1 | 1 |
| III-2857 | B7 | HOC(Me)$_2$ | 1 | 1 |
| III-2858 | B8 | HOC(Me)$_2$ | 1 | 1 |
| III-2859 | B9 | HOC(Me)$_2$ | 1 | 1 |
| III-2860 | B10 | HOC(Me)$_2$ | 1 | 1 |
| III-2861 | B11 | HOC(Me)$_2$ | 1 | 1 |
| III-2862 | B12 | HOC(Me)$_2$ | 1 | 1 |
| III-2863 | B15 | HOC(Me)$_2$ | 1 | 1 |
| III-2864 | B17 | HOC(Me)$_2$ | 1 | 1 |
| III-2865 | B18 | HOC(Me)$_2$ | 1 | 1 |
| III-2866 | B19 | HOC(Me)$_2$ | 1 | 1 |
| III-2867 | B20 | HOC(Me)$_2$ | 1 | 1 |
| III-2868 | B21 | HOC(Me)$_2$ | 1 | 1 |
| III-2869 | B22 | HOC(Me)$_2$ | 1 | 1 |
| III-2870 | B24 | HOC(Me)$_2$ | 1 | 1 |
| III-2871 | B27 | HOC(Me)$_2$ | 1 | 1 |
| III-2872 | B28 | HOC(Me)$_2$ | 1 | 1 |
| III-2873 | B29 | HOC(Me)$_2$ | 1 | 1 |
| III-2874 | B30 | HOC(Me)$_2$ | 1 | 1 |

TABLE 67

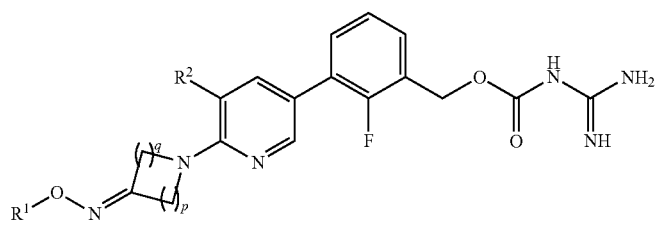

(III)

| Compound No. | R¹ | R² | p | q |
| --- | --- | --- | --- | --- |
| III-2875 | B31 | HOC(Me)$_2$ | 1 | 1 |
| III-2876 | B33 | HOC(Me)$_2$ | 1 | 1 |
| III-2877 | B34 | HOC(Me)$_2$ | 1 | 1 |
| III-2878 | B35 | HOC(Me)$_2$ | 1 | 1 |
| III-2879 | B37 | HOC(Me)$_2$ | 1 | 1 |
| III-2880 | B38 | HOC(Me)$_2$ | 1 | 1 |
| III-2881 | B39 | HOC(Me)$_2$ | 1 | 1 |
| III-2882 | B40 | HOC(Me)$_2$ | 1 | 1 |
| III-2883 | B41 | HOC(Me)$_2$ | 1 | 1 |
| III-2884 | B42 | HOC(Me)$_2$ | 1 | 1 |
| III-2885 | B43 | HOC(Me)$_2$ | 1 | 1 |
| III-2886 | B44 | HOC(Me)$_2$ | 1 | 1 |
| III-2887 | B45 | HOC(Me)$_2$ | 1 | 1 |
| III-2888 | B46 | HOC(Me)$_2$ | 1 | 1 |
| III-2889 | B47 | HOC(Me)$_2$ | 1 | 1 |
| III-2890 | B48 | HOC(Me)$_2$ | 1 | 1 |
| III-2891 | B49 | HOC(Me)$_2$ | 1 | 1 |
| III-2892 | B50 | HOC(Me)$_2$ | 1 | 1 |
| III-2893 | B51 | HOC(Me)$_2$ | 1 | 1 |
| III-2894 | B54 | HOC(Me)$_2$ | 1 | 1 |
| III-2895 | B57 | HOC(Me)$_2$ | 1 | 1 |
| III-2896 | B58 | HOC(Me)$_2$ | 1 | 1 |
| III-2897 | B59 | HOC(Me)$_2$ | 1 | 1 |
| III-2898 | B60 | HOC(Me)$_2$ | 1 | 1 |
| III-2899 | B61 | HOC(Me)$_2$ | 1 | 1 |
| III-2900 | B62 | HOC(Me)$_2$ | 1 | 1 |
| III-2901 | B63 | HOC(Me)$_2$ | 1 | 1 |
| III-2902 | B66 | HOC(Me)$_2$ | 1 | 1 |
| III-2903 | B69 | HOC(Me)$_2$ | 1 | 1 |
| III-2904 | B70 | HOC(Me)$_2$ | 1 | 1 |
| III-2905 | B71 | HOC(Me)$_2$ | 1 | 1 |
| III-2906 | B72 | HOC(Me)$_2$ | 1 | 1 |
| III-2907 | B73 | HOC(Me)$_2$ | 1 | 1 |
| III-2908 | B74 | HOC(Me)$_2$ | 1 | 1 |
| III-2909 | B75 | HOC(Me)$_2$ | 1 | 1 |
| III-2910 | B76 | HOC(Me)$_2$ | 1 | 1 |
| III-2911 | B77 | HOC(Me)$_2$ | 1 | 1 |
| III-2912 | B78 | HOC(Me)$_2$ | 1 | 1 |
| III-2913 | B79 | HOC(Me)$_2$ | 1 | 1 |
| III-2914 | B83 | HOC(Me)$_2$ | 1 | 1 |
| III-2915 | B86 | HOC(Me)$_2$ | 1 | 1 |
| III-2916 | B87 | HOC(Me)$_2$ | 1 | 1 |
| III-2917 | B88 | HOC(Me)$_2$ | 1 | 1 |

TABLE 68

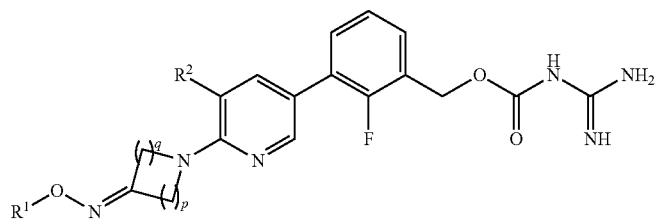

(III)

| Compound No. | R¹ | R² | p | q |
|---|---|---|---|---|
| III-2918 | B63 | HOC(Me)$_2$ | 2 | 1 |
| III-2919 | B66 | HOC(Me)$_2$ | 2 | 1 |
| III-2920 | B69 | HOC(Me)$_2$ | 2 | 1 |
| III-2921 | B77 | HOC(Me)$_2$ | 2 | 1 |
| III-2922 | B79 | HOC(Me)$_2$ | 2 | 1 |
| III-2923 | B83 | HOC(Me)$_2$ | 2 | 1 |
| III-2924 | B87 | HOC(Me)$_2$ | 2 | 1 |
| III-2925 | B88 | HOC(Me)$_2$ | 2 | 1 |
| III-2926 | B63 | HOC(Me)$_2$ | 3 | 1 |
| III-2927 | B66 | HOC(Me)$_2$ | 3 | 1 |
| III-2928 | B69 | HOC(Me)$_2$ | 3 | 1 |
| III-2929 | B77 | HOC(Me)$_2$ | 3 | 1 |
| III-2930 | B79 | HOC(Me)$_2$ | 3 | 1 |
| III-2931 | B83 | HOC(Me)$_2$ | 3 | 1 |
| III-2932 | B87 | HOC(Me)$_2$ | 3 | 1 |
| III-2933 | B88 | HOC(Me)$_2$ | 3 | 1 |
| III-2934 | B63 | HOC(Me)$_2$ | 2 | 2 |
| III-2935 | B66 | HOC(Me)$_2$ | 2 | 2 |
| III-2936 | B69 | HOC(Me)$_2$ | 2 | 2 |
| III-2937 | B77 | HOC(Me)$_2$ | 2 | 2 |
| III-2938 | B79 | HOC(Me)$_2$ | 2 | 2 |
| III-2939 | B83 | HOC(Me)$_2$ | 2 | 2 |
| III-2940 | B87 | HOC(Me)$_2$ | 2 | 2 |
| III-2941 | B88 | HOC(Me)$_2$ | 2 | 2 |
| III-2942 | B63 | THPOC(Me)$_2$ | 1 | 1 |
| III-2943 | B66 | THPOC(Me)$_2$ | 1 | 1 |
| III-2944 | B69 | THPOC(Me)$_2$ | 1 | 1 |
| III-2945 | B77 | THPOC(Me)$_2$ | 1 | 1 |
| III-2946 | B79 | THPOC(Me)$_2$ | 1 | 1 |
| III-2947 | B83 | THPOC(Me)$_2$ | 1 | 1 |
| III-2948 | B87 | THPOC(Me)$_2$ | 1 | 1 |
| III-2949 | B88 | THPOC(Me)$_2$ | 1 | 1 |
| III-2950 | B1 | MeOCH$_2$ | 1 | 1 |
| III-2951 | B3 | MeOCH$_2$ | 1 | 1 |
| III-2952 | B6 | MeOCH$_2$ | 1 | 1 |
| III-2953 | B7 | MeOCH$_2$ | 1 | 1 |
| III-2954 | B8 | MeOCH$_2$ | 1 | 1 |
| III-2955 | B9 | MeOCH$_2$ | 1 | 1 |
| III-2956 | B10 | MeOCH$_2$ | 1 | 1 |
| III-2957 | B11 | MeOCH$_2$ | 1 | 1 |
| III-2958 | B12 | MeOCH$_2$ | 1 | 1 |
| III-2959 | B15 | MeOCH$_2$ | 1 | 1 |
| III-2960 | B17 | MeOCH$_2$ | 1 | 1 |
| III-2961 | B18 | MeOCH$_2$ | 1 | 1 |
| III-2962 | B19 | MeOCH$_2$ | 1 | 1 |

TABLE 69

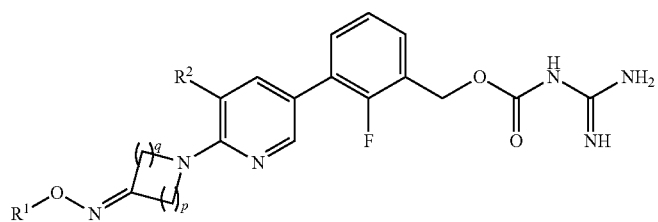

(III)

| Compound No. | R¹ | R² | p | q |
|---|---|---|---|---|
| III-2963 | B20 | MeOCH$_2$ | 1 | 1 |
| III-2964 | B21 | MeOCH$_2$ | 1 | 1 |
| III-2965 | B22 | MeOCH$_2$ | 1 | 1 |
| III-2966 | B24 | MeOCH$_2$ | 1 | 1 |
| III-2967 | B27 | MeOCH$_2$ | 1 | 1 |
| III-2968 | B28 | MeOCH$_2$ | 1 | 1 |
| III-2969 | B29 | MeOCH$_2$ | 1 | 1 |
| III-2970 | B30 | MeOCH$_2$ | 1 | 1 |
| III-2971 | B31 | MeOCH$_2$ | 1 | 1 |
| III-2972 | B33 | MeOCH$_2$ | 1 | 1 |
| III-2973 | B34 | MeOCH$_2$ | 1 | 1 |
| III-2974 | B35 | MeOCH$_2$ | 1 | 1 |
| III-2975 | B37 | MeOCH$_2$ | 1 | 1 |
| III-2976 | B38 | MeOCH$_2$ | 1 | 1 |
| III-2977 | B39 | MeOCH$_2$ | 1 | 1 |
| III-2978 | B40 | MeOCH$_2$ | 1 | 1 |
| III-2979 | B41 | MeOCH$_2$ | 1 | 1 |
| III-2980 | B42 | MeOCH$_2$ | 1 | 1 |
| III-2981 | B43 | MeOCH$_2$ | 1 | 1 |
| III-2982 | B44 | MeOCH$_2$ | 1 | 1 |
| III-2983 | B45 | MeOCH$_2$ | 1 | 1 |
| III-2984 | B46 | MeOCH$_2$ | 1 | 1 |
| III-2985 | B47 | MeOCH$_2$ | 1 | 1 |
| III-2986 | B48 | MeOCH$_2$ | 1 | 1 |
| III-2987 | B49 | MeOCH$_2$ | 1 | 1 |
| III-2988 | B50 | MeOCH$_2$ | 1 | 1 |
| III-2989 | B51 | MeOCH$_2$ | 1 | 1 |
| III-2990 | B54 | MeOCH$_2$ | 1 | 1 |
| III-2991 | B57 | MeOCH$_2$ | 1 | 1 |
| III-2992 | B58 | MeOCH$_2$ | 1 | 1 |
| III-2993 | B59 | MeOCH$_2$ | 1 | 1 |
| III-2994 | B60 | MeOCH$_2$ | 1 | 1 |
| III-2995 | B61 | MeOCH$_2$ | 1 | 1 |
| III-2996 | B62 | MeOCH$_2$ | 1 | 1 |
| III-2997 | B63 | MeOCH$_2$ | 1 | 1 |
| III-2998 | B66 | MeOCH$_2$ | 1 | 1 |
| III-2999 | B69 | MeOCH$_2$ | 1 | 1 |
| III-3000 | B70 | MeOCH$_2$ | 1 | 1 |
| III-3001 | B71 | MeOCH$_2$ | 1 | 1 |
| III-3002 | B72 | MeOCH$_2$ | 1 | 1 |
| III-3003 | B73 | MeOCH$_2$ | 1 | 1 |
| III-3004 | B74 | MeOCH$_2$ | 1 | 1 |
| III-3005 | B75 | MeOCH$_2$ | 1 | 1 |
| III-3006 | B76 | MeOCH$_2$ | 1 | 1 |
| III-3007 | B77 | MeOCH$_2$ | 1 | 1 |

TABLE 70

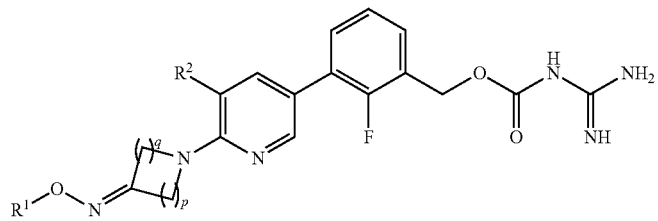

(III)

| Compound No. | R¹ | R² | p | q |
| --- | --- | --- | --- | --- |
| III-3008 | B78 | MeOCH$_2$ | 1 | 1 |
| III-3009 | B79 | MeOCH$_2$ | 1 | 1 |
| III-3010 | B83 | MeOCH$_2$ | 1 | 1 |
| III-3011 | B86 | MeOCH$_2$ | 1 | 1 |
| III-3012 | B87 | MeOCH$_2$ | 1 | 1 |
| III-3013 | B88 | MeOCH$_2$ | 1 | 1 |
| III-3014 | B63 | MeOCH$_2$ | 2 | 1 |
| III-3015 | B66 | MeOCH$_2$ | 2 | 1 |
| III-3016 | B69 | MeOCH$_2$ | 2 | 1 |
| III-3017 | B77 | MeOCH$_2$ | 2 | 1 |
| III-3018 | B79 | MeOCH$_2$ | 2 | 1 |
| III-3019 | B83 | MeOCH$_2$ | 2 | 1 |
| III-3020 | B87 | MeOCH$_2$ | 2 | 1 |
| III-3021 | B88 | MeOCH$_2$ | 2 | 1 |
| III-3022 | B63 | MeOCH$_2$ | 3 | 1 |
| III-3023 | B66 | MeOCH$_2$ | 3 | 1 |
| III-3024 | B69 | MeOCH$_2$ | 3 | 1 |
| III-3025 | B77 | MeOCH$_2$ | 3 | 1 |
| III-3026 | B79 | MeOCH$_2$ | 3 | 1 |
| III-3027 | B83 | MeOCH$_2$ | 3 | 1 |
| III-3028 | B87 | MeOCH$_2$ | 3 | 1 |
| III-3029 | B88 | MeOCH$_2$ | 3 | 1 |
| III-3030 | B63 | MeOCH$_2$ | 2 | 2 |
| III-3031 | B66 | MeOCH$_2$ | 2 | 2 |
| III-3032 | B69 | MeOCH$_2$ | 2 | 2 |
| III-3033 | B77 | MeOCH$_2$ | 2 | 2 |
| III-3034 | B79 | MeOCH$_2$ | 2 | 2 |
| III-3035 | B83 | MeOCH$_2$ | 2 | 2 |
| III-3036 | B87 | MeOCH$_2$ | 2 | 2 |
| III-3037 | B88 | MeOCH$_2$ | 2 | 2 |
| III-3038 | B63 | EtOCH$_2$ | 1 | 1 |
| III-3039 | B66 | EtOCH$_2$ | 1 | 1 |
| III-3040 | B69 | EtOCH$_2$ | 1 | 1 |
| III-3041 | B77 | EtOCH$_2$ | 1 | 1 |
| III-3042 | B79 | EtOCH$_2$ | 1 | 1 |
| III-3043 | B83 | EtOCH$_2$ | 1 | 1 |
| III-3044 | B87 | EtOCH$_2$ | 1 | 1 |
| III-3045 | B88 | EtOCH$_2$ | 1 | 1 |
| III-3046 | B1 | cPr | 1 | 1 |
| III-3047 | B3 | cPr | 1 | 1 |
| III-3048 | B6 | cPr | 1 | 1 |
| III-3049 | B7 | cPr | 1 | 1 |
| III-3050 | B8 | cPr | 1 | 1 |
| III-3051 | B9 | cPr | 1 | 1 |
| III-3052 | B10 | cPr | 1 | 1 |
| III-3053 | B11 | cPr | 1 | 1 |
| III-3054 | B12 | cPr | 1 | 1 |

TABLE 71

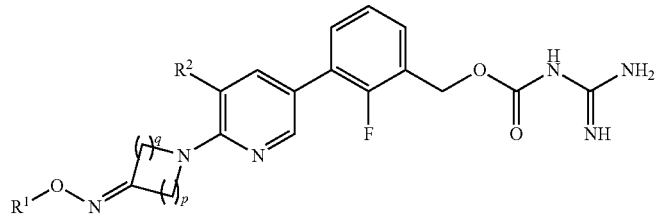

(III)

| Compound No. | R¹ | R² | p | q |
|---|---|---|---|---|
| III-3055 | B15 | cPr | 1 | 1 |
| III-3056 | B17 | cPr | 1 | 1 |
| III-3057 | B18 | cPr | 1 | 1 |
| III-3058 | B19 | cPr | 1 | 1 |
| III-3059 | B20 | cPr | 1 | 1 |
| III-3060 | B21 | cPr | 1 | 1 |
| III-3061 | B22 | cPr | 1 | 1 |
| III-3062 | B24 | cPr | 1 | 1 |
| III-3063 | B27 | cPr | 1 | 1 |
| III-3064 | B28 | cPr | 1 | 1 |
| III-3065 | B29 | cPr | 1 | 1 |
| III-3066 | B30 | cPr | 1 | 1 |
| III-3067 | B31 | cPr | 1 | 1 |
| III-3068 | B33 | cPr | 1 | 1 |
| III-3069 | B34 | cPr | 1 | 1 |
| III-3070 | B35 | cPr | 1 | 1 |
| III-3071 | B37 | cPr | 1 | 1 |
| III-3072 | B38 | cPr | 1 | 1 |
| III-3073 | B39 | cPr | 1 | 1 |
| III-3074 | B40 | cPr | 1 | 1 |
| III-3075 | B41 | cPr | 1 | 1 |
| III-3076 | B42 | cPr | 1 | 1 |
| III-3077 | B43 | cPr | 1 | 1 |
| III-3078 | B44 | cPr | 1 | 1 |
| III-3079 | B45 | cPr | 1 | 1 |
| III-3080 | B46 | cPr | 1 | 1 |
| III-3081 | B47 | cPr | 1 | 1 |
| III-3082 | B48 | cPr | 1 | 1 |
| III-3083 | B49 | cPr | 1 | 1 |
| III-3084 | B50 | cPr | 1 | 1 |
| III-3085 | B51 | cPr | 1 | 1 |
| III-3086 | B54 | cPr | 1 | 1 |
| III-3087 | B57 | cPr | 1 | 1 |
| III-3088 | B58 | cPr | 1 | 1 |
| III-3089 | B59 | cPr | 1 | 1 |
| III-3090 | B60 | cPr | 1 | 1 |
| III-3091 | B61 | cPr | 1 | 1 |
| III-3092 | B62 | cPr | 1 | 1 |
| III-3093 | B63 | cPr | 1 | 1 |
| III-3094 | B66 | cPr | 1 | 1 |
| III-3095 | B69 | cPr | 1 | 1 |
| III-3096 | B70 | cPr | 1 | 1 |
| III-3097 | B71 | cPr | 1 | 1 |
| III-3098 | B72 | cPr | 1 | 1 |
| III-3099 | B73 | cPr | 1 | 1 |
| III-3100 | B74 | cPr | 1 | 1 |
| III-3101 | B75 | cPr | 1 | 1 |
| III-3102 | B76 | cPr | 1 | 1 |
| III-3103 | B77 | cPr | 1 | 1 |
| III-3104 | B78 | cPr | 1 | 1 |
| III-3105 | B79 | cPr | 1 | 1 |
| III-3106 | B83 | cPr | 1 | 1 |
| III-3107 | B86 | cPr | 1 | 1 |
| III-3108 | B87 | cPr | 1 | 1 |
| III-3109 | B88 | cPr | 1 | 1 |

TABLE 72

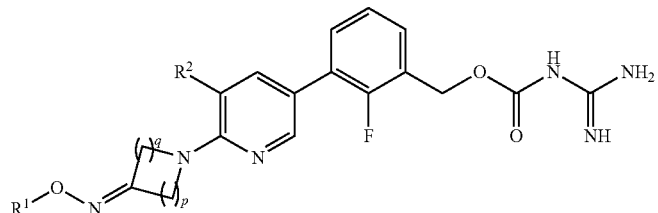

(III)

| Compound No. | R¹ | R² | p | q |
|---|---|---|---|---|
| III-3110 | B63 | cPr | 2 | 1 |
| III-3111 | B66 | cPr | 2 | 1 |
| III-3112 | B69 | cPr | 2 | 1 |
| III-3113 | B77 | cPr | 2 | 1 |
| III-3114 | B79 | cPr | 2 | 1 |
| III-3115 | B83 | cPr | 2 | 1 |
| III-3116 | B87 | cPr | 2 | 1 |
| III-3117 | B88 | cPr | 2 | 1 |
| III-3118 | B63 | cPr | 3 | 1 |
| III-3119 | B66 | cPr | 3 | 1 |
| III-3120 | B69 | cPr | 3 | 1 |
| III-3121 | B77 | cPr | a | 1 |
| III-3122 | B79 | cPr | 3 | 1 |
| III-3123 | B83 | cPr | 3 | 1 |
| III-3124 | B87 | cPr | 3 | 1 |
| III-3125 | B88 | cPr | 3 | 1 |
| III-3126 | B63 | cPr | 2 | 2 |
| III-3127 | B66 | cPr | 2 | 2 |
| III-3128 | B69 | cPr | 2 | 2 |
| III-3129 | B77 | cPr | 2 | 2 |
| III-3130 | B79 | cPr | 2 | 2 |
| III-3131 | B83 | cPr | 2 | 2 |
| III-3132 | B87 | cPr | 2 | 2 |
| III-3133 | B88 | cPr | 2 | 2 |
| III-3134 | B63 | cBu | 1 | 1 |
| III-3135 | B66 | cBu | 1 | 1 |
| III-3136 | B69 | cBu | 1 | 1 |
| III-3137 | B77 | cBu | 1 | 1 |
| III-3138 | B79 | cBu | 1 | 1 |
| III-3139 | B83 | cBu | 1 | 1 |
| III-3140 | B87 | cBu | 1 | 1 |
| III-3141 | B88 | cBu | 1 | 1 |
| III-3142 | B1 | MeO | 1 | 1 |
| III-3143 | B3 | MeO | 1 | 1 |
| III-3144 | B6 | MeO | 1 | 1 |
| III-3145 | B7 | MeO | 1 | 1 |
| III-3146 | B8 | MeO | 1 | 1 |
| III-3147 | B9 | MeO | 1 | 1 |
| III-3148 | B10 | MeO | 1 | 1 |
| III-3149 | B11 | MeO | 1 | 1 |
| III-3150 | B12 | MeO | 1 | 1 |
| III-3151 | B15 | MeO | 1 | 1 |
| III-3152 | B17 | MeO | 1 | 1 |
| III-3153 | B18 | MeO | 1 | 1 |
| III-3154 | B19 | MeO | 1 | 1 |
| III-3155 | B20 | MeO | 1 | 1 |
| III-3156 | B21 | MeO | 1 | 1 |
| III-3157 | B22 | MeO | 1 | 1 |
| III-3158 | B24 | MeO | 1 | 1 |
| III-3159 | B27 | MeO | 1 | 1 |
| III-3160 | B28 | MeO | 1 | 1 |
| III-3161 | B29 | MeO | 1 | 1 |
| III-3162 | B30 | MeO | 1 | 1 |
| III-3163 | B31 | MeO | 1 | 1 |
| III-3164 | B33 | MeO | 1 | 1 |
| III-3165 | B34 | MeO | 1 | 1 |

TABLE 73

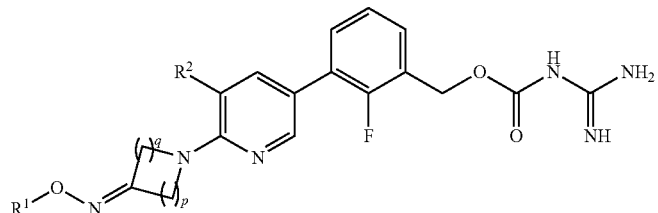

(III)

| Compound No. | R¹ | R² | p | q |
|---|---|---|---|---|
| III-3166 | B35 | MeO | 1 | 1 |
| III-3167 | B37 | MeO | 1 | 1 |
| III-3168 | B38 | MeO | 1 | 1 |
| III-3169 | B39 | MeO | 1 | 1 |
| III-3170 | B40 | MeO | 1 | 1 |
| III-3171 | B41 | MeO | 1 | 1 |
| III-3172 | B42 | MeO | 1 | 1 |
| III-3173 | B43 | MeO | 1 | 1 |
| III-3174 | B44 | MeO | 1 | 1 |
| III-3175 | B45 | MeO | 1 | 1 |
| III-3176 | B46 | MeO | 1 | 1 |
| III-3177 | B47 | MeO | 1 | 1 |
| III-3178 | B48 | MeO | 1 | 1 |
| III-3179 | B49 | MeO | 1 | 1 |
| III-3180 | B50 | MeO | 1 | 1 |
| III-3181 | B51 | MeO | 1 | 1 |
| III-3182 | B54 | MeO | 1 | 1 |
| III-3183 | B57 | MeO | 1 | 1 |
| III-3184 | B58 | MeO | 1 | 1 |
| III-3185 | B59 | MeO | 1 | 1 |
| III-3186 | B60 | MeO | 1 | 1 |
| III-3187 | B61 | MeO | 1 | 1 |
| III-3188 | B62 | MeO | 1 | 1 |
| III-3189 | B63 | MeO | 1 | 1 |
| III-3190 | B66 | MeO | 1 | 1 |
| III-3191 | B69 | MeO | 1 | 1 |
| III-3192 | B70 | MeO | 1 | 1 |
| III-3193 | B71 | MeO | 1 | 1 |
| III-3194 | B72 | MeO | 1 | 1 |
| III-3195 | B73 | MeO | 1 | 1 |
| III-3196 | B74 | MeO | 1 | 1 |
| III-3197 | B75 | MeO | 1 | 1 |
| III-3198 | B76 | MeO | 1 | 1 |
| III-3199 | B77 | MeO | 1 | 1 |
| III-3200 | B78 | MeO | 1 | 1 |
| III-3201 | B79 | MeO | 1 | 1 |
| III-3202 | B83 | MeO | 1 | 1 |
| III-3203 | B86 | MeO | 1 | 1 |
| III-3204 | B87 | MeO | 1 | 1 |
| III-3205 | B88 | MeO | 1 | 1 |
| III-3206 | B63 | MeO | 2 | 1 |
| III-3207 | B66 | MeO | 2 | 1 |
| III-3208 | B69 | MeO | 2 | 1 |
| III-3209 | B77 | MeO | 2 | 1 |
| III-3210 | B79 | MeO | 2 | 1 |
| III-3211 | B83 | MeO | 2 | 1 |
| III-3212 | B87 | MeO | 2 | 1 |
| III-3213 | B88 | MeO | 2 | 1 |
| III-3214 | B63 | MeO | 3 | 1 |
| III-3215 | B66 | MeO | 3 | 1 |
| III-3216 | B69 | MeO | 3 | 1 |
| III-3217 | B77 | MeO | 3 | 1 |
| III-3218 | B79 | MeO | 3 | 1 |
| III-3219 | B83 | MeO | 3 | 1 |
| III-3220 | B87 | MeO | 3 | 1 |
| III-3221 | B88 | MeO | 3 | 1 |

TABLE 74

(III)

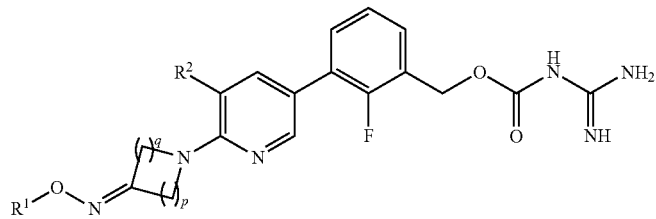

| Compound No. | R¹ | R² | p | q |
|---|---|---|---|---|
| III-3222 | B63 | MeO | 2 | 2 |
| III-3223 | B66 | MeO | 2 | 2 |
| III-3224 | B69 | MeO | 2 | 2 |
| III-3225 | B77 | MeO | 2 | 2 |
| III-3226 | B79 | MeO | 2 | 2 |
| III-3227 | B83 | MeO | 2 | 2 |
| III-3228 | B87 | MeO | 2 | 2 |
| III-3229 | B88 | MeO | 2 | 2 |
| III-3230 | B63 | EtO | 1 | 1 |
| III-3231 | B66 | EtO | 1 | 1 |
| III-3232 | B69 | EtO | 1 | 1 |
| III-3233 | B77 | EtO | 1 | 1 |
| III-3234 | B79 | EtO | 1 | 1 |
| III-3235 | B83 | EtO | 1 | 1 |
| III-3236 | B87 | EtO | 1 | 1 |
| III-3237 | B88 | EtO | 1 | 1 |
| III-3238 | B1 | NC | 1 | 1 |
| III-3239 | B3 | NC | 1 | 1 |
| III-3240 | B6 | NC | 1 | 1 |
| III-3241 | B7 | NC | 1 | 1 |
| III-3242 | B8 | NC | 1 | 1 |
| III-3243 | B9 | NC | 1 | 1 |
| III-3244 | B10 | NC | 1 | 1 |
| III-3245 | B11 | NC | 1 | 1 |
| III-3246 | B12 | NC | 1 | 1 |
| III-3247 | B15 | NC | 1 | 1 |
| III-3248 | B17 | NC | 1 | 1 |
| III-3249 | B18 | NC | 1 | 1 |
| III-3250 | B19 | NC | 1 | 1 |
| III-3251 | B20 | NC | 1 | 1 |
| III-3252 | B21 | NC | 1 | 1 |
| III-3253 | B22 | NC | 1 | 1 |
| III-3254 | B24 | NC | 1 | 1 |
| III-3255 | B27 | NC | 1 | 1 |
| III-3256 | B28 | NC | 1 | 1 |
| III-3257 | B29 | NC | 1 | 1 |
| III-3258 | B30 | NC | 1 | 1 |
| III-3259 | B31 | NC | 1 | 1 |
| III-3260 | B33 | NC | 1 | 1 |
| III-3261 | B34 | NC | 1 | 1 |
| III-3262 | B35 | NC | 1 | 1 |
| III-3263 | B37 | NC | 1 | 1 |
| III-3264 | B38 | NC | 1 | 1 |
| III-3265 | B39 | NC | 1 | 1 |
| III-3266 | B40 | NC | 1 | 1 |
| III-3267 | B41 | NC | 1 | 1 |
| III-3268 | B42 | NC | 1 | 1 |
| III-3269 | B43 | NC | 1 | 1 |
| III-3270 | B44 | NC | 1 | 1 |
| III-3271 | B45 | NC | 1 | 1 |
| III-3272 | B46 | NC | 1 | 1 |
| III-3273 | B47 | NC | 1 | 1 |

TABLE 75

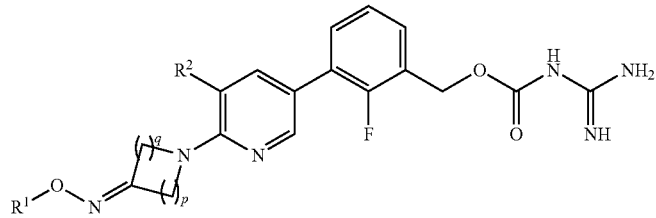

(III)

| Compound No. | R¹ | R² | p | q |
|---|---|---|---|---|
| III-3274 | B48 | NC | 1 | 1 |
| III-3275 | B49 | NC | 1 | 1 |
| III-3276 | B50 | NC | 1 | 1 |
| III-3277 | B51 | NC | 1 | 1 |
| III-3278 | B54 | NC | 1 | 1 |
| III-3279 | B57 | NC | 1 | 1 |
| III-3280 | B58 | NC | 1 | 1 |
| III-3281 | B59 | NC | 1 | 1 |
| III-3282 | B60 | NC | 1 | 1 |
| III-3283 | B61 | NC | 1 | 1 |
| III-3284 | B62 | NC | 1 | 1 |
| III-3285 | B63 | NC | 1 | 1 |
| III-3286 | B66 | NC | 1 | 1 |
| III-3287 | B69 | NC | 1 | 1 |
| III-3288 | B70 | NC | 1 | 1 |
| III-3289 | B71 | NC | 1 | 1 |
| III-3290 | B72 | NC | 1 | 1 |
| III-3291 | B73 | NC | 1 | 1 |
| III-3292 | B74 | NC | 1 | 1 |
| III-3293 | B75 | NC | 1 | 1 |
| III-3294 | B76 | NC | 1 | 1 |
| III-3295 | B77 | NC | 1 | 1 |
| III-3296 | B78 | NC | 1 | 1 |
| III-3297 | B79 | NC | 1 | 1 |
| III-3298 | B83 | NC | 1 | 1 |
| III-3299 | B86 | NC | 1 | 1 |
| III-3300 | B87 | NC | 1 | 1 |
| III-3301 | B88 | NC | 1 | 1 |
| III-3302 | B63 | NC | 2 | 1 |
| III-3303 | B66 | NC | 2 | 1 |
| III-3304 | B69 | NC | 2 | 1 |
| III-3305 | B77 | NC | 2 | 1 |
| III-3306 | B79 | NC | 2 | 1 |
| III-3307 | B83 | NC | 2 | 1 |
| III-3308 | B87 | NC | 2 | 1 |
| III-3309 | B88 | NC | 2 | 1 |
| III-3310 | B63 | NC | 3 | 1 |
| III-3311 | B66 | NC | 3 | 1 |
| III-3312 | B69 | NC | 3 | 1 |
| III-3313 | B77 | NC | 3 | 1 |
| III-3314 | B79 | NC | 3 | 1 |
| III-3315 | B83 | NC | 3 | 1 |
| III-3316 | B87 | NC | 3 | 1 |
| III-3317 | B88 | NC | 3 | 1 |
| III-3318 | B63 | NC | 2 | 2 |
| III-3319 | B66 | NC | 2 | 2 |
| III-3320 | B69 | NC | 2 | 2 |
| III-3321 | B77 | NC | 2 | 2 |
| III-3322 | B79 | NC | 2 | 2 |
| III-3323 | B83 | NC | 2 | 2 |
| III-3324 | B87 | NC | 2 | 2 |
| III-3325 | B88 | NC | 2 | 2 |

The following indicates a typical method for producing a compound of general formula (I) of the present invention, or a pharmacologically acceptable salt thereof. Furthermore, the compound of the present invention, or a pharmacologically acceptable salt thereof, is not limited to a compound, or pharmacologically acceptable salt thereof, produced according to the production method indicated below.

In the production method indicated below, in the case a partial structure is present that inhibits a desired reaction within the compound or is subjected to a side reaction (such as a hydroxyl group, amino group, carbonyl group, carboxyl group, amide group or thiol group), the desired reaction can be carried out by introducing a protecting group into that partial structure and the target compound can be obtained by subsequently removing the protecting group. Reactions for introducing and removing protecting groups can be carried out according to methods routinely used in synthetic organic chemistry (such as the method described in Protective Groups in Organic Synthesis, 4th Edition, T. W. Greene and P. G. M. Wuts, ed., John Wiley & Sons Inc. (2006)). In addition, specific production methods for individual compounds of the present invention are explained in the examples to be subsequently described.

(Production Method 1)

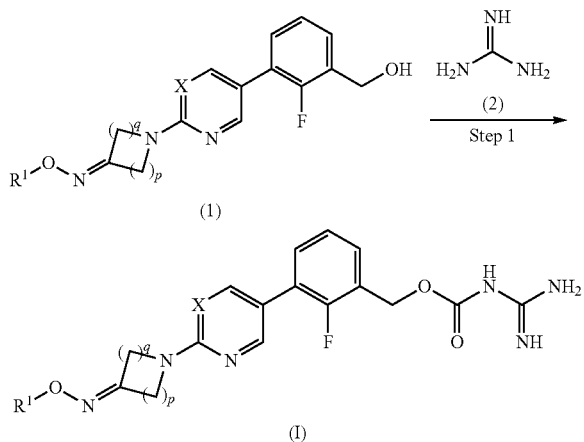

R[1] represents a hydrogen atom, protecting group, optionally substituted $C_1$-$C_6$ alkyl group, optionally substituted $C_2$-$C_6$ alkenyl group, optionally substituted $C_3$-$C_8$ cycloalkyl group, optionally substituted $C_1$-$C_6$ alkoxy-$C_1$-$C_6$ alkyl group, —$CONR^{11}R^{12}$, optionally substituted heterocyclyl group, optionally substituted heterocyclyl-$C_1$-$C_6$ alkyl group, optionally substituted aryl group or optionally substituted $C_7$-$C_{16}$ aralkyl group, and X represents N or C—$R^2$, wherein, R[2] represents a hydrogen atom, halogen atom, optionally substituted $C_1$-$C_6$ alkyl group, optionally substituted $C_3$-$C_8$ cycloalkyl group, optionally substituted $C_1$-$C_6$ alkoxy group or cyano group, and p and q, independently of each other, represent a natural number of 1 to 3, provided that the sum of p and q is a natural number of 2 to 4, wherein, the term "substituted" refers to being substituted with at least one substituent selected from the group consisting of a deuterium atom, halogen atom, $C_1$-$C_6$ alkyl group, $C_1$-$C_6$ alkoxy group, $C_1$-$C_6$ alkoxy-$C_1$-$C_6$ alkyl group, $R^{13}$O—$C_1$-$C_6$ alkyl group, halo-$C_1$-$C_6$ alkyl group, $C_7$-$C_{16}$ aralkyl group, $C_1$-$C_7$ acyl group, cyano group, oxo group, —$CONR^{11}R^{12}$, —$OR^{13}$, —$COOR^{14}$, —$NR^{15}R^{16}$ and —$S(O)_nR^{17}$, and R[11] and R[12] independently represent a hydrogen atom or $C_1$-$C_6$ alkyl group, R[13] represents a hydrogen atom, $C_1$-$C_7$ acyl group or protecting group, R[14] represents a hydrogen atom or $C_1$-$C_6$ alkyl group, R[15] and R[16] independently represent a hydrogen atom, $C_1$-$C_6$ alkyl group, $C_7$-$C_{16}$ aralkyl group, $C_1$-$C_7$ acyl group, —$COOR^{14}$ or —$S(O)_nR^{17}$, R[17] represents a $C_1$-$C_6$ alkyl group, and n represents 0, 1 or 2.

Step 1 of Production Method 1 is a step for reacting Compound (1) and a guanidine or guanidine acid salt of Compound (2) in a solvent in the presence of 1,1'-carbonyldiimidazole to produce a compound of general formula (I).

Compound (1) can be produced according to Syntheses 1 to 10 to be subsequently described and the reference examples of the present description.

Examples of guanidine acid salts of Compound (2) include guanidine hydrochloride, guanidine sulfate and guanidine carbonate.

Compound (2) is a known and is available from a reagent supplier such as Tokyo Chemical Industry Co., Ltd. The amounts of guanidine or guanidine acid salt used based on 1 mole of Compound (1) is normally 0.9 times to 5 times the molar amount, and preferably 1.1 times to 3 times the molar amount, of Compound (1).

There are no particular limitations on the solvent used provided it does not inhibit the reaction and dissolves the raw materials to a certain degree, and examples thereof include aromatic hydrocarbons such as benzene, toluene or xylene, halogenated aliphatic hydrocarbons such as methylene chloride, chloroform or 1,2-dichloroethane, ethers such as tetrahydrofuran, 1,2-dimethoxyethane or 1,4-dioxane, nitriles such as acetonitrile or propionitrile, amides such as N,N-dimethylformamide, N,N-dimethylacetamide or N-methylpyrrolidone, and arbitrarily mixed solvents thereof. N,N-dimethylformamide is used preferably. Although there are no particular limitations thereon, the amount of solvent used is normally 1 time to 20 times, and preferably 2 times to 10 times, the mass of Compound (1).

The amount of 1,1'-carbonyldiimidazole used based on 1 mole of Compound (1) is normally 0.9 times to 5 times the molar amount, and preferably 1.1 times to 3 times the molar amount, of Compound (1).

Although varying according to such factors as the types and amounts used of the raw materials, solvent and the like, the reaction temperature is normally −20° C. to 150° C. and preferably 0° C. to 40° C.

Although varying according to such factors as the reaction temperature, the reaction time is normally 1 minute to 24 hours and preferably 1 hour to 12 hours.

Although the reaction pressure may be suitably set as necessary and the reaction may be carried out under pressure, reduced pressure or atmospheric pressure, the reaction pressure is preferably atmospheric pressure. Although the reaction can be carried out in an atmosphere suitably selected as necessary, the reaction atmosphere is preferably an air atmosphere or an inert gas atmosphere such as that of nitrogen or argon.

In the case a protecting group is present in Compound (1), Compound (1) can be further subjected to a deprotection step as necessary.

In the case Compound (1) has at least two different types of protecting groups, only one type of protecting group can be selectively removed by selecting the deprotection conditions.

Deprotection conditions can be suitably selected according to a method routinely used in synthetic organic chemistry (such as the method described in Protective Groups in Organic Synthesis, 4th Edition, T. W. Greene and P. G. M. Wuts, ed., John Wiley & Sons Inc. (2006)) or the examples of the present description.

The aforementioned Compound (1) can be suitably prepared according to, for example, the following Syntheses 1 to 10 and the reference examples of the present description.

Synthesis 1

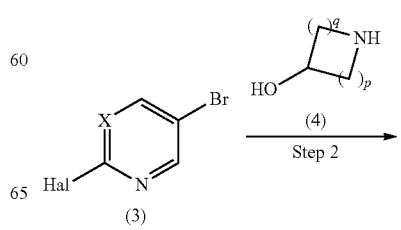

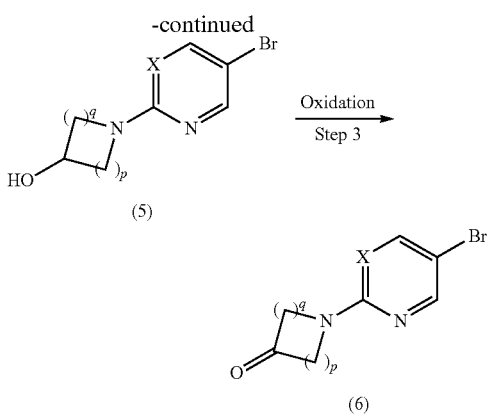

X, p and q are as previously described and Hal represents a halogen atom.

Step 2 of Synthesis 1 is a step for obtaining Compound (5) by reacting Compound (3) and Compound (4) in a solvent and in the presence of a base. Compound (3) and Compound (4) are known or can be produced from known compounds according to known methods.

Examples of Compound (3) include 5-bromo-2-chloropyridine, 5-bromo-2-chloropyrimidine, 5-bromo-2,3-difluoropyridine and 5-bromo-2-fluoro-3-methylpyridine.

Examples of Compound (4) include azetidin-3-ol, pyrrolidin-3-ol, piperidin-4-ol and acid salts thereof.

Examples of acid salts of Compound (4) include hydrochlorides, sulfates and acetates.

The amount of Compound (4) used based on 1 mole of Compound (3) is normally 0.9 times to 5 times the molar amount, and preferably 1.1 times to 3 times the molar amount, of Compound (3).

There are no particular limitations on the solvent used provided it does not inhibit the reaction and dissolves the raw materials to a certain degree, and examples thereof include alcohols such as methanol, ethanol, propanol or isopropanol, aromatic hydrocarbons such as benzene, toluene or xylene, halogenated aliphatic hydrocarbons such as methylene chloride, chloroform or 1,2-dichloroethane, ethers such as tetrahydrofuran, 1,2-dimethoxyethane or 1,4-dioxane, nitriles such as acetonitrile or propionitrile, amides such as N,N-dimethylformamide, N,N-dimethylacetamide or N-methylpyrrolidone, sulfoxides such as dimethylsulfoxide, and arbitrarily mixed solvents thereof. Alcohols such as ethanol, amides such as N,N-dimethylformamide or N-methylpyrrolidone, or sulfoxides such as dimethylsulfoxide are used preferably. Although there are no particular limitations thereon, the amount of solvent used is normally 1 time to 50 times, and preferably 5 times to 20 times, the mass of Compound (3).

Examples of base used include alkaline metal acetates such as sodium acetate or potassium acetate, alkaline metal carbonates such as sodium carbonate, potassium carbonate or cesium carbonate, and organic bases such as triethylamine or diisopropylethylamine, with potassium carbonate, cesium carbonate, triethylamine or diisopropylethylamine being preferable. The amount of base used based on 1 mole of Compound (3) is normally 0.9 times to 10 times the molar amount, and preferably 1 time to 5 times the molar amount, of Compound (3).

Although varying according to such factors as the types and amounts used of the raw materials, solvent and the like, the reaction temperature is normally 0° C. to 150° C. and preferably 40° C. to 120° C.

Although varying according to such factors as the reaction temperature, the reaction time is normally 1 minute to 48 hours and preferably 0.5 hours to 24 hours. Although the reaction pressure may be suitably set as necessary and the reaction may be carried out under pressure, reduced pressure or atmospheric pressure, the reaction pressure is preferably atmospheric pressure. Although the reaction can be carried out in an atmosphere suitably selected as necessary, the reaction atmosphere is preferably an air atmosphere or an inert gas atmosphere such as that of nitrogen or argon.

Step 3 of Synthesis 1 is a step for obtaining Compound (6) by oxidizing Compound (5) using an oxidizing agent in a solvent and optionally in the presence of base.

Examples of oxidizing agents include manganese dioxide, pyridinium chlorochromate (PCC), pyridinium dichloride (PDC) and 1,1,1-triacetoxy-1,1-dihydro-1,2-benzoiodoquinol-3(1H)-one (Dess-Martin Periodinane).

There are no particular limitations on the solvent used provided it does not inhibit the reaction and dissolves the raw materials to a certain degree, and examples thereof include halogenated aliphatic hydrocarbons such as methylene chloride, chloroform or 1,2-dichloroethane, nitriles such as acetonitrile, and esters such as methyl acetate, ethyl acetate or isopropyl acetate, with methylene chloride being preferable.

Although varying according to the type of oxidizing agent, the amount of oxidizing agent used based on 1 mole of Compound (5) is normally 0.9 times to 100 times the molar amount, and preferably 1 time to 20 times the molar amount, of Compound (5).

Examples of base used include organic bases such as triethylamine or pyridine, and inorganic bases such as sodium bicarbonate, potassium bicarbonate, sodium carbonate or potassium carbonate, with pyridine or sodium bicarbonate being preferable. The amount of base used based on 1 mole of Compound (5) is normally 0.9 times to 20 times the molar amount, and preferably 1 time to 10 times the molar amount, of Compound (5).

Although varying according to such factors as the types and amounts used of the raw materials, solvent and the like, the reaction temperature is normally 0° C. to 150° C. and preferably 0° C. to 100° C.

Although varying according to such factors as the reaction temperature, the reaction time is normally 30 minutes to 24 hours and preferably 1 hour to 12 hours. Although the reaction pressure may be suitably set as necessary and the reaction may be carried out under pressure, reduced pressure or atmospheric pressure, the reaction pressure is preferably atmospheric pressure. Although the reaction can be carried out in an atmosphere suitably selected as necessary, the reaction atmosphere is preferably an air atmosphere or an inert gas atmosphere such as that of nitrogen or argon.

Synthesis 2

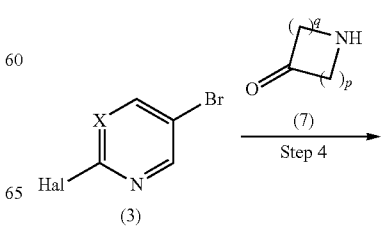

-continued

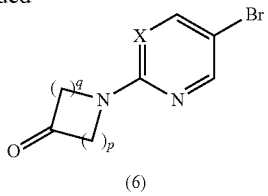

X, Hal, p and q are as previously described.

Step 4 of Synthesis 2 is a step for obtaining Compound (6) by reacting Compound (3) and Compound (7) in a solvent and in the presence of base. Compound (3) and Compound (7) are known or can be produced from known compounds according to a known method. Examples of Compound (3) are as previously described.

Examples of Compound (7) include azetidin-3-one, pyrrolidine-3-one, piperidin-4-one and acid salts thereof.

Examples of acid salts of Compound (7) include hydrochlorides, sulfates and acetates.

Step 4 of Synthesis 2 can be carried out using the same conditions as Step 2 of the aforementioned Synthesis 1.

Synthesis 3

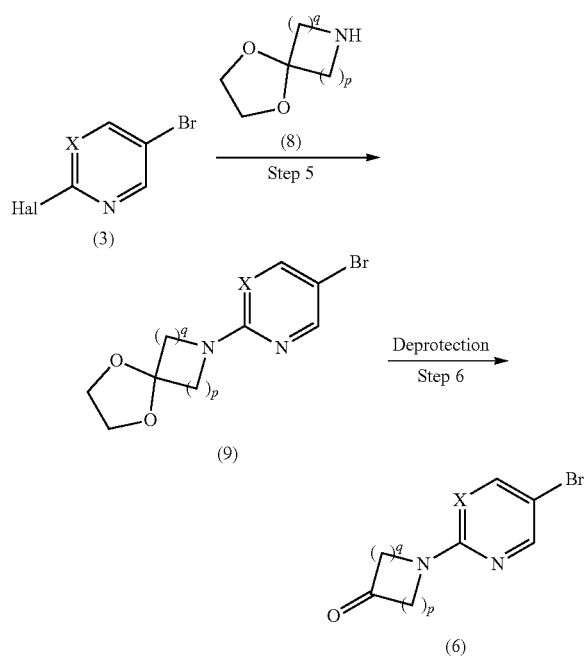

X, Hal, p and q are as previously described.

Step 5 of Synthesis 3 is a step for obtaining Compound (9) by reacting Compound (3) and Compound (8) in a solvent and in the presence of base. Compound (3) and Compound (8) are known or can be produced from known compounds according to a known method. Examples of Compound (3) are as previously described.

Examples of Compound (8) include 5,8-dioxa-2-azaspiro[3.4]octane, 1,4-dioxa-7-azaspiro[4.4]nonane, 1,4-dioxa-8-azaspiro[4.5]decane, and acid salts thereof.

Examples of acid salts of Compound (8) include hydrochlorides, sulfates and acetates.

Step 5 of Synthesis 3 can be carried out using the same conditions as Step 2 of the aforementioned Synthesis 1.

Step 6 of Synthesis 3 includes a step for obtaining Compound (6) by deprotecting the carbonyl protecting group from Compound (9) in a solvent using acid. Examples of acid include organic acids such as acetic acid, para-toluenesulfonic acid or pyridinium para-toluenesulfonate, and inorganic acids such as hydrochloric acid or perchloric acid, with hydrochloric acid being preferable. The amount of acid used based on 1 mole of Compound (9) is normally 1 time to 20 times the molar amount, and preferably 1 time to 10 times the molar amount, of Compound (9).

There are no particular limitations on the solvent used provided it does not inhibit the reaction and dissolves the raw materials to a certain degree, and examples thereof include water, aromatic hydrocarbons such as benzene, toluene or xylene, ethers such as diethyl ether, tetrahydrofuran, 1,4-dioxane or 1,2-dimethoxyethane, ketones such as acetone, methyl ethyl ketone, methyl isobutyl ketone or methyl tert-butyl ketone, and arbitrarily mixed solvents thereof, with acetone being preferable. Although there are no particular limitations thereon, the amount of solvent used is normally 1 time to 50 times, and preferably 5 times to 20 times, the mass of Compound (9).

Although varying according to such factors as the types and amounts used of the raw materials, solvent and the like, the reaction temperature is normally 0° C. to 150° C. and preferably 0° C. to 100° C.

Although varying according to such factors as the reaction temperature, the reaction time is normally 1 minute to 48 hours and preferably 0.5 hours to 24 hours.

Although the reaction pressure may be suitably set as necessary and the reaction may be carried out under pressure, reduced pressure or atmospheric pressure, the reaction pressure is preferably atmospheric pressure. Although the reaction can be carried out in an atmosphere suitably selected as necessary, the reaction atmosphere is preferably an air atmosphere or an inert gas atmosphere such as that of nitrogen or argon.

Synthesis 4

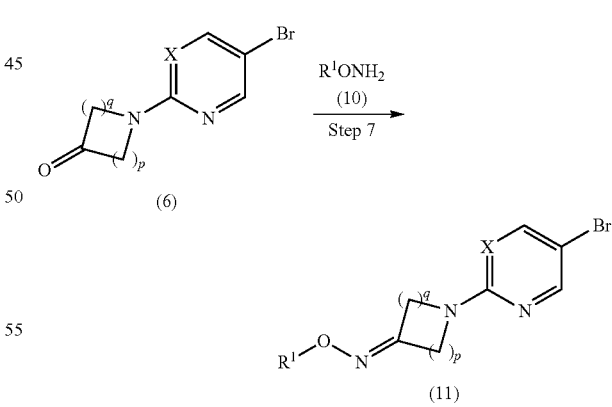

X, $R^1$, p and q are as previously described.

Step 7 of Synthesis 4 is a step for obtaining Compound (11) by reacting Compound (6) and Compound (10) in a solvent and optionally in the presence of base.

Compound (6) can be produced according to any of the aforementioned Syntheses 1 to 3. Compound (10) is known or can be produced from known compounds according to a known method.

Compound (10) is known or can be produced from known compounds according to the reference examples of the present description to be subsequently described.

Compound (10) may be an acid salt. Examples of acid salts include hydrochlorides, sulfates and acetates.

The amount of Compound (10) used based on 1 mole of Compound (6) is normally 0.9 times to 10 times the molar amount, and preferably 1.1 times to 5 times the molar amount, of Compound (6).

There are no particular limitations on the solvent used provided it does not inhibit the reaction and dissolves the raw materials to a certain degree, and examples thereof include water, alcohols such as methanol, ethanol, propanol or isopropanol, ethers such as tetrahydrofuran, 1,2-dimethoxyethane or 1,4-dioxane, nitriles such as acetonitrile or propionitrile, and arbitrarily mixed solvents thereof. Water, ethanol, tetrahydrofuran or an arbitrarily mixed solvent thereof is preferable. Although there are no particular limitations thereon, the amount of solvent used is normally 1 time to 50 times, and preferably 5 times to 30 times, the mass of Compound (6).

Examples of base used include alkaline metal acetates such as sodium acetate or potassium acetate, alkaline metal carbonates such as sodium carbonate, potassium carbonate or cesium carbonate, and organic bases such as triethylamine or diisopropylethylamine, with alkaline metal carbonates such as sodium carbonate or potassium carbonate being used preferably. The amount of base used based on 1 mole of Compound (6) is normally 0.9 times to 10 times the molar amount, and preferably 1 time to 5 times the molar amount, of Compound (6).

Although varying according to such factors as the types and amounts used of the raw materials, solvent and the like, the reaction temperature is normally 0° C. to 150° C. and preferably 20° C. to 120° C.

Although varying according to such factors as the reaction temperature, the reaction time is normally 1 minute to 48 hours and preferably 0.5 hours to 24 hours.

Although the reaction pressure may be suitably set as necessary and the reaction may be carried out under pressure, reduced pressure or atmospheric pressure, the reaction pressure is preferably atmospheric pressure. Although the reaction can be carried out in an atmosphere suitably selected as necessary, the reaction atmosphere is preferably an air atmosphere or an inert gas atmosphere such as that of nitrogen or argon.

Synthesis 5

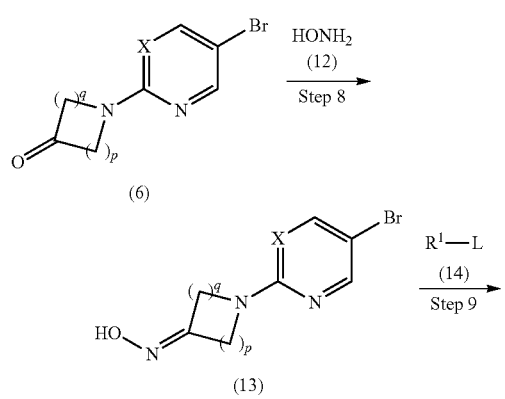

-continued

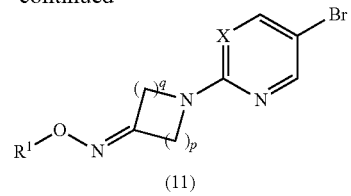

X, $R^1$, p and q are as previously described and L represents a leaving group. Examples of the leaving group L include a halogen atom, methanesulfonyloxy group, trifluoromethanesulfonyloxy group and para-toluenesulfonyloxy group.

Step 8 of Synthesis 5 is a step for obtaining Compound (13) by reacting Compound (6) with a hydroxylamine of Compound (12) or an acid salt of hydroxylamine in a solvent.

Compound (6) can be produced according to any of the aforementioned Syntheses 1 to 3.

Examples of acid salts of the hydroxylamine of Compound (12) include hydroxylamine hydrochloride and hydroxylamine sulfate.

The hydroxylamine of Compound (12) or acid salts of the hydroxylamine are known and is available from a reagent supplier such as Tokyo Chemical Industry Co., Ltd. The amount of hydroxylamine hydrochloride used based on 1 mole of Compound (6) is normally 0.9 times to 5 times the molar amount, and preferably 1.1 times to 3 times the molar amount, of Compound (6).

There are no particular limitations on the solvent used provided it does not inhibit the reaction and dissolves the raw materials to a certain degree, and examples thereof include water, alcohols such as methanol, ethanol, propanol or isopropanol, ethers such as tetrahydrofuran, 1,2-dimethoxyethane or 1,4-dioxane, nitriles such as acetonitrile or propionitrile, and arbitrarily mixed solvents thereof. Water, ethanol, tetrahydrofuran or an arbitrarily mixed solvent thereof is preferable. Although there are no particular limitations thereon, the amount of solvent used is normally 1 time to 50 times, and preferably 5 times to 30 times, the mass of Compound (6).

Although varying according to such factors as the types and amounts used of the raw materials, solvent and the like, the reaction temperature is normally 0° C. to 150° C. and preferably 40° C. to 120° C.

Although varying according to such factors as the reaction temperature, the reaction time is normally 1 minute to 48 hours and preferably 0.5 hours to 24 hours.

Although the reaction pressure may be suitably set as necessary and the reaction may be carried out under pressure, reduced pressure or atmospheric pressure, the reaction pressure is preferably atmospheric pressure. Although the reaction can be carried out in an atmosphere suitably selected as necessary, the reaction atmosphere is preferably an air atmosphere or an inert gas atmosphere such as that of nitrogen or argon.

Step 9 of Synthesis 5 is a step for obtaining Compound (11) by reacting Compound (13) and Compound (14) in a solvent and in the presence of base.

Compound (14) is known or can be produced from known compounds according to the reference examples of the present description to be subsequently described and the like. The amount of Compound (14) used based on 1 mole of Compound (13) is normally 0.9 times to 5 times the molar amount, and preferably 1.1 times to 3 times the molar amount, of Compound (13).

There are no particular limitations on the solvent used provided it does not inhibit the reaction and dissolves the raw materials to a certain degree, and examples thereof include aromatic hydrocarbons such as benzene, toluene or xylene, halogenated aliphatic hydrocarbons such as methylene chloride, chloroform or 1,2-dichloroethane, ethers such as tetrahydrofuran, 1,2-dimethoxyethane or 1,4-dioxane, nitriles such as acetonitrile or propionitrile, amides such as N,N-dimethylformamide, N,N-dimethylacetamide or N-methylpyrrolidone, sulfoxides such as dimethylsulfoxide, and arbitrarily mixed solvents thereof. Amides such as N,N-dimethylformamide or N-methylpyrrolidone are used preferably. Although there are no particular limitations thereon, the amount of solvent used is normally 1 time to 50 times, and preferably 5 times to 30 times, the mass of Compound (13).

Examples of base used include alkaline metal acetates such as sodium acetate or potassium acetate, alkaline metal carbonates such as sodium carbonate, potassium carbonate or cesium carbonate, and organic bases such as triethylamine or diisopropylethylamine, with potassium carbonate, cesium carbonate, triethylamine or diisopropylethylamine being preferable. The amount of base used based on 1 mole of Compound (13) is normally 0.9 times to 10 times the molar amount, and preferably 1 time to 5 times the molar amount, of Compound (13).

Although varying according to such factors as the types and amounts used of the raw materials, solvent and the like, the reaction temperature is normally 0° C. to 150° C. and preferably 20° C. to 120° C.

Although varying according to such factors as the reaction temperature, the reaction time is normally 1 minute to 48 hours and preferably 0.5 hours to 24 hours.

Although the reaction pressure may be suitably set as necessary and the reaction may be carried out under pressure, reduced pressure or atmospheric pressure, the reaction pressure is preferably atmospheric pressure. Although the reaction can be carried out in an atmosphere suitably selected as necessary, the reaction atmosphere is preferably an air atmosphere or an inert gas atmosphere such as that of nitrogen or argon.

Synthesis 6

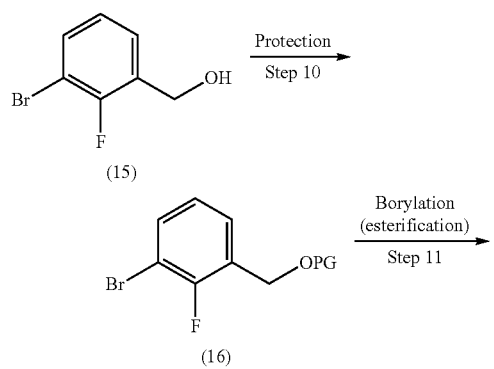

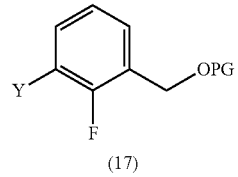

PG represents a protecting group, and Y represents a boronic acid group or boronate ester substituent. Examples of the boronate substituent Y include a diisopropyl boronate group, pinacol boronate group, neopentyl glycol boronate group and catechol boronate group.

Step 10 of Synthesis 6 is a step for obtaining Compound (16) by introducing a protecting group for the hydroxyl group of Compound (15) in a solvent.

Compound (15), namely (2-bromo-3-fluorophenyl)methanol, is known or can be produced from known compounds according to a known method.

Introduction of a protecting group for a hydroxyl group can be suitably carried out according to the known art, such as that described in Protective Groups in Organic Synthesis, 4th Edition, T. W. Greene and P. G. M. Wuts, ed., John Wiley & Sons Inc., or the examples of the present description.

Step 11 of Synthesis 6 is a step for obtaining Compound (17) by reacting Compound (16) with a borylation reagent in the presence of a palladium catalyst and base and in a solvent and in an inert gas atmosphere to introduce a boronic acid group or boronate ester substituent.

The borylation reagent is known or can be produced from known compounds according to a known method. Examples of borylation reagents include trimethyl borate, triisopropyl borate, bis(pinacolato)diborane, bis(neopentylglycolato)diborane and bis(catecholato)diborane. The amount of the borylation reagent used based on 1 mole of Compound (16) is normally 0.9 times to 5 times the molar amount, and preferably 1.1 times to 3 times the molar amount, of Compound (16).

There are no particular limitations on the solvent used provided it does not inhibit the reaction and dissolves the raw materials, base and catalyst to a certain degree, and examples thereof include aromatic hydrocarbons such as benzene or toluene, ethers such as tetrahydrofuran, 1,2-dimethoxyethane or 1,4-dioxane, alcohols such as methanol, ethanol, propanol or isopropanol, amides such as N,N-dimethylformamide, N,N-dimethylacetamide or N-methylpyrrolidone, sulfoxides such as dimethylsulfoxide, nitriles such as acetonitrile, water, and arbitrarily mixed solvents thereof, with toluene, 1,4-dioxane, N,N-dimethylformamide, dimethylsulfoxide or acetonitrile being preferable.

Examples of the inert gas used include nitrogen, helium and argon.

Examples of the palladium catalyst used include organic palladium complexes such as tetrakis(triphenylphosphine)palladium, bis(triphenylphosphine)palladium dichloride or 1,1'-bis(diphenylphosphino)ferrocene palladium dichloride, with 1,1'-bis(diphenylphosphino)ferrocene palladium (II) dichloride being preferable. The amount of palladium used as catalyst based on 1 mole of Compound (16) is normally 0.0001 times to 1 time the molar amount, and preferably 0.005 times to 0.3 times the molar amount, of Compound (16).

Examples of base used include alkaline metal acetates such as sodium acetate or potassium acetate, alkaline metal carbonates such as sodium carbonate, potassium carbonate or cesium carbonate, and organic bases such as triethylamine or diisopropylethylamine, with sodium acetate, potassium acetate or triethylamine being preferable. The amount of base used based on 1 mole of Compound (16) is normally 1 time to 10 times the molar amount, and preferably 1 time to 5 times the molar amount, of Compound (16).

Although varying according to such factors as the types and amounts used of the raw materials, solvent and the like, the reaction temperature is normally 0° C. to 200° C. and preferably 30° C. to 150° C.

Although varying according to such factors as the reaction temperature, the reaction time is normally 10 minutes to 120 hours and preferably 0.5 hours to 48 hours.

Although the reaction pressure may be suitably set as necessary and the reaction may be carried out under pressure, reduced pressure or atmospheric pressure, the reaction pressure is preferably atmospheric pressure.

Synthesis 7

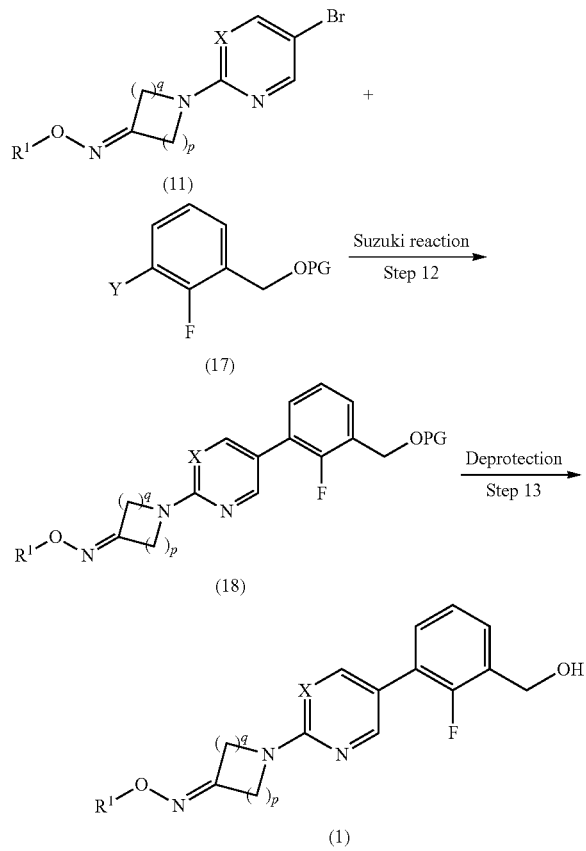

X, $R^1$, Y, PG, p and q are as previously described.

Step 12 of Synthesis 7 is a so-called Suzuki reaction for obtaining Compound (18) by reacting Compound (11) and Compound (17) in a solvent and in the presence of a base or fluoride and a palladium catalyst in an inert gas atmosphere.

Compound (11) can be produced according to the aforementioned Synthesis 4 or 5. Compound (17) can be produced according to the aforementioned Synthesis 6. The amount of Compound (17) used based on 1 mole of Compound (11) is normally 0.8 times to 3 times the molar amount, and preferably 0.9 times to 1.5 times the molar amount, of Compound (11).

There are no particular limitations on the inert solvent used provided it does not inhibit the reaction and dissolves the raw materials, catalyst and base (or fluoride) to a certain degree, and examples thereof include aromatic hydrocarbons such as benzene or toluene, ethers such as tetrahydrofuran, 1,2-dimethoxyethane or 1,4-dioxane, alcohols such as methanol, ethanol, propanol or isopropanol, amides such as N,N-dimethylformamide, N,N-dimethylacetamide or N-methylpyrrolidone, sulfoxides such as dimethylsulfoxide, nitriles such as acetonitrile, water, and arbitrarily mixed solvents thereof, with 1,2-dimethoxyethane, mixed solvent of 1,2-dimethoxyethane and water, 1,4-dioxane, mixed solvent of 1,4-dioxane and water, toluene, mixed solvent of toluene, ethanol and water, or mixed solvent of toluene and water being preferable.

Examples of the inert gas used include nitrogen, helium and argon.

Examples of the palladium catalyst used include metal palladium catalysts such as palladium-activated carbon or palladium black, organic palladium complexes such as tetrakis(triphenylphosphine)palladium, bis(triphenylphosphine)palladium dichloride, 1,1'-bis(diphenylphosphino)ferrocene palladium dichloride or tris(dibenyzlideneacetone) dipalladium, and palladium salts such as palladium chloride or palladium acetate, with tetrakis(triphenylphosphine)palladium or palladium acetate being preferable. The amount of palladium used as catalyst based on 1 mole of Compound (11) is normally 0.0001 times to 1 time the molar amount, and preferably 0.005 times to 0.3 times the molar amount, of Compound (11).

In the case of using tris(dibenzylideneacetone)dipalladium, palladium chloride or palladium acetate for the catalyst, it is preferable that an organic phosphine compound also be present. Examples of organic phosphine compounds used include tri-n-butylphosphine, tri-tert-butylphosphine, tricyclohexylphosphine, butyldi-1-adamantylphosphine, triphenylphosphine, tri(o-tolyl)phosphine, 2-dicyclohexylphosphino-2',6'-dimethoxybiphenyl, 1,1'-bis(diphenylphosphino)ferrocene and 1,2,3,4,5-pentaphenyl-1'-(di-tert-butylphosphino)ferrocene, with tricyclohexylphosphine, butyldi-1-adamantylphosphine, triphenylphosphine or 2-dicyclohexylphosphino-2',6'-dimethoxybiphenyl being preferable. The amount of organic phosphine compound used based on 1 mole of palladium is normally 1 time to 5 times the molar amount, and preferably 1.5 times to 2.5 times the molar amount, of palladium.

Examples of base or fluoride include alkaline metal acetates such as sodium acetate or potassium acetate, alkaline metal carbonates such as sodium carbonate, potassium carbonate or cesium carbonate, alkaline metal phosphates such as trisodium phosphate or tripotassium phosphate, alkaline metal hydroxides such as lithium hydroxide, sodium hydroxide or potassium hydroxide, quaternary ammonium hydroxides such as tetramethylammonium hydroxide, tetraethylammonium hydroxide or tetrabutylammonium hydroxide, and fluorides such as cesium fluoride, tetramethylammonium fluoride, tetraethylammonium fluoride or tetrabutylammonium fluoride, with sodium carbonate or tripotassium phosphate being preferable. The amount of base or fluoride used based on 1 mole of Compound (11) is normally 1 time to 10 times the molar amount, and preferably 1.5 times to 5 times the molar amount, of Compound (11).

Although varying according to such factors as the types and amounts used of the raw materials, solvent and the like, the reaction temperature is normally 0° C. to 200° C. and preferably 50° C. to 150° C.

Although varying according to such factors as the reaction temperature, the reaction time is normally 10 minutes to 120 hours and preferably 0.5 hours to 48 hours.

Although the reaction pressure may be suitably set as necessary and the reaction may be carried out under pressure, reduced pressure or atmospheric pressure, the reaction pressure is preferably atmospheric pressure.

Step 13 of Synthesis 7 is a step for obtaining Compound (1) by being subject to the deprotection of Compound (18) to remove protecting group PG thereof.

Deprotection conditions can be suitably selected according to a method described in the known art, such as the aforementioned Protective Groups in Organic Synthesis, 4th Edition, T. W. Greene and P. G. M. Wuts, ed., John Wiley & Sons Inc., or the examples of the present description.

Furthermore, in the case Compound (18) has a protecting group other than protecting group PG, preferably only protecting group PG is removed by suitably selecting the deprotection conditions.

Step 14 of Synthesis 8 is a so-called Suzuki reaction for obtaining Compound (19) by reacting Compound (6) and Compound (17) in a solvent and in the presence of a base or fluoride and a palladium catalyst in an inert gas atmosphere.

Compound (6) can be produced according to any of the aforementioned Syntheses 1 to 3. Compound (17) can be produced according to the aforementioned Synthesis 6.

Step 14 of Synthesis 8 can be carried out using the same conditions as Step 12 of the aforementioned Synthesis 7.

Step 15 of Synthesis 8 is a step for obtaining Compound (20) by being subject to the deprotection of Compound (19) to remove protecting group PG thereof.

Deprotection conditions can be suitably selected according to a method described in the known art, such as the aforementioned Protective Groups in Organic Synthesis, 4th Edition, T. W. Greene and P. G. M. Wuts, ed., John Wiley & Sons Inc., or the examples of the present description.

Furthermore, in the case Compound (20) has a protecting group other than protecting group PG, preferably only protecting group PG is removed by suitably selecting the deprotection conditions.

Step 16 of Synthesis 8 is a step for obtaining Compound (1) by reacting Compound (20) and Compound (10) in the presence of solvent and optionally base. Step 16 of Synthesis 8 can be carried out using the same conditions as Step 7 of the aforementioned Synthesis 4.

Synthesis 8

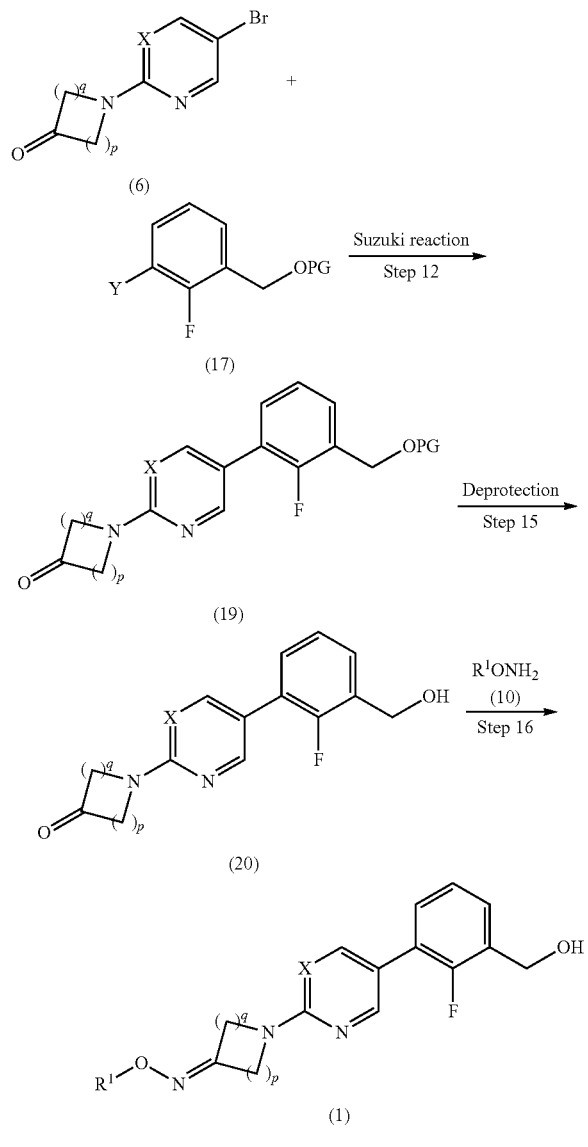

Synthesis 9

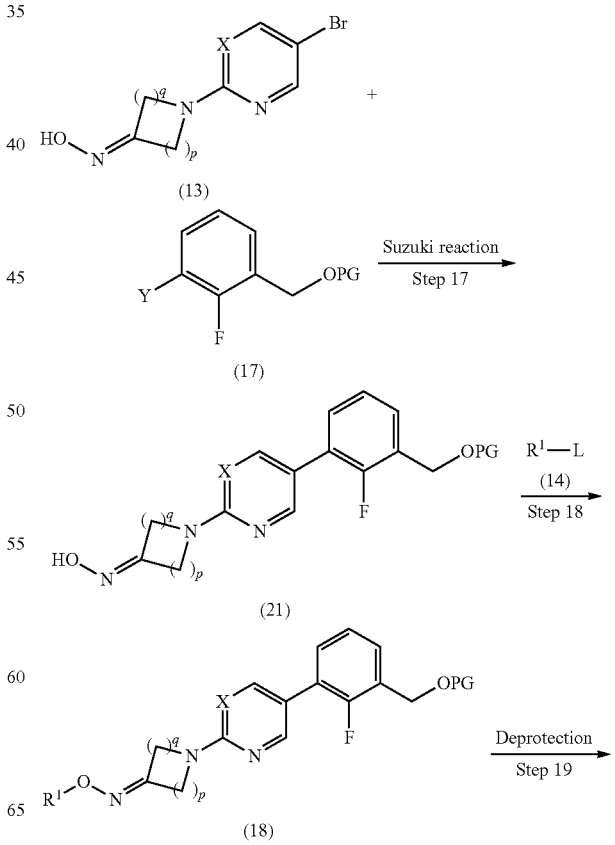

X, $R^1$, Y, PG, p and q are as previously described.

153
-continued

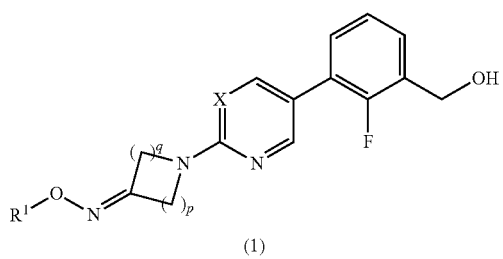

(1)

X, R¹, Y, PG, p and q are as previously described.

Step 17 of Synthesis 9 is a so-called Suzuki reaction for obtaining Compound (21) by reacting Compound (13) and Compound (17) in a solvent and in the presence of a base or fluoride and a palladium catalyst in an inert gas atmosphere.

Compound (13) can be produced according to Step 8 of the aforementioned Synthesis 5. Compound (17) can be produced according to the aforementioned Synthesis 6.

Step 17 of Synthesis 9 can be carried out using the same conditions as Step 12 of the aforementioned Synthesis 7.

Step 18 of Synthesis 9 is a step for obtaining Compound (18) by reacting Compound (21) and Compound (14) in a solvent and in the presence of base.

Step 18 of Synthesis 9 can be carried out using the same conditions as Step 9 of the aforementioned Synthesis 5.

Step 19 of Synthesis 9 is a step for obtaining Compound (1) by being subject to the deprotection of Compound (18) to remove protecting group PG thereof, and can be carried out using the same conditions as Step 13 of the aforementioned Synthesis 7.

Synthesis 10

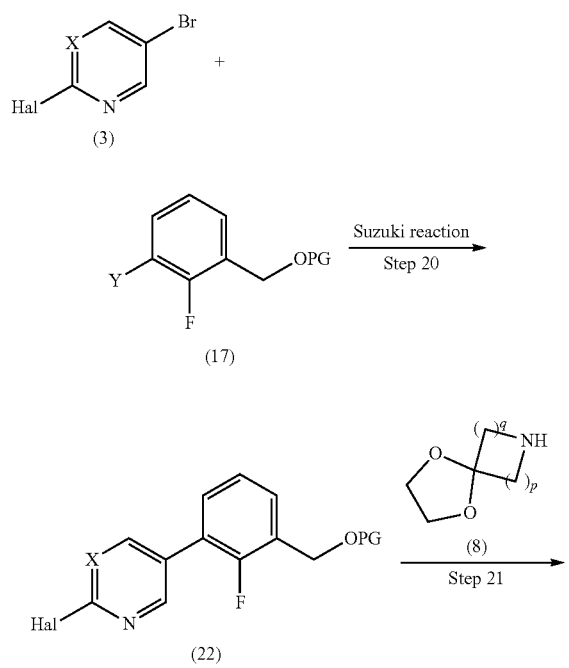

154
-continued

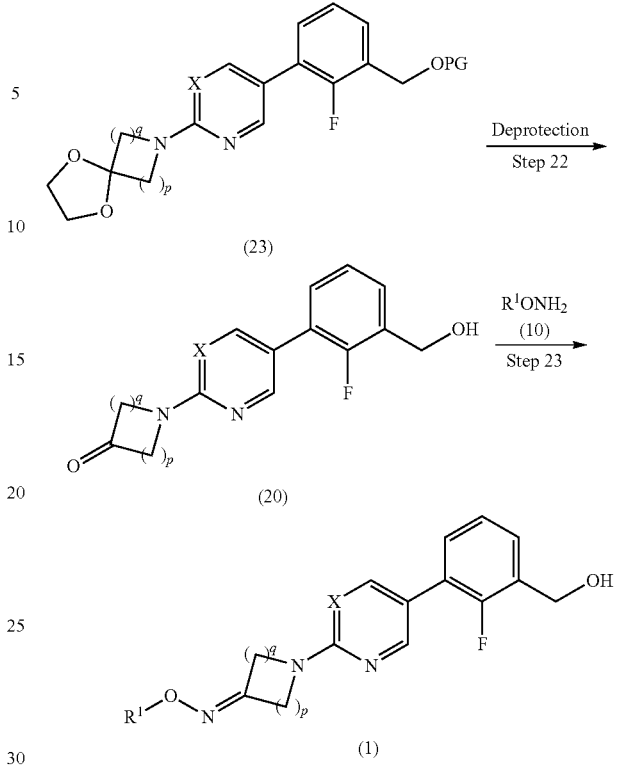

X, R¹, Hal, Y, PG, p and q are as previously described.

Step 20 of Synthesis 10 is a so-called Suzuki reaction for obtaining Compound (22) by reacting Compound (3) and Compound (17) in a solvent and in the presence of base or fluoride and a palladium catalyst in an inert gas atmosphere.

Compound (3) is known or can be produced from known compounds according to a known method. Compound (17) can be produced according to the aforementioned Synthesis 6.

Step 20 of Synthesis 10 can be carried out using the same conditions as Step 12 of the aforementioned Synthesis 7.

Step 21 of Synthesis 10 is a step for obtaining Compound (23) by reacting Compound (22) and Compound (8) in a solvent and in the presence of base.

Compound (8) is known or can be produced from known compounds according to a known method.

Step 21 of Synthesis 10 can be carried out using the same conditions as Step 5 of the aforementioned Synthesis 3.

Step 22 of Synthesis 10 is a step for obtaining Compound (20) by deprotecting protecting group PG of Compound (23) together with the carbonyl protecting group of Compound (23) using acid in a solvent.

Deprotection conditions can be suitably selected according to a method described in the known art, such as the aforementioned Protective Groups in Organic Synthesis, 4th Edition, T. W. Greene and P. G. M. Wuts, ed., John Wiley & Sons Inc., or the reference examples of the present description.

Step 23 of Synthesis 10 is a step for obtaining Compound (1) by reacting Compound (20) and Compound (10) in a solvent and in the presence of base.

Step 23 of Synthesis 10 can be carried out using the same conditions as Step 7 of the aforementioned Synthesis 4.

Compound (1) used in Production Method 1 is obtained according to the aforementioned Syntheses 1 to 10. However, Compound (1) used in the Production Method 1 can also be obtained by a reaction scheme other than that indicated in the aforementioned Syntheses 1 to 10 by interchanging the suitable combinations and/or suitable reaction orders of each of the steps and raw materials indicated in the aforementioned Syntheses 1 to 10 and by introducing and/or removing suitable protecting groups.

Although compounds obtained in each step may be isolated and purified by known means, the compounds may also be used in the subsequent step as is. Isolation and purification can be carried out using ordinary filtration, extraction, crystallization and various column chromatography procedures.

In a specific embodiment, the present invention relates to a pharmaceutical composition containing the compound of general formula (I), as indicated in each of the aforementioned specific embodiments, or a pharmacologically acceptable salt thereof, and preferably relates to a pharmaceutical composition containing the compound of general formula (I), as indicated in each of the aforementioned specific embodiments, or a pharmacologically acceptable salt thereof, and at least one type of pharmacologically acceptable additive.

In a specific embodiment, the present invention relates to a pharmaceutical composition containing the compound of general formula (I), as indicated in each of the aforementioned specific embodiments, or a pharmacologically acceptable salt thereof, for treating a disease prevented, alleviated and/or treated by inhibiting VAP-1, and preferably relates to a pharmaceutical composition containing the compound of general formula (I), as indicated in each of the aforementioned specific embodiments, or a pharmacologically acceptable salt thereof, and at least one type of pharmacologically acceptable additive, for treating a disease prevented, alleviated and/or treated by inhibiting VAP-1.

In a specific embodiment, the present invention relates to a pharmaceutical composition containing the compound of general formula (I), as indicated in each of the aforementioned specific embodiments, or a pharmacologically acceptable salt thereof, for treating diabetic nephropathy, and preferably relates to a pharmaceutical composition containing the compound of general formula (I), as indicated in each of the aforementioned specific embodiments, or a pharmacologically acceptable salt thereof, and at least one type of pharmacologically acceptable additive, for treating diabetic nephropathy.

In a specific embodiment, the present invention relates to a pharmaceutical composition containing the compound of general formula (I), as indicated in each of the aforementioned specific embodiments, or a pharmacologically acceptable salt thereof, for treating non-alcoholic steatohepatitis, and preferably relates to a pharmaceutical composition containing the compound of general formula (I), as indicated in each of the aforementioned specific embodiments, or a pharmacologically acceptable salt thereof, and at least one type of pharmacologically acceptable additive, for treating non-alcoholic steatohepatitis.

The pharmaceutical composition containing the compound of general formula (I), or a pharmacologically acceptable salt thereof, can be in the form of the compound per se (in the form of a bulk powder), or can be in the form of a preparation, such as a tablet, capsule, powder, syrup, granule, grain, pill, suspension, emulsion, percutaneous absorbent, suppository, ointment, lotion, inhalant, ophthalmic solution or injection, produced by mixing with suitable pharmacologically acceptable additives and the like, and can be administered orally or parenterally (such as by intravenous, intramuscular, intraperitoneal, transdermal, transnasal, transtracheal, transpulmonary, ophthalmic, intradermal or subcutaneous administration).

These preparations are produced by known methods using additives such as excipients, lubricants, binders, disintegrating agents, emulsifiers, stabilizers, correctives, diluents, isotonic agents, buffers, pH adjusters, solubilizers, thickeners, dispersants or preservatives (antiseptics).

Examples of excipients include organic excipients and inorganic excipients. Examples of organic excipients include sugar derivatives such as lactose, sucrose, glucose, mannitol or sorbitol, starch derivatives such as cornstarch, potato starch, α-starch or dextrin, cellulose derivatives such as crystalline cellulose, gum arabic, dextran and pullulan. Examples of inorganic excipients include light anhydrous silicic acid, and sulfates such as calcium sulfate.

Examples of lubricants include stearic acid, metal stearates such as calcium stearate or magnesium stearate, talc, colloidal silica, waxes such as beeswax or spermaceti, boric acid, adipic acid, sulfates such as sodium sulfate, glycol, fumaric acid, sodium benzoate, D,L-leucine, sodium lauryl sulfate, silicic acids such as anhydrous silicic acid or silicic acid hydrate, and starch derivatives listed as examples of the aforementioned excipients.

Examples of binders include hydroxypropyl cellulose, hydroxypropyl methyl cellulose, polyvinylpyrrolidone, macrogol, and compounds listed as examples of the aforementioned excipients.

Examples of disintegrating agents include cellulose derivatives such as low substituted hydroxypropyl cellulose, carboxymethyl cellulose, calcium carboxymethyl cellulose or internally crosslinked calcium carboxymethyl cellulose, crosslinked polyvinylpyrrolidone, and chemically modified starch or cellulose derivatives such as carboxymethyl starch or sodium carboxymethyl starch.

Examples of emulsifiers include colloidal clay such as bentonite or veegum, anionic surfactants such as sodium lauryl sulfate, cationic surfactants such as benzalkonium chloride, and nonionic surfactants such as polyoxyethylene alkyl ether, polyoxyethylene sorbitan fatty acid ester or sucrose fatty acid ester.

Examples of stabilizers include parahydroxybenzoates such as methyl paraben or propyl paraben, alcohols such as chlorobutanol, benzyl alcohol or phenyl ethyl alcohol, benzalkonium chloride, phenols such as phenol or cresol, thimerosal, acetic anhydride and sorbic acid.

Examples of correctives include sweeteners such as sodium saccharin or aspartame, acidifiers such as citric acid, malic acid or tartaric acid, and aromatics such as menthol, lemon extract or orange extract.

Examples of diluents include water, lactose, mannitol, glucose, sucrose, calcium sulfate, hydroxypropyl cellulose, microcrystalline cellulose, water, ethanol, polyethylene glycol, propylene glycol, glycerol, starch, polyvinylpyrrolidone and mixtures thereof.

Examples of isotonic agents include glycerin, propylene glycol, sodium chloride, potassium chloride, sorbitol and mannitol.

Examples of buffers include phosphoric acid, phosphates, citric acid, acetic acid and ε-aminocaproic acid.

Examples of pH adjusters include hydrochloric acid, citric acid, phosphoric acid, acetic acid, sodium hydroxide, potassium hydroxide, boric acid, borax, sodium carbonate and sodium bicarbonate.

Examples of solubilizers include Polysorbate 80, polyoxyethylene hydrogenated castor oil 60 and macrogol 4000.

Examples of thickeners and dispersants include cellulose polymers such as hydroxypropyl methyl cellulose or hydroxypropyl cellulose, polyvinyl alcohol and polyvinylpyrrolidone, while examples of stabilizers include edetic acid and sodium edetate.

Examples of preservatives (antiseptics) include general purpose sorbic acid, potassium sorbate, benzalkonium chloride, benzethonium chloride, methyl parahydroxybenzoate, propyl parahydroxybenzoate and chlorobutanol, and these preservatives can also be used in combination.

Other suitable additives can also be used corresponding to the administration form. For example, in the case the compound of general formula (I) of the present invention, or a pharmacologically acceptable salt thereof, is in the form of an aerosol for transnasal or transtracheal administration, carbon dioxide or a chlorofluorocarbon (CFC), such as dichlorodifluoromethane, trichlorofluoromethane or dichlorotetrafluoroethane, can be used for the propellant.

Although able to be varied according to conditions such as the symptoms, age or body weight of a patient, the dosage of the active ingredient of the pharmaceutical composition of the present invention is a lower limit of 0.001 mg/Kg (and preferably 0.01 mg/Kg) and upper limit of 20 mg/Kg (and preferably 10 mg/Kg) each per administration in the case of oral administration, or a lower limit of 0.0001 mg/Kg (and preferably 0.0005 mg/Kg) and upper limit of 10 mg/Kg (and preferably 5 mg/Kg) each per administration in the case of parental administration, administered one to six times per day to an adult corresponding to symptoms.

In a specific embodiment, the present invention relates to the compound of general formula (I), as indicated in each of the aforementioned specific embodiments, or a pharmacologically acceptable salt thereof, for use in treating a disease prevented, alleviated and/or treated by inhibiting VAP-1.

In a specific embodiment, the present invention relates to the compound of general formula (I), as indicated in each of the aforementioned specific embodiments, or a pharmacologically acceptable salt thereof, for producing a medicament for treating a disease prevented, alleviated and/or treated by inhibiting VAP-1.

In a specific embodiment, the present invention relates to a method for treating a disease prevented, alleviated and/or treated by inhibiting VAP-1, which includes administering a therapeutically effective amount of the compound of general formula (I), as indicated in each of the aforementioned specific embodiments, or a pharmacologically acceptable salt thereof, to a patient in need thereof.

In the present invention, the terms "treating" a disease or "treatment" of a disease include (1) preventing a disease, or in other words, not allowing the onset of clinical symptoms of a disease in a subject for which, although there is the possibility of having been exposed to a disease or being susceptible to a disease, does not yet manifest or exhibit symptoms of the disease, (2) suppressing a disease, or in other words, suppressing the onset of a disease or clinical symptoms thereof, or (3) alleviating a disease, or in other words, inducing a temporary or permanent regression of the disease or clinical symptoms thereof.

In the present invention, a "therapeutically effective amount" refers to, in the case of administering to a subject, an amount of the compound of general formula (I) of the present invention that (i) treats or prevents a disease, (ii) relieves, improves or eliminates one or more symptoms of a disease, or (iii) prevents or delays the manifestation of one or more symptoms of a disease. A therapeutically effective amount varies according to the compound of general formula (I) of the present invention used, the disease state being treated, the severity of the disease being treated, the age and relative health status of the subject, the administration route and form, the discretion of the examining physician or veterinarian, and other factors.

Examples

DIOL silica gel in silica gel column chromatography indicates CHROMATOREX (trade name) DIOL MB 100-40/75 manufactured by Fuji Silysia Chemical Ltd.

DNH silica gel in silica gel column chromatography indicates CHROMATOREX (trade name) DNH MB 100-40/75 manufactured by Fuji Silysia Chemical Ltd.

DUIS of the ionization mode in mass spectroscopy is the ESI and APCI mixed mode.

Unless otherwise mentioned, $^1$H-NMR is indicated by chemical shifts (δ) relative to tetramethylsilane as the internal standard (0 ppm), and the coupling constants (J values) are indicated in Hz unit. The peak splitting patterns are indicated by the following abbreviations: s: singlet, d: doublet, t: triplet, q: quartet, quin: quintet, sext: sextet, sep: septet, br s: broad singlet, m: multiplet.

The abbreviations described in Examples and Reference Examples have general meanings that are usually used in the fields of organic chemistry and pharmaceuticals. Specifically, the abbreviations are understood by skilled artisans as follows.

TEA: triethylamine
DIPEA: N,N-diisopropylethylamine
DMF: N,N-dimethylformamide
DMSO: dimethylsulfoxide
THF: tetrahydrofuran
CDI: 1,1'-carbonyldiimidazole
TBME: tert-butyl methyl ether
DHP: 3,4-dihydro-2H-pyran
PPTS: pyridinium para-toluenesulfonate
DMAP: N,N-dimethyl-4-aminopyridine
BAST: bis(2-methoxyethyl)aminosulfur trifluoride
NMP: N-methylpyrrolidone
TBS: tert-butyldimethylsilyl
THP: tetrahydropyran-2-yl Compounds used in Examples were synthesized as follows.

EXAMPLES

Example 1

2-Fluoro-3-{2-[3-(methoxyimino)azetidin-1-yl]pyrimidin-5-yl}benzyl carbamimidoylcarbamate
(Compound II-2

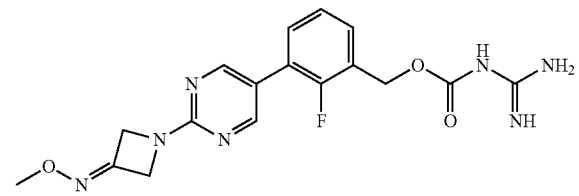 [SMILES: CON=C1CN(c2ncc(-c3cccc(COC(=O)NC(=N)N)c3F)cn2)C1]

CDI 1.91 g (11.8 mmol) was added to a DMF (20 mL) solution of 1-[5-(2-fluoro-3-hydroxymethylphenyl)pyrimidin-2-yl]azetidin-3-one O-methyl oxime 1.78 g (5.89 mmol) synthesized in the same manner as in Reference Example 7-1, and the mixture was stirred at room temperature for 2 hours. Next, guanidine carbonate 2.12 g (11.8 mmol) was added, and the mixture was stirred at room temperature for 4 hours. After the completion of the reaction, water was added to the reaction mixture, the mixture was stirred at room temperature, and the precipitated solid was collected by filtration. Ethyl acetate was added to the obtained solid, and the mixture was stirred at 50° C. for 1 hour. The solid was then collected by filtration and dried under reduced pressure to give the title compound 2.09 g (5.40 mmol, yield 92%) as a white solid. Mass spectrum (ESI, m/z):388[M+1]$^+$.

$^1$H-NMR spectrum (400 MHz, DMSO-d$_6$+D$_2$O) δ:8.63 (br s, 2H), 7.54-7.47 (m, 1H), 7.45-7.39 (m, 1H), 7.33-7.26 (m, 1H), 5.06 (s, 2H), 4.85-4.78 (m, 4H), 3.83 (s, 3H).

Example 2

3-{2-[3-(Ethoxyimino)azetidin-1-yl]pyrimidin-5-yl}-2-fluorobenzyl carbamimidoylcarbamate (Compound II-3)

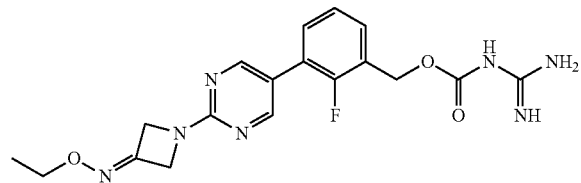 [SMILES: CCON=C1CN(c2ncc(-c3cccc(COC(=O)NC(=N)N)c3F)cn2)C1]

DMF 2.6 mL was added to 1-{5-[2-fluoro-3-(hydroxymethyl)phenyl]pyrimidin-2-yl}azetidin-3-one O-ethyl oxime 80.5 mg (0.254 mmol) synthesized in the same manner as in Reference Example 7-2, and CDI 96.3 mg (0.594 mmol). The mixture was ultrasonicated and was stirred at room temperature for 1 hour. Next, guanidine carbonate 98.4 mg (0.546 mmol) was added, and the mixture was ultrasonicated and was stirred at room temperature for 2 hours. After the completion of the reaction, methylene chloride 15 mL and water 25 mL were added to the reaction mixture, and the mixture was stirred and cooled with ice. The precipitated solid was collected by filtration, washed with water and diethyl ether, and dried under reduced pressure to give the title compound 59.7 mg (0.149 mmol, yield 58%) as a grayish white solid.

Mass spectrum (DUIS, m/z):402[M+1]$^+$.

$^1$H-NMR spectrum (400 MHz, DMSO-d$_6$+D$_2$O) δ:8.63 (s, 2H), 7.58-7.47 (m, 1H), 7.46-7.39 (m, 1H), 7.36-7.27 (m, 1H), 5.06 (s, 2H), 4.87-4.76 (m, 4H), 4.09 (q, J=7.0 Hz, 2H), 1.22 (t, J=7.0 Hz, 3H).

Example 3

2-Fluoro-3-(2-{3-[(methoxy-d$_3$)imino]azetidin-1-yl}pyrimidin-5-yl)benzyl carbamimidoylcarbamate (Compound II-12)

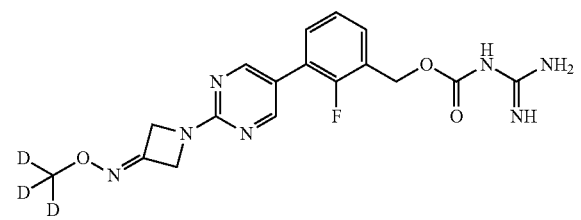 [SMILES: [2H]C([2H])([2H])ON=C1CN(c2ncc(-c3cccc(COC(=O)NC(=N)N)c3F)cn2)C1]

CDI 140 mg (0.863 mmol) was added to a DMF (6 mL) solution of 1-{5-[2-fluoro-3-(hydroxymethyl)phenyl]pyrimidin-2-yl}azetidin-3-one O-methyl-d$_3$ oxime 124 mg (0.406 mmol) synthesized in the same manner as in Reference Example 7-3, and the mixture was stirred at room temperature for 3 hours. Next, guanidine carbonate 150 mg (0.833 mmol) was added, and the mixture was stirred at room temperature for 3 hours. After the completion of the reaction, water was added to the reaction mixture and the mixture was stirred at room temperature. The precipitated solid was collected by filtration and was dried under reduced pressure to give the title compound 143 mg (0.366 mmol, yield 90%) as a white solid.

Mass spectrum (ESI, m/z):391[M+1].

$^1$H-NMR spectrum (400 MHz, DMSO-d$_6$+D$_2$O) δ:8.63 (br s, 2H), 7.55-7.47 (m, 1H), 7.46-7.38 (m, 1H), 7.34-7.25 (m, 1H), 5.06 (s, 2H), 4.86-4.76 (m, 4H).

Example 4

3-[2-(3-{[(tert-Butyldimethylsilyl)oxy]imino}azetidin-1-yl)pyrimidin-5-yl]-2-fluorobenzyl carbamimidoylcarbamate (Compound II-62)

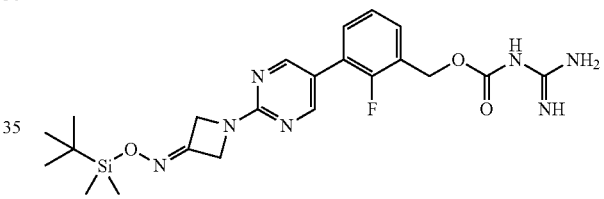

DMF 3 mL was added to 1-{5-[2-fluoro-3-(hydroxymethyl)phenyl]pyrimidin-2-yl}azetidin-3-one O-(tert-butyldimethylsilyl) oxime 129 mg (0.320 mmol) synthesized in the same manner as in Reference Example 13-1, and CDI 119 mg (0.734 mmol), and the mixture was stirred at room temperature for 2 hours. Next, guanidine carbonate 125 mg (0.694 mmol) was added, and the mixture was stirred at room temperature for 3 hours. After the completion of the reaction, water 20 mL was added to the reaction mixture, and the mixture was stirred. The precipitated solid was collected by filtration and was dried under reduced pressure. Ethyl acetate was added to the obtained solid, and the mixture was stirred at 75° C. After natural cooling, diisopropyl ether was added, and the mixture was stirred at room temperature. The solid was collected by filtration and was dried under reduced pressure to give the title compound 94.6 mg (0.194 mmol, yield 61%) as a white solid.

Mass spectrum (DUIS, m/z):488[M+1]$^+$.

$^1$H-NMR spectrum (400 MHz, DMSO-d$_6$) δ:8.63 (d, J=1.4 Hz, 2H), 7.55-7.47 (m, 1H), 7.45-7.37 (m, 1H), 7.32-7.26 (m, 1H), 5.06 (s, 2H), 4.89-4.78 (m, 4H), 0.92 (s, 9H), 0.16 (s, 6H).

Example 5

2-Fluoro-3-(2-{3-[(2-fluoroethoxy)imino]azetidin-1-yl}pyrimidin-5-yl)benzyl carbamimidoylcarbamate (Compound II-15)

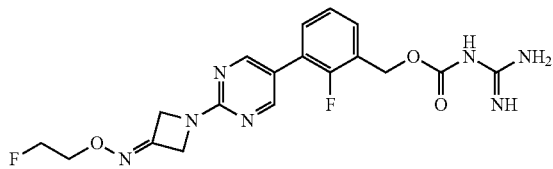 [SMILES: N=C(N)NC(=O)OCc1cccc(-c2cnc(N3CC(=NOCCF)C3)nc2)c1F]

CDI 160 mg (0.99 mmol) was added to a DMF (5 mL) solution of 1-{5-[2-fluoro-3-(hydroxymethyl)phenyl]pyrimidin-2-yl}azetidin-3-one O-(2-fluoroethyl) oxime 150 mg (0.45 mmol) synthesized in the same manner as in Reference Example 7-4, and the mixture was stirred at room temperature for 2 hours. Next, guanidine carbonate 160 mg (0.89 mmol) was added, and the mixture was stirred at room temperature for 2.5 hours. After the completion of the reaction, water was added to the reaction mixture, and followed by extraction with methylene chloride. The organic layer was washed with brine, dried over anhydrous sodium sulfate, and filtered. The filtrate was concentrated under reduced pressure. The concentrated residue was purified by silica gel column chromatography (DNH silica gel, eluting solvent: 1,2-dichloroethane:methanol) to give the title compound 63 mg (0.15 mmol, yield 33%) as a white solid.

Mass spectrum (APCI, m/z):420[M+1]$^+$.

$^1$H-NMR spectrum (400 MHz, DMSO-d$_6$+D$_2$O) δ:8.64 (d, J=1.0 Hz, 2H), 7.55-7.47 (m, 1H), 7.45-7.39 (m, 1H), 7.33-7.27 (m, 1H), 5.06 (s, 2H), 4.88-4.80 (m, 4H), 4.73-4.55 (m, 2H), 4.34-4.21 (m, 2H).

Example 6

3-(2-{3-[(2,2-Difluoroethoxy)imino]azetidin-1-yl}pyrimidin-5-yl)-2-fluorobenzyl carbamimidoylcarbamate (Compound II-18)

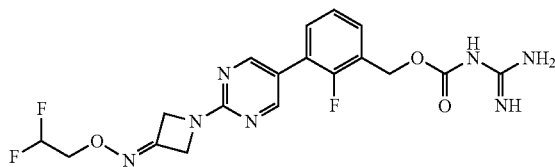 [SMILES: N=C(N)NC(=O)OCc1cccc(-c2cnc(N3CC(=NOCC(F)F)C3)nc2)c1F]

CDI 74 mg (0.46 mmol) was added to a DMF (3 mL) solution of 1-{5-[2-fluoro-3-(hydroxymethyl)phenyl]pyrimidin-2-yl}azetidin-3-one O-(2,2-difluoroethyl) oxime 80 mg (0.23 mmol) synthesized in the same manner as in Reference Example 7-5, and the mixture was stirred at room temperature for 16 hours. Next, guanidine carbonate 82 mg (0.46 mmol) was added, and the mixture was stirred at room temperature for 2 hours. After the completion of the reaction, water was added to the reaction mixture and the mixture was stirred. The precipitated solid was collected by filtration and was dried under reduced pressure to give the title compound 66 mg (0.15 mmol, yield 65%) as a white solid.

Mass spectrum (ESI, m/z):438[M+1]$^+$.

$^1$H-NMR spectrum (400 MHz, DMSO-d$_6$+D$_2$O) δ:8.66-8.61 (m, 2H), 7.55-7.47 (m, 1H), 7.46-7.38 (m, 1H), 7.34-7.26 (m, 1H), 6.25 (tt, J=3.6, 54.8 Hz, 1H), 5.06 (s, 2H), 4.89-4.81 (m, 4H), 4.32 (dt, J=3.6, 14.6 Hz, 2H).

Example 7

2-Fluoro-3-(2-{3-[(2,2,2-trifluoroethoxy)imino]azetidin-1-yl}pyrimidin-5-yl)benzyl carbamimidoylcarbamate (Compound II-19)

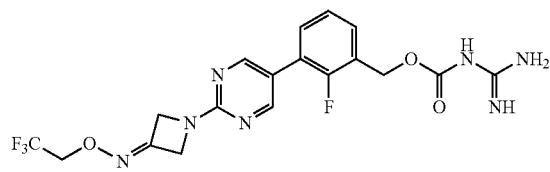 [SMILES: N=C(N)NC(=O)OCc1cccc(-c2cnc(N3CC(=NOCC(F)(F)F)C3)nc2)c1F]

CDI 120 mg (0.740 mmol) was added to a DMF (4 mL) solution of 1-{5-[2-fluoro-3-(hydroxymethyl)phenyl]pyrimidin-2-yl}azetidin-3-one O-(2,2,2-trifluoroethyl) oxime 124 mg (0.335 mmol) synthesized in the same manner as in Reference Example 7-6, and the mixture was stirred at room temperature for 1.5 hours. Next, guanidine carbonate 120 mg (0.666 mmol) was added, and the mixture was stirred at room temperature for 16 hours. After the completion of the reaction, water was added to the reaction mixture, and followed by extraction with methylene chloride. The organic layer was washed with brine, dried over anhydrous sodium sulfate, and filtered. The filtrate was concentrated under reduced pressure. The concentrated residue was purified by silica gel column chromatography (DNH silica gel, eluting solvent:ethyl acetate:methanol) to give the title compound 80.8 mg (0.177 mmol, yield 53%) as a white solid.

Mass spectrum (ESI, m/z):456[M+1]$^+$.

$^1$H-NMR spectrum (400 MHz, DMSO-d$_6$+D$_2$O) δ:8.64 (d, J=1.4 Hz, 2H), 7.54-7.48 (m, 1H), 7.45-7.40 (m, 1H), 7.33-7.27 (m, 1H), 5.06 (s, 2H), 4.92-4.83 (m, 4H), 4.70 (q, J=9.0 Hz, 2H).

Example 8

2-Fluoro-3-(2-{3-[(3-fluoropropoxy)imino]azetidin-1-yl}pyrimidin-5-yl)benzyl carbamimidoylcarbamate (Compound II-20)

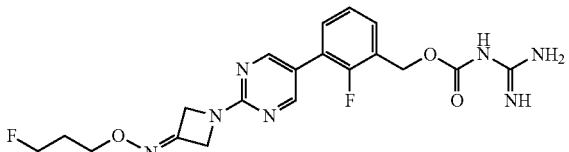

CDI 89 mg (0.55 mmol) was added to a DMF (4 mL) solution of 1-{5-[2-fluoro-3-(hydroxymethyl)phenyl]pyrimidin-2-yl}azetidin-3-one O-(3-fluoropropyl) oxime 96 mg (0.28 mmol) synthesized in the same manner as in Reference Example 7-7, and the mixture was stirred at room temperature for 17 hours. Next, guanidine carbonate 99 mg (0.55 mmol) was added, and the mixture was stirred at room temperature for 4 hours. After the completion of the reaction, water was added to the reaction mixture, and followed by extraction with methylene chloride. The organic layer was washed with water, dried over anhydrous sodium sulfate, and filtered. The filtrate was concentrated under reduced pressure. The concentrated residue was purified by silica gel column chromatography (DNH silica gel, eluting solvent:ethyl acetate:methanol) to give the title compound 0.10 g (0.23 mmol, yield 82%) as a white solid.

Mass spectrum (ESI, m/z):434[M+1]$^+$.

$^1$H-NMR spectrum (400 MHz, DMSO-d$_6$+D$_2$O) δ:8.66-8.60 (m, 2H), 7.54-7.48 (m, 1H), 7.45-7.39 (m, 1H), 7.33-7.27 (m, 1H), 5.06 (s, 2H), 4.86-4.79 (m, 4H), 4.54 (td, J=6.0, 47.2 Hz, 2H), 4.14 (t, J=6.3 Hz, 2H), 2.12-1.90 (m, 2H).

Example 9

2-Fluoro-3-{2-[3-({2-[(tetrahydropyran-2-yl)oxy]ethoxy}imino)azetidin-1-yl]pyrimidin-5-yl}benzyl carbamimidoylcarbamate (Compound II-67)

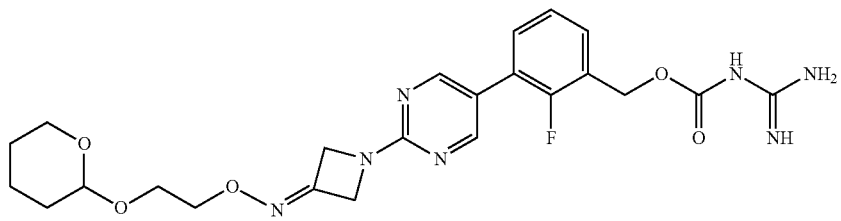 [SMILES: N=C(N)NC(=O)OCc1cccc(-c2cnc(N3CC(=NOCCOC4CCCCO4)C3)nc2)c1F]

CDI 74 mg (0.46 mmol) was added to a DMF (6 mL) solution of 1-{5-[2-fluoro-3-(hydroxymethyl)phenyl]pyrimidin-2-yl}azetidin-3-one O-{2-[(tetrahydropyran-2-yl)oxy]ethyl} oxime 94 mg (0.23 mmol) synthesized in the same manner as in Reference Example 7-8, and the mixture was stirred at room temperature for 7 hours. Next, guanidine carbonate 81 mg (0.45 mmol) was added, and the mixture was stirred at room temperature for 14 hours. After the completion of the reaction, water was added to the reaction mixture, and followed by extraction with methylene chloride. The organic layer was washed with water, dried over anhydrous sodium sulfate, and filtered. The filtrate was concentrated under reduced pressure. The concentrated residue was purified by silica gel column chromatography (DNH silica gel, eluting solvent:ethyl acetate:methanol) to give the title compound 85 mg (0.17 mmol, yield 74%) as a white solid.

$^1$H-NMR spectrum (400 MHz, DMSO-d$_6$) δ:8.64 (d, J=1.3 Hz, 2H), 7.56-7.46 (m, 1H), 7.45-7.37 (m, 1H), 7.33-7.25 (m, 1H), 5.06 (s, 2H), 4.90-4.75 (m, 4H), 4.63-4.57 (m, 1H), 4.23-4.12 (m, 2H), 3.87-3.70 (m, 2H), 3.67-3.57 (m, 1H), 3.49-3.38 (m, 1H), 1.82-1.34 (m, 6H).

Example 10

2-Fluoro-3-{2-[3-({3-[(tetrahydropyran-2-yl)oxy]propoxy}imino)azetidin-1-yl]pyrimidin-5-yl}benzyl carbamimidoylcarbamate (Compound II-68)

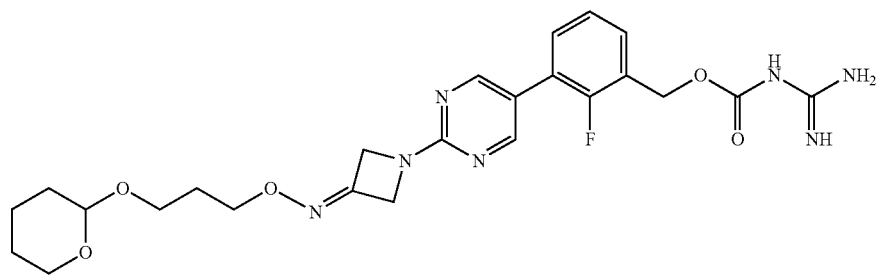 [SMILES: N=C(N)NC(=O)OCc1cccc(-c2cnc(N3CC(=NOCCCOC4CCCCO4)C3)nc2)c1F]

CDI 136 mg (0.839 mmol) was added to a DMF (4 mL) solution of 1-{5-[2-fluoro-3-(hydroxymethyl)phenyl]pyrimidin-2-yl}azetidin-3-one O-{3-[(tetrahydropyran-2-yl)oxy]propyl} oxime 180 mg (0.418 mmol) synthesized in the same manner as in Reference Example 7-9, and the mixture was stirred at room temperature for 3 hours. Next, guanidine carbonate 151 mg (0.838 mmol) was added, and the mixture was stirred at room temperature for 3 hours. After the completion of the reaction, water was added to the reaction mixture, and followed by extraction with methylene chloride. The organic layer was washed with water, dried over anhydrous sodium sulfate, and filtered. The filtrate was concentrated under reduced pressure. The concentrated residue was purified by silica gel column chromatography (DNH silica gel, eluting solvent:ethyl acetate:methanol) to give the title compound 145 mg (0.281 mmol, yield 67%) as a white solid.

$^1$H-NMR spectrum (400 MHz, DMSO-$d_6$+$D_2O$) δ:8.63 (d, J=1.4 Hz, 2H), 7.57-7.47 (m, 1H), 7.46-7.39 (m, 1H), 7.34-7.24 (m, 1H), 5.07 (s, 2H), 4.86-4.78 (m, 4H), 4.62-4.48 (m, 1H), 4.11 (t, J=6.4 Hz, 2H), 3.81-3.63 (m, 2H), 3.52-3.37 (m, 2H), 1.87 (quin, J=6.4 Hz, 2H), 1.76-1.38 (m, 6H).

Example 11

2-Fluoro-3-{2-[3-({4-[(tetrahydropyran-2-yl)oxy]butoxy}imino)azetidin-1-yl]pyrimidin-5-yl}benzyl carbamimidoylcarbamate (Compound II-69)

Mass spectrum (APCI, m/z):530[M+1]$^+$.

$^1$H-NMR spectrum (400 MHz, DMSO-$d_6$+$D_2O$) δ:8.63 (d, J=1.0 Hz, 2H), 7.54-7.47 (m, 1H), 7.45-7.38 (m, 1H), 7.33-7.26 (m, 1H), 5.06 (s, 2H), 4.86-4.77 (m, 4H), 4.56-4.52 (m, 1H), 4.09-4.01 (m, 2H), 3.77-3.31 (m, 4H), 1.76-1.36 (m, 10H).

Example 12

2-Fluoro-3-(2-{3-[(2-methoxyethoxy)imino]azetidin-1-yl}pyrimidin-5-yl)benzyl carbamimidoylcarbamate (Compound II-26)

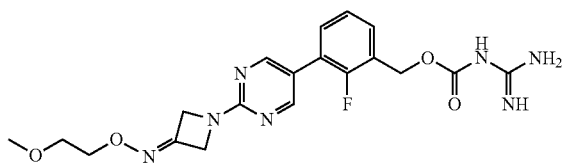

CDI 62 mg (0.38 mmol) was added to a DMF (6 mL) solution of 1-{5-[2-fluoro-3-(hydroxymethyl)phenyl]pyrimidin-2-yl}azetidin-3-one O-(2-methoxyethyl) oxime 66 mg (0.19 mmol) synthesized in the same manner as in Reference Example 7-11, and the mixture was stirred at room temperature for 7 hours. Next, guanidine carbonate 70 mg (0.39 mmol) was added, and the mixture was stirred at

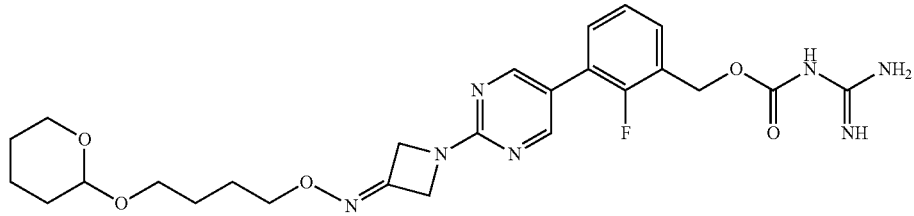 [SMILES: N=C(N)NC(=O)OCc1cccc(-c2cnc(N3CC(=NOCCCCOC4CCCCO4)C3)nc2)c1F]

CDI 160 mg (0.987 mmol) was added to a DMF (6 mL) solution of 1-{5-[2-fluoro-3-(hydroxymethyl)phenyl]pyrimidin-2-yl}azetidin-3-one O-{4-[(tetrahydropyran-2-yl)oxy]butyl} oxime 190 mg (0.427 mmol) synthesized in the same manner as in Reference Example 7-10, and the mixture was stirred at room temperature for 2 hours. Next, guanidine carbonate 160 mg (0.888 mmol) was added, and the mixture was stirred at room temperature for 16 hours. After the completion of the reaction, water was added to the reaction mixture, and the mixture was stirred at room temperature. The precipitated solid was collected by filtration. Ethyl acetate was added to the obtained solid, and the mixture was stirred at 50° C. for 30 minutes. Thereafter, the solid was collected by filtration and was dried under reduced pressure to give the title compound 166 mg (0.313 mmol, yield 73%) as a white solid.

room temperature for 19 hours. After the completion of the reaction, water was added to the reaction mixture, and followed by extraction with methylene chloride. The organic layer was washed with water, dried over anhydrous sodium sulfate, and filtered. The filtrate was concentrated under reduced pressure. The concentrated residue was purified by silica gel column chromatography (DNH silica gel, eluting solvent:ethyl acetate:methanol) to give the title compound 73 mg (0.17 mmol, yield 89%) as a white solid.

Mass spectrum (ESI, m/z):432[M+1]$^+$.

$^1$H-NMR spectrum (400 MHz, DMSO-$d_6$+$D_2O$) δ:8.63 (d, J=1.4 Hz, 2H), 7.54-7.47 (m, 1H), 7.45-7.39 (m, 1H), 7.33-7.27 (m, 1H), 5.06 (s, 2H), 4.86-4.78 (m, 4H), 4.18-4.12 (m, 2H), 3.60-3.54 (m, 2H), 3.27 (s, 3H).

Example 13

2-Fluoro-3-(2-{3-[(2-{2-[(tetrahydropyran-2-yl)oxy]ethoxy}ethoxy)imino]azetidin-1-yl}pyrimidin-5-yl)benzyl carbamimidoylcarbamate (Compound II-70)

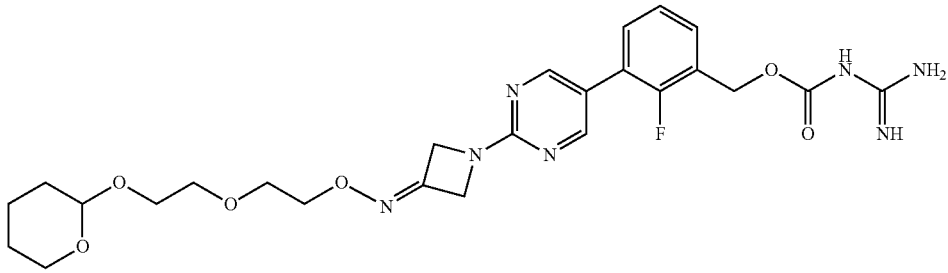 [SMILES: N=C(N)NC(=O)OCc1cccc(-c2cnc(N3CC(=NOCCOCCOC4CCCCO4)C3)nc2)c1F]

CDI 85 mg (0.52 mmol) was added to a DMF (2 mL) solution of 1-{5-[2-fluoro-3-(hydroxymethyl)phenyl]pyrimidin-2-yl}azetidin-3-one O-[2-{2-[(tetrahydropyran-2-yl)oxy]ethoxy}ethyl] oxime 105 mg (0.228 mmol) synthesized in the same manner as in Reference Example 7-12, and the mixture was stirred at room temperature for 1.5 hours. Next, guanidine carbonate 85 mg (0.47 mmol) was added, and the mixture was stirred at room temperature for 16 hours. After the completion of the reaction, water was added to the reaction mixture, and followed by extraction with methylene chloride. The organic layer was washed with brine, dried over anhydrous sodium sulfate, and filtered. The filtrate was concentrated under reduced pressure. The concentrated residue was purified by silica gel column chromatography (DNH silica gel, eluting solvent:ethyl acetate: methanol) to give the title compound 98 mg (0.18 mmol, yield 79%) as a white foam.

$^1$H-NMR spectrum (400 MHz, DMSO-$d_6$+$D_2O$) δ:8.63 (d, J=1.3 Hz, 2H), 7.54-7.48 (m, 1H), 7.46-7.39 (m, 1H), 7.33-7.27 (m, 1H), 5.06 (s, 2H), 4.86-4.78 (m, 4H), 4.60-4.56 (m, 1H), 4.18-4.12 (m, 2H), 3.78-3.38 (m, 8H), 1.76-1.34 (m, 6H).

Example 14

[({1-[5-(3-{[(Carbamimidoylcarbamoyl)oxy]methyl}-2-fluorophenyl)pyrimidin-2-yl]azetidin-3-ylidene}amino)oxy]methyl pivalate (Compound II-31)

CDI 30 mg (0.19 mmol) was added to a DMF (2 mL) solution of {[(1-{5-[2-fluoro-3-(hydroxymethyl)phenyl]pyrimidin-2-yl}azetidin-3-ylidene)amino]oxy}methyl pivalate 34 mg (0.084 mmol) synthesized in the same manner as in Reference Example 7-13, and the mixture was stirred at room temperature for 2 hours. Next, guanidine carbonate 30 mg (0.17 mmol) was added, and the mixture was stirred at room temperature for 16 hours. After the completion of the reaction, water was added to the reaction mixture, and followed by extraction with methylene chloride. The organic layer was washed with brine, dried over anhydrous sodium sulfate, and filtered. The filtrate was concentrated under reduced pressure. The concentrated residue was purified by silica gel column chromatography (DIOL silica gel, eluting solvent:ethyl acetate:methanol) and (DNH silica gel, eluting solvent: ethyl acetate:methanol) to give the title compound 22 mg (0.045 mmol, yield 54%) as a white solid.

Mass spectrum (ESI, m/z):488[M+1]$^+$.

$^1$H-NMR spectrum (400 MHz, DMSO-d$_6$+D$_2$O) δ:8.64 (s, 2H), 7.54-7.47 (m, 1H), 7.46-7.39 (m, 1H), 7.33-7.26 (m, 1H), 5.68 (s, 2H), 5.06 (s, 2H), 4.90-4.80 (m, 4H), 1.17 (s, 9H).

Example 15

3-[2-(3-{[(2,2-Dimethyl-1,3-dioxan-5-yl)methoxy]imino}azetidin-1-yl)pyrimidin-5-yl]-2-fluorobenzyl carbamimidoylcarbamate (Compound II-76)

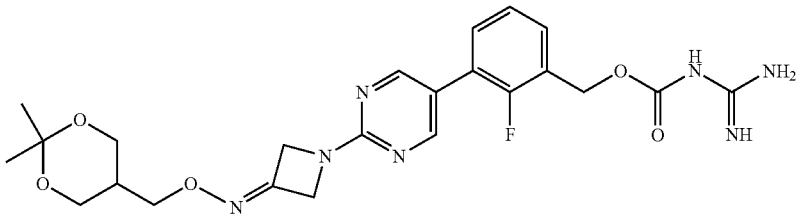 [SMILES: CC1(C)OCC(CON=C2CN(c3ncc(-c4cccc(COC(=O)NC(=N)N)c4F)cn3)C2)CO1]

CDI 183 mg (1.13 mmol) was added to a DMF (4 mL) solution of 1-{5-[2-fluoro-3-(hydroxymethyl)phenyl]pyrimidin-2-yl}azetidin-3-one O-[(2,2-dimethyl-1,3-dioxan-5-yl)methyl] oxime 147 mg (0.353 mmol) synthesized in the same manner as in Reference Example 7-14, and the mixture was stirred at room temperature for 2 hours. Next, guanidine carbonate 130 mg (0.722 mmol) was added, and the mixture was stirred at room temperature for 3 hours. After the completion of the reaction, water and a saturated aqueous sodium carbonate solution were added to the reaction mixture, and followed by extraction with ethyl acetate. The organic layer was washed with brine, dried over anhydrous sodium sulfate, and filtered. The filtrate was concentrated under reduced pressure. The concentrated residue was purified by silica gel column chromatography (DNH silica gel, eluting solvent: ethyl acetate:methanol=100:0 to 90:10 (V/V)) to give the title compound 149 mg (0.297 mmol, yield 84%) as a white solid.

Mass spectrum (ESI, m/z):502[M+1]$^+$.

$^1$H-NMR spectrum (400 MHz, DMSO-d$_6$+D$_2$O) δ:8.63 (d, J=1.1 Hz, 2H), 7.54-7.48 (m, 1H), 7.44-7.39 (m, 1H), 7.32-7.27 (m, 1H), 5.06 (s, 2H), 4.86-4.79 (m, 4H), 4.09 (d, J=7.0 Hz, 2H), 3.91 (dd, J=4.0, 11.9 Hz, 2H), 3.66 (dd, J=6.1, 11.9 Hz, 2H), 2.02-1.95 (m, 1H), 1.34 (s, 3H), 1.31 (s, 3H).

Example 16

3-[2-(3-{[(2,2-Dimethyl-1,3-dioxolan-4-yl)methoxy)]imino}azetidin-1-yl)pyrimidin-5-yl]-2-fluorobenzyl carbamimidoylcarbamate (Compound II-77)

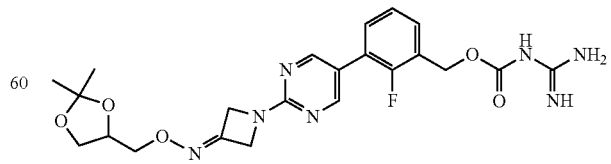

CDI 173 mg (1.07 mmol) was added to a DMF (4 mL) solution of 1-{5-[2-fluoro-3-(hydroxymethyl)phenyl]pyrimidin-2-yl}azetidin-3-one O-[(2,2-dimethyl-1,3-dioxolan- 4-yl)methyl] oxime 143 mg (0.355 mmol) synthesized in the same manner as in Reference Example 7-15, and the mixture was stirred at room temperature for 2 hours. Next, guanidine carbonate 128 mg (0.710 mmol) was added, and the mixture was stirred at room temperature for 3 hours. After the completion of the reaction, water and a saturated aqueous sodium carbonate solution were added to the reaction mixture, and followed by extraction with ethyl acetate. The organic layer was washed with brine, dried over anhydrous sodium sulfate, and filtered. The filtrate was concentrated under reduced pressure. The concentrated residue was purified by silica gel column chromatography (DNH silica gel, eluting solvent: ethyl acetate:methanol=100:0 to 90:10 (V/V)) to give the title compound 137 mg (0.281 mmol, yield 79%) as a white solid.

Mass spectrum (ESI, m/z):488[M+1].

$^1$H-NMR spectrum (400 MHz, DMSO-d$_6$+D$_2$O) δ:8.63 (d, J=1.3 Hz, 2H), 7.54-7.48 (m, 1H), 7.44-7.40 (m, 1H), 7.33-7.27 (m, 1H), 5.06 (s, 2H), 4.87-4.79 (m, 4H), 4.34-4.27 (m, 1H), 4.10-4.02 (m, 3H), 3.68 (dd, J=6.4, 8.4 Hz, 1H), 1.34 (s, 3H), 1.28 (s, 3H).

Example 17

2-Fluoro-3-(2-{3-[(3-methoxy-2-{[(tetrahydropyran-2-yl)oxy]methyl}propoxy)imino]azetidin-1-yl}pyrimidin-5-yl)benzyl carbamimidoylcarbamate (Compound II-80)

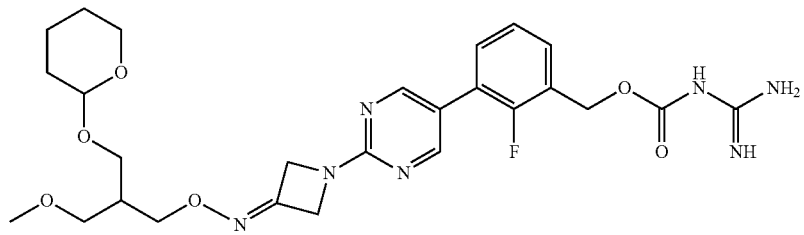 [SMILES: COCC(CON=C1CN(c2ncc(-c3cccc(COC(=O)NC(=N)N)c3F)cn2)C1)COC1CCCCO1]

CDI 92 mg (0.57 mmol) was added to a DMF (6 mL) solution of 1-{5-[2-fluoro-3-(hydroxymethyl)phenyl]pyrimidin-2-yl}azetidin-3-one O-(3-methoxy-2-{[(tetrahydropyran-2-yl)oxy]methyl}propyl) oxime 134 mg (0.282 mmol) synthesized in the same manner as in Reference Example 7-16, and the mixture was stirred at room temperature for 4 hours. Next, guanidine carbonate 102 mg (0.566 mmol) was added, and the mixture was stirred at room temperature for 14 hours. After the completion of the reaction, water was added to the reaction mixture, and followed by extraction with methylene chloride. The organic layer was washed with water, dried over anhydrous sodium sulfate, and filtered. The filtrate was concentrated under reduced pressure. The concentrated residue was purified by silica gel column chromatography (DNH silica gel, eluting solvent: ethyl acetate:methanol) to give the title compound 129 mg (0.231 mmol, yield 82%) as a colorless oil.

$^1$H-NMR spectrum (400 MHz, DMSO-d$_6$+D$_2$O) δ:8.63 (d, J=1.3 Hz, 2H), 7.55-7.48 (m, 1H), 7.46-7.38 (m, 1H), 7.35-7.26 (m, 1H), 5.06 (s, 2H), 4.88-4.77 (m, 4H), 4.58-4.52 (m, 1H), 4.12-4.03 (m, 2H), 3.77-3.56 (m, 2H), 3.47-3.34 (m, 4H), 3.25 (s, 3H), 2.29-2.12 (m, 1H), 1.86-1.36 (m, 6H).

Example 18

2-Fluoro-3-[2-(3-{[2-methoxy-3-(trityloxy)propoxy]imino}azetidin-1-yl)pyrimidin-5-yl]benzyl carbamimidoylcarbamate (Compound II-89)

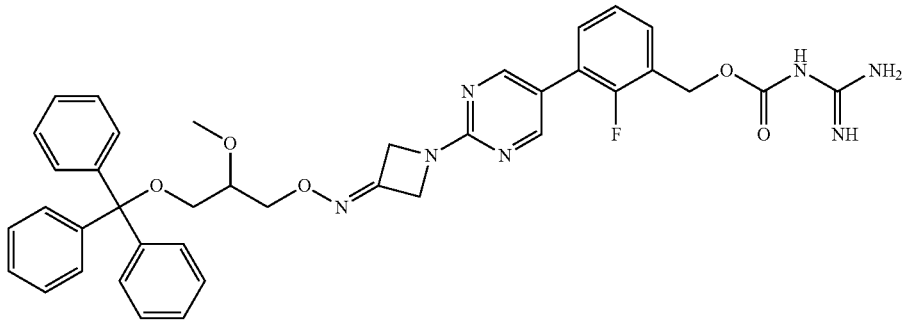 [SMILES: COC(CON=C1CN(c2ncc(-c3cccc(COC(=O)NC(=N)N)c3F)cn2)C1)COC(c1ccccc1)(c1ccccc1)c1ccccc1]

CDI 62 mg (0.38 mmol) was added to a DMF (6 mL) solution of 1-{5-[2-fluoro-3-(hydroxymethyl)phenyl]pyrimidin-2-yl}azetidin-3-one O-[2-methoxy-3-(trityloxy)propyl] oxime 0.12 g (0.19 mmol) synthesized in the same manner as in Reference Example 7-17, and the mixture was stirred at room temperature for 16 hours. Next, guanidine carbonate 68 mg (0.38 mmol) was added, and the mixture was stirred at room temperature for 5 hours. After the completion of the reaction, water was added to the reaction mixture, and followed by extraction with methylene chloride. The organic layer was washed with water, dried over anhydrous sodium sulfate, and filtered. The filtrate was concentrated under reduced pressure. The concentrated residue was purified by silica gel column chromatography (DNH silica gel, eluting solvent: ethyl acetate:methanol) to give the title compound 0.12 g (0.17 mmol, yield 89%) as a white foam.

$^1$H-NMR spectrum (400 MHz, DMSO-$d_6$+$D_2O$) δ:8.65 (d, J=1.3 Hz, 2H), 7.57-7.19 (m, 18H), 5.07 (s, 2H), 4.85-4.77 (m, 2H), 4.73-4.53 (m, 2H), 4.18-4.06 (m, 2H), 3.66-3.59 (m, 1H), 3.34 (s, 3H), 3.21-2.98 (m, 2H).

Example 19

3-[2-(3-{[2-(2,2-Dimethyl-1,3-dioxolan-4-yl)ethoxy]imino}azetidin-1-yl)pyrimidin-5-yl]-2-fluorobenzyl carbamimidoylcarbamate (Compound II-78)

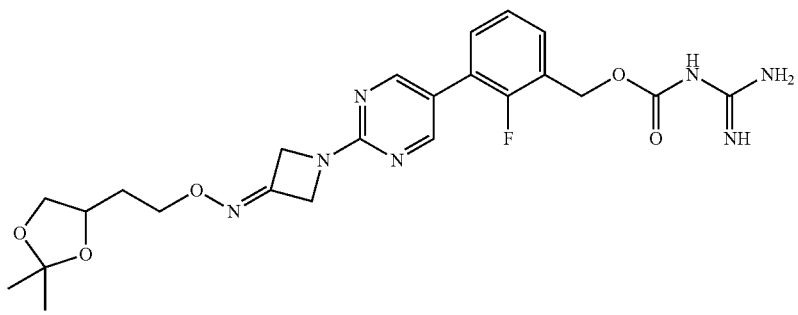 [SMILES: CC1(C)OCC(CCON=C2CN(c3ncc(-c4cccc(COC(=O)NC(=N)N)c4F)cn3)C2)O1]

CDI 70 mg (0.43 mmol) was added to a DMF (6 mL) solution of 1-{5-[2-fluoro-3-(hydroxymethyl)phenyl]pyrimidin-2-yl}azetidin-3-one O-[2-(2,2-dimethyl-1,3-dioxolan-4-yl)ethyl] oxime 90 mg (0.22 mmol) synthesized in the same manner as in Reference Example 7-18, and the mixture was stirred at room temperature for 6 hours. Next, guanidine carbonate 78 mg (0.43 mmol) was added, and the mixture was stirred at room temperature for 16 hours. After the completion of the reaction, water was added to the reaction mixture, and followed by extraction with methylene chloride. The organic layer was washed with water, dried over anhydrous sodium sulfate, and filtered. The filtrate was concentrated under reduced pressure. The concentrated residue was purified by silica gel column chromatography (DNH silica gel, eluting solvent: ethyl acetate: methanol) to give the title compound 0.10 g (0.20 mmol, yield 91%) as a white solid.

$^1$H-NMR spectrum (400 MHz, DMSO-$d_6$+$D_2$O) δ:8.63 (d, J=1.3 Hz, 2H), 7.55-7.48 (m, 1H), 7.46-7.39 (m, 1H), 7.33-7.26 (m, 1H), 5.06 (s, 2H), 4.86-4.78 (m, 4H), 4.17-4.05 (m, 3H), 4.02 (dd, J=6.0, 8.0 Hz, 1H), 3.61-3.44 (m, 1H), 1.95-1.78 (m, 2H), 1.32 (s, 3H), 1.27 (s, 3H).

Example 20

1-[({1-[5-(3-{[(Carbamimidoylcarbamoyl)oxy] methyl}-2-fluorophenyl)pyrimidin-2-yl]azetidin-3-ylidene}amino)oxy]-3-methoxypropan-2-yl acetate
(Compound II-52)

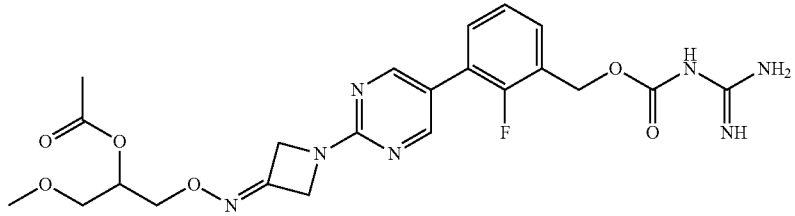 [SMILES: COCC(CON=C1CN(c2ncc(-c3cccc(COC(=O)NC(=N)N)c3F)cn2)C1)OC(C)=O]

CDI 52 mg (0.32 mmol) was added to a DMF (4 mL) solution of 1-{[(1-{5-[2-fluoro-3-(hydroxymethyl)phenyl] pyrimidin-2-yl}azetidin-3-ylidene)amino]oxy}-3-methoxy-propan-2-yl acetate 66 mg (0.16 mmol) synthesized in the same manner as in Reference Example 7-19, and the mixture was stirred at room temperature for 17 hours. Next, guanidine carbonate 57 mg (0.32 mmol) was added, and the mixture was stirred at room temperature for 6 hours. After the completion of the reaction, water was added to the reaction mixture, and followed by extraction with methylene chloride. The organic layer was washed with water, dried over anhydrous sodium sulfate, and filtered. The filtrate was concentrated under reduced pressure. The concentrated residue was purified by silica gel column chromatography (DNH silica gel, eluting solvent: ethyl acetate:methanol) to give the title compound 58 mg (0.12 mmol, yield 75%) as a white solid.

Mass spectrum (ESI, m/z):504[M+1]$^+$.

$^1$H-NMR spectrum (400 MHz, DMSO-$d_6$+$D_2$O) δ:8.63 (d, J=1.3 Hz, 2H), 7.56-7.47 (m, 1H), 7.47-7.39 (m, 1H), 7.34-7.27 (m, 1H), 5.20-5.13 (m, 1H), 5.07 (s, 2H), 4.88-4.73 (m, 4H), 4.22-4.09 (m, 2H), 3.57-3.44 (m, 2H), 3.27 (s, 3H), 2.04 (s, 3H).

Example 21

2-Fluoro-3-(2-{3-[(3-fluoro-2-{[(tetrahydropyran-2-yl)oxy]methyl}propoxy)imino]azetidin-1-yl}pyrimidin-5-yl)benzyl carbamimidoylcarbamate
(Compound II-75)

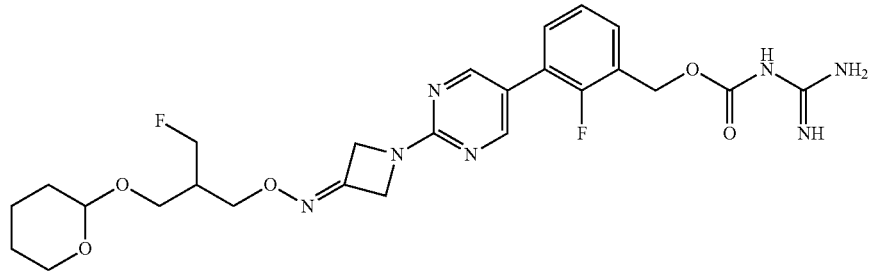 [SMILES: N=C(N)NC(=O)OCc1cccc(-c2cnc(N3CC(=NOCC(CF)COC4CCCCO4)C3)nc2)c1F]

CDI 68 mg (0.42 mmol) was added to a DMF (3 mL) solution of 1-{5-[2-fluoro-3-(hydroxymethyl)phenyl]pyrimidin-2-yl}azetidin-3-one O-(3-fluoro-2-{[(tetrahydropyran-2-yl)oxy]methyl}propyl) oxime 65 mg (0.14 mmol) synthesized in the same manner as in Reference Example 7-20, and the mixture was stirred at room temperature for 2 hours. Next, CDI 30 mg (0.23 mmol) was added, and the mixture was stirred at room temperature for 16 hours. Next, guanidine carbonate 51 mg (0.28 mmol) was added, and the mixture was stirred at room temperature for 2 hours. After the completion of the reaction, water and a saturated aqueous sodium carbonate solution were added to the reaction mixture, and followed by extraction with ethyl acetate three times. The organic layer was washed with brine, dried over anhydrous sodium sulfate, and filtered. The filtrate was concentrated under reduced pressure. The concentrated residue was purified by silica gel column chromatography (DNH silica gel, eluting solvent: ethyl acetate:methanol=100:0 to 90:10 (V/V)) to give the title compound 52 mg (0.095 mmol, yield 68%) as a white solid.

Mass spectrum (ESI, m/z):548[M+1]$^+$.

$^1$H-NMR spectrum (400 MHz, DMSO-$d_6$+$D_2O$) δ:8.63 (d, J=1.4 Hz, 2H), 7.54-7.48 (m, 1H), 7.45-7.40 (m, 1H), 7.33-7.28 (m, 1H), 5.06 (s, 2H), 4.87-4.80 (m, 4H), 4.64-4.42 (m, 3H), 4.16-4.07 (m, 2H), 3.77-3.62 (m, 2H), 3.49-3.40 (m, 2H), 2.42-2.30 (m, 1H), 1.76-1.58 (m, 2H), 1.54-1.41 (m, 4H).

Example 22

2-Fluoro-3-[2-(3-{[2-fluoro-3-(trityloxy)propoxy]imino}azetidin-1-yl)pyrimidin-5-yl]benzyl carbamimidoylcarbamate (Compound II-90)

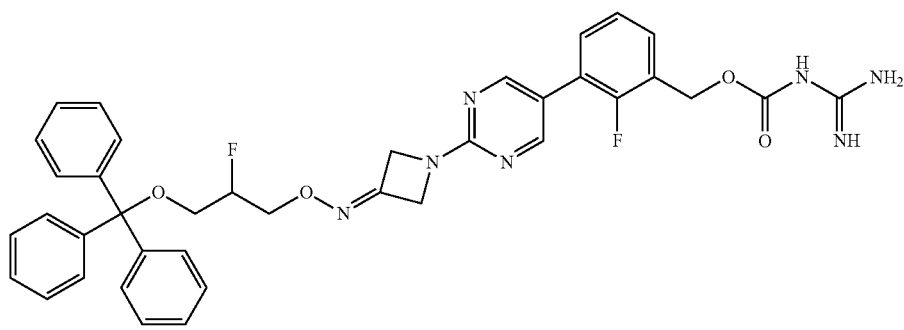 [SMILES: N=C(N)NC(=O)OCc1cccc(-c2cnc(N3CC(=NOCC(F)COC(c4ccccc4)(c4ccccc4)c4ccccc4)C3)nc2)c1F]

CDI 1.0 g (6.2 mmol) was added to a DMF (16 mL) solution of 1-{5-[2-fluoro-3-(hydroxymethyl)phenyl]pyrimidin-2-yl}azetidin-3-one O-[2-fluoro-3-(trityloxy)propyl] oxime 1.7 g (2.8 mmol) synthesized in the same manner as in Reference Example 7-21, and the mixture was stirred at room temperature for 18 hours. Next, guanidine carbonate 1.1 g (6.1 mmol) was added, and the mixture was stirred at room temperature for 20 hours. After the completion of the reaction, water was added to the reaction mixture, and followed by extraction with methylene chloride. The organic layer was washed with water, dried over anhydrous sodium sulfate, and filtered. The filtrate was concentrated under reduced pressure. The concentrated residue was purified by silica gel column chromatography (DNH silica gel, eluting solvent: ethyl acetate:methanol) to give the title compound 1.9 g (2.7 mmol, yield 96%) as a white solid.

$^1$H-NMR spectrum (400 MHz, DMSO-$d_6$+$D_2O$) δ:8.65 (d, J=1.4 Hz, 2H), 7.58-7.22 (m, 18H), 5.08 (s, 2H), 5.04-4.85 (m, 1H), 4.84-4.78 (m, 2H), 4.76-4.62 (m, 2H), 4.47-

4.14 (m, 2H), 3.37-3.13 (m, 2H).

Example 23

2-Fluoro-3-{2-[3-({3-methoxy-4-[(tetrahydropyran-2-yl)oxy]butoxy}imino)azetidin-1-yl]pyrimidin-5-yl}benzyl carbamimidoylcarbamate (Compound II-81)

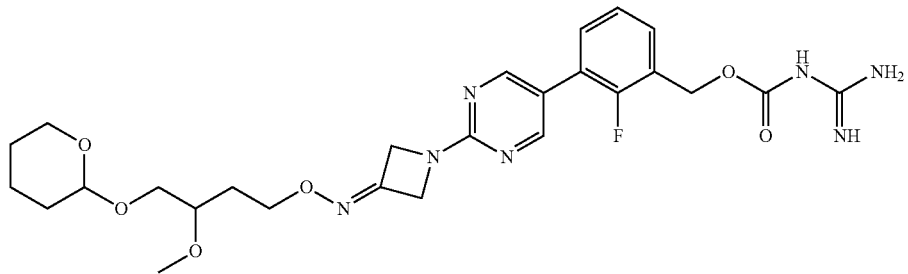 [SMILES: COC(CCON=C1CN(c2ncc(-c3cccc(COC(=O)NC(=N)N)c3F)cn2)C1)COC1CCCCO1]

CDI 108 mg (0.666 mmol) was added to a DMF (2 mL) solution of 1-{5-[2-fluoro-3-(hydroxymethyl)phenyl]pyrimidin-2-yl}azetidin-3-one O-{3-methoxy-4-[(tetrahydropyran-2-yl)oxy]butyl} oxime 79 mg (0.17 mmol) synthesized in the same manner as in Reference Example 7-22, and the mixture was stirred at room temperature for 3 hours. Next, guanidine carbonate 120 mg (0.666 mmol) was added, and the mixture was stirred at room temperature for 1 hour. After the completion of the reaction, water was added to the reaction mixture, and followed by extraction with ethyl acetate. The organic layer was washed with brine, dried over anhydrous magnesium sulfate, and filtered. The filtrate was concentrated under reduced pressure. The concentrated residue was purified by silica gel column chromatography (DIOL silica gel, eluting solvent: ethyl acetate:methanol) to give the title compound 62 mg (0.11 mmol, yield 65%) as a white solid.

Mass spectrum (ESI, m/z):560[M+1]$^+$.

$^1$H-NMR spectrum (400 MHz, DMSO-d$_6$+D$_2$O) δ:8.63 (d, J=1.3 Hz, 2H), 7.55-7.46 (m, 1H), 7.46-7.38 (m, 1H), 7.34-7.26 (m, 1H), 5.06 (s, 2H), 4.88-4.76 (m, 4H), 4.67-4.53 (m, 1H), 4.17-4.07 (m, 2H), 3.87-3.23 (m, 8H), 1.95-1.34 (m, 8H).

Example 24

4-[({1-[5-(3-{[(Carbamimidoylcarbamoyl)oxy]methyl}-2-fluorophenyl)pyrimidin-2-yl]azetidin-3-ylidene}amino)oxy]butane-1,2-diyl diacetate (Compound II-53)

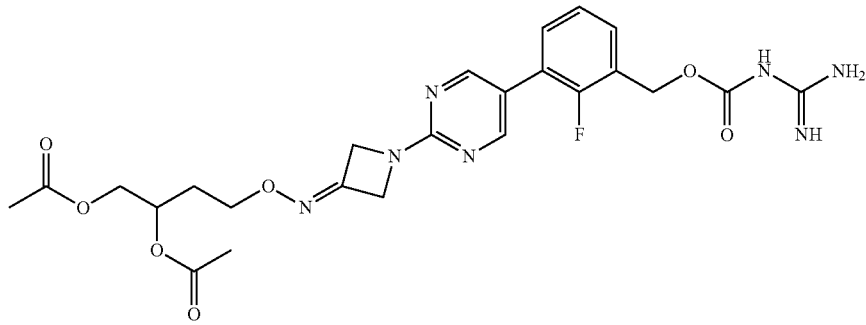 [SMILES: CC(=O)OCC(CCON=C1CN(c2ncc(-c3cccc(COC(=O)NC(=N)N)c3F)cn2)C1)OC(C)=O]

CDI 47 mg (0.29 mmol) was added to a DMF (2 mL) solution of 4-{[(1-{5-[2-fluoro-3-(hydroxymethyl)phenyl]pyrimidin-2-yl}azetidin-3-ylidene)amino]oxy}butane-1,2-diyl diacetate 53 mg (0.12 mmol) synthesized in the same manner as in Reference Example 26, and the mixture was stirred at room temperature for 6 hours. Next, guanidine carbonate 52 mg (0.29 mmol) was added, and the mixture was stirred at room temperature for 18 hours. After the completion of the reaction, water was added to the reaction mixture, and the mixture was stirred. The precipitated solid was collected by filtration. Ethyl acetate was added to the obtained solid, and the mixture was stirred. Thereafter, the solid was collected by filtration and was dried under reduced pressure to give the title compound 20 mg (0.037 mmol, yield 31%) as a white solid.

Mass spectrum (ESI, m/z):546[M+1]$^+$.

$^1$H-NMR spectrum (400 MHz, DMSO-d$_6$+D$_2$O) δ:8.63 (d, J=1.4 Hz, 2H), 7.55-7.47 (m, 1H), 7.46-7.39 (m, 1H), 7.34-7.25 (m, 1H), 5.15-5.02 (m, 3H), 4.87-4.76 (m, 4H), 4.22 (dd, J=3.2, 12.0 Hz, 1H), 4.16-4.01 (m, 3H), 2.03 (s, 3H), 2.01 (s, 3H), 1.99-1.82 (m, 2H).

Example 25

2-[({1-[5-(3-{[(Carbamimidoylcarbamoyl)oxy]methyl}-2-fluorophenyl)pyrimidin-2-yl]azetidin-3-ylidene}amino)oxy]ethyl acetate (Compound II-36)

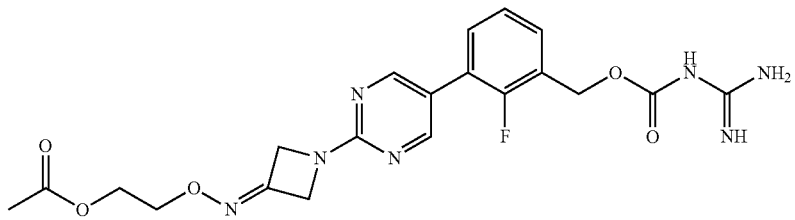 [SMILES: CC(=O)OCCON=C1CN(c2ncc(-c3cccc(COC(=O)NC(=N)N)c3F)cn2)C1]

CDI 24 mg (0.15 mmol) was added to a DMF (2 mL) solution of 2-{[(1-{5-[2-fluoro-3-(hydroxymethyl)phenyl]pyrimidin-2-yl}azetidin-3-ylidene)amino]oxy}ethyl acetate 28 mg (0.075 mmol) synthesized in the same manner as in Reference Example 7-23, and the mixture was stirred at room temperature for 16 hours. Next, CDI 12 mg (0.074 mmol) was added, and the mixture was stirred at room temperature for 2 hours. Next, guanidine carbonate 41 mg (0.23 mmol) was added, and the mixture was stirred at room temperature for 1 hour. After the completion of the reaction, water was added to the reaction mixture, and followed by extraction with ethyl acetate. The organic layer was washed with brine, dried over anhydrous magnesium sulfate, and filtered. The filtrate was concentrated under reduced pressure. The concentrated residue was purified by silica gel column chromatography (DNH silica gel, eluting solvent: ethyl acetate:methanol). Ethyl acetate was added to the crude product thus obtained, and the mixture was stirred. The solid was collected by filtration and was dried under reduced pressure to give the title compound 8.0 mg (0.017 mmol, yield 23%) as a white solid.

Mass spectrum (ESI, m/z):460[M+1]$^+$.

$^1$H-NMR spectrum (400 MHz, DMSO-d$_6$+D$_2$O) δ:8.63 (d, J=1.4 Hz, 2H), 7.54-7.47 (m, 1H), 7.46-7.38 (m, 1H), 7.33-7.27 (m, 1H), 5.06 (s, 2H), 4.88-4.76 (m, 4H), 4.27-4.20 (m, 4H), 2.04 (s, 3H).

Example 26

2-[({1-[5-(3-{[(Carbamimidoylcarbamoyl)oxy]methyl}-2-fluorophenyl)pyrimidin-2-yl]azetidin-3-ylidene}amino)oxy]ethyl propionate (Compound II-37)

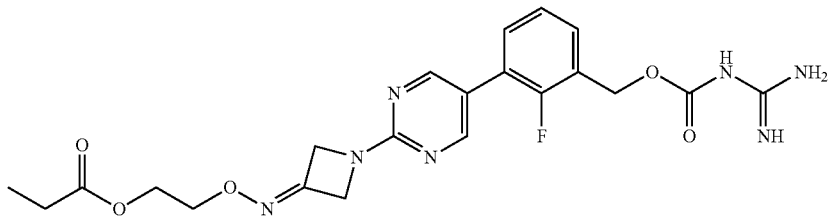 [SMILES: CCC(=O)OCCON=C1CN(c2ncc(-c3cccc(COC(=O)NC(=N)N)c3F)cn2)C1]

CDI 70.0 mg (0.432 mmol) was added to a DMF (2 mL) solution of 2-{[(1-{5-[2-fluoro-3-(hydroxymethyl)phenyl]pyrimidin-2-yl}azetidin-3-ylidene)amino]oxy}ethyl propionate 82.2 mg (0.212 mmol) synthesized in the same manner as in Reference Example 7-24, and the mixture was stirred at room temperature for 4.25 hours. Next, DMF 2 mL and guanidine carbonate 94.2 mg (0.523 mmol) were added, and the mixture was stirred at room temperature for 2.5 hours. After the completion of the reaction, the reaction mixture was poured to water 30 mL. The precipitated solid was collected by filtration and was dried under reduced pressure to give the title compound 85.4 mg (0.180 mmol, yield 85%) as a white solid.

Mass spectrum (ESI, m/z):474[M+1]$^+$.

$^1$H-NMR spectrum (400 MHz, DMSO-d$_6$+D$_2$O) δ:8.66-8.61 (m, 2H), 7.54-7.47 (m, 1H), 7.45-7.38 (m, 1H), 7.33-7.27 (m, 1H), 5.06 (s, 2H), 4.87-4.77 (m, 4H), 4.28-4.20 (m, 4H), 2.34 (q, J=7.5 Hz, 2H), 1.04 (t, J=7.5 Hz, 3H).

Example 27

2-[({1-[5-(3-{[(Carbamimidoylcarbamoyl)oxy]methyl}-2-fluorophenyl)pyrimidin-2-yl]azetidin-3-ylidene}amino)oxy]ethyl butyrate (Compound II-38)

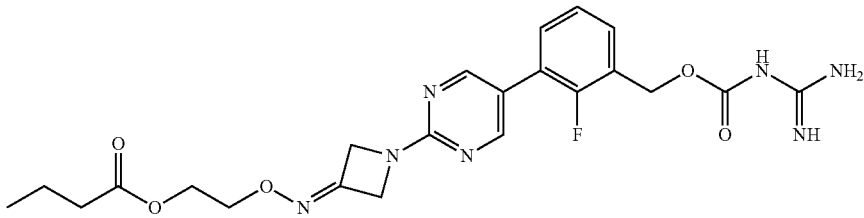 [SMILES: CCCC(=O)OCCON=C1CN(c2ncc(-c3cccc(COC(=O)NC(=N)N)c3F)cn2)C1]

CDI 79 mg (0.49 mmol) was added to a DMF (2 mL) solution of 2-{[(1-{5-[2-fluoro-3-(hydroxymethyl)phenyl]pyrimidin-2-yl}azetidin-3-ylidene)amino]oxy}ethyl butyrate 93 mg (0.23 mmol) synthesized in the same manner as in Reference Example 7-25, and the mixture was stirred at room temperature for 1 hour. Next, guanidine carbonate 91 mg (0.51 mmol) was added, and the mixture was stirred at room temperature for 15 hours. After the completion of the reaction, the reaction mixture was poured to water 25 mL. The precipitated solid was collected by filtration and was dried under reduced pressure to give the title compound 104 mg (0.21 mmol, yield 91%) as a white solid.

Mass spectrum (ESI, m/z):488[M+1]$^+$.

$^1$H-NMR spectrum (400 MHz, DMSO-d$_6$+D$_2$O) δ:8.64 (d, J=1.3 Hz, 2H), 7.54-7.48 (m, 1H), 7.45-7.39 (m, 1H), 7.33-7.27 (m, 1H), 5.06 (s, 2H), 4.86-4.77 (m, 4H), 4.28-4.20 (m, 4H), 2.30 (t, J=7.3 Hz, 2H), 1.55 (sext, J=7.3 Hz, 2H), 0.89 (t, J=7.3 Hz, 3H).

Example 28

2-[({1-[5-(3-{[(Carbamimidoylcarbamoyl)oxy]methyl}-2-fluorophenyl)pyrimidin-2-yl]azetidin-3-ylidene}amino)oxy]ethyl benzoate (Compound II-39)

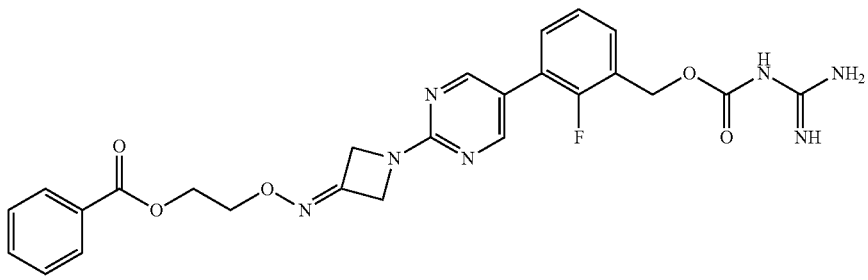 [SMILES: N=C(N)NC(=O)OCc1cccc(-c2cnc(N3CC(=NOCCOC(=O)c4ccccc4)C3)nc2)c1F]

CDI 68.2 mg (0.427 mmol) was added to a DMF (3 mL) solution of 2-{[(1-{5-[2-fluoro-3-(hydroxymethyl)phenyl]pyrimidin-2-yl}azetidin-3-ylidene)amino]oxy}ethyl benzoate 90.9 mg (0.208 mmol) synthesized in the same manner as in Reference Example 7-26, and the mixture was stirred at room temperature for 4 hours. Next, DMF 2 mL and guanidine carbonate 91.3 mg (0.507 mmol) were added, and the mixture was stirred at room temperature for 4 hours. After the completion of the reaction, the reaction mixture was poured to water 30 mL. The precipitated solid was collected by filtration and was dried under reduced pressure to give the title compound 90.7 mg (0.174 mmol, yield 84%) as a white solid.

Mass spectrum (ESI, m/z): 522[M+1]$^+$.

$^1$H-NMR spectrum (400 MHz, DMSO-d$_6$+D$_2$O) δ:8.62 (d, J=0.8 Hz, 2H), 8.03-7.96 (m, 2H), 7.71-7.64 (m, 1H), 7.59-7.38 (m, 4H), 7.33-7.21 (m, 1H), 5.07 (s, 2H), 4.84-4.76 (m, 4H), 4.56-4.50 (m, 2H), 4.41-4.34 (m, 2H).

Example 29

3-[({1-[5-(3-{[(Carbamimidoylcarbamoyl)oxy]methyl}-2-fluorophenyl)pyrimidin-2-yl]azetidin-3-ylidene}amino)oxy]-2-{[(tetrahydropyran-2-yl)oxy]methyl}propyl acetate (Compound II-82)

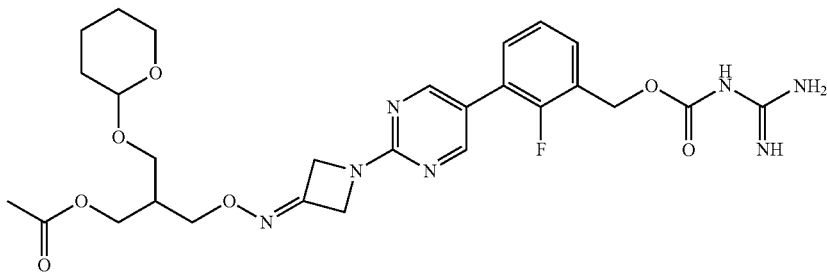 [SMILES: CC(=O)OCC(CON=C1CN(c2ncc(-c3cccc(COC(=O)NC(=N)N)c3F)cn2)C1)COC1CCCCO1]

CDI 65 mg (0.40 mmol) was added to a DMF (4 mL) solution of 3-{[(1-{5-[2-fluoro-3-(hydroxymethyl)phenyl]pyrimidin-2-yl}azetidin-3-ylidene)amino]oxy}-2-{[(tetrahydropyran-2-yl)oxy]methyl}propyl acetate 90 mg (0.18 mmol) synthesized in the same manner as in Reference Example 7-27, and the mixture was stirred at room temperature for 1.5 hours. Next, guanidine carbonate 65 mg (0.36 mmol) was added, and the mixture was stirred at room temperature for 16 hours. After the completion of the reaction, water was added to the reaction mixture, and followed by extraction with ethyl acetate. The organic layer was washed with brine, dried over anhydrous sodium sulfate, and filtered. The filtrate was concentrated under reduced pressure. The concentrated residue was purified by silica gel column chromatography (DNH silica gel, eluting solvent: ethyl acetate:methanol) to give the title compound 114 mg (including impurities) as a colorless oil.

$^1$H-NMR spectrum (400 MHz, DMSO-d$_6$+D$_2$O) δ:8.63 (d, J=1.3 Hz, 2H), 7.55-7.48 (m, 1H), 7.45-7.39 (m, 1H), 7.33-7.27 (m, 1H), 5.06 (s, 2H), 4.87-4.79 (m, 4H), 4.59-4.53 (m, 1H), 4.11-4.07 (m, 4H), 3.76-3.36 (m, 4H), 2-63-2.42 (m, 1H), 2.02 (s, 3H), 1.75-1.38 (m, 6H).

Example 30

3-[({1-[5-(3-{[(Carbamimidoylcarbamoyl)oxy]methyl}-2-fluorophenyl)pyrimidin-2-yl]azetidin-3-ylidene}amino)oxy]-2-{[(tetrahydropyran-2-yl)oxy]methyl}propyl propionate (Compound II-83)

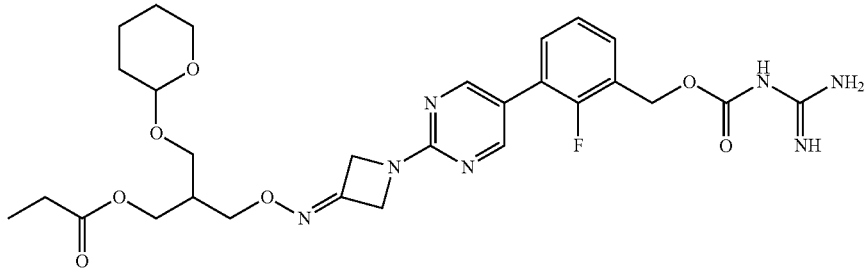 [SMILES: CCC(=O)OCC(CON=C1CN(c2ncc(-c3cccc(COC(=O)NC(=N)N)c3F)cn2)C1)COC1CCCCO1]

CDI 60 mg (0.37 mmol) was added to a DMF (2 mL) solution of 3-{[(1-{5-[2-fluoro-3-(hydroxymethyl)phenyl]pyrimidin-2-yl}azetidin-3-ylidene)amino]oxy}-2-{[(tetrahydropyran-2-yl)oxy]methyl}propyl propionate 85 mg (0.17 mmol) synthesized in the same manner as in Reference Example 7-28, and the mixture was stirred at room temperature for 2 hours. Next, guanidine carbonate 60 mg (0.33 mmol) was added, and the mixture was stirred at room temperature for 2 hours. After the completion of the reaction, water was added to the reaction mixture, and followed by extraction with ethyl acetate. The organic layer was washed with brine, dried over anhydrous sodium sulfate, and filtered. The filtrate was concentrated under reduced pressure. The concentrated residue was purified by silica gel column chromatography (DNH silica gel, eluting solvent: ethyl acetate:methanol) to give the title compound 98 mg (including impurities) as a colorless oil.

$^1$H-NMR spectrum (400 MHz, DMSO-d$_6$+D$_2$O) δ:8.65-8.61 (m, 2H), 7.54-7.48 (m, 1H), 7.45-7.39 (m, 1H), 7.33-7.27 (m, 1H), 5.06 (s, 2H), 4.86-4.78 (m, 4H), 4.57-4.53 (m, 1H), 4.15-4.04 (m, 4H), 3.75-3.34 (m, 4H), 2.36-2.29 (m, 3H), 1.75-1.37 (m, 6H), 1.03 (t, J=7.5 Hz, 3H).

Example 31

3-[({1-[5-(3-{[(Carbamimidoylcarbamoyl)oxy]methyl}-2-fluorophenyl)pyrimidin-2-yl]azetidin-3-ylidene}amino)oxy]-2-{[(tetrahydropyran-2-yl)oxy]methyl}propyl butyrate (Compound II-84)

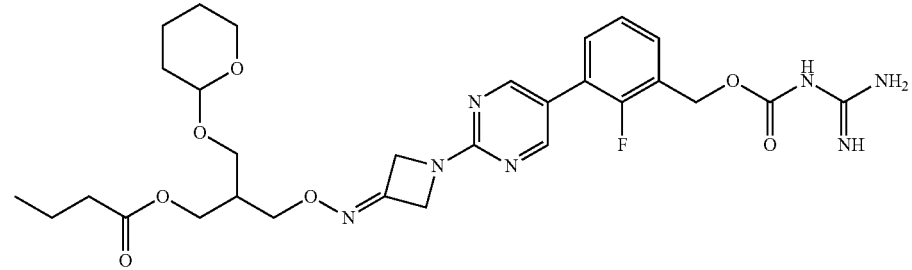 [SMILES: CCCC(=O)OCC(CON=C1CN(c2ncc(-c3cccc(COC(=O)NC(=N)N)c3F)cn2)C1)COC1CCCCO1]

CDI 60 mg (0.37 mmol) was added to a DMF (2 mL) solution of 3-{[(1-{5-[2-fluoro-3-(hydroxymethyl)phenyl]pyrimidin-2-yl}azetidin-3-ylidene)amino]oxy}-2-{[(tetrahydropyran-2-yl)oxy]methyl}propyl butyrate 89 mg (0.17 mmol) synthesized in the same manner as in Reference Example 7-29, and the mixture was stirred at room temperature for 2 hours. Next, guanidine carbonate 60 mg (0.33 mmol) was added, and the mixture was stirred at room temperature for 2 hours. After the completion of the reaction, water was added to the reaction mixture, and followed by extraction with ethyl acetate. The organic layer was washed with brine, dried over anhydrous sodium sulfate, and 9filtered. The filtrate was concentrated under reduced pressure. The concentrated residue was purified by silica gel column chromatography (DNH silica gel, eluting solvent: ethyl acetate:methanol) to give the title compound 92 mg (including impurities) as a white solid.

$^1$H-NMR spectrum (400 MHz, DMSO-d$_6$+D$_2$O) δ:8.63 (d, J=1.1 Hz, 2H), 7.54-7.48 (m, 1H), 7.45-7.39 (m, 1H), 7.34-7.27 (m, 1H), 5.06 (s, 2H), 4.87-4.77 (m, 4H), 4.57-4.53 (m, 1H), 4.16-4.03 (m, 4H), 3.75-3.64 (m, 2H), 3.47-3.35 (m, 2H), 2.37-2.32 (m, 1H), 2.29 (t, J=7.3 Hz, 2H), 1.74-1.38 (m, 8H), 0.88 (t, J=7.3 Hz, 3H).

Example 32

3-[({1-[5-(3-{[(Carbamimidoylcarbamoyl)oxy]methyl}-2-fluorophenyl)pyrimidin-2-yl]azetidin-3-ylidene}amino)oxy]-2-{[(tetrahydropyran-2-yl)oxy]methyl}propyl isobutyrate (Compound II-85)

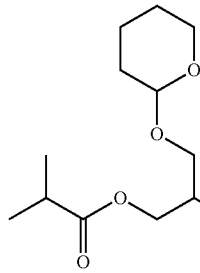
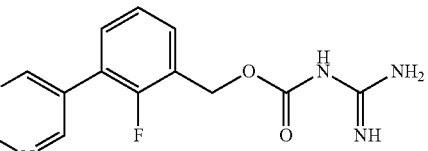

CDI 72.0 mg (0.444 mmol) was added to a DMF (4 mL) solution of 3-{[(1-{5-[2-fluoro-3-(hydroxymethyl)phenyl]pyrimidin-2-yl}azetidin-3-ylidene)amino]oxy}-2-{[(tetrahydropyran-2-yl)oxy]methyl}propyl isobutyrate 117 mg (0.221 mmol) synthesized in the same manner as in Reference Example 7-30, and the mixture was stirred at room temperature for 15 hours. Next, guanidine carbonate 80.0 mg (0.444 mmol) was added, and the mixture was stirred at room temperature for 3 hours. After the completion of the reaction, water was added to the reaction mixture, and followed by extraction with methylene chloride. The organic layer was washed with water, dried over anhydrous sodium sulfate, and filtered. The filtrate was concentrated under reduced pressure. The concentrated residue was purified by silica gel column chromatography (DNH silica gel, eluting solvent: ethyl acetate:methanol) to give the title compound 119 mg (0.193 mmol, yield 88%) as a white foam.

$^1$H-NMR spectrum (400 MHz, DMSO-d$_6$+D$_2$O) δ:8.63 (d, J=1.4 Hz, 2H), 7.54-7.48 (m, 1H), 7.45-7.39 (m, 1H), 7.33-7.26 (m, 1H), 5.06 (s, 2H), 4.87-4.78 (m, 4H), 4.62-4.49 (m, 1H), 4.16-4.02 (m, 4H), 3.74-3.58 (m, 2H), 3.49-3.33 (m, 2H), 2.55 (sep, J=7.0 Hz, 1H), 2.41-2.27 (m, 1H), 1.80-1.35 (m, 6H), 1.09 (d, J=7.0 Hz, 6H).

Example 33

3-[({1-[5-(3-{[(Carbamimidoylcarbamoyl)oxy]methyl}-2-fluorophenyl)pyrimidin-2-yl]azetidin-3-ylidene}amino)oxy]-2-{[(tetrahydropyran-2-yl)oxy]methyl}propyl pivalate (Compound II-86)

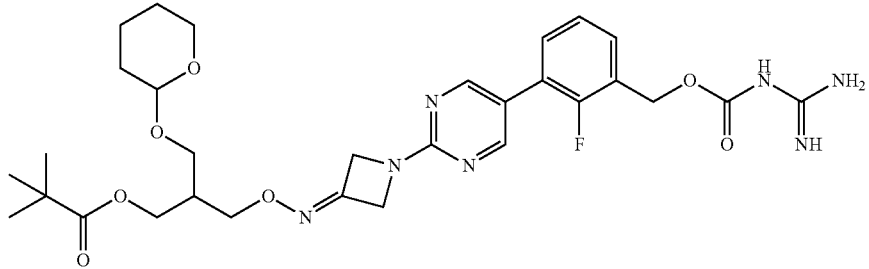 [SMILES: CC(C)(C)C(=O)OCC(CON=C1CN(c2ncc(-c3cccc(COC(=O)NC(=N)N)c3F)cn2)C1)COC1CCCCO1]

CDI 65 mg (0.40 mmol) was added to a DMF (4 mL) solution of 3-{[(1-{5-[2-fluoro-3-(hydroxymethyl)phenyl]pyrimidin-2-yl}azetidin-3-ylidene)amino]oxy}-2-{[(tetrahydropyran-2-yl)oxy]methyl}propyl pivalate 99 mg (0.18 mmol) synthesized in the same manner as in Reference Example 7-31, and the mixture was stirred at room temperature for 15 hours. Next, guanidine carbonate 70 mg (0.39 mmol) was added, and the mixture was stirred at room temperature for 21 hours. After the completion of the reaction, water was added to the reaction mixture, and followed by extraction with methylene chloride. The organic layer was washed with water, dried over anhydrous sodium sulfate, and filtered. The filtrate was concentrated under reduced pressure. The concentrated residue was purified by silica gel column chromatography (DNH silica gel, eluting solvent: ethyl acetate:methanol) to give the title compound 0.11 g (0.17 mmol, yield 94%) as a white foam.

$^1$H-NMR spectrum (400 MHz, DMSO-$d_6$) δ:8.64 (d, J=1.3 Hz, 2H), 7.56-7.47 (m, 1H), 7.45-7.38 (m, 1H), 7.33-7.25 (m, 1H), 5.06 (s, 2H), 4.87-4.78 (m, 4H), 4.59-4.53 (m, 1H), 4.18-4.01 (m, 4H), 3.84-3.61 (m, 2H), 3.49-3.34 (m, 2H), 2.40-2.28 (m, 1H), 1.82-1.35 (m, 6H), 1.15 (s, 9H).

Example 34

3-[({1-[5-(3-{[(Carbamimidoylcarbamoyl)oxy]methyl}-2-fluorophenyl)pyrimidin-2-yl]azetidin-3-ylidene}amino)oxy]-2-{[(tetrahydropyran-2-yl)oxy]methyl}propyl hexanoate (Compound II-87)

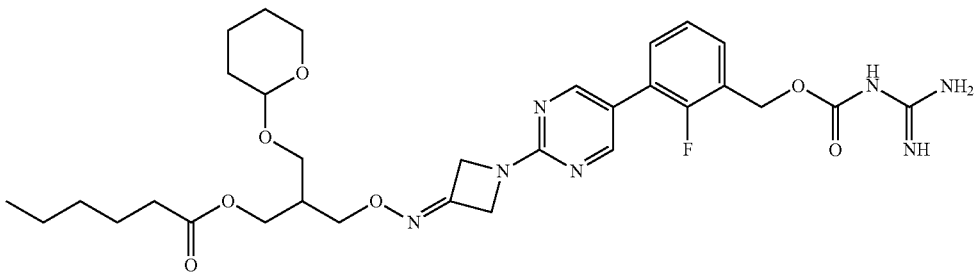 [SMILES: CCCCCC(=O)OCC(CON=C1CN(c2ncc(-c3cccc(COC(=O)NC(=N)N)c3F)cn2)C1)COC1CCCCO1]

CDI 109 mg (0.672 mmol) was added to a DMF (4 mL) solution of 3-{[(1-{5-[2-fluoro-3-(hydroxymethyl)phenyl]pyrimidin-2-yl}azetidin-3-ylidene)amino]oxy}-2-{[(tetrahydropyran-2-yl)oxy]methyl}propyl hexanoate 188 mg (0.337 mmol) synthesized in the same manner as in Reference Example 7-32, and the mixture was stirred at room temperature for 3 hours. Next, guanidine carbonate 121 mg (0.672 mmol) was added, and the mixture was stirred at room temperature for 16 hours. After the completion of the reaction, a saturated aqueous ammonium chloride solution was added to the reaction mixture, and followed by extraction with ethyl acetate. The organic layer was washed with brine, dried over anhydrous magnesium sulfate, and filtered. The filtrate was concentrated under reduced pressure. The concentrated residue was purified by silica gel column chromatography (DNH silica gel, eluting solvent: ethyl acetate:methanol) to give the title compound 163 mg (0.253 mmol, yield 75%) as a white solid.

Mass spectrum (ESI, m/z):644[M+1]$^+$.

Example 35

3-[({1-[5-(3-{[(Carbamimidoylcarbamoyl)oxy]methyl}-2-fluorophenyl)pyrimidin-2-yl]azetidin-3-ylidene}amino)oxy]-2-{[(tetrahydropyran-2-yl)oxy]methyl}propyl benzoate (Compound II-88)

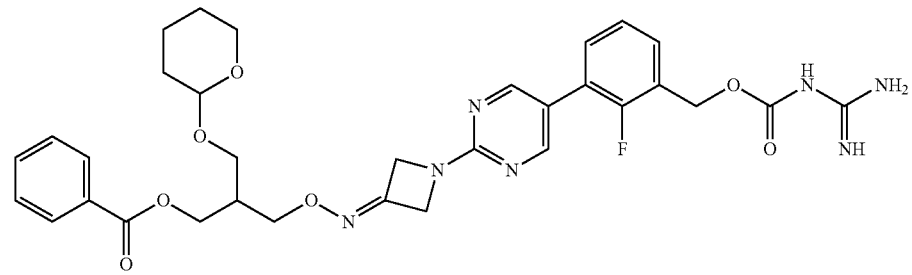 [SMILES: N=C(N)NC(=O)OCc1cccc(-c2cnc(N3CC(=NOCC(COC(=O)c4ccccc4)COC4CCCCO4)C3)nc2)c1F]

CDI 65.2 mg (0.402 mmol) was added to a DMF (3 mL) solution of 3-{[(1-{5-[2-fluoro-3-(hydroxymethyl)phenyl]pyrimidin-2-yl}azetidin-3-ylidene)amino]oxy}-2-{[(tetrahydropyran-2-yl)oxy]methyl}propyl benzoate 109 mg (0.193 mmol) synthesized in the same manner as in Reference Example 7-33, and the mixture was stirred at room temperature for 3 hours. Next, CDI 65.0 mg (0.401 mmol) was added, and the mixture was stirred at room temperature for 2 hours. Next, guanidine carbonate 70.0 mg (0.389 mmol) was added, and the mixture was stirred at room temperature for 2 hours. After the completion of the reaction, water and a saturated aqueous sodium carbonate solution were added to the reaction mixture, and followed by extraction with ethyl acetate. The organic layer was washed with brine, dried over anhydrous sodium sulfate, and filtered. The filtrate was concentrated under reduced pressure. The concentrated residue was purified by silica gel column chromatography (DNH silica gel, eluting solvent: ethyl acetate:methanol=100:0 to 88:12 (V/V)) to give the title compound 102 mg (0.157 mmol, yield 81%) as a colorless oil.

Mass spectrum (ESI, m/z):650[M+1]$^+$.

$^1$H-NMR spectrum (400 MHz, DMSO-d$_6$) δ:8.63 (d, J=1.3 Hz, 2H), 8.00-7.96 (m, 2H), 7.66-7.61 (m, 1H), 7.54-7.48 (m, 3H), 7.44-7.39 (m, 1H), 7.32-7.27 (m, 1H), 5.06 (s, 2H), 4.82-4.75 (m, 4H), 4.61-4.57 (m, 1H), 4.42-4.35 (m, 2H), 4.26-4.16 (m, 2H), 3.82-3.74 (m, 1H), 3.74-3.67 (m, 1H), 3.53-3.36 (m, 2H), 2.54-2.45 (m, 1H), 1.75-1.53 (m, 2H), 1.51-1.39 (m, 4H).

Example 36)

2-Fluoro-3-{5-fluoro-6-[3-(methoxyimino)azetidin-1-yl]pyridin-3-yl}benzyl carbamimidoylcarbamate (Compound III-78)

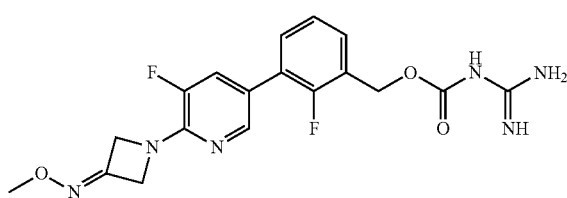 [SMILES: CON=C1CN(c2ncc(-c3cccc(COC(=O)NC(=N)N)c3F)cc2F)C1]

CDI 1.4 g (8.6 mmol) was added to a DMF (15 mL) solution of 1-{3-fluoro-5-[2-fluoro-3-(hydroxymethyl)phenyl]pyridin-2-yl}azetidin-3-one O-methyl oxime 1.22 g (3.82 mmol) synthesized in the same manner as in Reference Example 7-34, and the mixture was stirred at room temperature for 1.5 hours. Next, guanidine carbonate 1.4 g (7.8 mmol) was added, and the mixture was stirred at room temperature for 16 hours. After the completion of the reaction, water was added to the reaction mixture, and the mixture was stirred at room temperature. The precipitated solid was collected by filtration. Ethyl acetate was added to the obtained solid, and the mixture was stirred at 50° C. for 1 hour. The solid was collected by filtration and was dried under reduced pressure to give the title compound 1.31 g (3.24 mmol, yield 85%) as a white solid.

Mass spectrum (ESI, m/z):405[M+1]$^+$.

$^1$H-NMR spectrum (400 MHz, DMSO-d$_6$+D$_2$O) δ:8.19-8.15 (m, 1H), 7.78-7.71 (m, 1H), 7.53-7.46 (m, 1H), 7.44-7.37 (m, 1H), 7.31-7.24 (m, 1H), 5.06 (s, 2H), 4.90-4.83 (m, 4H), 3.82 (s, 3H).

Example 37

2-Fluoro-3-(5-fluoro-6-{3-[(methoxy-d$_3$)imino]azetidin-1-yl}pyridin-3-yl)benzyl carbamimidoylcarbamate (Compound III-88)

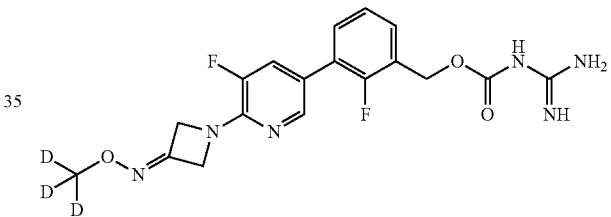

CDI 110 mg (0.678 mmol) was added to a DMF (4 mL) suspension of 1-{3-fluoro-5-[2-fluoro-3-(hydroxymethyl)phenyl]pyridin-2-yl}azetidin-3-one O-methyl-d$_3$ oxime 99 mg (0.31 mmol) synthesized in the same manner as in Reference Example 7-35, and the mixture was stirred at room temperature for 1 hour. Next, guanidine carbonate 110 mg (0.611 mmol) was added, and the mixture was stirred at room temperature for 16 hours. After the completion of the reaction, water was added to the reaction mixture, and the mixture was stirred at room temperature. The precipitated solid was collected by filtration. Ethyl acetate was added to the obtained solid, and the mixture was stirred at 50° C. for 1 hour. Thereafter, the solid was collected by filtration and was dried under reduced pressure to give the title compound 88 mg (0.22 mmol, yield 71%) as a white solid.

Mass spectrum (ESI, m/z):408[M+1]$^+$.

$^1$H-NMR spectrum (400 MHz, DMSO-d$_6$+D$_2$O) δ:8.20-8.15 (m, 1H), 7.79-7.70 (m, 1H), 7.53-7.47 (m, 1H), 7.43-7.37 (m, 1H), 7.32-7.25 (m, 1H), 5.06 (s, 2H), 4.90-4.82 (m, 4H).

Example 38

3-[6-(3-{[2-(2,2-Dimethyl-1,3-dioxolan-4-yl)ethoxy]imino}azetidin-1-yl)-5-fluoropyridin-3-yl]-2-fluorobenzyl carbamimidoylcarbamate (Compound III-154)

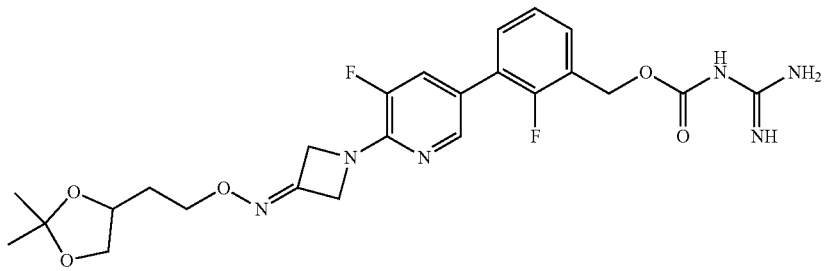 [SMILES: CC1(C)OCC(CCON=C2CN(c3ncc(-c4cccc(COC(=O)NC(=N)N)c4F)cc3F)C2)O1]

CDI 215 mg (1.33 mmol) was added to a DMF (6 mL) suspension of 1-{3-fluoro-5-[2-fluoro-3-(hydroxymethyl)phenyl]pyridin-2-yl}azetidin-3-one O-[2-(2,2-dimethyl-1,3-dioxolan-4-yl)ethyl] oxime 255 mg (0.588 mmol) synthesized in the same manner as in Reference Example 7-36, and the mixture was stirred at room temperature for 3 hours. Next, guanidine carbonate 215 mg (1.19 mmol) was added, and the mixture was stirred at room temperature for 1.5 hours. After the completion of the reaction, water was added to the reaction mixture and the mixture was stirred at room temperature. The precipitated solid was collected by filtration and was dried under reduced pressure to give the title compound 244 mg (0.471 mmol, yield 80%) as a white solid.

$^1$H-NMR spectrum (400 MHz, DMSO-d$_6$+D$_2$O) δ:8.20-8.15 (m, 1H), 7.79-7.71 (m, 1H), 7.53-7.46 (m, 1H), 7.44-7.38 (m, 1H), 7.31-7.25 (m, 1H), 5.06 (s, 2H), 4.91-4.83 (m, 4H), 4.17-4.05 (m, 3H), 4.05-3.99 (m, 1H), 3.53-3.46 (m, 1H), 1.91-1.79 (m, 2H), 1.32 (s, 3H), 1.27 (s, 3H).

Example 39

3-[6-(3-{[(2,2-Dimethyl-1,3-dioxan-5-yl)methoxy]imino}azetidin-1-yl)-5-fluoropyridin-3-yl]-2-fluorobenzyl carbamimidoylcarbamate (Compound III-152)

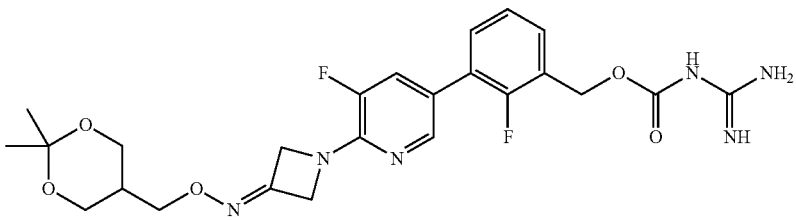 [SMILES: CC1(C)OCC(CON=C2CN(c3ncc(-c4cccc(COC(=O)NC(=N)N)c4F)cc3F)C2)CO1]

CDI 45 mg (0.28 mmol) was added to a DMF (4 mL) suspension of 1-{3-fluoro-5-[2-fluoro-3-(hydroxymethyl)phenyl]pyridin-2-yl}azetidin-3-one O-[(2,2-dimethyl-1,3-dioxan-5-yl)methyl] oxime 54 mg (0.12 mmol) synthesized in the same manner as in Reference Example 7-37, and the mixture was stirred at room temperature for 2 hours. Next, guanidine carbonate 45 mg (0.25 mmol) was added, and the mixture was stirred at room temperature for 16 hours. After the completion of the reaction, water was added to the reaction mixture, and followed by extraction with methylene chloride. The organic layer was washed with brine, dried over anhydrous sodium sulfate, and filtered. The filtrate was concentrated under reduced pressure. The resultant oil was dried under reduced pressure to give a crude product 116 mg including the title compound as a colorless oil.

Example 40

2-Fluoro-3-[5-fluoro-6-(3-{[2-fluoro-3-(trityloxy)propoxy]imino}azetidin-1-yl)pyridin-3-yl]benzyl carbamimidoylcarbamate (Compound III-166)

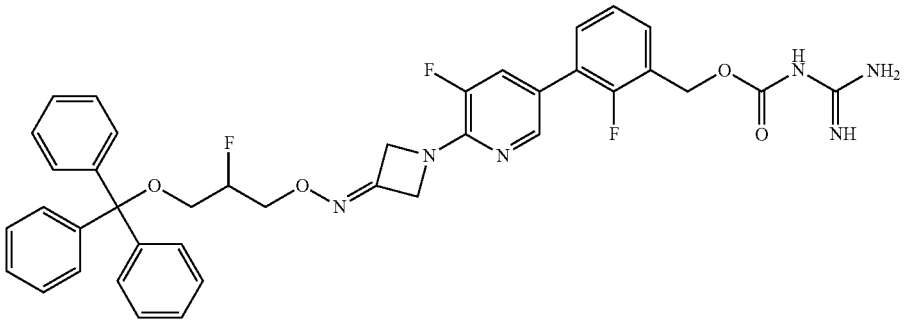 [SMILES: N=C(N)NC(=O)OCc1cccc(-c2cnc(N3CC(=NOCC(F)COC(c4ccccc4)(c4ccccc4)c4ccccc4)C3)c(F)c2)c1F]

CDI 300 mg (1.85 mmol) was added to a DMF (6 mL) solution of 1-{3-fluoro-5-[2-fluoro-3-(hydroxymethyl)phenyl]pyridin-2-yl}azetidin-3-one O-[2-fluoro-3-(trityloxy)propyl] oxime 576 mg (0.924 mmol) synthesized in the same manner as in Reference Example 7-38, and the mixture was stirred at room temperature for 3 hours. Next, guanidine carbonate 333 mg (1.85 mmol) was added, and the mixture was stirred at room temperature for 15 hours. After the completion of the reaction, water was added to the reaction mixture, and followed by extraction with methylene chloride. The organic layer was washed with a saturated aqueous sodium hydrogen carbonate solution, dried over anhydrous sodium sulfate, and filtered. The filtrate was concentrated under reduced pressure. The concentrated residue was purified by silica gel column chromatography (DNH silica gel, eluting solvent: ethyl acetate:methanol) to give the title compound 631 mg (0.890 mmol, yield 96%) as a white foam.

$^1$H-NMR spectrum (400 MHz, DMSO-d$_6$) δ:8.24-8.18 (m, 1H), 7.84-7.74 (m, 1H), 7.56-7.46 (m, 1H), 7.44-7.22 (m, 17H), 5.06 (s, 2H), 5.03-4.66 (m, 5H), 4.43-4.15 (m, 2H), 3.31-3.12 (m, 2H).

Example 41

2-Fluoro-3-{6-[3-(methoxyimino)azetidin-1-yl]pyridin-3-yl}benzyl carbamimidoylcarbamate (Compound III-2)

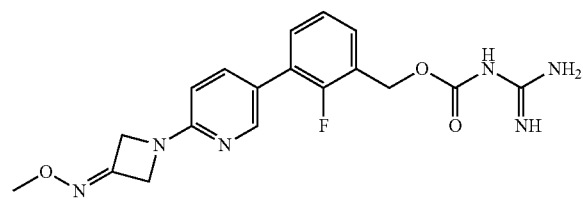 [SMILES: CON=C1CN(c2ccc(-c3cccc(COC(=O)NC(=N)N)c3F)cn2)C1]

CDI 105 mg (0.648 mmol) was added to a DMF (2 mL) solution of 1-{5-[2-fluoro-3-(hydroxymethyl)phenyl]pyridin-2-yl}azetidin-3-one O-methyl oxime 49 mg (0.16 mmol) synthesized in the same manner as in Reference Example 7-39, and the mixture was stirred at room temperature for 14 hours. Next, guanidine carbonate 60 mg (0.33 mmol) was added, and the mixture was stirred at room temperature for 2 hours. After the completion of the reaction, water and a saturated aqueous sodium carbonate solution were added to the reaction mixture, and followed by extraction with ethyl acetate. The organic layer was washed with brine, dried over anhydrous sodium sulfate, and filtered. The filtrate was concentrated under reduced pressure. The concentrated residue was purified by silica gel column chromatography (DNH silica gel, eluting solvent: ethyl acetate:methanol=100:0 to 88:12 (V/V)) to give the title compound 44 mg (0.11 mmol, yield 69%) as a white solid.

Mass spectrum (ESI, m/z):387[M+1]$^+$.

$^1$H-NMR spectrum (400 MHz, DMSO-d$_6$+D$_2$O) δ:8.32-8.29 (m, 1H), 7.81-7.77 (m, 1H), 7.49-7.33 (m, 2H), 7.31-7.23 (m, 1H), 6.71-6.66 (m, 1H), 5.06 (s, 2H), 4.76-4.69 (m, 4H), 3.82 (s, 3H).

Example 42

2-Fluoro-3-{6-[3-(methoxyimino)azetidin-1-yl]-5-methylpyridin-3-yl}benzyl carbamimidoylcarbamate (Compound III-716)

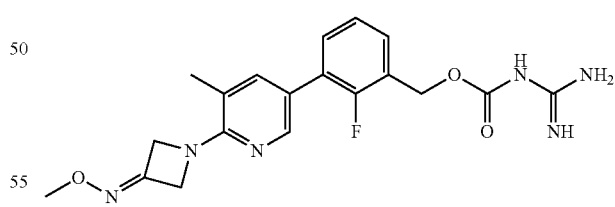

CDI 175 mg (1.08 mmol) was added to a DMF (2 mL) solution of 1-{5-[2-fluoro-3-(hydroxymethyl)phenyl]-3-methylpyridin-2-yl}azetidin-3-one O-methyl oxime 85 mg (0.27 mmol) synthesized in the same manner as in Reference Example 7-40, and the mixture was stirred at room temperature for 3 hours. Next, guanidine carbonate 194 mg (1.08 mmol) was added, and the mixture was stirred at room temperature for 1 hour. After the completion of the reaction, water was added to the reaction mixture, and the mixture was stirred. The precipitated solid was collected by filtration. Ethyl acetate was added to the obtained solid, and the mixture was stirred. Thereafter, the solid was collected by filtration and was dried under reduced pressure to give the title compound 21 mg (0.052 mmol, yield 19%) as a white solid.

Mass spectrum (ESI, m/z):401[M+1]$^+$.

$^1$H-NMR spectrum (400 MHz, DMSO-$d_6$+$D_2O$) δ:8.20-8.16 (m, 1H), 7.63-7.58 (m, 1H), 7.49-7.41 (m, 1H), 7.41-7.34 (m, 1H), 7.31-7.22 (m, 1H), 5.06 (s, 2H), 4.87-4.81 (m, 4H), 3.81 (s, 3H), 2.25 (s, 3H).

Example 43

3-{5-Cyano-6-[3-(methoxyimino)azetidin-1-yl]pyridin-3-yl}-2-fluorobenzyl carbamimidoylcarbamate (Compound III-1482)

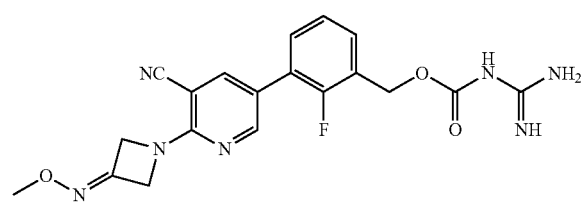

CDI 130 mg (0.802 mmol) was added to a DMF (6 mL) solution of 5-[2-fluoro-3-(hydroxymethyl)phenyl]-2-[3-(methoxyimino)azetidin-1-yl]nicotinonitrile 129 mg (0.395 mmol) synthesized in the same manner as in Reference Example 7-41, and the mixture was stirred at room temperature for 3 hours. Next, guanidine carbonate 150 mg (0.833 mmol) was added, and the mixture was stirred at room temperature for 17 hours. After the completion of the reaction, water was added to the reaction mixture, and the mixture was stirred. The precipitated solid was collected by filtration. Ethyl acetate was added to the obtained solid, and the mixture was stirred at room temperature for 1 hour. The solid was collected by filtration and was dried under reduced pressure to give the title compound 98.0 mg (0.238 mmol, yield 60%) as a white solid.

Mass spectrum (ESI, m/z):412[M+1]$^+$.

$^1$H-NMR spectrum (400 MHz, DMSO-$d_6$+$D_2O$) δ:8.59-8.54 (m, 1H), 8.26-8.22 (m, 1H), 7.55-7.47 (m, 1H), 7.46-7.39 (m, 1H), 7.34-7.25 (m, 1H), 5.06 (s, 2H), 5.03-4.99 (m, 4H), 3.84 (s, 3H).

Example 44

3-{5-Chloro-6-[3-(methoxyimino)azetidin-1-yl]pyridin-3-yl}-2-fluorobenzyl carbamimidoylcarbamate (Compound III-324)

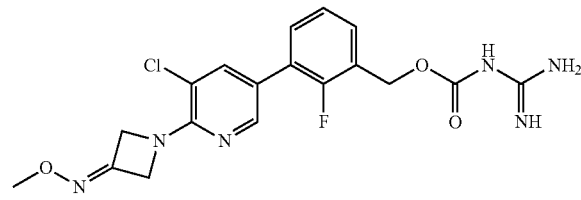 [SMILES: CON=C1CN(c2ncc(-c3cccc(COC(=O)NC(=N)N)c3F)cc2Cl)C1]

CDI 43 mg (0.27 mmol) was added to a DMF (2 mL) suspension of 1-{3-chloro-5-[2-fluoro-3-(hydroxymethyl)phenyl]pyridin-2-yl}azetidin-3-one O-methyl oxime 40 mg (0.12 mmol) synthesized in the same manner as in Reference Example 7-42, and the mixture was stirred at room temperature for 1 hour. Next, guanidine carbonate 43 mg (0.24 mmol) was added, and the mixture was stirred at room temperature for 2.5 hours. After the completion of the reaction, water was added to the reaction mixture, and the mixture was stirred at room temperature. The precipitated solid was collected by filtration. Ethyl acetate was added to the obtained solid, and the mixture was stirred at 50° C. for 1 hour. Thereafter, the solid was collected by filtration and was dried under reduced pressure to give the title compound 39 mg (0.093 mmol, yield 78%) as a white solid.

Mass spectrum (ESI, m/z):421[M+1]$^+$.

$^1$H-NMR spectrum (400 MHz, DMSO-$d_6$+$D_2O$) δ:8.34-8.28 (m, 1H), 7.93-7.88 (m, 1H), 7.54-7.47 (m, 1H), 7.44-7.39 (m, 1H), 7.31-7.25 (m, 1H), 5.06 (s, 2H), 4.96-4.89 (m, 4H), 3.82 (s, 3H).

Example 45

3-{5-(Difluoromethyl)-6-[3-(methoxyimino)azetidin-1-yl]pyridin-3-yl}-2-fluorobenzyl carbamimidoylcarbamate (Compound III-960)

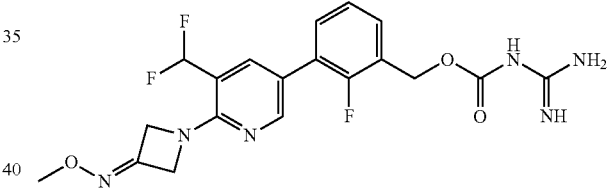

CDI 125 mg (0.771 mmol) was added to a DMF (3 mL) solution of 1-{3-(difluoromethyl)-5-[2-fluoro-3-(hydroxymethyl)phenyl]pyridin-2-yl}azetidin-3-on e O-methyl oxime 108 mg (0.307 mmol) synthesized in the same manner as in Reference Example 7-43, and the mixture was stirred at room temperature for 1.5 hours. Next, CDI 50 mg (0.31 mmol) was added, and the mixture was stirred at room temperature for 1 hour. Next, guanidine carbonate 112 mg (0.622 mmol) was added, and the mixture was stirred at room temperature for 2 hours. After the completion of the reaction, water was added to the reaction mixture, and the mixture was stirred at room temperature for 30 minutes. The precipitated solid was collected by filtration and was dried under reduced pressure to give the title compound 104 mg (0.238 mmol, yield 78%) as a white solid.

Mass spectrum (ESI, m/z):437[M+1]$^+$.

$^1$H-NMR spectrum (400 MHz, DMSO-$d_6$+$D_2O$) δ:8.51-8.47 (m, 1H), 8.01-7.98 (m, 1H), 7.53-7.47 (m, 1H), 7.44-7.38 (m, 1H), 7.34-6.97 (m, 2H), 5.07 (s, 2H), 4.94-4.83 (m, 4H), 3.83 (s, 3H).

Example 46

3-{5-Cyclopropyl-6-[3-(methoxyimino)azetidin-1-yl]pyridin-3-yl}-2-fluorobenzyl carbamimidoylcarbamate (Compound III-1308)

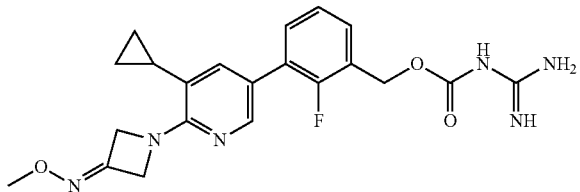 [SMILES: CON=C1CN(c2ncc(-c3cccc(COC(=O)NC(=N)N)c3F)cc2C2CC2)C1]

CDI 200 mg (1.23 mmol) was added to a DMF (3 mL) solution of 1-{3-cyclopropyl-5-[2-fluoro-3-(hydroxymethyl)phenyl]pyridin-2-yl}azetidin-3-one O-methyl oxime 121 mg (0.354 mmol) synthesized in the same manner as in Reference Example 7-44, and the mixture was stirred at room temperature for 14 hours. Next, guanidine carbonate 130 mg (0.722 mmol) was added, and the mixture was stirred at room temperature for 2 hours. After the completion of the reaction, water was added to the reaction mixture, and the mixture was stirred at room temperature for 30 minutes. The precipitated solid was collected by filtration and was dried under reduced pressure to give the title compound 97.1 mg (0.228 mmol, yield 64%) as a white solid.

Mass spectrum (ESI, m/z):427[M+1]$^+$.

$^1$H-NMR spectrum (400 MHz, DMSO-d$_6$+D$_2$O) δ:8.20-8.13 (m, 1H), 7.47-7.40 (m, 2H), 7.40-7.35 (m, 1H), 7.29-7.22 (m, 1H), 5.05 (s, 2H), 4.94-4.90 (m, 4H), 3.82 (s, 3H), 1.98-1.82 (m, 1H), 0.98-0.91 (m, 2H), 0.75-0.69 (m, 2H).

Example 47

3-{5-Ethyl-6-[3-(methoxyimino)azetidin-1-yl]pyridin-3-yl}-2-fluorobenzyl carbamimidoylcarbamate (Compound III-851)

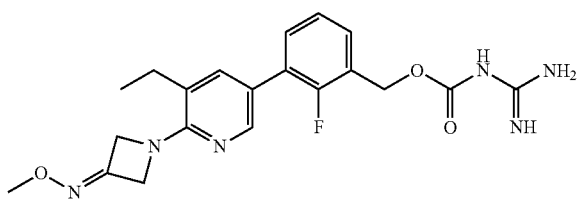 [SMILES: CCc1cc(-c2cccc(COC(=O)NC(=N)N)c2F)cnc1N1CC(=NOC)C1]

CDI 195 mg (1.20 mmol) was added to a DMF (3 mL) solution of 1-{3-ethyl-5-[2-fluoro-3-(hydroxymethyl)phenyl]pyridin-2-yl}azetidin-3-one O-methyloxime 113 mg (0.343 mmol) synthesized in the same manner as in Reference Example 7-45, and the mixture was stirred at room temperature for 1.5 hours. Next, guanidine carbonate 124 mg (0.688 mmol) was added, and the mixture was stirred at room temperature for 1.5 hours. After the completion of the reaction, water was added to the reaction mixture, and the mixture was stirred at room temperature for 30 minutes. The precipitated solid was collected by filtration and was dried under reduced pressure to give the title compound 96.0 mg (0.232 mmol, yield 68%) as a white solid.

Mass spectrum (ESI, m/z):415[M+1]$^+$.

$^1$H-NMR spectrum (400 MHz, DMSO-d$_6$+D$_2$O) δ:8.21-8.19 (m, 1H), 7.62-7.59 (m, 1H), 7.49-7.43 (m, 1H), 7.40-7.36 (m, 1H), 7.30-7.24 (m, 1H), 5.06 (s, 2H), 4.85-4.81 (m, 4H), 3.81 (s, 3H), 2.59 (q, J=7.4 Hz, 2H), 1.20 (t, J=7.5 Hz, 3H).

Example 48

2-Fluoro-3-{6-[3-(methoxyimino)azetidin-1-yl]-5-{2-[(tetrahydropyran-2-yl)oxy]propan-2-yl}pyridin-3-yl}benzyl carbamimidoylcarbamate (Compound III-1210)

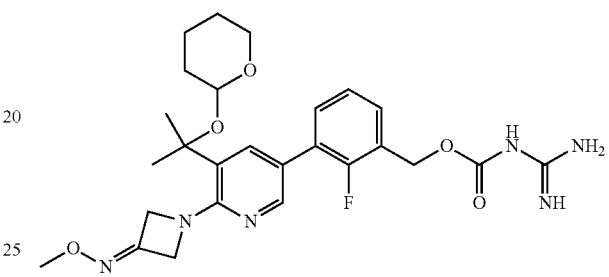

CDI 140 mg (0.863 mmol) was added to a DMF (6 mL) solution of 1-{5-[2-fluoro-3-(hydroxymethyl)phenyl]-3-{2-[(tetrahydropyran-2-yl)oxy]propan-2-yl}pyridin-2-yl}azetidin-3-one O-methyl oxime 189 mg (0.426 mmol) synthesized in the same manner as in Reference Example 7-46, and the mixture was stirred at room temperature for 6 hours. Next, guanidine carbonate 160 mg (0.888 mmol) was added, and the mixture was stirred at room temperature for 20 hours. After the completion of the reaction, water was added to the reaction mixture, and followed by extraction with methylene chloride. The organic layer was washed with water, dried over anhydrous sodium sulfate, and filtered. The filtrate was concentrated under reduced pressure. The concentrated residue was purified by silica gel column chromatography (DNH silica gel, eluting solvent: ethyl acetate: methanol) to give the title compound 175 mg (0.331 mmol, yield 78%) as a colorless oil.

$^1$H-NMR spectrum (400 MHz, DMSO-d$_6$) δ:8.33-8.28 (m, 1H), 7.83-7.76 (m, 1H), 7.54-7.47 (m, 1H), 7.43-7.35 (m, 1H), 7.31-7.21 (m, 1H), 5.06 (s, 2H), 4.93-4.77 (m, 4H), 4.57-4.47 (m, 1H), 3.85-3.69 (m, 4H), 3.44-3.20 (m, 1H), 1.88-1.27 (m, 12H).

Example 49

2-Fluoro-3-{6-[3-(methoxyimino)azetidin-1-yl]-5-(methoxymethyl)pyridin-3-yl}benzyl carbamimidoylcarbamate (Compound III-1221)

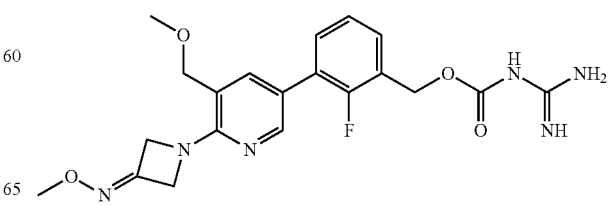

CDI 150 mg (0.925 mmol) was added to a DMF (6 mL) solution of 1-{5-[2-fluoro-3-(hydroxymethyl)phenyl]-3-(methoxymethyl)pyridin-2-yl}azetidin-3-one O-methyl oxime 157 mg (0.455 mmol) synthesized in the same manner as in Reference Example 7-47, and the mixture was stirred at room temperature for 20 hours. Next, guanidine carbonate 170 mg (0.944 mmol) was added, and the mixture was stirred at room temperature for 16 hours. After the completion of the reaction, water was added to the reaction mixture, and the mixture was stirred at room temperature for 2 hours. Thereafter, the precipitated solid was collected by filtration and was dried under reduced pressure to give the title compound 164 mg (0.381 mmol, yield 84%) as a white solid.

Mass spectrum (ESI, m/z):431[M+1]$^+$.

$^1$H-NMR spectrum (400 MHz, DMSO-d$_6$+D$_2$O) δ:8.32-8.25 (m, 1H), 7.77-7.72 (m, 1H), 7.50-7.43 (m, 1H), 7.42-7.35 (m, 1H), 7.30-7.24 (m, 1H), 5.06 (s, 2H), 4.93-4.81 (m, 4H), 4.39 (s, 2H), 3.82 (s, 3H), 3.33 (s, 3H).

Example 50

2-Fluoro-3-{5-methoxy-6-[3-(methoxyimino)azetidin-1-yl]pyridin-3-yl}benzyl carbamimidoylcarbamate (Compound III-1395)

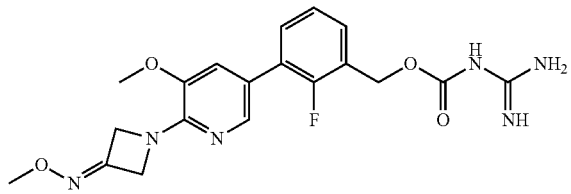 [SMILES: CON=C1CN(c2ncc(-c3cccc(COC(=O)NC(=N)N)c3F)cc2OC)C1]

CDI 153 mg (0.944 mmol) was added to a DMF (3 mL) solution of 1-{5-[2-fluoro-3-(hydroxymethyl)phenyl]-3-methoxypyridin-2-yl}azetidin-3-one O-methyl oxime 104 mg (0.314 mmol) synthesized in the same manner as in Reference Example 7-48, and the mixture was stirred at room temperature for 1.5 hours. Next, guanidine carbonate 170 mg (0.944 mmol) was added, and the mixture was stirred at room temperature for 1.5 hours. After the completion of the reaction, water was added to the reaction mixture, and the mixture was stirred. The precipitated solid was collected by filtration. Ethyl acetate was added to the obtained solid, and the mixture was stirred at 40° C. Thereafter, the solid was collected by filtration and was purified by silica gel column chromatography (DIOL silica gel, eluting solvent: ethyl acetate:methanol) to give the title compound 13 mg (0.031 mmol, yield 10%) as a white solid.

Mass spectrum (ESI, m/z):417[M+1]$^+$.

$^1$H-NMR spectrum (400 MHz, DMSO-d$_6$+D$_2$O) δ:7.91-7.89 (m, 1H), 7.54-7.45 (m, 1H), 7.44-7.35 (m, 1H), 7.34-7.30 (m, 1H), 7.30-7.22 (m, 1H), 5.06 (s, 2H), 4.83-4.71 (m, 4H), 3.83 (s, 3H), 3.81 (s, 3H).

Example 51

2-Fluoro-3-{2-[4-(methoxyimino)piperidin-1-yl]pyrimidin-5-yl}benzyl carbamimidoylcarbamate (Compound II-205)

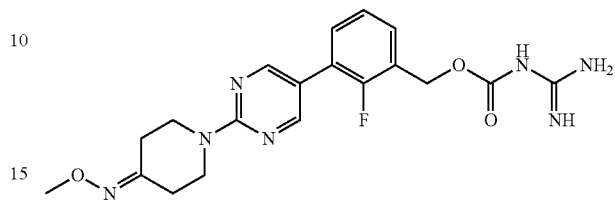

CDI 112 mg (0.691 mmol) was added to a DMF (4 mL) solution of 1-{5-[2-fluoro-3-(hydroxymethyl)phenyl]pyrimidin-2-yl}piperidin-4-one O-methyloxime 100 mg (0.303 mmol) synthesized in the same manner as in Reference Example 7-49, and the mixture was stirred at room temperature for 6 hours. Next, guanidine carbonate 109 mg (0.605 mmol) was added, and the mixture was stirred at room temperature for 16 hours. After the completion of the reaction, water was added to the reaction mixture, and followed by extraction with methylene chloride. The organic layer was washed with water, dried over anhydrous sodium sulfate, and filtered. The filtrate was concentrated under reduced pressure. The concentrated residue was purified by silica gel column chromatography (DNH silica gel, eluting solvent: ethyl acetate:methanol) to give the title compound 117 mg (0.282 mmol, yield 93%) as a white solid.

Mass spectrum (ESI, m/z):416[M+1]$^+$.

$^1$H-NMR spectrum (400 MHz, DMSO-d$_6$+D$_2$O) δ:8.59 (d, J=1.3 Hz, 2H), 7.55-7.47 (m, 1H), 7.43-7.37 (m, 1H), 7.33-7.24 (m, 1H), 5.06 (s, 2H), 3.99-3.85 (m, 4H), 3.76 (s, 3H), 2.60-2.53 (m, 2H), 2.42-2.35 (m, 2H).

Example 52

2-Fluoro-3-[2-(4-{[(tetrahydropyran-2-yl)oxy]imino}piperidin-1-yl)pyrimidin-5-yl]benzyl carbamimidoylcarbamate (Compound II-249)

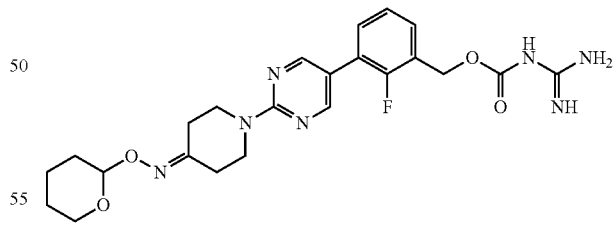

CDI 189 mg (0.117 mmol) was added to a DMF (2 mL) solution of 1-{5-[2-fluoro-3-(hydroxymethyl)phenyl]pyrimidin-2-yl}piperidin-4-one O-tetrahydropyran-2-yl oxime 210 mg (0.524 mmol) synthesized in the same manner as in Reference Example 61, and the mixture was stirred at room temperature for 1 hour. Next, guanidine carbonate 190 mg (0.105 mmol) was added, and the mixture was stirred at room temperature for 11 hours. After the completion of the reaction, the reaction mixture was poured to water 20 mL, and the mixture was stirred for 20 minutes. The precipitated solid was collected by filtration and was dried under reduced pressure to give the title compound 151 mg (0.311 mmol, yield 59%) as a white solid.

Mass spectrum (ESI, m/z):486[M+1]$^+$.

$^1$H-NMR spectrum (400 MHz, DMSO-d$_6$+D$_2$O) δ:8.60 (d, J=1.0 Hz, 2H), 7.54-7.48 (m, 1H), 7.44-7.37 (m, 1H), 7.33-7.26 (m, 1H), 5.18-5.14 (m, 1H), 5.07 (s, 2H), 4.01-3.87 (m, 4H), 3.78-3.73 (m, 1H), 3.52-3.43 (m, 1H), 2.71-2.60 (m, 2H), 2.45-2.38 (m, 2H), 1.91-1.37 (m, 6H).

Example 53

3-{2-[4-(Ethoxyimino)piperidin-1-yl]pyrimidin-5-yl}-2-fluorobenzyl carbamimidoylcarbamate (Compound II-206)

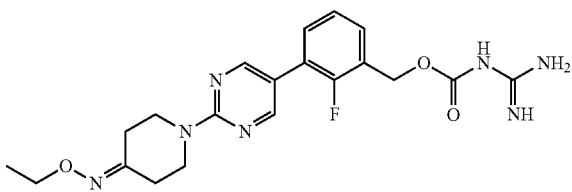 [SMILES: CCON=C1CCN(c2ncc(-c3cccc(COC(=O)NC(=N)N)c3F)cn2)CC1]

CDI 110 mg (0.678 mmol) was added to a DMF (4 mL) solution of 1-{5-[2-fluoro-3-(hydroxymethyl)phenyl]pyrimidin-2-yl}piperidin-4-one O-ethyl oxime 100 mg (0.290 mmol) synthesized in the same manner as in Reference Example 62-1, and the mixture was stirred at room temperature for 6 hours. Next, guanidine carbonate 113 mg (0.627 mmol) was added, and the mixture was stirred at room temperature for 16 hours. After the completion of the reaction, water was added to the reaction mixture, and followed by extraction with methylene chloride. The organic layer was washed with water, dried over anhydrous sodium sulfate, and filtered. The filtrate was concentrated under reduced pressure. The concentrated residue was purified by silica gel column chromatography (DNH silica gel, eluting solvent: ethyl acetate:methanol) to give the title compound 114 mg (0.265 mmol, yield 91%) as a white solid.

Mass spectrum (ESI, m/z):430[M+1].

$^1$H-NMR spectrum (400 MHz, DMSO-d$_6$+D$_2$O) δ:8.59 (d, J=1.0 Hz, 2H), 7.56-7.46 (m, 1H), 7.44-7.36 (m, 1H), 7.32-7.23 (m, 1H), 5.06 (s, 2H), 4.02 (q, J=7.1 Hz, 2H), 3.95-3.89 (m, 4H), 2.60-2.54 (m, 2H), 2.41-2.35 (m, 2H), 1.19 (t, J=7.1 Hz, 3H).

Example 54

2-Fluoro-3-{2-[4-(isopropoxyimino)piperidin-1-yl]pyrimidin-5-yl}benzyl carbamimidoylcarbamate (Compound II-208)

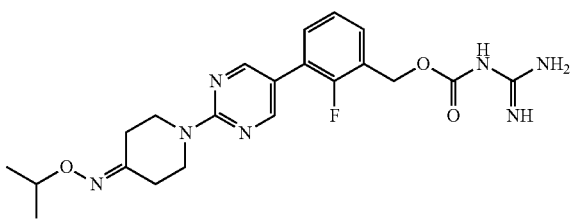 [SMILES: CC(C)ON=C1CCN(c2ncc(-c3cccc(COC(=O)NC(=N)N)c3F)cn2)CC1]

CDI 79.6 mg (0.491 mmol) was added to a DMF (2 mL) solution of 1-{5-[2-fluoro-3-(hydroxymethyl)phenyl]pyrimidin-2-yl}piperidin-4-one O-isopropyl oxime 77.1 mg (0.215 mmol) synthesized in the same manner as in Reference Example 62-2, and the mixture was stirred at room temperature for 1 hour. Next, guanidine carbonate 80.8 mg (0.448 mmol) was added, and the mixture was stirred at room temperature for 1.5 hours. After the completion of the reaction, methylene chloride and water were added to the reaction mixture, and followed by extraction with methylene chloride. The organic layer was dried over anhydrous sodium sulfate, and filtered. The filtrate was concentrated under reduced pressure. The concentrated residue was purified by silica gel column chromatography (DNH silica gel, eluting solvent: ethyl acetate:methanol=100:0 to 68:32 (V/V)). Ethyl acetate was added to the obtained solid, and the mixture was ultrasonicated. The solid was collected by filtration and was dried under reduced pressure to give the title compound 45.3 mg (0.102 mmol, yield 47%) as a white solid.

$^1$H-NMR spectrum (400 MHz, DMSO-d$_6$+D$_2$O) δ: 8.59 (d, J=1.4 Hz, 2H), 7.55-7.47 (m, 1H), 7.43-7.37 (m, 1H), 7.32-7.22 (m, 1H), 5.06 (s, 2H), 4.22 (sep, J=6.2 Hz, 1H), 3.98-3.87 (m, 4H), 2.60-2.54 (m, 2H), 2.43-2.36 (m, 2H), 1.18 (d, J=6.2 Hz, 6H).

Example 55

2-Fluoro-3-{2-[4-(propoxyimino)piperidin-1-yl]pyrimidin-5-yl}benzyl carbamimidoylcarbamate (Compound II-207)

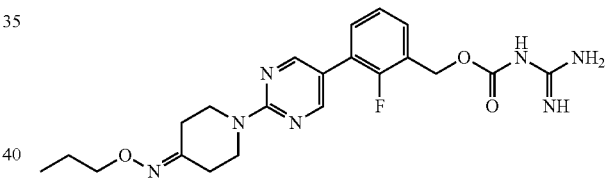

CDI 100 mg (0.617 mmol) was added to a DMF (2.5 mL) solution of 1-{5-[2-fluoro-3-(hydroxymethyl)phenyl]pyrimidin-2-yl}piperidin-4-one O-propyl oxime 88.8 mg (0.248 mmol) synthesized in the same manner as in Reference Example 62-3, and the mixture was stirred at room temperature for 2 hours. Next, guanidine carbonate 100 mg (0.555 mmol) was added, and the mixture was stirred at room temperature for 1.5 hours. After the completion of the reaction, water was added to the reaction mixture, and followed by extraction with methylene chloride. The organic layer was dried over anhydrous sodium sulfate, and filtered. The filtrate was concentrated under reduced pressure. Toluene was added to the concentrated residue, which was then concentrated under reduced pressure, and this operation was repeated several times. Ethyl acetate was added to the obtained solid, and the mixture was ultrasonicated. The solid was collected by filtration and was dried under reduced pressure to give the title compound 106 mg (0.239 mmol, yield 96%) as a white solid.

Mass spectrum (DUIS, m/z):444[M+1]$^+$.

$^1$H-NMR spectrum (400 MHz, DMSO-d$_6$) δ:8.59 (d, J=1.4 Hz, 2H), 7.54-7.47 (m, 1H), 7.43-7.36 (m, 1H), 7.32-7.25 (m, 1H), 5.06 (s, 2H), 3.96-3.89 (m, 6H), 2.61-2.55 (m, 2H), 2.41-2.34 (m, 2H), 1.60 (sext, J=7.3 Hz, 2H), 0.89 (t, J=7.3 Hz, 3H).

Example 56

3-(2-{4-[(Allyloxy)imino]piperidin-1-yl}pyrimidin-5-yl)-2-fluorobenzyl carbamimidoylcarbamate (Compound II-209)

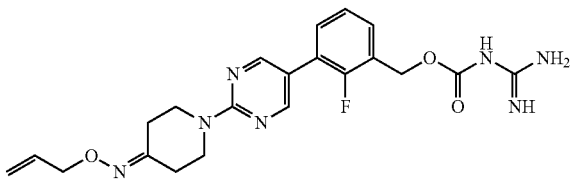 [SMILES: C=CCON=C1CCN(c2ncc(-c3cccc(COC(=O)NC(=N)N)c3F)cn2)CC1]

CDI 100 mg (0.617 mmol) was added to a DMF (2.5 mL) solution of 1-{5-[2-fluoro-3-(hydroxymethyl)phenyl]pyrimidin-2-yl}piperidin-4-one O-allyl oxime 92.7 mg (0.260 mmol) synthesized in the same manner as in Reference Example 63, and the mixture was stirred at room temperature for 2 hours. Next, guanidine carbonate 100 mg (0.555 mmol) was added, and the mixture was stirred at room temperature for 1.5 hours. After the completion of the reaction, water was added to the reaction mixture, and followed by extraction with methylene chloride. The organic layer was dried over anhydrous sodium sulfate, and filtered. The filtrate was concentrated under reduced pressure. Toluene was added to the concentrated residue, which was then concentrated under reduced pressure, and this operation was repeated several times. Ethyl acetate was added to the obtained solid, and the mixture was ultrasonicated. The solid was collected by filtration and was dried under reduced pressure to give the title compound 107 mg (0.242 mmol, yield 93%) as a white solid.

Mass spectrum (DUIS, m/z):442[M+1]$^+$.

$^1$H-NMR spectrum (400 MHz, DMSO-$d_6$) δ:8.60 (d, J=1.4 Hz, 2H), 7.58-7.44 (m, 1H), 7.42-7.33 (m, 1H), 7.31-7.23 (m, 1H), 6.02-5.92 (m, 1H), 5.31-5.24 (m, 1H), 5.21-5.16 (m, 1H), 5.06 (s, 2H), 4.53-4.48 (m, 2H), 3.97-3.89 (m, 4H), 2.64-2.56 (m, 2H), 2.42-2.34 (m, 2H).

Example 57)

2-Fluoro-3-{2-[4-({2-[(tetrahydropyran-2-yl)oxy]ethoxy}imino)piperidin-1-yl]pyrimidin-5-yl}benzyl carbamimidoylcarbamate (Compound II-250)

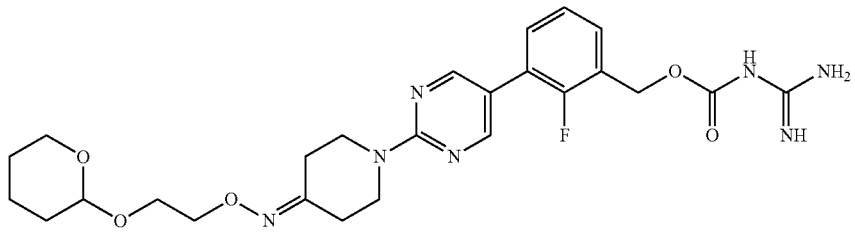 [SMILES: N=C(N)NC(=O)OCc1cccc(-c2cnc(N3CCC(=NOCCOC4CCCCO4)CC3)nc2)c1F]

CDI 35 mg (0.22 mmol) was added to a DMF (1 mL) solution of 1-{5-[2-fluoro-3-(hydroxymethyl)phenyl]pyrimidin-2-yl}piperidin-4-one O-{2-[(tetrahydropyran-2-yl)oxy]ethyl} oxime 38 mg (0.085 mmol) synthesized in the same manner as in Reference Example 65, and the mixture was stirred at room temperature for 1 hour. Next, guanidine carbonate 32 mg (0.18 mmol) was added, and the mixture was stirred at room temperature for 11 hours. After the completion of the reaction, the reaction mixture was poured to water 10 mL, and followed by extraction with a mixed solvent consisting of methylene chloride:methanol=80:20 (V/V). The organic layer was dried over anhydrous magnesium sulfate, and filtered. The filtrate was concentrated under reduced pressure. The concentrated residue was purified by silica gel column chromatography (DIOL silica gel, eluting solvent: ethyl acetate:methanol=100:0 to 90:10 (V/V)) to give the title compound 43 mg (0.081 mmol, yield 95%) as a white solid.

Mass spectrum (ESI, m/z):530[M+1]$^+$.

$^1$H-NMR spectrum (400 MHz, DMSO-$d_6$+$D_2O$) δ:8.59 (s, 2H), 7.54-7.46 (m, 1H), 7.43-7.36 (m, 1H), 7.32-7.25 (m, 1H), 5.06 (s, 2H), 4.61-4.56 (m, 1H), 4.16-4.07 (m, 2H), 3.97-3.87 (m, 4H), 3.85-3.70 (m, 2H), 3.63-3.55 (m, 1H), 3.42-3.37 (m, 1H), 2.63-2.54 (m, 2H), 2.43-2.36 (m, 2H), 1.80-1.36 (m, 6H).

Example 58

2-Fluoro-3-{2-[4-({3-[(tetrahydropyran-2-yl)oxy]propoxy}imino)piperidin-1-yl]pyrimidin-5-yl}benzyl carbamimidoylcarbamate (Compound II-251)

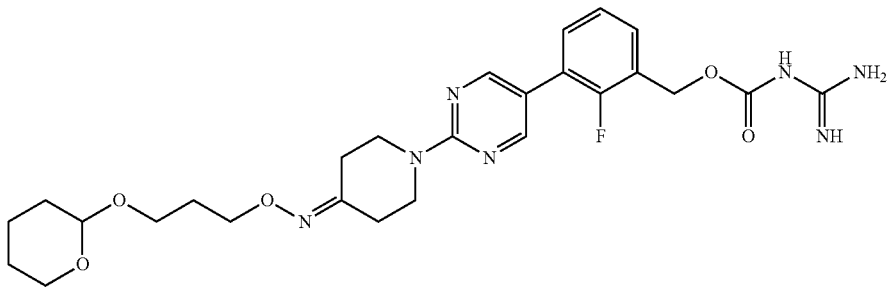 [SMILES: N=C(N)NC(=O)OCc1cccc(-c2cnc(N3CCC(=NOCCCOC4CCCCO4)CC3)nc2)c1F]

CDI 69 mg (0.43 mmol) was added to a DMF (4 mL) solution of 1-{5-[2-fluoro-3-(hydroxymethyl)phenyl]pyrimidin-2-yl}piperidin-4-one O-{3-[(tetrahydropyran-2-yl)oxy]propyl} oxime 97 mg (0.21 mmol) synthesized in the same manner as in Reference Example 7-51, and the mixture was stirred at room temperature for 8 hours. Next, guanidine carbonate 77 mg (0.43 mmol) was added, and the mixture was stirred at room temperature for 22 hours. After the completion of the reaction, water was added to the reaction mixture, and followed by extraction with methylene chloride. The organic layer was washed with water, dried over anhydrous sodium sulfate, and filtered. The filtrate was concentrated under reduced pressure. The concentrated residue was purified by silica gel column chromatography (DNH silica gel, eluting solvent: ethyl acetate:methanol) to give the title compound 92 mg (0.17 mmol, yield 81%) as a white solid.

$^1$H-NMR spectrum (400 MHz, DMSO-$d_6$+$D_2O$) δ:8.59 (d, J=1.3 Hz, 2H), 7.58-7.47 (m, 1H), 7.44-7.37 (m, 1H), 7.32-7.24 (m, 1H), 5.06 (s, 2H), 4.59-4.51 (m, 1H), 4.11-4.00 (m, 2H), 3.98-3.86 (m, 4H), 3.78-3.64 (m, 2H), 3.47-3.35 (m, 2H), 2.63-2.54 (m, 2H), 2.46-2.36 (m, 2H), 1.97-1.79 (m, 2H), 1.78-1.39 (m, 6H).

Example 59

2-Fluoro-3-{2-[4-({4-[(tetrahydropyran-2-yl)oxy]butoxy}imino)piperidin-1-yl]pyrimidin-5-yl}benzyl carbamimidoylcarbamate (Compound II-252)

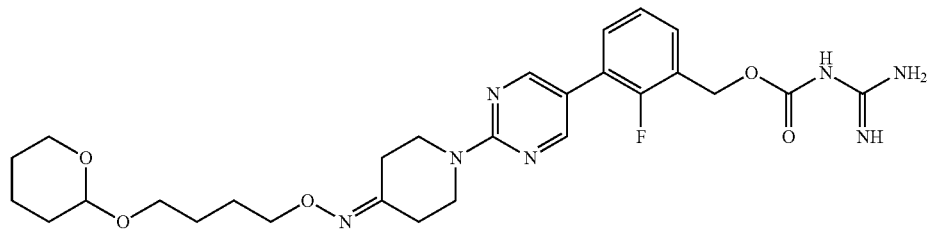 [SMILES: N=C(N)NC(=O)OCc1cccc(-c2cnc(N3CCC(=NOCCCCOC4CCCCO4)CC3)nc2)c1F]

CDI 84.0 mg (0.518 mmol) was added to a DMF (6 mL) solution of 1-{5-[2-fluoro-3-(hydroxymethyl)phenyl]pyrimidin-2-yl}piperidin-4-one O-{4-[(tetrahydropyran-2-yl)oxy]butyl} oxime 123 mg (0.260 mmol) synthesized in the same manner as in Reference Example 7-52, and the mixture was stirred at room temperature for 7 hours. Next, guanidine carbonate 94.0 mg (0.522 mmol) was added, and the mixture was stirred at room temperature for 21 hours. After the completion of the reaction, water was added to the reaction mixture, and followed by extraction with methylene chloride. The organic layer was washed with water, dried over anhydrous sodium sulfate, and filtered. The filtrate was concentrated under reduced pressure. The concentrated residue was purified by silica gel column chromatography (DNH silica gel, eluting solvent: ethyl acetate:methanol) to give the title compound 112 mg (0.201 mmol, yield 77%) as a white solid.

$^1$H-NMR spectrum (400 MHz, DMSO-d$_6$+D$_2$O) δ:8.59 (d, J=1.4 Hz, 2H), 7.54-7.47 (m, 1H), 7.43-7.36 (m, 1H), 7.33-7.24 (m, 1H), 5.06 (s, 2H), 4.56-4.52 (m, 1H), 4.02-3.95 (m, 2H), 3.95-3.87 (m, 4H), 3.77-3.69 (m, 1H), 3.68-3.60 (m, 1H), 3.45-3.30 (m, 2H), 2.62-2.55 (m, 2H), 2.42-2.34 (m, 2H), 1.79-1.36 (m, 10H).

Example 60

2-Fluoro-3-(2-{4-[(2-methoxyethoxy)imino]piperidin-1-yl}pyrimidin-5-yl)benzyl carbamimidoylcarbamate (Compound II-218)

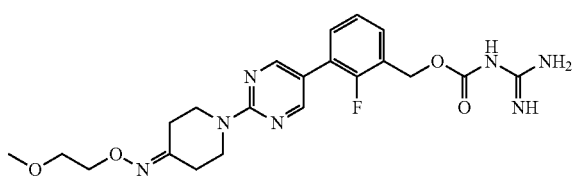 [SMILES: COCCON=C1CCN(c2ncc(-c3cccc(COC(=O)NC(=N)N)c3F)cn2)CC1]

CDI 107 mg (0.660 mmol) was added to a DMF (6 mL) solution of 1-{5-[2-fluoro-3-(hydroxymethyl)phenyl]pyrimidin-2-yl}piperidin-4-one O-(2-methoxyethyl) oxime 124 mg (0.331 mmol) synthesized in the same manner as in Reference Example 7-53, and the mixture was stirred at room temperature for 5 hours. Next, guanidine carbonate 119 mg (0.661 mmol) was added, and the mixture was stirred at room temperature for 16 hours. After the completion of the reaction, water was added to the reaction mixture, and followed by extraction with methylene chloride. The organic layer was washed with water, dried over anhydrous sodium sulfate, and filtered. The filtrate was concentrated under reduced pressure. The concentrated residue was purified by silica gel column chromatography (DNH silica gel, eluting solvent: ethyl acetate:methanol) to give the title compound 126 mg (0.274 mmol, yield 83%) as a white solid.

Mass spectrum (ESI, m/z):460[M+1]$^+$.

$^1$H-NMR spectrum (400 MHz, DMSO-d$_6$+D$_2$O) δ:8.60 (d, J=1.4 Hz, 2H), 7.53-7.47 (m, 1H), 7.42-7.36 (m, 1H), 7.31-7.25 (m, 1H), 5.06 (s, 2H), 4.11-4.07 (m, 2H), 3.96-3.89 (m, 4H), 3.57-3.52 (m, 2H), 3.26 (s, 3H), 2.63-2.55 (m, 2H), 2.42-2.33 (m, 2H).

Example 61

3-{2-[4-({2,2-Dimethyl-3-[(tetrahydropyran-2-yl)oxy]propoxy}imino)piperidin-1-yl]pyrimidin-5-yl}-2-fluorobenzyl carbamimidoylcarbamate (Compound II-254)

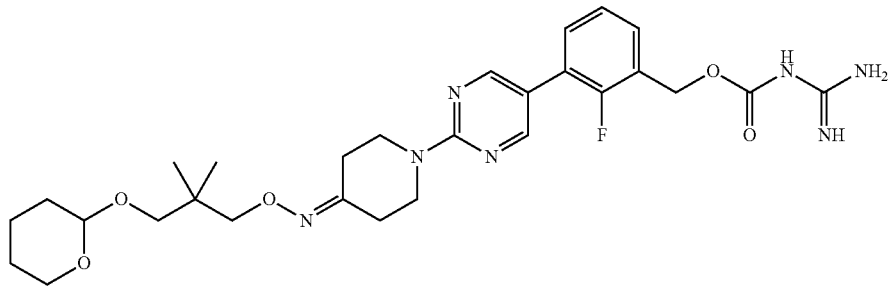 [SMILES: CC(C)(CON=C1CCN(c2ncc(-c3cccc(COC(=O)NC(=N)N)c3F)cn2)CC1)COC1CCCCO1]

CDI 100 mg (0.617 mmol) was added to a DMF (3 mL) solution of 1-{5-[2-fluoro-3-(hydroxymethyl)phenyl]pyrimidin-2-yl}piperidin-4-one O-{2,2-dimethyl-3-[(tetrahydropyran-2-yl)oxy]propyl} oxime 131 mg (0.269 mmol) synthesized in the same manner as in Reference Example 7-54, and the mixture was stirred at room temperature for 4 hours. Next, guanidine carbonate 100 mg (0.555 mmol) was added, and the mixture was stirred at room temperature for 16 hours. After the completion of the reaction, water was added to the reaction mixture, and followed by extraction with methylene chloride. The organic layer was washed with brine, dried over anhydrous sodium sulfate, and filtered. The filtrate was concentrated under reduced pressure. The concentrated residue was purified by silica gel column chromatography (DNH silica gel, eluting solvent: ethyl acetate: methanol). Ethyl acetate was added to the obtained solid, and the mixture was stirred at 50° C. for 1 hour. Thereafter, the solid was collected by filtration and was dried under reduced pressure to give the title compound 121 mg (0.212 mmol, yield 79%) as a white solid.

Mass spectrum (APCI, m/z):572[M+1]+.

1H-NMR spectrum (400 MHz, DMSO-d6+D2O) δ:8.59 (d, J=1.3 Hz, 2H), 7.53-7.47 (m, 1H), 7.43-7.37 (m, 1H), 7.31-7.26 (m, 1H), 5.06 (s, 2H), 4.54-4.50 (m, 1H), 3.96-3.88 (m, 4H), 3.83 (s, 2H), 3.76-3.66 (m, 1H), 3.47-3.37 (m, 2H), 3.07 (d, J=9.2 Hz, 1H), 2.63-2.56 (m, 2H), 2.43-2.35 (m, 2H), 1.77-1.36 (m, 6H), 0.91 (s, 3H), 0.91 (s, 3H).

Example 62

2-Fluoro-3-{2-[4-({3-methyl-3-[(tetrahydropyran-2-yl)oxy]butoxy}imino)piperidin-1-yl]pyrimidin-5-yl}benzyl carbamimidoylcarbamate (Compound II-255)

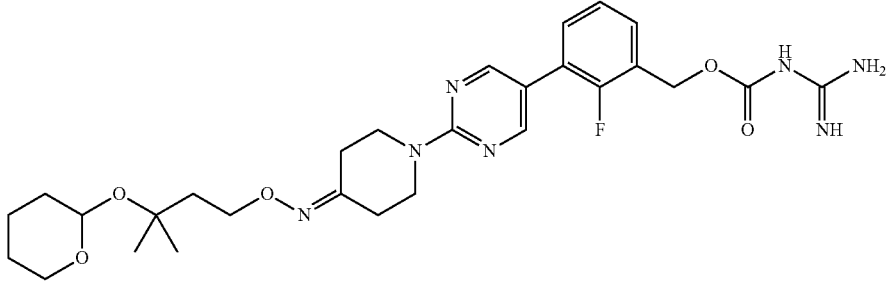 [SMILES: CC(C)(CCON=C1CCN(c2ncc(-c3cccc(COC(=O)NC(=N)N)c3F)cn2)CC1)OC1CCCCO1]

CDI 160 mg (0.987 mmol) was added to a DMF (4 mL) solution of 1-{5-[2-fluoro-3-(hydroxymethyl)phenyl]pyrimidin-2-yl}piperidin-4-one O-{3-methyl-3-[(tetrahydropyran-2-yl)oxy]butyl} oxime 193 mg (0.397 mmol) synthesized in the same manner as in Reference Example 7-55, and the mixture was stirred at room temperature for 14 hours. Next, guanidine carbonate 145 mg (0.805 mmol) was added, and the mixture was stirred at room temperature for 2 hours. After the completion of the reaction, water was added to the reaction mixture, and followed by extraction with ethyl acetate. The organic layer was washed with brine, dried over anhydrous sodium sulfate, and filtered. The filtrate was concentrated under reduced pressure. Ethyl acetate was added to the concentrated residue, and the mixture was stirred at 70° C. for 1 hour and at room temperature for 14 hours. The solid was collected by filtration and was dried under reduced pressure to give the title compound 186 mg (0.325 mmol, yield 82%) as a white solid.

Mass spectrum (ESI, m/z):572[M+1]+.

1H-NMR spectrum (400 MHz, DMSO-d6+D2O) δ:8.59 (d, J=1.4 Hz, 2H), 7.53-7.48 (m, 1H), 7.42-7.37 (m, 1H), 7.31-7.26 (m, 1H), 5.06 (s, 2H), 4.77 (dd, J=2.7, 5.5 Hz, 1H), 4.13-4.04 (m, 2H), 3.95-3.88 (m, 4H), 3.84-3.77 (m, 1H), 3.44-3.37 (m, 1H), 2.60-2.52 (m, 2H), 2.43-2.36 (m, 2H), 1.86-1.68 (m, 3H), 1.59-1.32 (m, 5H), 1.19 (s, 3H), 1.18 (s, 3H).

Example 63

2-Fluoro-3-{2-[4-({2-[(tetrahydropyran-2-yl)oxy]propoxy}imino)piperidin-1-yl]pyrimidin-5-yl}benzyl carbamimidoylcarbamate (Compound II-256)

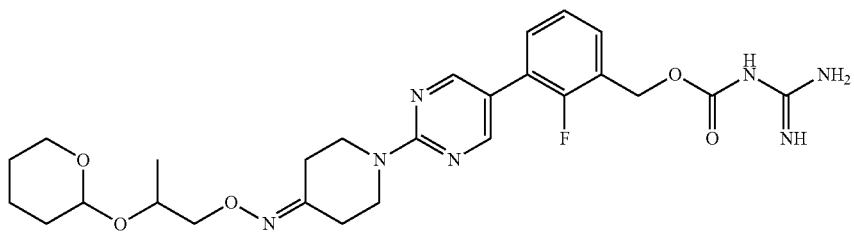 [SMILES: CC(CON=C1CCN(c2ncc(-c3cccc(COC(=O)NC(=N)N)c3F)cn2)CC1)OC1CCCCO1]

CDI 49 mg (0.30 mmol) was added to a DMF (1.2 mL) solution of 1-{5-[2-fluoro-3-(hydroxymethyl)phenyl]pyrimidin-2-yl}piperidin-4-one O-{2-[(tetrahydropyran-2-yl)oxy]propyl} oxime 57 mg (0.12 mmol) synthesized in the same manner as in Reference Example 7-56, and the mixture was stirred at room temperature for 1.5 hours. Next, guanidine carbonate 52 mg (0.29 mmol) was added, and the mixture was stirred at room temperature for 4 hours. After the completion of the reaction, water was added to the reaction mixture, and followed by extraction with methylene chloride three times. The organic layer was dried over anhydrous sodium sulfate, and filtered. The filtrate was concentrated under reduced pressure. Toluene was added to the concentrated residue, which was then concentrated under reduced pressure, and this operation was repeated several times. Diisopropyl ether was added, and the mixture was ultrasonicated. The solid was collected by filtration and was dried under reduced pressure to give the title compound 49 mg (0.090 mmol, yield 75%) as a white solid.

Mass spectrum (DUIS, m/z):544[M+1]$^+$.

$^1$H-NMR spectrum (400 MHz, DMSO-d$_6$+D$_2$O) δ:8.61-8.57 (m, 2H), 7.54-7.46 (m, 1H), 7.43-7.37 (m, 1H), 7.33-7.24 (m, 1H), 5.06 (s, 2H), 4.79-4.61 (m, 1H), 4.10-3.73 (m, 8H), 3.45-3.34 (m, 1H), 2.63-2.56 (m, 2H), 2.44-2.34 (m, 2H), 1.86-1.36 (m, 6H), 1.17-1.03 (m, 3H).

Example 64

2-Fluoro-3-{2-[4-({2-methyl-3-[(tetrahydropyran-2-yl)oxy]propoxy}imino)piperidin-1-yl]pyrimidin-5-yl}benzyl carbamimidoylcarbamate (Compound II-257)

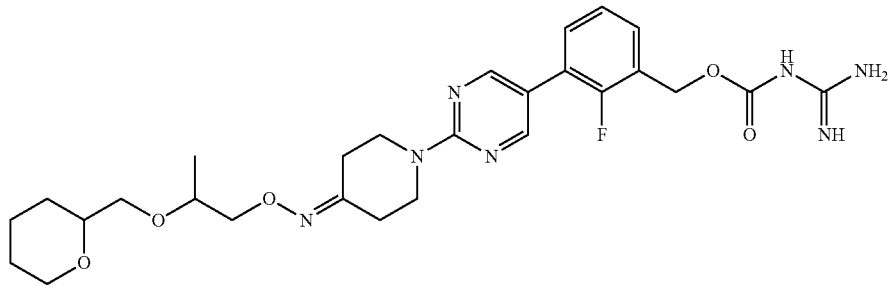 [SMILES: CC(CON=C1CCN(c2ncc(-c3cccc(COC(=O)NC(=N)N)c3F)cn2)CC1)OCC1CCCCO1]

CDI 135 mg (0.833 mmol) was added to a DMF (4 mL) solution of 1-{5-[2-fluoro-3-(hydroxymethyl)phenyl]pyrimidin-2-yl}piperidin-4-one O-{2-methyl-3-[(tetrahydropyran-2-yl)oxy]propyl)}oxime 175 mg (0.370 mmol) synthesized in the same manner as in Reference Example 7-57, and the mixture was stirred at room temperature for 1.5 hours. Next, guanidine carbonate 135 mg (0.749 mmol) was added, and the mixture was stirred at room temperature for 16 hours. After the completion of the reaction, water was added to the reaction mixture, and followed by extraction with methylene chloride. The organic layer was washed with brine, dried over anhydrous sodium sulfate, and filtered. The filtrate was concentrated under reduced pressure. The concentrated residue was purified by silica gel column chromatography (DNH silica gel, eluting solvent: ethyl acetate: methanol). Ethyl acetate was added to the obtained solid, and the mixture was stirred at 50° C. for 1 hour. Thereafter, the solid was collected by filtration and was dried under reduced pressure to give the title compound 117 mg (0.210 mmol, yield 57%) as a white solid.

Mass spectrum (APCI, m/z):558[M+1].

$^1$H-NMR spectrum (400 MHz, DMSO-d$_6$+D$_2$O) δ:8.63-8.56 (m, 2H), 7.54-7.47 (m, 1H), 7.42-7.36 (m, 1H), 7.31-7.25 (m, 1H), 5.06 (s, 2H), 4.56-4.51 (m, 1H), 4.02-3.80 (m, 6H), 3.77-3.67 (m, 1H), 3.63-3.37 (m, 2H), 3.34-3.18 (m, 1H), 2.63-2.55 (m, 2H), 2.43-2.36 (m, 2H), 2.11-2.01 (m, 1H), 1.76-1.37 (m, 6H), 0.97-0.87 (m, 3H).

Example 65

3-[2-(4-{[(2,2-Dimethyl-1,3-dioxan-5-yl)methoxy]imino}piperidin-1-yl)pyrimidin-5-yl]-2-fluorobenzyl carbamimidoylcarbamate (Compound II-259)

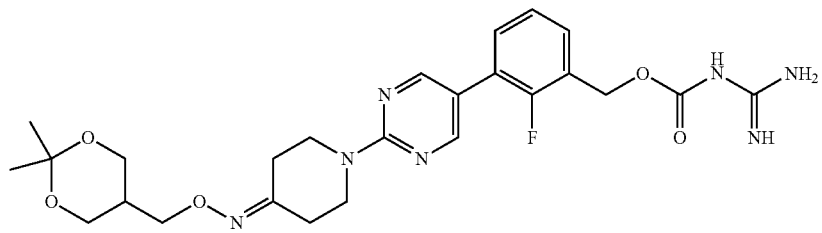 [SMILES: CC1(C)OCC(CON=C2CCN(c3ncc(-c4cccc(COC(=O)NC(=N)N)c4F)cn3)CC2)CO1]

CDI 252 mg (1.55 mmol) was added to a DMF (4 mL) solution of 1-{5-[2-fluoro-3-(hydroxymethyl)phenyl]pyrimidin-2-yl}piperidin-4-one O-[(2,2-dimethyl-1,3-dioxan-5-yl)methyl] oxime 345 mg (0.776 mmol) synthesized in the same manner as in Reference Example 7-58, and the mixture was stirred at room temperature for 14 hours. Next, guanidine carbonate 280 mg (1.55 mmol) was added, and the mixture was stirred at room temperature for 2 hours. After the completion of the reaction, water and a saturated aqueous sodium carbonate solution were added to the reaction mixture, and followed by extraction with ethyl acetate. The organic layer was washed with brine, dried over anhydrous sodium sulfate, and filtered. The filtrate was concentrated under reduced pressure. The concentrated residue was purified by silica gel column chromatography (DNH silica gel, eluting solvent: ethyl acetate:methanol=100:0 to 88:12 (V/V)). Ethyl acetate 5 mL was added to the obtained solid, and the mixture was stirred at 70° C. for 30 minutes. Thereafter, the solid was collected by filtration and was dried under reduced pressure to give the title compound 393 mg (0.742 mmol, yield 96%) as a white solid.

Mass spectrum (ESI, m/z):530[M+1]$^+$.

$^1$H-NMR spectrum (400 MHz, DMSO-d$_6$+D$_2$O) δ:8.59 (d, J=1.3 Hz, 2H), 7.53-7.47 (m, 1H), 7.44-7.36 (m, 1H), 7.34-7.24 (m, 1H), 5.06 (s, 2H), 4.02 (d, J=7.0 Hz, 2H), 3.97-3.85 (m, 6H), 3.77-3.45 (m, 2H), 2.62-2.55 (m, 2H), 2.43-2.37 (m, 2H), 2.03-1.94 (m, 1H), 1.33 (s, 3H), 1.32 (s, 3H).

Example 66

2-Fluoro-3-[2-(4-{[(2,2,5-trimethyl-1,3-dioxan-5-yl)methoxy]imino}piperidin-1-yl)pyrimidin-5-yl]benzyl carbamimidoylcarbamate (Compound II-262)

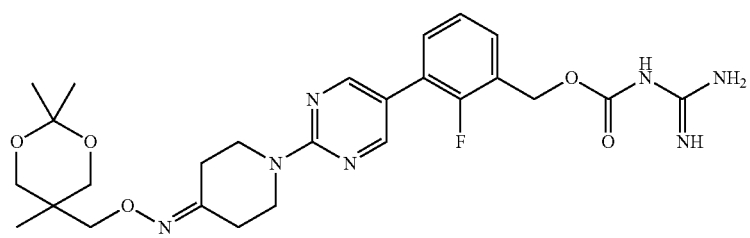 [SMILES: CC1(CON=C2CCN(c3ncc(-c4cccc(COC(=O)NC(=N)N)c4F)cn3)CC2)COC(C)(C)OC1]

CDI 80 mg (0.49 mmol) was added to a DMF (3 mL) solution of 1-{5-[2-fluoro-3-(hydroxymethyl)phenyl]pyrimidin-2-yl}piperidin-4-one O-[(2,2,5-trimethyl-1,3-dioxan-5-yl)methyl] oxime 97 mg (0.21 mmol) synthesized in the same manner as in Reference Example 7-59, and the mixture was stirred at room temperature for 4 hours. Next, guanidine carbonate 80 mg (0.44 mmol) was added, and the mixture was stirred at room temperature for 15 hours. After the completion of the reaction, water was added to the reaction mixture, and followed by extraction with methylene chloride. The organic layer was washed with brine, dried over anhydrous sodium sulfate, and filtered. The filtrate was concentrated under reduced pressure. The concentrated residue was purified by silica gel column chromatography (DNH silica gel, eluting solvent: 1,2-dichloroethane:methanol) and (DNH silica gel, eluting solvent: ethyl acetate:methanol) to give the title compound 83 mg (including impurities) as a white foam.

Mass spectrum (APCI, m/z):544[M+1]$^+$.

$^1$H-NMR spectrum (400 MHz, DMSO-$d_6$+$D_2O$) δ:8.59 (d, J=1.3 Hz, 2H), 7.54-7.47 (m, 1H), 7.42-7.36 (m, 1H), 7.31-7.25 (m, 1H), 5.06 (s, 2H), 4.01 (s, 2H), 3.97-3.89 (m, 4H), 3.61 (d, J=11.7 Hz, 2H), 3.52 (d, J=11.7 Hz, 2H), 2.63-2.57 (m, 2H), 2.42-2.36 (m, 2H), 1.35 (s, 3H), 1.29 (s, 3H), 0.85 (s, 3H).

Example 67

3-[2-(4-{[(2,2-Dimethyl-1,3-dioxolan-4-yl)methoxy]imino}piperidin-1-yl)pyrimidin-5-yl]-2-fluorobenzyl carbamimidoylcarbamate (Compound II-260)

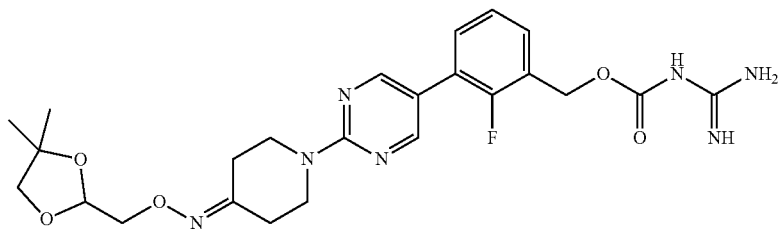 [SMILES: CC1(C)COC(CON=C2CCN(c3ncc(-c4cccc(COC(=O)NC(=N)N)c4F)cn3)CC2)O1]

CDI 100 mg (0.617 mmol) was added to a DMF (6 mL) solution of 1-{5-[2-fluoro-3-(hydroxymethyl)phenyl]pyrimidin-2-yl}piperidin-4-one O-[(2,2-dimethyl-1,3-dioxolan-4-yl)methyl] oxime 130 mg (0.302 mmol) synthesized in the same manner as in Reference Example 7-60, and the mixture was stirred at room temperature for 15 hours. Next, guanidine carbonate 110 mg (0.611 mmol) was added, and the mixture was stirred at room temperature for 4 hours. After the completion of the reaction, water was added to the reaction mixture, and followed by extraction with methylene chloride. The organic layer was washed with water, dried over anhydrous sodium sulfate, and filtered. The filtrate was concentrated under reduced pressure. The concentrated residue was purified by silica gel column chromatography (DNH silica gel, eluting solvent: ethyl acetate:methanol) to give the title compound 118 mg (0.229 mmol, yield 76%) as a white solid.

$^1$H-NMR spectrum (400 MHz, DMSO-$d_6$+$D_2O$) δ:8.60 (d, J=1.5 Hz, 2H), 7.55-7.46 (m, 1H), 7.44-7.37 (m, 1H), 7.32-7.24 (m, 1H), 5.06 (s, 2H), 4.33-4.21 (m, 1H), 4.06-3.98 (m, 3H), 3.96-3.89 (m, 4H), 3.67 (dd, J=6.5, 8.3 Hz, 1H), 2.62-2.55 (m, 2H), 2.42-2.36 (m, 2H), 1.33 (s, 3H), 1.28 (s, 3H).

Example 68

2-[({1-[5-(3-{[(Carbamimidoylcarbamoyl)oxy]methyl}-2-fluorophenyl)pyrimidin-2-yl]piperidin-4-ylidene}amino)oxy]ethyl acetate (Compound III-225)

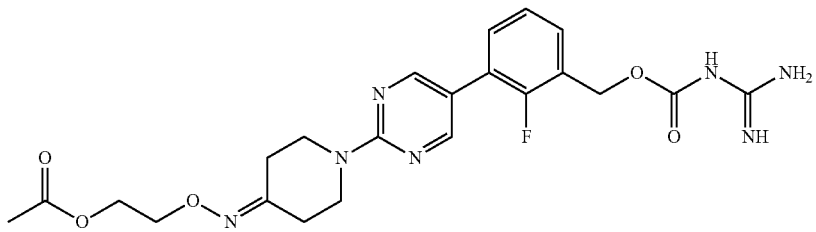 [SMILES: CC(=O)OCCON=C1CCN(c2ncc(-c3cccc(COC(=O)NC(=N)N)c3F)cn2)CC1]

CDI 56 mg (0.35 mmol) was added to a DMF (4 mL) solution of 2-{[(1-{5-[2-fluoro-3-(hydroxymethyl)phenyl]pyrimidin-2-yl}piperidin-4-ylidene)amino]oxy}ethyl acetate 69 mg (0.17 mmol) synthesized in the same manner as in Reference Example 7-61, and the mixture was stirred at room temperature for 8 hours. Next, guanidine carbonate 62 mg (0.34 mmol) was added, and the mixture was stirred at room temperature for 14 hours. After the completion of the reaction, water was added to the reaction mixture, and followed by extraction with methylene chloride. The organic layer was washed with water, dried over anhydrous sodium sulfate, and filtered. The filtrate was concentrated under reduced pressure. The concentrated residue was purified by silica gel column chromatography (DNH silica gel, eluting solvent: ethyl acetate:methanol) to give the title compound 62 mg (0.13 mmol, yield 76%) as a white solid.

Mass spectrum (ESI, m/z):488[M+l]$^+$.

$^1$H-NMR spectrum (400 MHz, DMSO-d$_6$+D$_2$O) 5:8.60 (d, J=1.1 Hz, 2H), 7.55-7.46 (m, 1H), 7.44-7.36 (m, 1H), 7.32-7.23 (m, 1H), 5.06 (s, 2H), 4.25-4.13 (m, 4H), 3.96-3.89 (m, 4H), 2.63-2.55 (m, 2H), 2.44-2.36 (m, 2H), 2.03 (s, 3H).

Example 69

(E/Z)-2-fluoro-3-{2-[3-(methoxyimino)pyrrolidin-1-yl]pyrimidin-5-yl}benzyl carbamimidoylcarbamate (Compound II-92)

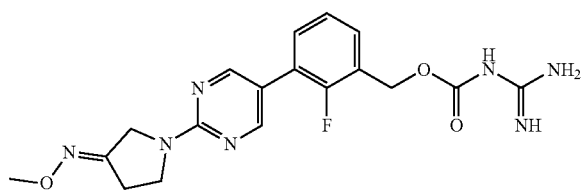 [SMILES: CO/N=C1\CCN(c2ncc(-c3cccc(COC(=O)NC(=N)N)c3F)cn2)C1]

CDI 52.4 mg (0.323 mmol) was added to a DMF (2 mL) solution of 1-{5-[2-fluoro-3-(hydroxymethyl)phenyl]pyrimidin-2-yl}pyrrolidin-3-one O-methyloxime EZ mixture 51.1 mg (0.162 mmol) synthesized in the same manner as in Reference Example 76, and the mixture was stirred at room temperature for 1.5 hours. Next, guanidine carbonate 64.2 mg (0.356 mmol) was added, and the mixture was stirred at room temperature for 13 hours. After the completion of the reaction, the reaction mixture was poured to water 20 mL, and the mixture was stirred at room temperature for 5 minutes. The precipitated solid was collected by filtration and was dried under reduced pressure to give the title compound 41.5 mg (0.103 mmol, yield 64%) as a brown solid.

Mass spectrum (ESI, m/z):402[M+l]$^+$.

$^1$H-NMR spectrum (400 MHz, DMSO-d$_6$+D$_2$O) 5:8.63-8.59 (m, 2H), 7.53-7.46 (m, 1H), 7.43-7.37 (m, 1H), 7.33-7.24 (m, 1H), 5.06 (s, 2H), 4.26-4.20 (m, 2H), 3.87-3.77 (m, 5H), 2.87-2.80 (m, 2H).

Example 70

2-Fluoro-3-{2-[3-(hydroxyimino)azetidin-1-yl]pyrimidin-5-yl}benzyl carbamimidoylcarbamate (Compound II-1)

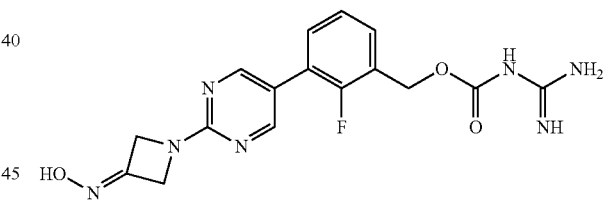

1 M tetrabutylammonium fluoride/THF solution 230 μl (0.230 mmol) was added to a THF (5 mL) suspension of 3-[2-(3-{[(tert-butyldimethylsilyl)oxy]imino}azetidin-1-yl)pyrimidin-5-yl]-2-fluorobenzyl carbamimidoylcarbamate 91.6 mg (0.188 mmol) synthesized in the same manner as in Example 4, and the mixture was stirred at room temperature for 2 hours. After the completion of the reaction, the reaction mixture was concentrated under reduced pressure, and water was added. The precipitated solid was collected by filtration, and was washed with water and diethyl ether. Ethyl acetate was added to the obtained solid, and the mixture was stirred at 75° C. for 30 minutes. Thereafter, the solid was collected by filtration and was purified by silica gel column chromatography (DNH silica gel, eluting solvent: 1,2-dichloroethane:methanol=99:1 to 50:50 (V/V)) to give the title compound 19.9 mg (0.0533 mmol, yield 28%) as a white solid.

Mass spectrum (DUIS, m/z):374[M+l]$^+$.

$^1$H-NMR spectrum (400 MHz, DMSO-d$_6$+D$_2$O) δ:8.63 (s, 2H), 7.57-7.47 (m, 1H), 7.46-7.38 (m, 1H), 7.34-7.24 (m, 1H), 5.06 (s, 2H), 4.88-4.70 (m, 4H).

Example 71

2-Fluoro-3-(2-{3-[(2-hydroxyethoxy)imino]azetidin-1-yl}pyrimidin-5-yl)benzyl carbamimidoylcarbamate hydrochloride (Compound II-21 hydrochloride)

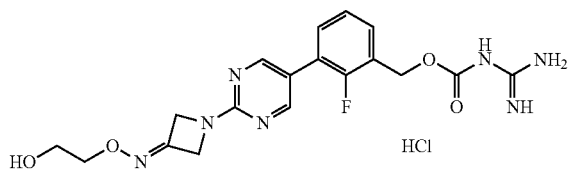 [SMILES: N=C(N)NC(=O)OCc1cccc(-c2cnc(N3CC(=NOCCO)C3)nc2)c1F ; Cl]

At 0° C., 2 M hydrogen chloride/ethanol solution 1 mL (2 mmol) was added to an ethanol (2 mL) suspension of 2-fluoro-3-{2-[3-({2-[(tetrahydropyran-2-yl)oxy]ethoxy}imino)azetidin-1-yl]pyrimidin-5-yl}benzyl carbamimidoylcarbamate 85 mg (0.17 mmol) synthesized in the same manner as in Example 9, and the mixture was stirred at room temperature for 2 hours. After the completion of the reaction, the reaction mixture was concentrated under reduced pressure. TBME was added to the concentrated residue, and the solid was collected by filtration and was dried under reduced pressure to give the title compound 59 mg (0.13 mmol, yield 76%) as a white solid.

Mass spectrum (APCI, m/z):418[M+1]$^+$.

$^1$H-NMR spectrum (400 MHz, DMSO-d$_6$+D$_2$O) δ:8.64 (d, J=1.1 Hz, 2H), 7.67-7.59 (m, 1H), 7.58-7.50 (m, 1H), 7.40-7.31 (m, 1H), 5.37 (s, 2H), 4.86-4.80 (m, 4H), 4.05 (t, J=5.2 Hz, 2H), 3.61 (t, J=5.2 Hz, 2H).

Example 72

2-Fluoro-3-(2-{3-[(3-hydroxypropoxy)imino]azetidin-1-yl}pyrimidin-5-yl)benzyl carbamimidoylcarbamate (Compound II-22)

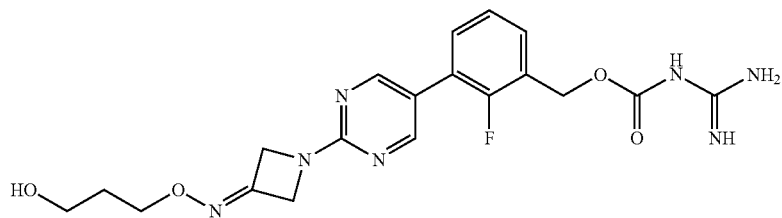 [SMILES: N=C(N)NC(=O)OCc1cccc(-c2cnc(N3CC(=NOCCCO)C3)nc2)c1F]

At room temperature, 2 M hydrogen chloride/ethanol solution 2 mL (4 mmol) was added to 2-fluoro-3-{2-[3-({3-[(tetrahydropyran-2-yl)oxy]propoxy}imino)azetidin-1-yl]pyrimidin-5-yl}benzyl carbamimidoylcarbamate 145 mg (0.281 mmol) synthesized in the same manner as in Example 10, and the mixture was stirred at room temperature for 30 minutes. After the completion of the reaction, the reaction mixture was concentrated under reduced pressure. Methylene chloride, TEA and water were added to the concentrated residue, and the mixture was stirred. The precipitated solid was collected by filtration and was dried under reduced pressure to give the title compound 69 mg (0.16 mmol, yield 57%) as a white solid.

Mass spectrum (ESI, m/z):432[M+1]$^+$.

1H-NMR spectrum (400 MHz, DMSO-d$_6$) δ:8.63 (d, J=1.4 Hz, 2H), 7.56-7.46 (m, 1H), 7.45-7.35 (m, 1H), 7.32-7.25 (m, 1H), 5.06 (s, 2H), 4.85-4.77 (m, 4H), 4.48 (t, J=5.1 Hz, 1H), 4.10 (t, J=6.5 Hz, 2H), 3.52-3.44 (m, 2H), 1.76 (quin, J=6.5 Hz, 2H).

Example 73

2-Fluoro-3-(2-{3-[(4-hydroxybutoxy)imino]azetidin-1-yl}pyrimidin-5-yl)benzyl carbamimidoylcarbamate (Compound II-23)

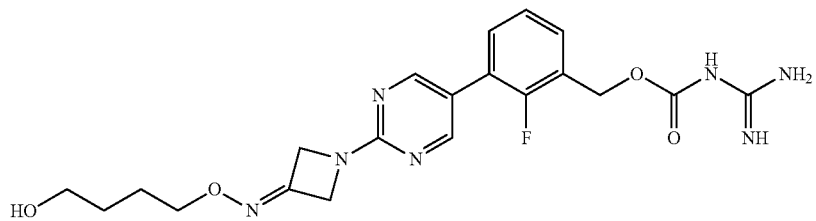 [SMILES: N=C(N)NC(=O)OCc1cccc(-c2cnc(N3CC(=NOCCCCO)C3)nc2)c1F]

2 M hydrogen chloride/ethanol solution 0.3 mL (0.6 mmol) was added to a methylene chloride (2 mL) suspension of 2-fluoro-3-{2-[3-({4-[(tetrahydropyran-2-yl)oxy]butoxy}imino)azetidin-1-yl]pyrimidin-5-yl}benzyl carbamimidoylcarbamate 90 mg (0.17 mmol) synthesized in the same manner as in Example 11, and the mixture was stirred at room temperature for 1 hour. After the completion of the reaction, the reaction mixture was concentrated under reduced pressure. The concentrated residue was purified by silica gel column chromatography (DNH silica gel, eluting solvent: 1,2-dichloroethane:methanol) to give the title compound 63 mg (0.14 mmol, yield 82%) as a white solid.

Mass spectrum (APCI, m/z):446[M+1]$^+$.

$^1$H-NMR spectrum (400 MHz, DMSO-d$_6$+D$_2$O) δ:8.66-8.60 (m, 2H), 7.54-7.47 (m, 1H), 7.45-7.39 (m, 1H), 7.33-7.26 (m, 1H), 5.06 (s, 2H), 4.86-4.77 (m, 4H), 4.07-4.01 (m, 2H), 3.44-3.38 (m, 2H), 1.69-1.59 (m, 2H), 1.53-1.43 (m, 2H).

Example 74

2-Fluoro-3-[2-(3-{[2-(2-hydroxyethoxy)ethoxy]imino}azetidin-1-yl)pyrimidin-5-yl]benzyl carbamimidoylcarbamate (Compound II-30)

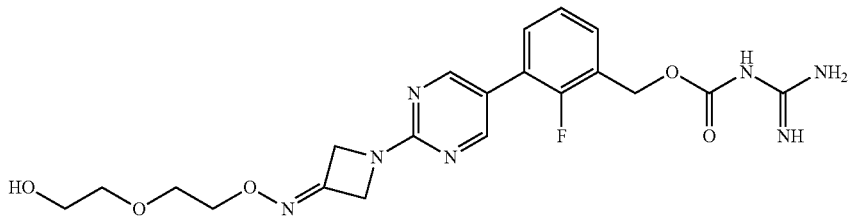 [SMILES: N=C(N)NC(=O)OCc1cccc(-c2cnc(N3CC(=NOCCOCCO)C3)nc2)c1F]

2 M hydrogen chloride/ethanol solution 0.20 mL (0.40 mmol) was added to an ethanol (2 mL) solution of 2-fluoro-3-(2-{3-[(2-{2-[(tetrahydropyran-2-yl)oxy]ethoxy}ethoxy)imino]azetidin-1-yl}pyrimidin-5-yl)benzyl carbamimidoylcarbamate 70 mg (0.13 mmol) synthesized in the same manner as in Example 13, and the mixture was stirred at room temperature for 1 hour. After the completion of the reaction, TEA 55 μl (0.40 mmol) was added to the reaction mixture, and the reaction mixture was concentrated under reduced pressure. The concentrated residue was purified by silica gel column chromatography (DNH silica gel, eluting solvent: 1,2-dichloroethane:methanol). Ethyl acetate was added to the obtained solid, and the mixture was stirred at 50° C. for 1 hour. Thereafter, the solid was collected by filtration and was dried under reduced pressure to give the title compound 52 mg (0.11 mmol, yield 85%) as a white solid.

Mass spectrum (ESI, m/z):462[M+1]$^+$.

$^1$H-NMR spectrum (400 MHz, DMSO-d$_6$) δ:8.63 (s, 2H), 7.54-7.47 (m, 1H), 7.45-7.38 (m, 1H), 7.32-7.25 (m, 1H), 5.06 (s, 2H), 4.88-4.76 (m, 4H), 4.64-4.56 (m, 1H), 4.20-4.11 (m, 2H), 3.69-3.60 (m, 2H), 3.55-3.40 (m, 4H).

Example 75

2-Fluoro-3-[2-(3-{[3-fluoro-2-(hydroxymethyl)propoxy]imino}azetidin-1-yl)pyrimidin-5-yl]benzyl carbamimidoylcarbamate (Compound II-50)

2 M hydrogen chloride/ethanol solution 0.10 mL (0.20 mmol) was added to a methylene chloride (0.10 mL) solution of 2-fluoro-3-(2-{3-[(3-fluoro-2-{[(tetrahydropyran-2-yl)oxy]methyl}propoxy)imino]azetidin-1-yl}pyrimidin-5-yl)benzyl carbamimidoylcarbamate 52 mg (0.095 mmol) synthesized in the same manner as in Example 21, and the mixture was stirred at room temperature for 1 hour. After the completion of the reaction, TEA and a saturated aqueous sodium hydrogen carbonate solution were added to the reaction mixture, and followed by extraction with ethyl acetate. The organic layer was washed with brine, dried over anhydrous sodium sulfate, and filtered. The filtrate was concentrated under reduced pressure. The concentrated residue was purified by silica gel column chromatography (DNH silica gel, eluting solvent: ethyl acetate:methanol=100:0 to 88:12 (V/V)) to give the title compound 25 mg (0.054 mmol, yield 57%) as a white solid.

Mass spectrum (ESI, m/z):464[M+1]$^+$.

$^1$H-NMR spectrum (400 MHz, DMSO-d$_6$+D$_2$O) δ:8.63 (d, J=1.1 Hz, 2H), 7.54-7.49 (m, 1H), 7.45-7.40 (m, 1H), 7.33-7.28 (m, 1H), 5.07 (s, 2H), 4.87-4.80 (m, 4H), 4.52 (dd, J=5.2 Hz, J=47.4 Hz, 2H), 4.14-4.02 (m, 2H), 3.53-3.44 (m, 2H), 2.25-2.12 (m, 1H).

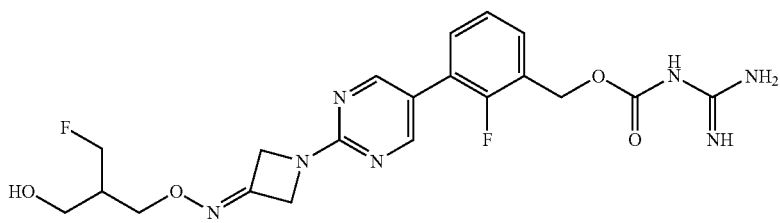 [SMILES: N=C(N)NC(=O)OCc1cccc(-c2cnc(N3CC(=NOCC(CO)CF)C3)nc2)c1F]

Example 76

2-Fluoro-3-(2-{3-[(4-hydroxy-3-methoxybutoxy)imino]azetidin-1-yl}pyrimidin-5-yl)benzyl carbamimidoylcarbamate (Compound II-51)

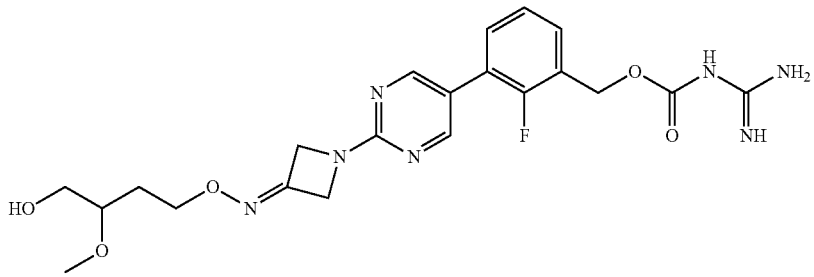 [SMILES: COC(CO)CCON=C1CN(c2ncc(-c3cccc(COC(=O)NC(=N)N)c3F)cn2)C1]

At 0° C., 2 M hydrogen chloride/ethanol solution 0.56 mL (1.1 mmol) was added to an ethanol (2 mL) solution of 2-fluoro-3-{2-[3-({3-methoxy-4-[(tetrahydropyran-2-yl)oxy]butoxy}imino)azetidin-1-yl]pyrimidin-5-yl}benzyl carbamimidoylcarbamate 63 mg (0.11 mmol) synthesized in the same manner as in Example 23, and the mixture was stirred at room temperature for 3 hours. After the completion of the reaction, TEA and water were added to the reaction mixture. The precipitated solid was collected by filtration, washed with water and ethyl acetate, and dried under reduced pressure to give the title compound 20 mg (0.042 mmol, yield 38%) as a white solid.

Mass spectrum (ESI, m/z):476[M+1]$^+$.

$^1$H-NMR spectrum (400 MHz, DMSO-d$_6$+D$_2$O) δ:8.69-8.60 (m, 2H), 7.67-7.57 (m, 1H), 7.56-7.47 (m, 1H), 7.42-7.31 (m, 1H), 5.31 (s, 2H), 4.90-4.76 (m, 4H), 4.17-4.05 (m, 2H), 3.41 (d, J=5.0 Hz, 2H), 3.30 (s, 3H), 3.28-3.20 (m, 1H), 1.90-1.78 (m, 1H), 1.76-1.63 (m, 1H).

Example 77

3-[({1-[5-(3-{[(Carbamimidoylcarbamoyl)oxy]methyl}-2-fluorophenyl)pyrimidin-2-yl]azetidin-3-ylidene}amino)oxy]-2-(hydroxymethyl)propyl acetate (Compound II-54)

2 M hydrogen chloride/ethanol solution 0.30 mL (0.60 mmol) was added to an ethanol (2 mL) solution of 3-[({1-[5-(3-{[(carbamimidoylcarbamoyl)oxy]methyl}-2-fluorophenyl)pyrimidin-2-yl]azetidin-3-ylidene}amino)oxy]-2-{[(tetrahydropyran-2-yl)oxy]methyl}propyl acetate 114 mg (0.194 mmol) synthesized in the same manner as in Example 29, and the mixture was stirred at room temperature for 1 hour. After the completion of the reaction, TEA 0.20 mL (1.4 mmol) was added to the reaction mixture, and the mixture was concentrated under reduced pressure. The concentrated residue was purified by silica gel column chromatography (DNH silica gel, eluting solvent: 1,2-dichloroethane:methanol). To the oil thus obtained, hexane was added. The precipitated solid was collected by filtration and was dried under reduced pressure to give the title compound 44 mg (0.087 mmol, yield 45%) as a white solid.

Mass spectrum (ESI, m/z):504[M+1]$^+$.

$^1$H-NMR spectrum (400 MHz, DMSO-d$_6$+D$_2$O) δ:8.66-8.60 (m, 2H), 7.54-7.47 (m, 1H), 7.46-7.39 (m, 1H), 7.33-7.26 (m, 1H), 5.06 (s, 2H), 4.87-4.77 (m, 4H), 4.13-3.99 (m, 4H), 3.49-3.42 (m, 2H), 2.19-2.11 (m, 1H), 2.02 (s, 3H).

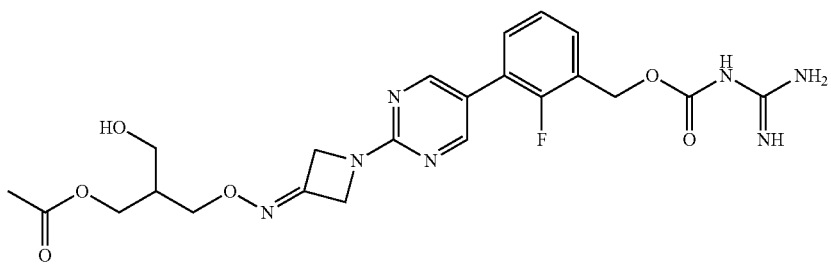 [SMILES: CC(=O)OCC(CO)CON=C1CN(c2ncc(-c3cccc(COC(=O)NC(=N)N)c3F)cn2)C1]

Example 78

3-[({1-[5-(3-{[(Carbamimidoylcarbamoyl)oxy]methyl}-2-fluorophenyl)pyrimidin-2-yl]azetidin-3-ylidene}amino)oxy]-2-(hydroxymethyl)propyl propionate (Compound II-55)

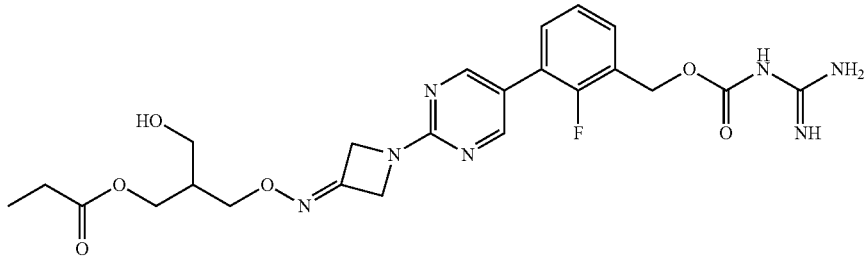 [SMILES: CCC(=O)OCC(CO)CON=C1CN(c2ncc(-c3cccc(COC(=O)NC(=N)N)c3F)cn2)C1]

2 M hydrogen chloride/ethanol solution 0.25 mL (0.50 mmol) was added to an ethanol (2 mL) solution of 3-[({1-[5-(3-{[(carbamimidoylcarbamoyl)oxy]methyl}-2-fluorophenyl)pyrimidin-2-yl]azetidin-3-ylidene}amino)oxy]-2-{[(tetrahydropyran-2-yl)oxy]methyl}propyl propionate 98 mg (0.16 mmol) synthesized in the same manner as in Example 30, and the mixture was stirred at room temperature for 1 hour. After the completion of the reaction, TEA 0.20 mL (1.4 mmol) was added to the reaction mixture, and the mixture was concentrated under reduced pressure. The concentrated residue was purified by silica gel column chromatography (DNH silica gel, eluting solvent: 1,2-dichloroethane:methanol). To the oil thus obtained, hexane was added. The precipitated solid was collected by filtration and was dried under reduced pressure to give the title compound 49 mg (0.095 mmol, yield 59%) as a white solid.

Mass spectrum (ESI, m/z):518[M+1]$^+$.

$^1$H-NMR spectrum (400 MHz, DMSO-$d_6$) δ:8.67-8.57 (m, 2H), 7.54-7.48 (m, 1H), 7.44-7.37 (m, 1H), 7.33-7.26 (m, 1H), 5.06 (s, 2H), 4.87-4.77 (m, 4H), 4.66 (t, J=5.2 Hz, 1H), 4.14-3.99 (m, 4H), 3.52-3.40 (m, 2H), 2.32 (q, J=7.5 Hz, 2H), 2.19-2.10 (m, 1H), 1.03 (t, J=7.5 Hz, 3H).

Example 79

3-[({1-[5-(3-{[(Carbamimidoylcarbamoyl)oxy]methyl}-2-fluorophenyl)pyrimidin-2-yl]azetidin-3-ylidene}amino)oxy]-2-(hydroxymethyl)propyl butyrate (Compound II-56)

2 M hydrogen chloride/ethanol solution 0.25 mL (0.50 mmol) was added to an ethanol (2 mL) solution of 3-[({1-[5-(3-{[(carbamimidoylcarbamoyl)oxy]methyl}-2-fluorophenyl)pyrimidin-2-yl]azetidin-3-ylidene}amino)oxy]-2-{[(tetrahydropyran-2-yl)oxy]methyl}propyl butyrate 92 mg (0.15 mmol) synthesized in the same manner as in Example 31, and the mixture was stirred at room temperature for 1 hour. After the completion of the reaction, TEA 0.20 mL (1.4 mmol) was added to the reaction mixture, and the mixture was concentrated under reduced pressure. The concentrated residue was purified by silica gel column chromatography (DNH silica gel, eluting solvent: 1,2-dichloroethane:methanol) to give the title compound 39 mg (0.073 mmol, yield 49%) as a white foam.

Mass spectrum (ESI, m/z):532[M+1]$^+$.

$^1$H-NMR spectrum (400 MHz, DMSO-$d_6$+$D_2O$) δ:8.63 (d, J=1.3 Hz, 2H), 7.54-7.48 (m, 1H), 7.45-7.40 (m, 1H), 7.33-7.27 (m, 1H), 5.06 (s, 2H), 4.86-4.78 (m, 4H), 4.14-3.99 (m, 4H), 3.48-3.43 (m, 2H), 2.28 (t, J=7.3 Hz, 2H), 2.19-2.12 (m, 1H), 1.55 (sext, J=7.3 Hz, 2H), 0.88 (t, J=7.3 Hz, 3H).

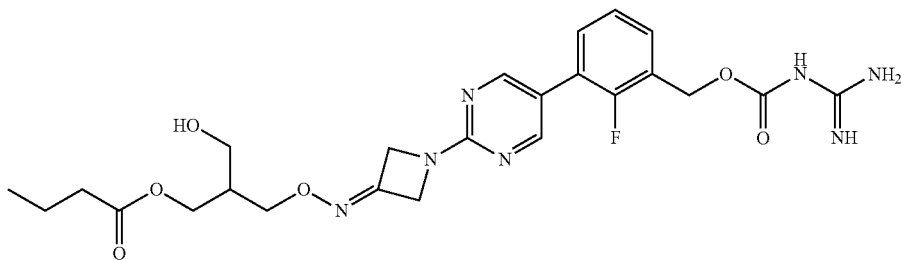 [SMILES: CCCC(=O)OCC(CO)CON=C1CN(c2ncc(-c3cccc(COC(=O)NC(=N)N)c3F)cn2)C1]

Example 80

3-[({1-[5-(3-{[(Carbamimidoylcarbamoyl)oxy]methyl}-2-fluorophenyl)pyrimidin-2-yl]azetidin-3-ylidene}amino)oxy]-2-(hydroxymethyl)propyl isobutyrate (Compound II-57)

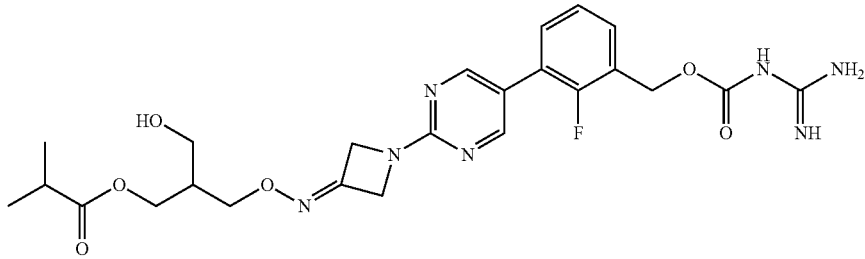 [SMILES: CC(C)C(=O)OCC(CO)CON=C1CN(c2ncc(-c3cccc(COC(=O)NC(=N)N)c3F)cn2)C1]

At 0° C., 2 M hydrogen chloride/ethanol solution 1 mL (2 mmol) was added to an ethanol (2 mL) solution of 3-[({1-[5-(3-{[(carbamimidoylcarbamoyl)oxy]methyl}-2-fluorophenyl)pyrimidin-2-yl]azetidin-3-ylidene}amino)oxy]-2-{[(tetrahydropyran-2-yl)oxy]methyl}propyl isobutyrate 0.12 g (0.19 mmol) synthesized in the same manner as in Example 32, and the mixture was stirred at room temperature for 1 hour. After the completion of the reaction, TEA and water were added to the reaction mixture, and followed by extraction with methylene chloride. The organic layer was washed with water, dried over anhydrous sodium sulfate, and filtered. The filtrate was concentrated under reduced pressure. The concentrated residue was purified by silica gel column chromatography (DNH silica gel, eluting solvent: ethyl acetate:methanol) to give the title compound 53 mg (0.10 mmol, yield 53%) as a white solid.

Mass spectrum (ESI, m/z):532[M+1]$^+$.

$^1$H-NMR spectrum (400 MHz, DMSO-d$_6$+D$_2$O) δ:8.71-8.57 (m, 2H), 7.56-7.47 (m, 1H), 7.47-7.39 (m, 1H), 7.36-7.25 (m, 1H), 5.09 (s, 2H), 4.86-4.78 (m, 4H), 4.15-4.00 (m, 4H), 3.57-3.35 (m, 2H), 2.54 (sep, J=7.0 Hz, 1H), 2.25-2.08 (m, 1H), 1.09 (d, J=7.0 Hz, 6H).

Example 81

3-[({1-[5-(3-{[(Carbamimidoylcarbamoyl)oxy]methyl}-2-fluorophenyl)pyrimidin-2-yl]azetidin-3-ylidene}amino)oxy]-2-(hydroxymethyl)propyl pivalate (Compound II-58)

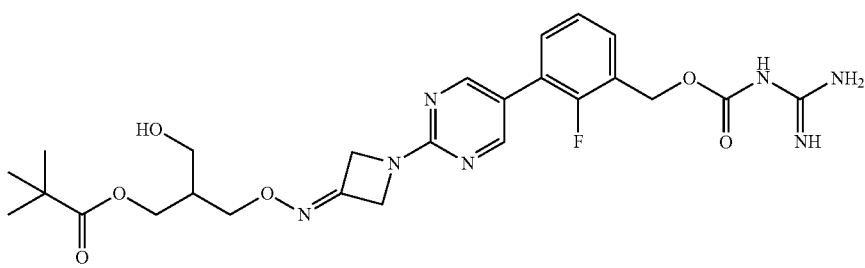 [SMILES: CC(C)(C)C(=O)OCC(CO)CON=C1CN(c2ncc(-c3cccc(COC(=O)NC(=N)N)c3F)cn2)C1]

At 0° C., 2 M hydrogen chloride/ethanol solution 1 mL (2 mmol) was added to an ethanol (4 mL) solution of 3-[({1-[5-(3-{[(carbamimidoylcarbamoyl)oxy]methyl}-2-fluorophenyl)pyrimidin-2-yl]azetidin-3-ylidene}amino)oxy]-2-{[(tetrahydropyran-2-yl)oxy]methyl}propyl pivalate 0.11 g (0.17 mmol) synthesized in the same manner as in Example 33, and the mixture was stirred at room temperature for 1 hour. After the completion of the reaction, TEA and water were added to the reaction mixture, and followed by extraction with methylene chloride. The organic layer was washed with water, dried over anhydrous sodium sulfate, and filtered. The filtrate was concentrated under reduced pressure. The concentrated residue was purified by silica gel column chromatography (DNH silica gel, eluting solvent: ethyl acetate:methanol) to give the title compound 53 mg (0.097 mmol, yield 57%) as a white solid.

Mass spectrum (ESI, m/z):546[M+1]$^+$.

$^1$H-NMR spectrum (400 MHz, DMSO-d$_6$+D$_2$O) δ:8.63 (d, J=1.3 Hz, 2H), 7.56-7.47 (m, 1H), 7.45-7.38 (m, 1H), 7.33-7.26 (m, 1H), 5.06 (s, 2H), 4.87-4.77 (m, 4H), 4.14-3.99 (m, 4H), 3.56-3.39 (m, 2H), 2.26-2.07 (m, 1H), 1.15 (s, 9H).

Example 82

3-[({1-[5-(3-{[(Carbamimidoylcarbamoyl)oxy]methyl}-2-fluorophenyl)pyrimidin-2-yl]azetidin-3-ylidene}amino)oxy]-2-(hydroxymethyl)propyl hexanoate (Compound II-59)

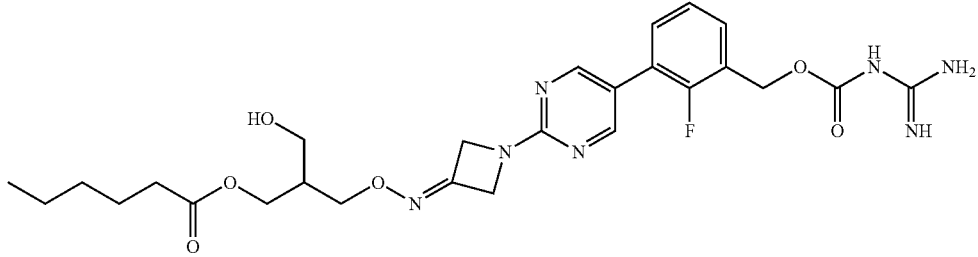 [SMILES: CCCCCC(=O)OCC(CO)CON=C1CN(c2ncc(-c3cccc(COC(=O)NC(=N)N)c3F)cn2)C1]

2 M hydrogen chloride/ethanol solution 1.26 mL (2.52 mmol) was added to an ethanol (2.5 mL) solution of 3-[({1-[5-(3-{[(carbamimidoylcarbamoyl)oxy]methyl}-2-fluorophenyl)pyrimidin-2-yl]azetidin-3-ylidene}amino)oxy]-2-{[(tetrahydropyran-2-yl)oxy]methyl}propyl hexanoate 163 mg (0.253 mmol) synthesized in the same manner as in Example 34, and the mixture was stirred at room temperature for 2 hours. After the completion of the reaction, TEA 0.35 mL (2.5 mmol) was added to the reaction mixture, and the mixture was concentrated under reduced pressure. The concentrated residue was purified by silica gel column chromatography (DNH silica gel, eluting solvent: ethyl acetate:methanol) to give the title compound 62 mg (0.11 mol, yield 43%) as a light yellow solid.

Mass spectrum (ESI, m/z):560[M+1]$^+$.

$^1$H-NMR spectrum (400 MHz, DMSO-$d_6$+$D_2O$) δ:8.63 (d, J=1.1 Hz, 2H), 7.55-7.47 (m, 1H), 7.46-7.38 (m, 1H), 7.34-7.25 (m, 1H), 5.06 (s, 2H), 4.87-4.77 (m, 4H), 4.15-3.98 (m, 4H), 3.56-3.38 (m, 2H), 2.29 (t, J=7.4 Hz, 2H), 2.21-2.09 (m, 1H), 1.58-1.47 (m, 2H), 1.33-1.20 (m, 4H), 0.85 (t, J=6.8 Hz, 3H).

Example 83

3-[({1-[5-(3-{[(Carbamimidoylcarbamoyl)oxy]methyl}-2-fluorophenyl)pyrimidin-2-yl]azetidin-3-ylidene}amino)oxy]-2-(hydroxymethyl)propyl benzoate (Compound II-60)

2 M hydrogen chloride/ethanol solution 1.0 mL (2.0 mmol) was added to an ethanol (1 mL) solution of 3-[({1-[5-(3-{[(carbamimidoylcarbamoyl)oxy]methyl}-2-fluorophenyl)pyrimidin-2-yl]azetidin-3-ylidene}amino)oxy]-2-{[(tetrahydropyran-2-yl)oxy]methyl}propyl benzoate 102 mg (0.157 mmol) synthesized in the same manner as in Example 35, and the mixture was stirred at room temperature for 30 minutes. After the completion of the reaction, TEA and a saturated aqueous sodium hydrogen carbonate solution were added to the reaction mixture, and followed by extraction with ethyl acetate. The organic layer was washed with brine, dried over anhydrous sodium sulfate, and filtered. The filtrate was concentrated under reduced pressure. The concentrated residue was purified by silica gel column chromatography (DNH silica gel, eluting solvent: ethyl acetate:methanol=100:0 to 88:12 (V/V)). Ethyl acetate was added to the crude product thus obtained, and the mixture was stirred at room temperature for 30 minutes. Thereafter, the solid was collected by filtration and was dried under reduced pressure to give the title compound 65.0 mg (0.115 mmol, yield 73%) as a white solid.

Mass spectrum (ESI, m/z):566[M+1]$^+$.

$^1$H-NMR spectrum (400 MHz, DMSO-$d_6$+$D_2O$) δ:8.63 (s, 2H), 8.01-7.96 (m, 2H), 7.68-7.57 (m, 1H), 7.55-7.48 (m, 3H), 7.46-7.39 (m, 1H), 7.34-7.27 (m, 1H), 5.07 (s, 2H), 4.84-4.71 (m, 4H), 4.35 (d, J=5.8 Hz, 2H), 4.25-4.11 (m, 2H), 3.62-3.53 (m, 2H), 2.41-2.30 (m, 1H).

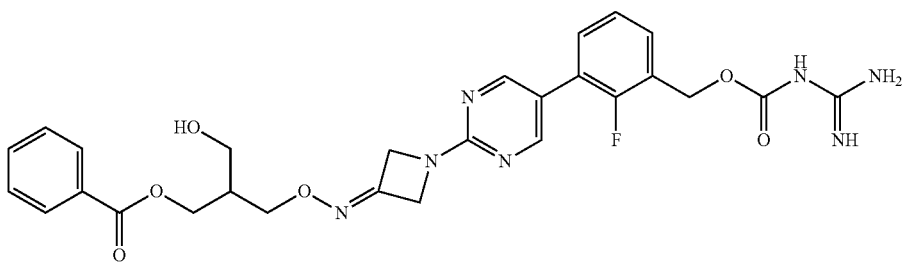 [SMILES: N=C(N)NC(=O)OCc1cccc(-c2cnc(N3CC(=NOCC(CO)COC(=O)c4ccccc4)C3)nc2)c1F]

Example 84

2-Fluoro-3-{5-(2-hydroxypropan-2-yl)-6-[3-(methoxyimino)azetidin-1-yl]pyridin-3-yl}benzyl carbamimidoylcarbamate (Compound III-1134)

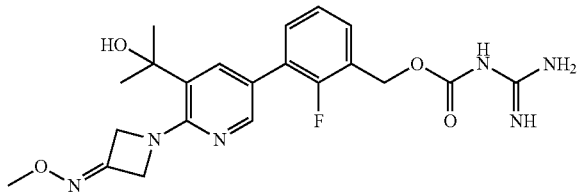 [SMILES: CON=C1CN(c2ncc(-c3cccc(COC(=O)NC(=N)N)c3F)cc2C(C)(C)O)C1]

At 0° C., 2 M hydrogen chloride/ethanol solution 1.7 mL (3.4 mmol) was added to an ethanol (4 mL) solution of 2-fluoro-3-{6-[3-(methoxyimino)azetidin-1-yl]-5-{2-[(tetrahydropyran-2-yl)oxy]propan-2-yl}pyridin-3-yl}benzyl carbamimidoylcarbamate 175 mg (0.331 mmol) synthesized in the same manner as in Example 48, and the mixture was stirred at room temperature for 1 hour. After the completion of the reaction, TEA and water were added to the reaction mixture, and followed by extraction with methylene chloride. The organic layer was washed with a saturated aqueous sodium hydrogen carbonate solution, dried over anhydrous sodium sulfate, and filtered. The filtrate was concentrated under reduced pressure. The concentrated residue was purified by silica gel column chromatography (DNH silica gel, eluting solvent: ethyl acetate:methanol) to give the title compound 114 mg (0.256 mmol, yield 77%) as a white solid.

Mass spectrum (ESI, m/z):445[M+1]$^+$.

$^1$H-NMR spectrum (400 MHz, DMSO-d$_6$+D$_2$O) δ:8.32-8.25 (m, 1H), 7.80-7.74 (m, 1H), 7.51-7.44 (m, 1H), 7.42-7.35 (m, 1H), 7.34-7.22 (m, 1H), 5.06 (s, 2H), 4.88-4.79 (m, 4H), 3.81 (s, 3H), 1.56 (s, 6H).

Example 85

2-Fluoro-3-(2-{4-[(2-hydroxyethoxy)imino]piperidin-1-yl}pyrimidin-5-yl)benzyl carbamimidoylcarbamate (Compound II-215)

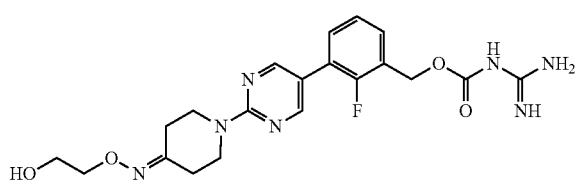 [SMILES: N=C(N)NC(=O)OCc1cccc(-c2cnc(N3CCC(=NOCCO)CC3)nc2)c1F]

2 M hydrogen chloride/ethanol solution 1.0 mL (2.0 mmol) was added to 2-fluoro-3-{2-[4-({2-[(tetrahydropyran-2-yl)oxy]ethoxy}imino)piperidin-1-yl]pyrimidin-5-yl}benzyl carbamimidoylcarbamate 26 mg (0.049 mmol) synthesized in the same manner as in Example 57, and the mixture was stirred at room temperature for 20 minutes. After the completion of the reaction, the reaction mixture was washed with a saturated aqueous sodium hydrogen carbonate solution, dried over anhydrous sodium sulfate, and filtered. The filtrate was concentrated under reduced pressure to give the title compound 13 mg (0.029 mmol, yield 59%) as a white solid.

Mass spectrum (ESI, m/z):446[M+1]$^+$.

$^1$H-NMR spectrum (400 MHz, DMSO-d$_6$+D$_2$O) δ:8.59 (d, J=1.3 Hz, 2H), 7.55-7.48 (m, 1H), 7.43-7.36 (m, 1H), 7.33-7.24 (m, 1H), 5.06 (s, 2H), 4.01-3.96 (m, 2H), 3.96-3.90 (m, 4H), 3.63-3.55 (m, 2H), 2.62-2.55 (m, 2H), 2.42-2.33 (m, 2H).

Example 86

2-Fluoro-3-(2-{4-[(3-hydroxypropoxy)imino]piperidin-1-yl}pyrimidin-5-yl)benzyl carbamimidoylcarbamate hydrochloride (Compound II-216 hydrochloride)

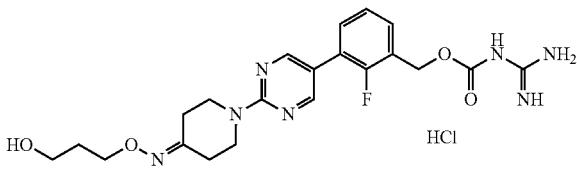 [SMILES: N=C(N)NC(=O)OCc1cccc(-c2cnc(N3CCC(=NOCCCO)CC3)nc2)c1F ; Cl]

2 M hydrogen chloride/ethanol solution 1 mL (2 mmol) was added to an ethanol (4 mL) suspension of 2-fluoro-3-{2-[4-({3-[(tetrahydropyran-2-yl)oxy]propoxy}imino)piperidin-1-yl]pyrimidin-5-yl}benzyl carbamimidoylcarbamate 92 mg (0.17 mmol) synthesized in the same manner as in Example 58, and the mixture was stirred at room temperature for 2 hours. After the completion of the reaction, the precipitated solid was collected by filtration, washed with TBME, and dried under reduced pressure to give the title compound 53 mg (0.11 mmol, yield 65%) as a white solid.

Mass spectrum (ESI, m/z):460[M+1]$^+$.

$^1$H-NMR spectrum (400 MHz, DMSO-d$_6$+D$_2$O) δ:8.60 (br s, 2H), 7.69-7.58 (m, 1H), 7.56-7.48 (m, 1H), 7.40-7.30 (m, 1H), 5.36 (s, 2H), 4.04 (t, J=6.5 Hz, 2H), 3.98-3.86 (m, 4H), 3.47 (t, J=6.4 Hz, 2H), 2.62-2.54 (m, 2H), 2.43-2.34 (m, 2H), 1.83-1.68 (m, 2H).

Example 87

2-Fluoro-3-(2-{4-[(4-hydroxybutoxy)imino]piperidin-1-yl}pyrimidin-5-yl)benzyl carbamimidoylcarbamate hydrochloride (Compound II-217 hydrochloride)

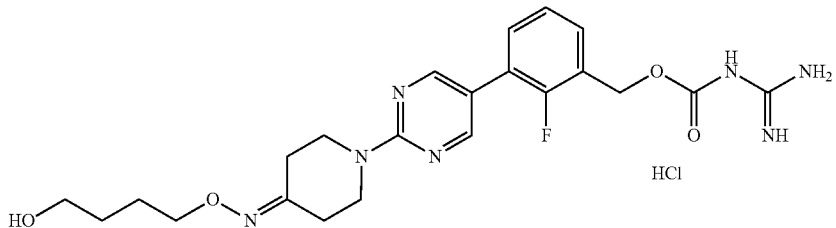 [SMILES: N=C(N)NC(=O)OCc1cccc(-c2cnc(N3CCC(=NOCCCCO)CC3)nc2)c1F ; Cl]

2 M hydrogen chloride/ethanol solution 1 mL (2 mmol) was added to an ethanol (2 mL) solution of 2-fluoro-3-{2-[4-({4-[(tetrahydropyran-2-yl)oxy]butoxy}imino)piperidin-1-yl]pyrimidin-5-yl}benzyl carbamimidoylcarbamate 0.11 g (0.20 mmol) synthesized in the same manner as in Example 59, and the mixture was stirred at room temperature for 2 hours. After the completion of the reaction, the precipitated solid was collected by filtration, washed with TBME, and dried under reduced pressure to give the title compound 74 mg (0.15 mmol, yield 75%) as a white solid.

Mass spectrum (ESI, m/z):474[M+1]$^+$.

$^1$H-NMR spectrum (400 MHz, DMSO-d$_6$+D$_2$O) δ:8.60 (d, J=1.3 Hz, 2H), 7.66-7.59 (m, 1H), 7.56-7.47 (m, 1H), 7.39-7.31 (m, 1H), 5.36 (s, 2H), 3.98 (t, J=6.6 Hz, 2H), 3.96-3.89 (m, 4H), 3.41 (t, J=6.5 Hz, 2H), 2.62-2.54 (m, 2H), 2.44-2.35 (m, 2H), 1.69-1.41 (m, 4H).

Example 88

2-Fluoro-3-(2-{4-[(3-hydroxy-2,2-dimethylpropoxy)imino]piperidin-1-yl}pyrimidin-5-yl)benzyl carbamimidoylcarbamate (Compound II-221)

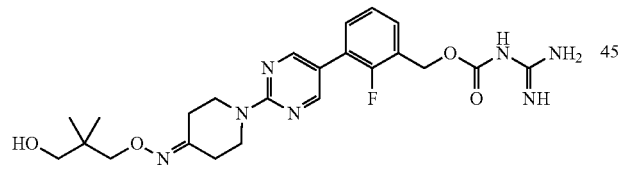

2 M hydrogen chloride/ethanol solution 0.30 mL (0.60 mmol) was added to a methylene chloride (2 mL) suspension of 3-{2-[4-({2,2-dimethyl-3-[(tetrahydropyran-2-yl)oxy]propoxy}imino)piperidin-1-yl]pyrimidin-5-yl}-2-fluorobenzyl carbamimidoylcarbamate 90 mg (0.16 mmol) synthesized in the same manner as in Example 61, and the mixture was stirred at room temperature for 1 hour. After the completion of the reaction, the reaction mixture was concentrated under reduced pressure. The concentrated residue was purified by silica gel column chromatography (DNH silica gel, eluting solvent: 1,2-dichloroethane:methanol) to give the title compound 56 mg (0.11 mmol, yield 69%) as a white solid.

Mass spectrum (APCI, m/z):488[M+1]$^+$.

$^1$H-NMR spectrum (400 MHz, DMSO-d$_6$+D$_2$O) δ:8.59 (s, 2H), 7.54-7.47 (m, 1H), 7.43-7.36 (m, 1H), 7.32-7.25 (m, 1H), 5.06 (s, 2H), 3.97-3.87 (m, 4H), 3.78 (s, 2H), 3.18 (s, 2H), 2.63-2.56 (m, 2H), 2.41-2.34 (m, 2H), 0.84 (s, 6H).

Example 89

2-Fluoro-3-(2-{4-[(3-hydroxy-3-methylbutoxy)imino]piperidin-1-yl}pyrimidin-5-yl)benzyl carbamimidoylcarbamate (Compound II-222)

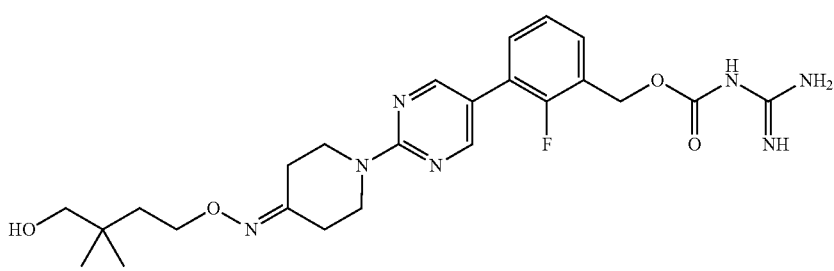 [SMILES: CC(C)(CO)CCON=C1CCN(c2ncc(-c3cccc(COC(=O)NC(=N)N)c3F)cn2)CC1]

2 M hydrogen chloride/ethanol solution 1.1 mL (2.2 mmol) was added to an ethanol(0.57 mL) suspension of 2-fluoro-3-{2-[4-({3-methyl-3-[(tetrahydropyran-2-yl)oxy]butoxy}imino)piperidin-1-yl]pyrimidin-5-yl}benzyl carbamimidoylcarbamate 130 mg (0.23 mmol) synthesized in the same manner as in Example 62, and the mixture was stirred at room temperature for 2 hours. After the completion of the reaction, TEA and a saturated aqueous sodium hydrogen carbonate solution were added to the reaction mixture, and followed by extraction with ethyl acetate. The organic layer was washed with brine, dried over anhydrous sodium sulfate, and filtered. The filtrate was concentrated under reduced pressure. The concentrated residue was purified by silica gel column chromatography (DNH silica gel, eluting solvent: ethyl acetate:methanol=100:0 to 88:12 (V/V)) to give the title compound 95 mg (0.20 mmol, yield 87%) as a white solid.

Mass spectrum (ESI, m/z):488[M+1]$^+$.

$^1$H-NMR spectrum (400 MHz, DMSO-d$_6$+D$_2$O) δ:8.59 (d, J=1.3 Hz, 2H), 7.53-7.47 (m, 1H), 7.42-7.37 (m, 1H), 7.31-7.26 (m, 1H), 5.06 (s, 2H), 4.08 (t, J=7.3 Hz, 2H), 3.95-3.88 (m, 4H), 2.59-2.54 (m, 2H), 2.41-2.36 (m, 2H), 1.72 (t, J=7.3 Hz, 2H), 1.12 (s, 6H).

Example 90

2-Fluoro-3-(2-{4-[(2-hydroxypropoxy)imino]piperidin-1-yl}pyrimidin-5-yl)benzyl carbamimidoylcarbamate (Compound II-223)

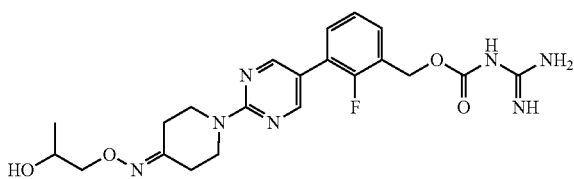 [SMILES: CC(O)CON=C1CCN(c2ncc(-c3cccc(COC(=O)NC(=N)N)c3F)cn2)CC1]

2 M hydrogen chloride/ethanol solution 0.4 mL (0.8 mmol) was added to an ethanol (0.6 mL) suspension of 2-fluoro-3-{2-[4-({2-[(tetrahydropyran-2-yl)oxy]propoxy}imino)piperidin-1-yl]pyrimidin-5-yl}benzyl carbamimidoylcarbamate 47 mg (0.086 mmol) synthesized in the same manner as in Example 63, and the mixture was stirred at room temperature for 45 minutes. After the completion of the reaction, the reaction mixture was concentrated under reduced pressure. A saturated aqueous sodium hydrogen carbonate solution 3 mL was added to the concentrated residue, and the mixture was stirred. The precipitated solid was collected by filtration, washed with water and diethyl ether, and dried under reduced pressure. The obtained solid was purified by silica gel column chromatography (DNH silica gel, eluting solvent: 1,2-dichloroethane:methanol=99:1 to 70:30 (V/V)). TBME was added to the crude product thus obtained, and the mixture was ultrasonicated. The solid was collected by filtration and was dried under reduced pressure to give the title compound 12 mg (0.026 mmol, yield 30%) as a white solid.

Mass spectrum (DUIS, m/z):460[M+1]$^+$.

$^1$H-NMR spectrum (400 MHz, DMSO-d$_6$+D$_2$O) δ:8.59 (d, J=1.3 Hz, 2H), 7.54-7.47 (m, 1H), 7.43-7.36 (m, 1H), 7.32-7.25 (m, 1H), 5.06 (s, 2H), 3.96-3.74 (m, 7H), 2.64-2.58 (m, 2H), 2.43-2.33 (m, 2H), 1.06 (d, J=6.1 Hz, 3H).

Example 91

2-Fluoro-3-(2-{4-[(3-hydroxy-2-methylpropoxy)imino]piperidin-1-yl}pyrimidin-5-yl)benzyl carbamimidoylcarbamate (Compound II-224)

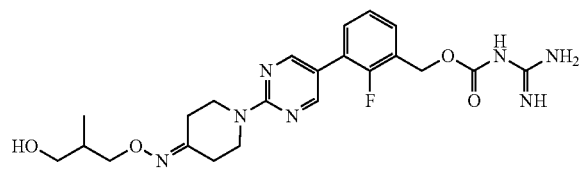 [SMILES: CC(CO)CON=C1CCN(c2ncc(-c3cccc(COC(=O)NC(=N)N)c3F)cn2)CC1]

2 M hydrogen chloride/ethanol solution 0.40 mL (0.80 mmol) was added to a methylene chloride (2 mL) suspension of 2-fluoro-3-{2-[4-({2-methyl-3-[(tetrahydropyran-2-yl)oxy]propoxy}imino)piperidin-1-yl]pyrimidin-5-yl}benzyl carbamimidoylcarbamate 100 mg (0.179 mmol) synthesized in the same manner as in Example 64, and the mixture was stirred at room temperature for 1 hour. After the completion of the reaction, the reaction mixture was concentrated under reduced pressure. The concentrated residue was purified by silica gel column chromatography (DNH silica gel, eluting solvent: 1,2-dichloroethane:methanol) to give the title compound 65 mg (0.14 mmol, yield 78%) as a white solid.

Mass spectrum (APCI, m/z):474[M+1]$^+$.

$^1$H-NMR spectrum (400 MHz, DMSO-d$_6$+D$_2$O) δ:8.59 (d, J=1.4 Hz, 2H), 7.53-7.47 (m, 1H), 7.43-7.37 (m, 1H), 7.31-7.26 (m, 1H), 5.06 (s, 2H), 4.00-3.88 (m, 5H), 3.83-3.75 (m, 1H), 3.41-3.33 (m, 1H), 3.33-3.24 (m, 1H), 2.62-2.55 (m, 2H), 2.42-2.36 (m, 2H), 1.95-1.85 (m, 1H), 0.87 (d, J=6.9 Hz, 3H).

Example 92

2-Fluoro-3-[2-(3-{[3-hydroxy-2-(hydroxymethyl)propoxy]imino}azetidin-1-yl)pyrimidin-5-yl]benzyl carbamimidoylcarbamate (Compound II-42)

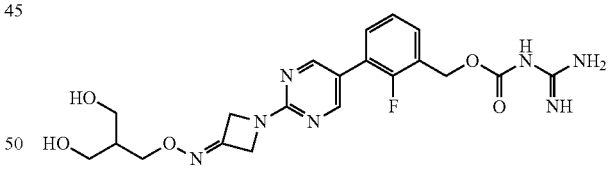

2 M hydrogen chloride/ethanol solution 2.40 mL (4.80 mmol) was added to a methylene chloride (2 mL) suspension of 3-[2-(3-{[(2,2-dimethyl-1,3-dioxan-5-yl)methoxy]imino}azetidin-1-yl)pyrimidin-5-yl]-2-fluorobenzyl carbamimidoylcarbamate 121 mg (0.241 mmol) synthesized in the same manner as in Example 15, and the mixture was stirred at room temperature for 14 hours. After the completion of the reaction, TEA and water were added to the reaction mixture, and followed by extraction with ethyl acetate. The organic layer was washed with brine, dried over anhydrous sodium sulfate, and filtered. The filtrate was concentrated under reduced pressure. The concentrated residue was purified by silica gel column chromatography (DNH silica gel, eluting solvent: ethyl acetate:methanol=100:0 to 90:10 (V/V)). Ethyl acetate 5 mL was added to the crude product thus obtained, and the mixture was stirred at 70° C. for 1 hour. Thereafter, the solid was collected by filtration and was dried under reduced pressure to give the title compound 46.6 mg (0.101 mmol, yield 42%) as a white solid.

Mass spectrum (ESI, m/z):462[M+1]$^+$.

$^1$H-NMR spectrum (400 MHz, DMSO-d$_6$+D$_2$O) δ:8.63 (s, 2H), 7.54-7.48 (m, 1H), 7.45-7.39 (m, 1H), 7.33-7.27 (m, 1H), 5.06 (s, 2H), 4.85-4.78 (m, 4H), 4.04 (d, J=6.4 Hz, 2H), 3.47-3.41 (m, 4H), 1.96-1.88 (m, 1H).

Example 93

3-(2-{3-[(2,3-Dihydroxypropoxy)imino]azetidin-1-yl}pyrimidin-5-yl)-2-fluorobenzyl carbamimidoyl-carbamate (Compound II-43)

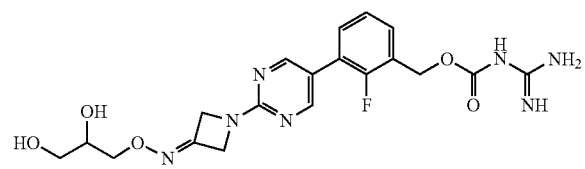 [SMILES: N=C(N)NC(=O)OCc1cccc(-c2cnc(N3CC(=NOCC(O)CO)C3)nc2)c1F]

2 M hydrogen chloride/ethanol solution 1.0 mL (2.0 mmol) was added to a methylene chloride (1.0 mL) solution of 3-[2-(3-{[(2,2-dimethyl-1,3-dioxolan-4-yl)methoxy]imino}azetidin-1-yl)pyrimidin-5-yl]-2-fluorobenzyl carbamimidoylcarbamate 100 mg (0.21 mmol) synthesized in the same manner as in Example 16, and the mixture was stirred at room temperature for 14 hours. After the completion of the reaction, TEA and a saturated aqueous sodium carbonate solution were added to the reaction mixture, and followed by extraction with ethyl acetate. The organic layer was washed with brine, dried over anhydrous sodium sulfate, and filtered. The filtrate was concentrated under reduced pressure. The concentrated residue was purified by silica gel column chromatography (DNH silica gel, eluting solvent: ethyl acetate:methanol=100:0 to 88:12 (V/V)) two times to give the title compound 16 mg (0.036 mmol, yield 17%) as a white solid.

Mass spectrum (ESI, m/z):448[M+1]$^+$.

$^1$H-NMR spectrum (400 MHz, DMSO-d$_6$+D$_2$O) δ:8.65-8.61 (m, 2H), 7.54-7.47 (m, 1H), 7.45-7.38 (m, 1H), 7.33-7.27 (m, 1H), 5.06 (s, 2H), 4.86-4.79 (m, 4H), 4.07 (dd, J=4.5, 11.2 Hz, 1H), 3.92 (dd, J=6.7, 11.2 Hz, 1H), 3.75-3.60 (m, 1H), 3.36 (d, J=5.6 Hz, 2H).

Example 94

3-(2-{3-[(3,4-Dihydroxybutoxy)imino]azetidin-1-yl}pyrimidin-5-yl)-2-fluorobenzyl carbamimidoyl-carbamate (Compound II-47)

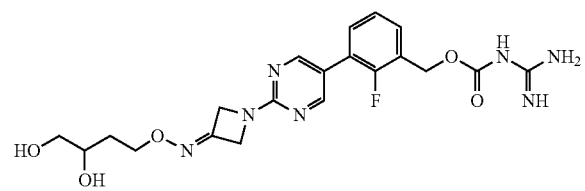 [SMILES: N=C(N)NC(=O)OCc1cccc(-c2cnc(N3CC(=NOCCC(O)CO)C3)nc2)c1F]

2 M hydrogen chloride/ethanol solution 1 mL (2 mmol) was added to an ethanol (2 mL) suspension of 3-[2-(3-{[2-(2,2-dimethyl-1,3-dioxolan-4-yl)ethoxy]imino}azetidin-1-yl)pyrimidin-5-yl]-2-fluorobenzyl carbamimidoylcarbamate 0.10 g (0.20 mmol) synthesized in the same manner as in Example 19, and the mixture was stirred at room temperature for 4 hours. After the completion of the reaction, TEA and ethanol were added to the reaction mixture. The mixture was filtered, and the filtrate was concentrated under reduced pressure. The concentrated residue was purified by silica gel column chromatography (DNH silica gel, eluting solvent: ethyl acetate:methanol) to give the title compound 22 mg (0.048 mmol, yield 24%) as a white solid.

Mass spectrum (ESI, m/z):462[M+1]$^+$.

$^1$H-NMR spectrum (400 MHz, DMSO-d$_6$+D$_2$O) 5:8.63 (br s, 2H), 7.56-7.47 (m, 1H), 7.46-7.39 (m, 1H), 7.34-7.26 (m, 1H), 5.06 (s, 2H), 4.90-4.73 (m, 4H), 4.13 (br t, J=6.5 Hz, 2H), 3.62-3.45 (m, 1H), 3.36-3.21 (m, 2H), 1.92-1.75 (m, 1H), 1.65-1.47 (m, 1H).

Example 95

3-(6-{3-[(3,4-Dihydroxybutoxy)imino]azetidin-1-yl}-5-fluoropyridin-3-yl)-2-fluorobenzyl carbamim-idoylcarbamate (Compound III-123)

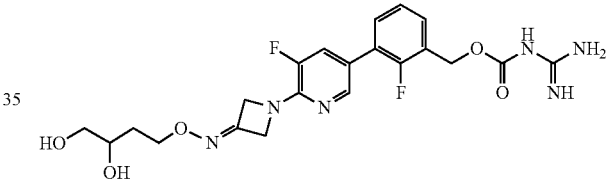

2 M hydrogen chloride/ethanol solution 0.71 mL (1.4 mmol) was added to an ethanol (5 mL) solution of 3-[6-(3-{[2-(2,2-dimethyl-1,3-dioxolan-4-yl)ethoxy]imino}azetidin-1-yl)-5-fluoropyridin-3-yl]-2-fluorobenzyl carbamimidoylcarbamate 244 mg (0.471 mmol) synthesized in the same manner as in Example 38, and the mixture was stirred at room temperature for 1 hour. After the completion of the reaction, TEA 0.20 mL (1.4 mmol) was added to the reaction mixture, and the mixture was concentrated under reduced pressure. A methanol-methylene chloride (5:95 (V/V)) mixed solution was added to the concentrated residue, and the precipitated solid was collected by filtration. The filtrate was concentrated under reduced pressure and was purified by silica gel column chromatography (DNH silica gel, eluting solvent: 1,2-dichloroethane:methanol). The solid thus obtained and the solid obtained by the previous filtration were combined, ethyl acetate was added thereto, and the mixture was stirred at 50° C. for 1 hour. Thereafter, the solid was collected by filtration and was dried under reduced pressure to give the title compound 123 mg (0.257 mmol, yield 55%) as a white solid.

Mass spectrum (ESI, m/z):479[M+1]$^+$.

$^1$H-NMR spectrum (400 MHz, DMSO-d$_6$+D$_2$O) δ:8.21-8.13 (m, 1H), 7.78-7.71 (m, 1H), 7.53-7.46 (m, 1H), 7.44-7.38 (m, 1H), 7.32-7.25 (m, 1H), 5.06 (s, 2H), 4.90-4.82 (m, 4H), 4.16-4.09 (m, 2H), 3.58-3.48 (m, 1H), 3.35-3.22 (m, 2H), 1.88-1.78 (m, 1H), 1.59-1.47 (m, 1H).

Example 96

2-Fluoro-3-{5-fluoro-6-[3-{[3-hydroxy-2-(hydroxymethyl)propoxy]imino}azetidin-1-yl]pyridin-3-yl}benzyl carbamimidoylcarbamate (Compound III-118)

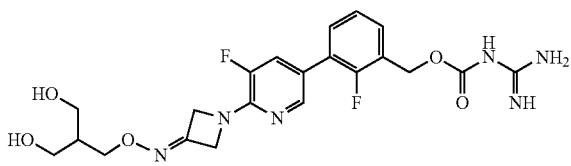 [SMILES: N=C(N)NC(=O)OCc1cccc(-c2cnc(N3CC(=NOCC(CO)CO)C3)c(F)c2)c1F]

2 M hydrogen chloride/ethanol solution 0.18 mL (0.36 mmol) was added to an ethanol (2 mL) solution of 3-[6-(3-{[(2,2-dimethyl-1,3-dioxan-5-yl)methoxy]imino}azetidin-1-yl)-5-fluoropyridin-3-yl]-2-fluorobenzyl carbamimidoylcarbamate 62 mg (0.12 mmol) synthesized in the same manner as in Example 39, and the mixture was stirred at room temperature for 1 hour. After the completion of the reaction, TEA 50 μl (0.36 mmol) was added to the reaction mixture, and the mixture was concentrated under reduced pressure. The concentrated residue was purified by silica gel column chromatography (DNH silica gel, eluting solvent: 1,2-dichloroethane:methanol) to give the title compound 24 mg (0.050 mmol, yield 42%) as a white solid.

Mass spectrum (ESI, m/z):479[M+1]$^+$.

$^1$H-NMR spectrum (400 MHz, DMSO-d$_6$+D$_2$O) δ:8.22-8.13 (m, 1H), 7.79-7.71 (m, 1H), 7.53-7.47 (m, 1H), 7.44-7.38 (m, 1H), 7.32-7.25 (m, 1H), 5.06 (s, 2H), 4.90-4.83 (m, 4H), 4.04 (d, J=6.3 Hz, 2H), 3.47-3.43 (m, 4H), 1.96-1.86 (m, 1H).

Example 97

2-Fluoro-3-[2-(4-{[3-hydroxy-2-(hydroxymethyl)propoxy]imino}piperidin-1-yl)pyrimidin-5-yl]benzyl carbamimidoylcarbamate (Compound II-230)

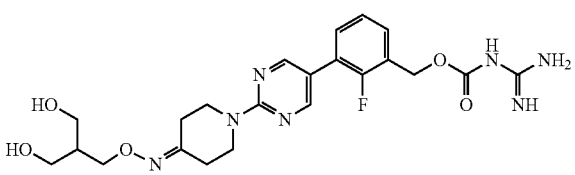 [SMILES: N=C(N)NC(=O)OCc1cccc(-c2cnc(N3CCC(=NOCC(CO)CO)CC3)nc2)c1F]

2 M hydrogen chloride/ethanol solution 1.41 mL (2.82 mmol) was added to an ethanol (0.3 mL) solution of 3-[2-(4-{[(2,2-dimethyl-1,3-dioxan-5-yl)methoxy]imino}piperidin-1-yl)pyrimidin-5-yl]-2-fluorobenzyl carbamimidoylcarbamate 150 mg (0.283 mmol) synthesized in the same manner as in Example 65, and the mixture was stirred at room temperature for 30 minutes. After the completion of the reaction, TEA and a saturated aqueous sodium hydrogen carbonate solution were added to the reaction mixture, and followed by extraction with ethyl acetate. The organic layer was washed with brine, dried over anhydrous sodium sulfate, and filtered. The filtrate was concentrated under reduced pressure. The concentrated residue was purified by silica gel column chromatography (DNH silica gel, eluting solvent: ethyl acetate:methanol=100:0 to 92:8 (V/V)) to give the title compound 112 mg (0.229 mmol, yield 81%) as a white solid.

Mass spectrum (ESI, m/z):490[M+1]$^+$.

$^1$H-NMR spectrum (400 MHz, DMSO-d$_6$+D$_2$O) δ:8.59 (d, J=1.3 Hz, 2H), 7.53-7.47 (m, 1H), 7.42-7.37 (m, 1H), 7.31-7.26 (m, 1H), 5.06 (s, 2H), 3.98 (d, J=6.4 Hz, 2H), 3.96-3.89 (m, 4H), 3.47-3.39 (m, 4H), 2.61-2.55 (m, 2H), 2.43-2.36 (m, 2H), 1.93-1.85 (m, 1H).

Example 98

2-Fluoro-3-[2-(4-{[3-hydroxy-2-(hydroxymethyl)-2-methylpropoxy]imino}piperidin-1-yl)pyrimidin-5-yl]benzyl carbamimidoylcarbamate (Compound II-232)

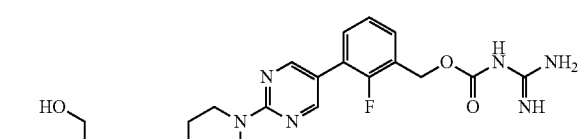

2 M hydrogen chloride/ethanol solution 0.30 mL (0.60 mmol) was added to a methylene chloride (2 mL) solution of 2-fluoro-3-[2-(4-{[(2,2,5-trimethyl-1,3-dioxan-5-yl)methoxy]imino}piperidin-1-yl)pyrimidin-5-yl]benzyl carbamimidoylcarbamate 68 mg (0.13 mmol) synthesized in the same manner as in Example 66, and the mixture was stirred at room temperature for 3 hours. After the completion of the reaction, TEA 0.10 mL (0.72 mmol) was added to the reaction mixture, and the mixture was concentrated under reduced pressure. The concentrated residue was purified by silica gel column chromatography (DNH silica gel, eluting solvent: 1,2-dichloroethane:methanol). Ethyl acetate was added to the obtained solid, and the mixture was stirred at 50° C. for 1 hour. Thereafter, the solid was collected by filtration and was dried under reduced pressure to give the title compound 28 mg (0.056 mmol, yield 43%) as a white solid.

Mass spectrum (APCI, m/z):504[M+1]$^+$.

$^1$H-NMR spectrum (400 MHz, DMSO-d$_6$+D$_2$O) δ:8.59 (d, J=1.4 Hz, 2H), 7.53-7.47 (m, 1H), 7.42-7.37 (m, 1H), 7.31-7.25 (m, 1H), 5.06 (s, 2H), 3.96-3.89 (m, 4H), 3.86 (s, 2H), 3.28 (s, 4H), 2.61-2.55 (m, 2H), 2.40-2.35 (m, 2H), 0.81 (s, 3H).

Example 99

3-(2-{4-[(2,3-Dihydroxypropoxy)imino]piperidin-1-yl}pyrimidin-5-yl)-2-fluorobenzyl carbamimidoylcarbamate (Compound II-231)

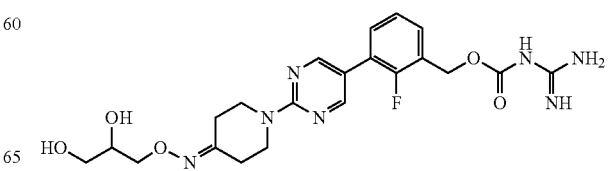

At 0° C., 2 M hydrogen chloride/ethanol solution 1 mL (2 mmol) was added to 3-[2-(4-{[(2,2-dimethyl-1,3-dioxolan-4-yl)methoxy]imino}piperidin-1-yl)pyrimidin-5-yl]-2-fluorobenzyl carbamimidoylcarbamate 0.11 g (0.21 mmol) synthesized in the same manner as in Example 67, and the mixture was stirred at room temperature for 4 hours. After the completion of the reaction, TEA and ethanol were added to the reaction mixture. The mixture was filtered, and the filtrate was concentrated under reduced pressure. The concentrated residue was purified by silica gel column chromatography (DNH silica gel, eluting solvent: ethyl acetate:methanol) to give the title compound 72 mg (0.15 mmol, yield 71%) as a white solid.

Mass spectrum (ESI, m/z):476[M+1]$^+$.

$^1$H-NMR spectrum (400 MHz, DMSO-d$_6$+D$_2$O) δ:8.59 (br s, 2H), 7.56-7.47 (m, 1H), 7.43-7.36 (m, 1H), 7.32-7.25 (m, 1H), 5.06 (s, 2H), 4.07-3.82 (m, 6H), 3.76-3.64 (m, 1H), 3.41-3.31 (m, 2H), 2.65-2.55 (m, 2H), 2.44-2.35 (m, 2H).

Example 100

2-Fluoro-3-[2-(3-{[3-hydroxy-2-(methoxymethyl)propoxy]imino}azetidin-1-yl)pyrimidin-5-yl]benzyl carbamimidoylcarbamate (Compound III-45)

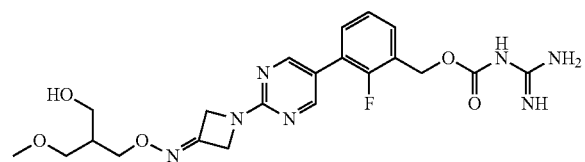 [SMILES: COCC(CO)CON=C1CN(c2ncc(-c3cccc(COC(=O)NC(=N)N)c3F)cn2)C1]

Acetic acid 1.0 mL was added to a THF (2 mL)-water (1 mL) solution of 2-fluoro-3-(2-{3-[(3-methoxy-2-{[(tetrahydropyran-2-yl)oxy]methyl}propoxy)imino]azetidin-1l-yl}pyrimidin-5-yl)benzyl carbamimidoylcarbamate 126 mg (0.225 mmol) synthesized in the same manner as in Example 17, and the mixture was stirred at 60° C. for 15 hours. After the completion of the reaction, the reaction mixture was purified by silica gel column chromatography (DNH silica gel, eluting solvent: ethyl acetate:methanol) to give the title compound 31 mg (0.065 mmol, yield 29%) as a white solid.

Mass spectrum (ESI, m/z):476[M+1]$^+$.

$^1$H-NMR spectrum (400 MHz, DMSO-d$_6$+D$_2$O) δ:8.63 (d, J=1.3 Hz, 2H), 7.55-7.47 (m, 1H), 7.45-7.39 (m, 1H), 7.33-7.26 (m, 1H), 5.07 (s, 2H), 4.90-4.71 (m, 4H), 4.12-3.84 (m, 2H), 3.44 (d, J=5.6 Hz, 2H), 3.39-3.32 (m, 2H), 3.23 (s, 3H), 2.12-2.00 (m, 1H).

Example 101

2-Fluoro-3-(2-{3-[(3-hydroxy-2-methoxypropoxy)imino]azetidin-1-yl}pyrimidin-5-yl)benzyl carbamimidoylcarbamate (Compound II-46)

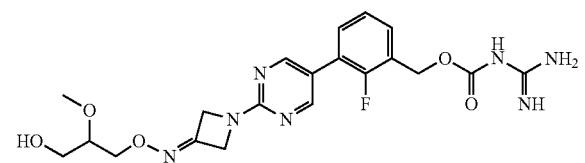 [SMILES: COC(CO)CON=C1CN(c2ncc(-c3cccc(COC(=O)NC(=N)N)c3F)cn2)C1]

At 0° C., 2 M hydrogen chloride/ethanol solution 1 mL (2 mmol) was added to an ethanol (2 mL) solution of 2-fluoro-3-[2-(3-{[2-methoxy-3-(trityloxy)propoxy]imino}azetidin-1-yl)pyrimidin-5-yl]benzyl carbamimidoylcarbamate 123 mg (0.175 mmol) synthesized in the same manner as in Example 18, and the mixture was stirred at room temperature for 1 hour. After the completion of the reaction, TEA was added to the reaction mixture. The mixture was filtered, and the filtrate was concentrated under reduced pressure. The concentrated residue was purified by silica gel column chromatography (DNH silica gel, eluting solvent: ethyl acetate:methanol) to give the title compound 54 mg (0.12 mmol, yield 69%) as a white solid.

Mass spectrum (ESI, m/z):462[M+1]$^+$.

$^1$H-NMR spectrum (400 MHz, DMSO-d$_6$+D$_2$O) δ:8.63 (d, J=1.3 Hz, 2H), 7.56-7.48 (m, 1H), 7.46-7.39 (m, 1H), 7.34-7.25 (m, 1H), 5.06 (s, 2H), 4.87-4.79 (m, 4H), 4.19-3.96 (m, 2H), 3.48-3.40 (m, 3H), 3.34 (s, 3H).

Example 102

2-Fluoro-3-(2-{3-[(2-fluoro-3-hydroxypropoxy)imino]azetidin-1-yl}pyrimidin-5-yl)benzyl carbamimidoylcarbamate (Compound II-40)

At 0° C., 2 M hydrogen chloride/ethanol solution 9 mL (18 mmol) was added to an ethanol (10 mL) suspension of 2-fluoro-3-[2-(3-{[2-fluoro-3-(trityloxy)propoxy]imino}azetidin-1-yl)pyrimidin-5-yl]benzyl carbamimidoylcarbamate 2.45 g (3.54 mmol) synthesized in the same manner as in Example 22, and the mixture was stirred at room temperature for 2 hours. After the completion of the reaction, TEA (6 mL) was added to the reaction mixture, and the mixture was concentrated under reduced pressure. Water was added to the concentrated residue, and the precipitated solid was collected by filtration. Ethyl acetate was added to the obtained solid, and the mixture was stirred at 50° C. for 1 hour. Thereafter, the solid was collected by filtration and was purified by silica gel column chromatography (DNH silica gel, eluting solvent: ethyl acetate:methanol) to give the title compound 1.20 g (2.67 mmol, yield 75%) as a white solid.

Mass spectrum (ESI, m/z):450[M+1]$^+$.

$^1$H-NMR spectrum (400 MHz, DMSO-d$_6$+D$_2$O) δ:8.64 (s, 2H), 7.57-7.47 (m, 1H), 7.45-7.39 (m, 1H), 7.34-7.25 (m, 1H), 5.06 (s, 2H), 4.93-4.57 (m, 5H), 4.34-4.13 (m, 2H), 3.72-3.49 (m, 2H).

Example 103

2-Fluoro-3-(5-fluoro-6-{3-[(2-fluoro-3-hydroxypropoxy)imino]azetidin-1-yl}pyridin-3-yl)benzyl carbamimidoylcarbamate (Compound III-116)

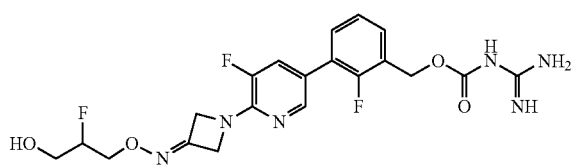 [SMILES: N=C(N)NC(=O)OCc1cccc(-c2cnc(N3CC(=NOCC(F)CO)C3)c(F)c2)c1F]

At 0° C., 2 M hydrogen chloride/ethanol solution 4.5 mL (9.0 mmol) was added to an ethanol (4 mL) solution of 2-fluoro-3-[5-fluoro-6-(3-{[2-fluoro-3-(trityloxy)propoxy]imino}azetidin-1-yl)pyridin-3-yl]benzyl carbamimidoylcarbamate 631 mg (0.890 mmol) synthesized in the same manner as in Example 40, and the mixture was stirred at room temperature for 2 hours. After the completion of the reaction, TEA (2 mL) and water were added to the reaction mixture, and followed by extraction with methylene chloride. The organic layer was washed with a saturated aqueous sodium hydrogen carbonate solution, dried over anhydrous sodium sulfate, and filtered. The filtrate was concentrated under reduced pressure. The concentrated residue was purified by silica gel column chromatography (DNH silica gel, eluting solvent: ethyl acetate:methanol). Ethyl acetate was added to the crude product thus obtained, and the mixture was stirred at room temperature for 30 minutes. Thereafter, the solid was collected by filtration and was dried under reduced pressure to give the title compound 332 mg (0.712 mmol, yield 80%) as a white solid.

Mass spectrum (ESI, m/z):467[M+1]$^+$.

$^1$H-NMR spectrum (400 MHz, DMSO-d$_6$+D$_2$O) δ:8.21-8.16 (m, 1H), 7.80-7.71 (m, 1H), 7.54-7.45 (m, 1H), 7.44-7.37 (m, 1H), 7.33-7.24 (m, 1H), 5.06 (s, 2H), 4.93-4.85 (m, 4H), 4.84-4.61 (m, 1H), 4.31-4.12 (m, 2H), 3.70-3.50 (m, 2H).

Example 104

2-Fluoro-3-(2-{3-[(2-hydroxy-3-methoxypropoxy)imino]azetidin-1-yl}pyrimidin-5-yl)benzyl carbamimidoylcarbamate (Compound II-49)

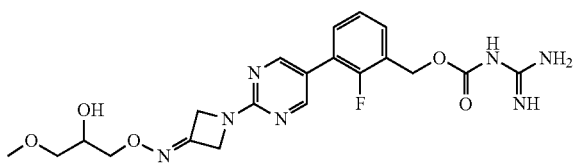 [SMILES: COCC(O)CON=C1CN(c2ncc(-c3cccc(COC(=O)NC(=N)N)c3F)cn2)C1]

Lithium hydroxide 4.0 mg (0.17 mmol) was added to a THF (2 mL)-water (0.4 mL) solution of 1-[({1-[5-(3-{[(carbamimidoylcarbamoyl)oxy]methyl}-2-fluorophenyl)pyrimidin-2-yl]azetidin-3-ylidene}amino)oxy]-3-methoxypropan-2-yl acetate 43 mg (0.085 mmol) synthesized in the same manner as in Example 20, and the mixture was stirred at 50° C. for 2 hours. After the completion of the reaction, acetic acid 10 μl (0.17 mmol) was added to the reaction mixture. The mixture was purified by silica gel column chromatography (DNH silica gel, eluting solvent: ethyl acetate:methanol) to give the title compound 42 mg (including impurities) as a white solid.

Mass spectrum (ESI, m/z):462[M+1]$^+$.

$^1$H-NMR spectrum (400 MHz, DMSO-d$_6$+D$_2$O) δ:8.63 (d, J=1.4 Hz, 2H), 7.58-7.48 (m, 1H), 7.45-7.37 (m, 1H), 7.33-7.27 (m, 1H), 5.06 (s, 2H), 4.86-4.79 (m, 4H), 4.04-3.90 (m, 2H), 3.89-3.81 (m, 1H), 3.37-3.28 (m, 2H), 3.27 (s, 3H).

Example 105

2-Fluoro-3-{2-[4-(hydroxyimino)piperidin-1-yl]pyrimidin-5-yl}benzyl carbamimidoylcarbamate hydrochloride (Compound II-204 hydrochloride)

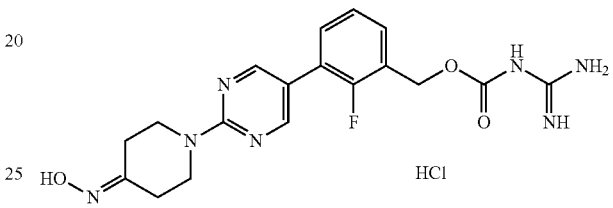

2 M hydrogen chloride/ethanol solution 3.0 mL (6.0 mmol) was added to 2-fluoro-3-[2-(4-{[(tetrahydropyran-2-yl)oxy]imino}piperidin-1-yl)pyrimidin-5-yl]benzyl carbamimidoylcarbamate 117 mg (0.241 mmol) synthesized in the same manner as in Example 52, and the mixture was stirred at room temperature for 1 hour. After the completion of the reaction, the precipitated solid was collected by filtration and was dried under reduced pressure to give the title compound 106 mg (including impurities) as a white solid.

Mass spectrum (ESI, m/z):402[M+1]$^+$.

$^1$H-NMR spectrum (400 MHz, DMSO-d$_6$+D$_2$O) δ:8.61 (d, J=1.4 Hz, 2H), 7.67-7.58 (m, 1H), 7.55-7.49 (m, 1H), 7.38-7.32 (m, 1H), 5.36 (s, 2H), 3.95-3.89 (m, 4H), 2.60-2.54 (m, 2H), 2.40-2.34 (m, 2H).

Example 106

3-[6-(3-{[(tert-butyldimethylsilyl)oxy]imino}azetidin-1-yl)-5-fluoropyridin-3-yl]-2-fluorobenzyl carbamimidoylcarbamate (Compound III-138)

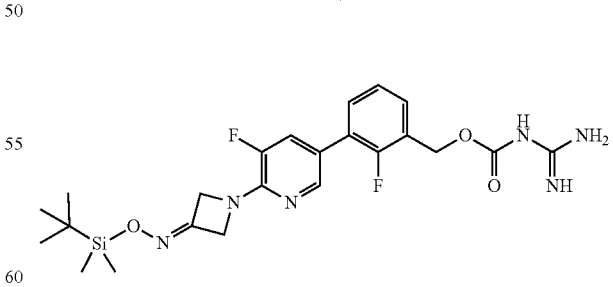

CDI 350 mg (2.16 mmol) was added to a DMF (6 mL) solution of 1-{3-fluoro-5-[2-fluoro-3-(hydroxymethyl)phenyl]pyridin-2-yl}azetidin-3-one O-(tert-butyldimethylsilyl) oxime 450 mg (1.07 mmol) synthesized in the same manner as in Reference Example 13-2, and the mixture was stirred at room temperature for 26 hours. Next, guanidine carbonate 580 mg (3.22 mmol) was added, and the mixture was stirred at room temperature for 3 hours. After the completion of the reaction, water was added to the reaction mixture, and followed by extraction with methylene chloride. The organic layer was washed with brine, dried over anhydrous sodium sulfate, and filtered. The filtrate was concentrated under reduced pressure. The concentrated residue was purified by silica gel column chromatography (DNH silica gel, eluting solvent: ethyl acetate:methanol) to give the title compound 422 mg (0.836 mmol, yield 78%) as a white solid.

$^1$H-NMR spectrum (400 MHz, DMSO-$d_6$+$D_2O$) δ:8.25-8.18 (m, 1H), 7.84-7.75 (m, 1H), 7.58-7.50 (m, 1H), 7.49-7.41 (m, 1H), 7.38-7.28 (m, 1H), 5.10 (s, 2H), 4.95-4.89 (m, 4H), 0.96 (s, 9H), 0.20 (s, 6H).

Example 107

2-Fluoro-3-{5-fluoro-6-[3-(hydroxyimino)azetidin-1-yl]pyridin-3-yl}benzyl carbamimidoylcarbamate (Compound III-77)

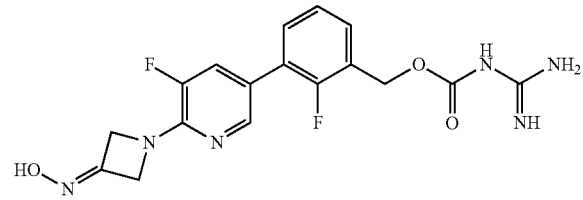 [SMILES: N=C(N)NC(=O)OCc1cccc(-c2cnc(N3CC(=NO)C3)c(F)c2)c1F]

1 M tetrabutylammonium fluoride/THF solution 0.24 mL (0.24 mmol) was added to a THF (2 mL) solution of 3-[6-(3-{[(tert-butyldimethylsilyl)oxy]imino}azetidin-1-yl)-5-fluoropyridin-3-yl]-2-fluorobenzyl carbamimidoylcarbamate 100 mg (0.20 mmol) synthesized in the same manner as in Example 106, and the mixture was stirred at room temperature for 1 hour. After the completion of the reaction, water was added to the reaction mixture, and the mixture was stirred at room temperature. The precipitated solid was collected by filtration. Next, ethyl acetate was added, and the mixture was stirred at room temperature for 3 hours. Thereafter, the solid was collected by filtration and was dried under reduced pressure to give the title compound 35 mg (0.090 mmol, yield 45%) as a white solid.

Mass spectrum (ESI, m/z):391[M+1].

$^1$H-NMR spectrum (400 MHz, DMSO-$d_6$+$D_2O$) δ:8.17 (s, 1H), 7.81-7.68 (m, 1H), 7.55-7.46 (m, 1H), 7.45-7.37 (m, 1H), 7.33-7.24 (m, 1H), 5.06 (s, 2H), 4.89-4.78 (m, 4H).

Example 108 tert-Butyl 2-[({1-[5-(3-{[(carbamimidoylcarbamoyl)oxy]methyl}-2-fluorophenyl)pyrimidin-2-yl]azetidin-3-ylidene}amino)oxy]acetate (Compound II-279)

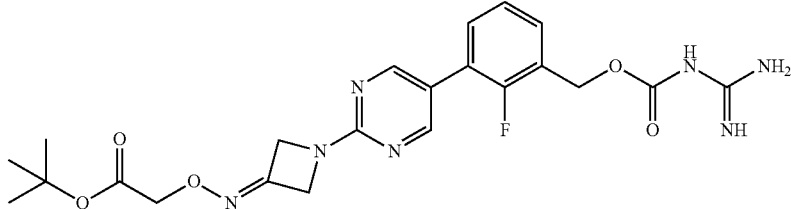 [SMILES: CC(C)(C)OC(=O)CON=C1CN(c2ncc(-c3cccc(COC(=O)NC(=N)N)c3F)cn2)C1]

CDI 82 mg (0.51 mmol) was added to a DMF (3 mL) solution of tert-butyl 2-{[(1-{5-[2-fluoro-3-(hydroxymethyl)phenyl]pyrimidin-2-yl}azetidin-3-ylidene)amino]oxy}acetate 92 mg (0.23 mmol) synthesized in the same manner as in Reference Example 7-62, and the mixture was stirred at room temperature for 2.5 hours. Next, guanidine carbonate 82 mg (0.46 mmol) was added, and the mixture was stirred at room temperature for 16 hours. After the completion of the reaction, water was added to the reaction mixture, and followed by extraction with methylene chloride. The organic layer was washed with brine, dried over anhydrous sodium sulfate, and filtered. The filtrate was concentrated under reduced pressure. Toluene was added to the concentrated residue, which was then concentrated under reduced pressure, and this operation was repeated several times. Ethyl acetate was added, and the mixture was ultrasonicated. The solid was collected by filtration and was dried under reduced pressure to give the title compound 88 mg (0.18 mmol, yield 78%) as a white solid.

Mass spectrum (APCI, m/z):488[M+1]$^+$.

$^1$H-NMR spectrum (400 MHz, DMSO-$d_6$+$D_2O$) δ:8.64 (s, 2H), 7.55-7.47 (m, 1H), 7.45-7.38 (m, 1H), 7.34-7.25 (m, 1H), 5.06 (s, 2H), 4.90-4.80 (m, 4H), 4.54 (s, 2H), 1.44 (s, 9H).

Example 109

2-[({1-[5-(3-{[(Carbamimidoylcarbamoyl)oxy]methyl}-2-fluorophenyl)pyrimidin-2-yl]azetidin-3-ylidene}amino)oxy]acetic acid hydrochloride (Compound II-274 hydrochloride)

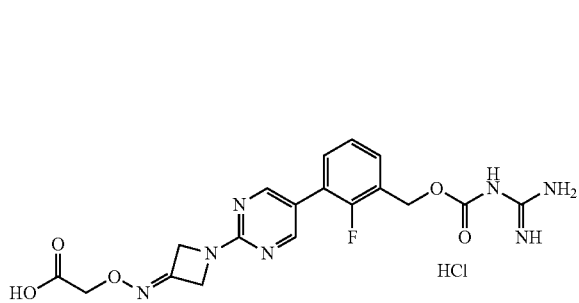 [SMILES: N=C(N)NC(=O)OCc1cccc(-c2cnc(N3CC(=NOCC(=O)O)C3)nc2)c1F ; Cl]

4 M hydrogen chloride/1,4-dioxane solution 500 μl (2.00 mmol) was added to a methylene chloride (1 mL) suspension of tert-butyl 2-[({1-[5-(3-{[(carbamimidoylcarbamoyl)oxy]methyl}-2-fluorophenyl)pyrimidin-2-yl]azetidin-3-ylidene}amino)oxy]acetate 70 mg (0.14 mmol) synthesized in the same manner as in Example 108, and the mixture was stirred at room temperature for 20 hours. After the completion of the reaction, the reaction mixture was concentrated under reduced pressure. TBME was added to the concentrated residue, and the mixture was stirred at 50° C. for 1 hour. Thereafter, the solid was collected by filtration and was dried under reduced pressure. 1 N aqueous sodium hydroxide solution 6.00 mL (6.00 mmol) was added to a solution of the solid obtained above in a mixed solvent (2 mL) consisting of methylene chloride:methanol=90:10 (V/V), and the mixture was stirred at room temperature for 14 hours. After the completion of the reaction, the reaction mixture was neutralized by the addition of 1 N hydrochloric acid. The precipitated solid was collected by filtration and was dried under reduced pressure. 4 M hydrogen chloride/1,4-dioxane solution 1.00 mL (1.00 mmol) was added to a suspension of the solid in methylene chloride (1 mL), and the mixture was stirred at room temperature for 1 hour. After the completion of the reaction, the reaction mixture was concentrated under reduced pressure. TBME was added to the concentrated residue, and the mixture was stirred at 50° C. for 1 hour. Thereafter, the solid was collected by filtration and was dried under reduced pressure to give the title compound 25 mg (0.053 mmol, yield 38%) as a light yellow solid.

Mass spectrum (APCI, m/z):432[M+1]+.

1H-NMR spectrum (400 MHz, DMSO-d6+D2O) δ:8.65 (d, J=1.3 Hz, 2H), 7.67-7.60 (m, 1H), 7.57-7.51 (m, 1H), 7.40-7.33 (m, 1H), 5.37 (s, 2H), 4.89-4.82 (m, 4H), 4.59 (s, 2H).

Example 110

3-[2-(3-{[(Dimethylcarbamoyl)oxy]imino}azetidin-1-yl)pyrimidin-5-yl]-2-fluorobenzyl carbamimidoylcarbamate (Compound II-282)

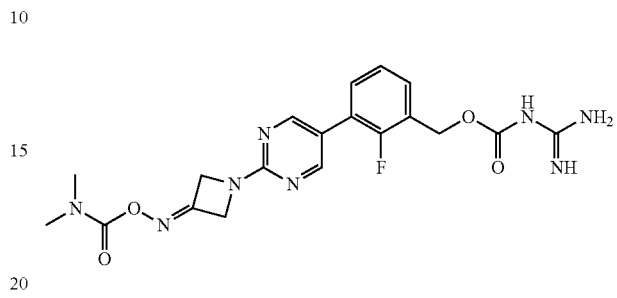

CDI 41 mg (0.25 mmol) was added to a DMF (2 mL) solution of 1-{5-[2-fluoro-3-(hydroxymethyl)phenyl]pyrimidin-2-yl}azetidin-3-one O-dimethylcarbamoyl oxime 41 mg (0.11 mmol) synthesized in the same manner as in Reference Example 7-63, and the mixture was stirred at room temperature for 16 hours. Next, guanidine carbonate 41 mg (0.23 mmol) was added, and the mixture was stirred at room temperature for 4 hours. After the completion of the reaction, water was added to the reaction mixture, and the mixture was stirred at room temperature. The precipitated solid was collected by filtration. Ethyl acetate was added to the solid, and the mixture was stirred at room temperature for 1 hour. Thereafter, the solid was collected by filtration and was dried under reduced pressure to give the title compound 22 mg (0.050 mmol, yield 45%) as a white solid.

Mass spectrum (ESI, m/z):445[M+1]+.

1H-NMR spectrum (400 MHz, DMSO-d6+D2O) δ:8.65 (d, J=1.1 Hz, 2H), 7.55-7.49 (m, 1H), 7.45-7.39 (m, 1H), 7.33-7.27 (m, 1H), 5.07 (s, 2H), 4.96 (s, 4H), 2.89 (s, 6H).

Example 111

2-Fluoro-3-[2-(3-{[2-(methylamino)-2-oxoethoxy]imino}azetidin-1-yl)pyrimidin-5-yl]benzyl carbamimidoylcarbamate (Compound II-283)

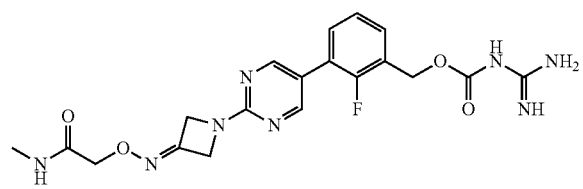 [SMILES: CNC(=O)CON=C1CN(c2ncc(-c3cccc(COC(=O)NC(=N)N)c3F)cn2)C1]

CDI 60 mg (0.37 mmol) was added to a DMF (4 mL) solution of 2-({[1-{5-[2-fluoro-3-(hydroxymethyl)phenyl]pyrimidin-2-yl}azetidin-3-ylidene]amino}oxy)-N-methylacetamide 58 mg (0.16 mmol) synthesized in the same manner as Reference Compound 7-64, and the mixture was stirred at room temperature for 2 hours. Next, guanidine carbonate 60 mg (0.33 mmol) was added, and the mixture was stirred at room temperature for 16 hours. After the completion of the reaction, water was added to the reaction mixture, and followed by extraction with methylene chloride. The organic layer was washed with brine, dried over anhydrous sodium sulfate, and filtered. The filtrate was concentrated under reduced pressure. The concentrated residue was purified by silica gel column chromatography (DNH silica gel, eluting solvent: 1,2-dichloroethane:methanol). Ethyl acetate was added to the obtained crude product, and the mixture was stirred at room temperature. Thereafter, the solid was collected by filtration and was dried under reduced pressure. Next, methanol was added, and the mixture was stirred. The solid was collected by filtration and was dried under reduced pressure. The solid thus obtained was purified by silica gel column chromatography (DNH silica gel, eluting solvent: ethyl acetate:methanol). The crude product obtained was dissolved by the addition of a mixed solvent consisting of methylene chloride:methanol=90:10 (V/V). The solution was concentrated under reduced pressure and the concentrated residue was dried under reduced pressure to give the title compound 13 mg (0.029 mmol, yield 18%) as a white solid.

Mass spectrum (APCI, m/z):445[M+1]$^+$.

$^1$H-NMR spectrum (400 MHz, DMSO-$d_6$) δ:8.65 (s, 2H), 7.66 (br d, J=4.3 Hz, 1H), 7.57-7.48 (m, 1H), 7.46-7.38 (m, 1H), 7.33-7.25 (m, 1H), 5.06 (s, 2H), 4.98-4.80 (m, 4H), 4.44 (s, 2H), 2.64 (d, J=4.5 Hz, 3H).

Example 112

3-(2-{3-[(3-Amino-3-oxopropoxy)imino]azetidin-1-yl}pyrimidin-5-yl)-2-fluorobenzyl carbamimidoylcarbamate (Compound II-284)

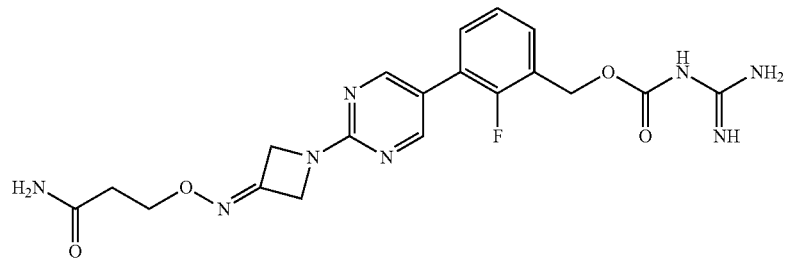 [SMILES: N=C(N)NC(=O)OCc1cccc(-c2cnc(N3CC(=NOCCC(N)=O)C3)nc2)c1F]

CDI 226 mg (1.39 mmol) was added to a DMF (4 ml) solution of 3-{[(1-{5-[2-fluoro-3-(hydroxymethyl)phenyl]pyrimidin-2-yl}azetidin-3-ylidene)amino]oxy}propanamide 165 mg (0.459 mmol) synthesized in the same manner as in Reference Example 7-65, and the mixture was stirred at room temperature for 3 hours. Next, guanidine carbonate 170 mg (0.944 mmol) was added, and the mixture was stirred at room temperature for 3 hours. After the completion of the reaction, water was added to the reaction mixture, and the mixture was stirred at room temperature for 30 minutes. The precipitated solid was collected by filtration. The obtained solid was purified by silica gel column chromatography (DNH silica gel, eluting solvent: ethyl acetate:methanol). Ethyl acetate was added to the crude product thus obtained, and the mixture was stirred at 70° C. for 30 minutes. Thereafter, the solid was collected by filtration and was dried under reduced pressure to give the title compound 69.5 mg (0.156 mmol, yield 34%) as a white solid.

Mass spectrum (ESI, m/z):445[M+1]$^+$.

$^1$H-NMR spectrum (400 MHz, DMSO-$d_6$) 5:8.63 (d, J=1.3 Hz, 2H), 7.58-7.48 (m, 1H), 7.45-7.35 (m, 2H), 7.34-7.26 (m, 1H), 6.87 (br s, 1H), 5.06 (s, 2H), 4.92-4.68 (m, 4H), 4.22 (t, J=6.5 Hz, 2H), 2.42 (t, J=6.5 Hz, 2H).

Example 113

2-Fluoro-3-[2-(3-{[3-(methylamino)-3-oxopropoxy]imino}azetidin-1-yl)pyrimidin-5-yl]benzyl carbamimidoylcarbamate (Compound II-285)

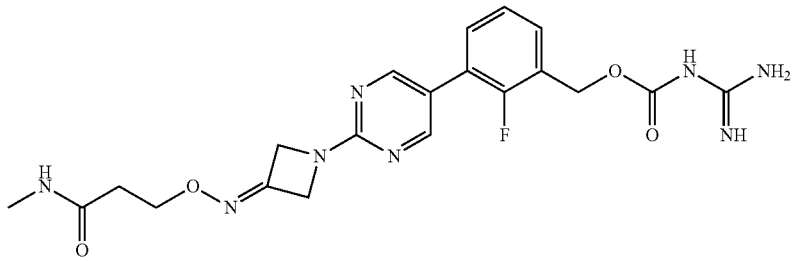 [SMILES: CNC(=O)CCON=C1CN(c2ncc(-c3cccc(COC(=O)NC(=N)N)c3F)cn2)C1]

CDI 293 mg (1.81 mmol) was added to a DMF (4 ml) solution of 3-{[(1-{5-[2-fluoro-3-(hydroxymethyl)phenyl]pyrimidin-2-yl}azetidin-3-ylidene)amino]oxy}-N-methylpropanamide 168 mg (0.450 mmol) synthesized in the same manner as in Reference Example 7-66, and the mixture was stirred at room temperature for 2 hours. Next, guanidine carbonate 165 mg (0.916 mmol) was added, and the mixture was stirred at room temperature for 2 hours. After the completion of the reaction, water and a saturated aqueous sodium carbonate solution were added to the reaction mixture, and followed by extraction with ethyl acetate. The organic layer was washed with brine, dried over anhydrous sodium sulfate, and filtered. The filtrate was concentrated under reduced pressure. The concentrated residue was purified by silica gel column chromatography (DNH silica gel, eluting solvent: ethyl acetate:methanol). Ethyl acetate was added to the crude product thus obtained, and the mixture was stirred at 70° C. for 1 hour. Thereafter, the solid was purified by being collected by filtration and being dried under reduced pressure to give the title compound 51.0 mg (0.111 mmol, yield 25%) as a white solid.

Mass spectrum (ESI, m/z):459[M+1]$^+$.

$^1$H-NMR spectrum (400 MHz, DMSO-d$_6$) δ:8.63 (d, J=1.4 Hz, 2H), 7.83 (br d, J=4.3 Hz, 1H), 7.54-7.47 (m, 1H), 7.45-7.37 (m, 1H), 7.34-7.24 (m, 1H), 5.06 (s, 2H), 4.90-4.64 (m, 4H), 4.22 (t, J=6.5 Hz, 2H), 2.57 (d, J=4.3 Hz, 3H), 2.43 (t, J=6.5 Hz, 2H).

Example 114

Ethyl 4-[({1-[5-(3-{[(carbamimidoylcarbamoyl)oxy]methyl}-2-fluorophenyl)pyrimidin-2-yl]azetidin-3-ylidene}amino)oxy]butanoate (Compound II-281)

CDI 127 mg (0.783 mmol) was added to a DMF (6 mL) solution of ethyl 4-{[(1-{5-[2-fluoro-3-(hydroxymethyl)phenyl]pyrimidin-2-yl}azetidin-3-ylidene)amino]oxy}butanoate 157 mg (0.390 mmol) synthesized in the same manner as in Reference Example 7-67, and the mixture was stirred at room temperature for 16 hours. Next, guanidine carbonate 141 mg (0.783 mmol) was added, and the mixture was stirred at room temperature for 5 hours. After the completion of the reaction, water was added to the reaction mixture, and followed by extraction with methylene chloride. The organic layer was washed with water, dried over anhydrous sodium sulfate, and filtered. The filtrate was concentrated under reduced pressure. The concentrated residue was purified by silica gel column chromatography (DNH silica gel, eluting solvent: ethyl acetate:methanol) to give the title compound 153 mg (0.314 mmol, yield 81%) as a white solid.

Mass spectrum (ESI, m/z):488[M+1]$^+$.

$^1$H-NMR spectrum (400 MHz, DMSO-d$_6$+D$_2$O) δ:8.63 (d, J=1.3 Hz, 2H), 7.55-7.47 (m, 1H), 7.46-7.39 (m, 1H), 7.33-7.27 (m, 1H), 5.06 (s, 2H), 4.87-4.77 (m, 4H), 4.23-3.93 (m, 4H), 2.38 (t, J=7.3 Hz, 2H), 1.92-1.82 (m, 2H), 1.19 (t, J=7.1 Hz, 3H).

Example 115

4-[({1-[5-(3-{[(Carbamimidoylcarbamoyl)oxy] methyl}-2-fluorophenyl)pyrimidin-2-yl]azetidin-3-ylidene}amino)oxy]butanoic acid (Compound III-276)

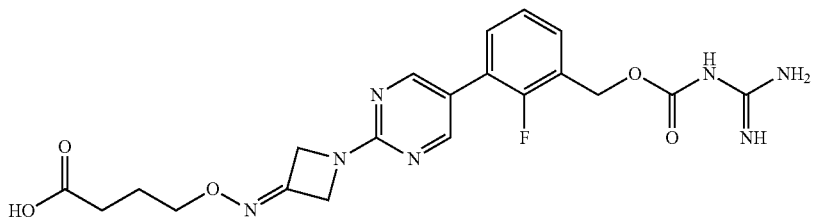 [SMILES: N=C(N)NC(=O)OCc1cccc(-c2cnc(N3CC(=NOCCCC(=O)O)C3)nc2)c1F]

Lithium hydroxide 13 mg (0.543 mmol) was added to a THF (4 mL)-water (1 mL) suspension of ethyl 4-[({1-[5-(3-{[(carbamimidoylcarbamoyl)oxy]methyl}-2-fluorophenyl)pyrimidin-2-yl]azetidin-3-ylidene}amino)oxy]butanoate 130 mg (0.267 mmol) synthesized in the same manner as in Example 114, and the mixture was stirred at 50° C. for 3 hours. After the completion of the reaction, acetic acid 0.12 ml (2.10 mmol) and water were added to the reaction mixture, and the mixture was stirred at room temperature. The precipitated solid was collected by filtration. The obtained solid was dried under reduced pressure to give the title compound 103 mg (0.224 mmol, yield 84%) as a white solid.

Mass spectrum (ESI, m/z):460[M+1]$^+$.

$^1$H-NMR spectrum (400 MHz, DMSO-d$_6$) δ:8.59 (d, J=1.5 Hz, 2H), 7.49-7.37 (m, 2H), 7.31-7.20 (m, 1H), 5.09 (s, 2H), 4.86-4.74 (m, 4H), 4.05 (t, J=6.5 Hz, 2H), 2.27 (t, J=7.3 Hz, 2H), 1.92-1.82 (m, 2H).

Example 116

2-Fluoro-3-[2-(3-{[4-(methylamino)-4-oxobutoxy]imino}azetidin-1-yl)pyrimidin-5-yl]benzyl carbamimidoylcarbamate (Compound II-290)

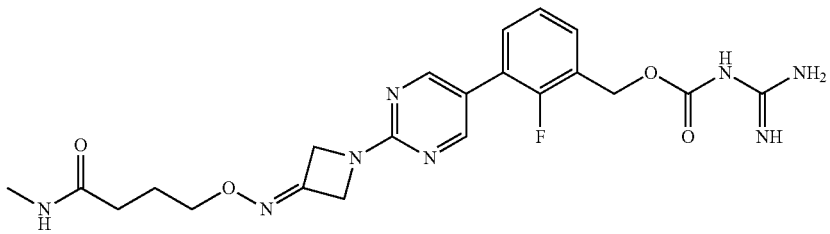 [SMILES: CNC(=O)CCCON=C1CN(c2ncc(-c3cccc(COC(=O)NC(=N)N)c3F)cn2)C1]

CDI 110 mg (0.678 mmol) was added to a DMF (4 mL) solution of 4-{[(1-{5-[2-fluoro-3-(hydroxymethyl)phenyl]pyrimidin-2-yl}azetidin-3-ylidene)amino]oxy}-N-methylbutanamide 116 mg (0.299 mmol) synthesized in the same manner as Reference Compound 7-68, and the mixture was stirred at room temperature for 30 minutes. Next, guanidine carbonate 110 mg (0.611 mmol) was added, and the mixture was stirred at room temperature for 16 hours. After the completion of the reaction, water was added to the reaction mixture, and followed by extraction with methylene chloride. The organic layer was washed with brine, dried over anhydrous sodium sulfate, and filtered. The filtrate was concentrated under reduced pressure. The concentrated residue was purified by silica gel column chromatography (DNH silica gel, eluting solvent: 1,2-dichloroethane:methanol). Ethyl acetate was added to the crude product thus obtained, and the mixture was stirred at 50° C. for 1 hour.

Thereafter, the solid was collected by filtration and was dried under reduced pressure to give the title compound 88.2 mg (0.187 mmol, yield 63%) as a white solid.

Mass spectrum (APCI, m/z):473[M+1]$^+$.

$^1$H-NMR spectrum (400 MHz, DMSO-d$_6$) δ:8.64 (d, J=1.4 Hz, 2H), 7.83-7.68 (m, 1H), 7.55-7.47 (m, 1H), 7.46-7.37 (m, 1H), 7.33-7.25 (m, 1H), 5.06 (s, 2H), 4.91-4.68 (m, 4H), 4.01 (t, J=6.5 Hz, 2H), 2.56 (d, J=4.6 Hz, 3H), 2.13 (t, J=7.5 Hz, 2H), 1.90-1.75 (m, 2H).

Example 117

3-[2-(3-{[2-(Dimethylamino)ethoxy]imino}azetidin-1-yl)pyrimidin-5-yl]-2-fluorobenzyl carbamimidoyl-carbamate (Compound III-293)

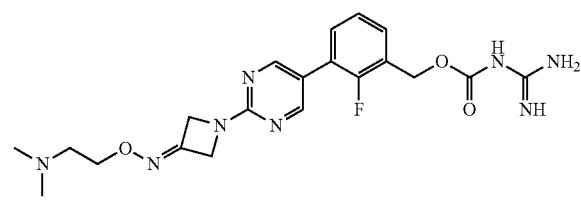 [SMILES: CN(C)CCON=C1CN(c2ncc(-c3cccc(COC(=O)NC(=N)N)c3F)cn2)C1]

CDI 124 mg (0.765 mmol) was added to a DMF (2 mL) solution of 1-{5-[2-fluoro-3-(hydroxymethyl)phenyl]pyrimidin-2-yl}azetidin-3-one O-[2-(dimethylamino)ethyl] oxime 55.0 mg (0.153 mmol) synthesized in the same manner as in Reference Example 7-69, and the mixture was stirred at room temperature for 16 hours. Next, guanidine carbonate 138 mg (0.766 mmol) was added, and the mixture was stirred at room temperature for 2 hours. After the completion of the reaction, water was added to the reaction mixture, and the mixture was concentrated under reduced pressure. The concentrated residue was purified by silica gel column chromatography (DNH silica gel, eluting solvent: ethyl acetate:methanol). The crude product thus obtained was washed with ethyl acetate and water, and was dried under reduced pressure to give the title compound 20.0 mg (0.0450 mmol, yield 29%) as a white solid.

Mass spectrum (ESI, m/z):445[M+1]$^+$.

$^1$H-NMR (400 MHz, DMSO-d$_6$+D$_2$O) δ:8.63 (d, J=1.3 Hz, 2H), 7.55-7.47 (m, 1H), 7.45-7.39 (m, 1H), 7.34-7.26 (m, 1H), 5.06 (s, 2H), 4.86-4.77 (m, 4H), 4.11 (t, J=6.0 Hz, 2H), 2.57-2.47 (m, 2H), 2.17 (s, 6H).

Example 118

3-{2-[3-({2-[Benzyl(methyl)amino]ethoxy}imino)azetidin-1-yl]pyrimidin-5-yl}-2-fluorobenzyl carbamimidoylcarbamate (Compound II-294)

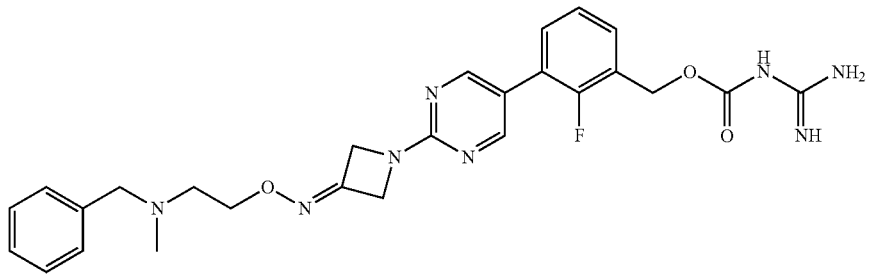 [SMILES: CN(CCON=C1CN(c2ncc(-c3cccc(COC(=O)NC(=N)N)c3F)cn2)C1)Cc1ccccc1]

CDI 62 mg (0.38 mmol) was added to a DMF (3 mL) solution of 1-{5-[2-fluoro-3-(hydroxymethyl)phenyl]pyrimidin-2-yl}azetidin-3-one O-{2-[benzyl(methyl)amino]ethyl} oxime 83 mg (0.19 mmol) synthesized in the same manner as in Reference Example 7-70, and the mixture was stirred at room temperature for 16 hours. Next, guanidine carbonate 69 mg (0.38 mmol) was added, and the mixture was stirred at room temperature for 2 hours. After the completion of the reaction, water was added to the reaction mixture, and the mixture was stirred at room temperature. The precipitated solid was collected by filtration. The crude product thus obtained was washed with water and ethyl acetate, and was dried under reduced pressure to give the title compound 32 mg (0.061 mmol, yield 32%) as a white solid.

Mass spectrum (ESI, m/z):521[M+1]$^+$.

$^1$H-NMR (400 MHz, DMSO-d$_6$+D$_2$O) δ:8.64 (d, J=1.0 Hz, 2H), 7.55-7.48 (m, 1H), 7.46-7.38 (m, 1H), 7.34-7.18 (m, 6H), 5.06 (s, 2H), 4.84-4.75 (m, 4H), 4.14 (t, J=5.8 Hz, 2H), 3.59-3.40 (m, 2H), 2.62 (t, J=6.0 Hz, 2H), 2.20 (s, 3H).

Example 119

3-(2-{3-[(3-Acetamido-2-{[(tetrahydropyran-2-yl)oxy]methyl}propoxy)imino]azetidin-1-yl}pyrimidin-5-yl)-2-fluorobenzyl carbamimidoylcarbamate (Compound II-362)

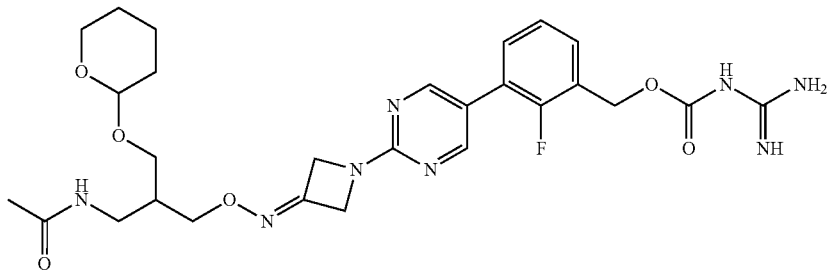 [SMILES: CC(=O)NCC(CON=C1CN(c2ncc(-c3cccc(COC(=O)NC(=N)N)c3F)cn2)C1)COC1CCCCO1]

CDI 67 mg (0.41 mmol) was added to a DMF (4 mL) solution of N-(3-{[(1-{5-[2-fluoro-3-(hydroxymethyl)phenyl]pyrimidin-2-yl}azetidin-3-ylidene)amino]oxy}-2-{[(tetrahydropyran-2-yl)oxy]methyl}propyl)acetamide 69 mg (0.14 mmol) synthesized in the same manner as in Reference Example 7-71, and the mixture was stirred at room temperature for 20 hours. Next, guanidine carbonate 50 mg (0.28 mmol) was added, and the mixture was stirred at room temperature for 2 hours. After the completion of the reaction, water was added to the reaction mixture, and followed by extraction with methylene chloride. The organic layer was washed with water, dried over anhydrous sodium sulfate, and filtered. The filtrate was concentrated under reduced pressure. The concentrated residue was purified by silica gel column chromatography (DNH silica gel, eluting solvent: ethyl acetate:methanol) to give the title compound 62 mg (0.11 mmol, yield 79%) as a white foam.

$^1$H-NMR spectrum (400 MHz, DMSO-$d_6$+$D_2O$) δ:8.63 (d, J=1.1 Hz, 2H), 7.91-7.84 (m, 1H), 7.54-7.47 (m, 1H), 7.45-7.39 (m, 1H), 7.33-7.26 (m, 1H), 5.06 (s, 2H), 4.87-4.78 (m, 4H), 4.57-4.52 (m, 1H), 4.09-3.99 (m, 2H), 3.78-3.58 (m, 2H), 3.48-3.40 (m, 1H), 3.37-3.27 (m, 1H), 3.20-3.06 (m, 2H), 2.18-2.06 (m, 1H), 1.82 (s, 3H), 1.74-1.37 (m, 6H).

Example 120

3-[2-(3-{[3-Acetamido-2-(hydroxymethyl)propoxy]imino}azetidin-1-yl)pyrimidin-5-yl]-2-fluorobenzyl carbamimidoylcarbamate (Compound II-302)

At 0° C., 2 M hydrogen chloride/ethanol solution 0.50 mL (1.0 mmol) was added to an ethanol (2 mL) solution of 3-(2-{3-[(3-acetamido-2-{[(tetrahydropyran-2-yl)oxy]methyl}propoxy)imino]azetidin-1-yl}pyrimidin-5-yl)-2-fluorobenzyl carbamimidoylcarbamate 62 mg (0.11 mmol) synthesized in the same manner as in Example 119, and the mixture was stirred at room temperature for 1 hour. After the completion of the reaction, TEA was added to the reaction mixture. The mixture was purified by silica gel column chromatography (DNH silica gel, eluting solvent: ethyl acetate:methanol) to give the title compound 41 mg (0.082 mmol, yield 77%) as a white solid.

Mass spectrum (ESI, m/z):503[M+1]$^+$.

$^1$H-NMR spectrum (400 MHz, DMSO-$d_6$+$D_2O$) δ:8.63 (d, J=1.3 Hz, 2H), 7.94-7.84 (m, 1H), 7.53-7.46 (m, 1H), 7.45-7.38 (m, 1H), 7.34-7.27 (m, 1H), 5.06 (s, 2H), 4.86-4.78 (m, 4H), 4.07-3.94 (m, 2H), 3.44-3.35 (m, 2H), 3.17-3.04 (m, 2H), 1.99-1.90 (m, 1H), 1.82 (s, 3H).

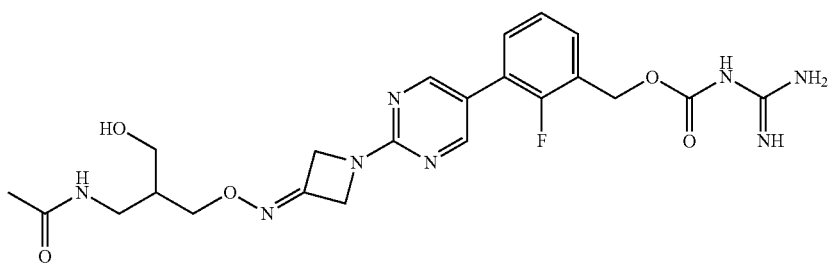 [SMILES: CC(=O)NCC(CO)CON=C1CN(c2ncc(-c3cccc(COC(=O)NC(=N)N)c3F)cn2)C1]

Example 121

3-{(2-[3-({3-(Dimethylamino)-2-[(tetrahydropyran-2-yloxy)methyl]propoxy}imino)azetidin-1-yl]pyrimidin-5-yl}-2-fluorobenzyl carbamimidoylcarbamate (Compound II-363)

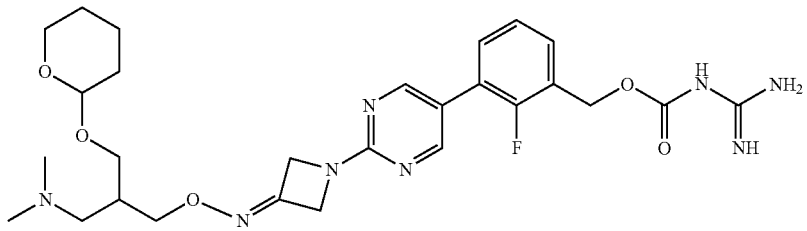 [SMILES: CN(C)CC(CON=C1CN(c2ncc(-c3cccc(COC(=O)NC(=N)N)c3F)cn2)C1)COC1CCCCO1]

CDI 50 mg (0.31 mmol) was added to a DMF (4 mL) solution of 1-{5-[2-fluoro-3-(hydroxymethyl)phenyl]pyrimidin-2-yl}azetidin-3-one O-(3-(dimethylamino)-2-{[(tetrahydropyran-2-yl)oxy]methyl}propyl) oxime 50 mg (0.10 mmol) synthesized in the same manner as in Reference Example 7-72, and the mixture was stirred at room temperature for 19 hours. Next, guanidine carbonate 37 mg (0.21 mmol) was added, and the mixture was stirred at room temperature for 3 hours. After the completion of the reaction, water was added to the reaction mixture, and followed by extraction with methylene chloride. The organic layer was washed with water, dried over anhydrous sodium sulfate, and filtered. The filtrate was concentrated under reduced pressure. The concentrated residue was purified by silica gel column chromatography (DNH silica gel, eluting solvent: ethyl acetate:methanol) to give the title compound 48 mg (0.084 mmol, yield 84%) as a colorless oil.

$^1$H-NMR spectrum (400 MHz, DMSO-$d_6$+$D_2$O) δ:8.63 (d, J=1.3 Hz, 2H), 7.55-7.47 (m, 1H), 7.45-7.38 (m, 1H), 7.33-7.26 (m, 1H), 5.06 (s, 2H), 4.87-4.74 (m, 4H), 4.59-4.51 (m, 1H), 4.12-4.01 (m, 2H), 3.78-3.60 (m, 2H), 3.49-3.28 (m, 2H), 2.30-2.19 (m, 2H), 2.18-2.09 (m, 7H), 1.76-1.37 (m, 6H).

Example 122

3-[2-(3-{[3-(Dimethylamino)-2-(hydroxymethyl)propoxy]imino}azetidin-1-yl)pyrimidin-5-yl]-2-fluorobenzyl carbamimidoylcarbamate (Compound II-303)

At 0° C., 2 M hydrogen chloride/ethanol solution 0.40 mL (0.80 mmol) was added to an ethanol (1 mL) solution of 3-(2-{3-[(3-(dimethylamino)-2-{[(tetrahydropyran-2-yloxy)methyl]propoxy}imino)azetidin-1-yl]pyrimidin-5-yl}-2-fluorobenzyl carbamimidoylcarbamate 48 mg (0.084 mmol) synthesized in the same manner as in Example 121, and the mixture was stirred at room temperature for 0.5 hours. After the completion of the reaction, TEA was added to the reaction mixture. The mixture was purified by silica gel column chromatography (DNH silica gel, eluting solvent: ethyl acetate:methanol) to give the title compound 20 mg (0.041 mmol, yield 49%) as a white solid.

Mass spectrum (ESI, m/z):489[M+1]$^+$.

$^1$H-NMR spectrum (400 MHz, DMSO-$d_6$) δ:8.63 (d, J=1.0 Hz, 2H), 7.54-7.46 (m, 1H), 7.45-7.35 (m, 1H), 7.34-7.25 (m, 1H), 5.06 (s, 2H), 4.86-4.77 (m, 4H), 4.57 (br s, 1H), 4.06-3.97 (m, 2H), 3.49-3.41 (m, 2H), 2.27-2.15 (m, 2H), 2.13 (s, 6H), 2.06-1.94 (m, 1H).

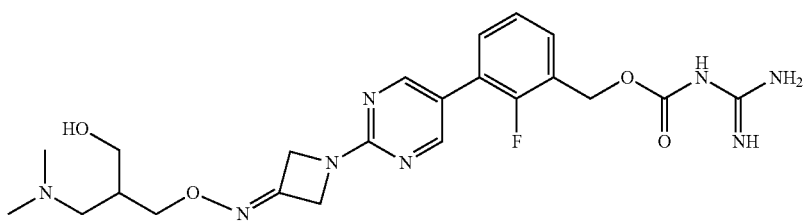 [SMILES: CN(C)CC(CO)CON=C1CN(c2ncc(-c3cccc(COC(=O)NC(=N)N)c3F)cn2)C1]

Example 123

3-(2-{3-[(3-Acetamido-2-methoxypropoxy)imino]azetidin-1-yl}pyrimidin-5-yl)-2-fluorobenzyl carbamimidoylcarbamate (Compound II-304)

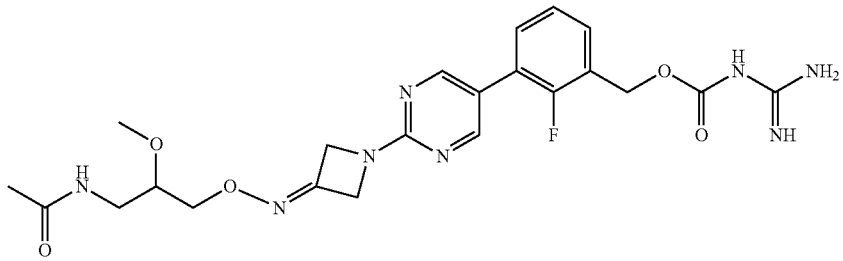 [SMILES: COC(CNC(C)=O)CON=C1CN(c2ncc(-c3cccc(COC(=O)NC(=N)N)c3F)cn2)C1]

CDI 40 mg (0.25 mmol) was added to a DMF (4 mL) solution of N-(3-{[(1-{5-[2-fluoro-3-(hydroxymethyl)phenyl]pyrimidin-2-yl}azetidin-3-ylidene)amino]oxy}-2-methoxypropyl)acetamide 50 mg (0.12 mmol) synthesized in the same manner as in Reference Example 7-73, and the mixture was stirred at room temperature for 15 hours. Next, guanidine carbonate 45 mg (0.25 mmol) was added, and the mixture was stirred at room temperature for 4 hours. After the completion of the reaction, water was added to the reaction mixture, and followed by extraction with methylene chloride. The organic layer was washed with water, dried over anhydrous sodium sulfate, and filtered. The filtrate was concentrated under reduced pressure. The concentrated residue was purified by silica gel column chromatography (DNH silica gel, eluting solvent: ethyl acetate:methanol) to give the title compound 33 mg (0.066 mmol, yield 55%) as a light yellow solid.

Mass spectrum (ESI, m/z):503[M+1]$^+$.

$^1$H-NMR spectrum (400 MHz, DMSO-d$_6$) δ:8.63 (s, 2H), 7.89 (t, J=5.6 Hz, 1H), 7.57-7.46 (m, 1H), 7.46-7.36 (m, 1H), 7.35-7.22 (m, 1H), 5.06 (s, 2H), 4.88-4.77 (m, 4H), 4.13-3.95 (m, 2H), 3.51-3.44 (m, 1H), 3.34 (s, 3H), 3.26-3.08 (m, 2H), 1.82 (s, 3H).

Example 124

2-Fluoro-3-[2-(3-{[2-(piperidin-1-yl)ethoxy]imino}azetidin-1-yl)pyrimidin-5-yl]benzyl carbamimidoylcarbamate (Compound III-311)

CDI 94 mg (0.58 mmol) was added to a DMF (3 mL) solution of 1-{5-[2-fluoro-3-(hydroxymethyl)phenyl]pyrimidin-2-yl}azetidin-3-one O-[2-(piperidin-1-yl)ethyl] oxime 77 mg (0.19 mmol) synthesized in the same manner as in Reference Example 7-74, and the mixture was stirred at room temperature for 16 hours. Next, guanidine carbonate 104 mg (0.58 mmol) was added, and the mixture was stirred at room temperature for 2 hours. After the completion of the reaction, water was added to the reaction mixture, and the mixture was stirred at room temperature. The precipitated solid was collected by filtration. The crude product thus obtained was washed with water and ethyl acetate, and was dried under reduced pressure to give the title compound 45 mg (0.093 mmol, yield 49%) as a white solid.

Mass spectrum (ESI, m/z):485[M+1]$^+$.

$^1$H-NMR (400 MHz, DMSO-d$_6$+D$_2$O) δ:8.63 (d, J=1.3 Hz, 2H), 7.55-7.47 (m, 1H), 7.46-7.39 (m, 1H), 7.33-7.26 (m, 1H), 5.06 (s, 2H), 4.87-4.75 (m, 4H), 4.13 (t, J=6.1 Hz, 2H), 2.59-2.47 (m, 2H), 2.45-2.30 (m, 4H), 1.54-1.44 (m, 4H), 1.41-1.32 (m, 2H).

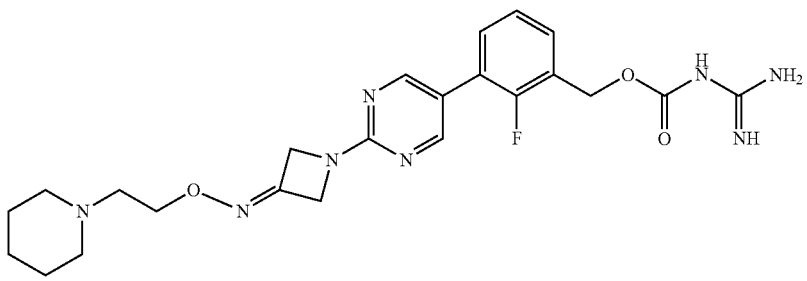 [SMILES: N=C(N)NC(=O)OCc1cccc(-c2cnc(N3CC(=NOCCN4CCCCC4)C3)nc2)c1F]

Example 125

2-Fluoro-3-(2-{3-[(2-morpholinoethoxy)imino]azetidin-1-yl}pyrimidin-5-yl)benzyl carbamimidoylcarbamate (Compound II-312)

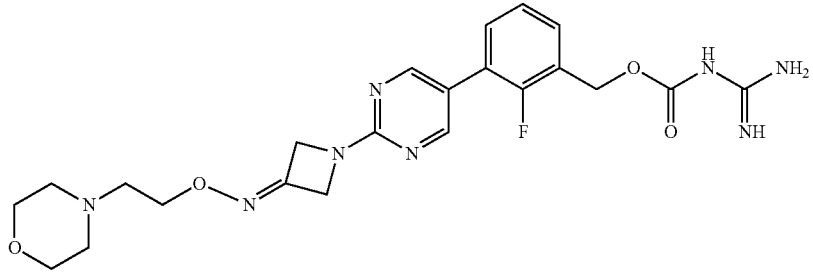 [SMILES: N=C(N)NC(=O)OCc1cccc(-c2cnc(N3CC(=NOCCN4CCOCC4)C3)nc2)c1F]

CDI 126 mg (0.777 mmol) was added to a DMF (3 ml) solution of 1-{5-[2-fluoro-3-(hydroxymethyl)phenyl]pyrimidin-2-yl}azetidin-3-one O-(2-morpholinoethyl) oxime 104 mg (0.259 mmol) synthesized in the same manner as in Reference Example 7-75, and the mixture was stirred at room temperature for 14 hours. Next, guanidine carbonate 95.2 mg (0.528 mmol) was added, and the mixture was stirred at room temperature for 1.5 hours. After the completion of the reaction, water was added to the reaction mixture and the mixture was stirred at room temperature. The precipitated solid was collected by filtration and was dried under reduced pressure to give the title compound 103 mg (0.212 mmol, yield 82%) as a white solid.

Mass spectrum (APCI, m/z):487[M+1]$^+$.

$^1$H-NMR spectrum (400 MHz, DMSO-d$_6$+D$_2$O) δ:8.63 (d, J=1.3 Hz, 2H), 7.53-7.48 (m, 1H), 7.45-7.39 (m, 1H), 7.34-7.26 (m, 1H), 5.06 (s, 2H), 4.87-4.76 (m, 4H), 4.15 (t, J=6.0 Hz, 2H), 3.60-3.55 (m, 4H), 2.59 (t, J=6.0 Hz, 2H), 2.46-2.39 (m, 4H).

Example 126

3-[2-(3-{[2-(Azetidin-1-yl)ethoxy]imino}azetidin-1-yl)pyrimidin-5-yl]-2-fluorobenzyl carbamimidoylcarbamate (Compound II-313)

CDI 35 mg (0.22 mmol) was added to a DMF (2 ml) solution of 1-{5-[2-fluoro-3-(hydroxymethyl)phenyl]pyrimidin-2-yl}azetidin-3-one O-[2-(azetidin-1-yl)ethyl] oxime 27 mg (0.071 mmol) synthesized in the same manner as in Reference Example 7-76, and the mixture was stirred at room temperature for 14 hours. Next, CDI 12 mg (0.074 mmol) was added, and the mixture was stirred at room temperature for 3 hours. Next, guanidine carbonate 26 mg (0.14 mmol) was added, and the mixture was stirred at room temperature for 2 hours. After the completion of the reaction, water and a saturated aqueous sodium carbonate solution were added to the reaction mixture, and followed by extraction with ethyl acetate. The organic layer was washed with brine, dried over anhydrous sodium sulfate, and filtered. The filtrate was concentrated under reduced pressure. The concentrated residue was purified by silica gel column chromatography (DNH silica gel, eluting solvent: ethyl acetate:methanol) to give the title compound 24 mg (0.053 mmol, yield 74%) as a white solid.

Mass spectrum (ESI, m/z):457[M+1]$^+$.

$^1$H-NMR spectrum (400 MHz, DMSO-d$_6$+D$_2$O) δ:8.63 (d, J=1.3 Hz, 2H), 7.55-7.47 (m, 1H), 7.46-7.39 (m, 1H), 7.33-7.28 (m, 1H), 5.07 (s, 2H), 4.85-4.77 (m, 4H), 3.98 (t, J=5.6 Hz, 2H), 3.17-3.10 (m, 4H), 2.60 (t, J=5.6 Hz, 2H), 1.99-1.92 (m, 2H).

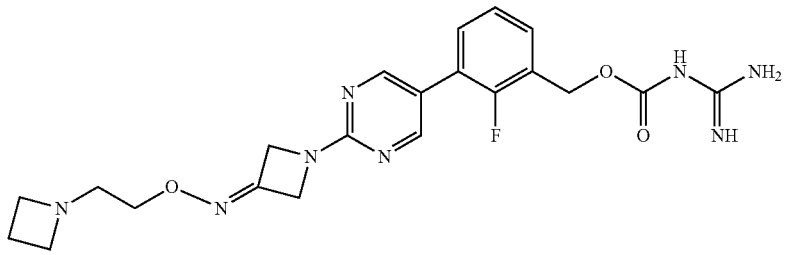 [SMILES: N=C(N)NC(=O)OCc1cccc(-c2cnc(N3CC(=NOCCN4CCC4)C3)nc2)c1F]

Example 127

3-[2-(3-{[2-(3,3-Difluoroazetidin-1-yl)ethoxy]imino}azetidin-1-yl)pyrimidin-5-yl]-2-fluorobenzyl carbamimidoylcarbamate (Compound II-315)

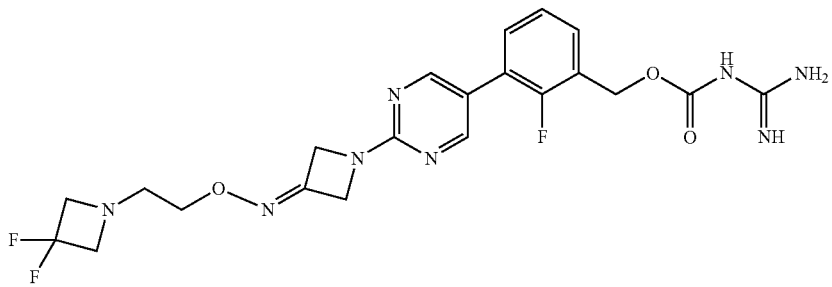 [SMILES: N=C(N)NC(=O)OCc1cccc(-c2cnc(N3CC(=NOCCN4CC(F)(F)C4)C3)nc2)c1F]

CDI 22 mg (0.14 mmol) was added to a DMF (2 mL) solution of 1-{5-[2-fluoro-3-(hydroxymethyl)phenyl]pyrimidin-2-yl}azetidin-3-one O-[2-(3,3-difluoroazetidin-1-yl)ethyl] oxime 28 mg (0.069 mmol) synthesized in the same manner as in Reference Example 7-77, and the mixture was stirred at room temperature for 3 hours. Next, guanidine carbonate 25 mg (0.14 mmol) was added, and the mixture was stirred at room temperature for 16 hours. After the completion of the reaction, water was added to the reaction mixture, and the mixture was stirred at room temperature. The precipitated solid was collected by filtration. The crude product thus obtained was washed with water and ethyl acetate, and was dried under reduced pressure to give the title compound 13 mg (0.026 mmol, yield 38%) as a white solid.

Mass spectrum (ESI, m/z):493[M+1]$^+$.

$^1$H-NMR (400 MHz, DMSO-d$_6$+D$_2$O) δ:8.66-8.60 (m, 2H), 7.55-7.48 (m, 1H), 7.45-7.38 (m, 1H), 7.33-7.26 (m, 1H), 5.06 (s, 2H), 4.86-4.78 (m, 4H), 4.07 (t, J=5.3 Hz, 2H), 3.62 (t, J=12.5 Hz, 4H), 2.81 (t, J=5.3 Hz, 2H).

Example 128

2-Fluoro-3-[2-(3-{[2-(3-fluoroazetidin-1-yl)ethoxy]imino}azetidin-1-yl)pyrimidin-5-yl]benzyl carbamimidoylcarbamate (Compound II-314)

CDI 38 mg (0.23 mmol) was added to a DMF (2 mL) solution of 1-{5-[2-fluoro-3-(hydroxymethyl)phenyl]pyrimidin-2-yl}azetidin-3-one O-[2-(3-fluoroazetidin-1-yl)ethyl] oxime 36 mg (0.092 mmol) synthesized in the same manner as in Reference Example 7-78, and the mixture was stirred at room temperature for 3 hours. Next, guanidine carbonate 42 mg (0.23 mmol) was added, and the mixture was stirred at room temperature for 16 hours. After the completion of the reaction, water was added to the reaction mixture, and followed by extraction with ethyl acetate. The organic layer was washed with water, dried over anhydrous magnesium sulfate, and filtered. The filtrate was concentrated under reduced pressure. The concentrated residue was purified by silica gel column chromatography (DNH silica gel, eluting solvent: ethyl acetate:methanol). The crude product thus obtained was washed with TBME and was dried under reduced pressure to give the title compound 22 mg (0.046 mmol, yield 50%) as a white solid.

Mass spectrum (ESI, m/z):475[M+1]$^+$.

$^1$H-NMR (400 MHz, DMSO-d$_6$+D$_2$O) δ:8.63 (d, J=1.4 Hz, 2H), 7.55-7.48 (m, 1H), 7.46-7.39 (m, 1H), 7.33-7.26 (m, 1H), 5.25-5.02 (m, 3H), 4.87-4.76 (m, 4H), 4.03 (t, J=5.5 Hz, 2H), 3.67-3.49 (m, 2H), 3.21-3.07 (m, 2H), 2.71 (t, J=5.5 Hz, 2H).

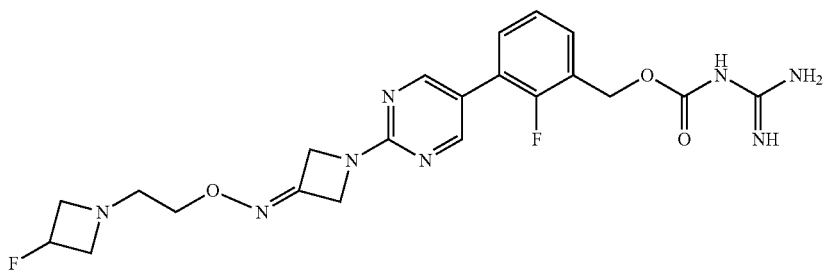 [SMILES: N=C(N)NC(=O)OCc1cccc(-c2cnc(N3CC(=NOCCN4CC(F)C4)C3)nc2)c1F]

Example 129

2-Fluoro-3-[2-(3-{[2-(3-methoxyazetidin-1-yl)ethoxy]imino}azetidin-1-yl)pyrimidin-5-yl]benzyl carbamimidoylcarbamate (Compound II-316)

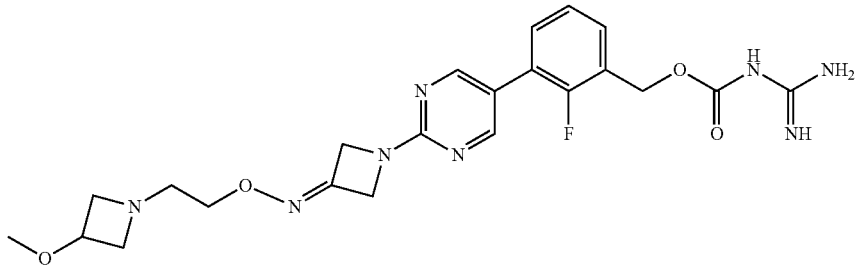 [SMILES: COC1CN(CCON=C2CN(c3ncc(-c4cccc(COC(=O)NC(=N)N)c4F)cn3)C2)C1]

CDI 40 mg (0.25 mmol) was added to a DMF (2 mL) solution of 1-{5-[2-fluoro-3-(hydroxymethyl)phenyl]pyrimidin-2-yl}azetidin-3-one O-[2-(3-methoxyazetidin-1-yl)ethyl] oxime 39 mg (0.097 mmol) synthesized in the same manner as in Reference Example 7-79, and the mixture was stirred at room temperature for 3 hours. Next, guanidine carbonate 44 mg (0.24 mmol) was added, and the mixture was stirred at room temperature for 18 hours. After the completion of the reaction, water was added to the reaction mixture, and the mixture was stirred at room temperature. The precipitated solid was collected by filtration. The crude product thus obtained was washed with ethyl acetate and was dried under reduced pressure to give the title compound 21 mg (0.043 mmol, yield 44%) as a white solid.

Mass spectrum (ESI, m/z):487[M+1]$^+$.

$^1$H-NMR (400 MHz, DMSO-d$_6$+D$_2$O) δ:8.63 (d, J=1.1 Hz, 2H), 7.55-7.47 (m, 1H), 7.45-7.38 (m, 1H), 7.34-7.25 (m, 1H), 5.06 (s, 2H), 4.87-4.76 (m, 4H), 4.05-3.88 (m, 3H), 3.62-3.36 (m, 2H), 3.14 (s, 3H), 2.88-2.79 (m, 2H), 2.71-2.62 (m, 2H).

Example 130

2-Fluoro-3-[2-(3-{[(4-methylmorpholin-2-yl)methoxy]imino}azetidin-1-yl)pyrimidin-5-yl]benzyl carbamimidoylcarbamate (Compound II-317)

CDI 130 mg (0.82 mmol) was added to a DMF (3 ml) solution of 1-{5-[2-fluoro-3-(hydroxymethyl)phenyl]pyrimidin-2-yl}azetidin-3-one O-[(4-methylmorpholin-2-yl)methyl] oxime 110 mg (0.27 mmol) synthesized in the same manner as in Reference Example 7-80, and the mixture was stirred at room temperature for 14 hours. Next, guanidine carbonate 100 mg (0.56 mmol) was added, and the mixture was stirred at room temperature for 2 hours. After the completion of the reaction, water and a saturated aqueous sodium carbonate solution were added to the reaction mixture, and followed by extraction with ethyl acetate. The organic layer was washed with brine, dried over anhydrous sodium sulfate, and filtered. The filtrate was concentrated under reduced pressure. The concentrated residue was purified by silica gel column chromatography (DNH silica gel, eluting solvent: ethyl acetate:methanol) to give the title compound 63 mg (0.13 mmol, yield 47%) as a white solid.

Mass spectrum (APCI, m/z):487[M+1].

$^1$H-NMR spectrum (400 MHz, DMSO-d$_6$) δ:8.63 (d, J=1.4 Hz, 2H), 7.55-7.47 (m, 1H), 7.45-7.37 (m, 1H), 7.33-7.25 (m, 1H), 5.06 (s, 2H), 4.87-4.77 (m, 4H), 4.08-3.91 (m, 2H), 3.80-3.74 (m, 1H), 3.73-3.65 (m, 1H), 3.54-3.44 (m, 1H), 2.75-2.68 (m, 1H), 2.60-2.55 (m, 1H), 2.17 (s, 3H), 2.00-1.91 (m, 1H), 1.78-1.69 (m, 1H).

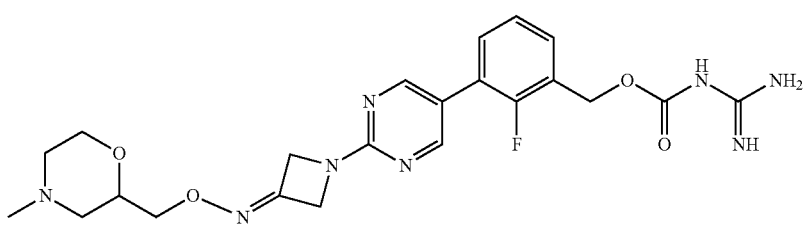 [SMILES: CN1CCOC(CON=C2CN(c3ncc(-c4cccc(COC(=O)NC(=N)N)c4F)cn3)C2)C1]

Example 131

3-[2-(3-{[(4-Acetylmorpholin-2-yl)methoxy]imino}azetidin-1-yl)pyrimidin-5-yl]-2-fluorobenzyl carbamimidoylcarbamate (Compound II-318)

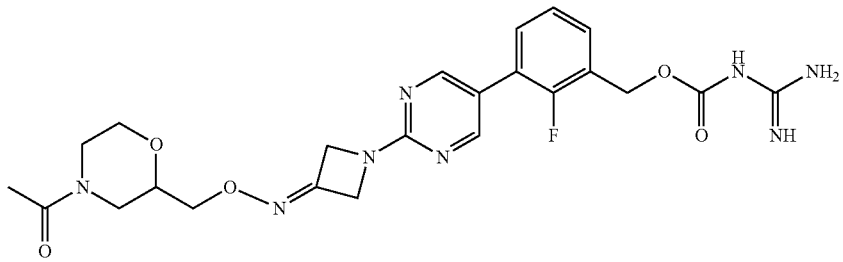 [SMILES: CC(=O)N1CCOC(CON=C2CN(c3ncc(-c4cccc(COC(=O)NC(=N)N)c4F)cn3)C2)C1]

CDI 100 mg (0.62 mmol) was added to a DMF (3 ml) solution of 1-[2-({[(1-{5-[2-fluoro-3-(hydroxymethyl)phenyl]pyrimidin-2-yl}azetidin-3-ylidene)amino]oxy}methyl)morpholino]ethanone 88 mg (0.21 mmol) synthesized in the same manner as in Reference Example 7-81, and the mixture was stirred at room temperature for 14 hours. Next, guanidine carbonate 74 mg (0.41 mmol) was added, and the mixture was stirred at room temperature for 2 hours. After the completion of the reaction, water and a saturated aqueous sodium carbonate solution were added to the reaction mixture, and followed by extraction with ethyl acetate. The organic layer was washed with brine, dried over anhydrous sodium sulfate, and filtered. The filtrate was concentrated under reduced pressure. The concentrated residue was purified by silica gel column chromatography (DNH silica gel, eluting solvent: ethyl acetate:methanol) to give the title compound 87 mg (0.17 mmol, yield 81%) as a white solid.

Mass spectrum (APCI, m/z):515[M+1]$^+$.

$^1$H-NMR spectrum (400 MHz, DMSO-d$_6$+D$_2$O) δ:8.63 (d, J=1.3 Hz, 2H), 7.55-7.48 (m, 1H), 7.46-7.38 (m, 1H), 7.33-7.27 (m, 1H), 5.06 (s, 2H), 4.87-4.80 (m, 4H), 4.32-3.98 (m, 3H), 3.90-3.82 (m, 1H), 3.79-3.53 (m, 2H), 3.50-3.32 (m, 1H), 3.22-2.95 (m, 1H), 2.73-2.43 (m, 1H), 2.04-1.99 (m, 3H).

Example 132

2-Fluoro-3-[2-(3-{[(5-oxotetrahydrofuran-2-yl)methoxy]imino}azetidin-1-yl)pyrimidin-5-yl]benzyl carbamimidoylcarbamate (Compound II-319)

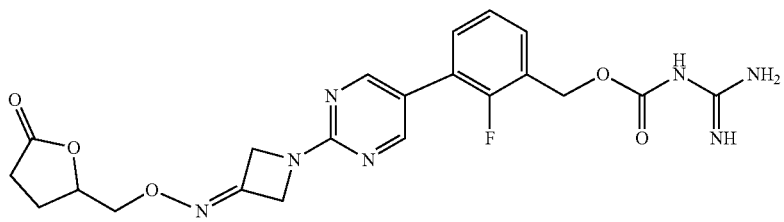 [SMILES: N=C(N)NC(=O)OCc1cccc(-c2cnc(N3CC(=NOCC4CCC(=O)O4)C3)nc2)c1F]

CDI 115 mg (0.709 mmol) was added to a DMF (4 mL) solution of 5-({[(1-{5-[2-fluoro-3-(hydroxymethyl)phenyl]pyrimidin-2-yl}azetidin-3-ylidene)amino]oxy}methyl)dihydrofuran-2(3H)-one 121 mg (0.313 mmol) synthesized in the same manner as Reference Compound 7-82, and the mixture was stirred at room temperature for 1 hour. Next, guanidine carbonate 115 mg (0.638 mmol) was added, and the mixture was stirred at room temperature for 2 hours. After the completion of the reaction, water was added to the reaction mixture, and the mixture was stirred at room temperature. The precipitated solid was collected by filtration. The obtained solid was purified by silica gel column chromatography (DNH silica gel, eluting solvent: 1,2-dichloroethane:methanol). Ethyl acetate was added to the crude product thus obtained, and the mixture was stirred at room temperature. Thereafter, the solid was collected by filtration and was dried under reduced pressure to give the title compound 57.3 mg (0.122 mmol, yield 39%) as a white solid.

Mass spectrum (APCI, m/z):472[M+1]$^+$.

$^1$H-NMR spectrum (400 MHz, DMSO-d$_6$+D$_2$O) δ:8.64 (d, J=1.4 Hz, 2H), 7.54-7.48 (m, 1H), 7.45-7.39 (m, 1H), 7.33-7.27 (m, 1H), 5.06 (s, 2H), 4.88-4.74 (m, 5H), 4.26-4.14 (m, 2H), 2.60-2.43 (m, 2H), 2.32-2.21 (m, 1H), 2.01-1.90 (m, 1H).

Example 133

3-[({1-[5-(3-{[(Carbamimidoylcarbamoyl)oxy]methyl}-2-fluorophenyl)pyrimidin-2-yl]azetidin-3-ylidene}amino)oxy]cyclobutyl acetate (Compound II-339)

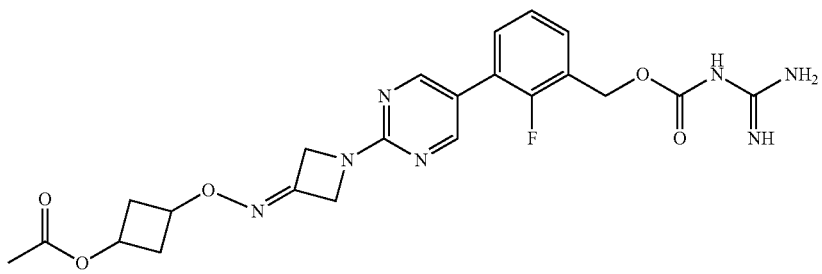 [SMILES: CC(=O)OC1CC(ON=C2CN(c3ncc(-c4cccc(COC(=O)NC(=N)N)c4F)cn3)C2)C1]

CDI 53 mg (0.33 mmol) was added to a DMF (3 ml) solution of 3-{[(1-{5-[2-fluoro-3-(hydroxymethyl)phenyl]pyrimidin-2-yl}azetidin-3-ylidene)amino]oxy}cyclobutyl acetate 65 mg (0.16 mmol) synthesized in the same manner as in Reference Example 7-83, and the mixture was stirred at room temperature for 14 hours. Further, CDI 26 mg (0.16 mmol) was added, and the mixture was stirred at room temperature for 1 hour. Next, guanidine carbonate 59 mg (0.33 mmol) was added, and the mixture was stirred at room temperature for 3 hours. After the completion of the reaction, water was added to the reaction mixture, and the mixture was stirred at room temperature. The precipitated solid was collected by filtration. Ethyl acetate was added to the crude product thus obtained, and the mixture was stirred at 70° C. for 1 hour. Thereafter, the solid was collected by filtration and was dried under reduced pressure to give the title compound 70 mg (0.14 mmol, yield 88%) as a white solid.

Mass spectrum (ESI, m/z):486[M+1]$^+$.

$^1$H-NMR spectrum (400 MHz, DMSO-d$_6$+D$_2$O) δ:8.63 (d, J=1.3 Hz, 2H), 7.55-7.47 (m, 1H), 7.45-7.38 (m, 1H), 7.34-7.26 (m, 1H), 5.09-5.01 (m, 3H), 4.87-4.79 (m, 5H), 2.50-2.44 (m, 2H), 2.40-2.32 (m, 2H), 2.01 (s, 3H).

Example 134

2-Fluoro-3-(2-{3-[(3-hydroxycyclobutoxy)imino]azetidin-1-yl}pyrimidin-5-yl)benzyl carbamimidoylcarbamate (Compound II-336)

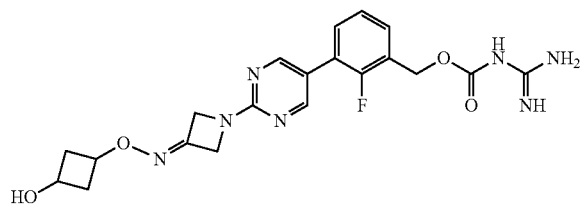 [SMILES: N=C(N)NC(=O)OCc1cccc(-c2cnc(N3CC(=NOC4CC(O)C4)C3)nc2)c1F]

Lithium hydroxide 6.3 mg (0.26 mmol) was added to a THF (1 ml)-water (1 ml) solution of 3-[({1-[5-(3-{[(carbamimidoylcarbamoyl)oxy]methyl}-2-fluorophenyl)pyrimidin-2-yl]azetidin-3-ylidene}amino)oxy]cyclobutyl acetate 57 mg (0.12 mmol) synthesized in the same manner as in Example 133, and the mixture was stirred at room temperature for 2 hours. After the completion of the reaction, a saturated aqueous sodium bicarbonate solution was added to the reaction mixture, and followed by extraction with methylene chloride. The organic layer was washed with brine, dried over anhydrous sodium sulfate, and filtered. The filtrate was concentrated under reduced pressure. The concentrated residue was purified by silica gel column chromatography (DNH silica gel, eluting solvent: ethyl acetate:methanol) to give the title compound 6.0 mg (0.014 mmol, yield 12%) as a white solid.

Mass spectrum (ESI, m/z):444[M+1]$^+$.

$^1$H-NMR spectrum (400 MHz, DMSO-d$_6$+D$_2$O) δ:8.63 (d, J=1.0 Hz, 2H), 7.55-7.47 (m, 1H), 7.45-7.38 (m, 1H), 7.34-7.24 (m, 1H), 5.06 (s, 2H), 4.88-4.78 (m, 4H), 4.78-4.70 (m, 1H), 4.33-4.26 (m, 1H), 2.35-2.27 (m, 2H), 2.16-2.08 (m, 2H).

Example 135

3-(2-{3-[(Benzyloxy)imino]azetidin-1-yl}pyrimidin-5-yl)-2-fluorobenzyl carbamimidoylcarbamate (Compound II-334)

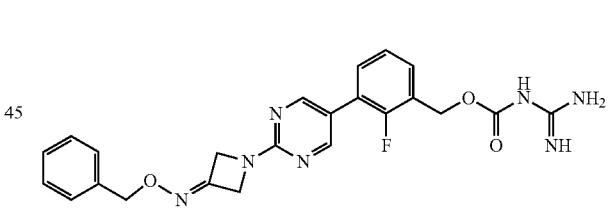

CDI 58 mg (0.36 mmol) was added to a DMF (4 mL) solution of 1-(5-(2-fluoro-3-(hydroxymethyl)phenyl)pyrimidin-2-yl)azetidin-3-one O-benzyl oxime 68 mg (0.18 mmol) synthesized in the same manner as in Reference Example 7-84, and the mixture was stirred at room temperature for 5 hours. Next, guanidine carbonate 65 mg (0.36 mmol) was added, and the mixture was stirred at room temperature for 2 hours and was allowed to stand at room temperature for 4 days. After the completion of the reaction, water was added to the reaction mixture, and followed by extraction with methylene chloride. The organic layer was washed with water, dried over anhydrous sodium sulfate, and filtered. The filtrate was concentrated under reduced pressure. The concentrated residue was purified by silica gel column chromatography (DNH silica gel, eluting solvent: ethyl acetate:methanol) to give the title compound 66 mg (0.14 mmol, yield 78%) as a white solid.

Mass spectrum (ESI, m/z):464[M+1]+.

1H-NMR spectrum (400 MHz, DMSO-d6+D2O) δ:8.63 (d, J=1.3 Hz, 2H), 7.54-7.48 (m, 1H), 7.45-7.25 (m, 7H), 5.09 (s, 2H), 5.06 (s, 2H), 4.83 (s, 4H).

Example 136

2-Fluoro-3-[2-(3-{[(4-methoxybenzyl)oxy]imino}azetidin-1-yl)pyrimidin-5-yl]benzyl carbamimidoylcarbamate (Compound II-335)

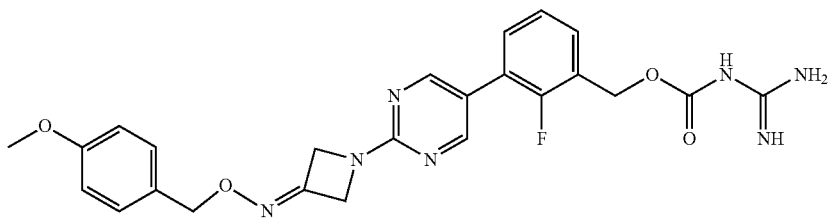 [SMILES: COc1ccc(CON=C2CN(c3ncc(-c4cccc(COC(=O)NC(=N)N)c4F)cn3)C2)cc1]

CDI 110 mg (0.678 mmol) was added to a DMF (4 mL) solution of 1-{5-[2-fluoro-3-(hydroxymethyl)phenyl]pyrimidin-2-yl}azetidin-3-one O-(4-methoxybenzyl) oxime 126 mg (0.309 mmol) synthesized in the same manner as Reference Compound 7-85, and the mixture was stirred at room temperature for 3 hours. Further, CDI 40 mg (0.25 mmol) was added, and the mixture was stirred at room temperature for 17 hours. Next, guanidine carbonate 110 mg (0.678 mmol) was added, and the mixture was stirred at room temperature for 2 hours. After the completion of the reaction, water was added to the reaction mixture, and the mixture was stirred at room temperature. The precipitated solid was collected by filtration. The obtained solid was purified by silica gel column chromatography (DNH silica gel, eluting solvent: 1,2-dichloroethane:methanol). Ethyl acetate was added to the crude product thus obtained, and the mixture was stirred at room temperature. Thereafter, the solid was collected by filtration and was dried under reduced pressure to give the title compound 66.6 mg (0.135 mmol, yield 44%) as a white solid.

Mass spectrum (ESI, m/z):494[M+1]+.

1H-NMR spectrum (400 MHz, DMSO-d6+D2O) δ:8.62 (d, J=1.4 Hz, 2H), 7.54-7.47 (m, 1H), 7.45-7.39 (m, 1H), 7.36-7.26 (m, 3H), 6.96-6.90 (m, 2H), 5.06 (s, 2H), 5.01 (s, 2H), 4.85-4.77 (m, 4H), 3.76 (s, 3H).

Example 137

2-Fluoro-3-[2-(3-{[(1-methylazetidin-3-yl)oxy]imino}azetidin-1-yl)pyrimidin-5-yl]benzyl carbamimidoylcarbamate (Compound II-342)

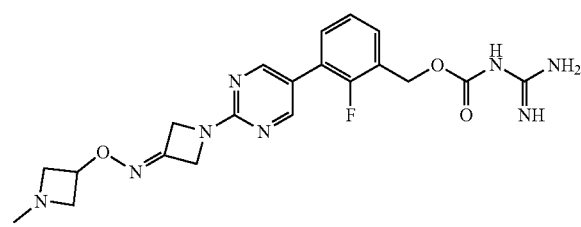 [SMILES: CN1CC(ON=C2CN(c3ncc(-c4cccc(COC(=O)NC(=N)N)c4F)cn3)C2)C1]

CDI 55 mg (0.34 mmol) was added to a DMF (3 ml) solution of 1-{5-[2-fluoro-3-(hydroxymethyl)phenyl]pyrimidin-2-yl}azetidin-3-one O-(1-methylazetidin-3-yl) oxime 40 mg (0.11 mmol) synthesized in the same manner as in Reference Example 7-86, and the mixture was stirred at room temperature for 1 hour. Next, guanidine carbonate 46 mg (0.26 mmol) was added, and the mixture was stirred at room temperature for 1.5 hours. After the completion of the reaction, water and a saturated aqueous sodium carbonate solution were added to the reaction mixture, and followed by extraction with ethyl acetate. The organic layer was washed with brine, dried over anhydrous sodium sulfate, and filtered. The filtrate was concentrated under reduced pressure. The concentrated residue was purified by silica gel column chromatography (DNH silica gel, eluting solvent: ethyl acetate:methanol). Ethyl acetate was added to the crude product thus obtained, and the mixture was stirred at 70° C. for 1 hour. Thereafter, the solid was collected by filtration and was dried under reduced pressure to give the title compound 19 mg (0.043 mmol, yield 39%) as a white solid.

Mass spectrum (ESI, m/z):443[M+1]+.

1H-NMR spectrum (400 MHz, DMSO-d6+D2O) δ:8.63 (d, J=0.6 Hz, 2H), 7.55-7.47 (m, 1H), 7.45-7.38 (m, 1H), 7.33-7.26 (m, 1H), 5.06 (s, 2H), 4.88-4.79 (m, 4H), 4.75-4.66 (m, 1H), 3.54-3.48 (m, 2H), 3.03-2.97 (m, 2H), 2.25 (s, 3H).

Example 138

3-[2-(3-{[(1-Acetylazetidin-3-yl)oxy]imino}azetidin-1-yl)pyrimidin-5-yl]-2-fluorobenzyl carbamimidoylcarbamate (Compound II-350)

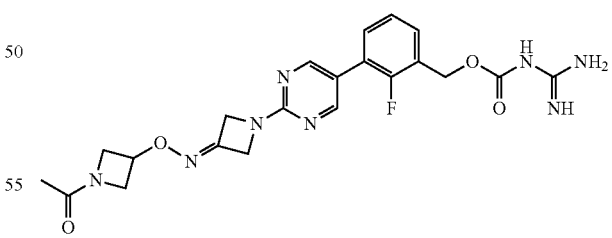

CDI 89 mg (0.55 mmol) was added to a DMF (3 ml) solution of 1-(3-{[(1-{5-[2-fluoro-3-(hydroxymethyl)phenyl]pyrimidin-2-yl}azetidin-3-ylidene)amino]oxy}azetidin-1-yl)ethanone 70 mg (0.18 mmol) synthesized in the same manner as in Reference Example 7-87, and the mixture was stirred at room temperature for 5 hours. Next, guanidine carbonate 66 mg (0.37 mmol) was added, and the mixture was stirred at room temperature for 1 hour. After the completion of the reaction, water and a saturated aqueous sodium carbonate solution were added to the reaction mixture, and followed by extraction with ethyl acetate. The organic layer was washed with brine, dried over anhydrous sodium sulfate, and filtered. The filtrate was concentrated under reduced pressure. The concentrated residue was purified by silica gel column chromatography (DNH silica gel, eluting solvent: ethyl acetate:methanol). Ethyl acetate was added to the crude product thus obtained, and the mixture was stirred at 70° C. for 1 hour. Thereafter, the solid was collected by filtration and was dried under reduced pressure to give the title compound 18 mg (0.038 mmol, yield 21%) as a white solid.

Mass spectrum (ESI, m/z):487[M+1]$^+$.

$^1$H-NMR spectrum (400 MHz, DMSO-d$_6$+D$_2$O) δ:8.64 (d, J=1.3 Hz, 2H), 7.55-7.47 (m, 1H), 7.46-7.38 (m, 1H), 7.34-7.26 (m, 1H), 5.06 (s, 2H), 5.01-4.91 (m, 1H), 4.90-4.83 (m, 4H), 4.41-4.34 (m, 1H), 4.15-4.06 (m, 2H), 3.83-3.77 (m, 1H), 1.78 (s, 3H).

Example 139

3-[2-(3-{[(1-Benzylazetidin-3-yl)oxy]imino}azetidin-1-yl)pyrimidin-5-yl]-2-fluorobenzyl carbamimidoylcarbamate (Compound III-344)

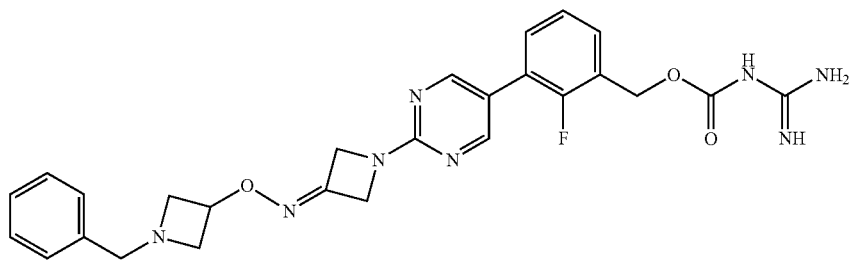 [SMILES: N=C(N)NC(=O)OCc1cccc(-c2cnc(N3CC(=NOC4CN(Cc5ccccc5)C4)C3)nc2)c1F]

CDI 21 mg (0.13 mmol) was added to a DMF (3 ml) solution of 1-{5-[2-fluoro-3-(hydroxymethyl)phenyl]pyrimidin-2-yl}azetidin-3-one O-(1-benzylazetidin-3-yl) oxime 28 mg (0.065 mmol) synthesized in the same manner as in Reference Example 7-88, and the mixture was stirred at room temperature for 3 hours. Further, CDI 11 mg (0.068 mmol) was added, and the mixture was stirred at room temperature for 2 hours. Further, CDI 11 mg (0.068 mmol) was added, and the mixture was stirred at room temperature for 30 minutes. Next, guanidine carbonate 23 mg (0.13 mmol) was added, and the mixture was stirred at room temperature for 1 hour. After the completion of the reaction, water was added to the reaction mixture and the mixture was stirred at room temperature. The precipitated solid was collected by filtration and was dried under reduced pressure to give the title compound 26 mg (0.050 mmol, yield 77%) as a white solid.

Mass spectrum (ESI, m/z):519[M+1]$^+$.

$^1$H-NMR spectrum (400 MHz, DMSO-d$_6$) δ:8.64 (br d, J=1.0 Hz, 2H), 7.55-7.46 (m, 1H), 7.45-7.36 (m, 1H), 7.34-7.21 (m, 6H), 5.06 (s, 2H), 4.87-4.75 (m, 5H), 3.60 (s, 2H), 3.55-3.39 (m, 2H), 3.13-3.02 (m, 2H).

Example 140

2-Fluoro-3-{2-[3-({[1-(2,2,2-trifluoroethyl)azetidin-3-yl]oxy}imino)azetidin-1-yl]pyrimidin-5-yl}benzyl carbamimidoylcarbamate (Compound II-346)

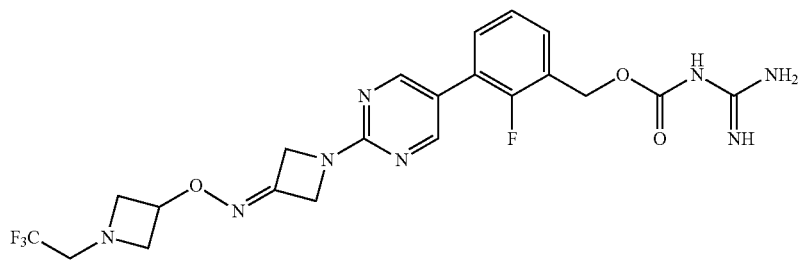 [SMILES: N=C(N)NC(=O)OCc1cccc(-c2cnc(N3CC(=NOC4CN(CC(F)(F)F)C4)C3)nc2)c1F]

CDI 19 mg (0.12 mmol) was added to a DMF (3 ml) solution of 1-{5-[2-fluoro-3-(hydroxymethyl)phenyl]pyrimidin-2-yl}azetidin-3-one O-[1-(2,2,2-trifluoroethyl)azetidin-3-yl] oxime 25 mg (0.059 mmol) synthesized in the same manner as in Reference Example 7-89, and the mixture was stirred at room temperature for 2 hours. Further, CDI 10 mg (0.062 mmol) was added, and the mixture was stirred at room temperature for 30 minutes. Next, guanidine carbonate 21 mg (0.12 mmol) was added, and the mixture was stirred at room temperature for 40 minutes. After the completion of the reaction, water was added to the reaction mixture and the mixture was stirred at room temperature. The precipitated solid was collected by filtration and was dried under reduced pressure to give the title compound 25 mg (0.049 mmol, yield 83%) as a white solid.

Mass spectrum (ESI, m/z):511[M+1]$^+$.

$^1$H-NMR spectrum (400 MHz, DMSO-$d_6$+$D_2O$) δ:8.64 (d, J=1.3 Hz, 2H), 7.55-7.47 (m, 1H), 7.46-7.38 (m, 1H), 7.34-7.25 (m, 1H), 5.06 (s, 2H), 4.87-4.79 (m, 5H), 3.74-3.63 (m, 2H), 3.37-3.30 (m, 2H), 3.25 (q, J=10.1 Hz, 2H).

Example 141

2-Fluoro-3-{2-[3-({[1-(methylsulfonyl)azetidin-3-yl]oxy}imino)azetidin-1-yl]pyrimidin-5-yl}benzyl carbamimidoylcarbamate (Compound II-352)

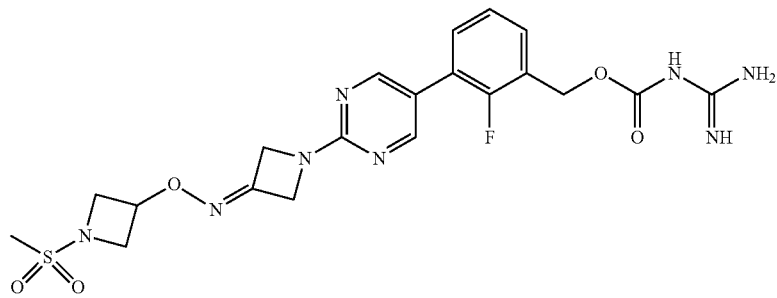 [SMILES: CS(=O)(=O)N1CC(ON=C2CN(c3ncc(-c4cccc(COC(=O)NC(=N)N)c4F)cn3)C2)C1]

CDI 31 mg (0.19 mmol) was added to a DMF (3 ml) solution of 1-{5-[2-fluoro-3-(hydroxymethyl)phenyl]pyrimidin-2-yl}azetidin-3-one O-[1-(methylsulfonyl)azetidin-3-yl] oxime 27 mg (0.064 mmol) synthesized in the same manner as in Reference Example 7-90, and the mixture was stirred at room temperature for 3 hours. Further, CDI 11 mg (0.068 mmol) was added, and the mixture was stirred at room temperature for 1 hour. Next, guanidine carbonate 24 mg (0.13 mmol) was added, and the mixture was stirred at room temperature for 2 hours. After the completion of the reaction, water and a saturated aqueous sodium carbonate solution were added to the reaction mixture, and followed by extraction with ethyl acetate. The organic layer was washed with brine, dried over anhydrous sodium sulfate, and filtered. The filtrate was concentrated under reduced pressure. The concentrated residue was purified by silica gel column chromatography (DNH silica gel, eluting solvent: ethyl acetate:methanol) to give the title compound 14 mg (0.028 mmol, yield 44%) as a white solid.

Mass spectrum (ESI, m/z):507[M+1]$^+$.

$^1$H-NMR spectrum (400 MHz, DMSO-$d_6$+$D_2O$) δ:8.64 (d, J=1.3 Hz, 2H), 7.56-7.47 (m, 1H), 7.46-7.38 (m, 1H), 7.35-7.24 (m, 1H), 5.06 (s, 2H), 5.01-4.93 (m, 1H), 4.90-4.84 (m, 4H), 4.18-4.11 (m, 2H), 3.95-3.89 (m, 2H), 3.04 (s, 3H).

Example 142

3-[2-(3-{[(1-Ethylazetidin-3-yl)oxy]imino}azetidin-1-yl)pyrimidin-5-yl]-2-fluorobenzyl carbamimidoylcarbamate (Compound II-343)

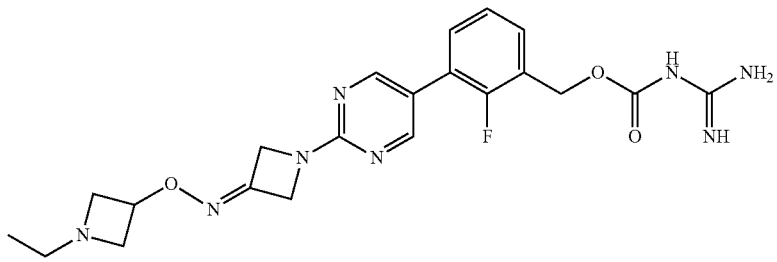 [SMILES: CCN1CC(ON=C2CN(c3ncc(-c4cccc(COC(=O)NC(=N)N)c4F)cn3)C2)C1]

CDI 42 mg (0.26 mmol) was added to a DMF (3 ml) solution of 1-{5-[2-fluoro-3-(hydroxymethyl)phenyl]pyrimidin-2-yl}azetidin-3-one O-(1-ethylazetidin-3-yl) oxime 30 mg (0.081 mmol) synthesized in the same manner as in Reference Example 7-91, and the mixture was stirred at room temperature for 4 hours. Further, CDI 60 mg (0.37 mmol) was added, and the mixture was stirred at room temperature for 17 hours. Next, guanidine carbonate 29 mg (0.16 mmol) was added, and the mixture was stirred at room temperature for 2 hours. After the completion of the reaction, water and a saturated aqueous sodium carbonate solution were added to the reaction mixture, and followed by extraction with ethyl acetate. The organic layer was washed with brine, dried over anhydrous sodium sulfate, and filtered. The filtrate was concentrated under reduced pressure. The concentrated residue was purified by silica gel column chromatography (DNH silica gel, eluting solvent: ethyl acetate:methanol) to give the title compound 28 mg (0.061 mmol, yield 75%) as a white solid.

Mass spectrum (ESI, m/z):457[M+1]$^+$.

$^1$H-NMR spectrum (400 MHz, DMSO-$d_6$+$D_2O$) δ:8.63 (d, J=1.3 Hz, 2H), 7.54-7.48 (m, 1H), 7.45-7.39 (m, 1H), 7.33-7.27 (m, 1H), 5.06 (s, 2H), 4.87-4.80 (m, 4H), 4.77-4.70 (m, 1H), 3.51-3.45 (m, 2H), 3.02-2.89 (m, 2H), 2.42 (q, J=7.2 Hz, 2H), 0.87 (t, J=7.2 Hz, 3H).

Example 143

Methyl 3-[({1-[5-(3-{[(carbamimidoylcarbamoyl)oxy]methyl}-2-fluorophenyl)pyrimidin-2-yl]azetidin-3-ylidene}amino)oxy]azetidin-1-carboxylate (Compound II-351)

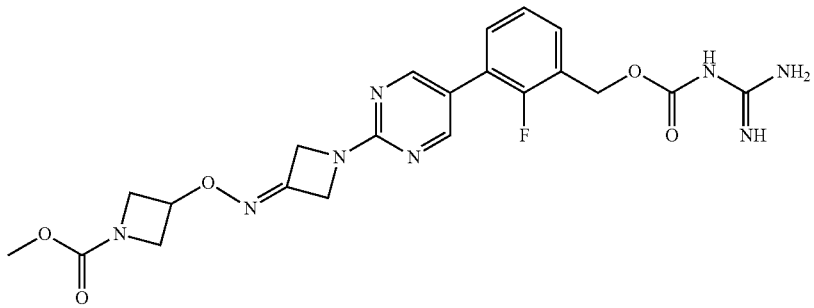 [SMILES: COC(=O)N1CC(ON=C2CN(c3ncc(-c4cccc(COC(=O)NC(=N)N)c4F)cn3)C2)C1]

CDI 90 mg (0.56 mmol) was added to a DMF (3 ml) solution of methyl 3-{[(1-{5-[2-fluoro-3-(hydroxymethyl)phenyl]pyrimidin-2-yl}azetidin-3-ylidene)amino]oxy}azetidin-1-carboxylate 56 mg (0.14 mmol) synthesized in the same manner as in Reference Example 7-92, and the mixture was stirred at room temperature for 2.5 hours. Next, guanidine carbonate 50 mg (0.28 mmol) was added, and the mixture was stirred at room temperature for 2 hours. After the completion of the reaction, water was added to the reaction mixture and the mixture was stirred at room temperature. The precipitated solid was collected by filtration and was dried under reduced pressure to give the title compound 49 mg (0.10 mmol, yield 71%) as a white solid.

Mass spectrum (ESI, m/z):487[M+1]$^+$.

$^1$H-NMR spectrum (400 MHz, DMSO-$d_6$) δ:8.64 (d, J=1.0 Hz, 2H), 7.56-7.47 (m, 1H), 7.46-7.38 (m, 1H), 7.33-7.26 (m, 1H), 5.06 (s, 2H), 5.01-4.93 (m, 1H), 4.91-4.81 (m, 4H), 4.30-4.08 (m, 2H), 3.98-3.84 (m, 2H), 3.57 (s, 3H).

Example 144

2-Fluoro-3-(2-{3-[(oxetan-3-yloxy)imino]azetidin-1-yl}pyrimidin-5-yl)benzyl carbamimidoylcarbamate (Compound II-356)

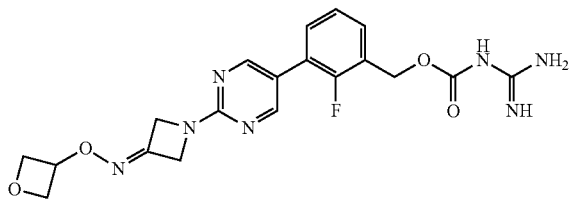 [SMILES: N=C(N)NC(=O)OCc1cccc(-c2cnc(N3CC(=NOC4COC4)C3)nc2)c1F]

CDI 50 mg (0.31 mmol) was added to a DMF (4 mL) solution of 1-{5-[2-fluoro-3-(hydroxymethyl)phenyl]pyrimidin-2-yl}azetidin-3-one O-oxetan-3-yl oxime 50 mg (0.15 mmol) synthesized in the same manner as in Reference Example 7-93, and the mixture was stirred at room temperature for 5 hours. Next, guanidine carbonate 60 mg (0.33 mmol) was added, and the mixture was stirred at room temperature for 15 hours. After the completion of the reaction, water was added to the reaction mixture and the mixture was stirred at room temperature. The precipitated solid was collected by filtration and was dried under reduced pressure to give the title compound 30 mg (0.070 mmol, yield 47%) as a white solid.

Mass spectrum (ESI, m/z):430[M+1]$^+$.

1H-NMR spectrum (400 MHz, DMSO-d6+D2O) δ:8.64 (d, J=1.1 Hz, 2H), 7.56-7.48 (m, 1H), 7.46-7.40 (m, 1H), 7.34-7.28 (m, 1H), 5.25-5.18 (m, 1H), 5.07 (s, 2H), 4.91-4.83 (m, 4H), 4.81-4.74 (m, 2H), 4.60-4.54 (m, 2H).

Example 145

2-{3-[({1-[5-(3-{[(Carbamimidoylcarbamoyl)oxy]methyl}-2-fluorophenyl)pyrimidin-2-yl]azetidin-3-ylidene}amino)oxy]azetidin-1-yl}ethyl acetate (Compound II-349)

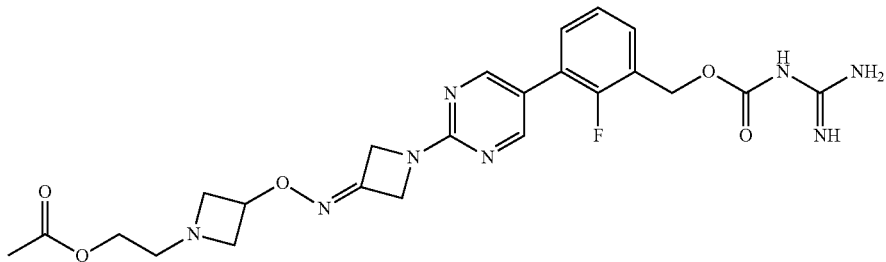 [SMILES: CC(=O)OCCN1CC(ON=C2CN(c3ncc(-c4cccc(COC(=O)NC(=N)N)c4F)cn3)C2)C1]

CDI 68 mg (0.42 mmol) was added to a DMF (3 ml) solution of 2-(3-{[(1-{5-[2-fluoro-3-(hydroxymethyl)phenyl]pyrimidin-2-yl}azetidin-3-ylidene)amino]oxy}azetidin-1-yl)ethyl acetate 43 mg (0.10 mmol) synthesized in the same manner as in Reference Example 7-94, and the mixture was stirred at room temperature for 3 hours. Further, CDI 45 mg (0.28 mmol) was added, and the mixture was stirred at room temperature for 14 hours. Next, guanidine carbonate 36 mg (0.20 mmol) was added, and the mixture was stirred at room temperature for 1 hour. After the completion of the reaction, water and a saturated aqueous sodium carbonate solution were added to the reaction mixture, and followed by extraction with methylene chloride. The organic layer was washed with brine, dried over anhydrous sodium sulfate, and filtered. The filtrate was concentrated under reduced pressure. The concentrated residue was purified by silica gel column chromatography (DNH silica gel, eluting solvent: ethyl acetate:methanol) to give the title compound 42 mg (0.082 mmol, yield 82%) as a white solid.

Mass spectrum (ESI, m/z):515[M+1]$^+$.

$^1$H-NMR spectrum (400 MHz, DMSO-$d_6$) δ:8.64 (d, J=1.3 Hz, 2H), 7.55-7.46 (m, 1H), 7.45-7.37 (m, 1H), 7.33-7.25 (m, 1H), 5.06 (s, 2H), 4.88-4.80 (m, 4H), 4.80-4.72 (m, 1H), 3.96 (t, J=5.5 Hz, 2H), 3.59-3.52 (m, 2H), 3.10-3.04 (m, 2H), 2.65 (t, J=5.5 Hz, 2H), 2.00 (s, 3H).

Example 146

2-Fluoro-3-{2-[3-({[1-(2-hydroxyethyl)azetidin-3-yl]oxy}imino)azetidin-1-yl]pyrimidin-5-yl}benzyl carbamimidoylcarbamate (Compound II-347)

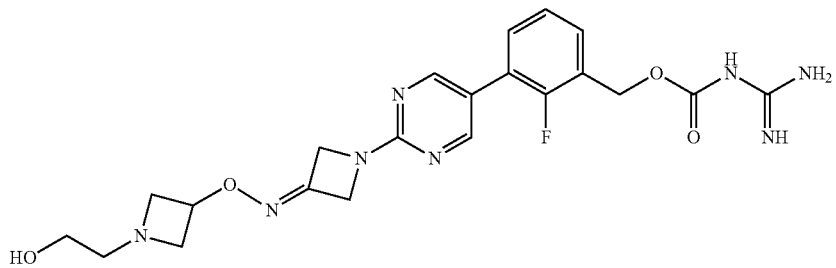 [SMILES: N=C(N)NC(=O)OCc1cccc(-c2cnc(N3CC(=NOC4CN(CCO)C4)C3)nc2)c1F]

Lithium hydroxide 4.0 mg (0.167 mmol) was added to a THF (1 ml)-water (1 ml) solution of 2-{3-[({1-[5-(3-{[(carbamimidoylcarbamoyl)oxy]methyl}-2-fluorophenyl)pyrimidin-2-yl]azetidin-3-ylidene}amino)oxy]azetidin-1-yl}ethyl acetate 35 mg (0.068 mmol) synthesized in the same manner as in Example 145, and the mixture was stirred at room temperature for 2 hours. After the completion of the reaction, a saturated aqueous sodium bicarbonate solution was added to the reaction mixture, and followed by extraction with methylene chloride. The organic layer was washed with brine, dried over anhydrous sodium sulfate, and filtered. The filtrate was concentrated under reduced pressure. The concentrated residue was purified by silica gel column chromatography (DNH silica gel, eluting solvent: ethyl acetate:methanol) to give the title compound 4.8 mg (0.010 mmol, yield 15%) as a white solid.

Mass spectrum (ESI, m/z):473[M+1]$^+$.

$^1$H-NMR spectrum (400 MHz, DMSO-$d_6$+$D_2O$) δ:8.63 (d, J=0.8 Hz, 2H), 7.55-7.47 (m, 1H), 7.46-7.38 (m, 1H), 7.34-7.26 (m, 1H), 5.06 (s, 2H), 4.90-4.68 (m, 5H), 3.58-3.46 (m, 2H), 3.35 (t, J=6.0 Hz, 2H), 3.12-2.97 (m, 2H), 2.59-2.45 (m, 2H).

Example 147

2-Fluoro-3-{2-[3-({[1-(2-methoxyethyl)azetidin-3-yl]oxy}imino)azetidin-1-yl]pyrimidin-5-yl}benzyl carbamimidoylcarbamate (Compound II-348)

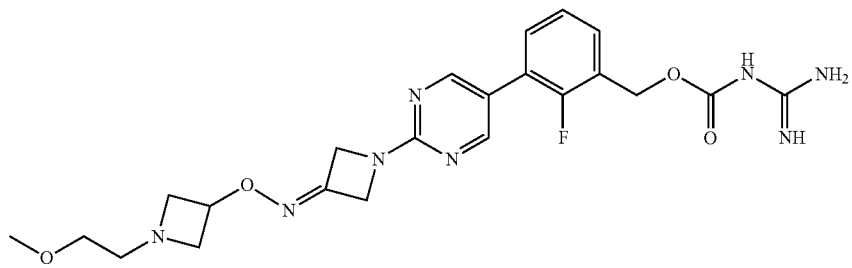 [SMILES: COCCN1CC(ON=C2CN(c3ncc(-c4cccc(COC(=O)NC(=N)N)c4F)cn3)C2)C1]

CDI 76 mg (0.47 mmol) was added to a DMF (3 ml) solution of 1-{5-[2-fluoro-3-(hydroxymethyl)phenyl]pyrimidin-2-yl}azetidin-3-one O-[1-(2-methoxyethyl)azetidin-3-yl] oxime 47 mg (0.12 mmol) synthesized in the same manner as in Reference Example 7-95, and the mixture was stirred at room temperature for 14 hours. Further, CDI 38 mg (0.23 mmol) was added, and the mixture was stirred at room temperature for 1 hour. Next, guanidine carbonate 42 mg (0.23 mmol) was added, and the mixture was stirred at room temperature for 2 hours. After the completion of the reaction, water was added to the reaction mixture and the mixture was stirred at room temperature. The precipitated solid was collected by filtration and was dried under reduced pressure to give the title compound 45 mg (0.093 mmol, yield 78%) as a white solid.

Mass spectrum (ESI, m/z):487[M+1]$^+$.

$^1$H-NMR spectrum (400 MHz, DMSO-$d_6$) δ:8.64 (d, J=1.4 Hz, 2H), 7.54-7.47 (m, 1H), 7.45-7.38 (m, 1H), 7.33-7.25 (m, 1H), 5.06 (s, 2H), 4.88-4.79 (m, 4H), 4.76-4.70 (m, 1H), 3.56-3.48 (m, 2H), 3.29 (t, J=5.8 Hz, 2H), 3.21 (s, 3H), 3.07-3.01 (m, 2H), 2.57 (t, J=5.8 Hz, 2H).

Example 148

2-Fluoro-3-{2-[3-({[1-(2-fluoroethyl)azetidin-3-yl]oxy}imino)azetidin-1-yl]pyrimidin-5-yl}benzyl carbamimidoylcarbamate (Compound II-345)

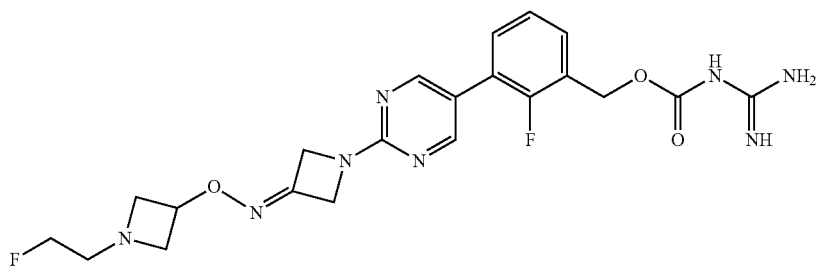 [SMILES: N=C(N)NC(=O)OCc1cccc(-c2cnc(N3CC(=NOC4CN(CCF)C4)C3)nc2)c1F]

CDI 81 mg (0.50 mmol) was added to a DMF (2 ml) solution of 1-{5-[2-fluoro-3-(hydroxymethyl)phenyl]pyrimidin-2-yl}azetidin-3-one O-[1-(2-fluoroethyl)azetidin-3-yl] oxime 39 mg (0.10 mmol) synthesized in the same manner as in Reference Example 7-96, and the mixture was stirred at room temperature for 16 hours. Next, guanidine carbonate 36 mg (0.20 mmol) was added, and the mixture was stirred at room temperature for 2 hours. After the completion of the reaction, water and a saturated aqueous sodium carbonate solution were added to the reaction mixture, and followed by extraction with ethyl acetate. The organic layer was washed with brine, dried over anhydrous sodium sulfate, and filtered. The filtrate was concentrated under reduced pressure. The concentrated residue was purified by silica gel column chromatography (DNH silica gel, eluting solvent: ethyl acetate:methanol) to give the title compound 38 mg (0.080 mmol, yield 80%) as a white solid.

Mass spectrum (ESI, m/z):475[M+1]$^+$.

1H-NMR spectrum (400 MHz, DMSO-$d_6$) δ:8.64 (br s, 2H), 7.54-7.47 (m, 1H), 7.45-7.37 (m, 1H), 7.34-7.25 (m, 1H), 5.06 (s, 2H), 4.88-4.74 (m, 5H), 4.50-4.28 (m, 2H), 3.62-3.52 (m, 2H), 3.16-3.06 (m, 2H), 2.85-2.61 (m, 2H).

Example 149

Ethyl 3-[({1-[5-(3-{[(carbamimidoylcarbamoyl)oxy]methyl}-2-fluorophenyl)pyrimidin-2-yl]piperidin-4-ylidene}amino)oxy]propanoate (Compound II-507)

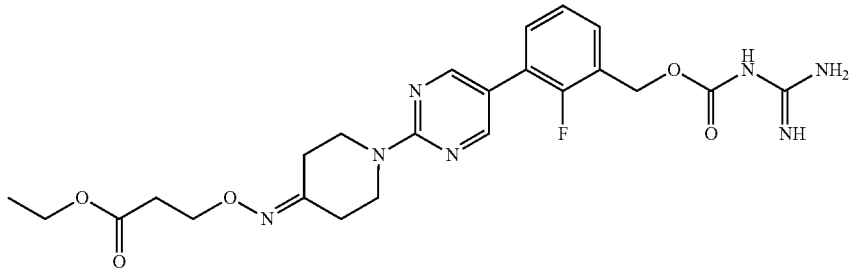 [SMILES: CCOC(=O)CCON=C1CCN(c2ncc(-c3cccc(COC(=O)NC(=N)N)c3F)cn2)CC1]

CDI 27 mg (0.17 mmol) was added to a DMF (2 mL) solution of ethyl 3-{[(1-{5-[2-fluoro-3-(hydroxymethyl)phenyl]pyrimidin-2-yl}piperidin-4-ylidene)amino]oxy}propanoate 34 mg (0.082 mmol) synthesized in the same manner as in Reference Example 7-97, and the mixture was stirred at room temperature for 16 hours. Next, guanidine carbonate 30 mg (0.17 mmol) was added, and the mixture was stirred at room temperature for 6 hours. After the completion of the reaction, water was added to the reaction mixture, and followed by extraction with methylene chloride. The organic layer was washed with water, dried over anhydrous sodium sulfate, and filtered. The filtrate was concentrated under reduced pressure. The concentrated residue was purified by silica gel column chromatography (DNH silica gel, eluting solvent: ethyl acetate:methanol) to give the title compound 20 mg (0.040 mmol, yield 49%) as a white solid.

Mass spectrum (ESI, m/z):502[M+1]$^+$.

$^1$H-NMR spectrum (400 MHz, DMSO-$d_6$+$D_2O$) δ:8.59 (d, J=1.3 Hz, 2H), 7.54-7.47 (m, 1H), 7.43-7.36 (m, 1H), 7.31-7.25 (m, 1H), 5.06 (s, 2H), 4.20 (t, J=6.1 Hz, 2H), 4.08 (q, J=7.1 Hz, 2H), 3.95-3.87 (m, 4H), 2.66-2.60 (m, 2H), 2.57-2.52 (m, 2H), 2.43-2.33 (m, 2H), 1.18 (t, J=7.1 Hz, 3H).

Example 150

3-(2-{4-[(3-Amino-3-oxopropoxy)imino]piperidin-1-yl}pyrimidin-5-yl)-2-fluorobenzyl carbamimidoylcarbamate (Compound II-511)

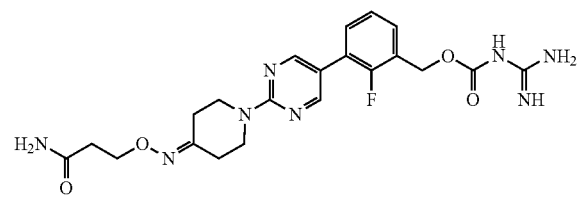 [SMILES: N=C(N)NC(=O)OCc1cccc(-c2cnc(N3CCC(=NOCCC(N)=O)CC3)nc2)c1F]

CDI 59 mg (0.37 mmol) was added to a DMF (4 ml) solution of 3-{[(1-{5-[2-fluoro-3-(hydroxymethyl)phenyl]pyrimidin-2-yl}piperidin-4-ylidene)amino]oxy}propanamide 65 mg (0.17 mmol) synthesized in the same manner as in Reference Example 7-98, and the mixture was stirred at room temperature for 3 hours. Next, guanidine carbonate 61 mg (0.34 mmol) was added, and the mixture was stirred at room temperature for 1 hour. After the completion of the reaction, water was added to the reaction mixture, and followed by extraction with methylene chloride. The organic layer was washed with brine, dried over anhydrous sodium sulfate, and filtered. The filtrate was concentrated under reduced pressure. The concentrated residue was purified by silica gel column chromatography (DNH silica gel, eluting solvent: ethyl acetate:methanol). Ethyl acetate was added to the crude product thus obtained, and the mixture was stirred at 70° C. for 30 minutes. Thereafter, the solid was collected by filtration and was dried under reduced pressure to give the title compound 15 mg (0.031 mmol, yield 18%) as a white solid.

Mass spectrum (ESI, m/z):473[M+1]$^+$.

$^1$H-NMR spectrum (400 MHz, DMSO-$d_6$) δ:8.59 (d, J=1.4 Hz, 2H), 7.54-7.46 (m, 1H), 7.42-7.32 (m, 2H), 7.30-7.24 (m, 1H), 6.83 (br s, 1H), 5.06 (s, 2H), 4.16 (t, J=6.6 Hz, 2H), 3.96-3.88 (m, 4H), 2.58-2.53 (m, 2H), 2.42-2.32 (m, 4H).

Example 151

2-Fluoro-3-[2-(4-{[3-(methylamino)-3-oxopropoxy]imino}piperidin-1-yl)pyrimidin-5-yl]benzyl carbamimidoylcarbamate (Compound II-512)

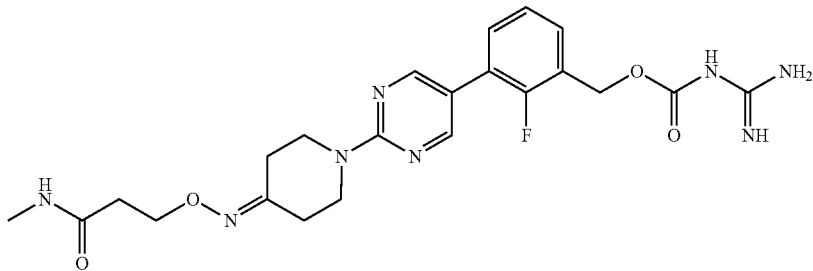 [SMILES: CNC(=O)CCON=C1CCN(c2ncc(-c3cccc(COC(=O)NC(=N)N)c3F)cn2)CC1]

CDI 65 mg (0.40 mmol) was added to a DMF (4 mL) solution of a crude product 80 mg synthesized in the same manner as in Reference Example 7-99 which included 3-{[(1-{5-[2-fluoro-3-(hydroxymethyl)phenyl]pyrimidin-2-yl}piperidin-4-ylidene)amino]oxy}-N-methylpropanamide, and the mixture was stirred at room temperature for 3 hours. Next, guanidine carbonate 72 mg (0.40 mmol) was added, and the mixture was stirred at room temperature for 17 hours. After the completion of the reaction, water was added to the reaction mixture, and followed by extraction with methylene chloride. The organic layer was washed with water, dried over anhydrous sodium sulfate, and filtered. The filtrate was concentrated under reduced pressure. The concentrated residue was purified by silica gel column chromatography (DNH silica gel, eluting solvent: 1,2-dichloroethane:methanol) to give the title compound 32 mg (0.066 mmol) as a white solid.

Mass spectrum (ESI, m/z):487[M+1]$^+$.

$^1$H-NMR spectrum (400 MHz, DMSO-$d_6$+$D_2O$) δ:8.59 (s, 2H), 7.53-7.47 (m, 1H), 7.42-7.36 (m, 1H), 7.31-7.25 (m, 1H), 5.06 (s, 2H), 4.16 (t, J=6.5 Hz, 2H), 3.96-3.87 (m, 4H), 2.60-2.53 (m, 5H), 2.44-2.34 (m, 4H).

Example 152

Ethyl 4-[({1-[5-(3-{[(carbamimidoylcarbamoyl)oxy]methyl}-2-fluorophenyl)pyrimidin-2-yl]piperidin-4-ylidene}amino)oxy]butanoate (Compound II-508)

CDI 85 mg (0.52 mmol) was added to a DMF (4 mL) solution of ethyl 4-{[(1-{5-[2-fluoro-3-(hydroxymethyl)phenyl]pyrimidin-2-yl}piperidin-4-ylidene)amino]oxy}butanoate 0.11 g (0.26 mmol) synthesized in the same manner as in Reference Example 7-100, and the mixture was stirred at room temperature for 7 hours. Next, guanidine carbonate 95 mg (0.53 mmol) was added, and the mixture was stirred at room temperature for 16 hours. After the completion of the reaction, water was added to the reaction mixture, and followed by extraction with methylene chloride. The organic layer was washed with water, dried over anhydrous sodium sulfate, and filtered. The filtrate was concentrated under reduced pressure. The concentrated residue was purified by silica gel column chromatography (DNH silica gel, eluting solvent: ethyl acetate:methanol) to give the title compound 98 mg (0.19 mmol, yield 73%) as a white solid.

Mass spectrum (ESI, m/z):516[M+1]$^+$.

$^1$H-NMR spectrum (400 MHz, DMSO-$d_6$+$D_2O$) δ:8.59 (d, J=1.4 Hz, 2H), 7.55-7.47 (m, 1H), 7.43-7.36 (m, 1H), 7.32-7.23 (m, 1H), 5.06 (s, 2H), 4.05 (q, J=7.2 Hz, 2H), 3.98 (t, J=6.4 Hz, 2H), 3.95-3.89 (m, 4H), 2.61-2.54 (m, 2H), 2.44-2.32 (m, 4H), 1.90-1.81 (m, 2H), 1.18 (t, J=7.2 Hz, 3H).

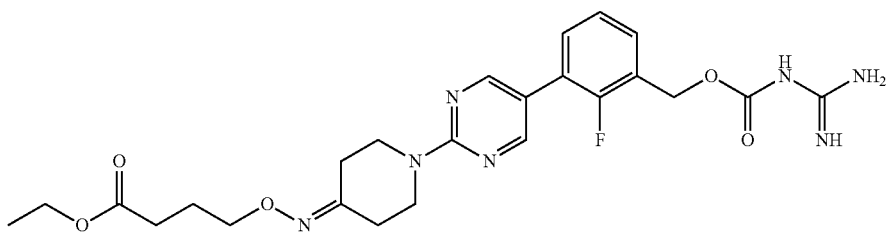 [SMILES: CCOC(=O)CCCON=C1CCN(c2ncc(-c3cccc(COC(=O)NC(=N)N)c3F)cn2)CC1]

Example 153

4-[({1-[5-(3-{[(Carbamimidoylcarbamoyl)oxy]methyl}-2-fluorophenyl)pyrimidin-2-yl]piperidin-4-ylidene}amino)oxy]butanoic acid (Compound II-505)

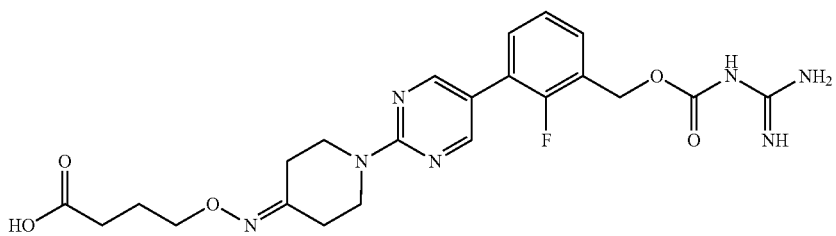 [SMILES: N=C(N)NC(=O)OCc1cccc(-c2cnc(N3CCC(=NOCCCC(=O)O)CC3)nc2)c1F]

Lithium hydroxide 11 mg (0.46 mmol) was added to a THF (6 mL)-water (2 mL) suspension of ethyl 4-[({1-[5-(3-{[(carbamimidoylcarbamoyl)oxy]methyl}-2-fluorophenyl)pyrimidin-2-yl]piperidin-4-ylidene}amino)oxy]butanoate 85 mg (0.17 mmol) synthesized in the same manner as in Example 152, and the mixture was stirred at 50° C. for 6 hours. After the completion of the reaction, acetic acid 0.1 ml (1.7 mmol) and water were added to the reaction mixture, and the mixture was stirred at room temperature. The precipitated solid was collected by filtration. The obtained solid was dried under reduced pressure to give the title compound 65 mg (0.13 mmol, yield 77%) as a white solid.

Mass spectrum (ESI, m/z):488[M+1]$^+$.

$^1$H-NMR spectrum (400 MHz, DMSO-d$_6$+D$_2$O) δ:8.59 (d, J=1.4 Hz, 2H), 7.54-7.47 (m, 1H), 7.43-7.37 (m, 1H), 7.32-7.26 (m, 1H), 5.06 (s, 2H), 3.98 (t, J=6.4 Hz, 2H), 3.95-3.88 (m, 4H), 2.61-2.55 (m, 2H), 2.43-2.33 (m, 2H), 2.28 (t, J=7.3 Hz, 2H), 1.88-1.77 (m, 2H).

Example 154

3-[2-(4-{[3-(Dimethylamino)-3-oxopropoxy]imino}piperidin-1-yl)pyrimidin-5-yl]-2-fluorobenzyl carbamimidoylcarbamate (Compound II-513)

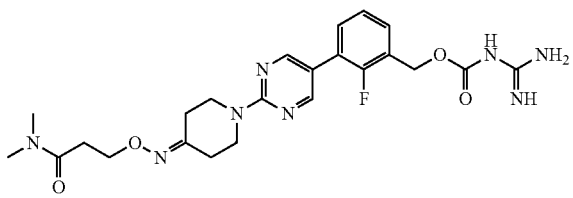 [SMILES: CN(C)C(=O)CCON=C1CCN(c2ncc(-c3cccc(COC(=O)NC(=N)N)c3F)cn2)CC1]

CDI 117 mg (0.722 mmol) was added to a DMF (6 mL) solution of 3-{[(1-{5-[2-fluoro-3-(hydroxymethyl)phenyl]pyrimidin-2-yl}piperidin-4-ylidene)amino]oxy}-N,N-dimethylpropanamide 150 mg (0.361 mmol) synthesized in the same manner as in Reference Example 7-101, and the mixture was stirred at room temperature for 7 hours. Next, guanidine carbonate 130 mg (0.722 mmol) was added, and the mixture was stirred at room temperature for 14 hours. After the completion of the reaction, water was added to the reaction mixture, and followed by extraction with methylene chloride. The organic layer was washed with water, dried over anhydrous sodium sulfate, and filtered. The filtrate was concentrated under reduced pressure. The concentrated residue was purified by silica gel column chromatography (DNH silica gel, eluting solvent: ethyl acetate:methanol) to give the title compound 123 mg (0.246 mmol, yield 68%) as a white solid.

Mass spectrum (ESI, m/z):501[M+1]$^+$.

$^1$H-NMR spectrum (400 MHz, DMSO-d$_6$+D$_2$O) δ:8.59 (d, J=1.4 Hz, 2H), 7.54-7.47 (m, 1H), 7.43-7.36 (m, 1H), 7.32-7.25 (m, 1H), 5.06 (s, 2H), 4.19 (t, J=6.7 Hz, 2H), 3.97-3.87 (m, 4H), 2.96 (s, 3H), 2.81 (s, 3H), 2.65 (t, J=6.7 Hz, 2H), 2.58-2.53 (m, 2H), 2.42-2.36 (m, 2H).

Example 155

3-(2-{4-[(2-Acetamidoethoxy)imino]piperidin-1-yl}pyrimidin-5-yl)-2-fluorobenzyl carbamimidoylcarbamate (Compound II-519)

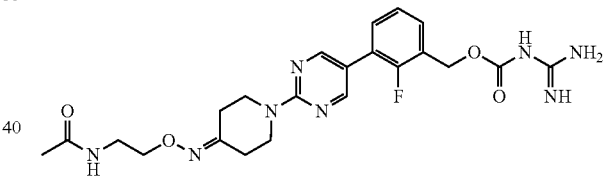

CDI 30 mg (0.19 mmol) was added to a DMF (4 mL) solution of N-(2-{[(1-{5-[2-fluoro-3-(hydroxymethyl)phenyl]pyrimidin-2-yl}piperidin-4-ylidene)amino]oxy}ethyl)acetamide 37 mg (0.092 mmol) synthesized in the same manner as in Reference Example 7-102, and the mixture was stirred at room temperature for 7 hours. Next, guanidine carbonate 34 mg (0.19 mmol) was added, and the mixture was stirred at room temperature for 16 hours. After the completion of the reaction, water was added to the reaction mixture, and followed by extraction with methylene chloride. The organic layer was washed with water, dried over anhydrous sodium sulfate, and filtered. The filtrate was concentrated under reduced pressure. The concentrated residue was purified by silica gel column chromatography (DNH silica gel, eluting solvent: ethyl acetate:methanol) to give the title compound 37 mg (0.076 mmol, yield 83%) as a white solid.

Mass spectrum (ESI, m/z):487[M+1]$^+$.

$^1$H-NMR spectrum (400 MHz, DMSO-d$_6$+D$_2$O) δ:8.60 (d, J=1.4 Hz, 2H), 7.56-7.47 (m, 1H), 7.44-7.37 (m, 1H), 7.32-7.25 (m, 1H), 5.06 (s, 2H), 4.01-3.89 (m, 6H), 3.33-3.26 (m, 2H), 2.64-2.56 (m, 3H), 2.43-2.36 (m, 2H), 1.82 (s, 3H).

Example 156

2-Fluoro-3-[2-(4-{[2-(N-methylacetamido)ethoxy]imino}piperidin-1-yl)pyrimidin-5-yl]benzyl carbamimidoylcarbamate (Compound III-520)

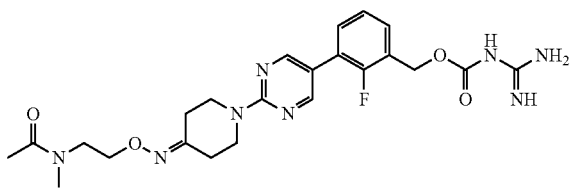 [SMILES: CC(=O)N(C)CCON=C1CCN(c2ncc(-c3cccc(COC(=O)NC(=N)N)c3F)cn2)CC1]

CDI 75 mg (0.46 mmol) was added to a DMF (4 mL) solution of N-(2-{[(1-{5-[2-fluoro-3-(hydroxymethyl)phenyl]pyrimidin-2-yl}piperidin-4-ylidene)amino]oxy}ethyl)-N-methylacetamide 95 mg (0.23 mmol) synthesized in the same manner as in Reference Example 7-103, and the mixture was stirred at room temperature for 7 hours. Next, guanidine carbonate 83 mg (0.46 mmol) was added, and the mixture was stirred at room temperature for 14 hours. After the completion of the reaction, water was added to the reaction mixture, and followed by extraction with methylene chloride. The organic layer was washed with water, dried over anhydrous sodium sulfate, and filtered. The filtrate was concentrated under reduced pressure. The concentrated residue was purified by silica gel column chromatography (DNH silica gel, eluting solvent: ethyl acetate:methanol) to give the title compound 73 mg (0.15 mmol, yield 65%) as a white solid.

Mass spectrum (ESI, m/z):501[M+1]$^+$.

$^1$H-NMR spectrum (400 MHz, DMSO-d$_6$+D$_2$O) δ:8.60 (d, J=1.4 Hz, 2H), 7.54-7.47 (m, 1H), 7.43-7.36 (m, 1H), 7.32-7.25 (m, 1H), 5.06 (s, 2H), 4.17-4.02 (m, 2H), 3.97-3.88 (m, 4H), 3.59-3.47 (m, 2H), 3.02-2.77 (m, 3H), 2.62-2.54 (m, 2H), 2.42-2.35 (m, 2H), 2.00-1.96 (m, 3H).

Example 157

2-Fluoro-3-[2-(4-{[2-(N-methylmethylsulfonamido)ethoxy]imino}piperidin-1-yl)pyrimidin-5-yl]benzyl carbamimidoylcarbamate hydrochloride (Compound II-522 hydrochloride)

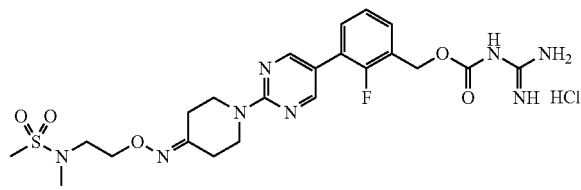 [SMILES: CN(CCON=C1CCN(c2ncc(-c3cccc(COC(=O)NC(=N)N)c3F)cn2)CC1)S(C)(=O)=O ; Cl]

CDI 59 mg (0.36 mmol) was added to a DMF (2.5 mL) solution of N-(2-{[(1-{5-[2-fluoro-3-(hydroxymethyl)phenyl]pyrimidin-2-yl}piperidin-4-ylidene)amino]oxy}ethyl)-N-methylmethanesulfonamide 55 mg (0.12 mmol) synthesized in the same manner as in Reference Example 7-104, and the mixture was stirred at room temperature for 17 hours. Next, guanidine carbonate 66 mg (0.37 mmol) was added, and the mixture was stirred at room temperature for 2 hours. After the completion of the reaction, water was added to the reaction mixture, and the mixture was stirred at room temperature. The precipitated solid was collected by filtration and was washed with TBME. The crude product thus obtained was purified by silica gel column chromatography (DNH silica gel, eluting solvent: ethyl acetate:methanol). The crude product obtained was dissolved into 2 N HCl/ethanol, and the solution was concentrated under reduced pressure. The crude product thus obtained was washed with ethyl acetate and was dried under reduced pressure to give the title compound 51 mg (0.089 mmol, yield 74%) as a white solid.

Mass spectrum (ESI, m/z):537[M+1]$^+$.

$^1$H-NMR (400 MHz, DMSO-d$_6$+D$_2$O) δ:8.61 (d, J=1.3 Hz, 2H), 7.67-7.59 (m, 1H), 7.55-7.49 (m, 1H), 7.39-7.32 (m, 1H), 5.36 (s, 2H), 4.16-4.08 (m, 2H), 3.98-3.89 (m, 4H), 3.38-3.30 (m, 2H), 2.88 (s, 3H), 2.81 (s, 3H), 2.63-2.56 (m, 2H), 2.44-2.38 (m, 2H).

Example 158

3-{2-[4-({2-[N-(tert-butoxycarbonyl)methylsulfonamido]ethoxy}imino)piperidin-1-yl]pyrimidin-5-yl}-2-fluorobenzyl carbamimidoylcarbamate (Compound II-570)

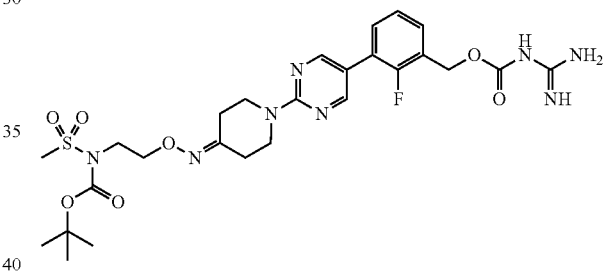

CDI 78 mg (0.48 mmol) was added to a DMF (3 mL) solution of tert-butyl (2-{[(1-{5-[2-fluoro-3-(hydroxymethyl)phenyl]pyrimidin-2-yl}piperidin-4-ylidene)amino]oxy}ethyl)(methylsulfonyl)carbamate 86 mg (0.16 mmol) synthesized in the same manner as in Reference Example 7-105, and the mixture was stirred at room temperature for 16 hours. Next, guanidine carbonate 86 mg (0.48 mmol) was added, and the mixture was stirred at room temperature for 2 hours. After the completion of the reaction, a saturated aqueous ammonium chloride solution was added to the reaction mixture, and followed by extraction with ethyl acetate. The organic layer was washed with brine, dried over anhydrous magnesium sulfate, and filtered. The filtrate was concentrated under reduced pressure. The concentrated residue was purified by silica gel column chromatography (DNH silica gel, eluting solvent: ethyl acetate:methanol) to give the title compound 62 mg (0.10 mmol, yield 63%) as a colorless oil.

Mass spectrum (ESI, m/z):623[M+1]$^+$.

$^1$H-NMR (400 MHz, DMSO-d$_6$+D$_2$O) δ:8.60 (d, J=1.3 Hz, 2H), 7.55-7.47 (m, 1H), 7.43-7.36 (m, 1H), 7.33-7.23 (m, 1H), 5.06 (s, 2H), 4.14-4.08 (m, 2H), 3.97-3.82 (m, 6H), 3.34 (s, 3H), 2.62-2.46 (m, 2H), 2.43-2.35 (m, 2H), 1.47 (s, 9H).

Example 159

2-Fluoro-3-[2-(4-{[2-(methylsulfonamido)ethoxy]imino}piperidin-1-yl)pyrimidin-5-yl]benzyl carbamimidoylcarbamate (Compound II-521)

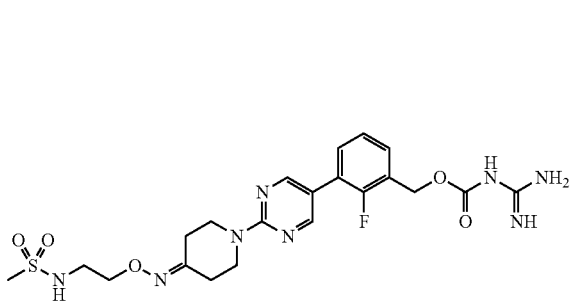 [SMILES: CS(=O)(=O)NCCON=C1CCN(c2ncc(-c3cccc(COC(=O)NC(=N)N)c3F)cn2)CC1]

2 M hydrogen chloride/ethanol solution (2 mL) was added to 3-{2-[4-({2-[N-(tert-butoxycarbonyl)methylsulfonamido]ethoxy}imino)piperidin-1-yl]pyrimidin-5-yl}-2-fluorobenzyl carbamimidoylcarbamate 62 mg (0.10 mmol) synthesized in the same manner as in Example 158, and the mixture was stirred at room temperature for 22 hours. After the completion of the reaction, the reaction mixture was concentrated under reduced pressure. The concentrated residue was washed with TBME and was filtered. The crude product thus obtained was dissolved into ethanol and was neutralized with triethylamine. The resultant solution was purified by silica gel column chromatography (DNH silica gel, eluting solvent: ethyl acetate:methanol) to give the title compound 23 mg (0.044 mmol, yield 44%) as a white solid.

Mass spectrum (ESI, m/z):523[M+].

$^1$H-NMR (400 MHz, DMSO-$d_6$+$D_2O$) δ:8.63-8.57 (m, 2H), 7.55-7.47 (m, 1H), 7.44-7.36 (m, 1H), 7.33-7.25 (m, 1H), 5.06 (s, 2H), 4.03 (t, J=5.7 Hz, 2H), 3.97-3.89 (m, 4H), 3.21 (t, J=5.7 Hz, 2H), 2.91 (s, 3H), 2.65-2.58 (m, 2H), 2.44-2.36 (m, 2H).

Example 160

3-[2-(4-{[2-(Dimethylamino)ethoxy]imino}piperidin-1-yl)pyrimidin-5-yl]-2-fluorobenzyl carbamimidoylcarbamate (Compound II-517)

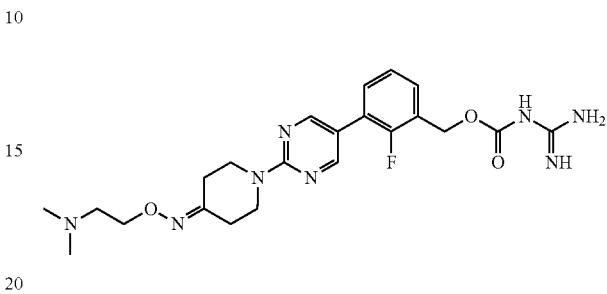

CDI 28 mg (0.17 mmol) was added to a DMF (1.5 mL) solution of 1-{5-[2-fluoro-3-(hydroxymethyl)phenyl]pyrimidin-2-yl}piperidin-4-one O-[2-(dimethylamino)ethyl] oxime 14 mg (0.036 mmol) synthesized in the same manner as in Reference Example 7-106, and the mixture was stirred at room temperature for 3 hours. Next, guanidine carbonate 31 mg (0.17 mmol) was added, and the mixture was stirred at room temperature for 1 hour. After the completion of the reaction, water was added to the reaction mixture, and the mixture was stirred at room temperature. The precipitated solid was collected by filtration. The crude product thus obtained was washed with TBME and was dried under reduced pressure to give the title compound 14 mg (0.030 mmol, yield 83%) as a white solid.

Mass spectrum (ESI, m/z):473[M+1]$^+$.

$^1$H-NMR (400 MHz, DMSO-$d_6$+$D_2O$) δ:8.59 (d, J=1.4 Hz, 2H), 7.55-7.46 (m, 1H), 7.43-7.37 (m, 1H), 7.33-7.24 (m, 1H), 5.06 (s, 2H), 4.06 (t, J=6.0 Hz, 2H), 3.96-3.88 (m, 4H), 2.63-2.45 (m, 4H), 2.42-2.36 (m, 2H), 2.17 (s, 6H).

Example 161

3-{2-[4-({2-[(tert-Butoxycarbonyl)(methyl)amino]ethoxy}imino)piperidin-1-yl]pyrimidin-5-yl}-2-fluorobenzyl carbamimidoylcarbamate (Compound II-571)

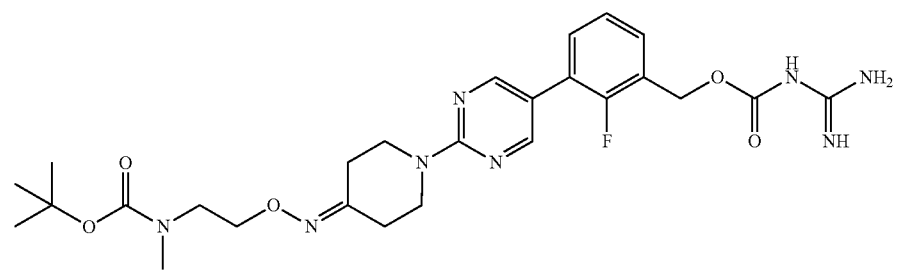 [SMILES: CN(CCON=C1CCN(c2ncc(-c3cccc(COC(=O)NC(=N)N)c3F)cn2)CC1)C(=O)OC(C)(C)C]

CDI 71.0 mg (0.438 mmol) was added to a DMF (2 mL) solution of tert-butyl (2-{[(1-{5-[2-fluoro-3-(hydroxymethyl)phenyl]pyrimidin-2-yl}piperidin-4-ylidene)amino]oxy}ethyl)(methyl)carbamate 103 mg (0.218 mmol) synthesized in the same manner as in Reference Example 7-107, and the mixture was stirred at room temperature for 2 hours. Next, guanidine carbonate 78.0 mg (0.433 mmol) was added, and the mixture was stirred at room temperature for 2 hours. After the completion of the reaction, a saturated aqueous ammonium chloride solution was added to the reaction mixture, and followed by extraction with ethyl acetate. The organic layer was washed with brine, dried over anhydrous magnesium sulfate, and filtered. The filtrate was concentrated under reduced pressure. The concentrated residue was purified by silica gel column chromatography (DIOL silica gel, eluting solvent: ethyl acetate:methanol) to give the title compound 87.0 mg (0.156 mmol, yield 72%) as a white solid.

Mass spectrum (ESI, m/z):559[M+1]$^+$.

$^1$H-NMR (400 MHz, DMSO-d$_6$) δ:8.60 (d, J=1.4 Hz, 2H), 7.54-7.47 (m, 1H), 7.43-7.35 (m, 1H), 7.32-7.24 (m, 1H), 5.06 (s, 2H), 4.10-4.01 (m, 2H), 3.98-3.87 (m, 4H), 3.45-3.37 (m, 2H), 2.86-2.75 (m, 2H), 2.63-2.45 (m, 2H), 2.43-2.36 (m, 2H), 1.38 (s, 9H).

Example 162

2-Fluoro-3-[2-(4-{[2-(methylamino)ethoxy]imino}piperidin-1-yl)pyrimidin-5-yl]benzyl carbamimidoylcarbamate dihydrochloride (Compound II-516 dihydrochloride)

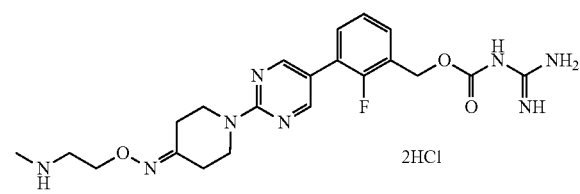 [SMILES: CNCCON=C1CCN(c2ncc(-c3cccc(COC(=O)NC(=N)N)c3F)cn2)CC1]

2 M hydrogen chloride/ethanol solution (3 mL) was added to 3-{2-[4-({2-[(tert-butoxycarbonyl)(methyl)amino]ethoxy}imino)piperidin-1-yl]pyrimidin-5-yl}-2-fluorobenzyl carbamimidoylcarbamate 87 mg (0.16 mmol) synthesized in the same manner as in Example 161, and the mixture was stirred at room temperature for 14 hours. After the completion of the reaction, the reaction mixture was concentrated under reduced pressure. The concentrated residue was washed with TBME to give the title compound 66 mg (0.12 mmol, yield 75%) as a white solid.

Mass spectrum (ESI, m/z):459[M+1]$^+$.

$^1$H-NMR (400 MHz, DMSO-d$_6$+D$_2$O) δ:8.61 (d, J=1.3 Hz, 2H), 7.66-7.58 (m, 1H), 7.56-7.48 (m, 1H), 7.39-7.30 (m, 1H), 5.36 (s, 2H), 4.26-4.18 (m, 2H), 4.00-3.90 (m, 4H), 3.24-3.16 (m, 2H), 2.69-2.62 (m, 2H), 2.60 (s, 3H), 2.46-2.38 (m, 2H).

Example 163

3-{2-[4-({2-[(Di-tert-butoxycarbonyl)amino]ethoxy}imino)piperidin-1-yl]pyrimidin-5-yl}-2-fluorobenzyl carbamimidoylcarbamate (Compound II-572)

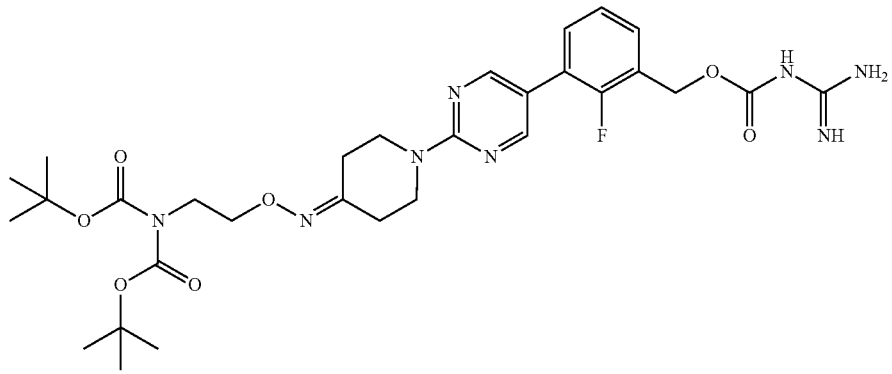 [SMILES: CC(C)(C)OC(=O)N(CCON=C1CCN(c2ncc(-c3cccc(COC(=O)NC(=N)N)c3F)cn2)CC1)C(=O)OC(C)(C)C]

CDI 61.0 mg (0.376 mmol) was added to a DMF (2 mL) solution of di-tert-butyl (2-{[(1-{5-[2-fluoro-3-(hydroxymethyl)phenyl]pyrimidin-2-yl}piperidin-4-ylidene)amino]oxy}ethyl)carbamate 105 mg (0.188 mmol) synthesized in the same manner as in Reference Example 7-108, and the mixture was stirred at room temperature for 2 hours. Next, guanidine carbonate 68 mg (0.377 mmol) was added, and the mixture was stirred at room temperature for 2 hours. After the completion of the reaction, a saturated aqueous ammonium chloride solution was added to the reaction mixture, and followed by extraction with ethyl acetate. The organic layer was washed with brine, dried over anhydrous magnesium sulfate, and filtered. The filtrate was concentrated under reduced pressure. The concentrated residue was purified by silica gel column chromatography (DIOL silica gel, eluting solvent: ethyl acetate:methanol) to give the title compound 99.0 mg (0.154 mmol, yield 82%) as a colorless oil.

Mass spectrum (ESI, m/z):645[M+1]$^+$.

$^1$H-NMR (400 MHz, DMSO-d$_6$) δ:8.59 (d, J=1.4 Hz, 2H), 7.53-7.46 (m, 1H), 7.42-7.36 (m, 1H), 7.31-7.24 (m, 1H), 5.06 (s, 2H), 4.11-4.05 (m, 2H), 3.95-3.87 (m, 4H), 3.79-3.73 (m, 2H), 2.58-2.47 (m, 2H), 2.42-2.35 (m, 2H), 1.43 (s, 18H).

Example 164

3-(2-{4-[(2-Aminoethoxy)imino]piperidin-1-yl}pyrimidin-5-yl)-2-fluorobenzyl carbamimidoylcarbamate (Compound II-515)

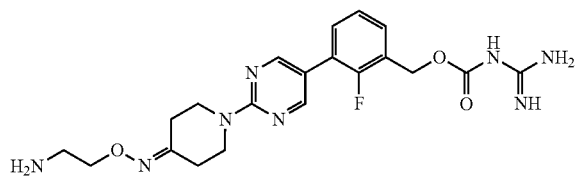 [SMILES: N=C(N)NC(=O)OCc1cccc(-c2cnc(N3CCC(=NOCCN)CC3)nc2)c1F]

2 M hydrogen chloride/ethanol solution (3 mL) was added to 3-{2-[4-({2-[(di-tert-butoxycarbonyl)amino]ethoxy}imino)piperidin-1-yl]pyrimidin-5-yl}-2-fluorobenzyl carbamimidoylcarbamate 99 mg (0.15 mmol) synthesized in the same manner as in Example 163, and the mixture was stirred at room temperature for 14 hours. After the completion of the reaction, the reaction mixture was concentrated under reduced pressure. The concentrated residue was washed with TBME and was filtered. The residue obtained was dissolved into ethanol and was neutralized with triethylamine. The solution thus obtained was purified by silica gel column chromatography (DIOL silica gel, eluting solvent: ethyl acetate:methanol). The crude product thus obtained was washed with TBME and was dried under reduced pressure to give the title compound 43 mg (0.097 mmol, yield 65%) as a white solid.

Mass spectrum (ESI, m/z):445[M+1]$^+$.

$^1$H-NMR (400 MHz, DMSO-d$_6$+D$_2$O) δ:8.59 (d, J=1.3 Hz, 2H), 7.54-7.47 (m, 1H), 7.43-7.36 (m, 1H), 7.32-7.25 (m, 1H), 5.06 (s, 2H), 3.98-3.89 (m, 6H), 2.76-2.70 (m, 2H), 2.63-2.57 (m, 2H), 2.42-2.35 (m, 2H).

Example 165

3-(2-{4-[(2-Cyanoethoxy)imino]piperidin-1-yl}pyrimidin-5-yl)-2-fluorobenzyl carbamimidoylcarbamate (Compound II-526)

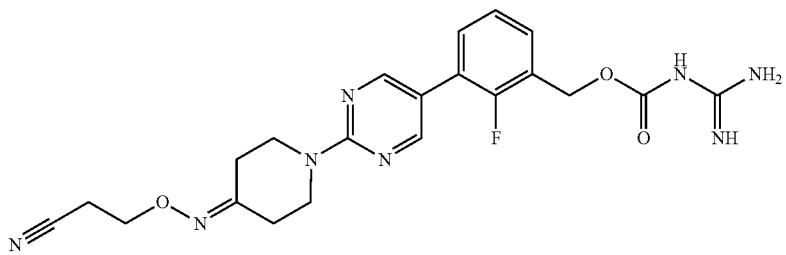 [SMILES: N#CCCON=C1CCN(c2ncc(-c3cccc(COC(=O)NC(=N)N)c3F)cn2)CC1]

CDI 53 mg (0.33 mmol) was added to a DMF (4 ml) solution of 3-{[(1-{5-[2-fluoro-3-(hydroxymethyl)phenyl]pyrimidin-2-yl}piperidin-4-ylidene)amino]oxy}propanenitrile 60 mg (0.16 mmol) synthesized in the same manner as in Reference Example 7-109, and the mixture was stirred at room temperature for 14 hours. Next, guanidine carbonate 59 mg (0.33 mmol) was added, and the mixture was stirred at room temperature for 1 hour. After the completion of the reaction, water was added to the reaction mixture, and followed by extraction with methylene chloride. The organic layer was washed with water, dried over anhydrous sodium sulfate, and filtered. The filtrate was concentrated under reduced pressure. The concentrated residue was purified by silica gel column chromatography (DNH silica gel, eluting solvent: ethyl acetate:methanol) to give the title compound 67 mg (0.15 mmol, yield 91%) as a white solid.

Mass spectrum (ESI, m/z):455[M+1]$^+$.

$^1$H-NMR spectrum (400 MHz, DMSO-d$_6$+D$_2$O) δ:8.60 (d, J=1.4 Hz, 2H), 7.54-7.47 (m, 1H), 7.43-7.37 (m, 1H), 7.31-7.26 (m, 1H), 5.06 (s, 2H), 4.17 (t, J=6.0 Hz, 2H), 3.99-3.91 (m, 4H), 2.85 (t, J=6.0 Hz, 2H), 2.65-2.55 (m, 2H), 2.48-2.39 (m, 2H).

Example 166

3-(2-{4-[(3-Cyanopropoxy)imino]piperidin-1-yl}pyrimidin-5-yl)-2-fluorobenzyl carbamimidoylcarbamate (Compound II-527)

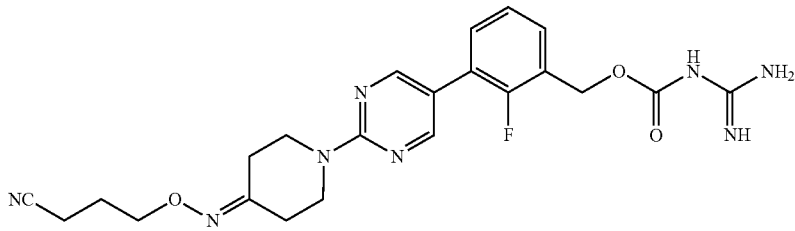 [SMILES: N#CCCCON=C1CCN(c2ncc(-c3cccc(COC(=O)NC(=N)N)c3F)cn2)CC1]

CDI 60 mg (0.37 mmol) was added to a DMF (4 mL) solution of 4-{[(1-{5-[2-fluoro-3-(hydroxymethyl)phenyl]pyrimidin-2-yl}piperidin-4-ylidene)amino]oxy}butanenitrile 69 mg (0.18 mmol) synthesized in the same manner as in Reference Example 7-110, and the mixture was stirred at room temperature for 7 hours. Next, guanidine carbonate 65 mg (0.36 mmol) was added, and the mixture was stirred at room temperature for 16 hours. After the completion of the reaction, water was added to the reaction mixture, and followed by extraction with methylene chloride. The organic layer was washed with water, dried over anhydrous sodium sulfate, and filtered. The filtrate was concentrated under reduced pressure. The concentrated residue was purified by silica gel column chromatography (DNH silica gel, eluting solvent: ethyl acetate:methanol) to give the title compound 69 mg (0.15 mmol, yield 83%) as a white solid.

Mass spectrum (ESI, m/z):469[M+1]$^+$.

$^1$H-NMR spectrum (400 MHz, DMSO-d$_6$+D$_2$O) δ:8.59 (d, J=1.4 Hz, 2H), 7.55-7.47 (m, 1H), 7.44-7.36 (m, 1H), 7.33-7.25 (m, 1H), 5.06 (s, 2H), 4.05 (t, J=6.0 Hz, 2H), 3.97-3.89 (m, 4H), 2.64-2.49 (m, 4H), 2.44-2.37 (m, 2H), 1.96-1.85 (m, 2H).

Example 167

2-Fluoro-3-[2-(4-{[2-(methylsulfonyl)ethoxy]imino}piperidin-1-yl)pyrimidin-5-yl]benzyl carbamimidoylcarbamate (Compound II-528)

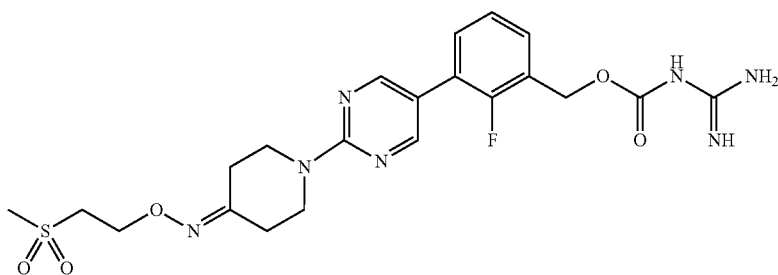 [SMILES: CS(=O)(=O)CCON=C1CCN(c2ncc(-c3cccc(COC(=O)NC(=N)N)c3F)cn2)CC1]

CDI 52 mg (0.29 mmol) was added to a DMF (6 mL) solution of 1-{5-[2-fluoro-3-(hydroxymethyl)phenyl]pyrimidin-2-yl}piperidin-4-one O-[2-(methylsulfonyl)ethyl]oxime 61 mg (0.14 mmol) synthesized in the same manner as in Reference Example 7-111, and the mixture was stirred at room temperature for 14 hours. Next, guanidine carbonate 47 mg (0.29 mmol) was added, and the mixture was stirred at room temperature for 7 hours. After the completion of the reaction, water and methylene chloride were added to the reaction mixture, and the mixture was stirred at room temperature. The precipitated solid was collected by filtration and was dried under reduced pressure to give the title compound 19 mg (0.037 mmol, yield 26%) as a white solid.

Mass spectrum (ESI, m/z):508[M+1]$^+$.

$^1$H-NMR spectrum (400 MHz, DMSO-d$_6$+D$_2$O) δ:8.60 (d, J=1.3 Hz, 2H), 7.55-7.47 (m, 1H), 7.43-7.36 (m, 1H), 7.33-7.24 (m, 1H), 5.06 (s, 2H), 4.35 (t, J=5.8 Hz, 2H), 3.96-3.87 (m, 4H), 3.52-3.43 (m, 2H), 2.99 (s, 3H), 2.63-2.56 (m, 2H), 2.46-2.38 (m, 2H).

Example 168

2-Fluoro-3-[2-(4-{[3-(methylsulfonyl)propoxy]imino}piperidin-1-yl)pyrimidin-5-yl]benzyl carbamimidoylcarbamate (Compound II-529)

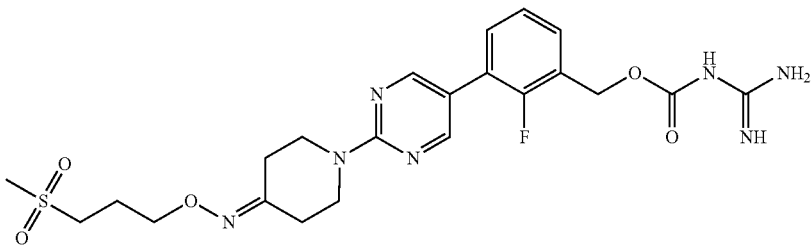 [SMILES: CS(=O)(=O)CCCON=C1CCN(c2ncc(-c3cccc(COC(=O)NC(=N)N)c3F)cn2)CC1]

CDI 6.0 mg (0.037 mmol) was added to a DMF (1 ml) solution of 1-{5-[2-fluoro-3-(hydroxymethyl)phenyl]pyrimidin-2-yl}piperidin-4-one O-[3-(methylsulfonyl)propyl] oxime 8.0 mg (0.018 mmol) synthesized in the same manner as in Reference Example 7-112, and the mixture was stirred at room temperature for 14 hours. Further, CDI 12 mg (0.074 mmol) was added, and the mixture was stirred at room temperature for 2 hours. Further, CDI 12 mg (0.074 mmol) was added, and the mixture was stirred at room temperature for 2 hours. Next, guanidine carbonate 6.0 mg (0.033 mmol) was added, and the mixture was stirred at room temperature for 2 hours. After the completion of the reaction, water was added to the reaction mixture, and followed by extraction with ethyl acetate. The organic layer was washed with brine, dried over anhydrous sodium sulfate, and filtered. The filtrate was concentrated under reduced pressure. The concentrated residue was purified by silica gel column chromatography (DNH silica gel, eluting solvent: ethyl acetate:methanol). Ethyl acetate was added to the crude product thus obtained, and the mixture was stirred at 70° C. for 30 minutes. Thereafter, the solid was collected by filtration and was dried under reduced pressure to give the title compound 5.6 mg (0.011 mmol, yield 61%) as a white solid.

Mass spectrum (ESI, m/z):522[M+1]$^+$.

$^1$H-NMR spectrum (400 MHz, DMSO-d$_6$+D$_2$O) δ:8.60 (d, J=1.1 Hz, 2H), 7.55-7.46 (m, 1H), 7.44-7.35 (m, 1H), 7.32-7.25 (m, 1H), 5.06 (s, 2H), 4.08 (t, J=6.3 Hz, 2H), 3.98-3.88 (m, 4H), 3.23-3.11 (m, 2H), 2.98 (s, 3H), 2.64-2.57 (m, 2H), 2.44-2.36 (m, 2H), 2.08-1.98 (m, 2H).

Example 169

2-Fluoro-3-[2-(4-{[(1-methyl-1H-pyrazol-3-yl)methoxy]imino}piperidin-1-yl)pyrimidin-5-yl]benzyl carbamimidoylcarbamate (Compound II-541)

CDI 73 mg (0.45 mmol) was added to a DMF (3 mL) solution of 1-{5-[2-fluoro-3-(hydroxymethyl)phenyl]pyrimidin-2-yl}piperidin-4-one O-[(1-methyl-1H-pyrazol-3-yl)methyl] oxime 83 mg (0.20 mmol) synthesized in the same manner as Reference Compound 7-113, and the mixture was stirred at room temperature for 14 hours. Next, guanidine carbonate 73 mg (0.41 mmol) was added, and the mixture was stirred at room temperature for 3.5 hours. After the completion of the reaction, water was added to the reaction mixture, and followed by extraction with methylene chloride. The organic layer was washed with brine, dried over anhydrous sodium sulfate, and filtered. The filtrate was concentrated under reduced pressure. The concentrated residue was purified by silica gel column chromatography (DNH silica gel, eluting solvent: 1,2-dichloroethane:methanol). Ethyl acetate was added to the crude product thus obtained, and the mixture was ultrasonicated. The solid was collected by filtration and was dried under reduced pressure to give the title compound 55 mg (0.11 mmol, yield 55%) as a white solid Mass spectrum (APCI, m/z):496[M+1]$^+$.

$^1$H-NMR spectrum (400 MHz, DMSO-d$_6$+D$_2$O) δ:8.59 (d, J=1.3 Hz, 2H), 7.61 (d, J=2.1 Hz, 1H), 7.53-7.47 (m, 1H), 7.42-7.36 (m, 1H), 7.31-7.25 (m, 1H), 6.23 (d, J=2.1 Hz, 1H), 5.06 (s, 2H), 4.93 (s, 2H), 3.95-3.87 (m, 4H), 3.80 (s, 3H), 2.60-2.48 (m, 2H), 2.42-2.35 (m, 2H).

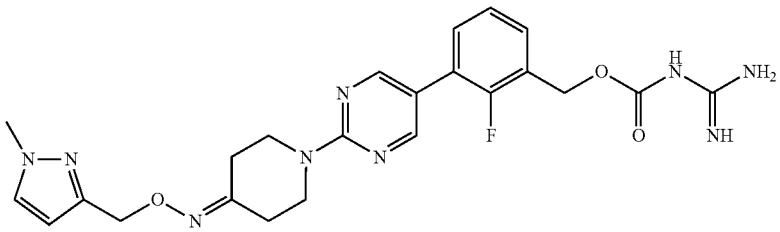 [SMILES: Cn1ccc(CON=C2CCN(c3ncc(-c4cccc(COC(=O)NC(=N)N)c4F)cn3)CC2)n1]

Example 170

2-Fluoro-3-{2-[4-({[1-(tetrahydropyran-2-yl)-1H-pyrazol-3-yl]methoxy}imino)piperidin-1-yl]pyrimidin-5-yl}benzyl carbamimidoylcarbamate (Compound II-573)

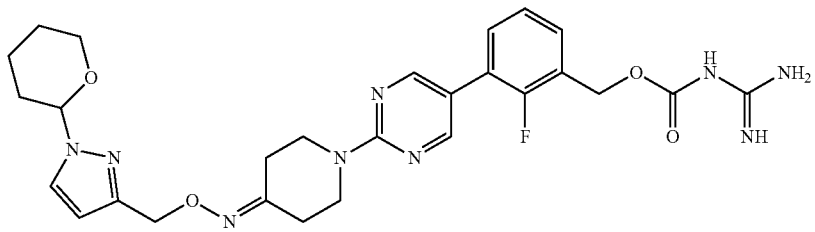 [SMILES: N=C(N)NC(=O)OCc1cccc(-c2cnc(N3CCC(=NOCc4ccn(C5CCCCO5)n4)CC3)nc2)c1F]

CDI 16 mg (0.10 mmol) was added to a DMF (4 ml) solution of 1-{5-[2-fluoro-3-(hydroxymethyl)phenyl]pyrimidin-2-yl}piperidin-4-one O-{[1-(tetrahydropyran-2-yl)-1H-pyrazol-3-yl]methyl} oxime 23 mg (0.048 mmol) synthesized in the same manner as in Reference Example 7-114, and the mixture was stirred at room temperature for 14 hours. Further, CDI 8.0 mg (0.049 mmol) was added, and the mixture was stirred at room temperature for 1.5 hours. Next, guanidine carbonate 18 mg (0.10 mmol) was added, and the mixture was stirred at room temperature for 2 hours. After the completion of the reaction, water was added to the reaction mixture, and followed by extraction with methylene chloride. The organic layer was washed with water, dried over anhydrous sodium sulfate, and filtered. The filtrate was concentrated under reduced pressure. The concentrated residue was purified by silica gel column chromatography (DNH silica gel, eluting solvent: ethyl acetate:methanol) to give the title compound 27 mg (0.047 mmol, yield 98%) as a white solid.

Mass spectrum (ESI, m/z):566[M+1]$^+$.

$^1$H-NMR spectrum (400 MHz, CDCl$_3$) δ:8.52 (d, J=1.4 Hz, 2H), 7.57 (d, J=2.4 Hz, 1H), 7.46-7.40 (m, 1H), 7.32-7.27 (m, 1H), 7.22-7.14 (m, 1H), 6.36 (d, J=2.4 Hz, 1H), 5.40-5.33 (m, 1H), 5.24 (s, 2H), 5.12 (s, 2H), 4.11-4.03 (m, 1H), 4.03-3.94 (m, 4H), 3.75-3.63 (m, 1H), 2.72-2.67 (m, 2H), 2.49-2.44 (m, 2H), 2.19-1.97 (m, 3H), 1.80-1.49 (m, 3H).

Example 171

3-[2-(4-{[(1H-pyrazol-3-yl)methoxy]imino}piperidin-1-yl)pyrimidin-5-yl]-2-fluorobenzyl carbamimidoylcarbamate (Compound II-539)

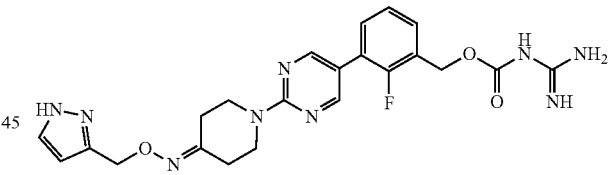

2 M hydrogen chloride/ethanol solution (1.6 ml) was added to 2-fluoro-3-{2-[4-({[1-(tetrahydropyran-2-yl)-1H-pyrazol-3-yl]methoxy}imino)piperidin-1-yl]pyrimidin-5-yl}benzyl carbamimidoylcarbamate 25 mg (0.044 mmol) synthesized in the same manner as in Example 170, and the mixture was stirred at room temperature for 2 hours. After the completion of the reaction, TEA and ethanol were added to the reaction mixture under ice cooling. The mixture was stirred at room temperature for 30 minutes, and the precipitated solid was collected by filtration and was dried under reduced pressure to give the title compound 9.9 mg (0.021 mmol, yield 48%) as a white solid.

Mass spectrum (ESI, m/z):482[M+1]$^+$.

$^1$H-NMR spectrum (400 MHz, DMSO-d$_6$+D$_2$O) δ:8.59 (d, J=1.3 Hz, 2H), 7.67-7.46 (m, 2H), 7.43-7.35 (m, 1H), 7.31-7.25 (m, 1H), 6.27 (d, J=2.1 Hz, 1H), 5.06 (s, 2H), 5.00 (s, 2H), 3.97-3.86 (m, 4H), 2.60-2.54 (m, 2H), 2.42-2.36 (m, 2H).

Example 172

2-Fluoro-3-{2-[4-({[1-(tetrahydropyran-2-yl)-1H-pyrazol-4-yl]methoxy}imino)piperidin-1-yl]pyrimidin-5-yl}benzyl carbamimidoylcarbamate (Compound II-574)

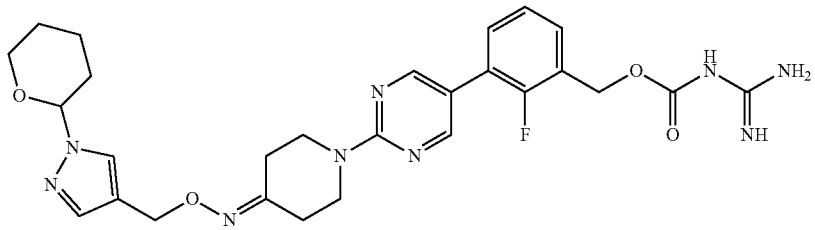 [SMILES: N=C(N)NC(=O)OCc1cccc(-c2cnc(N3CCC(=NOCc4cnn(C5CCCCO5)c4)CC3)nc2)c1F]

CDI 65 mg (0.40 mmol) was added to a DMF (4 mL) solution of 1-{5-[2-fluoro-3-(hydroxymethyl)phenyl]pyrimidin-2-yl}piperidin-5-one O-{[1-(tetrahydropyran-2-yl)-1H-pyrazol-4-yl]methyl} oxime 89 mg (0.19 mmol) synthesized in the same manner as in Reference Example 7-115, and the mixture was stirred at room temperature for 3 hours. Next, guanidine carbonate 70 mg (0.39 mmol) was added, and the mixture was stirred at room temperature for 3 hours. After the completion of the reaction, water was added to the reaction mixture, and followed by extraction with methylene chloride. The organic layer was washed with water, dried over anhydrous sodium sulfate, and filtered. The filtrate was concentrated under reduced pressure. The concentrated residue was purified by silica gel column chromatography (DNH silica gel, eluting solvent: ethyl acetate:methanol) to give the title compound 91 mg (0.16 mmol, yield 84%) as a white solid.

Mass spectrum (ESI, m/z):566[M+1]$^+$.

$^1$H-NMR spectrum (400 MHz, DMSO-$d_6$+$D_2O$) δ:8.59 (s, 2H), 7.89 (s, 1H), 7.53-7.47 (m, 2H), 7.42-7.36 (m, 1H), 7.31-7.25 (m, 1H), 5.38-5.33 (m, 1H), 5.06 (s, 2H), 4.90 (s, 2H), 3.95-3.87 (m, 5H), 3.65-3.55 (m, 1H), 2.59-2.53 (m, 2H), 2.44-2.33 (m, 2H), 2.14-1.82 (m, 3H), 1.74-1.43 (m, 3H).

Example 173

3-[2-(4-{[(1H-pyrazol-4-yl)methoxy]imino}piperidin-1-yl)pyrimidin-5-yl]-2-fluorobenzyl carbamimidoylcarbamate (Compound II-540)

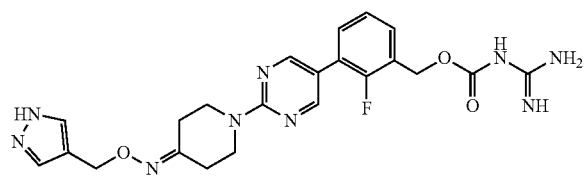 [SMILES: N=C(N)NC(=O)OCc1cccc(-c2cnc(N3CCC(=NOCc4cn[nH]c4)CC3)nc2)c1F]

2 M hydrogen chloride/ethanol solution 2.0 mL (4.0 mmol) was added to 2-fluoro-3-{2-[4-({[1-(tetrahydropyran-2-yl)-1H-pyrazol-4-yl]methoxy}imino)piperidin-1-yl]pyrimidin-5-yl}benzyl carbamimidoylcarbamate 80 mg (0.14 mmol) synthesized in the same manner as in Example 172, and the mixture was stirred at room temperature for 2 hours. After the completion of the reaction, the reaction mixture was concentrated under reduced pressure. Methylene chloride and TEA were added to the concentrated residue, and subsequently water was added. The precipitated solid was collected by filtration and was dried under reduced pressure to give the title compound 41 mg (0.085 mmol, yield 61%) as a white solid.

Mass spectrum (ESI, m/z):482[M+1]$^+$.

$^1$H-NMR spectrum (400 MHz, DMSO-$d_6$+$D_2O$) δ:8.59 (d, J=1.4 Hz, 2H), 7.87-7.65 (m, 1H), 7.61-7.45 (m, 2H), 7.43-7.36 (m, 1H), 7.33-7.22 (m, 1H), 5.06 (s, 2H), 4.93 (s, 2H), 4.02-3.83 (m, 4H), 2.59-2.53 (m, 2H), 2.45-2.37 (m, 2H).

Example 174

2-Fluoro-3-[2-(4-{[(1-methyl-1H-pyrazol-4-yl)methoxy]imino}piperidin-1-yl)pyrimidin-5-yl]benzyl carbamimidoylcarbamate (Compound II-542)

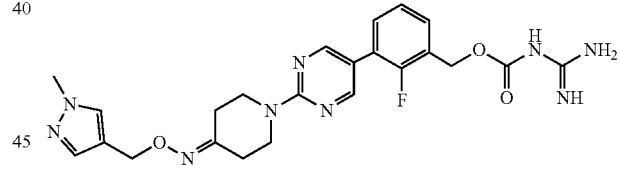

CDI 84 mg (0.52 mmol) was added to a DMF (6 mL) solution of 1-{5-[2-fluoro-3-(hydroxymethyl)phenyl]pyrimidin-2-yl}piperidin-4-one O-[(1-methyl-1H-pyrazol-4-yl)methyl] oxime 0.11 g (0.26 mmol) synthesized in the same manner as in Reference Example 7-116, and the mixture was stirred at room temperature for 15 hours. Next, guanidine carbonate 93 mg (0.52 mmol) was added, and the mixture was stirred at room temperature for 5 hours. After the completion of the reaction, water was added to the reaction mixture, and followed by extraction with methylene chloride. The organic layer was washed with water, dried over anhydrous sodium sulfate, and filtered. The filtrate was concentrated under reduced pressure. The concentrated residue was purified by silica gel column chromatography (DNH silica gel, eluting solvent: ethyl acetate:methanol). Ethyl acetate was added to the crude product thus obtained, and the mixture was stirred. The solid was collected by filtration and was dried under reduced pressure to give the title compound 78 mg (0.16 mmol, yield 62%) as a white solid.

Mass spectrum (ESI, m/z):496[M+1]$^+$.

$^1$H-NMR spectrum (400 MHz, DMSO-d$_6$+D$_2$O) δ:8.59 (d, J=1.4 Hz, 2H), 7.70 (s, 1H), 7.54-7.47 (m, 1H), 7.42 (s, 1H), 7.42-7.37 (m, 1H), 7.32-7.25 (m, 1H), 5.06 (s, 2H), 4.87 (s, 2H), 3.95-3.87 (m, 4H), 3.81 (s, 3H), 2.57-2.53 (m, 2H), 2.43-2.33 (m, 2H).

Example 175

3-[2-(4-{[2-(1H-pyrazol-1-yl)ethoxy]imino}piperidin-1-yl)pyrimidin-5-yl]-2-fluorobenzyl carbamimidoylcarbamate (Compound II-543)

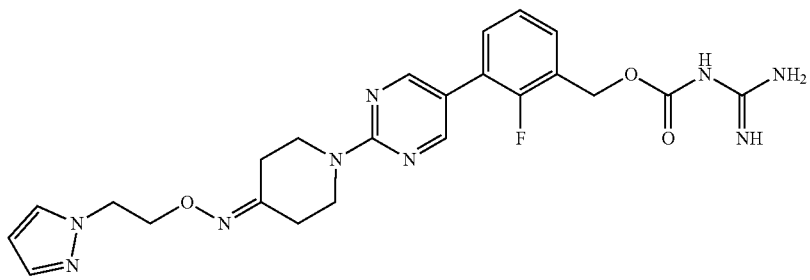 [SMILES: N=C(N)NC(=O)OCc1cccc(-c2cnc(N3CCC(=NOCCn4cccn4)CC3)nc2)c1F]

CDI 24 mg (0.15 mmol) was added to a DMF (1 mL) solution of 1-{5-[2-fluoro-3-(hydroxymethyl)phenyl]pyrimidin-2-yl}piperidin-4-one O-[2-(1H-pyrazol-1-yl)ethyl] oxime 30 mg (0.073 mmol) synthesized in the same manner as in Reference Example 7-117, and the mixture was stirred at room temperature for 3 hours. Next, guanidine carbonate 26 mg (0.15 mmol) was added, and the mixture was stirred at room temperature for 3 hours. After the completion of the reaction, water was added to the reaction mixture, and the mixture was stirred at room temperature. The precipitated solid was collected by filtration. The crude product thus obtained was washed with TBME and was dried under reduced pressure to give the title compound 16 mg (0.032 mmol, yield 44%) as a white solid.

Mass spectrum (ESI, m/z):496[M+1]$^+$.

$^1$H-NMR (400 MHz, DMSO-d$_6$+D$_2$O) δ:8.59 (d, J=1.4 Hz, 2H), 7.67 (dd, J=0.6, 2.3 Hz, 1H), 7.54-7.47 (m, 1H), 7.45 (dd, J=0.6, 1.9 Hz, 1H), 7.43-7.36 (m, 1H), 7.32-7.25 (m, 1H), 6.23 (dd, J=1.9, 2.3 Hz, 1H), 5.06 (s, 2H), 4.39-4.32 (m, 2H), 4.32-4.25 (m, 2H), 3.97-3.85 (m, 4H), 2.56-2.46 (m, 2H), 2.42-2.36 (m, 2H).

Example 176

2-Fluoro-3-(2-{4-[(pyridin-4-ylmethoxy)imino]piperidin-1-yl}pyrimidin-5-yl)benzyl carbamimidoylcarbamate (Compound II-544)

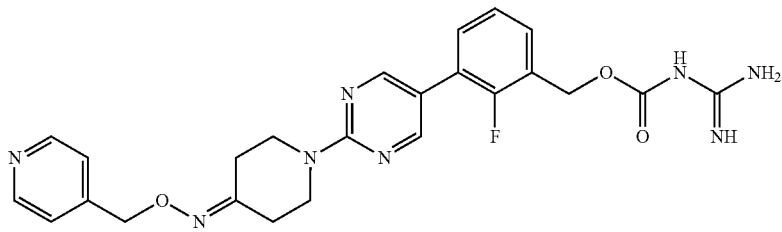 [SMILES: N=C(N)NC(=O)OCc1cccc(-c2cnc(N3CCC(=NOCc4ccncc4)CC3)nc2)c1F]

CDI 95 mg (0.586 mmol) was added to a DMF (4 mL) solution of 1-{5-[2-fluoro-3-(hydroxymethyl)phenyl]pyrimidin-2-yl}piperidin-4-one O-pyridin-4-ylmethyl oxime 104 mg (0.255 mmol) synthesized in the same manner as Reference Compound 7-118, and the mixture was stirred at room temperature for 2 hours. Next, guanidine carbonate 95 mg (0.527 mmol) was added, and the mixture was stirred at room temperature for 16 hours. After the completion of the reaction, water was added to the reaction mixture, and the mixture was stirred at room temperature. The precipitated solid was collected by filtration. Ethyl acetate was added to the obtained solid, and the mixture was stirred at room temperature. Thereafter, the solid was collected by filtration and was dried under reduced pressure to give the title compound 99.5 mg (0.202 mmol, yield 79%) as a white solid.

Mass spectrum (ESI, m/z):493[M+1]$^+$.

$^1$H-NMR spectrum (400 MHz, DMSO-d$_6$+D$_2$O) δ:8.60 (d, J=1.0 Hz, 2H), 8.56-8.51 (m, 2H), 7.54-7.47 (m, 1H), 7.43-7.36 (m, 1H), 7.36-7.32 (m, 2H), 7.31-7.25 (m, 1H), 5.11 (s, 2H), 5.06 (s, 2H), 4.00-3.88 (m, 4H), 2.73-2.66 (m, 2H), 2.43-2.36 (m, 2H).

Example 177

3-[2-(4-{[2-(2,5-Dioxopyrrolidin-1-yl)ethoxy]imino}piperidin-1-yl)pyrimidin-5-yl]-2-fluorobenzyl carbamimidoylcarbamate (Compound II-545)

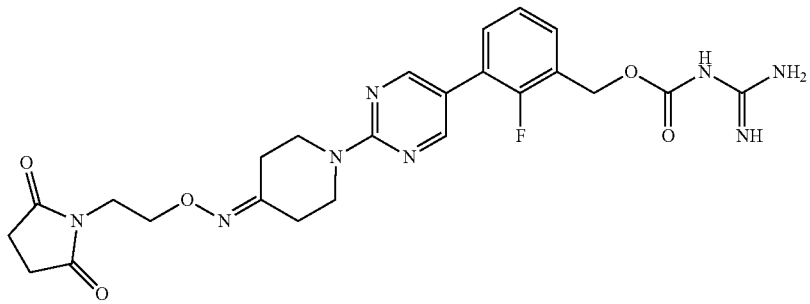 [SMILES: N=C(N)NC(=O)OCc1cccc(-c2cnc(N3CCC(=NOCCN4C(=O)CCC4=O)CC3)nc2)c1F]

CDI 101 mg (0.62 mmol) was added to a DMF (4 ml) solution of 1-(2-{[(1-{5-[2-fluoro-3-(hydroxymethyl)phenyl]pyrimidin-2-yl}piperidin-4-ylidene)amino]oxy}ethyl)pyrrolidine-2,5-dione 138 mg (0.31 mmol) synthesized in the same manner as in Reference Example 7-119, and the mixture was stirred at room temperature for 4 hours. Next, guanidine carbonate 115 mg (0.64 mmol) was added, and the mixture was stirred at room temperature for 1 hour. After the completion of the reaction, water was added to the reaction mixture, and followed by extraction with methylene chloride. The organic layer was washed with water, dried over anhydrous sodium sulfate, and filtered. The filtrate was concentrated under reduced pressure. The concentrated residue was purified by silica gel column chromatography (DNH silica gel, eluting solvent: ethyl acetate:methanol). Ethyl acetate was added to the crude product thus obtained, and the mixture was stirred at 70° C. for 30 minutes. Thereafter, the solid was collected by filtration and was dried under reduced pressure to give the title compound 93 mg (0.18 mmol, yield 58%) as a white solid.

Mass spectrum (ESI, m/z):527[M+1]$^+$.

$^1$H-NMR spectrum (400 MHz, DMSO-$d_6$+$D_2O$) δ:8.60 (d, J=1.3 Hz, 2H), 7.55-7.47 (m, 1H), 7.43-7.36 (m, 1H), 7.32-7.25 (m, 1H), 5.06 (s, 2H), 4.11-4.05 (m, 2H), 3.95-3.86 (m, 4H), 3.67-3.55 (m, 2H), 2.63 (s, 4H), 2.52-2.47 (m, 2H), 2.40-2.32 (m, 2H).

Example 178

2-Fluoro-3-[2-(4-{[2-(2-oxopyrrolidin-1-yl)ethoxy]imino}piperidin-1-yl)pyrimidin-5-yl]benzyl carbamimidoylcarbamate (Compound II-546)

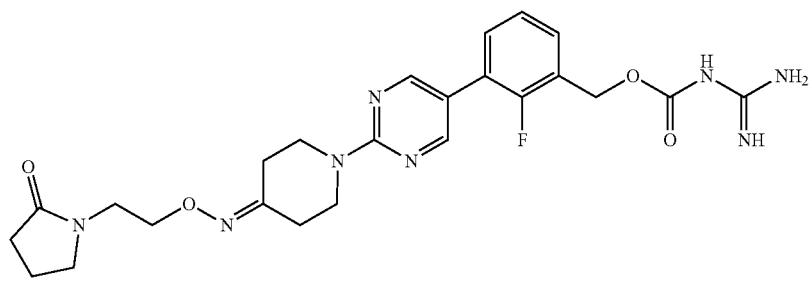 [SMILES: N=C(N)NC(=O)OCc1cccc(-c2cnc(N3CCC(=NOCCN4CCCC4=O)CC3)nc2)c1F]

CDI 61 mg (0.38 mmol) was added to a DMF (2 ml) solution of 1-(2-{[(1-{5-[2-fluoro-3-(hydroxymethyl)phenyl]pyrimidin-2-yl}piperidin-4-ylidene)amino]oxy}ethyl)pyrrolidin-2-one 80 mg (0.19 mmol) synthesized in the same manner as in Reference Example 7-120, and the mixture was stirred at room temperature for 4 hours. Next, guanidine carbonate 67 mg (0.37 mmol) was added, and the mixture was stirred at room temperature for 15 hours. After the completion of the reaction, water was added to the reaction mixture and the mixture was stirred at room temperature. The precipitated solid was collected by filtration and was dried under reduced pressure to give the title compound 82 mg (0.16 mmol, yield 84%) as a white solid.

Mass spectrum (ESI, m/z):513[M+1]⁺.
¹H-NMR spectrum (400 MHz, DMSO-d₆+D₂O) δ:8.59 (d, J=1.1 Hz, 2H), 7.55-7.47 (m, 1H), 7.44-7.36 (m, 1H), 7.33-7.24 (m, 1H), 5.06 (s, 2H), 4.11-4.04 (m, 2H), 3.96-3.87 (m, 4H), 3.45-3.36 (m, 4H), 2.60-2.54 (m, 2H), 2.48-2.36 (m, 2H), 2.25-2.16 (m, 2H), 2.00-1.83 (m, 2H).

Example 179

2-Fluoro-3-[2-(4-{[2-(2-oxooxazolidin-3-yl)ethoxy]imino}piperidin-1-yl)pyrimidin-5-yl]benzyl carbamimidoylcarbamate (Compound II-547)

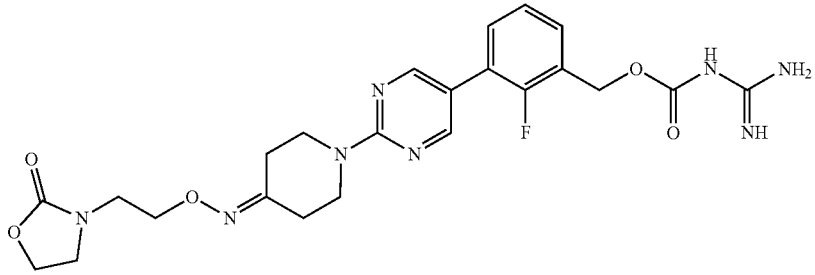 [SMILES: N=C(N)NC(=O)OCc1cccc(-c2cnc(N3CCC(=NOCCN4CCOC4=O)CC3)nc2)c1F]

CDI 76 mg (0.47 mmol) was added to a DMF (4 ml) solution of 3-(2-{[(1-{5-[2-fluoro-3-(hydroxymethyl)phenyl]pyrimidin-2-yl}piperidin-4-ylidene)amino]oxy}ethyl)oxazolidin-2-one 67 mg (0.16 mmol) synthesized in the same manner as in Reference Example 7-121, and the mixture was stirred at room temperature for 14 hours. Further, CDI 25 mg (0.15 mmol) was added, and the mixture was stirred at room temperature for 1 hour. Next, guanidine carbonate 58 mg (0.32 mmol) was added, and the mixture was stirred at room temperature for 1.5 hours. After the completion of the reaction, water was added to the reaction mixture and the mixture was stirred at room temperature. The precipitated solid was collected by filtration and was dried under reduced pressure to give the title compound 62 mg (0.12 mmol, yield 75%) as a white solid.

Mass spectrum (ESI, m/z):515[M+1]⁺.
¹H-NMR spectrum (400 MHz, DMSO-d₆+D₂O) δ:8.59 (br s, 2H), 7.55-7.46 (m, 1H), 7.43-7.36 (m, 1H), 7.32-7.25 (m, 1H), 5.06 (s, 2H), 4.29-4.21 (m, 2H), 4.17-4.07 (m, 2H), 3.97-3.87 (m, 4H), 3.64-3.55 (m, 2H), 3.44-3.38 (m, 2H), 2.60-2.54 (m, 2H), 2.43-2.36 (m, 2H).

Example 180

2-Fluoro-3-[2-(4-{[2-(3-oxomorpholino)ethoxy]imino}piperidin-1-yl)pyrimidin-5-yl]benzyl carbamimidoylcarbamate (Compound II-548)

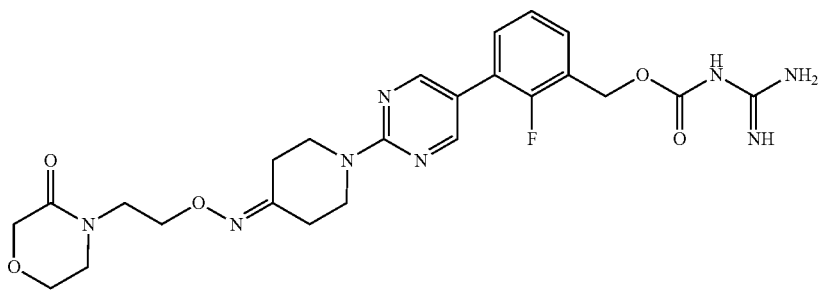 [SMILES: N=C(N)NC(=O)OCc1cccc(-c2cnc(N3CCC(=NOCCN4CCOCC4=O)CC3)nc2)c1F]

CDI 130 mg (0.802 mmol) was added to a DMF (4 ml) solution of 4-(2-{[(1-{5-[2-fluoro-3-(hydroxymethyl)phenyl]pyrimidin-2-yl}piperidin-4-ylidene)amino]oxy}ethyl)morpholin-3-one 118 mg (0.266 mmol) synthesized in the same manner as in Reference Example 7-122, and the mixture was stirred at room temperature for 4 hours. Next, guanidine carbonate 106 mg (0.588 mmol) was added, and the mixture was stirred at room temperature for 2 hours. After the completion of the reaction, water was added to the reaction mixture and the mixture was stirred at room temperature. The precipitated solid was collected by filtration and was dried under reduced pressure to give the title compound 106 mg (0.201 mmol, yield 76%) as a white solid.

Mass spectrum (ESI, m/z):529[M+1]$^+$.

$^1$H-NMR spectrum (400 MHz, DMSO-d$_6$) δ:8.60 (d, J=1.4 Hz, 2H), 7.55-7.47 (m, 1H), 7.42-7.35 (m, 1H), 7.31-7.24 (m, 1H), 5.06 (s, 2H), 4.17-4.08 (m, 2H), 4.02 (s, 2H), 3.96-3.89 (m, 4H), 3.84-3.76 (m, 2H), 3.60-3.52 (m, 2H), 3.43-3.35 (m, 2H), 2.60-2.52 (m, 2H), 2.43-2.36 (m, 2H).

Example 181

2-Fluoro-3-{2-[4-(phenoxyimino)piperidin-1-yl]pyrimidin-5-yl}benzyl carbamimidoylcarbamate (Compound II-565)

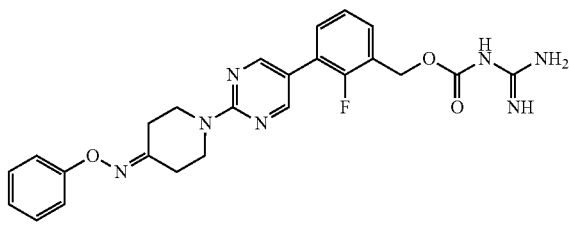 [SMILES: N=C(N)NC(=O)OCc1cccc(-c2cnc(N3CCC(=NOc4ccccc4)CC3)nc2)c1F]

CDI 69 mg (0.43 mmol) was added to a DMF (1 mL) solution of 1-{5-[2-fluoro-3-(hydroxymethyl)phenyl]pyrimidin-2-yl}piperidin-4-one O-phenyl oxime 68 mg (0.17 mmol) synthesized in the same manner as in Reference Example 120, and the mixture was stirred at room temperature for 1 hour. Further, DMF 1 mL was added. Next, guanidine carbonate 67 mg (0.37 mmol) was added, and the mixture was stirred at room temperature for 11 hours. After the completion of the reaction, water was added to the reaction mixture, and the mixture was stirred at room temperature. The precipitated solid was collected by filtration. The obtained solid was purified by silica gel column chromatography (DIOL silica gel, eluting solvent: ethyl acetate:methanol). The resultant fraction including the target compound was concentrated under reduced pressure. Ethanol was added to the concentrated residue, and the mixture was stirred at 65° C. for 30 minutes. Thereafter, the solid was collected by filtration and was dried under reduced pressure to give the title compound 58 mg (0.11 mmol, yield 65%) as a white solid.

Mass spectrum (ESI, m/z):478[M+1].

$^1$H-NMR spectrum (400 MHz, DMSO-d$_6$+D$_2$O) δ:8.62 (s, 2H), 7.55-7.48 (m, 1H), 7.43-7.27 (m, 4H), 7.20-7.13 (m, 2H), 7.05-6.97 (m, 1H), 5.07 (s, 2H), 4.07-3.98 (m, 4H), 2.86-2.80 (m, 2H), 2.61-2.54 (m, 2H).

Example 182

2-Fluoro-3-(2-{4-[(pyrimidin-5-yloxy)imino]piperidin-1-yl}pyrimidin-5-yl)benzyl carbamimidoylcarbamate (Compound III-566)

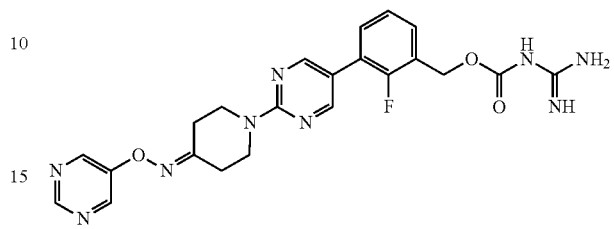

CDI 36 mg (0.22 mmol) was added to a DMF (2 mL) solution of 1-{5-[2-fluoro-3-(hydroxymethyl)phenyl]pyrimidin-2-yl}piperidin-4-one O-pyrimidin-5-yl oxime 44 mg (0.11 mmol) synthesized in the same manner as in Reference Example 7-123, and the mixture was stirred at room temperature for 3.5 hours. Further, CDI 18 mg (0.11 mmol) was added, and the mixture was stirred at room temperature for 3.5 hours. Next, guanidine carbonate 50 mg (0.28 mmol) was added, and the mixture was stirred at room temperature for 19 hours. After the completion of the reaction, water was added to the reaction mixture, and the mixture was stirred at room temperature. The precipitated solid was collected by filtration. The obtained solid was purified by silica gel column chromatography (DIOL silica gel, eluting solvent: ethyl acetate:methanol) and then purified by silica gel column chromatography (eluting solvent: ethyl acetate:methanol) to give the title compound 17 mg (0.035 mmol, yield 32%) as a light yellow solid.

Mass spectrum (ESI, m/z):480[M+1]$^+$.

$^1$H-NMR spectrum (400 MHz, DMSO-d$_6$+D$_2$O) δ:8.89 (d, J=1.3 Hz, 1H), 8.74 (d, J=1.0 Hz, 2H), 8.65-8.61 (m, 2H), 7.55-7.49 (m, 1H), 7.44-7.38 (m, 1H), 7.33-7.27 (m, 1H), 5.07 (s, 2H), 4.09-4.00 (m, 4H), 2.91-2.84 (m, 2H), 2.64-2.56 (m, 2H).

Example 183

2-Fluoro-3-(2-{4-[(pyrimidin-2-yloxy)imino]piperidin-1-yl}pyrimidin-5-yl)benzyl carbamimidoylcarbamate (Compound II-567)

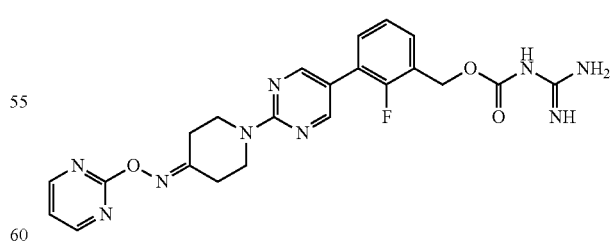

CDI 13.6 mg (0.084 mmol) was added to a DMF (1 mL) solution of 1-{5-[2-fluoro-3-(hydroxymethyl)phenyl]pyrimidin-2-yl}piperidin-4-one O-pyrimidin-2-yl oxime 15.4 mg (0.039 mmol) synthesized in the same manner as in Reference Example 7-124, and the mixture was stirred at room temperature for 3.5 hours. Further, CDI 4.1 mg (0.025 mmol) was added, and the mixture was stirred at room temperature for 1.5 hours. Next, guanidine carbonate 18.1 mg (0.10 mmol) was added, and the mixture was stirred at room temperature for 18.5 hours. After the completion of the reaction, water was added to the reaction mixture and the mixture was stirred at room temperature. The precipitated solid was collected by filtration and was dried under reduced pressure to give the title compound 13.6 mg (0.028 mmol, yield 72%) as a white solid.

Mass spectrum (ESI, m/z):480[M+1]+.

$^1$H-NMR spectrum (400 MHz, DMSO-$d_6$+$D_2O$) δ:8.67 (d, J=4.8 Hz, 2H), 8.63 (d, J=1.3 Hz, 2H), 7.57-7.48 (m, 1H), 7.45-7.36 (m, 1H), 7.32-7.21 (m, 2H), 5.07 (s, 2H), 4.09-3.98 (m, 4H), 2.87-2.80 (m, 2H), 2.63-2.57 (m, 2H).

Example 184

2-Fluoro-3-{2-[3-(methoxyimino)azetidin-1-yl]pyrimidin-5-yl}benzyl carbamimidoylcarbamate 1/2 L-tartrate (Compound II-2 1/2 L-tartrate)

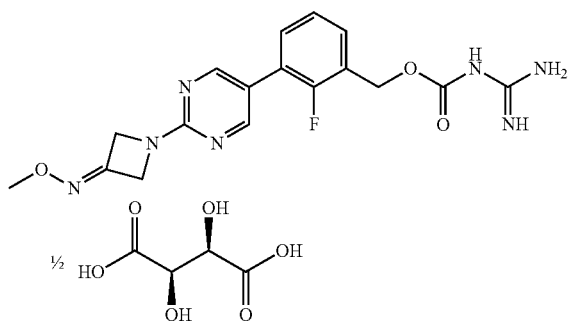

DMSO (5 mL) was added to 2-fluoro-3-{2-[3-(methoxyimino)azetidin-1-yl]pyrimidin-5-yl}benzyl carbamimidoylcarbamate (Compound II-2) 500 mg (1.29 mmol) synthesized in the same manner as in Example 1, and the mixture was heated to 50° C. to give a solution. Next, L-tartaric acid 198 mg (1.32 mmol) was added, and the mixture was cooled to room temperature. Ethyl acetate (20 ml) was dropped thereto, and the mixture was stirred at room temperature for 16 hours. The precipitated solid was collected by filtration and was dried under reduced pressure to give the title compound 545 mg (1.18 mmol, yield 91%) as a white solid.

Mass spectrum (ESI, m/z):388[M+1]+.

$^1$H-NMR spectrum (400 MHz, DMSO-$d_6$+$D_2O$) δ:8.63 (d, J=1.4 Hz, 2H), 7.56-7.48 (m, 1H), 7.48-7.38 (m, 1H), 7.35-7.24 (m, 1H), 5.09 (s, 2H), 4.85-4.78 (m, 4H), 4.19 (s, 1H), 3.83 (s, 3H).

Example 185

2-Fluoro-3-{2-[3-(methoxyimino)azetidin-1-yl]pyrimidin-5-yl}benzyl carbamimidoylcarbamate 1/2 D-tartrate (Compound II-2 1/2 D-tartrate)

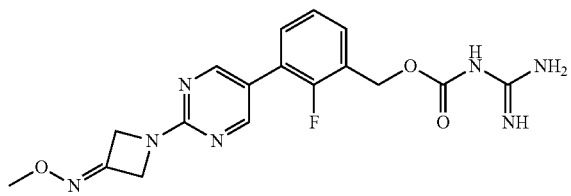

-continued

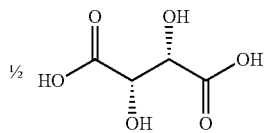

DMSO (5 mL) was added to 2-fluoro-3-{2-[3-(methoxyimino)azetidin-1-yl]pyrimidin-5-yl}benzyl carbamimidoylcarbamate (Compound II-2) 500 mg (1.29 mmol) synthesized in the same manner as in Example 1, and the mixture was heated to 50° C. to give a solution. Next, D-tartaric acid 201 mg (1.34 mmol) was added, and the mixture was cooled to room temperature. Ethyl acetate (20 ml) was dropped thereto, and the mixture was stirred at room temperature for 16 hours. The precipitated solid was collected by filtration and was dried under reduced pressure to give the title compound 558 mg (1.21 mmol, yield 94%) as a white solid.

Mass spectrum (ESI, m/z):388[M+1]+.

$^1$H-NMR spectrum (400 MHz, DMSO-$d_6$+$D_2O$) δ:8.63 (d, J=1.4 Hz, 2H), 7.57-7.49 (m, 1H), 7.47-7.40 (m, 1H), 7.37-7.25 (m, 1H), 5.10 (s, 2H), 4.87-4.76 (m, 4H), 4.20 (s, 1H), 3.83 (s, 3H).

Example 186

2-Fluoro-3-{2-[3-(methoxyimino)azetidin-1-yl]pyrimidin-5-yl}benzyl carbamimidoylcarbamate maleate (Compound II-2 maleate)

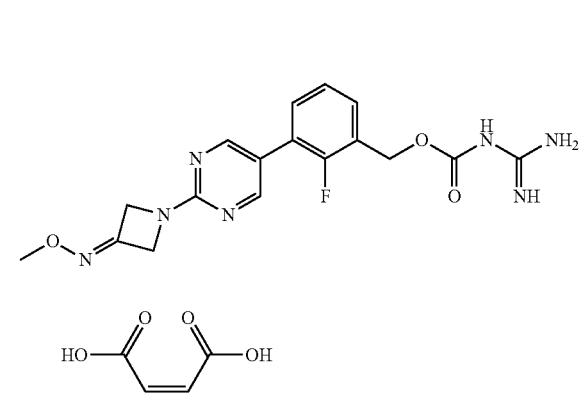

DMSO (5 mL) was added to 2-fluoro-3-{2-[3-(methoxyimino)azetidin-1-yl]pyrimidin-5-yl}benzyl carbamimidoylcarbamate (Compound II-2) 500 mg (1.29 mmol) synthesized in the same manner as in Example 1, and the mixture was heated to 50° C. to give a solution. Next, maleic acid 152 mg (1.31 mmol) was added, and the mixture was cooled to room temperature. Ethyl acetate (20 ml) was dropped thereto, and the mixture was stirred at room temperature for 16 hours. The precipitated solid was collected by filtration and was dried under reduced pressure to give the title compound 556 mg (1.10 mmol, yield 85%) as a white solid.

Mass spectrum (ESI, m/z):388[M+1]+.

$^1$H-NMR spectrum (400 MHz, DMSO-$d_6$+$D_2O$) δ:8.64 (d, J=1.1 Hz, 2H), 7.66-7.57 (m, 1H), 7.56-7.49 (m, 1H), 7.39-7.31 (m, 1H), 6.08 (s, 2H), 5.33 (s, 2H), 4.87-4.77 (m, 4H), 3.83 (s, 3H).

Example 187

2-Fluoro-3-{2-[3-(methoxyimino)azetidin-1-yl]pyrimidin-5-yl}benzyl carbamimidoylcarbamate 1/2 succinate (Compound II-2 1/2 succinate)

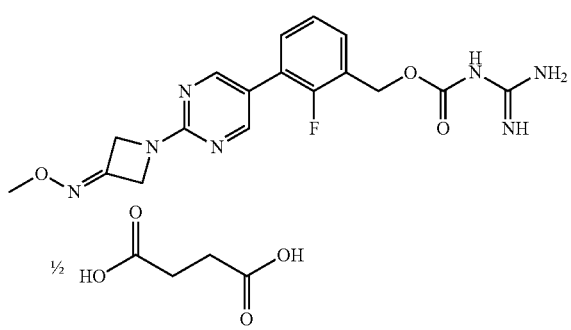

DMSO (5 mL) was added to 2-fluoro-3-{2-[3-(methoxyimino)azetidin-1-yl]pyrimidin-5-yl}benzyl carbamimidoylcarbamate (Compound III-2) 500 mg (1.29 mmol) synthesized in the same manner as in Example 1, and the mixture was heated to 50° C. to give a solution. Next, succinic acid 153 mg (1.30 mmol) was added, and the mixture was cooled to room temperature. Ethyl acetate (20 ml) was dropped thereto, and the mixture was stirred at room temperature for 16 hours. The precipitated solid was collected by filtration and was dried under reduced pressure to give the title compound 506 mg (1.13 mmol, yield 88%) as a white solid.

Mass spectrum (ESI, m/z):388[M+1]$^+$.

$^1$H-NMR spectrum (400 MHz, DMSO-d$_6$+D$_2$O) δ:8.63 (d, J=1.3 Hz, 2H), 7.54-7.38 (m, 2H), 7.34-7.26 (m, 1H), 5.07 (s, 2H), 4.86-4.77 (m, 4H), 3.83 (s, 3H), 2.41 (s, 2H).

Example 188

3-{2-[3-(Ethoxyimino)azetidin-1-yl]pyrimidin-5-yl}-2-fluorobenzyl carbamimidoylcarbamate 1/2 L-tartrate (Compound II-3 1/2 L-tartrate)

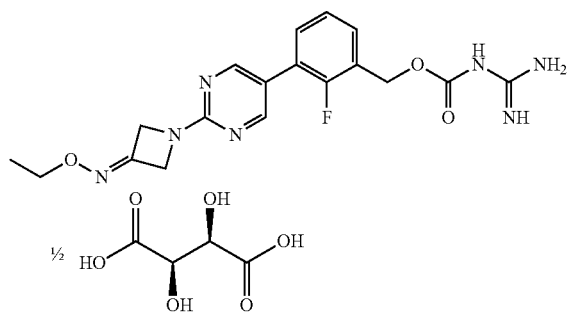

DMSO (5 mL) was added to 3-{2-[3-(ethoxyimino)azetidin-1-yl]pyrimidin-5-yl}-2-fluorobenzyl carbamimidoylcarbamate (Compound II-3) 500 mg (1.25 mmol) synthesized in the same manner as in Example 2, and the mixture was heated to 50° C. to give a solution. Next, L-tartaric acid 190 mg (1.27 mmol) was added, and the mixture was cooled to room temperature. Ethyl acetate (20 ml) was dropped thereto, and the mixture was stirred at room temperature for 16 hours. The precipitated solid was collected by filtration and was dried under reduced pressure to give the title compound 561 mg (1.18 mmol, yield 94%) as a white solid.

Mass spectrum (ESI, m/z):402[M+1]$^+$.

$^1$H-NMR spectrum (400 MHz, DMSO-d$_6$+D$_2$O) δ:8.63 (d, J=1.3 Hz, 2H), 7.57-7.48 (m, 1H), 7.47-7.39 (m, 1H), 7.34-7.25 (m, 1H), 5.09 (s, 2H), 4.87-4.75 (m, 4H), 4.19 (s, 1H), 4.08 (q, J=7.0 Hz, 2H), 1.22 (t, J=7.0 Hz, 3H).

Example 189

3-{2-[3-(Ethoxyimino)azetidin-1-yl]pyrimidin-5-yl}-2-fluorobenzyl carbamimidoylcarbamate 1/2 D-tartrate (Compound III-3 1/2 D-tartrate)

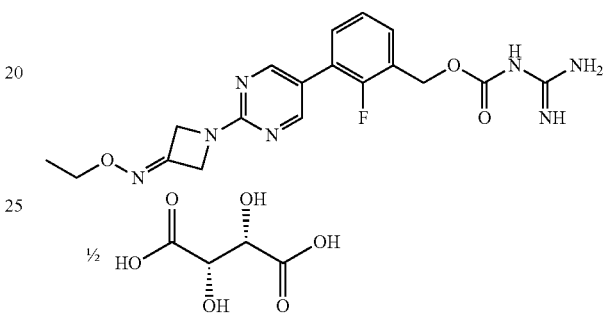

DMSO (5 mL) was added to 3-{2-[3-(ethoxyimino)azetidin-1-yl]pyrimidin-5-yl}-2-fluorobenzyl carbamimidoylcarbamate (Compound II-3) 500 mg (1.25 mmol) synthesized in the same manner as in Example 2, and the mixture was heated to 50° C. to give a solution. Next, D-tartaric acid 188 mg (1.25 mmol) was added, and the mixture was cooled to room temperature. Ethyl acetate (20 ml) was dropped thereto, and the mixture was stirred at room temperature for 16 hours. The precipitated solid was collected by filtration and was dried under reduced pressure to give the title compound 534 mg (1.12 mmol, yield 90%) as a white solid.

Mass spectrum (ESI, m/z):402[M+1]$^+$.

$^1$H-NMR spectrum (400 MHz, DMSO-d$_6$+D$_2$O) δ:8.63 (d, J=1.3 Hz, 2H), 7.58-7.48 (m, 1H), 7.46-7.39 (m, 1H), 7.35-7.25 (m, 1H), 5.08 (s, 2H), 4.89-4.74 (m, 4H), 4.17 (s, 1H), 4.08 (q, J=7.1 Hz, 2H), 1.22 (t, J=0.1 Hz, 3H).

Example 190

3-{2-[3-(Ethoxyimino)azetidin-1-yl]pyrimidin-5-yl}-2-fluorobenzyl carbamimidoylcarbamate maleate (Compound III-3 maleate)

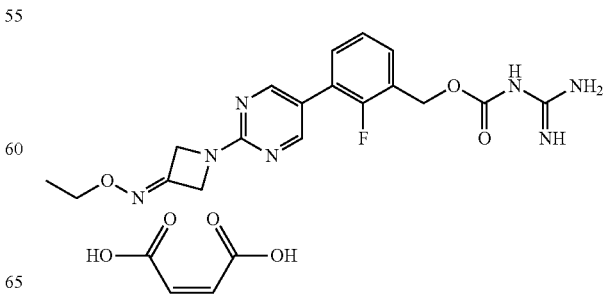

DMSO (5 mL) was added to 3-{2-[3-(ethoxyimino)azetidin-1-yl]pyrimidin-5-yl}-2-fluorobenzyl carbamimidoylcarbamate (Compound II-3) 500 mg (1.25 mmol) synthesized in the same manner as in Example 2, and the mixture was heated to 50° C. to give a solution. Next, maleic acid 151 mg (1.30 mmol) was added, and the mixture was cooled to room temperature. Ethyl acetate (20 ml) was dropped thereto, and the mixture was stirred at room temperature for 16 hours. The precipitated solid was collected by filtration and was dried under reduced pressure to give the title compound 597 mg (1.15 mmol, yield 92%) as a white solid.

Mass spectrum (ESI, m/z):402[M+1]$^+$.

$^1$H-NMR spectrum (400 MHz, DMSO-d$_6$+D$_2$O) δ:8.64 (d, J=1.1 Hz, 2H), 7.66-7.56 (m, 1H), 7.56-7.48 (m, 1H), 7.39-7.32 (m, 1H), 6.07 (s, 2H), 5.30 (s, 2H), 4.93-4.74 (m, 4H), 4.09 (q, J=7.0 Hz, 2H), 1.22 (t, J=7.0 Hz, 3H).

Example 191

3-{2-[3-(Ethoxyimino)azetidin-1-yl]pyrimidin-5-yl}-2-fluorobenzyl carbamimidoylcarbamate 1/2 succinate (Compound II-3 1/2 succinate)

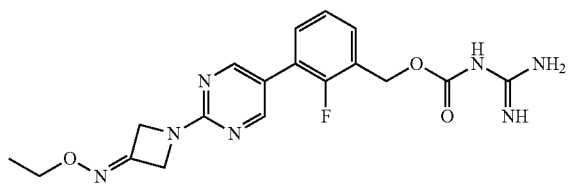

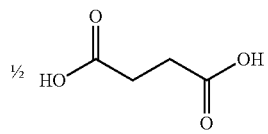

DMSO (5 mL) was added to 3-{2-[3-(ethoxyimino)azetidin-1-yl]pyrimidin-5-yl}-2-fluorobenzyl carbamimidoylcarbamate (Compound II-3) 500 mg (1.25 mmol) synthesized in the same manner as in Example 2, and the mixture was heated to 50° C. to give a solution. Next, succinic acid 147 mg (1.25 mmol) was added, and the mixture was cooled to room temperature. Ethyl acetate (20 ml) was dropped thereto, and the mixture was stirred at room temperature for 16 hours. The precipitated solid was collected by filtration and was dried under reduced pressure to give the title compound 560 mg (1.22 mmol, yield 98%) as a white solid.

Mass spectrum (ESI, m/z):402[M+1]$^+$.

$^1$H-NMR spectrum (400 MHz, DMSO-d$_6$+D$_2$O) δ:8.67-8.59 (m, 2H), 7.55-7.48 (m, 1H), 7.46-7.39 (m, 1H), 7.33-7.27 (m, 1H), 5.07 (s, 2H), 4.88-4.76 (m, 4H), 4.08 (q, J=7.0 Hz, 2H), 2.42 (s, 2H), 1.22 (t, J=7.0 Hz, 3H).

Example 192

2-Fluoro-3-(2-{3-[(methoxy-d$_3$)imino]azetidin-1-yl}pyrimidin-5-yl)benzyl carbamimidoylcarbamate 1/2 L-tartrate (Compound II-12 1/2 L-tartrate)

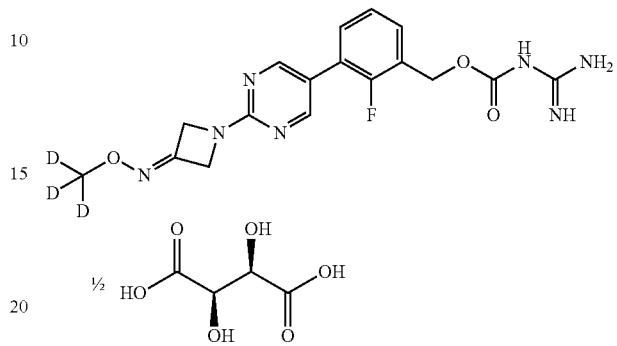

DMSO (5 mL) was added to 2-fluoro-3-(2-{3-[(methoxy-d$_3$)imino]azetidin-1-yl}pyrimidin-5-yl)benzyl carbamimidoylcarbamate (Compound II-12) 500 mg (1.28 mmol) synthesized in the same manner as in Example 3, and the mixture was heated to 50° C. to give a solution. Next, L-tartaric acid 199 mg (1.33 mmol) was added, and the mixture was cooled to room temperature. Ethyl acetate (20 ml) was dropped thereto, and the mixture was stirred at room temperature for 16 hours. The precipitated solid was collected by filtration and was dried under reduced pressure to give the title compound 573 mg (1.23 mmol, yield 96%) as a white solid.

Mass spectrum (ESI, m/z):391[M+1]$^+$.

$^1$H-NMR spectrum (400 MHz, DMSO-d$_6$+D$_2$O) δ:8.63 (s, 2H), 7.56-7.49 (m, 1H), 7.46-7.40 (m, 1H), 7.33-7.26 (m, 1H), 5.10 (s, 2H), 4.87-4.77 (m, 4H), 4.19 (s, 1H).

Example 193

2-Fluoro-3-(2-{3-[(methoxy-d$_3$)imino]azetidin-1-yl}pyrimidin-5-yl)benzyl carbamimidoylcarbamate 1/2 D-tartrate (Compound II-12 1/2 D-tartrate)

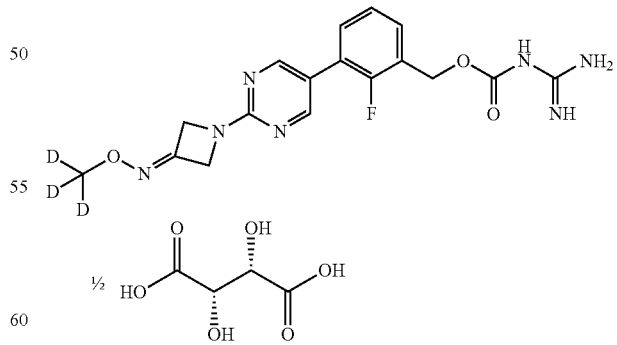

DMSO (5 mL) was added to 2-fluoro-3-(2-{3-[(methoxy-d$_3$)imino]azetidin-1-yl}pyrimidin-5-yl)benzyl carbamimidoylcarbamate (Compound II-12) 500 mg (1.28 mmol) synthesized in the same manner as in Example 3, and the mixture was heated to 50° C. to give a solution. Next, D-tartaric acid 194 mg (1.29 mmol) was added, and the mixture was cooled to room temperature. Ethyl acetate (20 ml) was dropped thereto, and the mixture was stirred at room temperature for 16 hours. The precipitated solid was collected by filtration and was dried under reduced pressure to give the title compound 555 mg (1.19 mmol, yield 93%) as a white solid.

Mass spectrum (ESI, m/z):391[M+1]$^+$.

$^1$H-NMR spectrum (400 MHz, DMSO-d$_6$+D$_2$O) δ:8.63 (d, J=1.1 Hz, 2H), 7.57-7.49 (m, 1H), 7.47-7.40 (m, 1H), 7.34-7.27 (m, 1H), 5.09 (s, 2H), 4.85-4.78 (m, 4H), 4.18 (s, 1H).

Example 194

2-Fluoro-3-(2-{3-[(methoxy-d$_3$)imino]azetidin-1-yl}pyrimidin-5-yl)benzyl carbamimidoylcarbamate maleate (Compound II-12 maleate)

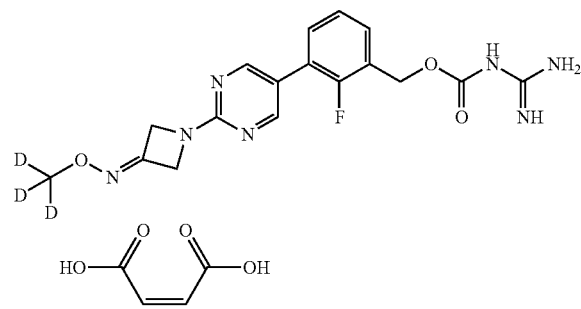

DMSO (5 mL) was added to 2-fluoro-3-(2-{3-[(methoxy-d$_3$)imino]azetidin-1-yl}pyrimidin-5-yl)benzyl carbamimidoylcarbamate (Compound II-12) 500 mg (1.28 mmol) synthesized in the same manner as in Example 3, and the mixture was heated to 50° C. to give a solution. Next, maleic acid 151 mg (1.30 mmol) was added, and the mixture was cooled to room temperature. Ethyl acetate (20 ml) was dropped thereto, and the mixture was stirred at room temperature for 16 hours. The precipitated solid was collected by filtration and was dried under reduced pressure to give the title compound 543 mg (1.07 mmol, yield 84%) as a white solid.

Mass spectrum (ESI, m/z):391[M+1]$^+$.

$^1$H-NMR spectrum (400 MHz, DMSO-d$_6$+D$_2$O) δ:8.64 (d, J=1.1 Hz, 2H), 7.65-7.57 (m, 1H), 7.56-7.49 (m, 1H), 7.39-7.32 (m, 1H), 6.08 (s, 2H), 5.32 (s, 2H), 4.85-4.78 (m, 4H).

Example 195

2-Fluoro-3-(2-{3-[(methoxy-d$_3$)imino]azetidin-1-yl}pyrimidin-5-yl)benzyl carbamimidoylcarbamate 1/2 succinate (Compound II-12 1/2 succinate)

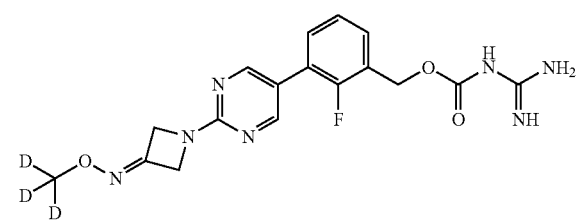

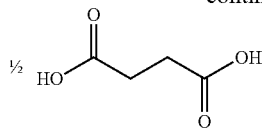

DMSO (5 mL) was added to 2-fluoro-3-(2-{3-[(methoxy-d$_3$)imino]azetidin-1-yl}pyrimidin-5-yl)benzyl carbamimidoylcarbamate (Compound II-12) 500 mg (1.28 mmol) synthesized in the same manner as in Example 3, and the mixture was heated to 50° C. to give a solution. Next, succinic acid 153 mg (1.30 mmol) was added, and the mixture was cooled to room temperature. Ethyl acetate (20 ml) was dropped thereto, and the mixture was stirred at room temperature for 16 hours. The precipitated solid was collected by filtration and was dried under reduced pressure to give the title compound 506 mg (1.13 mmol, yield 88%) as a white solid.

Mass spectrum (ESI, m/z):391[M+1]$^+$.

$^1$H-NMR spectrum (400 MHz, DMSO-d$_6$+D$_2$O) δ:8.63 (d, J=1.3 Hz, 2H), 7.54-7.47 (m, 1H), 7.45-7.39 (m, 1H), 7.33-7.27 (m, 1H), 5.07 (s, 2H), 4.85-4.78 (m, 4H), 2.41 (s, 2H).

Example 196

2-Fluoro-3-(2-{3-[(2-fluoroethoxy)imino]azetidin-1-yl}pyrimidin-5-yl)benzyl carbamimidoylcarbamate 1/2 L-tartrate (Compound II-15 1/2 L-tartrate)

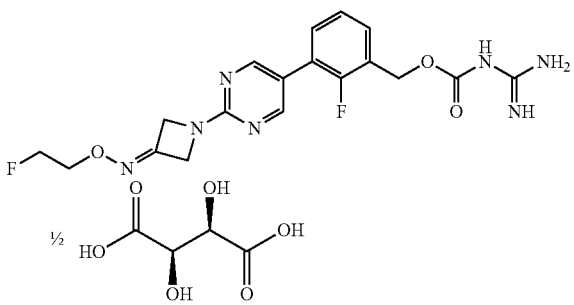

DMSO (5 mL) was added to 2-fluoro-3-(2-{3-[(2-fluoroethoxy)imino]azetidin-1-yl}pyrimidin-5-yl)benzyl carbamimidoylcarbamate (Compound II-15) 500 mg (1.19 mmol) synthesized in the same manner as in Example 5, and the mixture was heated to 50° C. to give a solution. Next, L-tartaric acid 179 mg (1.20 mmol) was added, and the mixture was cooled to room temperature. Ethyl acetate (20 ml) was dropped thereto, and the mixture was stirred at room temperature for 16 hours. The precipitated solid was collected by filtration and was dried under reduced pressure to give the title compound 541 mg (1.09 mmol, yield 92%) as a white solid.

Mass spectrum (ESI, m/z):420[M+1]$^+$.

$^1$H-NMR spectrum (400 MHz, DMSO-d$_6$+D$_2$O) δ:8.64 (d, J=1.3 Hz, 2H), 7.58-7.49 (m, 1H), 7.48-7.40 (m, 1H), 7.36-7.27 (m, 1H), 5.10 (s, 2H), 4.90-4.80 (m, 4H), 4.75-4.55 (m, 2H), 4.36-4.22 (m, 2H), 4.18 (s, 1H).

Example 197

2-Fluoro-3-(2-{3-[(2-fluoroethoxy)imino]azetidin-1-yl}pyrimidin-5-yl)benzyl carbamimidoylcarbamate 1/2 D-tartrate (Compound II-15 1/2 D-tartrate)

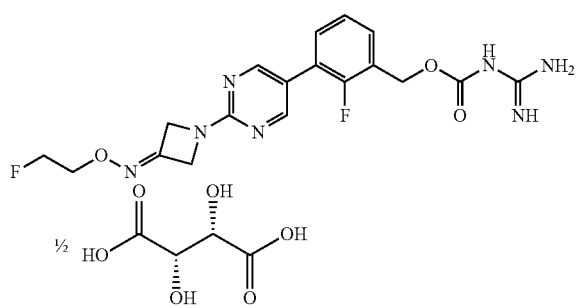

DMSO (5 mL) was added to 2-fluoro-3-(2-{3-[(2-fluoroethoxy)imino]azetidin-1-yl}pyrimidin-5-yl)benzyl carbamimidoylcarbamate (Compound II-15) 500 mg (1.19 mmol) synthesized in the same manner as in Example 5, and the mixture was heated to 50° C. to give a solution. Next, D-tartaric acid 181 mg (1.21 mmol) was added, and the mixture was cooled to room temperature. Ethyl acetate (20 ml) was dropped thereto, and the mixture was stirred at room temperature for 16 hours. The precipitated solid was collected by filtration and was dried under reduced pressure to give the title compound 529 mg (1.07 mmol, yield 90%) as a white solid.

Mass spectrum (ESI, m/z):420[M+1]$^+$.
$^1$H-NMR spectrum (400 MHz, DMSO-d$_6$+D$_2$O) δ:8.64 (d, J=1.3 Hz, 2H), 7.58-7.48 (m, 1H), 7.47-7.40 (m, 1H), 7.34-7.27 (m, 1H), 5.09 (s, 2H), 4.89-4.80 (m, 4H), 4.74-4.54 (m, 2H), 4.37-4.20 (m, 2H), 4.17 (s, 1H).

Example 198

2-Fluoro-3-(2-{3-[(2-fluoroethoxy)imino]azetidin-1-yl}pyrimidin-5-yl)benzyl carbamimidoylcarbamate maleate (Compound II-15 maleate)

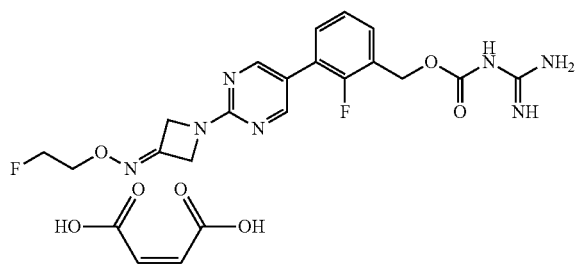

DMSO (5 mL) was added to 2-fluoro-3-(2-{3-[(2-fluoroethoxy)imino]azetidin-1-yl}pyrimidin-5-yl)benzyl carbamimidoylcarbamate (Compound II-15) 500 mg (1.19 mmol) synthesized in the same manner as in Example 5, and the mixture was heated to 50° C. to give a solution. Next, maleic acid 138 mg (1.19 mmol) was added, and the mixture was cooled to room temperature. Ethyl acetate (20 ml) was dropped thereto, and the mixture was stirred at room temperature for 48 hours. The precipitated solid was collected by filtration and was dried under reduced pressure to give the title compound 518 mg (0.967 mmol, yield 81%) as a white solid.

Mass spectrum (ESI, m/z):420[M+1]$^+$.
$^1$H-NMR spectrum (400 MHz, DMSO-d$_6$+D$_2$O) δ:8.64 (d, J=1.3 Hz, 2H), 7.65-7.58 (m, 1H), 7.56-7.49 (m, 1H), 7.40-7.33 (m, 1H), 6.08 (s, 2H), 5.32 (s, 2H), 4.90-4.81 (m, 4H), 4.74-4.55 (m, 2H), 4.35-4.20 (m, 2H).

Example 199

2-Fluoro-3-(2-{3-[(2-fluoroethoxy)imino]azetidin-1-yl}pyrimidin-5-yl)benzyl carbamimidoylcarbamate 1/2 succinate (Compound II-15 1/2 succinate)

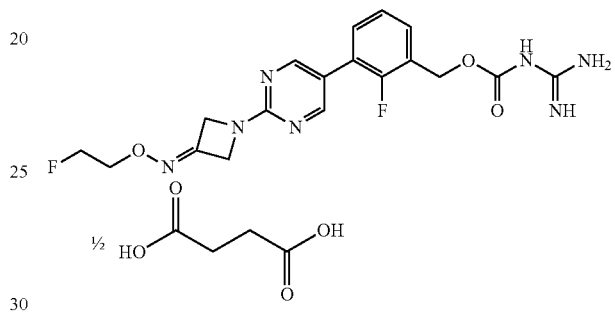

DMSO (5 mL) was added to 2-fluoro-3-(2-{3-[(2-fluoroethoxy)imino]azetidin-1-yl}pyrimidin-5-yl)benzyl carbamimidoylcarbamate (Compound II-15) 500 mg (1.19 mmol) synthesized in the same manner as in Example 5, and the mixture was heated to 50° C. to give a solution. Next, succinic acid 145 mg (1.23 mmol) was added, and the mixture was cooled to room temperature. Ethyl acetate (20 ml) was dropped thereto, and the mixture was stirred at room temperature for 20 hours. The precipitated solid was collected by filtration and was dried under reduced pressure to give the title compound 492 mg (1.03 mmol, yield 87%) as a white solid.

Mass spectrum (ESI, m/z):420[M+1]$^+$.
$^1$H-NMR spectrum (400 MHz, DMSO-d$_6$+D$_2$O) δ:8.64 (s, 2H), 7.54-7.48 (m, 1H), 7.45-7.39 (m, 1H), 7.35-7.24 (m, 1H), 5.07 (s, 2H), 4.88-4.80 (m, 4H), 4.75-4.54 (m, 2H), 4.36-4.20 (m, 2H), 2.41 (s, 2H).

Example 200

2-Fluoro-3-{5-fluoro-6-[3-(methoxyimino)azetidin-1-yl]pyridin-3-yl}benzyl carbamimidoylcarbamate 1/2 L-tartrate (Compound III-78 1/2 L-tartrate)

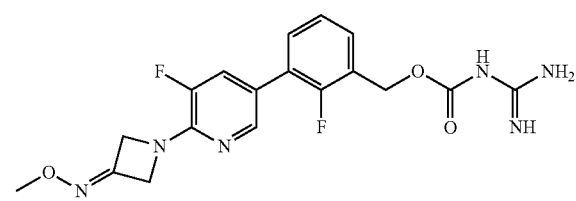

-continued

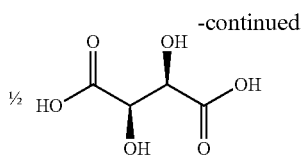

DMSO (5 mL) was added to 2-fluoro-3-{5-fluoro-6-[3-(methoxyimino)azetidin-1-yl]pyridin-3-yl}benzyl carbamimidoylcarbamate (Compound III-78) 500 mg (1.24 mmol) synthesized in the same manner as in Example 36, and the mixture was heated to 50° C. to give a solution. Next, L-tartaric acid 188 mg (1.25 mmol) was added, and the mixture was cooled to room temperature. Ethyl acetate (20 ml) was dropped thereto, and the mixture was stirred at room temperature for 16 hours. The precipitated solid was collected by filtration and was dried under reduced pressure to give the title compound 515 mg (1.07 mmol, yield 86%) as a white solid.

Mass spectrum (ESI, m/z):405[M+1]$^+$.

$^1$H-NMR spectrum (400 MHz, DMSO-d$_6$+D$_2$O) δ:8.21-8.15 (m, 1H), 7.79-7.72 (m, 1H), 7.55-7.48 (m, 1H), 7.45-7.38 (m, 1H), 7.33-7.25 (m, 1H), 5.09 (s, 2H), 4.90-4.82 (m, 4H), 4.19 (s, 1H), 3.82 (s, 3H).

Example 201

2-Fluoro-3-{5-fluoro-6-[3-(methoxyimino)azetidin-1-yl]pyridin-3-yl}benzyl carbamimidoylcarbamate 1/2 D-tartrate (Compound III-78 1/2 D-tartrate)

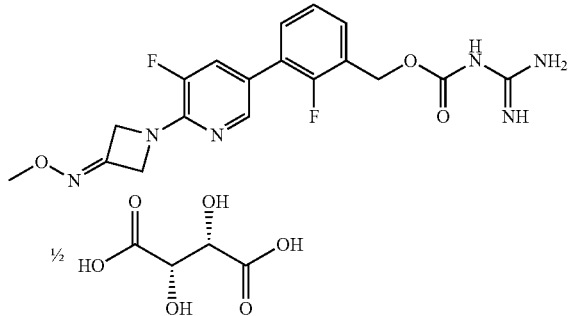

DMSO (5 mL) was added to 2-fluoro-3-{5-fluoro-6-[3-(methoxyimino)azetidin-1-yl]pyridin-3-yl}benzyl carbamimidoylcarbamate (Compound III-78) 500 mg (1.24 mmol) synthesized in the same manner as in Example 36, and the mixture was heated to 50° C. to give a solution. Next, D-tartaric acid 186 mg (1.24 mmol) was added, and the mixture was cooled to room temperature. Ethyl acetate (20 ml) was dropped thereto, and the mixture was stirred at room temperature for 16 hours. The precipitated solid was collected by filtration and was dried under reduced pressure to give the title compound 525 mg (1.10 mmol, yield 89%) as a white solid.

Mass spectrum (ESI, m/z):405[M+1]$^+$.

$^1$H-NMR spectrum (400 MHz, DMSO-d$_6$+D$_2$O) δ:8.22-8.15 (m, 1H), 7.79-7.72 (m, 1H), 7.55-7.47 (m, 1H), 7.46-7.38 (m, 1H), 7.32-7.25 (m, 1H), 5.09 (s, 2H), 4.92-4.80 (m, 4H), 4.20 (s, 1H), 3.82 (s, 3H).

Example 202

2-Fluoro-3-{5-fluoro-6-[3-(methoxyimino)azetidin-1-yl]pyridin-3-yl}benzyl carbamimidoylcarbamate maleate (Compound III-78 maleate)

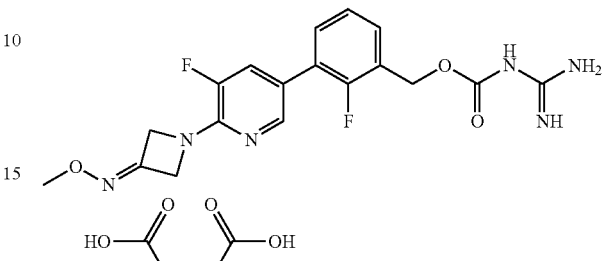

DMSO (5 mL) was added to 2-fluoro-3-{5-fluoro-6-[3-(methoxyimino)azetidin-1-yl]pyridin-3-yl}benzyl carbamimidoylcarbamate (Compound III-78) 500 mg (1.24 mmol) synthesized in the same manner as in Example 36, and the mixture was heated to 50° C. to give a solution. Next, maleic acid 150 mg (1.29 mmol) was added, and the mixture was cooled to room temperature. Ethyl acetate (20 ml) was dropped thereto, and the mixture was stirred at room temperature for 40 hours. The precipitated solid was collected by filtration and was dried under reduced pressure to give the title compound 455 mg (0.874 mmol, yield 71%) as a white solid.

Mass spectrum (ESI, m/z):405[M+1]$^+$.

$^1$H-NMR spectrum (400 MHz, DMSO-d$_6$+D$_2$O) δ:8.21-8.17 (m, 1H), 7.81-7.70 (m, 1H), 7.63-7.56 (m, 1H), 7.56-7.47 (m, 1H), 7.40-7.28 (m, 1H), 6.07 (s, 2H), 5.32 (s, 2H), 4.90-4.84 (m, 4H), 3.82 (s, 3H).

Example 203

2-Fluoro-3-{5-fluoro-6-[3-(methoxyimino)azetidin-1-yl]pyridin-3-yl}benzyl carbamimidoylcarbamate 1/2 succinate (Compound III-78 1/2 succinate)

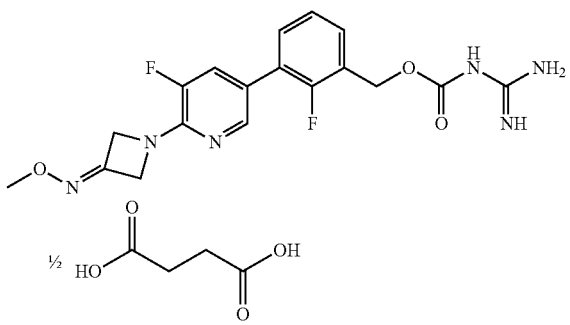

DMSO (4 mL) was added to 2-fluoro-3-{5-fluoro-6-[3-(methoxyimino)azetidin-1-yl]pyridin-3-yl}benzyl carbamimidoylcarbamate (Compound III-78) 500 mg (1.24 mmol) synthesized in the same manner as in Example 36, and the mixture was heated to 50° C. to give a solution. Next, succinic acid 150 mg (1.27 mmol) was added, and the mixture was cooled to room temperature. Ethyl acetate (20 ml) was dropped thereto, and the mixture was stirred at room temperature for 20 hours. The precipitated solid was collected by filtration and was dried under reduced pressure to give the title compound 488 mg (1.05 mmol, yield 85%) as a white solid.

Mass spectrum (ESI, m/z):405[M+1]$^+$.

$^1$H-NMR spectrum (400 MHz, DMSO-d$_6$+D$_2$O) δ:8.22-8.13 (m, 1H), 7.81-7.70 (m, 1H), 7.55-7.45 (m, 1H), 7.44-7.37 (m, 1H), 7.33-7.23 (m, 1H), 5.06 (s, 2H), 4.90-4.83 (m, 4H), 3.82 (s, 3H), 2.40 (s, 2H).

Example 204

2-Fluoro-3-(5-fluoro-6-{3-[(methoxy-d$_3$)imino]azetidin-1-yl}pyridin-3-yl)benzyl carbamimidoylcarbamate 1/2 L-tartrate (Compound III-88 1/2 L-tartrate)

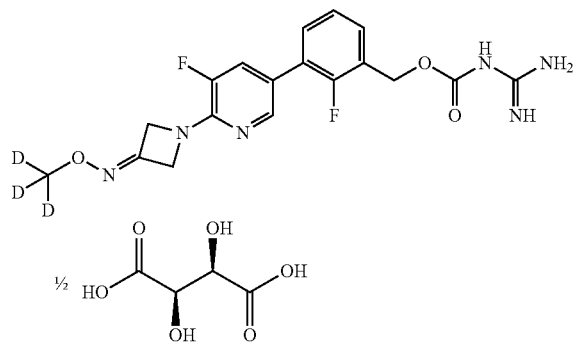

DMSO (5 mL) was added to 2-fluoro-3-(5-fluoro-6-{3-[(methoxy-d$_3$)imino]azetidin-1-yl}pyridin-3-yl)benzyl carbamimidoylcarbamate (Compound III-88) 500 mg (1.23 mmol) synthesized in the same manner as in Example 37, and the mixture was heated to 50° C. to give a solution. Next, L-tartaric acid 185 mg (1.23 mmol) was added, and the mixture was cooled to room temperature. Ethyl acetate (20 ml) was dropped thereto, and the mixture was stirred at room temperature for 16 hours. The precipitated solid was collected by filtration and was dried under reduced pressure to give the title compound 567 mg (1.18 mmol, yield 96%) as a white solid.

Mass spectrum (ESI, m/z):408[M+1]$^+$.

$^1$H-NMR spectrum (400 MHz, DMSO-d$_6$+D$_2$O) δ:8.20-8.16 (m, 1H), 7.78-7.72 (m, 1H), 7.55-7.47 (m, 1H), 7.46-7.39 (m, 1H), 7.36-7.22 (m, 1H), 5.10 (s, 2H), 4.90-4.82 (m, 4H), 4.20 (s, 1H).

Example 205

2-Fluoro-3-(5-fluoro-6-{3-[(methoxy-d$_3$)imino]azetidin-1-yl}pyridin-3-yl)benzyl carbamimidoylcarbamate 1/2 D-tartrate (Compound III-88 1/2 D-tartrate)

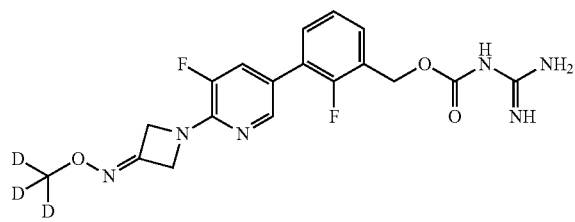

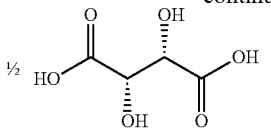

DMSO (5 mL) was added to 2-fluoro-3-(5-fluoro-6-{3-[(methoxy-d$_3$)imino]azetidin-1-yl}pyridin-3-yl)benzyl carbamimidoylcarbamate (Compound III-88) 500 mg (1.23 mmol) synthesized in the same manner as in Example 37, and the mixture was heated to 50° C. to give a solution. Next, D-tartaric acid 184 mg (1.23 mmol) was added, and the mixture was cooled to room temperature. Ethyl acetate (20 ml) was dropped thereto, and the mixture was stirred at room temperature for 16 hours. The precipitated solid was collected by filtration and was dried under reduced pressure to give the title compound 573 mg (1.19 mmol, yield 97%) as a white solid.

Mass spectrum (ESI, m/z):408[M+1]$^+$.

$^1$H-NMR spectrum (400 MHz, DMSO-d$_6$+D$_2$O) δ:8.20-8.15 (m, 1H), 7.80-7.71 (m, 1H), 7.55-7.48 (m, 1H), 7.46-7.38 (m, 1H), 7.34-7.25 (m, 1H), 5.10 (s, 2H), 4.90-4.83 (m, 4H), 4.20 (s, 1H).

Example 206

2-Fluoro-3-(5-fluoro-6-{3-[(methoxy-d$_3$)imino]azetidin-1-yl}pyridin-3-yl)benzyl carbamimidoylcarbamate maleate (Compound III-88 maleate)

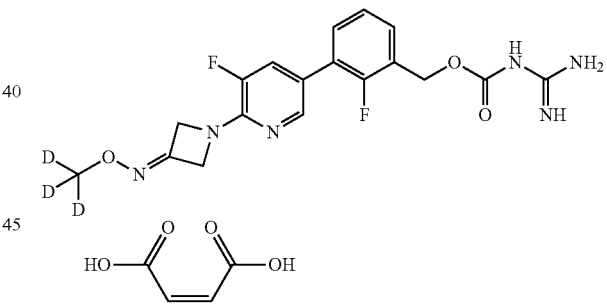

DMSO (5 mL) was added to 2-fluoro-3-(5-fluoro-6-{3-[(methoxy-d$_3$)imino]azetidin-1-yl}pyridin-3-yl)benzyl carbamimidoylcarbamate (Compound III-88) 500 mg (1.23 mmol) synthesized in the same manner as in Example 37, and the mixture was heated to 50° C. to give a solution. Next, maleic acid 148 mg (1.28 mmol) was added, and the mixture was cooled to room temperature. Ethyl acetate (20 ml) was dropped thereto, and the mixture was stirred at room temperature for 16 hours. The precipitated solid was collected by filtration and was dried under reduced pressure to give the title compound 527 mg (1.01 mmol, yield 82%) as a white solid.

Mass spectrum (ESI, m/z):408[M+1]$^+$.

$^1$H-NMR spectrum (400 MHz, DMSO-d$_6$+D$_2$O) δ:8.20-8.17 (m, 1H), 7.80-7.71 (m, 1H), 7.63-7.57 (m, 1H), 7.54-7.48 (m, 1H), 7.37-7.31 (m, 1H), 6.08 (s, 2H), 5.32 (s, 2H), 4.90-4.84 (m, 4H).

Example 207

2-Fluoro-3-(5-fluoro-6-{3-[(methoxy-d₃)imino]azetidin-1-yl}pyridin-3-yl)benzyl carbamimidoylcarbamate 1/2 succinate (Compound III-88 1/2 succinate)

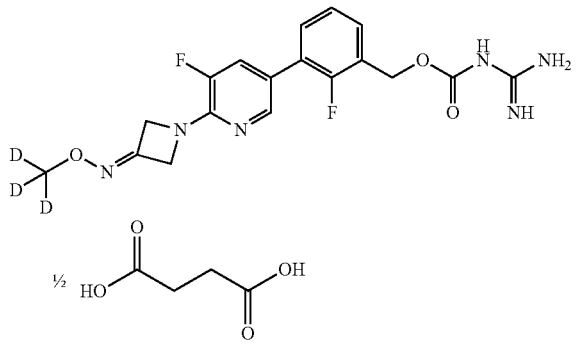

DMSO (5 mL) was added to 2-fluoro-3-(5-fluoro-6-{3-[(methoxy-d₃)imino]azetidin-1-yl}pyridin-3-yl)benzyl carbamimidoylcarbamate (Compound III-88) 500 mg (1.23 mmol) synthesized in the same manner as in Example 37, and the mixture was heated to 50° C. to give a solution. Next, succinic acid 146 mg (1.24 mmol) was added, and the mixture was cooled to room temperature. Ethyl acetate (20 ml) was dropped thereto, and the mixture was stirred at room temperature for 20 hours. The precipitated solid was collected by filtration and was dried under reduced pressure to give the title compound 497 mg (1.07 mmol, yield 87%) as a white solid.

Mass spectrum (ESI, m/z):408[M+1]⁺.

¹H-NMR spectrum (400 MHz, DMSO-d₆+D₂O) δ:8.19-8.16 (m, 1H), 7.78-7.72 (m, 1H), 7.53-7.46 (m, 1H), 7.44-7.37 (m, 1H), 7.32-7.25 (m, 1H), 5.07 (s, 2H), 4.89-4.83 (m, 4H), 2.42 (s, 2H).

Example 208

2-Fluoro-3-(5-fluoro-6-{3-[(methoxy-d₃)imino]azetidin-1-yl}pyridin-3-yl)benzyl carbamimidoylcarbamate monosuccinate (Compound III-88 succinate)

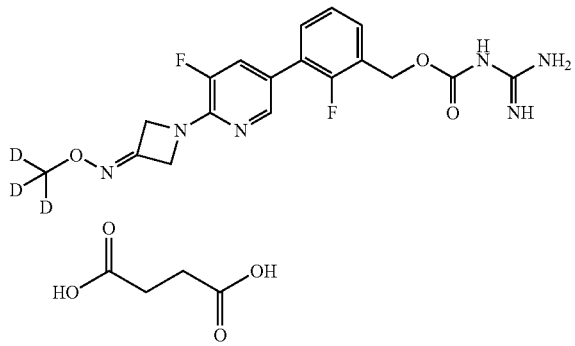

DMSO (0.4 mL) was added to 2-fluoro-3-(5-fluoro-6-{3-[(methoxy-d₃)imino]azetidin-1-yl}pyridin-3-yl)benzyl carbamimidoylcarbamate (Compound III-88) 100 mg (0.245 mmol) synthesized in the same manner as in Example 37, and the mixture was heated to 60° C. to give a solution. Next, succinic acid 29 mg (0.246 mmol) was added, and the mixture was cooled to room temperature. Ethyl acetate (2 ml) was dropped thereto, and the mixture was stirred at room temperature. The precipitated solid was collected by filtration and was dried under reduced pressure to give the title compound 123 mg (0.234 mmol, yield 96%) as a white solid.

Mass spectrum (ESI, m/z):408[M+1]⁺.

¹H-NMR spectrum (400 MHz, DMSO-d₆+D₂O) δ:8.20-8.16 (m, 1H), 7.79-7.72 (m, 1H), 7.54-7.46 (m, 1H), 7.44-7.37 (m, 1H), 7.33-7.24 (m, 1H), 5.07 (s, 2H), 4.90-4.83 (m, 4H), 2.42 (s, 4H).

REFERENCE EXAMPLES

Reference Example 1

1-(5-Bromopyrimidin-2-yl)azetidin-3-ol (Reference Compound 1)

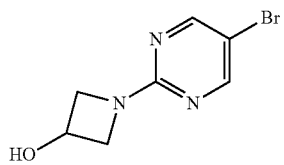 [SMILES: OC1CN(c2ncc(Br)cn2)C1]

TEA 54 mL (0.39 mol) was added to an ethanol (300 mL) solution of 5-bromo-2-chloropyrimidine 25 g (0.13 mol) and azetidin-3-ol hydrochloride 16 g (0.15 mol), and the mixture was stirred at 60° C. for 4 hours. After the completion of the reaction, the solvent of the reaction mixture was concentrated under reduced pressure to approximately half volume. Water 200 mL was added, and the mixture was stirred at room temperature for 3 hours. The precipitated solid was collected by filtration and was dried under reduced pressure to give the title compound 28 g (0.12 mol, yield 92%) as a white solid.

Mass spectrum (CI, m/z):230, 232[M+1]⁺.

¹H-NMR spectrum (400 MHz, DMSO-d₆) δ:8.43 (s, 2H), 5.73 (d, J=6.5 Hz, 1H), 4.59-4.51 (m, 1H), 4.25-4.18 (m, 2H), 3.79-3.73 (m, 2H).

Reference Example 2

1-(5-Bromopyrimidin-2-yl)azetidin-3-one (Reference Compound 2)

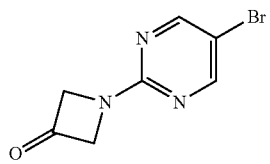 [SMILES: O=C1CN(c2ncc(Br)cn2)C1]

Dess-Martin Periodinane 50 g (120 mmol) and sodium hydrogen carbonate 10 g (120 mmol) were added to a methylene chloride (400 mL) suspension of 1-(5-bromopyrimidin-2-yl)azetidin-3-ol 19 g (83 mmol) synthesized in the same manner as in Reference Example 1, and the mixture was stirred at room temperature for 20 hours. After the completion of the reaction, sodium thiosulfate pentahydrate and a saturated aqueous sodium hydrogen carbonate solution were added to the reaction mixture, and followed by extraction with methylene chloride. The organic layer was washed with a saturated aqueous sodium hydrogen carbonate solution, dried over anhydrous sodium sulfate, and filtered. The filtrate was concentrated under reduced pressure. Diisopropyl ether was added to the concentrated residue. The solid was collected by filtration and was dried under reduced pressure to give the title compound 16 g (70 mmol, yield 84%) as a white solid.

Mass spectrum (CI, m/z):228, 230[M+1]⁺.
$^1$H-NMR spectrum (400 MHz, DMSO-$d_6$) δ:8.58 (s, 2H), 4.87 (s, 4H).

The title compound was synthesized also in the following manner.

TEA 3.0 mL (22 mmol) was added to an ethanol (10 mL) solution of 5-bromo-2-chloropyrimidine 2.0 g (10 mmol) and azetidin-3-one hydrochloride 1.0 g (9.3 mmol), and the mixture was stirred at 80° C. for 3 hours. After the completion of the reaction, water was added to the reaction mixture, and followed by extraction with ethyl acetate. The organic layer was washed with water, dried over anhydrous magnesium sulfate, and filtered. The filtrate was concentrated under reduced pressure. The concentrated residue was purified by silica gel column chromatography (eluting solvent: 1,2-dichloroethane:ethyl acetate) to give the title compound 0.55 g (2.4 mmol, yield 24%) as a colorless oil.

The title compound was synthesized also in the following manner.

Azadol 7.0 mg (0.046 mmol) and iodobenzene diacetate 0.40 g (1.2 mmol) were added to a methylene chloride (5 mL) solution of 1-(5-bromopyrimidin-2-yl)azetidin-3-ol 0.20 g (0.87 mmol) synthesized in the same manner as in Reference Example 1, and the mixture was stirred at room temperature for 4 hours. After the completion of the reaction, a saturated aqueous sodium bicarbonate solution and a 20% aqueous sodium thiosulfate solution were added to the reaction mixture, and the mixture was stirred for 1 hour and followed by extraction with ethyl acetate. The organic layer was washed with brine, dried over anhydrous sodium sulfate, and filtered. The filtrate was concentrated under reduced pressure. Hexane was added to the concentrated residue, and the mixture was stirred at 50° C. The solid was collected by filtration to give the title compound 0.19 g (0.82 mmol, yield 94%) as a white solid.

Reference Example 3-1

1-(5-Bromopyrimidin-2-yl)azetidin-3-one O-methyl oxime (Reference Compound 3-1)

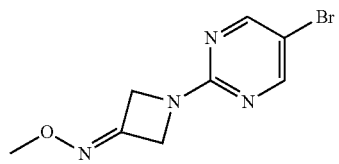

O-methylhydroxylamine hydrochloride 1.5 g (18 mmol) was added to a THF (40 mL) solution of 1-(5-bromopyrimidin-2-yl)azetidin-3-one 2.0 g (8.8 mmol) synthesized in the same manner as in Reference Example 2, and the mixture was stirred at 50° C. for 12 hours. After the completion of the reaction, a saturated aqueous sodium hydrogen carbonate solution was added to the reaction mixture. The precipitated solid was collected by filtration, washed with TBME, and dried under reduced pressure to give the title compound 1.5 g (5.8 mmol, yield 66%) as a white solid.

Mass spectrum (CI, m/z):257, 259[M+1]⁺.
$^1$H-NMR spectrum (400 MHz, DMSO-$d_6$) δ:8.54 (s, 2H), 4.80-4.66 (m, 4H), 3.81 (s, 3H).

Reference Example 3-2

1-(5-Bromopyridin-2-yl)azetidin-3-one O-methyl oxime (Reference Compound 3-2)

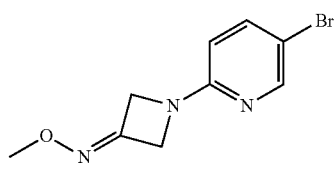

O-methylhydroxylamine hydrochloride 38 mg (0.46 mmol) was added to a THF (4 mL) solution of 1-(5-bromopyridin-2-yl)azetidin-3-one 52 mg (0.23 mmol) synthesized in the same manner as in Reference Example 32-2, and the mixture was stirred at 50° C. for 8 hours. After the completion of the reaction, a saturated aqueous sodium hydrogen carbonate solution was added to the reaction mixture, and followed by extraction with ethyl acetate. The organic layer was washed with water, dried over anhydrous magnesium sulfate, and filtered. The filtrate was concentrated under reduced pressure. The concentrated residue was purified by silica gel column chromatography (eluting solvent: 1,2-dichloroethane:ethyl acetate) to give the title compound 55 mg (0.22 mmol, yield 96%) as a white solid.

Reference Example 3-3

1-(5-Bromo-3-methylpyridin-2-yl)azetidin-3-one O-methyl oxime (Reference Compound 3-3)

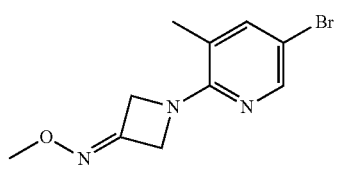

The reaction was performed by the method described in Reference Example 3-2, except that 1-(5-bromopyridin-2-yl)azetidin-3-one (Reference Compound 32-2) was replaced by 1-(5-bromo-3-methylpyridin-2-yl)azetidin-3-one synthesized in the same manner as in Reference Example 32-3, and the reaction temperature was ambient. Consequently, the title compound (yield 81%) was obtained as a light brown solid.

Mass spectrum (ESI, m/z):270, 272[M+1]⁺.
$^1$H-NMR spectrum (400 MHz, DMSO-$d_6$) δ:8.09 (d, J=2.1 Hz, 1H), 7.65-7.60 (m, 1H), 4.77 (s, 4H), 3.79 (s, 3H), 2.17 (s, 3H).

Reference Example 3-4

1-(5-Bromo-3-chloropyridin-2-yl)azetidin-3-one O-methyl oxime (Reference Compound 3-4)

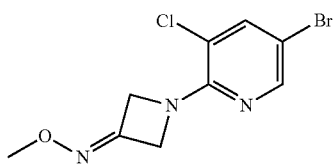

The reaction was performed by the method described in Reference Example 3-2, except that 1-(5-bromopyridin-2-yl)azetidin-3-one (Reference Compound 32-2) was replaced by 1-(5-bromo-3-chloropyridin-2-yl)azetidin-3-one synthesized in the same manner as in Reference Example 32-4. Consequently, the title compound (yield 75%) was obtained as a white solid.

Mass spectrum (CI, m/z):290, 292[M+1]$^+$.

$^1$H-NMR spectrum (400 MHz, CDCl$_3$) δ:8.12 (d, J=2.1 Hz, 1H), 7.63 (d, J=2.1 Hz, 1H), 4.92-4.84 (m, 4H), 3.89 (s, 3H).

Reference Example 3-5

1-[5-Bromo-3-(difluoromethyl)pyridin-2-yl]azetidin-3-one O-methyl oxime (Reference Compound 3-5)

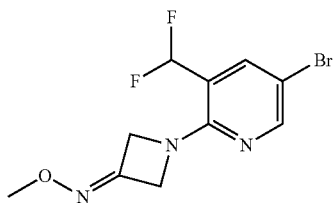 [SMILES: CON=C1CN(c2ncc(Br)cc2C(F)F)C1]

The reaction was performed by the method described in Reference Example 3-2, except that 1-(5-bromopyridin-2-yl)azetidin-3-one (Reference Compound 32-2) was replaced by 1-[5-bromo-3-(difluoromethyl)pyridin-2-yl]azetidin-3-one synthesized in the same manner as in Reference Example 32-5, and the reaction temperature was changed to 70° C. Consequently, the title compound (yield 87%) was obtained as a white solid.

Mass spectrum (CI, m/z):306, 308[M+1]$^+$.

$^1$H-NMR spectrum (400 MHz, DMSO-d$_6$) δ:8.42-8.39 (m, 1H), 7.99-7.96 (m, 1H), 7.07 (t, J=54.2 Hz, 1H), 4.85-4.80 (m, 4H), 3.81 (s, 3H).

Reference Example 3-6

1-(5-Bromo-3-cyclopropylpyridin-2-yl)azetidin-3-one O-methyl oxime (Reference Compound 3-6)

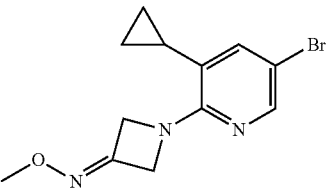 [SMILES: CON=C1CN(c2ncc(Br)cc2C2CC2)C1]

The reaction was performed by the method described in Reference Example 3-2, except that 1-(5-bromopyridin-2-yl)azetidin-3-one (Reference Compound 32-2) was replaced by 1-(5-bromo-3-cyclopropylpyridin-2-yl)azetidin-3-one synthesized in the same manner as in Reference Example 32-6, and the reaction temperature was changed to 70° C. Consequently, the title compound (yield 37%) was obtained as a white solid.

Mass spectrum (CI, m/z):296, 298[M+1]$^+$.

$^1$H-NMR spectrum (400 MHz, DMSO-d$_6$) δ:8.08-8.05 (m, 1H), 7.41 (dd, J=0.7, 2.3 Hz, 1H), 4.88-4.83 (m, 4H), 3.80 (s, 3H), 1.88-1.79 (m, 1H), 0.95-0.86 (m, 2H), 0.78-0.69 (m, 2H).

Reference Example 3-7

1-(5-Bromo-3-ethylpyridin-2-yl)azetidin-3-one O-methyl oxime (Reference Compound 3-7)

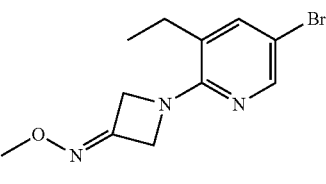 [SMILES: CCc1cc(Br)cnc1N1CC(=NOC)C1]

The reaction was performed by the method described in Reference Example 3-2, except that 1-(5-bromopyridin-2-yl)azetidin-3-one (Reference Compound 32-2) was replaced by 1-(5-bromo-3-ethylpyridin-2-yl)azetidin-3-one synthesized in the same manner as in Reference Example 32-7, and the reaction temperature was changed to 70° C. Consequently, the title compound (yield 84%) was obtained as a white solid.

Mass spectrum (CI, m/z):284, 286[M+1]$^+$.

$^1$H-NMR spectrum (400 MHz, DMSO-d$_6$) δ:8.10 (d, J=2.3 Hz, 1H), 7.63-7.59 (m, 1H), 4.80-4.72 (m, 4H), 3.80 (s, 3H), 2.58-2.42 (m, 2H), 1.15 (t, J=7.5 Hz, 3H).

Reference Example 3-8

1-[5-Bromo-3-(methoxymethyl)pyridin-2-yl]azetidin-3-one O-methyl oxime (Reference Compound 3-8)

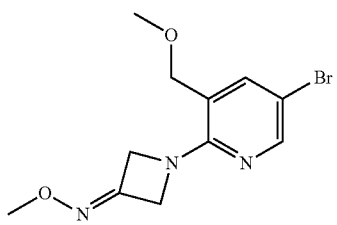 [SMILES: COCc1cc(Br)cnc1N1CC(=NOC)C1]

The reaction was performed by the method described in Reference Example 3-2, except that 1-(5-bromopyridin-2-yl)azetidin-3-one (Reference Compound 32-2) was replaced by 1-[5-bromo-3-(methoxymethyl)pyridin-2-yl]azetidin-3-one synthesized in the same manner as in Reference Example 50-2. Consequently, the title compound (yield 76%) was obtained as a white solid.

Mass spectrum (CI, m/z):300, 302[M+1]$^+$.

$^1$H-NMR spectrum (400 MHz, DMSO-d$_6$) δ:8.19 (d, J=2.4 Hz, 1H), 7.71 (d, J=2.4 Hz, 1H), 4.82-4.78 (m, 4H), 4.31 (s, 2H), 3.80 (s, 3H), 3.31 (s, 3H).

Reference Example 4) [(3-Bromo-2-fluorobenzyl)oxy](tert-butyl)dimethylsilane (Reference Compound 4)

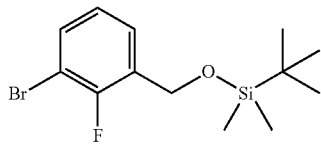 [SMILES: CC(C)(C)[Si](C)(C)OCc1cccc(Br)c1F]

(Tert-butyl)dimethylsilyl chloride 22 g (0.15 mol) and imidazole 14 g (0.21 mol) were added to a THF (200 mL) solution of (3-bromo-2-fluorophenyl)methanol 25 g (0.12 mol), and the mixture was stirred at room temperature for 5 hours and was allowed to stand at room temperature for 2 days. After the completion of the reaction, water was added to the reaction mixture, and followed by extraction with ethyl acetate. The organic layer was washed with water, dried over anhydrous magnesium sulfate, and filtered. The filtrate was concentrated under reduced pressure. The concentrated residue was purified by silica gel column chromatography (eluting solvent: hexane:ethyl acetate) to give the title compound 35 g (0.11 mol, yield 92%) as a colorless oil.

Mass spectrum (CI, m/z):319, 321[M+1]$^+$.

$^1$H-NMR spectrum (400 MHz, DMSO-d$_6$) δ:7.65-7.59 (m, 1H), 7.48-7.42 (m, 1H), 7.22-7.15 (m, 1H), 4.78 (s, 2H), 0.90 (s, 9H), 0.09 (s, 6H).

Reference Example 5) tert-Butyl {[2-fluoro-3-(4,4,5,5-tetramethyl-1,3,2-dioxaborolan-2-yl)benzyl]oxy}dimethylsilane (Reference Compound 5)

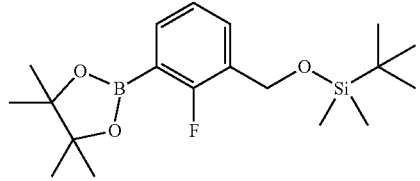 [SMILES: CC1(C)OB(c2cccc(CO[Si](C)(C)C(C)(C)C)c2F)OC1(C)C]

1,4-Dioxane (100 mL) solution of [(3-bromo-2-fluorobenzyl)oxy](tert-butyl)dimethylsilane 14.4 g (45.0 mmol) synthesized in the same manner as in Reference Example 4, bis(pinacolato)diborane 12.6 g (49.6 mmol) and potassium acetate 6.00 g (61.1 mmol) was degassed and purged with nitrogen. Next, [1,1'-bis(diphenylphosphino)ferrocene]palladium (II) dichloride 1.84 g (2.25 mmol) was added. Under a stream of argon, the mixture was stirred at 100° C. for 20 hours. After the completion of the reaction, the reaction mixture was filtered through Celite, water was added, and followed by extraction with ethyl acetate. The organic layer was washed with water, dried over anhydrous magnesium sulfate, and filtered. The filtrate was concentrated under reduced pressure. The concentrated residue was purified by silica gel column chromatography (eluting solvent: hexane:ethyl acetate) to give the title compound 9.64 g (26.3 mmol, yield 43%) as a light yellow oil.

Mass spectrum (CI, m/z):367[M+1]$^+$.

$^1$H-NMR spectrum (400 MHz, DMSO-d$_6$) δ:7.60-7.52 (m, 2H), 7.25-7.17 (m, 1H), 4.74 (s, 2H), 1.29 (s, 12H), 0.90 (s, 9H), 0.09 (s, 6H).

Reference Example 6-1

1-[5-(3-{[(tert-Butyldimethylsilyl)oxy]methyl}-2-fluorophenyl)pyrimidin-2-yl]azetidin-3-one O-methyl oxime (Reference Compound 6-1)

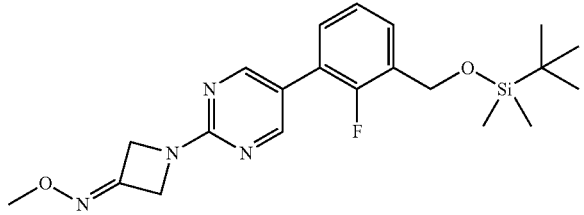 [SMILES: CON=C1CN(c2ncc(-c3cccc(CO[Si](C)(C)C(C)(C)C)c3F)cn2)C1]

1,2-Dimethoxyethane (70 mL) suspension of 1-(5-bromopyrimidin-2-yl)azetidin-3-one O-methyl oxime 2.00 g (7.78 mmol) synthesized in the same manner as in Reference Example 3-1, tert-butyl {[2-fluoro-3-(4,4,5,5-tetramethyl-1,3,2-dioxaborolan-2-yl)benzyl]oxy}dimethylsilane 2.85 g (7.78 mmol) synthesized in the same manner as in Reference Example 5 and a 2 M aqueous sodium carbonate solution 12 mL (24 mmol) was degassed and purged with nitrogen. Next, tetrakis(triphenylphosphine)palladium (0) 1.35 g (1.17 mmol) was added. Under a stream of argon, the mixture was stirred at 80° C. for 3 hours. After the completion of the reaction, water was added to the reaction mixture, and followed by extraction with ethyl acetate. The organic layer was washed with water, dried over anhydrous magnesium sulfate, and filtered. The filtrate was concentrated under reduced pressure. The concentrated residue was purified by silica gel column chromatography (eluting solvent: 1,2-dichloroethane:ethyl acetate) to give the title compound 2.75 g (6.60 mmol, yield 85%) as a white solid.

Mass spectrum (CI, m/z):417[M+1]$^+$.

$^1$H-NMR spectrum (400 MHz, DMSO-d$_6$) δ:8.62 (d, J=1.4 Hz, 2H), 7.55-7.42 (m, 2H), 7.35-7.27 (m, 1H), 4.84-4.78 (m, 6H), 3.83 (s, 3H), 0.91 (s, 9H), 0.11 (s, 6H).

Reference Example 6-2

1-[5-(3-{[(tert-Butyldimethylsilyl)oxy]methyl}-2-fluorophenyl)pyrimidin-2-yl]azetidin-3-one O-ethyl oxime (Reference Compound 6-2)

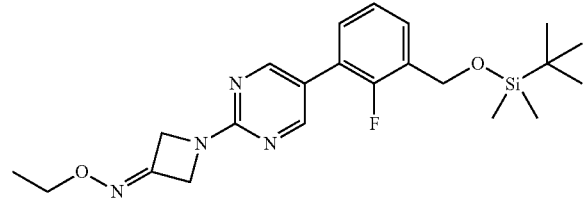 [SMILES: CCON=C1CN(c2ncc(-c3cccc(CO[Si](C)(C)C(C)(C)C)c3F)cn2)C1]

The reaction was performed by the method described in Reference Example 6-1, except that 1-(5-bromopyrimidin-2-yl)azetidin-3-one O-methyl oxime (Reference Compound 3-1) was replaced by 1-(5-bromopyrimidin-2-yl)azetidin-3-one O-ethyl oxime synthesized in the same manner as in Reference Example 8. Consequently, the title compound (yield 82%) was obtained as a light yellow solid.

Mass spectrum (CI, m/z):431 [M+1]$^+$.

$^1$H-NMR spectrum (400 MHz, DMSO-d$_6$) δ:8.62 (d, J=1.5 Hz, 2H), 7.53-7.42 (m, 2H), 7.35-7.29 (m, 1H), 4.85-4.77 (m, 6H), 4.08 (q, J=7.0 Hz, 2H), 1.22 (t, J=7.0 Hz, 3H), 0.91 (s, 9H), 0.11 (s, 6H).

Reference Example 6-3

1-[5-(3-{[(tert-Butyldimethylsilyl)oxy]methyl}-2-fluorophenyl)pyrimidin-2-yl]azetidin-3-one O-methyl-d$_3$ oxime (Reference Compound 6-3)

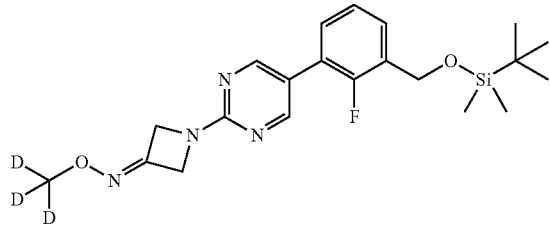 [SMILES: [2H]C([2H])([2H])ON=C1CN(c2ncc(-c3cccc(CO[Si](C)(C)C(C)(C)C)c3F)cn2)C1]

The reaction was performed by the method described in Reference Example 6-1, except that 1-(5-bromopyrimidin-2-yl)azetidin-3-one O-methyl oxime (Reference Compound 3-1) was replaced by 1-(5-bromopyrimidin-2-yl)azetidin-3-one O-methyl-d$_3$ oxime synthesized in the same manner as in Reference Example 10-1. Consequently, the title compound (yield 77%) was obtained as a gray solid.

Mass spectrum (CI, m/z):420[M+1]$^+$.

$^1$H-NMR spectrum (400 MHz, DMSO-d$_6$) δ:8.62 (d, J=1.4 Hz, 2H), 7.52-7.42 (m, 2H), 7.35-7.27 (m, 1H), 4.85-4.77 (m, 6H), 0.91 (s, 9H), 0.11 (s, 6H).

Reference Example 6-4

1-[5-(3-{[(tert-Butyldimethylsilyl)oxy]methyl}-2-fluorophenyl)pyrimidin-2-yl]azetidin-3-one O-(2-fluoroethyl) oxime (Reference Compound 6-4)

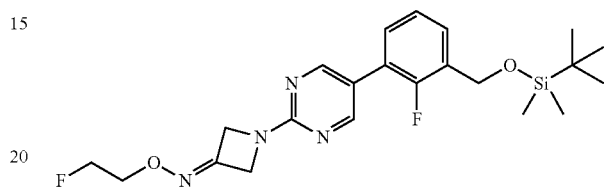

The reaction was performed by the method described in Reference Example 6-1, except that 1-(5-bromopyrimidin-2-yl)azetidin-3-one O-methyl oxime (Reference Compound 3-1) was replaced by 1-(5-bromopyrimidin-2-yl)azetidin-3-one O-(2-fluoroethyl) oxime synthesized in the same manner as in Reference Example 10-2. Consequently, the title compound (including impurities) was obtained as a light yellow solid.

Mass spectrum (CI, m/z):449[M+1]$^+$.

$^1$H-NMR spectrum (400 MHz, CDCl$_3$) δ:8.57 (d, J=1.0 Hz, 2H), 7.56-7.47 (m, 1H), 7.31-7.19 (m, 2H), 4.93-4.87 (m, 4H), 4.85 (s, 2H), 4.75-4.59 (m, 2H), 4.40-4.28 (m, 2H), 0.96 (s, 9H), 0.14 (s, 6H).

Reference Example 6-5

1-[5-(3-{[(tert-Butyldimethylsilyl)oxy]methyl}-2-fluorophenyl)pyrimidin-2-yl]azetidin-3-one oxime (Reference Compound 6-5)

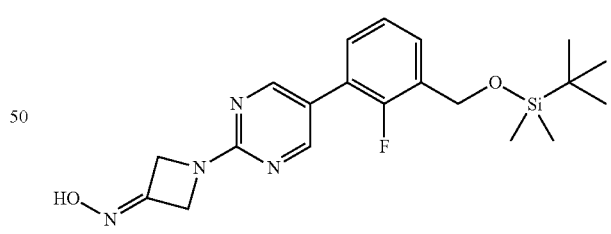

The reaction was performed by the method described in Reference Example 6-1, except that 1-(5-bromopyrimidin-2-yl)azetidin-3-one O-methyl oxime (Reference Compound 3-1) was replaced by 1-(5-bromopyrimidin-2-yl)azetidin-3-one oxime synthesized in the same manner as in Reference Example 9-1. Consequently, the title compound (yield 83%) was obtained as a light yellow solid.

Mass spectrum (CI, m/z):403[M+1]$^+$.

$^1$H-NMR spectrum (400 MHz, CDCl$_3$) δ:8.57 (d, J=1.5 Hz, 2H), 7.54-7.48 (m, 1H), 7.30-7.20 (m, 2H), 7.15 (s, 1H), 4.95-4.88 (m, 4H), 4.85 (s, 2H), 0.96 (s, 9H), 0.14 (s, 6H).

Reference Example 6-6

1-[5-(3-{[(tert-Butyldimethylsilyl)oxy]methyl}-2-fluorophenyl)pyrimidin-2-yl]azetidin-3-one O-(3-fluoropropyl) oxime (Reference Compound 6-6)

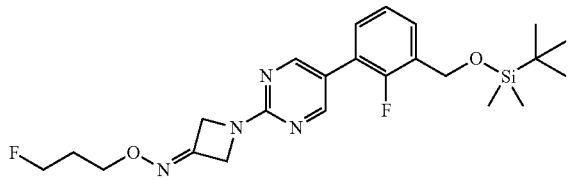 [SMILES: CC(C)(C)[Si](C)(C)OCc1cccc(-c2cnc(N3CC(=NOCCCF)C3)nc2)c1F]

The reaction was performed by the method described in Reference Example 6-1, except that 1-(5-bromopyrimidin-2-yl)azetidin-3-one O-methyl oxime (Reference Compound 3-1) was replaced by 1-(5-bromopyrimidin-2-yl)azetidin-3-one O-(3-fluoropropyl) oxime synthesized in the same manner as in Reference Example 10-3. Consequently, the title compound (yield 70%) was obtained as a white solid.

Mass spectrum (CI, m/z):463[M+1]$^+$.

$^1$H-NMR spectrum (400 MHz, DMSO-d$_6$) δ:8.63 (d, J=1.4 Hz, 2H), 7.53-7.43 (m, 2H), 7.36-7.26 (m, 1H), 4.85-4.79 (m, 6H), 4.53 (td, J=6.0, 47.3 Hz, 2H), 4.13 (t, J=6.3 Hz, 2H), 2.08-1.93 (m, 2H), 0.91 (s, 9H), 0.11 (s, 6H).

Reference Example 6-7

1-[5-(3-{[(tert-Butyldimethylsilyl)oxy]methyl}-2-fluorophenyl)pyrimidin-2-yl]azetidin-3-one O-{2-[(tetrahydropyran-2-yl)oxy]ethyl} oxime (Reference Compound 6-7)

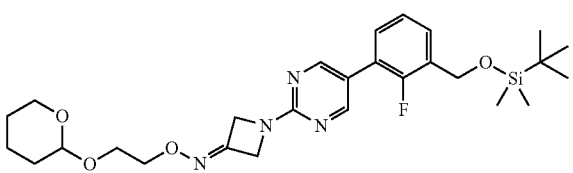 [SMILES: CC(C)(C)[Si](C)(C)OCc1cccc(-c2cnc(N3CC(=NOCCOC4CCCCO4)C3)nc2)c1F]

The reaction was performed by the method described in Reference Example 6-1, except that 1-(5-bromopyrimidin-2-yl)azetidin-3-one O-methyl oxime (Reference Compound 3-1) was replaced by 1-(5-bromopyrimidin-2-yl)azetidin-3-one O-{2-[(tetrahydropyran-2-yl)oxy]ethyl} oxime synthesized in the same manner as in Reference Example 10-4, and the reaction temperature was changed to 85° C. Consequently, the title compound (yield 72%) was obtained as a light yellow solid.

Mass spectrum (CI, m/z):531[M+1]$^+$.

$^1$H-NMR spectrum (400 MHz, DMSO-d$_6$) δ:8.63 (d, J=1.4 Hz, 2H), 7.54-7.41 (m, 2H), 7.38-7.22 (m, 1H), 4.88-4.77 (m, 6H), 4.63-4.58 (m, 1H), 4.22-4.12 (m, 2H), 3.87-3.70 (m, 2H), 3.67-3.57 (m, 1H), 3.49-3.38 (m, 1H), 1.81-1.41 (m, 6H), 0.91 (s, 9H), 0.11 (s, 6H).

Reference Example 6-8

1-[5-(3-{[(tert-Butyldimethylsilyl)oxy]methyl}-2-fluorophenyl)pyrimidin-2-yl]azetidin-3-one O-{3-[(tetrahydropyran-2-yl)oxy]propyl} oxime (Reference Compound 6-8)

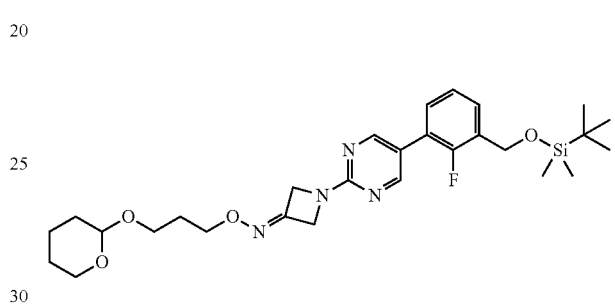

The reaction was performed by the method described in Reference Example 6-1, except that 1-(5-bromopyrimidin-2-yl)azetidin-3-one O-methyl oxime (Reference Compound 3-1) was replaced by 1-(5-bromopyrimidin-2-yl)azetidin-3-one O-{3-[(tetrahydropyran-2-yl)oxy]propyl} oxime synthesized in the same manner as in Reference Example 10-5. Consequently, the title compound (yield 66%) was obtained as a light yellow solid.

Mass spectrum (CI, m/z):545[M+1]$^+$.

$^1$H-NMR spectrum (400 MHz, DMSO-d$_6$) δ:8.63 (d, J=1.4 Hz, 2H), 7.52-7.44 (m, 2H), 7.35-7.28 (m, 1H), 4.89-4.73 (m, 6H), 4.59-4.51 (m, 1H), 4.18-4.05 (m, 2H), 3.80-3.63 (m, 2H), 3.48-3.37 (m, 2H), 1.91-1.79 (m, 2H), 1.78-1.39 (m, 6H), 0.91 (s, 9H), 0.11 (s, 6H).

Reference Example 6-9

1-[5-(3-{[(tert-Butyldimethylsilyl)oxy]methyl}-2-fluorophenyl)pyrimidin-2-yl]azetidin-3-one O-{4-[(tetrahydropyran-2-yl)oxy]butyl} oxime (Reference Compound 6-9)

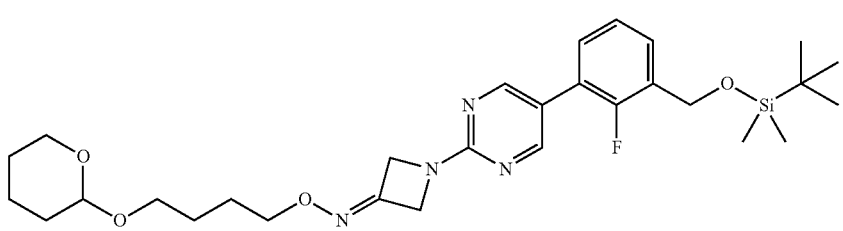 [SMILES: CC(C)(C)[Si](C)(C)OCc1cccc(-c2cnc(N3CC(=NOCCCCOC4CCCCO4)C3)nc2)c1F]

The reaction was performed by the method described in Reference Example 6-1, except that 1-(5-bromopyrimidin-2-yl)azetidin-3-one O-methyl oxime (Reference Compound 3-1) was replaced by 1-(5-bromopyrimidin-2-yl)azetidin-3-one O-{4-[(tetrahydropyran-2-yl)oxy]butyl} oxime synthesized in the same manner as in Reference Example 10-6. Consequently, the title compound (yield 93%) was obtained as a light yellow solid.

Mass spectrum (CI, m/z):559[M+1]$^+$.

$^1$H-NMR spectrum (400 MHz, CDCl$_3$) δ:8.56 (d, J=1.4 Hz, 2H), 7.54-7.46 (m, 1H), 7.30-7.19 (m, 2H), 4.89-4.86 (m, 4H), 4.85 (s, 2H), 4.61-4.56 (m, 1H), 4.20-4.10 (m, 2H), 3.92-3.73 (m, 2H), 3.55-3.37 (m, 2H), 1.88-1.47 (m, 10H), 0.96 (s, 9H), 0.14 (s, 6H).

Reference Example 6-10

1-[5-(3-{[(tert-Butyldimethylsilyl)oxy]methyl}-2-fluorophenyl)pyrimidin-2-yl]azetidin-3-one O-(2-methoxyethyl) oxime (Reference Compound 6-10)

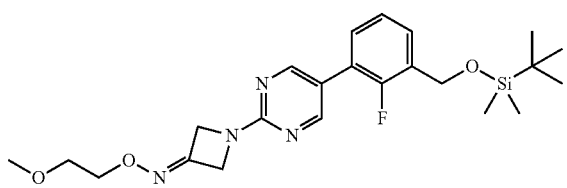 [SMILES: COCCON=C1CN(c2ncc(-c3cccc(CO[Si](C)(C)C(C)(C)C)c3F)cn2)C1]

The reaction was performed by the method described in Reference Example 6-1, except that 1-(5-bromopyrimidin-2-yl)azetidin-3-one O-methyl oxime (Reference Compound 3-1) was replaced by 1-(5-bromopyrimidin-2-yl)azetidin-3-one O-(2-methoxyethyl) oxime synthesized in the same manner as in Reference Example 10-7, and the reaction temperature was changed to 85° C. Consequently, the title compound (yield 66%) was obtained as a white solid.

Mass spectrum (CI, m/z):461[M+1]$^+$.

$^1$H-NMR spectrum (400 MHz, DMSO-d$_6$) δ:8.63 (d, J=1.5 Hz, 2H), 7.55-7.42 (m, 2H), 7.37-7.20 (m, 1H), 4.85-4.78 (m, 6H), 4.16-4.13 (m, 2H), 3.58-3.54 (m, 2H), 3.27 (s, 3H), 0.91 (s, 9H), 0.11 (s, 6H).

Reference Example 6-11

1-[5-(3-{[(tert-Butyldimethylsilyl)oxy]methyl}-2-fluorophenyl)pyrimidin-2-yl]azetidin-3-one 0-(2-{2-[(tetrahydropyran-2-yl)oxy]ethoxy}ethyl) oxime (Reference Compound 6-11)

The reaction was performed by the method described in Reference Example 6-1, except that 1-(5-bromopyrimidin-2-yl)azetidin-3-one O-methyl oxime (Reference Compound 3-1) was replaced by 1-(5-bromopyrimidin-2-yl)azetidin-3-one O-(2-{2-[(tetrahydropyran-2-yl)oxy]ethoxy}ethyl) oxime synthesized in the same manner as in Reference Example 16. Consequently, the title compound (yield 80%) was obtained as a yellow oil.

Mass spectrum (CI, m/z):575[M+1]$^+$.

$^1$H-NMR spectrum (400 MHz, CDCl$_3$) δ:8.56 (d, J=1.5 Hz, 2H), 7.54-7.47 (m, 1H), 7.29-7.19 (m, 2H), 4.91-4.87 (m, 4H), 4.85 (s, 2H), 4.67-4.63 (m, 1H), 4.29-4.24 (m, 2H), 3.91-3.84 (m, 2H), 3.80-3.76 (m, 2H), 3.72-3.68 (m, 2H), 3.66-3.59 (m, 1H), 3.54-3.47 (m, 1H), 1.90-1.41 (m, 6H), 0.96 (s, 9H), 0.14 (s, 6H).

Reference Example 6-12

1-[5-(3-{[(tert-Butyldimethylsilyl)oxy]methyl}-2-fluorophenyl)pyrimidin-2-yl]azetidin-3-one 0-[(2,2-dimethyl-1,3-dioxan-5-yl)methyl] oxime (Reference Compound 6-12)

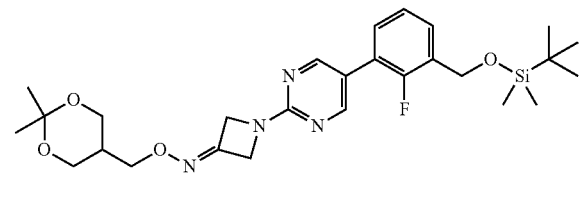

The reaction was performed by the method described in Reference Example 6-1, except that 1-(5-bromopyrimidin-2-yl)azetidin-3-one O-methyl oxime (Reference Compound 3-1) was replaced by 1-(5-bromopyrimidin-2-yl)azetidin-3-one O-[(2,2-dimethyl-1,3-dioxan-5-yl)methyl] oxime synthesized in the same manner as in Reference Example 10-8. Consequently, the title compound (yield 89%) was obtained as a white solid.

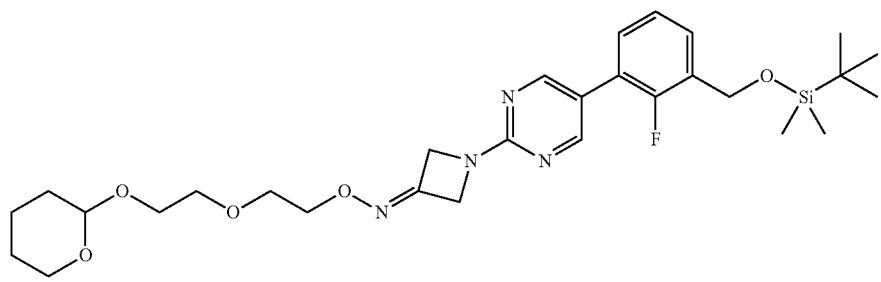 [SMILES: CC(C)(C)[Si](C)(C)OCc1cccc(-c2cnc(N3CC(=NOCCOCCOC4CCCCO4)C3)nc2)c1F]

Reference Example 6-13

1-[5-(3-{[(tert-Butyldimethylsilyl)oxy]methyl}-2-fluorophenyl)pyrimidin-2-yl]azetidin-3-one O-[(2,2-dimethyl-1,3-dioxolan-4-yl)methyl] oxime (Reference Compound 6-13)

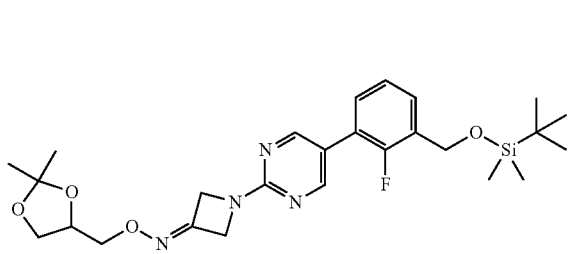 [SMILES: CC1(C)OCC(CON=C2CN(c3ncc(-c4cccc(CO[Si](C)(C)C(C)(C)C)c4F)cn3)C2)O1]

The reaction was performed by the method described in Reference Example 6-1, except that 1-(5-bromopyrimidin-2-yl)azetidin-3-one O-methyl oxime (Reference Compound 3-1) was replaced by 1-(5-bromopyrimidin-2-yl)azetidin-3-one O-[(2,2-dimethyl-1,3-dioxolan-4-yl)methyl] oxime synthesized in the same manner as in Reference Example 10-9. Consequently, the title compound (yield 94%) was obtained as a light yellow solid.

Mass spectrum (CI, m/z):517[M+1]$^+$.

$^1$H-NMR spectrum (400 MHz, DMSO-d$_6$) δ:8.63 (d, J=1.4 Hz, 2H), 7.53-7.42 (m, 2H), 7.36-7.27 (m, 1H), 4.85-4.78 (m, 6H), 4.34-4.26 (m, 1H), 4.10-4.01 (m, 3H), 3.68 (dd, J=6.4, 8.4 Hz, 1H), 1.33 (s, 3H), 1.28 (s, 3H), 0.91 (s, 9H), 0.11 (s, 6H).

Reference Example 6-14

1-[5-(3-{[(tert-Butyldimethylsilyl)oxy]methyl}-2-fluorophenyl)pyrimidin-2-yl]azetidin-3-one O-(3-methoxy-2-{[(tetrahydropyran-2-yl)oxy]methyl}propyl) oxime (Reference Compound 6-14)

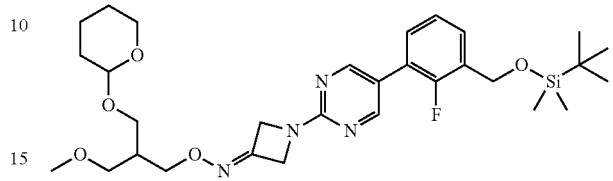

The reaction was performed by the method described in Reference Example 6-1, except that 1-(5-bromopyrimidin-2-yl)azetidin-3-one O-methyl oxime (Reference Compound 3-1) was replaced by 1-(5-bromopyrimidin-2-yl)azetidin-3-one O-(3-methoxy-2-{[(tetrahydropyran-2-yl)oxy]methyl}propyl) oxime synthesized in the same manner as in Reference Example 19-1. Consequently, the title compound (yield 85%) was obtained as a light yellow oil.

Mass spectrum (CI, m/z):589[M+1]$^+$.

$^1$H-NMR spectrum (400 MHz, DMSO-d$_6$) δ:8.63 (d, J=1.5 Hz, 2H), 7.59-7.40 (m, 2H), 7.37-7.26 (m, 1H), 4.86-4.77 (m, 6H), 4.60-4.33 (m, 1H), 4.16-4.01 (m, 2H), 3.80-3.63 (m, 2H), 3.48-3.33 (m, 4H), 3.24 (s, 3H), 2.27-2.13 (m, 1H), 1.81-1.36 (m, 6H), 0.91 (s, 9H), 0.11 (s, 6H).

Reference Example 6-15

1-[5-(3-{[(tert-Butyldimethylsilyl)oxy]methyl}-2-fluorophenyl)pyrimidin-2-yl]azetidin-3-one O-[2-methoxy-3-(trityloxy)propyl] oxime (Reference Compound 6-15)

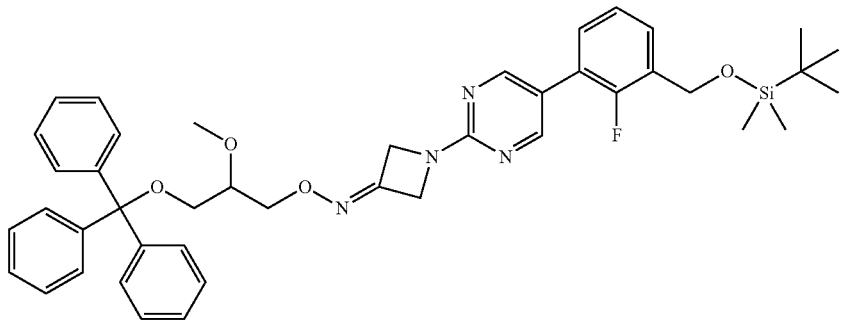 [SMILES: COC(CON=C1CN(c2ncc(-c3cccc(CO[Si](C)(C)C(C)(C)C)c3F)cn2)C1)COC(c1ccccc1)(c1ccccc1)c1ccccc1]

The reaction was performed by the method described in Reference Example 6-1, except that 1-(5-bromopyrimidin-2-yl)azetidin-3-one O-methyl oxime (Reference Compound 3-1) was replaced by 1-(5-bromopyrimidin-2-yl)azetidin-3-one O-[2-methoxy-3-(trityloxy)propyl] oxime synthesized in the same manner as in Reference Example 19-2. Consequently, the title compound (yield 84%) was obtained as a light yellow foam.

Mass spectrum (CI, m/z):733[M+1]$^+$.

$^1$H-NMR spectrum (400 MHz, DMSO-d$_6$) δ:8.65 (d, J=1.5 Hz, 2H), 7.52-7.21 (m, 18H), 4.87-4.76 (m, 4H), 4.75-4.53 (m, 2H), 4.21-4.05 (m, 2H), 3.67-3.58 (m, 1H), 3.34 (s, 3H), 3.18-2.98 (m, 2H), 0.91 (s, 9H), 0.11 (s, 6H).

Reference Example 6-16

1-[5-(3-{[(tert-Butyldimethylsilyl)oxy]methyl}-2-fluorophenyl)pyrimidin-2-yl]azetidin-3-one 0-[2-(2,2-dimethyl-1,3-dioxolan-4-yl)ethyl] oxime (Reference Compound 6-16)

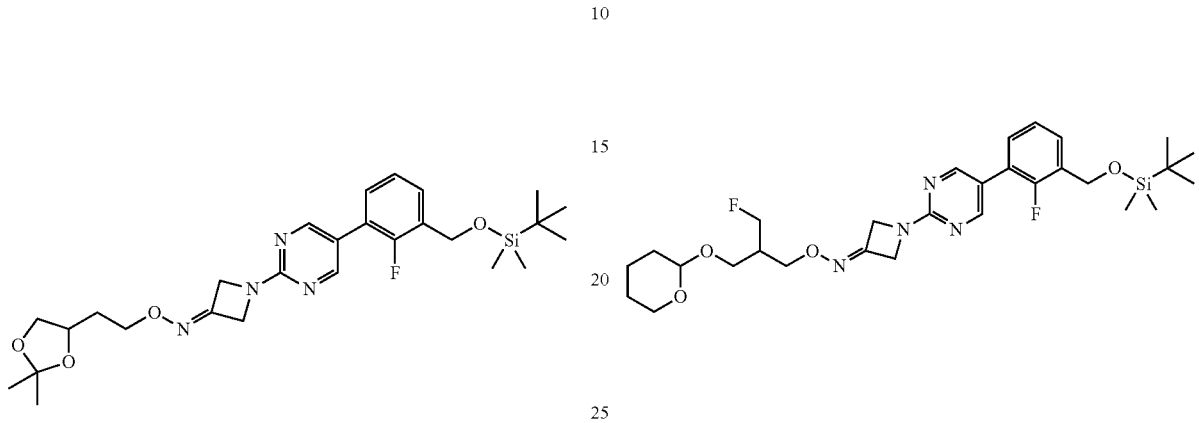

The reaction was performed by the method described in Reference Example 6-1, except that 1-(5-bromopyrimidin-2-yl)azetidin-3-one O-methyl oxime (Reference Compound 3-1) was replaced by 1-(5-bromopyrimidin-2-yl)azetidin-3-one 0-[2-(2,2-dimethyl-1,3-dioxolan-4-yl)ethyl] oxime synthesized in the same manner as in Reference Example 10-10. Consequently, the title compound (yield 98%) was obtained as a light yellow solid.

Mass spectrum (CI, m/z):531[M+1]$^+$.

$^1$H-NMR spectrum (400 MHz, DMSO-d$_6$) δ:8.63 (d, J=1.4 Hz, 2H), 7.52-7.43 (m, 2H), 7.38-7.24 (m, 1H), 4.85-4.77 (m, 6H), 4.18-4.05 (m, 3H), 4.02 (dd, J=6.1, 8.0 Hz, 1H), 3.49 (dd, J=7.3, 8.0 Hz, 1H), 1.91-1.79 (m, 2H), 1.31 (s, 3H), 1.27 (s, 3H), 0.90 (s, 9H), 0.11 (s, 6H).

Reference Example 6-17

1-[5-(3-{[(tert-Butyldimethylsilyl)oxy]methyl}-2-fluorophenyl)pyrimidin-2-yl]azetidin-3-one 0-(3-fluoro-2-{[(tetrahydropyran-2-yl)oxy]methyl}propyl) oxime (Reference Compound 6-17)

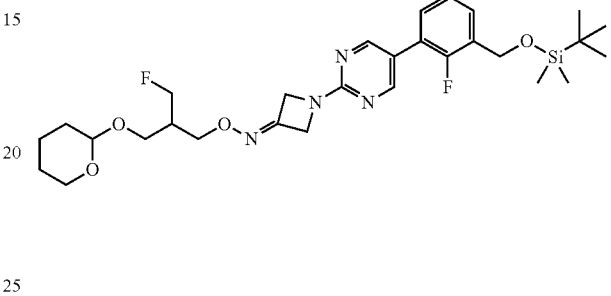

The reaction was performed by the method described in Reference Example 6-1, except that 1-(5-bromopyrimidin-2-yl)azetidin-3-one O-methyl oxime (Reference Compound 3-1) was replaced by 1-(5-bromopyrimidin-2-yl)azetidin-3-one O-(3-fluoro-2-{[(tetrahydropyran-2-yl)oxy]methyl}propyl) oxime synthesized in the same manner as in Reference Example 23. Consequently, the title compound (yield 97%) was obtained as a light yellow oil.

Mass spectrum (ESI, m/z):577[M+1]$^+$.

$^1$H-NMR spectrum (400 MHz, DMSO-d$_6$) δ:8.63 (d, J=1.4 Hz, 2H), 7.54-7.39 (m, 2H), 7.37-7.26 (m, 1H), 4.86-4.79 (m, 6H), 4.65-4.41 (m, 3H), 4.17-4.07 (m, 2H), 3.78-3.67 (m, 2H), 3.48-3.38 (m, 2H), 2.43-2.30 (m, 1H), 1.77-1.57 (m, 2H), 1.53-1.41 (m, 4H), 0.91 (s, 9H), 0.11 (s, 6H).

Reference Example 6-18

1-[5-(3-{[(tert-Butyldimethylsilyl)oxy]methyl}-2-fluorophenyl)pyrimidin-2-yl]azetidin-3-one O-[2-fluoro-3-(trityloxy)propyl] oxime (Reference Compound 6-18)

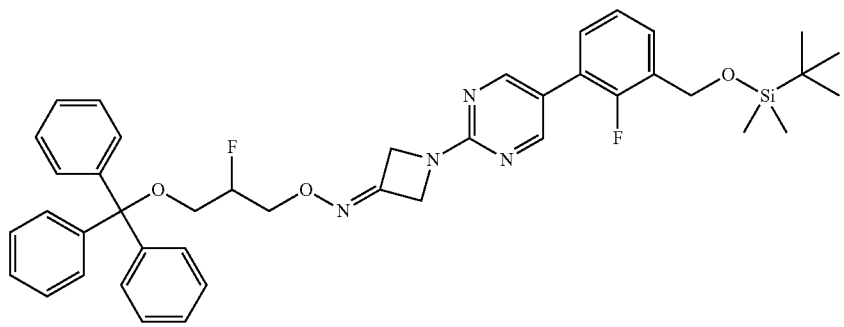 [SMILES: CC(C)(C)[Si](C)(C)OCc1cccc(-c2cnc(N3CC(=NOCC(F)COC(c4ccccc4)(c4ccccc4)c4ccccc4)C3)nc2)c1F]

The reaction was performed by the method described in Reference Example 6-1, except that 1-(5-bromopyrimidin-2-yl)azetidin-3-one O-methyl oxime (Reference Compound 3-1) was replaced by 1-(5-bromopyrimidin-2-yl)azetidin-3-one O-[2-fluoro-3-(trityloxy)propyl] oxime synthesized in the same manner as in Reference Example 24-1. Consequently, the title compound (yield 60%) was obtained as a white foam.

Mass spectrum (ESI, m/z):721[M+1]$^+$.

$^1$H-NMR spectrum (400 MHz, DMSO-$d_6$) δ:8.64 (d, J=1.4 Hz, 2H), 7.51-7.24 (m, 18H), 5.03-4.84 (m, 1H), 4.83-4.78 (m, 4H), 4.76-4.59 (m, 2H), 4.42-4.15 (m, 2H), 3.33-3.13 (m, 2H), 0.91 (s, 9H), 0.11 (s, 6H).

Reference Example 6-19

1-[5-(3-{[(tert-Butyldimethylsilyl)oxy]methyl}-2-fluorophenyl)pyrimidin-2-yl]azetidin-3-one O-{3-methoxy-4-[(tetrahydropyran-2-yl)oxy]butyl} oxime (Reference Compound 6-19)

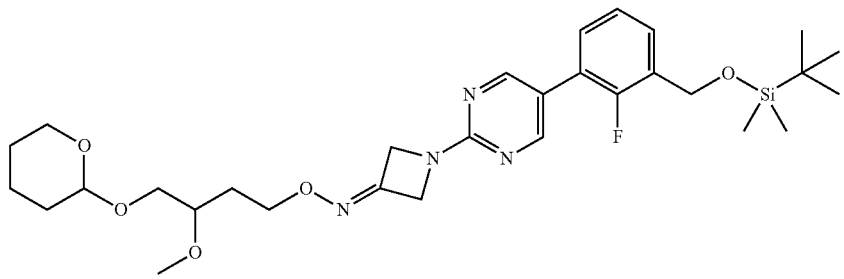 [SMILES: COC(CCON=C1CN(c2ncc(-c3cccc(CO[Si](C)(C)C(C)(C)C)c3F)cn2)C1)COC1CCCCO1]

The reaction was performed by the method described in Reference Example 6-1, except that 1-(5-bromopyrimidin-2-yl)azetidin-3-one O-methyl oxime (Reference Compound 3-1) was replaced by 1-(5-bromopyrimidin-2-yl)azetidin-3-one O-{3-methoxy-4-[(tetrahydropyran-2-yl)oxy]butyl} oxime synthesized in the same manner as in Reference Example 19-3, and the reaction temperature was changed to 70° C. Consequently, the title compound (yield 92%) was obtained as a light yellow oil.

Mass spectrum (ESI, m/z):589[M+1]$^+$.

$^1$H-NMR spectrum (400 MHz, CDCl$_3$) δ:8.57 (d, J=1.3 Hz, 2H), 7.55-7.47 (m, 1H), 7.31-7.18 (m, 2H), 4.91-4.86 (m, 4H), 4.85 (s, 2H), 4.68-4.60 (m, 1H), 4.27-4.18 (m, 2H), 3.92-3.83 (m, 1H), 3.83-3.73 (m, 1H), 3.58-3.37 (m, 6H), 2.03-1.46 (m, 8H), 0.96 (s, 9H), 0.14 (s, 6H).

Reference Example 6-20)

4-[({1-[5-(3-{[(tert-Butyldimethylsilyl)oxy]methyl}-2-fluorophenyl)pyrimidin-2-yl]azetidin-3-ylidene}amino)oxy]butane-1,2-diyl diacetate (Reference Compound 6-20)

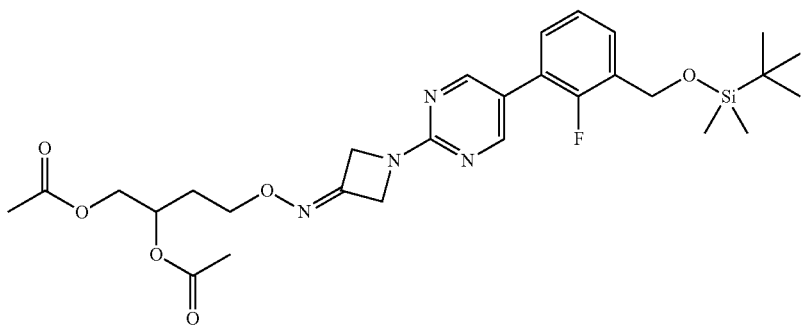 [SMILES: CC(=O)OCC(CCON=C1CN(c2ncc(-c3cccc(CO[Si](C)(C)C(C)(C)C)c3F)cn2)C1)OC(C)=O]

The reaction was performed by the method described in Reference Example 6-1, except that 1-(5-bromopyrimidin-2-yl)azetidin-3-one O-methyl oxime (Reference Compound 3-1) was replaced by 4-({[1-(5-bromopyrimidin-2-yl)azetidin-3-ylidene]amino}oxy)butane-1,2-diyl diacetate synthesized in the same manner as in Reference Example 25, and the reaction temperature was changed to 70° C. Consequently, the title compound (yield 35%) was obtained as a light yellow solid.

Mass spectrum (ESI, m/z):575[M+1]+.

1H-NMR spectrum (400 MHz, CDCl3) δ:8.56 (d, J=1.4 Hz, 2H), 7.54-7.47 (m, 1H), 7.30-7.19 (m, 2H), 5.24-5.17 (m, 1H), 4.87 (s, 4H), 4.85 (s, 2H), 4.29 (dd, J=3.3, 12.0 Hz, 1H), 4.22-4.12 (m, 2H), 4.09 (dd, J=6.2, 12.0 Hz, 1H), 2.08 (s, 3H), 2.07 (s, 3H), 2.06-1.94 (m, 2H), 0.96 (s, 9H), 0.14 (s, 6H).

Reference Example 6-21

2-[({1-[5-(3-{[(tert-Butyldimethylsilyl)oxy]methyl}-2-fluorophenyl)pyrimidin-2-yl]azetidin-3-ylidene}amino)oxy]ethyl acetate (Reference Compound 6-21)

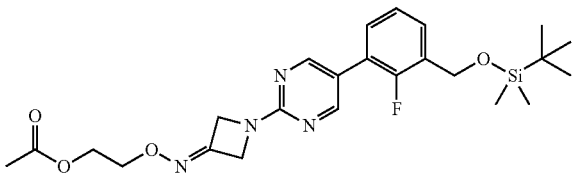 [SMILES: CC(=O)OCCON=C1CN(c2ncc(-c3cccc(CO[Si](C)(C)C(C)(C)C)c3F)cn2)C1]

The reaction was performed by the method described in Reference Example 6-1, except that 1-(5-bromopyrimidin-2-yl)azetidin-3-one O-methyl oxime (Reference Compound 3-1) was replaced by 2-({[1-(5-bromopyrimidin-2-yl)azetidin-3-ylidene]amino}oxy)ethyl acetate synthesized in the same manner as in Reference Example 10-11. Consequently, the title compound (yield 80%) was obtained as a colorless oil.

Mass spectrum (ESI, m/z):489[M+1]+.

1H-NMR spectrum (400 MHz, CDCl3) δ:8.57 (d, J=1.3 Hz, 2H), 7.55-7.47 (m, 1H), 7.31-7.19 (m, 2H), 4.94-4.87 (m, 4H), 4.85 (s, 2H), 4.38-4.25 (m, 4H), 2.10 (s, 3H), 0.96 (s, 9H), 0.14 (s, 6H).

Reference Example 6-22

2-[({1-[5-(3-{[(tert-Butyldimethylsilyl)oxy]methyl}-2-fluorophenyl)pyrimidin-2-yl]azetidin-3-ylidene}amino)oxy]ethyl propionate (Reference Compound 6-22)

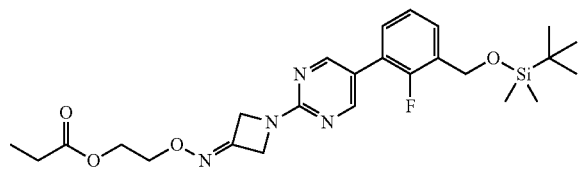 [SMILES: CCC(=O)OCCON=C1CN(c2ncc(-c3cccc(CO[Si](C)(C)C(C)(C)C)c3F)cn2)C1]

The reaction was performed by the method described in Reference Example 6-1, except that 1-(5-bromopyrimidin-2-yl)azetidin-3-one O-methyl oxime (Reference Compound 3-1) was replaced by 2-({[1-(5-bromopyrimidin-2-yl)azetidin-3-ylidene]amino}oxy)ethyl propionate synthesized in the same manner as in Reference Example 28-1. Consequently, the title compound (yield 38%) was obtained as a white solid.

Mass spectrum (CI, m/z):503[M+1]+.

1H-NMR spectrum (400 MHz, CDCl3) δ:8.57 (d, J=1.4 Hz, 2H), 7.56-7.46 (m, 1H), 7.32-7.18 (m, 2H), 4.90-4.86 (m, 4H), 4.85 (s, 2H), 4.36-4.27 (m, 4H), 2.38 (q, J=7.6 Hz, 2H), 1.16 (t, J=7.6 Hz, 3H), 0.96 (s, 9H), 0.14 (s, 6H).

Reference Example 6-23

2-[({1-[5-(3-{[(tert-Butyldimethylsilyl)oxy]methyl}-2-fluorophenyl)pyrimidin-2-yl]azetidin-3-ylidene}amino)oxy]ethyl butyrate (Reference Compound 6-23)

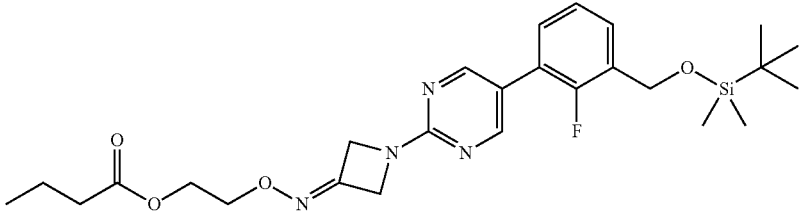 [SMILES: CCCC(=O)OCCON=C1CN(c2ncc(-c3cccc(CO[Si](C)(C)C(C)(C)C)c3F)cn2)C1]

The reaction was performed by the method described in Reference Example 6-1, except that 1-(5-bromopyrimidin-2-yl)azetidin-3-one O-methyl oxime (Reference Compound 3-1) was replaced by 2-({[1-(5-bromopyrimidin-2-yl)azetidin-3-ylidene]amino}oxy)ethyl butyrate synthesized in the same manner as in Reference Example 28-2, and the product was purified by HPLC separation. Consequently, the title compound (yield 65%) was obtained as a colorless oil.

Mass spectrum (CI, m/z):517[M+1]+.

1H-NMR spectrum (400 MHz, CDCl3) δ:8.57 (d, J=1.4 Hz, 2H), 7.54-7.48 (m, 1H), 7.29-7.20 (m, 2H), 4.91-4.86 (m, 4H), 4.85 (s, 2H), 4.36-4.26 (m, 4H), 2.33 (t, J=7.4 Hz, 2H), 1.67 (sext, J=7.4 Hz, 2H), 0.99-0.93 (m, 12H), 0.14 (s, 6H).

Reference Example 6-24

2-[({1-[5-(3-{[(tert-Butyldimethylsilyl)oxy]methyl}-2-fluorophenyl)pyrimidin-2-yl]azetidin-3-ylidene}amino)oxy]ethyl benzoate (Reference Compound 6-24)

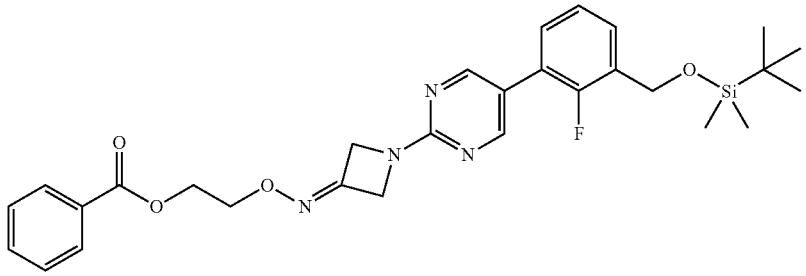 [SMILES: CC(C)(C)[Si](C)(C)OCc1cccc(-c2cnc(N3CC(=NOCCOC(=O)c4ccccc4)C3)nc2)c1F]

The reaction was performed by the method described in Reference Example 6-1, except that 1-(5-bromopyrimidin-2-yl)azetidin-3-one O-methyl oxime (Reference Compound 3-1) was replaced by 2-({[1-(5-bromopyrimidin-2-yl)azetidin-3-ylidene]amino}oxy)ethyl benzoate synthesized in the same manner as in Reference Example 28-3. Consequently, the title compound (yield 72%) was obtained as a light yellow oil.

Reference Compound 6-24 Mass spectrum (CI, m/z):551 [M+1]$^+$.

$^1$H-NMR spectrum (400 MHz, CDCl$_3$) δ:8.56 (d, J=1.4 Hz, 2H), 8.12-7.97 (m, 2H), 7.60-7.54 (m, 1H), 7.53-7.42 (m, 3H), 7.28-7.22 (m, 2H), 4.88 (s, 4H), 4.85 (s, 2H), 4.62-4.51 (m, 2H), 4.47-4.39 (m, 2H), 0.96 (s, 9H), 0.13 (s, 6H).

Reference Example 6-25

1-[5-(3-{[(tert-Butyldimethylsilyl)oxy]methyl}-2-fluorophenyl)pyrimidin-2-yl]azetidin-3-one O-(3-hydroxy-2-{[(tetrahydropyran-2-yl)oxy]methyl}propyl) oxime (Reference Compound 6-25)

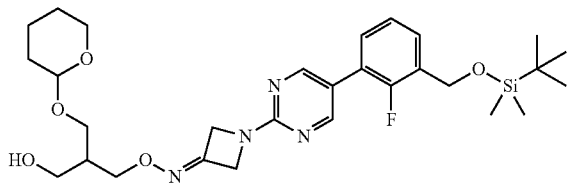 [SMILES: CC(C)(C)[Si](C)(C)OCc1cccc(-c2cnc(N3CC(=NOCC(CO)COC4CCCCO4)C3)nc2)c1F]

The reaction was performed by the method described in Reference Example 6-1, except that 1-(5-bromopyrimidin-2-yl)azetidin-3-one O-methyl oxime (Reference Compound 3-1) was replaced by 1-(5-bromopyrimidin-2-yl)azetidin-3-one O-(3-hydroxy-2-{[(tetrahydropyran-2-yl)oxy]methyl}propyl) oxime synthesized in the same manner as in Reference Example 18-1. Consequently, the title compound (yield 91%) was obtained as a light yellow oil.

Mass spectrum (CI, m/z):575[M+1]$^+$.

$^1$H-NMR spectrum (400 MHz, CDCl$_3$) δ:8.57 (d, J=1.4 Hz, 2H), 7.54-7.48 (m, 1H), 7.29-7.20 (m, 2H), 4.89-4.86 (m, 4H), 4.85 (s, 2H), 4.62-4.57 (m, 1H), 4.27-4.16 (m, 2H), 3.92-3.70 (m, 4H), 3.63-3.49 (m, 2H), 2.56-2.46 (m, 1H), 2.34-2.23 (m, 1H), 1.84-1.48 (m, 6H), 0.96 (s, 9H), 0.14 (s, 6H).

Reference Example 6-26)

1-[5-(3-{[(tert-Butyldimethylsilyl)oxy]methyl}-2-fluorophenyl)-3-fluoropyridin-2-yl]azetidin-3-one O-methyl oxime (Reference Compound 6-26)

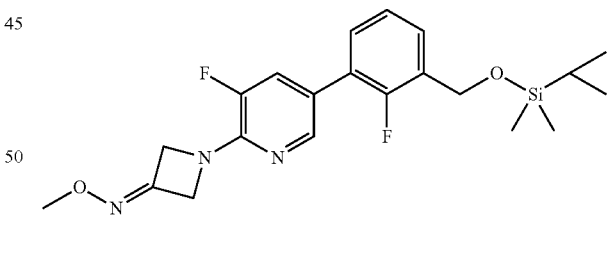

The reaction was performed by the method described in Reference Example 6-1, except that 1-(5-bromopyrimidin-2-yl)azetidin-3-one O-methyl oxime (Reference Compound 3-1) was replaced by 1-(5-bromo-3-fluoropyridin-2-yl)azetidin-3-one O-methyl oxime synthesized in the same manner as in Reference Example 33-1. Consequently, the title compound (including impurities) was obtained as a white solid.

Mass spectrum (CI, m/z):434[M+1]$^+$.

$^1$H-NMR spectrum (400 MHz, CDCl$_3$) δ:8.17-8.14 (m, 1H), 7.53-7.43 (m, 2H), 7.31-7.18 (m, 2H), 4.90-4.88 (m, 4H), 4.84 (s, 2H), 3.91 (s, 3H), 0.96 (s, 9H), 0.13 (s, 6H).

Reference Example 6-27

1-[5-(3-{[(tert-Butyldimethylsilyl)oxy]methyl}-2-fluorophenyl)-3-fluoropyridin-2-yl]azetidin-3-one O-methyl-d₃ oxime (Reference Compound 6-27)

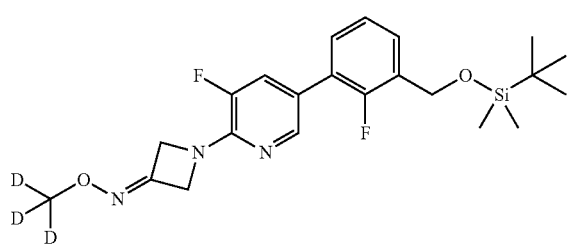 [SMILES: [2H]C([2H])([2H])ON=C1CN(c2ncc(-c3cccc(CO[Si](C)(C)C(C)(C)C)c3F)cc2F)C1]

The reaction was performed by the method described in Reference Example 6-1, except that 1-(5-bromopyrimidin-2-yl)azetidin-3-one O-methyl oxime (Reference Compound 3-1) was replaced by 1-(5-bromo-3-fluoropyridin-2-yl)azetidin-3-one O-methyl-d₃ oxime synthesized in the same manner as in Reference Example 33-2. Consequently, the title compound (including impurities) was obtained as a white solid.

Mass spectrum (CI, m/z):437[M+1]⁺.
¹H-NMR spectrum (400 MHz, CDCl₃) δ:8.17-8.13 (m, 1H), 7.53-7.43 (m, 2H), 7.31-7.24 (m, 1H), 7.24-7.16 (m, 1H), 4.91-4.87 (m, 4H), 4.84 (s, 2H), 0.96 (s, 9H), 0.13 (s, 6H).

Reference Example 6-28

1-[5-(3-{[(tert-Butyldimethylsilyl)oxy]methyl}-2-fluorophenyl)-3-fluoropyridin-2-yl]azetidin-3-one O-[2-(2,2-dimethyl-1,3-dioxolan-4-yl)ethyl] oxime (Reference Compound 6-28)

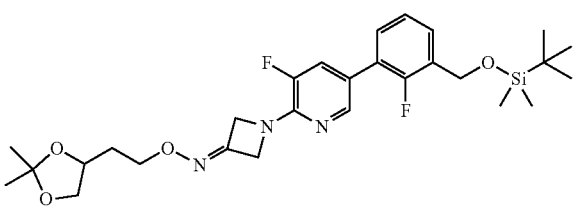 [SMILES: CC1(C)OCC(CCON=C2CN(c3ncc(-c4cccc(CO[Si](C)(C)C(C)(C)C)c4F)cc3F)C2)O1]

The reaction was performed by the method described in Reference Example 6-1, except that 1-(5-bromopyrimidin-2-yl)azetidin-3-one O-methyl oxime (Reference Compound 3-1) was replaced by 1-(5-bromo-3-fluoropyridin-2-yl)azetidin-3-one O-[2-(2,2-dimethyl-1,3-dioxolan-4-yl)ethyl] oxime synthesized in the same manner as in Reference Example 34-1. Consequently, the title compound (including impurities) was obtained as a colorless oil.

Mass spectrum (CI, m/z):548[M+1]⁺.
¹H-NMR spectrum (400 MHz, CDCl₃) δ:8.17-8.13 (m, 1H), 7.53-7.42 (m, 2H), 7.31-7.17 (m, 2H), 4.91-4.88 (m, 4H), 4.84 (s, 2H), 4.26-4.15 (m, 3H), 4.12-4.06 (m, 1H), 3.61-3.55 (m, 1H), 2.01-1.92 (m, 2H), 1.42 (s, 3H), 1.37 (s, 3H), 0.96 (s, 9H), 0.13 (s, 6H).

Reference Example 6-29

1-[5-(3-{[(tert-Butyldimethylsilyl)oxy]methyl}-2-fluorophenyl)-3-fluoropyridin-2-yl]azetidin-3-one O-[(2,2-dimethyl-1,3-dioxan-5-yl)methyl] oxime (Reference Compound 6-29)

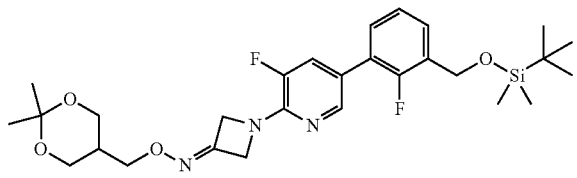 [SMILES: CC1(C)OCC(CON=C2CN(c3ncc(-c4cccc(CO[Si](C)(C)C(C)(C)C)c4F)cc3F)C2)CO1]

The reaction was performed by the method described in Reference Example 6-1, except that 1-(5-bromopyrimidin-2-yl)azetidin-3-one O-methyl oxime (Reference Compound 3-1) was replaced by 1-(5-bromo-3-fluoropyridin-2-yl)azetidin-3-one O-[(2,2-dimethyl-1,3-dioxan-5-yl)methyl] oxime synthesized in the same manner as in Reference Example 34-2. Consequently, the title compound (including impurities) was obtained as a light yellow oil.

Mass spectrum (CI, m/z):548[M+1]⁺.
¹H-NMR spectrum (400 MHz, CDCl₃) δ:8.17-8.14 (m, 1H), 7.76-7.18 (m, 4H), 4.91-4.87 (m, 4H), 4.85 (s, 2H), 4.18 (d, J=6.9 Hz, 2H), 4.01 (dd, J=4.0, 12.0 Hz, 2H), 3.76 (dd, J=5.9, 12.0 Hz, 2H), 2.14-2.06 (m, 1H), 1.45 (s, 3H), 1.42 (s, 3H), 0.96 (s, 9H), 0.14 (s, 6H).

Reference Example 6-30

1-[5-(3-{[(tert-Butyldimethylsilyl)oxy]methyl}-2-fluorophenyl)-3-fluoropyridin-2-yl]azetidin-3-one O-[2-fluoro-3-(trityloxy)propyl] oxime (Reference Compound 6-30)

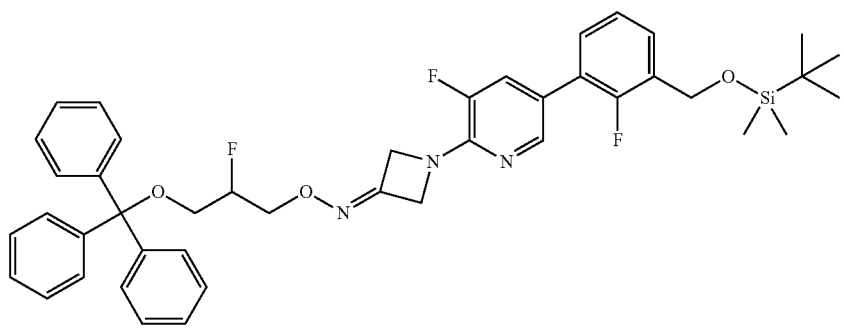 [SMILES: CC(C)(C)[Si](C)(C)OCc1cccc(-c2cnc(N3CC(=NOCC(F)COC(c4ccccc4)(c4ccccc4)c4ccccc4)C3)c(F)c2)c1F]

The reaction was performed by the method described in Reference Example 6-1, except that 1-(5-bromopyrimidin-2-yl)azetidin-3-one O-methyl oxime (Reference Compound 3-1) was replaced by 1-(5-bromo-3-fluoropyridin-2-yl)azetidin-3-one O-[2-fluoro-3-(trityloxy)propyl] oxime synthesized in the same manner as in Reference Example 24-2. Consequently, the title compound (yield 81%) was obtained as a colorless foam.

Mass spectrum (CI, m/z):738[M+1]$^+$.

$^1$H-NMR spectrum (400 MHz, DMSO-d$_6$) δ:8.21-8.18 (m, 1H), 7.79-7.73 (m, 1H), 7.51-7.17 (m, 18H), 5.02-4.67 (m, 7H), 4.39-4.14 (m, 2H), 3.31-3.13 (m, 2H), 0.91 (s, 9H), 0.11 (s, 6H).

Reference Example 6-31

1-[5-(3-{[(tert-Butyldimethylsilyl)oxy]methyl}-2-fluorophenyl)pyridin-2-yl]azetidin-3-one O-methyl oxime (Reference Compound 6-31)

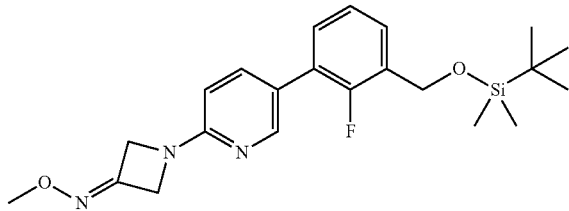 [SMILES: CON=C1CN(c2ccc(-c3cccc(CO[Si](C)(C)C(C)(C)C)c3F)cn2)C1]

The reaction was performed by the method described in Reference Example 6-1, except that 1-(5-bromopyrimidin-2-yl)azetidin-3-one O-methyl oxime (Reference Compound 3-1) was replaced by 1-(5-bromopyridin-2-yl)azetidin-3-one O-methyloxime synthesized in the same manner as in Reference Example 3-2. Consequently, the title compound (yield 97%) was obtained as a light yellow oil.

Mass spectrum (CI, m/z):416[M+1]$^+$.

$^1$H-NMR spectrum (400 MHz, DMSO-d$_6$) δ:8.32-8.29 (m, 1H), 7.80-7.75 (m, 1H), 7.45-7.39 (m, 2H), 7.31-7.25 (m, 1H), 6.69-6.65 (m, 1H), 4.81 (s, 2H), 4.76-4.65 (m, 4H), 3.82 (s, 3H), 0.91 (s, 9H), 0.11 (s, 6H).

Reference Example 6-32

1-[5-(3-{[(tert-Butyldimethylsilyl)oxy]methyl}-2-fluorophenyl)-3-methylpyridin-2-yl]azetidin-3-one O-methyl oxime (Reference Compound 6-32)

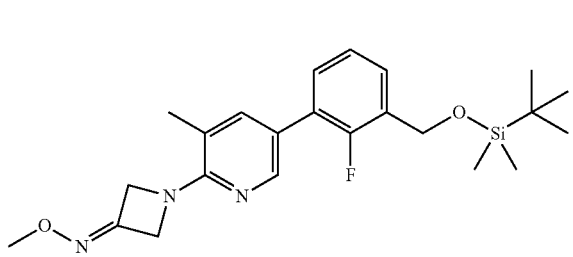 [SMILES: CON=C1CN(c2ncc(-c3cccc(CO[Si](C)(C)C(C)(C)C)c3F)cc2C)C1]

The reaction was performed by the method described in Reference Example 6-1, except that 1-(5-bromopyrimidin-2-yl)azetidin-3-one O-methyl oxime (Reference Compound 3-1) was replaced by 1-(5-bromo-3-methylpyridin-2-yl)azetidin-3-one O-methyl oxime synthesized in the same manner as in Reference Example 3-3. Consequently, the title compound (yield 58%) was obtained as a yellow oil.

Mass spectrum (ESI, m/z):430[M+1]$^+$.

$^1$H-NMR spectrum (400 MHz, CDCl$_3$) δ:8.27-8.23 (m, 1H), 7.53-7.49 (m, 1H), 7.49-7.43 (m, 1H), 7.31-7.24 (m, 1H), 7.23-7.16 (m, 1H), 4.89-4.82 (m, 6H), 3.90 (s, 3H), 2.27 (s, 3H), 0.96 (s, 9H), 0.13 (s, 6H).

Reference Example 6-33

5-(3-{[(tert-Butyldimethylsilyl)oxy]methyl}-2-fluorophenyl)-2-[3-(methoxyimino)azetidin-1-yl]nicotinonitrile (Reference Compound 6-33)

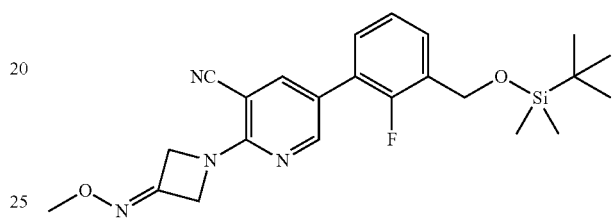

The reaction was performed by the method described in Reference Example 6-1, except that 1-(5-bromopyrimidin-2-yl)azetidin-3-one O-methyl oxime (Reference Compound 3-1) was replaced by 5-bromo-2-[3-(methoxyimino)azetidin-1-yl]nicotinonitrile synthesized in the same manner as in Reference Example 39, and the reaction temperature was changed to 85° C. Consequently, the title compound (yield 50%) was obtained as a white solid.

Mass spectrum (CI, m/z):441[M+1]$^+$.

$^1$H-NMR spectrum (400 MHz, DMSO-d$_6$) δ:8.58-8.54 (m, 1H), 8.24 (dd, J=0.9, 2.3 Hz, 1H), 7.54-7.41 (m, 2H), 7.36-7.25 (m, 1H), 5.06-4.96 (m, 4H), 4.80 (s, 2H), 3.83 (s, 3H), 0.91 (s, 9H), 0.11 (s, 6H).

Reference Example 6-34

1-[5-(3-{[(tert-Butyldimethylsilyl)oxy]methyl}-2-fluorophenyl)-3-chloropyridin-2-yl]azetidin-3-one O-methyl oxime (Reference Compound 6-34)

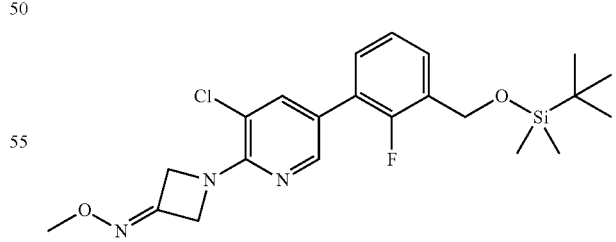

The reaction was performed by the method described in Reference Example 6-1, except that 1-(5-bromopyrimidin-2-yl)azetidin-3-one O-methyl oxime (Reference Compound 3-1) was replaced by 1-(5-bromo-3-chloropyridin-2-yl)azetidin-3-one O-methyl oxime synthesized in the same manner as in Reference Example 3-4. Consequently, the title compound (including impurities) was obtained as a white solid.

Mass spectrum (CI, m/z):450[M+1]$^+$.

$^1$H-NMR spectrum (400 MHz, CDCl$_3$) δ:8.29-8.27 (m, 1H), 7.74-7.71 (m, 1H), 7.52-7.46 (m, 1H), 7.29-7.18 (m, 2H), 4.99-4.94 (m, 4H), 4.84 (s, 2H), 3.90 (s, 3H), 0.96 (s, 9H), 0.13 (s, 6H).

Reference Example 6-35

1-[5-(3-{[(tert-Butyldimethylsilyl)oxy]methyl}-2-fluorophenyl)-3-(difluoromethyl)pyridin-2-yl]azetidin-3-one O-methyl oxime (Reference Compound 6-35)

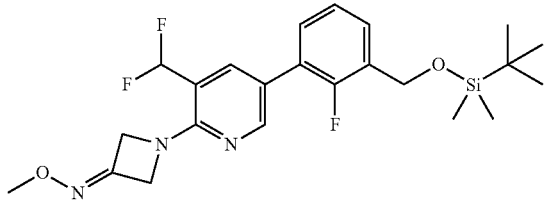 [SMILES: CON=C1CN(c2ncc(-c3cccc(CO[Si](C)(C)C(C)(C)C)c3F)cc2C(F)F)C1]

The reaction was performed by the method described in Reference Example 6-1, except that 1-(5-bromopyrimidin-2-yl)azetidin-3-one O-methyl oxime (Reference Compound 3-1) was replaced by 1-[5-bromo-3-(difluoromethyl)pyridin-2-yl]azetidin-3-one O-methyl oxime synthesized in the same manner as in Reference Example 3-5. Consequently, the title compound (yield 89%) was obtained as a colorless oil.

Mass spectrum (CI, m/z):466[M+1]$^+$.

$^1$H-NMR spectrum (400 MHz, DMSO-d$_6$) δ:8.51-8.47 (m, 1H), 8.00-7.97 (m, 1H), 7.50-7.43 (m, 2H), 7.36-6.99 (m, 2H), 4.93-4.86 (m, 4H), 4.81 (s, 2H), 3.83 (s, 3H), 0.91 (s, 9H), 0.11 (s, 6H).

Reference Example 6-36

1-[5-(3-{[(tert-Butyldimethylsilyl)oxy]methyl}-2-fluorophenyl)-3-cyclopropylpyridin-2-yl]azetidin-3-one O-methyl oxime (Reference Compound 6-36)

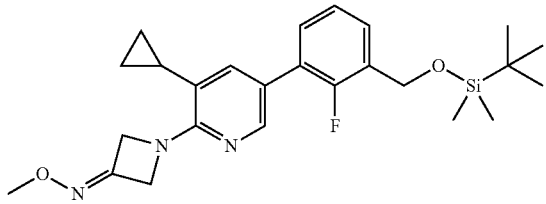 [SMILES: CON=C1CN(c2ncc(-c3cccc(CO[Si](C)(C)C(C)(C)C)c3F)cc2C2CC2)C1]

The reaction was performed by the method described in Reference Example 6-1, except that 1-(5-bromopyrimidin-2-yl)azetidin-3-one O-methyl oxime (Reference Compound 3-1) was replaced by 1-(5-bromo-3-cyclopropylpyridin-2-yl)azetidin-3-one O-methyl oxime synthesized in the same manner as in Reference Example 3-6. Consequently, the title compound (yield 90%) was obtained as a colorless oil.

Mass spectrum (CI, m/z):456[M+1]$^+$.

$^1$H-NMR spectrum (400 MHz, DMSO-d$_6$) δ:8.18-8.15 (m, 1H), 7.44-7.38 (m, 3H), 7.31-7.23 (m, 1H), 4.94-4.90 (m, 4H), 4.80 (s, 2H), 3.81 (s, 3H), 1.94-1.86 (m, 1H), 0.98-0.85 (m, 11H), 0.75-0.69 (m, 2H), 0.11 (s, 6H).

Reference Example 6-37

1-[5-(3-{[(tert-Butyldimethylsilyl)oxy]methyl}-2-fluorophenyl)-3-ethylpyridin-2-yl]azetidin-3-one O-methyl oxime (Reference Compound 6-37)

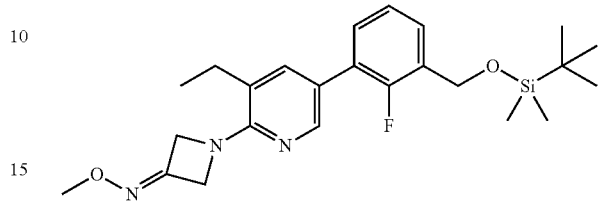

The reaction was performed by the method described in Reference Example 6-1, except that 1-(5-bromopyrimidin-2-yl)azetidin-3-one O-methyl oxime (Reference Compound 3-1) was replaced by 1-(5-bromo-3-ethylpyridin-2-yl)azetidin-3-one O-methyl oxime synthesized in the same manner as in Reference Example 3-7. Consequently, the title compound (yield 83%) was obtained as a colorless oil.

Mass spectrum (CI, m/z):444[M+1]$^+$.

$^1$H-NMR spectrum (400 MHz, DMSO-d$_6$) δ:8.22-8.17 (m, 1H), 7.61-7.59 (m, 1H), 7.46-7.40 (m, 2H), 7.32-7.25 (m, 1H), 4.85-4.79 (m, 6H), 3.81 (s, 3H), 2.63-2.53 (m, 2H), 1.19 (t, J=7.4 Hz, 3H), 0.91 (s, 9H), 0.11 (s, 6H).

Reference Example 6-38

1-[5-(3-{[(tert-Butyldimethylsilyl)oxy]methyl}-2-fluorophenyl)-3-{2-[(tetrahydropyran-2-yl)oxy]propan-2-yl}pyridin-2-yl]azetidin-3-one O-methyl oxime (Reference Compound 6-38)

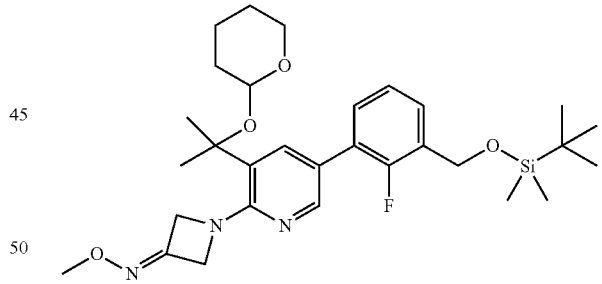

The reaction was performed by the method described in Reference Example 6-1, except that 1-(5-bromopyrimidin-2-yl)azetidin-3-one O-methyl oxime (Reference Compound 3-1) was replaced by 1-(5-bromo-3-{2-[(tetrahydropyran-2-yl)oxy]propan-2-yl}pyridin-2-yl)azetidin-3-one O-methyl oxime synthesized in the same manner as in Reference Example 51. Consequently, the title compound (yield 85%) was obtained as a colorless oil.

Mass spectrum (CI, m/z):558[M+1]$^+$.

$^1$H-NMR spectrum (400 MHz, DMSO-d$_6$) δ:8.32-8.28 (m, 1H), 7.82-7.75 (m, 1H), 7.56-7.37 (m, 2H), 7.35-7.24 (m, 1H), 4.87-4.80 (m, 6H), 4.54-4.50 (m, 1H), 3.85-3.72 (m, 4H), 3.40-3.23 (m, 1H), 1.83-1.28 (m, 12H), 0.91 (s, 9H), 0.11 (s, 6H).

Reference Example 6-39

1-[5-(3-{[(tert-Butyldimethylsilyl)oxy]methyl}-2-fluorophenyl)-3-(methoxymethyl)pyridin-2-yl]azetidin-3-one O-methyl oxime (Reference Compound 6-39)

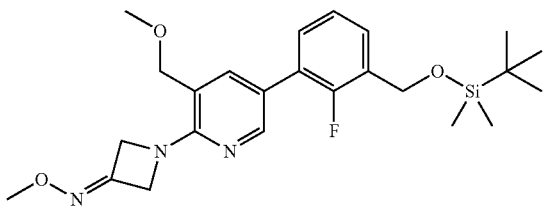 [SMILES: COCc1cc(-c2cccc(CO[Si](C)(C)C(C)(C)C)c2F)cnc1N1CC(=NOC)C1]

The reaction was performed by the method described in Reference Example 6-1, except that 1-(5-bromopyrimidin-2-yl)azetidin-3-one O-methyl oxime (Reference Compound 3-1) was replaced by 1-[5-bromo-3-(methoxymethyl)pyridin-2-yl]azetidin-3-one O-methyl oxime synthesized in the same manner as in Reference Example 3-8. Consequently, the title compound (yield 81%) was obtained as a light yellow oil.

Mass spectrum (CI, m/z):460[M+1].

$^1$H-NMR spectrum (400 MHz, DMSO-$d_6$) δ:8.31-8.25 (m, 1H), 7.76-7.70 (m, 1H), 7.49-7.38 (m, 2H), 7.34-7.24 (m, 1H), 4.89-4.84 (m, 4H), 4.81 (s, 2H), 4.39 (s, 2H), 3.81 (s, 3H), 3.33 (s, 3H), 0.91 (s, 9H), 0.11 (s, 6H).

Reference Example 6-40

1-[5-(3-{[(tert-Butyldimethylsilyl)oxy]methyl}-2-fluorophenyl)-3-methoxypyridin-2-yl]azetidin-3-one O-methyl oxime (Reference Compound 6-40)

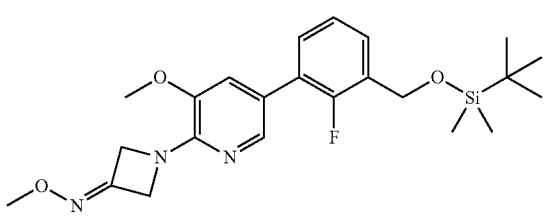 [SMILES: CON=C1CN(c2ncc(-c3cccc(CO[Si](C)(C)C(C)(C)C)c3F)cc2OC)C1]

The reaction was performed by the method described in Reference Example 6-1, except that 1-(5-bromopyrimidin-2-yl)azetidin-3-one O-methyl oxime (Reference Compound 3-1) was replaced by 1-(5-bromo-3-methoxypyridin-2-yl)azetidin-3-one O-methyl oxime synthesized in the same manner as in Reference Example 57. Consequently, the title compound (including impurities) was obtained as a yellow oil.

Mass spectrum (ESI, m/z):446[M+1]$^+$.

$^1$H-NMR spectrum (400 MHz, DMSO-$d_6$) δ:7.92-7.89 (m, 1H), 7.50-7.40 (m, 2H), 7.34-7.26 (m, 2H), 4.81 (s, 2H), 4.79-4.74 (m, 4H), 3.82 (s, 3H), 3.80 (s, 3H), 0.91 (s, 9H), 0.11 (s, 6H).

Reference Example 6-41

1-[5-(3-{[(tert-Butyldimethylsilyl)oxy]methyl}-2-fluorophenyl)pyrimidin-2-yl]piperidin-4-one (Reference Compound 6-41)

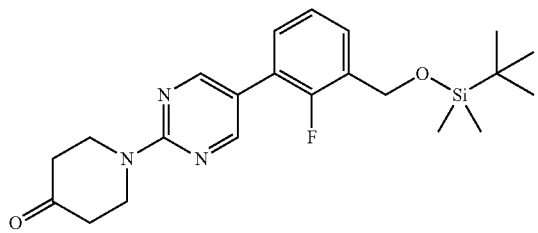 [SMILES: CC(C)(C)[Si](C)(C)OCc1cccc(-c2cnc(N3CCC(=O)CC3)nc2)c1F]

The reaction was performed by the method described in Reference Example 6-1, except that 1-(5-bromopyrimidin-2-yl)azetidin-3-one O-methyl oxime (Reference Compound 3-1) was replaced by 1-(5-bromopyrimidin-2-yl)piperidin-4-one synthesized in the same manner as in Reference Example 59. Consequently, the title compound (yield 91%) was obtained as a light yellow solid.

Mass spectrum (CI, m/z):416[M+1]$^+$.

$^1$H-NMR spectrum (400 MHz, DMSO-$d_6$) δ:8.63 (d, J=1.5 Hz, 2H), 7.53-7.41 (m, 2H), 7.37-7.24 (m, 1H), 4.82 (s, 2H), 4.14-4.07 (m, 4H), 2.48-2.43 (m, 4H), 0.92 (s, 9H), 0.11 (s, 6H).

Reference Example 6-42

1-[5-(3-{[(tert-Butyldimethylsilyl)oxy]methyl}-2-fluorophenyl)pyrimidin-2-yl]piperidin-4-one O-{3-[(tetrahydropyran-2-yl)oxy]propyl} oxime (Reference Compound 6-42)

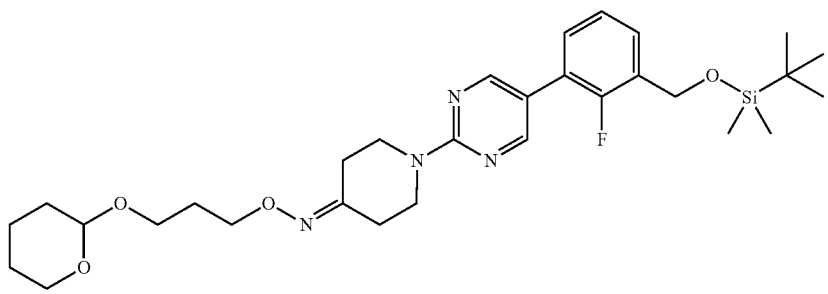 [SMILES: CC(C)(C)[Si](C)(C)OCc1cccc(-c2cnc(N3CCC(=NOCCCOC4CCCCO4)CC3)nc2)c1F]

The reaction was performed by the method described in Reference Example 6-1, except that 1-(5-bromopyrimidin-2-yl)azetidin-3-one O-methyl oxime (Reference Compound 3-1) was replaced by 1-(5-bromopyrimidin-2-yl)piperidin-4-one O-{3-[(tetrahydropyran-2-yl)oxy]propyl} oxime synthesized in the same manner as in Reference Example 67-1. Consequently, the title compound (yield 72%) was obtained as a light yellow oil.

Mass spectrum (CI, m/z):573[M+1]$^+$.

$^1$H-NMR spectrum (400 MHz, DMSO-d$_6$) δ:8.59 (d, J=1.4 Hz, 2H), 7.52-7.38 (m, 2H), 7.34-7.26 (m, 1H), 4.83 (s, 2H), 4.57-4.54 (m, 1H), 4.08-4.02 (m, 2H), 3.97-3.87 (m, 4H), 3.76-3.62 (m, 2H), 3.47-3.35 (m, 2H), 2.61-2.54 (m, 2H), 2.42-2.36 (m, 2H), 1.93-1.32 (m, 8H), 0.91 (s, 9H), 0.11 (s, 6H).

Reference Example 6-43

1-[5-(3-{[(tert-Butyldimethylsilyl)oxy]methyl}-2-fluorophenyl)pyrimidin-2-yl]piperidin-4-one O-{4-[(tetrahydropyran-2-yl)oxy]butyl} oxime (Reference Compound 6-43)

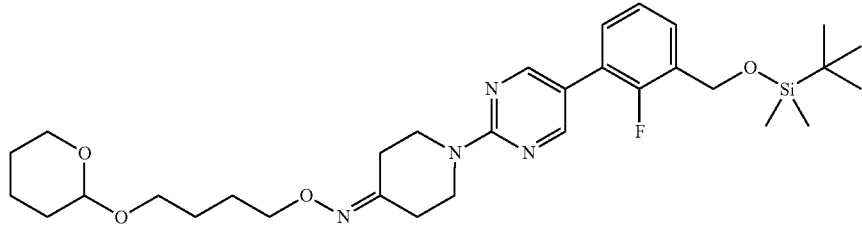 [SMILES: CC(C)(C)[Si](C)(C)OCc1cccc(-c2cnc(N3CCC(=NOCCCCOC4CCCCO4)CC3)nc2)c1F]

The reaction was performed by the method described in Reference Example 6-1, except that 1-(5-bromopyrimidin-2-yl)azetidin-3-one O-methyl oxime (Reference Compound 3-1) was replaced by 1-(5-bromopyrimidin-2-yl)piperidin-4-one O-{4-[(tetrahydropyran-2-yl)oxy]butyl} oxime synthesized in the same manner as in Reference Example 67-2. Consequently, the title compound (yield 80%) was obtained as a light yellow oil.

Mass spectrum (CI, m/z):587[M+1]$^+$.

$^1$H-NMR spectrum (400 MHz, DMSO-d$_6$) δ:8.59 (d, J=1.4 Hz, 2H), 7.53-7.41 (m, 2H), 7.34-7.24 (m, 1H), 4.81 (s, 2H), 4.64-4.47 (m, 1H), 4.02-3.96 (m, 2H), 3.95-3.86 (m, 4H), 3.77-3.57 (m, 2H), 3.46-3.34 (m, 2H), 2.60-2.54 (m, 2H), 2.41-2.35 (m, 2H), 1.86-1.36 (m, 10H), 0.91 (s, 9H), 0.11 (s, 6H).

Reference Example 6-44

1-[5-(3-{[(tert-Butyldimethylsilyl)oxy]methyl}-2-fluorophenyl)pyrimidin-2-yl]piperidin-4-one O-(2-methoxyethyl) oxime (Reference Compound 6-44)

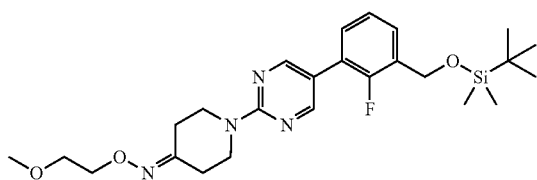 [SMILES: COCCON=C1CCN(c2ncc(-c3cccc(CO[Si](C)(C)C(C)(C)C)c3F)cn2)CC1]

The reaction was performed by the method described in Reference Example 6-1, except that 1-(5-bromopyrimidin-2-yl)azetidin-3-one O-methyl oxime (Reference Compound 3-1) was replaced by 1-(5-bromopyrimidin-2-yl)piperidin-4-one O-(2-methoxyethyl) oxime synthesized in the same manner as in Reference Example 67-3, and the reaction temperature was changed to 85° C. Consequently, the title compound (yield 75%) was obtained as a light yellow oil.

Mass spectrum (CI, m/z):489[M+1]$^+$.

$^1$H-NMR spectrum (400 MHz, DMSO-d$_6$) δ:8.59 (d, J=1.4 Hz, 2H), 7.51-7.39 (m, 2H), 7.34-7.23 (m, 1H), 4.83 (s, 2H), 4.13-4.05 (m, 2H), 3.98-3.89 (m, 4H), 3.59-3.50 (m, 2H), 3.26 (s, 3H), 2.62-2.54 (m, 2H), 2.40-2.35 (m, 2H), 0.91 (s, 9H), 0.11 (s, 6H).

Reference Example 6-45

1-[5-(3-{[(tert-Butyldimethylsilyl)oxy]methyl}-2-fluorophenyl)pyrimidin-2-yl]piperidin-4-one O-{2,2-dimethyl-3-[(tetrahydropyran-2-yl)oxy]propyl} oxime (Reference Compound 6-45)

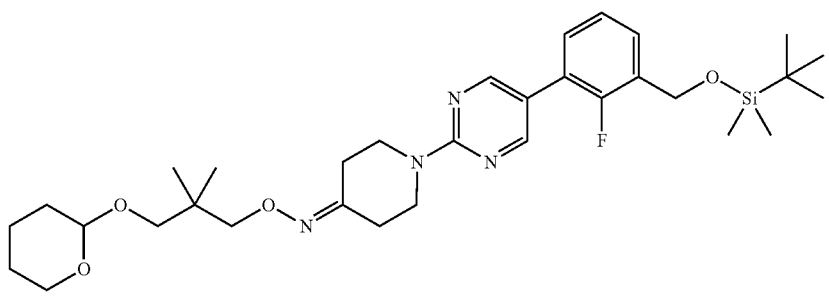 [SMILES: CC(C)(CON=C1CCN(c2ncc(-c3cccc(CO[Si](C)(C)C(C)(C)C)c3F)cn2)CC1)COC1CCCCO1]

The reaction was performed by the method described in Reference Example 6-1, except that 1-(5-bromopyrimidin-2-yl)azetidin-3-one O-methyl oxime (Reference Compound 3-1) was replaced by 1-(5-bromopyrimidin-2-yl)piperidin-4-one O-{2,2-dimethyl-3-[(tetrahydropyran-2-yl)oxy]propyl} oxime synthesized in the same manner as in Reference Example 67-4. Consequently, the title compound (including impurities) was obtained as a light yellow oil.

Mass spectrum (CI, m/z):601 [M+1]$^+$.

$^1$H-NMR spectrum (400 MHz, CDCl$_3$) δ:8.53 (d, J=1.5 Hz, 2H), 7.51-7.45 (m, 1H), 7.30-7.18 (m, 2H), 4.85 (s, 2H), 4.60-4.56 (m, 1H), 4.03-3.97 (m, 4H), 3.93-3.91 (m, 2H), 3.90-3.80 (m, 1H), 3.56 (d, J=9.3 Hz, 1H), 3.53-3.45 (m, 1H), 3.12 (d, J=9.3 Hz, 1H), 2.73-2.67 (m, 2H), 2.50-2.43 (m, 2H), 1.90-1.46 (m, 6H), 0.98 (s, 3H), 0.97 (s, 3H), 0.96 (s, 9H), 0.14 (s, 6H).

Reference Example 6-46

1-[5-(3-{[(tert-Butyldimethylsilyl)oxy]methyl}-2-fluorophenyl)pyrimidin-2-yl]piperidin-4-one O-{3-methyl-3-[(tetrahydropyran-2-yl)oxy]butyl} oxime (Reference Compound 6-46)

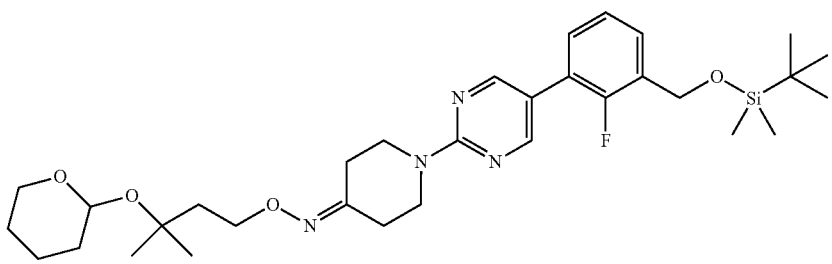 [SMILES: CC(C)(CCON=C1CCN(c2ncc(-c3cccc(CO[Si](C)(C)C(C)(C)C)c3F)cn2)CC1)OC1CCCCO1]

The reaction was performed by the method described in Reference Example 6-1, except that 1-(5-bromopyrimidin-2-yl)azetidin-3-one O-methyl oxime (Reference Compound 3-1) was replaced by 1-(5-bromopyrimidin-2-yl)piperidin-4-one O-{3-methyl-3-[(tetrahydropyran-2-yl)oxy]butyl} oxime synthesized in the same manner as in Reference Example 69-1. Consequently, the title compound (yield 84%) was obtained as a colorless oil.

Mass spectrum (CI, m/z):601[M+1]$^+$.

$^1$H-NMR spectrum (400 MHz, CDCl$_3$) δ:8.52 (d, J=1.5 Hz, 2H), 7.51-7.45 (m, 1H), 7.31-7.18 (m, 2H), 4.85 (s, 2H), 4.81-4.75 (m, 1H), 4.24-4.16 (m, 2H), 4.04-3.92 (m, 5H), 3.57-3.38 (m, 1H), 2.70-2.64 (m, 2H), 2.49-2.44 (m, 2H), 1.97-1.80 (m, 3H), 1.72-1.41 (m, 5H), 1.28 (s, 3H), 1.26 (s, 3H), 0.96 (s, 9H), 0.14 (s, 6H).

Reference Example 6-47

1-[5-(3-{[(tert-Butyldimethylsilyl)oxy]methyl}-2-fluorophenyl)pyrimidin-2-yl]piperidin-4-one O-{2-methyl-3-[(tetrahydropyran-2-yl)oxy]propyl} oxime (Reference Compound 6-47)

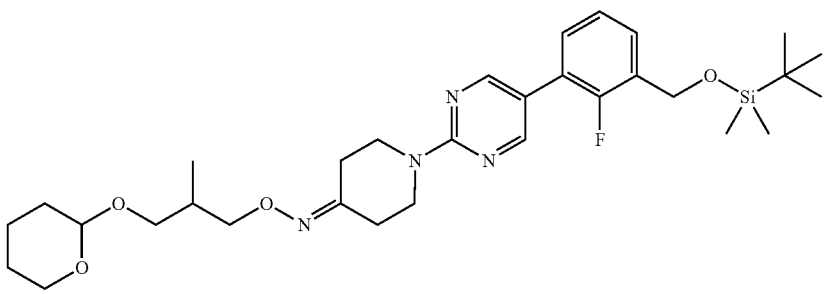 [SMILES: CC(CON=C1CCN(c2ncc(-c3cccc(CO[Si](C)(C)C(C)(C)C)c3F)cn2)CC1)COC1CCCCO1]

The reaction was performed by the method described in Reference Example 6-1, except that 1-(5-bromopyrimidin-2-yl)azetidin-3-one O-methyl oxime (Reference Compound 3-1) was replaced by 1-(5-bromopyrimidin-2-yl)piperidin-4-one O-{2-methyl-3-[(tetrahydropyran-2-yl)oxy]propyl} oxime synthesized in the same manner as in Reference Example 67-6. Consequently, the title compound (including impurities) was obtained as a colorless oil.

Mass spectrum (CI, m/z):587[M+1]$^+$.

$^1$H-NMR spectrum (400 MHz, CDCl$_3$) 5:8.53 (d, J=1.4 Hz, 2H), 7.51-7.44 (m, 1H), 7.30-7.18 (m, 2H), 4.85 (s, 2H), 4.61-4.55 (m, 1H), 4.22-3.23 (m, 10H), 2.72-2.65 (m, 2H), 2.50-2.44 (m, 2H), 2.23-2.10 (m, 1H), 1.88-1.46 (m, 6H), 1.04-0.98 (m, 3H), 0.96 (s, 9H), 0.14 (s, 6H).

Reference Example 6-48

1-[5-(3-{[(tert-Butyldimethylsilyl)oxy]methyl}-2-fluorophenyl)pyrimidin-2-yl]piperidin-4-one O-[(2,2-dimethyl-1,3-dioxan-5-yl)methyl] oxime (Reference Compound 6-48)

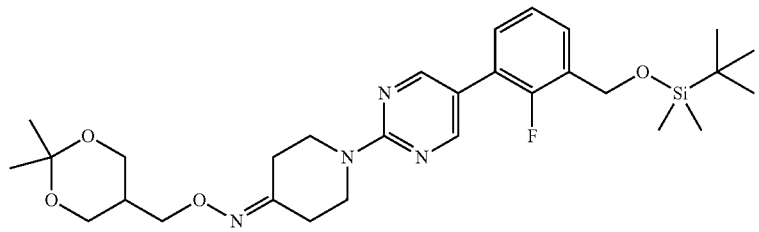 [SMILES: CC1(C)OCC(CON=C2CCN(c3ncc(-c4cccc(CO[Si](C)(C)C(C)(C)C)c4F)cn3)CC2)CO1]

The reaction was performed by the method described in Reference Example 6-1, except that 1-(5-bromopyrimidin-2-yl)azetidin-3-one O-methyl oxime (Reference Compound 3-1) was replaced by 1-(5-bromopyrimidin-2-yl)piperidin-4-one O-[(2,2-dimethyl-1,3-dioxan-5-yl)methyl] oxime synthesized in the same manner as in Reference Example 67-7. Consequently, the title compound (yield 96%) was obtained as a colorless oil.

Mass spectrum (CI, m/z):559[M+1]$^+$.

$^1$H-NMR spectrum (400 MHz, CDCl$_3$) δ:8.53 (d, J=1.4 Hz, 2H), 7.51-7.45 (m, 1H), 7.30-7.18 (m, 2H), 4.85 (s, 2H), 4.16-4.07 (m, 2H), 4.04-3.95 (m, 6H), 3.77 (dd, J=6.5, 11.9 Hz, 2H), 2.70-2.64 (m, 2H), 2.48-2.42 (m, 2H), 2.19-2.10 (m, 1H), 1.44 (s, 3H), 1.42 (s, 3H), 0.96 (s, 9H), 0.14 (s, 6H).

Reference Example 6-49

1-[5-(3-{[(tert-Butyldimethylsilyl)oxy]methyl}-2-fluorophenyl)pyrimidin-2-yl]piperidin-4-one O-[(2,2,5-trimethyl-1,3-dioxan-5-yl)methyl] oxime (Reference Compound 6-49)

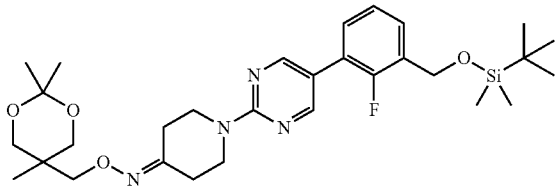 [SMILES: CC1(CON=C2CCN(c3ncc(-c4cccc(CO[Si](C)(C)C(C)(C)C)c4F)cn3)CC2)COC(C)(C)OC1]

The reaction was performed by the method described in Reference Example 6-1, except that 1-(5-bromopyrimidin-2-yl)azetidin-3-one O-methyl oxime (Reference Compound 3-1) was replaced by 1-(5-bromopyrimidin-2-yl)piperidin-4-one O-[(2,2,5-trimethyl-1,3-dioxan-5-yl)methyl] oxime synthesized in the same manner as in Reference Example 67-8. Consequently, the title compound (including impurities) was obtained as a light yellow oil.

Mass spectrum (CI, m/z):346[M+1]$^+$.

$^1$H-NMR spectrum (400 MHz, CDCl$_3$) δ:8.53 (d, J=1.4 Hz, 2H), 7.51-7.45 (m, 1H), 7.29-7.18 (m, 2H), 4.85 (s, 2H), 4.11 (s, 2H), 4.03-3.97 (m, 4H), 3.78-3.73 (m, 2H), 3.60-3.55 (m, 2H), 2.71-2.66 (m, 2H), 2.49-2.45 (m, 2H), 1.44 (s, 3H), 1.42 (s, 3H), 0.96 (s, 9H), 0.95 (s, 3H), 0.14 (s, 6H).

Reference Example 6-50

1-[5-(3-{[(tert-Butyldimethylsilyl)oxy]methyl}-2-fluorophenyl)pyrimidin-2-yl]piperidin-4-one 0-[(2,2-dimethyl-1,3-dioxolan-4-yl)methyl] oxime (Reference Compound 6-50)

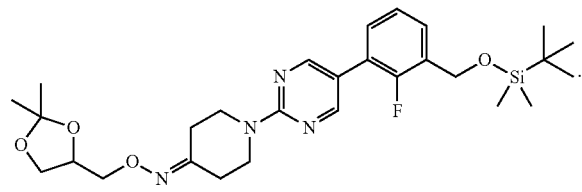 [SMILES: CC1(C)OCC(CON=C2CCN(c3ncc(-c4cccc(CO[Si](C)(C)C(C)(C)C)c4F)cn3)CC2)O1]

The reaction was performed by the method described in Reference Example 6-1, except that 1-(5-bromopyrimidin-2-yl)azetidin-3-one O-methyl oxime (Reference Compound 3-1) was replaced by 1-(5-bromopyrimidin-2-yl)piperidin-4-one O-[(2,2-dimethyl-1,3-dioxolan-4-yl)methyl] oxime synthesized in the same manner as in Reference Example 67-9. Consequently, the title compound (yield 80%) was obtained as a light yellow oil.

Mass spectrum (CI, m/z):545[M+1]$^+$.

$^1$H-NMR spectrum (400 MHz, DMSO-d$_6$) δ:8.59 (d, J=1.5 Hz, 2H), 7.52-7.40 (m, 2H), 7.37-7.28 (m, 1H), 4.81 (s, 2H), 4.34-4.19 (m, 1H), 4.06-3.98 (m, 3H), 3.96-3.88 (m, 4H), 3.67 (dd, J=6.5, 8.3 Hz, 1H), 2.62-2.55 (m, 2H), 2.42-2.32 (m, 2H), 1.33 (s, 3H), 1.28 (s, 3H), 0.91 (s, 9H), 0.11 (s, 6H).

Reference Example 6-51

2-[({1-[5-(3-{[(tert-Butyldimethylsilyl)oxy]methyl}-2-fluorophenyl)pyrimidin-2-yl]piperidin-4-ylidene}amino)oxy]ethyl acetate (Reference Compound 6-51)

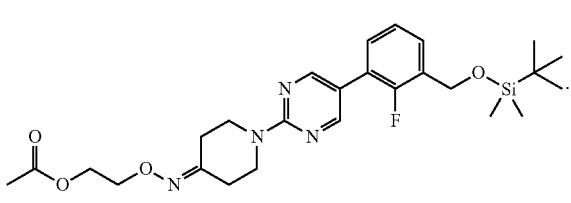 [SMILES: CC(=O)OCCON=C1CCN(c2ncc(-c3cccc(CO[Si](C)(C)C(C)(C)C)c3F)cn2)CC1]

The reaction was performed by the method described in Reference Example 6-1, except that 1-(5-bromopyrimidin-2-yl)azetidin-3-one O-methyl oxime (Reference Compound 3-1) was replaced by 2-({[1-(5-bromopyrimidin-2-yl)piperidin-4-ylidene]amino}oxy)ethyl acetate synthesized in the same manner as in Reference Example 29-3. Consequently, the title compound (yield 85%) was obtained as a light brown solid.

Mass spectrum (CI, m/z):517[M+1]$^+$.

$^1$H-NMR spectrum (400 MHz, DMSO-d$_6$) δ:8.59 (d, J=1.5 Hz, 2H), 7.52-7.41 (m, 2H), 7.35-7.24 (m, 1H), 4.81 (s, 2H), 4.31-4.12 (m, 4H), 3.97-3.86 (m, 4H), 2.62-2.55 (m, 2H), 2.43-2.34 (m, 2H), 2.03 (s, 3H), 0.91 (s, 9H), 0.11 (s, 6H).

Reference Example 6-52) tert-Butyl 2-[({1-[5-(3-{[(tert-butyldimethylsilyl)oxy]methyl}-2-fluorophenyl)pyrimidin-2-yl]azetidin-3-ylidene}amino)oxy]acetate (Reference Compound 6-52)

The reaction was performed by the method described in Reference Example 6-1, except that 1-(5-bromopyrimidin-2-yl)azetidin-3-one O-methyl oxime (Reference Compound 3-1) was replaced by tert-butyl 2-({[1-(5-bromopyrimidin-2-yl)azetidin-3-ylidene]amino}oxy)acetate synthesized in the same manner as in Reference Example 10-12. Consequently, the title compound (including impurities) was obtained as a yellow oil.

Mass spectrum (CI, m/z):517[M+1]$^+$.

$^1$H-NMR spectrum (400 MHz, CDCl$_3$) δ:8.57 (d, J=1.4 Hz, 2H), 7.55-7.47 (m, 1H), 7.29-7.20 (m, 2H), 4.99-4.89 (m, 4H), 4.85 (s, 2H), 4.52 (s, 2H), 1.50 (s, 9H), 0.96 (s, 9H), 0.14 (s, 6H).

Reference Example 6-53

2-[({1-[5-(3-{[(tert-Butyldimethylsilyl)oxy]methyl}-2-fluorophenyl)pyrimidin-2-yl]azetidin-3-ylidene}amino)oxy]-N-methylacetamide (Reference Compound 6-53)

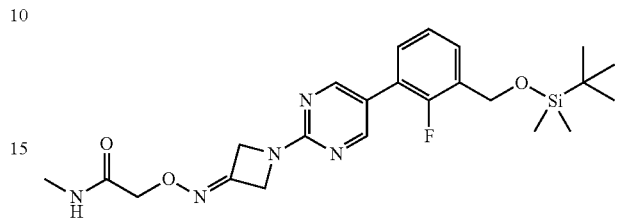

The reaction was performed by the method described in Reference Example 6-1, except that 1-(5-bromopyrimidin-2-yl)azetidin-3-one O-methyl oxime (Reference Compound 3-1) was replaced by 2-({[1-(5-bromopyrimidin-2-yl)azetidin-3-ylidene]amino}oxy)-N-methylacetamide synthesized in the same manner as in Reference Example 77. Consequently, the title compound (including impurities) was obtained as a light yellow solid.

Mass spectrum (CI, m/z):474[M+1]$^+$.

$^1$H-NMR spectrum (400 MHz, CDCl$_3$) δ:8.58 (d, J=1.4 Hz, 2H), 7.58-7.43 (m, 1H), 7.29-7.21 (m, 2H), 6.16 (br s, 1H), 4.85 (s, 2H), 4.58 (s, 2H), 2.91 (d, J=4.9 Hz, 3H), 0.96 (s, 9H), 0.14 (s, 6H).

Reference Example 6-54

3-[({1-[5-(3-{[(tert-Butyldimethylsilyl)oxy]methyl}-2-fluorophenyl)pyrimidin-2-yl]azetidin-3-ylidene}amino)oxy]propanamide (Reference Compound 6-54)

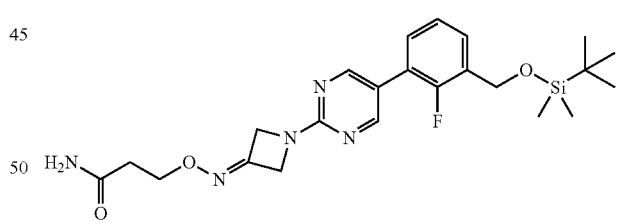

The reaction was performed by the method described in Reference Example 6-1, except that 1-(5-bromopyrimidin-2-yl)azetidin-3-one O-methyl oxime (Reference Compound 3-1) was replaced by 3-({[1-(5-bromopyrimidin-2-yl)azetidin-3-ylidene]amino}oxy)propanamide synthesized in the same manner as in Reference Example 78-1. Consequently, the title compound (including impurities) was obtained as a white solid.

Mass spectrum (ESI, m/z):474[M+1]$^+$.

$^1$H-NMR spectrum (400 MHz, DMSO-d$_6$) δ:8.63 (d, J=1.4 Hz, 2H), 7.52-7.43 (m, 2H), 7.37 (br s, 1H), 7.34-7.27 (m, 1H), 6.87 (br s, 1H), 4.87-4.72 (m, 6H), 4.22 (t, J=6.5 Hz, 2H), 2.42 (t, J=6.5 Hz, 2H), 0.91 (s, 9H), 0.11 (s, 6H).

Reference Example 6-55

3-[({1-[5-(3-{[(tert-Butyldimethylsilyl)oxy]methyl}-2-fluorophenyl)pyrimidin-2-yl]azetidin-3-ylidene}amino)oxy]-N-methylpropanamide (Reference Compound 6-55)

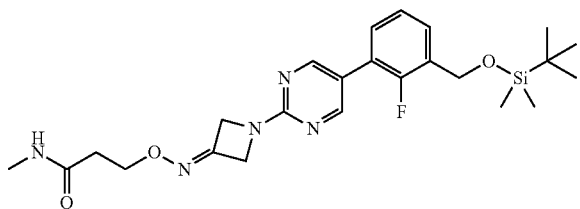 [SMILES: CNC(=O)CCON=C1CN(c2ncc(-c3cccc(CO[Si](C)(C)C(C)(C)C)c3F)cn2)C1]

The reaction was performed by the method described in Reference Example 6-1, except that 1-(5-bromopyrimidin-2-yl)azetidin-3-one O-methyl oxime (Reference Compound 3-1) was replaced by 3-({[1-(5-bromopyrimidin-2-yl)azetidin-3-ylidene]amino}oxy)-N-methylpropanamide synthesized in the same manner as in Reference Example 78-2. Consequently, the title compound (including impurities) was obtained as a white solid.

Mass spectrum (CI, m/z):488[M+1]$^+$.

$^1$H-NMR spectrum (400 MHz, DMSO-d$_6$) δ:8.63 (d, J=1.4 Hz, 2H), 7.90-7.77 (m, 1H), 7.52-7.42 (m, 2H), 7.36-7.25 (m, 1H), 4.87-4.71 (m, 6H), 4.22 (t, J=6.5 Hz, 2H), 2.57 (d, J=4.5 Hz, 3H), 2.43 (t, J=6.5 Hz, 2H), 0.91 (s, 9H), 0.11 (s, 6H).

Reference Example 6-56

Ethyl 4-[({1-[5-(3-{[(tert-butyldimethylsilyl)oxy]methyl}-2-fluorophenyl)pyrimidin-2-yl]azetidin-3-ylidene}amino)oxy]butanoate (Reference Compound 6-56)

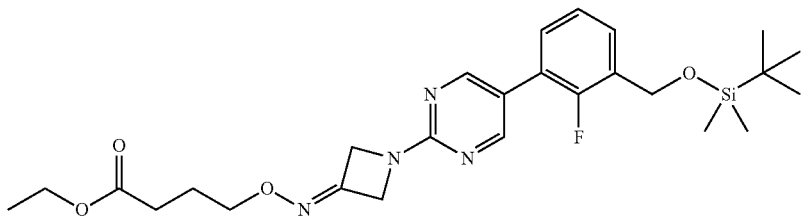 [SMILES: CCOC(=O)CCCON=C1CN(c2ncc(-c3cccc(CO[Si](C)(C)C(C)(C)C)c3F)cn2)C1]

The reaction was performed by the method described in Reference Example 6-1, except that 1-(5-bromopyrimidin-2-yl)azetidin-3-one O-methyl oxime (Reference Compound 3-1) was replaced by ethyl 4-({[1-(5-bromopyrimidin-2-yl)azetidin-3-ylidene]amino}oxy)butanoate synthesized in the same manner as in Reference Example 10-13. Consequently, the title compound (yield 86%) was obtained as a colorless oil.

Mass spectrum (CI, m/z):517[M+1]$^+$.

$^1$H-NMR spectrum (400 MHz, DMSO-d$_6$) δ:8.63 (d, J=1.4 Hz, 2H), 7.54-7.43 (m, 2H), 7.35-7.27 (m, 1H), 4.85-4.77 (m, 6H), 4.10-4.01 (m, 4H), 2.38 (t, J=7.4 Hz, 2H), 1.93-1.82 (m, 2H), 1.18 (t, J=7.2 Hz, 3H), 0.91 (s, 9H), 0.11 (s, 6H).

Reference Example 6-57

4-[({1-[5-(3-{[(tert-Butyldimethylsilyl)oxy]methyl}-2-fluorophenyl)pyrimidin-2-yl]azetidin-3-ylidene}amino)oxy]-N-methylbutanamide (Reference Compound 6-57)

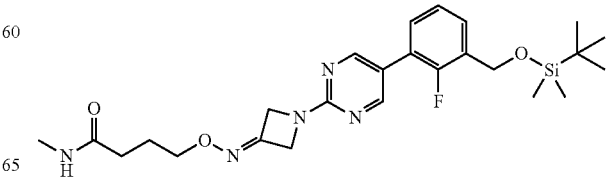

The reaction was performed by the method described in Reference Example 6-1, except that 1-(5-bromopyrimidin-2-yl)azetidin-3-one O-methyl oxime (Reference Compound 3-1) was replaced by 4-({[1-(5-bromopyrimidin-2-yl)azetidin-3-ylidene]amino}oxy)-N-methylbutanamide synthesized in the same manner as in Reference Example 80. Consequently, the title compound (including impurities) was obtained as a light yellow solid.

Mass spectrum (CI, m/z):502[M+1]$^+$.

$^1$H-NMR spectrum (400 MHz, CDCl$_3$) δ:8.57 (d, J=1.5 Hz, 2H), 7.58-7.43 (m, 1H), 7.29-7.20 (m, 2H), 5.48 (br s, 1H), 4.91-4.82 (m, 6H), 4.13 (t, J=6.1 Hz, 2H), 2.83 (d, J=4.8 Hz, 3H), 2.28 (t, J=7.4 Hz, 2H), 2.08-1.99 (m, 2H), 0.96 (s, 9H), 0.14 (s, 6H).

Reference Example 6-58

2-{3-[({1-[5-(3-{[(tert-Butyldimethylsilyl)oxy]methyl}-2-fluorophenyl)pyrimidin-2-yl]azetidin-3-ylidene}amino)oxy]-2-{[(tetrahydropyran-2-yl)oxy]methyl}propyl}isoindoline-1,3-dione (Reference Compound 6-58)

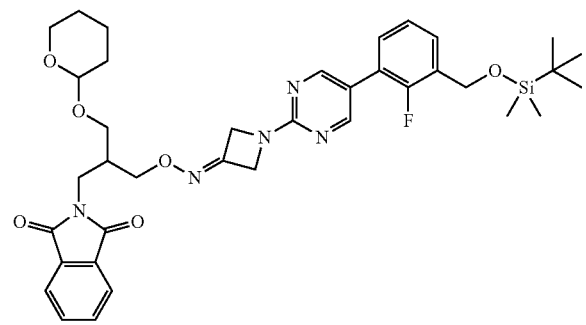 [SMILES: CC(C)(C)[Si](C)(C)OCc1cccc(-c2cnc(N3CC(=NOCC(COC4CCCCO4)CN4C(=O)c5ccccc5C4=O)C3)nc2)c1F]

The reaction was performed by the method described in Reference Example 6-1, except that 1-(5-bromopyrimidin-2-yl)azetidin-3-one O-methyl oxime (Reference Compound 3-1) was replaced by 2-[3-({[1-(5-bromopyrimidin-2-yl)azetidin-3-ylidene]amino}oxy)-2-{[(tetrahydropyran-2-yl)oxy]methyl}propyl]isoindoline-1,3-dione synthesized in the same manner as in Reference Example 85-1. Consequently, the title compound (yield 73%) was obtained as a yellow oil.

Mass spectrum (EI, m/z):703[M]$^+$.

$^1$H-NMR spectrum (400 MHz, DMSO-d$_6$) δ:8.62 (d, J=1.3 Hz, 2H), 7.88-7.83 (m, 2H), 7.80-7.74 (m, 2H), 7.52-7.44 (m, 2H), 7.35-7.29 (m, 1H), 4.82 (s, 2H), 4.77-4.62 (m, 2H), 4.57-4.46 (m, 3H), 4.17-4.04 (m, 2H), 3.76-3.60 (m, 4H), 3.43-3.35 (m, 2H), 2.60-2.47 (m, 1H), 1.70-1.22 (m, 6H), 0.91 (s, 9H), 0.11 (s, 6H).

Reference Example 6-59

2-{3-[({1-[5-(3-{[(tert-Butyldimethylsilyl)oxy]methyl}-2-fluorophenyl)pyrimidin-2-yl]azetidin-3-ylidene}amino)oxy]-2-methoxypropyl}isoindoline-1,3-dione (Reference Compound 6-59)

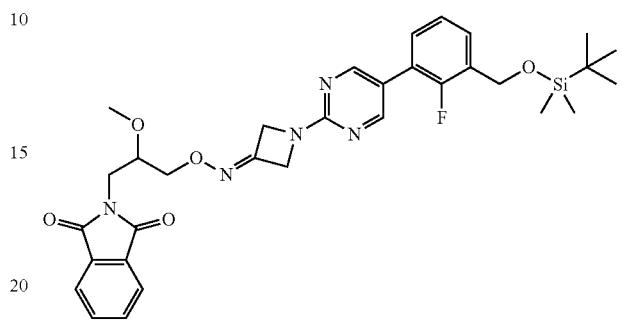

The reaction was performed by the method described in Reference Example 6-1, except that 1-(5-bromopyrimidin-2-yl)azetidin-3-one O-methyl oxime (Reference Compound 3-1) was replaced by 2-[3-({[1-(5-bromopyrimidin-2-yl)azetidin-3-ylidene]amino}oxy)-2-methoxypropyl]iso indoline-1,3-dione synthesized in the same manner as in Reference Example 85-2. Consequently, the title compound (yield 80%) was obtained as a light yellow oil.

Mass spectrum (CI, m/z):620[M+1]$^+$.

$^1$H-NMR spectrum (400 MHz, DMSO-d$_6$+D$_2$O) δ:8.63 (d, J=1.4 Hz, 2H), 7.91-7.85 (m, 2H), 7.85-7.80 (m, 2H), 7.55-7.41 (m, 2H), 7.37-7.24 (m, 1H), 4.82 (s, 2H), 4.79-4.68 (m, 4H), 4.17-4.07 (m, 2H), 3.87-3.64 (m, 3H), 3.32 (s, 3H), 0.91 (s, 9H), 0.11 (s, 6H).

Reference Example 6-60

1-[5-(3-{[(tert-Butyldimethylsilyl)oxy]methyl}-2-fluorophenyl)pyrimidin-2-yl]azetidin-3-one O-(2-morpholinoethyl) oxime (Reference Compound 6-60)

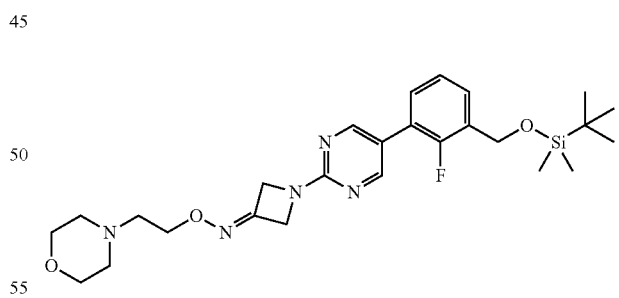

The reaction was performed by the method described in Reference Example 6-1, except that 1-(5-bromopyrimidin-2-yl)azetidin-3-one O-methyl oxime (Reference Compound 3-1) was replaced by 1-(5-bromopyrimidin-2-yl)azetidin-3-one O-(2-morpholinoethyl) oxime synthesized in the same manner as in Reference Example 90-1. Consequently, the title compound (yield 83%)) was obtained as a dark brown solid.

Mass spectrum (CI, m/z):516[M+1]$^+$.

$^1$H-NMR spectrum (400 MHz, DMSO-d$_6$) δ:8.62 (d, J=1.4 Hz, 2H), 7.51-7.43 (m, 2H), 7.35-7.28 (m, 1H), 4.85-4.77 (m, 6H), 4.15 (t, J=6.0 Hz, 2H), 3.61-3.52 (m, 4H), 2.58 (t, J=6.0 Hz, 2H), 2.45-2.38 (m, 4H), 0.91 (s, 9H), 0.11 (s, 6H).

Reference Example 6-61

1-[5-(3-{[(tert-Butyldimethylsilyl)oxy]methyl}-2-fluorophenyl)pyrimidin-2-yl]azetidin-3-one O-[2-(azetidin-1-yl)ethyl] oxime (Reference Compound 6-61)

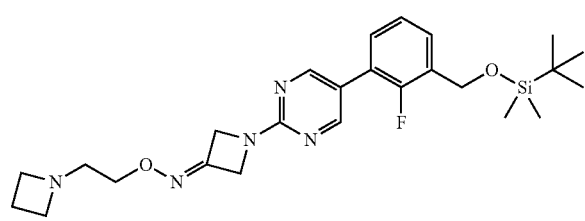 [SMILES: CC(C)(C)[Si](C)(C)OCc1cccc(-c2cnc(N3CC(=NOCCN4CCC4)C3)nc2)c1F]

The reaction was performed by the method described in Reference Example 6-1, except that 1-(5-bromopyrimidin-2-yl)azetidin-3-one O-methyl oxime (Reference Compound 3-1) was replaced by 1-(5-bromopyrimidin-2-yl)azetidin-3-one O-[2-(azetidin-1-yl)ethyl] oxime synthesized in the same manner as in Reference Example 90-2. Consequently, the title compound (yield 74%) was obtained as a colorless oil.

Mass spectrum (ESI, m/z):486[M+1].

$^1$H-NMR spectrum (400 MHz, DMSO-d$_6$) δ:8.62 (d, J=1.4 Hz, 2H), 7.50-7.44 (m, 2H), 7.34-7.29 (m, 1H), 4.85-4.76 (m, 6H), 3.97 (t, J=5.7 Hz, 2H), 3.16-3.09 (m, 4H), 2.59 (t, J=5.7 Hz, 2H), 1.99-1.89 (m, 2H), 0.91 (s, 9H), 0.11 (s, 6H).

Reference Example 6-62

1-[5-(3-{[(tert-Butyldimethylsilyl)oxy]methyl}-2-fluorophenyl)pyrimidin-2-yl]azetidin-3-one O-[(4-methylmorpholin-2-yl)methyl] oxime (Reference Compound 6-62)

The reaction was performed by the method described in Reference Example 6-1, except that 1-(5-bromopyrimidin-2-yl)azetidin-3-one O-methyl oxime (Reference Compound 3-1) was replaced by 1-(5-bromopyrimidin-2-yl)azetidin-3-one O-[(4-methylmorpholin-2-yl)methyl] oxime synthesized in the same manner as in Reference Example 92-1. Consequently, the title compound (including impurities) was obtained as a brown oil.

Mass spectrum (ESI, m/z):516[M+1]$^+$.

Reference Example 6-63

1-(2-{[({1-[5-(3-{[(tert-Butyldimethylsilyl)oxy]methyl}-2-fluorophenyl)pyrimidin-2-yl]azetidin-3-ylidene}amino)oxy]methyl}morpholino)ethanone (Reference Compound 6-63)

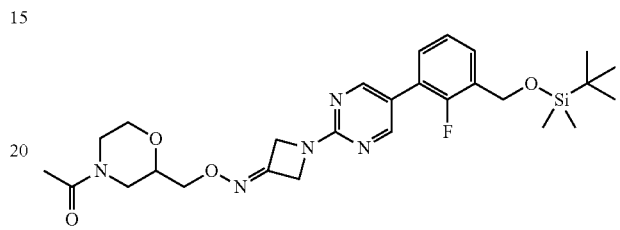

The reaction was performed by the method described in Reference Example 6-1, except that 1-(5-bromopyrimidin-2-yl)azetidin-3-one O-methyl oxime (Reference Compound 3-1) was replaced by 1-{2-[({[1-(5-bromopyrimidin-2-yl)azetidin-3-ylidene]amino}oxy)methyl]morpholino}ethanone synthesized in the same manner as in Reference Example 87-3. Consequently, the title compound (including impurities) was obtained as a brown oil.

Mass spectrum (ESI, m/z):544[M+1]$^+$.

$^1$H-NMR spectrum (400 MHz, DMSO-d$_6$) δ:8.63 (d, J=1.3 Hz, 2H), 7.52-7.42 (m, 2H), 7.36-7.28 (m, 1H), 4.86-4.78 (m, 6H), 4.32-3.98 (m, 3H), 3.90-3.82 (m, 1H), 3.79-3.53 (m, 2H), 3.50-3.39 (m, 1H), 3.22-2.89 (m, 1H), 2.70-2.40 (m, 1H), 2.03-1.99 (m, 3H), 0.91 (s, 9H), 0.11 (s, 6H).

Reference Example 6-64

3-[({(1-[5-(3-{[(tert-Butyldimethylsilyl)oxy]methyl}-2-fluorophenyl)pyrimidin-2-yl]azetidin-3-ylidene}amino)oxy]cyclobutyl acetate (Reference Compound 6-64)

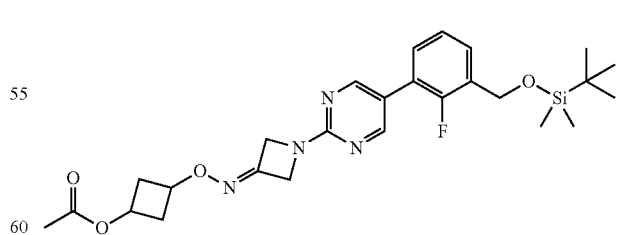

The reaction was performed by the method described in Reference Example 6-1, except that 1-(5-bromopyrimidin-2-yl)azetidin-3-one O-methyl oxime (Reference Compound 3-1) was replaced by 3-({[1-(5-bromopyrimidin-2-yl)azetidin-3-ylidene]amino}oxy)cyclobutyl acetate synthesized in the same manner as in Reference Example 29-4. Consequently, the title compound (including impurities) was obtained as a light yellow oil.

Mass spectrum (CI, m/z):515[M+1]+.

1H-NMR spectrum (400 MHz, DMSO-d6) δ:8.63 (d, J=1.3 Hz, 2H), 7.53-7.41 (m, 2H), 7.37-7.27 (m, 1H), 5.12-4.98 (m, 1H), 4.90-4.75 (m, 7H), 2.54-2.44 (m, 2H), 2.40-2.29 (m, 2H), 2.01 (s, 3H), 0.91 (s, 9H), 0.11 (s, 6H).

Reference Example 6-65

1-[5-(3-{[(tert-Butyldimethylsilyl)oxy]methyl}-2-fluorophenyl)pyrimidin-2-yl]azetidin-3-one O-benzyl oxime (Reference Compound 6-65)

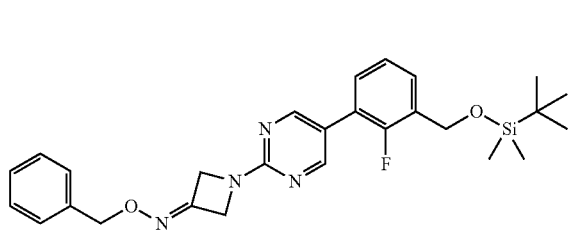 [SMILES: CC(C)(C)[Si](C)(C)OCc1cccc(-c2cnc(N3CC(=NOCc4ccccc4)C3)nc2)c1F]

The reaction was performed by the method described in Reference Example 6-1, except that 1-(5-bromopyrimidin-2-yl)azetidin-3-one O-methyl oxime (Reference Compound 3-1) was replaced by 1-(5-bromopyrimidin-2-yl)azetidin-3-one O-benzyl oxime synthesized in the same manner as in Reference Example 98. Consequently, the title compound (including impurities) was obtained as a white solid.

Mass spectrum (CI, m/z):493[M+1]+.

1H-NMR spectrum (400 MHz, DMSO-d6) δ:8.62 (d, J=1.4 Hz, 2H), 7.52-7.27 (m, 8H), 5.09 (s, 2H), 4.85-4.79 (m, 6H), 0.91 (s, 9H), 0.11 (s, 6H).

Reference Example 6-66

1-[5-(3-{[(tert-Butyldimethylsilyl)oxy]methyl}-2-fluorophenyl)pyrimidin-2-yl]azetidin-3-one O-(1-methylazetidin-3-yl) oxime (Reference Compound 6-66)

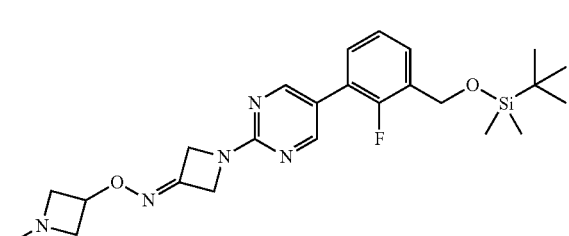

The reaction was performed by the method described in Reference Example 6-1, except that 1-(5-bromopyrimidin-2-yl)azetidin-3-one O-methyl oxime (Reference Compound 3-1) was replaced by 1-(5-bromopyrimidin-2-yl)azetidin-3-one O-(1-methylazetidin-3-yl) oxime synthesized in the same manner as in Reference Example 92-2. Consequently, the title compound (including impurities) was obtained as a brown oil.

Mass spectrum (ESI, m/z):472[M+1]+.

Reference Example 6-67

1-{3-[({1-[5-(3-{[(tert-Butyldimethylsilyl)oxy]methyl}-2-fluorophenyl)pyrimidin-2-yl]azetidin-3-ylidene}amino)oxy]azetidin-1-yl}ethanone (Reference Compound 6-67)

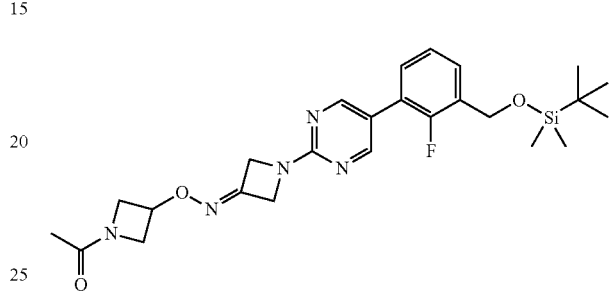

The reaction was performed by the method described in Reference Example 6-1, except that 1-(5-bromopyrimidin-2-yl)azetidin-3-one O-methyl oxime (Reference Compound 3-1) was replaced by 1-[3-({[1-(5-bromopyrimidin-2-yl)azetidin-3-ylidene]amino}oxy)azetidin-1-yl]ethanone synthesized in the same manner as in Reference Example 87-4. Consequently, the title compound (including impurities) was obtained as a brown oil.

Mass spectrum (ESI, m/z):500[M+1]+.

Reference Example 6-68

1-[5-(3-{[(tert-Butyldimethylsilyl)oxy]methyl}-2-fluorophenyl)pyrimidin-2-yl]azetidin-3-one O-(1-benzylazetidin-3-yl) oxime (Reference Compound 6-68)

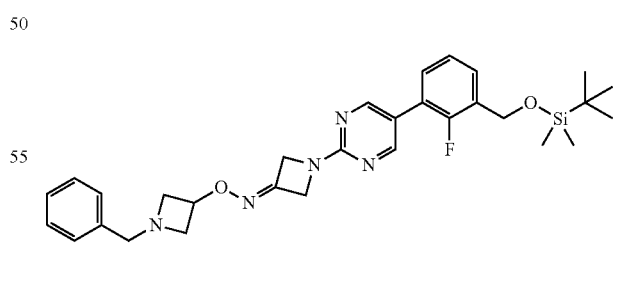

The reaction was performed by the method described in Reference Example 6-1, except that 1-(5-bromopyrimidin-2-yl)azetidin-3-one O-methyl oxime (Reference Compound 3-1) was replaced by 1-(5-bromopyrimidin-2-yl)azetidin-3-one O-(1-benzylazetidin-3-yl) oxime synthesized in the

Reference Example 6-69

1-[5-(3-{[(tert-Butyldimethylsilyl)oxy]methyl}-2-fluorophenyl)pyrimidin-2-yl]azetidin-3-one O-[1-(2,2,2-trifluoroethyl)azetidin-3-yl] oxime (Reference Compound 6-69)

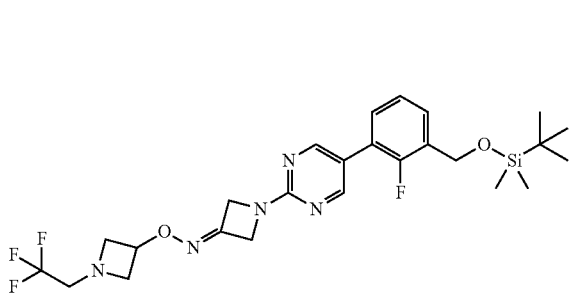 [SMILES: CC(C)(C)[Si](C)(C)OCc1cccc(-c2cnc(N3CC(=NOC4CN(CC(F)(F)F)C4)C3)nc2)c1F]

The reaction was performed by the method described in Reference Example 6-1, except that 1-(5-bromopyrimidin-2-yl)azetidin-3-one O-methyl oxime (Reference Compound 3-1) was replaced by 1-(5-bromopyrimidin-2-yl)azetidin-3-one O-[1-(2,2,2-trifluoroethyl)azetidin-3-yl] oxime synthesized in the same manner as in Reference Example 101-1. Consequently, the title compound (including impurities) was obtained as a colorless oil.

Mass spectrum (ESI, m/z):540[M+1]$^+$.

Reference Example 6-70

1-[5-(3-{[(tert-Butyldimethylsilyl)oxy]methyl}-2-fluorophenyl)pyrimidin-2-yl]azetidin-3-one O-[1-(methylsulfonyl)azetidin-3-yl] oxime (Reference Compound 6-70)

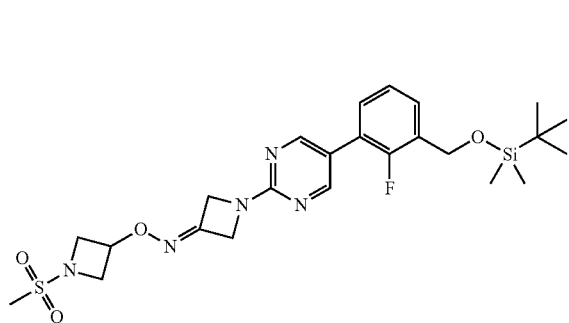 [SMILES: CC(C)(C)[Si](C)(C)OCc1cccc(-c2cnc(N3CC(=NOC4CN(S(C)(=O)=O)C4)C3)nc2)c1F]

The reaction was performed by the method described in Reference Example 6-1, except that 1-(5-bromopyrimidin-2-yl)azetidin-3-one O-methyl oxime (Reference Compound 3-1) was replaced by 1-(5-bromopyrimidin-2-yl)azetidin-3-one O-[1-(methylsulfonyl)azetidin-3-yl] oxime synthesized in the same manner as in Reference Example 102-1. Consequently, the title compound (including impurities) was obtained as a colorless oil.

same manner as in Reference Example 100-1. Consequently, the title compound (including impurities) was obtained as a light yellow oil.

Mass spectrum (ESI, m/z):548[M+1]$^+$.

Reference Example 6-71

1-[5-(3-{[(tert-Butyldimethylsilyl)oxy]methyl}-2-fluorophenyl)pyrimidin-2-yl]azetidin-3-one O-(1-ethylazetidin-3-yl) oxime (Reference Compound 6-71)

The reaction was performed by the method described in Reference Example 6-1, except that 1-(5-bromopyrimidin-2-yl)azetidin-3-one O-methyl oxime (Reference Compound 3-1) was replaced by 1-(5-bromopyrimidin-2-yl)azetidin-3-one O-(1-ethylazetidin-3-yl) oxime synthesized in the same manner as in Reference Example 100-2. Consequently, the title compound (including impurities) was obtained as a brown oil.

Mass spectrum (ESI, m/z):486[M+1]$^+$.

Reference Example 6-72

Methyl 3-[({1-[5-(3-{[(tert-butyldimethylsilyl)oxy]methyl}-2-fluorophenyl)pyrimidin-2-yl]azetidin-3-ylidene}amino)oxy]azetidin-1-carboxylate (Reference Compound 6-72)

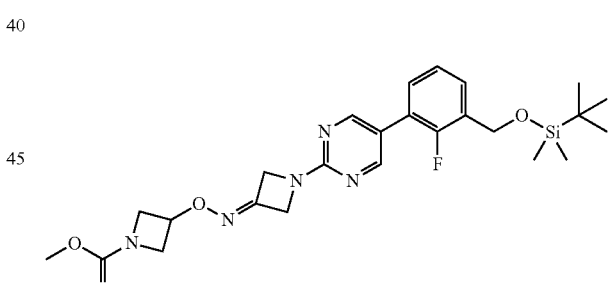

The reaction was performed by the method described in Reference Example 6-1, except that 1-(5-bromopyrimidin-2-yl)azetidin-3-one O-methyl oxime (Reference Compound 3-1) was replaced by methyl 3-({[1-(5-bromopyrimidin-2-yl)azetidin-3-ylidene]amino}oxy)azetidin-1-carboxylate synthesized in the same manner as in Reference Example 102-2. Consequently, the title compound (yield 81%) was obtained as a colorless oil.

Mass spectrum (ESI, m/z):516[M+1]$^+$.

$^1$H-NMR spectrum (400 MHz, DMSO-d$_6$) δ:8.63 (d, J=1.4 Hz, 2H), 7.50-7.45 (m, 2H), 7.36-7.24 (m, 1H), 5.02-4.91 (m, 1H), 4.89-4.83 (m, 4H), 4.81 (s, 2H), 4.27-4.08 (m, 2H), 4.01-3.79 (m, 2H), 3.57 (s, 3H), 0.91 (s, 9H), 0.11 (s, 6H).

Reference Example 6-73

1-[5-(3-{[(tert-Butyldimethylsilyl)oxy]methyl}-2-fluorophenyl)pyrimidin-2-yl]azetidin-3-one O-oxetan-3-yl oxime (Reference Compound 6-73)

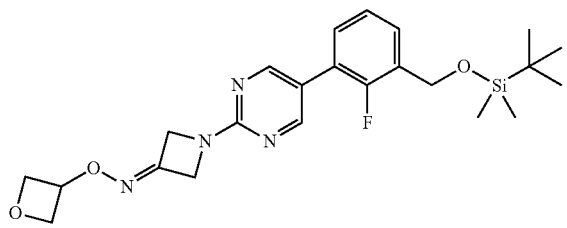 [SMILES: CC(C)(C)[Si](C)(C)OCc1cccc(-c2cnc(N3CC(=NOC4COC4)C3)nc2)c1F]

The reaction was performed by the method described in Reference Example 6-1, except that 1-(5-bromopyrimidin-2-yl)azetidin-3-one O-methyl oxime (Reference Compound 3-1) was replaced by 1-(5-bromopyrimidin-2-yl)azetidin-3-one O-oxetan-3-yl oxime synthesized in the same manner as in Reference Example 10-15. Consequently, the title compound (yield 51%) was obtained as a light yellow solid.

Mass spectrum (CI, m/z):459[M+1]$^+$.

$^1$H-NMR spectrum (400 MHz, DMSO-d$_6$) δ:8.64 (d, J=1.4 Hz, 2H), 7.53-7.43 (m, 2H), 7.35-7.28 (m, 1H), 5.26-5.17 (m, 1H), 4.90-4.84 (m, 4H), 4.81 (s, 2H), 4.79-4.74 (m, 2H), 4.59-4.53 (m, 2H), 0.91 (s, 9H), 0.11 (s, 6H).

Reference Example 6-74

2-{3-[({1-[5-(3-{[(tert-Butyldimethylsilyl)oxy]methyl}-2-fluorophenyl)pyrimidin-2-yl]azetidin-3-ylidene}amino)oxy]azetidin-1-yl}ethyl acetate (Reference Compound 6-74)

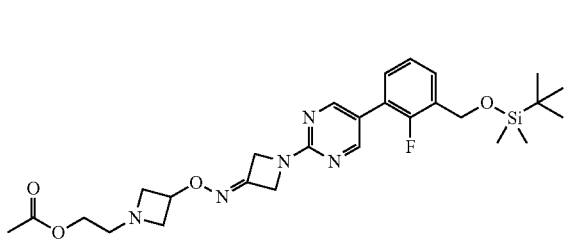 [SMILES: CC(=O)OCCN1CC(ON=C2CN(c3ncc(-c4cccc(CO[Si](C)(C)C(C)(C)C)c4F)cn3)C2)C1]

The reaction was performed by the method described in Reference Example 6-1, except that 1-(5-bromopyrimidin-2-yl)azetidin-3-one O-methyl oxime (Reference Compound 3-1) was replaced by 2-[3-({[1-(5-bromopyrimidin-2-yl)azetidin-3-ylidene]amino}oxy)azetidin-1-yl]ethyl acetate synthesized in the same manner as in Reference Example 29-5. Consequently, the title compound (including impurities) was obtained as a white solid.

Reference Example 6-75

1-[5-(3-{[(tert-Butyldimethylsilyl)oxy]methyl}-2-fluorophenyl)pyrimidin-2-yl]azetidin-3-one 0-[1-(2-methoxyethyl)azetidin-3-yl] oxime (Reference Compound 6-75)

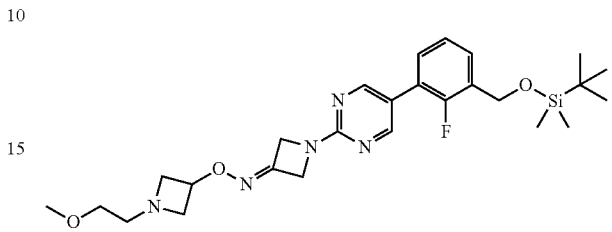

The reaction was performed by the method described in Reference Example 6-1, except that 1-(5-bromopyrimidin-2-yl)azetidin-3-one O-methyl oxime (Reference Compound 3-1) was replaced by 1-(5-bromopyrimidin-2-yl)azetidin-3-one O-[1-(2-methoxyethyl)azetidin-3-yl] oxime synthesized in the same manner as in Reference Example 101-2. Consequently, the title compound (including impurities) was obtained as a brown oil.

Mass spectrum (ESI, m/z):516[M+1]$^+$.

Reference Example 6-76

1-[5-(3-{[(tert-Butyldimethylsilyl)oxy]methyl}-2-fluorophenyl)pyrimidin-2-yl]azetidin-3-one 0-[1-(2-fluoroethyl)azetidin-3-yl] oxime (Reference Compound 6-76)

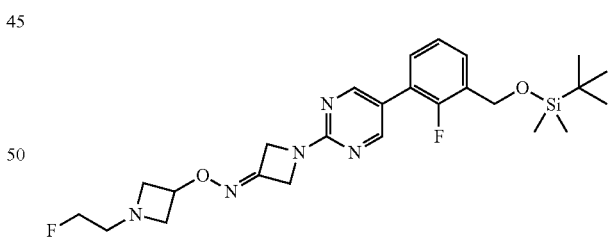

The reaction was performed by the method described in Reference Example 6-1, except that 1-(5-bromopyrimidin-2-yl)azetidin-3-one O-methyl oxime (Reference Compound 3-1) was replaced by 1-(5-bromopyrimidin-2-yl)azetidin-3-one O-[1-(2-fluoroethyl)azetidin-3-yl] oxime synthesized in the same manner as in Reference Example 101-3. Consequently, the title compound (including impurities) was obtained as a light yellow oil.

Reference Example 6-77

Ethyl 3-[({1-[5-(3-{[(tert-butyldimethylsilyl)oxy]methyl}-2-fluorophenyl)pyrimidin-2-yl]piperidin-4-ylidene}amino)oxy]propanoate (Reference Compound 6-77)

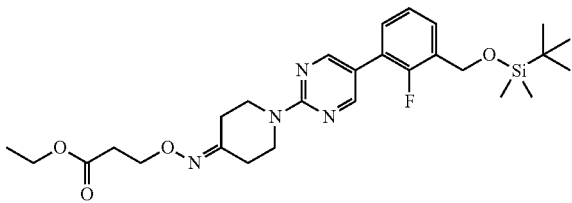 [SMILES: CCOC(=O)CCON=C1CCN(c2ncc(-c3cccc(CO[Si](C)(C)C(C)(C)C)c3F)cn2)CC1]

The reaction was performed by the method described in Reference Example 6-1, except that 1-(5-bromopyrimidin-2-yl)azetidin-3-one O-methyl oxime (Reference Compound 3-1) was replaced by ethyl 3-({[1-(5-bromopyrimidin-2-yl)piperidin-4-ylidene]amino}oxy)propanoate synthesized in the same manner as in Reference Example 104. Consequently, the title compound (including impurities) was obtained as a light yellow solid.

Mass spectrum (CI, m/z):531[M+1]$^+$.

$^1$H-NMR spectrum (400 MHz, DMSO-d$_6$) δ:8.59 (d, J=1.4 Hz, 2H), 7.51-7.41 (m, 2H), 7.33-7.27 (m, 1H), 4.81 (s, 2H), 4.20 (t, J=6.1 Hz, 2H), 4.07 (q, J=7.1 Hz, 2H), 3.96-3.86 (m, 4H), 2.65-2.61 (m, 2H), 2.56-2.51 (m, 2H), 2.41-2.35 (m, 2H), 1.18 (t, J=7.1 Hz, 4H), 0.91 (s, 9H), 0.11 (s, 6H).

Reference Example 6-78

3-[({1-[5-(3-{[(tert-Butyldimethylsilyl)oxy]methyl}-2-fluorophenyl)pyrimidin-2-yl]piperidin-4-ylidene}amino)oxy]propanamide (Reference Compound 6-78)

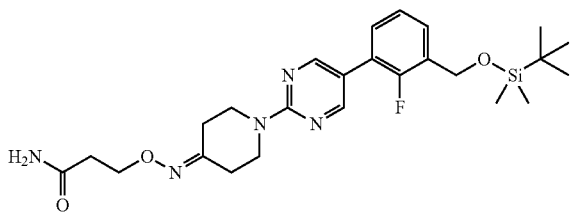 [SMILES: CC(C)(C)[Si](C)(C)OCc1cccc(-c2cnc(N3CCC(=NOCCC(N)=O)CC3)nc2)c1F]

The reaction was performed by the method described in Reference Example 6-1, except that 1-(5-bromopyrimidin-2-yl)azetidin-3-one O-methyl oxime (Reference Compound 3-1) was replaced by 3-({[1-(5-bromopyrimidin-2-yl)piperidin-4-ylidene]amino}oxy)propanamide synthesized in the same manner as in Reference Example 105-1. Consequently, the title compound (including impurities) was obtained as a white foam.

Mass spectrum (ESI, m/z):502[M+1]$^+$.

$^1$H-NMR spectrum (400 MHz, CDCl$_3$) δ:8.53 (d, J=1.4 Hz, 2H), 7.51-7.43 (m, 2H), 7.26-7.19 (m, 1H), 5.86 (br s, 1H), 5.31 (br s, 1H), 4.85 (s, 2H), 4.33 (t, J=5.9 Hz, 2H), 4.04-3.96 (m, 4H), 2.73-2.59 (m, 4H), 2.50-2.44 (m, 2H), 0.96 (s, 9H), 0.14 (s, 6H).

Reference Example 6-79

3-[({1-[5-(3-{[(tert-Butyldimethylsilyl)oxy]methyl}-2-fluorophenyl)pyrimidin-2-yl]piperidin-4-ylidene}amino)oxy]-N-methylpropanamide (Reference Compound 6-79)

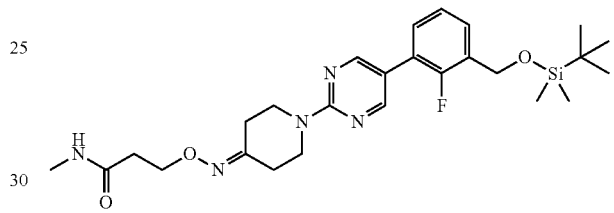

The reaction was performed by the method described in Reference Example 6-1, except that 1-(5-bromopyrimidin-2-yl)azetidin-3-one O-methyl oxime (Reference Compound 3-1) was replaced by 3-({[1-(5-bromopyrimidin-2-yl)piperidin-4-ylidene]amino}oxy)-N-methylpropanamide synthesized in the same manner as in Reference Example 105-2. Consequently, the title compound (yield 88%) was obtained as a gray solid.

Mass spectrum (CI, m/z):516[M+1]$^+$.

$^1$H-NMR spectrum (400 MHz, DMSO-d$_6$) δ:8.59 (d, J=1.4 Hz, 2H), 7.86-7.76 (m, 1H), 7.68-7.40 (m, 2H), 7.34-7.25 (m, 1H), 4.81 (s, 2H), 4.16 (t, J=6.5 Hz, 2H), 3.97-3.87 (m, 4H), 2.59-2.52 (m, 5H), 2.43-2.35 (m, 4H), 0.92 (s, 9H), 0.11 (s, 6H).

Reference Example 6-80

Ethyl 4-[({1-[5-(3-{[(tert-butyldimethylsilyl)oxy]methyl}-2-fluorophenyl)pyrimidin-2-yl]piperidin-4-ylidene}amino)oxy]butanoate (Reference Compound 6-80)

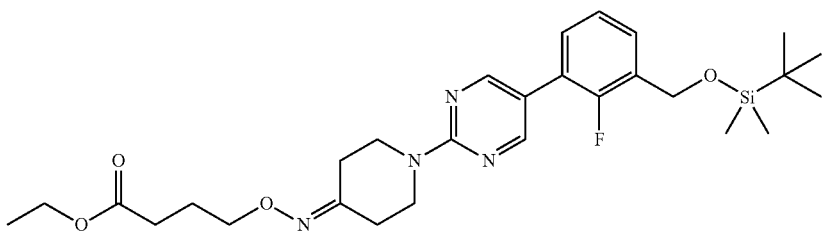 [SMILES: CCOC(=O)CCCON=C1CCN(c2ncc(-c3cccc(CO[Si](C)(C)C(C)(C)C)c3F)cn2)CC1]

The reaction was performed by the method described in Reference Example 6-1, except that 1-(5-bromopyrimidin-2-yl)azetidin-3-one O-methyl oxime (Reference Compound 3-1) was replaced by ethyl 4-(﹛[1-(5-bromopyrimidin-2-yl)piperidin-4-ylidene]amino﹜oxy)butanoate synthesized in the same manner as in Reference Example 67-11. Consequently, the title compound (including impurities) was obtained as a light yellow oil.

Reference Example 6-81

3-[(﹛1-[5-(3-﹛[(tert-Butyldimethylsilyl)oxy]methyl﹜-2-fluorophenyl)pyrimidin-2-yl]piperidin-4-ylidene﹜amino)oxy]-N,N-dimethylpropanamide (Reference Compound 6-81)

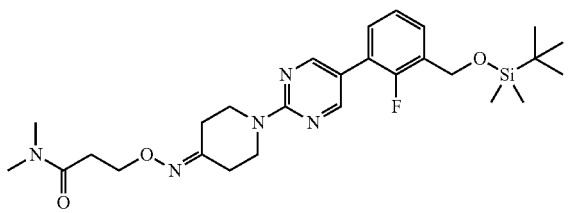 [SMILES: CN(C)C(=O)CCON=C1CCN(c2ncc(-c3cccc(CO[Si](C)(C)C(C)(C)C)c3F)cn2)CC1]

The reaction was performed by the method described in Reference Example 6-1, except that 1-(5-bromopyrimidin-2-yl)azetidin-3-one O-methyl oxime (Reference Compound 3-1) was replaced by 3-(﹛[1-(5-bromopyrimidin-2-yl)piperidin-4-ylidene]amino﹜oxy)-N,N-dimethylpropanamide synthesized in the same manner as in Reference Example 105-3. Consequently, the title compound (yield 95%) was obtained as a gray solid.

Mass spectrum (CI, m/z):530[M+1]$^+$.

$^1$H-NMR spectrum (400 MHz, DMSO-$d_6$) δ:8.59 (d, J=1.4 Hz, 2H), 7.51-7.41 (m, 2H), 7.34-7.26 (m, 1H), 4.81 (s, 2H), 4.19 (t, J=6.8 Hz, 2H), 3.96-3.89 (m, 4H), 2.96 (s, 3H), 2.81 (s, 3H), 2.68-2.62 (m, 2H), 2.57-2.53 (m, 2H), 2.41-2.36 (m, 2H), 0.91 (s, 9H), 0.11 (s, 6H).

Reference Example 6-82

2-﹛2-[(﹛1-[5-(3-﹛[(tert-Butyldimethylsilyl)oxy]methyl﹜-2-fluorophenyl)pyrimidin-2-yl]piperidin-4-ylidene﹜amino)oxy]ethyl﹜isoindoline-1,3-dione (Reference Compound 6-82)

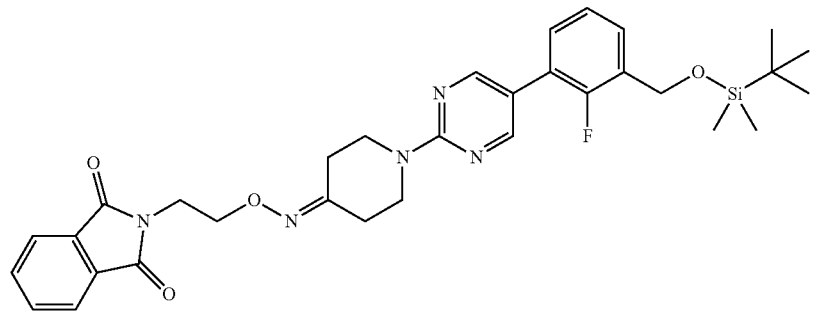 [SMILES: CC(C)(C)[Si](C)(C)OCc1cccc(-c2cnc(N3CCC(=NOCCN4C(=O)c5ccccc5C4=O)CC3)nc2)c1F]

The reaction was performed by the method described in Reference Example 6-1, except that 1-(5-bromopyrimidin-2-yl)azetidin-3-one O-methyl oxime (Reference Compound 3-1) was replaced by 2-[2-(﹛[1-(5-bromopyrimidin-2-yl)piperidin-4-ylidene]amino﹜oxy)ethyl]isoindoline-1,3-dione synthesized in the same manner as in Reference Example 85-3. Consequently, the title compound (yield 84%) was obtained as a dark brown oil.

Mass spectrum (CI, m/z):604[M+1]$^+$.

$^1$H-NMR spectrum (400 MHz, DMSO-$d_6$) δ:8.58 (d, J=1.4 Hz, 2H), 7.91-7.82 (m, 4H), 7.52-7.39 (m, 2H), 7.34-7.26 (m, 1H), 4.81 (s, 2H), 4.26-4.16 (m, 2H), 3.87-3.82 (m, 4H), 3.79-3.68 (m, 2H), 2.48-2.39 (m, 2H), 2.19-2.08 (m, 2H), 0.91 (s, 9H), 0.11 (s, 6H).

Reference Example 6-83

1-[5-(3-﹛[(tert-Butyldimethylsilyl)oxy]methyl﹜-2-fluorophenyl)pyrimidin-2-yl]piperidin-4-one O-[2-(dimethylamino)ethyl] oxime (Reference Compound 6-83)

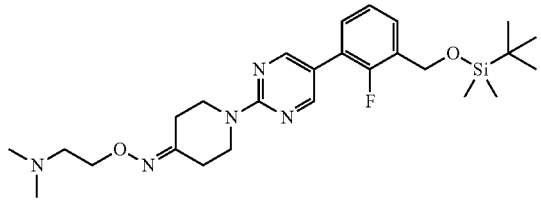 [SMILES: CN(C)CCON=C1CCN(c2ncc(-c3cccc(CO[Si](C)(C)C(C)(C)C)c3F)cn2)CC1]

The reaction was performed by the method described in Reference Example 6-1, except that 1-(5-bromopyrimidin-2-yl)azetidin-3-one O-methyl oxime (Reference Compound 3-1) was replaced by 1-﹛5-(3-﹛[(tert-butyldimethylsilyl)oxy]methyl﹜-2-fluorophenyl)pyrimidin-2-yl﹜azetidin-3-one O-[2-(dimethylamino)ethyl] oxime synthesized in the same manner as in Reference Example 110-1. Consequently, the title compound (yield 86%) was obtained as a white solid.

Mass spectrum (ESI, m/z):502[M+1]⁺.

Reference Example 6-84) tert-Butyl {2-[({1-[5-(3-{[(tert-butyldimethylsilyl)oxy]methyl}-2-fluorophenyl)pyrimidin-2-yl]piperidin-4-ylidene}amino)oxy]ethyl}(methyl)carbamate (Reference Compound 6-84)

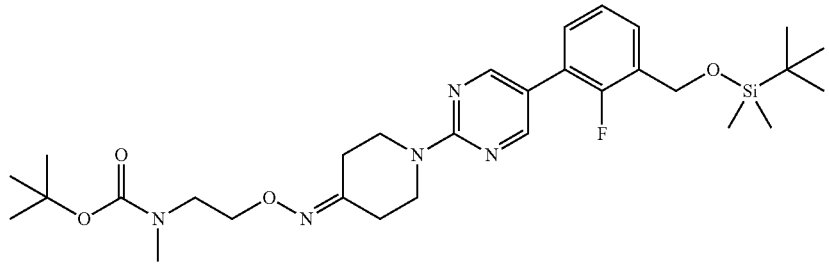 [SMILES: CN(CCON=C1CCN(c2ncc(-c3cccc(CO[Si](C)(C)C(C)(C)C)c3F)cn2)CC1)C(=O)OC(C)(C)C]

The reaction was performed by the method described in Reference Example 6-1, except that 1-(5-bromopyrimidin-2-yl)azetidin-3-one O-methyl oxime (Reference Compound 3-1) was replaced by tert-butyl [2-({[1-(5-bromopyrimidin-2-yl)piperidin-4-ylidene]amino}oxy)ethyl](methyl)carbamate synthesized in the same manner as in Reference Example 109-2. Consequently, the title compound (yield 84%) was obtained as a white foam.

Mass spectrum (ESI, m/z):588[M+1]⁺.
¹H-NMR (400 MHz, CDCl₃) δ:8.53 (d, J=1.4 Hz, 2H), 7.52-7.44 (m, 1H), 7.30-7.16 (m, 2H), 4.85 (s, 2H), 4.23-4.10 (m, 2H), 4.06-3.95 (m, 4H), 3.56-3.42 (m, 2H), 2.95-2.86 (m, 3H), 2.71-2.65 (m, 2H), 2.51-2.43 (m, 2H), 1.46 (s, 9H), 0.96 (s, 9H), 0.14 (s, 6H).

Reference Example 6-85

Di-tert-butyl {2-[({1-[5-(3-{[(tert-butyldimethylsilyl)oxy]methyl}-2-fluorophenyl)pyrimidin-2-yl]piperidin-4-ylidene}amino)oxy]ethyl}carbamate (Reference Compound 6-85)

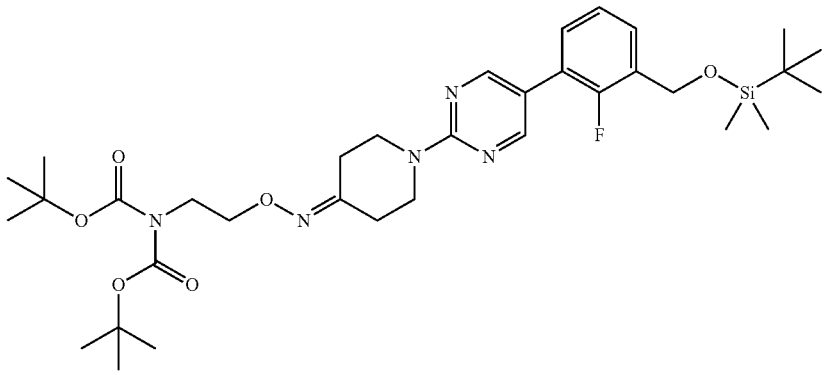 [SMILES: CC(C)(C)OC(=O)N(CCON=C1CCN(c2ncc(-c3cccc(CO[Si](C)(C)C(C)(C)C)c3F)cn2)CC1)C(=O)OC(C)(C)C]

The reaction was performed by the method described in Reference Example 6-1, except that 1-(5-bromopyrimidin-2-yl)azetidin-3-one O-methyl oxime (Reference Compound 3-1) was replaced by di-tert-butyl [2-({[1-(5-bromopyrimidin-2-yl)piperidin-4-ylidene]amino}oxy)ethyl]carbamate synthesized in the same manner as in Reference Example 111. Consequently, the title compound (yield 95%) was obtained as a colorless oil.

Reference Example 6-86

3-[({1-[5-(3-{[(tert-Butyldimethylsilyl)oxy]methyl}-2-fluorophenyl)pyrimidin-2-yl]piperidin-4-ylidene}amino)oxy]propanenitrile (Reference Compound 6-86)

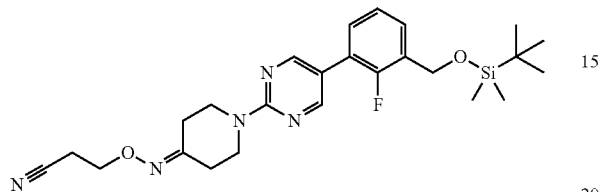

The reaction was performed by the method described in Reference Example 6-1, except that 1-(5-bromopyrimidin-2-yl)azetidin-3-one O-methyl oxime (Reference Compound 3-1) was replaced by 3-({[1-(5-bromopyrimidin-2-yl)piperidin-4-ylidene]amino}oxy)propanenitrile synthesized in the same manner as in Reference Example 112. Consequently, the title compound (yield 87%) was obtained as a light yellow oil.

Mass spectrum (CI, m/z):484[M+1]$^+$.

$^1$H-NMR spectrum (400 MHz, CDCl$_3$) δ:8.53 (d, J=1.5 Hz, 2H), 7.52-7.45 (m, 1H), 7.29-7.20 (m, 2H), 4.85 (s, 2H), 4.25 (t, J=6.3 Hz, 2H), 4.04-3.98 (m, 4H), 2.74 (t, J=6.3 Hz, 2H), 2.73-2.68 (m, 2H), 2.48-2.43 (m, 2H), 0.96 (s, 9H), 0.14 (s, 6H).

Reference Example 6-87

4-[({1-[5-(3-{[(tert-Butyldimethylsilyl)oxy]methyl}-2-fluorophenyl)pyrimidin-2-yl]piperidin-4-ylidene}amino)oxy]butanenitrile (Reference Compound 6-87)

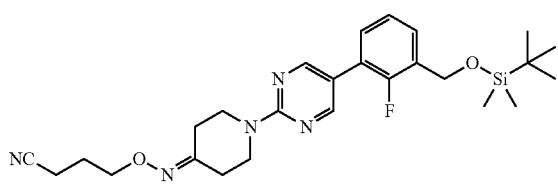 [SMILES: CC(C)(C)[Si](C)(C)OCc1cccc(-c2cnc(N3CCC(=NOCCCC#N)CC3)nc2)c1F]

The reaction was performed by the method described in Reference Example 6-1, except that 1-(5-bromopyrimidin-2-yl)azetidin-3-one O-methyl oxime (Reference Compound 3-1) was replaced by 4-({[1-(5-bromopyrimidin-2-yl)piperidin-4-ylidene]amino}oxy)butanenitrile synthesized in the same manner as in Reference Example 67-12. Consequently, the title compound (yield 72%) was obtained as a light yellow oil.

Mass spectrum (ESI, m/z):674[M+1]$^+$.

Mass spectrum (CI, m/z):498[M+1]$^+$.

$^1$H-NMR spectrum (400 MHz, DMSO-d$_6$) δ:8.59 (d, J=1.5 Hz, 2H), 7.52-7.41 (m, 2H), 7.34-7.25 (m, 1H), 4.81 (s, 2H), 4.04 (t, J=6.0 Hz, 2H), 3.96-3.89 (m, 4H), 2.63-2.53 (m, 4H), 2.42-2.36 (m, 2H), 1.93-1.86 (m, 2H), 0.91 (s, 9H), 0.11 (s, 6H).

Reference Example 6-88

1-[5-(3-{[(tert-Butyldimethylsilyl)oxy]methyl}-2-fluorophenyl)pyrimidin-2-yl]piperidin-4-one O-[2-(methylsulfonyl)ethyl] oxime (Reference Compound 6-88)

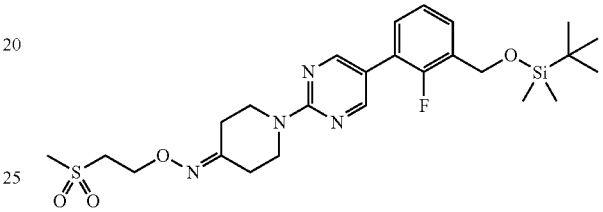

The reaction was performed by the method described in Reference Example 6-1, except that 1-(5-bromopyrimidin-2-yl)azetidin-3-one O-methyl oxime (Reference Compound 3-1) was replaced by 1-(5-bromopyrimidin-2-yl)piperidin-4-one O-[2-(methylsulfonyl)ethyl] oxime synthesized in the same manner as in Reference Example 113. Consequently, the title compound (including impurities) was obtained as a white solid.

Reference Example 6-89

1-[5-(3-{[(tert-Butyldimethylsilyl)oxy]methyl}-2-fluorophenyl)pyrimidin-2-yl]piperidin-4-one O-[3-(methylsulfonyl)propyl] oxime (Reference Compound 6-89)

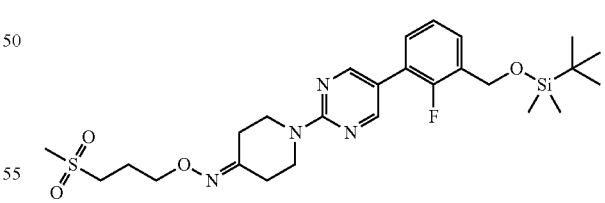

The reaction was performed by the method described in Reference Example 6-1, except that 1-(5-bromopyrimidin-2-yl)azetidin-3-one O-methyl oxime (Reference Compound 3-1) was replaced by 1-(5-bromopyrimidin-2-yl)piperidin-4-one O-[3-(methylsulfonyl)propyl] oxime synthesized in the same manner as in Reference Example 67-13. Consequently, the title compound (including impurities) was obtained as a white solid.

Reference Example 6-90

1-[5-(3-{[(tert-Butyldimethylsilyl)oxy]methyl}-2-fluorophenyl)pyrimidin-2-yl]piperidin-4-one O-[(1-methyl-1H-pyrazol-3-yl)methyl] oxime (Reference Compound 6-90)

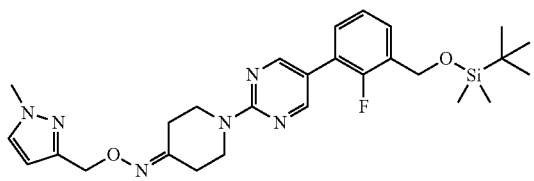 [SMILES: Cn1ccc(CON=C2CCN(c3ncc(-c4cccc(CO[Si](C)(C)C(C)(C)C)c4F)cn3)CC2)n1]

The reaction was performed by the method described in Reference Example 6-1, except that 1-(5-bromopyrimidin-2-yl)azetidin-3-one O-methyl oxime (Reference Compound 3-1) was replaced by 1-(5-bromopyrimidin-2-yl)piperidin-4-one O-[(1-methyl-1H-pyrazol-3-yl)methyl] oxime synthesized in the same manner as in Reference Example 67-14. Consequently, the title compound (yield 74%) was obtained as a light yellow oil.

Mass spectrum (CI, m/z):525[M+1]⁺.

¹H-NMR spectrum (400 MHz, CDCl₃) δ:8.52 (d, J=1.5 Hz, 2H), 7.51-7.44 (m, 1H), 7.32 (d, J=2.1 Hz, 1H), 7.29-7.18 (m, 2H), 6.30 (d, J=2.1 Hz, 1H), 5.09 (s, 2H), 4.85 (s, 2H), 4.03-3.93 (m, 4H), 3.90 (s, 3H), 2.74-2.67 (m, 2H), 2.51-2.45 (m, 2H), 0.96 (s, 9H), 0.13 (s, 6H).

Reference Example 6-91)

1-[5-(3-{[(tert-Butyldimethylsilyl)oxy]methyl}-2-fluorophenyl)pyrimidin-2-yl]piperidin-4-one O-{[1-(tetrahydropyran-2-yl)-1H-pyrazol-3-yl]methyl} oxime (Reference Compound 6-91)

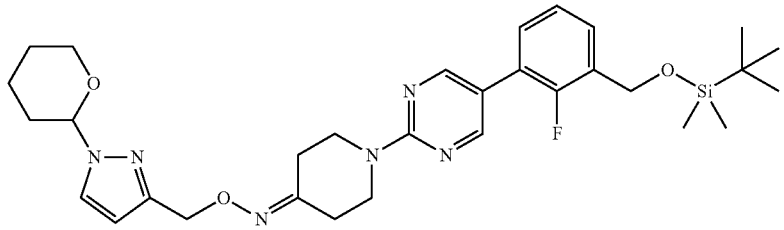 [SMILES: CC(C)(C)[Si](C)(C)OCc1cccc(-c2cnc(N3CCC(=NOCc4ccn(C5CCCCO5)n4)CC3)nc2)c1F]

The reaction was performed by the method described in Reference Example 6-1, except that 1-(5-bromopyrimidin-2-yl)azetidin-3-one O-methyl oxime (Reference Compound 3-1) was replaced by 1-(5-bromopyrimidin-2-yl)piperidin-4-one O-{[1-(tetrahydropyran-2-yl)-1H-pyrazol-3-yl]methyl} oxime synthesized in the same manner as in Reference Example 67-15. Consequently, the title compound (including impurities) was obtained as a colorless oil.

Mass spectrum (ESI, m/z):595[M+1]⁺.

¹H-NMR spectrum (400 MHz, CDCl₃) δ:8.52 (d, J=1.4 Hz, 2H), 7.57 (d, J=2.4 Hz, 1H), 7.50-7.44 (m, 1H), 7.27-7.16 (m, 2H), 6.36 (d, J=2.4 Hz, 1H), 5.36 (dd, J=2.7, 9.6 Hz, 1H), 5.12 (s, 2H), 4.85 (s, 2H), 4.11-4.04 (m, 1H), 4.02-3.93 (m, 4H), 3.77-3.59 (m, 1H), 2.72-2.67 (m, 2H), 2.50-2.45 (m, 2H), 2.20-1.96 (m, 3H), 1.76-1.52 (m, 3H), 0.96 (s, 9H), 0.13 (s, 6H).

Reference Example 6-92

1-[5-(3-{[(tert-Butyldimethylsilyl)oxy]methyl}-2-fluorophenyl)pyrimidin-2-yl]piperidin-4-one O-{[1-(tetrahydropyran-2-yl)-1H-pyrazol-4-yl]methyl} oxime (Reference Compound 6-92)

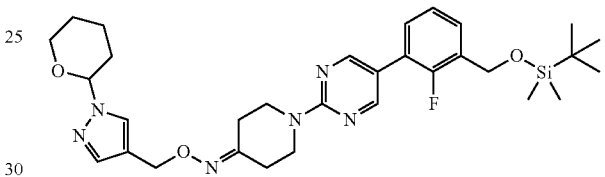

The reaction was performed by the method described in Reference Example 6-1, except that 1-(5-bromopyrimidin-2-yl)azetidin-3-one O-methyl oxime (Reference Compound 3-1) was replaced by 1-(5-bromopyrimidin-2-yl)piperidin-4-one O-{[1-(tetrahydropyran-2-yl)-1H-pyrazol-4-yl]methyl} oxime synthesized in the same manner as in Reference Example 67-16. Consequently, the title compound (yield 76%) was obtained as a light yellow oil.

Mass spectrum (CI, m/z):595[M+1]⁺.

¹H-NMR spectrum (400 MHz, DMSO-d₆) δ:8.58 (d, J=1.5 Hz, 2H), 7.90 (s, 1H), 7.53-7.40 (m, 3H), 7.34-7.26 (m, 1H), 5.36 (dd, J=2.3, 10.1 Hz, 1H), 4.89 (s, 2H), 4.80 (s, 2H), 3.98-3.86 (m, 5H), 3.68-3.56 (m, 1H), 2.59-2.52 (m, 2H), 2.43-2.36 (m, 2H), 2.11-1.46 (m, 6H), 0.91 (s, 9H), 0.11 (s, 6H).

Reference Example 6-93

1-[5-(3-{[(tert-Butyldimethylsilyl)oxy]methyl}-2-fluorophenyl)pyrimidin-2-yl]piperidin-4-one O-[(1-methyl-1H-pyrazol-4-yl)methyl] oxime (Reference Compound 6-93)

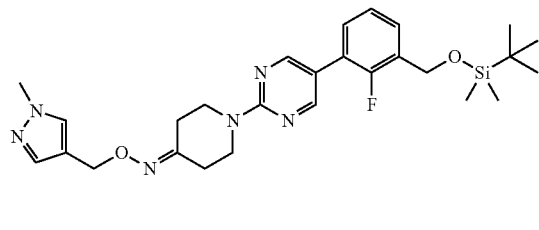 [SMILES: Cn1cc(CON=C2CCN(c3ncc(-c4cccc(CO[Si](C)(C)C(C)(C)C)c4F)cn3)CC2)cn1]

The reaction was performed by the method described in Reference Example 6-1, except that 1-(5-bromopyrimidin-2-yl)azetidin-3-one O-methyl oxime (Reference Compound 3-1) was replaced by 1-(5-bromopyrimidin-2-yl)piperidin-4-one O-[(1-methyl-1H-pyrazol-4-yl)methyl] oxime synthesized in the same manner as in Reference Example 116. Consequently, the title compound (yield 70%) was obtained as a light yellow oil.

Mass spectrum (CI, m/z):525[M+1]+.

$^1$H-NMR spectrum (400 MHz, DMSO-d$_6$) δ:8.58 (d, J=1.4 Hz, 2H), 7.70 (s, 1H), 7.50-7.41 (m, 3H), 7.33-7.26 (m, 1H), 4.87 (s, 2H), 4.81 (s, 2H), 3.95-3.87 (m, 4H), 3.81 (s, 3H), 2.56-2.52 (m, 2H), 2.42-2.36 (m, 2H), 0.91 (s, 9H), 0.11 (s, 6H).

Reference Example 6-94

1-[5-(3-{[(tert-Butyldimethylsilyl)oxy]methyl}-2-fluorophenyl)pyrimidin-2-yl]piperidin-4-one O-[2-(1H-pyrazol-1-yl)ethyl] oxime (Reference Compound 6-94)

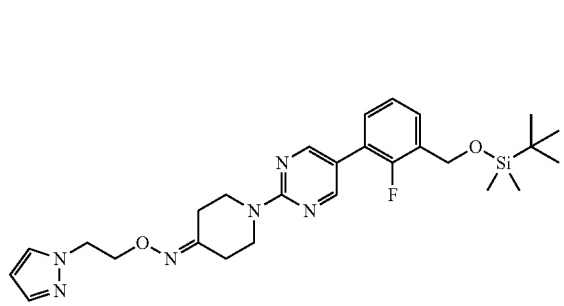 [SMILES: CC(C)(C)[Si](C)(C)OCc1cccc(-c2cnc(N3CCC(=NOCCn4cccn4)CC3)nc2)c1F]

The reaction was performed by the method described in Reference Example 6-1, except that 1-(5-bromopyrimidin-2-yl)azetidin-3-one O-methyl oxime (Reference Compound 3-1) was replaced by 1-(5-bromopyrimidin-2-yl)piperidin-4-one O-[2-(1H-pyrazol-1-yl)ethyl] oxime synthesized in the same manner as in Reference Example 110-3. Consequently, the title compound (including impurities) was obtained as a white solid.

Mass spectrum (ESI, m/z):525[M+1]+.

Reference Example 6-95

1-[5-(3-{[(tert-Butyldimethylsilyl)oxy]methyl}-2-fluorophenyl)pyrimidin-2-yl]piperidin-4-one O-pyridin-4-ylmethyl oxime (Reference Compound 6-95)

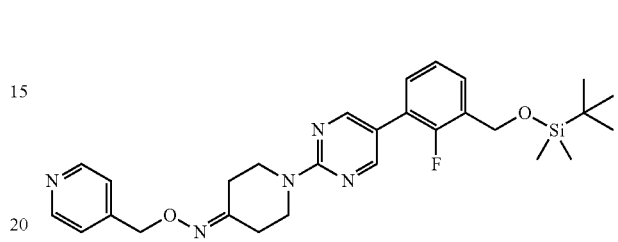

The reaction was performed by the method described in Reference Example 6-1, except that 1-(5-bromopyrimidin-2-yl)azetidin-3-one O-methyl oxime (Reference Compound 3-1) was replaced by 1-(5-bromopyrimidin-2-yl)piperidin-4-one O-pyridin-4-ylmethyl oxime synthesized in the same manner as in Reference Example 117. Consequently, the title compound (including impurities) was obtained as a light yellow solid.

Mass spectrum (CI, m/z):522[M+1]+.

$^1$H-NMR spectrum (400 MHz, CDCl$_3$) δ:8.61-8.56 (m, 2H), 8.53 (d, J=1.4 Hz, 2H), 7.58-7.43 (m, 1H), 7.32-7.18 (m, 4H), 5.11 (s, 2H), 4.85 (s, 2H), 4.07-3.96 (m, 4H), 2.81-2.73 (m, 2H), 2.50-2.42 (m, 2H), 0.96 (s, 9H), 0.14 (s, 6H).

Reference Example 6-96

1-{2-[({1-[5-(3-{[(tert-Butyldimethylsilyl)oxy]methyl}-2-fluorophenyl)pyrimidin-2-yl]piperidin-4-ylidene}amino)oxy]ethyl}pyrrolidine-2,5-dione (Reference Compound 6-96)

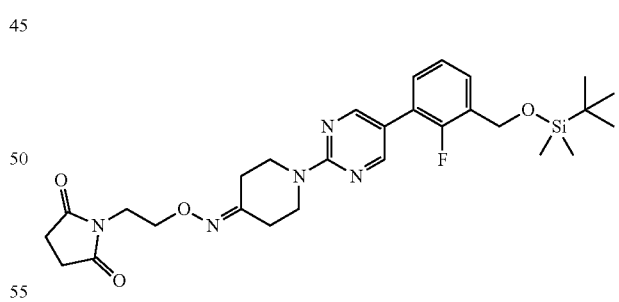

The reaction was performed by the method described in Reference Example 6-1, except that 1-(5-bromopyrimidin-2-yl)azetidin-3-one O-methyl oxime (Reference Compound 3-1) was replaced by 1-[2-({[1-(5-bromopyrimidin-2-yl)piperidin-4-ylidene)amino]oxy}ethyl)pyrrolidine-2,5-dione synthesized in the same manner as in Reference Example 118. Consequently, the title compound (yield 88%) was obtained as a light brown oil.

Mass spectrum (CI, m/z):556[M+1]+.

$^1$H-NMR spectrum (400 MHz, CDCl$_3$) δ:8.52 (d, J=1.4 Hz, 2H), 7.52-7.43 (m, 1H), 7.32-7.16 (m, 2H), 4.85 (s, 2H), 4.25-4.16 (m, 2H), 4.04-3.95 (m, 4H), 3.86-3.77 (m, 2H), 2.71 (s, 4H), 2.64-2.55 (m, 2H), 2.46-2.41 (m, 2H), 0.96 (s, 9H), 0.14 (s, 6H).

Reference Example 6-97

1-{2-[({1-[5-(3-{[(tert-Butyldimethylsilyl)oxy]methyl}-2-fluorophenyl)pyrimidin-2-yl]piperidin-4-ylidene}amino)oxy]ethyl}pyrrolidin-2-one (Reference Compound 6-97)

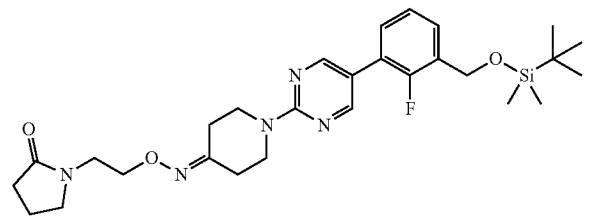 [SMILES: CC(C)(C)[Si](C)(C)OCc1cccc(-c2cnc(N3CCC(=NOCCN4CCCC4=O)CC3)nc2)c1F]

The reaction was performed by the method described in Reference Example 6-1, except that 1-(5-bromopyrimidin-2-yl)azetidin-3-one O-methyl oxime (Reference Compound 3-1) was replaced by 1-[2-({[1-(5-bromopyrimidin-2-yl)piperidin-4-ylidene]amino}oxy)ethyl]pyrrolidin-2-on e synthesized in the same manner as in Reference Example 119-1. Consequently, the title compound (including impurities) was obtained as a colorless oil.

Mass spectrum (CI, m/z):542[M+1]$^+$.

$^1$H-NMR spectrum (400 MHz, DMSO-d$_6$) δ:8.59 (d, J=1.4 Hz, 2H), 7.51-7.42 (m, 2H), 7.33-7.27 (m, 1H), 4.81 (s, 2H), 4.09-4.04 (m, 2H), 3.97-3.86 (m, 4H), 3.44-3.36 (m, 4H), 2.59-2.53 (m, 2H), 2.42-2.35 (m, 2H), 2.24-2.13 (m, 2H), 1.98-1.84 (m, 2H), 0.91 (s, 9H), 0.11 (s, 6H).

Reference Example 6-98

3-{2-[({1-[5-(3-{[(tert-Butyldimethylsilyl)oxy]methyl}-2-fluorophenyl)pyrimidin-2-yl]piperidin-4-ylidene}amino)oxy]ethyl}oxazolidin-2-one (Reference Compound 6-98)

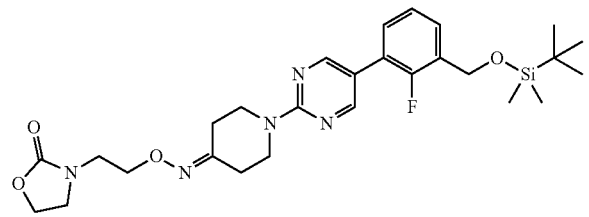 [SMILES: CC(C)(C)[Si](C)(C)OCc1cccc(-c2cnc(N3CCC(=NOCCN4CCOC4=O)CC3)nc2)c1F]

The reaction was performed by the method described in Reference Example 6-1, except that 1-(5-bromopyrimidin-2-yl)azetidin-3-one O-methyl oxime (Reference Compound 3-1) was replaced by 3-[2-({[1-(5-bromopyrimidin-2-yl)piperidin-4-ylidene]amino}oxy)ethyl]oxazolidin-2-one synthesized in the same manner as in Reference Example 119-2. Consequently, the title compound (including impurities) was obtained as a colorless oil.

Mass spectrum (CI, m/z):544[M+1]$^+$.

$^1$H-NMR spectrum (400 MHz, DMSO-d$_6$) δ:8.59 (d, J=1.5 Hz, 2H), 7.51-7.42 (m, 2H), 7.34-7.26 (m, 1H), 4.81 (s, 2H), 4.28-4.21 (m, 2H), 4.15-4.08 (m, 2H), 3.96-3.88 (m, 4H), 3.64-3.54 (m, 2H), 3.44-3.38 (m, 2H), 2.60-2.52 (m, 2H), 2.43-2.35 (m, 2H), 0.91 (s, 9H), 0.11 (s, 6H).

Reference Example 6-99

4-{2-[({1-[5-(3-{[(tert-Butyldimethylsilyl)oxy]methyl}-2-fluorophenyl)pyrimidin-2-yl]piperidin-4-ylidene}amino)oxy]ethyl}morpholin-3-one (Reference Compound 6-99)

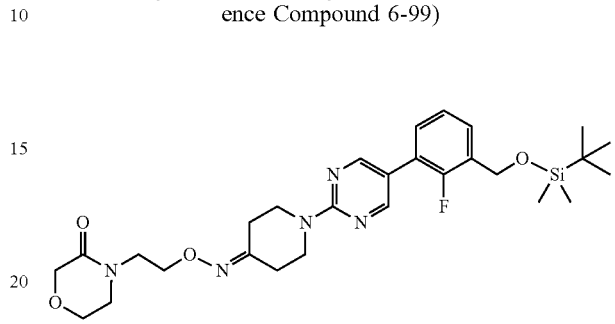

The reaction was performed by the method described in Reference Example 6-1, except that 1-(5-bromopyrimidin-2-yl)azetidin-3-one O-methyl oxime (Reference Compound 3-1) was replaced by 4-[2-({[1-(5-bromopyrimidin-2-yl)piperidin-4-ylidene]amino}oxy)ethyl]morpholin-3-one synthesized in the same manner as in Reference Example 119-3. Consequently, the title compound (including impurities) was obtained as a colorless oil.

Mass spectrum (CI, m/z):558[M+1]$^+$.

$^1$H-NMR spectrum (400 MHz, DMSO-d$_6$) δ:8.59 (d, J=1.5 Hz, 2H), 7.51-7.41 (m, 2H), 7.35-7.25 (m, 1H), 4.81 (s, 2H), 4.15-4.09 (m, 2H), 4.02 (s, 2H), 3.95-3.89 (m, 4H), 3.85-3.78 (m, 2H), 3.59-3.53 (m, 2H), 3.42-3.36 (m, 2H), 2.60-2.52 (m, 2H), 2.42-2.34 (m, 2H), 1.99 (s, 1H), 0.91 (s, 9H), 0.11 (s, 6H).

Reference Example 7-1

1-[5-(2-Fluoro-3-hydroxymethylphenyl)pyrimidin-2-yl]azetidin-3-one O-methyl oxime (Reference Compound 7-1)

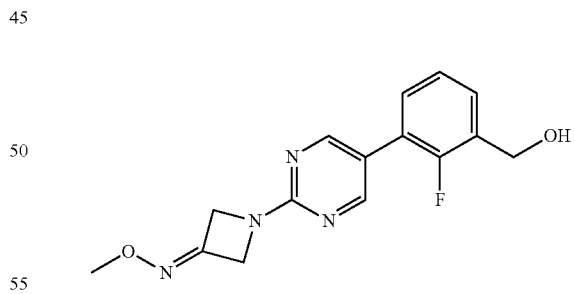

1 M tetrabutylammonium fluoride/THF solution 8.0 mL (8.0 mmol) was added to a THF (30 mL) solution of 1-[5-(3-{[(tert-butyldimethylsilyl)oxy]methyl}-2-fluorophenyl)pyrimidin-2-yl]azetidin-3-one O-methyl oxime 2.75 g (6.60 mmol) synthesized in the same manner as in Reference Example 6-1, and the mixture was stirred at room temperature for 1 hour. After the completion of the reaction, water was added to the reaction mixture, and followed by extraction with ethyl acetate. The organic layer was washed with water, dried over anhydrous magnesium sulfate, and filtered. The filtrate was concentrated under reduced pressure. TBME was added to the concentrated residue, and the mixture was stirred at room temperature. Thereafter, the solid was collected by filtration and was dried under reduced pressure to give the title compound 1.78 g (5.89 mmol, yield 89%) as a gray solid.

Mass spectrum (CI, m/z):303[M+1]$^+$.

$^1$H-NMR spectrum (400 MHz, DMSO-d$_6$) δ:8.62 (d, J=1.5 Hz, 2H), 7.53-7.41 (m, 2H), 7.32-7.26 (m, 1H), 5.33 (t, J=5.6 Hz, 1H), 4.84-4.77 (m, 4H), 4.60 (d, J=5.6 Hz, 2H), 3.83 (s, 3H).

Reference Example 7-2

1-{5-[2-Fluoro-3-(hydroxymethyl)phenyl]pyrimidin-2-yl}azetidin-3-one O-ethyl oxime (Reference Compound 7-2)

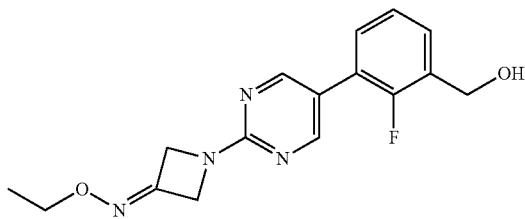 [SMILES: CCON=C1CN(c2ncc(-c3cccc(CO)c3F)cn2)C1]

1 M tetrabutylammonium fluoride/THF solution 0.38 mL (0.38 mmol) was added to a THF (2.6 mL) solution of 1-[5-(3-{[(tert-butyldimethylsilyl)oxy]methyl}-2-fluorophenyl)pyrimidin-2-yl]azetidin-3-one O-ethyl oxime 130 mg (0.302 mmol) synthesized in the same manner as in Reference Example 6-2, and the mixture was stirred at room temperature for 1.5 hours. After the completion of the reaction, the reaction mixture was concentrated under reduced pressure. The concentrated residue was purified by silica gel column chromatography (eluting solvent: 1,2-dichloroethane:methanol) to give the title compound 83.6 mg (0.264 mmol, yield 87%) as a light yellow solid.

Mass spectrum (DUIS, m/z):317[M+1]$^+$.

$^1$H-NMR spectrum (400 MHz, DMSO-d$_6$) δ:8.62 (d, J=1.4 Hz, 2H), 7.54-7.41 (m, 2H), 7.32-7.26 (m, 1H), 5.34 (t, J=5.7 Hz, 1H), 4.85-4.76 (m, 4H), 4.60 (d, J=5.7 Hz, 2H), 4.08 (q, J=7.0 Hz, 2H), 1.22 (t, J=7.0 Hz, 3H).

Reference Example 7-3

1-{5-[2-Fluoro-3-(hydroxymethyl)phenyl]pyrimidin-2-yl}azetidin-3-one O-methyl-d$_3$ oxime (Reference Compound 7-3)

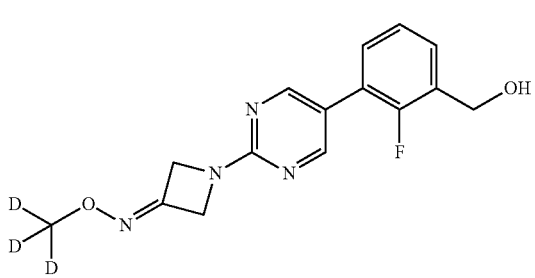 [SMILES: [2H]C([2H])([2H])ON=C1CN(c2ncc(-c3cccc(CO)c3F)cn2)C1]

The reaction was performed by the method described in Reference Example 7-2, except that 1-[5-(3-{[(tert-butyldimethylsilyl)oxy]methyl}-2-fluorophenyl)pyrimidin-2-yl]azetidin-3-one O-ethyl oxime (Reference Compound 6-2) was replaced by 1-[5-(3-{[(tert-butyldimethylsilyl)oxy]methyl}-2-fluorophenyl)pyrimidin-2-yl]azetidin-3-one O-methyl-d$_3$ oxime synthesized in the same manner as in Reference Example 6-3. Consequently, the title compound (yield 83%) was obtained as a white solid.

Mass spectrum (CI, m/z):306[M+1]$^+$.

$^1$H-NMR spectrum (400 MHz, DMSO-d$_6$) δ:8.62 (d, J=1.4 Hz, 2H), 7.54-7.40 (m, 2H), 7.34-7.25 (m, 1H), 5.34 (br s, 1H), 4.86-4.76 (m, 4H), 4.60 (br s, 2H).

Reference Example 7-4

1-{5-[2-Fluoro-3-(hydroxymethyl)phenyl]pyrimidin-2-yl}azetidin-3-one O-(2-fluoroethyl) oxime (Reference Compound 7-4)

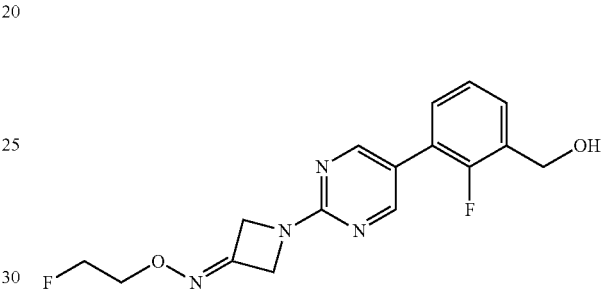

The reaction was performed by the method described in Reference Example 7-2, except that 1-[5-(3-{[(tert-butyldimethylsilyl)oxy]methyl}-2-fluorophenyl)pyrimidin-2-yl]azetidin-3-one O-ethyl oxime (Reference Compound 6-2) was replaced by 1-[5-(3-{[(tert-butyldimethylsilyl)oxy]methyl}-2-fluorophenyl)pyrimidin-2-yl]azetidin-3-one O-(2-fluoroethyl) oxime synthesized in the same manner as in Reference Example 6-4. Consequently, the title compound (including impurities) was obtained as a light yellow solid.

Mass spectrum (CI, m/z):335[M+1]$^+$.

$^1$H-NMR spectrum (400 MHz, CDCl$_3$)δ:8.57 (d, J=1.0 Hz, 2H), 7.51-7.41 (m, 1H), 7.35-7.20 (m, 2H), 4.94-4.88 (m, 4H), 4.84 (d, J=6.1 Hz, 2H), 4.74-4.58 (m, 2H), 4.39-4.28 (m, 2H), 1.85 (t, J=6.1 Hz, 1H).

Reference Example 7-5

1-{5-[2-Fluoro-3-(hydroxymethyl)phenyl]pyrimidin-2-yl}azetidin-3-one O-(2,2-difluoroethyl) oxime (Reference Compound 7-5)

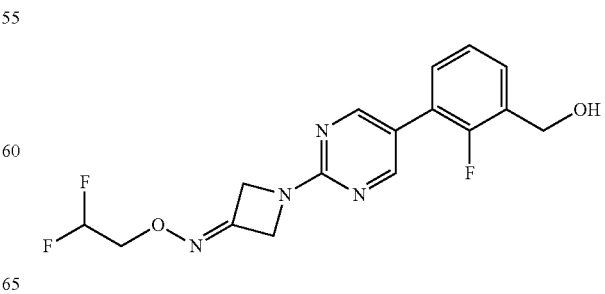

The reaction was performed by the method described in Reference Example 7-2, except that 1-[5-(3-{[(tert-butyldimethylsilyl)oxy]methyl}-2-fluorophenyl)pyrimidin-2-yl]azetidin-3-one O-ethyl oxime (Reference Compound 6-2) was replaced by 1-[5-(3-{[(tert-butyldimethylsilyl)oxy]methyl}-2-fluorophenyl)pyrimidin-2-yl]azetidin-3-one O-(2,2-difluoroethyl) oxime synthesized in the same manner as in Reference Example 15-1. Consequently, the title compound (yield 83%) was obtained as a white solid.

Mass spectrum (ESI, m/z):353[M+1]$^+$.

$^1$H-NMR spectrum (400 MHz, DMSO-d$_6$) δ:8.64 (d, J=1.4 Hz, 2H), 7.53-7.41 (m, 2H), 7.33-7.26 (m, 1H), 6.25 (tt, J=3.8, 54.8 Hz, 1H), 5.34 (t, J=5.2 Hz, 1H), 4.90-4.80 (m, 4H), 4.60 (d, J=5.2 Hz, 2H), 4.31 (dt, J=3.8, 14.7 Hz, 2H).

Reference Example 7-6

1-{5-[2-Fluoro-3-(hydroxymethyl)phenyl]pyrimidin-2-yl}azetidin-3-one O-(2,2,2-trifluoroethyl) oxime (Reference Compound 7-6)

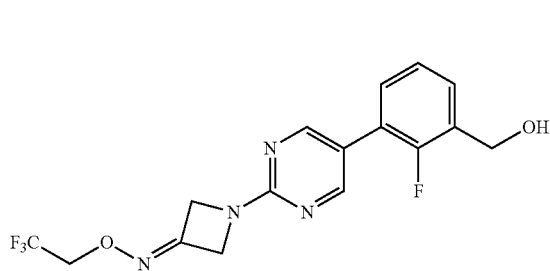 [SMILES: OCc1cccc(-c2cnc(N3CC(=NOCC(F)(F)F)C3)nc2)c1F]

The reaction was performed by the method described in Reference Example 7-2, except that 1-[5-(3-{[(tert-butyldimethylsilyl)oxy]methyl}-2-fluorophenyl)pyrimidin-2-yl]azetidin-3-one O-ethyl oxime (Reference Compound 6-2) was replaced by 1-[5-(3-{[(tert-butyldimethylsilyl)oxy]methyl}-2-fluorophenyl)pyrimidin-2-yl]azetidin-3-one O-(2,2,2-trifluoroethyl) oxime synthesized in the same manner as in Reference Example 15-2. Consequently, the title compound (yield 90%) was obtained as a white solid.

Mass spectrum (CI, m/z):371[M+1]$^+$.

$^1$H-NMR spectrum (400 MHz, CDCl$_3$) δ:8.58 (d, J=1.4 Hz, 2H), 7.49-7.42 (m, 1H), 7.34-7.22 (m, 2H), 4.94-4.89 (m, 4H), 4.84 (d, J=6.1 Hz, 2H), 4.45 (q, J=8.5 Hz, 2H), 1.85 (t, J=6.1 Hz, 1H).

Reference Example 7-7

1-{5-[2-Fluoro-3-(hydroxymethyl)phenyl]pyrimidin-2-yl}azetidin-3-one O-(3-fluoropropyl) oxime (Reference Compound 7-7)

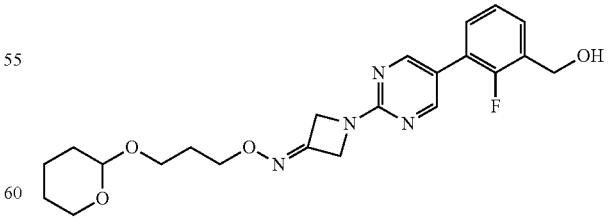

The reaction was performed by the method described in Reference Example 7-2, except that 1-[5-(3-{[(tert-butyldimethylsilyl)oxy]methyl}-2-fluorophenyl)pyrimidin-2-yl]azetidin-3-one O-ethyl oxime (Reference Compound 6-2) was replaced by 1-[5-(3-{[(tert-butyldimethylsilyl)oxy]methyl}-2-fluorophenyl)pyrimidin-2-yl]azetidin-3-one O-(3-fluoropropyl) oxime synthesized in the same manner as in Reference Example 6-6. Consequently, the title compound (yield 80%) was obtained as a white solid.

Mass spectrum (CI, m/z):349[M+1]$^+$.

$^1$H-NMR spectrum (400 MHz, DMSO-d$_6$) δ:8.63 (d, J=1.4 Hz, 2H), 7.53-7.40 (m, 2H), 7.33-7.25 (m, 1H), 5.34 (t, J=5.7 Hz, 1H), 4.85-4.79 (m, 4H), 4.64-4.44 (m, 4H), 4.13 (t, J=6.3 Hz, 2H), 2.10-1.92 (m, 2H).

Reference Example 7-8

1-{5-[2-Fluoro-3-(hydroxymethyl)phenyl]pyrimidin-2-yl}azetidin-3-one O-{2-[(tetrahydropyran-2-yl)oxy]ethyl} oxime (Reference Compound 7-8)

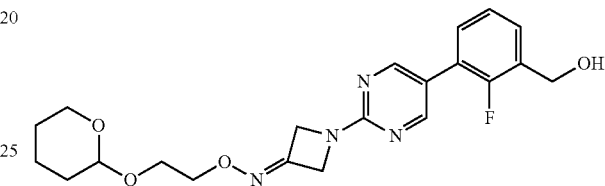

The reaction was performed by the method described in Reference Example 7-2, except that 1-[5-(3-{[(tert-butyldimethylsilyl)oxy]methyl}-2-fluorophenyl)pyrimidin-2-yl]azetidin-3-one O-ethyl oxime (Reference Compound 6-2) was replaced by 1-[5-(3-{[(tert-butyldimethylsilyl)oxy]methyl}-2-fluorophenyl)pyrimidin-2-yl]azetidin-3-one O-{2-[(tetrahydropyran-2-yl)oxy]ethyl} oxime synthesized in the same manner as in Reference Example 6-7. Consequently, the title compound (yield 80%) was obtained as a white solid.

Mass spectrum (CI, m/z):417[M+1]$^+$.

$^1$H-NMR spectrum (400 MHz, DMSO-d$_6$) δ:8.63 (d, J=1.5 Hz, 2H), 7.54-7.40 (m, 2H), 7.34-7.24 (m, 1H), 5.36 (br s, 1H), 4.92-4.74 (m, 4H), 4.66-4.52 (m, 3H), 4.26-4.08 (m, 2H), 3.88-3.70 (m, 2H), 3.69-3.56 (m, 1H), 3.49-3.38 (m, 1H), 1.84-1.35 (m, 6H).

Reference Example 7-9

1-{5-[2-Fluoro-3-(hydroxymethyl)phenyl]pyrimidin-2-yl}azetidin-3-one O-{3-[(tetrahydropyran-2-yl)oxy]propyl} oxime (Reference Compound 7-9)

The reaction was performed by the method described in Reference Example 7-2, except that 1-[5-(3-{[(tert-butyldimethylsilyl)oxy]methyl}-2-fluorophenyl)pyrimidin-2-yl]azetidin-3-one O-ethyl oxime (Reference Compound 6-2) was replaced by 1-[5-(3-{[(tert-butyldimethylsilyl)oxy]

methyl}-2-fluorophenyl)pyrimidin-2-yl]azetidin-3-one O-{3-[(tetrahydropyran-2-yl)oxy]propyl} oxime synthesized in the same manner as in Reference Example 6-8. Consequently, the title compound (yield 97%) was obtained as a white solid.

Mass spectrum (CI, m/z):431[M+1]⁺.

1H-NMR spectrum (400 MHz, DMSO-$d_6$) δ:8.63 (d, J=1.4 Hz, 2H), 7.53-7.41 (m, 2H), 7.32-7.26 (m, 1H), 5.34 (t, J=5.5 Hz, 1H), 4.85-4.77 (m, 4H), 4.60 (d, J=5.5 Hz, 2H), 4.58-4.55 (m, 1H), 4.11 (t, J=6.5 Hz, 2H), 3.78-3.64 (m, 2H), 3.49-3.39 (m, 2H), 1.87 (quin, J=6.5 Hz, 2H), 1.78-1.39 (m, 6H).

Reference Example 7-10

1-{5-[2-Fluoro-3-(hydroxymethyl)phenyl]pyrimidin-2-yl}azetidin-3-one O-{4-[(tetrahydropyran-2-yl)oxy]butyl} oxime (Reference Compound 7-10)

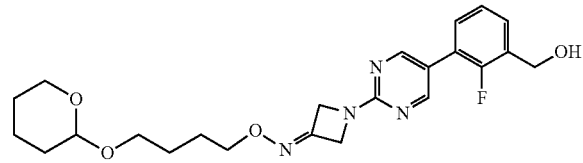 [SMILES: OCc1cccc(-c2cnc(N3CC(=NOCCCCOC4CCCCO4)C3)nc2)c1F]

The reaction was performed by the method described in Reference Example 7-2, except that 1-[5-(3-{[(tert-butyldimethylsilyl)oxy]methyl}-2-fluorophenyl)pyrimidin-2-yl]azetidin-3-one O-ethyl oxime (Reference Compound 6-2) was replaced by 1-[5-(3-{[(tert-butyldimethylsilyl)oxy]methyl}-2-fluorophenyl)pyrimidin-2-yl]azetidin-3-one O-{4-[(tetrahydropyran-2-yl)oxy]butyl} oxime synthesized in the same manner as in Reference Example 6-9. Consequently, the title compound (yield 88%) was obtained as a white solid.

Mass spectrum (CI, m/z):445[M+1]⁺.

¹H-NMR spectrum (400 MHz, CDCl₃) δ:8.57 (d, J=1.4 Hz, 2H), 7.48-7.41 (m, 1H), 7.35-7.21 (m, 2H), 4.91-4.86 (m, 4H), 4.84 (d, J=6.1 Hz, 2H), 4.61-4.58 (m, 1H), 4.16-4.11 (m, 2H), 3.91-3.83 (m, 1H), 3.83-3.74 (m, 1H), 3.55-3.47 (m, 1H), 3.47-3.39 (m, 1H), 1.88-1.47 (m, 10H).

Reference Example 7-11

1-{5-[2-Fluoro-3-(hydroxymethyl)phenyl]pyrimidin-2-yl}azetidin-3-one O-(2-methoxyethyl) oxime (Reference Compound 7-11)

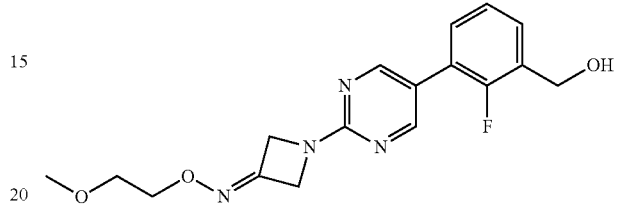

The reaction was performed by the method described in Reference Example 7-2, except that 1-[5-(3-{[(tert-butyldimethylsilyl)oxy]methyl}-2-fluorophenyl)pyrimidin-2-yl]azetidin-3-one O-ethyl oxime (Reference Compound 6-2) was replaced by 1-[5-(3-{[(tert-butyldimethylsilyl)oxy]methyl}-2-fluorophenyl)pyrimidin-2-yl]azetidin-3-one O-(2-methoxyethyl) oxime synthesized in the same manner as in Reference Example 6-10. Consequently, the title compound (yield 75%) was obtained as a white solid.

¹H-NMR spectrum (400 MHz, DMSO-$d_6$) δ:8.63 (d, J=1.5 Hz, 2H), 7.52-7.41 (m, 2H), 7.32-7.26 (m, 1H), 5.34 (t, J=5.1 Hz, 1H), 4.87-4.77 (m, 4H), 4.60 (d, J=5.1 Hz, 2H), 4.19-4.12 (m, 2H), 3.59-3.53 (m, 2H), 3.27 (s, 3H).

Reference Example 7-12

1-{5-[2-Fluoro-3-(hydroxymethyl)phenyl]pyrimidin-2-yl}azetidin-3-one O-(2-{2-[(tetrahydropyran-2-yl)oxy]ethoxy}ethyl) oxime (Reference Compound 7-12)

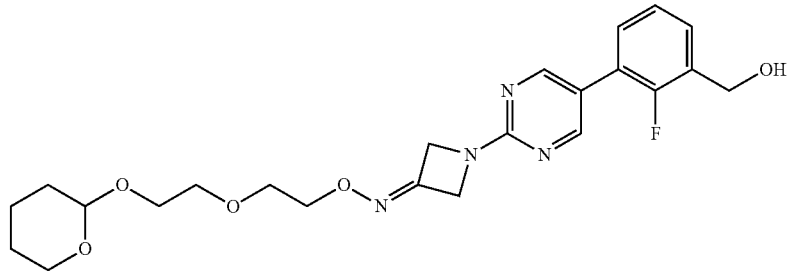 [SMILES: OCc1cccc(-c2cnc(N3CC(=NOCCOCCOC4CCCCO4)C3)nc2)c1F]

The reaction was performed by the method described in Reference Example 7-2, except that 1-[5-(3-{[(tert-butyldimethylsilyl)oxy]methyl}-2-fluorophenyl)pyrimidin-2-yl]azetidin-3-one O-ethyl oxime (Reference Compound 6-2) was replaced by 1-[5-(3-{[(tert-butyldimethylsilyl)oxy]methyl}-2-fluorophenyl)pyrimidin-2-yl]azetidin-3-one O-(2-{2-[(tetrahydropyran-2-yl)oxy]ethoxy}ethyl) oxime synthesized in the same manner as in Reference Example 6-11. Consequently, the title compound (yield 86%) was obtained as a white solid.

Mass spectrum (CI, m/z):461 [M+1]+.

¹H-NMR spectrum (400 MHz, CDCl₃) δ:8.56 (d, J=1.4 Hz, 2H), 7.48-7.42 (m, 1H), 7.34-7.20 (m, 2H), 4.91-4.87 (m, 4H), 4.83 (d, J=5.9 Hz, 2H), 4.66-4.63 (m, 1H), 4.29-4.24 (m, 2H), 3.91-3.84 (m, 2H), 3.80-3.76 (m, 2H), 3.72-3.69 (m, 2H), 3.66-3.59 (m, 1H), 3.54-3.47 (m, 1H), 1.91 (t, J=5.9 Hz, 1H), 1.88-1.46 (m, 6H).

Mass spectrum (CI, m/z):595[M+1]+.

Reference Example 7-13) {[(1-{5-[2-Fluoro-3-(hydroxymethyl)phenyl]pyrimidin-2-yl}azetidin-3-ylidene)amino]oxy}methyl pivalate (Reference Compound 7-13)

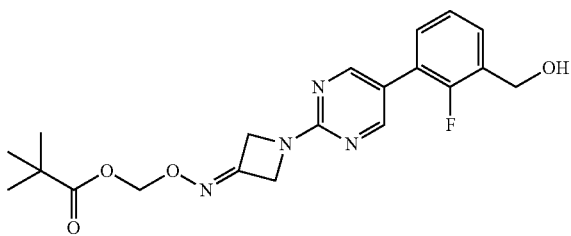 [SMILES: CC(C)(C)C(=O)OCON=C1CN(c2ncc(-c3cccc(CO)c3F)cn2)C1]

The reaction was performed by the method described in Reference Example 7-2, except that 1-[5-(3-{[(tert-butyldimethylsilyl)oxy]methyl}-2-fluorophenyl)pyrimidin-2-yl]azetidin-3-one O-ethyl oxime (Reference Compound 6-2) was replaced by [({1-[5-(3-{[(tert-butyldimethylsilyl)oxy]methyl}-2-fluorophenyl)pyrimidin-2-yl]azetidin-3-ylidene}amino)oxy]methyl pivalate synthesized in the same manner as in Reference Example 15-3. Consequently, the title compound (including impurities) was obtained as a white solid.

Mass spectrum (CI, m/z):403[M+1]+.

¹H-NMR spectrum (400 MHz, CDCl₃) δ:8.57 (d, J=1.5 Hz, 2H), 7.49-7.42 (m, 1H), 7.42-7.20 (m, 2H), 5.73 (s, 2H), 4.92-4.88 (m, 4H), 4.84 (d, J=5.9 Hz, 2H), 1.83 (t, J=5.9 Hz, 1H), 1.24 (s, 9H).

Reference Example 7-14

1-{5-[2-Fluoro-3-(hydroxymethyl)phenyl]pyrimidin-2-yl}azetidin-3-one O-[(2,2-dimethyl-1,3-dioxan-5-yl)methyl] oxime (Reference Compound 7-14)

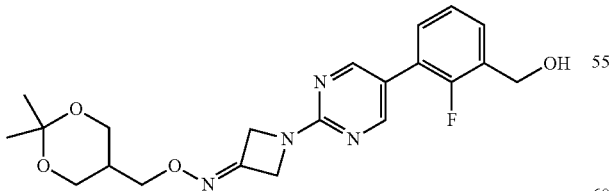

The reaction was performed by the method described in Reference Example 7-2, except that 1-[5-(3-{[(tert-butyldimethylsilyl)oxy]methyl}-2-fluorophenyl)pyrimidin-2-yl]azetidin-3-one O-ethyl oxime (Reference Compound 6-2) was replaced by 1-[5-(3-{[(tert-butyldimethylsilyl)oxy]methyl}-2-fluorophenyl)pyrimidin-2-yl]azetidin-3-one O-[(2,2-dimethyl-1,3-dioxan-5-yl)methyl] oxime synthesized in the same manner as in Reference Example 6-12. Consequently, the title compound (yield 88%) was obtained as a white solid.

Mass spectrum (CI, m/z):417[M+1]+.

¹H-NMR spectrum (400 MHz, DMSO-d₆) δ:8.63 (d, J=1.4 Hz, 2H), 7.51-7.42 (m, 2H), 7.32-7.26 (m, 1H), 5.34 (br s, 1H), 4.85-4.79 (m, 4H), 4.60 (s, 2H), 4.08 (d, J=7.0 Hz, 2H), 3.91 (dd, J=4.0, 11.8 Hz, 2H), 3.65 (dd, J=6.1, 11.8 Hz, 2H), 2.02-1.95 (m, 1H), 1.34 (s, 3H), 1.31 (s, 3H).

Reference Example 7-15

1-{5-[2-Fluoro-3-(hydroxymethyl)phenyl]pyrimidin-2-yl}azetidin-3-one O-[(2,2-dimethyl-1,3-dioxolan-4-yl)methyl] oxime (Reference Compound 7-15)

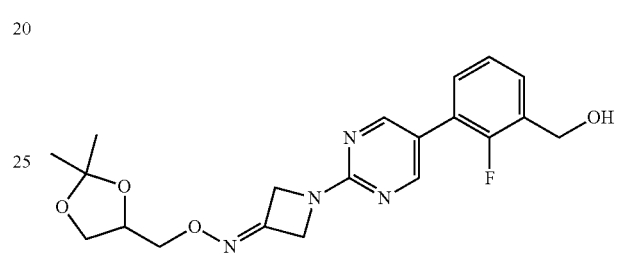

The reaction was performed by the method described in Reference Example 7-2, except that 1-[5-(3-{[(tert-butyldimethylsilyl)oxy]methyl}-2-fluorophenyl)pyrimidin-2-yl]azetidin-3-one O-ethyl oxime (Reference Compound 6-2) was replaced by 1-[5-(3-{[(tert-butyldimethylsilyl)oxy]methyl}-2-fluorophenyl)pyrimidin-2-yl]azetidin-3-one O-[(2,2-dimethyl-1,3-dioxolan-4-yl)methyl] oxime synthesized in the same manner as in Reference Example 6-13. Consequently, the title compound (yield 93%) was obtained as a white solid.

Mass spectrum (CI, m/z):403[M+1]+.

¹H-NMR spectrum (400 MHz, DMSO-d₆) δ:8.63 (d, J=1.5 Hz, 2H), 7.51-7.42 (m, 2H), 7.33-7.25 (m, 1H), 5.34 (t, J=5.7 Hz, 1H), 4.86-4.78 (m, 4H), 4.60 (d, J=5.7 Hz, 2H), 4.34-4.26 (m, 1H), 4.10-4.00 (m, 3H), 3.68 (dd, J=6.4, 8.4 Hz, 1H), 1.33 (s, 3H), 1.28 (s, 3H).

Reference Example 7-16

1-{5-[2-Fluoro-3-(hydroxymethyl)phenyl]pyrimidin-2-yl}azetidin-3-one O-(3-methoxy-2-{[(tetrahydropyran-2-yl)oxy]methyl}propyl) oxime (Reference Compound 7-16)

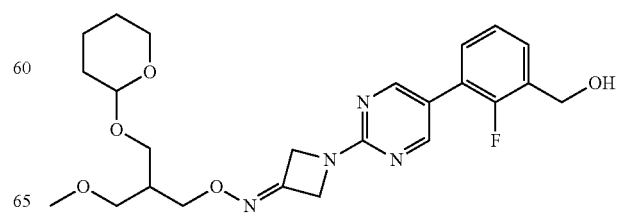

The reaction was performed by the method described in Reference Example 7-2, except that 1-[5-(3-{[(tert-butyldimethylsilyl)oxy]methyl}-2-fluorophenyl)pyrimidin-2-yl]azetidin-3-one O-ethyl oxime (Reference Compound 6-2) was replaced by 1-[5-(3-{[(tert-butyldimethylsilyl)oxy]methyl}-2-fluorophenyl)pyrimidin-2-yl]azetidin-3-one O-(3-methoxy-2-{[(tetrahydropyran-2-yl)oxy]methyl}propyl) oxime synthesized in the same manner as in Reference Example 6-14. Consequently, the title compound (yield 90%) was obtained as a white solid.

Mass spectrum (CI, m/z):475[M+1]⁺.

¹H-NMR spectrum (400 MHz, DMSO-$d_6$) 5:8.63 (d, J=1.4 Hz, 2H), 7.54-7.40 (m, 2H), 7.34-7.21 (m, 1H), 5.34 (t, J=5.6 Hz, 1H), 4.88-4.76 (m, 4H), 4.60 (d, J=5.6 Hz, 2H), 4.57-4.52 (m, 1H), 4.12-3.93 (m, 2H), 3.79-3.63 (m, 2H), 3.47-3.33 (m, 4H), 3.24 (s, 3H), 2.28-2.16 (m, 1H), 1.78-1.37 (m, 6H).

Reference Example 7-17

1-{5-[2-Fluoro-3-(hydroxymethyl)phenyl]pyrimidin-2-yl}azetidin-3-one O-[2-methoxy-3-(trityloxy)propyl] oxime (Reference Compound 7-17)

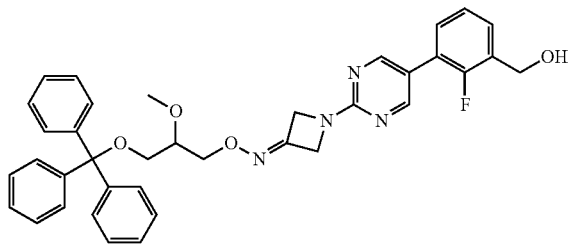 [SMILES: COC(CON=C1CN(c2ncc(-c3cccc(CO)c3F)cn2)C1)COC(c1ccccc1)(c1ccccc1)c1ccccc1]

The reaction was performed by the method described in Reference Example 7-2, except that 1-[5-(3-{[(tert-butyldimethylsilyl)oxy]methyl}-2-fluorophenyl)pyrimidin-2-yl]azetidin-3-one O-ethyl oxime (Reference Compound 6-2) was replaced by 1-[5-(3-{[(tert-butyldimethylsilyl)oxy]methyl}-2-fluorophenyl)pyrimidin-2-yl]azetidin-3-one O-[2-methoxy-3-(trityloxy)propyl] oxime synthesized in the same manner as in Reference Example 6-15. Consequently, the title compound (yield 80%) was obtained as a colorless oil.

Mass spectrum (CI, m/z):619[M+1]⁺.

¹H-NMR spectrum (400 MHz, DMSO-$d_6$) δ:8.65 (d, J=1.4 Hz, 2H), 7.53-7.21 (m, 18H), 5.34 (t, J=5.7 Hz, 1H), 4.82-4.79 (m, 2H), 4.74-4.44 (m, 4H), 4.18-4.06 (m, 2H), 3.69-3.57 (m, 1H), 3.34 (s, 3H), 3.23-2.96 (m, 2H).

Reference Example 7-18

1-{5-[2-Fluoro-3-(hydroxymethyl)phenyl]pyrimidin-2-yl}azetidin-3-one O-[2-(2,2-dimethyl-1,3-dioxolan-4-yl)ethyl] oxime (Reference Compound 7-18)

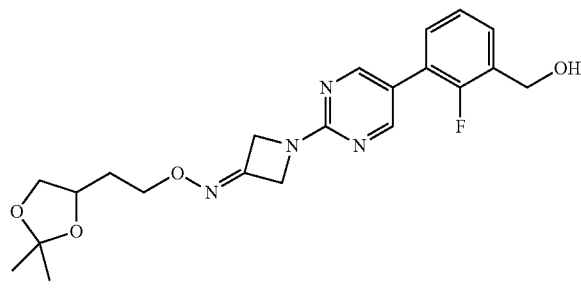 [SMILES: CC1(C)OCC(CCON=C2CN(c3ncc(-c4cccc(CO)c4F)cn3)C2)O1]

The reaction was performed by the method described in Reference Example 7-2, except that 1-[5-(3-{[(tert-butyldimethylsilyl)oxy]methyl}-2-fluorophenyl)pyrimidin-2-yl]azetidin-3-one O-ethyl oxime (Reference Compound 6-2) was replaced by 1-[5-(3-{[(tert-butyldimethylsilyl)oxy]methyl}-2-fluorophenyl)pyrimidin-2-yl]azetidin-3-one O-[2-(2,2-dimethyl-1,3-dioxolan-4-yl)ethyl] oxime synthesized in the same manner as in Reference Example 6-16. Consequently, the title compound (yield 55%) was obtained as a white solid.

Mass spectrum (CI, m/z):417[M+1]⁺.

¹H-NMR spectrum (400 MHz, DMSO-$d_6$) δ:8.63 (d, J=1.5 Hz, 2H), 7.53-7.40 (m, 2H), 7.35-7.24 (m, 1H), 5.34 (t, J=5.7 Hz, 1H), 4.86-4.77 (m, 4H), 4.60 (d, J=5.7 Hz, 2H), 4.16-4.07 (m, 3H), 4.02 (dd, J=6.0, 8.0 Hz, 1H), 3.49 (dd, J=7.2, 8.0 Hz, 1H), 1.93-1.77 (m, 2H), 1.31 (s, 3H), 1.27 (s, 3H).

Reference Example 7-19

1-{[(1-{5-[2-Fluoro-3-(hydroxymethyl)phenyl]pyrimidin-2-yl}azetidin-3-ylidene)amino]oxy}-3-methoxypropan-2-yl acetate (Reference Compound 7-19)

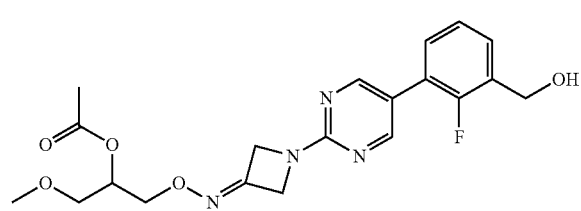 [SMILES: COCC(CON=C1CN(c2ncc(-c3cccc(CO)c3F)cn2)C1)OC(C)=O]

The reaction was performed by the method described in Reference Example 7-2, except that 1-[5-(3-{[(tert-butyldimethylsilyl)oxy]methyl}-2-fluorophenyl)pyrimidin-2-yl]azetidin-3-one O-ethyl oxime (Reference Compound 6-2) was replaced by 1-[({1-[5-(3-{[(tert-butyldimethylsilyl)oxy]methyl}-2-fluorophenyl)pyrimidin-2-yl]azetidin-3-ylidene}amino)oxy]-3-methoxypropan-2-yl acetate synthesized in the same manner as in Reference Example 22.

Consequently, the title compound (yield 60%) was obtained as a light yellow solid.

Mass spectrum (CI, m/z):419[M+1].

$^1$H-NMR spectrum (400 MHz, DMSO-d$_6$) δ:8.63 (d, J=1.3 Hz, 2H), 7.52-7.41 (m, 2H), 7.35-7.25 (m, 1H), 5.34 (t, J=5.6 Hz, 1H), 5.22-5.09 (m, 1H), 4.87-4.73 (m, 4H), 4.60 (d, J=5.6 Hz, 2H), 4.22-4.07 (m, 2H), 3.54-3.44 (m, 2H), 3.27 (s, 3H), 2.04 (s, 3H).

Reference Example 7-20

1-{5-[2-Fluoro-3-(hydroxymethyl)phenyl]pyrimidin-2-yl}azetidin-3-one O-(3-fluoro-2-{[(tetrahydropyran-2-yl)oxy]methyl}propyl) oxime (Reference Compound 7-20)

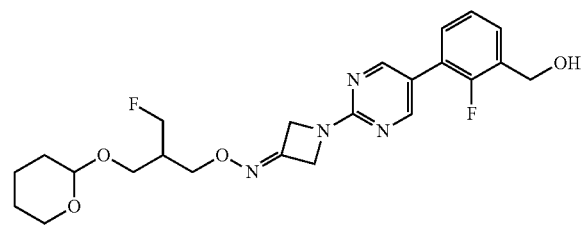 [SMILES: OCc1cccc(-c2cnc(N3CC(=NOCC(CF)COC4CCCCO4)C3)nc2)c1F]

The reaction was performed by the method described in Reference Example 7-2, except that 1-[5-(3-{[(tert-butyldimethylsilyl)oxy]methyl}-2-fluorophenyl)pyrimidin-2-yl]azetidin-3-one O-ethyl oxime (Reference Compound 6-2) was replaced by 1-[5-(3-{[(tert-butyldimethylsilyl)oxy]methyl}-2-fluorophenyl)pyrimidin-2-yl]azetidin-3-one O-(3-fluoro-2-{[(tetrahydropyran-2-yl)oxy]methyl}propyl) oxime synthesized in the same manner as in Reference Example 6-17. Consequently, the title compound (yield 36%) was obtained as a white solid.

Mass spectrum (ESI, m/z):463[M+1]$^+$.

$^1$H-NMR spectrum (400 MHz, DMSO-d$_6$) δ:8.63 (d, J=1.5 Hz, 2H), 7.53-7.40 (m, 2H), 7.32-7.26 (m, 1H), 5.33 (t, J=5.7 Hz, 1H), 4.87-4.79 (m, 4H), 4.66-4.41 (m, 5H), 4.16-4.05 (m, 2H), 3.76-3.68 (m, 2H), 3.47-3.38 (m, 2H), 2.43-2.29 (m, 1H), 1.76-1.57 (m, 2H), 1.53-1.41 (m, 4H).

Reference Example 7-21

1-{5-[2-Fluoro-3-(hydroxymethyl)phenyl]pyrimidin-2-yl}azetidin-3-one O-[2-fluoro-3-(trityloxy)propyl] oxime (Reference Compound 7-21)

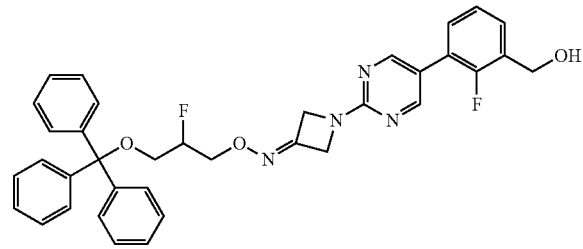 [SMILES: OCc1cccc(-c2cnc(N3CC(=NOCC(F)COC(c4ccccc4)(c4ccccc4)c4ccccc4)C3)nc2)c1F]

The reaction was performed by the method described in Reference Example 7-1, except that 1-[5-(3-{[(tert-butyldimethylsilyl)oxy]methyl}-2-fluorophenyl)pyrimidin-2-yl]azetidin-3-one O-methyl oxime (Reference Compound 6-1) was replaced by 1-[5-(3-{[(tert-butyldimethylsilyl)oxy]methyl}-2-fluorophenyl)pyrimidin-2-yl]azetidin-3-one O-[2-fluoro-3-(trityloxy)propyl] oxime synthesized in the same manner as in Reference Example 6-18, and the concentrated residue was purified by silica gel column chromatography. Consequently, the title compound (yield 90%) was obtained as a white solid.

Mass spectrum (ESI, m/z):607[M+1]$^+$.

$^1$H-NMR spectrum (400 MHz, DMSO-d$_6$) δ:8.64 (d, J=1.4 Hz, 2H), 7.55-7.19 (m, 18H), 5.34 (t, J=5.6 Hz, 1H), 5.04-4.84 (m, 1H), 4.83-4.77 (m, 2H), 4.76-4.63 (m, 2H), 4.61 (d, J=5.6 Hz, 2H), 4.43-4.15 (m, 2H), 3.31-3.11 (m, 2H).

Reference Example 7-22

1-{5-[2-Fluoro-3-(hydroxymethyl)phenyl]pyrimidin-2-yl}azetidin-3-one O-{3-methoxy-4-[(tetrahydropyran-2-yl)oxy]butyl} oxime (Reference Compound 7-22)

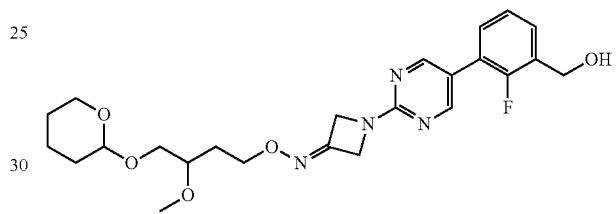

The reaction was performed by the method described in Reference Example 7-2, except that 1-[5-(3-{[(tert-butyldimethylsilyl)oxy]methyl}-2-fluorophenyl)pyrimidin-2-yl]azetidin-3-one O-ethyl oxime (Reference Compound 6-2) was replaced by 1-[5-(3-{[(tert-butyldimethylsilyl)oxy]methyl}-2-fluorophenyl)pyrimidin-2-yl]azetidin-3-one O-{3-methoxy-4-[(tetrahydropyran-2-yl)oxy]butyl} oxime synthesized in the same manner as in Reference Example 6-19. Consequently, the title compound (yield 96%) was obtained as a white solid.

Mass spectrum (ESI, m/z):475[M+1]$^+$.

$^1$H-NMR spectrum (400 MHz, CDCl$_3$) δ:8.57 (d, J=1.4 Hz, 2H), 7.50-7.41 (m, 1H), 7.35-7.28 (m, 1H), 7.28-7.19 (m, 1H), 4.93-4.86 (m, 4H), 4.83 (d, J=5.4 Hz, 2H), 4.69-4.59 (m, 1H), 4.31-4.16 (m, 2H), 4.00-3.73 (m, 2H), 3.60-3.36 (m, 6H), 2.03-1.46 (m, 9H).

Reference Example 7-23

2-{[(1-{5-[2-Fluoro-3-(hydroxymethyl)phenyl]pyrimidin-2-yl}azetidin-3-ylidene)amino]oxy}ethyl acetate (Reference Compound 7-23)

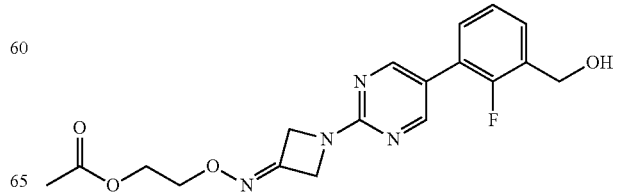

The reaction was performed by the method described in Reference Example 7-2, except that 1-[5-(3-{[(tert-butyldimethylsilyl)oxy]methyl}-2-fluorophenyl)pyrimidin-2-yl]azetidin-3-one O-ethyl oxime (Reference Compound 6-2) was replaced by 2-[({1-[5-(3-{[(tert-butyldimethylsilyl)oxy]methyl}-2-fluorophenyl)pyrimidin-2-yl]azetidin-3-ylidene}amino)oxy]ethyl acetate synthesized in the same manner as in Reference Example 6-21. Consequently, the title compound (yield 61%) was obtained as a white solid.

Mass spectrum (ESI, m/z):375[M+1]$^+$.

$^1$H-NMR spectrum (400 MHz, CDCl$_3$) δ:8.57 (d, J=1.4 Hz, 2H), 7.49-7.42 (m, 1H), 7.35-7.21 (m, 2H), 4.92-4.87 (m, 4H), 4.84 (d, J=6.1 Hz, 2H), 4.37-4.26 (m, 4H), 2.10 (s, 3H), 1.83 (t, J=6.1 Hz, 1H).

Reference Example 7-24

2-{[(1-{5-[2-Fluoro-3-(hydroxymethyl)phenyl]pyrimidin-2-yl}azetidin-3-ylidene)amino]oxy}ethyl propionate (Reference Compound 7-24)

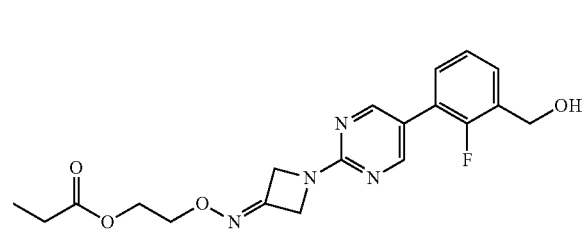 [SMILES: CCC(=O)OCCON=C1CN(c2ncc(-c3cccc(CO)c3F)cn2)C1]

The reaction was performed by the method described in Reference Example 7-2, except that 1-[5-(3-{[(tert-butyldimethylsilyl)oxy]methyl}-2-fluorophenyl)pyrimidin-2-yl]azetidin-3-one O-ethyl oxime (Reference Compound 6-2) was replaced by 2-[({1-[5-(3-{[(tert-butyldimethylsilyl)oxy]methyl}-2-fluorophenyl)pyrimidin-2-yl]azetidin-3-ylidene}amino)oxy]ethyl propionate synthesized in the same manner as in Reference Example 6-22. Consequently, the title compound (yield 88%) was obtained as a light yellow oil.

Mass spectrum (CI, m/z):389[M+1]$^+$.

$^1$H-NMR spectrum (400 MHz, DMSO-d$_6$) δ:8.63 (d, J=1.5 Hz, 2H), 7.53-7.39 (m, 2H), 7.34-7.25 (m, 1H), 5.34 (t, J=5.5 Hz, 1H), 4.87-4.76 (m, 4H), 4.60 (d, J=5.5 Hz, 2H), 4.28-4.19 (m, 4H), 2.34 (q, J=7.5 Hz, 2H), 1.03 (t, J=7.5 Hz, 3H).

Reference Example 7-25

2-{[(1-{5-[2-Fluoro-3-(hydroxymethyl)phenyl]pyrimidin-2-yl}azetidin-3-ylidene)amino]oxy}ethyl butyrate (Reference Compound 7-25)

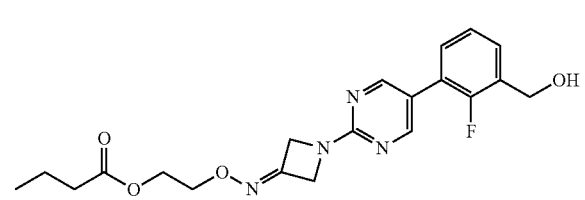 [SMILES: CCCC(=O)OCCON=C1CN(c2ncc(-c3cccc(CO)c3F)cn2)C1]

The reaction was performed by the method described in Reference Example 7-2, except that 1-[5-(3-{[(tert-butyldimethylsilyl)oxy]methyl}-2-fluorophenyl)pyrimidin-2-yl]azetidin-3-one O-ethyl oxime (Reference Compound 6-2) was replaced by 2-[({1-[5-(3-{[(tert-butyldimethylsilyl)oxy]methyl}-2-fluorophenyl)pyrimidin-2-yl]azetidin-3-ylidene}amino)oxy]ethyl butyrate synthesized in the same manner as in Reference Example 6-23. Consequently, the title compound (yield 89%) was obtained as a colorless foam.

Mass spectrum (CI, m/z):403[M+1]$^+$.

$^1$H-NMR spectrum (400 MHz, DMSO-d$_6$) δ:8.63 (d, J=1.1 Hz, 2H), 7.56-7.38 (m, 2H), 7.34-7.24 (m, 1H), 5.34 (t, J=5.0 Hz, 1H), 4.90-4.70 (m, 4H), 4.60 (d, J=5.0 Hz, 2H), 4.34-4.17 (m, 4H), 2.30 (t, J=7.3 Hz, 2H), 1.55 (sext, J=7.3 Hz, 2H), 0.89 (t, J=7.3 Hz, 3H).

Reference Example 7-26

2-{[(1-{5-[2-Fluoro-3-(hydroxymethyl)phenyl]pyrimidin-2-yl}azetidin-3-ylidene)amino]oxy}ethyl benzoate (Reference Compound 7-26)

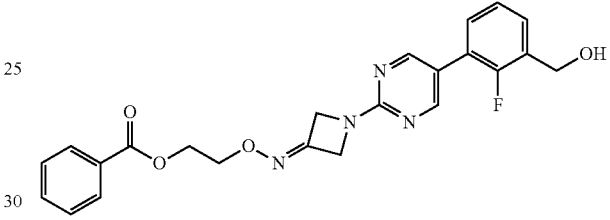

The reaction was performed by the method described in Reference Example 7-2, except that 1-[5-(3-{[(tert-butyldimethylsilyl)oxy]methyl}-2-fluorophenyl)pyrimidin-2-yl]azetidin-3-one O-ethyl oxime (Reference Compound 6-2) was replaced by 2-[({1-[5-(3-{[(tert-butyldimethylsilyl)oxy]methyl}-2-fluorophenyl)pyrimidin-2-yl]azetidin-3-ylidene}amino)oxy]ethyl benzoate synthesized in the same manner as in Reference Example 6-24. Consequently, the title compound (yield 82%) was obtained as a light yellow oil.

Mass spectrum (CI, m/z):437[M+1]$^+$.

$^1$H-NMR spectrum (400 MHz, DMSO-d$_6$) δ:8.62 (d, J=1.4 Hz, 2H), 8.02-7.92 (m, 2H), 7.73-7.63 (m, 1H), 7.59-7.40 (m, 4H), 7.33-7.23 (m, 1H), 5.34 (t, J=5.5 Hz, 1H), 4.90-4.72 (m, 4H), 4.60 (d, J=5.5 Hz, 2H), 4.56-4.49 (m, 2H), 4.41-4.34 (m, 2H).

Reference Example 7-27

3-{[(1-{5-[2-Fluoro-3-(hydroxymethyl)phenyl]pyrimidin-2-yl}azetidin-3-ylidene)amino]oxy}-2-{[(tetrahydropyran-2-yl)oxy]methyl}propyl acetate (Reference Compound 7-27)

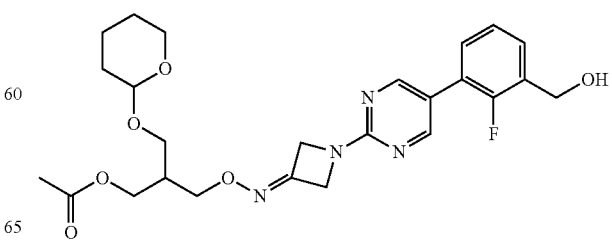

The reaction was performed by the method described in Reference Example 7-2, except that 1-[5-(3-{[(tert-bu- The reaction was performed by the method described in Reference Example 7-2, except that 1-[5-(3-{[(tert-butyldimethylsilyl)oxy]methyl}-2-fluorophenyl)pyrimidin-2-yl]azetidin-3-one O-ethyl oxime (Reference Compound 6-2) was replaced by 3-[({1-[5-(3-{[(tert-butyldimethylsilyl)oxy]methyl}-2-fluorophenyl)pyrimidin-2-yl]azetidin-3-ylidene}amino)oxy]-2-{[(tetrahydropyran-2-yl)oxy]methyl}propyl acetate synthesized in the same manner as in Reference Example 29-1. Consequently, the title compound (yield 79%) was obtained as a white solid.

Mass spectrum (CI, m/z):503[M+1]⁺.

¹H-NMR spectrum (400 MHz, CDCl₃) δ:8.57 (d, J=1.5 Hz, 2H), 7.48-7.42 (m, 1H), 7.35-7.21 (m, 2H), 4.90-4.86 (m, 4H), 4.83 (d, J=6.0 Hz, 2H), 4.62-4.57 (m, 1H), 4.25-4.13 (m, 4H), 3.87-3.76 (m, 2H), 3.58-3.47 (m, 1H), 3.47-3.39 (m, 1H), 2.46-2.38 (m, 1H), 2.07 (s, 3H), 1.89 (t, J=6.0 Hz, 1H), 1.84-1.48 (m, 6H).

Reference Example 7-28

3-{[(1-{5-[2-Fluoro-3-(hydroxymethyl)phenyl]pyrimidin-2-yl}azetidin-3-ylidene)amino]oxy}-2-{[(tetrahydropyran-2-yl)oxy]methyl}propyl propionate (Reference Compound 7-28)

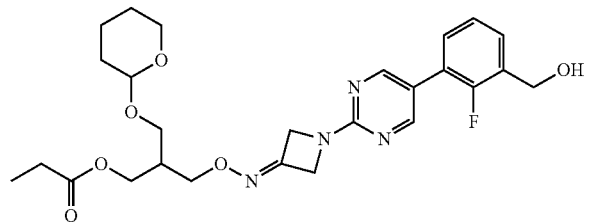 [SMILES: CCC(=O)OCC(CON=C1CN(c2ncc(-c3cccc(CO)c3F)cn2)C1)COC1CCCCO1]

The reaction was performed by the method described in Reference Example 7-2, except that 1-[5-(3-{[(tert-butyldimethylsilyl)oxy]methyl}-2-fluorophenyl)pyrimidin-2-yl]azetidin-3-one O-ethyl oxime (Reference Compound 6-2) was replaced by 3-[({1-[5-(3-{[(tert-butyldimethylsilyl)oxy]methyl}-2-fluorophenyl)pyrimidin-2-yl]azetidin-3-ylidene}amino)oxy]-2-{[(tetrahydropyran-2-yl)oxy]methyl}propyl propionate synthesized in the same manner as in Reference Example 29-2. Consequently, the title compound (yield 89%) was obtained as a white solid.

Mass spectrum (CI, m/z):517[M+1]⁺.

¹H-NMR spectrum (400 MHz, CDCl₃) δ:8.57 (d, J=1.4 Hz, 2H), 7.48-7.42 (m, 1H), 7.35-7.21 (m, 2H), 4.90-4.86 (m, 4H), 4.83 (d, J=6.0 Hz, 2H), 4.61-4.57 (m, 1H), 4.25-4.13 (m, 4H), 3.87-3.78 (m, 2H), 3.56-3.48 (m, 1H), 3.47-3.38 (m, 1H), 2.46-2.39 (m, 1H), 2.35 (q, J=7.6 Hz, 2H), 1.86 (t, J=6.0 Hz, 1H), 1.83-1.47 (m, 6H), 1.15 (t, J=7.6 Hz, 3H).

Reference Example 7-29

3-{[(1-{5-[2-Fluoro-3-(hydroxymethyl)phenyl]pyrimidin-2-yl}azetidin-3-ylidene)amino]oxy}-2-{[(tetrahydropyran-2-yl)oxy]methyl}propyl butyrate (Reference Compound 7-29)

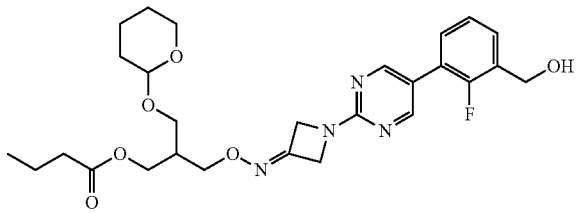 [SMILES: CCCC(=O)OCC(CON=C1CN(c2ncc(-c3cccc(CO)c3F)cn2)C1)COC1CCCCO1]

The reaction was performed by the method described in Reference Example 7-2, except that 1-[5-(3-{[(tert-butyldimethylsilyl)oxy]methyl}-2-fluorophenyl)pyrimidin-2-yl]azetidin-3-one O-ethyl oxime (Reference Compound 6-2) was replaced by 3-[({1-[5-(3-{[(tert-butyldimethylsilyl)oxy]methyl}-2-fluorophenyl)pyrimidin-2-yl]azetidin-3-ylidene}amino)oxy]-2-{[(tetrahydropyran-2-yl)oxy]methyl}propyl butyrate synthesized in the same manner as in Reference Example 30-1. Consequently, the title compound (yield 85%) was obtained as a white solid.

Mass spectrum (CI, m/z):531[M+1]⁺.

¹H-NMR spectrum (400 MHz, CDCl₃) δ:8.57 (d, J=1.5 Hz, 2H), 7.49-7.42 (m, 1H), 7.35-7.21 (m, 2H), 4.90-4.85 (m, 4H), 4.83 (d, J=6.1 Hz, 2H), 4.61-4.57 (m, 1H), 4.24-4.14 (m, 4H), 3.87-3.77 (m, 2H), 3.55-3.48 (m, 1H), 3.46-3.38 (m, 1H), 2.46-2.38 (m, 1H), 2.30 (t, J=7.4 Hz, 2H), 1.88 (t, J=6.1 Hz, 1H), 1.85-1.47 (m, 8H), 0.95 (t, J=7.4 Hz, 3H).

Reference Example 7-30

3-{[(1-{5-[2-Fluoro-3-(hydroxymethyl)phenyl]pyrimidin-2-yl}azetidin-3-ylidene)amino]oxy}-2-{[(tetrahydropyran-2-yl)oxy]methyl}propyl isobutyrate (Reference Compound 7-30)

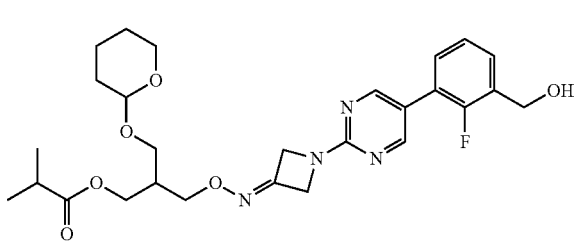 [SMILES: CC(C)C(=O)OCC(CON=C1CN(c2ncc(-c3cccc(CO)c3F)cn2)C1)COC1CCCCO1]

The reaction was performed by the method described in Reference Example 7-1, except that 1-[5-(3-{[(tert-butyldimethylsilyl)oxy]methyl}-2-fluorophenyl)pyrimidin-2-yl]azetidin-3-one O-methyl oxime (Reference Compound 6-1) was replaced by 3-[({1-[5-(3-{[(tert-butyldimethylsilyl)oxy]methyl}-2-fluorophenyl)pyrimidin-2-yl]azetidin-3-ylidene}amino)oxy]-2-{[(tetrahydropyran-2-yl)oxy]methyl}propyl isobutyrate synthesized in the same manner as in Reference Example 30-2, and the concentrated residue was purified by silica gel column chromatography. Consequently, the title compound (yield 82%) was obtained as a white solid.

Mass spectrum (CI, m/z):531 [M+1]+.

$^1$H-NMR spectrum (400 MHz, DMSO-d$_6$) δ:8.63 (d, J=1.4 Hz, 2H), 7.54-740 (m, 2H), 7.35-7.24 (m, 1H), 5.40 (br. s, 1H), 4.88-4.77 (m, 4H), 4.61 (br. s, 2H), 4.58-4.54 (m, 1H), 4.20-4.01 (m, 4H), 3.77-3.61 (m, 2H), 3.48-3.35 (m, 2H), 2.55 (sep, J=7.0 Hz, 1H), 2.39-2.26 (m, 1H), 1.78-1.38 (m, 6H), 1.09 (d, J=7.0 Hz, 6H).

Reference Example 7-31

3-{[(1-{5-[2-Fluoro-3-(hydroxymethyl)phenyl]pyrimidin-2-yl}azetidin-3-ylidene)amino]oxy}-2-{[(tetrahydropyran-2-yl)oxy]methyl}propyl pivalate (Reference Compound 7-31)

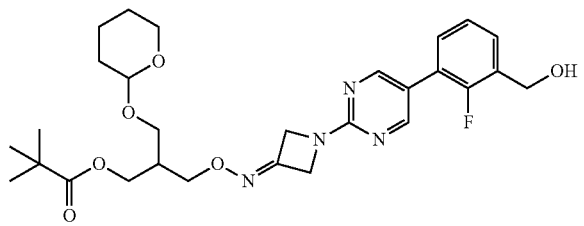 [SMILES: CC(C)(C)C(=O)OCC(CON=C1CN(c2ncc(-c3cccc(CO)c3F)cn2)C1)COC1CCCCO1]

The reaction was performed by the method described in Reference Example 7-1, except that 1-[5-(3-{[(tert-butyldimethylsilyl)oxy]methyl}-2-fluorophenyl)pyrimidin-2-yl]azetidin-3-one O-methyl oxime (Reference Compound 6-1) was replaced by 3-[({1-[5-(3-{[(tert-butyldimethylsilyl)oxy]methyl}-2-fluorophenyl)pyrimidin-2-yl]azetidin-3-ylidene}amino)oxy]-2-{[(tetrahydropyran-2-yl)oxy]methyl}propyl pivalate synthesized in the same manner as in Reference Example 30-3, and the concentrated residue was purified by silica gel column chromatography. Consequently, the title compound (yield 89%) was obtained as a white solid.

Mass spectrum (CI, m/z):545[M+1]+.

$^1$H-NMR spectrum (400 MHz, DMSO-d$_6$) δ:8.63 (d, J=1.5 Hz, 2H), 7.52-7.41 (m, 2H), 7.32-7.26 (m, 1H), 5.34 (t, J=5.1 Hz, 1H), 4.87-4.77 (m, 4H), 4.60 (d, J=5.1 Hz, 2H), 4.58-4.53 (m, 1H), 4.19-4.02 (m, 4H), 3.78-3.65 (m, 2H), 3.48-3.34 (m, 2H), 2.40-2.28 (m, 1H), 1.79-1.38 (m, 6H), 1.15 (s, 9H).

Reference Example 7-32

3-{[(1-{5-[2-Fluoro-3-(hydroxymethyl)phenyl]pyrimidin-2-yl}azetidin-3-ylidene)amino]oxy}-2-{[(tetrahydropyran-2-yl)oxy]methyl}propyl hexanoate (Reference Compound 7-32)

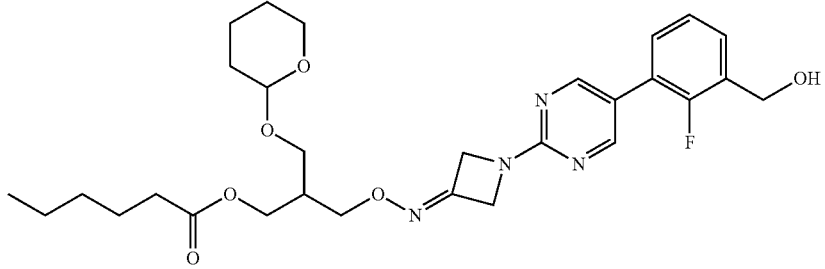 [SMILES: CCCCCC(=O)OCC(CON=C1CN(c2ncc(-c3cccc(CO)c3F)cn2)C1)COC1CCCCO1]

The reaction was performed by the method described in Reference Example 7-2, except that 1-[5-(3-{[(tert-butyldimethylsilyl)oxy]methyl}-2-fluorophenyl)pyrimidin-2-yl]azetidin-3-one O-ethyl oxime (Reference Compound 6-2) was replaced by 3-[({1-[5-(3-{[(tert-butyldimethylsilyl)oxy]methyl}-2-fluorophenyl)pyrimidin-2-yl]azetidin-3-ylidene}amino)oxy]-2-{[(tetrahydropyran-2-yl)oxy]methyl}propyl hexanoate synthesized in the same manner as in Reference Example 30-4. Consequently, the title compound (yield 98%) was obtained as a colorless oil.

Mass spectrum (ESI, m/z):559[M+1]+.

$^1$H-NMR spectrum (400 MHz, CDCl$_3$) δ:8.57 (d, J=1.5 Hz, 2H), 7.49-7.42 (m, 1H), 7.36-7.20 (m, 2H), 4.92-4.86 (m, 4H), 4.84 (d, J=5.3 Hz, 2H), 4.62-4.56 (m, 1H), 4.25-4.15 (m, 4H), 3.87-3.77 (m, 2H), 3.56-3.48 (m, 1H), 3.47-3.38 (m, 1H), 2.48-2.38 (m, 1H), 2.32 (t, J=7.5 Hz, 2H), 1.92-1.75 (m, 2H), 1.75-1.47 (m, 7H), 1.39-1.24 (m, 4H), 0.90 (t, J=7.0 Hz, 3H).

Reference Example 7-33

3-{[(1-{5-[2-Fluoro-3-(hydroxymethyl)phenyl]pyrimidin-2-yl}azetidin-3-ylidene)amino]oxy}-2-{[(tetrahydropyran-2-yl)oxy]methyl}propyl benzoate (Reference Compound 7-33)

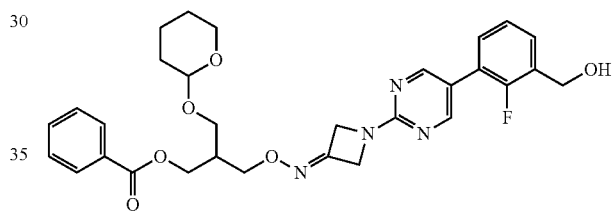

The reaction was performed by the method described in Reference Example 7-2, except that 1-[5-(3-{[(tert-butyldimethylsilyl)oxy]methyl}-2-fluorophenyl)pyrimidin-2-yl]azetidin-3-one O-ethyl oxime (Reference Compound 6-2) was replaced by 3-[({1-[5-(3-{[(tert-butyldimethylsilyl)oxy]methyl}-2-fluorophenyl)pyrimidin-2-yl]azetidin-3-ylidene}amino)oxy]-2-{[(tetrahydropyran-2-yl)oxy]methyl}propyl benzoate synthesized in the same manner as in Reference Example 30-5. Consequently, the title compound (yield 96%) was obtained as a colorless oil.

Mass spectrum (CI, m/z):565[M+1]+.

$^1$H-NMR spectrum (400 MHz, DMSO-d$_6$) δ:8.62 (d, J=1.4 Hz, 2H), 8.00-7.96 (m, 2H), 7.66-7.60 (m, 1H), 7.54-7.42 (m, 4H), 7.32-7.26 (m, 1H), 5.33 (t, J=5.2 Hz, 1H), 4.83-4.73 (m, 4H), 4.63-4.57 (m, 3H), 4.43-4.34 (m, 2H), 4.26-4.16 (m, 2H), 3.82-3.67 (m, 2H), 3.52-3.36 (m, 2H), 1.75-1.55 (m, 2H), 1.52-1.38 (m, 4H).

Reference Example 7-34

1-{3-Fluoro-5-[2-fluoro-3-(hydroxymethyl)phenyl]pyridin-2-yl}azetidin-3-one O-methyl oxime (Reference Compound 7-34)

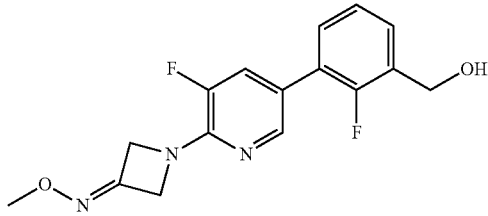 [SMILES: CON=C1CN(c2ncc(-c3cccc(CO)c3F)cc2F)C1]

The reaction was performed by the method described in Reference Example 7-2, except that 1-[5-(3-{[(tert-butyldimethylsilyl)oxy]methyl}-2-fluorophenyl)pyrimidin-2-yl]azetidin-3-one O-ethyl oxime (Reference Compound 6-2) was replaced by 1-[5-(3-{[(tert-butyldimethylsilyl)oxy]methyl}-2-fluorophenyl)-3-fluoropyridin-2-yl]azetidin-3-one O-methyl oxime synthesized in the same manner as in Reference Example 6-26. Consequently, the title compound (yield 79%) was obtained as a white solid.

Mass spectrum (CI, m/z):320[M+1]$^+$.

$^1$H-NMR spectrum (400 MHz, CDCl$_3$) δ:8.17-8.14 (m, 1H), 7.50-7.40 (m, 2H), 7.36-7.30 (m, 1H), 7.25-7.19 (m, 1H), 4.92-4.88 (m, 4H), 4.83 (d, J=5.9 Hz, 2H), 3.91 (s, 3H), 1.86 (t, J=5.9 Hz, 1H).

Reference Example 7-35

1-{3-Fluoro-5-[2-fluoro-3-(hydroxymethyl)phenyl]pyridin-2-yl}azetidin-3-one O-methyl-d$_3$ oxime (Reference Compound 7-35)

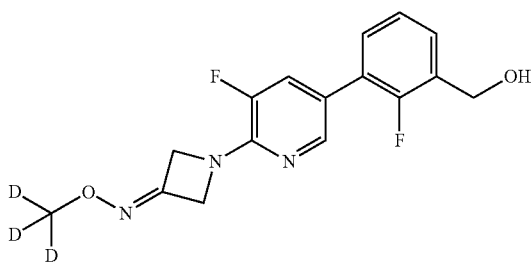 [SMILES: [2H]C([2H])([2H])ON=C1CN(c2ncc(-c3cccc(CO)c3F)cc2F)C1]

The reaction was performed by the method described in Reference Example 7-2, except that 1-[5-(3-{[(tert-butyldimethylsilyl)oxy]methyl}-2-fluorophenyl)pyrimidin-2-yl]azetidin-3-one O-ethyl oxime (Reference Compound 6-2) was replaced by 1-[5-(3-{[(tert-butyldimethylsilyl)oxy]methyl}-2-fluorophenyl)-3-fluoropyridin-2-yl]azetidin-3-one O-methyl-d$_3$ oxime synthesized in the same manner as in Reference Example 6-27. Consequently, the title compound (including impurities) was obtained as a white solid.

Mass spectrum (CI, m/z):323[M+1]$^+$.

$^1$H-NMR spectrum (400 MHz, CDCl$_3$) δ:8.19-8.12 (m, 1H), 7.50-7.40 (m, 2H), 7.36-7.30 (m, 1H), 7.25-7.20 (m, 1H), 4.92-4.87 (m, 4H), 4.83 (d, J=6.2 Hz, 2H), 1.86-1.81 (m, 1H).

Reference Example 7-36

1-{3-Fluoro-5-[2-fluoro-3-(hydroxymethyl)phenyl]pyridin-2-yl}azetidin-3-one O-[2-(2,2-dimethyl-1,3-dioxolan-4-yl)ethyl] oxime (Reference Compound 7-36)

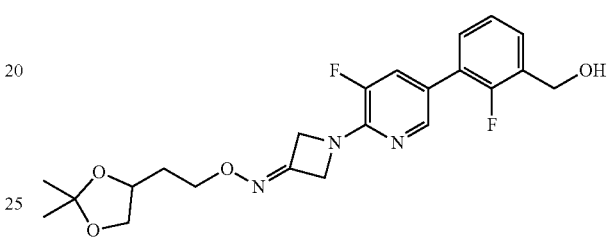

The reaction was performed by the method described in Reference Example 7-2, except that 1-[5-(3-{[(tert-butyldimethylsilyl)oxy]methyl}-2-fluorophenyl)pyrimidin-2-yl]azetidin-3-one O-ethyl oxime (Reference Compound 6-2) was replaced by 1-[5-(3-{[(tert-butyldimethylsilyl)oxy]methyl}-2-fluorophenyl)-3-fluoropyridin-2-yl]azetidin-3-one O-[2-(2,2-dimethyl-1,3-dioxolan-4-yl)ethyl] oxime synthesized in the same manner as in Reference Example 6-28. Consequently, the title compound (including impurities) was obtained as a white solid.

Mass spectrum (CI, m/z):434[M+1]$^+$.

$^1$H-NMR spectrum (400 MHz, CDCl$_3$) δ:8.17-8.13 (m, 1H), 7.50-7.40 (m, 2H), 7.37-7.28 (m, 1H), 7.25-7.19 (m, 1H), 4.91-4.87 (m, 4H), 4.85-4.80 (m, 2H), 4.26-4.16 (m, 3H), 4.12-4.06 (m, 1H), 3.61-3.55 (m, 1H), 2.00-1.90 (m, 3H), 1.42 (s, 3H), 1.37 (s, 3H).

Reference Example 7-37

1-{3-Fluoro-5-[2-fluoro-3-(hydroxymethyl)phenyl]pyridin-2-yl}azetidin-3-one O-[(2,2-dimethyl-1,3-dioxan-5-yl)methyl] oxime (Reference Compound 7-37)

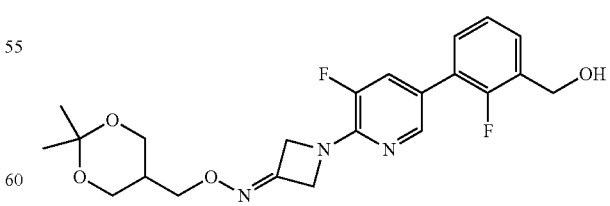

The reaction was performed by the method described in Reference Example 7-2, except that 1-[5-(3-{[(tert-butyldimethylsilyl)oxy]methyl}-2-fluorophenyl)pyrimidin-2-yl]azetidin-3-one O-ethyl oxime (Reference Compound 6-2) was replaced by 1-[5-(3-{[(tert-butyldimethylsilyl)oxy]

methyl}-2-fluorophenyl)-3-fluoropyridin-2-yl]azetidin-3-one O-[(2,2-dimethyl-1,3-dioxan-5-yl)methyl] oxime synthesized in the same manner as in Reference Example 6-29. Consequently, the title compound (including impurities) was obtained as a light yellow oil.

Mass spectrum (CI, m/z):434[M+1]⁺.

¹H-NMR spectrum (400 MHz, CDCl₃) δ:8.17-8.14 (m, 1H), 7.51-7.40 (m, 2H), 7.37-7.29 (m, 1H), 7.25-7.19 (m, 1H), 4.91-4.87 (m, 4H), 4.83 (d, J=6.0 Hz, 2H), 4.19 (d, J=6.9 Hz, 2H), 4.01 (dd, J=4.1, 12.0 Hz, 2H), 3.76 (dd, J=5.9, 12.0 Hz, 2H), 2.14-2.06 (m, 1H), 1.82 (t, J=6.0 Hz, 1H), 1.45 (s, 3H), 1.42 (s, 3H).

Reference Example 7-38

1-{3-Fluoro-5-[2-fluoro-3-(hydroxymethyl)phenyl]pyridin-2-yl}azetidin-3-one O-[2-fluoro-3-(trityloxy)propyl] oxime (Reference Compound 7-38)

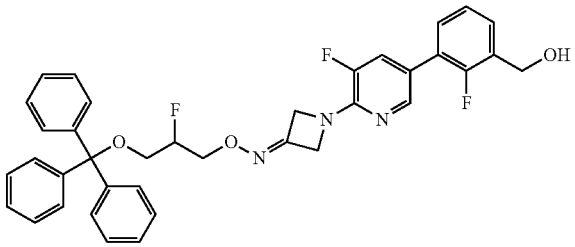 [SMILES: OCc1cccc(-c2cnc(N3CC(=NOCC(F)COC(c4ccccc4)(c4ccccc4)c4ccccc4)C3)c(F)c2)c1F]

The reaction was performed by the method described in Reference Example 7-1, except that 1-[5-(3-{[(tert-butyldimethylsilyl)oxy]methyl}-2-fluorophenyl)pyrimidin-2-yl]azetidin-3-one O-methyl oxime (Reference Compound 6-1) was replaced by 1-[5-(3-{[(tert-butyldimethylsilyl)oxy]methyl}-2-fluorophenyl)-3-fluoropyridin-2-yl]azetidin-3-one O-[2-fluoro-3-(trityloxy)propyl] oxime synthesized in the same manner as in Reference Example 6-30, and the concentrated residue was purified by silica gel column chromatography. Consequently, the title compound (yield 80%) was obtained as a white foam.

Mass spectrum (ESI, m/z):624[M+1].

¹H-NMR spectrum (400 MHz, DMSO-d₆) δ:8.22-8.15 (m, 1H), 7.81-7.73 (m, 1H), 7.54-7.21 (m, 18H), 5.34 (t, J=5.1 Hz, 1H), 5.06-4.67 (m, 5H), 4.61 (d, J=5.1 Hz, 2H), 4.39-4.11 (m, 2H), 3.33-3.12 (m, 2H).

Reference Example 7-39

1-{5-[2-Fluoro-3-(hydroxymethyl)phenyl]pyridin-2-yl}azetidin-3-one O-methyl oxime (Reference Compound 7-39)

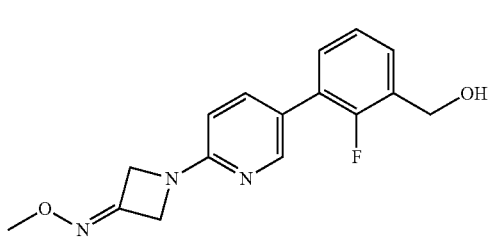 [SMILES: CON=C1CN(c2ccc(-c3cccc(CO)c3F)cn2)C1]

The reaction was performed by the method described in Reference Example 7-2, except that 1-[5-(3-{[(tert-butyldimethylsilyl)oxy]methyl}-2-fluorophenyl)pyrimidin-2-yl]azetidin-3-one O-ethyl oxime (Reference Compound 6-2) was replaced by 1-[5-(3-{[(tert-butyldimethylsilyl)oxy]methyl}-2-fluorophenyl)pyridin-2-yl]azetidin-3-one O-methyl oxime synthesized in the same manner as in Reference Example 6-31. Consequently, the title compound (yield 83%) was obtained as a white solid.

Mass spectrum (CI, m/z):302[M+1]⁺.

¹H-NMR spectrum (400 MHz, DMSO-d₆) δ:8.32-8.29 (m, 1H), 7.80-7.75 (m, 1H), 7.47-7.35 (m, 2H), 7.29-7.23 (m, 1H), 6.69-6.64 (m, 1H), 5.30 (t, J=5.6 Hz, 1H), 4.76-4.68 (m, 4H), 4.60 (d, J=5.6 Hz, 2H), 3.82 (s, 3H).

Reference Example 7-40

1-{5-[2-Fluoro-3-(hydroxymethyl)phenyl]-3-methylpyridin-2-yl}azetidin-3-one O-methyl oxime (Reference Compound 7-40)

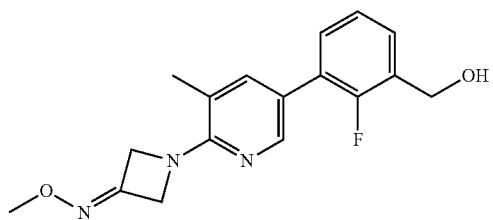 [SMILES: CON=C1CN(c2ncc(-c3cccc(CO)c3F)cc2C)C1]

The reaction was performed by the method described in Reference Example 7-2, except that 1-[5-(3-{[(tert-butyldimethylsilyl)oxy]methyl}-2-fluorophenyl)pyrimidin-2-yl]azetidin-3-one O-ethyl oxime (Reference Compound 6-2) was replaced by 1-[5-(3-{[(tert-butyldimethylsilyl)oxy]methyl}-2-fluorophenyl)-3-methylpyridin-2-yl]azetidin-3-one O-methyl oxime synthesized in the same manner as in Reference Example 6-32. Consequently, the title compound (yield 84%) was obtained as a white solid.

Mass spectrum (ESI, m/z):316[M+1]⁺.

¹H-NMR spectrum (400 MHz, CDCl₃) δ:8.27-8.22 (m, 1H), 7.55-7.50 (m, 1H), 7.44-7.37 (m, 1H), 7.37-7.29 (m, 1H), 7.24-7.16 (m, 1H), 4.89-4.84 (m, 4H), 4.82 (s, 2H), 3.90 (s, 3H), 2.27 (s, 3H).

Reference Example 7-41

5-[2-Fluoro-3-(hydroxymethyl)phenyl]-2-[3-(methoxyimino)azetidin-1-yl]nicotinonitrile (Reference Compound 7-41)

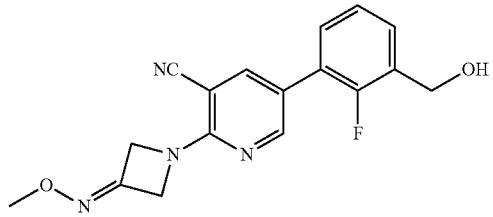 [SMILES: CON=C1CN(c2ncc(-c3cccc(CO)c3F)cc2C#N)C1]

The reaction was performed by the method described in Reference Example 7-1, except that 1-[5-(3-{[(tert-butyldimethylsilyl)oxy]methyl}-2-fluorophenyl)pyrimidin-2-yl]azetidin-3-one O-methyl oxime (Reference Compound 6-1) was replaced by 5-(3-{[(tert-butyldimethylsilyl)oxy]methyl}-2-fluorophenyl)-2-[3-(methoxyimino)azetidin-1-yl]nicotinonitrile synthesized in the same manner as in Reference Example 6-33, and the concentrated residue was purified by silica gel column chromatography. Consequently, the title compound (yield 78%) was obtained as a white solid.

Mass spectrum (CI, m/z):327[M+1]$^+$.

$^1$H-NMR spectrum (400 MHz, DMSO-d$_6$) δ:8.59-8.54 (m, 1H), 8.24 (dd, J=1.0, 2.3 Hz, 1H), 7.53-7.42 (m, 2H), 7.31-7.26 (m, 1H), 5.33 (t, J=5.6 Hz, 1H), 5.03-4.98 (m, 4H), 4.60 (d, J=5.6 Hz, 2H), 3.83 (s, 3H).

Reference Example 7-42

1-{3-Chloro-5-[2-fluoro-3-(hydroxymethyl)phenyl]pyridin-2-yl}azetidin-3-one O-methyl oxime (Reference Compound 7-42)

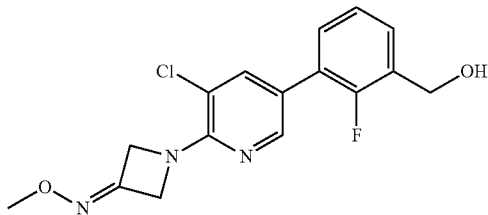

The reaction was performed by the method described in Reference Example 7-2, except that 1-[5-(3-{[(tert-butyldimethylsilyl)oxy]methyl}-2-fluorophenyl)pyrimidin-2-yl]azetidin-3-one O-ethyl oxime (Reference Compound 6-2) was replaced by 1-[5-(3-{[(tert-butyldimethylsilyl)oxy]methyl}-2-fluorophenyl)-3-chloropyridin-2-yl]azetidin-3-one O-methyl oxime synthesized in the same manner as in Reference Example 6-34. Consequently, the title compound (yield 80%) was obtained as a white solid.

Mass spectrum (CI, m/z):336[M+1]$^+$.

$^1$H-NMR spectrum (400 MHz, CDCl$_3$) δ:8.29-8.27 (m, 1H), 7.75-7.72 (m, 1H), 7.46-7.40 (m, 1H), 7.35-7.29 (m, 1H), 7.25-7.19 (m, 1H), 4.99-4.93 (m, 4H), 4.83 (d, J=6.0 Hz, 2H), 3.90 (s, 3H), 1.81 (t, J=6.0 Hz, 1H).

Reference Example 7-43

1-{3-(Difluoromethyl)-5-[2-fluoro-3-(hydroxymethyl)phenyl]pyridin-2-yl}azetidin-3-one O-methyl oxime (Reference Compound 7-43)

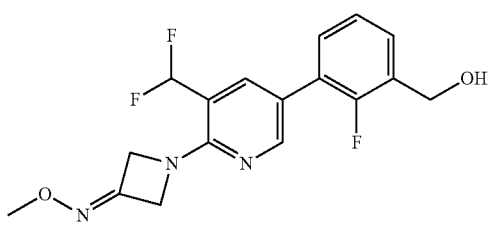 [SMILES: CON=C1CN(c2ncc(-c3cccc(CO)c3F)cc2C(F)F)C1]

The reaction was performed by the method described in Reference Example 7-2, except that 1-[5-(3-{[(tert-butyldimethylsilyl)oxy]methyl}-2-fluorophenyl)pyrimidin-2-yl]azetidin-3-one O-ethyl oxime (Reference Compound 6-2) was replaced by 1-[5-(3-{[(tert-butyldimethylsilyl)oxy]methyl}-2-fluorophenyl)-3-(difluoromethyl)pyridin-2-yl]azetidin-3-one O-methyl oxime synthesized in the same manner as in Reference Example 6-35. Consequently, the title compound (yield 87%) was obtained as a colorless oil.

Mass spectrum (CI, m/z):352[M+1]$^+$.

$^1$H-NMR spectrum (400 MHz, DMSO-d$_6$) δ:8.50-8.47 (m, 1H), 8.00-7.97 (m, 1H), 7.50-7.42 (m, 2H), 7.33-6.97 (m, 2H), 5.36-5.28 (m, 1H), 4.92-4.86 (m, 4H), 4.64-4.58 (m, 2H), 3.83 (s, 3H).

Reference Example 7-44

1-{3-Cyclopropyl-5-[2-fluoro-3-(hydroxymethyl)phenyl]pyridin-2-yl}azetidin-3-one O-methyl oxime (Reference Compound 7-44)

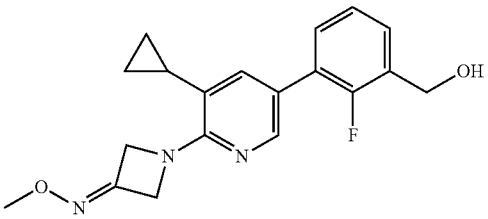 [SMILES: CON=C1CN(c2ncc(-c3cccc(CO)c3F)cc2C2CC2)C1]

The reaction was performed by the method described in Reference Example 7-2, except that 1-[5-(3-{[(tert-butyldimethylsilyl)oxy]methyl}-2-fluorophenyl)pyrimidin-2-yl]azetidin-3-one O-ethyl oxime (Reference Compound 6-2) was replaced by 1-[5-(3-{[(tert-butyldimethylsilyl)oxy]methyl}-2-fluorophenyl)-3-cyclopropylpyridin-2-yl]azetidin-3-one O-methyl oxime synthesized in the same manner as in Reference Example 6-36. Consequently, the title compound (yield 92%) was obtained as a colorless oil.

Mass spectrum (CI, m/z):342[M+1].

$^1$H-NMR spectrum (400 MHz, DMSO-d$_6$) δ:8.18-8.15 (m, 1H), 7.46-7.36 (m, 3H), 7.28-7.21 (m, 1H), 5.33-5.25 (m, 1H), 4.94-4.90 (m, 4H), 4.62-4.56 (m, 2H), 3.81 (s, 3H), 1.94-1.86 (m, 1H), 0.97-0.91 (m, 2H), 0.75-0.69 (m, 2H).

Reference Example 7-45

1-{3-Ethyl-5-[2-fluoro-3-(hydroxymethyl)phenyl]pyridin-2-yl}azetidin-3-one O-methyloxime (Reference Compound 7-45)

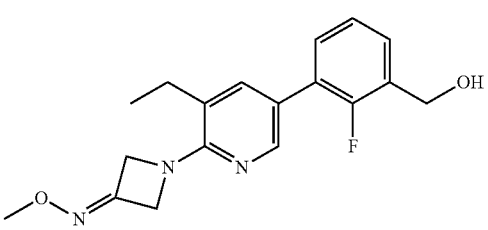 [SMILES: CCc1cc(-c2cccc(CO)c2F)cnc1N1CC(=NOC)C1]

The reaction was performed by the method described in Reference Example 7-2, except that 1-[5-(3-{[(tert-butyldimethylsilyl)oxy]methyl}-2-fluorophenyl)pyrimidin-2-yl]azetidin-3-one O-ethyl oxime (Reference Compound 6-2)

was replaced by 1-[5-(3-{[(tert-butyldimethylsilyl)oxy]methyl}-2-fluorophenyl)-3-ethylpyridin-2-yl]azetidin-3-one O-methyl oxime synthesized in the same manner as in Reference Example 6-37. Consequently, the title compound (yield 53%) was obtained as a colorless foam.

Mass spectrum (ESI, m/z):330[M+1]$^+$.

$^1$H-NMR spectrum (400 MHz, DMSO-d$_6$) δ:8.21-8.19 (m, 1H), 7.61-7.59 (m, 1H), 7.47-7.38 (m, 2H), 7.28-7.24 (m, 1H), 5.34-5.28 (m, 1H), 4.84-4.80 (m, 4H), 4.62-4.58 (m, 2H), 3.81 (s, 3H), 2.58 (q, J=7.5 Hz, 2H), 1.19 (t, J=7.5 Hz, 3H).

Reference Example 7-46

1-(5-[2-Fluoro-3-(hydroxymethyl)phenyl]-3-{2-[(tetrahydropyran-2-yl)oxy]propan-2-yl}pyridin-2-yl)azetidin-3-one O-methyl oxime (Reference Compound 7-46)

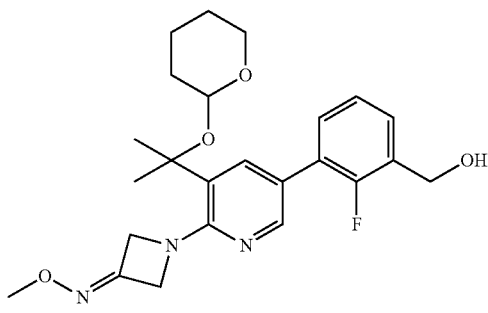 [SMILES: CON=C1CN(c2ncc(-c3cccc(CO)c3F)cc2C(C)(C)OC2CCCCO2)C1]

The reaction was performed by the method described in Reference Example 7-1, except that 1-[5-(3-{[(tert-butyldimethylsilyl)oxy]methyl}-2-fluorophenyl)pyrimidin-2-yl]azetidin-3-one O-methyl oxime (Reference Compound 6-1) was replaced by 1-[5-(3-{[(tert-butyldimethylsilyl)oxy]methyl}-2-fluorophenyl)-3-{2-[(tetrahydropyran-2-yl)oxy]propan-2-yl}pyridin-2-yl]azetidin-3-one O-methyl oxime synthesized in the same manner as in Reference Example 6-38, and the concentrated residue was purified by silica gel column chromatography. Consequently, the title compound (yield 80%) was obtained as a colorless oil.

Mass spectrum (CI, m/z):444[M+1]$^+$.

$^1$H-NMR spectrum (400 MHz, DMSO-d$_6$) δ:8.33-8.28 (m, 1H), 7.81-7.76 (m, 1H), 7.51-7.39 (m, 2H), 7.33-7.21 (m, 1H), 5.33 (br s, 1H), 4.93-4.76 (m, 4H), 4.61 (br s, 2H), 4.55-4.48 (m, 1H), 3.85-3.72 (m, 4H), 3.41-3.22 (m, 1H), 1.87-1.28 (m, 12H).

Reference Example 7-47

1-{5-[2-Fluoro-3-(hydroxymethyl)phenyl]-3-(methoxymethyl)pyridin-2-yl}azetidin-3-one O-methyl oxime (Reference Compound 7-47)

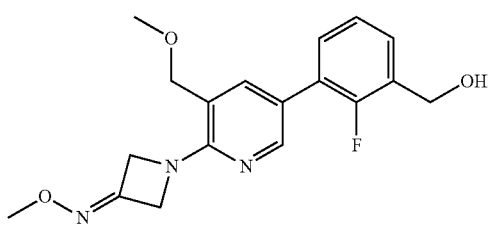 [SMILES: COCc1cc(-c2cccc(CO)c2F)cnc1N1CC(=NOC)C1]

The reaction was performed by the method described in Reference Example 7-2, except that 1-[5-(3-{[(tert-butyldimethylsilyl)oxy]methyl}-2-fluorophenyl)pyrimidin-2-yl]azetidin-3-one O-ethyl oxime (Reference Compound 6-2) was replaced by 1-[5-(3-{[(tert-butyldimethylsilyl)oxy]methyl}-2-fluorophenyl)-3-(methoxymethyl)pyridin-2-yl]azetidin-3-one O-methyl oxime synthesized in the same manner as in Reference Example 6-39. Consequently, the title compound (yield 83%) was obtained as a white solid.

Mass spectrum (CI, m/z): 346[M+1]$^+$.

$^1$H-NMR spectrum (400 MHz, DMSO-d$_6$) δ:8.30-8.27 (m, 1H), 7.75-7.72 (m, 1H), 7.49-7.36 (m, 2H), 7.29-7.20 (m, 1H), 5.31 (t, J=5.6 Hz, 1H), 4.92-4.80 (m, 4H), 4.60 (d, J=5.6 Hz, 2H), 4.39 (s, 2H), 3.81 (s, 3H).

Reference Example 7-48

1-{5-[2-Fluoro-3-(hydroxymethyl)phenyl]-3-methoxypyridin-2-yl}azetidin-3-one O-methyl oxime (Reference Compound 7-48)

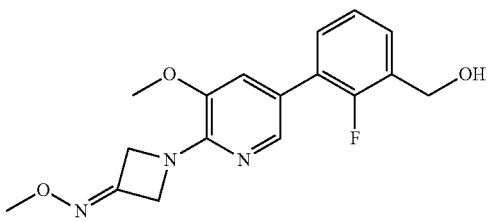 [SMILES: CON=C1CN(c2ncc(-c3cccc(CO)c3F)cc2OC)C1]

The reaction was performed by the method described in Reference Example 7-2, except that 1-[5-(3-{[(tert-butyldimethylsilyl)oxy]methyl}-2-fluorophenyl)pyrimidin-2-yl]azetidin-3-one O-ethyl oxime (Reference Compound 6-2) was replaced by 1-[5-(3-{[(tert-butyldimethylsilyl)oxy]methyl}-2-fluorophenyl)-3-methoxypyridin-2-yl]azetidin-3-one O-methyl oxime synthesized in the same manner as in Reference Example 6-40. Consequently, the title compound (yield 84%) was obtained as a white solid.

Mass spectrum (ESI, m/z):332[M+1]$^+$.

$^1$H-NMR spectrum (400 MHz, DMSO-d$_6$) δ:7.92-7.88 (m, 1H), 7.48-7.40 (m, 2H), 7.34-7.30 (m, 1H), 7.29-7.23 (m, 1H), 5.31 (t, J=5.4 Hz, 1H), 4.80-4.72 (m, 4H), 4.60 (d, J=5.4 Hz, 2H), 3.82 (s, 3H), 3.80 (s, 3H).

Reference Example 7-49

1-{5-[2-Fluoro-3-(hydroxymethyl)phenyl]pyrimidin-2-yl}piperidin-4-one O-methyloxime (Reference Compound 7-49)

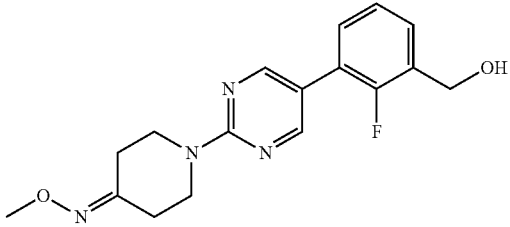 [SMILES: CON=C1CCN(c2ncc(-c3cccc(CO)c3F)cn2)CC1]

The reaction was performed by the method described in Reference Example 7-1, except that 1-[5-(3-{[(tert-butyldimethylsilyl)oxy]methyl}-2-fluorophenyl)pyrimidin-2-yl]azetidin-3-one O-methyl oxime (Reference Compound 6-1) was replaced by 1-[5-(3-{[(tert-butyldimethylsilyl)oxy]methyl}-2-fluorophenyl)pyrimidin-2-yl]piperidin-4-one O-methyl oxime synthesized in the same manner as in Reference Example 60. Consequently, the title compound (including impurities) was obtained as a white solid.

Mass spectrum (CI, m/z):331[M+1]$^+$.

$^1$H-NMR spectrum (400 MHz, DMSO-d$_6$) δ:8.59 (d, J=1.4 Hz, 2H), 7.51-7.38 (m, 2H), 7.33-7.21 (m, 1H), 5.34 (br s, 1H), 4.60 (br s, 2H), 3.95-3.89 (m, 4H), 3.76 (s, 3H), 2.59-2.53 (m, 2H), 2.41-2.24 (m, 2H).

Reference Example 7-50

1-{5-[2-Fluoro-3-(hydroxymethyl)phenyl]pyrimidin-2-yl}piperidin-4-one (Reference Compound 7-50)

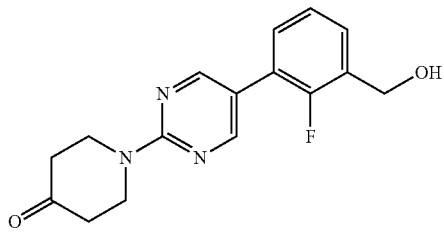 [SMILES: O=C1CCN(c2ncc(-c3cccc(CO)c3F)cn2)CC1]

The reaction was performed by the method described in Reference Example 7-1, except that 1-[5-(3-{[(tert-butyldimethylsilyl)oxy]methyl}-2-fluorophenyl)pyrimidin-2-yl]azetidin-3-one O-methyl oxime (Reference Compound 6-1) was replaced by 1-[5-(3-{[(tert-butyldimethylsilyl)oxy]methyl}-2-fluorophenyl)pyrimidin-2-yl]piperidin-4-one synthesized in the same manner as in Reference Example 6-41, and the concentrated residue was purified by silica gel column chromatography. Consequently, the title compound (including impurities) was obtained as a white oil.

Mass spectrum (CI, m/z):302[M+1]$^+$.

$^1$H-NMR spectrum (400 MHz, CDCl$_3$) δ:8.57 (d, J=1.5 Hz, 2H), 7.52-7.41 (m, 1H), 7.36-7.29 (m, 1H), 7.28-7.22 (m, 1H), 4.84 (d, J=6.0 Hz, 2H), 4.22-4.17 (m, 4H), 2.58-2.52 (m, 4H), 1.90 (t, J=6.0 Hz, 1H).

Reference Example 7-51

1-{5-[2-Fluoro-3-(hydroxymethyl)phenyl]pyrimidin-2-yl}piperidin-4-one O-{3-[(tetrahydropyran-2-yl)oxy]propyl} oxime (Reference Compound 7-51)

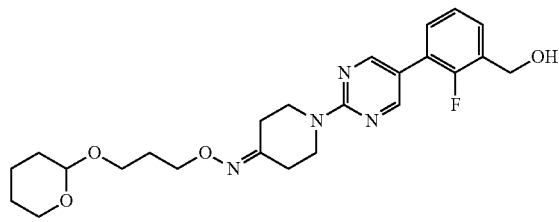 [SMILES: OCc1cccc(-c2cnc(N3CCC(=NOCCCOC4CCCCO4)CC3)nc2)c1F]

The reaction was performed by the method described in Reference Example 7-2, except that 1-[5-(3-{[(tert-butyldimethylsilyl)oxy]methyl}-2-fluorophenyl)pyrimidin-2-yl]azetidin-3-one O-ethyl oxime (Reference Compound 6-2) was replaced by 1-[5-(3-{[(tert-butyldimethylsilyl)oxy]methyl}-2-fluorophenyl)pyrimidin-2-yl]piperidin-4-one O-{3-[(tetrahydropyran-2-yl)oxy]propyl} oxime synthesized in the same manner as in Reference Example 6-42. Consequently, the title compound (yield 85%) was obtained as a colorless oil.

Reference Example 7-52

1-{5-[2-Fluoro-3-(hydroxymethyl)phenyl]pyrimidin-2-yl}piperidin-4-one O-{4-[(tetrahydropyran-2-yl)oxy]butyl} oxime (Reference Compound 7-52)

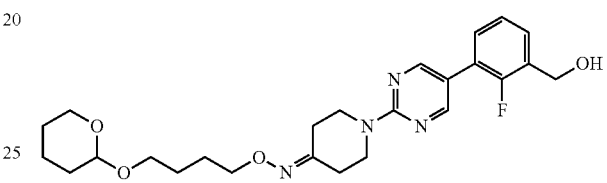

The reaction was performed by the method described in Reference Example 7-2, except that 1-[5-(3-{[(tert-butyldimethylsilyl)oxy]methyl}-2-fluorophenyl)pyrimidin-2-yl]azetidin-3-one O-ethyl oxime (Reference Compound 6-2) was replaced by 1-[5-(3-{[(tert-butyldimethylsilyl)oxy]methyl}-2-fluorophenyl)pyrimidin-2-yl]piperidin-4-one O-{4-[(tetrahydropyran-2-yl)oxy]butyl} oxime synthesized in the same manner as in Reference Example 6-43. Consequently, the title compound (yield 77%) was obtained as a colorless oil.

Mass spectrum (CI, m/z):473 [M+1].

$^1$H-NMR spectrum (400 MHz, DMSO-d$_6$) δ:8.59 (d, J=1.5 Hz, 2H), 7.52-7.39 (m, 2H), 7.32-7.21 (m, 1H), 5.33 (t, J=4.2 Hz, 1H), 4.60 (d, J=4.2 Hz, 2H), 4.56-4.51 (m, 1H), 4.02-3.96 (m, 2H), 3.95-3.88 (m, 4H), 3.77-3.68 (m, 1H), 3.67-3.60 (m, 1H), 3.46-3.34 (m, 2H), 2.62-2.55 (m, 2H), 2.42-2.34 (m, 2H), 1.80-1.34 (m, 10H).

Reference Example 7-53

1-{5-[2-Fluoro-3-(hydroxymethyl)phenyl]pyrimidin-2-yl}piperidin-4-one O-(2-methoxyethyl) oxime (Reference Compound 7-53)

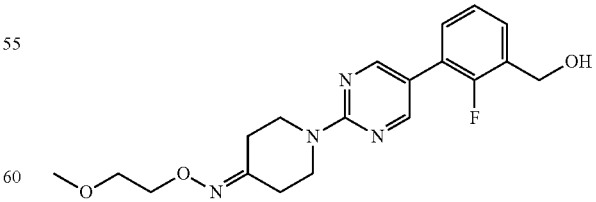

The reaction was performed by the method described in Reference Example 7-1, except that 1-[5-(3-{[(tert-butyldimethylsilyl)oxy]methyl}-2-fluorophenyl)pyrimidin-2-yl]azetidin-3-one O-methyl oxime (Reference Compound 6-1) was replaced by 1-[5-(3-{[(tert-butyldimethylsilyl)oxy]

methyl}-2-fluorophenyl)pyrimidin-2-yl]piperidin-4-one O-(2-methoxyethyl) oxime synthesized in the same manner as in Reference Example 6-44, and the concentrated residue was purified by silica gel column chromatography. Consequently, the title compound (yield 79%) was obtained as a white solid.

Mass spectrum (CI, ml/z):375[M+1]⁺.

¹H-NMR spectrum (400 MHz, DMSO-d₆) δ:8.59 (d, J=1.5 Hz, 2H), 7.49-7.41 (m, 2H), 7.31-7.24 (m, 1H), 5.33 (t, J=5.6 Hz, 1H), 4.60 (d, J=5.6 Hz, 2H), 4.13-4.05 (m, 2H), 3.96-3.88 (m, 4H), 3.57-3.51 (m, 2H), 3.26 (s, 3H), 2.62-2.55 (m, 2H), 2.42-2.34 (m, 2H).

Reference Example 7-54

1-{5-[2-Fluoro-3-(hydroxymethyl)phenyl]pyrimidin-2-yl}piperidin-4-one O-{2,2-dimethyl-3-[(tetrahydropyran-2-yl)oxy]propyl} oxime (Reference Compound 7-54)

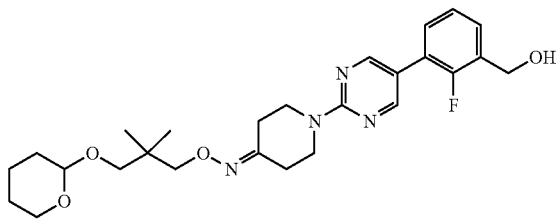 [SMILES: CC(C)(CON=C1CCN(c2ncc(-c3cccc(CO)c3F)cn2)CC1)COC1CCCCO1]

The reaction was performed by the method described in Reference Example 7-2, except that 1-[5-(3-{[(tert-butyldimethylsilyl)oxy]methyl}-2-fluorophenyl)pyrimidin-2-yl]azetidin-3-one O-ethyl oxime (Reference Compound 6-2) was replaced by 1-[5-(3-{[(tert-butyldimethylsilyl)oxy]methyl}-2-fluorophenyl)pyrimidin-2-yl]piperidin-4-one 0-{2,2-dimethyl-3-[(tetrahydropyran-2-yl)oxy]propyl} oxime synthesized in the same manner as in Reference Example 6-45. Consequently, the title compound (yield 89%) was obtained as a white foam.

Mass spectrum (CI, m/z):487[M+1]⁺.

¹H-NMR spectrum (400 MHz, CDCl₃) δ:8.53 (d, J=1.5 Hz, 2H), 7.46-7.39 (m, 1H), 7.35-7.19 (m, 2H), 4.86-4.80 (m, 2H), 4.60-4.56 (m, 1H), 4.03-3.97 (m, 4H), 3.95-3.89 (m, 2H), 3.88-3.80 (m, 1H), 3.56 (d, J=9.3 Hz, 1H), 3.53-3.45 (m, 1H), 3.12 (d, J=9.3 Hz, 1H), 2.75-2.66 (m, 2H), 2.50-2.44 (m, 2H), 1.90-1.45 (m, 6H), 0.98 (s, 3H), 0.97 (s, 3H).

Reference Example 7-55

1-{5-[2-Fluoro-3-(hydroxymethyl)phenyl]pyrimidin-2-yl}piperidin-4-one O-{3-methyl-3-[(tetrahydropyran-2-yl)oxy]butyl} oxime (Reference Compound 7-55)

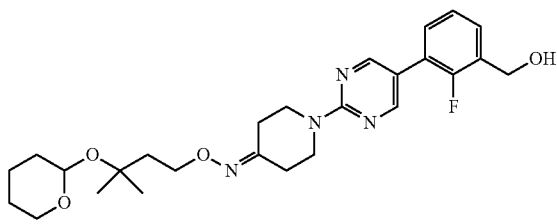 [SMILES: CC(C)(CCON=C1CCN(c2ncc(-c3cccc(CO)c3F)cn2)CC1)OC1CCCCO1]

The reaction was performed by the method described in Reference Example 7-2, except that 1-[5-(3-{[(tert-butyldimethylsilyl)oxy]methyl}-2-fluorophenyl)pyrimidin-2-yl]azetidin-3-one O-ethyl oxime (Reference Compound 6-2) was replaced by 1-[5-(3-{[(tert-butyldimethylsilyl)oxy]methyl}-2-fluorophenyl)pyrimidin-2-yl]piperidin-4-one O-{3-methyl-3-[(tetrahydropyran-2-yl)oxy]butyl} oxime synthesized in the same manner as in Reference Example 6-46. Consequently, the title compound (yield 94%) was obtained as a colorless oil.

Mass spectrum (CI, m/z):487[M+1]⁺.

¹H-NMR spectrum (400 MHz, CDCl₃) 5:8.53 (d, J=1.5 Hz, 2H), 7.45-7.40 (m, 1H), 7.34-7.27 (m, 1H), 7.25-7.21 (m, 1H), 4.83 (d, J=4.9 Hz, 2H), 4.80-4.77 (m, 1H), 4.25-4.15 (m, 2H), 4.07-3.89 (m, 5H), 3.51-3.41 (m, 1H), 2.71-2.64 (m, 2H), 2.50-2.43 (m, 2H), 1.97-1.80 (m, 4H), 1.74-1.60 (m, 1H), 1.55-1.40 (m, 4H), 1.28 (s, 3H), 1.26 (s, 3H).

Reference Example 7-56

1-{5-[2-Fluoro-3-(hydroxymethyl)phenyl]pyrimidin-2-yl}piperidin-4-one O-{2-[(tetrahydropyran-2-yl)oxy]propyl} oxime (Reference Compound 7-56)

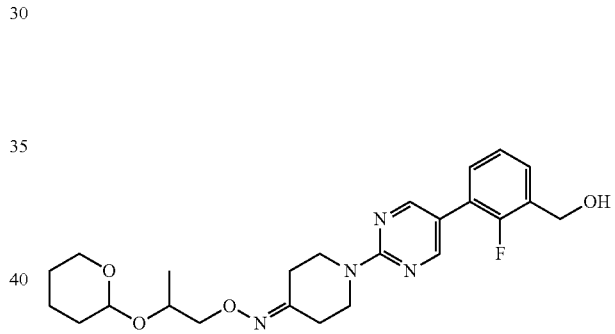

The reaction was performed by the method described in Reference Example 7-2, except that 1-[5-(3-{[(tert-butyldimethylsilyl)oxy]methyl}-2-fluorophenyl)pyrimidin-2-yl]azetidin-3-one O-ethyl oxime (Reference Compound 6-2) was replaced by 1-[5-(3-{[(tert-butyldimethylsilyl)oxy]methyl}-2-fluorophenyl)pyrimidin-2-yl]piperidin-4-one 0-{2-[(tetrahydropyran-2-yl)oxy]propyl} oxime synthesized in the same manner as in Reference Example 71. Consequently, the title compound (yield 94%) was obtained as a light yellow foam.

Mass spectrum (DUIS, m/z):459[M+1]⁺.

¹H-NMR spectrum (400 MHz, CDCl₃) δ:8.55-8.51 (m, 2H), 7.46-7.40 (m, 1H), 7.35-7.29 (m, 1H), 7.25-7.20 (m, 1H), 4.83 (s, 2H), 4.81-4.73 (m, 1H), 4.19-4.07 (m, 2H), 4.07-3.90 (m, 6H), 3.62-3.42 (m, 1H), 2.75-2.65 (m, 2H), 2.50-2.43 (m, 2H), 1.93-1.44 (m, 7H), 1.26-1.11 (m, 3H).

Reference Example 7-57

1-{5-[2-Fluoro-3-(hydroxymethyl)phenyl]pyrimidin-2-yl}piperidin-4-one O-{2-methyl-3-[(tetrahydropyran-2-yl)oxy]propyl)}oxime (Reference Compound 7-57)

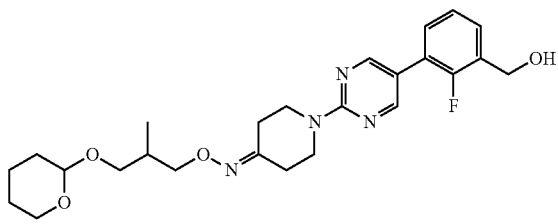 [SMILES: CC(CON=C1CCN(c2ncc(-c3cccc(CO)c3F)cn2)CC1)COC1CCCCO1]

The reaction was performed by the method described in Reference Example 7-2, except that 1-[5-(3-{[(tert-butyldimethylsilyl)oxy]methyl}-2-fluorophenyl)pyrimidin-2-yl]azetidin-3-one O-ethyl oxime (Reference Compound 6-2) was replaced by 1-[5-(3-{[(tert-butyldimethylsilyl)oxy]methyl}-2-fluorophenyl)pyrimidin-2-yl]piperidin-4-one O-{2-methyl-3-[(tetrahydropyran-2-yl)oxy]propyl} oxime synthesized in the same manner as in Reference Example 6-47. Consequently, the title compound (yield 78%) was obtained as a white foam.

Mass spectrum (CI, m/z):473[M+1]$^+$.

$^1$H-NMR spectrum (400 MHz, CDCl$_3$) δ:8.53 (d, J=1.5 Hz, 2H), 7.45-7.39 (m, 1H), 7.35-7.20 (m, 2H), 4.83 (d, J=6.0 Hz, 2H), 4.61-4.58 (m, 1H), 4.12-3.24 (m, 10H), 2.73-2.65 (m, 2H), 2.50-2.43 (m, 2H), 2.24-2.13 (m, 1H), 1.89-1.46 (m, 7H), 1.04-0.98 (m, 3H).

Reference Example 7-58

1-{5-[2-Fluoro-3-(hydroxymethyl)phenyl]pyrimidin-2-yl}piperidin-4-one O-[(2,2-dimethyl-1,3-dioxan-5-yl)methyl] oxime (Reference Compound 7-58)

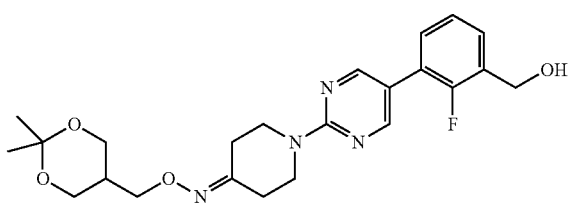 [SMILES: CC1(C)OCC(CON=C2CCN(c3ncc(-c4cccc(CO)c4F)cn3)CC2)CO1]

The reaction was performed by the method described in Reference Example 7-2, except that 1-[5-(3-{[(tert-butyldimethylsilyl)oxy]methyl}-2-fluorophenyl)pyrimidin-2-yl]azetidin-3-one O-ethyl oxime (Reference Compound 6-2) was replaced by 1-[5-(3-{[(tert-butyldimethylsilyl)oxy]methyl}-2-fluorophenyl)pyrimidin-2-yl]piperidin-4-one O-[(2,2-dimethyl-1,3-dioxan-5-yl)methyl] oxime synthesized in the same manner as in Reference Example 6-48. Consequently, the title compound (yield 85%) was obtained as a white solid.

Mass spectrum (EI, m/z):444[M]$^+$.

$^1$H-NMR spectrum (400 MHz, CDCl$_3$) δ:8.53 (d, J=1.5 Hz, 2H), 7.45-7.40 (m, 1H), 7.34-7.28 (m, 1H), 7.26-7.21 (m, 1H), 4.83 (d, J=6.1 Hz, 2H), 4.12 (d, J=6.9 Hz, 2H), 4.03-3.96 (m, 6H), 3.77 (dd, J=6.5, 12.0 Hz, 2H), 2.70-2.65 (m, 2H), 2.48-2.43 (m, 2H), 2.19-2.10 (m, 1H), 1.82 (t, J=6.1 Hz, 1H), 1.44 (s, 3H), 1.42 (s, 3H).

Reference Example 7-59

1-{5-[2-Fluoro-3-(hydroxymethyl)phenyl]pyrimidin-2-yl}piperidin-4-one O-[(2,2,5-trimethyl-1,3-dioxan-5-yl)methyl] oxime (Reference Compound 7-59)

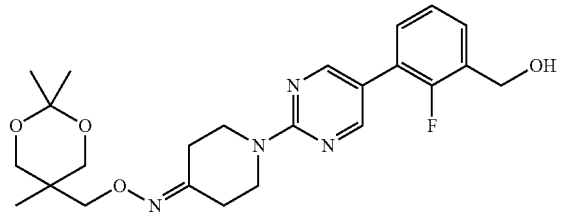 [SMILES: CC1(CON=C2CCN(c3ncc(-c4cccc(CO)c4F)cn3)CC2)COC(C)(C)OC1]

The reaction was performed by the method described in Reference Example 7-2, except that 1-[5-(3-{[(tert-butyldimethylsilyl)oxy]methyl}-2-fluorophenyl)pyrimidin-2-yl]azetidin-3-one O-ethyl oxime (Reference Compound 6-2) was replaced by 1-[5-(3-{[(tert-butyldimethylsilyl)oxy]methyl}-2-fluorophenyl)pyrimidin-2-yl]piperidin-4-one O-[(2,2,5-trimethyl-1,3-dioxan-5-yl)methyl] oxime synthesized in the same manner as in Reference Example 6-49. Consequently, the title compound (yield 76%) was obtained as a white foam.

Mass spectrum (CI, m/z):459[M+1]$^+$.

$^1$H-NMR spectrum (400 MHz, CDCl$_3$) δ:8.53 (d, J=1.4 Hz, 2H), 7.45-7.39 (m, 1H), 7.35-7.21 (m, 7H), 4.86-4.80 (m, 2H), 4.11 (s, 2H), 4.03-3.97 (m, 4H), 3.75 (d, J=11.9 Hz, 2H), 3.58 (d, J=11.9 Hz, 2H), 2.71-2.66 (m, 2H), 2.51-2.44 (m, 2H), 1.85-1.78 (m, 1H), 1.44 (s, 3H), 1.42 (s, 3H), 0.95 (s, 3H).

Reference Example 7-60

1-{5-[2-Fluoro-3-(hydroxymethyl)phenyl]pyrimidin-2-yl}piperidin-4-one O-[(2,2-dimethyl-1,3-dioxolan-4-yl)methyl] oxime (Reference Compound 7-60)

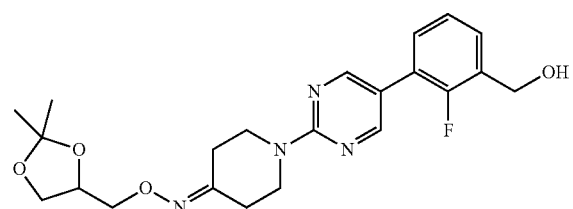

The reaction was performed by the method described in Reference Example 7-2, except that 1-[5-(3-{[(tert-butyldimethylsilyl)oxy]methyl}-2-fluorophenyl)pyrimidin-2-yl]azetidin-3-one O-ethyl oxime (Reference Compound 6-2) was replaced by 1-[5-(3-{[(tert-butyldimethylsilyl)oxy]methyl}-2-fluorophenyl)pyrimidin-2-yl]piperidin-4-one O-[(2,2-dimethyl-1,3-dioxolan-4-yl)methyl] oxime synthesized in the same manner as in Reference Example 6-50. Consequently, the title compound (yield 81%) was obtained as a white solid.

Mass spectrum (CI, m/z):431[M+1]+.

$^1$H-NMR spectrum (400 MHz, DMSO-d$_6$) δ:8.59 (d, J=1.5 Hz, 2H), 7.49-7.41 (m, 2H), 7.31-7.24 (m, 1H), 5.32 (t, J=5.7 Hz, 1H), 4.60 (d, J=5.7 Hz, 2H), 4.31-4.25 (m, 1H), 4.07-3.97 (m, 3H), 3.97-3.88 (m, 4H), 3.67 (dd, J=6.5. 8.3 Hz, 1H), 2.62-2.55 (m, 2H), 2.43-2.33 (m, 2H), 1.33 (s, 3H), 1.28 (s, 3H).

Reference Example 7-61

2-{[(1-{5-[2-Fluoro-3-(hydroxymethyl)phenyl]pyrimidin-2-yl}piperidin-4-ylidene)amino]oxy}ethyl acetate (Reference Compound 7-61)

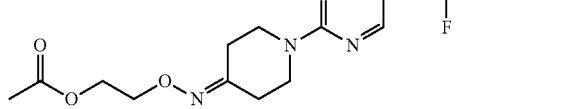

The reaction was performed by the method described in Reference Example 7-2, except that 1-[5-(3-{[(tert-butyldimethylsilyl)oxy]methyl}-2-fluorophenyl)pyrimidin-2-yl]azetidin-3-one O-ethyl oxime (Reference Compound 6-2) was replaced by 2-[({1-[5-(3-{[(tert-butyldimethylsilyl)oxy]methyl}-2-fluorophenyl)pyrimidin-2-yl]piperidin-4-ylidene}amino)oxy]ethyl acetate synthesized in the same manner as in Reference Example 6-51. Consequently, the title compound (yield 81%) was obtained as a white solid.

Mass spectrum (CI, m/z):403[M+1]+.

$^1$H-NMR spectrum (400 MHz, DMSO-d$_6$) δ:8.59 (d, J=1.5 Hz, 2H), 7.49-7.41 (m, 2H), 7.30-7.25 (m, 1H), 5.33 (t, J=5.3 Hz, 1H), 4.60 (d, J=5.3 Hz, 2H), 4.27-4.12 (m, 4H), 3.96-3.89 (m, 4H), 2.64-2.54 (m, 2H), 2.44-2.32 (m, 2H), 2.03 (s, 3H).

Reference Example 7-62 tert-Butyl 2-{[(1-{5-[2-fluoro-3-(hydroxymethyl)phenyl]pyrimidin-2-yl}azetidin-3-ylidene)amino]oxy}acetate (Reference Compound 7-62)

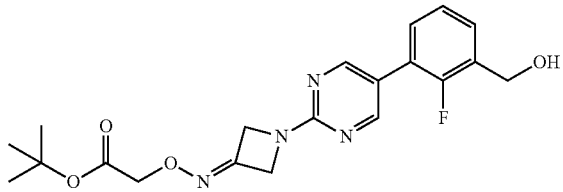 [SMILES: CC(C)(C)OC(=O)CON=C1CN(c2ncc(-c3cccc(CO)c3F)cn2)C1]

The reaction was performed by the method described in Reference Example 7-2, except that 1-[5-(3-{[(tert-butyldimethylsilyl)oxy]methyl}-2-fluorophenyl)pyrimidin-2-yl]azetidin-3-one O-ethyl oxime (Reference Compound 6-2) was replaced by tert-butyl 2-[({1-[5-(3-{[(tert-butyldimethylsilyl)oxy]methyl}-2-fluorophenyl)pyrimidin-2-yl]azetidin-3-ylidene}amino)oxy]acetate synthesized in the same manner as in Reference Example 6-52. Consequently, the title compound (yield 46%) was obtained as a white solid.

Mass spectrum (CI, m/z):403[M+1]+.

$^1$H-NMR spectrum (400 MHz, CDCl$_3$) δ:8.57 (d, J=1.4 Hz, 2H), 7.48-7.42 (m, 1H), 7.34-7.21 (m, 2H), 4.99-4.88 (m, 4H), 4.83 (br s, 2H), 4.52 (s, 2H), 1.50 (s, 9H).

Reference Example 7-63

1-{5-[2-Fluoro-3-(hydroxymethyl)phenyl]pyrimidin-2-yl}azetidin-3-one O-dimethylcarbamoyl oxime (Reference Compound 7-63)

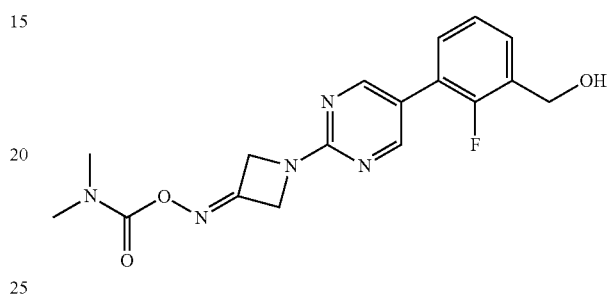

The reaction was performed by the method described in Reference Example 7-2, except that 1-[5-(3-{[(tert-butyldimethylsilyl)oxy]methyl}-2-fluorophenyl)pyrimidin-2-yl]azetidin-3-one O-ethyl oxime (Reference Compound 6-2) was replaced by 1-[5-(3-{[(tert-butyldimethylsilyl)oxy]methyl}-2-fluorophenyl)pyrimidin-2-yl]azetidin-3-one O-dimethylcarbamoyl oxime synthesized in the same manner as in Reference Example 15-4. Consequently, the title compound (yield 49%) was obtained as a light yellow solid.

Mass spectrum (CI, m/z):360[M+1]+.

$^1$H-NMR spectrum (400 MHz, CDCl$_3$) δ:8.58 (d, J=1.4 Hz, 2H), 7.50-7.44 (m, 1H), 7.35-7.23 (m, 2H), 5.04-4.95 (m, 4H), 4.84 (s, 2H), 3.02 (br s, 3H), 2.96 (br s, 3H).

Reference Example 7-64)

2-({[1-{5-[2-Fluoro-3-(hydroxymethyl)phenyl]pyrimidin-2-yl}azetidin-3-ylidene]amino}oxy)-N-methylacetamide (Reference Compound 7-64)

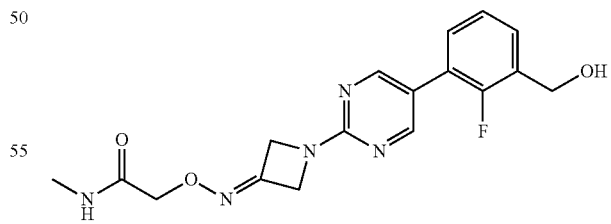

The reaction was performed by the method described in Reference Example 7-2, except that 1-[5-(3-{[(tert-butyldimethylsilyl)oxy]methyl}-2-fluorophenyl)pyrimidin-2-yl]azetidin-3-one O-ethyl oxime (Reference Compound 6-2) was replaced by 2-[({1-[5-(3-{[(tert-butyldimethylsilyl)oxy]methyl}-2-fluorophenyl)pyrimidin-2-yl]azetidin-3-ylidene}amino)oxy]-N-methylacetamide synthesized in the same manner as in Reference Example 6-53. Consequently, the title compound (yield 64%) was obtained as a white solid.

Mass spectrum (CI, m/z):360[M+1]⁺.

¹H-NMR spectrum (400 MHz, CDCl₃) δ:8.59 (d, J=1.5 Hz, 2H), 7.50-7.43 (m, 1H), 7.35-7.22 (m, 2H), 6.16 (br s, 1H), 4.96-4.90 (m, 4H), 4.84 (d, J=5.8 Hz, 2H), 4.58 (s, 2H), 2.91 (d, J=4.9 Hz, 3H), 1.86 (t, J=5.8 Hz, 1H).

Reference Example 7-65

3-{[(1-{5-[2-Fluoro-3-(hydroxymethyl)phenyl]pyrimidin-2-yl}azetidin-3-ylidene]amino}oxy)propanamide (Reference Compound 7-65)

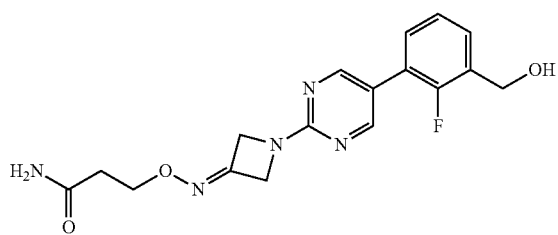 [SMILES: NC(=O)CCON=C1CN(c2ncc(-c3cccc(CO)c3F)cn2)C1]

The reaction was performed by the method described in Reference Example 7-2, except that 1-[5-(3-{[(tert-butyldimethylsilyl)oxy]methyl}-2-fluorophenyl)pyrimidin-2-yl]azetidin-3-one O-ethyl oxime (Reference Compound 6-2) was replaced by 3-[({1-[5-(3-{[(tert-butyldimethylsilyl)oxy]methyl}-2-fluorophenyl)pyrimidin-2-yl]azetidin-3-ylidene}amino)oxy]propanamide synthesized in the same manner as in Reference Example 6-54, that the purification by silica gel column chromatography was not performed, and that ethyl acetate was added to the product, and the mixture was stirred at room temperature and was thereafter filtered to afford the solid. Consequently, the title compound (including impurities) was obtained as a light yellow solid.

Mass spectrum (ESI, m/z):360[M+1]⁺.

¹H-NMR spectrum (400 MHz, DMSO-d₆) δ:8.62 (d, J=1.3 Hz, 2H), 7.55-7.47 (m, 1H), 7.47-7.36 (m, 2H), 7.31-7.25 (m, 1H), 6.86 (br s, 1H), 4.85-4.74 (m, 4H), 4.59 (s, 2H), 4.22 (t, J=6.5 Hz, 2H), 2.42 (t, J=6.5 Hz, 2H).

Reference Example 7-66

3-{[(1-{5-[2-Fluoro-3-(hydroxymethyl)phenyl]pyrimidin-2-yl]azetidin-3-ylidene}amino)oxy]-N-methylpropanamide (Reference Compound 7-66)

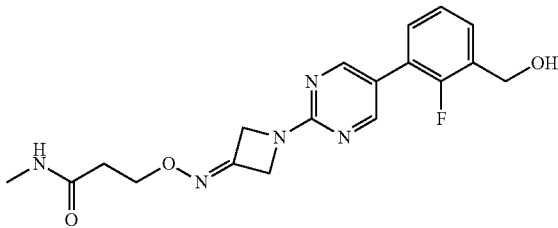 [SMILES: CNC(=O)CCON=C1CN(c2ncc(-c3cccc(CO)c3F)cn2)C1]

The reaction was performed by the method described in Reference Example 7-2, except that 1-[5-(3-{[(tert-butyldimethylsilyl)oxy]methyl}-2-fluorophenyl)pyrimidin-2-yl]azetidin-3-one O-ethyl oxime (Reference Compound 6-2) was replaced by 3-[({1-[5-(3-{[(tert-butyldimethylsilyl)oxy]methyl}-2-fluorophenyl)pyrimidin-2-yl]azetidin-3-ylidene}amino)oxy]-N-methylpropanamide synthesized in the same manner as in Reference Example 6-55, and the purification by silica gel column chromatography was not performed. Consequently, the title compound (including impurities) was obtained as a light yellow solid.

¹H-NMR spectrum (400 MHz, DMSO-d₆) δ:8.62 (d, J=1.5 Hz, 2H), 8.05-7.88 (m, 1H), 7.53-7.47 (m, 1H), 7.46-7.38 (m, 1H), 7.32-7.23 (m, 1H), 4.86-4.73 (m, 4H), 4.59 (s, 2H), 4.22 (t, J=6.5 Hz, 2H), 2.57 (d, J=3.4 Hz, 3H), 2.43 (t, J=6.5 Hz, 2H).

Reference Example 7-67

Ethyl 4-{[(1-{5-[2-fluoro-3-(hydroxymethyl)phenyl]pyrimidin-2-yl}azetidin-3-ylidene)amino]oxy}butanoate (Reference Compound 7-67)

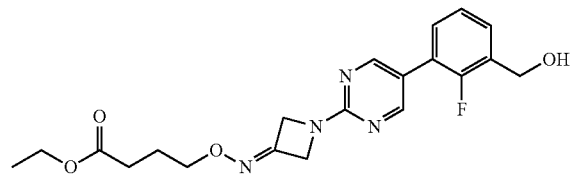 [SMILES: CCOC(=O)CCCON=C1CN(c2ncc(-c3cccc(CO)c3F)cn2)C1]

The reaction was performed by the method described in Reference Example 7-2, except that 1-[5-(3-{[(tert-butyldimethylsilyl)oxy]methyl}-2-fluorophenyl)pyrimidin-2-yl]azetidin-3-one O-ethyl oxime (Reference Compound 6-2) was replaced by ethyl 4-[({1-[5-(3-{[(tert-butyldimethylsilyl)oxy]methyl}-2-fluorophenyl)pyrimidin-2-yl]azetidin-3-ylidene}amino)oxy]butanoate synthesized in the same manner as in Reference Example 6-56. Consequently, the title compound (yield 82%) was obtained as a white solid.

Mass spectrum (CI, m/z):403[M+1]⁺.

¹H-NMR spectrum (400 MHz, DMSO-d₆) δ:8.63 (d, J=1.5 Hz, 2H), 7.52-7.41 (m, 2H), 7.31-7.26 (m, 1H), 5.34 (t, J=4.1 Hz, 1H), 4.90-4.74 (m, 4H), 4.60 (d, J=4.1 Hz, 2H), 4.11-4.01 (m, 4H), 2.38 (t, J=7.3 Hz, 2H), 1.92-1.82 (m, 2H), 1.18 (t, J=7.2 Hz, 3H).

Reference Example 7-68

4-{[(1-{5-[2-Fluoro-3-(hydroxymethyl)phenyl]pyrimidin-2-yl}azetidin-3-ylidene)amino]oxy}-N-methylbutanamide (Reference Compound 7-68)

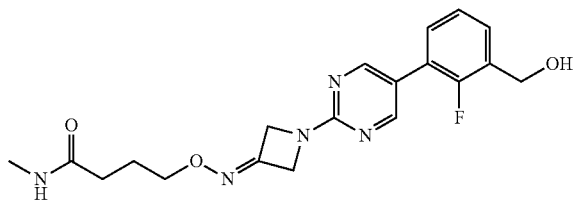 [SMILES: CNC(=O)CCCON=C1CN(c2ncc(-c3cccc(CO)c3F)cn2)C1]

The reaction was performed by the method described in Reference Example 7-1, except that 1-[5-(3-{[(tert-butyldimethylsilyl)oxy]methyl}-2-fluorophenyl)pyrimidin-2-yl]azetidin-3-one O-methyl oxime (Reference Compound 6-1) was replaced by 4-[({1-[5-(3-{[(tert-butyldimethylsilyl)oxy]methyl}-2-fluorophenyl)pyrimidin-2-yl]azetidin-3-ylidene}amino)oxy]-N-methylbutanamide synthesized in the same manner as in Reference Example 6-57, and that ethyl acetate, instead of TBME, was added to the concentrated residue, and the mixture was stirred at room temperature. Consequently, the title compound (yield 64%) was obtained as a white solid.

Mass spectrum (CI, m/z):388[M+1]$^+$.

$^1$H-NMR spectrum (400 MHz, CDCl$_3$) δ:8.57 (d, J=1.5 Hz, 2H), 7.48-7.43 (m, 1H), 7.34-7.21 (m, 2H), 5.48 (br s, 1H), 4.92-4.79 (m, 6H), 4.13 (t, J=6.1 Hz, 2H), 2.83 (d, J=4.9 Hz, 3H), 2.31-2.25 (m, 2H), 2.08-1.99 (m, 2H), 1.90 (br s, 1H).

Reference Example 7-69

1-{5-[2-Fluoro-3-(hydroxymethyl)phenyl]pyrimidin-2-yl}azetidin-3-one O-[2-(dimethylamino)ethyl] oxime (Reference Compound 7-69)

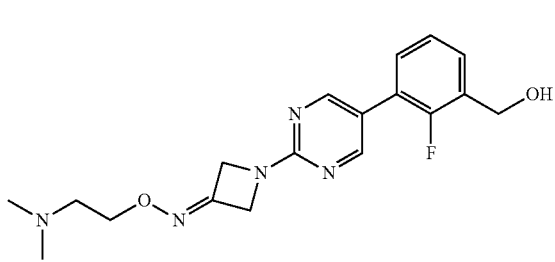 [SMILES: CN(C)CCON=C1CN(c2ncc(-c3cccc(CO)c3F)cn2)C1]

The reaction was performed by the method described in Reference Example 7-1, except that 1-[5-(3-{[(tert-butyldimethylsilyl)oxy]methyl}-2-fluorophenyl)pyrimidin-2-yl]azetidin-3-one O-methyl oxime (Reference Compound 6-1) was replaced by 1-[5-(3-{[(tert-butyldimethylsilyl)oxy]methyl}-2-fluorophenyl)pyrimidin-2-yl]azetidin-3-one O-[2-(dimethylamino)ethyl] oxime synthesized in the same manner as in Reference Example 83, and the concentrated residue was purified by silica gel column chromatography. Consequently, the title compound (yield 16%) was obtained as a white solid.

Mass spectrum (ESI, m/z):360[M+1]$^+$.

Reference Example 7-70

1-{5-[2-Fluoro-3-(hydroxymethyl)phenyl]pyrimidin-2-yl}azetidin-3-one O-{2-[benzyl(methyl)amino]ethyl} oxime (Reference Compound 7-70)

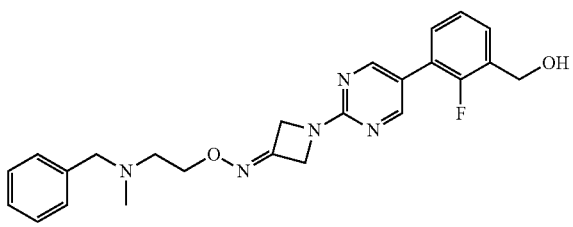 [SMILES: CN(CCON=C1CN(c2ncc(-c3cccc(CO)c3F)cn2)C1)Cc1ccccc1]

The reaction was performed by the method described in Reference Example 7-2, except that 1-[5-(3-{[(tert-butyldimethylsilyl)oxy]methyl}-2-fluorophenyl)pyrimidin-2-yl]azetidin-3-one O-ethyl oxime (Reference Compound 6-2) was replaced by 1-[5-(3-{[(tert-butyldimethylsilyl)oxy)methyl)-2-fluorophenyl)pyrimidin-2-yl)azetidin-3-one O-{2-[benzyl(methyl)amino]ethyl} oxime synthesized in the same manner as in Reference Example 84-1. Consequently, the title compound (quantitative yield) was obtained as a white solid.

Mass spectrum (ESI, m/z):436[M+1]$^+$.

$^1$H-NMR (400 MHz, DMSO-d$_6$) δ:8.63 (d, J=1.5 Hz, 2H), 7.53-7.41 (m, 2H), 7.35-7.17 (m, 6H), 5.34 (t, J=5.6 Hz, 1H), 4.82-4.75 (m, 4H), 4.60 (d, J=5.6 Hz, 2H), 4.14 (t, J=6.0 Hz, 2H), 3.52 (s, 2H), 2.62 (t, J=6.0 Hz, 2H), 2.20 (s, 3H).

Reference Example 7-71

N-(3-{[(1-{5-[2-fluoro-3-(hydroxymethyl)phenyl]pyrimidin-2-yl}azetidin-3-ylidene)amino]oxy}-2-{[(tetrahydropyran-2-yl)oxy]methyl}propyl)acetamide (Reference Compound 7-71)

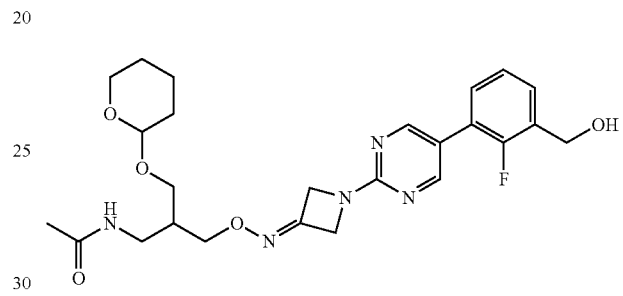

The reaction was performed by the method described in Reference Example 7-2, except that 1-[5-(3-{[(tert-butyldimethylsilyl)oxy]methyl}-2-fluorophenyl)pyrimidin-2-yl]azetidin-3-one O-ethyl oxime (Reference Compound 6-2) was replaced by N-{3-[({1-[5-(3-{[(tert-butyldimethylsilyl)oxy]methyl}-2-fluorophenyl)pyrimidin-2-yl]azetidin-3-ylidene}amino)oxy]-2-{[(tetrahydropyran-2-yl)oxy]methyl}propyl}acetamide synthesized in the same manner as in Reference Example 87-1. Consequently, the title compound (yield 97%) was obtained as a white solid.

Mass spectrum (CI, m/z):502[M+1]$^+$.

$^1$H-NMR spectrum (400 MHz, DMSO-d$_6$) 5:8.63 (d, J=1.5 Hz, 2H), 7.88-7.80 (m, 1H), 7.52-7.41 (m, 2H), 7.34-7.26 (m, 1H), 5.34 (t, J=5.6 Hz, 1H), 4.89-4.76 (m, 4H), 4.60 (d, J=5.6 Hz, 2H), 4.56-4.52 (m, 1H), 4.13-3.95 (m, 2H), 3.80-3.55 (m, 2H), 3.48-3.26 (m, 2H), 3.17-3.08 (m, 2H), 2.17-2.05 (m, 1H), 1.81 (s, 3H), 1.77-1.39 (m, 6H).

Reference Example 7-72

1-{5-[2-Fluoro-3-(hydroxymethyl)phenyl]pyrimidin-2-yl}azetidin-3-one O-[3-(dimethylamino)-2-{[(tetrahydropyran-2-yl)oxy]methyl}propyl] oxime (Reference Compound 7-72)

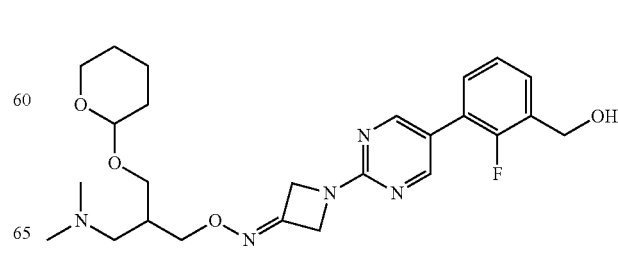

The reaction was performed by the method described in Reference Example 7-2, except that 1-[5-(3-{[(tert-butyldimethylsilyl)oxy]methyl}-2-fluorophenyl)pyrimidin-2-yl]azetidin-3-one O-ethyl oxime (Reference Compound 6-2) was replaced by 1-[5-(3-{[(tert-butyldimethylsilyl)oxy]methyl}-2-fluorophenyl)pyrimidin-2-yl]azetidin-3-one O-[3-(dimethylamino)-2-{[(tetrahydropyran-2-yl)oxy]methyl}propyl] oxime synthesized in the same manner as in Reference Example 88. Consequently, the title compound (yield 38%) was obtained as a white solid.

$^1$H-NMR spectrum (400 MHz, DMSO-$d_6$) δ:8.63 (d, J=1.4 Hz, 2H), 7.52-7.41 (m, 2H), 7.32-7.26 (m, 1H), 5.40-5.28 (m, 1H), 4.91-4.74 (m, 4H), 4.63-4.59 (m, 2H), 4.57-4.52 (m, 1H), 4.10-4.02 (m, 2H), 3.81-3.57 (m, 2H), 3.47-3.34 (m, 2H), 2.30-2.19 (m, 2H), 2.18-2.09 (m, 7H), 1.81-1.39 (m, 6H).

Reference Example 7-73

N-(3-{[(1-{5-[2-fluoro-3-(hydroxymethyl)phenyl]pyrimidin-2-yl}azetidin-3-ylidene)amino]oxy}-2-methoxypropyl)acetamide (Reference Compound 7-73)

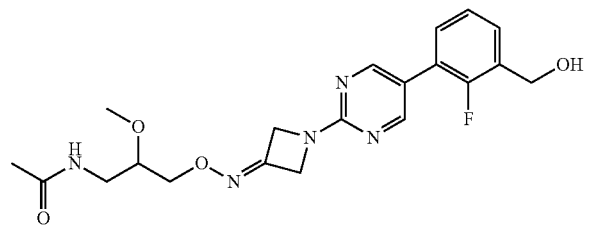 [SMILES: COC(CNC(C)=O)CON=C1CN(c2ncc(-c3cccc(CO)c3F)cn2)C1]

The reaction was performed by the method described in Reference Example 7-1, except that 1-[5-(3-{[(tert-butyldimethylsilyl)oxy]methyl}-2-fluorophenyl)pyrimidin-2-yl]azetidin-3-one O-methyl oxime (Reference Compound 6-1) was replaced by N-{3-[({1-[5-(3-{[(tert-butyldimethylsilyl)oxy]methyl}-2-fluorophenyl)pyrimidin-2-yl]azetidin-3-ylidene}amino)oxy]-2-methoxypropyl}acetamide synthesized in the same manner as in Reference Example 87-2. Consequently, the title compound (yield 68%) was obtained as a white solid.

Mass spectrum (CI, m/z):418[M+1]$^+$.

$^1$H-NMR spectrum (400 MHz, DMSO-$d_6$) δ:8.63 (d, J=1.1 Hz, 2H), 7.88 (t, J=5.5 Hz, 1H), 7.54-7.37 (m, 2H), 7.34-7.23 (m, 1H), 5.32 (t, J=5.7 Hz, 1H), 4.89-4.77 (m, 4H), 4.60 (d, J=5.7 Hz, 2H), 4.13-3.95 (m, 2H), 3.54-3.43 (m, 1H), 3.34 (s, 3H), 3.25-3.08 (m, 2H), 1.83 (s, 3H).

Reference Example 7-74

1-{5-[2-Fluoro-3-(hydroxymethyl)phenyl]pyrimidin-2-yl}azetidin-3-one O-[2-(piperidin-1-yl)ethyl] oxime (Reference Compound 7-74)

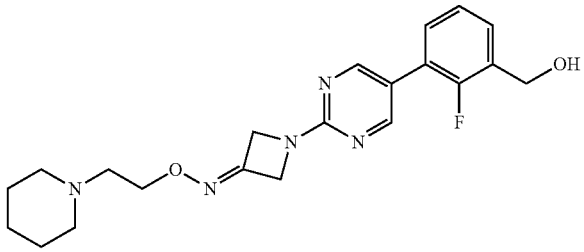 [SMILES: OCc1cccc(-c2cnc(N3CC(=NOCCN4CCCCC4)C3)nc2)c1F]

The reaction was performed by the method described in Reference Example 7-2, except that 1-[5-(3-{[(tert-butyldimethylsilyl)oxy]methyl}-2-fluorophenyl)pyrimidin-2-yl]azetidin-3-one O-ethyl oxime (Reference Compound 6-2) was replaced by 1-[5-(3-{[(tert-butyldimethylsilyl)oxy]methyl}-2-fluorophenyl)pyrimidin-2-yl]azetidin-3-one O-[2-(piperidin-1-yl)ethyl] oxime synthesized in the same manner as in Reference Example 84-2. Consequently, the title compound (yield 94%) was obtained as a white solid.

Mass spectrum (ESI, m/z):400[M+1]$^+$.

$^1$H-NMR (400 MHz, CDCl$_3$) δ:8.57 (d, J=1.5 Hz, 2H), 7.49-7.42 (m, 1H), 7.35-7.21 (m, 2H), 4.91-4.86 (m, 4H), 4.83 (s, 2H), 4.25 (t, J=6.0 Hz, 2H), 2.67 (t, J=6.0 Hz, 2H), 2.53-2.42 (m, 4H), 1.69-1.39 (m, 6H).

Reference Example 7-75

1-{5-[2-Fluoro-3-(hydroxymethyl)phenyl]pyrimidin-2-yl}azetidin-3-one O-(2-morpholinoethyl) oxime (Reference Compound 7-75)

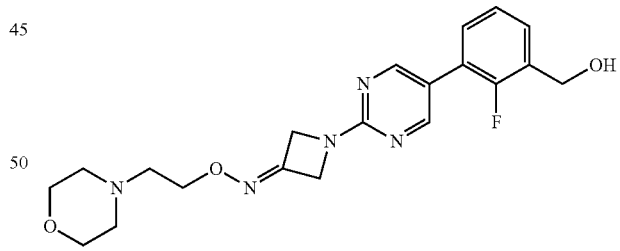

The reaction was performed by the method described in Reference Example 7-2, except that 1-[5-(3-{[(tert-butyldimethylsilyl)oxy]methyl}-2-fluorophenyl)pyrimidin-2-yl]azetidin-3-one O-ethyl oxime (Reference Compound 6-2) was replaced by 1-[5-(3-{[(tert-butyldimethylsilyl)oxy]methyl}-2-fluorophenyl)pyrimidin-2-yl]azetidin-3-one O-(2-morpholinoethyl) oxime synthesized in the same manner as in Reference Example 6-60. Consequently, the title compound (yield 99%) was obtained as a white solid.

Mass spectrum (ESI, m/z):402[M+1]$^+$.

$^1$H-NMR spectrum (400 MHz, DMSO-$d_6$) δ:8.63 (d, J=1.5 Hz, 2H), 7.51-7.42 (m, 2H), 7.31-7.27 (m, 1H), 5.34

(t, J=5.3 Hz, 1H), 4.84-4.77 (m, 4H), 4.60 (d, J=5.3 Hz, 2H), 4.15 (t, J=6.0 Hz, 2H), 3.59-3.54 (m, 4H), 2.58 (t, J=6.0 Hz, 2H), 2.46-2.38 (m, 4H).

Reference Example 7-76

1-{5-[2-Fluoro-3-(hydroxymethyl)phenyl]pyrimidin-2-yl}azetidin-3-one O-[2-(azetidin-1-yl)ethyl] oxime (Reference Compound 7-76)

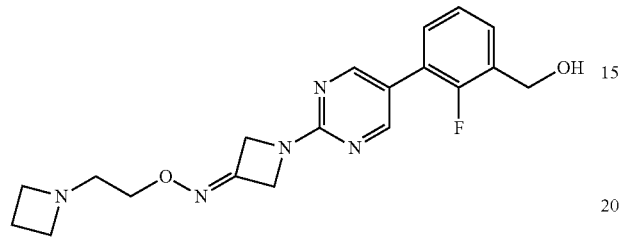

The reaction was performed by the method described in Reference Example 7-2, except that 1-[5-(3-{[(tert-butyldimethylsilyl)oxy]methyl}-2-fluorophenyl)pyrimidin-2-yl]azetidin-3-one O-ethyl oxime (Reference Compound 6-2) was replaced by 1-[5-(3-{[(tert-butyldimethylsilyl)oxy]methyl}-2-fluorophenyl)pyrimidin-2-yl]azetidin-3-one O-[2-(azetidin-1-yl)ethyl] oxime synthesized in the same manner as in Reference Example 6-61. Consequently, the title compound (yield 78%) was obtained as a white solid.

Mass spectrum (ESI, m/z):372[M+1]⁺.

$^1$H-NMR spectrum (400 MHz, DMSO-$d_6$) δ:8.62 (d, J=1.4 Hz, 2H), 7.51-7.42 (m, 2H), 7.32-7.26 (m, 1H), 5.34 (t, J=5.5 Hz, 1H), 4.85-4.75 (m, 4H), 4.60 (d, J=5.5 Hz, 2H), 3.97 (t, J=5.8 Hz, 2H), 3.16-3.09 (m, 4H), 2.59 (t, J=5.8 Hz, 2H), 2.07-1.78 (m, 2H).

Reference Example 7-77

1-{5-[2-Fluoro-3-(hydroxymethyl)phenyl]pyrimidin-2-yl}azetidin-3-one O-[2-(3,3-difluoroazetidin-1-yl)ethyl] oxime (Reference Compound 7-77)

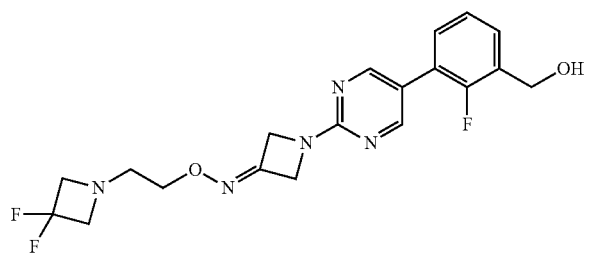 [SMILES: OCc1cccc(-c2cnc(N3CC(=NOCCN4CC(F)(F)C4)C3)nc2)c1F]

The reaction was performed by the method described in Reference Example 7-2, except that 1-[5-(3-{[(tert-butyldimethylsilyl)oxy]methyl}-2-fluorophenyl)pyrimidin-2-yl]azetidin-3-one O-ethyl oxime (Reference Compound 6-2) was replaced by 1-[5-(3-{[(tert-butyldimethylsilyl)oxy]methyl}-2-fluorophenyl)pyrimidin-2-yl]azetidin-3-one O-[2-(3,3-difluoroazetidin-1-yl)ethyl] oxime synthesized in the same manner as in Reference Example 84-3. Consequently, the title compound (yield 72%) was obtained as a white solid.

Mass spectrum (ESI, m/z):408[M+1]⁺.

$^1$H-NMR (400 MHz, CDCl$_3$) δ:8.57 (d, J=1.5 Hz, 2H), 7.49-7.42 (m, 1H), 7.36-7.21 (m, 2H), 4.93-4.80 (m, 6H), 4.17 (t, J=5.3 Hz, 2H), 3.66 (t, J=12.0 Hz, 4H), 2.88 (t, J=5.3 Hz, 2H).

Reference Example 7-78

1-{5-[2-Fluoro-3-(hydroxymethyl)phenyl]pyrimidin-2-yl}azetidin-3-one O-[2-(3-fluoroazetidin-1-yl)ethyl] oxime (Reference Compound 7-78)

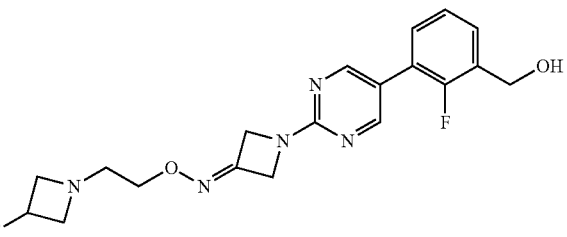

The reaction was performed by the method described in Reference Example 7-2, except that 1-[5-(3-{[(tert-butyldimethylsilyl)oxy]methyl}-2-fluorophenyl)pyrimidin-2-yl]azetidin-3-one O-ethyl oxime (Reference Compound 6-2) was replaced by 1-[5-(3-{[(tert-butyldimethylsilyl)oxy]methyl}-2-fluorophenyl)pyrimidin-2-yl]azetidin-3-one O-[2-(3-fluoroazetidin-1-yl)ethyl] oxime synthesized in the same manner as in Reference Example 84-4. Consequently, the title compound (yield 78%) was obtained as a white solid.

Mass spectrum (ESI, m/z):390[M+1]⁺.

$^1$H-NMR (400 MHz, DMSO-$d_6$) δ:8.63 (d, J=1.4 Hz, 2H), 7.52-7.41 (m, 2H), 7.32-7.25 (m, 1H), 5.33 (t, J=5.7 Hz, 1H), 5.24-5.02 (m, 1H), 4.88-4.75 (m, 4H), 4.60 (d, J=5.7 Hz, 2H), 4.02 (t, J=5.5 Hz, 2H), 3.65-3.53 (m, 2H), 3.20-3.05 (m, 2H), 2.71 (t, J=5.5 Hz, 2H).

Reference Example 7-79

1-{5-[2-Fluoro-3-(hydroxymethyl)phenyl]pyrimidin-2-yl}azetidin-3-one O-[2-(3-methoxyazetidin-1-yl)ethyl] oxime (Reference Compound 7-79)

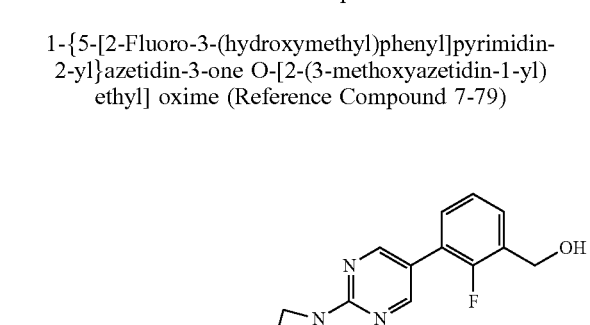

The reaction was performed by the method described in Reference Example 7-2, except that 1-[5-(3-{[(tert-butyldimethylsilyl)oxy]methyl}-2-fluorophenyl)pyrimidin-2-yl]azetidin-3-one O-ethyl oxime (Reference Compound 6-2) was replaced by 1-[5-(3-{[(tert-butyldimethylsilyl)oxy]methyl}-2-fluorophenyl)pyrimidin-2-yl]azetidin-3-one O-[2-(3-methoxyazetidin-1-yl)ethyl] oxime synthesized in the same manner as in Reference Example 84-5. Consequently, the title compound (yield 66%) was obtained as a white solid.

Mass spectrum (ESI, m/z):402[M+1]$^+$.

$^1$H-NMR (400 MHz, DMSO-d$_6$) δ:8.62 (d, J=1.4 Hz, 2H), 7.52-7.40 (m, 2H), 7.32-7.25 (m, 1H), 5.33 (t, J=5.7 Hz, 1H), 4.86-4.75 (m, 4H), 4.60 (d, J=5.7 Hz, 2H), 4.03-3.88 (m, 3H), 3.55-3.48 (m, 2H), 3.13 (s, 3H), 2.86-2.78 (m, 2H), 2.69-2.61 (m, 2H).

Reference Example 7-80

1-{5-[2-Fluoro-3-(hydroxymethyl)phenyl]pyrimidin-2-yl}azetidin-3-one O-[(4-methylmorpholin-2-yl)methyl] oxime (Reference Compound 7-80)

The reaction was performed by the method described in Reference Example 7-2, except that 1-[5-(3-{[(tert-butyldimethylsilyl)oxy]methyl}-2-fluorophenyl)pyrimidin-2-yl]azetidin-3-one O-ethyl oxime (Reference Compound 6-2) was replaced by 1-[5-(3-{[(tert-butyldimethylsilyl)oxy]methyl}-2-fluorophenyl)pyrimidin-2-yl]azetidin-3-one O-[(4-methylmorpholin-2-yl)methyl] oxime synthesized in the same manner as in Reference Example 6-62. Consequently, the title compound (yield 79%) was obtained as a white solid.

$^1$H-NMR spectrum (400 MHz, DMSO-d$_6$) δ:8.63 (d, J=1.4 Hz, 2H), 7.51-7.42 (m, 2H), 7.32-7.26 (m, 1H), 5.34 (t, J=5.5 Hz, 1H), 4.86-4.78 (m, 4H), 4.60 (d, J=5.5 Hz, 2H), 4.06-3.93 (m, 2H), 3.80-3.74 (m, 1H), 3.74-3.66 (m, 1H), 3.53-3.45 (m, 1H), 2.73-2.68 (m, 1H), 2.60-2.53 (m, 1H), 2.17 (s, 3H), 2.00-1.92 (m, 1H), 1.77-1.71 (m, 1H).

Reference Example 7-81

1-[2-({[(1-{5-[2-Fluoro-3-(hydroxymethyl)phenyl]pyrimidin-2-yl}azetidin-3-ylidene)amino)oxy]methyl)morpholino}ethanone (Reference Compound 7-81)

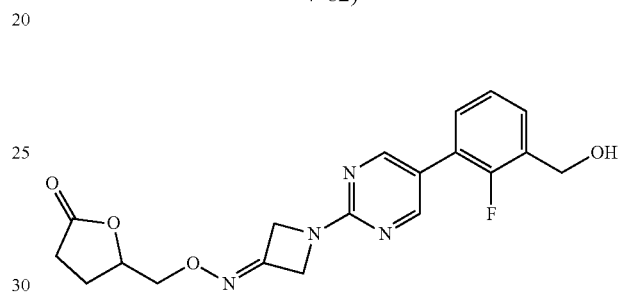

The reaction was performed by the method described in Reference Example 7-2, except that 1-[5-(3-{[(tert-butyldimethylsilyl)oxy]methyl}-2-fluorophenyl)pyrimidin-2-yl]azetidin-3-one O-ethyl oxime (Reference Compound 6-2) was replaced by 1-(2-{[({1-[5-(3-{[(tert-butyldimethylsilyl)oxy]methyl}-2-fluorophenyl)pyrimidin-2-yl]azetidin-3-ylidene}amino)oxy]methyl}morpholino)ethanone synthesized in the same manner as in Reference Example 6-63. Consequently, the title compound (yield 74%) was obtained as a white solid.

$^1$H-NMR spectrum (400 MHz, DMSO-d$_6$) δ:8.63 (d, J=1.4 Hz, 2H), 7.51-7.42 (m, 2H), 7.32-7.26 (m, 1H), 5.34 (t, J=5.7 Hz, 1H), 4.86-4.79 (m, 4H), 4.60 (d, J=5.7 Hz, 2H), 4.33-3.98 (m, 3H), 3.88-3.82 (m, 1H), 3.79-3.52 (m, 2H), 3.49-3.26 (m, 1H), 3.21-2.92 (m, 1H), 2.73-2.45 (m, 1H), 2.03-1.98 (m, 3H).

Reference Example 7-82

5-({[(1-{5-[2-Fluoro-3-(hydroxymethyl)phenyl]pyrimidin-2-yl}azetidin-3-ylidene)amino]oxy}methyl)dihydrofuran-2(3H)-one (Reference Compound 7-82)

The reaction was performed by the method described in Reference Example 7-2, except that 1-[5-(3-{[(tert-butyldimethylsilyl)oxy]methyl}-2-fluorophenyl)pyrimidin-2-yl]azetidin-3-one O-ethyl oxime (Reference Compound 6-2) was replaced by 5-{[({1-[5-(3-{[(tert-butyldimethylsilyl)oxy]methyl}-2-fluorophenyl)pyrimidin-2-yl]azetidin-3-ylidene}amino)oxy]methyl}dihydrofuran-2(3H)-one synthesized in the same manner as in Reference Example 15-5. Consequently, the title compound (yield 72%) was obtained as a white solid.

Mass spectrum (CI, m/z):387[M+1]$^+$.

$^1$H-NMR spectrum (400 MHz, CDCl$_3$) δ:8.57 (d, J=1.4 Hz, 2H), 7.49-7.43 (m, 1H), 7.35-7.21 (m, 2H), 4.92-4.86 (m, 4H), 4.86-4.76 (m, 3H), 4.33-4.20 (m, 2H), 2.60-2.53 (m, 2H), 2.41-2.31 (m, 1H), 2.16-2.04 (m, 1H), 1.89-1.81 (m, 1H).

Reference Example 7-83

3-{[(1-{5-[2-Fluoro-3-(hydroxymethyl)phenyl]pyrimidin-2-yl}azetidin-3-ylidene)amino]oxy}cyclobutyl acetate (Reference Compound 7-83)

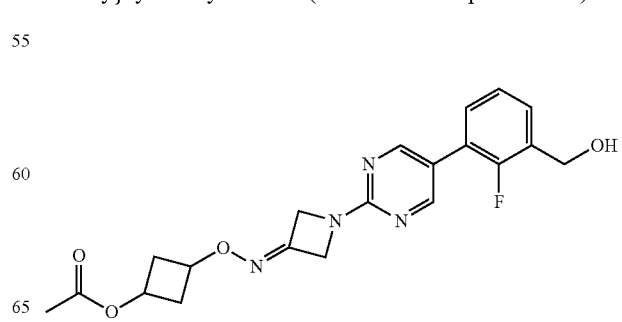

The reaction was performed by the method described in Reference Example 7-2, except that 1-[5-(3-{[(tert-butyldimethylsilyl)oxy]methyl}-2-fluorophenyl)pyrimidin-2-yl]azetidin-3-one O-ethyl oxime (Reference Compound 6-2) was replaced by 3-[({1-[5-(3-{[(tert-butyldimethylsilyl)oxy]methyl}-2-fluorophenyl)pyrimidin-2-yl]azetidin-3-ylidene}amino)oxy]cyclobutyl acetate synthesized in the same manner as in Reference Example 6-64, and the reaction temperature was changed to 0° C. Consequently, the title compound (yield 82%) was obtained as a white solid.

Mass spectrum (CI, m/z):401[M+1]$^+$.

$^1$H-NMR spectrum (400 MHz, DMSO-d$_6$) δ:8.63 (d, J=1.4 Hz, 2H), 7.51-7.42 (m, 2H), 7.32-7.27 (m, 1H), 5.34 (t, J=5.7 Hz, 1H), 5.08-5.01 (m, 1H), 4.86-4.79 (m, 5H), 4.60 (d, J=5.7 Hz, 2H), 2.51-2.44 (m, 2H), 2.40-2.31 (m, 2H), 2.01 (s, 3H).

Reference Example 7-84

1-{5-[2-Fluoro-3-(hydroxymethyl)phenyl]pyrimidin-2-yl}azetidin-3-one O-benzyl oxime (Reference Compound 7-84)

The reaction was performed by the method described in Reference Example 7-2, except that 1-[5-(3-{[(tert-butyldimethylsilyl)oxy]methyl}-2-fluorophenyl)pyrimidin-2-yl]azetidin-3-one O-ethyl oxime (Reference Compound 6-2) was replaced by 1-[5-(3-{[(tert-butyldimethylsilyl)oxy]methyl}-2-fluorophenyl)pyrimidin-2-yl]azetidin-3-one O-benzyl oxime synthesized in the same manner as in Reference Example 6-65. Consequently, the title compound (yield 68%) was obtained as a white solid.

Mass spectrum (CI, m/z):379[M+1]$^+$.

$^1$H-NMR spectrum (400 MHz, DMSO-d$_6$) δ:8.62 (d, J=1.5 Hz, 2H), 7.51-7.26 (m, 8H), 5.34 (t, J=5.6 Hz, 1H), 5.09 (s, 2H), 4.83 (s, 4H), 4.60 (d, J=5.6 Hz, 2H).

Reference Example 7-85

1-{5-[2-Fluoro-3-(hydroxymethyl)phenyl]pyrimidin-2-yl}azetidin-3-one O-(4-methoxybenzyl) oxime (Reference Compound 7-85)

The reaction was performed by the method described in Reference Example 7-2, except that 1-[5-(3-{[(tert-butyldimethylsilyl)oxy]methyl}-2-fluorophenyl)pyrimidin-2-yl]azetidin-3-one O-ethyl oxime (Reference Compound 6-2) was replaced by 1-[5-(3-{[(tert-butyldimethylsilyl)oxy]methyl}-2-fluorophenyl)pyrimidin-2-yl]azetidin-3-one O-(4-methoxybenzyl) oxime synthesized in the same manner as in Reference Example 15-6. Consequently, the title compound (yield 98%) was obtained as a white solid.

Mass spectrum (CI, m/z):409[M+1]$^+$.

$^1$H-NMR spectrum (400 MHz, CDCl$_3$) δ:8.55 (d, J=1.5 Hz, 2H), 7.48-7.41 (m, 1H), 7.35-7.20 (m, 4H), 6.93-6.87 (m, 2H), 5.05 (s, 2H), 4.90-4.80 (m, 6H), 3.82 (s, 3H), 1.84 (t, J=5.9 Hz, 1H).

Reference Example 7-86

1-{5-[2-Fluoro-3-(hydroxymethyl)phenyl]pyrimidin-2-yl}azetidin-3-one O-(1-methylazetidin-3-yl) oxime (Reference Compound 7-86)

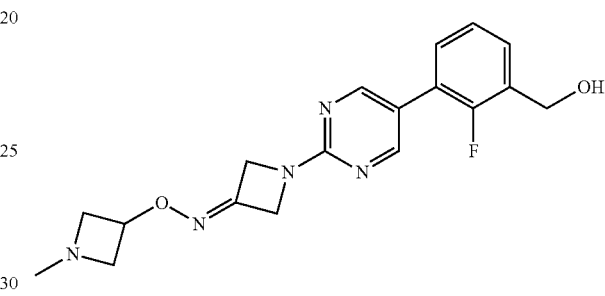

The reaction was performed by the method described in Reference Example 7-2, except that 1-[5-(3-{[(tert-butyldimethylsilyl)oxy]methyl}-2-fluorophenyl)pyrimidin-2-yl]azetidin-3-one O-ethyl oxime (Reference Compound 6-2) was replaced by 1-[5-(3-{[(tert-butyldimethylsilyl)oxy]methyl}-2-fluorophenyl)pyrimidin-2-yl]azetidin-3-one O-(1-methylazetidin-3-yl) oxime synthesized in the same manner as in Reference Example 6-66. Consequently, the title compound (including impurities) was obtained as a brown oil.

Mass spectrum (ESI, m/z):358[M+1]$^+$.

$^1$H-NMR spectrum (400 MHz, DMSO-d$_6$) δ:8.63 (d, J=1.4 Hz, 2H), 7.54-7.37 (m, 2H), 7.35-7.20 (m, 1H), 4.87-4.79 (m, 4H), 4.75-4.65 (m, 1H), 4.59 (s, 2H), 3.58-3.46 (m, 2H), 3.04-2.92 (m, 2H), 2.25 (s, 3H).

Reference Example 7-87

1-(3-{[(1-{5-[2-Fluoro-3-(hydroxymethyl)phenyl]pyrimidin-2-yl}azetidin-3-ylidene)amino]oxy}azetidin-1-yl)ethanone (Reference Compound 7-87)

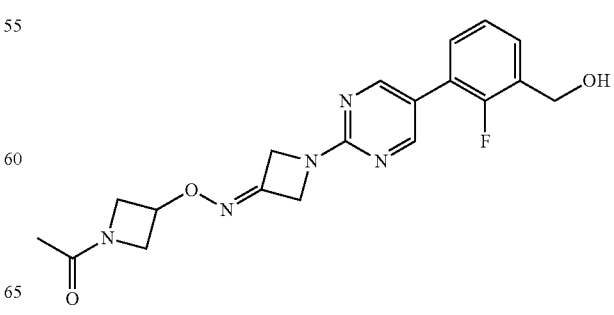

The reaction was performed by the method described in Reference Example 7-2, except that 1-[5-(3-{[(tert-butyldimethylsilyl)oxy]methyl}-2-fluorophenyl)pyrimidin-2-yl]azetidin-3-one O-ethyl oxime (Reference Compound 6-2) was replaced by 1-{3-[({1-[5-(3-{[(tert-butyldimethylsilyl)oxy]methyl}-2-fluorophenyl)pyrimidin-2-yl]azetidin-3-ylidene}amino)oxy]azetidin-1-yl}ethanone synthesized in the same manner as in Reference Example 6-67. Consequently, the title compound (including impurities) was obtained as a yellow solid.

¹H-NMR spectrum (400 MHz, DMSO-d₆) δ:8.63 (d, J=1.5 Hz, 2H), 7.55-7.37 (m, 2H), 7.33-7.21 (m, 1H), 5.01-4.92 (m, 1H), 4.90-4.83 (m, 4H), 4.60 (s, 2H), 4.42-4.32 (m, 1H), 4.15-4.03 (m, 2H), 3.83-3.72 (m, 1H), 1.78 (s, 3H).

Reference Example 7-88

1-{5-[2-Fluoro-3-(hydroxymethyl)phenyl]pyrimidin-2-yl}azetidin-3-one O-(1-benzylazetidin-3-yl) oxime (Reference Compound 7-88)

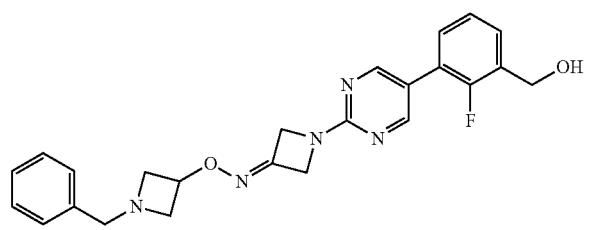 [SMILES: OCc1cccc(-c2cnc(N3CC(=NOC4CN(Cc5ccccc5)C4)C3)nc2)c1F]

The reaction was performed by the method described in Reference Example 7-2, except that 1-[5-(3-{[(tert-butyldimethylsilyl)oxy]methyl}-2-fluorophenyl)pyrimidin-2-yl]azetidin-3-one O-ethyl oxime (Reference Compound 6-2) was replaced by 1-[5-(3-{[(tert-butyldimethylsilyl)oxy]methyl}-2-fluorophenyl)pyrimidin-2-yl]azetidin-3-one O-(1-benzylazetidin-3-yl) oxime synthesized in the same manner as in Reference Example 6-68. Consequently, the title compound (yield 82%) was obtained as a white solid.

Mass spectrum (ESI, m/z):434[M+1]⁺.

¹H-NMR spectrum (400 MHz, DMSO-d₆) δ:8.63 (d, J=1.4 Hz, 2H), 7.51-7.42 (m, 2H), 7.33-7.21 (m, 6H), 5.34 (t, J=5.5 Hz, 1H), 4.86-4.75 (m, 5H), 4.60 (d, J=5.5 Hz, 2H), 3.60 (s, 2H), 3.55-3.47 (m, 2H), 3.11-3.03 (m, 2H).

Reference Example 7-89

1-{5-[2-Fluoro-3-(hydroxymethyl)phenyl]pyrimidin-2-yl}azetidin-3-one O-[1-(2,2,2-trifluoroethyl)azetidin-3-yl] oxime (Reference Compound 7-89)

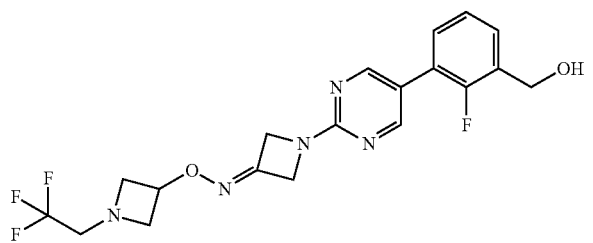 [SMILES: OCc1cccc(-c2cnc(N3CC(=NOC4CN(CC(F)(F)F)C4)C3)nc2)c1F]

The reaction was performed by the method described in Reference Example 7-2, except that 1-[5-(3-{[(tert-butyldimethylsilyl)oxy]methyl}-2-fluorophenyl)pyrimidin-2-yl]azetidin-3-one O-ethyl oxime (Reference Compound 6-2) was replaced by 1-[5-(3-{[(tert-butyldimethylsilyl)oxy]methyl}-2-fluorophenyl)pyrimidin-2-yl]azetidin-3-one O-[1-(2,2,2-trifluoroethyl)azetidin-3-yl] oxime synthesized in the same manner as in Reference Example 6-69. Consequently, the title compound (yield 81%) was obtained as a white solid.

Mass spectrum (ESI, m/z):426[M+1]⁺.

¹H-NMR spectrum (400 MHz, DMSO-d₆) δ:8.63 (d, J=1.4 Hz, 2H), 7.51-7.42 (m, 2H), 7.32-7.26 (m, 1H), 5.34 (t, J=5.7 Hz, 1H), 4.86-4.78 (m, 5H), 4.60 (d, J=5.7 Hz, 2H), 3.71-3.65 (m, 2H), 3.37-3.30 (m, 2H), 3.25 (q, J=10.1 Hz, 2H).

Reference Example 7-90

1-{5-[2-Fluoro-3-(hydroxymethyl)phenyl]pyrimidin-2-yl}azetidin-3-one O-[1-(methylsulfonyl)azetidin-3-yl] oxime (Reference Compound 7-90)

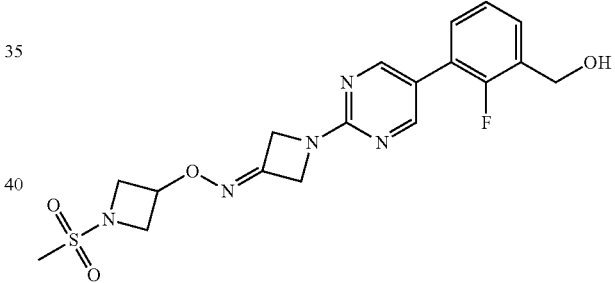

The reaction was performed by the method described in Reference Example 7-2, except that 1-[5-(3-{[(tert-butyldimethylsilyl)oxy]methyl}-2-fluorophenyl)pyrimidin-2-yl]azetidin-3-one O-ethyl oxime (Reference Compound 6-2) was replaced by 1-[5-(3-{[(tert-butyldimethylsilyl)oxy]methyl}-2-fluorophenyl)pyrimidin-2-yl]azetidin-3-one O-[1-(methylsulfonyl)azetidin-3-yl] oxime synthesized in the same manner as in Reference Example 6-70. Consequently, the title compound (yield 79%) was obtained as a white solid.

Mass spectrum (ESI, m/z):422[M+1]⁺.

¹H-NMR spectrum (400 MHz, DMSO-d₆) δ:8.64 (d, J=1.4 Hz, 2H), 7.54-7.40 (m, 2H), 7.33-7.25 (m, 1H), 5.34 (t, J=5.5 Hz, 1H), 4.96 (tt, J=4.6, 6.7 Hz, 1H), 4.90-4.83 (m, 4H), 4.60 (d, J=5.5 Hz, 2H), 4.14 (dd, J=6.7, 9.9 Hz, 2H), 3.92 (dd, J=4.6, 9.9 Hz, 2H), 3.04 (s, 3H).

Reference Example 7-91

1-{5-[2-Fluoro-3-(hydroxymethyl)phenyl]pyrimidin-2-yl}azetidin-3-one O-(1-ethylazetidin-3-yl) oxime (Reference Compound 7-91)

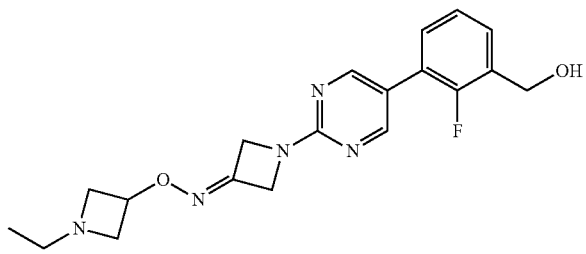 [SMILES: CCN1CC(ON=C2CN(c3ncc(-c4cccc(CO)c4F)cn3)C2)C1]

The reaction was performed by the method described in Reference Example 7-2, except that 1-[5-(3-{[(tert-butyldimethylsilyl)oxy]methyl}-2-fluorophenyl)pyrimidin-2-yl]azetidin-3-one O-ethyl oxime (Reference Compound 6-2) was replaced by 1-[5-(3-{[(tert-butyldimethylsilyl)oxy]methyl}-2-fluorophenyl)pyrimidin-2-yl]azetidin-3-one O-(1-ethylazetidin-3-yl) oxime synthesized in the same manner as in Reference Example 6-71. Consequently, the title compound (yield 78%) was obtained as a brown oil.

Mass spectrum (CI, m/z):372[M+1]$^+$.

$^1$H-NMR spectrum (400 MHz, DMSO-d$_6$) δ:8.63 (d, J=1.4 Hz, 2H), 7.51-7.42 (m, 2H), 7.32-7.26 (m, 1H), 5.34 (t, J=5.4 Hz, 1H), 4.87-4.80 (m, 4H), 4.77-4.69 (m, 1H), 4.60 (d, J=5.4 Hz, 2H), 3.51-3.44 (m, 2H), 2.97-2.90 (m, 2H), 2.41 (q, J=7.2 Hz, 2H), 0.87 (t, J=7.2 Hz, 3H).

Reference Example 7-92

Methyl 3-{[(1-{5-[2-fluoro-3-(hydroxymethyl)phenyl]pyrimidin-2-yl}azetidin-3-ylidene)amino]oxy}azetidine-1-carboxylate (Reference Compound 7-92)

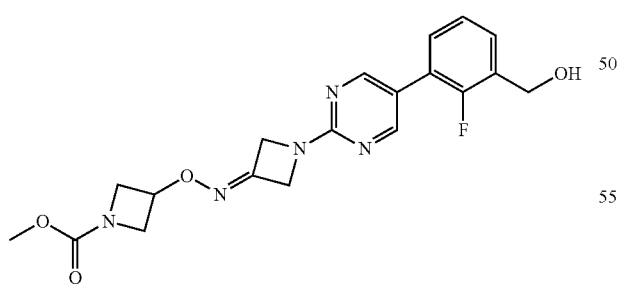

The reaction was performed by the method described in Reference Example 7-2, except that 1-[5-(3-{[(tert-butyldimethylsilyl)oxy]methyl}-2-fluorophenyl)pyrimidin-2-yl]azetidin-3-one O-ethyl oxime (Reference Compound 6-2) was replaced by methyl 3-[({1-[5-(3-{[(tert-butyldimethylsilyl)oxy]methyl}-2-fluorophenyl)pyrimidin-2-yl]azetidin-3-ylidene}amino)oxy]azetidine-1-carboxylate synthesized in the same manner as in Reference Example 6-72. Consequently, the title compound (including impurities) was obtained as a white solid.

Mass spectrum (ESI, m/z):402[M+1]$^+$.

$^1$H-NMR spectrum (400 MHz, DMSO-d$_6$) δ:8.63 (d, J=1.4 Hz, 2H), 7.53-7.40 (m, 2H), 7.34-7.22 (m, 1H), 5.35 (t, J=5.3 Hz, 1H), 5.00-4.93 (m, 1H), 4.89-4.82 (m, 4H), 4.60 (d, J=5.3 Hz, 2H), 4.25-4.10 (m, 2H), 3.97-3.83 (m, 2H), 3.57 (s, 3H).

Reference Example 7-93

1-(5-(2-Fluoro-3-(hydroxymethyl)phenyl)pyrimidin-2-yl)azetidin-3-one O-oxetan-3-yl oxime (Reference Compound 7-93)

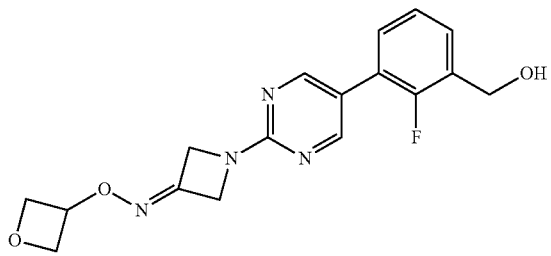 [SMILES: OCc1cccc(-c2cnc(N3CC(=NOC4COC4)C3)nc2)c1F]

The reaction was performed by the method described in Reference Example 7-2, except that 1-[5-(3-{[(tert-butyldimethylsilyl)oxy]methyl}-2-fluorophenyl)pyrimidin-2-yl]azetidin-3-one O-ethyl oxime (Reference Compound 6-2) was replaced by 1-[5-(3-{[(tert-butyldimethylsilyl)oxy]methyl}-2-fluorophenyl)pyrimidin-2-yl]azetidin-3-one O-oxetan-3-yl oxime synthesized in the same manner as in Reference Example 6-73. Consequently, the title compound (yield 59%) was obtained as a white solid.

Mass spectrum (CI, m/z):345[M+1]$^+$.

$^1$H-NMR spectrum (400 MHz, DMSO-d$_6$) δ:8.64 (d, J=1.1 Hz, 2H), 7.53-7.41 (m, 2H), 7.33-7.25 (m, 1H), 5.34 (t, J=5.7 Hz, 1H), 5.25-5.18 (m, 1H), 4.91-4.83 (m, 4H), 4.80-4.72 (m, 2H), 4.60 (d, J=5.7 Hz, 2H), 4.58-4.52 (m, 2H).

Reference Example 7-94

2-(3-{[(1-{5-[2-Fluoro-3-(hydroxymethyl)phenyl]pyrimidin-2-yl}azetidin-3-ylidene)amino]oxy}azetidin-1-yl)ethyl acetate (Reference Compound 7-94)

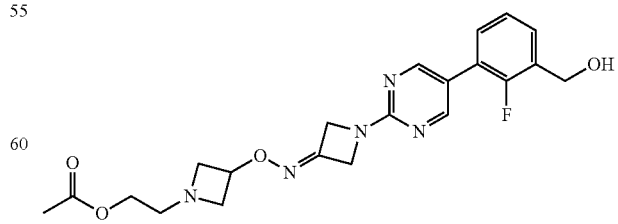

The reaction was performed by the method described in Reference Example 7-1, except that 1-[5-(3-{[(tert-butyldimethylsilyl)oxy]methyl}-2-fluorophenyl)pyrimidin-2- yl]azetidin-3-one O-methyl oxime (Reference Compound 6-1) was replaced by 2-{3-[({1-[5-(3-{[(tert-butyldimethylsilyl)oxy]methyl}-2-fluorophenyl)pyrimidin-2-yl]azetidin-3-ylidene}amino)oxy]azetidin-1-yl}ethyl acetate synthesized in the same manner as in Reference Example 6-74, and the concentrated residue was purified by silica gel column chromatography. Consequently, the title compound (yield 91%) was obtained as a white solid.

Mass spectrum (CI, m/z):430[M+1]$^+$.

$^1$H-NMR spectrum (400 MHz, DMSO-$d_6$) δ:8.63 (d, J=1.4 Hz, 2H), 7.51-7.42 (m, 2H), 7.32-7.26 (m, 1H), 5.33 (t, J=5.5 Hz, 1H), 4.88-4.79 (m, 4H), 4.79-4.71 (m, 1H), 4.60 (d, J=5.5 Hz, 2H), 3.96 (t, J=5.6 Hz, 2H), 3.58-3.52 (m, 2H), 3.10-3.04 (m, 2H), 2.65 (t, J=5.6 Hz, 2H), 2.00 (s, 3H).

Reference Example 7-95

1-{5-[2-Fluoro-3-(hydroxymethyl)phenyl]pyrimidin-2-yl}azetidin-3-one O-[1-(2-methoxyethyl)azetidin-3-yl] oxime (Reference Compound 7-95)

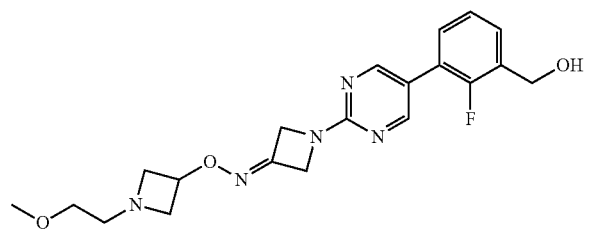 [SMILES: COCCN1CC(ON=C2CN(c3ncc(-c4cccc(CO)c4F)cn3)C2)C1]

The reaction was performed by the method described in Reference Example 7-1, except that 1-[5-(3-{[(tert-butyldimethylsilyl)oxy]methyl}-2-fluorophenyl)pyrimidin-2-yl]azetidin-3-one O-methyl oxime (Reference Compound 6-1) was replaced by 1-[5-(3-{[(tert-butyldimethylsilyl)oxy]methyl}-2-fluorophenyl)pyrimidin-2-yl]azetidin-3-one O-[1-(2-methoxyethyl)azetidin-3-yl] oxime synthesized in the same manner as in Reference Example 6-75, and the concentrated residue was purified by silica gel column chromatography. Consequently, the title compound (yield 71%) was obtained as a white solid.

Mass spectrum (CI, m/z):402[M+1]$^+$.

$^1$H-NMR spectrum (400 MHz, DMSO-$d_6$) δ:8.63 (d, J=1.4 Hz, 2H), 7.51-7.42 (m, 2H), 7.32-7.26 (m, 1H), 5.33 (t, J=5.4 Hz, 1H), 4.85-4.80 (m, 4H), 4.77-4.70 (m, 1H), 4.60 (d, J=5.4 Hz, 2H), 3.56-3.48 (m, 2H), 3.29 (t, J=5.8 Hz, 2H), 3.21 (s, 3H), 3.08-3.01 (m, 2H), 2.57 (t, J=5.8 Hz, 2H).

Reference Example 7-96

1-{5-[2-Fluoro-3-(hydroxymethyl)phenyl]pyrimidin-2-yl}azetidin-3-one O-[1-(2-fluoroethyl)azetidin-3-yl] oxime (Reference Compound 7-96)

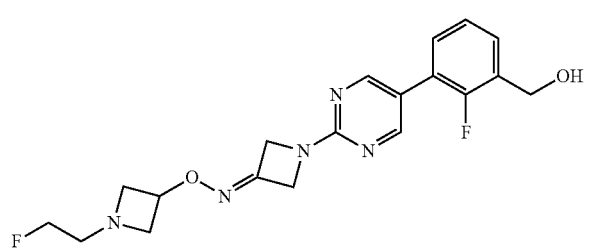 [SMILES: OCc1cccc(-c2cnc(N3CC(=NOC4CN(CCF)C4)C3)nc2)c1F]

The reaction was performed by the method described in Reference Example 7-1, except that 1-[5-(3-{[(tert-butyldimethylsilyl)oxy]methyl}-2-fluorophenyl)pyrimidin-2-yl]azetidin-3-one O-methyl oxime (Reference Compound 6-1) was replaced by 1-[5-(3-{[(tert-butyldimethylsilyl)oxy]methyl}-2-fluorophenyl)pyrimidin-2-yl]azetidin-3-one O-[1-(2-fluoroethyl)azetidin-3-yl] oxime synthesized in the same manner as in Reference Example 6-76, and the concentrated residue was purified by silica gel column chromatography. Consequently, the title compound (yield 71%) was obtained as a colorless oil.

Mass spectrum (CI, m/z):390[M+1]$^+$.

$^1$H-NMR spectrum (400 MHz, DMSO-$d_6$) δ:8.63 (d, J=1.4 Hz, 2H), 7.51-7.42 (m, 2H), 7.32-7.26 (m, 1H), 5.34 (t, J=5.3 Hz, 1H), 4.87-4.80 (m, 4H), 4.80-4.72 (m, 1H), 4.60 (d, J=5.3 Hz, 2H), 4.40 (td, J=4.8, 47.7 Hz, 2H), 3.61-3.53 (m, 2H), 3.15-3.05 (m, 2H), 2.71 (td, J=4.8, 29.1 Hz, 2H).

Reference Example 7-97

Ethyl 3-{[(1-{5-[2-fluoro-3-(hydroxymethyl)phenyl]pyrimidin-2-yl}piperidin-4-ylidene)amino]oxy}propanoate (Reference Compound 7-97)

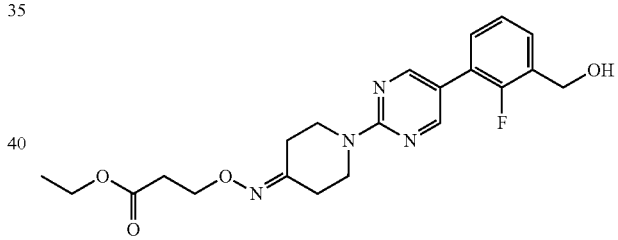

The reaction was performed by the method described in Reference Example 7-2, except that 1-[5-(3-{[(tert-butyldimethylsilyl)oxy]methyl}-2-fluorophenyl)pyrimidin-2-yl]azetidin-3-one O-ethyl oxime (Reference Compound 6-2) was replaced by ethyl 3-[({1-[5-(3-{[(tert-butyldimethylsilyl)oxy]methyl}-2-fluorophenyl)pyrimidin-2-yl]piperidin-4-ylidene}amino)oxy]propanoate synthesized in the same manner as in Reference Example 6-77. Consequently, the title compound (yield 39%) was obtained as a white solid.

Mass spectrum (CI, m/z):417[M+1]$^+$.

$^1$H-NMR spectrum (400 MHz, DMSO-$d_6$) δ:8.59 (d, J=1.5 Hz, 2H), 7.51-7.41 (m, 2H), 7.32-7.24 (m, 1H), 7.32-7.24 (m, 1H), 5.37-5.30 (m, 1H), 4.63-4.57 (m, 2H), 4.20 (t, J=6.1 Hz, 2H), 4.07 (q, J=7.2 Hz, 2H), 3.95-3.87 (m, 4H), 2.65-2.60 (m, 2H), 2.53 (t, J=6.1 Hz, 2H), 2.41-2.35 (m, 2H), 1.18 (t, J=7.2 Hz, 3H).

Reference Example 7-98

3-{[(1-{5-[2-Fluoro-3-(hydroxymethyl)phenyl]pyrimidin-2-yl}piperidin-4-ylidene)amino]oxy}propanamide (Reference Compound 7-98)

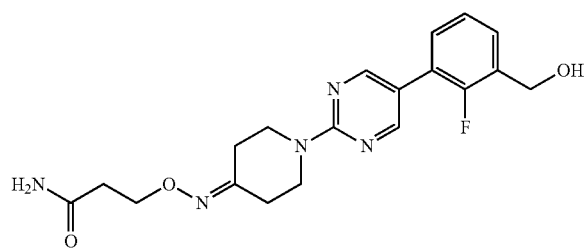 [SMILES: NC(=O)CCON=C1CCN(c2ncc(-c3cccc(CO)c3F)cn2)CC1]

The reaction was performed by the method described in Reference Example 7-2, except that 1-[5-(3-{[(tert-butyldimethylsilyl)oxy]methyl}-2-fluorophenyl)pyrimidin-2-yl]azetidin-3-one O-ethyl oxime (Reference Compound 6-2) was replaced by 3-[({1-[5-(3-{[(tert-butyldimethylsilyl)oxy]methyl}-2-fluorophenyl)pyrimidin-2-yl]piperidin-4-ylidene}amino)oxy]propanamide synthesized in the same manner as in Reference Example 6-78. Consequently, the title compound (including impurities) was obtained as a white solid.

Mass spectrum (ESI, m/z):388[M+1]$^+$.

$^1$H-NMR spectrum (400 MHz, CDCl$_3$) δ:8.53 (d, J=1.5 Hz, 2H), 7.48-7.38 (m, 1H), 7.36-7.18 (m, 2H), 5.86 (br s, 1H), 5.31 (br s, 1H), 4.83 (s, 2H), 4.37-4.30 (m, 2H), 4.04-3.96 (m, 4H), 2.70-2.62 (m, 4H), 2.50-2.44 (m, 2H).

Reference Example 7-99

3-{[(1-{5-[2-Fluoro-3-(hydroxymethyl)phenyl]pyrimidin-2-yl}piperidin-4-ylidene)amino]oxy}-N-methylpropanamide (Reference Compound 7-99)

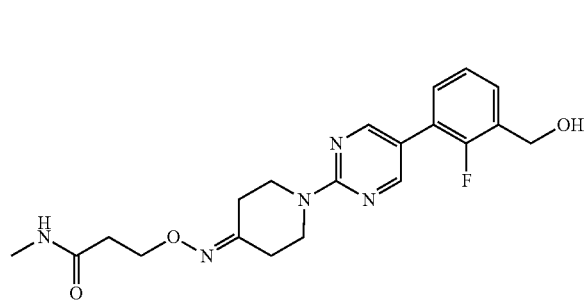 [SMILES: CNC(=O)CCON=C1CCN(c2ncc(-c3cccc(CO)c3F)cn2)CC1]

The reaction was performed by the method described in Reference Example 7-2, except that 1-[5-(3-{[(tert-butyldimethylsilyl)oxy]methyl}-2-fluorophenyl)pyrimidin-2-yl]azetidin-3-one O-ethyl oxime (Reference Compound 6-2) was replaced by 3-[({1-[5-(3-{[(tert-butyldimethylsilyl)oxy]methyl}-2-fluorophenyl)pyrimidin-2-yl]piperidin-4-ylidene}amino)oxy]-N-methylpropanamide synthesized in the same manner as in Reference Example 6-79, and the purification by silica gel column chromatography was not performed. Consequently, a crude product including the title compound was obtained as a light yellow solid.

Reference Example 7-100

Ethyl 4-{[(1-{5-[2-fluoro-3-(hydroxymethyl)phenyl]pyrimidin-2-yl}piperidin-4-ylidene)amino]oxy}butanoate (Reference Compound 7-100)

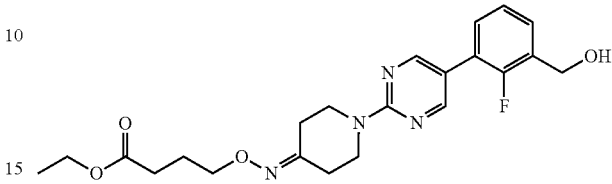

The reaction was performed by the method described in Reference Example 7-2, except that 1-[5-(3-{[(tert-butyldimethylsilyl)oxy]methyl}-2-fluorophenyl)pyrimidin-2-yl]azetidin-3-one O-ethyl oxime (Reference Compound 6-2) was replaced by ethyl 4-[({1-[5-(3-{[(tert-butyldimethylsilyl)oxy]methyl}-2-fluorophenyl)pyrimidin-2-yl]piperidin-4-ylidene}amino)oxy]butanoate synthesized in the same manner as in Reference Example 6-80. Consequently, the title compound (yield 70%) was obtained as a light yellow solid.

Mass spectrum (CI, m/z):431[M+1]$^+$.

$^1$H-NMR spectrum (400 MHz, DMSO-d$_6$) δ:8.59 (d, J=1.5 Hz, 2H), 7.49-7.41 (m, 2H), 7.31-7.24 (m, 1H), 5.33 (t, J=5.7 Hz, 1H), 4.60 (d, J=5.7 Hz, 2H), 4.05 (q, J=7.2 Hz, 2H), 3.98 (t, J=6.4 Hz, 2H), 3.95-3.89 (m, 4H), 2.59-2.54 (m, 2H), 2.41-2.32 (m, 4H), 1.89-1.81 (m, 2H), 1.18 (t, J=7.2 Hz, 3H).

Reference Example 7-101

3-{[(1-{5-[2-Fluoro-3-(hydroxymethyl)phenyl]pyrimidin-2-yl}piperidin-4-ylidene)amino]oxy}-N,N-dimethylpropanamide (Reference Compound 7-101)

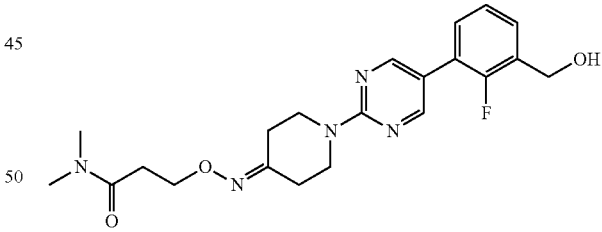

The reaction was performed by the method described in Reference Example 7-2, except that 1-[5-(3-{[(tert-butyldimethylsilyl)oxy]methyl}-2-fluorophenyl)pyrimidin-2-yl]azetidin-3-one O-ethyl oxime (Reference Compound 6-2) was replaced by 3-[({1-[5-(3-{[(tert-butyldimethylsilyl)oxy]methyl}-2-fluorophenyl)pyrimidin-2-yl]piperidin-4-ylidene}amino)oxy]-N,N-dimethylpropanamide synthesized in the same manner as in Reference Example 6-81. Consequently, the title compound (yield 71%) was obtained as a white solid.

Mass spectrum (CI, m/z):416[M+1]$^+$.

$^1$H-NMR spectrum (400 MHz, DMSO-d$_6$) δ:8.59 (d, J=1.5 Hz, 2H), 7.49-7.41 (m, 2H), 7.31-7.24 (m, 1H), 5.36-5.31 (m, 1H), 4.63-4.57 (m, 2H), 4.19 (t, J=6.8 Hz, 2H), 3.95-3.89 (m, 4H), 2.96 (s, 3H), 2.81 (s, 3H), 2.65 (t, J=6.8 Hz, 2H), 2.58-2.52 (m, 2H), 2.41-2.36 (m, 2H).

Reference Example 7-102

N-(2-{[(1-{5-[2-fluoro-3-(hydroxymethyl)phenyl]pyrimidin-2-yl}piperidin-4-ylidene)amino]oxy}ethyl)acetamide (Reference Compound 7-102)

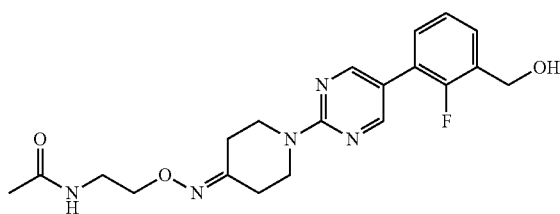 [SMILES: CC(=O)NCCON=C1CCN(c2ncc(-c3cccc(CO)c3F)cn2)CC1]

The reaction was performed by the method described in Reference Example 7-2, except that 1-[5-(3-{[(tert-butyldimethylsilyl)oxy]methyl}-2-fluorophenyl)pyrimidin-2-yl]azetidin-3-one O-ethyl oxime (Reference Compound 6-2) was replaced by N-{2-[({1-[5-(3-{[(tert-butyldimethylsilyl)oxy]methyl}-2-fluorophenyl)pyrimidin-2-yl]piperidin-4-ylidene}amino)oxy]ethyl}acetamide synthesized in the same manner as in Reference Example 87-5. Consequently, the title compound (yield 94%) was obtained as a white solid.

Mass spectrum (CI, m/z):402[M+1].

$^1$H-NMR spectrum (400 MHz, DMSO-$d_6$) δ:8.59 (d, J=1.5 Hz, 2H), 7.96-7.89 (m, 1H), 7.51-7.40 (m, 2H), 7.32-7.24 (m, 1H), 5.34 (br. s, 1H), 4.60 (s, 2H), 4.05-3.83 (m, 6H), 3.32-3.22 (m, 2H), 2.63-2.56 (m, 2H), 2.43-2.36 (m, 2H), 1.81 (s, 3H).

Reference Example 7-103

N-(2-{[(1-{5-[2-fluoro-3-(hydroxymethyl)phenyl]pyrimidin-2-yl}piperidin-4-ylidene)amino]oxy}ethyl)-N-methylacetamide (Reference Compound 7-103)

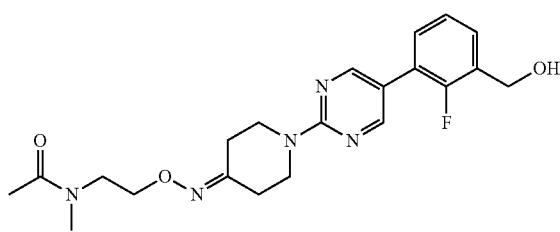 [SMILES: CC(=O)N(C)CCON=C1CCN(c2ncc(-c3cccc(CO)c3F)cn2)CC1]

The reaction was performed by the method described in Reference Example 7-2, except that 1-[5-(3-{[(tert-butyldimethylsilyl)oxy]methyl}-2-fluorophenyl)pyrimidin-2-yl]azetidin-3-one O-ethyl oxime (Reference Compound 6-2) was replaced by N-{2-[({1-[5-(3-{[(tert-butyldimethylsilyl)oxy]methyl}-2-fluorophenyl)pyrimidin-2-yl]piperidin-4-ylidene}amino)oxy]ethyl}-N-methylacetamide synthesized in the same manner as in Reference Example 106. Consequently, the title compound (quantitative yield) was obtained as a white solid.

Mass spectrum (CI, m/z):416[M+1]$^+$.

$^1$H-NMR spectrum (400 MHz, DMSO-$d_6$) δ:8.59 (d, J=1.5 Hz, 2H), 7.50-7.41 (m, 2H), 7.31-7.24 (m, 1H), 5.33 (t, J=5.6 Hz, 1H), 4.60 (d, J=5.6 Hz, 2H), 4.17-4.02 (m, 2H), 3.96-3.88 (m, 4H), 3.58-3.47 (m, 2H), 3.01-2.77 (m, 3H), 2.60-2.54 (m, 2H), 2.42-2.35 (m, 2H), 2.00-1.96 (m, 3H).

Reference Example 7-104

N-(2-{[(1-{5-[2-fluoro-3-(hydroxymethyl)phenyl]pyrimidin-2-yl}piperidin-4-ylidene)amino]oxy}ethyl)-N-methylmethanesulfonamide (Reference Compound 7-104)

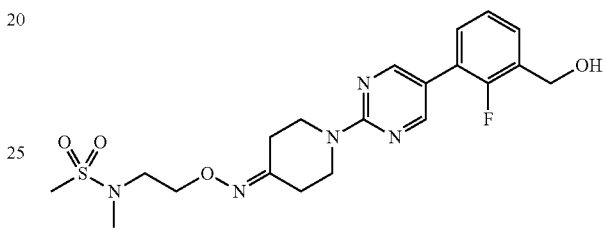

The reaction was performed by the method described in Reference Example 7-1, except that 1-[5-(3-{[(tert-butyldimethylsilyl)oxy]methyl}-2-fluorophenyl)pyrimidin-2-yl]azetidin-3-one O-methyl oxime (Reference Compound 6-1) was replaced by N-{2-[({1-[5-(3-{[(tert-butyldimethylsilyl)oxy]methyl}-2-fluorophenyl)pyrimidin-2-yl]piperidin-4-ylidene}amino)oxy]ethyl}-N-methylmethanesulfonamide synthesized in the same manner as in Reference Example 108, and the concentrated residue was purified by silica gel column chromatography. Consequently, the title compound (yield 83%) was obtained as a white solid.

Mass spectrum (ESI, m/z):452[M+1]$^+$.

Reference Example 7-105 tert-Butyl (2-{[(1-{5-[2-fluoro-3-(hydroxymethyl)phenyl]pyrimidin-2-yl}piperidin-4-ylidene)amino]oxy}ethyl)(methylsulfonyl)carbamate (Reference Compound 7-105)

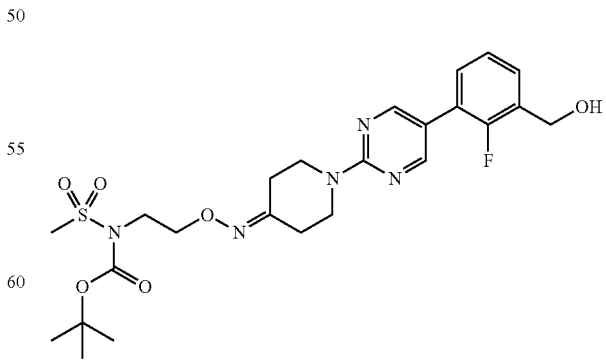

The reaction was performed by the method described in Reference Example 7-2, except that 1-[5-(3-{[(tert-butyldimethylsilyl)oxy]methyl}-2-fluorophenyl)pyrimidin-2- yl]azetidin-3-one O-ethyl oxime (Reference Compound 6-2) was replaced by tert-butyl {2-[({1-[5-(3-{[(tert-butyldimethylsilyl)oxy]methyl}-2-fluorophenyl)pyrimidin-2-yl]piperidin-4-ylidene}amino)oxy]ethyl}(methylsulfonyl)carbamate synthesized in the same manner as in Reference Example 109-1. Consequently, the title compound (yield 87%) was obtained as a colorless oil.

Mass spectrum (ESI, m/z):538[M+1]⁺.

$^1$H-NMR (400 MHz, DMSO-$d_6$) δ:8.59 (d, J=1.4 Hz, 2H), 7.50-7.40 (m, 2H), 7.31-7.23 (m, 1H), 4.60 (s, 2H), 4.16-4.07 (m, 2H), 3.97-3.80 (m, 6H), 3.50-3.14 (m, 3H), 2.61-2.54 (m, 2H), 2.41-2.34 (m, 2H), 1.47 (s, 9H).

Reference Example 7-106

1-{5-[2-Fluoro-3-(hydroxymethyl)phenyl]pyrimidin-2-yl}piperidin-4-one O-[2-(dimethylamino)ethyl] oxime (Reference Compound 7-106)

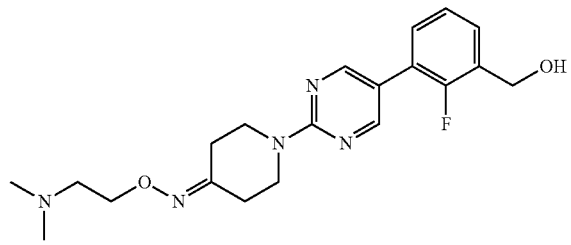 [SMILES: CN(C)CCON=C1CCN(c2ncc(-c3cccc(CO)c3F)cn2)CC1]

The reaction was performed by the method described in Reference Example 7-1, except that 1-[5-(3-{[(tert-butyldimethylsilyl)oxy]methyl}-2-fluorophenyl)pyrimidin-2-yl]azetidin-3-one O-methyl oxime (Reference Compound 6-1) was replaced by 1-[5-(3-{[(tert-butyldimethylsilyl)oxy]methyl}-2-fluorophenyl)pyrimidin-2-yl]piperidin-4-one O-[2-(dimethylamino)ethyl] oxime synthesized in the same manner as in Reference Example 6-83, and the concentrated residue was purified by silica gel column chromatography. Consequently, the title compound (yield 16%) was obtained as a white solid.

Mass spectrum (ESI, m/z):388[M+1]⁺.

$^1$H-NMR (400 MHz, DMSO-$d_6$) δ:8.59 (d, J=1.5 Hz, 2H), 7.49-7.41 (m, 2H), 7.31-7.24 (m, 1H), 5.40-5.25 (m, 1H), 4.63-4.57 (m, 2H), 4.05 (t, J=6.1 Hz, 2H), 3.95-3.88 (m, 4H), 2.61-2.44 (m, 4H), 2.41-2.35 (m, 2H), 2.16 (s, 6H).

Reference Example 7-107 tert-Butyl (2-{[(1-{5-[2-fluoro-3-(hydroxymethyl)phenyl]pyrimidin-2-yl}piperidin-4-ylidene)amino]oxy}ethyl)(methyl)carbamate (Reference Compound 7-107)

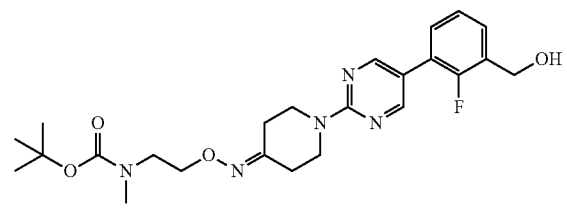 [SMILES: CN(CCON=C1CCN(c2ncc(-c3cccc(CO)c3F)cn2)CC1)C(=O)OC(C)(C)C]

The reaction was performed by the method described in Reference Example 7-2, except that 1-[5-(3-{[(tert-butyldimethylsilyl)oxy]methyl}-2-fluorophenyl)pyrimidin-2-yl]azetidin-3-one O-ethyl oxime (Reference Compound 6-2) was replaced by tert-butyl {2-[({1-[5-(3-{[(tert-butyldimethylsilyl)oxy]methyl}-2-fluorophenyl)pyrimidin-2-yl]piperidin-4-ylidene}amino)oxy]ethyl}(methyl)carbamate synthesized in the same manner as in Reference Example 6-84. Consequently, the title compound (yield 71%) was obtained as a colorless oil.

Mass spectrum (ESI, m/z):474[M+1]⁺.

$^1$H-NMR (400 MHz, CDCl$_3$) δ:8.53 (d, J=1.5 Hz, 2H), 7.47-7.39 (m, 1H), 7.35-7.29 (m, 1H), 7.28-7.20 (m, 1H), 4.83 (d, J=4.8 Hz, 2H), 4.21-4.09 (m, 3H), 4.05-3.95 (m, 4H), 3.55-3.43 (m, 2H), 2.96-2.85 (m, 3H), 2.72-2.64 (m, 2H), 2.51-2.43 (m, 2H), 1.46 (s, 9H).

Reference Example 7-108

Di-tert-butyl (2-{[(1-{5-[2-fluoro-3-(hydroxymethyl)phenyl]pyrimidin-2-yl}piperidin-4-ylidene)amino]oxy}ethyl)carbamate (Reference Compound 7-108)

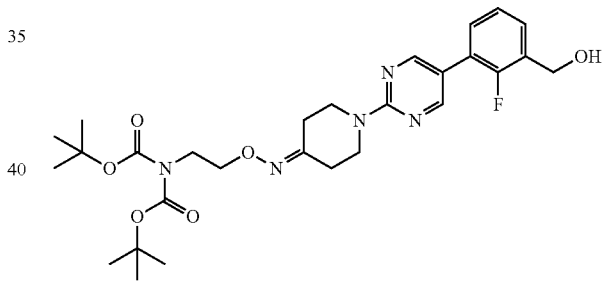

The reaction was performed by the method described in Reference Example 7-2, except that 1-[5-(3-{[(tert-butyldimethylsilyl)oxy]methyl}-2-fluorophenyl)pyrimidin-2-yl]azetidin-3-one O-ethyl oxime (Reference Compound 6-2) was replaced by di-tert-butyl {2-[({1-[5-(3-{[(tert-butyldimethylsilyl)oxy]methyl}-2-fluorophenyl)pyrimidin-2-yl]piperidin-4-ylidene}amino)oxy]ethyl}carbamate synthesized in the same manner as in Reference Example 6-85. Consequently, the title compound (yield 70%) was obtained as a colorless oil.

Mass spectrum (ESI, m/z):560[M+1]⁺.

$^1$H-NMR (400 MHz, CDCl$_3$) δ:8.53 (d, J=1.5 Hz, 2H), 7.46-7.40 (m, 1H), 7.35-7.28 (m, 1H), 7.28-7.20 (m, 1H), 4.83 (d, J=6.0 Hz, 2H), 4.22-4.16 (m, 2H), 4.04-3.94 (m, 4H), 3.94-3.86 (m, 2H), 2.69-2.63 (m, 2H), 2.49-2.42 (m, 2H), 1.85 (t, J=6.0 Hz, 1H), 1.51 (s, 18H).

Reference Example 7-109

3-{[(1-{5-[2-Fluoro-3-(hydroxymethyl)phenyl]pyrimidin-2-yl}piperidin-4-ylidene)amino]oxy}propanenitrile (Reference Compound 7-109)

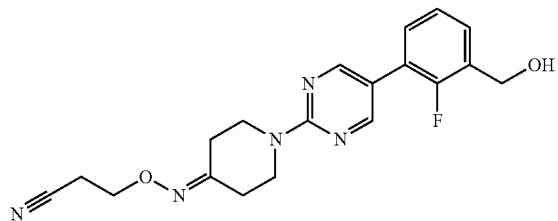 [SMILES: N#CCCON=C1CCN(c2ncc(-c3cccc(CO)c3F)cn2)CC1]

The reaction was performed by the method described in Reference Example 7-2, except that 1-[5-(3-{[(tert-butyldimethylsilyl)oxy]methyl}-2-fluorophenyl)pyrimidin-2-yl]azetidin-3-one O-ethyl oxime (Reference Compound 6-2) was replaced by 3-[({1-[5-(3-{[(tert-butyldimethylsilyl)oxy]methyl}-2-fluorophenyl)pyrimidin-2-yl]piperidin-4-ylidene}amino)oxy]propanenitrile synthesized in the same manner as in Reference Example 6-86. Consequently, the title compound (yield 45%) was obtained as a white solid.

Mass spectrum (CI, m/z):370[M+1]$^+$.

$^1$H-NMR spectrum (400 MHz, CDCl$_3$) δ:8.54 (d, J=1.5 Hz, 2H), 7.47-7.40 (m, 1H), 7.35-7.29 (m, 1H), 7.27-7.21 (m, 1H), 4.83 (d, J=6.0 Hz, 2H), 4.25 (t, J=6.3 Hz, 2H), 4.05-3.98 (m, 4H), 2.74 (t, J=6.3 Hz, 2H), 2.73-2.66 (m, 2H), 2.49-2.43 (m, 2H), 1.83 (t, J=6.0 Hz, 1H).

Reference Example 7-110

4-{[(1-{5-[2-Fluoro-3-(hydroxymethyl)phenyl]pyrimidin-2-yl}piperidin-4-ylidene)amino]oxy}butanenitrile (Reference Compound 7-110)

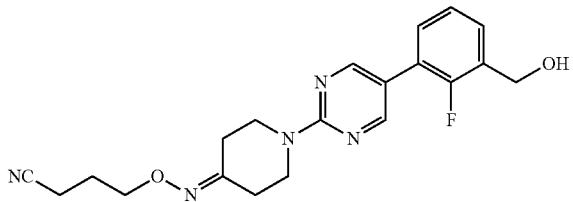 [SMILES: N#CCCCON=C1CCN(c2ncc(-c3cccc(CO)c3F)cn2)CC1]

The reaction was performed by the method described in Reference Example 7-2, except that 1-[5-(3-{[(tert-butyldimethylsilyl)oxy]methyl}-2-fluorophenyl)pyrimidin-2-yl]azetidin-3-one O-ethyl oxime (Reference Compound 6-2) was replaced by 4-[({1-[5-(3-{[(tert-butyldimethylsilyl)oxy]methyl}-2-fluorophenyl)pyrimidin-2-yl]piperidin-4-ylidene}amino)oxy]butanenitrile synthesized in the same manner as in Reference Example 6-87. Consequently, the title compound (yield 78%) was obtained as a white solid.

Mass spectrum (CI, m/z):384[M+1]$^+$.

$^1$H-NMR spectrum (400 MHz, DMSO-d$_6$) δ:8.59 (d, J=1.4 Hz, 2H), 7.50-7.41 (m, 2H), 7.30-7.25 (m, 1H), 5.38-5.30 (m, 1H), 4.64-4.56 (m, 2H), 4.04 (t, J=6.0 Hz, 2H), 3.96-3.90 (m, 4H), 2.63-2.58 (m, 2H), 2.55 (t, J=7.1 Hz, 2H), 2.43-2.35 (m, 2H), 1.95-1.84 (m, 2H).

Reference Example 7-111

1-{5-[2-Fluoro-3-(hydroxymethyl)phenyl]pyrimidin-2-yl}piperidin-4-one O-[2-(methylsulfonyl)ethyl] oxime (Reference Compound 7-111)

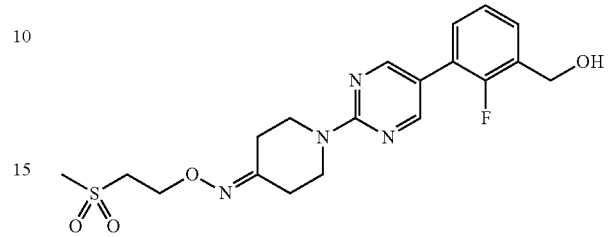

The reaction was performed by the method described in Reference Example 7-2, except that 1-[5-(3-{[(tert-butyldimethylsilyl)oxy]methyl}-2-fluorophenyl)pyrimidin-2-yl]azetidin-3-one O-ethyl oxime (Reference Compound 6-2) was replaced by 1-[5-(3-{[(tert-butyldimethylsilyl)oxy]methyl}-2-fluorophenyl)pyrimidin-2-yl]piperidin-4-one O-[2-(methylsulfonyl)ethyl] oxime synthesized in the same manner as in Reference Example 6-88. Consequently, the title compound (yield 99%) was obtained as a white solid.

Mass spectrum (CI, m/z):423[M+1]$^+$.

$^1$H-NMR spectrum (400 MHz, DMSO-d$_6$) δ:8.59 (d, J=1.5 Hz, 2H), 7.51-7.40 (m, 2H), 7.31-7.24 (m, 1H), 5.33 (t, J=5.5 Hz, 1H), 4.60 (d, J=5.5 Hz, 2H), 4.35 (t, J=5.8 Hz, 2H), 3.97-3.90 (m, 4H), 3.48 (t, J=5.8 Hz, 2H), 2.99 (s, 3H), 2.62-2.55 (m, 2H), 2.43-2.37 (m, 2H).

Reference Example 7-112

1-{5-[2-Fluoro-3-(hydroxymethyl)phenyl]pyrimidin-2-yl}piperidin-4-one O-[3-(methylsulfonyl)propyl] oxime (Reference Compound 7-112)

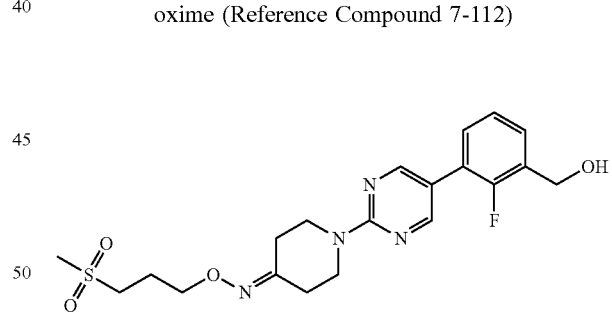

The reaction was performed by the method described in Reference Example 7-2, except that 1-[5-(3-{[(tert-butyldimethylsilyl)oxy]methyl}-2-fluorophenyl)pyrimidin-2-yl]azetidin-3-one O-ethyl oxime (Reference Compound 6-2) was replaced by 1-[5-(3-{[(tert-butyldimethylsilyl)oxy]methyl}-2-fluorophenyl)pyrimidin-2-yl]piperidin-4-one O-[3-(methylsulfonyl)propyl] oxime synthesized in the same manner as in Reference Example 6-89. Consequently, the title compound (yield 67%) was obtained as a white solid.

Mass spectrum (ESI, m/z):437[M+1]$^+$.

$^1$H-NMR spectrum (400 MHz, CDCl$_3$) δ:8.54 (d, J=1.5 Hz, 2H), 7.47-7.39 (m, 1H), 7.35-7.20 (m, 2H), 4.83 (d, J=6.0 Hz, 2H), 4.17 (t, J=6.0 Hz, 2H), 4.06-3.95 (m, 4H), 3.17-3.12 (m, 2H), 2.93 (s, 3H), 2.70-2.63 (m, 2H), 2.50-2.42 (m, 2H), 2.30-2.18 (m, 2H), 1.81 (t, J=6.3 Hz, 1H).

Reference Example 7-113

1-{5-[2-Fluoro-3-(hydroxymethyl)phenyl]pyrimidin-2-yl}piperidin-4-one O-[(1-methyl-1H-pyrazol-3-yl)methyl] oxime (Reference Compound 7-113)

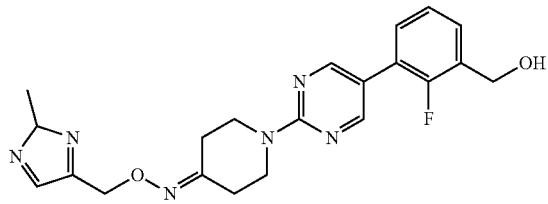 [SMILES: CC1N=CC(CON=C2CCN(c3ncc(-c4cccc(CO)c4F)cn3)CC2)=N1]

The reaction was performed by the method described in Reference Example 7-2, except that 1-[5-(3-{[(tert-butyldimethylsilyl)oxy]methyl}-2-fluorophenyl)pyrimidin-2-yl]azetidin-3-one O-ethyl oxime (Reference Compound 6-2) was replaced by 1-[5-(3-{[(tert-butyldimethylsilyl)oxy]methyl}-2-fluorophenyl)pyrimidin-2-yl]piperidin-4-one O-[(1-methyl-1H-pyrazol-3-yl)methyl] oxime synthesized in the same manner as in Reference Example 6-90. Consequently, the title compound (yield 91%) was obtained as a white solid.

Mass spectrum (CI, m/z):411[M+1]$^+$.

$^1$H-NMR spectrum (400 MHz, CDCl$_3$) δ:8.52 (d, J=1.5 Hz, 2H), 7.45-7.39 (m, 1H), 7.35-7.19 (m, 3H), 6.30 (d, J=2.3 Hz, 1H), 5.09 (s, 2H), 4.83 (d, J=6.1 Hz, 2H), 4.03-3.94 (m, 4H), 3.90 (s, 3H), 2.74-2.67 (m, 2H), 2.51-2.45 (m, 2H), 1.84 (t, J=6.1 Hz, 1H).

Reference Example 7-114

1-{5-[2-Fluoro-3-(hydroxymethyl)phenyl]pyrimidin-2-yl}piperidin-4-one O-{[1-(tetrahydropyran-2-yl)-1H-pyrazol-3-yl]methyl} oxime (Reference Compound 7-114)

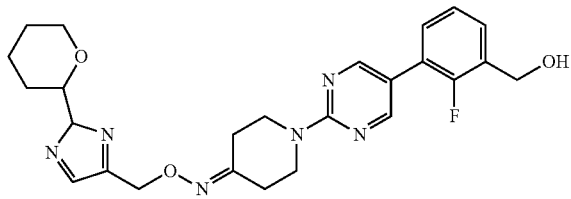 [SMILES: OCc1cccc(-c2cnc(N3CCC(=NOCC4=NC(C5CCCCO5)N=C4)CC3)nc2)c1F]

The reaction was performed by the method described in Reference Example 7-2, except that 1-[5-(3-{[(tert-butyldimethylsilyl)oxy]methyl}-2-fluorophenyl)pyrimidin-2-yl]azetidin-3-one O-ethyl oxime (Reference Compound 6-2) was replaced by 1-[5-(3-{[(tert-butyldimethylsilyl)oxy]methyl}-2-fluorophenyl)pyrimidin-2-yl]piperidin-4-one O-{[1-(tetrahydropyran-2-yl)-1H-pyrazol-3-yl]methyl} oxime synthesized in the same manner as in Reference Example 6-91. Consequently, the title compound (yield 66%) was obtained as a white solid.

Mass spectrum (CI, m/z):481 [M+1]$^+$.

$^1$H-NMR spectrum (400 MHz, CDCl$_3$) δ:8.52 (d, J=1.5 Hz, 2H), 7.57 (d, J=2.4 Hz, 1H), 7.45-7.39 (m, 1H), 7.34-7.27 (m, 1H), 7.25-7.21 (m, 1H), 6.36 (d, J=2.4 Hz, 1H), 5.36 (dd, J=2.8, 9.5 Hz, 1H), 5.12 (s, 2H), 4.83 (br d, J=4.5 Hz, 2H), 4.11-4.04 (m, 1H), 4.04-3.95 (m, 4H), 3.74-3.65 (m, 1H), 2.72-2.67 (m, 2H), 2.50-2.45 (m, 2H), 2.17-2.00 (m, 3H), 1.83 (br t, J=4.5 Hz, 1H), 1.75-1.46 (m, 3H).

Reference Example 7-115

1-{5-[2-Fluoro-3-(hydroxymethyl)phenyl]pyrimidin-2-yl}piperidin-4-one O-{[1-(tetrahydropyran-2-yl)-1H-pyrazol-4-yl]methyl} oxime (Reference Compound 7-115)

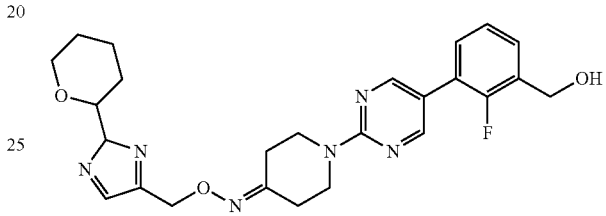

The reaction was performed by the method described in Reference Example 7-2, except that 1-[5-(3-{[(tert-butyldimethylsilyl)oxy]methyl}-2-fluorophenyl)pyrimidin-2-yl]azetidin-3-one O-ethyl oxime (Reference Compound 6-2) was replaced by 1-[5-(3-{[(tert-butyldimethylsilyl)oxy]methyl}-2-fluorophenyl)pyrimidin-2-yl]piperidin-4-one O-{[1-(tetrahydropyran-2-yl)-1H-pyrazol-4-yl]methyl} oxime synthesized in the same manner as in Reference Example 6-92. Consequently, the title compound (yield 60%) was obtained as a white solid.

Mass spectrum (CI, m/z):481 [M+1]$^+$.

$^1$H-NMR spectrum (400 MHz, DMSO-d$_6$) δ:8.58 (d, J=1.4 Hz, 2H), 7.90 (s, 1H), 7.51 (s, 1H), 7.49-7.40 (m, 2H), 7.32-7.23 (m, 1H), 5.36 (dd, J=2.2, 10.1 Hz, 1H), 5.32 (t, J=5.3 Hz, 1H), 4.89 (s, 2H), 4.60 (d, J=5.3 Hz, 2H), 3.97-3.83 (m, 5H), 3.69-3.55 (m, 1H), 2.57-2.52 (m, 2H), 2.41-2.36 (m, 2H), 2.14-1.46 (m, 6H).

Reference Example 7-116

1-{5-[2-Fluoro-3-(hydroxymethyl)phenyl]pyrimidin-2-yl}piperidin-4-one O-[(1-methyl-1H-pyrazol-4-yl)methyl] oxime (Reference Compound 7-116)

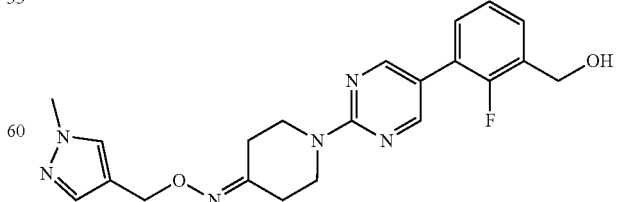

The reaction was performed by the method described in Reference Example 7-2, except that 1-[5-(3-{[(tert-butyldimethylsilyl)oxy]methyl}-2-fluorophenyl)pyrimidin-2- yl]azetidin-3-one O-ethyl oxime (Reference Compound 6-2) was replaced by 1-[5-(3-{[(tert-butyldimethylsilyl)oxy]methyl}-2-fluorophenyl)pyrimidin-2-yl]piperidin-4-one O-[(1-methyl-1H-pyrazol-4-yl)methyl] oxime synthesized in the same manner as in Reference Example 6-93. Consequently, the title compound (quantitative yield) was obtained as a white solid.

Mass spectrum (CI, m/z):411[M+1]$^+$.

$^1$H-NMR spectrum (400 MHz, DMSO-d$_6$) δ:8.58 (d, J=1.5 Hz, 2H), 7.70 (s, 1H), 7.49-7.40 (m, 3H), 7.31-7.23 (m, 1H), 5.32 (t, J=5.3 Hz, 1H), 4.87 (s, 2H), 4.60 (d, J=5.3 Hz, 2H), 3.95-3.87 (m, 4H), 3.81 (s, 3H), 2.56-2.52 (m, 2H), 2.41-2.35 (m, 2H).

Reference Example 7-117

1-{5-[2-Fluoro-3-(hydroxymethyl)phenyl]pyrimidin-2-yl}piperidin-4-one O-[2-(1H-pyrazol-1-yl)ethyl] oxime (Reference Compound 7-117)

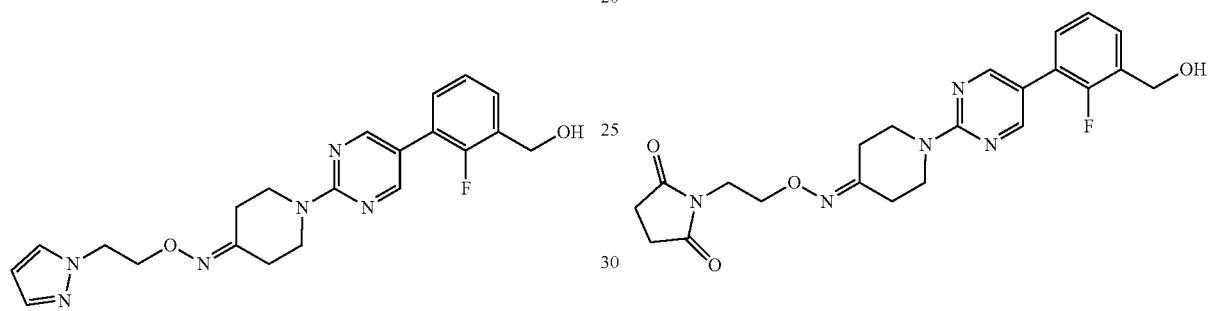

The reaction was performed by the method described in Reference Example 7-1, except that 1-[5-(3-{[(tert-butyldimethylsilyl)oxy]methyl}-2-fluorophenyl)pyrimidin-2-yl]azetidin-3-one O-methyl oxime (Reference Compound 6-1) was replaced by 1-[5-(3-{[(tert-butyldimethylsilyl)oxy]methyl}-2-fluorophenyl)pyrimidin-2-yl]piperidin-4-one O-[2-(1H-pyrazol-1-yl)ethyl] oxime synthesized in the same manner as in Reference Example 6-94, and the concentrated residue was purified by silica gel column chromatography. Consequently, the title compound (yield 32%) was obtained as a white solid.

Mass spectrum (ESI, m/z):411[M+1]$^+$.

Reference Example 7-118

1-{5-[2-Fluoro-3-(hydroxymethyl)phenyl]pyrimidin-2-yl}piperidin-4-one O-pyridin-4-ylmethyl oxime (Reference Compound 7-118)

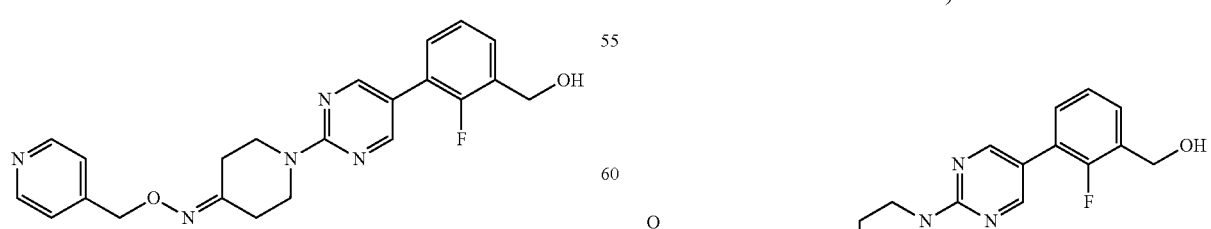

The reaction was performed by the method described in Reference Example 7-2, except that 1-[5-(3-{[(tert-butyldimethylsilyl)oxy]methyl}-2-fluorophenyl)pyrimidin-2-yl]azetidin-3-one O-ethyl oxime (Reference Compound 6-2) was replaced by 1-[5-(3-{[(tert-butyldimethylsilyl)oxy]methyl}-2-fluorophenyl)pyrimidin-2-yl]piperidin-4-one O-pyridin-4-ylmethyl oxime synthesized in the same manner as in Reference Example 6-95. Consequently, the title compound (including impurities) was obtained as a colorless oil.

Mass spectrum (CI, m/z):408[M+1]$^+$.

$^1$H-NMR spectrum (400 MHz, CDCl$_3$) δ:8.60-8.56 (m, 2H), 8.54 (d, J=1.5 Hz, 2H), 7.51-7.39 (m, 1H), 7.35-7.20 (m, 4H), 5.11 (s, 2H), 4.84 (br s, 2H), 4.07-3.97 (m, 4H), 2.81-2.73 (m, 2H), 2.50-2.43 (m, 2H), 1.96-1.85 (m, 1H).

Reference Example 7-119

1-(2-{[(1-{5-[2-Fluoro-3-(hydroxymethyl)phenyl]pyrimidin-2-yl}piperidin-4-ylidene)amino]oxy}ethyl)pyrrolidine-2,5-dione (Reference Compound 7-119)

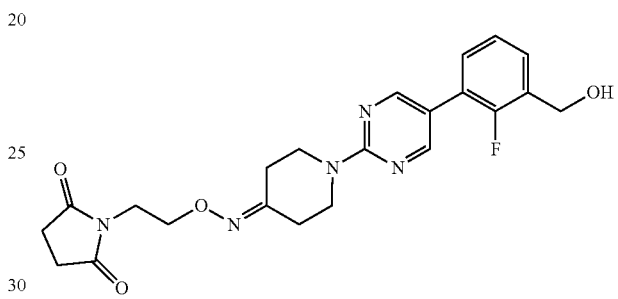

The reaction was performed by the method described in Reference Example 7-2, except that 1-[5-(3-{[(tert-butyldimethylsilyl)oxy]methyl}-2-fluorophenyl)pyrimidin-2-yl]azetidin-3-one O-ethyl oxime (Reference Compound 6-2) was replaced by 1-{2-[({1-[5-(3-{[(tert-butyldimethylsilyl)oxy]methyl}-2-fluorophenyl)pyrimidin-2-yl]piperidin-4-ylidene}amino)oxy]ethyl}pyrrolidine-2,5-dione synthesized in the same manner as in Reference Example 6-96. Consequently, the title compound (including impurities) was obtained as a white solid.

Mass spectrum (CI, m/z):442[M+1]$^+$.

$^1$H-NMR spectrum (400 MHz, CDCl$_3$) δ:8.53 (d, J=1.5 Hz, 2H), 7.46-7.39 (m, 1H), 7.35-7.28 (m, 1H), 7.26-7.21 (m, 1H), 4.83 (d, J=5.7 Hz, 2H), 4.24-4.17 (m, 2H), 4.05-3.95 (m, 4H), 3.85-3.78 (m, 2H), 2.71 (s, 4H), 2.63-2.56 (m, 2H), 2.47-2.40 (m, 2H), 1.84 (br t, J=5.7 Hz, 1H).

Reference Example 7-120

1-(2-{[(1-{5-[2-Fluoro-3-(hydroxymethyl)phenyl]pyrimidin-2-yl}piperidin-4-ylidene)amino]oxy}ethyl)pyrrolidin-2-one (Reference Compound 7-120)

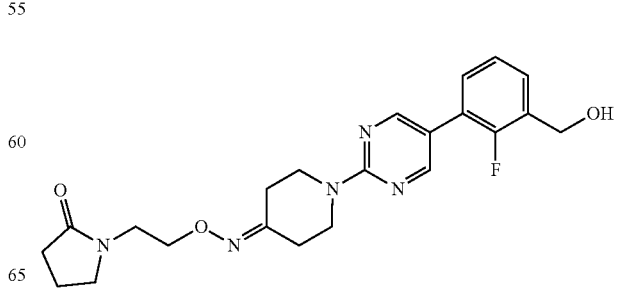

The reaction was performed by the method described in Reference Example 7-2, except that 1-[5-(3-{[(tert-butyldimethylsilyl)oxy]methyl}-2-fluorophenyl)pyrimidin-2-yl]azetidin-3-one O-ethyl oxime (Reference Compound 6-2) was replaced by 1-{2-[({1-[5-(3-{[(tert-butyldimethylsilyl)oxy]methyl}-2-fluorophenyl)pyrimidin-2-yl]piperidin-4-ylidene}amino)oxy]ethyl}pyrrolidin-2-one synthesized in the same manner as in Reference Example 6-97. Consequently, the title compound (yield 69%) was obtained as a white solid.

Mass spectrum (CI, m/z):428[M+1]$^+$.

$^1$H-NMR spectrum (400 MHz, DMSO-$d_6$) δ:8.59 (d, J=1.4 Hz, 2H), 7.49-7.42 (m, 2H), 7.31-7.22 (m, 1H), 5.32 (t, J=5.7 Hz, 1H), 4.60 (d, J=5.7 Hz, 2H), 4.11-4.01 (m, 2H), 3.96-3.88 (m, 4H), 3.44-3.35 (m, 4H), 2.59-2.53 (m, 2H), 2.41-2.35 (m, 2H), 2.25-2.14 (m, 2H), 1.97-1.86 (m, 2H).

Reference Example 7-121

3-(2-{[(1-{5-[2-Fluoro-3-(hydroxymethyl)phenyl]pyrimidin-2-yl}piperidin-4-ylidene)amino]oxy}ethyl)oxazolidin-2-one (Reference Compound 7-121)

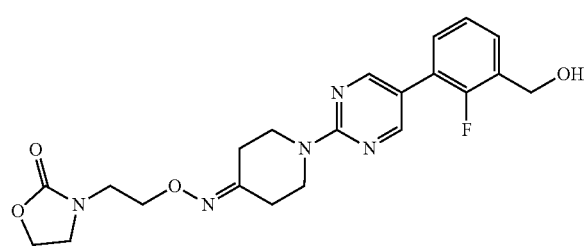 [SMILES: O=C1OCCN1CCON=C1CCN(c2ncc(-c3cccc(CO)c3F)cn2)CC1]

The reaction was performed by the method described in Reference Example 7-2, except that 1-[5-(3-{[(tert-butyldimethylsilyl)oxy]methyl}-2-fluorophenyl)pyrimidin-2-yl]azetidin-3-one O-ethyl oxime (Reference Compound 6-2) was replaced by 3-{2-[({1-[5-(3-{[(tert-butyldimethylsilyl)oxy]methyl}-2-fluorophenyl)pyrimidin-2-yl]piperidin-4-ylidene}amino)oxy]ethyl}oxazolidin-2-one synthesized in the same manner as in Reference Example 6-98. Consequently, the title compound (yield 72%) was obtained as a white solid.

Mass spectrum (CI, m/z):430[M+1]$^+$.

$^1$H-NMR spectrum (400 MHz, DMSO-$d_6$) δ:8.59 (d, J=1.4 Hz, 2H), 7.49-7.42 (m, 2H), 7.30-7.25 (m, 1H), 5.33 (br t, J=4.9 Hz, 1H), 4.60 (br d, J=4.9 Hz, 2H), 4.29-4.21 (m, 2H), 4.15-4.08 (m, 2H), 3.96-3.89 (m, 4H), 3.63-3.55 (m, 2H), 3.45-3.36 (m, 2H), 2.60-2.54 (m, 2H), 2.41-2.36 (m, 2H).

Reference Example 7-122

4-(2-{[(1-{5-[2-Fluoro-3-(hydroxymethyl)phenyl]pyrimidin-2-yl}piperidin-4-ylidene)amino]oxy}ethyl)morpholin-3-one (Reference Compound 7-122)

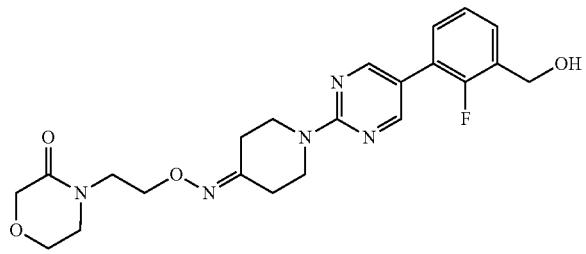 [SMILES: O=C1COCCN1CCON=C1CCN(c2ncc(-c3cccc(CO)c3F)cn2)CC1]

The reaction was performed by the method described in Reference Example 7-2, except that 1-[5-(3-{[(tert-butyldimethylsilyl)oxy]methyl}-2-fluorophenyl)pyrimidin-2-yl]azetidin-3-one O-ethyl oxime (Reference Compound 6-2) was replaced by 4-{2-[({1-[5-(3-{[(tert-butyldimethylsilyl)oxy]methyl}-2-fluorophenyl)pyrimidin-2-yl]piperidin-4-ylidene}amino)oxy]ethyl}morpholin-3-one synthesized in the same manner as in Reference Example 6-99. Consequently, the title compound (including impurities) was obtained as a white solid.

Mass spectrum (CI, m/z):444[M+1]$^+$.

$^1$H-NMR spectrum (400 MHz, DMSO-$d_6$) δ:8.59 (d, J=1.4 Hz, 2H), 7.49-7.42 (m, 2H), 7.31-7.25 (m, 1H), 5.32 (t, J=5.6 Hz, 1H), 4.60 (d, J=5.6 Hz, 2H), 4.16-4.08 (m, 2H), 4.02 (s, 2H), 3.96-3.88 (m, 4H), 3.85-3.75 (m, 2H), 3.62-3.50 (m, 2H), 3.43-3.34 (m, 2H), 2.60-2.53 (m, 2H), 2.42-2.36 (m, 2H).

Reference Example 7-123

1-{5-[2-Fluoro-3-(hydroxymethyl)phenyl]pyrimidin-2-yl}piperidin-4-one O-pyrimidin-5-yl oxime (Reference Compound 7-123)

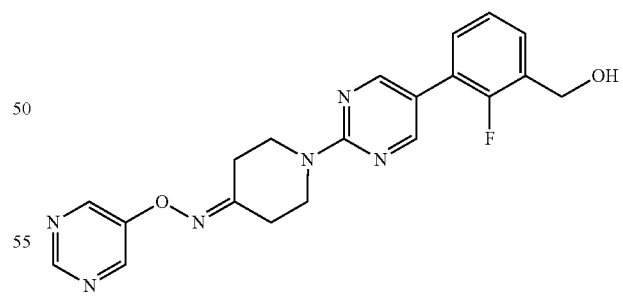

The reaction was performed by the method described in Reference Example 7-2, except that 1-[5-(3-{[(tert-butyldimethylsilyl)oxy]methyl}-2-fluorophenyl)pyrimidin-2-yl]azetidin-3-one O-ethyl oxime (Reference Compound 6-2) was replaced by 1-[5-(3-{[(tert-butyldimethylsilyl)oxy]methyl}-2-fluorophenyl)pyrimidin-2-yl]piperidin-4-one O-pyrimidin-5-yl oxime synthesized in the same manner as in Reference Example 121. Consequently, the title compound (yield 92%) was obtained as a dark brown solid.

Mass spectrum (CI, m/z):395[M+1]+.
¹H-NMR spectrum (400 MHz, DMSO-d₆) δ:8.90 (s, 1H), 8.73 (s, 2H), 8.62 (d, J=1.4 Hz, 2H), 7.50-7.43 (m, 2H), 7.32-7.25 (m, 1H), 5.34 (t, J=5.4 Hz, 1H), 4.61 (d, J=5.4 Hz, 2H), 4.10-4.00 (m, 4H), 2.90-2.84 (m, 2H), 2.63-2.57 (m, 2H).

Reference Example 7-124

1-{5-[2-Fluoro-3-(hydroxymethyl)phenyl]pyrimidin-2-yl}piperidin-4-one O-pyrimidin-2-yl oxime (Reference Compound 7-124)

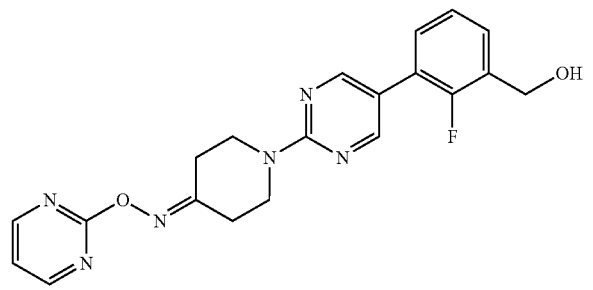 [SMILES: OCc1cccc(-c2cnc(N3CCC(=NOc4ncccn4)CC3)nc2)c1F]

The reaction was performed by the method described in Reference Example 7-2, except that 1-[5-(3-{[(tert-butyldimethylsilyl)oxy]methyl}-2-fluorophenyl)pyrimidin-2-yl]azetidin-3-one O-ethyl oxime (Reference Compound 6-2) was replaced by 1-[5-(3-{[(tert-butyldimethylsilyl)oxy]methyl}-2-fluorophenyl)pyrimidin-2-yl]piperidin-4-one O-pyrimidin-2-yl oxime synthesized in the same manner as in Reference Example 74-2. Consequently, the title compound (yield 93%) was obtained as a dark brown solid.
Mass spectrum (CI, m/z):395[M+1]+.
¹H-NMR spectrum (400 MHz, DMSO-d₆) δ:8.67 (d, J=4.8 Hz, 2H), 8.62 (d, J=1.4 Hz, 2H), 7.51-7.43 (m, 2H), 7.31-7.23 (m, 2H), 5.38-5.30 (m, 1H), 4.64-4.58 (m, 2H), 4.07-3.99 (m, 4H), 2.86-2.80 (m, 2H), 2.63-2.56 (m, 2H).

Reference Example 8

1-(5-Bromopyrimidin-2-yl)azetidin-3-one O-ethyl oxime (Reference Compound 8)

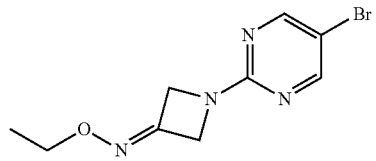

Sodium carbonate 70 mg (0.66 mmol) and O-ethylhydroxylamine hydrochloride 48 mg (0.49 mmol) were added to a THF (1 mL)-ethanol (2 mL)-water (1 mL) solution of 1-(5-bromopyrimidin-2-yl)azetidin-3-one 0.10 g (0.44 mmol) synthesized in the same manner as in Reference Example 2. The mixture was stirred at 50° C. for 2 hours, allowed to stand still at room temperature overnight, and stirred at 50° C. for 1 hour. After the completion of the reaction, water was added to the reaction mixture, and followed by extraction with ethyl acetate. The organic layer was washed with water, dried over anhydrous sodium sulfate, and filtered. The filtrate was concentrated under reduced pressure. The concentrated residue was purified by silica gel column chromatography (eluting solvent: 1,2-dichloroethane:ethyl acetate) to give the title compound 0.10 g (0.37 mmol, yield 84%) as a white solid.
Mass spectrum (CI, m/z):270, 272[M+1]+.
¹H-NMR spectrum (400 MHz, DMSO-d₆) δ:8.54 (s, 2H), 4.77-4.71 (m, 4H), 4.06 (q, J=7.0 Hz, 2H), 1.20 (t, J=7.0 Hz, 3H).

Reference Example 9-1

1-(5-Bromopyrimidin-2-yl)azetidin-3-one oxime (Reference Compound 9-1)

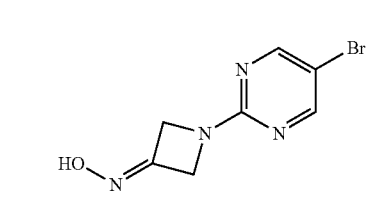 [SMILES: ON=C1CN(c2ncc(Br)cn2)C1]

Under stirring, hydroxylamine hydrochloride 12.1 g (174 mmol) was added to a THF (300 mL) suspension of 1-(5-bromopyrimidin-2-yl)azetidin-3-one 15.9 g (69.7 mmol) synthesized in the same manner as in Reference Example 2, and the mixture was stirred at 55° C. for 10 hours. After the completion of the reaction, a saturated aqueous sodium hydrogen carbonate solution was added to the reaction mixture. The precipitated solid was collected by filtration and was dried under reduced pressure to give the title compound 18.0 g (including impurities) as a white solid.
Mass spectrum (CI, m/z):243, 245[M+1]+.
¹H-NMR spectrum (400 MHz, DMSO-d₆) δ:10.95 (br s, 1H), 8.54 (s, 2H), 4.75-4.67 (m, 4H).

Reference Example 9-2

1-(5-Bromo-3-fluoropyridin-2-yl)azetidin-3-one oxime (Reference Compound 9-2)

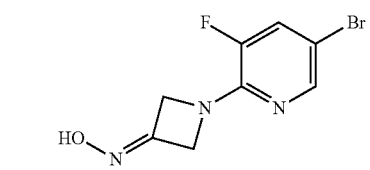 [SMILES: ON=C1CN(c2ncc(Br)cc2F)C1]

The reaction was performed by the method described in Reference Example 9-1, except that 1-(5-bromopyrimidin-2-yl)azetidin-3-one (Reference Compound 2) was replaced by 1-(5-bromo-3-fluoropyridin-2-yl)azetidin-3-one synthesized in the same manner as in Reference Example 32-1, that extraction was performed with ethyl acetate, and that the product was purified by recrystallization from methylene chloride. Consequently, the title compound (yield 89%) was obtained as a white solid.
Mass spectrum (CI, m/z):260, 262[M+1]+.
¹H-NMR spectrum (400 MHz, CDCl₃) δ:8.03 (dd, J=0.8, 1.9 Hz, 1H), 7.38 (dd, J=1.9, 10.7 Hz, 1H), 7.33 (s, 1H), 4.90-4.82 (m, 4H).

Reference Example 9-3

2-({[1-(5-Bromopyrimidin-2-yl)azetidin-3-ylidene]amino}oxy)acetic acid (Reference Compound 9-3)

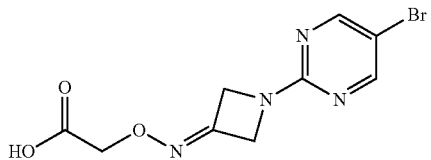 [SMILES: O=C(O)CON=C1CN(c2ncc(Br)cn2)C1]

The reaction was performed by the method described in Reference Example 9-1, except that the hydroxylamine hydrochloride was replaced by carboxymethoxyamine hemihydrochloride, that the reaction temperature was always ambient, and that after the completion of the reaction, the reaction mixture was concentrated under reduced pressure. Consequently, the title compound (including impurities) was obtained.

Reference Example 9-4

3-({[1-(5-Bromopyrimidin-2-yl)azetidin-3-ylidene]amino}oxy)propionic acid (Reference Compound 9-4)

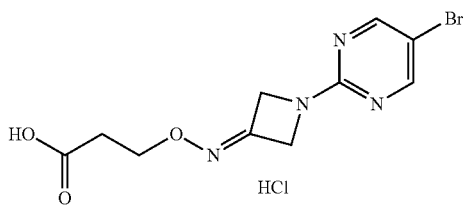 [SMILES: O=C(O)CCON=C1CN(c2ncc(Br)cn2)C1 ; Cl]

The reaction was performed by the method described in Reference Example 9-1, except that the hydroxylamine hydrochloride was replaced by 3-(aminooxy)propionic acid hydrochloride and that after the completion of the reaction, the reaction mixture was concentrated under reduced pressure. Consequently, the title compound (including impurities) was obtained.

Reference Example 10-1

1-(5-Bromopyrimidin-2-yl)azetidin-3-one O-methyl-$d_3$ oxime (Reference Compound 10-1)

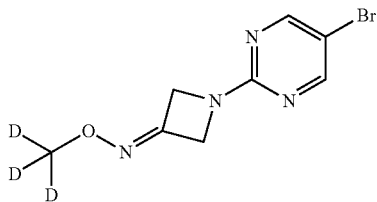 [SMILES: [2H]C([2H])([2H])ON=C1CN(c2ncc(Br)cn2)C1]

Iodomethane-$d_3$ 0.10 mL (1.6 mmol) and cesium carbonate 0.80 g (2.5 mmol) were added to a DMF (6.0 mL) solution of 1-(5-bromopyrimidin-2-yl)azetidin-3-one oxime 0.20 g (0.82 mmol) synthesized in the same manner as in Reference Example 9-1, and the mixture was stirred at room temperature for 18 hours. After the completion of the reaction, water was added to the reaction mixture, and followed by extraction with ethyl acetate. The organic layer was washed with water, dried over anhydrous magnesium sulfate, and filtered. The filtrate was concentrated under reduced pressure. The concentrated residue was purified by silica gel column chromatography (eluting solvent: 1,2-dichloroethane:ethyl acetate) to give the title compound 0.17 g (0.65 mmol, yield 79%) as a white solid.

Mass spectrum (CI, m/z):260, 262[M+1]$^+$.

$^1$H-NMR spectrum (400 MHz, DMSO-$d_6$) δ:8.52 (s, 2H), 4.80-4.70 (m, 4H).

Reference Example 10-2

1-(5-Bromopyrimidin-2-yl)azetidin-3-one O-(2-fluoroethyl) oxime (Reference Compound 10-2)

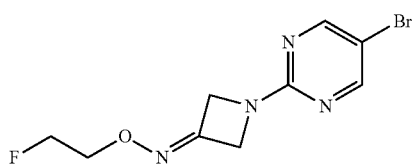 [SMILES: FCCON=C1CN(c2ncc(Br)cn2)C1]

The reaction was performed by the method described in Reference Example 10-1, except that iodomethane-$d_3$ was replaced by 2-fluoroethyl methanesulfonate synthesized in the same manner as in Reference Example 14-1, and the reaction temperature was changed to 90° C. Consequently, the title compound (yield 81%) was obtained as a white solid.

Mass spectrum (CI, m/z):289, 291[M+1]$^+$.

$^1$H-NMR spectrum (400 MHz, CDCl$_3$) δ:8.37 (s, 2H), 4.85-4.79 (m, 4H), 4.74-4.57 (m, 2H), 4.39-4.25 (m, 2H).

Reference Example 10-3

1-(5-Bromopyrimidin-2-yl)azetidin-3-one O-(3-fluoropropyl) oxime (Reference Compound 10-3)

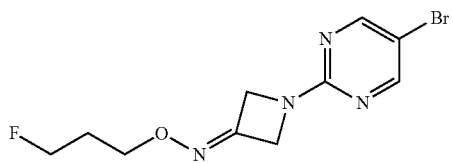 [SMILES: FCCCON=C1CN(c2ncc(Br)cn2)C1]

The reaction was performed by the method described in Reference Example 10-1, except that iodomethane-$d_3$ was replaced by 3-fluoropropyl methanesulfonate synthesized in the same manner as in Reference Example 14-3, and the reaction temperature was changed to 80° C. Consequently, the title compound (yield 60%) was obtained as a white solid.

Mass spectrum (CI, m/z):303, 305[M+1]$^+$.

$^1$H-NMR spectrum (400 MHz, DMSO-$d_6$) δ:8.55 (s, 2H), 4.79-4.72 (m, 4H), 4.62-4.41 (m, 2H), 4.12 (t, J=6.3 Hz, 2H), 2.06-1.92 (m, 2H).

Reference Example 10-4

1-(5-Bromopyrimidin-2-yl)azetidin-3-one O-{2-[(tetrahydropyran-2-yl)oxy]ethyl}oxime (Reference Compound 10-4)

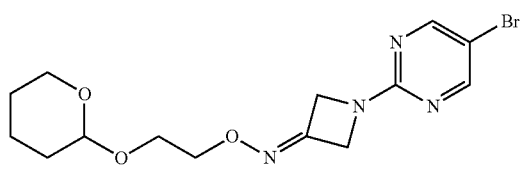 [SMILES: Brc1cnc(N2CC(=NOCCOC3CCCCO3)C2)nc1]

The reaction was performed by the method described in Reference Example 10-1, except that iodomethane-d$_3$ was replaced by 2-(2-bromoethoxy)tetrahydropyran, and the reaction temperature was changed to 80° C. Consequently, the title compound (yield 79%) was obtained as a white solid.

Mass spectrum (CI, m/z):371, 373[M+1]$^+$.

$^1$H-NMR spectrum (400 MHz, DMSO-d$_6$) δ:8.55 (s, 2H), 4.79-4.70 (m, 4H), 4.63-4.53 (m, 1H), 4.23-4.11 (m, 2H), 3.86-3.69 (m, 2H), 3.65-3.56 (m, 1H), 3.50-3.38 (m, 1H), 1.89-1.24 (m, 6H).

Reference Example 10-5

1-(5-Bromopyrimidin-2-yl)azetidin-3-one O-{3-[(tetrahydropyran-2-yl)oxy]propyl}oxime (Reference Compound 10-5)

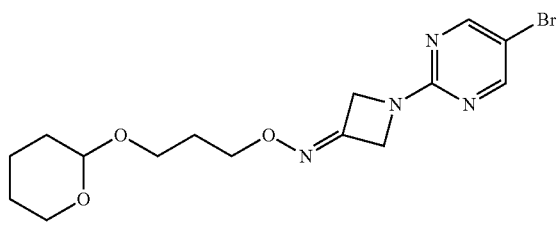 [SMILES: Brc1cnc(N2CC(=NOCCCOC3CCCCO3)C2)nc1]

The reaction was performed by the method described in Reference Example 10-1, except that iodomethane-d$_3$ was replaced by 2-(3-bromopropoxy)tetrahydropyran, and the reaction temperature was changed to 80° C. Consequently, the title compound (including impurities) was obtained as a light yellow solid.

Mass spectrum (CI, m/z):385,387[M+1]$^+$.

1H-NMR spectrum (400 MHz, DMSO-d$_6$) δ:8.54 (s, 2H), 4.81-4.68 (m, 4H), 4.59-4.51 (m, 1H), 4.19-4.03 (m, 2H), 3.77-3.63 (m, 2H), 3.48-3.36 (m, 2H), 1.89-1.80 (m, 2H), 1.75-1.39 (m, 6H).

Reference Example 10-6

1-(5-Bromopyrimidin-2-yl)azetidin-3-one O-{4-[(tetrahydropyran-2-yl)oxy]butyl}oxime (Reference Compound 10-6)

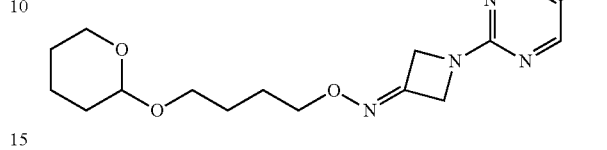

The reaction was performed by the method described in Reference Example 10-1, except that iodomethane-d$_3$ was replaced by 2-(4-bromobutoxy)tetrahydropyran, and the reaction temperature was changed to 80° C. Consequently, the title compound (yield 89%) was obtained as a white solid.

Mass spectrum (CI, m/z):399,401[M+1]$^+$.

$^1$H-NMR spectrum (400 MHz, DMSO-d$_6$) δ:8.54 (s, 2H), 4.80-4.71 (m, 4H), 4.57-4.50 (m, 1H), 4.07-4.01 (m, 2H), 3.78-3.58 (m, 2H), 3.47-3.33 (m, 2H), 1.84-1.36 (m, 10H).

Reference Example 10-7

1-(5-Bromopyrimidin-2-yl)azetidin-3-one O-(2-methoxyethyl) oxime (Reference Compound 10-7)

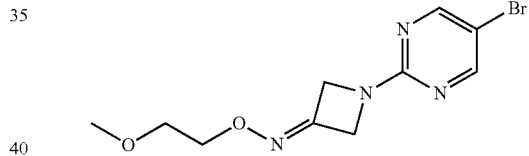

The reaction was performed by the method described in Reference Example 10-1, except that iodomethane-d$_3$ was replaced by 2-bromoethyl methyl ether, and the reaction temperature was changed to 80° C. Consequently, the title compound (yield 89%) was obtained as a white solid.

Mass spectrum (CI, m/z):301, 303[M+1]$^+$.

$^1$H-NMR spectrum (400 MHz, DMSO-d$_6$) δ:8.55 (s, 2H), 4.79-4.71 (m, 4H), 4.17-4.10 (m, 2H), 3.58-3.51 (m, 2H), 3.26 (s, 3H).

Reference Example 10-8

1-(5-Bromopyrimidin-2-yl)azetidin-3-one O-[(2,2-dimethyl-1,3-dioxan-5-yl)methyl]oxime (Reference Compound 10-8)

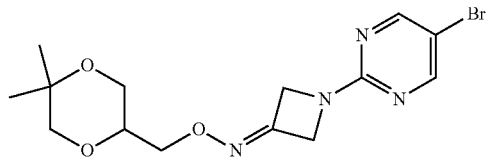 [SMILES: CC1(C)COC(CON=C2CN(c3ncc(Br)cn3)C2)CO1]

The reaction was performed by the method described in Reference Example 10-1, except that iodomethane-d₃ was replaced by (2,2-dimethyl-1,3-dioxan-5-yl)methyl methanesulfonate synthesized in the same manner as in Reference Example 14-4, and the reaction temperature was changed to 80° C. Consequently, the title compound (yield 74%) was obtained as a white solid.

Mass spectrum (CI, m/z):371, 373[M+1]⁺.

¹H-NMR spectrum (400 MHz, DMSO-d₆) δ:8.55 (s, 2H), 4.79-4.72 (m, 4H), 4.07 (d, J=7.2 Hz, 2H), 3.89 (dd, J=4.0, 11.9 Hz, 2H), 3.64 (dd, J=6.1, 11.9 Hz, 2H), 2.01-1.93 (m, 1H), 1.33 (s, 3H), 1.30 (s, 3H).

Reference Example 10-9

1-(5-Bromopyrimidin-2-yl)azetidin-3-one O-[(2,2-dimethyl-1,3-dioxolan-4-yl)methyl]oxime (Reference Compound 10-9)

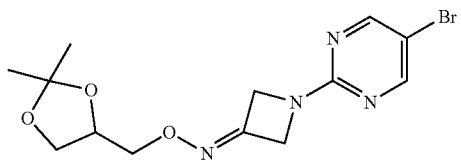 [SMILES: CC1(C)OCC(CON=C2CN(c3ncc(Br)cn3)C2)O1]

The reaction was performed by the method described in Reference Example 10-1, except that iodomethane-d₃ was replaced by (2,2-dimethyl-1,3-dioxolan-4-yl)methyl methanesulfonate synthesized in the same manner as in Reference Example 14-5, and the reaction temperature was changed to 80° C. Consequently, the title compound (yield 66%) was obtained as a white solid.

Mass spectrum (CI, m/z):357, 359[M+1]⁺.

¹H-NMR spectrum (400 MHz, DMSO-d₆) δ:8.55 (s, 2H), 4.79-4.72 (m, 4H), 4.33-4.24 (m, 1H), 4.09-4.00 (m, 3H), 3.66 (dd, J=6.5, 8.3 Hz, 1H), 1.32 (s, 3H), 1.27 (s, 3H).

Reference Example 10-10

1-(5-Bromopyrimidin-2-yl)azetidin-3-one O-[2-(2,2-dimethyl-1,3-dioxolan-4-yl)ethyl]oxime (Reference Compound 10-10)

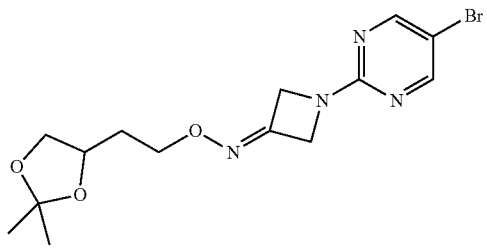 [SMILES: CC1(C)OCC(CCON=C2CN(c3ncc(Br)cn3)C2)O1]

The reaction was performed by the method described in Reference Example 10-1, except that iodomethane-d₃ was replaced by 2-(2,2-dimethyl-1,3-dioxolan-4-yl)ethyl methanesulfonate synthesized in the same manner as in Reference Example 14-6, and the reaction temperature was changed to 80° C. Consequently, the title compound (yield 82%) was obtained as a white solid.

Mass spectrum (CI, m/z):371, 373[M+1]⁺.

¹H-NMR spectrum (400 MHz, DMSO-d₆) δ:8.54 (s, 2H), 4.79-4.70 (m, 4H), 4.17-4.03 (m, 3H), 4.01 (dd, J=6.0, 8.0 Hz, 1H), 3.48 (dd, J=7.2, 8.0 Hz, 1H), 1.89-1.79 (m, 2H), 1.31 (s, 3H), 1.26 (s, 3H).

Reference Example 10-11

2-({[1-(5-Bromopyrimidin-2-yl)azetidin-3-ylidene]amino}oxy)ethyl acetate (Reference Compound 10-11)

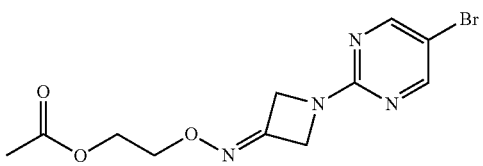 [SMILES: CC(=O)OCCON=C1CN(c2ncc(Br)cn2)C1]

The reaction was performed by the method described in Reference Example 10-1, except that iodomethane-d₃ was replaced by 2-bromoethyl acetate, and the reaction temperature was changed to 80° C. Consequently, the title compound (yield 65%) was obtained as a white solid.

Mass spectrum (ESI, m/z):329, 331[M+1]⁺.

¹H-NMR spectrum (400 MHz, CDCl₃) δ:8.37 (s, 2H), 4.85-4.75 (m, 4H), 4.35-4.24 (m, 4H), 2.09 (s, 3H).

Reference Example 10-12) tert-Butyl 2-({[1-(5-bromopyrimidin-2-yl)azetidin-3-ylidene]amino}oxy)acetate (Reference Compound 10-12)

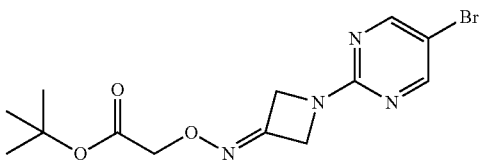 [SMILES: CC(C)(C)OC(=O)CON=C1CN(c2ncc(Br)cn2)C1]

The reaction was performed by the method described in Reference Example 10-1, except that iodomethane-d₃ was replaced by tert-butyl bromoacetate. Consequently, the title compound (yield 83%) was obtained as a light yellow oil.

Mass spectrum (CI, m/z):357, 359[M+1]⁺.

¹H-NMR spectrum (400 MHz, CDCl₃) δ:8.37 (s, 2H), 4.89-4.81 (m, 4H), 4.51 (s, 2H), 1.49 (s, 9H).

Reference Example 10-13

Ethyl 4-({[1-(5-bromopyrimidin-2-yl)azetidin-3-ylidene]amino}oxy)butanoate (Reference Compound 10-13)

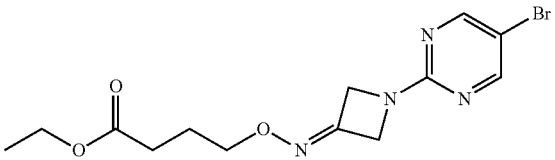 [SMILES: CCOC(=O)CCCON=C1CN(c2ncc(Br)cn2)C1]

The reaction was performed by the method described in Reference Example 10-1, except that iodomethane-d₃ was replaced by ethyl 4-bromobutyrate, and the reaction temperature was changed to 80° C. Consequently, the title compound (yield 90%) was obtained as a white solid.

Mass spectrum (CI, m/z):357, 359[M+1]⁺.

¹H-NMR spectrum (400 MHz, DMSO-d₆) δ:8.55 (s, 2H), 4.78-4.70 (m, 4H), 4.09-4.00 (m, 4H), 2.36 (t, J=7.4 Hz, 2H), 1.92-1.79 (m, 2H), 1.18 (t, J=7.1 Hz, 3H).

Reference Example 10-14) tert-Butyl 2-[({[1-(5-bromopyrimidin-2-yl)azetidin-3-ylidene]amino}oxy)methyl]morpholine-4-carboxylate (Reference Compound 10-14)

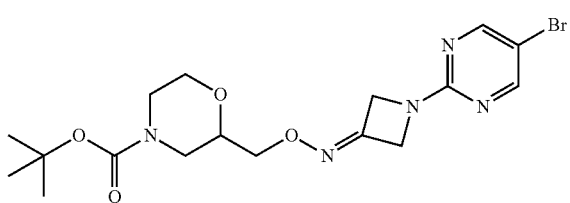 [SMILES: CC(C)(C)OC(=O)N1CCOC(CON=C2CN(c3ncc(Br)cn3)C2)C1]

The reaction was performed by the method described in Reference Example 10-1, except that iodomethane-d₃ was replaced by tert-butyl 2-{[(methylsulfonyl)oxy]methyl}morpholine-4-carboxylate synthesized in the same manner as in Reference Example 14-9, and the reaction temperature was changed to 80° C. Consequently, the title compound (yield 50%) was obtained as a white solid.

Mass spectrum (CI, m/z):442, 444[M+1]⁺.

¹H-NMR spectrum (400 MHz, DMSO-d₆) δ:8.55 (s, 2H), 4.80-4.72 (m, 4H), 4.08-3.98 (m, 2H), 3.88-3.76 (m, 2H), 3.76-3.65 (m, 1H), 3.63-3.53 (m, 1H), 3.45-3.33 (m, 1H), 2.97-2.77 (m, 1H), 2.76-2.54 (m, 1H), 1.40 (s, 9H).

Reference Example 10-15

1-(5-Bromopyrimidin-2-yl)azetidin-3-one O-oxetan-3-yl oxime (Reference Compound 10-15)

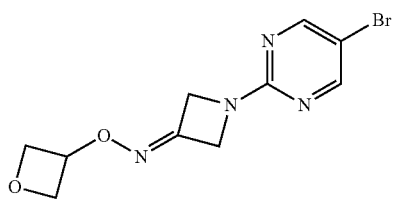 [SMILES: Brc1cnc(N2CC(=NOC3COC3)C2)nc1]

The reaction was performed by the method described in Reference Example 10-1, except that iodomethane-d₃ was replaced by oxetan-3-yl 4-methylbenzenesulfonate, and the reaction temperature was changed to 80° C. Consequently, the title compound (including impurities) was obtained as a white solid.

Mass spectrum (CI, m/z):299, 301[M+1]⁺.

¹H-NMR spectrum (400 MHz, DMSO-d₆) δ:8.56 (s, 2H), 5.23-5.16 (m, 1H), 4.83-4.78 (m, 4H), 4.78-4.73 (m, 2H), 4.57-4.52 (m, 2H).

Reference Example 11-1

1-(5-Bromopyrimidin-2-yl)azetidin-3-one O-(tert-butyldimethylsilyl) oxime (Reference Compound 11-1)

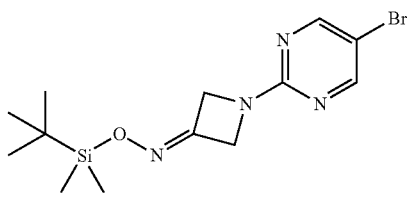 [SMILES: CC(C)(C)[Si](C)(C)ON=C1CN(c2ncc(Br)cn2)C1]

TEA 300 μl (2.15 mmol) was added to a DMF (3 mL) suspension of 1-(5-bromopyrimidin-2-yl)azetidin-3-one oxime 261 mg (1.07 mmol) synthesized in the same manner as in Reference Example 9-1. Next, a DMF (2 mL) solution of tert-butylchlorodimethylsilane 244 mg (1.62 mmol) was dropped thereto, and the mixture was stirred at room temperature for 1 hour. Further, TEA 300 μl (2.15 mmol) and tert-butylchlorodimethylsilane 204 mg (1.35 mmol) were added, and the mixture was stirred at 60° C. for 1 hour. After the completion of the reaction, the reaction mixture was diluted with toluene, sequentially washed with a saturated aqueous sodium hydrogen carbonate solution and brine, dried over anhydrous magnesium sulfate, and filtered. The filtrate was concentrated under reduced pressure. The concentrated residue was purified by silica gel column chromatography (eluting solvent: hexane:ethyl acetate) to give the title compound 296 mg (0.828 mmol, yield 77%) as a light yellow solid.

Mass spectrum (DUIS, m/z):357, 359[M+1]⁺.

¹H-NMR spectrum (400 MHz, DMSO-d₆) δ:8.55 (s, 2H), 4.81-4.72 (m, 4H), 0.91 (s, 9H), 0.15 (s, 6H).

Reference Example 11-2

1-(5-Bromo-3-fluoropyridin-2-yl)azetidin-3-one O-(tert-butyldimethylsilyl) oxime (Reference Compound 11-2)

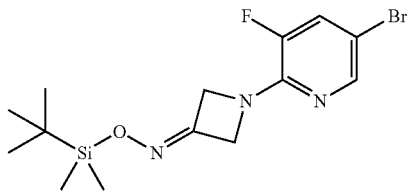 [SMILES: CC(C)(C)[Si](C)(C)ON=C1CN(c2ncc(Br)cc2F)C1]

(tert-Butyl)dimethylsilyl chloride 350 mg (2.32 mmol) and imidazole 172 mg (2.53 mmol) were added to a THF (10 ml) solution of 1-(5-bromopyrimidin-2-yl)azetidin-3-one O-(3-hydroxy-2-methoxypropyl) oxime 500 mg (1.92 mmol) synthesized in the same manner as in Reference Example 9-2, and the mixture was stirred at room temperature for 26 hours. After the completion of the reaction, water was added to the reaction mixture, and followed by extraction with ethyl acetate. The extract was concentrated, and the residue was purified by silica gel column chromatography (eluting solvent: hexane:ethyl acetate) to give the title compound 643 mg (yield 89%) as a white solid.

¹H-NMR spectrum (400 MHz, DMSO-d₆) δ:8.11-8.09 (m, 1H), 7.93-7.87 (m, 1H), 4.86-4.78 (m, 4H), 0.91 (s, 9H), 0.15 (s, 6H).

Reference Example 12

[2-Fluoro-3-(4,4,5,5-tetramethyl-1,3,2-dioxaborolan-2-yl)phenyl]methanol (Reference Compound 12)

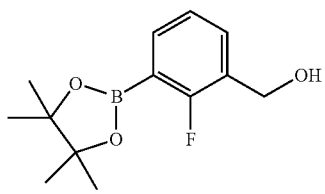 [SMILES: CC1(C)OB(c2cccc(CO)c2F)OC1(C)C]

1 M tetrabutylammonium fluoride/THF solution 1.35 mL (1.35 mmol) was added to a THF (10 mL) solution of tert-butyl {[2-fluoro-3-(4,4,5,5-tetramethyl-1,3,2-dioxaborolan-2-yl)benzyl]oxy}dimethyisilane 302 mg (0.824 mmol) synthesized in the same manner as in Reference Example 5, and the mixture was stirred at room temperature for 2.5 hours. After the completion of the reaction, the reaction mixture was concentrated under reduced pressure. The concentrated residue was purified by silica gel column chromatography (eluting solvent: hexane:ethyl acetate) to give the title compound 172 mg (0.682 mmol, yield 83%) as a colorless oil.

¹H-NMR spectrum (400 MHz, CDCl₃) δ:7.74-7.64 (m, 1H), 7.56-7.49 (m, 1H), 7.20-7.10 (m, 1H), 4.76 (s, 2H), 1.37 (s, 12H).

Reference Example 13-1

1-{5-[2-Fluoro-3-(hydroxymethyl)phenyl]pyrimidin-2-yl}azetidin-3-one O-(tert-butyldimethylsilyl) oxime (Reference Compound 13-1)

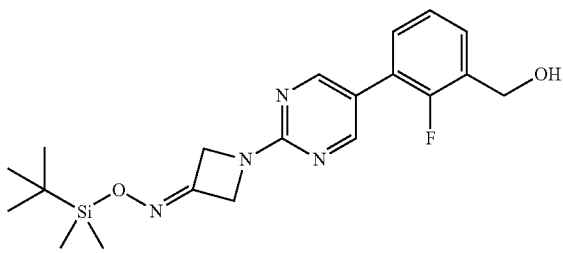 [SMILES: CC(C)(C)[Si](C)(C)ON=C1CN(c2ncc(-c3cccc(CO)c3F)cn2)C1]

A water (0.8 mL)-1,4-dioxane (4.0 mL) suspension of 1-(5-bromopyrimidin-2-yl)azetidin-3-one O-(tert-butyldimethylsilyl) oxime 180 mg (0.504 mmol) synthesized in the same manner as in Reference Example 11-1, [2-fluoro-3-(4,4,5,5-tetramethyl-1,3,2-dioxaborolan-2-yl)phenyl]methanol 164 mg (0.651 mmol) synthesized in the same manner as in Reference Example 12 and tripotassium phosphate 278 mg (1.31 mmol) was bubbled with nitrogen gas for 15 minutes. Next, tetrakis(triphenylphosphine)palladium (0) 31.1 mg (0.0269 mmol) was added. The mixture was fed to a microwave reaction device and was stirred at 120° C. for 1 hour. After the completion of the reaction, water was added to the reaction mixture, and followed by extraction with ethyl acetate. The organic layer was washed with brine, dried over anhydrous magnesium sulfate, and filtered. The filtrate was concentrated under reduced pressure. The concentrated residue was purified by silica gel column chromatography (eluting solvent: 1,2-dichloroethane:methanol=99:1 to 99:4 (V/V)) to give the title compound 131 mg (0.325 mmol, yield 64%) as a white solid.

Mass spectrum (DUIS, m/z):403[M+1]⁺.

¹H-NMR spectrum (400 MHz, DMSO-d₆) δ:8.63 (d, J=1.5 Hz, 2H), 7.66-7.42 (m, 2H), 7.32-7.26 (m, 1H), 5.34 (t, J=5.6 Hz, 1H), 4.88-4.73 (m, 4H), 4.61 (d, J=5.6 Hz, 2H), 0.93 (s, 9H), 0.16 (s, 6H).

Reference Example 13-2

1-{3-Fluoro-5-[2-fluoro-3-(hydroxymethyl)phenyl]pyridin-2-yl}azetidin-3-one O-(tert-butyldimethylsilyl) oxime (Reference Compound 13-2)

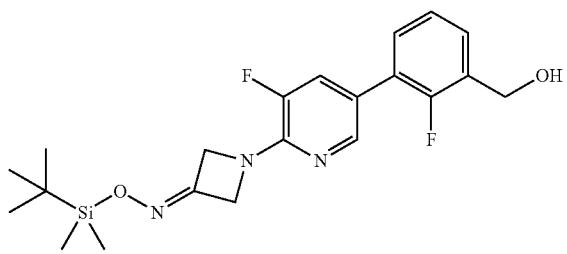 [SMILES: CC(C)(C)[Si](C)(C)ON=C1CN(c2ncc(-c3cccc(CO)c3F)cc2F)C1]

1,4-Dioxane (10 mL)-water (5 ml) solution of 1-(5-bromo-3-fluoropyridin-2-yl)azetidin-3-one O-(tert-butyldimethylsilyl) oxime 642 mg (1.72 mmol) synthesized in the same manner as in Reference Example 11-2, [2-fluoro-3-(4,4,5,5-tetramethyl-1,3,2-dioxaborolan-2-yl)phenyl]methanol 487 mg (1.93 mmol) synthesized in the same manner as in Reference Example 12 and sodium carbonate 545 mg (5.14 mmol) was degassed and purged with nitrogen. Next, tetrakis(triphenylphosphine)palladium (0) 99 mg (0.086 mmol) was added. Under a stream of argon, the mixture was stirred at 80° C. for 3 hours. After the completion of the reaction, water was added to the reaction mixture, and followed by extraction with ethyl acetate. The organic layer was washed with water, dried over anhydrous magnesium sulfate, and filtered. The filtrate was concentrated under reduced pressure. The concentrated residue was purified by silica gel column chromatography (eluting solvent: hexane:ethyl acetate) to give the title compound 450 mg (1.07 mmol, yield 62%) as a light yellow solid.

Mass spectrum (ESI, m/z):420[M+1]⁺.

¹H-NMR spectrum (400 MHz, DMSO-d₆+D₂O) δ:8.19-8.15 (m, 1H), 7.78-7.69 (m, 1H), 7.50-7.37 (m, 2H), 7.32-7.25 (m, 1H), 4.91-4.77 (m, 4H), 4.60 (s, 2H), 0.92 (s, 9H), 0.16 (s, 6H).

Reference Example 14-1

2-Fluoroethyl methanesulfonate (Reference Compound 14-1)

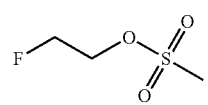

TEA 4.4 mL (32 mmol) and methanesulfonyl chloride 1.4 mL (18 mmol) were added to a methylene chloride (30 mL) solution of ethylene fluorohydrin 1.0 g (16 mmol), and the mixture was stirred at room temperature for 16 hours. After the completion of the reaction, water was added to the reaction mixture, and followed by extraction with methylene chloride. The organic layer was washed with brine, dried over anhydrous magnesium sulfate, and filtered. The filtrate was concentrated under reduced pressure to give a crude product 2.23 g including the title compound as a light yellow oil.

Mass spectrum (CI, m/z): 143 [M+1]$^+$.

$^1$H-NMR spectrum (400 MHz, CDCl$_3$) δ:4.76-4.60 (m, 2H), 4.53-4.41 (m, 2H), 3.08 (s, 3H).

Reference Example 14-2

2,2-Difluoroethyl methanesulfonate (Reference Compound 14-2)

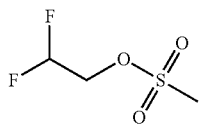

The reaction was performed by the method described in Reference Example 14-1, except that ethylene fluorohydrin was replaced by 2,2-difluoroethanol. Consequently, a crude product including the title compound was obtained.

Reference Example 14-3

3-Fluoropropyl methanesulfonate (Reference Compound 14-3)

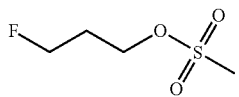

The reaction was performed by the method described in Reference Example 14-1, except that ethylene fluorohydrin was replaced by 3-fluoropropan-1-ol. Consequently, a crude product including the title compound was obtained as a brown oil.

Reference Example 14-4

(2,2-Dimethyl-1,3-dioxan-5-yl)methyl methanesulfonate (Reference Compound 14-4)

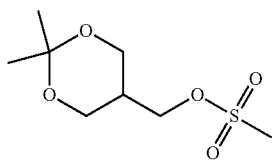

The reaction was performed by the method described in Reference Example 14-1, except that ethylene fluorohydrin was replaced by (2,2-dimethyl-1,3-dioxan-5-yl)methanol. Consequently, a crude product including the title compound was obtained as a yellow oil.

Reference Example 14-5

(2,2-Dimethyl-1,3-dioxolan-4-yl)methyl methanesulfonate (Reference Compound 14-5)

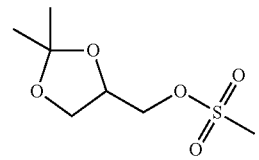

The reaction was performed by the method described in Reference Example 14-1, except that ethylene fluorohydrin was replaced by (2,2-dimethyl-1,3-dioxolan-4-yl)methanol. Consequently, a crude product including the title compound was obtained as a brown oil.

Reference Example 14-6

2-(2,2-Dimethyl-1,3-dioxolan-4-yl)ethyl methanesulfonate (Reference Compound 14-6)

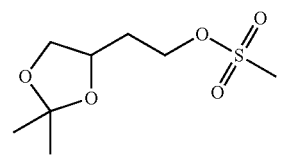

The reaction was performed by the method described in Reference Example 14-1, except that ethylene fluorohydrin was replaced by 2-(2,2-dimethyl-1,3-dioxolan-4-yl)ethanol. Consequently, a crude product including the title compound was obtained as a brown oil.

Reference Example 14-7

3-Hydroxy-3-methylbutyl methanesulfonate (Reference Compound 14-7)

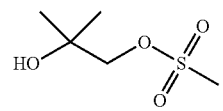

The reaction was performed by the method described in Reference Example 14-1, except that ethylene fluorohydrin was replaced by 3-methylbutane-1,3-diol. Consequently, a crude product including the title compound was obtained as a colorless oil.

Reference Example 14-8

(2,2,5-Trimethyl-1,3-dioxan-5-yl)methyl methanesulfonate (Reference Compound 14-8)

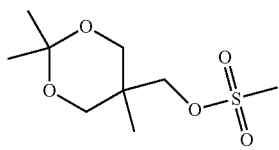

The reaction was performed by the method described in Reference Example 14-1, except that ethylene fluorohydrin was replaced by (2,2,5-trimethyl-1,3-dioxan-5-yl)methanol. Consequently, a crude product including the title compound was obtained as an orange oil.
Mass spectrum (CI, m/z):239[M+1]$^+$.
$^1$H-NMR spectrum (400 MHz, CDCl$_3$) δ:4.34 (s, 2H), 3.71-3.59 (m, 4H), 3.04 (s, 3H), 1.45 (s, 3H), 1.40 (s, 3H), 0.88 (s, 3H).

Reference Example 14-9 tert-Butyl 2-{[(methylsulfonyl)oxy]methyl}morpholine-4-carboxylate (Reference Compound 14-9)

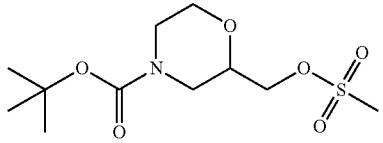 [SMILES: CC(C)(C)OC(=O)N1CCOC(COS(C)(=O)=O)C1]

The reaction was performed by the method described in Reference Example 14-1, except that ethylene fluorohydrin was replaced by tert-butyl 2-(hydroxymethyl)morpholine-4-carboxylate. Consequently, a crude product including the title compound was obtained.

Reference Example 14-10

(5-Oxotetrahydrofuran-2-yl)methyl methanesulfonate (Reference Compound 14-10)

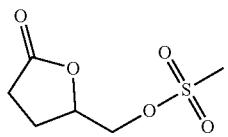

The reaction was performed by the method described in Reference Example 14-1, except that ethylene fluorohydrin was replaced by dihydro-5-(hydroxymethyl)-2(3H)-furanone. Consequently, the title compound (including impurities) was obtained.
Mass spectrum (CI, m/z):195[M+1]$^+$.
$^1$H-NMR spectrum (400 MHz, CDCl$_3$) δ:4.83-4.74 (m, 1H), 4.48-4.27 (m, 2H), 3.09 (s, 3H), 2.71-2.53 (m, 2H), 2.46-2.11 (m, 2H).

Reference Example 14-11

3-(Methylsulfonyl)propyl methanesulfonate (Reference Compound 14-11)

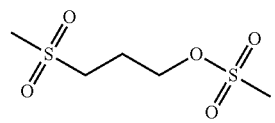

The reaction was performed by the method described in Reference Example 14-1, except that ethylene fluorohydrin was replaced by 3-(methylsulfonyl)propan-1-ol. Consequently, the title compound (including impurities) was obtained as a yellow solid.
$^1$H-NMR spectrum (400 MHz, CDCl$_3$) δ:4.48-4.36 (m, 2H), 3.23-3.16 (m, 2H), 3.06 (s, 3H), 2.97 (s, 3H), 2.44-2.25 (m, 2H).

Reference Example 14-12

(1-Methyl-1H-pyrazol-3-yl)methyl methanesulfonate (Reference Compound 14-12)

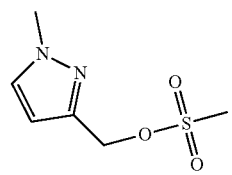

The reaction was performed by the method described in Reference Example 14-1, except that ethylene fluorohydrin was replaced by (1-methyl-1H-pyrazol-3-yl)methanol synthesized in the same manner as in Reference Example 114-1, and the product was purified by silica gel column chromatography. Consequently, the title compound (yield 22%) was obtained as a colorless oil.
$^1$H-NMR spectrum (400 MHz, CDCl$_3$) δ:7.31 (d, J=2.2 Hz, 1H), 6.30 (d, J=2.2 Hz, 1H), 4.60 (s, 2H), 3.89 (s, 3H).

Reference Example 14-13

3-(Chloromethyl)-1-(tetrahydropyran-2-yl)-1H-pyrazole (Reference Compound 14-13)

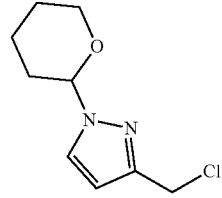 [SMILES: ClCc1ccn(C2CCCCO2)n1]

The reaction was performed by the method described in Reference Example 14-1, except that ethylene fluorohydrin was replaced by [2-(tetrahydropyran-2-yl)-1H-pyrazol-3-yl]methanol synthesized in the same manner as in Reference Example 114-2. Consequently, the title compound (yield 66%) was obtained as a colorless oil.

Mass spectrum (CI, m/z):201[M+1]+.

¹H-NMR spectrum (400 MHz, CDCl₃) δ:7.56 (d, J=2.5 Hz, 1H), 6.37 (d, J=2.5 Hz, 1H), 5.34 (dd, J=2.9, 9.4 Hz, 1H), 4.62 (s, 2H), 4.11-4.03 (m, 1H), 3.74-3.65 (m, 1H), 2.16-1.99 (m, 3H), 1.86-1.42 (m, 3H).

Reference Example 14-14

[1-(Tetrahydropyran-2-yl)-1H-pyrazol-4-yl]methyl methanesulfonate (Reference Compound 14-14)

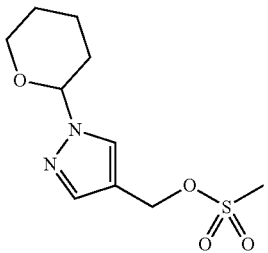 [SMILES: CS(=O)(=O)OCc1cnn(C2CCCCO2)c1]

The reaction was performed by the method described in Reference Example 14-1, except that ethylene fluorohydrin was replaced by [2-(tetrahydropyran-2-yl)-1H-pyrazol-4-yl]methanol synthesized in the same manner as in Reference Example 114-3. Consequently, a crude product including the title compound was obtained.

Reference Example 15-1

1-[5-(3-{[(tert-Butyldimethylsilyl)oxy]methyl}-2-fluorophenyl)pyrimidin-2-yl]azetidin-3-one O-(2,2-difluoroethyl) oxime (Reference Compound 15-1)

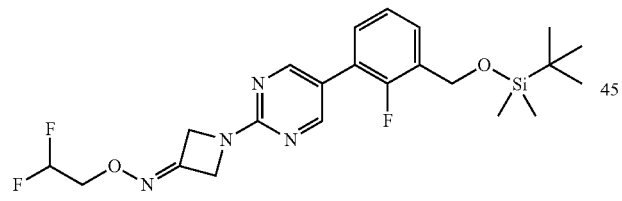

2,2-Difluoroethyl methanesulfonate 298 mg (1.86 mmol) synthesized in the same manner as in Reference Example 14-2 and cesium carbonate 607 mg (1.86 mmol) were added to a DMF (1 mL) solution of 1-[5-(3-{[(tert-butyldimethylsilyl)oxy]methyl}-2-fluorophenyl)pyrimidin-2-yl]azetidin-3-one oxime 150 mg (0.373 mmol) synthesized in the same manner as in Reference Example 6-5, and the mixture was stirred at room temperature for 15 hours and at 70° C. for 3 hours. After the completion of the reaction, a saturated aqueous ammonium chloride solution was added to the reaction mixture, and followed by extraction with ethyl acetate. The organic layer was washed with brine, dried over anhydrous magnesium sulfate, and filtered. The filtrate was concentrated under reduced pressure. The concentrated residue was purified by silica gel column chromatography (eluting solvent: hexane:ethyl acetate) to give the title compound 128 mg (0.274 mmol, yield 74%) as a white solid.

Mass spectrum (ESI, m/z):467[M+1]+.

¹H-NMR spectrum (400 MHz, CDCl₃) δ:8.57 (d, J=1.4 Hz, 2H), 7.55-7.47 (m, 1H), 7.31-7.19 (m, 2H), 6.01 (tt, J=4.2, 55.3 Hz, 1H), 4.92-4.88 (m, 4H), 4.85 (s, 2H), 4.26 (dt, J=4.2, 13.3 Hz, 2H), 0.96 (s, 9H), 0.14 (s, 6H).

Reference Example 15-2

1-[5-(3-{[(tert-Butyldimethylsilyl)oxy]methyl}-2-fluorophenyl)pyrimidin-2-yl]azetidin-3-one O-(2,2,2-trifluoroethyl) oxime (Reference Compound 15-2)

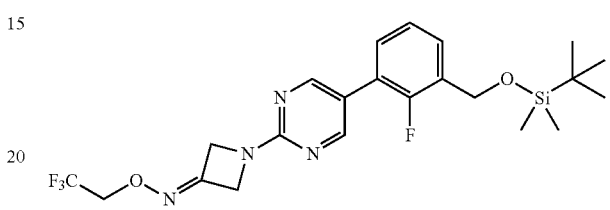

The reaction was performed by the method described in Reference Example 15-1, except that 2,2-difluoroethyl methanesulfonate (Reference Compound 14-2) was replaced by 2,2,2-trifluoroethyl trifluoromethanesulfonate, the reaction temperature was always ambient, and the purification by silica gel column chromatography was not performed. Consequently, a crude product including the title compound was obtained as a light yellow solid.

Mass spectrum (CI, m/z):485[M+1]+.

¹H-NMR spectrum (400 MHz, CDCl₃) δ:8.57 (d, J=1.4 Hz, 2H), 7.56-7.45 (m, 1H), 7.32-7.20 (m, 2H), 4.94-4.89 (m, 4H), 4.85 (s, 2H), 4.45 (q, J=8.5 Hz, 2H), 0.96 (s, 9H), 0.14 (s, 6H).

Reference Example 15-3

[({1-[5-(3-{[(tert-Butyldimethylsilyl)oxy]methyl}-2-fluorophenyl)pyrimidin-2-yl]azetidin-3-ylidene}amino)oxy]methyl pivalate (Reference Compound 15-3)

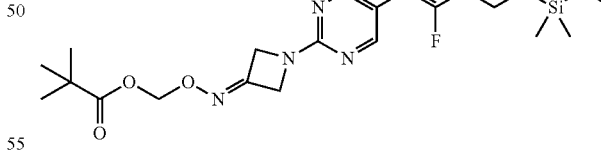

The reaction was performed by the method described in Reference Example 15-1, except that 2,2-difluoroethyl methanesulfonate (Reference Compound 14-2) was replaced by chloromethyl pivalate, and the reaction temperature was always ambient. Consequently, the title compound (yield 25%) was obtained as a white solid.

Mass spectrum (CI, m/z):517[M+1]+.

¹H-NMR spectrum (400 MHz, CDCl₃) δ:8.57 (d, J=1.5 Hz, 2H), 7.54-7.48 (m, 1H), 7.30-7.20 (m, 2H), 5.73 (s, 2H), 4.93-4.88 (m, 4H), 4.85 (s, 2H), 1.24 (s, 9H), 0.96 (s, 9H), 0.14 (s, 6H).

Reference Example 15-4

1-[5-(3-{[(tert-Butyldimethylsilyl)oxy]methyl}-2-fluorophenyl)pyrimidin-2-yl]azetidin-3-one O-dimethylcarbamoyl oxime (Reference Compound 15-4)

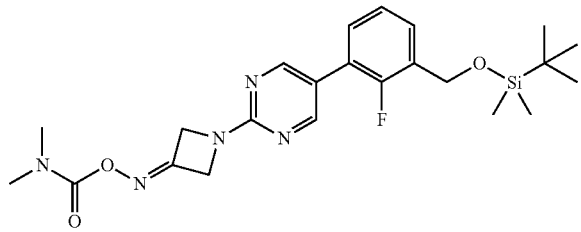 [SMILES: CN(C)C(=O)ON=C1CN(c2ncc(-c3cccc(CO[Si](C)(C)C(C)(C)C)c3F)cn2)C1]

The reaction was performed by the method described in Reference Example 15-1, except that 2,2-difluoroethyl methanesulfonate (Reference Compound 14-2) was replaced by dimethylcarbamoyl chloride, and the reaction temperature was always ambient. Consequently, the title compound (yield 63%) was obtained as a white solid.

Mass spectrum (CI, m/z):474[M+1]$^+$.

$^1$H-NMR spectrum (400 MHz, CDCl$_3$) δ:8.58 (d, J=1.4 Hz, 2H), 7.56-7.46 (m, 1H), 7.32-7.21 (m, 2H), 5.05-4.94 (m, 4H), 4.85 (s, 2H), 3.01 (br s, 3H), 2.95 (br s, 3H), 0.96 (s, 9H), 0.14 (s, 6H).

Reference Example 15-5

5-{[({1-[5-(3-{[(tert-Butyldimethylsilyl)oxy]methyl}-2-fluorophenyl)pyrimidin-2-yl]azetidin-3-ylidene}amino)oxy]methyl}dihydrofuran-2(3H)-one (Reference Compound 15-5)

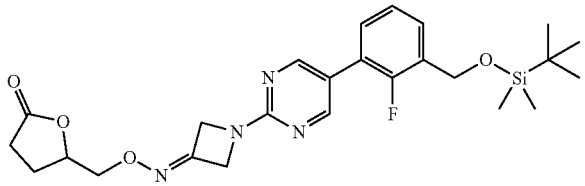 [SMILES: CC(C)(C)[Si](C)(C)OCc1cccc(-c2cnc(N3CC(=NOCC4CCC(=O)O4)C3)nc2)c1F]

The reaction was performed by the method described in Reference Example 15-1, except that 2,2-difluoroethyl methanesulfonate (Reference Compound 14-2) was replaced by (5-oxotetrahydrofuran-2-yl)methyl methanesulfonate synthesized in the same manner as in Reference Example 14-10, and the reaction temperature was always ambient. Consequently, the title compound (yield 53%) was obtained as a white solid.

Mass spectrum (CI, m/z):501[M+1]$^+$.

$^1$H-NMR spectrum (400 MHz, CDCl$_3$) δ:8.57 (d, J=1.4 Hz, 2H), 7.55-7.47 (m, 1H), 7.31-7.19 (m, 2H), 4.93-4.76 (m, 7H), 4.34-4.20 (m, 2H), 2.64-2.48 (m, 2H), 2.42-2.30 (m, 1H), 2.16-2.02 (m, 1H), 0.96 (s, 9H), 0.16-0.11 (m, 6H).

Reference Example 15-6

1-[5-(3-{[(tert-Butyldimethylsilyl)oxy]methyl}-2-fluorophenyl)pyrimidin-2-yl]azetidin-3-one O-(4-methoxybenzyl) oxime (Reference Compound 15-6)

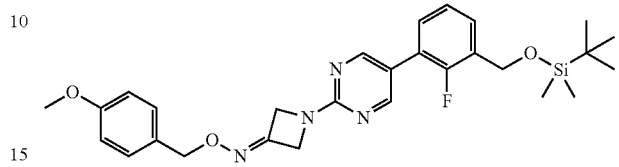

The reaction was performed by the method described in Reference Example 15-1, except that 2,2-difluoroethyl methanesulfonate (Reference Compound 14-2) was replaced by p-methoxybenzyl bromide, and the reaction temperature was always ambient. Consequently, the title compound (yield 85%) was obtained as a white solid.

Mass spectrum (CI, m/z):523[M+1]$^+$.

$^1$H-NMR spectrum (400 MHz, CDCl$_3$) δ:8.55 (d, J=1.3 Hz, 2H), 7.54-7.46 (m, 1H), 7.35-7.29 (m, 2H), 7.28-7.19 (m, 2H), 6.93-6.88 (m, 2H), 5.05 (s, 2H), 4.89-4.82 (m, 6H), 3.82 (s, 3H), 0.96 (s, 9H), 0.13 (s, 6H).

Reference Example 16

1-(5-Bromopyrimidin-2-yl)azetidin-3-one O-(2-{2-[(tetrahydropyran-2-yl)oxy]ethoxy}ethyl) oxime (Reference Compound 16)

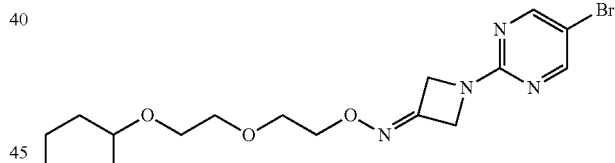

Under stirring at 0° C., 55% sodium hydride 50 mg (1.1 mmol) was added in portions to a THF (6 mL) suspension of 1-(5-bromopyrimidin-2-yl)azetidin-3-one O-(2-hydroxyethyl) oxime 160 mg (0.557 mmol) synthesized in the same manner as in Reference Example 27, and the mixture was stirred at 0° C. for 30 minutes. Next, 2-(2-bromoethoxy)tetrahydropyran 0.253 mL (1.67 mmol) was dropped thereto at 0° C., and the mixture was stirred at room temperature for 1 hour. DMF 6 mL was added, and the mixture was stirred at 60° C. for 2.5 hours. After the mixture was cooled naturally to room temperature, 2-(2-bromoethoxy)tetrahydropyran 0.253 mL (1.67 mmol) was dropped thereto, and the mixture was stirred at room temperature for 1.5 hours. After the completion of the reaction, ice water was added to the reaction mixture, and followed by extraction with ethyl acetate. The organic layer was washed with brine, dried over anhydrous sodium sulfate, and filtered. The filtrate was concentrated under reduced pressure. The concentrated residue was purified by silica gel column chromatography (eluting solvent: hexane:ethyl acetate) to give the title compound 138 mg (0.332 mmol, yield 60%) as a light yellow oil.

Mass spectrum (CI, m/z):415, 417[M+1]⁺.

¹H-NMR spectrum (400 MHz, CDCl₃) δ:8.37 (s, 2H), 4.82-4.78 (m, 4H), 4.66-4.62 (m, 1H), 4.27-4.23 (m, 2H), 3.91-3.83 (m, 2H), 3.79-3.74 (m, 2H), 3.71-3.67 (m, 2H), 3.65-3.58 (m, 1H), 3.54-3.47 (m, 1H), 1.89-1.45 (m, 6H).

Reference Example 17-1

1-(5-Bromopyrimidin-2-yl)azetidin-3-one O-[3-hydroxy-2-(hydroxymethyl)propyl]oxime (Reference Compound 17-1)

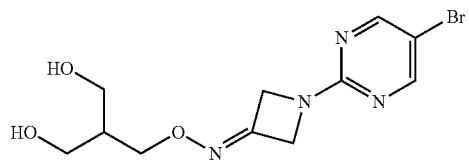 [SMILES: OCC(CO)CON=C1CN(c2ncc(Br)cn2)C1]

2 M hydrogen chloride/ethanol solution 22.0 mL (44.0 mmol) was added to a methylene chloride (11 mL) suspension of 1-(5-bromopyrimidin-2-yl)azetidin-3-one O-[(2,2-dimethyl-1,3-dioxan-5-yl)methyl] oxime 3.30 g (8.89 mmol) synthesized in the same manner as in Reference Example 10-8, and the mixture was stirred at room temperature for 30 minutes. After the completion of the reaction, TEA and water were added to the reaction mixture under ice cooling, and the mixture was concentrated under reduced pressure. Water 30 mL was added to the concentrated residue, and the mixture was stirred at room temperature for 30 minutes. Thereafter, the solid was collected by filtration and was dried under reduced pressure to give the title compound 2.11 g (6.37 mmol, yield 72%) as a pink solid.

Mass spectrum (ESI, m/z):331, 333[M+1]⁺.

¹H-NMR spectrum (400 MHz, DMSO-d₆) δ:8.55 (s, 2H), 4.79-4.70 (m, 4H), 4.42 (t, J=5.2 Hz, 2H), 4.02 (d, J=6.4 Hz, 2H), 3.49-3.38 (m, 4H), 1.95-1.92 (m, 1H).

Reference Example 17-2

1-(5-Bromopyrimidin-2-yl)azetidin-3-one O-(3,4-dihydroxybutyl) oxime (Reference Compound 17-2)

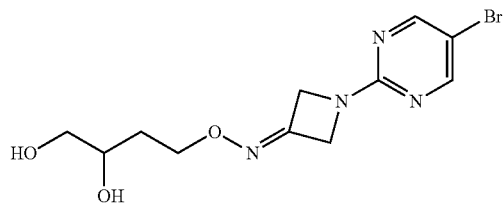 [SMILES: OCC(O)CCON=C1CN(c2ncc(Br)cn2)C1]

2 M hydrogen chloride/ethanol solution 20 mL (40 mmol) was added to an ethanol (67 mL) solution of 1-(5-bromopyrimidin-2-yl)azetidin-3-one O-[2-(2,2-dimethyl-1,3-dioxolan-4-yl)ethyl] oxime 2.5 g (6.7 mmol) synthesized in the same manner as in Reference Example 10-10, and the mixture was stirred at 70° C. for 4 hours. After the completion of the reaction, the reaction mixture was concentrated under reduced pressure. Ethyl acetate was added to the concentrated residue. The mixture was neutralized with an aqueous sodium hydrogen carbonate solution. The precipitated solid was collected by filtration, washed with ethyl acetate, and dried under reduced pressure to give the title compound 2.3 g (6.9 mmol, quantitative yield) as a beige solid.

Mass spectrum (ESI, m/z):331, 333[M+1]⁺.

¹H-NMR spectrum (400 MHz, DMSO-d₆+D₂O) δ:8.54 (s, 2H), 4.79-4.69 (m, 4H), 4.17-4.08 (m, 2H), 3.59-3.44 (m, 1H), 3.31 (dd, J=5.8, 10.8 Hz, 1H), 3.24 (dd, J=5.5, 10.8 Hz, 1H), 1.88-1.76 (m, 1H), 1.59-1.47 (m, 1H).

Reference Example 18-1

1-(5-Bromopyrimidin-2-yl)azetidin-3-one O-(3-hydroxy-2-{[(tetrahydropyran-2-yl)oxy]methyl}propyl) oxime (Reference Compound 18-1)

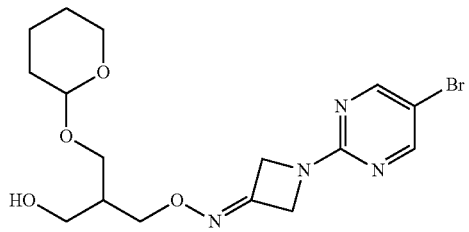 [SMILES: OCC(CON=C1CN(c2ncc(Br)cn2)C1)COC1CCCCO1]

DHP 0.65 mL (7.7 mmol) and PPTS 0.16 g (0.64 mmol) were added to a methylene chloride (10 mL) suspension of 1-(5-bromopyrimidin-2-yl)azetidin-3-one O-[3-hydroxy-2-(hydroxymethyl)propyl] oxime 2.1 g (6.3 mmol) synthesized in the same manner as in Reference Example 17-1, and the mixture was stirred at room temperature for 2 hours. Next, DMF 14 mL was added, and the mixture was stirred at room temperature for 25 hours. After the completion of the reaction, water was added to the reaction mixture, and followed by extraction with methylene chloride. The organic layer was washed with water, dried over anhydrous magnesium sulfate, and filtered. The filtrate was concentrated under reduced pressure. The concentrated residue was purified by silica gel column chromatography (eluting solvent: hexane:ethyl acetate) to give the title compound (including impurities) 1.35 g as a light yellow oil.

¹H-NMR spectrum (400 MHz, DMSO-d₆) δ:8.55 (s, 2H), 4.78-4.71 (m, 4H), 4.56-4.50 (m, 2H), 4.10-4.00 (m, 2H), 3.79-3.60 (m, 2H), 3.51-3.34 (m, 4H), 2.19-2.01 (m, 1H), 1.83-1.31 (m, 6H).

Reference Example 18-2

1-(5-Bromopyrimidin-2-yl)azetidin-3-one O-{3-hydroxy-4-[(tetrahydropyran-2-yl)oxy]butyl} oxime (Reference Compound 18-2)

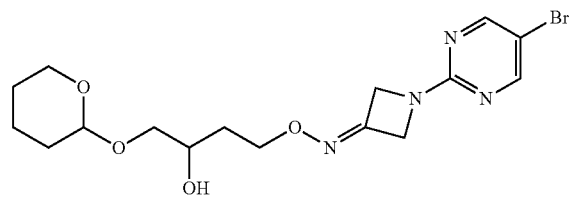 [SMILES: OC(CCON=C1CN(c2ncc(Br)cn2)C1)COC1CCCCO1]

The reaction was performed by the method described in Reference Example 18-1, except that 1-(5-bromopyrimidin-2-yl)azetidin-3-one O-[3-hydroxy-2-(hydroxymethyl)propyl] oxime (Reference Compound 17-1) was replaced by 1-(5-bromopyrimidin-2-yl)azetidin-3-one 0-(3,4-dihydroxybutyl) oxime synthesized in the same manner as in Reference Example 17-2. Consequently, the title compound (yield 46%) was obtained as a white solid.

Mass spectrum (ESI, m/z):415, 417[M+1]$^+$.

$^1$H-NMR spectrum (400 MHz, DMSO-d$_6$) δ:8.54 (s, 2H), 4.80-4.70 (m, 4H), 4.70-4.66 (m, 1H), 4.61-4.51 (m, 1H), 4.13 (t, J=6.6 Hz, 2H), 3.80-3.65 (m, 2H), 3.59-3.45 (m, 1H), 3.44-3.19 (m, 2H), 1.91-1.33 (m, 8H).

Reference Example 19-1

1-(5-Bromopyrimidin-2-yl)azetidin-3-one O-(3-methoxy-2-{[(tetrahydropyran-2-yl)oxy]methyl}propyl) oxime (Reference Compound 19-1)

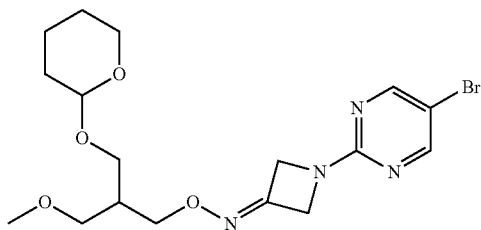 [SMILES: COCC(CON=C1CN(c2ncc(Br)cn2)C1)COC1CCCCO1]

At 0° C., iodomethane 0.037 mL (0.59 mmol) and 55% sodium hydride 25 mg (0.57 mmol) were added to a THF (6 mL) solution of 1-(5-bromopyrimidin-2-yl)azetidin-3-one O-(3-hydroxy-2-{[(tetrahydropyran-2-yl)oxy]methyl}propyl) oxime 0.16 g (0.39 mmol) synthesized in the same manner as in Reference Example 18-1, and the mixture was stirred at room temperature for 3 hours. After the completion of the reaction, water was added to the reaction mixture, and followed by extraction with ethyl acetate. The organic layer was washed with water, dried over anhydrous magnesium sulfate, and filtered. The filtrate was concentrated under reduced pressure. The concentrated residue was purified by silica gel column chromatography (eluting solvent: hexane:ethyl acetate) to give the title compound 0.16 g (0.37 mmol, yield 95%) as a colorless oil.

Mass spectrum (CI, m/z):429, 431[M+1]$^+$.

$^1$H-NMR spectrum (400 MHz, DMSO-d$_6$) δ:8.55 (s, 2H), 4.79-4.71 (m, 4H), 4.55-4.51 (m, 1H), 4.09-4.00 (m, 2H), 3.78-3.61 (m, 2H), 3.47-3.32 (m, 4H), 3.23 (s, 3H), 2.27-2.15 (m, 1H), 1.79-1.41 (m, 6H).

Reference Example 19-2

1-(5-Bromopyrimidin-2-yl)azetidin-3-one O-[2-methoxy-3-(trityloxy)propyl] oxime (Reference Compound 19-2)

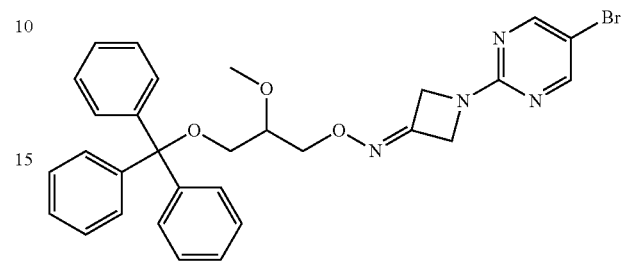

The reaction was performed by the method described in Reference Example 19-1, except that 1-(5-bromopyrimidin-2-yl)azetidin-3-one O-(3-hydroxy-2-{[(tetrahydropyran-2-yl)oxy]methyl}propyl) oxime (Reference Compound 18-1) was replaced by 1-(5-bromopyrimidin-2-yl)azetidin-3-one O-[2-hydroxy-3-(trityloxy)propyl] oxime synthesized in the same manner as in Reference Example 21-1. Consequently, the title compound (yield 85%) was obtained as a white foam.

Mass spectrum (CI, m/z):573, 575[M+1]$^+$.

$^1$H-NMR spectrum (400 MHz, DMSO-d$_6$) δ:8.57 (s, 2H), 7.44-7.20 (m, 15H), 4.77-4.71 (m, 2H), 4.66-4.47 (m, 2H), 4.18-4.05 (m, 2H), 3.66-3.56 (m, 1H), 3.33 (s, 3H), 3.17-2.96 (m, 2H).

Reference Example 19-3

1-(5-Bromopyrimidin-2-yl)azetidin-3-one O-{3-methoxy-4-[(tetrahydropyran-2-yl)oxy]butyl} oxime (Reference Compound 19-3)

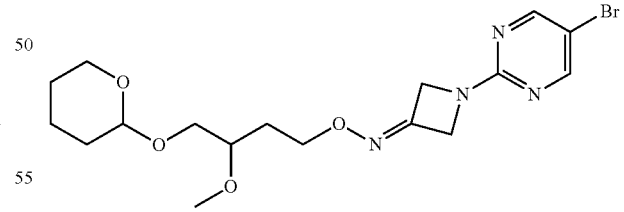

The reaction was performed by the method described in Reference Example 19-1, except that 1-(5-bromopyrimidin-2-yl)azetidin-3-one O-(3-hydroxy-2-{[(tetrahydropyran-2-yl)oxy]methyl}propyl) oxime (Reference Compound 18-1) was replaced by 1-(5-bromopyrimidin-2-yl) azetidin-3-one O-{3-hydroxy-4-[(tetrahydropyran-2-yl)oxy]butyl} oxime synthesized in the same manner as in Reference Example 18-2. Consequently, the title compound (yield 39%) was obtained as a white solid.

Mass spectrum (ESI, m/z):451, 453[M+Na]⁺.

Reference Example 20-1

1-(5-Bromopyrimidin-2-yl)azetidin-3-one O-(2,3-dihydroxypropyl) oxime (Reference Compound 20-1)

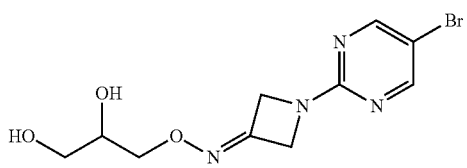 [SMILES: OCC(O)CON=C1CN(c2ncc(Br)cn2)C1]

PPTS 1.0 g (4.0 mmol) was added to a methanol (100 mL) suspension of 1-(5-bromopyrimidin-2-yl)azetidin-3-one 0-[(2,2-dimethyl-1,3-dioxolan-4-yl)methyl]oxime 6.6 g (18 mmol) synthesized in the same manner as in Reference Example 10-9, and the mixture was stirred at 70° C. for 15 hours. After the completion of the reaction, a saturated aqueous sodium hydrogen carbonate solution was added to the reaction mixture, and followed by extraction with ethyl acetate. The organic layer was washed with water three times, dried over anhydrous magnesium sulfate, and filtered. The filtrate was under reduced pressure to give a crude product 5.1 g including the title compound as a light brown solid.

Mass spectrum (ESI, m/z):317, 319[M+1]⁺.

¹H-NMR spectrum (400 MHz, DMSO-$d_6$) δ:8.55 (s, 2H), 4.80-4.72 (m, 5H), 4.57 (t, J=5.7 Hz, 1H), 4.09-3.98 (m, 1H), 3.93-3.87 (m, 1H), 3.74-3.65 (m, 1H), 3.35 (d, J=5.6 Hz, 2H).

The title compound was also synthesized in the following manner.

Acetic acid 3.0 mL (52 mmol) was added to a water (3 mL) suspension of 1-(5-bromopyrimidin-2-yl)azetidin-3-one O-[(2,2-dimethyl-1,3-dioxolan-4-yl)methyl]oxime 790 mg (2.12 mmol) synthesized in the same manner as in Reference Example 10-9, and the mixture was stirred at 80° C. for 1 hour. After the completion of the reaction, toluene was added to the reaction mixture. The mixture was concentrated under reduced pressure to give a crude product 701 mg including the title compound as a light red solid.

Reference Example 20-2

1-(5-Bromo-3-fluoropyridin-2-yl)azetidin-3-one O-(2,3-dihydroxypropyl) oxime (Reference Compound 20-2)

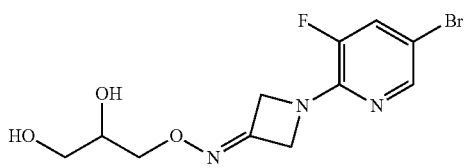 [SMILES: OCC(O)CON=C1CN(c2ncc(Br)cc2F)C1]

The reaction was performed by the method described in Reference Example 20-1, except that 1-(5-bromopyrimidin-2-yl)azetidin-3-one O-[(2,2-dimethyl-1,3-dioxolan-4-yl)methyl] oxime (Reference Compound 10-9) was replaced by 1-(5-bromo-3-fluoropyridin-2-yl)azetidin-3-one O-[(2,2-dimethyl-1,3-dioxolan-4-yl)methyl] oxime synthesized in the same manner as in Reference Example 34-3, and the concentrated residue was purified by silica gel column chromatography. Consequently, the title compound (yield 70%) was obtained as a light yellow solid.

Mass spectrum (CI, m/z):334, 336[M+1]⁺.

¹H-NMR spectrum (400 MHz, DMSO-$d_6$) δ:8.10 (dd, J=1.0, 1.9 Hz, 1H), 7.91 (dd, J=1.9, 11.3 Hz, 1H), 4.85-4.78 (m, 4H), 4.75 (d, J=5.1 Hz, 1H), 4.57 (t, J=5.7 Hz, 1H), 4.04 (dd, J=4.5, 11.0 Hz, 1H), 3.89 (dd, J=6.6, 11.0 Hz, 1H), 3.74-3.62 (m, 1H), 3.35 (t, J=5.6 Hz, 2H).

Reference Example 21-1

1-(5-Bromopyrimidin-2-yl)azetidin-3-one 0-[2-hydroxy-3-(trityloxy)propyl] oxime (Reference Compound 21-1)

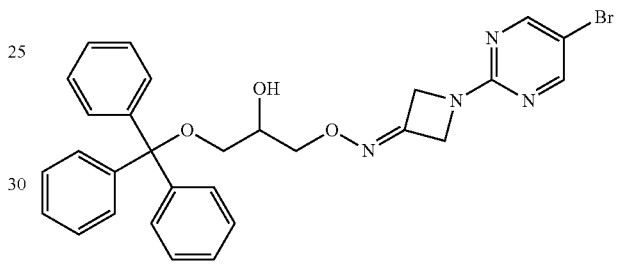

TEA 7.7 mL (55 mmol), DMAP 0.45 g (3.7 mmol) and trityl chloride 7.7 g (28 mmol) were added to a DMF (50 mL) solution of 1-(5-bromopyrimidin-2-yl)azetidin-3-one O-(2,3-dihydroxypropyl) oxime 5.8 g (18 mmol) synthesized in the same manner as in Reference Example 20-1, and the mixture was stirred at 60° C. for 8 hours. After the completion of the reaction, water was added to the reaction mixture, and followed by extraction ethyl acetate. The organic layer was washed with water, dried over anhydrous magnesium sulfate, and filtered. The filtrate was concentrated under reduced pressure. The concentrated residue was purified by silica gel column chromatography (eluting solvent: hexane:ethyl acetate) two times to give the title compound 5.4 g (9.7 mmol, yield 54%) as a light yellow solid.

Mass spectrum (ESI, m/z):559, 561[M+1]⁺.

¹H-NMR spectrum (400 MHz, DMSO-$d_6$) δ:8.57 (s, 2H), 7.43-7.20 (m, 15H), 5.06 (br s, 1H), 4.80-4.68 (m, 2H), 4.67-4.47 (m, 1H), 4.09-3.96 (m, 2H), 3.66-3.86 (m, 1H), 2.96 (d, J=5.3 Hz, 2H).

The title compound was also synthesized in the following manner.

Trityl chloride 677 mg (2.43 mmol) and TEA 0.615 mL (4.41 mmol) were added to a methylene chloride (15 mL) suspension of 1-(5-bromopyrimidin-2-yl)azetidin-3-one O-(2,3-dihydroxypropyl) oxime 700 mg (2.21 mmol) synthesized in the same manner as in Reference Example 20-1, and the mixture was stirred at room temperature for 23 hours. After the completion of the reaction, water was added to the reaction mixture, and followed by extraction with methylene chloride. The organic layer was washed with water, dried over anhydrous magnesium sulfate, and filtered. The filtrate was concentrated under reduced pressure. The concentrated residue was purified by silica gel column

Reference Example 21-2

1-(5-Bromo-3-fluoropyridin-2-yl)azetidin-3-one O-[2-hydroxy-3-(trityloxy)propyl]oxime (Reference Compound 21-2)

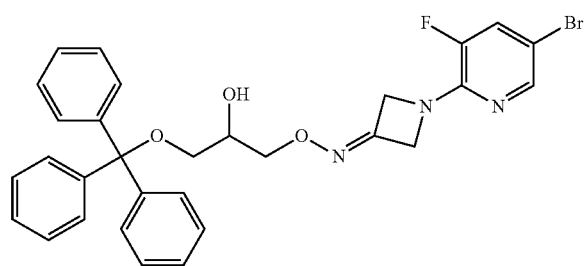 [SMILES: OC(CON=C1CN(c2ncc(Br)cc2F)C1)COC(c1ccccc1)(c1ccccc1)c1ccccc1]

The reaction was performed by the method described in Reference Example 21-1, except that 1-(5-bromopyrimidin-2-yl)azetidin-3-one O-(2,3-dihydroxypropyl) oxime (Reference Compound 20-1) was replaced by 1-(5-bromo-3-fluoropyridin-2-yl)azetidin-3-one O-(2,3-dihydroxypropyl) oxime synthesized in the same manner as in Reference Example 20-2. Consequently, the title compound (yield 80%) was obtained as a light brown foam.

Mass spectrum (ESI, m/z):576, 578[M+1]$^+$.

$^1$H-NMR spectrum (400 MHz, DMSO-d$_6$) δ:8.12 (dd, J=0.9, 2.0 Hz, 1H), 7.92 (dd, J=2.0, 11.3 Hz, 1H), 7.55-7.13 (m, 15H), 5.06 (d, J=5.1 Hz, 1H), 4.85-4.74 (m, 2H), 4.73-4.52 (m, 2H), 4.11-3.96 (m, 2H), 3.96-3.81 (m, 1H), 3.04-2.87 (m, 2H).

Reference Example 22

1-[({1-[5-(3-{[(tert-Butyldimethylsilyl)oxy]methyl}-2-fluorophenyl)pyrimidin-2-yl]azetidin-3-ylidene}amino)oxy]-3-methoxypropan-2-yl acetate (Reference Compound 22)

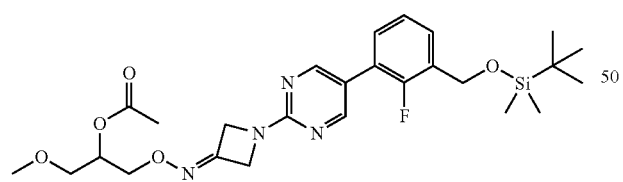

DMSO 1 mL, glycidyl methyl ether 0.17 mL (1.9 mmol) and 1-(5-bromopyrimidin-2-yl)azetidin-3-one oxime 0.30 g (1.2 mmol) synthesized in the same manner as in Reference Example 9-1 were added to a water (1 mL) solution of potassium hydroxide 0.10 g (1.8 mmol), and the mixture was stirred at room temperature for 20 hours. After the completion of the reaction, a saturated aqueous ammonium chloride solution was added to the reaction mixture, and the precipitated solid was collected by filtration. The filtrate was extracted with methylene chloride. The organic layer was washed with water, dried over anhydrous magnesium sulfate, and filtered. The filtrate was combined with the solid collected by the previous filtration, and the mixture was concentrated under reduced pressure. The concentrated residue was dried under reduced pressure to give a crude product 0.41 g including 1-(5-bromopyrimidin-2-yl)azetidin-3-one O-(2-hydroxy-3-methoxypropyl) oxime as a white solid.

Next, acetic anhydride 0.17 mL (1.8 mmol) and TEA 0.34 mL (2.4 mmol) were added to a methylene chloride (8 mL)-THF (4 mL) solution of the above-obtained crude product 0.40 g including 1-(5-bromopyrimidin-2-yl)azetidin-3-one O-(2-hydroxy-3-methoxypropyl) oxime, and the mixture was stirred at room temperature for 96 hours. After the completion of the reaction, water was added to the reaction mixture, and followed by extraction with methylene chloride. The organic layer was washed with water, dried over anhydrous magnesium sulfate, and filtered. The filtrate was concentrated under reduced pressure. The concentrated residue was purified by silica gel column chromatography (eluting solvent: hexane:ethyl acetate) to give a crude product 167 mg including 1-({[1-(5-bromopyrimidin-2-yl)azetidin-3-ylidene]amino}oxy)-3-methoxypropan-2-yl acetate as a white solid.

Next, the above obtained crude product 0.17 g including 1-({[1-(5-bromopyrimidin-2-yl)azetidin-3-ylidene]amino}oxy)-3-methoxypropan-2-yl acetate, tert-butyl {[2-fluoro-3-(4,4,5,5,-tetramethyl-1,3,2-dioxaborolan-2-yl)benzyl]oxy}dimethylsilane 0.16 g (0.45 mmol) synthesized in the same manner as in Reference Example 5, and a 2 M aqueous sodium carbonate solution 0.70 mL (1.4 mmol) were suspended in 1,2-dimethoxyethane (6 mL). The suspension was degassed and purged with nitrogen. Next, tetrakis(triphenylphosphine)palladium (0) 78 mg (0.067 mmol) was added. Under a stream of argon, the mixture was stirred at 80° C. for 3 hours. After the completion of the reaction, water was added to the reaction mixture, and followed by extraction with ethyl acetate. The organic layer was washed with water, dried over anhydrous magnesium sulfate, and filtered. The filtrate was concentrated under reduced pressure. The concentrated residue was purified by silica gel column chromatography (eluting solvent: hexane:ethyl acetate) to give the title compound 0.14 g (0.27 mmol, yield 23% [three steps]) as a light yellow oil.

Mass spectrum (CI, m/z):533[M+1]$^+$.

1H-NMR spectrum (400 MHz, DMSO-d6) δ:8.63 (d, J=1.4 Hz, 2H), 7.52-7.42 (m, 2H), 7.34-7.28 (m, 1H), 5.28-5.07 (m, 1H), 4.89-4.74 (m, 6H), 4.26-4.07 (m, 2H), 3.57-3.42 (m, 2H), 3.27 (s, 3H), 2.04 (s, 3H), 0.91 (s, 9H), 0.11 (s, 6H).

Reference Example 23

1-(5-Bromopyrimidin-2-yl)azetidin-3-one O-(3-fluoro-2-{[(tetrahydropyran-2-yl)oxy]methyl}propyl) oxime (Reference Compound 23)

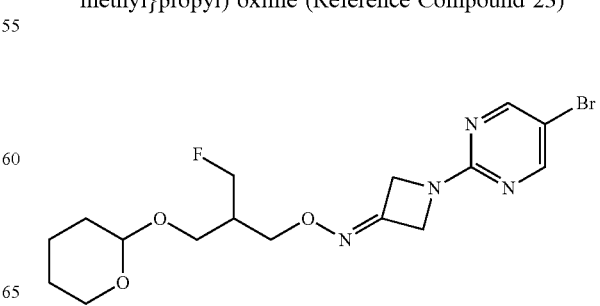

Methanesulfonyl chloride 51 µl (0.65 mmol) was added to a methylene chloride (6 mL) solution of 1-(5-bromopyrimidin-2-yl)azetidin-3-one O-(3-hydroxy-2-{[(tetrahydropyran-2-yl)oxy]methyl}propyl) oxime 210 mg (0.506 mmol) synthesized in the same manner as in Reference Example 18-1. Next, TEA 106 µl (0.761 mmol) was added under ice cooling, and the mixture was stirred at room temperature for 15 minutes. Next, methanesulfonyl chloride 51 µl (0.65 mmol) and TEA 106 µl (0.761 mmol) were added, and the mixture was stirred at room temperature for 10 minutes. After the completion of the reaction, a saturated aqueous sodium carbonate solution was added to the reaction mixture, and followed by extraction with methylene chloride. The organic layer was washed with brine, dried over anhydrous magnesium sulfate, and filtered. The filtrate was concentrated under reduced pressure. 1 M tetrabutylammonium fluoride/THF solution 1.15 mL (1.15 mmol) was added to a THF (6 mL) solution of the concentrated residue, and the mixture was stirred at 60° C. for 8 hours. After the completion of the reaction, the reaction mixture was concentrated under reduced pressure. The concentrated residue was purified by silica gel column chromatography (eluting solvent: hexane:ethyl acetate) to give the title compound 137 mg (0.328 mmol, yield 65% [two steps]) as a colorless oil.

Mass spectrum (CI, m/z):417, 419[M+1]+.

1H-NMR spectrum (400 MHz, DMSO-d6) δ:8.55 (s, 2H), 4.80-4.73 (m, 4H), 4.64-4.40 (m, 3H), 4.17-4.03 (m, 2H), 3.76-3.66 (m, 2H), 3.47-3.35 (m, 2H), 2.47-2.28 (m, 1H), 1.76-1.54 (m, 2H), 1.53-1.41 (m, 4H).

Reference Example 24-1

1-(5-Bromopyrimidin-2-yl)azetidin-3-one O-[2-fluoro-3-(trityloxy)propyl] oxime (Reference Compound 24-1)

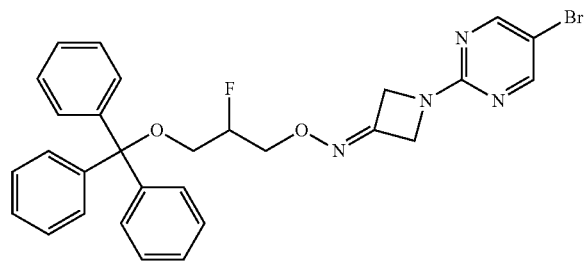 [SMILES: FC(CON=C1CN(c2ncc(Br)cn2)C1)COC(c1ccccc1)(c1ccccc1)c1ccccc1]

At 0° C., BAST 5.9 mL (29 mmol) was added to a methylene chloride (60 mL) solution of 1-(5-bromopyrimidin-2-yl)azetidin-3-one O-[2-hydroxy-3-(trityloxy)propyl] oxime 5.4 g (9.7 mmol) synthesized in the same manner as in Reference Example 21-1, and the mixture was stirred at room temperature for 24 hours. After the completion of the reaction, a saturated aqueous sodium hydrogen carbonate solution was added to the reaction mixture, and followed by extraction with methylene chloride. The organic layer was washed with water, dried over anhydrous magnesium sulfate, and filtered. The filtrate was concentrated under reduced pressure. TBME 30 mL was added to the concentrated residue, and the mixture was stirred at room temperature for 30 minutes. Thereafter, the solid was collected by filtration and was dried under reduced pressure to give the title compound 3.0 g (5.3 mmol, yield 55%) as a light yellow solid.

Mass spectrum (CI, m/z):561, 563[M+1]+.

1H-NMR spectrum (400 MHz, DMSO-d6) δ:8.57 (s, 2H), 7.45-7.19 (m, 15H), 5.03-4.84 (m, 1H), 4.78-4.71 (m, 2H), 4.69-4.55 (m, 2H), 4.41-4.11 (m, 2H), 3.33-3.11 (m, 2H).

Reference Example 24-2

1-(5-Bromo-3-fluoropyridin-2-yl)azetidin-3-one O-[2-fluoro-3-(trityloxy)propyl] oxime (Reference Compound 24-2)

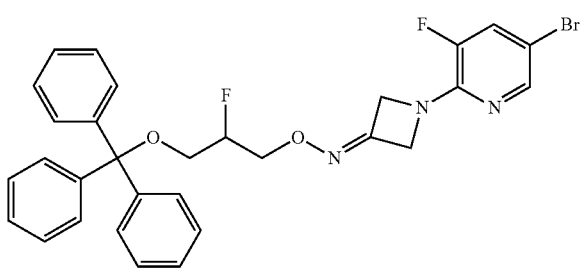 [SMILES: Fc1cc(Br)cnc1N1CC(=NOCC(F)COC(c2ccccc2)(c2ccccc2)c2ccccc2)C1]

The reaction was performed by the method described in Reference Example 24-1, except that 1-(5-bromopyrimidin-2-yl)azetidin-3-one O-[2-hydroxy-3-(trityloxy)propyl] oxime (Reference Compound 21-1) was replaced by 1-(5-bromo-3-fluoropyridin-2-yl)azetidin-3-one 0-[2-hydroxy-3-(trityloxy)propyl]oxime synthesized in the same manner as in Reference Example 21-2, and the concentrated residue was purified by silica gel column chromatography. Consequently, the title compound (yield 50%) was obtained as a light yellow solid.

Mass spectrum (CI, m/z):578, 580[M+1]+.

1H-NMR spectrum (400 MHz, DMSO-d6) 5:8.12 (dd, J=0.9, 1.9 Hz, 1H), 7.92 (dd, J=1.9, 11.2 Hz, 1H), 7.46-7.16 (m, 15H), 5.03-4.82 (m, 1H), 4.82-4.76 (m, 2H), 4.76-4.59 (m, 2H), 4.36-4.15 (m, 2H), 3.33-3.10 (m, 2H).

Reference Example 25

4-({[1-(5-Bromopyrimidin-2-yl)azetidin-3-ylidene]amino}oxy)butane-1,2-diyl diacetate (Reference Compound 25)

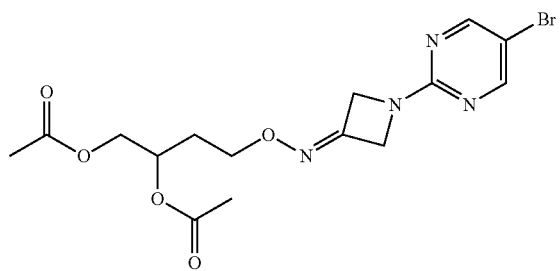 [SMILES: CC(=O)OCC(CCON=C1CN(c2ncc(Br)cn2)C1)OC(C)=O]

TEA 4.0 mL (29 mmol) and acetic anhydride 0.80 mL (8.5 mmol) were added to a DMF (58 mL) solution of 1-(5-bromopyrimidin-2-yl)azetidin-3-one O-(3,4-dihydroxybutyl) oxime 1.92 g (5.80 mmol) synthesized in the same manner as in Reference Example 17-2, and the mixture was stirred at room temperature for 24 hours. After the completion of the reaction, a saturated aqueous ammonium chloride solution was added to the reaction mixture, and followed by extraction with ethyl acetate. The organic layer was washed with brine, dried over anhydrous magnesium sulfate, and filtered. The filtrate was concentrated under reduced pressure. The concentrated residue was purified by silica gel column chromatography (eluting solvent: hexane:ethyl acetate) to give the title compound 340 mg (0.819 mmol, yield 14%) as a white solid.

Mass spectrum (ESI, m/z):415, 417[M+1]$^+$.

$^1$H-NMR spectrum (400 MHz, DMSO-d$_6$) δ:8.55 (s, 2H), 5.12-5.03 (m, 1H), 4.81-4.68 (m, 4H), 4.20 (dd, J=3.3, 12.0 Hz, 1H), 4.13-4.00 (m, 3H), 2.02 (s, 3H), 2.01 (s, 3H), 1.98-1.82 (m, 2H).

Reference Example 26

4-{[(1-{5-[2-Fluoro-3-(hydroxymethyl)phenyl]pyrimidin-2-yl}azetidin-3-ylidene)amino]oxy}butane-1,2-diyl diacetate (Reference Compound 26)

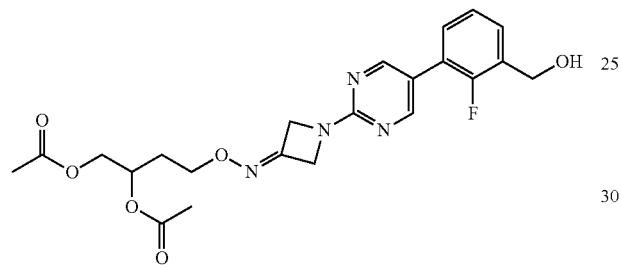

2 N hydrochloric acid 60 µl (0.13 mmol) was added to a THF (2 mL) solution of 4-[({1-[5-(3-{[(tert-butyldimethylsilyl)oxy]methyl}-2-fluorophenyl)pyrimidin-2-yl]azetidin-3-ylidene}amino)oxy]butane-1,2-diyl diacetate 72 mg (0.13 mmol) synthesized in the same manner as in Reference Example 6-20, and the mixture was stirred at room temperature for 20 hours. After the completion of the reaction, the reaction mixture was concentrated under reduced pressure. The concentrated residue was purified by silica gel column chromatography (eluting solvent: hexane:ethyl acetate) to give the title compound 53 mg (0.12 mmol, yield 92%) as a white solid.

Mass spectrum (ESI, m/z):461[M+1]$^+$.

$^1$H-NMR spectrum (400 MHz, DMSO-d$_6$) δ:8.63 (d, J=1.4 Hz, 2H), 7.53-7.41 (m, 2H), 7.33-7.26 (m, 1H), 5.34 (t, J=5.6 Hz, 1H), 5.13-5.05 (m, 1H), 4.86-4.75 (m, 4H), 4.60 (d, J=5.6 Hz, 2H), 4.21 (dd, J=3.2, 12.0 Hz, 1H), 4.14-4.01 (m, 3H), 2.03 (s, 3H), 2.01 (s, 3H), 1.99-1.83 (m, 2H).

Reference Example 27

1-(5-Bromopyrimidin-2-yl)azetidin-3-one O-(2-hydroxyethyl) oxime (Reference Compound 27)

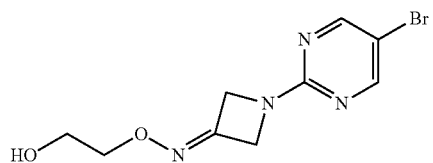 [SMILES: OCCON=C1CN(c2ncc(Br)cn2)C1]

2 M hydrogen chloride/ethanol solution 16 mL (32 mmol) was added to 1-(5-bromopyrimidin-2-yl)azetidin-3-one O-{2-[(tetrahydropyran-2-yl)oxy]ethyl}oxime 1.79 g (4.82 mmol) synthesized in the same manner as in Reference Example 10-4, and the mixture was stirred at room temperature for 8 hours. After the completion of the reaction, a saturated aqueous sodium hydrogen carbonate solution was added to the reaction mixture, and followed by extraction with ethyl acetate. The organic layer was washed with brine, dried over anhydrous magnesium sulfate, and filtered. The filtrate was concentrated under reduced pressure, and TBME (5 mL) was added to the concentrated residue. The solid was collected by filtration and was dried under reduced pressure to give the title compound 1.10 g (3.83 mmol, yield 79%) as a white solid.

Mass spectrum (ESI, m/z):287, 289[M+1]$^+$.

$^1$H-NMR spectrum (400 MHz, CDCl$_3$) δ:8.38 (s, 2H), 4.85-4.79 (m, 4H), 4.24-4.19 (m, 2H), 3.93-3.86 (m, 2H), 2.05 (t, J=6.0 Hz, 1H).

Reference Example 28-1

2-({[1-(5-Bromopyrimidin-2-yl)azetidin-3-ylidene]amino}oxy)ethyl propionate (Reference Compound 28-1)

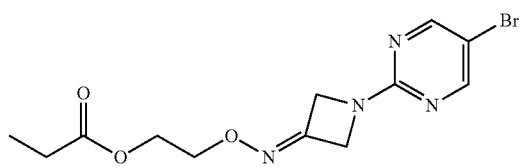 [SMILES: CCC(=O)OCCON=C1CN(c2ncc(Br)cn2)C1]

TEA 750 µl (5.38 mmol) was added to a methylene chloride (3 mL) suspension of 1-(5-bromopyrimidin-2-yl)azetidin-3-one O-(2-hydroxyethyl) oxime 303 mg (1.06 mmol) synthesized in the same manner as in Reference Example 27, and the mixture was stirred for 10 minutes under ice cooling. Next, propionyl chloride 182 µl (2.09 mmol) was dropped thereto under ice cooling, and the mixture was stirred at room temperature for 30 minutes. Next, methylene chloride (7 mL), TEA 750 µl (5.38 mmol) and propionyl chloride 182 µl (2:09 mmol) were added under ice cooling, and the mixture was stirred at room temperature for 15 hours. After the completion of the reaction, a saturated aqueous ammonium chloride solution was added to the reaction mixture, and followed by extraction with methylene chloride. The organic layer was dried over anhydrous magnesium sulfate, and filtered. The filtrate was concentrated under reduced pressure. The concentrated residue was purified by silica gel column chromatography (eluting solvent: hexane:ethyl acetate=87:13 to 66:34 (V/V)) to give the title compound 273 mg (0.796 mmol, yield 75%) as a light yellow oil.

Mass spectrum (CI, m/z):343, 345[M+1]$^+$.

$^1$H-NMR spectrum (400 MHz, CDCl$_3$) δ:8.37 (s, 2H), 4.84-4.76 (m, 4H), 4.36-4.24 (m, 4H), 2.37 (q, J=7.6 Hz, 2H), 1.15 (t, J=7.6 Hz, 3H).

Reference Example 28-2

2-({[1-(5-Bromopyrimidin-2-yl)azetidin-3-ylidene]amino}oxy)ethyl butyrate (Reference Compound 28-2)

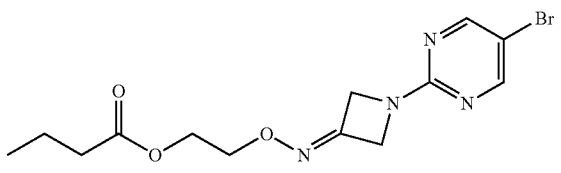 [SMILES: CCCC(=O)OCCON=C1CN(c2ncc(Br)cn2)C1]

The reaction was performed by the method described in Reference Example 28-1, except that propionyl chloride was replaced by butyryl chloride. Consequently, the title compound (yield 41%) was obtained as a light yellow oil.

Mass spectrum (CI, m/z):357, 359[M+1]$^+$.

$^1$H-NMR spectrum (400 MHz, CDCl$_3$) δ:8.37 (s, 2H), 4.82-4.77 (m, 4H), 4.35-4.25 (m, 4H), 2.32 (t, J=7.4 Hz, 2H), 1.66 (sext, J=7.4 Hz, 2H), 0.95 (t, J=7.4 Hz, 3H).

Reference Example 28-3

2-({[1-(5-Bromopyrimidin-2-yl)azetidin-3-ylidene]amino}oxy)ethyl benzoate (Reference Compound 28-3)

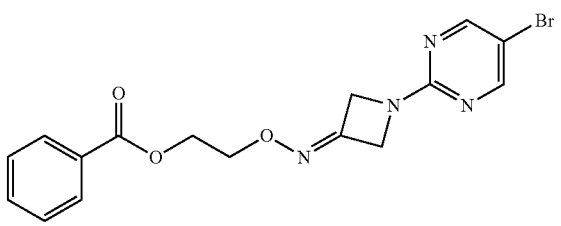 [SMILES: O=C(OCCON=C1CN(c2ncc(Br)cn2)C1)c1ccccc1]

The reaction was performed by the method described in Reference Example 28-1, except that propionyl chloride was replaced by benzoyl chloride. Consequently, the title compound (yield 41%) was obtained as a light yellow oil.

Mass spectrum (CI, m/z):391, 393[M+1]$^+$.

$^1$H-NMR spectrum (400 MHz, CDCl$_3$) δ:8.36 (s, 2H), 8.07-8.04 (m, 2H), 7.61-7.54 (m, 1H), 7.47-7.42 (m, 2H), 4.80 (s, 4H), 4.60-4.53 (m, 2H), 4.45-4.38 (m, 2H).

Reference Example 29-1

3-[({1-[5-(3-{[(tert-Butyldimethylsilyl)oxy]methyl}-2-fluorophenyl)pyrimidin-2-yl]azetidin-3-ylidene}amino)oxy]-2-{[(tetrahydropyran-2-yl)oxy]methyl}propyl acetate (Reference Compound 29-1)

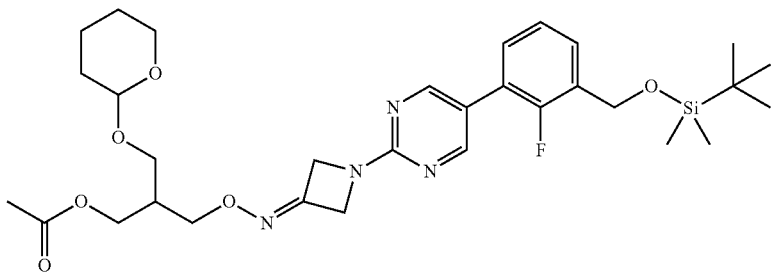 [SMILES: CC(=O)OCC(CON=C1CN(c2ncc(-c3cccc(CO[Si](C)(C)C(C)(C)C)c3F)cn2)C1)COC1CCCCO1]

TEA 32 μl (0.34 mmol) and acetic anhydride 103 μl (0.731 mmol) were added to a methylene chloride (4 mL) solution of 1-[5-(3-{[(tert-butyldimethylsilyl)oxy]methyl}-2-fluorophenyl)pyrimidin-2-yl]azetidin-3-one O-(3-hydroxy-2-{[(tetrahydropyran-2-yl)oxy]methyl}propyl) oxime 140 mg (0.244 mmol) synthesized in the same manner as in Reference Example 6-25, and the mixture was stirred at room temperature for 3 hours. Next, TEA 118 μl (1.25 mmol) and acetic anhydride 207 μl (1.48 mmol) were added, and the mixture was stirred at room temperature for 13 hours. After the completion of the reaction, water was added to the reaction mixture, and followed by extraction with methylene chloride. The organic layer was washed with brine, dried over anhydrous sodium sulfate, and filtered. The filtrate was concentrated under reduced pressure. The concentrated residue was purified by silica gel column chromatography (eluting solvent: hexane:ethyl acetate) to give the title compound 139 mg (0.225 mmol, yield 93%) as a colorless oil.

Mass spectrum (CI, m/z):617[M+1]$^+$.

$^1$H-NMR spectrum (400 MHz, CDCl$_3$) δ:8.56 (d, J=1.4 Hz, 2H), 7.54-7.48 (m, 1H), 7.30-7.19 (m, 2H), 4.90-4.86 (m, 4H), 4.85 (s, 2H), 4.61-4.57 (m, 1H), 4.25-4.09 (m, 4H), 3.88-3.77 (m, 2H), 3.57-3.48 (m, 1H), 3.47-3.38 (m, 1H), 2.47-2.39 (m, 1H), 2.07 (s, 3H), 1.86-1.47 (m, 6H), 0.96 (s, 9H), 0.14 (s, 6H).

Reference Example 29-2

3-[({1-[5-(3-{[(tert-Butyldimethylsilyl)oxy]methyl}-2-fluorophenyl)pyrimidin-2-yl]azetidin-3-ylidene}amino)oxy]-2-{[(tetrahydropyran-2-yl)oxy]methyl}propyl propionate (Reference Compound 29-2)

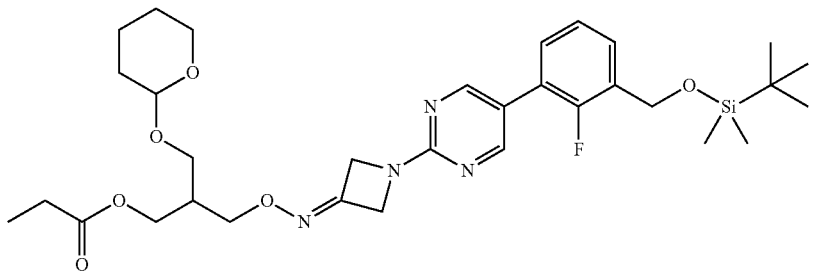 [SMILES: CCC(=O)OCC(CON=C1CN(c2ncc(-c3cccc(CO[Si](C)(C)C(C)(C)C)c3F)cn2)C1)COC1CCCCO1]

The reaction was performed by the method described in Reference Example 29-1, except that acetic anhydride was replaced by propanoic anhydride. Consequently, the title compound (yield 76%) was obtained as a light yellow oil.

Mass spectrum (CI, m/z):631 [M+1]$^+$.

$^1$H-NMR spectrum (400 MHz, CDCl$_3$) δ:8.57 (d, J=1.4 Hz, 2H), 7.53-7.47 (m, 1H), 7.30-7.20 (m, 2H), 4.90-4.86 (m, 4H), 4.85 (s, 2H), 4.61-4.57 (m, 1H), 4.24-4.13 (m, 4H), 3.89-3.78 (m, 2H), 3.56-3.48 (m, 1H), 3.47-3.39 (m, 1H), 2.46-2.30 (m, 3H), 1.85-1.40 (m, 6H), 1.19-1.12 (m, 3H), 0.96 (s, 9H), 0.14 (s, 6H).

Reference Example 29-3

2-({[1-(5-Bromopyrimidin-2-yl)piperidin-4-ylidene]amino}oxy)ethyl acetate (Reference Compound 29-3)

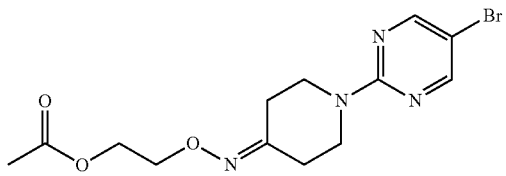 [SMILES: CC(=O)OCCON=C1CCN(c2ncc(Br)cn2)CC1]

The reaction was performed by the method described in Reference Example 29-1, except that 1-[5-(3-{[(tert-butyldimethylsilyl)oxy]methyl}-2-fluorophenyl)pyrimidin-2-yl]azetidin-3-one O-(3-hydroxy-2-{[(tetrahydropyran-2-yl)oxy]methyl}propyl) oxime (Reference Compound 6-25) was replaced by 1-(5-bromopyrimidin-2-yl)piperidin-4-one O-(2-hydroxyethyl) oxime synthesized in the same manner as in Reference Example 72. Consequently, the title compound (yield 79%) was obtained as a white solid.

Mass spectrum (CI, m/z):357, 359[M+1]$^+$.

$^1$H-NMR spectrum (400 MHz, DMSO-d$_6$) δ:8.49 (s, 2H), 4.24-4.11 (m, 4H), 3.92-3.77 (m, 4H), 2.57-2.51 (m, 2H), 2.39-2.32 (m, 2H), 2.02 (s, 3H).

Reference Example 29-4

3-({[1-(5-Bromopyrimidin-2-yl)azetidin-3-ylidene]amino}oxy)cyclobutyl acetate (Reference Compound 29-4)

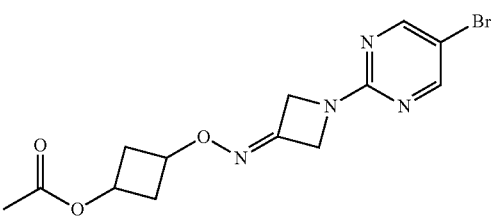 [SMILES: CC(=O)OC1CC(ON=C2CN(c3ncc(Br)cn3)C2)C1]

The reaction was performed by the method described in Reference Example 29-1, except that 1-[5-(3-{[(tert-butyldimethylsilyl)oxy]methyl}-2-fluorophenyl)pyrimidin-2-yl]azetidin-3-one O-(3-hydroxy-2-{[(tetrahydropyran-2-yl)oxy]methyl}propyl) oxime (Reference Compound 6-25) was replaced by 1-(5-bromopyrimidin-2-yl)azetidin-3-one O-(3-hydroxycyclobutyl) oxime synthesized in the same manner as in Reference Example 96-1, and DMAP was added. Consequently, the title compound (yield 98%) was obtained as a white solid.

$^1$H-NMR spectrum (400 MHz, DMSO-d$_6$) δ:8.55 (s, 2H), 5.08-4.99 (m, 1H), 4.84-4.71 (m, 5H), 2.49-2.41 (m, 2H), 2.39-2.28 (m, 2H), 2.01 (s, 3H).

Reference Example 29-5

2-[3-({[1-(5-Bromopyrimidin-2-yl)azetidin-3-ylidene]amino}oxy)azetidin-1-yl]ethyl acetate (Reference Compound 29-5)

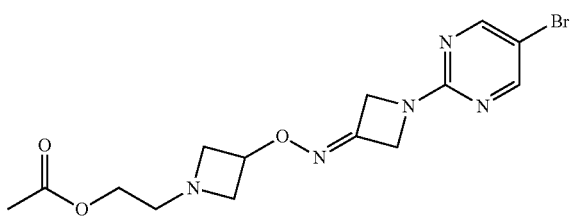 [SMILES: CC(=O)OCCN1CC(ON=C2CN(c3ncc(Br)cn3)C2)C1]

The reaction was performed by the method described in Reference Example 29-1, except that 1-[5-(3-{[(tert-butyldimethylsilyl)oxy]methyl}-2-fluorophenyl)pyrimidin-2-yl]azetidin-3-one O-(3-hydroxy-2-{[(tetrahydropyran-2-yl)oxy]methyl}propyl) oxime (Reference Compound 6-25) was replaced by 1-(5-bromopyrimidin-2-yl)azetidin-3-one O-[1-(2-hydroxyethyl)azetidin-3-yl] oxime synthesized in the same manner as in Reference Example 96-2. Consequently, the title compound (yield 88%) was obtained as a white solid.

Mass spectrum (CI, m/z):384, 386[M+1]$^+$.

$^1$H-NMR spectrum (400 MHz, DMSO-d$_6$) δ:8.55 (s, 2H), 4.79-4.70 (m, 5H), 3.96 (t, J=5.5 Hz, 2H), 3.58-3.50 (m, 2H), 3.10-3.01 (m, 2H), 2.64 (t, J=5.6 Hz, 2H), 1.99 (s, 3H).

Reference Example 30-1

3-[({1-[5-(3-{[(tert-Butyldimethylsilyl)oxy]methyl}-2-fluorophenyl)pyrimidin-2-yl]azetidin-3-ylidene}amino)oxy]-2-{[(tetrahydropyran-2-yl)oxy]methyl}propyl butyrate (Reference Compound 30-1)

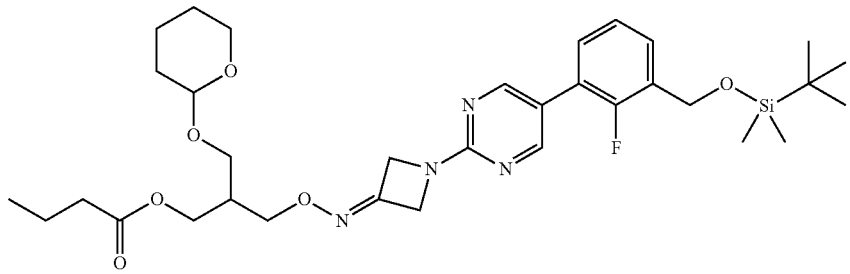 [SMILES: CCCC(=O)OCC(CON=C1CN(c2ncc(-c3cccc(CO[Si](C)(C)C(C)(C)C)c3F)cn2)C1)COC1CCCCO1]

Butyric anhydride 60 μl (0.37 mmol), TEA 80 μl (0.57 mmol) and DMAP 4.0 mg (0.033 mmol) were added to a methylene chloride (6 mL) solution of 1-[5-(3-{[(tert-butyldimethylsilyl)oxy]methyl}-2-fluorophenyl)pyrimidin-2-yl]azetidin-3-one O-(3-hydroxy-2-{[(tetrahydropyran-2-yl)oxy]methyl}propyl) oxime 0.16 g (0.28 mmol) synthesized in the same manner as in Reference Example 6-25, and the mixture was stirred at room temperature for 1.5 hours. After the completion of the reaction, water was added to the reaction mixture, and followed by extraction with methylene chloride. The organic layer was washed with water, dried over anhydrous magnesium sulfate, and filtered. The filtrate was concentrated under reduced pressure. The concentrated residue was purified by silica gel column chromatography (eluting solvent: hexane:ethyl acetate) to give the title compound 0.13 g (0.20 mmol, yield 71%) as a colorless oil.

Mass spectrum (CI, m/z):645[M+1]$^+$.

$^1$H-NMR spectrum (400 MHz, DMSO-d$_6$) δ:8.63 (d, J=1.3 Hz, 2H), 7.53-7.42 (m, 2H), 7.36-7.27 (m, 1H), 4.92-4.73 (m, 6H), 4.62-4.50 (m, 1H), 4.17-3.99 (m, 4H), 3.81-3.60 (m, 2H), 3.51-3.23 (m, 2H), 2.39-2.20 (m, 3H), 1.84-1.33 (m, 8H), 0.91 (s, 9H), 0.88 (t, J=7.4 Hz, 3H), 0.11 (s, 6H).

Reference Example 30-2

3-[({1-[5-(3-{[(tert-Butyldimethylsilyl)oxy]methyl}-2-fluorophenyl)pyrimidin-2-yl]azetidin-3-ylidene}amino)oxy]-2-{[(tetrahydropyran-2-yl)oxy]methyl}propyl isobutyrate (Reference Compound 30-2)

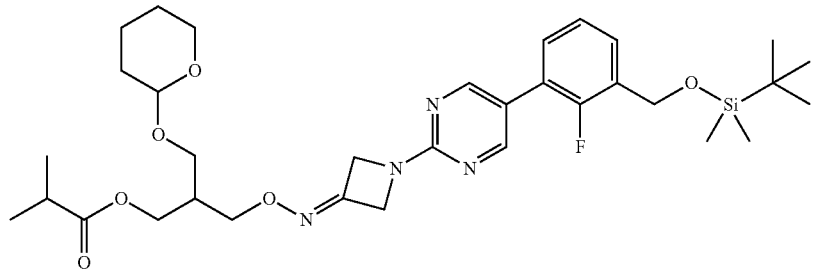 [SMILES: CC(C)C(=O)OCC(CON=C1CN(c2ncc(-c3cccc(CO[Si](C)(C)C(C)(C)C)c3F)cn2)C1)COC1CCCCO1]

The reaction was performed by the method described in Reference Example 30-1, except that butyric anhydride was replaced by isobutyric anhydride. Consequently, the title compound (yield 82%) was obtained as a colorless oil.

Mass spectrum (CI, m/z):645[M+1]$^+$.

$^1$H-NMR spectrum (400 MHz, DMSO-d$_6$) δ:8.63 (d, J=1.4 Hz, 2H), 7.53-7.42 (m, 2H), 7.34-7.29 (m, 1H), 4.88-4.76 (m, 6H), 4.60-4.52 (m, 1H), 4.16-4.04 (m, 4H), 3.77-3.65 (m, 2H), 3.48-3.34 (m, 2H), 2.55 (sep, J=7.0 Hz, 1H), 2.40-2.27 (m, 1H), 1.79-1.38 (m, 6H), 1.09 (d, J=7.0 Hz, 6H), 0.91 (s, 9H), 0.11 (s, 6H).

Reference Example 30-3

3-[({1-[5-(3-{[(tert-Butyldimethylsilyl)oxy]methyl}-2-fluorophenyl)pyrimidin-2-yl]azetidin-3-ylidene}amino)oxy]-2-{[(tetrahydropyran-2-yl)oxy]methyl}propyl pivalate (Reference Compound 30-3)

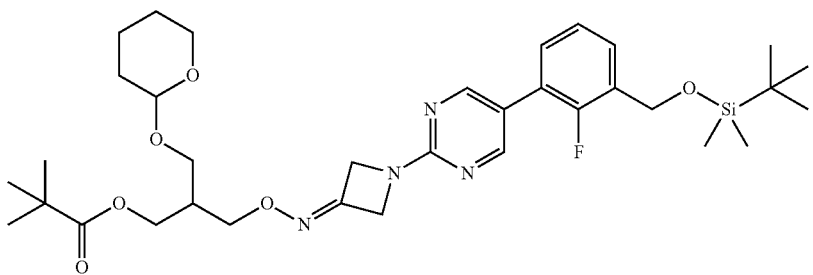 [SMILES: CC(C)(C)C(=O)OCC(CON=C1CN(c2ncc(-c3cccc(CO[Si](C)(C)C(C)(C)C)c3F)cn2)C1)COC1CCCCO1]

The reaction was performed by the method described in Reference Example 30-1, except that butyric anhydride was replaced by trimethylacetic anhydride. Consequently, the title compound (yield 73%) was obtained as a colorless oil.

Mass spectrum (CI, m/z):659[M+1]$^+$.

$^1$H-NMR spectrum (400 MHz, DMSO-d$_6$) δ:8.63 (d, J=1.3 Hz, 2H), 7.52-7.42 (m, 2H), 7.35-7.28 (m, 1H), 4.85-4.79 (m, 6H), 4.59-4.53 (m, 1H), 4.20-4.04 (m, 4H), 3.78-3.63 (m, 2H), 3.47-3.34 (m, 2H), 2.39-2.29 (m, 1H), 1.75-1.37 (m, 6H), 1.15 (s, 9H), 0.91 (s, 9H), 0.11 (s, 6H).

Reference Example 30-4

3-[({1-[5-(3-{[(tert-Butyldimethylsilyl)oxy]methyl}-2-fluorophenyl)pyrimidin-2-yl]azetidin-3-ylidene}amino)oxy]-2-{[(tetrahydropyran-2-yl)oxy]methyl}propyl hexanoate (Reference Example 30-4)

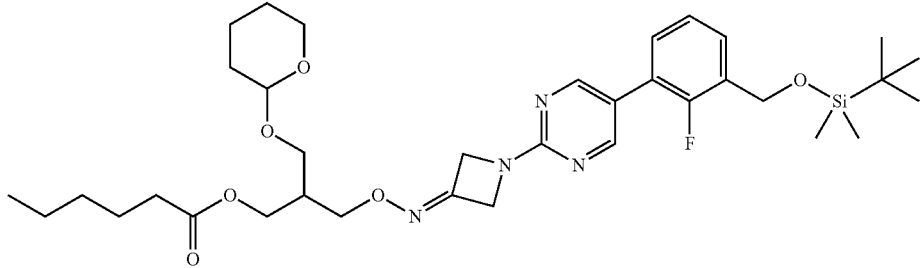 [SMILES: CCCCCC(=O)OCC(CON=C1CN(c2ncc(-c3cccc(CO[Si](C)(C)C(C)(C)C)c3F)cn2)C1)COC1CCCCO1]

The reaction was performed by the method described in Reference Example 30-1, except that butyric anhydride was replaced by hexanoic anhydride. Consequently, the title compound (yield 82%) was obtained as a colorless oil.

Mass spectrum (CI, m/z):673[M+1]$^+$.

$^1$H-NMR spectrum (400 MHz, DMSO-d$_6$) δ:8.63 (d, J=1.4 Hz, 2H), 7.55-7.43 (m, 2H), 7.36-7.28 (m, 1H), 4.90-4.74 (m, 6H), 4.61-4.51 (m, 1H), 4.19-4.00 (m, 4H), 3.76-3.56 (m, 2H), 3.49-3.26 (m, 3H), 2.40-2.20 (m, 3H), 1.83-1.16 (m, 12H), 0.91 (s, 9H), 0.85 (t, J=7.1 Hz, 3H), 0.11 (s, 6H).

Reference Example 30-5

3-[((1-[5-(3-{[(tert-Butyldimethylsilyl)oxy]methyl}-2-fluorophenyl)pyrimidin-2-yl]azetidin-3-ylidene}amino)oxy]-2-{[(tetrahydropyran-2-yl)oxy]methyl}propyl benzoate (Reference Compound 30-5)

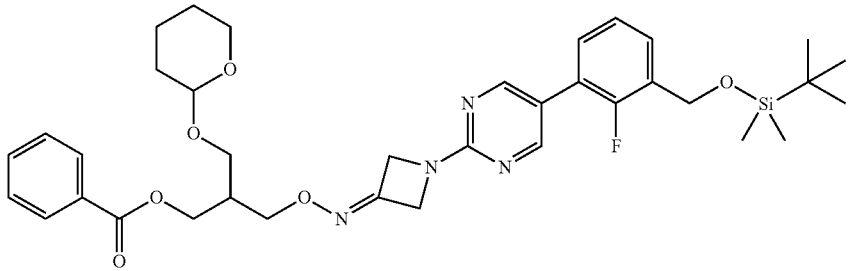 [SMILES: CC(C)(C)[Si](C)(C)OCc1cccc(-c2cnc(N3CC(=NOCC(COC(=O)c4ccccc4)COC4CCCCO4)C3)nc2)c1F]

The reaction was performed by the method described in Reference Example 30-1, except that butyric anhydride was replaced by benzoic anhydride. Consequently, the title compound (yield 78%) was obtained as a colorless oil.

Mass spectrum (CI, m/z):679[M+1]$^+$.

$^1$H-NMR spectrum (400 MHz, DMSO-d$_6$) δ:8.62 (d, J=1.4 Hz, 2H), 8.03-7.93 (m, 2H), 7.67-7.59 (m, 1H), 7.57-7.43 (m, 4H), 7.35-7.26 (m, 1H), 4.90-4.69 (m, 6H), 4.63-4.53 (m, 1H), 4.43-4.32 (m, 2H), 4.26-4.12 (m, 2H), 3.87-3.64 (m, 2H), 3.57-3.34 (m, 2H), 1.81-1.32 (m, 6H), 0.91 (s, 9H), 0.11 (s, 6H).

Reference Example 31-1

1-(5-Bromo-3-fluoropyridin-2-yl)azetidin-3-ol (Reference Compound 31-1)

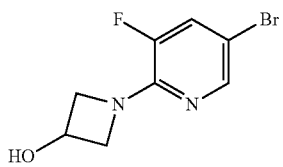

Cesium carbonate 19 g (58 mmol) and azetidin-3-ol hydrochloride 4.0 g (37 mmol) were added to an NMP (15 mL) solution of 5-bromo-2,3-difluoropyridine 2.85 g (14.7 mmol), and the mixture was stirred at 110° C. for 1 hour. After the completion of the reaction, the reaction mixture was naturally cooled to room temperature. Water was added thereto, and followed by extraction with methylene chloride. The organic layer was washed with brine, dried over anhydrous sodium sulfate, and filtered. The filtrate was concentrated under reduced pressure. The concentrated residue was purified by silica gel column chromatography (eluting solvent: hexane:ethyl acetate) to give the title compound 2.63 g (10.7 mmol, yield 73%) as a white solid.

Mass spectrum (CI, m/z):247, 249[M+1]$^+$.

$^1$H-NMR spectrum (400 MHz, CDCl$_3$) δ:7.96 (dd, J=0.9, 2.0 Hz, 1H), 7.30 (dd, J=2.0, 10.9 Hz, 1H), 4.83-4.74 (m, 1H), 4.43-4.36 (m, 2H), 4.01-3.95 (m, 2H), 2.31 (d, J=6.3 Hz, 1H).

The title compound was also synthesized in the following manner.

TEA 14 mL (100 mol) was added to an ethanol (70 mL) solution of 5-bromo-2,3-difluoropyridine 7.56 g (39.0 mmol) and azetidin-3-ol hydrochloride 5.00 g (45.6 mol), and the mixture was stirred at 55° C. for 3 hours. After the completion of the reaction, water 70 mL was added to the reaction mixture. The solvent was concentrated under reduced pressure to approximately half volume, and the residue was stirred at room temperature. The precipitated solid was collected by filtration and was dried under reduced pressure to give the title compound 8.06 g (32.6 mol, yield 84%) as a white solid.

Reference Example 31-2

1-(5-Bromo-3-chloropyridin-2-yl)azetidin-3-ol (Reference Compound 31-2)

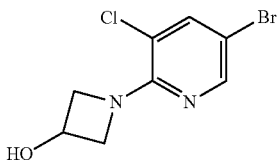 [SMILES: OC1CN(c2ncc(Br)cc2Cl)C1]

The reaction was performed by the method described in Reference Example 31-1, except that 5-bromo-2,3-difluoropyridine was replaced by 5-bromo-3-chloro-2-fluoropyridine. Consequently, the title compound (yield 80%) was obtained as a white solid.

Mass spectrum (CI, m/z):263, 265[M+1]$^+$.

$^1$H-NMR spectrum (400 MHz, DMSO-d$_6$) 5:8.15 (d, J=2.1 Hz, 1H), 7.91 (d, J=2.1 Hz, 1H), 5.63 (d, J=6.1 Hz, 1H), 4.54-4.45 (m, 1H), 4.38-4.31 (m, 2H), 3.89-3.82 (m, 2H).

Reference Example 31-3

1-(3-Methoxypyridin-2-yl)azetidin-3-ol (Reference Compound 31-3)

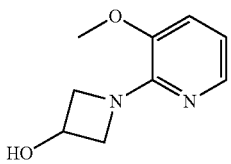

The reaction was performed by the method described in Reference Example 31-1, except that 5-bromo-2,3-difluoropyridine was replaced by 2-fluoro-3-methoxypyridine synthesized in the same manner as in Reference Example 55, that NMP was replaced by DMSO, and that the reaction temperature was changed to 100° C. Consequently, the title compound (yield 37%) was obtained as a white solid.

Mass spectrum (ESI, m/z): 181[M+1]$^+$.

1H-NMR spectrum (400 MHz, DMSO-d6) δ:7.64 (dd, J=1.4, 5.0 Hz, 1H), 7.07 (dd, J=1.4, 7.8 Hz, 1H), 6.64 (dd, J=5.0, 7.8 Hz, 1H), 5.46 (br s, 1H), 4.53-4.42 (m, 1H), 4.20-4.12 (m, 2H), 3.74-3.67 (m, 5H).

Reference Example 32-1

1-(5-Bromo-3-fluoropyridin-2-yl)azetidin-3-one (Reference Compound 32-1)

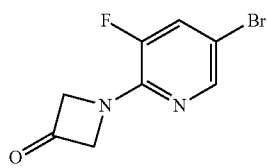 [SMILES: O=C1CN(c2ncc(Br)cc2F)C1]

At 0° C., Dess-Martin Periodinane 5.9 g (14 mmol) was added to a methylene chloride (30 mL) suspension of 1-(5-bromo-3-fluoropyridin-2-yl)azetidin-3-ol 2.63 g (10.7 mmol) synthesized in the same manner as in Reference Example 31-1, and the mixture was stirred at room temperature for 1 hour. After the completion of the reaction, an aqueous sodium thiosulfate solution and a saturated aqueous sodium hydrogen carbonate solution were added to the reaction mixture, and the mixture was stirred for 30 minutes, and followed by extraction with methylene chloride. The organic layer was washed with brine, dried over anhydrous sodium sulfate, and filtered. The filtrate was concentrated under reduced pressure to give a crude product 2.55 g including the title compound as a brown solid.

Mass spectrum (CI, m/z):245, 247[M+1]$^+$.

$^1$H-NMR spectrum (400 MHz, CDCl$_3$) δ:8.07 (dd, J=0.8, 1.9 Hz, 1H), 7.43 (dd, J=1.9, 10.5 Hz, 1H), 4.92-4.89 (m, 4H).

The title compound was synthesized also in the following manner.

Azadol 40 mg (0.26 mmol) and iodobenzene diacetate 1.80 g (5.59 mmol) were added to a methylene chloride (10 mL) solution of 1-(5-bromo-3-fluoropyridin-2-yl)azetidin-3-ol 1.00 g (4.05 mmol) synthesized in the same manner as in Reference Example 31-1, and the mixture was stirred at room temperature for 22 hours. After the completion of the reaction, a saturated aqueous sodium bicarbonate solution and sodium thiosulfate were added to the reaction mixture, and the mixture was stirred for 1 hour and followed by extraction with ethyl acetate. The organic layer was washed with a saturated aqueous sodium bicarbonate solution, dried over anhydrous magnesium sulfate, and filtered. The filtrate was concentrated under reduced pressure. TBME and hexane were added to the concentrated residue, and the mixture was stirred at room temperature. The solid was collected by filtration. Consequently, the title compound 504 mg (2.06 mmol, yield 51%) was obtained as a white solid.

Reference Example 32-2

1-(5-Bromopyridin-2-yl)azetidin-3-one (Reference Compound 32-2)

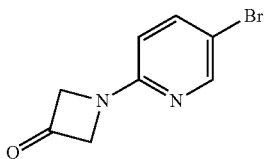 [SMILES: O=C1CN(c2ccc(Br)cn2)C1]

The reaction was performed by the method described in Reference Example 32-1, except that 1-(5-bromo-3-fluoropyridin-2-yl)azetidin-3-ol (Reference Compound 31-1) was replaced by 1-(5-bromopyridin-2-yl)azetidin-3-ol synthesized in the same manner as in Reference Example 35, and the concentrated residue was purified by silica gel column chromatography (eluting solvent: 1,2-dichloroethane:ethyl acetate). Consequently, the title compound (yield 27%) was obtained as a white solid.

Mass spectrum (CI, m/z):227, 229[M+1]$^+$.
$^1$H-NMR spectrum (400 MHz, DMSO-d$_6$) δ:8.25-8.23 (m, 1H), 7.79 (dd, J=2.5, 8.8 Hz, 1H), 6.65-6.61 (m, 1H), 4.79 (s, 4H).

Reference Example 32-3

1-(5-Bromo-3-methylpyridin-2-yl)azetidin-3-one (Reference Compound 32-3)

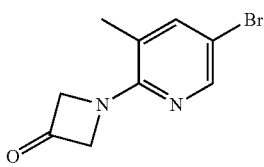

The reaction was performed by the method described in Reference Example 32-1, except that 1-(5-bromo-3-fluoropyridin-2-yl)azetidin-3-ol (Reference Compound 31-1) was replaced by 1-(5-bromo-3-methylpyridin-2-yl)azetidin-3-ol synthesized in the same manner as in Reference Example 36. Consequently, a crude product including the title compound was obtained.

Reference Example 32-4

1-(5-Bromo-3-chloropyridin-2-yl)azetidin-3-one (Reference Compound 32-4)

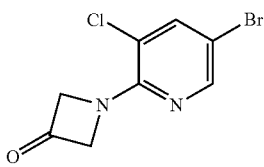 [SMILES: O=C1CN(c2ncc(Br)cc2Cl)C1]

The reaction was performed by the method described in Reference Example 32-1, except that 1-(5-bromo-3-fluoropyridin-2-yl)azetidin-3-ol (Reference Compound 31-1) was replaced by 1-(5-bromo-3-chloropyridin-2-yl)azetidin-3-ol synthesized in the same manner as in Reference Example 31-2. Consequently, a crude product including the title compound was obtained as a brown solid.

Mass spectrum (CI, m/z):261, 263[M+1]$^+$.
$^1$H-NMR spectrum (400 MHz, CDCl$_3$) δ:8.17 (d, J=2.1 Hz, 1H), 7.70 (d, J=2.1 Hz, 1H), 4.96 (s, 4H).

Reference Example 32-5

1-[5-Bromo-3-(difluoromethyl)pyridin-2-yl]azetidin-3-one (Reference Compound 32-5)

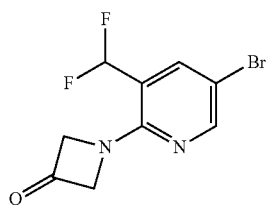 [SMILES: O=C1CN(c2ncc(Br)cc2C(F)F)C1]

The reaction was performed by the method described in Reference Example 32-1, except that 1-(5-bromo-3-fluoropyridin-2-yl)azetidin-3-ol (Reference Compound 31-1) was replaced by 1-[5-bromo-3-(difluoromethyl)pyridin-2-yl]azetidin-3-ol synthesized in the same manner as in Reference Example 43-2, and the concentrated residue was purified by silica gel column chromatography (eluting solvent: hexane:ethyl acetate). Consequently, the title compound (yield 83%) was obtained as a white solid.

Mass spectrum (CI, m/z):277, 279[M+1]$^+$.
$^1$H-NMR spectrum (400 MHz, DMSO-d$_6$) δ:8.46-8.42 (m, 1H), 8.05-8.01 (m, 1H), 7.09 (t, J=54.2 Hz, 1H), 4.95 (s, 4H).

Reference Example 32-6

1-(5-Bromo-3-cyclopropylpyridin-2-yl)azetidin-3-one (Reference Compound 32-6)

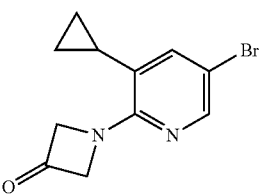 [SMILES: O=C1CN(c2ncc(Br)cc2C2CC2)C1]

The reaction was performed by the method described in Reference Example 32-1, except that 1-(5-bromo-3-fluoropyridin-2-yl)azetidin-3-ol (Reference Compound 31-1) was replaced by 1-(5-bromo-3-cyclopropylpyridin-2-yl)azetidin-3-ol synthesized in the same manner as in Reference Example 43-1, and the concentrated residue was purified by silica gel column chromatography (eluting solvent: hexane:ethyl acetate). Consequently, the title compound (yield 87%) was obtained as a white solid.

Mass spectrum (CI, m/z):267, 269[M+1]$^+$.
$^1$H-NMR spectrum (400 MHz, DMSO-d$_6$) δ:8.10 (d, J=2.3 Hz, 1H), 7.45 (dd, J=0.6, 2.3 Hz, 1H), 4.97 (s, 4H), 1.88-1.81 (m, 1H), 0.96-0.87 (m, 2H), 0.77-0.72 (m, 2H).

Reference Example 32-7

1-(5-Bromo-3-ethylpyridin-2-yl)azetidin-3-one (Reference Compound 32-7)

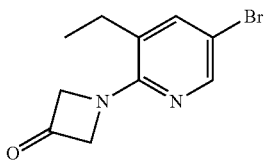

The reaction was performed by the method described in Reference Example 32-1, except that 1-(5-bromo-3-fluoropyridin-2-yl)azetidin-3-ol (Reference Compound 31-1) was replaced by 1-(5-bromo-3-ethylpyridin-2-yl)azetidin-3-ol synthesized in the same manner as in Reference Example 43-3, and the concentrated residue was purified by silica gel column chromatography (eluting solvent: hexane:ethyl acetate). Consequently, the title compound (yield 79%) was obtained as a white solid.

Mass spectrum (CI, m/z):255, 257[M+1]$^+$.
$^1$H-NMR spectrum (400 MHz, DMSO-d$_6$) δ:8.14 (d, J=2.4 Hz, 1H), 7.66-7.64 (m, 1H), 4.88 (s, 4H), 2.59-2.45 (m, 2H), 1.17 (t, J=7.5 Hz, 3H).

Reference Example 33-1

1-(5-Bromo-3-fluoropyridin-2-yl)azetidin-3-one O-methyl oxime (Reference Compound 33-1)

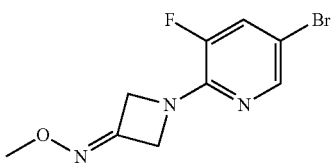

Cesium carbonate 6.2 g (19 mmol) and iodomethane 0.90 mL (14 mmol) were added to a DMF (8 mL) solution of 1-(5-bromo-3-fluoropyridin-2-yl)azetidin-3-one oxime 1.65 g (6.34 mmol) synthesized in the same manner as in Reference Example 9-2, and the mixture was stirred at room temperature for 2 hours. After the completion of the reaction, water was added to the reaction mixture, and followed by extraction with ethyl acetate. The organic layer was washed with brine, dried over anhydrous magnesium sulfate, and filtered. The filtrate was concentrated under reduced pressure. The concentrated residue was purified by silica gel column chromatography (eluting solvent: hexane:ethyl acetate) to give the title compound 1.33 g (4.85 mmol, yield 76%) as a light yellow solid.

Mass spectrum (CI, m/z):274, 276[M+1]$^+$.
$^1$H-NMR spectrum (400 MHz, CDCl$_3$) δ:8.02 (dd, J=0.8, 1.9 Hz, 1H), 7.37 (dd, J=1.9, 10.7 Hz, 1H), 4.83-4.81 (m, 4H), 3.89 (s, 3H).

The title compound was synthesized also in the following manner.

O-methylhydroxylamine hydrochloride 160 mg (1.92 mmol) was added to a THF (8 mL) solution of 1-(5-bromo-3-fluoropyridin-2-yl)azetidin-3-one 226 mg (0.922 mmol) synthesized in the same manner as in Reference Example 32-1, and the mixture was stirred at 50° C. for 8 hours. After the completion of the reaction, water was added to the reaction mixture, and followed by extraction with ethyl acetate. The organic layer was washed with water, dried over anhydrous magnesium sulfate, and filtered. The filtrate was concentrated under reduced pressure. The concentrated residue was purified by silica gel column chromatography (eluting solvent: 1,2-dichloroethane:ethyl acetate) to give the title compound 129 mg (0.471 mmol, yield 51%) as a white solid.

Reference Example 33-2

1-(5-Bromo-3-fluoropyridin-2-yl)azetidin-3-one O-methyl-d$_3$ oxime (Reference Compound 33-2)

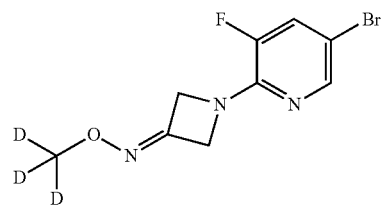 [SMILES: [2H]C([2H])([2H])ON=C1CN(c2ncc(Br)cc2F)C1]

The reaction was performed by the method described in Reference Example 33-1, except that iodomethane was replaced by iodomethane-d$_3$. Consequently, the title compound (yield 70%) was obtained as a white solid.

Mass spectrum (EI, m/z):276[M]$^+$, 278[M]$^+$.
$^1$H-NMR spectrum (400 MHz, CDCl$_3$) δ:8.02 (dd, J=0.9, 1.9 Hz, 1H), 7.37 (dd, J=1.9, 10.7 Hz, 1H), 4.85-4.77 (m, 4H).

Reference Example 34-1

1-(5-Bromo-3-fluoropyridin-2-yl)azetidin-3-one O-[2-(2,2-dimethyl-1,3-dioxolan-4-yl)ethyl] oxime (Reference Compound 34-1)

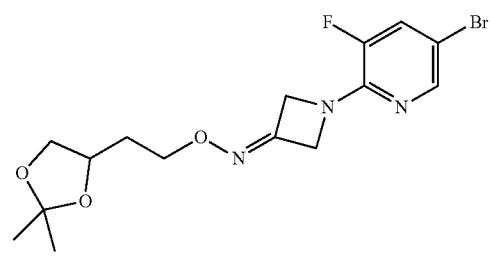 [SMILES: CC1(C)OCC(CCON=C2CN(c3ncc(Br)cc3F)C2)O1]

Cesium carbonate 1.10 g (3.38 mmol) and 2-(2,2-dimethyl-1,3-dioxolan-4-yl)ethyl methanesulfonate 570 mg (2.54 mmol) synthesized in the same manner as in Reference Example 14-6 were added to a DMF (2 mL) solution of 1-(5-bromo-3-fluoropyridin-2-yl)azetidin-3-one oxime 220 mg (0.846 mmol) synthesized in the same manner as in Reference Example 9-2, and the mixture was stirred at room temperature for 4 hours. After the completion of the reaction, water was added to the reaction mixture, and followed by extraction with ethyl acetate. The organic layer was washed with brine, dried over anhydrous sodium sulfate, and filtered. The filtrate was concentrated under reduced pressure. The concentrated residue was purified by silica gel column chromatography (eluting solvent: hexane:ethyl acetate) to give the title compound 265 mg (0.683 mmol, yield 81%) as a colorless oil.

Mass spectrum (CI, m/z):388, 340[M+1]$^+$.

$^1$H-NMR spectrum (400 MHz, CDCl$_3$) δ:8.02 (dd, J=0.9, 1.9 Hz, 1H), 7.37 (dd, J=1.9, 10.7 Hz, 1H), 4.83-4.80 (m, 4H), 4.24-4.13 (m, 3H), 4.10-4.05 (m, 1H), 3.60-3.54 (m, 1H), 1.99-1.91 (m, 2H), 1.41 (s, 3H), 1.36 (s, 3H).

Reference Example 34-2

1-(5-Bromo-3-fluoropyridin-2-yl)azetidin-3-one O-[(2,2-dimethyl-1,3-dioxan-5-yl)methyl] oxime (Reference Compound 34-2)

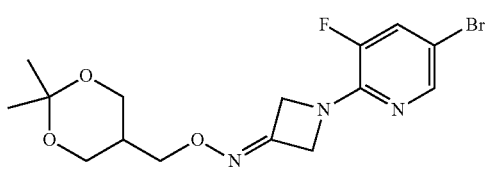 [SMILES: CC1(C)OCC(CON=C2CN(c3ncc(Br)cc3F)C2)CO1]

The reaction was performed by the method described in Reference Example 34-1, except that 2-(2,2-dimethyl-1,3-dioxolan-4-yl)ethyl methanesulfonate (Reference Compound 14-6) was replaced by (2,2-dimethyl-1,3-dioxan-5-yl)methyl methanesulfonate synthesized in the same manner as in Reference Example 14-4. Consequently, the title compound (including impurities) was obtained as a light yellow solid.

Mass spectrum (EI, m/z):387[M]$^+$, 389[M]$^+$.

$^1$H-NMR spectrum (400 MHz, CDCl$_3$) δ:8.02 (dd, J=0.8, 1.9 Hz, 1H), 7.37 (dd, J=1.9, 10.7 Hz, 1H), 4.83-4.79 (m, 4H), 4.17 (d, J=6.9 Hz, 2H), 4.00 (dd, J=4.0, 12.0 Hz, 2H), 3.75 (dd, J=5.8, 12.0 Hz, 2H), 2.13-2.04 (m, 1H), 1.45 (s, 3H), 1.41 (s, 3H).

Reference Example 34-3

1-(5-Bromo-3-fluoropyridin-2-yl)azetidin-3-one O-[(2,2-dimethyl-1,3-dioxolan-4-yl)methyl] oxime (Reference Compound 34-3)

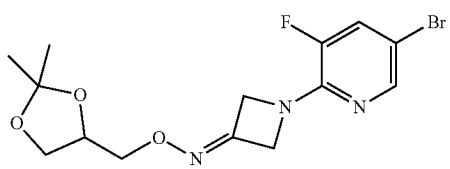 [SMILES: CC1(C)OCC(CON=C2CN(c3ncc(Br)cc3F)C2)O1]

The reaction was performed by the method described in Reference Example 34-1, except that 2-(2,2-dimethyl-1,3-dioxolan-4-yl)ethyl methanesulfonate (Reference Compound 14-6) was replaced by (2,2-dimethyl-1,3-dioxolan-4-yl)methyl methanesulfonate synthesized in the same manner as in Reference Example 14-5, and the reaction temperature was changed to 80° C. Consequently, the title compound (yield 41%) was obtained as a yellow solid.

Mass spectrum (CI, m/z):374, 376[M+1]$^+$.

$^1$H-NMR spectrum (400 MHz, DMSO-d$_6$) δ:8.10 (dd, J=0.9, 2.0 Hz, 1H), 7.91 (dd, J=2.0, 11.3 Hz, 1H), 4.85-4.77 (m, 4H), 4.32-4.23 (m, 1H), 4.07-4.00 (m, 3H), 3.66 (dd, J=6.4, 8.4 Hz, 1H), 1.32 (s, 3H), 1.27 (s, 3H).

Reference Example 35

1-(5-Bromopyridin-2-yl)azetidin-3-ol (Reference Compound 35)

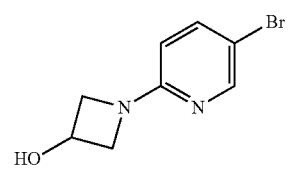 [SMILES: OC1CN(c2ccc(Br)cn2)C1]

DIPEA 2.72 mL (15.6 mmol) was added to a DMF (10 mL) suspension of 5-bromo-2-chloropyridine 1.00 g (5.20 mmol) and azetidin-3-ol hydrochloride 712 mg (6.50 mmol), and the mixture was stirred at 120° C. for 22 hours. After the completion of the reaction, water was added to the reaction mixture, and followed by extraction with toluene. The organic layer was washed with brine, dried over anhydrous magnesium sulfate, and filtered. The filtrate was concentrated under reduced pressure. The concentrated residue was purified by silica gel column chromatography (eluting solvent: hexane:ethyl acetate) to give the title compound 200 mg (0.873 mmol, yield 17%) as a colorless oil.

Mass spectrum (CI, m/z):229, 231[M+1]$^+$.

$^1$H-NMR spectrum (400 MHz, DMSO-d$_6$) 5:8.11 (dd, J=0.6, 2.7 Hz, 1H), 7.65 (dd, J=2.7, 8.8 Hz, 1H), 6.36 (dd, J=0.6, 8.8 Hz, 1H), 5.66 (d, J=6.4 Hz, 1H), 4.59-4.52 (m, 1H), 4.16-4.10 (m, 2H), 3.67-3.62 (m, 2H).

Reference Example 36

1-(5-Bromo-3-methylpyridin-2-yl)azetidin-3-ol (Reference Compound 36)

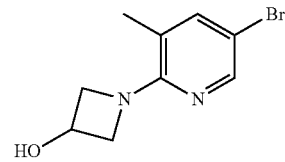

Azetidin-3-ol hydrochloride 1.2 g (11 mmol) and cesium carbonate 5.1 g (16 mmol) were added to a DMF (10 mL) solution of 5-bromo-2-fluoro-3-methylpyridine 1.0 g (5.3 mmol), and the mixture was stirred at room temperature for 15 hours and at 100° C. for 5 hours. After the completion of the reaction, a saturated aqueous ammonium chloride solution was added to the reaction mixture, and followed by extraction with ethyl acetate. The organic layer was washed with brine, dried over anhydrous magnesium sulfate, and filtered. The filtrate was concentrated under reduced pressure. The concentrated residue was purified by silica gel column chromatography (eluting solvent: hexane:ethyl acetate) to give the title compound 0.50 g (2.1 mmol, yield 40%) as a white solid.

Mass spectrum (ESI, m/z):243, 245[M+1]$^+$.

$^1$H-NMR spectrum (400 MHz, DMSO-d$_6$) δ:8.01 (d, J=2.4 Hz, 1H), 7.54-7.49 (m, 1H), 5.55 (d, J=4.8 Hz, 1H), 4.54-4.44 (m, 1H), 4.24-4.17 (m, 2H), 3.81-3.69 (m, 2H), 2.12 (s, 3H).

Reference Example 37-1)

tert-Butyl 3-(methoxyimino)azetidine-1-carboxylate (Reference Compound 37-1)

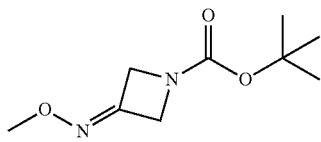

O-methylhydroxylamine hydrochloride 3.0 g (36 mmol) and sodium carbonate 5.6 g (53 mmol) were added to an ethanol (30 mL)-water (8 mL) solution of tert-butyl 3-oxoazetidine-1-carboxylate 3.0 g (17 mmol), and the mixture was stirred at 70° C. for 12 hours. After the completion of the reaction, water was added to the reaction mixture, and followed by extraction with ethyl acetate. The organic layer was washed with water, dried over anhydrous magnesium sulfate, and filtered. The filtrate was concentrated under reduced pressure to give a crude product 3.3 g including the title compound.

Mass spectrum (CI, m/z):201[M+1]$^+$.

$^1$H-NMR spectrum (400 MHz, DMSO-d$_6$) δ:4.61-4.47 (m, 4H), 3.78 (s, 3H), 1.40 (s, 9H).

Reference Example 37-2 tert-Butyl 3-[(benzyloxy)imino]azetidine-1-carboxylate (Reference Compound 37-2)

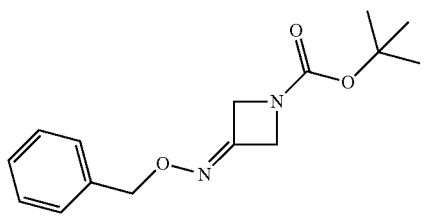 [SMILES: CC(C)(C)OC(=O)N1CC(=NOCc2ccccc2)C1]

The reaction was performed by the method described in Reference Example 37-1, except that O-methylhydroxylamine hydrochloride was replaced by O-benzylhydroxylamine hydrochloride. Consequently, a crude product including the title compound was obtained as a light yellow oil.

Reference Example 38

Azetidin-3-one O-methyl oxime hydrochloride (Reference Compound 38)

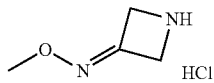

At 0° C., 2 M hydrogen chloride/ethanol solution 30 mL (60 mmol) was added to an ethanol(30 mL) solution of the crude product 3.3 g from Reference Example 37-1 which included tert-butyl 3-(methoxyimino)azetidine-1-carboxylate, and the mixture was stirred at room temperature for 7 hours. After the completion of the reaction, the reaction mixture was concentrated under reduced pressure to give a crude product 1.26 g including the title compound.

Mass spectrum (CI, m/z): 101[M+1]$^+$.

$^1$H-NMR spectrum (400 MHz, DMSO-d$_6$) δ:9.81 (br s., 2H), 4.83-4.70 (m, 4H), 3.82 (s, 3H).

Reference Example 39

5-Bromo-2-[3-(methoxyimino)azetidin-1-yl]nicotinonitrile (Reference Compound 39)

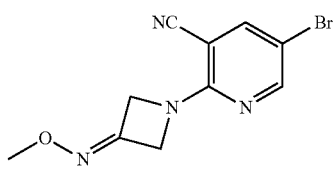 [SMILES: CON=C1CN(c2ncc(Br)cc2C#N)C1]

TEA 0.65 mL (4.7 mmol) was added to an ethanol (8 mL) suspension of the crude product 0.25 g from Reference Example 38 which included azetidin-3-one O-methyl oxime hydrochloride, and 5-bromo-2-chloronicotinonitrile 0.20 g (0.92 mmol), and the mixture was stirred at 70° C. for 1 hour. After the completion of the reaction, water was added to the reaction mixture, and followed by extraction with ethyl acetate. The organic layer was washed with brine, dried over anhydrous magnesium sulfate, and filtered. The filtrate was concentrated under reduced pressure. The concentrated residue was purified by silica gel column chromatography (eluting solvent: hexane:ethyl acetate) to give the title compound 0.12 g (including impurities) as a light brown solid.

Mass spectrum (CI, m/z):281, 283[M+1]$^+$.

$^1$H-NMR spectrum (400 MHz, DMSO-d$_6$) δ:8.48 (d, J=2.4 Hz, 1H), 8.36 (d, J=2.4 Hz, 1H), 4.96-4.92 (m, 4H), 3.82 (s, 3H).

Reference Example 40

1-[3-(Difluoromethyl)pyridin-2-yl]azetidin-3-ol
(Reference Compound 40)

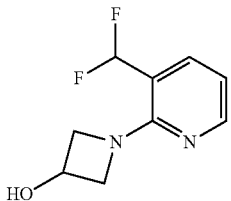 [SMILES: OC1CN(c2ncccc2C(F)F)C1]

Azetidin-3-ol hydrochloride 1.13 g (10.3 mmol) and DIPEA 4.20 mL (24.1 mmol) were added to a DMSO (10 mL) solution of 2-chloro-3-(difluoromethyl)pyridine 1.32 g (8.07 mmol), and the mixture was stirred at 110° C. for 13 hours. Next, cesium carbonate 7.89 g (24.2 mmol) and azetidin-3-ol hydrochloride 1.13 g (10.3 mmol) were added, and the mixture was stirred at 110° C. for 2 hours. After the completion of the reaction, water was added to the reaction mixture, and followed by extraction with ethyl acetate. The organic layer was washed with brine, dried over anhydrous magnesium sulfate, and filtered. The filtrate was concentrated under reduced pressure. The concentrated residue was purified by silica gel column chromatography (eluting solvent: hexane:ethyl acetate) to give the title compound 1.03 g (5.15 mmol, yield 64%) as a light yellow solid.

Mass spectrum (CI, m/z):201[M+1]$^+$.

$^1$H-NMR spectrum (400 MHz, DMSO-d$_6$) δ:8.24-8.20 (m, 1H), 7.74-7.70 (m, 1H), 7.01 (t, J=54.9 Hz, 1H), 6.75 (dd, J=4.9, 7.5 Hz, 1H), 5.63 (d, J=3.6 Hz, 1H), 4.59-4.50 (m, 1H), 4.31-4.24 (m, 2H), 3.88-3.82 (m, 2H).

Reference Example 41

1-(3-Iodopyridin-2-yl)azetidin-3-ol (Reference Compound 41)

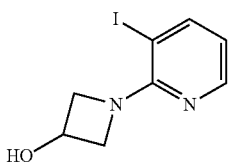 [SMILES: OC1CN(c2ncccc2I)C1]

Azetidin-3-ol hydrochloride 1.22 g (11.1 mmol) and DIPEA 4.64 mL (26.6 mmol) were added to a DMSO (10 mL) solution of 2-fluoro-3-iodopyridine 1.98 g (8.88 mmol), and the mixture was stirred at 100° C. for 9 hours. After the completion of the reaction, water was added to the reaction mixture, and followed by extraction with toluene. The organic layer was washed with brine, dried over anhydrous magnesium sulfate, and filtered. The filtrate was concentrated under reduced pressure. The concentrated residue was purified by silica gel column chromatography (eluting solvent: hexane:ethyl acetate) to give the title compound 1.66 g (6.01 mmol, yield 68%) as a white solid.

Mass spectrum (CI, m/z):277[M+1]$^+$.

$^1$H-NMR spectrum (400 MHz, DMSO-d$_6$) δ:8.12 (dd, J=1.6, 4.7 Hz, 1H), 8.00 (dd, J=1.6, 7.5 Hz, 1H), 6.52 (dd, J=4.7, 7.5 Hz, 1H), 5.56 (s, 1H), 4.46-4.36 (m, 3H), 3.87-3.81 (m, 2H).

Reference Example 42

1-(3-Cyclopropylpyridin-2-yl)azetidin-3-ol
(Reference Compound 42)

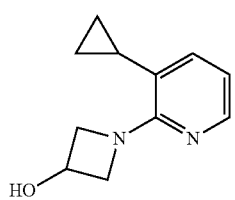 [SMILES: OC1CN(c2ncccc2C2CC2)C1]

Cyclopropylboronic acid 443 mg (5.16 mmol), 2 M aqueous sodium carbonate solution 5.16 mL (10.3 mmol), palladium (II) acetate 30 mg (0.13 mmol) and 2-dicyclohexylphosphino-2',6'-dimethoxy-1,1'-biphenyl 106 mg (0.258 mmol) were added to a toluene (20 mL) solution of 1-(3-iodopyridin-2-yl)azetidin-3-ol 712 mg (2.58 mmol) synthesized in the same manner as in Reference Example 41. The mixture was degassed, purged with nitrogen, and stirred at 110° C. for 2 hours under a stream of argon. Next, palladium (II) acetate 30 mg (0.13 mmol) and 2-dicyclohexylphosphino-2',6'-dimethoxy-1,1'-biphenyl 100 mg (0.244 mmol) were added. The mixture was degassed, purged with nitrogen, and stirred at 110° C. for 5 hours under a stream of argon. Next, palladium (II) acetate 60 mg (0.27 mmol) and 2-dicyclohexylphosphino-2',6'-dimethoxy-1,1'-biphenyl 200 mg (0.487 mmol) were added. The mixture was degassed, purged with nitrogen, and stirred at 110° C. for 4 hours under a stream of argon. After the completion of the reaction, a saturated aqueous sodium hydrogen carbonate solution was added to the reaction mixture, and followed by extraction with toluene. The organic layer was washed with brine, dried over anhydrous magnesium sulfate, and filtered. The filtrate was concentrated under reduced pressure. The concentrated residue was purified by silica gel column chromatography (eluting solvent: hexane:ethyl acetate) to give the title compound 276 mg (1.45 mmol, yield 56%) as a yellow oil.

Mass spectrum (CI, m/z): 191[M+1]$^+$.

$^1$H-NMR spectrum (400 MHz, DMSO-d$_6$) δ:7.93-7.90 (m, 1H), 7.19-7.16 (m, 1H), 6.61 (dd, J=4.9, 7.3 Hz, 1H), 5.49 (br s, 1H), 4.54-4.47 (m, 1H), 4.32-4.27 (m, 2H), 3.87-3.83 (m, 2H), 1.80-1.73 (m, 1H), 0.89-0.84 (m, 2H), 0.63-0.58 (m, 2H).

Reference Example 43-1

1-(5-Bromo-3-cyclopropylpyridin-2-yl)azetidin-3-ol
(Reference Compound 43-1)

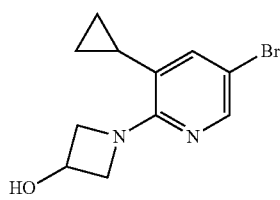 [SMILES: OC1CN(c2ncc(Br)cc2C2CC2)C1]

Under ice cooling, N-bromosuccinimide 326 mg (1.83 mmol) was added to an acetonitrile (10 mL) solution of 1-(3-cyclopropylpyridin-2-yl)azetidin-3-ol 332 mg (1.75 mmol) synthesized in the same manner as in Reference Example 42, and the mixture was stirred at 0° C. for 30 minutes. After the completion of the reaction, water was added to the reaction mixture, and followed by extraction with ethyl acetate. The organic layer was washed with brine, dried over anhydrous magnesium sulfate, and filtered. The filtrate was concentrated under reduced pressure. The concentrated residue was purified by silica gel column chromatography (eluting solvent: hexane:ethyl acetate) to give the title compound 383 mg (1.42 mmol, yield 82%) as a light yellow solid.

Mass spectrum (CI, m/z):269, 271[M+1]$^+$.

$^1$H-NMR spectrum (400 MHz, DMSO-d$_6$) δ:8.00-7.97 (m, 1H), 7.30 (dd, J=0.8, 2.3 Hz, 1H), 5.56 (br s, 1H), 4.55-4.47 (m, 1H), 4.35-4.28 (m, 2H), 3.88-3.83 (m, 2H), 1.81-1.73 (m, 1H), 0.91-0.85 (m, 2H), 0.70-0.65 (m, 2H).

Reference Example 43-2

1-[5-Bromo-3-(difluoromethyl)pyridin-2-yl]azetidin-3-ol (Reference Compound 43-2)

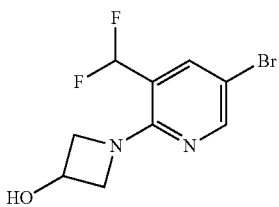 [SMILES: OC1CN(c2ncc(Br)cc2C(F)F)C1]

The reaction was performed by the method described in Reference Example 43-1, except that 1-(3-cyclopropylpyridin-2-yl)azetidin-3-ol (Reference Compound 42) was replaced by 1-[3-(difluoromethyl)pyridin-2-yl]azetidin-3-ol synthesized in the same manner as in Reference Example 40, and the reaction temperature was ambient. Consequently, the title compound (yield 95%) was obtained as a white solid.

Mass spectrum (CI, m/z):279, 281[M+1]$^+$.

$^1$H-NMR spectrum (400 MHz, DMSO-d$_6$) δ:8.33-8.29 (m, 1H), 7.88-7.85 (m, 1H), 6.96 (t, J=54.6 Hz, 1H), 5.68 (d, J=5.4 Hz, 1H), 4.59-4.50 (m, 1H), 4.32-4.25 (m, 2H), 3.88-3.82 (m, 2H).

Reference Example 43-3

1-(5-Bromo-3-ethylpyridin-2-yl)azetidin-3-ol (Reference Compound 43-3)

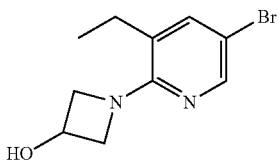

The reaction was performed by the method described in Reference Example 43-1, except that 1-(3-cyclopropylpyridin-2-yl)azetidin-3-ol (Reference Compound 42) was replaced by 1-(3-ethylpyridin-2-yl)azetidin-3-ol synthesized in the same manner as in Reference Example 45. Consequently, the title compound (yield 86%) was obtained as a white solid.

Mass spectrum (CI, m/z):257, 259[M+1]$^+$.

$^1$H-NMR spectrum (400 MHz, DMSO-d$_6$) δ:8.03 (d, J=2.3 Hz, 1H), 7.51-7.48 (m, 1H), 5.57 (d, J=4.1 Hz, 1H), 4.54-4.46 (m, 1H), 4.22-4.16 (m, 2H), 3.78-3.72 (m, 2H), 2.50-2.42 (m, 2H), 1.11 (t, J=7.5 Hz, 3H).

Reference Example 43-4

1-[5-Bromo-3-(methoxymethyl)pyridin-2-yl]azetidin-3-ol (Reference Compound 43-4)

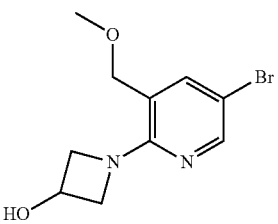

Under ice cooling, N-bromosuccinimide 900 mg (5.06 mmol) was added to an acetonitrile (10 mL) solution of 1-[3-(methoxymethyl)pyridin-2-yl]azetidin-3-ol 890 mg (4.58 mmol) synthesized in the same manner as in Reference Example 54, and the mixture was stirred at 0° C. for 1 hour. After the completion of the reaction, water was added to the reaction mixture, and followed by extraction with ethyl acetate. The organic layer was washed with water, dried over anhydrous magnesium sulfate, and filtered. The filtrate was concentrated under reduced pressure. Water was added to the concentrated residue. The solid was collected by filtration and was dried under reduced pressure to give the title compound 690 mg (2.53 mmol, yield 55%) as a white solid.

Mass spectrum (CI, m/z):273, 275[M+1]$^+$.

$^1$H-NMR spectrum (400 MHz, DMSO-d$_6$) δ:8.10 (d, J=2.4 Hz, 1H), 7.61 (d, J=2.4 Hz, 1H), 5.59 (d, J=6.0 Hz, 1H), 4.60-4.45 (m, 1H), 4.27-4.20 (m, 4H), 3.85-3.78 (m, 2H), 3.28 (s, 3H).

Reference Example 43-5

1-(5-Bromo-3-methoxypyridin-2-yl)azetidin-3-ol (Reference Compound 43-5)

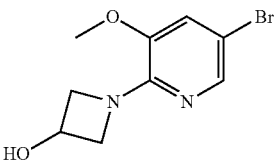

The reaction was performed by the method described in Reference Example 43-1, except that 1-(3-cyclopropylpyridin-2-yl)azetidin-3-ol (Reference Compound 42) was replaced by 1-(3-methoxypyridin-2-yl)azetidin-3-ol synthesized in the same manner as in Reference Example 31-3, and the reaction temperature was ambient. Consequently, the title compound (yield 76%) was obtained as a light yellow oil.

Mass spectrum (ESI, m/z):259, 261[M+1]⁺.

¹H-NMR spectrum (400 MHz, DMSO-$d_6$) δ:7.72 (d, J=2.0 Hz, 1H), 7.25 (d, J=2.0 Hz, 1H), 5.52 (d, J=5.6 Hz, 1H), 4.52-4.44 (m, 1H), 4.22-4.14 (m, 2H), 3.75 (s, 3H), 3.74-3.68 (m, 2H).

Reference Example 44

1-(3-Vinylpyridin-2-yl)azetidin-3-ol (Reference Compound 44)

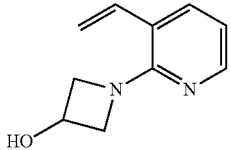

Potassium vinyltrifluoroborate 582 mg (4.34 mmol) and TEA 530 μl (3.80 mmol) were added to a 1-propanol (30 mL) solution of 1-(3-iodopyridin-2-yl)azetidin-3-ol 1.00 g (3.62 mmol) synthesized in the same manner as in Reference Example 41. The mixture was degassed and purged with nitrogen. 1,1'-Bis(diphenylphosphino)ferrocene dichloropalladium (II) 53.0 mg (0.072 mmol) was added, and the mixture was stirred at 100° C. for 2 hours under a stream of argon. Next, 1,1'-bis(diphenylphosphino)ferrocene dichloropalladium (II) 100 mg (0.137 mmol) was added. Under a stream of argon, the mixture was stirred at 100° C. for 10 hours. After the completion of the reaction, a saturated aqueous ammonium chloride solution was added to the reaction mixture, and followed by extraction with ethyl acetate. A saturated aqueous sodium carbonate solution was added to the aqueous layer, and followed by extraction with ethyl acetate. The organic layers were combined, washed with brine, dried over anhydrous sodium sulfate, and filtered. The filtrate was concentrated under reduced pressure. The concentrated residue was purified by silica gel column chromatography (eluting solvent: hexane:ethyl acetate) to give the title compound 370 mg (2.10 mmol, yield 58%) as a brown oil.

Mass spectrum (CI, m/z): 177[M+1]⁺.

¹H-NMR spectrum (400 MHz, DMSO-$d_6$) δ:8.04 (dd, J=1.8, 4.8 Hz, 1H), 7.61 (dd, J=1.8, 7.4 Hz, 1H), 6.76-6.67 (m, 2H), 5.60 (dd, J=1.4, 17.4 Hz, 1H), 5.53 (br s, 1H), 5.27 (dd, J=1.4, 11.0 Hz, 1H), 4.52-4.46 (m, 1H), 4.23-4.18 (m, 2H), 3.77-3.72 (m, 2H).

Reference Example 45

1-(3-Ethylpyridin-2-yl)azetidin-3-ol (Reference Compound 45)

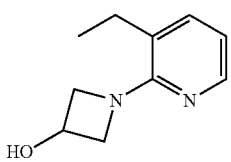

Palladium carbon (10% Pd carbon powder (hydrous) PE type (trade name), manufactured by N.E. CHEMCAT, containing 54% water) 38 mg was added to a THF (4 mL)-ethanol (8 mL) solution of 1-(3-vinylpyridin-2-yl)azetidin-3-ol 370 mg (2.10 mmol) synthesized in the same manner as in Reference Example 44. At a reduced pressure, the atmosphere was purged with hydrogen, and the mixture was stirred at room temperature for 30 minutes. After the completion of the reaction, the reaction mixture was filtered through Celite. The filtrate was concentrated under reduced pressure to give a crude product 388 mg including the title compound as a light yellow oil.

Reference Example 46

Methyl 5-bromo-2-fluoronicotinate (Reference Compound 46)

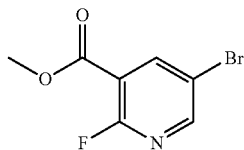

Iodomethane 0.75 mL (12 mmol) and potassium carbonate 2.5 g (18 mmol) were added to a DMF (8 mL) solution of 5-bromo-2-fluoronicotinic acid 2.0 g (9.1 mmol), and the mixture was stirred at room temperature for 20 hours. After the completion of the reaction, water was added to the reaction mixture, and followed by extraction with ethyl acetate. The organic layer was washed with water, dried over anhydrous magnesium sulfate, and filtered. The filtrate was concentrated under reduced pressure. The concentrated residue was purified by silica gel column chromatography (eluting solvent: hexane:ethyl acetate) to give the title compound 1.7 g (7.3 mmol, yield 80%) as a white solid.

Mass spectrum (CI, m/z):234, 236[M+1]⁺.

¹H-NMR spectrum (400 MHz, DMSO-$d_6$) δ:8.66 (dd, J=1.3, 2.6 Hz, 1H), 8.56 (dd, J=2.6, 8.2 Hz, 1H), 3.89 (s, 3H).

Reference Example 47

2-(5-Bromo-2-fluoropyridin-3-yl)propan-2-ol (Reference Compound 47)

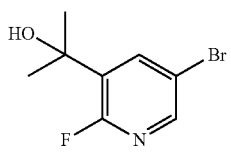

A THF (10 mL) solution of methyl 5-bromo-2-fluoronicotinate 1.65 g (7.05 mmol) synthesized in the same manner as in Reference Example 46 was degassed and purged with nitrogen. At 0° C., a 1.4 M methylmagnesium bromide THF-toluene solution 12.6 mL (17.6 mmol) was added, and the mixture was stirred at room temperature for 1 hour. After the completion of the reaction, a saturated aqueous ammonium chloride solution was added to the reaction mixture, and followed by extraction with ethyl acetate. The organic layer was washed with water, dried over anhydrous magnesium sulfate, and filtered. The filtrate was concentrated under reduced pressure. The concentrated residue was purified by silica gel column chromatography (eluting solvent: hexane:ethyl acetate) to give the title compound 1.71 g (including impurities) as a white solid.

Mass spectrum (CI, m/z):234, 236[M+1]$^+$.

$^1$H-NMR spectrum (400 MHz, DMSO-d$_6$) δ:8.26 (d, J=1.6, 2.6 Hz, 1H), 8.19 (d, J=2.6, 8.8 Hz, 1H), 5.60 (s, 1H), 1.51-1.43 (m, 6H).

Reference Example 48

5-Bromo-2-fluoro-3-{2-[(tetrahydropyran-2-yl)oxy]propan-2-yl}pyridine (Reference Compound 48)

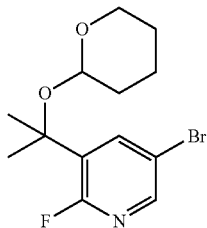 [SMILES: CC(C)(OC1CCCCO1)c1cc(Br)cnc1F]

PPTS 0.37 g (1.5 mmol) and DHP 3.1 mL (37 mmol) were added to a methylene chloride (10 mL) solution of 2-(5-bromo-2-fluoropyridin-3-yl)propan-2-ol 1.7 g (7.3 mmol) synthesized in the same manner as in Reference Example 47, and the mixture was stirred at room temperature for 20 hours. After the completion of the reaction, water was added to the reaction mixture, and followed by extraction with methylene chloride. The organic layer was washed with water, dried over anhydrous magnesium sulfate, and filtered. The filtrate was concentrated under reduced pressure. The concentrated residue was purified by silica gel column chromatography (eluting solvent: hexane:ethyl acetate) to give the title compound 2.1 g (6.6 mmol, yield 90%) as a colorless oil.

Mass spectrum (CI, m/z):318, 320[M+1]$^+$.

$^1$H-NMR spectrum (400 MHz, DMSO-d$_6$) δ:8.30 (dd, J=1.6, 2.4 Hz, 1H), 8.12 (dd, J=2.4, 8.8 Hz, 1H), 4.76-4.72 (m, 1H), 3.85-3.71 (m, 1H), 3.42-3.32 (m, 1H), 1.85-1.33 (m, 12H).

Reference Example 49

1-(5-Bromo-3-{2-[(tetrahydropyran-2-yl)oxy]propan-2-yl}pyridin-2-yl)azetidin-3-ol (Reference Compound 49)

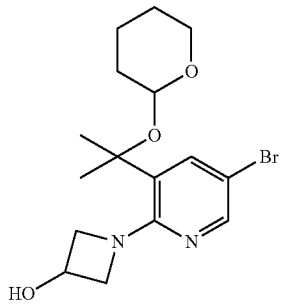 [SMILES: CC(C)(OC1CCCCO1)c1cc(Br)cnc1N1CC(O)C1]

Potassium carbonate 3.61 g (26.1 mmol) and azetidin-3-ol hydrochloride 1.43 g (13.1 mmol) were added to a DMSO (10 mL) solution of 5-bromo-2-fluoro-3-{2-[(tetrahydropyran-2-yl)oxy]propan-2-yl}pyridine 2.08 g (6.54 mmol) synthesized in the same manner as in Reference Example 48, and the mixture was stirred at 90° C. for 10 hours. After the completion of the reaction, water was added to the reaction mixture, and followed by extraction with ethyl acetate. The organic layer was washed with water, dried over anhydrous sodium sulfate, and filtered. The filtrate was concentrated under reduced pressure. The concentrated residue was purified by silica gel column chromatography (eluting solvent: hexane:ethyl acetate) to give the title compound 846 mg (2.28 mmol, yield 35%) as a colorless foam.

Mass spectrum (CI, m/z):371, 373[M+1]$^+$.

$^1$H-NMR spectrum (400 MHz, DMSO-d$_6$) δ:8.13 (d, J=2.3 Hz, 1H), 7.61 (d, J=2.3 Hz, 1H), 5.46 (br s, 1H), 4.46-4.35 (m, 2H), 4.30-4.13 (m, 2H), 3.88-3.71 (m, 3H), 3.41-3.22 (m, 1H), 1.87-1.29 (m, 12H).

Reference Example 50-1

1-(5-Bromo-3-{2-[(tetrahydropyran-2-yl)oxy]propan-2-yl}pyridin-2-yl)azetidin-3-one (Reference Compound 50-1)

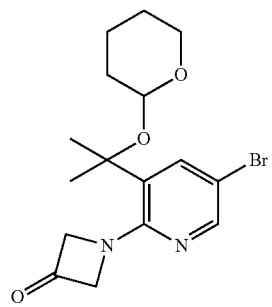 [SMILES: CC(C)(OC1CCCCO1)c1cc(Br)cnc1N1CC(=O)C1]

Dess-Martin Periodinane 1.45 g (3.42 mmol) and sodium hydrogen carbonate 300 mg (3.57 mmol) were added to a methylene chloride (20 mL) solution of 1-(5-bromo-3-{2-[(tetrahydropyran-2-yl)oxy]propan-2-yl}pyridin-2-yl)azetidin-3-ol 846 mg (2.28 mmol) synthesized in the same manner as in Reference Example 49, and the mixture was stirred at room temperature for 1 hour. After the completion of the reaction, water and sodium thiosulfate were added to the reaction mixture, and followed by extraction with methylene chloride. The organic layer was washed with water, dried over anhydrous sodium sulfate, and concentrated under reduced pressure. The concentrated residue was purified by silica gel column chromatography (eluting solvent: hexane:ethyl acetate) to give the title compound 554 mg (1.50 mmol, yield 66%) as a white solid.

Mass spectrum (CI, m/z):369, 371[M+1]$^+$.

$^1$H-NMR spectrum (400 MHz, DMSO-d$_6$) δ:8.24 (d, J=2.4 Hz, 1H), 7.77 (d, J=2.4 Hz, 1H), 4.95-4.82 (m, 4H), 4.58-4.48 (m, 1H), 3.81-3.67 (m, 1H), 3.36-3.28 (m, 1H), 1.87-1.24 (m, 12H).

Reference Example 50-2

1-[5-Bromo-3-(methoxymethyl)pyridin-2-yl]azetidin-3-one (Reference Compound 50-2)

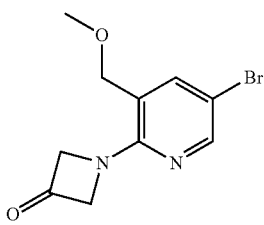

The reaction was performed by the method described in Reference Example 50-1, except that 1-(5-bromo-3-{2-[(tetrahydropyran-2-yl)oxy]propan-2-yl}pyridin-2-yl)azetidin-3-ol (Reference Compound 49) was replaced by 1-[5-bromo-3-(methoxymethyl)pyridin-2-yl]azetidin-3-ol synthesized in the same manner as in Reference Example 43-4. Consequently, the title compound (yield 80%) was obtained as a white solid.

Mass spectrum (CI, m/z):271, 273[M+1]$^+$.

$^1$H-NMR spectrum (400 MHz, DMSO-$d_6$) δ:8.23 (d, J=2.4 Hz, 1H), 7.76 (d, J=2.4 Hz, 1H), 4.92 (s, 4H), 4.33 (s, 2H), 3.31 (s, 3H).

Reference Example 51

1-(5-Bromo-3-{2-[(tetrahydropyran-2-yl)oxy]propan-2-yl}pyridin-2-yl)azetidin-3-one O-methyl oxime (Reference Compound 51)

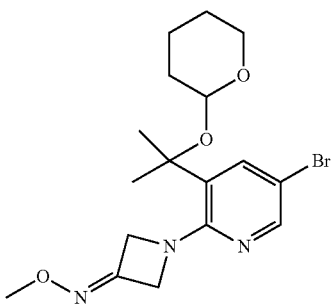 [SMILES: CON=C1CN(c2ncc(Br)cc2C(C)(C)OC2CCCCO2)C1]

Sodium carbonate 350 mg (3.30 mmol) and O-methylhydroxylamine hydrochloride 251 mg (3.01 mmol) were added to an ethanol (10 mL)-THF (10 mL)-water (6 mL) suspension of 1-(5-bromo-3-{2-[(tetrahydropyran-2-yl)oxy]propan-2-yl}pyridin-2-yl)azetidin-3-one 554 mg (1.50 mmol) synthesized in the same manner as in Reference Example 50-1, and the mixture was stirred at 60° C. for 4 hours. After the completion of the reaction, water was added to the reaction mixture, and followed by extraction with ethyl acetate. The organic layer was washed with water, dried over anhydrous magnesium sulfate, and filtered. The filtrate was concentrated under reduced pressure. The concentrated residue was purified by silica gel column chromatography (eluting solvent: 1,2-dichloroethane:ethyl acetate) to give the title compound 565 mg (including impurities) as a white solid.

Mass spectrum (CI, m/z):398, 400[M+1]$^+$.

$^1$H-NMR spectrum (400 MHz, DMSO-$d_6$) δ:8.20 (d, J=2.2 Hz, 1H), 7.71 (d, J=2.2 Hz, 1H), 4.86-4.70 (m, 4H), 4.51-4.45 (m, 1H), 3.80 (s, 3H), 3.78-3.69 (m, 1H), 3.42-3.22 (m, 1H), 1.85-1.26 (m, 12H).

Reference Example 52

(2-Fluoropyridin-3-yl)methanol (Reference Compound 52)

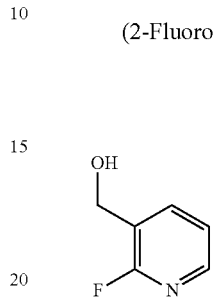

Sodium borohydride 1.0 g (26 mmol) was added to an ethanol (14 mL) solution of 2-fluoronicotinaldehyde 1.6 mL (16 mmol), and the mixture was stirred at room temperature for 1 hour. After the completion of the reaction, water was added to the reaction mixture, and followed by extraction with ethyl acetate. The organic layer was washed with brine, dried over anhydrous magnesium sulfate, and filtered. The filtrate was concentrated under reduced pressure to give the title compound 1.3 g (10 mmol, yield 63%) as a colorless oil.

Reference Example 53

2-Fluoro-3-(methoxymethyl)pyridine (Reference Compound 53)

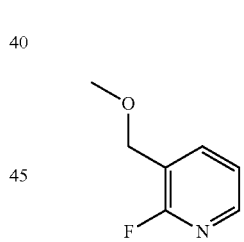

At 0° C., 55% sodium hydride 0.70 g (16 mmol) was added in portions to a THF (20 mL) solution of (2-fluoropyridin-3-yl)methanol 1.3 g (10 mmol) synthesized in the same manner as in Reference Example 52 and iodomethane 6.6 mL (110 mmol), and the mixture was stirred at room temperature for 2 hours. After the completion of the reaction, water was added to the reaction mixture, and followed by extraction with ethyl acetate. The organic layer was washed with water, dried over anhydrous magnesium sulfate, and filtered. The filtrate was concentrated under reduced pressure. The concentrated residue was purified by silica gel column chromatography (eluting solvent: hexane:ethyl acetate) to give the title compound 0.89 g (6.3 mmol, yield 63%) as a colorless oil.

$^1$H-NMR spectrum (400 MHz, DMSO-$d_6$) δ:8.23-8.14 (m, 1H), 8.02-7.92 (m, 1H), 7.40-7.35 (m, 1H), 4.46 (s, 2H), 3.33 (s, 3H).

525

Reference Example 54

1-[3-(Methoxymethyl)pyridin-2-yl]azetidin-3-ol (Reference Compound 54)

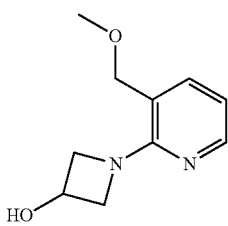

Azetidin-3-ol hydrochloride 1.4 g (13 mmol) and cesium carbonate 6.1 g (19 mmol) were added to a DMSO (10 mL) solution of 2-fluoro-3-(methoxymethyl)pyridine 0.89 g (6.3 mmol) synthesized in the same manner as in Reference Example 53, and the mixture was stirred at 100° C. for 10 hours. After the completion of the reaction, water was added to the reaction mixture, and followed by extraction with ethyl acetate. The organic layer was washed with brine, dried over anhydrous sodium sulfate, and filtered. The filtrate was concentrated under reduced pressure. The concentrated residue was purified by silica gel column chromatography (eluting solvent: hexane:ethyl acetate) to give the title compound 0.89 g (4.6 mmol, yield 73%) as a white solid.

Mass spectrum (CI, m/z):195[M+1]$^+$.

$^1$H-NMR spectrum (400 MHz, DMSO-d$_6$) 5:8.03 (dd, J=1.8, 4.9 Hz, 1H), 7.44 (dd, J=1.8, 7.3 Hz, 1H), 6.66 (dd, J=4.9, 7.3 Hz, 1H), 5.54 (br s, 1H), 4.59-4.44 (m, 1H), 4.26 (s, 2H), 4.24-4.14 (m, 2H), 3.84-3.78 (m, 2H), 3.27 (s, 3H).

Reference Example 55

2-Fluoro-3-methoxypyridine (Reference Compound 55)

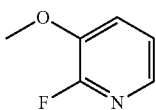

Iodomethane 1.7 mL (27 mmol) and cesium carbonate 4.3 g (13. mmol) were added to a DMSO (20 mL) solution of 2-fluoropyridin-3-ol 1.0 g (8.8 mmol), and the mixture was stirred at 60° C. for 1 hour. After the completion of the reaction, a saturated aqueous ammonium chloride solution was added to the reaction mixture, and followed by extraction with ethyl acetate. The organic layer was washed with brine, dried over anhydrous magnesium sulfate, and filtered. The filtrate was concentrated under reduced pressure to give the title compound 1.1 g (8.7 mmol, yield 99%) as a white solid.

$^1$H-NMR spectrum (400 MHz, DMSO-d$_6$) δ:7.76-7.69 (m, 1H), 7.65 (ddd, J=1.5, 8.0, 10.7 Hz, 1H), 7.31 (ddd, J=0.9, 4.8, 8.0 Hz, 1H), 3.88 (s, 3H).

526

Reference Example 56

1-(5-Bromo-3-methoxypyridin-2-yl)azetidin-3-one (Reference Compound 56)

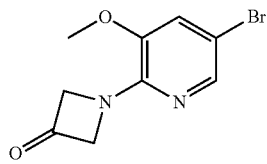

Pyridine 0.055 mL (0.68 mmol) and Dess-Martin Periodinane 110 mg (0.26 mmol) were added to a methylene chloride (2 mL) solution of 1-(5-bromo-3-methoxypyridin-2-yl)azetidin-3-ol 50 mg (0.19 mmol) synthesized in the same manner as in Reference Example 43-5, and the mixture was stirred at room temperature for 3 hours. After the completion of the reaction, the reaction mixture was diluted with ethyl acetate, sequentially washed with a saturated aqueous sodium thiosulfate solution and brine, dried over anhydrous magnesium sulfate, and filtered. The filtrate was concentrated under reduced pressure. The concentrated residue was purified by silica gel column chromatography (eluting solvent: hexane:ethyl acetate) to give the title compound 20 mg (0.078 mol, yield 40%) as a white solid.

Mass spectrum (CI, m/z):257, 259[M+1]$^+$.

$^1$H-NMR spectrum (400 MHz, DMSO-d$_6$) δ:7.84 (d, J=1.9 Hz, 1H), 7.41 (d, J=1.9 Hz, 1H), 4.82 (s, 4H), 3.81 (s, 3H).

Reference Example 57

1-(5-Bromo-3-methoxypyridin-2-yl)azetidin-3-one O-methyl oxime (Reference Compound 57)

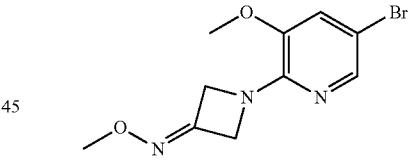

O-methylhydroxylamine hydrochloride 60 mg (0.72 mmol) and potassium carbonate 130 mg (0.94 mmol) were added to a THF (4 mL) solution of 1-(5-bromo-3-methoxypyridin-2-yl)azetidin-3-one 61 mg (0.24 mmol) synthesized in the same manner as in Reference Example 56, and the mixture was stirred at room temperature for 16 hours. After the completion of the reaction, a saturated aqueous sodium hydrogen carbonate solution was added to the reaction mixture, and followed by extraction with ethyl acetate. The organic layer was washed with brine, dried over anhydrous magnesium sulfate, and filtered. The filtrate was concentrated under reduced pressure. The concentrated residue was purified by silica gel column chromatography (eluting solvent: hexane:ethyl acetate) to give the title compound 45 mg (0.16 mmol, yield 67%) as a white solid.

Mass spectrum (ESI, m/z):286, 288[M+1]$^+$.

$^1$H-NMR spectrum (400 MHz, DMSO-d$_6$) δ:7.80 (d, J=2.0 Hz, 1H), 7.37 (d, J=2.0 Hz, 1H), 4.73-4.67 (m, 4H), 3.79 (s, 3H), 3.79 (s, 3H).

Reference Example 58

8-(5-Bromopyrimidin-2-yl)-1,4-dioxa-8-azaspiro[4.5]decane (Reference Compound 58)

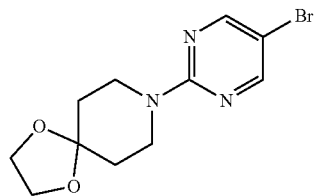 [SMILES: Brc1cnc(N2CCC3(CC2)OCCO3)nc1]

1,4-Dioxa-8-azaspiro[4.5]decane 0.74 mL (5.8 mmol) and DIPEA 1.8 mL (10 mmol) were added to a DMF (10 mL) solution of 5-bromo-2-chloropyrimidine 1.0 g (5.2 mmol), and the mixture was stirred at 100° C. for 3 hours. After the completion of the reaction, water was added to the reaction mixture, and followed by extraction with ethyl acetate. The organic layer was washed with water, dried over anhydrous sodium sulfate, and filtered. The filtrate was concentrated under reduced pressure. The concentrated residue was purified by silica gel column chromatography (eluting solvent: hexane:ethyl acetate) to give the title compound 1.5 g (5.0 mmol, yield 96%) as a white solid.

Mass spectrum (CI, m/z):300, 302[M+1]$^+$.

$^1$H-NMR spectrum (400 MHz, DMSO-d$_6$) δ:8.42 (s, 2H), 3.92 (s, 4H), 3.84-3.75 (m, 4H), 1.66-1.59 (m, 4H).

Reference Example 59

1-(5-Bromopyrimidin-2-yl)piperidin-4-one (Reference Compound 59)

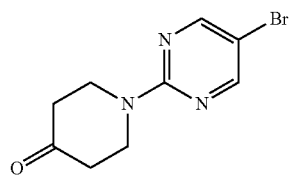 [SMILES: O=C1CCN(c2ncc(Br)cn2)CC1]

6 N hydrochloric acid 4.0 mL (24 mmol) was added to an acetone (20 mL) solution of 8-(5-bromopyrimidin-2-yl)-1,4-dioxa-8-azaspiro[4.5]decane 1.5 g (5.0 mmol) synthesized in the same manner as in Reference Example 58, and the mixture was stirred at room temperature for 20 hours and at 50° C. for 6 hours. After the completion of the reaction, a saturated aqueous sodium hydrogen carbonate solution was added to the reaction mixture, and followed by extraction with ethyl acetate. The organic layer was washed with brine, dried over anhydrous magnesium sulfate, and filtered. The filtrate was concentrated under reduced pressure. The concentrated residue was purified by silica gel column chromatography (eluting solvent: hexane:ethyl acetate) to give the title compound 1.0 g (3.9 mmol, yield 78%) as a white solid.

Mass spectrum (CI, m/z):256, 258[M+1]$^+$.

$^1$H-NMR spectrum (400 MHz, DMSO-d$_6$) δ:8.35 (s, 2H), 4.22-3.97 (m, 4H), 2.57-2.41 (m, 4H).

Reference Example 60

1-[5-(3-{[(tert-Butyldimethylsilyl)oxy]methyl}-2-fluorophenyl)pyrimidin-2-yl]piperidin-4-one O-methyl oxime (Reference Compound 60)

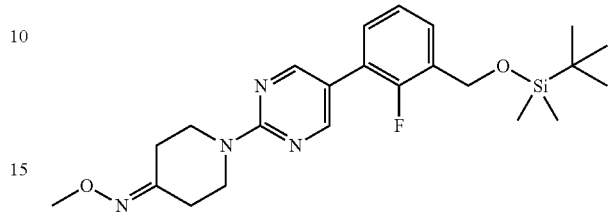

Sodium carbonate 242 mg (2.28 mmol) and O-methylhydroxylamine hydrochloride 188 mg (2.25 mmol) were added to an ethanol (8 mL)-THF (6 mL)-water (1 mL) suspension of 1-[5-(3-{[(tert-butyldimethylsilyl)oxy]methyl}-2-fluorophenyl)pyrimidin-2-yl]piperidin-4-one 440 mg (1.06 mmol) synthesized in the same manner as in Reference Example 6-41, and the mixture was stirred at 50° C. for 1 hour. After the completion of the reaction, water was added to the reaction mixture, and followed by extraction with ethyl acetate. The organic layer was washed with water and brine, dried over anhydrous sodium sulfate, and filtered. The filtrate was concentrated under reduced pressure. The concentrated residue was purified by silica gel column chromatography (eluting solvent: hexane:ethyl acetate) to give the title compound 392 mg (0.882 mmol, yield 83%) as a white solid.

Mass spectrum (CI, m/z):445[M+1]$^+$.

$^1$H-NMR spectrum (400 MHz, DMSO-d$_6$) δ:8.59 (d, J=1.4 Hz, 2H), 7.52-7.41 (m, 2H), 7.35-7.25 (m, 1H), 4.81 (s, 2H), 3.95-3.89 (m, 4H), 3.76 (s, 3H), 2.58-2.53 (m, 2H), 2.42-2.32 (m, 2H), 0.91 (s, 9H), 0.11 (s, 6H).

Reference Example 61

1-{5-[2-Fluoro-3-(hydroxymethyl)phenyl]pyrimidin-2-yl}piperidin-4-one O-tetrahydropyran-2-yl oxime (Reference Compound 61)

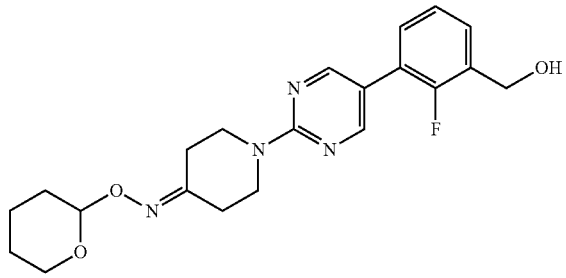 [SMILES: OCc1cccc(-c2cnc(N3CCC(=NOC4CCCCO4)CC3)nc2)c1F]

Sodium carbonate 115 mg (1.09 mmol) and O-(tetrahydropyran-2-yl)hydroxylamine 90.4 mg (0.772 mmol) were added to a THF (3 mL)-ethanol (4 mL)-water (0.5 mL) solution of 1-{5-[2-fluoro-3-(hydroxymethyl)phenyl]pyrimidin-2-yl}piperidin-4-one 150 mg (0.498 mmol) synthesized in the same manner as in Reference Example 7-50, and the mixture was stirred at room temperature for 2 hours.

Next, O-(tetrahydropyran-2-yl)hydroxylamine 53.1 mg (0.453 mmol) was added, and the mixture was stirred at room temperature for 3 hours. After the completion of the reaction, water was added to the reaction mixture, and followed by extraction with ethyl acetate. The organic layer was washed with brine, dried over anhydrous magnesium sulfate, and filtered. The filtrate was concentrated under reduced pressure. The concentrated residue was purified by silica gel column chromatography (eluting solvent: hexane:ethyl acetate=53:47 to 37:73 (V/V)) to give the title compound 215 mg (including impurities) as a white solid.

Mass spectrum (CI, m/z):401[M+1]$^+$.

$^1$H-NMR spectrum (400 MHz, CDCl$_3$) δ:8.53 (d, J=1.5 Hz, 2H), 7.46-7.40 (m, 1H), 7.35-7.29 (m, 1H), 7.25-7.20 (m, 1H), 5.26-5.22 (m, 1H), 4.83 (d, J=5.8 Hz, 2H), 4.06-3.97 (m, 4H), 3.97-3.88 (m, 1H), 3.67-3.56 (m, 1H), 2.79-2.74 (m, 2H), 2.59-2.48 (m, 2H), 1.92-1.50 (m, 7H).

Reference Example 62-1

1-{5-[2-Fluoro-3-(hydroxymethyl)phenyl]pyrimidin-2-yl}piperidin-4-one O-ethyl oxime (Reference Compound 62-1)

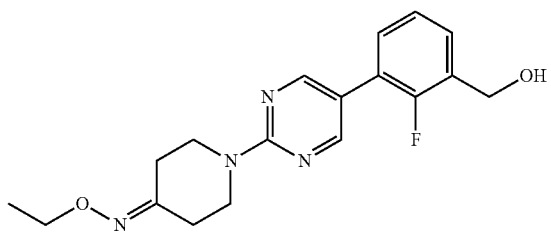 [SMILES: CCON=C1CCN(c2ncc(-c3cccc(CO)c3F)cn2)CC1]

Sodium carbonate 220 mg (2.08 mmol) and O-ethylhydroxylamine hydrochloride 192 mg (1.97 mmol) were added to an ethanol (8 mL)-THF (6 mL)-water (1 mL) solution of 1-[5-(3-{[(tert-butyldimethylsilyl)oxy]methyl}-2-fluorophenyl)pyrimidin-2-yl]piperidin-4-one 410 mg (0.987 mmol) synthesized in the same manner as in Reference Example 6-41, and the mixture was stirred at 50° C. for 1 hour. After the completion of the reaction, water was added to the reaction mixture, and followed by extraction with ethyl acetate. The organic layer was washed with water and brine, dried over anhydrous sodium sulfate, and filtered. The filtrate was concentrated under reduced pressure. The concentrated residue was purified by silica gel column chromatography (eluting solvent: 1,2-dichloroethane:ethyl acetate) to give the title compound 272 mg (0.790 mmol, yield 80%) as a white solid.

Mass spectrum (CI, m/z):345[M+1].

$^1$H-NMR spectrum (400 MHz, DMSO-d$_6$) δ:8.59 (d, J=1.4 Hz, 2H), 7.50-7.40 (m, 2H), 7.32-7.23 (m, 1H), 5.33 (t, J=5.2 Hz, 1H), 4.60 (d, J 5.2 Hz, 2H), 4.02 (q, J=7.0 Hz, 2H), 3.95-3.88 (m, 4H), 2.60-2.54 (m, 2H), 2.41-2.35 (m, 2H), 1.19 (t, J=7.0 Hz, 3H).

Reference Example 62-2

1-{5-[2-Fluoro-3-(hydroxymethyl)phenyl]pyrimidin-2-yl}piperidin-4-one O-isopropyl oxime (Reference Compound 62-2)

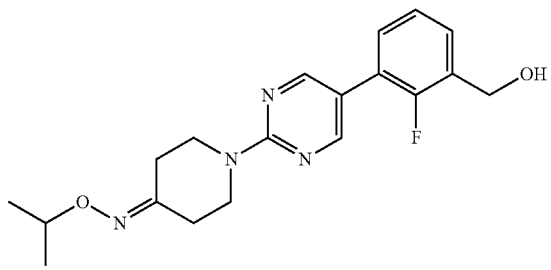 [SMILES: CC(C)ON=C1CCN(c2ncc(-c3cccc(CO)c3F)cn2)CC1]

The reaction was performed by the method described in Reference Example 62-1, except that O-ethylhydroxylamine hydrochloride was replaced by 2-(aminooxy)propane hydrochloride. Consequently, the title compound (yield 92%) was obtained as a white solid.

$^1$H-NMR spectrum (400 MHz, CDCl$_3$) δ:8.53 (d, J=1.5 Hz, 2H), 7.47-7.38 (m, 1H), 7.35-7.29 (m, 1H), 7.26-7.20 (m, 1H), 4.83 (d, J=6.1 Hz, 2H), 4.31 (sep, J=6.3 Hz, 1H), 4.03-3.97 (m, 4H), 2.72-2.66 (m, 2H), 2.50-2.45 (m, 2H), 1.85-1.81 (m, 1H), 1.25 (d, J=6.3 Hz, 6H).

Reference Example 62-3

1-{5-[2-Fluoro-3-(hydroxymethyl)phenyl]pyrimidin-2-yl}piperidin-4-one O-propyl oxime (Reference Compound 62-3)

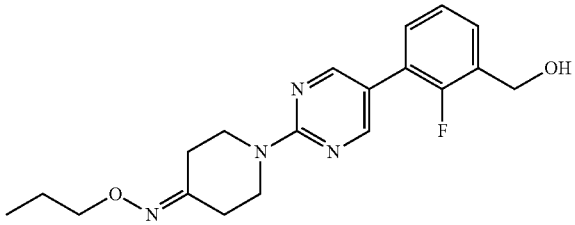 [SMILES: CCCON=C1CCN(c2ncc(-c3cccc(CO)c3F)cn2)CC1]

The reaction was performed by the method described in Reference Example 62-1, except that O-ethylhydroxylamine hydrochloride was replaced by O-propylhydroxylamine hydrochloride, and the reaction temperature was ambient. Consequently, the title compound (yield 87%) was obtained as a white solid.

$^1$H-NMR spectrum (400 MHz, DMSO-d$_6$) δ:8.59 (d, J=1.4 Hz, 2H), 7.49-7.42 (m, 2H), 7.30-7.25 (m, 1H), 5.33 (t, J=5.5 Hz, 1H), 4.60 (d, J=5.5 Hz, 2H), 3.96-3.88 (m, 6H), 2.61-2.55 (m, 2H), 2.43-2.33 (m, 2H), 1.60 (sext, J=7.3 Hz, 2H), 0.89 (t, J=7.3 Hz, 3H).

Reference Example 63

1-{5-[2-Fluoro-3-(hydroxymethyl)phenyl]pyrimidin-2-yl}piperidin-4-one O-allyl oxime (Reference Compound 63)

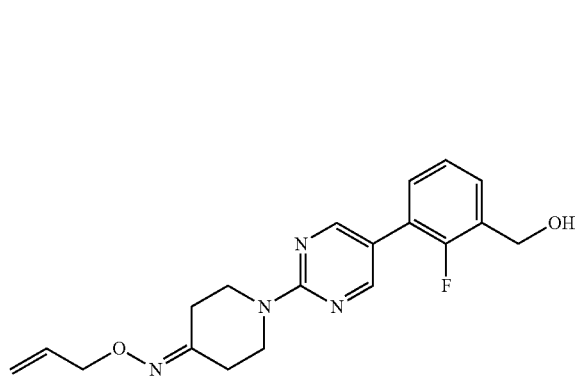 [SMILES: C=CCON=C1CCN(c2ncc(-c3cccc(CO)c3F)cn2)CC1]

O-allylhydroxylamine hydrochloride 67.2 mg (0.613 mmol) and sodium carbonate 62.4 mg (0.589 mmol) were added to a THF (1.7 mL)-ethanol (2.2 mL)-water (0.3 mL) solution of 1-[5-(3-{[(tert-butyldimethylsilyl)oxy]methyl}-2-fluorophenyl)pyrimidin-2-yl]piperidin-4-one 124 mg (0.298 mmol) synthesized in the same manner as in Reference Example 6-41, and the mixture was stirred at room temperature for 13.5 hours. The reaction mixture was filtered and washed with ethyl acetate. Thereafter, the filtrate was concentrated under reduced pressure. Ethanol 2 mL and acetic acid 0.4 mL were added to the concentrated residue, and the mixture was stirred at room temperature for 1.5 hours. Next, acetic acid 1 mL was added, and the mixture was stirred at room temperature for 1 hour. The reaction mixture was concentrated under reduced pressure. Ethanol 3 mL and 2 M hydrogen chloride/ethanol solution 0.15 mL (0.30 mmol) were added to the concentrated residue, and the mixture was stirred at room temperature for 4.5 hours. After the completion of the reaction, sodium carbonate 33.6 mg (0.317 mmol) and water (0.2 mL) were added to the reaction mixture, and the mixture was stirred at room temperature for 1 hour. The reaction mixture was filtered and washed with ethyl acetate, and the filtrate was concentrated under reduced pressure. The concentrated residue was purified by silica gel column chromatography (eluting solvent: hexane:ethyl acetate) to give the title compound 95.7 mg (0.269 mmol, yield 90%) as a white solid.

$^1$H-NMR spectrum (400 MHz, DMSO-$d_6$) δ:8.59 (d, J=1.5 Hz, 2H), 7.49-7.42 (m, 2H), 7.30-7.25 (m, 1H), 6.02-5.92 (m, 1H), 5.33 (t, J=5.6 Hz, 1H), 5.31-5.25 (m, 1H), 5.20-5.16 (m, 1H), 4.60 (d, J=5.6 Hz, 2H), 4.53-4.48 (m, 2H), 3.96-3.89 (m, 4H), 2.63-2.57 (m, 2H), 2.41-2.34 (m, 2H).

Reference Example 64

1-[5-(3-{[(tert-Butyldimethylsilyl)oxy]methyl}-2-fluorophenyl)pyrimidin-2-yl]piperidin-4-one oxime (Reference Compound 64)

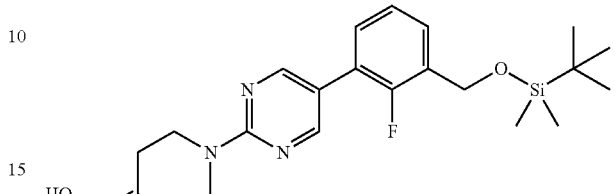

TEA 0.28 mL (2.0 mmol) was added to a THF (4 mL) suspension of hydroxylamine hydrochloride 92 mg (1.2 mmol), and the mixture was stirred at room temperature for 5 minutes. Next, there was added a THF (4 mL) solution of 1-[5-(3-{[(tert-butyldimethylsilyl)oxy]methyl}-2-fluorophenyl)pyrimidin-2-yl]piperidin-4-one 0.28 g (0.67 mmol) synthesized in the same manner as in Reference Example 6-41, and the mixture was stirred at room temperature for 1 hour and at 50° C. for 3 hours. After the completion of the reaction, water was added to the reaction mixture, and followed by extraction with ethyl acetate. The organic layer was washed with water, dried over anhydrous sodium sulfate, and filtered. The filtrate was concentrated under reduced pressure. The concentrated residue was dried under reduced pressure to give the title compound 0.26 g (0.60 mmol, yield 90%) as a white solid.

Mass spectrum (CI, m/z):431[M+1]$^+$.

$^1$H-NMR spectrum (400 MHz, DMSO) δ:10.47 (s, 1H), 8.59 (d, J=1.5 Hz, 2H), 7.54-7.40 (m, 2H), 7.35-7.27 (m, 1H), 4.81 (s, 2H), 3.95-3.86 (m, 4H), 2.60-2.53 (m, 2H), 2.39-2.33 (m, 2H), 0.91 (s, 9H), 0.11 (s, 6H).

Reference Example 65

1-{5-[2-Fluoro-3-(hydroxymethyl)phenyl]pyrimidin-2-yl}piperidin-4-one O-{2-[(tetrahydropyran-2-yl)oxy]ethyl} oxime (Reference Compound 65)

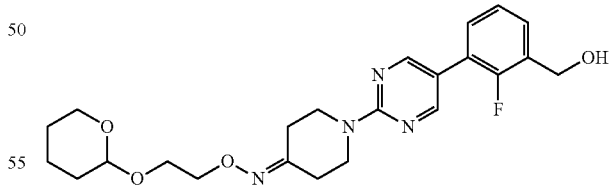

Cesium carbonate 168 mg (0.516 mmol) and 2-(2-bromoethoxy)tetrahydropyran 55 μl (0.36 mmol) were added to a DMF (2 mL) solution of 1-[5-(3-{[(tert-butyldimethylsilyl)oxy]methyl}-2-fluorophenyl)pyrimidin-2-yl]piperidin-4-one oxime 101 mg (0.235 mmol) synthesized in the same manner as in Reference Example 64, and the mixture was stirred at room temperature for 1 hour. Next, DMF 2 mL was added, and the mixture was stirred at room temperature for 2.5 hours. Next, methanol 1 mL was added, and the mixture was stirred at room temperature for 1.5 hours and at 85° C.

for 3 hours. After the completion of the reaction, the reaction mixture was purified by silica gel column chromatography (eluting solvent: hexane:ethyl acetate) and then purified by silica gel column chromatography (DIOL silica gel, eluting solvent: ethyl acetate:methanol=72:28 to 38:62 (V/V)) to give the title compound 39.4 mg (0.089 mmol, yield 38%) as a colorless oil.

Mass spectrum (ESI, m/z):445[M+1]$^+$.

$^1$H-NMR spectrum (400 MHz, DMSO-d$_6$) δ:8.59 (d, J=1.4 Hz, 2H), 7.51-7.33 (m, 2H), 7.32-7.14 (m, 1H), 5.33 (t, J=5.6 Hz, 1H), 4.62-4.56 (m, 3H), 4.16-4.08 (m, 2H), 3.95-3.85 (m, 4H), 3.84-3.69 (m, 2H), 3.64-3.55 (m, 1H), 3.46-3.37 (m, 1H), 2.63-2.56 (m, 2H), 2.41-2.36 (m, 2H), 1.78-1.36 (m, 6H).

Reference Example 66

1-(5-Bromopyrimidin-2-yl)piperidin-4-one oxime (Reference Compound 66)

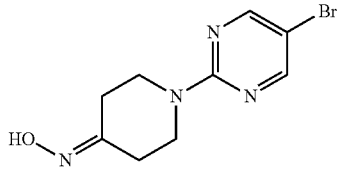 [SMILES: ON=C1CCN(c2ncc(Br)cn2)CC1]

Sodium carbonate 3.4 g (3.2 mmol) and hydroxylamine hydrochloride 1.7 g (25 mmol) were added to a THF (30 mL)-ethanol (30 mL)-water (10 mL) suspension of 1-(5-bromopyrimidin-2-yl)piperidin-4-one 4.0 g (16 mmol) synthesized in the same manner as in Reference Example 59, and the mixture was stirred at 50° C. for 1 hour. After the completion of the reaction, the precipitated solid was collected from the reaction mixture by filtration. Water was added to the filtrate, and followed by extraction with ethyl acetate. The organic layer was washed with water, dried over anhydrous magnesium sulfate, and filtered. The solid previously collected was added to the filtrate, and the mixture was concentrated under reduced pressure to give the title compound 2.5 g (9.8 mmol, yield 61%) as a white solid.

Mass spectrum (CI, m/z):271, 273[M+1]$^+$.

$^1$H-NMR spectrum (400 MHz, DMSO-d$_6$) δ:10.40 (br s, 1H), 8.48 (s, 2H), 3.84-3.78 (m, 4H), 2.55-2.50 (m, 2H), 2.36-2.29 (m, 2H).

Reference Example 67-1

1-(5-Bromopyrimidin-2-yl)piperidin-4-one O-{3-[(tetrahydropyran-2-yl)oxy]propyl}oxime (Reference Compound 67-1)

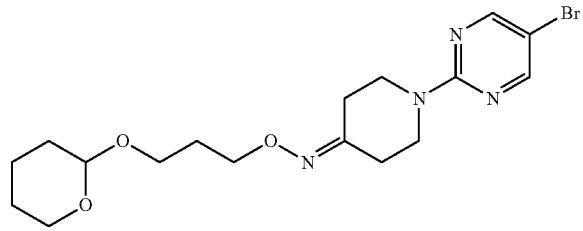 [SMILES: Brc1cnc(N2CCC(=NOCCCOC3CCCCO3)CC2)nc1]

Cesium carbonate 288 mg (0.884 mmol) and 2-(3-bromopropoxy)tetrahydropyran 0 120 mL (0.708 mmol) were added to a DMF (4 mL) solution of 1-(5-bromopyrimidin-2-yl)piperidin-4-one oxime 120 mg (0.443 mmol) synthesized in the same manner as in Reference Example 66, and the mixture was stirred at 80° C. for 9 hours. After the completion of the reaction, water was added to the reaction mixture, and followed by extraction with ethyl acetate. The organic layer was washed with water, dried over anhydrous sodium sulfate, and filtered. The filtrate was concentrated under reduced pressure. The concentrated residue was purified by silica gel column chromatography (eluting solvent: hexane:ethyl acetate) to give the title compound 143 mg (0.346 mmol, yield 78%) as a colorless oil.

Mass spectrum (CI, m/z):413, 415[M+1]$^+$.

$^1$H-NMR spectrum (400 MHz, DMSO-d$_6$) δ:8.48 (s, 2H), 4.59-4.49 (m, 1H), 4.08-3.98 (m, 2H), 3.88-3.60 (m, 6H), 3.48-3.36 (m, 2H), 2.58-2.50 (m, 2H), 2.38-2.30 (m, 2H), 1.93-1.77 (m, 2H), 1.75-1.32 (m, 6H).

Reference Example 67-2

1-(5-Bromopyrimidin-2-yl)piperidin-4-one O-{4-[(tetrahydropyran-2-yl)oxy]butyl}oxime (Reference Compound 67-2)

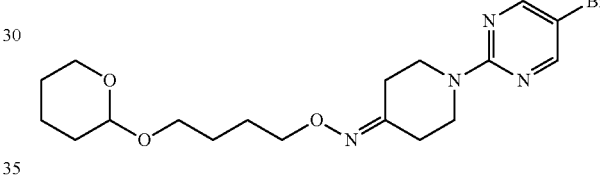

The reaction was performed by the method described in Reference Example 67-1, except that 2-(3-bromopropoxy)tetrahydropyran was replaced by 2-(4-bromobutoxy)tetrahydropyran. Consequently, the title compound (yield 95%) was obtained as a colorless oil.

Mass spectrum (CI, m/z):427, 429[M+1]$^+$.

$^1$H-NMR spectrum (400 MHz, DMSO-d$_6$) δ:8.48 (s, 2H), 4.65-4.41 (m, 1H), 4.02-3.92 (m, 2H), 3.88-3.79 (m, 4H), 3.76-3.57 (m, 2H), 3.49-3.34 (m, 2H), 2.56-2.50 (m, 2H), 2.39-2.31 (m, 2H), 1.85-1.31 (m, 10H).

Reference Example 67-3

1-(5-Bromopyrimidin-2-yl)piperidin-4-one O-(2-methoxyethyl) oxime (Reference Compound 67-3)

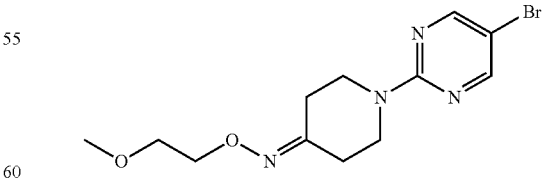

The reaction was performed by the method described in Reference Example 67-1, except that 2-(3-bromopropoxy)tetrahydropyran was replaced by 2-bromoethyl methyl ether, and the reaction temperature was changed to 85° C. Consequently, the title compound (yield 77%) was obtained as a white solid.

Mass spectrum (CI, m/z):329, 331[M+1]$^+$.

$^1$H-NMR spectrum (400 MHz, DMSO-d$_6$) δ:8.48 (s, 2H), 4.10-4.04 (m, 2H), 3.85-3.79 (m, 4H), 3.56-3.50 (m, 2H), 3.25 (s, 3H), 2.56-2.52 (m, 2H), 2.38-2.32 (m, 2H).

Reference Example 67-4

1-(5-Bromopyrimidin-2-yl)piperidin-4-one O-{2,2-dimethyl-3-[(tetrahydropyran-2-yl)oxy]propyl} oxime (Reference Compound 67-4)

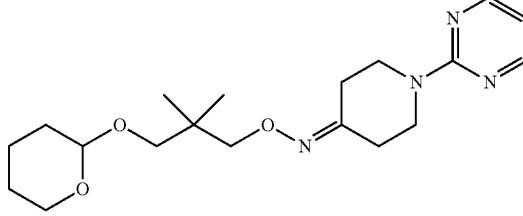

The reaction was performed by the method described in Reference Example 67-1, except that 2-(3-bromo-propoxy)tetrahydropyran was replaced by 2-(3-bromo-2,2-dimethyl-propoxy)tetrahydropyran synthesized in the same manner as in Reference Example 68-1. Consequently, the title compound (yield 49%) was obtained as a colorless oil.

Mass spectrum (CI, m/z):441, 443[M+1]$^+$.

$^1$H-NMR spectrum (400 MHz, CDCl$_3$) δ:8.30 (s, 2H), 4.59-4.55 (m, 1H), 3.94-3.80 (m, 7H), 3.55 (d, J=9.3 Hz, 1H), 3.51-3.45 (m, 1H), 3.11 (d, J=9.3 Hz, 1H), 2.68-2.63 (m, 2H), 2.45-2.39 (m, 2H), 1.89-1.46 (m, 6H), 0.97 (s, 3H), 0.96 (s, 3H).

Reference Example 67-5

1-(5-Bromopyrimidin-2-yl)piperidin-4-one O-(3-hydroxy-3-methylbutyl) oxime (Reference Compound 67-5)

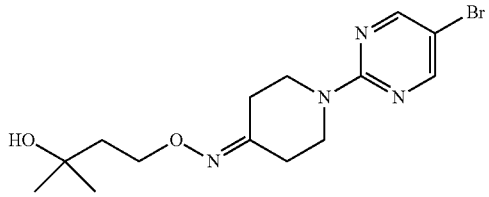 [SMILES: CC(C)(O)CCON=C1CCN(c2ncc(Br)cn2)CC1]

The reaction was performed by the method described in Reference Example 67-1, except that 2-(3-bromopropoxy)tetrahydropyran was replaced by 3-hydroxy-3-methylbutyl methanesulfonate synthesized in the same manner as in Reference Example 14-7. Consequently, the title compound (yield 88%) was obtained as a white solid.

Mass spectrum (CI, m/z):357, 359[M+1]$^+$.

$^1$H-NMR spectrum (400 MHz, CDCl$_3$) δ:8.31 (s, 2H), 4.26 (t, J=6.3 Hz, 2H), 3.94-3.86 (m, 4H), 2.64-2.58 (m, 2H), 2.46-2.40 (m, 2H), 2.24 (s, 1H), 1.89 (t, J=6.3 Hz, 2H), 1.28 (s, 6H).

Reference Example 67-6

1-(5-Bromopyrimidin-2-yl)piperidin-4-one O-{2-methyl-3-[(tetrahydropyran-2-yl)oxy]propyl} oxime (Reference Compound 67-6)

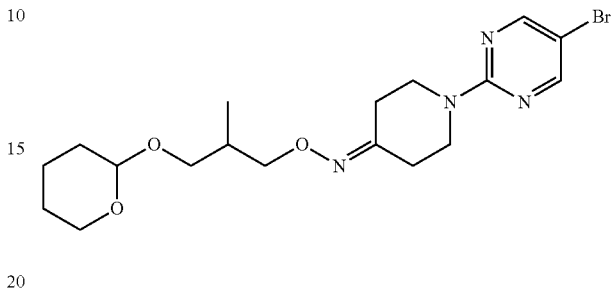

The reaction was performed by the method described in Reference Example 67-1, except that 2-(3-bromo-propoxy)tetrahydropyran was replaced by 2-(3-bromo-2-methyl-propoxy)tetrahydropyran synthesized in the same manner as in Reference Example 68-2, and the reaction temperature was changed to 90° C. Consequently, the title compound (quantitative yield) was obtained as a colorless oil.

Mass spectrum (CI, m/z):427, 429[M+1]$^+$.

$^1$H-NMR spectrum (400 MHz, CDCl$_3$) δ:8.31 (s, 2H), 4.62-4.54 (m, 1H), 4.23-3.23 (m, 10H), 2.68-2.61 (m, 2H), 2.45-2.39 (m, 2H), 2.21-2.09 (m, 1H), 1.90-1.44 (m, 6H), 1.04-0.93 (m, 3H).

Reference Example 67-7

1-(5-Bromopyrimidin-2-yl)piperidin-4-one O-[(2,2-dimethyl-1,3-dioxan-5-yl)methyl]oxime (Reference Compound 67-7)

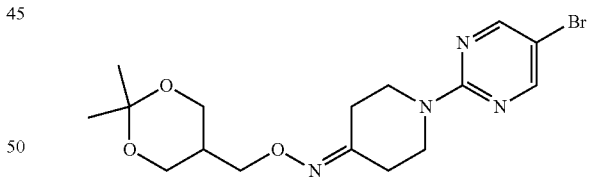

The reaction was performed by the method described in Reference Example 67-1, except that 2-(3-bromopropoxy)tetrahydropyran was replaced by (2,2-dimethyl-1,3-dioxan-5-yl)methyl methanesulfonate synthesized in the same manner as in Reference Example 14-4. Consequently, the title compound (yield 87%) was obtained as a white solid.

Mass spectrum (CI, m/z):399, 401[M+1]$^+$.

$^1$H-NMR spectrum (400 MHz, CDCl$_3$) δ:8.31 (s, 2H), 4.11 (d, J=6.9 Hz, 2H), 3.99 (dd, J=4.3, 12.0 Hz, 2H), 3.92-3.86 (m, 4H), 3.75 (dd, J=6.5, 12.0 Hz, 2H), 2.66-2.59 (m, 2H), 2.44-2.38 (m, 2H), 2.18-2.09 (m, 1H), 1.44 (s, 3H), 1.42 (s, 3H).

Reference Example 67-8

1-(5-Bromopyrimidin-2-yl)piperidin-4-one O-[(2,2,5-trimethyl-1,3-dioxan-5-yl)methyl]oxime (Reference Compound 67-8)

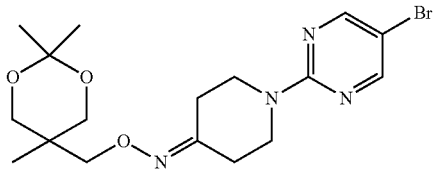 [SMILES: CC1(CON=C2CCN(c3ncc(Br)cn3)CC2)COC(C)(C)OC1]

The reaction was performed by the method described in Reference Example 67-1, except that 2-(3-bromo-propoxy)tetrahydropyran was replaced by (2,2,5-trimethyl-1,3-dioxan-5-yl)methyl methanesulfonate synthesized in the same manner as in Reference Example 14-8. Consequently, the title compound (including impurities) was obtained as a white solid.

Reference Example 67-9

1-(5-Bromopyrimidin-2-yl)piperidin-4-one O-[(2,2-dimethyl-1,3-dioxolan-4-yl)methyl]oxime (Reference Compound 67-9)

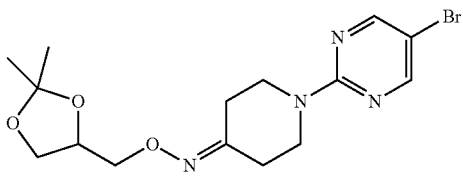 [SMILES: CC1(C)OCC(CON=C2CCN(c3ncc(Br)cn3)CC2)O1]

The reaction was performed by the method described in Reference Example 67-1, except that 2-(3-bromopropoxy)tetrahydropyran was replaced by (2,2-dimethyl-1,3-dioxolan-4-yl)methyl methanesulfonate synthesized in the same manner as in Reference Example 14-5. Consequently, the title compound (yield 71%) was obtained as a colorless oil.

$^1$H-NMR spectrum (400 MHz, DMSO-$d_6$) 5:8.48 (s, 2H), 4.20-4.33 (m, 1H), 3.93-4.06 (m, 3H), 3.77-3.89 (m, 4H), 3.59-3.71 (m, 1H), 2.52-2.59 (m, 2H), 2.31-2.39 (m, 2H), 1.32 (s, 3H), 1.27 (s, 3H).

Reference Example 67-10

1-(5-Bromopyrimidin-2-yl)piperidin-4-one O-{2-[(tetrahydropyran-2-yl)oxy]ethyl}oxime (Reference Compound 67-10)

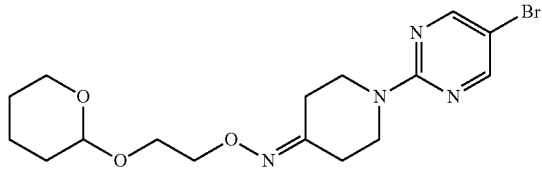 [SMILES: Brc1cnc(N2CCC(=NOCCOC3CCCCO3)CC2)nc1]

The reaction was performed by the method described in Reference Example 67-1, except that 2-(3-bromopropoxy)tetrahydropyran was replaced by 2-(2-bromoethoxy)tetrahydropyran. Consequently, the title compound (yield 79%) was obtained as a light yellow oil.

Mass spectrum (CI, m/z):399, 401[M+1]$^+$.

$^1$H-NMR spectrum (400 MHz, DMSO-$d_6$) δ:8.48 (s, 2H), 4.61-4.54 (m, 1H), 4.15-4.06 (m, 2H), 3.88-3.68 (m, 6H), 3.63-3.53 (m, 1H), 3.45-3.37 (m, 1H), 2.59-2.52 (m, 2H), 2.39-2.32 (m; 2H), 1.79-1.31 (m, 6H).

Reference Example 67-11

Ethyl 4-({[1-(5-bromopyrimidin-2-yl)piperidin-4-ylidene]amino}oxy)butanoate (Reference Compound 67-11)

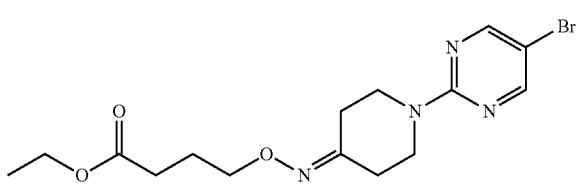 [SMILES: CCOC(=O)CCCON=C1CCN(c2ncc(Br)cn2)CC1]

The reaction was performed by the method described in Reference Example 67-1, except that 2-(3-bromopropoxy)tetrahydropyran was replaced by ethyl 4-bromobutyrate. Consequently, the title compound (yield 80%) was obtained as a white solid.

Mass spectrum (CI, m/z):385, 387[M+1]$^+$.

$^1$H-NMR spectrum (400 MHz, DMSO-$d_6$) δ:8.48 (s, 2H), 4.04 (q, J=7.2 Hz, 2H), 3.97 (t, J=6.4 Hz, 2H), 3.85-3.78 (m, 4H), 2.55-2.51 (m, 2H), 2.38-2.32 (m, 4H), 1.89-1.79 (m, 2H), 1.17 (t, J=7.2 Hz, 3H).

Reference Example 67-12

4-({[1-(5-Bromopyrimidin-2-yl)piperidin-4-ylidene]amino}oxy)butanenitrile (Reference Compound 67-12)

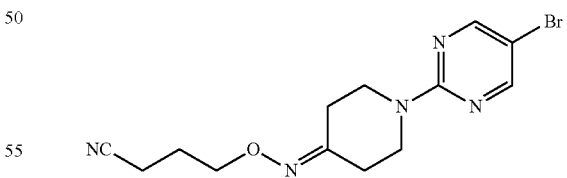

The reaction was performed by the method described in Reference Example 67-1, except that 2-(3-bromopropoxy)tetrahydropyran was replaced by 4-bromobutyronitrile. Consequently, the title compound (yield 85%) was obtained as a white solid.

Mass spectrum (CI, m/z):338, 340[M+1]$^+$.

$^1$H-NMR spectrum (400 MHz, DMSO-$d_6$) δ:8.49 (s, 2H), 4.03 (t, J=6.1 Hz, 2H), 3.87-3.79 (m, 4H), 2.61-2.52 (m, 4H), 2.39-2.32 (m, 2H), 1.94-1.83 (m, 2H).

Reference Example 67-13

1-(5-Bromopyrimidin-2-yl)piperidin-4-one O-[3-(methylsulfonyl)propyl] oxime (Reference Compound 67-13)

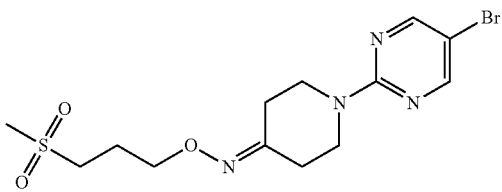 [SMILES: CS(=O)(=O)CCCON=C1CCN(c2ncc(Br)cn2)CC1]

The reaction was performed by the method described in Reference Example 67-1, except that 2-(3-bromopropoxy)tetrahydropyran was replaced by 3-(methylsulfonyl)propyl methanesulfonate synthesized in the same manner as in Reference Example 14-11, and the reaction temperature was changed to 100° C. Consequently, the title compound (including impurities) was obtained as a white solid.

Mass spectrum (CI, m/z):391, 393[M+1]$^+$.

$^1$H-NMR spectrum (400 MHz, CDCl$_3$) δ:8.31 (s, 2H), 4.16 (t, J=6.0 Hz, 2H), 3.97-3.84 (m, 4H), 3.17-3.10 (m, 2H), 2.93 (s, 3H), 2.66-2.57 (m, 2H), 2.44-2.38 (m, 2H), 2.29-2.17 (m, 2H).

Reference Example 67-14

1-(5-Bromopyrimidin-2-yl)piperidin-4-one O-[(1-methyl-1H-pyrazol-3-yl)methyl]oxime (Reference Compound 67-14)

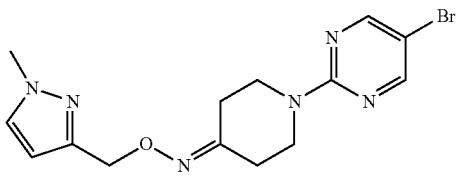 [SMILES: Cn1ccc(CON=C2CCN(c3ncc(Br)cn3)CC2)n1]

The reaction was performed by the method described in Reference Example 67-1, except that 2-(3-bromopropoxy)tetrahydropyran was replaced by (1-methyl-1H-pyrazol-3-yl)methyl methanesulfonate synthesized in the same manner as in Reference Example 14-12, and the reaction temperature was changed to 50° C. Consequently, the title compound (yield 57%) was obtained as a white solid.

Mass spectrum (CI, m/z):365, 367[M+1]$^+$.

$^1$H-NMR spectrum (400 MHz, CDCl$_3$) δ:8.30 (s, 2H), 7.31 (d, J=2.2 Hz, 1H), 6.29 (d, J=2.2 Hz, 1H), 5.08 (s, 2H), 3.92-3.84 (m, 7H), 2.69-2.63 (m, 2H), 2.46-2.41 (m, 2H).

Reference Example 67-15)

1-(5-Bromopyrimidin-2-yl)piperidin-4-one O-{[1-(tetrahydropyran-2-yl)-1H-pyrazol-3-yl]methyl} oxime (Reference Compound 67-15)

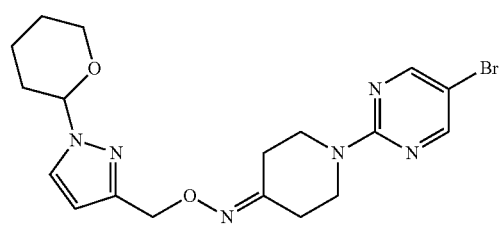 [SMILES: Brc1cnc(N2CCC(=NOCc3ccn(C4CCCCO4)n3)CC2)nc1]

The reaction was performed by the method described in Reference Example 67-1, except that 2-(3-bromopropoxy)tetrahydropyran was replaced by 3-(chloromethyl)-1-(tetrahydropyran-2-yl)-1H-pyrazole synthesized in the same manner as in Reference Example 14-13. Consequently, the title compound (yield 62%) was obtained as a white solid.

Mass spectrum (CI, m/z):435, 437[M+1]$^+$.

$^1$H-NMR spectrum (400 MHz, CDCl$_3$) δ:8.30 (s, 2H), 7.56 (d, J=2.5 Hz, 1H), 6.35 (d, J=2.5 Hz, 1H), 5.36 (dd, J=2.8, 9.7 Hz, 1H), 5.11 (s, 2H), 4.13-4.04 (m, 1H), 3.92-3.83 (m, 4H), 3.77-3.63 (m, 1H), 2.68-2.62 (m, 2H), 2.46-2.40 (m, 2H), 2.17-2.00 (m, 3H), 1.75-1.47 (m, 3H).

Reference Example 67-16

1-(5-Bromopyrimidin-2-yl)piperidin-4-one O-{[1-(tetrahydropyran-2-yl)-1H-pyrazol-4-yl]methyl} oxime (Reference Compound 67-16)

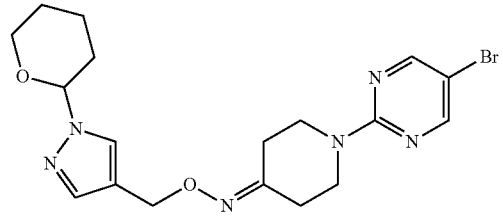 [SMILES: Brc1cnc(N2CCC(=NOCc3cnn(C4CCCCO4)c3)CC2)nc1]

The reaction was performed by the method described in Reference Example 67-1, except that 2-(3-bromopropoxy)tetrahydropyran was replaced by [2-(tetrahydropyran-2-yl)-1H-pyrazol-4-yl]methyl methanesulfonate synthesized in the same manner as in Reference Example 14-14, and the reaction temperature was ambient. Consequently, the title compound (yield 24%) was obtained as a light yellow solid.

Mass spectrum (CI, m/z):435, 437[M+1]$^+$.

$^1$H-NMR spectrum (400 MHz, DMSO-d$_6$) δ:8.48 (s, 2H), 7.89 (s, 1H), 7.49 (s, 1H), 5.36 (dd, J=2.3, 10.1 Hz, 1H), 4.88 (s, 2H), 3.95-3.87 (m, 1H), 3.85-3.76 (m, 4H), 3.66-3.56 (m, 1H), 2.54-2.48 (m, 2H), 2.42-2.32 (m, 2H), 2.14-1.81 (m, 3H), 1.74-1.42 (m, 3H).

Reference Example 68-1

2-(3-Bromo-2,2-dimethylpropoxy)tetrahydropyran
(Reference Compound 68-1)

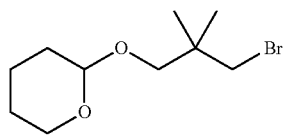

PPTS 0.3 g (1 mmol) and DHP 0.90 mL (10 mmol) were added to a methylene chloride (20 mL) solution of 3-bromo-2,2-dimethyl-1-propanol 1.0 g (6.0 mmol), and the mixture was stirred at room temperature for 16 hours. After the completion of the reaction, a saturated aqueous sodium hydrogen carbonate solution was added to the reaction mixture, and followed by extraction with methylene chloride. The organic layer was washed with brine, dried over anhydrous magnesium sulfate, and filtered. The filtrate was concentrated under reduced pressure. The concentrated residue was purified by silica gel column chromatography (eluting solvent: hexane:ethyl acetate) to give the title compound 1.5 g (6.0 mmol, yield 100%) as a colorless oil.

Mass spectrum (CI, m/z):251, 253[M+1]$^+$.

$^1$H-NMR spectrum (400 MHz, CDCl$_3$) δ:4.62-4.58 (m, 1H), 3.90-3.83 (m, 1H), 3.58 (d, J=9.4 Hz, 1H), 3.55-3.49 (m, 1H), 3.46-3.36 (m, 2H), 3.16 (d, J=9.4 Hz, 1H), 1.88-1.45 (m, 6H), 1.06 (s, 3H), 1.03 (s, 3H).

Reference Example 68-2

2-(3-Bromo-2-methylpropoxy)tetrahydropyran
(Reference Compound 68-2)

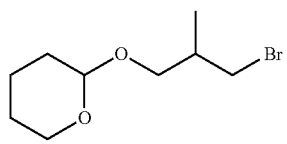

The reaction was performed by the method described in Reference Example 68-1, except that 3-bromo-2,2-dimethyl-1-propanol was replaced by 3-bromo-2-methylpropan-1-ol. Consequently, the title compound (yield 97%) was obtained as a colorless oil.

Mass spectrum (CI, m/z):237, 239[M+1]$^+$.

$^1$H-NMR spectrum (400 MHz, CDCl$_3$) δ:4.63-4.56 (m, 1H), 3.90-3.82 (m, 1H), 3.73-3.63 (m, 1H), 3.57-3.42 (m, 3H), 3.37-3.26 (m, 1H), 2.18-2.06 (m, 1H), 1.88-1.47 (m, 6H), 1.08-1.01 (m, 3H).

Reference Example 69-1

1-(5-Bromopyrimidin-2-yl)piperidin-4-one O-{3-methyl-3-[(tetrahydropyran-2-yl)oxy]butyl} oxime
(Reference Compound 69-1)

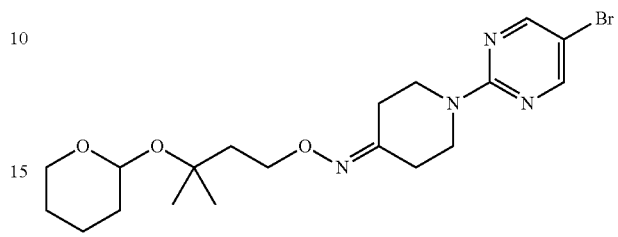

DHP 89 μl (0.98 mmol) and PPTS 25 mg (0.099 mmol) were added to a methylene chloride (5 mL) suspension of 1-(5-bromopyrimidin-2-yl)piperidin-4-one O-(3-hydroxy-3-methylbutyl) oxime 175 mg (0.490 mmol) synthesized in the same manner as in Reference Example 67-5, and the mixture was stirred at room temperature for 14 hours. Next, DHP 89 μl (0.98 mmol) and PPTS 25 mg (0.099 mmol) were added, and the mixture was stirred at room temperature for 3 hours. After the completion of the reaction, water was added to the reaction mixture, and followed by extraction with methylene chloride. The organic layer was washed with brine, dried over anhydrous magnesium sulfate, and filtered. The filtrate was concentrated under reduced pressure. The concentrated residue was purified by silica gel column chromatography (eluting solvent: hexane:ethyl acetate) to give the title compound 227 mg (including impurities) as a colorless oil.

Mass spectrum (CI, m/z):441, 443[M+1]$^+$.

$^1$H-NMR spectrum (400 MHz, CDCl$_3$) δ:8.30 (s, 2H), 4.80-4.75 (m, 1H), 4.23-4.11 (m, 2H), 3.99-3.83 (m, 5H), 3.50-3.37 (m, 1H), 2.66-2.59 (m, 2H), 2.46-2.40 (m, 2H), 1.97-1.78 (m, 3H), 1.75-1.47 (m, 5H), 1.27 (s, 3H), 1.25 (s, 3H).

Reference Example 69-2

1-(5-Bromopyrimidin-2-yl)piperidin-4-one O-{2-[(tetrahydropyran-2-yl)oxy]propyl}oxime (Reference Compound 69-2)

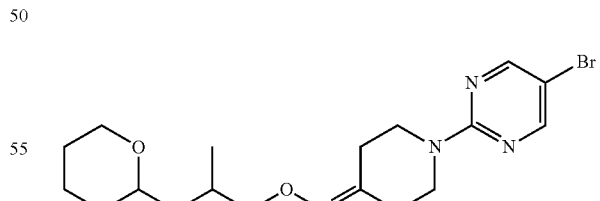

The reaction was performed by the method described in Reference Example 69-1, except that 1-(5-bromopyrimidin-2-yl)piperidin-4-one O-(3-hydroxy-3-methylbutyl) oxime (Reference Compound 67-5) was replaced by 1-(5-bromopyrimidin-2-yl)piperidin-4-one O-(2-hydroxypropyl) oxime synthesized in the same manner as in Reference Example 70. Consequently, the title compound (including impurities) was obtained as a colorless oil.

Mass spectrum (CI, m/z):357, 359[M+1]⁺.
¹H-NMR spectrum (400 MHz, CDCl₃) δ:8.31 (s, 2H), 4.26 (t, J=6.3 Hz, 2H), 3.94-3.86 (m, 4H), 2.64-2.58 (m, 2H), 2.46-2.40 (m, 2H), 2.24 (s, 1H), 1.89 (t, J=6.3 Hz, 2H), 1.28 (s, 6H).

Reference Example 70

1-(5-Bromopyrimidin-2-yl)piperidin-4-one O-(2-hydroxypropyl) oxime (Reference Compound 70)

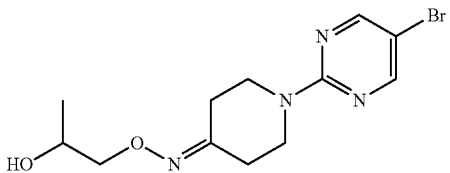 [SMILES: CC(O)CON=C1CCN(c2ncc(Br)cn2)CC1]

55% Sodium hydride 98.0 mg (2.25 mmol) was added to a DMF (3 mL) suspension of 1-(5-bromopyrimidin-2-yl)piperidin-4-one oxime 302 mg (1.11 mmol) synthesized in the same manner as in Reference Example 66, and the mixture was stirred at room temperature for 45 minutes. Next, 1-bromopropan-2-ol 100 μl (1.13 mmol) was added. The mixture was stirred at room temperature for 14 hours, at 50° C. for 10 hours, at 80° C. for 1 hour, and at 100° C. for 9 hours. After the completion of the reaction, water and 1 N hydrochloric acid were added to the reaction mixture to adjust the pH to 7. The reaction mixture was filtered and washed with water. Brine was added to the filtrate, and followed by extraction with ethyl acetate. The organic layer was dried over anhydrous magnesium sulfate, and filtered. The filtrate was concentrated under reduced pressure. The concentrated residue was purified by silica gel column chromatography (eluting solvent: hexane:ethyl acetate) to give the title compound 48.8 mg (0.148 mmol, yield 13%) as a white solid.
¹H-NMR spectrum (400 MHz, DMSO-d₆) δ:8.48 (s, 2H), 4.62 (d, J=4.3 Hz, 1H), 3.88-3.72 (m, 7H), 2.60-2.53 (m, 2H), 2.38-2.31 (m, 2H), 1.04 (d, J=6.1 Hz, 3H).

Reference Example 71

1-[5-(3-{[(tert-Butyldimethylsilyl)oxy]methyl}-2-fluorophenyl)pyrimidin-2-yl]piperidin-4-one 0-{2-[(tetrahydropyran-2-yl)oxy]propyl} oxime (Reference Compound 71)

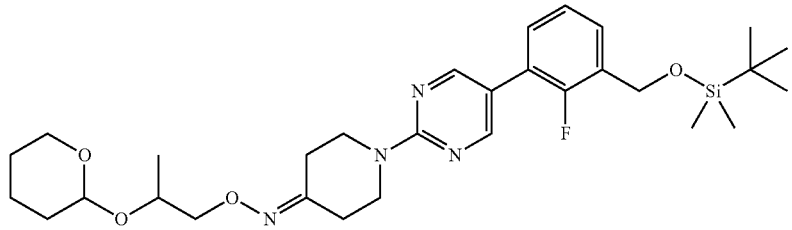 [SMILES: CC(CON=C1CCN(c2ncc(-c3cccc(CO[Si](C)(C)C(C)(C)C)c3F)cn2)CC1)OC1CCCCO1]

1-(5-Bromopyrimidin-2-yl)piperidin-4-one O-{2-[(tetrahydropyran-2-yl)oxy]propyl} oxime 59.1 mg (0.143 mmol) synthesized in the same manner as in Reference Example 69-2, tert-butyl {[2-fluoro-3-(4,4,5,5-tetramethyl-1,3,2-dioxaborolan-2-yl)benzyl]oxy}dimethylsilane 99.4 mg (0.271 mmol) synthesized in the same manner as in Reference Example 5, and tripotassium phosphate 80.3 mg (0.378 mmol) were suspended in water (0.2 mL)-1,4-dioxane (1 mL). The suspension was bubbled with nitrogen gas for 15 minutes. Next, tetrakis(triphenylphosphine)palladium (0) 10.3 mg (0.00891 mmol) was added. The mixture was fed to a microwave reaction device, and was stirred at 120° C. for 1 hour. After the completion of the reaction, water was added to the reaction mixture, and followed by extraction with ethyl acetate. The organic layer was washed with brine, dried over anhydrous magnesium sulfate, and filtered. The filtrate was concentrated under reduced pressure. The concentrated residue was purified by silica gel column chromatography (eluting solvent: hexane:ethyl acetate) to give the title compound 83.7 mg (including impurities) as a light yellow oil.
¹H-NMR spectrum (400 MHz, CDCl₃) 5:8.55-8.51 (m, 2H), 7.51-7.45 (m, 1H), 7.28-7.21 (m, 2H), 4.85 (s, 2H), 4.82-4.73 (m, 1H), 4.23-4.07 (m, 2H), 4.04-3.90 (m, 6H), 3.54-3.44 (m, 1H), 2.75-2.65 (m, 2H), 2.49-2.44 (m, 2H), 1.91-1.44 (m, 6H), 1.26-1.14 (m, 3H), 0.96 (s, 9H), 0.14 (s, 6H).

Reference Example 72

1-(5-Bromopyrimidin-2-yl)piperidin-4-one O-(2-hydroxyethyl) oxime (Reference Compound 72)

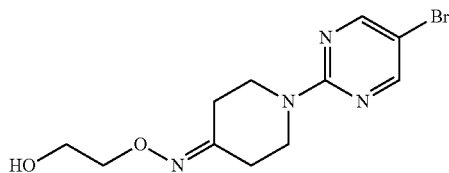 [SMILES: OCCON=C1CCN(c2ncc(Br)cn2)CC1]

2 M hydrogen chloride/ethanol solution 2.0 mL (4.0 mmol) was added to a dioxane (6 mL)-ethanol (6 mL) solution of 1-(5-bromopyrimidin-2-yl)piperidin-4-one O-{2-[(tetrahydropyran-2-yl)oxy]ethyl} oxime 0.45 g (1.1 mmol) synthesized in the same manner as in Reference Example 67-10, and the mixture was stirred at room temperature for 3 hours. After the completion of the reaction, TEA was added to the reaction mixture at 0° C. Next, water was added, and followed by extraction with ethyl acetate. The organic layer was washed with brine, dried over anhydrous magnesium sulfate, and filtered. The filtrate was concentrated under reduced pressure. The concentrated residue was dried under reduced pressure to give the title compound 0.30 g (0.95 mmol, yield 84%) as a white solid.

Mass spectrum (CI, m/z):315, 317[M+1]⁺.

¹H-NMR spectrum (400 MHz, DMSO-d₆) δ:8.50 (s, 2H), 4.62 (t, J=5.6 Hz, 1H), 4.01-3.95 (m, 2H), 3.87-3.76 (m, 4H), 3.62-3.55 (m, 2H), 2.59-2.53 (m, 2H), 2.38-2.31 (m, 2H).

Reference Example 73

5-(3-{[(tert-Butyldimethylsilyl)oxy]methyl}-2-fluorophenyl)-2-chloropyrimidine (Reference Compound 73)

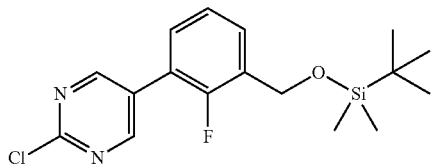 [SMILES: CC(C)(C)[Si](C)(C)OCc1cccc(-c2cnc(Cl)nc2)c1F]

tert-Butyl {[2-fluoro-3-(4,4,5,5-tetramethyl-1,3,2-dioxaborolan-2-yl)benzyl]oxy}dimethylsilane 1.81 g (4.94 mmol) synthesized in the same manner as in Reference Example 5, and 5-bromo-2-chloropyrimidine 1.17 g (6.05 mmol) were suspended in 1,4-dioxane (20 mL)-water (5.0 mL). Tripotassium phosphate n-hydrate 4.02 g (15.1 mmol) was added to the suspension, and the suspension was bubbled with argon gas for 5 minutes. Next, tetrakis(triphenylphosphine)palladium (0) 284 mg (0.246 mmol) was added, and the mixture was stirred at 100° C. for 1.5 hours under a stream of argon. After the completion of the reaction, water was added to the reaction mixture, and followed by extraction with ethyl acetate. The organic layer was washed with brine, dried over anhydrous magnesium sulfate, and filtered. The filtrate was concentrated under reduced pressure. The concentrated residue was purified by silica gel column chromatography (eluting solvent: hexane:ethyl acetate) to give the title compound 1.22 g (3.46 mmol, yield 70%) as a white solid.

Mass spectrum (CI, m/z):417[M+1]⁺.

¹H-NMR spectrum (400 MHz, CDCl₃) δ:8.81 (d, J=1.4 Hz, 2H), 7.66-7.60 (m, 1H), 7.34-7.28 (m, 2H), 4.86 (s, 2H), 0.96 (s, 9H), 0.14 (s, 6H).

Reference Example 74-1

7-[5-(3-{[(tert-Butyldimethylsilyl)oxy]methyl}-2-fluorophenyl)pyrimidin-2-yl]-1,4-dioxa-7-azaspiro[4.4]nonane (Reference Compound 74-1)

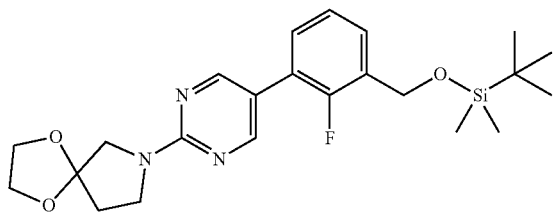 [SMILES: CC(C)(C)[Si](C)(C)OCc1cccc(-c2cnc(N3CCC4(C3)OCCO4)nc2)c1F]

TEA 0.50 mL (3.6 mmol) and 1,4-dioxa-7-azaspiro[4.4]nonane 156 mg (1.21 mmol) were added to an ethanol (5 mL) suspension of 5-(3-{[(tert-butyldimethylsilyl)oxy]methyl}-2-fluorophenyl)-2-chloropyrimidine 369 mg (1.05 mmol) synthesized in the same manner as in Reference Example 73, and the mixture was stirred at 100° C. for 1.75 hours. After the completion of the reaction, the reaction mixture was concentrated under reduced pressure. A saturated aqueous ammonium chloride solution was added thereto, and followed by extraction with ethyl acetate. The organic layer was washed with brine, dried over anhydrous magnesium sulfate, and filtered. The filtrate was concentrated under reduced pressure to give the title compound 472 mg (including impurities) as a light yellow oil.

Mass spectrum (CI, m/z):446[M+1]⁺.

¹H-NMR spectrum (400 MHz, CDCl₃) δ:8.52 (d, J=1.4 Hz, 2H), 7.52-7.41 (m, 1H), 7.26-7.18 (m, 2H), 4.85 (s, 2H), 4.07-3.99 (m, 4H), 3.80 (t, J=7.3 Hz, 2H), 3.71 (s, 2H), 2.24 (t, J=7.3 Hz, 2H), 0.96 (s, 9H), 0.13 (s, 6H).

Reference Example 74-2

1-[5-(3-{[(tert-Butyldimethylsilyl)oxy]methyl}-2-fluorophenyl)pyrimidin-2-yl]piperidin-4-one O-pyrimidin-2-yl oxime (Reference Compound 74-2)

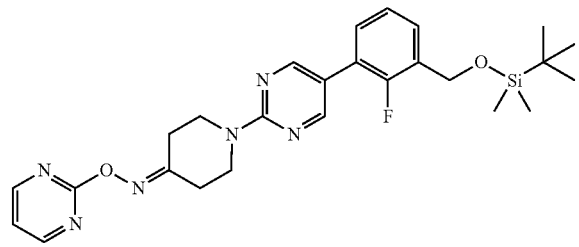 [SMILES: CC(C)(C)[Si](C)(C)OCc1cccc(-c2cnc(N3CCC(=NOc4ncccn4)CC3)nc2)c1F]

TEA 57 μl (0.41 mmol) was added to an ethanol suspension (2 mL) of piperidin-4-one O-pyrimidin-2-yl oxime 19 mg (0.099 mmol) synthesized in the same manner as in Reference Example 123, and 5-(3-{[(tert-butyldimethylsilyl)oxy]methyl}-2-fluorophenyl)-2-chloropyrimidine 30 mg (0.085 mmol). The mixture was stirred at 80° C. for 10 hours. After the completion of the reaction, the reaction mixture was concentrated under reduced pressure. The concentrated residue was purified by silica gel column chromatography (DIOL silica gel, eluting solvent: hexane:ethyl acetate) to give the title compound (including impurities) as a dark brown solid.

Mass spectrum (CI, m/z):509[M+1]⁺.

¹H-NMR spectrum (400 MHz, CDCl₃) δ:8.64 (d, J=4.8 Hz, 2H), 8.55 (d, J=1.4 Hz, 2H), 7.52-7.46 (m, 1H), 7.30-7.20 (m, 2H), 7.08-7.05 (m, 1H), 4.85 (s, 2H), 4.15-4.08 (m, 4H), 3.02-2.98 (m, 2H), 2.76-2.71 (m, 2H), 0.96 (s, 9H), 0.14 (s, 6H).

Reference Example 75

1-{5-[2-Fluoro-3-(hydroxymethyl)phenyl]pyrimidin-2-yl}pyrrolidin-3-one (Reference Compound 75)

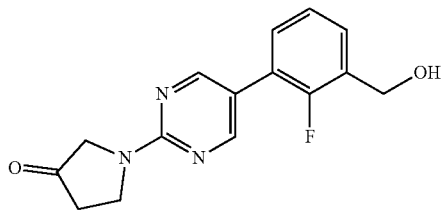 [SMILES: O=C1CCN(c2ncc(-c3cccc(CO)c3F)cn2)C1]

2 N sulfuric acid 0.01 mL (0.02 mmol) was added to a THF (10 mL) solution of 7-[5-(3-{[(tert-butyldimethylsilyl)oxy]methyl}-2-fluorophenyl)pyrimidin-2-yl]-1,4-dioxa-7-azaspiro[4.4]nonane 460 mg (1.03 mmol) synthesized in the same manner as in Reference Example 74-1, and the mixture was stirred at 80° C. for 11 hours. After the completion of the reaction, the precipitated solid was collected by filtration. The filtrate was concentrated under reduced pressure. The concentrated residue was combined with the previously collected solid. Purification by silica gel column chromatography (eluting solvent: hexane:ethyl acetate) gave the title compound 174 mg (0.606 mmol, yield 59%) as a white solid.

Mass spectrum (CI, m/z):288[M+1]$^+$.

$^1$H-NMR spectrum (400 MHz, DMSO-d$_6$) δ:8.63 (d, J=1.3 Hz, 2H), 7.52-7.40 (m, 2H), 7.33-7.24 (m, 1H), 5.33 (t, J=5.6 Hz, 1H), 4.61 (d, J=5.6 Hz, 2H), 3.98-3.92 (m, 4H), 2.77-2.69 (m, 2H).

Reference Example 76

1-{5-[2-Fluoro-3-(hydroxymethyl)phenyl]pyrimidin-2-yl}pyrrolidin-3-one O-methyloxime EZ mixture (Reference Compound 76)

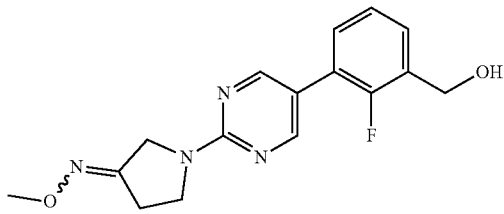 [SMILES: CON=C1CCN(c2ncc(-c3cccc(CO)c3F)cn2)C1]

THF 5 mL, methylene chloride 10 mL and O-methylhydroxylamine hydrochloride 50.2 mg (0.601 mmol) were added to a methanol (3 mL) suspension of 1-{5-[2-fluoro-3-(hydroxymethyl)phenyl]pyrimidin-2-yl}pyrrolidin-3-one 170 mg (0.592 mmol) synthesized in the same manner as in Reference Example 75, and the mixture was stirred at room temperature for 15 minutes. Next, O-methylhydroxylamine hydrochloride 152 mg (1.82 mmol) was added, and the mixture was stirred at room temperature for 1.5 hours. After the completion of the reaction, the reaction solution was concentrated under reduced pressure. A saturated aqueous sodium hydrogen carbonate solution was added, and followed by extraction with a mixed solvent consisting of methylene chloride:methanol=90:10 (V/V). The organic layer was dried over anhydrous sodium sulfate, and filtered. The filtrate was concentrated under reduced pressure. The concentrated residue was purified by silica gel column chromatography (eluting solvent: hexane:ethyl acetate:methanol) to give the title compound 51.1 mg (0.162 mmol, yield 27%) as a light yellow solid.

Mass spectrum (ESI, m/z):317[M+1]$^+$.

$^1$H-NMR spectrum (400 MHz, DMSO-d$_6$) δ:8.63-8.57 (m, 2H), 7.51-7.39 (m, 2H), 7.33-7.25 (m, 1H), 5.33 (br s, 1H), 4.60 (s, 2H), 4.27-4.19 (m, 2H), 3.87-3.76 (m, 5H), 2.92-2.76 (m, 2H).

Reference Example 77)

2-({[1-(5-Bromopyrimidin-2-yl)azetidin-3-ylidene]amino}oxy)-N-methylacetamide (Reference Compound 77)

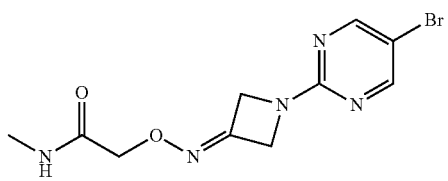 [SMILES: CNC(=O)CON=C1CN(c2ncc(Br)cn2)C1]

CDI 360 mg (2.22 mmol) was added to a DMF (6 mL) solution of 2-({[1-(5-bromopyrimidin-2-yl)azetidin-3-ylidene]amino}oxy)acetic acid 264 mg (0.877 mmol) synthesized in the same manner as in Reference Example 9-3, and the mixture was stirred at room temperature for 3 hours. Next, a 2.0 M methylamine THF solution 4.30 mL (8.60 mmol) was added, and the mixture was stirred at room temperature for 14 hours. After the completion of the reaction, water was added to the reaction mixture, and followed by extraction with methylene chloride. The organic layer was washed with brine, dried over anhydrous sodium sulfate, and filtered. The filtrate was concentrated under reduced pressure. The concentrated residue was purified by silica gel column chromatography (DNH silica gel, eluting solvent: ethyl acetate:methanol) to give the title compound 140 mg (0.446 mmol, yield 51%) as a white solid.

Mass spectrum (CI, m/z):314,316[M+1]$^+$.

$^1$H-NMR spectrum (400 MHz, CDCl$_3$) δ:8.39 (s, 2H), 6.13 (br s, 1H), 4.89-4.81 (m, 4H), 4.56 (s, 2H), 2.90 (d, J=5.0 Hz, 3H).

Reference Example 78-1

3-({[1-(5-Bromopyrimidin-2-yl)azetidin-3-ylidene]amino}oxy)propanamide (Reference Compound 78-1)

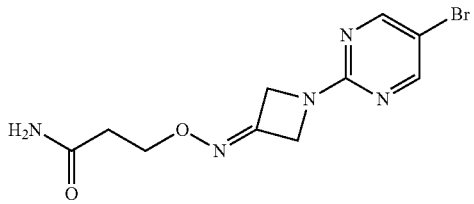 [SMILES: NC(=O)CCON=C1CN(c2ncc(Br)cn2)C1]

CDI 221 mg (1.36 mmol) was added to a DMF (4 ml) suspension of 3-({[1-(5-bromopyrimidin-2-yl)azetidin-3-ylidene]amino}oxy)propanoic acid hydrochloride 201 mg (0.572 mmol) synthesized in the same manner as in Reference Example 9-4, and the mixture was stirred at room temperature for 1 hour. Next, a 0.4 M ammonia/THF solution 8.00 ml (3.20 mmol) was added, and the mixture was stirred at room temperature for 1 hour. After the completion of the reaction, the reaction mixture was concentrated under reduced pressure. Toluene was added to the concentrated residue, which was then concentrated under reduced pressure, and this operation was repeated several times. Ethyl acetate was added to the concentrated residue, and the mixture was stirred at room temperature for 30 minutes. Thereafter, the solid was collected by filtration and was dried under reduced pressure to give a crude product 179 mg including the title compound as a white solid.

$^1$H-NMR spectrum (400 MHz, DMSO-$d_6$) δ:8.55 (s, 2H) 7.39 (s, 1H), 6.85 (s, 1H), 4.80-4.66 (m, 4H), 4.20 (t, J=6.5 Hz, 2H), 2.41 (t, J=6.5 Hz, 2H).

Reference Example 78-2

3-({[1-(5-Bromopyrimidin-2-yl)azetidin-3-ylidene]amino}oxy)-N-methylpropanamide (Reference Compound 78-2)

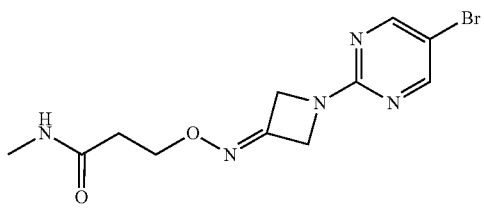 [SMILES: CNC(=O)CCON=C1CN(c2ncc(Br)cn2)C1]

The reaction was performed by the method described in Reference Example 78-1, except that the 0.4 M ammonia/THF solution was replaced by a 2 M methylamine/THF solution. Consequently, the title compound (yield 69%) was obtained as a white solid.

Mass spectrum (CI, m/z):328, 330[M+1]$^+$.

$^1$H-NMR spectrum (400 MHz, DMSO-$d_6$) δ:8.55 (s, 2H), 7.93-7.71 (m, 1H), 4.87-4.55 (m, 4H), 4.20 (t, J=6.5 Hz, 2H), 2.56 (d, J=4.6 Hz, 3H), 2.42 (t, J=6.5 Hz, 2H).

Reference Example 79

4-({[1-(5-Bromopyrimidin-2-yl)azetidin-3-ylidene]amino}oxy)butanoic acid (Reference Compound 79)

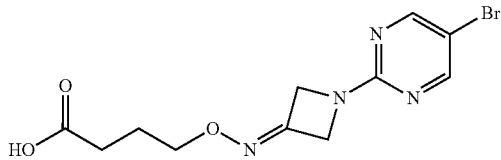 [SMILES: O=C(O)CCCON=C1CN(c2ncc(Br)cn2)C1]

Lithium hydroxide monohydrate 130 mg (3.10 mmol) was added to a methanol (6 mL) suspension of ethyl 4-({[1-(5-bromopyrimidin-2-yl)azetidin-3-ylidene]amino}oxy)butanoate 268 mg (0.750 mmol) synthesized in the same manner as in Reference Example 10-13, and the mixture was stirred at room temperature for 15 hours and was thereafter concentrated under reduced pressure. THF (6 mL) and water (3 mL) were added to the concentrated residue, and the mixture was stirred at room temperature for 3 hours. After the completion of the reaction, THF was distilled away under reduced pressure. 1 N hydrochloric acid was added to the concentrated residue to adjust the pH to 3, and the precipitated solid was collected by filtration. The collected solid was dried under reduced pressure. Further, the filtrate was extracted with ethyl acetate. The organic layer was washed with brine, dried over anhydrous sodium sulfate, and filtered. The filtrate was concentrated under reduced pressure. The precipitated solid was combined with the solid collected by the pervious filtration. Thus, the title compound 214 mg (0.650 mmol, yield 87%) was obtained as a light yellow solid.

Mass spectrum (CI, m/z):329, 331[M+1]$^+$.

$^1$H-NMR spectrum (400 MHz, CDCl$_3$) δ:8.38 (s, 2H), 4.82-4.76 (m, 4H), 4.14 (t, J=6.1 Hz, 2H), 2.47 (t, J=7.3 Hz, 2H), 2.02 (quin, J=6.6 Hz, 2H).

Reference Example 80

4-({[1-(5-Bromopyrimidin-2-yl)azetidin-3-ylidene]amino}oxy)-N-methylbutanamide (Reference Compound 80)

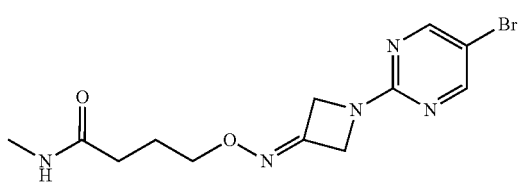 [SMILES: CNC(=O)CCCON=C1CN(c2ncc(Br)cn2)C1]

CDI 270 mg (1.67 mmol) was added to a DMF (6 mL) solution of 4-({[1-(5-bromopyrimidin-2-yl)azetidin-3-ylidene]amino}oxy)butanoic acid 214 mg (0.650 mmol) synthesized in the same manner as in Reference Example 79, and the mixture was stirred at room temperature for 2 hours. Next, a 2.0 M methylamine THF solution 3.25 mL (6.50 mmol) was added, and the mixture was stirred at room temperature for 20 hours. After the completion of the reaction, water was added to the reaction mixture, and followed by extraction with methylene chloride. The organic layer was washed with brine, dried over anhydrous sodium sulfate, and filtered. The filtrate was concentrated under reduced pressure. Ethyl acetate was added to the concentrated residue, and the mixture was ultrasonicated. The solid was collected by filtration and was dried under reduced pressure. The filtrate was concentrated under reduced pressure, and the concentrated residue was purified by silica gel column chromatography (eluting solvent: ethyl acetate: methanol). The concentrated under reduced pressure fraction including the target compound was combined with the solid collected by the previous filtration. Consequently, the title compound 170 mg (0.497 mmol, yield 76%) was obtained as a light yellow solid.

Mass spectrum (CI, m/z):342, 344[M+1]$^+$.

$^1$H-NMR spectrum (400 MHz, CDCl$_3$) δ:8.37 (s, 2H), 5.46 (br s, 1H), 4.82-4.76 (m, 4H), 4.12 (t, J=6.1 Hz, 2H), 2.82 (d, J=4.8 Hz, 3H), 2.26 (t, J=7.3 Hz, 2H), 2.06-1.98 (m, 2H).

Reference Example 81

1-[5-(3-{[(tert-Butyldimethylsilyl)oxy]methyl}-2-fluorophenyl)pyrimidin-2-yl]azetidin-3-one O-(2-hydroxyethyl) oxime (Reference Compound 81)

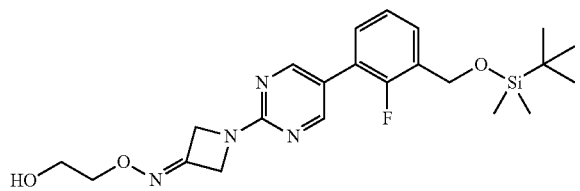 [SMILES: CC(C)(C)[Si](C)(C)OCc1cccc(-c2cnc(N3CC(=NOCCO)C3)nc2)c1F]

Lithium hydroxide 25.5 mg (1.06 mmol) was added to a THF (2 mL)-water (1 mL) solution of 2-[({1-[5-(3-{[(tert-butyldimethylsilyl)oxy]methyl}-2-fluorophenyl)pyrimidin-2-yl]azetidin-3-ylidene}amino)oxy]ethyl acetate 260 mg (0.532 mmol) synthesized in the same manner as in Reference Example 10-11, and the mixture was stirred at 70° C. for 5 hours. After the completion of the reaction, a saturated aqueous ammonium chloride solution was added to the reaction mixture, and followed by extraction with ethyl acetate. The organic layer was washed with brine, dried over anhydrous magnesium sulfate, and filtered. The filtrate was concentrated under reduced pressure. The concentrated residue was purified by silica gel column chromatography (eluting solvent: hexane:ethyl acetate) to give the title compound 170 mg (0.381 mmol, yield 72%) as a white solid.

Mass spectrum (ESI, m/z):447[M+1]$^+$.

Reference Example 82-1

2-[({1-[5-(3-{[(tert-Butyldimethylsilyl)oxy]methyl}-2-fluorophenyl)pyrimidin-2-yl]azetidin-3-ylidene}amino)oxy]ethyl methanesulfonate (Reference Compound 82-1)

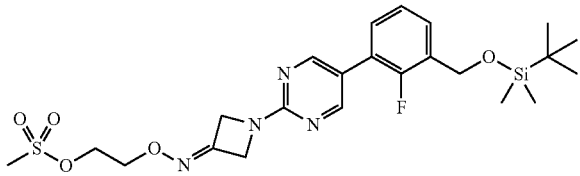 [SMILES: CC(C)(C)[Si](C)(C)OCc1cccc(-c2cnc(N3CC(=NOCCOS(C)(=O)=O)C3)nc2)c1F]

TEA 0.159 ml (1.14 mmol) and methanesulfonyl chloride 0.0591 ml (0.758 mmol) were added to a methylene chloride (3 mL) solution of 1-[5-(3-{[(tert-butyldimethylsilyl)oxy]methyl}-2-fluorophenyl)pyrimidin-2-yl]azetidin-3-one O-(2-hydroxyethyl) oxime 170 mg (0.381 mmol) synthesized in the same manner as in Reference Example 81, and the mixture was stirred at room temperature for 16 hours. After the completion of the reaction, a saturated aqueous ammonium chloride solution was added to the reaction mixture, and followed by extraction with ethyl acetate. The organic layer was washed with brine, dried over anhydrous magnesium sulfate, and filtered. The filtrate was concentrated under reduced pressure to give a crude product 199 mg including the title compound as a yellow oil.

Mass spectrum (ESI, m/z):525[M+1]$^+$.

Reference Example 82-2

2-({[1-(5-Bromopyrimidin-2-yl)azetidin-3-ylidene]amino}oxy)ethyl methanesulfonate (Reference Compound 82-2)

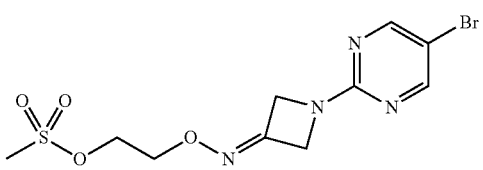 [SMILES: CS(=O)(=O)OCCON=C1CN(c2ncc(Br)cn2)C1]

The reaction was performed by the method described in Reference Example 82-1, except that 1-[5-(3-{[(tert-butyldimethylsilyl)oxy]methyl}-2-fluorophenyl)pyrimidin-2-yl]azetidin-3-one O-(2-hydroxyethyl) oxime (Reference Compound 81) was replaced by 1-(5-bromopyrimidin-2-yl)azetidin-3-one O-(2-hydroxyethyl) oxime synthesized in the same manner as in Reference Example 27. Consequently, a crude product including the title compound was obtained as a white solid.

$^1$H-NMR spectrum (400 MHz, DMSO-d$_6$) δ:8.55 (s, 2H), 4.81-4.74 (m, 4H), 4.46-4.36 (m, 2H), 4.32-4.23 (m, 2H), 3.19 (s, 3H).

Reference Example 82-3

2-({[1-(5-Bromopyrimidin-2-yl)piperidin-4-ylidene]amino}oxy)ethyl methanesulfonate (Reference Compound 82-3)

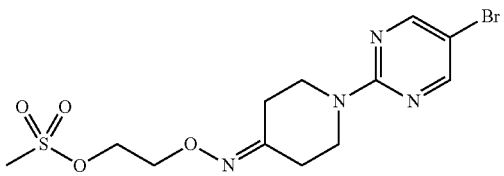 [SMILES: CS(=O)(=O)OCCON=C1CCN(c2ncc(Br)cn2)CC1]

The reaction was performed by the method described in Reference Example 82-1, except that 1-[5-(3-{[(tert-butyldimethylsilyl)oxy]methyl}-2-fluorophenyl)pyrimidin-2-yl]azetidin-3-one O-(2-hydroxyethyl) oxime (Reference Compound 81) was replaced by 1-(5-bromopyrimidin-2-yl)piperidin-4-one O-(2-hydroxyethyl) oxime synthesized in the same manner as in Reference Example 72. Consequently, the title compound (yield 96%) was obtained as a white solid.

Mass spectrum (ESI, m/z):393, 395[M+1]$^+$.

$^1$H-NMR (400 MHz, CDCl$_3$) δ:8.31 (s, 2H), 4.51-4.43 (m, 2H), 4.33-4.25 (m, 2H), 3.95-3.86 (m, 4H), 3.03 (s, 3H), 2.69-2.61 (m, 2H), 2.45-2.37 (m, 2H).

Reference Example 83

1-{5-(3-{[(tert-Butyldimethylsilyl)oxy]methyl}-2-fluorophenyl)pyrimidin-2-yl}azetidin-3-one O-[2-(dimethylamino)ethyl] oxime (Reference Compound 83)

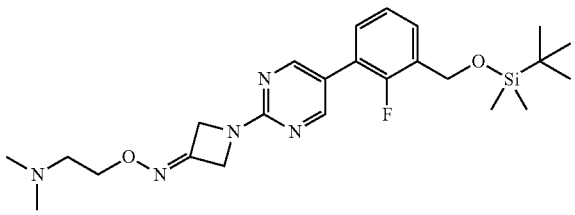 [SMILES: CN(C)CCON=C1CN(c2ncc(-c3cccc(CO[Si](C)(C)C(C)(C)C)c3F)cn2)C1]

2 M dimethylamine/THF solution 1.4 ml (2.8 mmol) was added to a DMF (5 mL) solution of 2-[({1-[5-(3-{[(tert-butyldimethylsilyl)oxy]methyl}-2-fluorophenyl)pyrimidin-2-yl]azetidin-3-ylidene}amino)oxy]ethyl methanesulfonate 100 mg (0.19 mmol) synthesized in the same manner as in Reference Example 82-1. The mixture was fed to a microwave reaction device and was stirred at 80° C. for 2 hours. After the completion of the reaction, a saturated aqueous ammonium chloride solution was added to the reaction mixture, and followed by extraction with ethyl acetate. The organic layer was washed with brine, dried over anhydrous magnesium sulfate, and filtered. The filtrate was concentrated under reduced pressure. The concentrated residue was purified by silica gel column chromatography (DIOL silica gel, eluting solvent: hexane:ethyl acetate) to give the title compound 67 mg (0.14 mmol, yield 74%) as a light yellow oil.

Mass spectrum (ESI, m/z):474[M+1]$^{+}$.

Reference Example 84-1

1-[5-(3-{[(tert-Butyldimethylsilyl)oxy]methyl}-2-fluorophenyl)pyrimidin-2-yl]azetidin-3-one O-{2-[benzyl(methyl)amino]ethyl} oxime (Reference Compound 84-1)

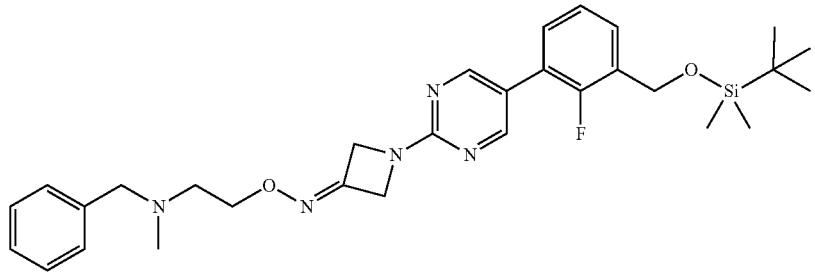 [SMILES: CN(CCON=C1CN(c2ncc(-c3cccc(CO[Si](C)(C)C(C)(C)C)c3F)cn2)C1)Cc1ccccc1]

N-methyl-1-phenylmethanamine 0.0737 ml (0.572 mmol) was added to a DMF (2 mL) solution of 2-[({1-[5-(3-{[(tert-butyldimethylsilyl)oxy]methyl}-2-fluorophenyl)pyrimidin-2-yl]azetidin-3-ylidene}amino)oxy]ethyl methanesulfonate 100 mg (0.191 mmol) synthesized in the same manner as in Reference Example 82-1, and the mixture was stirred at 70° C. for 7 hours and at room temperature for 17 hours. After the completion of the reaction, a saturated aqueous ammonium chloride solution was added to the reaction mixture, and followed by extraction with ethyl acetate. The organic layer was washed with brine, dried over anhydrous magnesium sulfate, and filtered. The filtrate was concentrated under reduced pressure. The concentrated residue was purified by silica gel column chromatography (eluting solvent: hexane:ethyl acetate) to give the title compound 104 mg (0.189 mmol, yield 99%) as a light yellow oil.

Mass spectrum (ESI, m/z):550[M+1]$^{+}$.
$^{1}$H-NMR (400 MHz, CDCl$_3$) δ:8.57 (d, J=1.5 Hz, 2H), 7.54-7.48 (m, 1H), 7.36-7.20 (m, 7H), 4.89-4.82 (m, 6H), 4.23 (t, J=5.8 Hz, 2H), 3.57 (s, 2H), 2.72 (t, J=5.8 Hz, 2H), 2.31 (s, 3H), 0.96 (s, 9H), 0.14 (s, 6H).

Reference Example 84-2

1-[5-(3-{[(tert-Butyldimethylsilyl)oxy]methyl}-2-fluorophenyl)pyrimidin-2-yl]azetidin-3-one O-[2-(piperidin-1-yl)ethyl] oxime (Reference Compound 84-2)

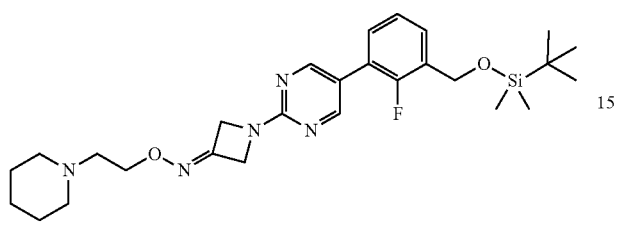

The reaction was performed by the method described in Reference Example 84-1, except that N-methyl-1-phenyl-methanamine was replaced by piperidine. Consequently, the title compound (quantitative yield) was obtained as a yellow solid.

Mass spectrum (ESI, m/z):514[M+1]$^+$.

Reference Example 84-3

1-[5-(3-{[(tert-Butyldimethylsilyl)oxy]methyl}-2-fluorophenyl)pyrimidin-2-yl]azetidin-3-one O-[2-(3,3-difluoroazetidin-1-yl)ethyl] oxime (Reference Compound 84-3)

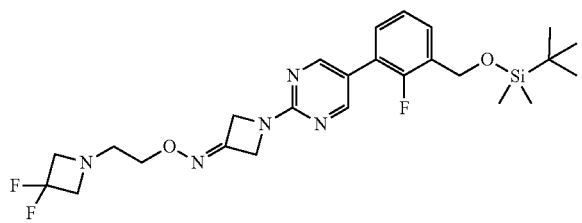 [SMILES: CC(C)(C)[Si](C)(C)OCc1cccc(-c2cnc(N3CC(=NOCCN4CC(F)(F)C4)C3)nc2)c1F]

The reaction was performed by the method described in Reference Example 84-1, except that N-methyl-1-phenyl-methanamine was replaced by 3,3-difluoroazetidine hydrochloride, and TEA was added. Consequently, the title compound (yield 52%) was obtained as a colorless oil.

Mass spectrum (ESI, m/z):522[M+1]$^+$.

$^1$H-NMR (400 MHz, CDCl$_3$) δ:8.57 (d, J=1.4 Hz, 2H), 7.55-7.47 (m, 1H), 7.30-7.20 (m, 2H), 4.91-4.82 (m, 6H), 4.21-4.14 (m, 2H), 3.66 (t, J=12.0 Hz, 4H), 2.92-2.84 (m, 2H), 0.96 (s, 9H), 0.14 (s, 6H).

Reference Example 84-4

1-[5-(3-{[(tert-Butyldimethylsilyl)oxy]methyl}-2-fluorophenyl)pyrimidin-2-yl]azetidin-3-one O-[2-(3-fluoroazetidin-1-yl)ethyl] oxime (Reference Compound 84-4)

The reaction was performed by the method described in Reference Example 84-1, except that N-methyl-1-phenyl-methanamine was replaced by 3-fluoroazetidine hydrochloride, that TEA was added, and that the reaction temperature was changed to 60° C. Consequently, the title compound (including impurities) was obtained as a yellow oil.

Mass spectrum (ESI, m/z):504[M+1]$^+$.

Reference Example 84-5

1-[5-(3-{[(tert-Butyldimethylsilyl)oxy]methyl}-2-fluorophenyl)pyrimidin-2-yl]azetidin-3-one O-[2-(3-methoxyazetidin-1-yl)ethyl] oxime (Reference Compound 84-5)

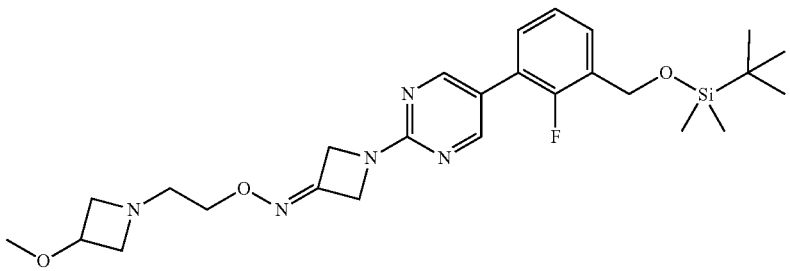 [SMILES: COC1CN(CCON=C2CN(c3ncc(-c4cccc(CO[Si](C)(C)C(C)(C)C)c4F)cn3)C2)C1]

The reaction was performed by the method describe in Reference Example 84-1, except that N-methyl-1-phenyl-methanamine was replaced by 3-methoxyazetidine hydrochloride, and TEA was added. Consequently, the title compound (including impurities) was obtained as a yellow oil.

Mass spectrum (ESI, m/z):516[M+1]$^+$.

Reference Example 85-1

2-[3-({[1-(5-Bromopyrimidin-2-yl)azetidin-3-ylidene]amino}oxy)-2-{[(tetrahydropyran-2-yl)oxy]methyl}propyl]isoindoline-1,3-dione (Reference Compound 85-1)

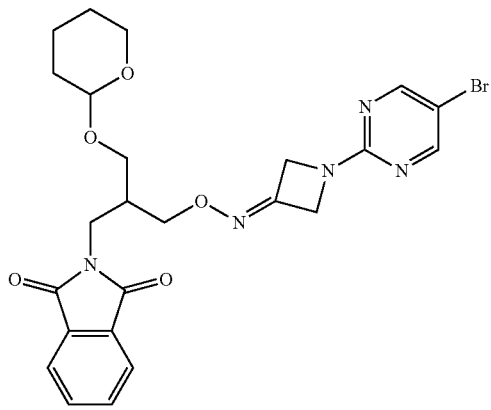 [SMILES: O=C1c2ccccc2C(=O)N1CC(CON=C1CN(c2ncc(Br)cn2)C1)COC1CCCCO1]

Phthalimide 0.19 g (1.3 mmol), 1,1'-azobis(N,N-dimethylformamide) 0.22 g (1.3 mmol) and tributylphosphine 0.32 mL (1.3 mmol) were added to a THF (8 mL) solution of 1-(5-bromopyrimidin-2-yl)azetidin-3-one O-(3-hydroxy-2-{[(tetrahydropyran-2-yl)oxy]methyl}propyl) oxime 0.36 g (0.87 mmol) synthesized in the same manner as in Reference Example 18-1, and the mixture was stirred at room temperature for 17 hours. After the completion of the reaction, water was added to the reaction mixture, and followed by extraction with ethyl acetate. The organic layer was washed with water, dried over anhydrous sodium sulfate, and filtered. The filtrate was concentrated under reduced pressure. The concentrated residue was purified by silica gel column chromatography (eluting solvent: hexane:ethyl acetate) to give the title compound 0.45 g (0.83 mmol, yield 95%) as a colorless oil.

$^1$H-NMR spectrum (400 MHz, DMSO-d$_6$) δ:8.54 (s, 2H), 7.89-7.82 (m, 2H), 7.81-7.75 (m, 2H), 4.73-4.56 (m, 2H), 4.54-4.40 (m, 3H), 4.14-4.00 (m, 2H), 3.77-3.61 (m, 4H), 3.43-3.33 (m, 3H), 1.67-1.22 (m, 6H).

Reference Example 85-2

2-[3-({[1-(5-Bromopyrimidin-2-yl)azetidin-3-ylidene]amino}oxy)-2-methoxypropyl]isoindoline-1,3-dione (Reference Compound 85-2)

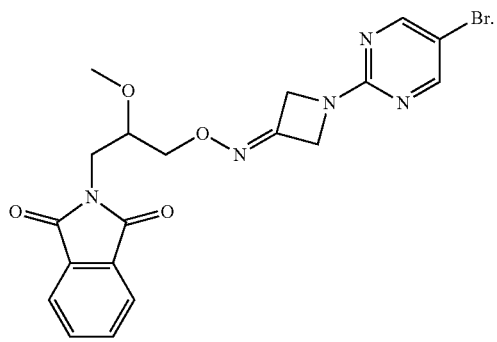 [SMILES: COC(CON=C1CN(c2ncc(Br)cn2)C1)CN1C(=O)c2ccccc2C1=O]

The reaction was performed by the method described in Reference Example 85-1, except that 1-(5-bromopyrimidin-2-yl)azetidin-3-one O-(3-hydroxy-2-{[(tetrahydropyran-2-yl)oxy]methyl}propyl) oxime (Reference Compound 18-1) was replaced by 1-(5-bromopyrimidin-2-yl)azetidin-3-one O-(3-hydroxy-2-methoxypropyl) oxime synthesized in the same manner as in Reference Example 89. Consequently, the title compound (yield 73%) was obtained as a white solid.

Mass spectrum (CI, m/z):460, 462[M+1]$^+$.

$^1$H-NMR spectrum (400 MHz, DMSO-d$_6$) δ:8.55 (s, 2H), 7.90-7.78 (m, 4H), 4.76-4.60 (m, 4H), 4.17-4.03 (m, 2H), 3.84-3.62 (m, 3H), 3.31 (s, 3H).

Reference Example 85-3

2-[2-({[1-(5-Bromopyrimidin-2-yl)piperidin-4-ylidene]amino}oxy)ethyl]isoindoline-1,3-dione (Reference Compound 85-3)

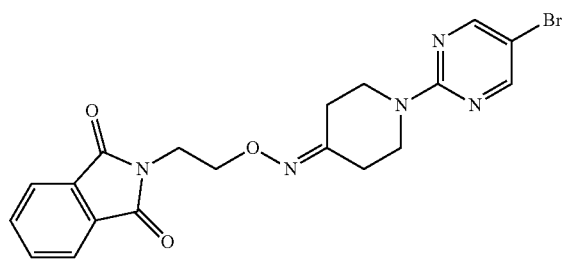 [SMILES: O=C1c2ccccc2C(=O)N1CCON=C1CCN(c2ncc(Br)cn2)CC1]

The reaction was performed by the method described in Reference Example 85-1, except that 1-(5-bromopyrimidin-2-yl)azetidin-3-one O-(3-hydroxy-2-{[(tetrahydropyran-2-yl)oxy]methyl}propyl) oxime (Reference Compound 18-1) was replaced by 1-(5-bromopyrimidin-2-yl)piperidin-4-one O-(2-hydroxyethyl) oxime synthesized in the same manner as in Reference Example 72. Consequently, the title compound (yield 79%) was obtained as a white solid.

Mass spectrum (CI, m/z):444, 446[M+1]⁺.

¹H-NMR spectrum (400 MHz, DMSO-d₆) δ:8.48 (s, 2H), 7.90-7.80 (m, 4H), 4.25-4.14 (m, 2H), 3.86-3.80 (m, 2H), 3.78-3.72 (m, 2H), 3.70-3.60 (m, 2H), 2.46-2.33 (m, 2H), 2.17-1.99 (m, 2H).

Reference Example 86-1

1-[5-(3-{[(tert-Butyldimethylsilyl)oxy]methyl}-2-fluorophenyl)pyrimidin-2-yl]azetidin-3-one O-(3-amino-2-{[(tetrahydropyran-2-yl)oxy]methyl}propyl) oxime (Reference Compound 86-1)

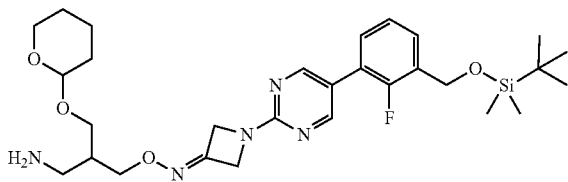 [SMILES: CC(C)(C)[Si](C)(C)OCc1cccc(-c2cnc(N3CC(=NOCC(CN)COC4CCCCO4)C3)nc2)c1F]

Hydrazine monohydrate 0.35 mL (7.2 mmol) was added to a methylene chloride (4 mL)-ethanol (6 mL) solution of 2-{3-[({1-[5-(3-{[(tert-butyldimethylsilyl)oxy]methyl}-2-fluorophenyl)pyrimidin-2-yl]azetidin-3-ylidene}amino)oxy]-2-{[(tetrahydropyran-2-yl)oxy]methyl}propyl}isoindoline-1,3-dione 465 mg (0.661 mmol) synthesized in the same manner as in Reference Example 6-58, and the mixture was stirred at room temperature for 18 hours. After the completion of the reaction, water was added to the reaction mixture, and followed by extraction with ethyl acetate. The organic layer was washed with brine, dried over anhydrous sodium sulfate, and filtered. The filtrate was concentrated under reduced pressure to give a crude product 360 mg including the title compound as a brown oil.

Reference Example 86-2

1-[5-(3-{[(tert-Butyldimethylsilyl)oxy]methyl}-2-fluorophenyl)pyrimidin-2-yl]azetidin-3-one O-(3-amino-2-methoxypropyl) oxime (Reference Compound 86-2)

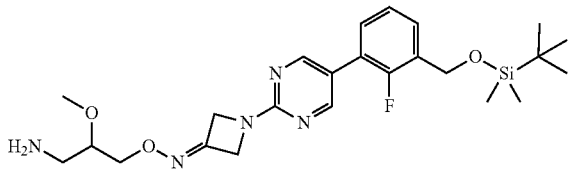 [SMILES: COC(CN)CON=C1CN(c2ncc(-c3cccc(CO[Si](C)(C)C(C)(C)C)c3F)cn2)C1]

The reaction was performed by the method described in Reference Example 86-1, except that 2-{3-[({1-[5-(3-{[(tert-butyldimethylsilyl)oxy]methyl}-2-fluorophenyl)pyrimidin-2-yl]azetidin-3-ylidene}amino)oxy]-2-{[(tetrahydropyran-2-yl)oxy]methyl}propyl}isoindoline-1,3-dione (Reference Compound 6-58) was replaced by 2-{3-[({1-[5-(3-{[(tert-butyldimethylsilyl)oxy]methyl}-2-fluorophenyl)pyrimidin-2-yl]azetidin-3-ylidene}amino)oxy]-2-methoxypropyl}isoindoline-1,3-dione synthesized in the same manner as in Reference Example 6-59. Consequently, a crude product including the title compound was obtained as a light yellow oil.

Mass spectrum (CI, m/z):490[M+1]⁺.

¹H-NMR spectrum (400 MHz, DMSO-d₆) δ:8.63 (d, J=1.4 Hz, 2H), 7.67-7.40 (m, 2H), 7.35-7.27 (m, 1H), 4.93-4.76 (m, 6H), 4.19-3.95 (m, 2H), 3.94-3.76 (m, 1H), 3.34 (s, 3H), 2.69-2.54 (m, 2H), 0.91 (s, 9H), 0.11 (s, 6H).

Reference Example 86-3

1-[5-(3-{[(tert-Butyldimethylsilyl)oxy]methyl}-2-fluorophenyl)pyrimidin-2-yl]piperidin-4-one O-(2-aminoethyl) oxime (Reference Compound 86-3)

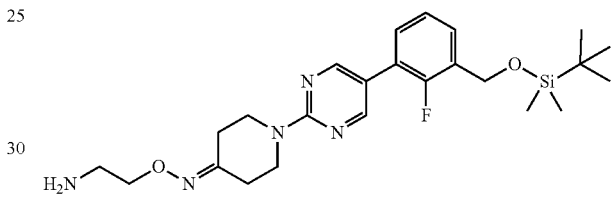

The reaction was performed by the method described in Reference Example 86-1, except that 2-{3-[({1-[5-(3-{[(tert-butyldimethylsilyl)oxy]methyl}-2-fluorophenyl)pyrimidin-2-yl]azetidin-3-ylidene}amino)oxy]-2-{[(tetrahydropyran-2-yl)oxy]methyl}propyl}isoindoline-1,3-dione (Reference Compound 6-58) was replaced by a crude product synthesized in the same manner as in Reference Example 6-82 which included 2-{2-[({1-[5-(3-{[(tert-butyldimethylsilyl)oxy]methyl}-2-fluorophenyl)pyrimidin-2-yl]piperidin-4-ylidene}amino)oxy]ethyl}isoindoline-1,3-dione, that the reaction solvent was ethanol alone, and that the reaction temperature was changed to 60° C. Consequently, a crude product including the title compound was obtained as a brown oil.

Reference Example 87-1

N-{3-[({1-[5-(3-{[(tert-butyldimethylsilyl)oxy]methyl}-2-fluorophenyl)pyrimidin-2-yl]azetidin-3-ylidene}amino)oxy]-2-{[(tetrahydropyran-2-yl)oxy]methyl}propyl}acetamide (Reference Compound 87-1)

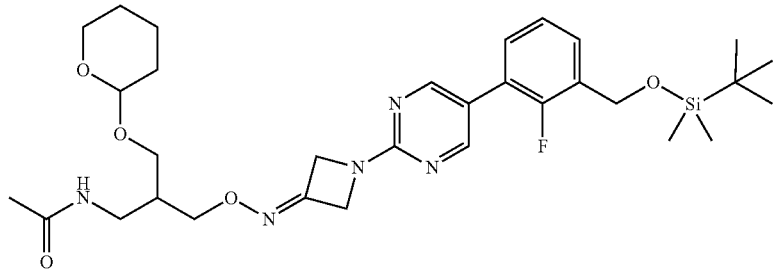 [SMILES: CC(=O)NCC(CON=C1CN(c2ncc(-c3cccc(CO[Si](C)(C)C(C)(C)C)c3F)cn2)C1)COC1CCCCO1]

TEA 0.075 mL (0.54 mmol) and acetic anhydride 0.050 mL (0.53 mmol) were added to a methylene chloride (6 mL) solution of a crude product 0.15 g synthesized in the same manner as in Reference Example 86-1 which included 1-[5-(3-{[(tert-butyldimethylsilyl)oxy]methyl}-2-fluorophenyl)pyrimidin-2-yl]azetidin-3-one O-(3-amino-2-{[(tetrahydropyran-2-yl)oxy]methyl}propyl) oxime, and the mixture was stirred at room temperature for 1 hour. After the completion of the reaction, water was added to the reaction mixture, and followed by extraction with methylene chloride. The organic layer was washed with water, dried over anhydrous sodium sulfate, and filtered. The filtrate was concentrated under reduced pressure. The concentrated residue was purified by silica gel column chromatography (eluting solvent: ethyl acetate:methanol) to give the title compound 0.087 g (0.14 mmol) as a colorless oil.

Mass spectrum (CI, m/z):616[M+1]$^+$.

$^1$H-NMR spectrum (400 MHz, DMSO-d$_6$) δ:8.63 (d, J=1.3 Hz, 2H), 7.89-7.80 (m, 1H), 7.54-7.42 (m, 2H), 7.36-7.28 (m, 1H), 4.86-4.78 (m, 6H), 4.56-4.52 (m, 1H), 4.08-3.99 (m, 2H), 3.77-3.57 (m, 2H), 3.45-3.37 (m, 2H), 3.15-3.10 (m, 2H), 2.16-2.08 (m, 1H), 1.82 (s, 3H), 1.77-1.29 (m, 6H), 0.91 (s, 9H), 0.11 (s, 6H).

Reference Example 87-2

N-{3-[({1-[5-(3-{[(tert-butyldimethylsilyl)oxy]methyl}-2-fluorophenyl)pyrimidin-2-yl]azetidin-3-ylidene}amino)oxy]-2-methoxypropyl}acetamide (Reference Compound 87-2)

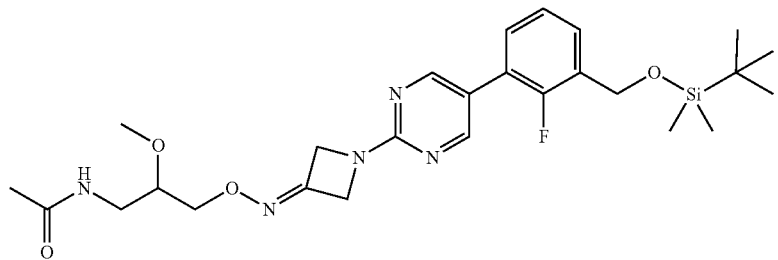 [SMILES: COC(CNC(C)=O)CON=C1CN(c2ncc(-c3cccc(CO[Si](C)(C)C(C)(C)C)c3F)cn2)C1]

The reaction was performed by the method described in Reference Example 87-1, except that the crude product including 1-[5-(3-{[(tert-butyldimethylsilyl)oxy]methyl}-2-fluorophenyl)pyrimidin-2-yl]azetidin-3-one O-(3-amino-2-{[(tetrahydropyran-2-yl)oxy]methyl}propyl) oxime (Reference Compound 86-1) was replaced by 1-[5-(3-{[(tert-butyldimethylsilyl)oxy]methyl}-2-fluorophenyl)pyrimidin-2-yl]azetidin-3-one O-(3-amino-2-methoxypropyl) oxime synthesized in the same manner as in Reference Example 86-2. Consequently, the title compound (yield 47%) was obtained as a white solid.

Mass spectrum (CI, m/z):532[M+1]$^+$.

$^1$H-NMR spectrum (400 MHz, DMSO-d$_6$) δ:8.63 (d, J=1.4 Hz, 2H), 7.89 (t, J=5.8 Hz, 1H), 7.52-7.43 (m, 2H), 7.35-7.28 (m, 1H), 4.88-4.76 (m, 6H), 4.11-3.97 (m, 2H), 3.52-3.45 (m, 1H), 3.34 (s, 3H), 3.26-3.08 (m, 2H), 1.82 (s, 3H), 0.91 (s, 9H), 0.11 (s, 6H).

Reference Example 87-3

1-{2-[({[1-(5-Bromopyrimidin-2-yl)azetidin-3-ylidene]amino}oxy)methyl]morpholino}ethanone (Reference Compound 87-3)

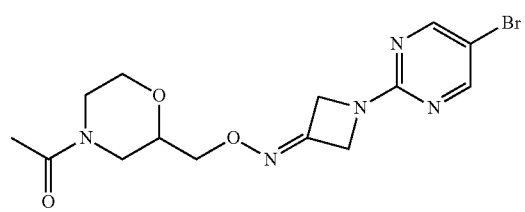 [SMILES: CC(=O)N1CCOC(CON=C2CN(c3ncc(Br)cn3)C2)C1]

The reaction was performed by the method described in Reference Example 87-1, except that 1-[5-(3-{[(tert-butyldimethylsilyl)oxy]methyl}-2-fluorophenyl)pyrimidin-2-yl]azetidin-3-one O-(3-amino-2-{[(tetrahydropyran-2-yl)oxy]methyl}propyl) oxime (Reference Compound 86-1) was replaced by 1-(5-bromopyrimidin-2-yl)azetidin-3-one O-morpholin-2-ylmethyl oxime synthesized in the same manner as in Reference Example 91. Consequently, the title compound (yield 94%) was obtained as a white solid.

Mass spectrum (CI, m/z):384, 386[M+1]$^+$.

$^1$H-NMR spectrum (400 MHz, DMSO-d$_6$) δ:8.55 (s, 2H), 4.80-4.72 (m, 4H), 4.28-4.09 (m, 1H), 4.08-3.98 (m, 2H), 3.88-3.80 (m, 1H), 3.77-3.51 (m, 2H), 3.49-3.28 (m, 1H), 3.19-2.90 (m, 1H), 2.73-2.42 (m, 1H), 2.01-1.99 (m, 3H).

Reference Example 87-4

1-[3-({[1-(5-Bromopyrimidin-2-yl)azetidin-3-ylidene]amino}oxy)azetidin-1-yl]ethanone (Reference Compound 87-4)

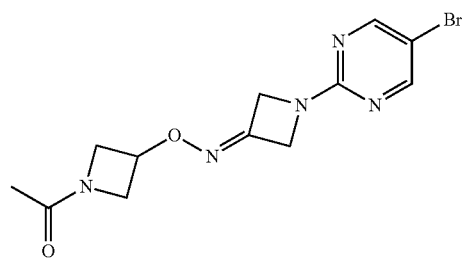 [SMILES: CC(=O)N1CC(ON=C2CN(c3ncc(Br)cn3)C2)C1]

The reaction was performed by the method described in Reference Example 87-1, except that 1-[5-(3-{[(tert-butyldimethylsilyl)oxy]methyl}-2-fluorophenyl)pyrimidin-2-yl]azetidin-3-one O-(3-amino-2-{[(tetrahydropyran-2-yl)

oxy]methyl}propyl) oxime (Reference Compound 86-1) was replaced by 1-(5-bromopyrimidin-2-yl)azetidin-3-one O-azetidin-3-yl oxime synthesized in the same manner as in Reference Example 99. Consequently, the title compound (yield 88%) was obtained as a white solid.

$^1$H-NMR spectrum (400 MHz, DMSO-d$_6$) δ:8.56 (s, 2H), 4.99-4.90 (m, 1H), 4.84-4.75 (m, 4H), 4.39-4.32 (m, 1H), 4.12-4.03 (m, 2H), 3.81-3.74 (m, 1H), 1.77 (s, 3H).

Reference Example 87-5

N-{2-[({1-[5-(3-{[(tert-butyldimethylsilyl)oxy]methyl}-2-fluorophenyl)pyrimidin-2-yl]piperidin-4-ylidene}amino)oxy]ethyl}acetamide (Reference Compound 87-5)

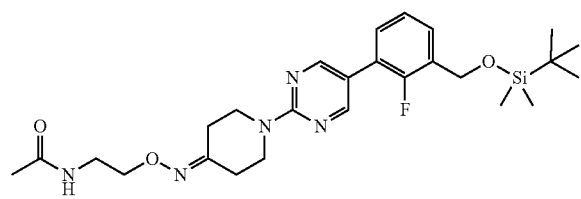 [SMILES: CC(=O)NCCON=C1CCN(c2ncc(-c3cccc(CO[Si](C)(C)C(C)(C)C)c3F)cn2)CC1]

The reaction was performed by the method described in Reference Example 87-1, except that the crude product including 1-[5-(3-{[(tert-butyldimethylsilyl)oxy]methyl}-2-fluorophenyl)pyrimidin-2-yl]azetidin-3-one O-(3-amino-2-{[(tetrahydropyran-2-yl)oxy]methyl}propyl) oxime (Reference Compound 86-1) was replaced by a crude product synthesized in the same manner as in Reference Example 86-3 which included 1-[5-(3-{[(tert-butyldimethylsilyl)oxy]methyl}-2-fluorophenyl)pyrimidin-2-yl]piperidin-4-one O-(2-aminoethyl) oxime. Consequently, the title compound (yield 82%) was obtained as a white solid.

Mass spectrum (CI, m/z):516[M+1]$^+$.

$^1$H-NMR spectrum (400 MHz, DMSO-d$_6$) δ:8.59 (d, J=1.5 Hz, 2H), 7.98-7.87 (m, 1H), 7.53-7.41 (m, 2H), 7.36-7.26 (m, 1H), 4.81 (s, 2H), 4.01-3.88 (m, 6H), 3.30-3.22 (m, 2H), 2.62-2.56 (m, 2H), 2.42-2.33 (m, 2H), 1.81 (s, 3H), 0.91 (s, 9H), 0.11 (s, 6H).

Reference Example 88

1-[5-(3-{[(tert-Butyldimethylsilyl)oxy]methyl}-2-fluorophenyl)pyrimidin-2-yl]azetidin-3-one O-[3-(dimethylamino)-2-{[(tetrahydropyran-2-yl)oxy]methyl}propyl] oxime (Reference Compound 88)

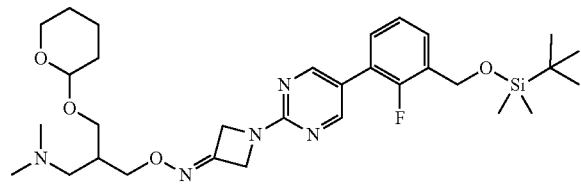 [SMILES: CN(C)CC(CON=C1CN(c2ncc(-c3cccc(CO[Si](C)(C)C(C)(C)C)c3F)cn2)C1)COC1CCCCO1]

A 36% aqueous formaldehyde solution 0.84 mL (11 mmol) and sodium triacetoxyborohydride 0.19 g (0.90 mmol) were added to a methanol (6 mL) solution of a crude product 0.21 g synthesized in the same manner as in Reference Example 86-1 which included 1-[5-(3-{[(tert-butyldimethylsilyl)oxy]methyl}-2-fluorophenyl)pyrimidin-2-yl]azetidin-3-one O-(3-amino-2-{[(tetrahydropyran-2-yl)oxy]methyl}propyl) oxime, and the mixture was stirred at room temperature for 1.5 hours. After the completion of the reaction, a saturated aqueous sodium bicarbonate solution was added to the reaction mixture, and followed by extraction with ethyl acetate. The organic layer was washed with brine, dried over anhydrous sodium sulfate, and filtered. The filtrate was concentrated under reduced pressure. The concentrated residue was purified by silica gel column chromatography (DNH silica gel, eluting solvent: hexane:ethyl acetate) to give the title compound 0.16 g (including impurities) as a colorless oil.

Mass spectrum (CI, m/z):602[M+1]$^+$.

$^1$H-NMR spectrum (400 MHz, DMSO-d$_6$) δ:8.63 (d, J=1.5 Hz, 2H), 7.54-7.41 (m, 2H), 7.36-7.27 (m, 1H), 4.89-4.75 (m, 6H), 4.57-4.50 (m, 1H), 4.11-3.95 (m, 2H), 3.78-3.57 (m, 2H), 3.50-3.35 (m, 2H), 2.30-2.02 (m, 9H), 1.80-1.35 (m, 6H), 0.91 (s, 9H), 0.11 (s, 6H).

Reference Example 89

1-(5-Bromopyrimidin-2-yl)azetidin-3-one O-(3-hydroxy-2-methoxypropyl) oxime (Reference Compound 89)

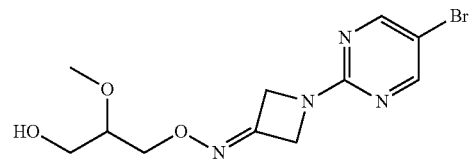 [SMILES: COC(CO)CON=C1CN(c2ncc(Br)cn2)C1]

At 0° C., 2 M hydrogen chloride/ethanol solution 1.0 mL (2.0 mmol) was added to an ethanol (6 mL)-THF (2 mL) solution of 1-(5-bromopyrimidin-2-yl)azetidin-3-one O-[2-methoxy-3-(trityloxy)propyl] oxime 0.46 g (0.80 mmol) synthesized in the same manner as in Reference Example 19-2, and the mixture was stirred at room temperature for 2 hours. After the completion of the reaction, TEA and water were added to the reaction mixture, and followed by extraction with ethyl acetate. The organic layer was washed with water, dried over anhydrous magnesium sulfate, and filtered. The filtrate was concentrated under reduced pressure. The concentrated residue was purified by silica gel column chromatography (eluting solvent: hexane:ethyl acetate) to give the title compound 0.25 g (0.75 mmol, yield 94%) as a white solid.

Mass spectrum (CI, m/z):331, 333[M+1]$^+$.

$^1$H-NMR spectrum (400 MHz, DMSO-d$_6$) δ:8.55 (s, 2H), 4.80-4.72 (m, 4H), 4.70-4.64 (m, 1H), 4.15-3.97 (m, 2H), 3.47-3.39 (m, 3H), 3.33 (s, 3H).

Reference Example 90-1

1-(5-Bromopyrimidin-2-yl)azetidin-3-one O-(2-morpholinoethyl) oxime (Reference Compound 90-1)

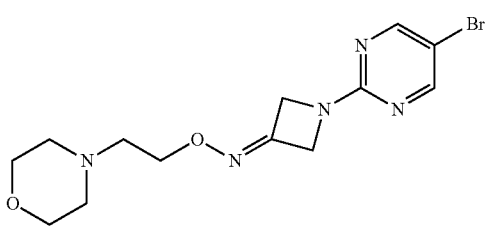 [SMILES: Brc1cnc(N2CC(=NOCCN3CCOCC3)C2)nc1]

DMF (2 ml) was added to 2-({[1-(5-bromopyrimidin-2-yl)azetidin-3-ylidene]amino}oxy)ethyl methanesulfonate 150 mg (0.411 mmol) synthesized in the same manner as in Reference Example 82-2, and morpholine 179 mg (2.06 mmol), and the mixture was stirred at 80° C. for 4 hours. After the completion of the reaction, a saturated aqueous ammonium chloride solution was added to the reaction mixture, and followed by extraction with ethyl acetate. The organic layer was washed with brine, dried over anhydrous sodium sulfate, and filtered. The filtrate was concentrated under reduced pressure. The concentrated residue was purified by silica gel column chromatography (DNH silica gel, eluting solvent: hexane:ethyl acetate) and then by silica gel column chromatography (eluting solvent: ethyl acetate:methanol) to give the title compound 116 mg (0.326 mmol, yield 79%) as a white solid.

Mass spectrum (CI, m/z):356, 358[M+1]$^+$.

$^1$H-NMR spectrum (400 MHz, DMSO-d$_6$) δ:8.55 (s, 2H), 4.80-4.69 (m, 4H), 4.13 (t, J=6.0 Hz, 2H), 3.58-3.52 (m, 4H), 2.57 (t, J=6.0 Hz, 2H), 2.43-2.37 (m, 4H).

Reference Example 90-2

1-(5-Bromopyrimidin-2-yl)azetidin-3-one O-[2-(azetidin-1-yl)ethyl] oxime (Reference Compound 90-2)

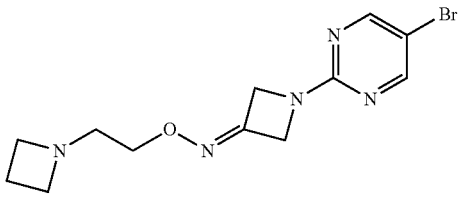 [SMILES: Brc1cnc(N2CC(=NOCCN3CCC3)C2)nc1]

The reaction was performed by the method described in Reference Example 90-1, except that morpholine was replaced by azetidine, and the reaction temperature was changed to 50° C. Consequently, the title compound (yield 26%) was obtained as a white solid.

$^1$H-NMR spectrum (400 MHz, DMSO-d$_6$) δ:8.54 (s, 2H), 4.78-4.69 (m, 4H), 3.95 (t, J=5.8 Hz, 2H), 3.16-3.04 (m, 4H), 2.57 (t, J=5.8 Hz, 2H), 1.98-1.89 (m, 2H).

Reference Example 91

1-(5-Bromopyrimidin-2-yl)azetidin-3-one O-morpholin-2-ylmethyl oxime (Reference Compound 91)

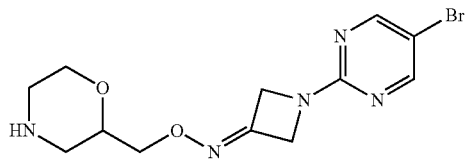 [SMILES: Brc1cnc(N2CC(=NOCC3CNCCO3)C2)nc1]

2 M hydrogen chloride/ethanol solution 5.00 ml (10.0 mmol) was added to an ethanol (2.5 mL) solution of tert-butyl 2-[({[1-(5-bromopyrimidin-2-yl)azetidin-3-ylidene]amino}oxy)methyl]morpholine-4-carboxylate 440 mg (0.995 mmol) synthesized in the same manner as in Reference Example 10-14, and the mixture was stirred at room temperature for 4 hours. After the completion of the reaction, a saturated aqueous sodium bicarbonate solution was added to the reaction mixture, and followed by extraction with methylene chloride. The organic layer was washed with brine, dried over anhydrous sodium sulfate, and filtered. The filtrate was concentrated under reduced pressure to give the title compound 260 mg (0.760 mmol, yield 76%) as a light yellow solid.

Mass spectrum (CI, m/z):342, 344[M+1]$^+$.

$^1$H-NMR spectrum (400 MHz, DMSO-d$_6$) δ:8.55 (s, 2H), 4.86-4.65 (m, 4H), 4.00-3.86 (m, 2H), 3.75-3.65 (m, 1H), 3.64-3.52 (m, 1H), 3.46-3.35 (m, 1H), 2.83-2.74 (m, 1H), 2.72-2.55 (m, 2H), 2.41-2.30 (m, 1H).

Reference Example 92-1

1-(5-Bromopyrimidin-2-yl)azetidin-3-one O-[(4-methylmorpholin-2-yl)methyl] oxime (Reference Compound 92-1)

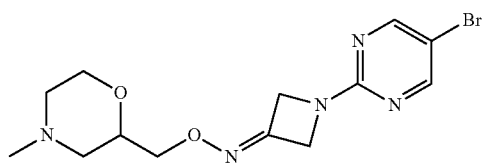 [SMILES: CN1CCOC(CON=C2CN(c3ncc(Br)cn3)C2)C1]

A 37% aqueous formaldehyde solution 0.13 ml (1.7 mmol) and sodium triacetoxyborohydride 16 mg (0.075 mmol) were added to a methanol (1 mL) solution of 1-(5-bromopyrimidin-2-yl)azetidin-3-one O-morpholin-2-ylmethyl oxime 20 mg (0.058 mmol) synthesized in the same manner as in Reference Example 91, and the mixture was stirred at room temperature for 15 minutes. Similarly, a 37% aqueous formaldehyde solution 0.64 ml (8.6 mmol) and sodium triacetoxyborohydride 75 mg (0.35 mmol) were added to a methanol (5 mL) solution of 1-(5-bromopyrimidin-2-yl)azetidin-3-one O-morpholin-2-ylmethyl oxime 100 mg (0.29 mmol) synthesized in the same manner as in Reference Example 91, and the mixture was stirred at room temperature for 15 minutes. After the completion of the reaction, the reaction mixtures were combined together. A saturated aqueous sodium carbonate solution and water were added thereto, and followed by extraction with ethyl acetate.

The organic layer was washed with brine, dried over anhydrous sodium sulfate, and filtered. The filtrate was concentrated under reduced pressure to give a crude product 130 mg including the title compound as a white solid.

Mass spectrum (CI, m/z):356, 358[M+1]+.

1H-NMR spectrum (400 MHz, DMSO-d6) δ:8.55 (s, 2H), 4.81-4.66 (m, 4H), 4.11-3.86 (m, 2H), 3.79-3.72 (m, 1H), 3.72-3.64 (m, 1H), 3.54-3.41 (m, 1H), 2.72-2.66 (m, 1H), 2.60-2.53 (m, 1H), 2.16 (s, 3H), 2.00-1.91 (m, 1H), 1.76-1.69 (m, 1H).

Reference Example 92-2

1-(5-Bromopyrimidin-2-yl)azetidin-3-one O-(1-methylazetidin-3-yl) oxime (Reference Compound 92-2)

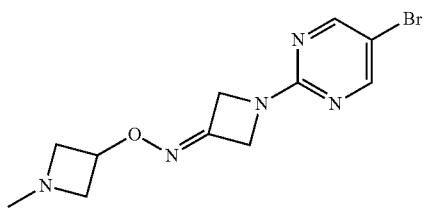 [SMILES: CN1CC(ON=C2CN(c3ncc(Br)cn3)C2)C1]

The reaction was performed by the method described in Reference Example 92-1, except that 1-(5-bromopyrimidin-2-yl)azetidin-3-one O-morpholin-2-ylmethyl oxime (Reference Compound 91) was replaced by 1-(5-bromopyrimidin-2-yl)azetidin-3-one O-azetidin-3-yl oxime synthesized in the same manner as in Reference Example 99, and the product was purified by silica gel column chromatography. Consequently, the title compound (yield 56%) was obtained as a white solid.

Mass spectrum (CI, m/z):312,314[M+1]+.

1H-NMR spectrum (400 MHz, DMSO-d6) δ:8.55 (s, 2H), 4.81-4.73 (m, 4H), 4.72-4.64 (m, 1H), 3.53-3.46 (m, 2H), 3.00-2.94 (m, 2H), 2.24 (s, 3H).

Reference Example 93-1

2-{3-[(tert-Butyldimethylsilyl)oxy]cyclobutoxy}isoindoline-1,3-dione (Reference Compound 93-1)

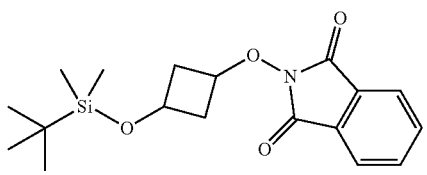 [SMILES: CC(C)(C)[Si](C)(C)OC1CC(ON2C(=O)c3ccccc3C2=O)C1]

Triphenylphosphine 190 mg (0.724 mmol) and a 40% diisopropyl azodicarboxylate/toluene solution 0.383 ml (0.728 mmol) were added to a THF (5 ml) suspension of 3-[(tert-butyldimethylsilyl)oxy]cyclobutanol 108 mg (0.534 mmol) and 2-hydroxyisoindoline-1,3-dione 80.0 mg (0.490 mmol), and the mixture was stirred at room temperature for 1 hour. After the completion of the reaction, water was added to the reaction mixture, and followed by extraction with ethyl acetate. The organic layer was washed with brine, dried over anhydrous magnesium sulfate, and filtered. The filtrate was concentrated under reduced pressure. The concentrated residue was purified by silica gel column chromatography (silica gel, eluting solvent: hexane:ethyl acetate) to give the title compound 121 mg (0.349 mmol, yield 71%) as a colorless oil.

Mass spectrum (CI, m/z):348[M+1]+.

1H-NMR spectrum (400 MHz, DMSO-d6) δ:7.87 (s, 4H), 4.91-4.83 (m, 1H), 4.71-4.61 (m, 1H), 2.50-2.43 (m, 2H), 2.20-2.10 (m, 2H), 0.86 (s, 9H), 0.04 (s, 6H).

Reference Example 93-2) tert-Butyl 3-[(1,3-dioxoisoindolin-2-yl)oxy]azetidine-1-carboxylate (Reference Compound 93-2)

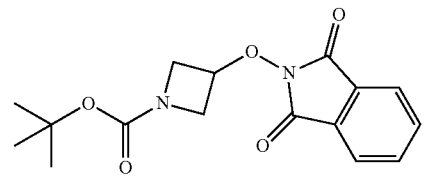 [SMILES: CC(C)(C)OC(=O)N1CC(ON2C(=O)c3ccccc3C2=O)C1]

The reaction was performed by the method described in Reference Example 93-1, except that 3-[(tert-butyldimethylsilyl)oxy]cyclobutanol was replaced by tert-butyl 3-hydroxyazetidine-1-carboxylate, and that the product was purified by silica gel column chromatography, TBME was added to the solid thus-obtained, the mixture was stirred at room temperature, and the solid was collected by filtration. Consequently, the title compound (yield 82%) was obtained as a white solid.

1H-NMR spectrum (400 MHz, DMSO-d6) δ:7.91-7.85 (m, 4H), 5.02-4.97 (m, 1H), 4.19-4.08 (m, 2H), 4.02-3.91 (m, 2H), 1.39 (s, 9H).

Reference Example 93-3

2-(Pyridin-4-ylmethoxy)isoindoline-1,3-dione (Reference Compound 93-3)

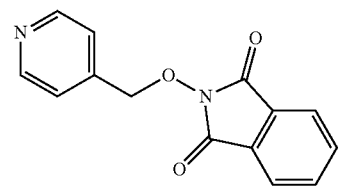 [SMILES: O=C1c2ccccc2C(=O)N1OCc1ccncc1]

The reaction was performed by the method described in Reference Example 93-1, except that 3-[(tert-butyldimethylsilyl)oxy]cyclobutanol was replaced by 4-pyridinemethanol, and that after the completion of the reaction, the reaction mixture was concentrated under reduced pressure, methanol was added to the concentrated residue without performing purification of the concentrated residue by silica gel column chromatography, and the mixture was stirred and filtered to afford the solid. Consequently, a crude product including the title compound was obtained as a light yellow solid.

Mass spectrum (CI, m/z):255[M+1]+.

1H-NMR spectrum (400 MHz, DMSO-d6) δ:8.64-8.59 (m, 2H), 7.89-7.86 (m, 4H), 7.56-7.52 (m, 2H), 5.25 (s, 2H).

Reference Example 94-1

O-{3-[(tert-butyldimethylsilyl)oxy]
cyclobutyl}hydroxylamine (Reference Compound
94-1)

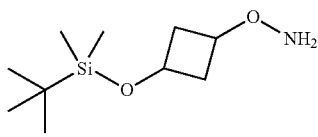

Hydrazine monohydrate 0.168 ml (3.46 mmol) was added to a methylene chloride (2 ml) solution of 2-{3-[(tert-butyldimethylsilyl)oxy]cyclobutoxy}isoindoline-1,3-dione 120 mg (0.345 mmol) synthesized in the same manner as in Reference Example 93-1, and the mixture was stirred at room temperature for 15 hours. After the completion of the reaction, the reaction mixture was filtered. The filtrate was concentrated under reduced pressure to give the title compound 73.8 mg (0.339 mmol, yield 98%) as a colorless oil.

$^1$H-NMR spectrum (400 MHz, DMSO-$d_6$) δ:5.83 (s, 2H), 4.48-4.34 (m, 1H), 4.16-4.05 (m, 1H), 2.30-2.20 (m, 2H), 2.00-1.88 (m, 2H), 0.85 (s, 9H), 0.01 (s, 6H).

Reference Example 94-2) tert-Butyl 3-(aminooxy)azetidine-1-carboxylate (Reference Compound 94-2)

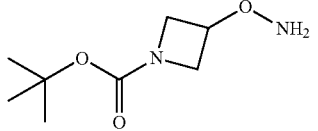

The reaction was performed by the method described in Reference Example 94-1, except that 2-{3-[(tert-butyldimethylsilyl)oxy]cyclobutoxy}isoindoline-1,3-dione (Reference Compound 93-1) was replaced by tert-butyl 3-[(1,3-dioxoisoindolin-2-yl)oxy]azetidine-1-carboxylate synthesized in the same manner as in Reference Example 93-2. Consequently, a crude product including the title compound was obtained as a colorless oil.

Mass spectrum (CI, m/z): 189[M+1]$^+$.

$^1$H-NMR spectrum (400 MHz, DMSO-$d_6$) δ:6.16 (s, 2H), 4.40-4.24 (m, 1H), 3.98-3.82 (m, 2H), 3.78-3.65 (m, 2H), 1.37 (s, 9H).

Reference Example 94-3

O-(pyridin-4-ylmethyl)hydroxylamine
dihydrochloride (Reference Compound 94-3)

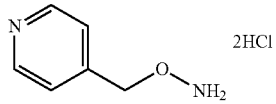

The reaction was performed by the method described in Reference Example 94-1, except that 2-{3-[(tert-butyldimethylsilyl)oxy]cyclobutoxy}isoindoline-1,3-dione (Reference Compound 93-1) was replaced by 2-(pyridin-4-ylmethoxy)isoindoline-1,3-dione synthesized in the same manner as in Reference Example 93-3, and that after the completion of the reaction, the reaction mixture was filtered, a saturated aqueous sodium bicarbonate solution was added to the filtrate, followed by extraction with methylene chloride, the organic layer was washed with brine, dried over anhydrous sodium sulfate, and filtered, the filtrate was concentrated under reduced pressure, diethyl ether and a 4 N hydrogen chloride-1,4-dioxane solution were added to the concentrated residue, and the precipitated solid was collected by filtration. Consequently, the title compound (yield 47%) was obtained as a white solid.

Mass spectrum (CI, m/z):125[M+1]$^+$.

$^1$H-NMR spectrum (400 MHz, DMSO-$d_6$) δ:8.93-8.87 (m, 2H), 7.97-7.92 (m, 2H), 5.36 (s, 2H).

Reference Example 95-1

1-(5-Bromopyrimidin-2-yl)azetidin-3-one O-{3-
[(tert-butyldimethylsilyl)oxy]cyclobutyl} oxime
(Reference Compound 95-1)

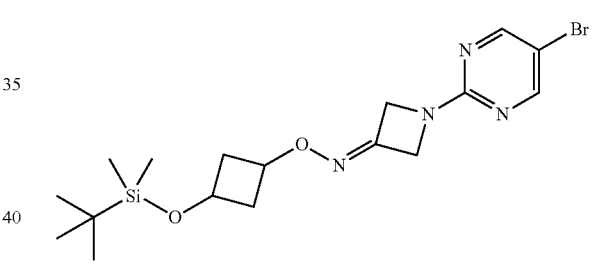

O-{3-[(tert-butyldimethylsilyl)oxy]
cyclobutyl}hydroxylamine 72 mg (0.33 mmol) synthesized in the same manner as in Reference Example 94-1 was added to an ethanol (2 ml) suspension of 1-(5-bromopyrimidin-2-yl)azetidin-3-one 69 mg (0.30 mmol) synthesized in the same manner as in Reference Example 2, and the mixture was stirred at 50° C. for 3 hours and at 100° C. for 8 hours. After the completion of the reaction, water was added to the reaction mixture, and followed by extraction with ethyl acetate. The organic layer was washed with brine, dried over anhydrous magnesium sulfate, and filtered. The filtrate was concentrated under reduced pressure. The concentrated residue was purified by silica gel column chromatography (silica gel, eluting solvent: hexane:ethyl acetate) to give the title compound 100 mg (0.23 mmol, yield 77%) as a white solid.

Mass spectrum (CI, m/z):427, 429[M+1]$^+$.

$^1$H-NMR spectrum (400 MHz, DMSO-$d_6$) δ:8.55 (s, 2H), 4.80-4.65 (m, 5H), 4.54-4.42 (m, 1H), 2.41-2.31 (m, 2H), 2.21-2.08 (m, 2H), 0.85 (s, 9H), 0.02 (s, 6H).

Reference Example 95-2 tert-Butyl 3-({[1-(5-bromopyrimidin-2-yl)azetidin-3-ylidene]amino}oxy)azetidine-1-carboxylate (Reference Compound 95-2)

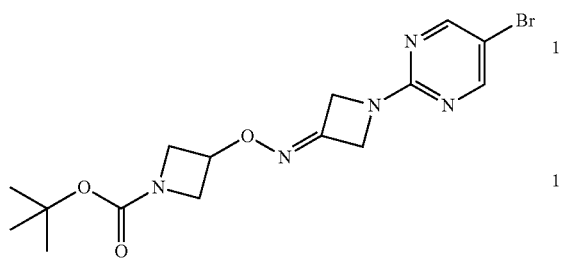

The reaction was performed by the method described in Reference Example 95-1, except that O-{3-[(tert-butyldimethylsilyl)oxy]cyclobutyl}hydroxylamine (Reference Compound 94-1) was replaced by tert-butyl 3-(aminooxy)azetidine-1-carboxylate synthesized in the same manner as in Reference Example 94-2, that the reaction temperature was always 100° C., and that after the completion of the reaction, the precipitated solid was collected by filtration. Consequently, the title compound (yield 49%) was obtained as a white solid.

$^1$H-NMR spectrum (400 MHz, DMSO-$d_6$) δ:8.56 (s, 2H), 4.96-4.85 (m, 1H), 4.82-4.76 (m, 4H), 4.16-4.02 (m, 2H), 3.88-3.74 (m, 2H), 1.38 (s, 9H).

Reference Example 96-1

1-(5-Bromopyrimidin-2-yl)azetidin-3-one O-(3-hydroxycyclobutyl) oxime (Reference Compound 96-1)

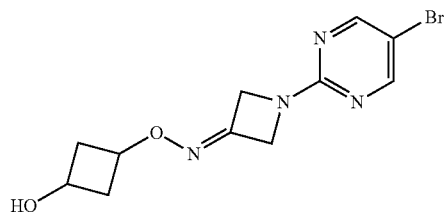 [SMILES: OC1CC(ON=C2CN(c3ncc(Br)cn3)C2)C1]

1 M tetrabutylammonium fluoride/THF solution 0.30 ml (0.30 mmol) was added to a THF (3 ml) solution of 1-(5-bromopyrimidin-2-yl)azetidin-3-one O-{3-[(tert-butyldimethylsilyl)oxy]cyclobutyl} oxime 99 mg (0.23 mmol) synthesized in the same manner as in Reference Example 95-1, and the mixture was stirred at room temperature for 2 hours. After the completion of the reaction, the reaction mixture was concentrated under reduced pressure. The concentrated residue was purified by silica gel column chromatography (eluting solvent: hexane:ethyl acetate) to give the title compound 69 mg (0.22 mmol, yield 96%) as a white solid.

Mass spectrum (CI, m/z):313, 315[M+1]$^+$.

$^1$H-NMR spectrum (400 MHz, DMSO-$d_6$) δ:8.55 (s, 2H), 5.08 (d, J=5.0 Hz, 1H), 4.81-4.67 (m, 5H), 4.34-4.22 (m, 1H), 2.32-2.23 (m, 2H), 2.15-2.04 (m, 2H).

Reference Example 96-2

1-(5-Bromopyrimidin-2-yl)azetidin-3-one O-[1-(2-hydroxyethyl)azetidin-3-yl] oxime (Reference Compound 96-2)

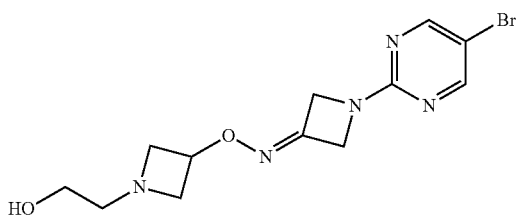 [SMILES: OCCN1CC(ON=C2CN(c3ncc(Br)cn3)C2)C1]

The reaction was performed by the method described in Reference Example 96-1, except that 1-(5-bromopyrimidin-2-yl)azetidin-3-one O-{3-[(tert-butyldimethylsilyl)oxy]cyclobutyl} oxime (Reference Compound 95-1) was replaced by 1-(5-bromopyrimidin-2-yl)azetidin-3-one O-(1-{2-[(tert-butyldimethylsilyl)oxy]ethyl}azetidin-3-yl) oxime synthesized in the same manner as in Reference Example 100-3. Consequently, the title compound (yield 57%) was obtained as a white solid.

Mass spectrum (ESI, m/z):342, 344[M+1]$^+$.

$^1$H-NMR spectrum (400 MHz, DMSO-$d_6$) δ:8.55 (s, 2H), 4.79-4.69 (m, 5H), 4.38 (t, J=5.5 Hz, 1H), 3.55-3.47 (m, 2H), 3.36-3.29 (m, 2H), 3.05-2.99 (m, 2H), 2.47 (t, J=6.0 Hz, 2H).

Reference Example 97

Azetidin-3-one O-benzyl oxime hydrochloride (Reference Compound 97)

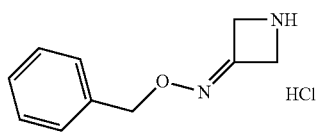 [SMILES: c1ccc(CON=C2CNC2)cc1 ; Cl]

4 M hydrogen chloride/1,4-dioxane solution 4.0 mL (16 mmol) was added to a methanol (30 mL) solution of a crude product 1.61 g synthesized in the same manner as in Reference Example 37-2 which included tert-butyl 3-[(benzyloxy)imino]azetidine-1-carboxylate, and the mixture was stirred at room temperature for 24 hours. After the completion of the reaction, the reaction mixture was concentrated under reduced pressure. The concentrated residue was dried under reduced pressure to give a crude product 1.86 g including the title compound as a white solid.

Reference Example 98

1-(5-Bromopyrimidin-2-yl)azetidin-3-one O-benzyl oxime (Reference Compound 98)

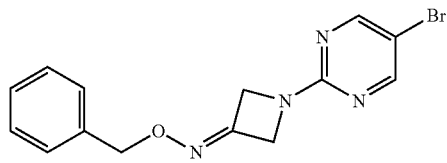 [SMILES: Brc1cnc(N2CC(=NOCc3ccccc3)C2)nc1]

5-Bromo-2-chloropyrimidine 300 mg (1.55 mmol) and DIPEA 1.00 mL (5.74 mmol) were added to an acetonitrile (8 mL) solution of a crude product 330 mg synthesized in the same manner as in Reference Example 97 which included azetidin-3-one O-benzyl oxime hydrochloride, and the mixture was stirred at 60° C. for 2 hours. After the completion of the reaction, water was added to the reaction mixture, and followed by extraction with ethyl acetate. The organic layer was washed with water, dried over anhydrous sodium sulfate, and filtered. The filtrate was concentrated under reduced pressure. The concentrated residue was purified by silica gel column chromatography (eluting solvent: 1,2-dichloroethane:ethyl acetate) to give the title compound 117 mg (0.351 mmol) as a white solid.

Mass spectrum (CI, m/z):333, 335[M+1]$^+$.

$^1$H-NMR spectrum (400 MHz, DMSO-d$_6$) δ:8.54 (s, 2H), 7.40-7.29 (m, 5H), 5.07 (s, 2H), 4.76 (s, 4H).

Reference Example 99

1-(5-Bromopyrimidin-2-yl)azetidin-3-one O-azetidin-3-yl oxime (Reference Compound 99)

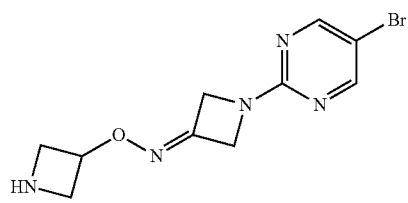 [SMILES: Brc1cnc(N2CC(=NOC3CNC3)C2)nc1]

TFA 5.00 ml (64.9 mmol) was added to a methylene chloride (10 ml) solution of tert-butyl 3-{[(1-(5-bromopyrimidin-2-yl)azetidin-3-ylidene)amino]oxy}azetidin-1-carboxylate 1.04 g (2.61 mmol) synthesized in the same manner as in Reference Example 95-2, and the mixture was stirred at room temperature for 15 hours. After the completion of the reaction, TEA and water were added to the reaction mixture, and followed by extraction with methylene chloride. The organic layer was washed with brine, dried over anhydrous sodium sulfate, and filtered. The filtrate was concentrated under reduced pressure to give the title compound 759 mg (2.55 mmol, yield 98%) as a white solid.

Mass spectrum (CI, m/z):298, 300[M+1]$^+$.

$^1$H-NMR spectrum (400 MHz, DMSO-d$_6$) δ:8.56 (s, 2H), 4.98-4.91 (m, 1H), 4.86-4.72 (m, 4H), 3.86-3.78 (m, 2H), 3.73-3.66 (m, 2H).

Reference Example 100-1

1-(5-Bromopyrimidin-2-yl)azetidin-3-one O-(1-benzylazetidin-3-yl) oxime (Reference Compound 100-1)

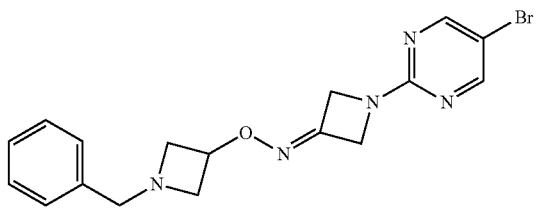 [SMILES: Brc1cnc(N2CC(=NOC3CN(Cc4ccccc4)C3)C2)nc1]

Benzaldehyde 0.034 ml (0.34 mmol) and sodium triacetoxyborohydride 53 mg (0.25 mmol) were added to a methylene chloride (2 ml)-MeOH (0.5 ml) solution of 1-(5-bromopyrimidin-2-yl)azetidin-3-one O-azetidin-3-yl oxime 50 mg (0.17 mmol) synthesized in the same manner as in Reference Example 99, and the mixture was stirred at room temperature for 3 hours. After the completion of the reaction, water was added to the reaction mixture, and followed by extraction with ethyl acetate. The organic layer was washed with brine, and dried over anhydrous sodium sulfate. The mixture was concentrated, and the residue was purified by silica gel column chromatography (silica gel, eluting solvent: hexane:ethyl acetate) to give the title compound 41 mg (0.11 mmol, yield 65%) as a white solid.

$^1$H-NMR spectrum (400 MHz, DMSO-d$_6$) δ:8.55 (s, 2H), 7.33-7.21 (m, 5H), 4.80-4.73 (m, 5H), 3.59 (s, 2H), 3.53-3.46 (m, 2H), 3.10-3.01 (m, 2H).

Reference Example 100-2

1-(5-Bromopyrimidin-2-yl)azetidin-3-one O-(1-ethylazetidin-3-yl) oxime (Reference Compound 100-2)

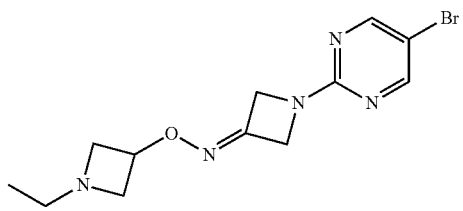 [SMILES: CCN1CC(ON=C2CN(c3ncc(Br)cn3)C2)C1]

The reaction was performed by the method described in Reference Example 100-1, except that benzaldehyde was replaced by acetaldehyde. Consequently, the title compound (yield 35%) was obtained as a white solid.

Mass spectrum (ESI, m/z):326, 328[M+1]$^+$.

$^1$H-NMR spectrum (400 MHz, DMSO-d$_6$) δ:8.55 (s, 2H), 4.79-4.68 (m, 5H), 3.51-3.42 (m, 2H), 2.97-2.88 (m, 2H), 2.40 (q, J=7.2 Hz, 2H), 0.86 (t, J=7.2 Hz, 3H).

Reference Example 100-3

1-(5-Bromopyrimidin-2-yl)azetidin-3-one O-(1-{2-[(tert-butyldimethylsilyl)oxy]ethyl}azetidin-3-yl) oxime (Reference Compound 100-3)

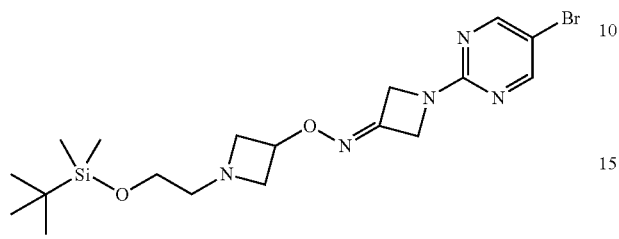

The reaction was performed by the method described in Reference Example 100-1, except that benzaldehyde was replaced by 2-[(tert-butyldimethylsilyl)oxy]acetaldehyde. Consequently, the title compound (yield 71%) was obtained as a colorless oil.

Mass spectrum (CI, m/z):456, 458[M+1]$^+$.

$^1$H-NMR spectrum (400 MHz, DMSO-d$_6$) δ:8.55 (s, 2H), 4.79-4.69 (m, 5H), 3.59-3.48 (m, 4H), 3.12-2.97 (m, 2H), 2.57-2.46 (m, 2H), 0.86 (s, 9H), 0.02 (s, 6H).

Reference Example 101-1

1-(5-Bromopyrimidin-2-yl)azetidin-3-one O-[1-(2,2,2-trifluoroethyl)azetidin-3-yl]oxime (Reference Compound 101-1)

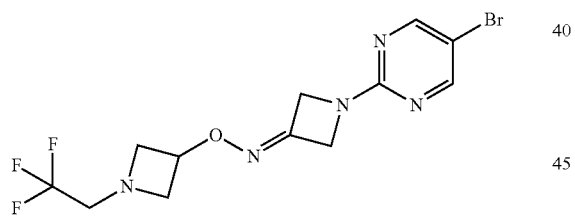

2,2,2-Trifluoroethyl trifluoromethanesulfonate 0.029 ml (0.20 mmol) and DIPEA 0.086 ml (0.50 mmol) were added to a DMF (1 ml) suspension of 1-(5-bromopyrimidin-2-yl)azetidin-3-one O-azetidin-3-yl oxime 50 mg (0.17 mmol) synthesized in the same manner as in Reference Example 99, and the mixture was stirred at room temperature for 14 hours. After the completion of the reaction, water was added to the reaction mixture, and followed by extraction with ethyl acetate. The organic layer was washed with brine, and dried over anhydrous magnesium sulfate. The mixture was concentrated, and the residue was purified by silica gel column chromatography (silica gel, eluting solvent: hexane:ethyl acetate) to give the title compound 39 mg (0.10 mmol, yield 59%) as a white solid.

Mass spectrum (CI, m/z):380, 382[M+1]$^+$.

$^1$H-NMR spectrum (400 MHz, DMSO-d$_6$) δ:8.55 (s, 2H), 4.83-4.75 (m, 5H), 3.69-3.64 (m, 2H), 3.37-3.29 (m, 2H), 3.25 (q, J=10.2 Hz, 2H).

Reference Example 101-2

1-(5-Bromopyrimidin-2-yl)azetidin-3-one O-[1-(2-methoxyethyl)azetidin-3-yl] oxime (Reference Compound 101-2)

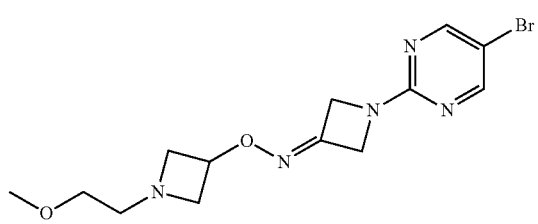 [SMILES: COCCN1CC(ON=C2CN(c3ncc(Br)cn3)C2)C1]

The reaction was performed by the method described in Reference Example 101-1, except that 2,2,2-trifluoroethyl trifluoromethanesulfonate was replaced by 2-bromoethyl methyl ether, and the reaction temperature was changed to 70° C. Consequently, the title compound (yield 43%) was obtained as a white solid.

Mass spectrum (ESI, m/z):356, 358[M+1]$^+$.

$^1$H-NMR spectrum (400 MHz, DMSO-d$_6$) δ:8.55 (s, 2H), 4.80-4.68 (m, 5H), 3.54-3.46 (m, 2H), 3.28 (t, J=5.8 Hz, 2H), 3.20 (s, 3H), 3.08-2.97 (m, 2H), 2.56 (t, J=5.8 Hz, 2H).

Reference Example 101-3

1-(5-Bromopyrimidin-2-yl)azetidin-3-one O-[1-(2-fluoroethyl)azetidin-3-yl] oxime (Reference Compound 101-3)

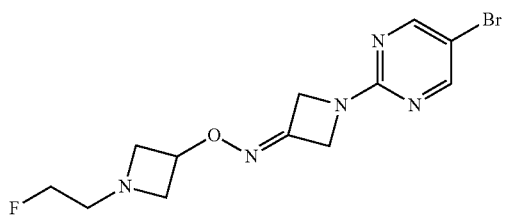 [SMILES: FCCN1CC(ON=C2CN(c3ncc(Br)cn3)C2)C1]

The reaction was performed by the method described in Reference Example 101-1, except that 2,2,2-trifluoroethyl trifluoromethanesulfonate was replaced by 2-fluoroethyl 4-methylbenzenesulfonate, and the reaction temperature was changed to 100° C. and then to 120° C. Consequently, the title compound (including impurities) was obtained as a colorless oil.

Mass spectrum (CI, m/z):344, 346[M+1]$^+$.

$^1$H-NMR spectrum (400 MHz, DMSO-d$_6$) δ:8.55 (s, 2H), 4.81-4.71 (m, 5H), 4.39 (td, J=4.8, 47.7 Hz, 2H), 3.60-3.51 (m, 2H), 3.13-3.03 (m, 2H), 2.70 (td, J=4.8, 29.0 Hz, 2H).

Reference Example 102-1

1-(5-Bromopyrimidin-2-yl)azetidin-3-one O-[1-(methylsulfonyl)azetidin-3-yl] oxime (Reference Compound 102-1)

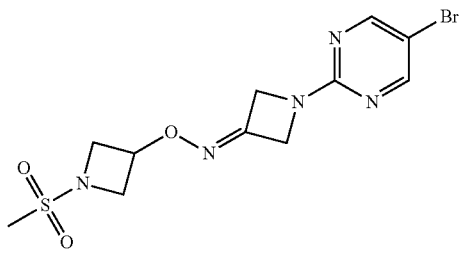 [SMILES: CS(=O)(=O)N1CC(ON=C2CN(c3ncc(Br)cn3)C2)C1]

Methanesulfonyl chloride 0.026 ml (0.34 mmol) and TEA 0.077 ml (0.55 mmol) were added to a methylene chloride (1 ml) solution of 1-(5-bromopyrimidin-2-yl)azetidin-3-one O-azetidin-3-yl oxime 82 mg (0.28 mmol) synthesized in the same manner as in Reference Example 99, and the mixture was stirred at room temperature for 14 hours. After the completion of the reaction, water was added to the reaction mixture, and followed by extraction with methylene chloride. The organic layer was washed with brine, and dried over anhydrous magnesium sulfate. The mixture was concentrated, and the residue was purified by silica gel column chromatography (silica gel, eluting solvent: hexane:ethyl acetate) to give the title compound 58 mg (0.15 mmol, yield 54%) as a white solid.

Mass spectrum (CI, m/z):376, 378[M+1]$^+$.

$^1$H-NMR spectrum (400 MHz, DMSO-$d_6$) δ:8.56 (s, 2H), 4.99-4.87 (m, 1H), 4.83-4.77 (m, 4H), 4.13 (dd, J=6.7, 9.7 Hz, 2H), 3.90 (dd, J=4.6, 9.7 Hz, 2H), 3.03 (s, 3H).

Reference Example 102-2

Methyl 3-({[1-(5-bromopyrimidin-2-yl)azetidin-3-ylidene]amino}oxy)azetidine-1-carboxylate (Reference Compound 102-2)

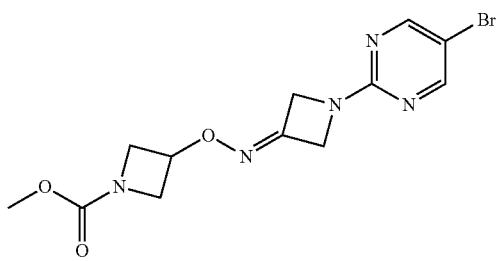 [SMILES: COC(=O)N1CC(ON=C2CN(c3ncc(Br)cn3)C2)C1]

The reaction was performed by the method described in Reference Example 102-1, except that methanesulfonyl chloride was replaced by methyl chloroformate. Consequently, the title compound (yield 78%) was obtained as a white solid.

Mass spectrum (CI, m/z):356, 358[M+1]$^+$.

$^1$H-NMR spectrum (400 MHz, DMSO-$d_6$) δ:8.56 (s, 2H), 4.98-4.92 (m, 1H), 4.84-4.74 (m, 4H), 4.24-4.09 (m, 2H), 3.95-3.82 (m, 2H), 3.56 (s, 3H).

Reference Example 103

3-({[1-(5-Bromopyrimidin-2-yl)piperidin-4-ylidene]amino}oxy)propanoic acid hydrochloride (Reference Compound 103)

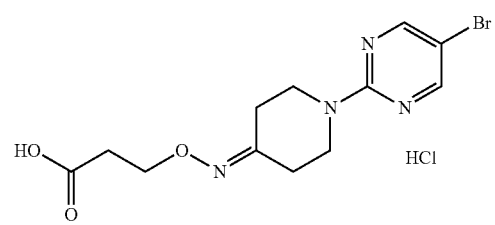 [SMILES: O=C(O)CCON=C1CCN(c2ncc(Br)cn2)CC1 ; Cl]

3-(Aminooxy)propanoic acid hydrochloride 67 mg (0.47 mmol) was added to a THF (2 mL)-ethanol (2 mL) solution of 1-(5-bromopyrimidin-2-yl)azetidin-3-one 0.10 g (0.39 mmol) synthesized in the same manner as in Reference Example 2, and the mixture was stirred at 50° C. for 2 hours. After the completion of the reaction, the reaction mixture was concentrated under reduced pressure. The concentrated residue was dried under reduced pressure to give a crude product 0.13 g including the title compound as a white solid.

Reference Example 104

Ethyl 3-({[1-(5-bromopyrimidin-2-yl)piperidin-4-ylidene]amino}oxy)propanoate (Reference Compound 104)

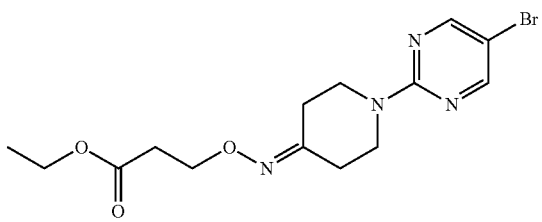 [SMILES: CCOC(=O)CCON=C1CCN(c2ncc(Br)cn2)CC1]

Potassium carbonate 0.11 g (0.80 mmol) and iodoethane 0.050 mL (0.62 mmol) were added to a DMF (4 mL) solution of a crude product 0.13 g synthesized in the same manner as in Reference Example 103 which included 3-({[1-(5-bromopyrimidin-2-yl)piperidin-4-ylidene]amino}oxy)propanoic acid, and the mixture was stirred at room temperature for 4 hours. After the completion of the reaction, water was added to the reaction mixture, and followed by extraction with ethyl acetate. The organic layer was washed with water, dried over anhydrous magnesium sulfate, and filtered. The filtrate was concentrated under reduced pressure. The concentrated residue was purified by silica gel column chromatography (eluting solvent: hexane:ethyl acetate) to give the title compound 99 mg (0.27 mmol) as a colorless oil.

Mass spectrum (CI, m/z):371, 373[M+1]$^+$.

$^1$H-NMR spectrum (400 MHz, DMSO-$d_6$) δ:8.48 (s, 2H), 4.19 (t, J=6.1 Hz, 2H), 4.07 (q, J=7.2 Hz, 2H), 3.87-3.76 (m, 4H), 2.66-2.58 (m, 2H), 2.38-2.32 (m, 2H), 1.17 (t, J=7.2 Hz, 3H).

Reference Example 105-1

3-({[1-(5-Bromopyrimidin-2-yl)piperidin-4-ylidene]amino}oxy)propanamide (Reference Compound 105-1)

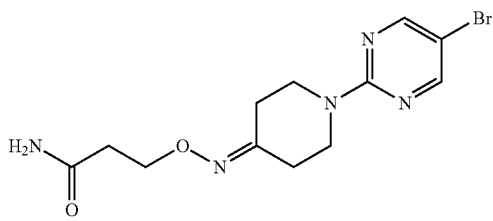 [SMILES: NC(=O)CCON=C1CCN(c2ncc(Br)cn2)CC1]

CDI 168 mg (1.04 mmol) was added to a THF (4 ml) solution of 3-({[1-(5-bromopyrimidin-2-yl)piperidin-4-ylidene]amino}oxy)propanoic acid hydrochloride 175 mg (0.461 mmol) synthesized in the same manner as in Reference Example 103, and the mixture was stirred at room temperature for 4 hours. Next, a 28% aqueous ammonia solution 0.965 ml (51.0 mmol) was added under ice cooling. The mixture was stirred for 15 minutes under ice cooling. After the completion of the reaction, a saturated aqueous ammonium chloride solution was added to the reaction mixture, and followed by extraction with ethyl acetate. The organic layer was washed with brine, dried over anhydrous magnesium sulfate, and filtered. The filtrate was concentrated under reduced pressure. Ethyl acetate was added to the crude product thus obtained, and the mixture was stirred at room temperature. Thereafter, the solid was collected by filtration and was dried under reduced pressure to give the title compound 93.9 mg (0.274 mmol, yield 59%) as a white solid.

Mass spectrum (CI, m/z):342, 344[M+1]$^+$.

$^1$H-NMR spectrum (400 MHz, CDCl$_3$) δ:8.31 (s, 2H), 5.83 (br s, 1H), 5.30 (br s, 1H), 4.32 (t, J=6.0 Hz, 2H), 3.95-3.85 (m, 4H), 2.68-2.57 (m, 4H), 2.47-2.39 (m, 2H).

Reference Example 105-2)

3-({[1-(5-Bromopyrimidin-2-yl)piperidin-4-ylidene]amino}oxy)-N-methylpropanamide (Reference Compound 105-2)

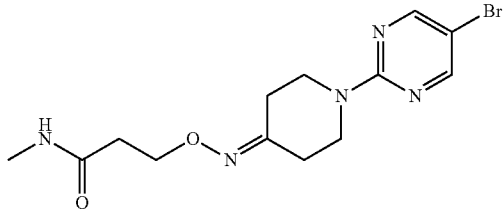 [SMILES: CNC(=O)CCON=C1CCN(c2ncc(Br)cn2)CC1]

The reaction was performed by the method described in Reference Example 105-1, except that the 28% aqueous ammonia solution was replaced by a 2 M methylamine/THF solution, that THF was replaced by DMF, and that the product was purified by silica gel column chromatography (eluting solvent: ethyl acetate:methanol) and the crude product thus obtained was washed with TBME. Consequently, the title compound (yield 36%) was obtained as a white solid.

$^1$H-NMR spectrum (400 MHz, DMSO-d$_6$) δ:8.48 (s, 2H), 7.84-7.74 (m, 1H), 4.14 (t, J=6.6 Hz, 2H), 3.88-3.77 (m, 4H), 2.56 (d, J=4.5 Hz, 3H), 2.43-2.29 (m, 4H).

Reference Example 105-3

3-({[1-(5-Bromopyrimidin-2-yl)piperidin-4-ylidene]amino}oxy)-N,N-dimethylpropanamide (Reference Compound 105-3)

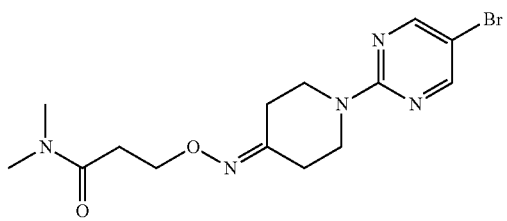 [SMILES: CN(C)C(=O)CCON=C1CCN(c2ncc(Br)cn2)CC1]

The reaction was performed by the method described in Reference Example 105-1, except that the 28% aqueous ammonia solution was replaced by a 2 M dimethylamine/THF solution, that THF was replaced by DMF, and that the product was purified by silica gel column chromatography (eluting solvent: ethyl acetate:methanol). Consequently, the title compound (yield 18%) was obtained as a white solid.

Mass spectrum (CI, m/z):370, 372[M+1]$^+$.

$^1$H-NMR spectrum (400 MHz, DMSO-d$_6$) δ:8.48 (s, 2H), 4.17 (t, J=6.8 Hz, 2H), 3.87-3.77 (m, 4H), 2.95 (s, 3H), 2.80 (s, 3H), 2.64 (t, J=6.7 Hz, 2H), 2.54-2.48 (m, 2H), 2.39-2.31 (m, 2H).

Reference Example 106

N-{2-[({1-[5-(3-{[(tert-butyldimethylsilyl)oxy]methyl}-2-fluorophenyl)pyrimidin-2-yl]piperidin-4-ylidene}amino)oxy]ethyl}-N-methylacetamide (Reference Compound 106)

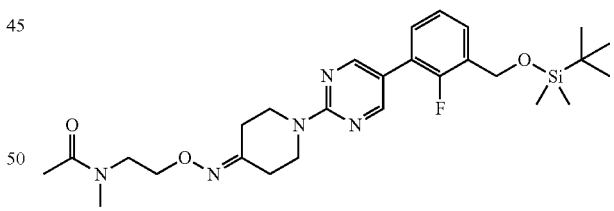

At 0° C., 55% sodium hydride 16 mg (0.37 mmol) was added to a THF (4 mL) solution of N-{2-[({1-[5-(3-{[(tert-butyldimethylsilyl)oxy]methyl}-2-fluorophenyl)pyrimidin-2-yl]5 piperidin-4-ylidene}amino)oxy]ethyl}acetamide 0.12 g (0.23 mmol) synthesized in the same manner as in Reference Example 87-5, and the mixture was stirred at 0° C. for 10 minutes. Next, iodomethane 0.030 mL (0.48 mmol) was added at 0° C., and the mixture was stirred at room temperature for 14 hours. After the completion of the reaction, water was added to the reaction mixture, and followed by extraction with ethyl acetate. The organic layer was washed with water, dried over anhydrous sodium sulfate, and filtered. The filtrate was concentrated under reduced pressure. The concentrated residue was purified by silica gel column chromatography (eluting solvent: ethyl acetate:methanol) to give the title compound 0.11 g (0.21 mmol, yield 91%) as a light yellow oil.

Mass spectrum (CI, m/z):530[M+1]$^+$.

$^1$H-NMR spectrum (400 MHz, DMSO-d$_6$) δ:8.59 (d, J=1.5 Hz, 2H), 7.51-7.41 (m, 2H), 7.33-7.27 (m, 1H), 4.81 (s, 2H), 4.16-4.02 (m, 2H), 3.96-3.89 (m, 4H), 3.59-3.46 (m, 2H), 3.00-2.79 (m, 3H), 2.60-2.53 (m, 2H), 2.42-2.36 (m, 2H), 2.00-1.96 (m, 3H), 0.92 (s, 9H), 0.11 (s, 6H).

Reference Example 107

N-{2-[({1-[5-(3-{[(tert-butyldimethylsilyl)oxy]methyl}-2-fluorophenyl)pyrimidin-2-yl]piperidin-4-ylidene}amino)oxy]ethyl}methanesulfonamide (Reference Compound 107)

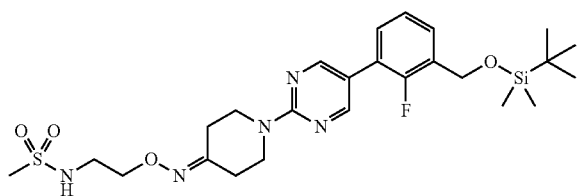 [SMILES: CC(C)(C)[Si](C)(C)OCc1cccc(-c2cnc(N3CCC(=NOCCNS(C)(=O)=O)CC3)nc2)c1F]

At 0° C., TEA 0.11 ml (0.79 mmol) and methanesulfonyl chloride 0.054 ml (0.69 mmol) were added to a methylene chloride (3 mL) solution of 1-[5-(3-{[(tert-butyldimethylsilyl)oxy]methyl}-2-fluorophenyl)pyrimidin-2-yl]piperidin-4-one O-(2-aminoethyl) oxime 300 mg (0.63 mmol) synthesized in the same manner as in Reference Example 86-3, and the mixture was stirred at room temperature for 16 hours. After the completion of the reaction, a saturated aqueous ammonium chloride solution was added to the reaction mixture, and followed by extraction with ethyl acetate. The organic layer was washed with brine, dried over anhydrous magnesium sulfate, and filtered. The filtrate was concentrated under reduced pressure. The concentrated residue was purified by silica gel column chromatography (DIOL silica gel, eluting solvent: hexane:ethyl acetate) to give the title compound (including impurities) 100 mg as a yellow oil.

Mass spectrum (ESI, m/z):552[M+1]$^+$.

$^1$H-NMR (400 MHz, CDCl$_3$) δ:8.53 (d, J=1.4 Hz, 2H), 7.53-7.44 (m, 1H), 7.30-7.18 (m, 2H), 4.85 (s, 2H), 4.83-4.74 (m, 1H), 4.23-4.15 (m, 2H), 4.06-3.96 (m, 4H), 3.50-3.42 (m, 2H), 2.99 (s, 3H), 2.72-2.63 (m, 2H), 2.49-2.42 (m, 2H), 0.96 (s, 9H), 0.14 (s, 6H).

Reference Example 108

N-{2-[({1-[5-(3-{[(tert-butyldimethylsilyl)oxy]methyl}-2-fluorophenyl)pyrimidin-2-yl]piperidin-4-ylidene}amino)oxy]ethyl}-N-methylmethanesulfonamide (Reference Compound 108)

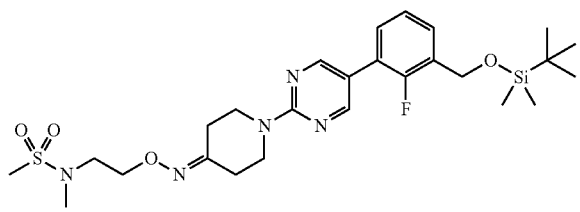 [SMILES: CN(CCON=C1CCN(c2ncc(-c3cccc(CO[Si](C)(C)C(C)(C)C)c3F)cn2)CC1)S(C)(=O)=O]

Iodomethane 0.056 ml (0.90 mmol) and potassium carbonate 50 mg (0.36 mmol) were added to a methylene chloride (3 mL) solution of N-{2-[({1-[5-(3-{[(tert-butyldimethylsilyl)oxy]methyl}-2-fluorophenyl)pyrimidin-2-yl]piperidin-4-ylidene}amino)oxy]ethyl}methanesulfonamide 100 mg (0.18 mmol) synthesized in the same manner as in Reference Example 107, and the mixture was stirred at room temperature for 66 hours. After the completion of the reaction, a saturated aqueous ammonium chloride solution was added to the reaction mixture, and followed by extraction with ethyl acetate. The organic layer was washed with brine, dried over anhydrous magnesium sulfate, and filtered. The filtrate was concentrated under reduced pressure. The concentrated residue was purified by silica gel column chromatography (DIOL silica gel, eluting solvent: hexane:ethyl acetate) to give the title compound (including impurities) 83 mg as a yellow oil.

Mass spectrum (ESI, m/z):566[M+1]$^+$.

Reference Example 109-1)

tert-Butyl {2-[({1-[5-(3-{[(tert-butyldimethylsilyl)oxy]methyl}-2-fluorophenyl)pyrimidin-2-yl]piperidin-4-ylidene}amino)oxy]ethyl}(methylsulfonyl)carbamate (Reference Compound 109-1)

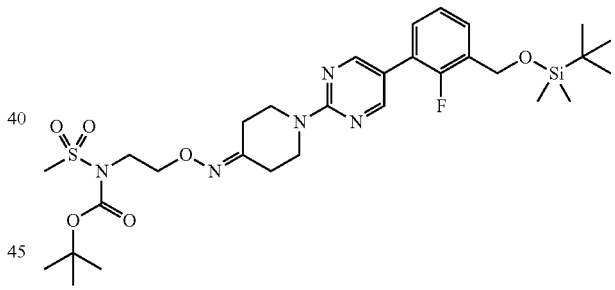

Di-tert-butyl carbonate 0.088 ml (0.38 mmol), TEA 0.079 ml (0.057 mmol) and DMAP 3.5 mg (0.029 mmol) were added to a methylene chloride (3 mL) solution of N-{2-[({1-[5-(3-{[(tert-butyldimethylsilyl)oxy]methyl}-2-fluorophenyl)pyrimidin-2-yl]piperidin-4-ylidene}amino)oxy]ethyl}methanesulfonamide 100 mg (0.19 mmol) synthesized in the same manner as in Reference Example 107, and the mixture was stirred at room temperature for 1 hour. After the completion of the reaction, a saturated aqueous ammonium chloride solution was added to the reaction mixture, and followed by extraction with ethyl acetate. The organic layer was washed with brine, dried over anhydrous magnesium sulfate, and filtered. The filtrate was concentrated under reduced pressure. The concentrated residue was purified by silica gel column chromatography (eluting solvent: hexane:ethyl acetate) to give the title compound 120 mg (0.18 mmol, yield 95%) as a yellow oil.

Mass spectrum (ESI, m/z):652[M+1]⁺.

Reference Example 109-2 tert-Butyl [2-({[1-(5-bromopyrimidin-2-yl)piperidin-4-ylidene]amino}oxy)ethyl](methyl)carbamate (Reference Compound 109-2)

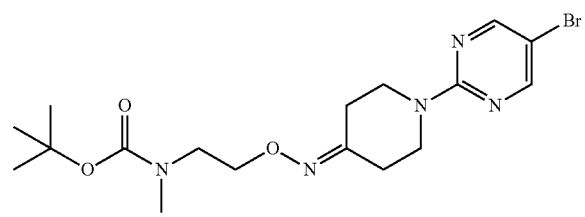 [SMILES: CN(CCON=C1CCN(c2ncc(Br)cn2)CC1)C(=O)OC(C)(C)C]

The reaction was performed by the method described in Reference Example 109-1, except that N-{2-[({1-[5-(3-{[(tert-butyldimethylsilyl)oxy]methyl}-2-fluorophenyl)pyrimidin-2-yl]piperidin-4-ylidene}amino)oxy]ethyl}methanesulfonamide (Reference Compound 107) was replaced by 1-(5-bromopyrimidin-2-yl)piperidin-4-one O-[2-(methylamino)ethyl]oxime synthesized in the same manner as in Reference Example 110-2. Consequently, the title compound (yield 92%) was obtained as a white solid.

Mass spectrum (ESI, m/z):428,430[M+1]⁺.

¹H-NMR (400 MHz, DMSO-$d_6$) δ:8.48 (s, 2H), 4.09-3.99 (m, 2H), 3.87-3.78 (m, 4H), 3.45-3.36 (m, 2H), 2.86-2.74 (m, 3H), 2.60-2.45 (m, 2H), 2.41-2.30 (m, 2H), 1.37 (s, 9H).

Reference Example 110-1

1-(5-Bromopyrimidin-2-yl)piperidin-4-one O-[2-(dimethylamino)ethyl] oxime (Reference Compound 110-1)

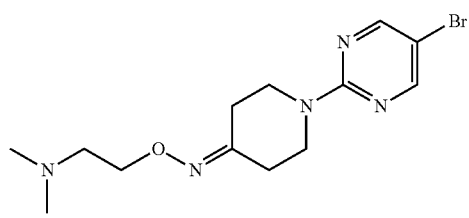 [SMILES: CN(C)CCON=C1CCN(c2ncc(Br)cn2)CC1]

2 M dimethylamine/THF solution 1.27 ml (2.54 mmol) was added to a DMF (3 mL) solution of 2-({[1-(5-bromopyrimidin-2-yl)piperidin-4-ylidene]amino}oxy)ethyl methanesulfonate 100 mg (0.254 mmol) synthesized in the same manner as in Reference Example 82-3. The mixture was fed to a microwave reaction device, and was stirred at 80° C. for 1 hour. After the completion of the reaction, a saturated aqueous ammonium chloride solution was added to the reaction mixture, and followed by extraction with ethyl acetate. The organic layer was washed with brine, dried over anhydrous magnesium sulfate, and filtered. The filtrate was concentrated under reduced pressure. The concentrated residue was purified by silica gel column chromatography (eluting solvent: hexane:ethyl acetate) to give the title compound 78.0 mg (0.228 mmol, yield 90%) as a colorless oil.

Mass spectrum (ESI, m/z):342, 344[M+1]⁺.

¹H-NMR (400 MHz, CDCl₃) δ:8.30 (s, 2H), 4.16 (t, J=5.8 Hz, 2H), 3.94-3.84 (m, 4H), 2.69-2.58 (m, 4H), 2.46-2.38 (m, 2H), 2.30 (s, 6H).

Reference Example 110-2

1-(5-Bromopyrimidin-2-yl)piperidin-4-one O-[2-(methylamino)ethyl] oxime (Reference Compound 110-2)

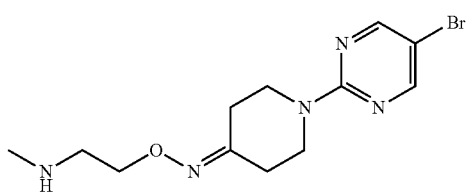 [SMILES: CNCCON=C1CCN(c2ncc(Br)cn2)CC1]

The reaction was performed by the method described in Reference Example 110-1, except that the 2 M dimethylamine/THF solution was replaced by 1 M methylamine/THF solution, that no solvents were used, that the mixture was stirred at a reaction temperature of 90° C. for 1 hour and at a reaction temperature of 110° C. for 1 hour, and that the purification by silica gel chromatography was not performed. Consequently, a crude product including the title compound was obtained as a yellow oil.

Mass spectrum (ESI, m/z):328, 330[M+1]⁺.

Reference Example 110-3

1-(5-Bromopyrimidin-2-yl)piperidin-4-one O-[2-(1H-pyrazol-1-yl)ethyl] oxime (Reference Compound 110-3)

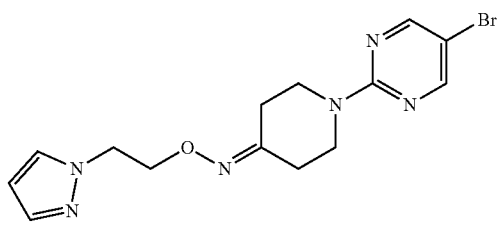 [SMILES: Brc1cnc(N2CCC(=NOCCn3cccn3)CC2)nc1]

The reaction was performed by the method described in Reference Example 110-1, except that the 2 M dimethylamine/THF solution was replaced by 1H-pyrazole, that cesium carbonate was added, and that the microwave reaction device was replaced by an oil bath. Consequently, the title compound (including impurities) was obtained as a white solid.

Mass spectrum (ESI, m/z):365, 367[M+1]⁺.

¹H-NMR (400 MHz, CDCl₃) δ:8.31 (s, 2H), 7.54-7.50 (m, 1H), 7.40-7.36 (m, 1H), 6.23 (t, J=2.1 Hz, 1H), 4.45-4.36 (m, 4H), 3.93-3.84 (m, 4H), 2.60-2.54 (m, 2H), 2.45-2.39 (m, 2H).

Reference Example 111

Di-tert-butyl [2-({[1-(5-bromopyrimidin-2-yl)piperidin-4-ylidene]amino}oxy)ethyl]carbamate (Reference Compound 111)

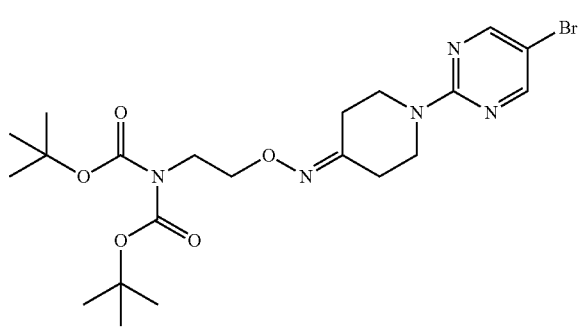 [SMILES: CC(C)(C)OC(=O)N(CCON=C1CCN(c2ncc(Br)cn2)CC1)C(=O)OC(C)(C)C]

Cesium carbonate 436 mg (1.34 mmol) was added to a DMF (3 mL) solution of 2-({[1-(5-bromopyrimidin-2-yl)piperidin-4-ylidene]amino}oxy)ethyl methanesulfonate 263 mg (0.669 mmol) synthesized in the same manner as in Reference Example 82-3, and di-tert-butyl iminocarboxylate 174 mg (0.801 mmol), and the mixture was stirred at 80° C. for 5 hours. After the completion of the reaction, a saturated aqueous ammonium chloride solution was added to the reaction mixture, and followed by extraction with ethyl acetate. The organic layer was washed with brine, dried over anhydrous magnesium sulfate, and filtered. The filtrate was concentrated under reduced pressure. The concentrated residue was purified by silica gel column chromatography (eluting solvent: hexane:ethyl acetate) to give the title compound 358 mg (including impurities) as a yellow oil.

Mass spectrum (ESI, m/z):514, 516[M+1]$^+$.

$^1$H-NMR (400 MHz, CDCl$_3$) δ:8.30 (s, 2H), 4.20-4.14 (m, 2H), 3.94-3.84 (m, 6H), 2.65-2.57 (m, 2H), 2.45-2.37 (m, 2H), 1.55 (s, 9H), 1.48 (s, 9H).

Reference Example 112

3-({[1-(5-Bromopyrimidin-2-yl)piperidin-4-ylidene]amino}oxy)propanenitrile (Reference Compound 112)

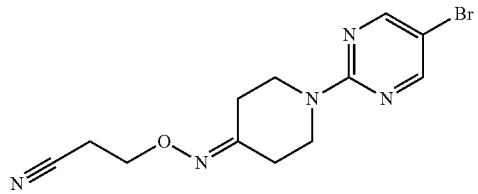 [SMILES: N#CCCON=C1CCN(c2ncc(Br)cn2)CC1]

Pyridine 0.290 ml (3.59 mmol) was added to a methylene chloride (20 ml) solution of 3-({[1-(5-bromopyrimidin-2-yl)piperidin-4-ylidene]amino}oxy)propanamide 558 mg (1.63 mmol) synthesized in the same manner as in Reference Example 105-1, and the mixture was stirred at room temperature. Next, trifluoroacetic anhydride 0.345 ml (2.44 mmol) was added under ice cooling. The mixture was stirred for 1 hour under ice cooling. After the completion of the reaction, water was added to the reaction mixture, and followed by extraction with methylene chloride. The organic layer was washed with brine, dried over anhydrous magnesium sulfate, and filtered. The filtrate was concentrated under reduced pressure. The concentrated residue was purified by silica gel column chromatography (eluting solvent: hexane:ethyl acetate) to give the title compound 442 mg (1.36 mmol, yield 83%) as a white solid.

Mass spectrum (CI, m/z):324, 326[M+1]$^+$.

$^1$H-NMR spectrum (400 MHz, CDCl$_3$) δ:8.31 (s, 2H), 4.24 (t, J=6.3 Hz, 2H), 3.94-3.88 (m, 4H), 2.73 (t, J=6.3 Hz, 2H), 2.69-2.63 (m, 2H), 2.45-2.39 (m, 2H).

Reference Example 113

1-(5-Bromopyrimidin-2-yl)piperidin-4-one O-[2-(methylsulfonyl)ethyl] oxime (Reference Compound 113)

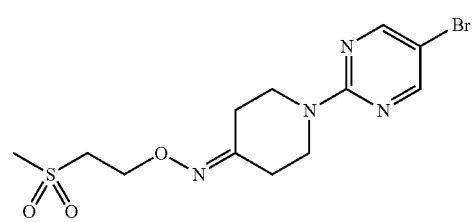 [SMILES: CS(=O)(=O)CCON=C1CCN(c2ncc(Br)cn2)CC1]

Methyl-(2-chloroethyl)sulfone 95 mg (0.67 mmol), cesium carbonate 0.29 g (0.89 mmol) and sodium iodide 15 mg (0.10 mmol) were added to a DMF (4 mL) solution of 1-(5-bromopyrimidin-2-yl)azetidin-3-one oxime 0.12 g (0.44 mmol) synthesized in the same manner as in Reference Example 66, and the mixture was stirred at 80° C. for 8 hours. After the completion of the reaction, water was added to the reaction mixture, and followed by extraction with ethyl acetate. The organic layer was washed with water, dried over anhydrous magnesium sulfate, and filtered. The filtrate was concentrated under reduced pressure. The concentrated residue was purified by silica gel column chromatography (eluting solvent: hexane:ethyl acetate) to give the title compound 0.11 g (0.29 mmol, yield 66%) as a white solid.

Mass spectrum (CI, m/z):377, 379[M+1]$^+$.

$^1$H-NMR spectrum (400 MHz, DMSO-d$_6$) δ:8.49 (s, 2H), 4.34 (t, J=5.8 Hz, 2H), 3.88-3.79 (m, 4H), 3.47 (t, J=5.8 Hz, 2H), 2.98 (s, 3H), 2.59-2.52 (m, 2H), 2.42-2.35 (m, 2H).

Reference Example 114-1

(1-Methyl-1H-pyrazol-3-yl)methanol (Reference Compound 114-1)

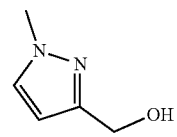

At 0° C., sodium borohydride 360 mg (9.52 mmol) was added to an ethanol (30 mL) solution of 1-methyl-1H-pyrazole-3-carbaldehyde 1.00 g (9.08 mmol), and the mixture was stirred at room temperature for 3 hours. After the completion of the reaction, the reaction mixture was concentrated under reduced pressure. The concentrated residue was purified by silica gel column chromatography (eluting solvent: ethyl acetate:methanol) to give the title compound 860 mg (7.67 mmol, yield 84%) as a colorless oil.

Mass spectrum (CI, m/z): 113[M+1]$^+$.

$^1$H-NMR spectrum (400 MHz, CDCl$_3$) δ:7.31 (d, J=2.2 Hz, 1H), 6.23 (d, J=2.2 Hz, 1H), 4.67 (s, 2H), 3.88 (s, 3H).

Reference Example 114-2

[1-(Tetrahydropyran-2-yl)-1H-pyrazol-3-yl]methanol (Reference Compound 114-2)

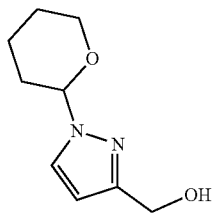 [SMILES: OCc1ccn(C2CCCCO2)n1]

The reaction was performed by the method described in Reference Example 114-1, except that 1-methyl-1H-pyrazole-3-carbaldehyde was replaced by 1-(tetrahydropyran-2-yl)-1H-pyrazole-3-carbaldehyde synthesized in the same manner as in Reference Example 115-1, that ethanol was replaced by methanol, that after the completion of the reaction, water was added to the reaction mixture and followed by extraction with ethyl acetate, and that the purification by silica gel column chromatography was not performed. Consequently, the title compound (yield 93%) was obtained as a colorless oil.

$^1$H-NMR spectrum (400 MHz, CDCl$_3$) δ:7.56 (d, J=2.5 Hz, 1H), 6.30 (d, J=2.5 Hz, 1H), 5.34 (dd, J=2.4, 9.9 Hz, 1H), 4.71 (d, J=6.0 Hz, 2H), 4.13-4.03 (m, 1H), 3.79-3.64 (m, 1H), 2.19-2.00 (m, 3H), 1.92 (t, J=6.0 Hz, 1H), 1.78-1.38 (m, 3H).

Reference Example 114-3

[1-(Tetrahydropyran-2-yl)-1H-pyrazol-4-yl]methanol (Reference Compound 114-3)

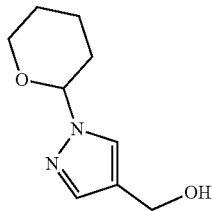 [SMILES: OCc1cnn(C2CCCCO2)c1]

The reaction was performed by the method described in Reference Example 114-1, except that 1-methyl-1H-pyrazole-3-carbaldehyde was replaced by 1-(tetrahydropyran-2-yl)-1H-pyrazole-4-carbaldehyde synthesized in the same manner as in Reference Example 115-2, that ethanol was replaced by methanol, that after the completion of the reaction, brine was added to the reaction mixture and followed by extraction with ethyl acetate, and that the purification by silica gel column chromatography was not performed. Consequently, the title compound (yield 85%) was obtained as a colorless oil.

Mass spectrum (CI, m/z):183[M+1]$^+$.

$^1$H-NMR spectrum (400 MHz, DMSO-d$_6$) δ:7.74-7.71 (m, 1H), 7.41-7.38 (m, 1H), 5.33 (dd, J=2.4, 10.0 Hz, 1H), 4.84 (t, J=5.5 Hz, 1H), 4.34 (d, J=5.4 Hz, 2H), 3.97-3.82 (m, 1H), 3.71-3.52 (m, 1H), 2.13-1.80 (m, 3H), 1.73-1.42 (m, 3H).

Reference Example 115-1

1-(Tetrahydropyran-2-yl)-1H-pyrazole-3-carbaldehyde (Reference Compound 115-1)

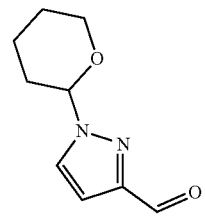 [SMILES: O=Cc1ccn(C2CCCCO2)n1]

para-Toluenesulfonic acid 206 mg (1.08 mmol) and DHP 1.85 ml (21.8 mmol) were added to a THF (30 ml) suspension of 1H-pyrazole-3-carbaldehyde 1.05 g (10.9 mmol), and the mixture was stirred at room temperature for 1 hour. Next, methylene chloride 30 ml was added, and the mixture was stirred at room temperature for 4.5 hours and at 60° C. for 5 hours. After the completion of the reaction, water was added to the reaction mixture, and followed by extraction with ethyl acetate. The organic layer was washed with brine, dried over anhydrous magnesium sulfate, and filtered. The filtrate was concentrated under reduced pressure. The concentrated residue was purified by silica gel column chromatography (eluting solvent: hexane:ethyl acetate) to give the title compound (including impurities).

Reference Example 115-2

1-(Tetrahydropyran-2-yl)-1H-pyrazole-4-carbaldehyde (Reference Compound 115-2)

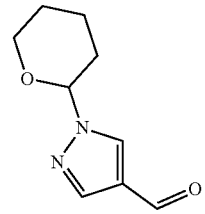 [SMILES: O=Cc1cnn(C2CCCCO2)c1]

The reaction was performed by the method described in Reference Example 115-1, except that 1H-pyrazole-3-carbaldehyde was replaced by 1H-pyrazole-4-carbaldehyde, that THF was replaced by methylene chloride, and that the reaction temperature was ambient. Consequently, the title compound (yield 86%) was obtained as a colorless oil.

Mass spectrum (CI, m/z):181[M+1]⁺.

¹H-NMR spectrum (400 MHz, DMSO-d₆) δ:9.83 (s, 1H), 8.64 (s, 1H), 8.02 (s, 1H), 5.50 (dd, J=2.5, 9.8 Hz, 1H), 3.99-3.90 (m, 1H), 3.72-3.59 (m, 1H), 2.16-1.86 (m, 3H), 1.75-1.47 (m, 3H).

Reference Example 116

1-(5-Bromopyrimidin-2-yl)piperidin-4-one O-[(1-methyl-1H-pyrazol-4-yl)methyl]oxime (Reference Compound 116)

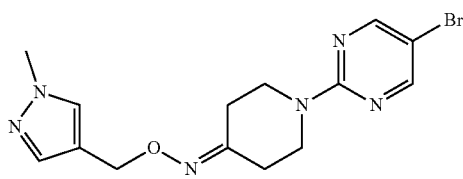 [SMILES: Cn1cc(CON=C2CCN(c3ncc(Br)cn3)CC2)cn1]

2 M hydrogen chloride/ethanol solution 2.0 mL (4.0 mmol) was added to 1-(5-bromopyrimidin-2-yl)piperidin-4-one O-{[1-(tetrahydropyran-2-yl)-1H-pyrazol-4-yl]methyl} oxime 0.18 g (0.41 mmol) synthesized in the same manner as in Reference Example 67-16, and the mixture was stirred at room temperature for 2 hours. After the completion of the reaction, TEA and water were added to the reaction mixture, and followed by extraction with ethyl acetate. The organic layer was washed with a saturated aqueous sodium bicarbonate solution, dried over anhydrous magnesium sulfate, and filtered. The filtrate was concentrated under reduced pressure. DMF 4 mL was added to the concentrated residue. Under stirring at room temperature, cesium carbonate 0.26 g (0.80 mmol) and iodomethane 0.040 mL (0.64 mmol) were added. The resultant mixture was stirred at room temperature for 17 hours. After the completion of the reaction, water was added to the reaction mixture, and followed by extraction with ethyl acetate. The organic layer was washed with water, dried over anhydrous sodium sulfate, and filtered. The filtrate was concentrated under reduced pressure. The concentrated residue was purified by silica gel column chromatography (eluting solvent: 1,2-dichloroethane:ethyl acetate) to give the title compound 0.14 g (0.38 mmol, yield 93%) as a white solid.

Mass spectrum (CI, m/z):366, 368[M+1]⁺.

¹H-NMR spectrum (400 MHz, DMSO-d₆) δ:8.47 (s, 2H), 7.69 (s, 1H), 7.41 (s, 1H), 4.86 (s, 2H), 3.84-3.78 (m, 7H), 2.52-2.47 (m, 2H), 2.39-2.32 (m, 2H).

Reference Example 117

1-(5-Bromopyrimidin-2-yl)piperidin-4-one O-pyridin-4-ylmethyl oxime (Reference Compound 117)

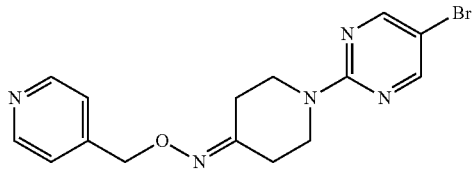 [SMILES: Brc1cnc(N2CCC(=NOCc3ccncc3)CC2)nc1]

Sodium carbonate 210 mg (1.98 mmol) and O-(pyridin-4-ylmethyl)hydroxylamine dihydrochloride 260 mg (1.32 mmol) synthesized in the same manner as in Reference Example 94-3 were added to a THF (6 mL) solution of 1-(5-bromopyrimidin-2-yl)piperidin-4-one 170 mg (0.664 mmol) synthesized in the same manner as in Reference Example 59, and the mixture was stirred at room temperature for 13 hours and at 50° C. for 1 hour. After the completion of the reaction, water was added to the reaction mixture, and followed by extraction with ethyl acetate. The organic layer was washed with brine, dried over anhydrous sodium sulfate, and filtered. The filtrate was concentrated under reduced pressure. The concentrated residue was purified by silica gel column chromatography (eluting solvent: hexane:ethyl acetate) to give the title compound 113 mg (0.312 mmol, yield 47%) as a white solid.

Mass spectrum (CI, m/z):362, 364[M+1]⁺.

¹H-NMR spectrum (400 MHz, CDCl₃) δ:8.60-8.56 (m, 2H), 8.31 (s, 2H), 7.27-7.22 (m, 2H), 5.10 (s, 2H), 3.95-3.88 (m, 4H), 2.74-2.69 (m, 2H), 2.45-2.39 (m, 2H).

Reference Example 118

1-[2-({[1-(5-Bromopyrimidin-2-yl)piperidin-4-ylidene]amino}oxy)ethyl)pyrrolidine-2,5-dione (Reference Compound 118)

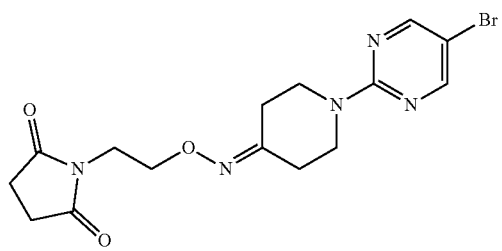 [SMILES: O=C1CCC(=O)N1CCON=C1CCN(c2ncc(Br)cn2)CC1]

Tributylphosphine 0.150 ml (0.608 mmol) and N,N,N',N'-tetramethylazodicarboxamide 150 mg (0.595 mmol) were added to a THF (3 ml) solution of 1-(5-bromopyrimidin-2-yl)piperidin-4-one O-(2-hydroxyethyl) oxime 125 mg (0.397 mmol) synthesized in the same manner as in Reference Example 72 and pyrrolidine-2,5-dione 58.2 mg (0.587 mmol), and the mixture was stirred at room temperature for 1 hour. After the completion of the reaction, water was added to the reaction mixture, and followed by extraction with ethyl acetate. The organic layer was washed with brine, dried over anhydrous magnesium sulfate, and filtered. The filtrate was concentrated under reduced pressure. The concentrated residue was purified by silica gel column chromatography (eluting solvent: hexane:ethyl acetate) to give the title compound 144 mg (0.364 mmol, yield 92%) as a white solid.

Mass spectrum (CI, m/z):396, 398[M+1]⁺.

¹H-NMR spectrum (400 MHz, CDCl₃) δ:8.30 (s, 2H), 4.24-4.15 (m, 2H), 3.94-3.85 (m, 4H), 3.84-3.76 (m, 2H), 2.70 (s, 4H), 2.58-2.52 (m, 2H), 2.42-2.36 (m, 2H).

Reference Example 119-1

1-[2-({[1-(5-Bromopyrimidin-2-yl)piperidin-4-ylidene]amino}oxy)ethyl]pyrrolidin-2-one (Reference Compound 119-1)

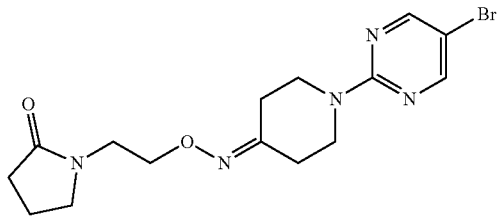 [SMILES: O=C1CCCN1CCON=C1CCN(c2ncc(Br)cn2)CC1]

55% Sodium hydride 25 mg (0.57 mmol) was added to a DMF (3 ml) solution of pyrrolidin-2-one 48 mg (0.56 mmol), and the mixture was stirred at room temperature for 30 minutes. Next, a crude product 149 mg synthesized in the same manner as in Reference Example 82-2 which included 2-({[1-(5-bromopyrimidin-2-yl)piperidin-4-ylidene]amino}oxy)ethyl methanesulfonate was added. The mixture was stirred at room temperature for 14 hours and at 60° C. for 2 hours. Next, pyrrolidin-2-one 16 mg (0.19 mmol) was added, and the mixture was stirred at 60° C. for 1 hour. After the completion of the reaction, a saturated aqueous ammonium chloride solution was added to the reaction mixture, and followed by extraction with ethyl acetate. The organic layer was washed with brine, dried over anhydrous magnesium sulfate, and filtered. The filtrate was concentrated under reduced pressure. The concentrated residue was purified by silica gel column chromatography (DIOL silica gel, eluting solvent: hexane:ethyl acetate) to give the title compound 100 mg (0.265 mmol) as a white solid.

Mass spectrum (CI, m/z):384, 386[M+1]$^+$.

$^1$H-NMR spectrum (400 MHz, CDCl$_3$) δ:8.31 (s, 2H), 4.21-4.14 (m, 2H), 3.94-3.86 (m, 4H), 3.62-3.53 (m, 2H), 3.50-3.41 (m, 2H), 2.66-2.58 (m, 2H), 2.44-2.35 (m, 4H), 2.06-1.98 (m, 2H).

Reference Example 119-2

3-[2-({[1-(5-Bromopyrimidin-2-yl)piperidin-4-ylidene]amino}oxy)ethyl]oxazolidin-2-one (Reference Compound 119-2)

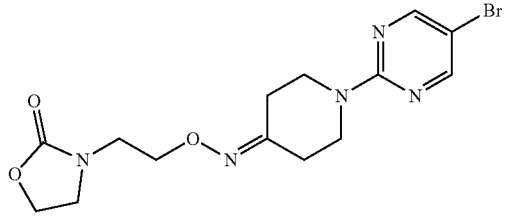 [SMILES: O=C1OCCN1CCON=C1CCN(c2ncc(Br)cn2)CC1]

The reaction was performed by the method described in Reference Example 119-1, except that pyrrolidin-2-one was replaced by oxazolidin-2-one. Consequently, the title compound (yield 57%) was obtained as a white solid.

Mass spectrum (CI, m/z):384, 386[M+1]$^+$.

$^1$H-NMR spectrum (400 MHz, CDCl$_3$) δ:8.31 (s, 2H), 4.37-4.28 (m, 2H), 4.27-4.17 (m, 2H), 3.95-3.85 (m, 4H), 3.69-3.62 (m, 2H), 3.59-3.53 (m, 2H), 2.66-2.56 (m, 2H), 2.45-2.37 (m, 2H).

Reference Example 119-3

4-[2-({[1-(5-Bromopyrimidin-2-yl)piperidin-4-ylidene]amino}oxy)ethyl]morpholin-3-one (Reference Compound 119-3)

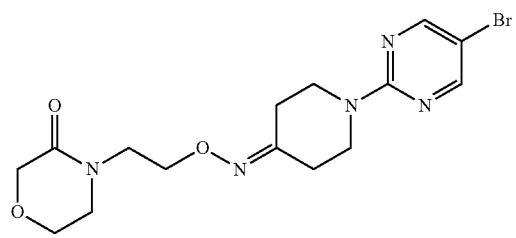 [SMILES: O=C1COCCN1CCON=C1CCN(c2ncc(Br)cn2)CC1]

The reaction was performed by the method described in Reference Example 119-1, except that pyrrolidin-2-one was replaced by morpholin-3-one, and the reaction temperature was changed to 40° C. Consequently, the title compound (yield 76%) was obtained as a white solid.

Mass spectrum (CI, m/z):398, 400[M+1]$^+$.

$^1$H-NMR spectrum (400 MHz, DMSO-d$_6$) δ:8.49 (s, 2H), 4.14-4.09 (m, 2H), 4.01 (s, 2H), 3.84-3.77 (m, 6H), 3.58-3.51 (m, 2H), 3.40-3.36 (m, 2H), 2.56-2.51 (m, 2H), 2.38-2.33 (m, 2H).

Reference Example 120

1-{5-[2-Fluoro-3-(hydroxymethyl)phenyl]pyrimidin-2-yl}piperidin-4-one O-phenyl oxime (Reference Compound 120)

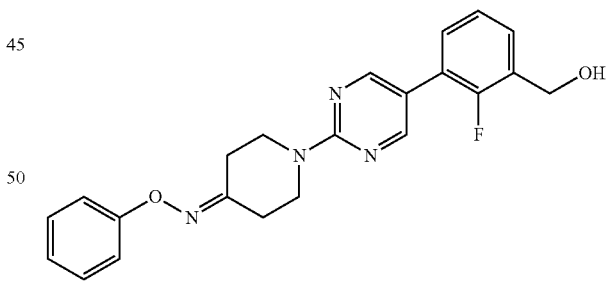

O-phenylhydroxylamine hydrochloride 36 mg (0.25 mmol) was added to an ethanol solution (1 mL) of 1-{5-[2-fluoro-3-(hydroxymethyl)phenyl]pyrimidin-2-yl}piperidin-4-one 61 mg (0.20 mmol) synthesized in the same manner as in Reference Example 7-50, and the mixture was stirred at room temperature for 1 hour. After the completion of the reaction, a saturated aqueous sodium bicarbonate solution was added to the reaction mixture, and followed by extraction with ethyl acetate. The organic layer was dried over anhydrous magnesium sulfate, and filtered. The filtrate was concentrated under reduced pressure. The concentrated residue was purified by silica gel column chromatography (DIOL silica gel, eluting solvent: 1,2-dichloroethane: ethyl acetate) to give the title compound 61 mg (0.16 mmol, yield 80%) as a light yellow solid.

Mass spectrum (CI, m/z):393[M+1]$^+$.

$^1$H-NMR spectrum (400 MHz, CDCl$_3$) δ:8.55 (d, J=1.5 Hz, 2H), 7.48-7.39 (m, 1H), 7.36-7.28 (m, 3H), 7.25-7.17 (m, 3H), 7.05-6.98 (m, 1H), 4.84 (d, J=6.1 Hz, 2H), 4.12-4.05 (m, 4H), 2.93-2.88 (m, 2H), 2.65-2.59 (m, 2H), 1.83 (t, J=6.1 Hz, 1H).

Reference Example 121

1-[5-(3-{[(tert-Butyldimethylsilyl)oxy]methyl}-2-fluorophenyl)pyrimidin-2-yl]piperidin-4-one O-pyrimidin-5-yl oxime (Reference Compound 121)

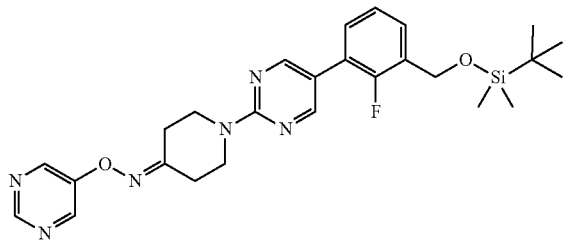 [SMILES: CC(C)(C)[Si](C)(C)OCc1cccc(-c2cnc(N3CCC(=NOc4cncnc4)CC3)nc2)c1F]

A toluene suspension (1 mL) of 5-bromopyrimidine 42 mg (0.26 mmol), 2-(di-tert-butylphosphino)-2',4',6'-triisopropyl-3,6-dimethoxy-1,1'-biphenyl 13 mg (0.027 mmol), allylpalladium chloride dimer 2.7 mg (0.0074 mmol) and cesium carbonate 0.12 g (0.37 mmol) was stirred while performing bubbling with argon, and 1-[5-(3-{[(tert-butyldimethylsilyl)oxy]methyl}-2-fluorophenyl)pyrimidin-2-yl]piperidin-4-one oxime 109 mg (0.25 mmol) synthesized in the same manner as in Reference Example 64 was added. The mixture was stirred at 65° C. for 5 hours. After the completion of the reaction, a saturated aqueous sodium bicarbonate solution was added to the reaction mixture, and followed by extraction with ethyl acetate. The organic layer was washed with a saturated aqueous sodium bicarbonate solution, dried over anhydrous sodium sulfate, and filtered. The filtrate was concentrated under reduced pressure. The concentrated residue was purified by silica gel column chromatography (DIOL silica gel, eluting solvent: 1,2-dichloroethane: ethyl acetate) to give the title compound 74 mg (0.15 mmol, yield 58%) as a light yellow solid.

$^1$H-NMR spectrum (400 MHz, CDCl$_3$) δ:8.91 (s, 1H), 8.68 (s, 2H), 8.56 (d, J=1.5 Hz, 2H), 7.53-7.46 (m, 1H), 7.30-7.20 (m, 2H), 4.86 (s, 2H), 4.15-4.07 (m, 4H), 2.94-2.87 (m, 2H), 2.66-2.59 (m, 2H), 0.96 (s, 9H), 0.14 (s, 6H).

Reference Example 122 tert-Butyl 4-[(pyrimidin-2-yloxy)imino]piperidine-1-carboxylate (Reference Compound 122)

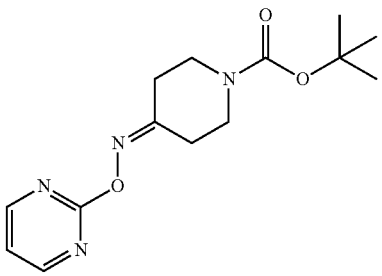 [SMILES: CC(C)(C)OC(=O)N1CCC(=NOc2ncccn2)CC1]

Cesium carbonate 288 mg (0.882 mmol) was added to a DMF solution (1 mL) of tert-butyl 4-(hydroxyimino)piperidine-1-carboxylate 148 mg (0.689 mmol) and 2-chloropyrimidine 51.9 mg (0.453 mmol), and the mixture was stirred at 85° C. for 4 hours. After the completion of the reaction, a saturated aqueous sodium bicarbonate solution was added to the reaction mixture, and followed by extraction with ethyl acetate. The organic layer was dried over anhydrous sodium sulfate, and filtered. The filtrate was concentrated under reduced pressure. The concentrated residue was purified by silica gel column chromatography (eluting solvent: ethyl acetate:methanol) to give the title compound 37.1 mg (0.127 mmol, yield 28%) as a dark brown solid.

$^1$H-NMR spectrum (400 MHz, CDCl$_3$) δ:8.63 (d, J=4.8 Hz, 2H), 7.08-7.04 (m, 1H), 3.69-3.49 (m, 4H), 2.95-2.85 (m, 2H), 2.71-2.52 (m, 2H), 1.49 (s, 9H).

Reference Example 123

Piperidin-4-one O-pyrimidin-2-yl oxime (Reference Compound 123)

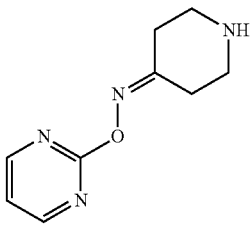 [SMILES: c1cnc(ON=C2CCNCC2)nc1]

2,6-Dimethylpyridine 28 µl (0.24 mmol) was added to a methylene chloride solution (1 mL) of tert-butyl 4-[(pyrimidin-2-yloxy)imino]piperidine-1-carboxylate 35 mg (0.12 mmol) synthesized in the same manner as in Reference Example 122, and the mixture was stirred at room temperature for 3 minutes. Next, trimethylsilyl trifluoromethanesulfonate 33 µl (0.18 mmol) was added, and the mixture was stirred at room temperature for 17 hours. Next, 2,6-dimethylpyridine 42 µl (0.36 mmol) and trimethylsilyl trifluoromethanesulfonate 44 µl (0.24 mmol) were added, and the mixture was stirred at room temperature for 3 hours. After the completion of the reaction, the reaction mixture was concentrated under reduced pressure. The concentrated residue was purified by silica gel column chromatography (DNH silica gel, eluting solvent: ethyl acetate:methanol) to give the title compound (including impurities) as a dark brown oil.

Test Example 1

Human VAP-1 enzyme inhibition test

This test was conducted by modifying the method of P. H. Yu et al. (Diabetologia 40 1243 (1997)). Human VAP-1 enzyme (R&D Systems, Inc.) was pre-incubated in a 96-well plate with the compound dissolved in dimethylsulfoxide at room temperature for 20 minutes. Next, in a solution to the final volume of 200 µL, the enzyme reaction solution was incubated with $^{14}$C-benzylamine (final concentration 100 µM) at 37° C. for 1 hour. The reaction was terminated by the addition of 100 µL of 2 M citric acid solution to the reaction solution. The oxidative product was extracted using a toluene/ethyl acetate mixture and the radioactivity was measured with a liquid scintillation counter. The inhibition ratio of the compound was calculated using the following equation.

Inhibition ratio={1−[VAP-1 enzyme activity after treatment with the compound]/[VAP-1 enzyme activity in the presence of dimethylsulfoxide alone without the compound]}×100

In this test, the compounds of the present invention showed excellent human VAP-1 inhibitory activity. For example, inhibition ratio of 50% or over was attained by the compounds, each 30 nM, of Examples 1, 2, 3, 5, 6, 7, 8, 12, 20, 25, 36, 37, 41, 42, 43, 44, 45, 46, 47, 49, 50, 57, 60, 68, 69, 70, 71, 72, 73, 74, 75, 76, 77, 85, 86, 87, 90, 91, 92, 93, 94, 95, 96, 97, 98, 99, 100, 101, 102, 103, 104, 105, 107, 108, 110, 111, 112, 113, 114, 115, 116, 117, 118, 120, 122, 123, 124, 125, 126, 128, 130, 131, 132, 133, 134, 135, 136, 137, 138, 139, 140, 141, 142, 143, 144, 146, 147, 148, 150, 151, 152, 153, 154, 155, 156, 157, 159, 162, 164, 165, 166, 167, 168, 169, 171, 172, 173, 174, 175, 176, 177, 178, 179, 180, 182, 183, 184, 185, 186, 187, 188, 189, 190, 191, 192, 193, 194, 195, 196, 197, 198, 199, 200, 201, 202, 203, 204, 205, 206, 207 and 208.

Test Example 2

Human plasma VAP-1 inhibition test

This test was conducted by modifying the method of P. H. Yu et al. (Diabetologia 40 1243 (1997)). Human blood was collected from a healthy donor in a heparin tube, and was centrifuged at 3000 rpm and 4° C. for 10 minutes to get plasma. The plasma was pre-incubated in a 96-well microplate with the compound dissolved in dimethylsulfoxide and Pargyline (final concentration 100 µM) at room temperature for 20 minutes. Next, in a solution to the final volume of 200 µL, the plasma reaction solution was incubated with $^{14}$C-benzylamine (final concentration 50 µM) at 37° C. for 1 hour. The reaction was terminated by the addition of 100 µL of 2 M citric acid solution to the reaction solution. The oxidative product was extracted using a toluene/ethyl acetate mixture and the radioactivity was measured with a liquid scintillation counter. The inhibition ratio of the compound was calculated using the following equation.

Inhibition ratio={1−[VAP-1 activity after treatment with the compound]/[VAP-1 activity in the presence of dimethylsulfoxide alone without the compound]}×100

Test Example 3

Rat Plasma VAP-1 Inhibition Test

This test was conducted by modifying the method of P. H. Yu et al. (Diabetologia 40 1243 (1997)). Blood was collected from 7-12 week old SD male rats in heparin tubes, and was centrifuged at 3000 rpm and 4° C. for 10 minutes to get plasma. The plasma was pre-incubated in a 96-well microplate with the compound dissolved in dimethylsulfoxide and Pargyline (final concentration 100 µM) at room temperature for 20 minutes. Next, in a solution to the final volume of 200 µL, the plasma reaction solution was incubated with $^{14}$C-benzylamine (final concentration 2.5 µM) at 37° C. for 3 hours. The reaction was terminated by the addition of 100 µL of 2 M citric acid solution to the reaction solution. The oxidative product was extracted using a toluene/ethyl acetate mixture and the radioactivity was measured with a liquid scintillation counter. The inhibition ratio of the compound was calculated using the following equation.

Inhibition ratio={1−[VAP-1 activity after treatment with the compound]/[VAP-1 activity in the presence of dimethylsulfoxide alone without the compound]}×100

Test Example 4

(Ex Vivo) Rat Plasma VAP-1 Inhibition Test after Oral Administration of the Compound The compound was orally administered (0.3-10 mg/kg) to 7-12 week old SD male rats in the non-fasting state. Under anesthesia, the blood was collected in heparin tubes from the jugular vein before the administration and 3, 8 and 24 hours after the administration. The blood was centrifuged at 14000 rpm for 10 minutes to get plasma. The VAP-1 enzyme activity in the plasma was measured by radiochemical enzyme assay.

The radiochemical enzyme assay was conducted by modifying the method of P. H. Yu et al. (Diabetologia 40 1243 (1997)). $^{14}$C-benzylamine (2.5 µM) was added to the obtained plasma, and was incubated at 37° C. for 3 hours. The reaction was terminated by the addition of 100 µL of 2 M citric acid solution to the reaction solution. The oxidative product was extracted using a toluene/ethyl acetate mixture and the radioactivity was measured with a liquid scintillation counter. The inhibition ratio of the compound was calculated using the following equation.

Inhibition ratio={1−[Plasma VAP-1 activity after administration of the compound]/[Plasma VAP-1 activity before administration]}×100

In this test, the compounds of the present invention showed excellent VAP-1 inhibitory activity. For example, inhibition ratio of 50% or over was attained 3 hours after the administration of the compounds, each at a dose of 0.3 mg/kg, of Examples 1, 2, 3, 5, 12, 20, 36, 37, 41, 42, 51, 53, 57, 60, 68, 69, 70, 72, 83, 85, 86, 87, 90, 91, 94, 95, 96, 97, 98, 99, 101, 102, 105, 133, 134, 141, 144, 149, 150, 151, 153, 154, 155, 156, 159, 165, 166, 167, 168, 169, 171, 173, 174, 175, 176, 177, 178, 182 and 183.

Test Example 5

Effect on Albuminuria of Diabetic Rats

Diabetes was induced by intravenous injection of 50 mg/mL/kg streptozotocin (STZ) in 2 mM citric acid buffer solution (pH 4.5) into 7 to 8 week old (weighing 180 to 250 g) SD rats. At the same time, normal rats were injected with the same amount of 2 mM citric acid buffer solution (pH 4.5) as control. The blood glucose level was measured by an enzyme electrode method. On the fourth day after the STZ injection, rats with a blood glucose level above 350 mg/dL were classfied as a diabetic model. The compound was administered daily for 4 weeks from the day of the STZ injection. After the treatment with the compound for 4 weeks, urine was collected for 24 hours using a metabolic cage, and the albumin concentration in the urine was measured.

Test Example 6

Effect on Livers in Non-Alcoholic Steatohepatitis (NASH) Models

This study was conducted using NASH model mice/ STAM (registered trademark) model mice (Medical Molecular Morphology 46 141 (2013)) from Stelic Institute & Co., Inc.

Fourteen-day-pregnant C57BL6J/JcL mice (CLEA Japan, Inc.) were fed and allowed to give the birth. Two-day-old mice were subcutaneously injected with streptozotocin (SIGMA-ALDRICH JAPAN) in physiological saline (Japanese Pharmacopoeia, Otsuka Pharmaceutical Co., Ltd.) one time to their backs. After 4 weeks of age, the mice were fed with high fat diet (High Fat Diet 32 (sterilized by radiation, CLEA Japan, Inc.) until the end of the experimental.

The compound was orally administered daily from 5- or 6-week-old. At 9- or 11-week-old, the animals were sacrificed under anesthesia. The livers were collected and their wet weights were measured. Paraffin sections or frozen sections were prepared from part of the livers, and were histopathologically examined, and the NAFLD activity score was measured. Further, RNA was extracted from the part of the livers, and the expression of fibrosis marker gene was measured by a quantitative PCR method. The results were statistically analyzed using EXSUS or Prism 4 (manufactured by GraphPad Software).

Test Example 7

The Cytotoxicity Inhibition Test in Human Normal Glomerular Microvascular Endothelial Cells Human normal glomerular microvascular endothelial cells were plated at 6000 cells/well in a collagen-coated 96-well culture plate. After one day of culture, the medium at each well was completely removed by aspiration and replaced with 50 μL of the compound solution diluted with the basal medium. The basal medium containing 0.1% DMSO was added to control wells. Following, the plate was incubated in $CO_2$ incubator for 30 minutes. Fifty microliter of 2 mM methylamine diluted with the basal medium was added (final concentration 1 mM) to each negative control well (0% inhibition) as well as the compound-containing well, and 50 μL of the basal medium was added to each positive control well (100% inhibition). The plate was incubated in $CO_2$ incubator for 2 days. Ten microliter of CCK-8 was added to each well and the mixtures were incubated in a plate incubator at 37° C. for approximately 2 hours after stirring with a plate shaker. The absorbance of the mixtures at 450 nm was measured with a multiplate reader. The cytotoxicity inhibition ratio of the compound was calculated from the following equation.

Inhibition ratio={[Average absorbance of the compound-containing wells]−[Average absorbance of negative control wells]}/{[Average absorbance of positive control wells]−[Average absorbance of negative control wells]}×100

In this test, the compounds of the present invention showed excellent cytotoxicity inhibitory effect in human normal glomerular microvascular endothelial cells. For example, inhibition ratio of 50% or over was attained by the compounds, each 100 nM, of Examples 1, 2, 3, 5, 36, 37, 95, 96, 102, 133, 134, 141 and 144.

Test Example 8

The Cytotoxicity Inhibition Test in Human Normal Hepatic Sinusoid-Like Microvascular Endothelial Cells Human normal hepatic sinusoid-like microvascular endothelial cells were plated at 6000 cells/well in a collagen-coated 96-well culture plate. After one day of culture, the medium at each well was completely removed by aspiration and replaced with 50 μL of the compound solution diluted with the basal medium. The basal medium containing 0.1% DMSO was added to control wells. Following, the plate was incubated in $CO_2$ incubator for 30 minutes. Fifty microliter of 2 mM methylamine diluted with the basal medium was added (final concentration 1 mM) to each negative control well (0% inhibition) as well as the compound-containing well, and 50 μL of the basal medium was added to each positive control well (100% inhibition). The plate was incubated in $CO_2$ incubator for 2 days. Ten microliter of CCK-8 was added to each well and the mixtures were incubated in a plate incubator at 37° C. for approximately 2 hours after stirring with a plate shaker. The absorbance of the mixtures at 450 nm was measured with a multiplate reader. The cytotoxicity inhibition ratio of the compound was calculated from the following equation.

Inhibition ratio={[Average absorbance of the compound-containing wells]−[Average absorbance of negative control wells]}/{[Average absorbance of positive control wells]−[Average absorbance of negative control wells]}×100

In this test, the compounds of the present invention showed excellent cytotoxicity inhibitory effect in human normal glomerular microvascular endothelial cells. For example, inhibition ratio of 50% or over was attained by the compounds, each 300 nM, of Examples 1, 2, 3, 5, 36, 37, 95, 96, 102, 133, 134, 141 and 144.

Test Example 9

Rat Pharmacokinetic (PK) Study (Concentration of Compound in Plasma after Oral Administration)

Seven to eight week old SD rats (weighing 180 to 250 g) were orally administered with a suspension of the compound in 0.5 W/V % methylcellulose 400 solution. Under anesthesia, the blood was collected from the jugular vein in EDTA tubes at 0.25, 0.5, 1, 2, 4, 6, 8 and 24 hours after the administration of the compound. The blood was centrifuged at 4° C. and 6000 g for 3 minutes to give plasma. Acetonitrile was added to the plasma, and the mixture was stirred with a shaker at 750 rpm for 3 minutes and was deproteinized by centrifugation at 3700 rpm for 2 minutes. Thus, the obtained sample was analyzed by LC/MS under the following conditions.

The concentration of the compound in the plasma at each blood sampling time was determined by an internal standard method, and AUC all (Area Under Curve) was calculated by a trapezoidal method.

The following LC and MS systems were used for measurement.

LC: CBM 30 series manufactured by Shimadzu Corporation
Column: Phenomenex Kinetex C18 (50×2.1 mm, 2.6 μm)
Column temperature: 40° C.
Flow rate: 0.3 mL/min
Mobile phase A: 0.1% aqueous formic acid solution, mobile phase B: 0.1% formic acid,
50% acetonitrile/methanol mixture
Gradient: 0-2 minutes: A/B=90/10 to 10/90, 2 to 3 minutes: A/B=10/90, 3-3.01 minutes: A/B=10/90 to 90/10
MS: 3200 manufactured by SCIEX
Ionization: ESI
Mode: positive In this study, the compounds of the present invention showed excellent PK. For example, 1000 ng·h/mL or higher AUC was attained by the compounds of Examples 1, 36, 37, 95, 96 and 102 at a dose of 3 mg/kg.

INDUSTRIAL APPLICABILITY

The compounds of the present invention of the general formula (I) or pharmacologically acceptable salts thereof have high VAP-1 inhibitory activity and excellent pharmacokinetic characteristics, and are therefore useful for the treatment of diseases that are prevented, alleviated and/or remedied by the inhibition of VAP-1, typically, nonalcoholic fatty liver diseases such as nonalcoholic steatohepatitis; inflammatory diseases such as atopic dermatitis and psoriasis; diabetic complications such as diabetic neuropathy, diabetic retinopathy (in particular, diabetic macular edema) and diabetic nephropathy; vascular diseases such as atherosclerosis: heart diseases such as myocardial infarction; and metabolic disorders such as obesity.

The invention claimed is:

1. A compound of formula (I):

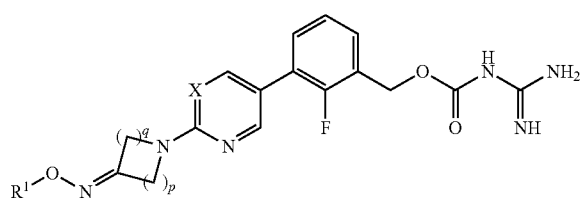

(I)

wherein,
$R^1$ represents a hydrogen atom, $C_1$-$C_7$ acyl group, tri($C_1$-$C_4$ alkyl)silyl group, tetrahydropyranyl group, triphenylmethyl group, optionally substituted $C_1$-$C_6$ alkyl group, optionally substituted $C_2$-$C_6$ alkenyl group, optionally substituted $C_3$-$C_8$ cycloalkyl group, optionally substituted $C_1$-$C_6$ alkoxy-$C_1$-$C_6$ alkyl group, —$CONR^{11}R^{12}$, optionally substituted heterocyclyl group, optionally substituted heterocyclyl-$C_1$-$C_6$ alkyl group, optionally substituted aryl group or optionally substituted $C_7$-$C_{16}$ aralkyl group, and X represents N or C—$R^2$, wherein, $R^2$ represents a hydrogen atom, halogen atom, optionally substituted $C_1$-$C_6$ alkyl group, optionally substituted $C_3$-$C_8$ cycloalkyl group, optionally substituted $C_1$-$C_6$ alkoxy group or cyano group, p and q, independently of each other, represent a natural number of 1 to 3, provided that the sum of p and q is a natural number of 2 to 4, wherein, the term "substituted" refers to being substituted with at least one substituent selected from the group consisting of a deuterium atom, halogen atom, $C_1$-$C_6$ alkyl group, $C_1$-$C_6$ alkoxy group, $C_1$-$C_6$ alkoxy-$C_1$-$C_6$ alkyl group, $R^{13}$O-$C_1$-$C_6$ alkyl group, halo-$C_1$-$C_6$ alkyl group, $C_7$-$C_{16}$ aralkyl group, $C_1$-$C_7$ acyl group, cyano group, oxo group, —$CONR^{11}R^{12}$, —$OR^{13}$, —$COOR^{14}$, —$NR^{15}R^{16}$ and —$S(O)_nR^{17}$, $R^{11}$ and $R^{12}$ independently represent a hydrogen atom or $C_1$-$C_6$ alkyl group, $R^{13}$ represents a hydrogen atom, $C_1$-$C_7$ acyl group, tri($C_1$-$C_4$ alkyl)silyl group, tetrahydropyranyl group or triphenylmethyl group, or if two —$OR^{13}$ groups are present and a 1,2- or 1,3-diol structure is formed, $R^{13}$ can represent acetonide, $R^{14}$ represents a hydrogen atom or $C_1$-$C_6$ alkyl group, $R^{15}$ and $R^{16}$ independently represent a hydrogen atom, $C_1$-$C_6$ alkyl group, $C_7$-$C_{16}$ aralkyl group, $C_1$-$C_7$ acyl group, —$COOR^{14}$ or —$S(O)_nR^{17}$, $R^{17}$ represents a $C_1$-$C_6$ alkyl group, and n represents 0, 1 or 2;

or a pharmacologically acceptable salt thereof.

2. The compound according to claim 1, of formula (II):

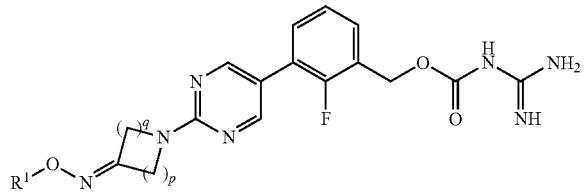

(II)

wherein,
$R^1$ represents a hydrogen atom, $C_1$-$C_7$ acyl group, tri($C_1$-$C_4$ alkyl)silyl group, tetrahydropyranyl group, triphenylmethyl group, optionally substituted $C_1$-$C_6$ alkyl group, optionally substituted $C_2$-$C_6$ alkenyl group, optionally substituted $C_3$-$C_8$ cycloalkyl group, optionally substituted $C_1$-$C_6$ alkoxy-$C_1$-$C_6$ alkyl group, —$CONR^{11}R^{12}$, optionally substituted heterocyclyl group, optionally substituted heterocyclyl-$C_1$-$C_6$ alkyl group, optionally substituted aryl group or optionally substituted $C_7$-$C_{16}$ aralkyl group, and p and q, independently of each other, represent a natural number of 1 to 3, provided that the sum of p and q is a natural number of 2 to 4, wherein, the term "substituted" refers to being substituted with at least one substituent selected from the group consisting of a deuterium atom, halogen atom, $C_1$-$C_6$ alkyl group, $C_1$-$C_6$ alkoxy group, $C_1$-$C_6$ alkoxy-$C_1$-$C_6$ alkyl group, $R^{13}$O-$C_1$-$C_6$ alkyl group, halo-$C_1$-$C_6$ alkyl group, $C_7$-$C_{16}$ aralkyl group, $C_1$-$C_7$ acyl group, cyano group, oxo group, —$CONR^{11}R^{12}$, —$OR^{13}$, —$COOR^{14}$, —$NR^{15}R^{16}$ and —$S(O)_nR^{17}$, R$^{11}$ and R$^{12}$ independently represent a hydrogen atom or C$_1$-C$_6$ alkyl group, R$^{13}$ represents a hydrogen atom, C$_1$-C$_7$ acyl group, tri(C$_1$-C$_4$ alkyl)silyl group, tetrahydropyranyl group or triphenylmethyl group, or if two —OR$^{13}$ groups are present and a 1,2- or 1,3-diol structure is formed, R$^{13}$ can represent acetonide, R$^{14}$ represents a hydrogen atom or C$_1$-C$_6$ alkyl group, R$^{15}$ and R$^{16}$ independently represent a hydrogen atom, C$_1$-C$_6$ alkyl group, C$_7$-C$_{16}$ aralkyl group, C$_1$-C$_7$ acyl group, —COOR$^{14}$ or —S(O)$_n$R$^{17}$, R$^{17}$ represents a C$_1$-C$_6$ alkyl group, and n represents 0, 1 or 2;

or a pharmacologically acceptable salt thereof.

3. The compound according to claim 2, or a pharmacologically acceptable salt thereof, wherein R$^1$ represents a hydrogen atom, optionally substituted C$_1$-C$_6$ alkyl group, C$_2$-C$_6$ alkenyl group, optionally substituted C$_3$-C$_8$ cycloalkyl group, optionally substituted C$_1$-C$_6$ alkoxy-C$_1$-C$_6$ alkyl group or optionally substituted heterocyclyl group, wherein, the term "substituted" refers to being substituted with at least one substituent selected from the group consisting of a deuterium atom, halogen atom, —OR$^{13}$ and —S(O)$_n$R$^{17}$, R$^{13}$ represents a hydrogen atom, C$_1$-C$_7$ acyl group, tri(C$_1$-C$_4$ alkyl)silyl group, tetrahydropyranyl group or triphenylmethyl group, or if two —OR$^{13}$ groups are present and a 1,2- or 1,3-diol structure is formed, R$^{13}$ can represent acetonide, R$^{17}$ represents a C$_1$-C$_6$ alkyl group, and n represents 0, 1 or 2.

4. The compound according to claim 3, or a pharmacologically acceptable salt thereof, wherein p and q represent 1.

5. The compound according to claim 4, or a pharmacologically acceptable salt thereof, wherein R$^1$ represents a C$_1$-C$_4$ alkyl group, or a C$_1$-C$_4$ alkyl group substituted with at least one substituent selected from the group consisting of a deuterium atom, fluorine atom and hydroxyl group.

6. The compound according to claim 1, of formula (III):

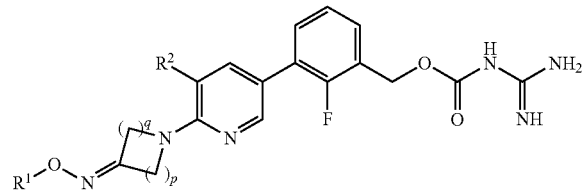

(III)

wherein,

R$^1$ represents a hydrogen atom, C$_1$-C$_7$ acyl group, tri(C$_1$-C$_4$ alkyl)silyl group, tetrahydropyranyl group, triphenylmethyl group, optionally substituted C$_1$-C$_6$ alkyl group, optionally substituted C$_2$-C$_6$ alkenyl group, optionally substituted C$_3$-C$_8$ cycloalkyl group, optionally substituted C$_1$-C$_6$ alkoxy-C$_1$-C$_6$ alkyl group, —CONR$^{11}$R$^{12}$, optionally substituted heterocyclyl group, optionally substituted heterocyclyl-C$_1$-C$_6$ alkyl group, optionally substituted aryl group or optionally substituted C$_7$-C$_{16}$ aralkyl group, and R$^2$ represents a hydrogen atom, halogen atom, optionally substituted C$_1$-C$_6$ alkyl group, optionally substituted C$_3$-C$_8$ cycloalkyl group, optionally substituted C$_1$-C$_6$ alkoxy group or cyano group, and p and q, independently of each other, represent a natural number of 1 to 3, provided that the sum of p and q is a natural number of 2 to 4, wherein, the term "substituted" refers to being substituted with at least one substituent selected from the group consisting of a deuterium atom, halogen atom, C$_1$-C$_6$ alkyl group, C$_1$-C$_6$ alkoxy group, C$_1$-C$_6$ alkoxy-C$_1$-C$_6$ alkyl group, R$^{13}$ O-C$_1$-C$_6$ alkyl group, halo-C$_1$-C$_6$ alkyl group, C$_7$-C$_{16}$ aralkyl group, C$_1$-C$_7$ acyl group, cyano group, oxo group, —CONR$^{11}$R$^{12}$, —OR$^{13}$, —COOR$^{14}$, —NR$^{15}$R$^{16}$ and —S(O)$_n$R$^{17}$, R$^{11}$ and R$^{12}$ independently represent a hydrogen atom or C$_1$-C$_6$ alkyl group, R$^{13}$ represents a hydrogen atom, C$_1$-C$_7$ acyl group, tri(C$_1$-C$_4$ alkyl)silyl group, tetrahydropyranyl group or triphenylmethyl group, or if two —OR$^{13}$ groups are present and a 1,2- or 1,3-diol structure is formed, R$^{13}$ can represent acetonide, R$^{14}$ represents a hydrogen atom or C$_1$-C$_6$ alkyl group, R$^{15}$ and R$^{16}$ independently represent a hydrogen atom, C$_1$-C$_6$ alkyl group, C$_7$-C$_{16}$ aralkyl group, C$_1$-C$_7$ acyl group, —COOR$^{14}$ or —S(O)$_n$R$^{17}$, R$^{17}$ represents a C$_1$-C$_6$ alkyl group, and n represents 0, 1 or 2;

or a pharmacologically acceptable salt thereof.

7. The compound according to claim 6, or a pharmacologically acceptable salt thereof, wherein R$^1$ represents a hydrogen atom, optionally substituted C$_1$-C$_6$ alkyl group, C$_2$-C$_6$ alkenyl group, optionally substituted C$_3$-C$_8$ cycloalkyl group, optionally substituted C$_1$-C$_6$ alkoxy-C$_1$-C$_6$ alkyl group or optionally substituted heterocyclyl group, wherein, the term "substituted" refers to being substituted with at least one substituent selected from the group consisting of a deuterium atom, halogen atom, —OR$^{13}$ and —S(O)$_n$R$^{17}$, R$^{13}$ represents a hydrogen atom, C$_1$-C$_7$ acyl group, tri(C$_1$-C$_4$ alkyl)silyl group, tetrahydropyranyl group or triphenylmethyl group, or if two —OR$^{13}$ groups are present and a 1,2- or 1,3-diol structure is formed, R$^{13}$ can represent acetonide, R$^{17}$ represents a C$_1$-C$_6$ alkyl group, and n represents 0, 1 or 2.

8. The compound according to claim 7, or a pharmacologically acceptable salt thereof, wherein R$^2$ represents a halogen atom.

9. The compound according to claim 8, or a pharmacologically acceptable salt thereof, wherein R$^2$ represents a fluorine atom.

10. The compound according to claim 9, or a pharmacologically acceptable salt thereof, wherein p and q represent 1.

11. The compound according to claim 10, or a pharmacologically acceptable salt thereof, wherein R$^1$ represents a C$_1$-C$_4$ alkyl group, or a C$_1$-C$_4$ alkyl group substituted with at least one substituent selected from the group consisting of a deuterium atom, fluorine atom and hydroxyl group.

12. The compound according to claim 1, or a pharmacologically acceptable salt thereof, wherein the compound is:

2-fluoro-3-{2-[3-(methoxyimino)azetidin-1-yl]pyrimidin-5-yl}benzyl carbamimidoylcarbamate, 3-{2-[3-(ethoxyimino)azetidin-1-yl]pyrimidin-5-yl}-2-fluorobenzyl carbamimidoylcarbamate, 2-fluoro-3-(2-{3-[(methoxy-d$_3$)imino]azetidin-1-yl}pyrimidin-5-yl)benzyl carbamimidoylcarbamate, 2-fluoro-3-(2-{3-[(2-fluoroethoxy)imino]azetidin-1-yl}pyrimidin-5-yl)benzyl carbamimidoylcarbamate, 3-{2-{3-[(2,2-difluoroethoxy)imino]azetidin-1-yl}pyrimidin-5-yl}-2-fluorobenzyl carbamimidoylcarbamate, 2-fluoro-3-(2-{3-[(2,2,2-trifluoroethoxy)imino]azetidin-1-yl}pyrimidin-5-yl)benzyl carbamimidoylcarbamate, 2-fluoro-3-(2-{3-[(3-fluoropropoxy)imino]azetidin-1-yl}pyrimidin-5-yl)benzyl carbamimidoylcarbamate, 2-fluoro-3-{2-[3-({4-[(tetrahydropyran-2-yl)oxy]butoxy}imino)azetidin-1-yl]pyrimidin-5-yl}benzyl carbamimidoylcarbamate, 2-fluoro-3-(2-{3-[(2-methoxyethoxy)imino]azetidin-1-yl}pyrimidin-5-yl)benzyl carbamimidoylcarbamate,

[({1-[5-(3-{[(carbamimidoylcarbamoyl)oxy]methyl}-2-fluorophenyl)pyrimidin-2-yl]azetidin-3-ylidene}amino)oxy]methyl pivalate, 1-[({1-[5-(3-{[(carbamimidoylcarbamoyl)oxy]methyl}-2-fluorophenyl)pyrimidin-2-yl]azetidin-3-ylidene}amino)oxy]-3-methoxypropan-2-yl acetate, 4-[({1-[5-(3-{[(carbamimidoylcarbamoyl)oxy]methyl}-2-fluorophenyl)pyrimidin-2-yl]azetidin-3-ylidene}amino)oxy]butan-1,2-diyl diacetate, 2-[({1-[5-(3-{[(carbamimidoylcarbamoyl)oxy]methyl}-2-fluorophenyl)pyrimidin-2-yl]azetidin-3-ylidene}amino)oxy]ethyl acetate, 2-[({1-[5-(3-{[(carbamimidoylcarbamoyl)oxy]methyl}-2-fluorophenyl)pyrimidin-2-yl]azetidin-3-ylidene}amino)oxy]ethyl propionate, 2-[({1-[5-(3-{[(carbamimidoylcarbamoyl)oxy]methyl}-2-fluorophenyl)pyrimidin-2-yl]azetidin-3-ylidene}amino)oxy]ethyl butyrate, 2-[({1-[5-(3-{[(carbamimidoylcarbamoyl)oxy]methyl}-2-fluorophenyl)pyrimidin-2-yl]azetidin-3-ylidene}amino)oxy]ethyl benzoate, 2-fluoro-3-{5-fluoro-6-[3-(methoxyimino)azetidin-1-yl]pyridin-3-yl}benzyl carbamimidoylcarbamate, 2-fluoro-3-{5-fluoro-6-{3-[(methoxy-$d_3$)imino]azetidin-1-yl}pyridin-3-yl}benzyl carbamimidoylcarbamate, 2-fluoro-3-{6-[3-(methoxyimino)azetidin-1-yl]pyridin-3-yl}benzyl carbamimidoylcarbamate, 2-fluoro-3-{6-[3-(methoxyimino)azetidin-1-yl]-5-methylpyridin-3-yl}benzyl carbamimidoylcarbamate, 3-{5-cyano-6-[3-(methoxyimino)azetidin-1-yl]pyridin-3-yl}-2-fluorobenzyl carbamimidoylcarbamate, 3-{5-chloro-6-[3-(methoxyimino)azetidin-1-yl]pyridin-3-yl}-2-fluorobenzyl carbamimidoylcarbamate, 3-{5-(difluoromethyl)-6-[3-(methoxyimino)azetidin-1-yl]pyridin-3-yl}-2-fluorobenzyl carbamimidoylcarbamate, 3-{5-(cyclopropyl)-6-[3-(methoxyimino)azetidin-1-yl]pyridin-3-yl}-2-fluorobenzyl carbamimidoylcarbamate, 3-{5-ethyl-6-[3-(methoxyimino)azetidin-1-yl]pyridin-3-yl}-2-fluorobenzyl carbamimidoylcarbamate, 2-fluoro-3-{6-[3-(methoxymino)azetidin-1-yl]-5-(methoxymethyl)pyridin-3-yl}benzyl carbamimidoylcarbamate, 2-fluoro-3-{5-methoxy-6-[3-(methoxyimino)azetidin-1-yl]pyridin-3-yl}benzyl carbamimidoylcarbamate, 2-fluoro-3-{2-[4-(methoxymino)piperidin-1-yl]pyrimidin-5-yl}benzyl carbamimidoylcarbamate, 3-{2-[4-(ethoxyimino)piperidin-1-yl]pyridimin-5-yl}-2-fluorobenzyl carbamimidoylcarbamate, 2-fluoro-3-{2-[4-(isopropoxyimino)piperidin-1-yl]pyrimidin-5-yl}benzyl carbamimidoylcarbamate, 2-fluoro-3-{2-[4-(propoxyimino)piperidin-1-yl]pyrimidin-5-yl}benzyl carbamimidoylcarbamate, 3-(2-{4-[(allyloxy)imino]piperidin-1-yl}pyridimin-5-yl)-2-fluorobenzyl carbamimidoylcarbamate, 2-fluoro-3-{2-[4-({2-[(tetrahydropyran-2-yl)oxy]ethoxy}imino)piperidin-1-yl]pyrimidin-5-yl}benzyl carbamimidoylcarbamate, 2-fluoro-3-(2-{4-[(2-methoxyethoxy)imino]piperidin-1-yl}pyridimin-5-yl)benzyl carbamimidoylcarbamate, 2-[({1-[5-(3-{[(carbamimidoylcarbamoyl)oxy]methyl}-2-fluorophenyl)pyrimidin-2-yl]piperidin-4-ylidene}amino)oxy]ethyl acetate, (E/Z)-2-fluoro-3-{2-[3-(methoxyimino)pyrrolidin-1-yl]pyrimidin-5-yl}benzyl carbamimidoylcarbamate, 2-fluoro-3-{2-[3-(hydroxymino)azetidin-1-yl]pyrimidin-5-yl}benzyl carbamimidoylcarbamate, 2-fluoro-3-(2-{3-[(2-hydroxyethoxy)imino]azetidin-1-yl}pyrimidin-5-yl)benzyl carbamimidoylcarbamate, 2-fluoro-3-(2-{3-[(3-hydroxypropoxy)imino]azetidin-1-yl}pyrimidin-5-yl)benzyl carbamimidoylcarbamate, 2-fluoro-3-(2-{3-[(4-hydroxybutoxy)imino]azetidin-1-yl}pyrimidin-5-yl)benzyl carbamimidoylcarbamate, 2-fluoro-3-[2-(3-{[2-(2-hydroxyethoxy)ethoxy]imino}azetidin-1-yl)pyrimidin-5-yl]benzyl carbamimidoylcarbamate, 2-fluoro-3-[2-(3-{[3-fluoro-2-(hydroxymethyl)propoxy]imino}azetidin-1-yl)pyrimidin-5-yl]benzyl carbamimidoylcarbamate, 2-fluoro-3-(2-{3-[(4-hydroxy-3-methoxybutoxy)imino]azetidin-1-yl}pyrimidin-5-yl)benzyl carbamimidoylcarbamate, 3-[({1-[5-(3-{[(carbamimidoylcarbamoyl)oxy]methyl}-2-fluorophenyl)pyrimidin-2-yl]azetidin-3-ylidene}amino)oxy]-2-(hydroxymethyl)propyl acetate, 3-[({1-[5-(3-{[(carbamimidoylcarbamoyl)oxy]methyl}-2-fluorophenyl)pyrimidin-2-yl]azetidin-3-ylidene}amino)oxy]-2-(hydroxymethyl)propyl propionate, 3-[({1-[5-(3-{[(carbamimidoylcarbamoyl)oxy]methyl}-2-fluorophenyl)pyrimidin-2-yl]azetidin-3-ylidene}amino)oxy]-2-(hydroxymethyl)propyl butyrate, 3-[({1-[5-(3-{[(carbamimidoylcarbamoyl)oxy]methyl}-2-fluorophenyl)pyrimidin-2-yl]azetidin-3-ylidene}amino)oxy]-2-(hydroxymethyl)propyl isobutyrate, 3-[({1-[5-(3-{[(carbamimidoylcarbamoyl)oxy]methyl}-2-fluorophenyl)pyrimidin-2-yl]azetidin-3-ylidene}amino)oxy]-2-(hydroxymethyl)propyl pivalate, 3-[({1-[5-(3-{[(carbamimidoylcarbamoyl)oxy]methyl}-2-fluorophenyl)pyrimidin-2-yl]azetidin-3-ylidene}amino)oxy]-2-(hydroxymethyl)propyl hexanoate, 3-[({1-[5-(3-{[(carbamimidoylcarbamoyl)oxy]methyl}-2-fluorophenyl)pyrimidin-2-yl]azetidin-3-ylidene}amino)oxy]-2-(hydroxymethyl)propyl benzoate, 2-fluoro-3-{5-(2-hydroxypropan-2-yl)-6-[3-(methoxyimino)azetidin-1-yl]pyridin-3-yl}benzyl carbamimidoylcarbamate, 2-fluoro-3-(2-{4-[(2-hydroxyethoxy)imino]piperidin-1-yl}pyrimidin-5-yl)benzyl carbamimidoylcarbamate, 2-fluoro-3-(2-{4-[(3-hydroxypropoxy)imino]piperidin-1-yl}pyrimidin-5-yl)benzyl carbamimidoylcarbamate, 2-fluoro-3-(2-{4-[(4-hydroxybutoxy)imino]piperidin-1-yl}pyrimidin-5-yl)benzyl carbamimidoylcarbamate, 2-fluoro-3-(2-{4-[(3-hydroxy-2,2-dimethylpropoxy)imino]piperidin-1-yl}pyrimidin-5-yl)benzyl carbamimidoylcarbamate,
2-fluoro-3-(2-{4-[(3-hydroxy-3-methylbutoxy)imino]piperidin-1-yl}pyrimidin-5-yl)benzyl carbamimidoylcarbamate,
2-fluoro-3-(2-{4-[(2-hydroxypropoxy)imino]piperidin-1-yl}pyrimidin-5-yl)benzyl carbamimidoylcarbamate,
2-fluoro-3-(2-{4-[(3-hydroxy-2-methylpropoxy)imino]piperidin-1-yl}pyrimidin-5-yl)benzyl carbamimidoylcarbamate,
2-fluoro-3-[2-(3-{[3-hydroxy-2-(hydroxymethyl)propoxy]imino}azetidin-1-yl)pyrimidin-5-yl]benzyl carbamimidoylcarbamate,
3-(2-{3-[(2,3-dihydroxypropoxy)imino]azetidin-1-yl}pyrimidin-5-yl)-2-fluorobenzyl carbamimidoylcarbamate,
3-(2-{3-[(3,4-dihydroxybutoxy)imino]azetidin-1-yl}pyrimidin-5-yl)-2-fluorobenzyl carbamimidoylcarbamate,
3-(6-{3-[(3,4-dihydroxybutoxy)imino]azetidin-1-yl}-5-fluoropyridin-3-yl)-2-fluorboenzyl carbamimidoylcarbamate,
2-fluoro-3-{5-fluoro-6-[3-{[3-hydroxy-2-(hydroxymethyl)propoxy]imino}azetidin-1-yl]pyridin-3-yl}benzyl carbamimidoylcarbamate,
2-fluoro-3-[2-(4-{[3-hydroxy-2-(hydroxymethyl)propoxy]imino}piperidin-1-yl)pyrimidin-5-yl]benzyl carbamimidoylcarbamate,
2-fluoro-3-[2-(4-{[3-hydroxy-2-(hydroxymethyl)-2-methylpropoxy]imino}piperidin-1-yl)pyrimidin-5-yl]benzyl carbamimidoylcarbamate,
3-(2-{4-[(2,3-dihydroxypropoxy)imino]piperidin-d-yl}pyrimidin-5-yl)-2-fluorobenzyl carbamimidoylcarbamate,
2-fluoro-3-[2-(3-{[3-hydroxy-2-(methoxymethyl)propoxy]imino}azetidin-1-yl)pyrimidin-5-yl]benzyl carbamimidoylcarbamate,
2-fluoro-3-(2-{3-[(3-hydroxy-2-methoxypropoxy)imino]azetidin-1-yl}pyrimidin-5-yl)benzyl carbamimidoylcarbamate,
2-fluoro-3-(2-{3-[(2-fluoro-3-hydroxypropoxy)imino]azetidin-1-yl}pyrimidin-5-yl)benzyl carbamimidoylcarbamate,
2-fluoro-3-(5-fluoro-6-{3-[(2-fluoro-3-hydroxypropoxy)imino]azetidin-1-yl}pyridin-3-yl)benzyl carbamimidoylcarbamate,
2-fluoro-3-(2-{3-[(2-hydroxy-3-methoxypropoxy)imino]azetidin-1-yl}pyrimidin-5-yl)benzyl carbamimidoylcarbamate,
2-fluoro-3-{2-[4-(hydroxyimino)piperidin-1-yl]pyrimidin-5-yl}benzyl carbamimidoylcarbamate,
2-fluoro-3-{5-fluoro-6-[3-(hydroxyimino)azetidin-1-yl]pyridin-3-yl}benzyl carbamimidoylcarbamate,
tert-butyl 2-[({1-[5-(3-{[(carbamimidoylcarbamoyl)oxy]methyl}-2-fluorophenyl)pyrimidin-2-yl]azetidin-3-ylidene}amino)oxy]acetate,
2-[({1-[5-(3-{[(carbamimidoylcarbamoyl)oxy]methyl}-2-fluorophenyl)pyrimidin-2-yl]azetidin-3-ylidene}amino)oxy]acetic acid,
3-[2-(3-{[(dimethylcarbamoyl)oxy]imino}azetidin-1-yl)pyrimidin-5-yl]-2-fluorobenzyl carbamimidoylcarbamate,
2-fluoro-3-[2-(3-{[2-(methylamino)-2-oxoethoxy]imino}azetidin-1-yl)pyrimidin-5-yl]benzyl carbamimidoylcarbamate,
3-(2-{3-[(3-amino-3-oxopropoxy)imino]azetidin-1-yl}pyrimidin-5-yl)-2-fluorobenzyl carbamimidoylcarbamate,
2-fluoro-3-[2-(3-{[3-(methylamino)-3-oxopropoxy]imino}azetidin-1-yl)pyrimidin-5-yl]benzyl carbamimidoylcarbamate,
ethyl 4-[({1-[5-(3-{[(carbamimidoylcarbamoyl)oxy]methyl}-2-fluorophenyl)pyrimidin-2-yl]azetidin-3-ylidene}amino)oxy]butanoate,
4-[({1-[5-(3-{[(carbamimidoylcarbamoyl)oxy]methyl}-2-fluorophenyl)pyrimidin-2-yl]azetidin-3-ylidene}amino)oxy]butanoic acid,
2-fluoro-3-[2-(3-{[4-(methylamino)-4-oxobutoxy]imino}azetidin-1-yl)pyrimidin-5-yl]benzyl carbamimidoylcarbamate,
3-[2-(3-{[2-(dimethylamino)ethoxy]imino}azetidin-1-yl)pyrimidin-5-yl]-2-fluorobenzyl carbamimidoylcarbamate,
3-{2-[3-{{2-[benzyl(methyl)amino]ethoxy}imino}azetidin-1-yl]pyrimidin-5-yl}-2-fluorobenzyl carbamimidoylcarbamate,
3-[2-(3-{[3-(acetamido-2-(hydroxymethyl)propoxy]imino}azetidin-1-yl)pyrimidin-5-yl]-2-fluorobenzyl carbamimidoylcarbamate,
3-[2-(3-{[3-(dimethylamino)-2-(hydroxymethyl)propoxy]imino}azetidin-1-yl)pyrimidin-5-yl]-2-fluorobenzyl carbamimidoylcarbamate,
3-(2-{3-[(3-acetamido-2-methoxypropoxy)imino]azetidin-1-yl}pyrimidin-5-yl)-2-fluorobenzyl carbamimidoylcarbamate,
2-fluoro-3-[2-(3-{[2-(piperidin-1-yl)ethoxy]imino}azetidin-1-yl)pyrimidin-5-yl]benzyl carbamimidoylcarbamate,
2-fluoro-3-(2-{3-[(morpholinoethoxy)imino]azetidin-1-yl}pyrimidin-5-yl)benzyl carbamimidoylcarbamate,
3-[2-(3-{[2-(azetidin-1-yl)ethoxy]imino}azetidin-1-yl)pyrimidin-5-yl]-2-fluorobenzyl carbamimidoylcarbamate,
3-[2-(3-{[2-(3,3-difluoroazetidin-1-yl)ethoxy]imino}azetidin-1-yl)pyrimidin-5-yl]-2-fluorobenzyl carbamimidoylcarbamate,
2-fluoro-3-[2-(3-{[2-(3-fluoroazetidin-1-yl)ethoxy]imino}azetidin-1-yl)pyrimidin-5-yl]benzyl carbamimidoylcarbamate,
2-fluoro-3-[2-(3-{[2-(3-methoxyazetidin-1-yl)ethoxy]imino}azetidin-1-yl)pyrimidin-5-yl]benzyl carbamimidoylcarbamate,
2-fluoro-3-[2-(3-{[(4-methylmorpholin-2-yl)methoxy]imino}azetidin-1-yl)pyrimidin-5-yl]benzyl carbamimidoylcarbamate,
3-[2-(3-{[(4-acetylmorpholin-2-yl)methoxy]imino}azetidin-1-yl)pyrimidin-5-yl]-2-fluorobenzyl carbamimidoylcarbamate,
2-fluoro-3-[2-(3-{[(5-oxotetrahydrofuran-2-yl)methoxy]imino}azetidin-1-yl)pyrimidin-5-yl]benzyl carbamimidoylcarbamate,
3-[({1-[5-(3-{[(carbamimidoylcarbamoyl)oxy]methyl}-2-fluorophenyl)pyrimidin-2-yl]azetidin-3-ylidene}amino)oxy]cyclobutyl acetate,
2-fluoro-3-(2-{3-[(3-hydroxycyclobutoxy)imino]azetidin-1-yl}pyrimidin-5-yl)benzyl carbamimidoylcarbamate,
3-(2-{3-[(benzyloxy)imino]azetidin-1-yl}pyrimidin-5-yl)-2-fluorobenzyl carbamimidoylcarbamate,
2-fluoro-3-[2-(3-{[(4-methoxybenzyl)oxy]imino}azetidin-1-yl)pyrimidin-5-yl]benzyl carbamimidoylcarbamate, 2-fluoro-3-[2-(3-{[(1-methylazetidin-3-yl)oxy]imino}azetidin-1-yl)pyrimidin-5-yl]benzyl carbamimidoylcarbamate,
3-[2-(3-{[(1-acetylazetidin-3-yl)oxy]imino}azetidin-1-yl)pyrimidin-5-yl]-2-fluorobenzyl carbamimidoylcarbamate,
3-[2-(3-{[(1-benzylazetidin-3-yl)oxy]imino}azetidin-1-yl)pyrimidin-5-yl]-2-fluorobenzyl carbamimidoylcarbamate,
2-fluoro-3-{2-{3-({[1-(2,2,2-trifluoroethyl)azetidin-3-yl]oxy}imino)azetidin-1-yl]pyrimidin-5-yl}benzyl carbamimidoylcarbamate,
2-fluoro-3-{2-[3-({[1-(methylsulfonyl)azetidin-3-yl]oxy}imino)azetidin-1-yl]pyrimidin-5-yl}benzyl carbamimidoylcarbamate,
3-[2-(3-{[(1-ethylazetidin-3-yl)oxy]imino}azetidin-1-yl)pyrimidin-5-yl]-2-fluorobenzyl carbamimidoylcarbamate,
methyl 3-[({1-[5-(3-{[(carbamimidoylcarbamoyl)oxy]methyl}-2-fluorophenyl)pyrimidin-2-yl]azetidin-3-ylidene}amino)oxy]azetidin-1-carboxylate,
2-fluoro-3-(2-{3-[(oxetan-3-yloxy)imino]azetidin-1-yl}pyrimidin-5-yl)benzyl carbamimidoylcarbamate,
2-{3-[({1-[5-(3-{[(carbamimidoylcarbamoyl)oxy]methyl}-2-fluorophenyl)pyrimidin-2-yl]azetidin-3-ylidene}amino)oxy]azetidin-1-yl}ethyl acetate,
2-fluoro-3-{2-[3-({[1-(2-hydroxyethyl)azetidin-3-yl]oxy}imino)azetidin-1-yl]pyrimidin-5-yl}benzyl carbamimidoylcarbamate,
2-fluoro-3-{2-[3-({[1-(2-methoxyethyl)azetidin-3-yl]oxy}imino)azetidin-1-yl]pyrimidin-5-yl}benzyl carbamimidoylcarbamate,
2-fluoro-3-{2-[3-({[1-(2-fluoroethyl)azetidin-3-yl]oxy}imino)azetidin-1-yl]pyrimidin-5-yl}benzyl carbamimidoylcarbamate,
ethyl 3-[({1-[5-(3-{[(carbamimidoylcarbamoyl)oxy]methyl}-2-fluorophenyl)pyrimidin-2-yl]piperidin-4-ylidene}amino)oxy]propanoate,
3-(2-{4-[(3-amino-3-oxopropoxy)imino]piperidin-1-yl}pyrimidin-5-yl)-2-fluorobenzyl carbamimidoylcarbamate,
2-fluoro-3-[2-(4-{[3-(methylamino)-3-oxopropoxy]imino}piperidin-1-yl)pyrimidin-5-yl]benzyl carbamimidoylcarbamate,
ethyl 4-[({1-[5-(3-{[(carbamimidoylcarbamoyl)oxy]methyl}-2-fluorophenyl)pyrimidin-2-yl]piperidin-4-ylidene}amino)oxy]butanoate,
4-[({1-[5-(3-{[(carbamimidoylcarbamoyl)oxy]methyl}-2-fluorophenyl)pyrimidin-2-yl]piperidin-4-ylidene}amino)oxy]butanoic acid,
3-[2-(4-{[3-(dimethylamino)-3-oxopropoxy]imino}piperidin-1-yl)pyrimidin-5-yl]-2-fluorobenzyl carbamimidoylcarbamate,
3-(2-{4-[(2-acetamidoethoxy)imino]piperidin-1-yl}pyrimidin-5-yl)-2-fluorobenzyl carbamimidoylcarbamate,
2-fluoro-3-[2-(4-{[2-(N-methylacetamido)ethoxy]imino}piperidin-1-yl)pyrimidin-5-yl]benzyl carbamimidoylcarbamate,
2-fluoro-3-[2-(4-{[2-(N-methylmethylsulfonamido)ethoxy]imino}piperidin-1-yl)pyrimidin-5-yl]benzyl carbamimidoylcarbamate,
2-fluoro-3-[2-(4-{[2-(methylsulfonamido)ethoxy]imino}piperidin-1-yl)pyrimidin-5-yl]benzyl carbamimidoylcarbamate,
3-[2-(4-{[2-(dimethylamino)ethoxy]imino}piperidin-1-yl)pyrimidin-5-yl]-2-fluorobenzyl carbamimidoylcarbamate,
2-fluoro-3-[2-(4-{[2-(methylamino)ethoxy]imino}piperidin-1-yl)pyrimidin-5-yl]benzyl carbamimidoylcarbamate,
3-(2-{4-[(2-aminoethoxy)imino]piperidin-1-yl}pyrimidin-5-yl)-2-fluorobenzyl carbamimidoylcarbamate,
3-(2-{4-[(2-cyanoethoxy)imino]piperidin-1-yl}pyrimidin-5-yl)-2-fluorobenzyl carbamimidoylcarbamate,
3-(2-{4-[(3-cyanopropoxy)imino]piperidin-1-yl}pyrimidin-5-yl)-2-fluorobenzyl carbamimidoylcarbamate,
2-fluoro-3-[2-(4-{[2-(methylsulfonyl)ethoxy]imino}piperidin-1-yl)pyrimidin-5-yl]benzyl carbamimidoylcarbamate,
2-fluoro-3-[2-(4-{[3-(methylsulfonyl)propoxy]imino}piperidin-1-yl)pyrimidin-5-yl]benzyl carbamimidoylcarbamate,
2-fluoro-3-[2-(4-{[1-(methyl-1H-pyrazol-3-yl)methoxy]imino}piperidin-1-yl)pyrimidin-5-yl]benzyl carbamimidoylcarbamate,
3-[2-(4-{[(1H-pyrazol-3-yl)methoxy]imino}piperidin-1-yl)pyrimidin-5-yl]-2-fluorobenzyl carbamimidoylcarbamate,
2-fluoro-3-{2-[4-({[1-(tetrahydropyran-2-yl)-1H-pyrazol-4-yl]methoxy}imino)piperidin-1-yl]pyrimidin-5-yl}benzyl carbamimidoylcarbamate,
3-[2-(4-{[(1H-pyrazol-4-yl)methoxy]imino}piperidin-1-yl)pyrimidin-5-yl]-2-fluorobenzyl carbamimidoylcarbamate,
2-fluoro-3-[2-(4-{[1-(methyl-1H-pyrazol-4-yl)methoxy]imino}piperidin-1-yl)pyrimidin-5-yl]benzyl carbamimidoylcarbamate,
3-[2-(4-{[2-(1H-pyrazol-2-yl)ethoxy]imino}piperidin-1-yl)pyrimidin-5-yl]-2-fluorobenzyl carbamimidoylcarbamate,
2-fluoro-3-(2-{4-[(pyridin-4-ylmethoxy)imino}piperidin-1-yl)pyrimidin-5-yl]benzyl carbamimidoylcarbamate,
3-[2-(4-{[2-(2,5-dioxopyrrolidin-1-yl)ethoxy]imino}piperidin-1-yl)pyrimidin-5-yl]-2-fluorobenzyl carbamimidoylcarbamate,
2-fluoro-3-[2-(4-{[2-(2-oxopyrrolidin-1-yl)ethoxy]imino}piperidin-1-yl)pyrimidin-5-yl]benzyl carbamimidoylcarbamate,
2-fluoro-3-[2-(4-{[2-(2-oxooxazolidin-3-yl)ethoxy]imino}piperidin-1-yl)pyrimidin-5-yl]benzyl carbamimidoylcarbamate,
2-fluoro-3-[2-(4-{[2-(3-oxomorpholino)ethoxy]imino}piperidin-1-yl)pyrimidin-5-yl]benzyl carbamimidoylcarbamate,
2-fluoro-3-{2-[4-(phenoxyimino)piperidin-1-yl]pyrimidin-5-yl}benzyl carbamimidoylcarbamate,
2-fluoro-3-(2-{4-[(pyrimidin-5-yloxy)imino]piperidin-1-yl}pyrimidin-5-yl)benzyl carbamimidoylcarbamate, or
2-fluoro-3-(2-{4-[(pyrimidin-2-yloxy)imino]piperidin-1-yl}pyrimidin-5-yl)benzyl carbamimidoylcarbamate.

13. 2-fluoro-3-{2-[3-(methoxyimino)azetidin-1-yl]pyrimidin-5-yl}benzyl carbamimidoylcarbamate or a pharmacologically acceptable salt thereof.

14. 3-{2-[3-(ethoxyimino)azetidin-1-yl]pyrimidin-5-yl}-2-fluorobenzyl carbamimidoylcarbamate or a pharmacologically acceptable salt thereof.

15. 2-fluoro-3-(2-{3-[(methoxy-d₃)imino]azetidin-1-yl}pyrimidin-5-yl)benzyl carbamimidoylcarbamate or a pharmacologically acceptable salt thereof.

16. 2-fluoro-3-(2-{3-[(2-fluoroethoxy)imino]azetidin-1-yl}pyrimidin-5-yl)benzyl carbamimidoylcarbamate or a pharmacologically acceptable salt thereof.

17. 2-fluoro-3-{5-fluoro-6-[3-(methoxyimino)azetidin-1-yl]pyridin-3-yl}benzyl carbamimidoylcarbamate or a pharmacologically acceptable salt thereof.

18. 2-fluoro-3-{5-fluoro-6-{3-[(methoxy-d₃)imino]azetidin-1-yl}pyridine-3-yl}benzyl carbamimidoylcarbamate or a pharmacologically acceptable salt thereof.

19. 3-(6-{3-[(3,4-dihydroxybutoxy)imino]azetidin-1-yl}-5-fluoropyridin-3-yl)-2-fluorobenzyl carbamimidoylcarbamate or a pharmacologically acceptable salt thereof.

20. 2-fluoro-3-{5-fluoro-6-[3-{[hydroxyl-2-(hydroxymethyl)propoxy]imino}azetidin-1-yl]pyridin-3-yl}benzyl carbamimidoylcarbamate or a pharmacologically acceptable salt thereof.

21. 2-fluoro-3-(2-{3-[(2-fluoro-3-hydroxypropoxy)imino]azetidin-1-yl}pyrimidin-5-yl)benzyl carbamimidoylcarbamate or a pharmacologically acceptable salt thereof.

22. 3-[({1-[5-(3-{[(carbamimidoylcarbamoyl)oxy]methyl}-2-fluorophenyl)pyrimidin-2-yl]azetidin-3-ylidene}amino)oxy]cyclobutyl acetate or a pharmacologically acceptable salt thereof.

23. 2-fluoro-3-(2-{3-[(3-hydroxycyclobutoxy)imino]azetidin-1-yl}pyrimidin-5-yl)benzyl carbamimidoylcarbamate or a pharmacologically acceptable salt thereof.

24. 2-fluoro-3-{2-[3-({[1-(methylsulfonyl)azetidin-3-yl]oxy}imino)azetidin-1-yl]pyrimidin-5-yl}benzyl carbamimidoylcarbamate or a pharmacologically acceptable salt thereof.

25. 2-fluoro-3-(2-{3-[(oxetan-3-yloxy)imino]azetidin-1-yl}pyrimidin-5-yl)benzyl carbamimidoylcarbamate or a pharmacologically acceptable salt thereof.

26. The compound according to claim 1, or a pharmacologically acceptable salt thereof, wherein the pharmacologically acceptable salt is a salt of an organic acid.

27. The compound according to claim 1, or a pharmacologically acceptable salt thereof, wherein the pharmacologically acceptable salt is a salt of a dicarboxylic acid.

28. A pharmaceutical composition containing the compound according to claim 1, or a pharmacologically acceptable salt thereof, and at least one type of pharmacologically acceptable additive.

29. A method for treating a disease by inhibiting VAP-1, comprising: administering a therapeutically effective amount of the compound according to claim 1, or a pharmacologically acceptable salt thereof, to a patient in need thereof, wherein the disease is selected from the group consisting of non-alcoholic steatohepatitis, and diabetic nephropathy.

30. A method for treating a non-alcoholic fatty liver disease by inhibiting VAP-1, comprising: administering a therapeutically effective amount of the compound according to claim 1, or a pharmacologically acceptable salt thereof, to a patient in need thereof.

* * * * *